United States Patent
Brandt

(10) Patent No.: US 12,247,037 B2
(45) Date of Patent: Mar. 11, 2025

(54) 1-(2,6-DIAZASPIRO[3.3]HEPTAN-6-YL)-5,6-DIHYDRO-4H-BENZO[F][1,2,4]TRIAZOLO[4,3-A][1,4]DIAZEPINE DERIVATIVES AND RELATED COMPOUNDS AS VASOPRESSIN ANTAGONISTS FOR THE TREATMENT OF NEURO-PSYCHOLOGICAL DISORDERS

(71) Applicant: Neumora Therapeutics, Inc., Watertown, MA (US)

(72) Inventor: Gary Brandt, Alameda, CA (US)

(73) Assignee: Neumora Therapeutics, Inc., Watertown, MA (US)

( * ) Notice: Subject to any disclaimer, the term of this patent is extended or adjusted under 35 U.S.C. 154(b) by 456 days.

(21) Appl. No.: 17/311,974

(22) PCT Filed: Dec. 12, 2019

(86) PCT No.: PCT/US2019/066082
§ 371 (c)(1),
(2) Date: Jun. 8, 2021

(87) PCT Pub. No.: WO2020/123872
PCT Pub. Date: Jun. 18, 2020

(65) Prior Publication Data
US 2023/0084719 A1    Mar. 16, 2023

Related U.S. Application Data

(60) Provisional application No. 62/778,831, filed on Dec. 12, 2018.

(51) Int. Cl.
*C07D 519/00* (2006.01)
*A61P 25/22* (2006.01)

(52) U.S. Cl.
CPC ............ *C07D 519/00* (2013.01); *A61P 25/22* (2018.01)

(58) Field of Classification Search
CPC ................................ C07D 519/00; A61P 25/22
See application file for complete search history.

(56) References Cited

U.S. PATENT DOCUMENTS 11,186,577 B2 * 11/2021 Jones .................. C07D 498/04

FOREIGN PATENT DOCUMENTS

| WO | 2010/054961 A1 | 5/2010 |
|----|----------------|--------|
| WO | 2011/131596 A1 | 10/2011 |
| WO | 2018/226769 A1 | 12/2018 |

OTHER PUBLICATIONS

Hyman, A glimmer of light for neuropsychiatric disorders, 2008, Nature, vol. 455, p. 890-893 (Year: 2008).*

* cited by examiner

*Primary Examiner* — Joseph K McKane
*Assistant Examiner* — Karen Cheng
(74) *Attorney, Agent, or Firm* — Seed IP Law Group LLP

(57) ABSTRACT

The present invention relates to 1-(2,6-diazaspiro[3.3]heptan-6-yl)-5,6-dihydro-4H-benzo[f][1,2,4]triazolo[4,3-a][1,4]diazepine derivatives and related compounds of Formula (I): wherein A, B, G, $R^1$, $R^{1b}$, $R^{1C}$, $R^2$ and X are as defined herein. The present compounds are vasopressin receptor antagonists (in particular of the Via receptor) for the treatment of neuro-psychological disorders, such as e.g. autism, anxiety, stress-related disorders, depression, schizophrenia or bipolar disorder. The present description discloses the synthesis of exemplary compounds, as well as pharmacological data thereof (e.g. pages 71 to 246; examples 1 to 49; tables 1 to 5). An exemplary compound is e.g. 8-chloro-1-(2-(5-fluoropyridin-2-yl)-2,6-diazaspiro[3.3]heptan-6-yl)-5-methyl-5,6-dihydro-4H-benzo[f][1,2,4]triazolo[4,3-a][1,4]diazepine (example 1, compound no. 1).

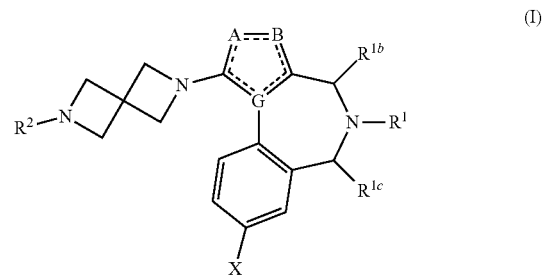

29 Claims, No Drawings

1-(2,6-DIAZASPIRO[3.3]HEPTAN-6-YL)-5,6-DIHYDRO-4H-BENZO[F][1,2,4]TRIAZOLO[4,3-A][1,4]DIAZEPINE DERIVATIVES AND RELATED COMPOUNDS AS VASOPRESSIN ANTAGONISTS FOR THE TREATMENT OF NEURO-PSYCHOLOGICAL DISORDERS

FIELD OF THE INVENTION

The invention relates to vasopressin receptor antagonists and to products containing the same, as well as to methods of their use and preparation.

BACKGROUND

Arginine vasopressin (AVP) is a naturally occurring neurohormone released in the brain and the blood stream. AVP is important in regulating water conservation, blood pressure and pituitary adrenocorticotropic hormone (ACTH) secretion and exerts its effects on physiology and behavior by binding to specific G protein-coupled receptors in the central nervous system and certain peripheral sites or tissues. Within the brain, AVP regulates circadian rhythms, facilitates hippocampal learning and memory and plays an important role in mediating social behaviors by acting in limbic circuits that are dysregulated in neurobehavioral disorders.

Three distinct AVP receptor subtypes have been identified on pharmacological and functional bases: V1a, V1b and V2. These receptors are located in the liver, vessels (coronary, renal, cerebral), platelets, kidney, uterus, adrenal glands, pancreas, central nervous system or pituitary gland. AVP is involved in the regulation of several functions, such as cardiovascular, hepatic, pancreatic, antidiuretic, and platelet-aggregating effects, and effects on the central and peripheral nervous system and on the uterine sphere. The effects of the AVP receptors depends on where they are located. The V1a receptor is found throughout the limbic system and cortex of the brain, and in the smooth muscle of blood vessels, uterus, and heart muscle. The V1b receptor is also located in limbic system and the pituitary gland. V2 receptors are located on the collecting ducts of nephrons in the kidney and have been a target for therapeutic approaches to the treatment of cardiovascular conditions.

Vasopressin functions as a neurochemical signal in the brain to affect social behavior. The V1a receptor is extensively expressed in the brain and particularly in limbic areas like the amygdala, lateral septum and hippocampus which are known to have an important role in the regulation of majority of the known effects of AVP, including anxiety, memory and learning, social cognition, aggressive behavior, affiliation, depression and the like. The V1a receptor is implicated in other neuropsychological disorders such as autistic spectrum disorders, schizophrenia, aggression, aggressive behavior and obsessive-compulsive disorders. The V1a receptor also mediates the cardiovascular effects of vasopressin in the brain by centrally regulating blood pressure and heart rate in the solitary tract nucleus and peripherally by inducing the contraction of vascular smooth muscles.

Use of vasopressin receptor antagonists, particularly V1a receptor antagonists, provides significant promise for the treatment of a variety of disorders which may benefit from antagonism of the V1a receptor. As a result, a number of V1a antagonists have been taken forward for clinical use and/or development. However, despite the advances made in this field, there remains a significant need for new and/or improved V1a receptor antagonists, as well as for pharmaceutical products containing the same, and for methods related to their use and manufacture.

SUMMARY OF THE INVENTION

The present invention is directed to compounds that antagonize vasopressin receptors, particularly the V1a receptor, to compositions containing the same, and to methods of their preparation and use for treatment of a malcondition wherein antagonism of the V1a receptor is medically indicated or beneficial.

In an embodiment, compounds are provided having the structure of Formula (I), or a pharmaceutically acceptable isomer, racemate, hydrate, solvate, isotope, or salt thereof:

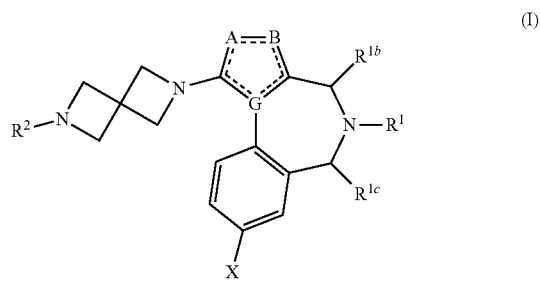

(I)

wherein A, B, G, $R^1$, $R^{1b}$, $R^{1c}$, $R^2$ and X are as defined below.

In an embodiment, a pharmaceutical composition is provided comprising a compound having the structure of Formula (I), or a pharmaceutically acceptable isomer, racemate, hydrate, solvate, isotope, or salt thereof, in combination with a pharmaceutically acceptable carrier, diluent, or excipient.

In an embodiment, use of a compound having the structure of Formula (I), or a pharmaceutically acceptable isomer, racemate, hydrate, solvate, isotope, or salt thereof, for the manufacture of a medicament is provided.

In an embodiment, a method is provided for antagonizing the V1a receptor, the method comprising contacting the receptor with an effective amount of a compound having the structure of Formula (I), or a pharmaceutically acceptable isomer, racemate, hydrate, solvate, isotope, or salt thereof, or a pharmaceutical composition comprising the same.

In an embodiment, a method is provided for treatment of a malcondition in a subject for which antagonism of the V1a receptor is medically indicated. Such method comprises administering to the subject an effective amount of a compound having the structure of Formula (I), or a pharmaceutically acceptable isomer, racemate, hydrate, solvate, isotope, or salt thereof, or a pharmaceutical composition comprising the same, at a frequency and for duration sufficient to provide a beneficial effect to the subject.

In an embodiment, a pharmaceutical composition is provided comprising a compound having the structure of Formula (I), or a pharmaceutically acceptable isomer, racemate, hydrate, solvate, isotope, or salt thereof, in combination with at least one pharmaceutically acceptable carrier, diluent, or excipient.

In an embodiment, a method of synthesis is provided for a compound having the structure of Formula (I), or a pharmaceutically acceptable isomer, racemate, hydrate, solvate, isotope, or salt thereof.

DETAILED DESCRIPTION OF THE INVENTION

As mentioned above, the invention relates to compounds that antagonize vasopressin receptors, particularly the V1a receptor, to products comprising the same, and to methods for their use and synthesis.

In one embodiment, compounds are provided having the structure of Formula (I), or a pharmaceutically acceptable isomer, racemate, hydrate, solvate, isotope, or salt thereof:

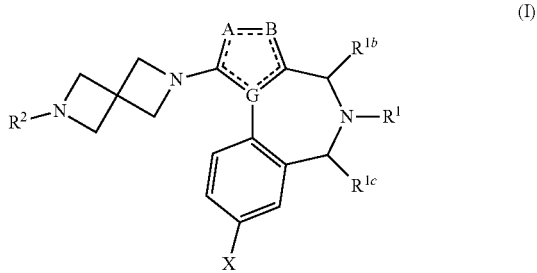

(I)

wherein
- ─ ─ ─ represents an optional double bond;
- A and B are independently nitrogen or oxygen, with the proviso that A and B are not both oxygen;
- G is nitrogen or carbon;
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ and $R^{1c}$ are independently hydrogen, lower alkyl, or spiroalkyl;
- $R^2$ is -Q-$(R^4)_n$, —S(=O)$_2R^5$, or —C(=O)$R^5$;
- $R^3$ is lower alkyl, lower haloalkyl, lower alkoxy, lower haloalkoxy, -cycloalkyl-$R^6$, —O-cycloalkyl-$R^6$, —O-heterocyclyl-$R^6$, —NH$R^5$, or —N$R^5R^5$;
- or $R^{1b}$ and $R^{1c}$ or $R^{1b}$ and $R^3$, together with the atoms to which they are attached, form a ring;
- Q is aryl or heteroaryl;
- each $R^4$ is independently halogen, hydroxy, lower alkyl, lower haloalkyl, lower alkoxy, lower haloalkoxyalkyl, or cyano;
- each $R^5$ is independently cycloalkyl, lower alkyl, lower haloalkyl, cycloalkylalkyl, lower alkoxy, heterocyclyl, or —O-heterocyclyl;
- $R^6$ is hydrogen, halo, alkyl, lower haloalkyl, or cyano; and
- n is 0, 1, or 2.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

"Halo" or "halogen" refers to fluorine, chlorine, bromine, and iodine.

"Hydroxy" refers to —OH.

"Cyano" refers to —CN.

"Lower haloalkyl" refers to a lower alkyl as defined above with one or more hydrogen atoms replaced with halogen. Examples of lower haloalkyl groups include, but are not limited to, —CF$_3$, —CH$_2$CF$_3$, and the like.

"Lower alkoxy" refers to a lower alkyl as defined above joined by way of an oxygen atom (i.e., —O-(lower alkyl). Examples of lower alkoxy groups include, but are not limited to, methoxy, ethoxy, n-propoxy, n-butoxy, iso-propoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, —OCF$_3$, —OCH$_2$CF$_3$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like "Cycloalkylalkyl" are alkyl groups as defined above in which a hydrogen or carbon bond of the alkyl group is replaced with a bond to a cycloalkyl group as defined above.

"Aryl" groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like). In one embodiment, aryl is phenyl or naphthyl, and in another embodiment aryl is phenyl.

"Heterocyclyl" or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups.

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of non-superimposable isomers that are called "enantiomers." Single enantiomers of a pure compound are optically active (i.e., they are capable of rotating the plane of plane polarized light and designated R or S).

"Spiroalkyl" refers to a geminally substituted di-lower alkyl substituents of 1 to 3 carbon atoms that form a continuous ring of 3 to 7 carbon atoms, respectively. The number of carbon atoms of the bonded geminal substituents are independent of each other, e.g. one germinal substituent may be 2 carbon atoms and the second germinal substituent may be 3 carbon atoms, with terminal carbons bonded to make a fused spiroalkyl of 6 carbon atoms, counting the geminally substituted carbon atom.

"Isolated optical isomer" means a compound which has been substantially purified from the corresponding optical isomer(s) of the same formula. For example, the isolated isomer may be at least about 80%, at least 80% or at least 85% pure. In other embodiments, the isolated isomer is at least 90% pure or at least 98% pure, or at least 99% pure by weight.

"Substantially enantiomerically or diasteromerically" pure means a level of enantiomeric or diasteromeric enrichment of one enantiomer with respect to the other enantiomer or diasteromer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out).

A "hydrate" is a compound that exists in combination with water molecules. The combination can include water in stoichiometric quantities, such as a monohydrate or a dehydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

Co-crystal forms of compounds having the structure of Formula (I) are also included within the scope of this invention; namely, solids that are crystalline single phase materials composed of two or more different molecular and/or ionic compounds generally in a stoichiometric ratio which are neither solvates nor simple salts.

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int J. Pharm.*, 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In one embodiment, compounds are provided having the structure of Formula (I), or a pharmaceutically acceptable isomer, racemate, hydrate, solvate, isotope, or salt thereof:

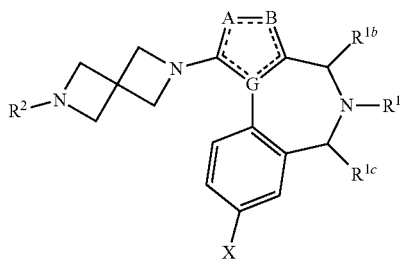

(I)

wherein
=== represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^1$ is hydrogen, lower alkyl, lower alkoxyalkyl, cycloalkyl, heterocyclyl, lower haloalkyl, or —C(=O)$R^3$;
$R^{1b}$ and $R^{1c}$ are independently hydrogen or lower alkyl;
$R^2$ is -Q-$(R^4)_n$, —S(=O)$_2R^5$, or —C(=O)$R^5$;
$R^3$ is lower alkyl, lower haloalkyl, lower alkoxy, lower haloalkoxy, or cycloalkyl-$R^6$;
Q is aryl or heteroaryl;
each $R^4$ is independently halogen, hydroxy, lower alkyl, lower alkoxy, or cyano;
$R^5$ is cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and n is 0, 1, or 2.

In one embodiment, compounds are provided having the structure of Formula (I-A), or a pharmaceutically acceptable isomer, racemate, hydrate, solvate, isotope, or salt thereof:

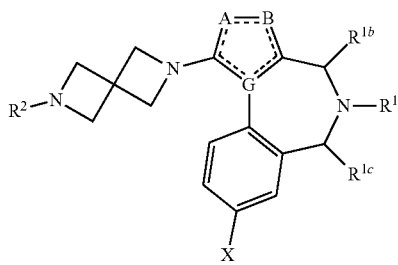

(I-A)

wherein
=== represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
$R^{1b}$ and $R^{1c}$ are independently hydrogen or lower alkyl; or $R^{1b}$ and $R^1$, together with the atoms to which they are attached, form a ring;
$R^2$ is -Q-$(R^4)_n$, —S(=O)$_2R^5$, or —C(=O)$R^5$;
Q is heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and n is 0, 1, or 2.

In one embodiment, compounds are provided having the structure of Formula (I-B), or a pharmaceutically acceptable isomer, racemate, hydrate, solvate, isotope, or salt thereof:

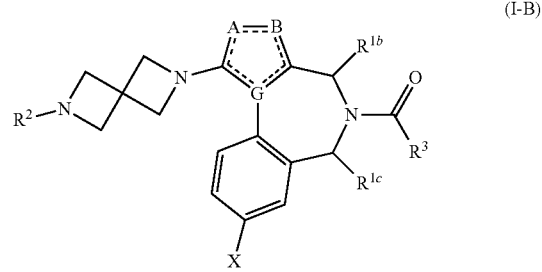

(I-B)

wherein
=== represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^{1b}$ and $R^{1c}$ are independently hydrogen or lower alkyl;
$R^2$ is -Q-$(R^4)_n$, —S(=O)$_2R^5$, or —C(=O)$R^5$;
$R^3$ is lower alkyl, lower haloalkyl, lower alkoxy, lower haloalkoxy, -cycloalkyl-$R^6$, —O-cycloalkyl-$R^6$, or —O-heterocyclyl-$R^6$; or $R^{1b}$ and $R^3$, together with the atoms to which they are attached, form a ring;
Q is heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and n is 0, 1, or 2.

In a more specific embodiment, $R^{1c}$ is hydrogen and compounds are provided having the structure of Formula (II), or a pharmaceutically acceptable isomer, racemate, hydrate, solvate, isotope or salt thereof:

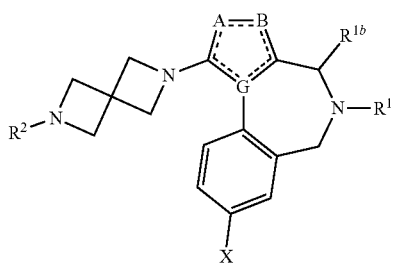

(II)

wherein
 --- represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^2$ is -Q-$(R^4)_n$, —S(=O)$_2R^5$, or —C(=O)$R^5$;
$R^3$ lower alkyl, lower haloalkyl, alkoxy, lower haloalkoxy, -cycloalkyl-$R^6$, —O-cycloalkyl-$R^6$, or —O-heterocyclyl-$R^6$;
or $R^{1b}$ and $R^1$ or $R^{1b}$ and $R^3$, together with the atoms to which they are attached, form a ring
Q is aryl or heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, lower haloalkoxy, heterocyclyl, or —O-heterocyclyl;
$R^6$ is hydrogen, halo, alkyl, lower haloalkyl, or cyano; and
n is 0, 1, or 2.

In a more specific embodiment, compounds are provided having the structure of Formula (II-A), or a pharmaceutically acceptable isomer, racemate, hydrate, solvate, isotope, or salt thereof:

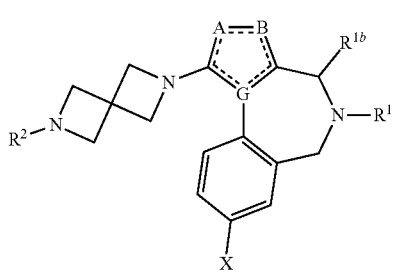

(II-A)

wherein
 --- represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
$R^{1b}$ is hydrogen or lower alkyl;
or $R^{1b}$ and $R^1$, together with the atoms to which they are attached, form a ring
$R^2$ is -Q-$(R^4)_n$, —S(=O)$_2R^5$, or —C(=O)$R^5$;
Q is heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and
n is 0, 1, or 2.

In a more specific embodiment, compounds are provided having the structure of Formula (II-B), or a pharmaceutically acceptable isomer, racemate, hydrate, solvate, isotope, or salt thereof:

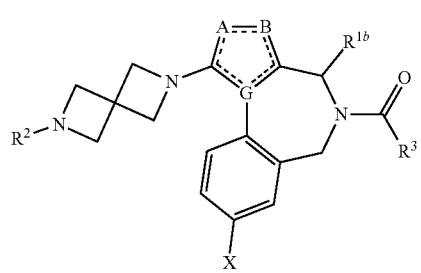

(II-B)

wherein
 --- represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^{1b}$ is hydrogen or lower alkyl;
$R^2$ is -Q-$(R^4)_n$, —S(=O)$_2R^5$, or —C(=O)$R^5$;
$R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
or $R^{1b}$ and $R^3$, together with the atoms to which they are attached, form a ring Q is heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and
n is 0, 1, or 2.

In a more specific embodiment, compounds are provided having the structure of Formula (III), or a pharmaceutically acceptable isomer, racemate, hydrate, solvate, isotope, or salt thereof:

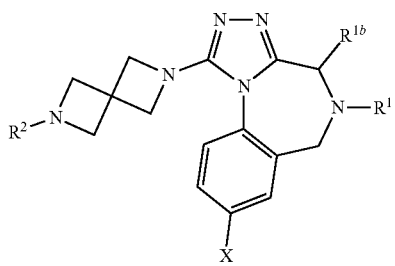

(III)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^2$ is -Q-$(R^4)_n$, —S(=O)$_2R^5$, or —C(=O)$R^5$;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- Q is heteroaryl;
- each $R^4$ is independently halogen, hydroxy, lower alkyl, lower haloalkyl, lower alkoxy, lower haloalkoxyalkyl, or cyano;
- $R^5$ is cycloalkyl, lower alkyl, lower haloalkyl, cycloalkylalkyl, lower alkoxy, heterocyclyl, or —O-heterocyclyl;
- $R^6$ is hydrogen, halo, alkyl, lower haloalkyl, or cyano; and
- n is 0, 1, or 2.

In a more specific embodiment, compounds are provided having the structure of Formula (III-A), or a pharmaceutically acceptable isomer, racemate, hydrate, solvate, isotope, or salt thereof:

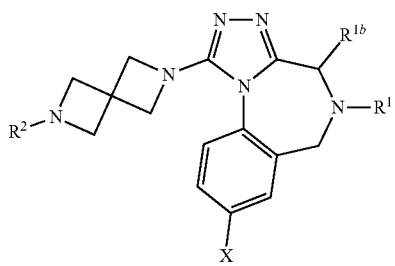

(III-A)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- $R^2$ is -Q-$(R^4)_n$, —S(=O)$_2R^5$, or —C(=O)$R^5$;
- Q is heteroaryl;
- each $R^4$ is independently halogen, hydroxy, lower alkyl, lower haloalkyl, lower alkoxy, lower haloalkoxyalkyl, or cyano;
- $R^5$ is cycloalkyl, lower alkyl, lower haloalkyl, cycloalkylalkyl, lower alkoxy, heterocyclyl, or —O-heterocyclyl;
- $R^6$ is hydrogen, halo, alkyl, lower haloalkyl, or cyano; and
- n is 0, 1, or 2.

In another embodiment, compounds are provided having the structure of Formula (III-B), or a pharmaceutically acceptable isomer, racemate, hydrate, solvate, isotope, or salt thereof:

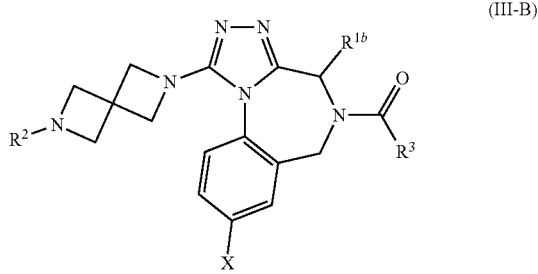

(III-B)

wherein
- X is halogen, lower alkyl, lower haloalkyl, lower alkoxy, or cyano;
- $R^{1b}$ is hydrogen or lower alkyl;
- $R^2$ is -Q-$(R^4)_n$, —S(=O)$_2R^5$, or —C(=O)$R^5$;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- Q is heteroaryl;
- each $R^4$ is independently halogen, hydroxy, lower alkyl, lower haloalkyl, lower alkoxy, lower haloalkoxyalkyl, or cyano;
- $R^5$ is cycloalkyl, lower alkyl, lower haloalkyl, cycloalkylalkyl, lower alkoxy, heterocyclyl, or —O-heterocyclyl;
- $R^6$ is hydrogen, halo, alkyl, lower haloalkyl, or cyano; and
- n is 0, 1, or 2.

In a more specific embodiment, compounds are provided having the structure of Formula (IV), or a pharmaceutically acceptable isomer, racemate, hydrate, solvate, isotope, or salt thereof:

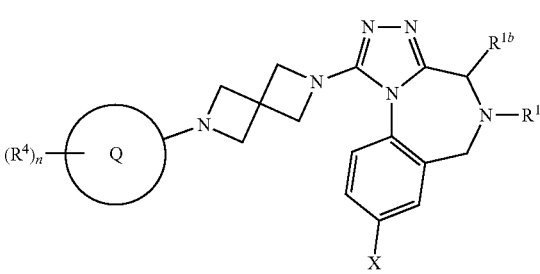

(IV)

wherein
- X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R$^{1b}$ is hydrogen or lower alkyl;

R³ is lower alkyl, lower haloalkyl, alkoxy, lower haloalkoxy, -cycloalkyl-R⁶, —O-cycloalkyl-R⁶, or —O-heterocyclyl-R⁶;

or R$^{1b}$ and R¹ or R$^{1b}$ and R³, together with the atoms to which they are attached, form a ring;

Q is heteroaryl;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (IV-A), or a pharmaceutically acceptable isomer, racemate, hydrate, solvate, isotope, or salt thereof:

(IV-A)

wherein

X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;

R$^{1b}$ is hydrogen or lower alkyl;

or R$^{1b}$ and R¹, together with the atoms to which they are attached, form a ring;

Q is heteroaryl;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (IV-A-1), or a pharmaceutically acceptable isomer, racemate, hydrate, solvate, isotope, or salt thereof:

(IV-A-1)

wherein

X is halogen;

R¹ is hydrogen, lower alkyl, lower haloalkyl, or cycloalkyl;

Q is heteroaryl;

each R⁴ is independently halogen, hydroxy, lower alkyl, lower haloalkyl, lower alkoxy, lower haloalkoxyalkyl, or cyano; and n is 0, 1, or 2.

In a more specific embodiment, compounds are provided having the structure of Formula (IV-B), or a pharmaceutically acceptable isomer, racemate, hydrate, solvate, isotope, or salt thereof:

(IV-B)

wherein

X is halogen, lower alkyl, lower haloalkyl, lower alkoxy, or cyano;

R$^{1b}$ is hydrogen or lower alkyl;

R³ is lower alkyl, lower haloalkyl, lower alkoxy, lower haloalkoxy, -cycloalkyl-R⁶, —O-cycloalkyl-R⁶, or —O-heterocyclyl-R⁶;

or R$^{1b}$ and R³, together with the atoms to which they are attached, form a ring;

Q is heteroaryl;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (V), or a pharmaceutically acceptable isomer, racemate, hydrate, solvate, isotope, or salt thereof:

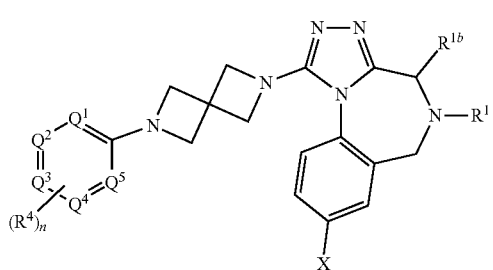

(V)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(═O)R$^3$, or —C(═O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
Q$^1$, Q$^2$, Q$^3$, Q$^4$, and Q$^5$ are independently N, CH, or CR$^4$;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (V-A), or a pharmaceutically acceptable isomer, racemate, hydrate, solvate, isotope, or salt thereof:

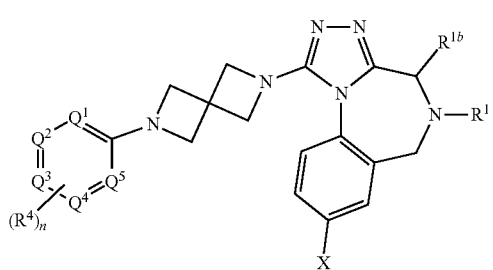

(V-A)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(═O)R$^3$;
R$^{1b}$ is hydrogen or lower alkyl;
or R$^{1b}$ and R$^1$, together with the atoms to which they are attached, form a ring;
Q$^1$, Q$^2$, Q$^3$, Q$^4$, and Q$^5$ are independently N, CH, or CR$^4$;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (V-A-1), or a pharmaceutically acceptable isomer, racemate, hydrate, solvate, isotope, or salt thereof:

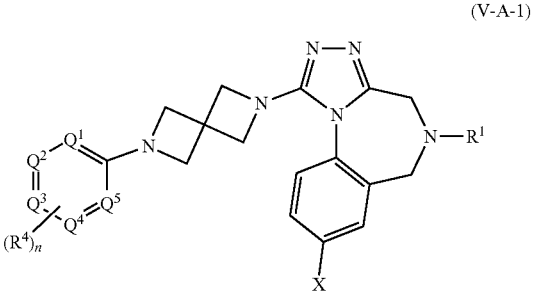

(V-A-1)

wherein
X is halogen;
R$^1$ is hydrogen, lower alkyl, lower haloalkyl, or cycloalkyl;
Q$^1$, Q$^2$, Q$^3$, Q$^4$, and Q$^5$ are independently N, CH, or CR$^4$;
each R$^4$ is independently halogen, hydroxy, lower alkyl, lower haloalkyl, lower alkoxy, lower haloalkoxyalkyl, or cyano; and
n is 0, 1, or 2.

In a more specific embodiment, compounds are provided having the structure of Formula (V-B), or a pharmaceutically acceptable isomer, racemate, hydrate, solvate, isotope, or salt thereof:

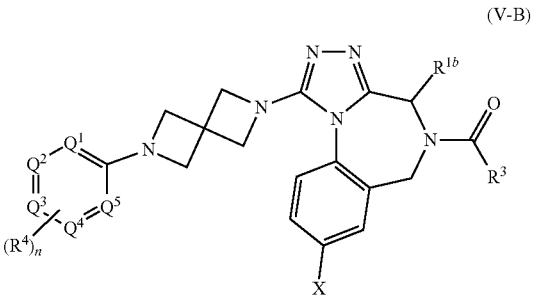

(V-B)

wherein
X is halogen, lower alkyl, lower haloalkyl, lower alkoxy, or cyano;
R$^{1b}$ is hydrogen or lower alkyl;
R$^3$ is lower alkyl, lower haloalkyl, lower alkoxy, lower haloalkoxy, -cycloalkyl-R$^6$, —O-cycloalkyl-R$^6$, or —O-heterocyclyl-R$^6$;
or R$^{1b}$ and R$^3$, together with the atoms to which they are attached, form a ring;
Q$^1$, Q$^2$, Q$^3$, Q$^4$, and Q$^5$ are independently N, CH, or CR$^4$;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (VI), or a pharmaceutically acceptable isomer, racemate, hydrate, solvate, isotope, or salt thereof:

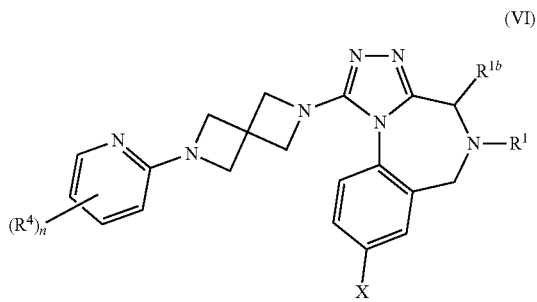

(VI)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (VI-A), or a pharmaceutically acceptable isomer, racemate, hydrate, solvate, isotope, or salt thereof:

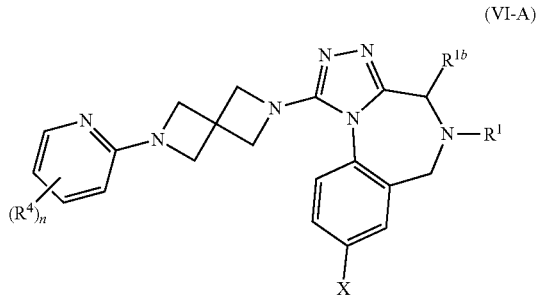

(VI-A)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (VI-A), or a pharmaceutically acceptable isomer, racemate, hydrate, solvate, isotope, or salt thereof:

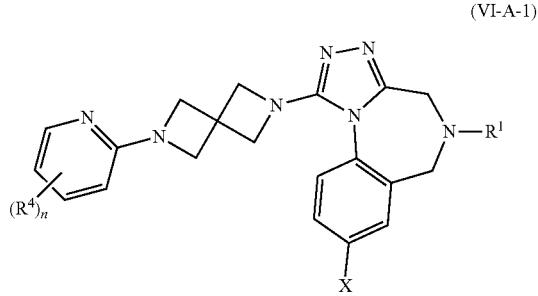

(VI-A-1)

wherein
- X is halogen;
- $R^1$ is hydrogen, lower alkyl, lower haloalkyl, or cycloalkyl;
- each $R^4$ is independently halogen, hydroxy, lower alkyl, lower haloalkyl, lower alkoxy, lower haloalkoxyalkyl, or cyano; and
- n is 0, 1, or 2.

In a more specific embodiment, compounds are provided having the structure of Formula (VI-B), or a pharmaceutically acceptable isomer, racemate, hydrate, solvate, isotope, or salt thereof:

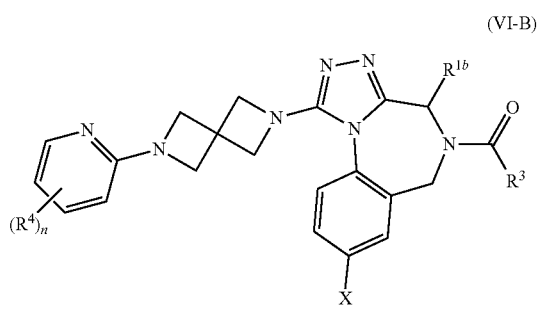

(VI-B)

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (VII), or a pharmaceutically acceptable isomer, racemate, hydrate, solvate, isotope, or salt thereof:

(VII)

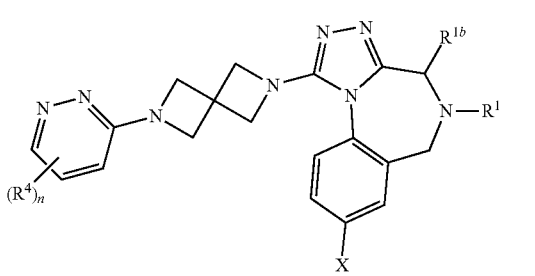

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (VII-A), or a pharmaceutically acceptable isomer, racemate, hydrate, solvate, isotope, or salt thereof:

(VII-A)

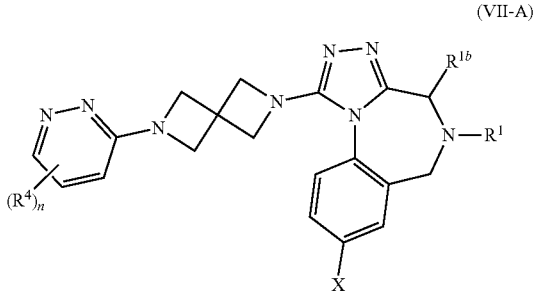

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;
R$^{1b}$ is hydrogen or lower alkyl;
or R$^{1b}$ and R$^1$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (VII-A-1), or a pharmaceutically acceptable isomer, racemate, hydrate, solvate, isotope, or salt thereof:

(VII-A-1)

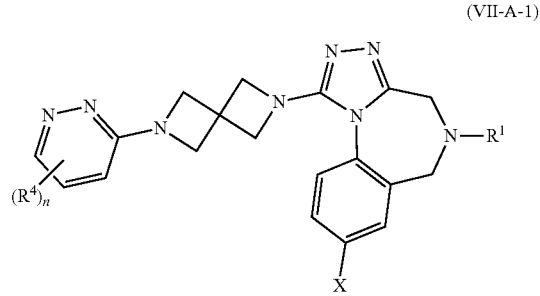

wherein
X is halogen;
R$^1$ is hydrogen, lower alkyl, lower haloalkyl, or cycloalkyl;
each R$^4$ is independently halogen, hydroxy, lower alkyl, lower haloalkyl, lower alkoxy, lower haloalkoxyalkyl, or cyano; and
n is 0, 1, or 2.

In a more specific embodiment, compounds are provided having the structure of Formula (VII-B), or a pharmaceutically acceptable isomer, racemate, hydrate, solvate, isotope, or salt thereof:

(VII-B)

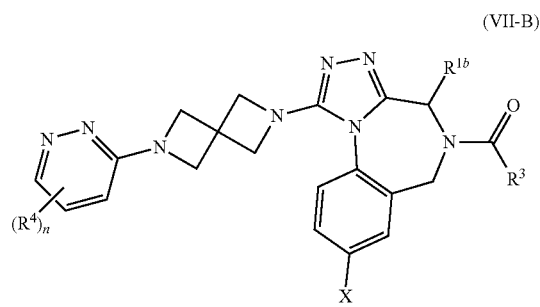

wherein
X is halogen, lower alkyl, lower haloalkyl, lower alkoxy, or cyano;
R$^{1b}$ is hydrogen or lower alkyl;
R$^3$ is lower alkyl, lower haloalkyl, lower alkoxy, lower haloalkoxy, -cycloalkyl-R$^6$, —O-cycloalkyl-R$^6$, or —O-heterocyclyl-R$^6$;
or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (VIII), or a pharmaceutically acceptable isomer, racemate, hydrate, solvate, isotope, or salt thereof:

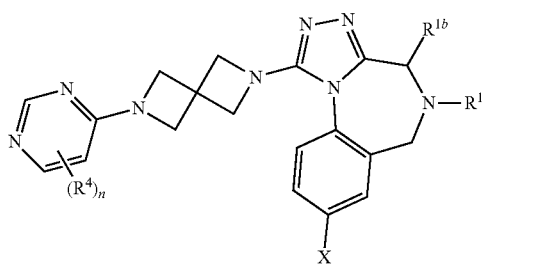

(VIII)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (VIII-A), or a pharmaceutically acceptable isomer, racemate, hydrate, solvate, isotope, or salt thereof:

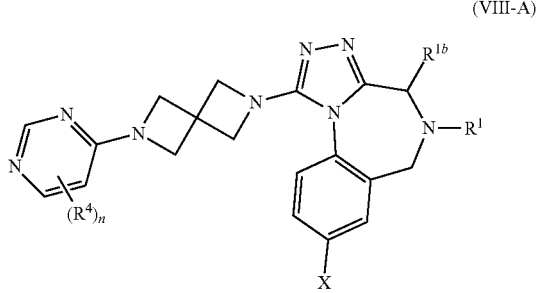

(VIII-A)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;
R$^{1b}$ is hydrogen or lower alkyl;
or R$^{1b}$ and R$^1$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (VIII-A-1), or a pharmaceutically acceptable isomer, racemate, hydrate, solvate, isotope, or salt thereof:

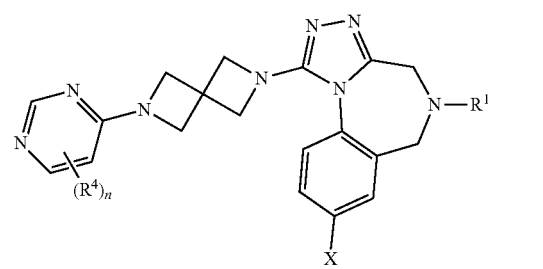

(VIII-A-1)

wherein
X is halogen;
R$^1$ is hydrogen, lower alkyl, lower haloalkyl, or cycloalkyl;
each R$^4$ is independently halogen, hydroxy, lower alkyl, lower haloalkyl, lower alkoxy, lower haloalkoxyalkyl, or cyano; and
n is 0, 1, or 2.

In a more specific embodiment, compounds are provided having the structure of Formula (VIII-B), or a pharmaceutically acceptable isomer, racemate, hydrate, solvate, isotope, or salt thereof:

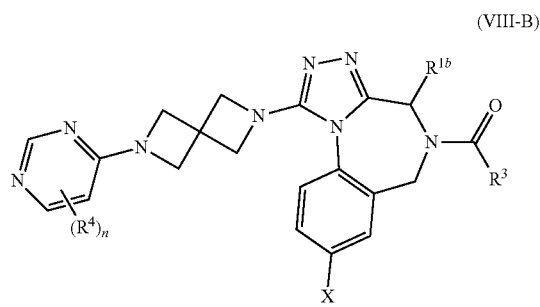

(VIII-B)

wherein
X is halogen, lower alkyl, lower haloalkyl, lower alkoxy, or cyano;
R$^{1b}$ is hydrogen or lower alkyl;
R$^3$ is lower alkyl, lower haloalkyl, lower alkoxy, lower haloalkoxy, -cycloalkyl-R$^6$, —O-cycloalkyl-R$^6$, or —O-heterocyclyl-R$^6$;
or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (IX), or a pharmaceutically acceptable isomer, racemate, hydrate, solvate, isotope, or salt thereof:

(IX)

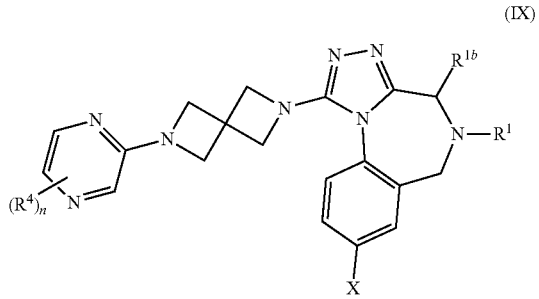

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (IX-A), or a pharmaceutically acceptable isomer, racemate, hydrate, solvate, isotope, or salt thereof:

(IX-A)

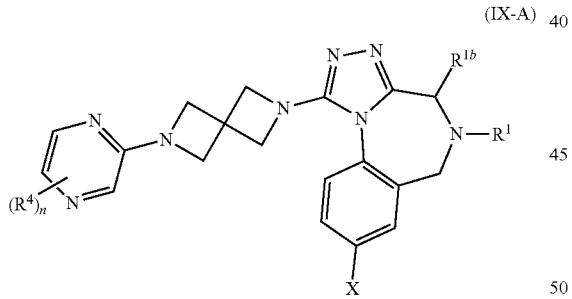

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (IX-A-1), or a pharmaceutically acceptable isomer, racemate, hydrate, solvate, isotope, or salt thereof:

(IX-A-1)

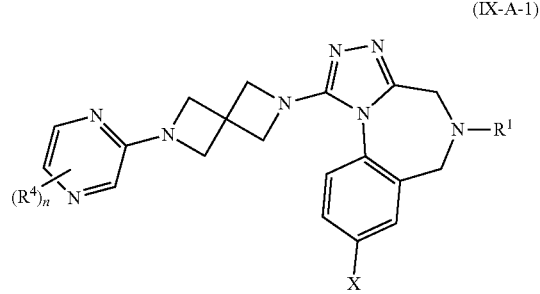

wherein
- X is halogen;
- $R^1$ is hydrogen, lower alkyl, lower haloalkyl, or cycloalkyl;
- each $R^4$ is independently halogen, hydroxy, lower alkyl, lower haloalkyl, lower alkoxy, lower haloalkoxyalkyl, or cyano; and
- n is 0, 1, or 2.

In a more specific embodiment, compounds are provided having the structure of Formula (IX-B), or a pharmaceutically acceptable isomer, racemate, hydrate, solvate, isotope, or salt thereof:

(IX-B)

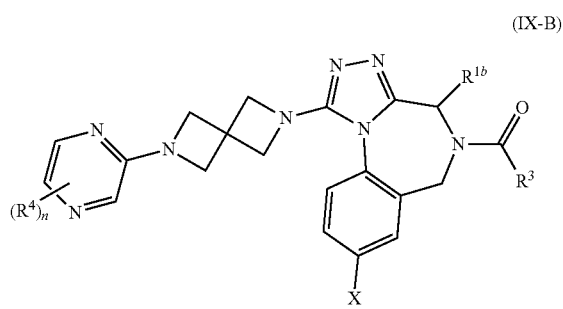

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (X), or a pharmaceutically acceptable isomer, racemate, hydrate, solvate, isotope, or salt thereof:

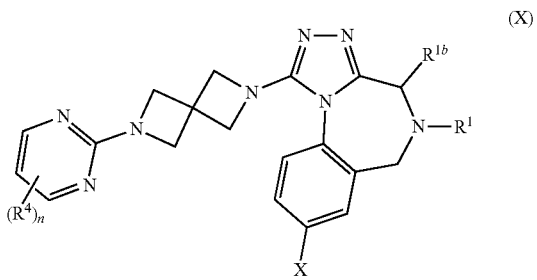

(X)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (X-A), or a pharmaceutically acceptable isomer, racemate, hydrate, solvate, isotope, or salt thereof:

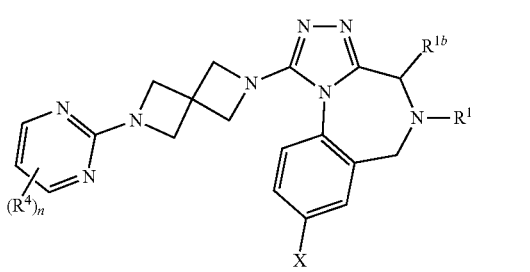

(X-A)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (X-A-1), or a pharmaceutically acceptable isomer, racemate, hydrate, solvate, isotope, or salt thereof:

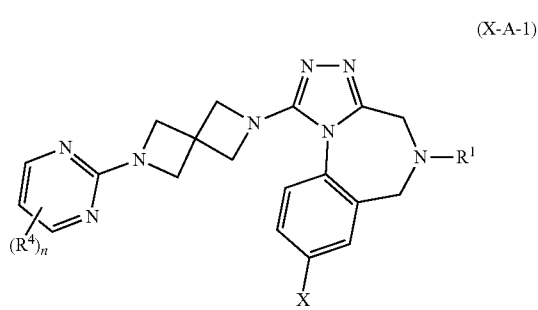

(X-A-1)

wherein
- X is halogen;
- $R^1$ is hydrogen, lower alkyl, lower haloalkyl, or cycloalkyl;
- each $R^4$ is independently halogen, hydroxy, lower alkyl, lower haloalkyl, lower alkoxy, lower haloalkoxyalkyl, or cyano; and
- n is 0, 1, or 2.

In a more specific embodiment, compounds are provided having the structure of Formula (X-B), or a pharmaceutically acceptable isomer, racemate, hydrate, solvate, isotope, or salt thereof:

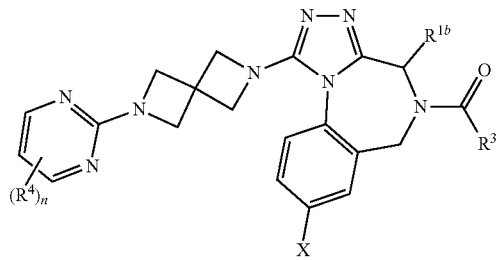

(X-B)

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (XI), or a pharmaceutically acceptable isomer, racemate, hydrate, solvate, isotope, or salt thereof:

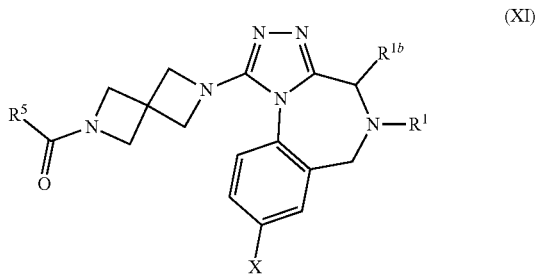

(XI)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano; and In a more specific embodiment, compounds are provided having the structure of Formula (XI-A), or a pharmaceutically acceptable isomer, racemate, hydrate, solvate, isotope, or salt thereof:

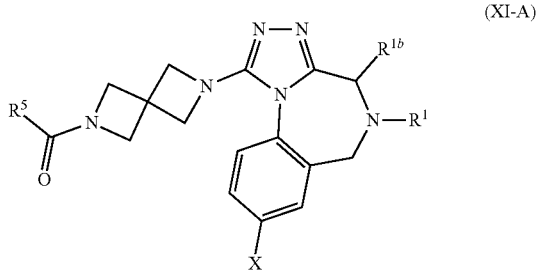

(XI-A)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

In a more specific embodiment, compounds are provided having the structure of Formula (XI-B), or a pharmaceutically acceptable isomer, racemate, hydrate, solvate, isotope, or salt thereof:

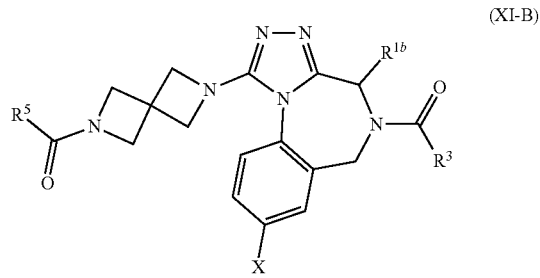

(XI-B)

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- $R^5$ is cycloalkyl, lower alkyl, lower haloalkyl, cycloalkylalkyl, alkoxy, heterocyclyl, or —O-heterocyclyl; and
- $R^6$ is hydrogen, halo, alkyl, lower haloalkyl, or cyano.

In another embodiment, compounds are provided having the structure of Formula (XII), or a pharmaceutically acceptable isomer, racemate, hydrate, solvate, isotope, or salt thereof.

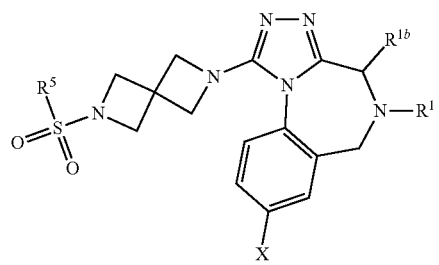

(XII)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

In a more specific embodiment, compounds are provided having the structure of Formula (XII-A), or a pharmaceutically acceptable isomer, racemate, hydrate, solvate, isotope, or salt thereof:

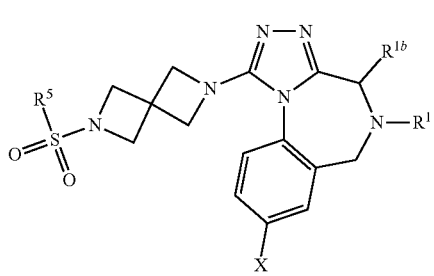

(XII-A)

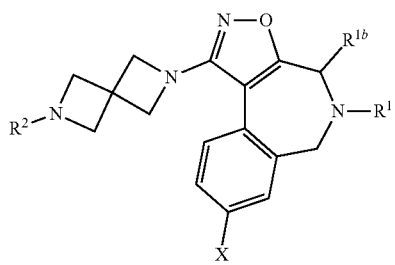

(XIII)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- $R^5$ is cycloalkyl, lower alkyl, lower haloalkyl, cycloalkylalkyl, heterocyclyl, lower alkoxy, or —O-heterocyclyl
- $R^6$ is hydrogen, halo, alkyl, lower haloalkyl, or cyano.

In a more specific embodiment, compounds are provided having the structure of Formula (XII-B), or a pharmaceutically acceptable isomer, racemate, hydrate, solvate, isotope, or salt thereof:

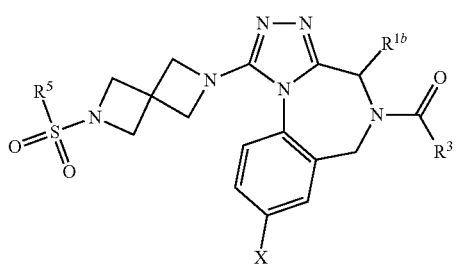

(XII-B)

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

In a more specific embodiment, compounds are provided having the structure of Formula (XIII), or a pharmaceutically acceptable isomer, racemate, hydrate, solvate, isotope, or salt thereof:

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^2$ is -Q-$(R^4)_n$, —S(=O)$_2R^5$, or —C(=O)$R^5$;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- Q is heteroaryl;
- each $R^4$ is independently halogen, hydroxy, lower alkyl, lower haloalkyl, lower alkoxy, lower haloalkoxyalkyl, or cyano;
- $R^5$ is cycloalkyl, lower alkyl, lower haloalkyl, cycloalkylalkyl, lower alkoxy, heterocyclyl, or —O-heterocyclyl;
- $R^6$ is hydrogen, halo, alkyl, lower haloalkyl, or cyano; and
- n is 0, 1, or 2.

In a more specific embodiment, compounds are provided having the structure of Formula (XIII-A), or a pharmaceutically acceptable isomer, racemate, hydrate, solvate, isotope, or salt thereof:

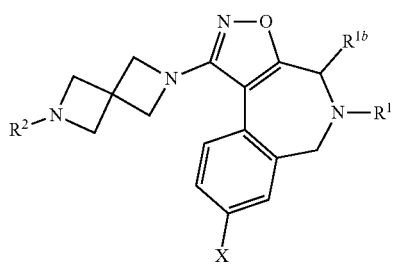

(XIII-A)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- $R^2$ is -Q-$(R^4)_n$, —S(=O)$_2R^5$, or —C(=O)$R^5$;
- Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O-heterocyclyl;

$R^6$ is hydrogen, halo, alkyl, lower haloalkyl, or cyano; and n is 0, 1, or 2.

In a more specific embodiment, compounds are provided having the structure of Formula (XIII-B), or a pharmaceutically acceptable isomer, racemate, hydrate, solvate, isotope, or salt thereof:

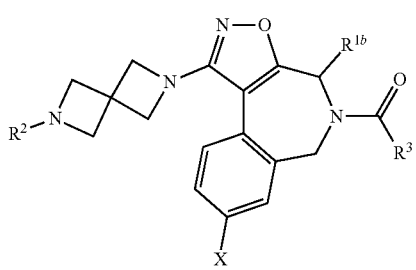

(XIII-B)

wherein
X is halogen, lower alkyl, lower haloalkyl, lower alkoxy, or cyano;

$R^{1b}$ is hydrogen or lower alkyl;

$R^2$ is -Q-$(R^4)_n$, —S(=O)$_2R^5$, or —C(=O)$R^5$;

$R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;

or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O-heterocyclyl;

$R^6$ is hydrogen, halo, alkyl, lower haloalkyl, or cyano; and n is 0, 1, or 2.

In a more specific embodiment, compounds are provided having the structure of Formula (XIV), or a pharmaceutically acceptable isomer, racemate, hydrate, solvate, isotope, or salt thereof:

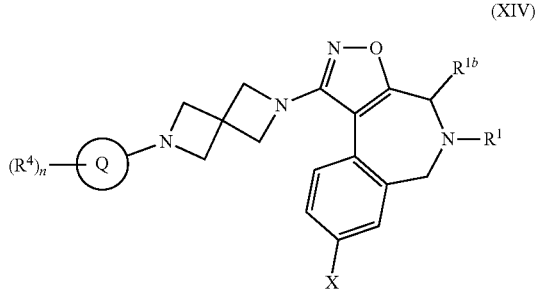

(XIV)

wherein
X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XIV-A), or a pharmaceutically acceptable isomer, racemate, hydrate, solvate, isotope, or salt thereof:

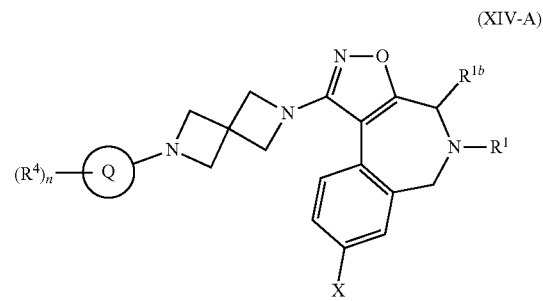

(XIV-A)

wherein
X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XIV-A-1), or a pharmaceutically acceptable isomer, racemate, hydrate, solvate, isotope, or salt thereof:

(XIV-A-1)

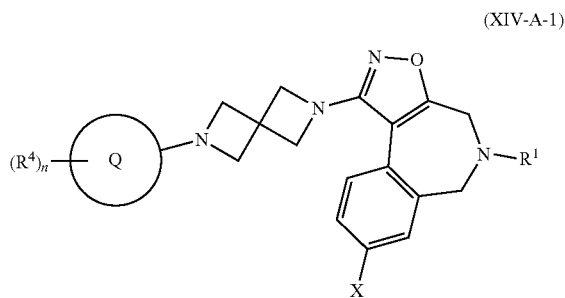

wherein

X is halogen;

R¹ is hydrogen, lower alkyl, lower haloalkyl, or cycloalkyl;

Q is heteroaryl;

each R⁴ is independently halogen, hydroxy, lower alkyl, lower haloalkyl, lower alkoxy, lower haloalkoxyalkyl, or cyano; and n is 0, 1, or 2.

In a more specific embodiment, compounds are provided having the structure of Formula (XIV-B), or a pharmaceutically acceptable isomer, racemate, hydrate, solvate, isotope, or salt thereof:

(XIV-B)

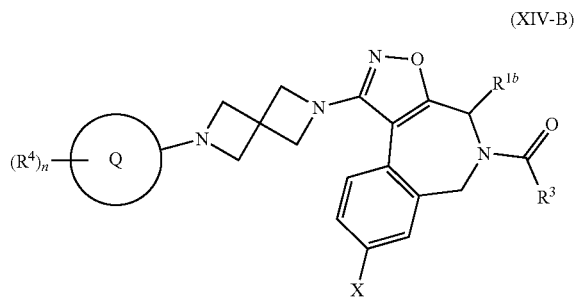

wherein

X is halogen, lower alkyl, lower haloalkyl, lower alkoxy, or cyano;

$R^{1b}$ is hydrogen or lower alkyl;

$R^3$ is lower alkyl lower haloalkyl, lower alkoxy, lower haloalkoxy, -cycloalkyl-$R^6$, —O-cycloalkyl-$R^6$, or —O-heterocyclyl-$R^6$;

or $R^{1b}$ and $R^3$, together with the atoms to which they are attached, form a ring;

Q is heteroaryl;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (XV), or a pharmaceutically acceptable isomer, racemate, hydrate, solvate, isotope, or salt thereof:

(XV)

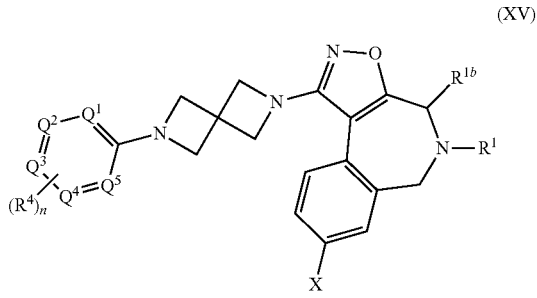

wherein

X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

$R^{1b}$ is hydrogen or lower alkyl;

R³ is lower alkyl, lower haloalkyl, alkoxy, lower haloalkoxy, -cycloalkyl-R⁶, —O-cycloalkyl-R⁶, or —O-heterocyclyl-R⁶;

or $R^{1b}$ and R¹ or $R^{1b}$ and R³, together with the atoms to which they are attached, form a ring;

Q¹, Q², Q³, Q⁴, and Q⁵ are independently N, CH, or CR⁴;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (XV-A), or a pharmaceutically acceptable isomer, racemate, hydrate, solvate, isotope, or salt thereof:

(XV-A)

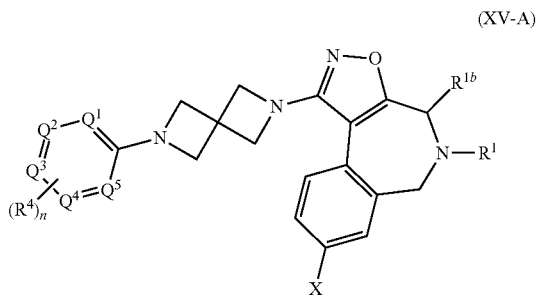

wherein

X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;

$R^{1b}$ is hydrogen or lower alkyl;

or $R^{1b}$ and R¹, together with the atoms to which they are attached, form a ring;

Q¹, Q², Q³, Q⁴, and Q⁵ are independently N, CH, or CR⁴;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (XV-A-1), or a pharmaceutically acceptable isomer, racemate, hydrate, solvate, isotope, or salt thereof:

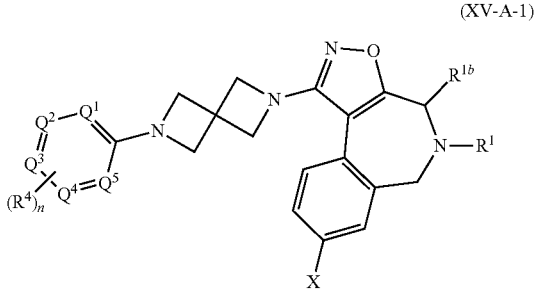

(XV-A-1)

wherein
X is halogen;
$R^1$ is hydrogen, lower alkyl, lower haloalkyl, or cycloalkyl;
$Q^1$, $Q^2$, $Q^3$, $Q^4$, and $Q^5$ are independently N, CH, or $CR^4$;
each $R^4$ is independently halogen, hydroxy, lower alkyl, lower haloalkyl, lower alkoxy, lower haloalkoxyalkyl, or cyano; and
n is 0, 1, or 2.

In a more specific embodiment, compounds are provided having the structure of Formula (XV-B), or a pharmaceutically acceptable isomer, racemate, hydrate, solvate, isotope, or salt thereof:

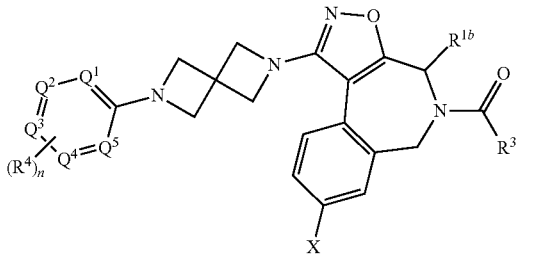

(XV-B)

wherein
X is halogen, lower alkyl, lower haloalkyl, lower alkoxy, or cyano;
$R^{1b}$ is hydrogen or lower alkyl;
$R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
or $R^{1b}$ and $R^3$, together with the atoms to which they are attached, form a ring;
$Q^1$, $Q^2$, $Q^3$, $Q^4$, and $Q^5$ are independently N, CH, or $CR^4$;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and
n is 0, 1, or 2.

In a more specific embodiment, compounds are provided having the structure of Formula (XVI), or a pharmaceutically acceptable isomer, racemate, hydrate, solvate, isotope, or salt thereof:

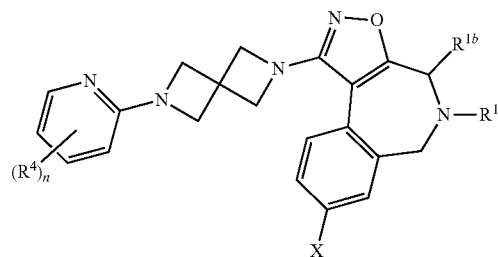

(XVI)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^3$ is lower alkyl, lower haloalkyl, alkoxy, lower haloalkoxy, -cycloalkyl-$R^6$, —O-cycloalkyl-$R^6$, or —O-heterocyclyl-$R^6$;
or $R^{1b}$ and $R^1$ or $R^{1b}$ and $R^3$, together with the atoms to which they are attached, form a ring;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and
n is 0, 1, or 2.

In a more specific embodiment, compounds are provided having the structure of Formula (XVI-A), or a pharmaceutically acceptable isomer, racemate, hydrate, solvate, isotope, or salt thereof:

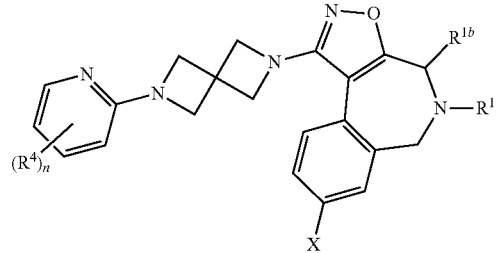

(XVI-A)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
$R^{1b}$ is hydrogen or lower alkyl;
or $R^{1b}$ and $R^1$, together with the atoms to which they are attached, form a ring;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and
n is 0, 1, or 2.

In a more specific embodiment, compounds are provided having the structure of Formula (XVI-A-1), or a pharmaceutically acceptable isomer, racemate, hydrate, solvate, isotope, or salt thereof:

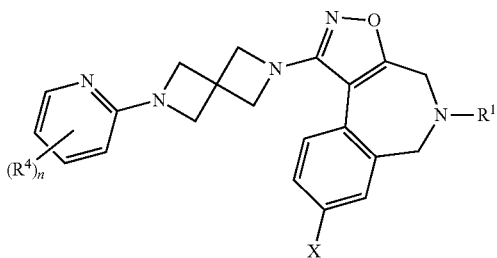

(XVI-A-1)

wherein

X is halogen;

R[1] is hydrogen, lower alkyl, lower haloalkyl, or cycloalkyl;

each R[4] is independently halogen, hydroxy, lower alkyl, lower haloalkyl, lower alkoxy, lower haloalkoxyalkyl, or cyano; and n is 0, 1, or 2.

In a more specific embodiment, compounds are provided having the structure of Formula (XVI-B), or a pharmaceutically acceptable isomer, racemate, hydrate, solvate, isotope, or salt thereof:

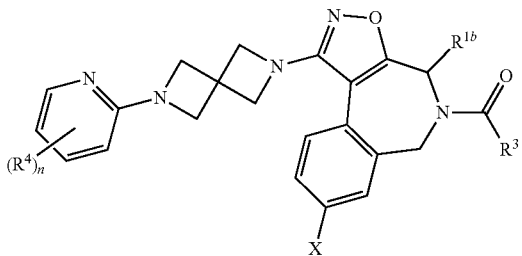

(XVI-B)

wherein

X is halogen, lower alkyl, lower haloalkyl, lower alkoxy, or cyano;

R[1b] is hydrogen or lower alkyl;

R[3] is lower alkyl, lower haloalkyl, lower alkoxy, lower haloalkoxy, -cycloalkyl-R[6], —O-cycloalkyl-R[6], or —O-heterocyclyl-R[6];

or R[1b] and R[3], together with the atoms to which they are attached, form a ring;

each R[4] is independently halogen, hydroxy, lower alkyl, lower haloalkyl, lower alkoxy, lower haloalkoxyalkyl, or cyano;

R[6] is hydrogen, halo, alkyl, lower haloalkyl, or cyano; and n is 0, 1, or 2.

In a more specific embodiment, compounds are provided having the structure of Formula (XVII), or a pharmaceutically acceptable isomer, racemate, hydrate, solvate, isotope, or salt thereof:

(XVII)

wherein

X is halogen, lower alkyl, lower haloalkyl, lower alkoxy, or cyano;

R[1] is hydrogen, lower alkyl-R[6], haloalkyl, lower alkoxyalkyl, -cycloalkyl-R[6], -alkyl-cycloalkyl-R[6], -aryl-R[6], -alkyl-aryl-R[6], -heterocyclyl-R[6], -alkyl-heterocyclyl-R[6], lower haloalkyl, -alkyl-C(=O)R[3], or —C(=O)R[3];

R[1b] is hydrogen or lower alkyl;

R[3] is lower alkyl, lower haloalkyl, alkoxy, lower haloalkoxy, -cycloalkyl-R[6], —O-cycloalkyl-R[6], or —O-heterocyclyl-R[6];

or R[1b] and R[1] or R[1b] and R[3], together with the atoms to which they are attached, form a ring;

each R[4] is independently halogen, hydroxy, lower alkyl, lower haloalkyl, lower alkoxy, lower haloalkoxyalkyl, or cyano;

R[6] is hydrogen, halo, alkyl, lower haloalkyl, or cyano; and n is 0, 1, or 2.

In a more specific embodiment, compounds are provided having the structure of Formula (XVII-A), or a pharmaceutically acceptable isomer, racemate, hydrate, solvate, isotope, or salt thereof:

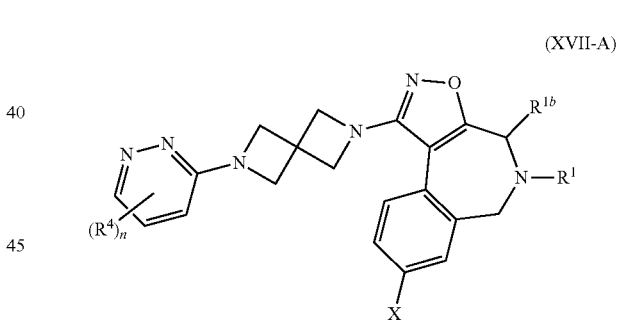

(XVII-A)

wherein

X is halogen, lower alkyl, lower haloalkyl, lower alkoxy, or cyano;

R[1] is hydrogen, lower alkyl-R[6], haloalkyl, lower alkoxyalkyl, -cycloalkyl-R[6], -alkyl-cycloalkyl-R[6], -aryl-R[6], -alkyl-aryl-R[6], -heterocyclyl-R[6], -alkyl-heterocyclyl-R[6], lower haloalkyl, or -alkyl-C(=O)R[3];

R[1b] is hydrogen or lower alkyl;

or R[1b] and R[1], together with the atoms to which they are attached, form a ring;

each R[4] is independently halogen, hydroxy, lower alkyl, lower haloalkyl, lower alkoxy, lower haloalkoxyalkyl, or cyano;

R[6] is hydrogen, halo, alkyl, lower haloalkyl, or cyano; and n is 0, 1, or 2.

In a more specific embodiment, compounds are provided having the structure of Formula (XVII-A-1), or a pharmaceutically acceptable isomer, racemate, hydrate, solvate, isotope, or salt thereof:

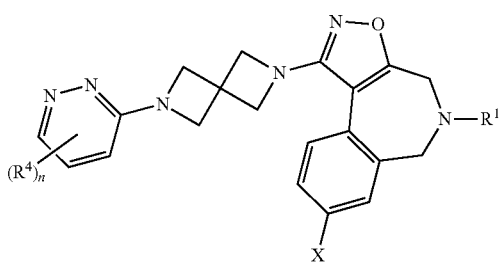

(XVII-A-1)

wherein
- X is halogen;
- $R^1$ is hydrogen, lower alkyl, lower haloalkyl, or cycloalkyl;
- each $R^4$ is independently halogen, hydroxy, lower alkyl, lower haloalkyl, lower alkoxy, lower haloalkoxyalkyl, or cyano; and
- n is 0, 1, or 2.

In a more specific embodiment, compounds are provided having the structure of Formula (XVII-B), or a pharmaceutically acceptable isomer, racemate, hydrate, solvate, isotope, or salt thereof:

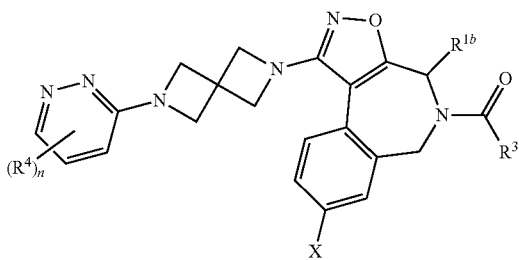

(XVII-B)

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (XVIII), or a pharmaceutically acceptable isomer, racemate, hydrate, solvate, isotope, or salt thereof:

(XVIII)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (XVIII-A), or a pharmaceutically acceptable isomer, racemate, hydrate, solvate, isotope, or salt thereof:

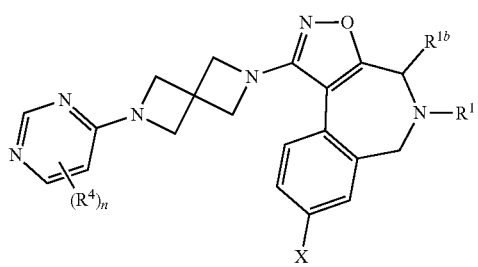

(XVIII-A)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- each $R^4$ is independently halogen, hydroxy, lower alkyl, lower haloalkyl, lower alkoxy, lower haloalkoxyalkyl, or cyano;
- $R^6$ is hydrogen, halo, alkyl, lower haloalkyl, or cyano; and
- n is 0, 1, or 2.

In a more specific embodiment, compounds are provided having the structure of Formula (XVIII-A-1), or a pharmaceutically acceptable isomer, racemate, hydrate, solvate, isotope, or salt thereof:

(XVIII-A-1)

wherein
X is halogen;
R$^1$ is hydrogen, lower alkyl, lower haloalkyl, or cycloalkyl;
each R$^4$ is independently halogen, hydroxy, lower alkyl, lower haloalkyl, lower alkoxy, lower haloalkoxyalkyl, or cyano; and
n is 0, 1, or 2.

In a more specific embodiment, compounds are provided having the structure of Formula (XVIII-B), or a pharmaceutically acceptable isomer, racemate, hydrate, solvate, isotope, or salt thereof:

(XVIII-B)

wherein
X is halogen, lower alkyl, lower haloalkyl, lower alkoxy, or cyano;
R$^{1b}$ is hydrogen or lower alkyl;
R$^3$ is lower alkyl, lower haloalkyl, lower alkoxy, lower haloalkoxy, -cycloalkyl-R$^6$, —O-cycloalkyl-R$^6$, or —O-heterocyclyl-R$^6$;
or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (XIX), or a pharmaceutically acceptable isomer, racemate, hydrate, solvate, isotope, or salt thereof:

(XIX)

wherein
X is halogen, lower alkyl, lower haloalkyl, lower alkoxy, or cyano;
R$^1$ is hydrogen, lower alkyl-R$^6$, haloalkyl, lower alkoxy-alkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (XIX-A), or a pharmaceutically acceptable isomer, racemate, hydrate, solvate, isotope, or salt thereof:

(XIX-A)

wherein
X is halogen, lower alkyl, lower haloalkyl, lower alkoxy, or cyano;
R$^1$ is hydrogen, lower alkyl-R$^6$, haloalkyl, lower alkoxy-alkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;
R$^{1b}$ is hydrogen or lower alkyl;
or R$^{1b}$ and R$^1$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (XIX-A-1), or a pharmaceutically acceptable isomer, racemate, hydrate, solvate, isotope, or salt thereof:

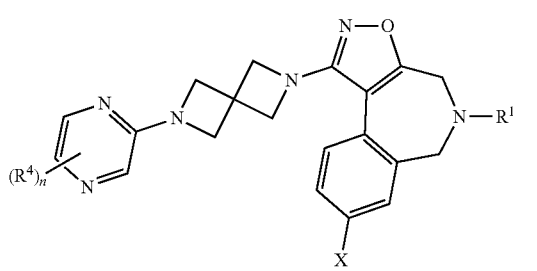

(XIX-A-1)

wherein
X is halogen;
R$^1$ is hydrogen, lower alkyl, lower haloalkyl, or cycloalkyl;
each R$^4$ is independently halogen, hydroxy, lower alkyl, lower haloalkyl, lower alkoxy, lower haloalkoxyalkyl, or cyano; and
n is 0, 1, or 2.

In a more specific embodiment, compounds are provided having the structure of Formula (XIX-B), or a pharmaceutically acceptable isomer, racemate, hydrate, solvate, isotope, or salt thereof:

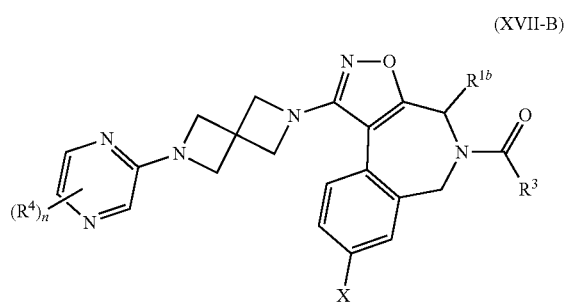

(XVII-B)

wherein
X is halogen, lower alkyl, lower haloalkyl, lower alkoxy, or cyano;
R$^{1b}$ is hydrogen or lower alkyl;
R$^3$ is lower alkyl, lower haloalkyl, lower alkoxy, lower haloalkoxy, -cycloalkyl-R$^6$, —O-cycloalkyl-R$^6$, or —O-heterocyclyl-R$^6$;
or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (XX), or a pharmaceutically acceptable isomer, racemate, hydrate, solvate, isotope, or salt thereof:

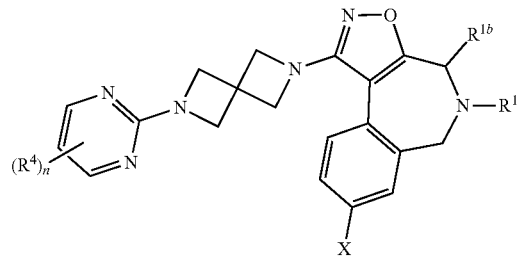

(XX)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (XX-A), or a pharmaceutically acceptable isomer, racemate, hydrate, solvate, isotope, or salt thereof:

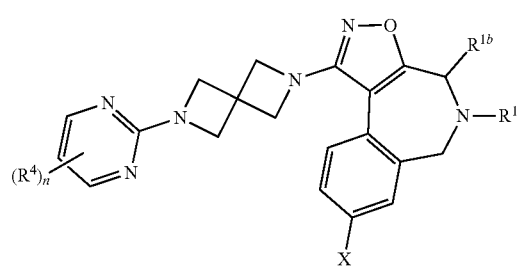

(XX-A)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;
R$^{1b}$ is hydrogen or lower alkyl;
or R$^{1b}$ and R$^1$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (XX-A-1), or a pharmaceutically acceptable isomer, racemate, hydrate, solvate, isotope, or salt thereof:

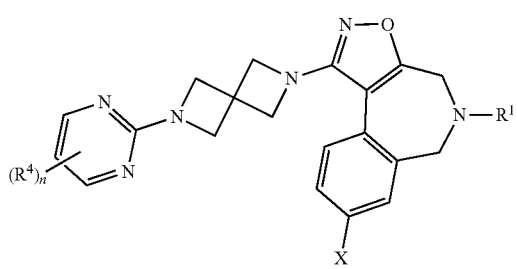

(XX-A-1)

wherein
X is halogen;
R$^1$ is hydrogen, lower alkyl, lower haloalkyl, or cycloalkyl;
each R$^4$ is independently halogen, hydroxy, lower alkyl, lower haloalkyl, lower alkoxy, lower haloalkoxyalkyl, or cyano; and
n is 0, 1, or 2.

In a more specific embodiment, compounds are provided having the structure of Formula (XX-B), or a pharmaceutically acceptable isomer, racemate, hydrate, solvate, isotope, or salt thereof:

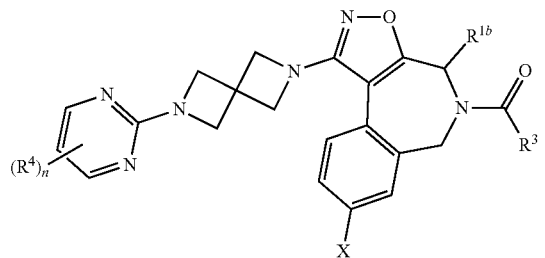

(XX-B)

wherein
X is halogen, lower alkyl, lower haloalkyl, lower alkoxy, or cyano;
R$^{1b}$ is hydrogen or lower alkyl;
R$^3$ is lower alkyl, lower haloalkyl, lower alkoxy, lower haloalkoxy, -cycloalkyl-R$^6$, —O-cycloalkyl-R$^6$, or —O-heterocyclyl-R$^6$;
or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

In a more specific embodiment, compounds are provided having the structure of Formula (XXI), or a pharmaceutically acceptable isomer, racemate, hydrate, solvate, isotope, or salt thereof:

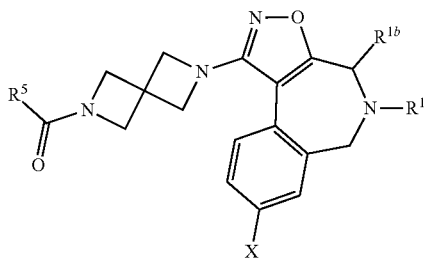

(XXI)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
R$^5$ is cycloalkyl, lower alkyl, lower haloalkyl, cycloalkylalkyl, lower alkoxy, heterocyclyl, or —O-heterocyclyl; and
R$^6$ is hydrogen, halo, alkyl, lower haloalkyl, or cyano.

In a more specific embodiment, compounds are provided having the structure of Formula (XXI-A), or a pharmaceutically acceptable isomer, racemate, hydrate, solvate, isotope, or salt thereof:

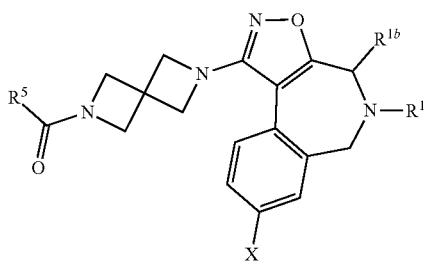

(XXI-A)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;
R$^{1b}$ is hydrogen or lower alkyl;
or R$^{1b}$ and R$^1$, together with the atoms to which they are attached, form a ring;
R$^5$ is cycloalkyl, lower alkyl, lower haloalkyl, cycloalkylalkyl, lower alkoxy, heterocyclyl, or —O-heterocyclyl
R$^6$ is hydrogen, halo, alkyl, lower haloalkyl, or cyano.

In a more specific embodiment, compounds are provided having the structure of Formula (XXI-B), or a pharmaceutically acceptable isomer, racemate, hydrate, solvate, isotope, or salt thereof:

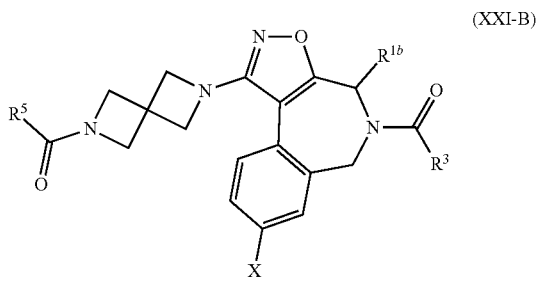
(XXI-B)

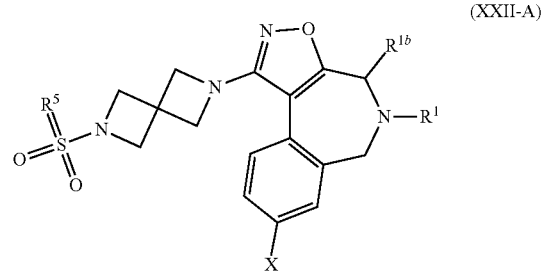
(XXII-A)

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

In a more specific embodiment, compounds are provided having the structure of Formula (XXII), or a pharmaceutically acceptable isomer, racemate, hydrate, solvate, isotope, or salt thereof:

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
- $R^{1b}$ is hydrogen or lower alkyl;
- or $R^{1b}$ and $R^1$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl;
- $R^6$ is hydrogen, halo, alkyl, lower haloalkyl, or cyano.

In a more specific embodiment, compounds are provided having the structure of Formula (XXII-B), or a pharmaceutically acceptable isomer, racemate, hydrate, solvate, isotope, or salt thereof:

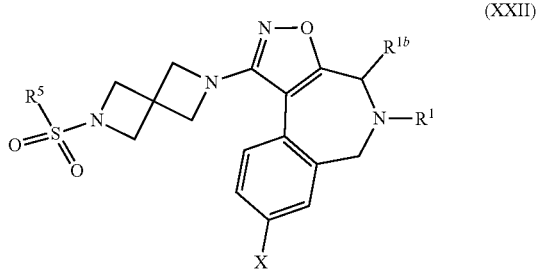
(XXII)

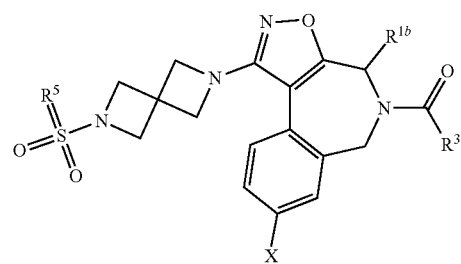
(XXII-B)

wherein
- X is halogen, lower alkyl, lower haloalkyl, lower alkoxy, or cyano;
- $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

In a more specific embodiment, compounds are provided having the structure of Formula (XXII-A), or a pharmaceutically acceptable isomer, racemate, hydrate, solvate, isotope, or salt thereof:

wherein
- X is halogen, lower alkyl, lower haloalkyl, lower alkoxy, or cyano;
- $R^{1b}$ is hydrogen or lower alkyl;
- $R^3$ is lower alkyl, lower haloalkyl, lower alkoxy, lower haloalkoxy, -cycloalkyl-$R^6$, —O-cycloalkyl-$R^6$, or —O-heterocyclyl-$R^6$;
- or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

In the following more specific embodiments, the various substituents (e.g., A, B, G, $R^1$, $R^{1b}$, $R^{1c}$, $R^2$ and X) are set forth in more detail with respect to the compounds of each of Formulas (I) through (XXII-B) above, as applicable to the substituents being further defined. For example, reference to $R^1$ below is intended to further limit the compounds of Formulas (I), (I-A), (II), (II-A), (III), (III-A), (IV), (IV-A), (V), (V-A), (VI), (VI-A), (VII), (VII-A), (VIII), (VIII-A), (IX), (IX-A), (X), (X-A), (XI), (XI-A), (XII), (XII-A), (XIII), (XIII-A), (XIV), (XIV-A), (XV), (XV-A), (XVI), (XVI-A), (XVII), (XVII-A), (XVIII), (XVIII-A), (XIX), (XIX-A), (XX), (XX-A), (XXI), (XXI-A), (XXII), and (XXII-A) above, but not Formulas (I-B), (II-B), (III-B), (IV-B), (V-B), (VI-B), (VII-B), (VIII-B), (IX-B), (X-B), (XI-B), (XII-B), (XIII-B), (XIV-B), (XV-B), (XVI-B), (XVII-B), (XVIII-B), (XIX-B), (XX-B), (XXI), (XXI-B), (XXII), and (XXII-B) since the $R^1$ substituent has already been further defined in the same. Thus, reference to the substituents below is intended to further modify Formulas (I) through (XXII-B) to the extent such formulas recite that particular substituent as a variable.

In further embodiments, compounds are provided having the structure of any one of Formulas (I) through (XXII-B), or a pharmaceutically acceptable isomer, racemate, hydrate, solvate, isotope, or salt thereof, wherein X is halogen. In more specific embodiments, compounds are provided having the structure of any one of Formulas (I) through (XXII-B), or a pharmaceutically acceptable isomer, racemate, hydrate, solvate, isotope, or salt thereof, wherein X is Cl, F, or Br. In more specific embodiments, compounds are provided having the structure of any one of Formulas (I) through (XXII-B), or a pharmaceutically acceptable isomer, racemate, hydrate, solvate, isotope, or salt thereof, wherein X is Cl.

In further embodiments, compounds are provided having the structure of any one of Formulas (I) through (XXII-B), or a pharmaceutically acceptable isomer, racemate, hydrate, solvate, isotope, or salt thereof, wherein X is lower alkyl. In more specific embodiments, compounds are provided having the structure of any one of Formulas (I) through (XXII-B), or a pharmaceutically acceptable isomer, racemate, hydrate, solvate, isotope, or salt thereof, wherein X is methyl, ethyl, or isopropyl.

In further embodiments, compounds are provided having the structure of any one of Formulas (I) through (XXII-B), or a pharmaceutically acceptable isomer, racemate, hydrate, solvate, isotope, or salt thereof, wherein X is lower haloalkyl. In more specific embodiments, compounds are provided having the structure of any one of Formulas (I) through (XXII-B), or a pharmaceutically acceptable isomer, racemate, hydrate, solvate, isotope, or salt thereof, wherein X is —$CF_3$.

In further embodiments, compounds are provided having the structure of any one of Formulas (I) through (XXII-B), or a pharmaceutically acceptable isomer, racemate, hydrate, solvate, isotope, or salt thereof, wherein X is lower alkoxy. In more specific embodiments, compounds are provided having the structure of any one of Formulas (I) through (XXII-B), or a pharmaceutically acceptable isomer, racemate, hydrate, solvate, isotope, or salt thereof, wherein X is methoxy, ethoxy, isopropoxy, or t-butoxy.

In further embodiments, compounds are provided having the structure of any one of Formulas (I) through (XXII-B), or a pharmaceutically acceptable isomer, racemate, hydrate, solvate, isotope, or salt thereof, wherein X is cyano.

In further embodiments, compounds are provided having the structure of any one of Formulas (I) through (XXII-B), or a pharmaceutically acceptable isomer, racemate, hydrate, solvate, isotope, or salt thereof, wherein $R^1$ is hydrogen.

In further embodiments, compounds are provided having the structure of any one of Formulas (I) through (XXII-B), or a pharmaceutically acceptable isomer, racemate, hydrate, solvate, isotope, or salt thereof, wherein $R^1$ is lower alkyl. In more specific embodiments, compounds are provided having the structure of any one of Formulas (I) through (XXII-B), or a pharmaceutically acceptable isomer, racemate, hydrate, solvate, isotope, or salt thereof, wherein $R^1$ is methyl, ethyl, or isopropyl.

In further embodiments, compounds are provided having the structure of any one of Formulas (I) through (XXII-B), or a pharmaceutically acceptable isomer, racemate, hydrate, solvate, isotope, or salt thereof, wherein $R^1$ is lower alkoxy. In more specific embodiments, compounds are provided having the structure of any one of Formulas (I) through (XXII-B), or a pharmaceutically acceptable isomer, racemate, hydrate, solvate, isotope, or salt thereof, wherein $R^1$ is methoxy, ethoxy, isopropoxy, or t-butoxy.

In further embodiments, compounds are provided having the structure of any one of Formulas (I) through (XXII-B), or a pharmaceutically acceptable isomer, racemate, hydrate, solvate, isotope, or salt thereof, wherein $R^1$ is cycloalkyl. In more specific embodiments, compounds are provided having the structure of any one of Formulas (I) through (XXII-B), or a pharmaceutically acceptable isomer, racemate, hydrate, solvate, isotope, or salt thereof, wherein $R^1$ is cyclopropyl or cyclobutyl.

In further embodiments, compounds are provided having the structure of any one of Formulas (I) through (XXII-B), or a pharmaceutically acceptable isomer, racemate, hydrate, solvate, isotope, or salt thereof, wherein $R^2$ is -Q-$(R^4)_n$. In further embodiments, n is 0. In further embodiments, n is 1, 2, or 3. In further embodiments, n is 1.

In further embodiments, compounds are provided having the structure of any one of Formulas (I) through (XXII-B) wherein $R^2$ is -Q-$(R^4)_n$ and $R^4$ is halogen. In more specific embodiments, compounds are provided wherein $R^4$ is F or Cl.

In further embodiments compounds are provided having the structure of any one of Formulas (I) through (XXII-B) wherein $R^2$ is -Q-$(R^4)_n$ and $R^4$ is lower alkyl. In more specific embodiments, compounds are provided wherein $R^4$ is methyl or ethyl.

In further embodiments compounds are provided having the structure of any one of Formulas (I) through (XXII-B) wherein $R^2$ is -Q-$(R^4)_n$ and $R^4$ is lower alkoxy. In more specific embodiments, compounds are provided wherein $R^4$ is methoxy or ethoxy.

In further embodiments compounds are provided having the structure of any one of Formulas (I) through (XXII-B) wherein $R^2$ is -Q-$(R^4)_n$ and $R^4$ is cyano.

In further embodiments compounds are provided having the structure of any one of Formulas (I) through (XXII-B) wherein $R^2$ is -Q-$(R^4)_n$ and $R^4$ is hydroxy.

In further embodiments, compounds are provided having the structure of any one of Formulas (I) through (XXII-B) wherein $R^2$ is —S(=O)$_2R^5$ or —C(=O)$R^5$ and $R^5$ is lower alkyl. In more specific embodiments, compounds are provided wherein $R^5$ is methyl, ethyl, or isopropyl.

In further embodiments, compounds are provided having the structure of any one of Formulas (I) through (XXII-B) wherein $R^2$ is —S(=O)$_2R^5$ or —C(=O)$R^5$ and $R^5$ is lower alkoxy. In more specific embodiments, compounds are provided wherein $R^5$ is t-butoxy.

In further embodiments, compounds are provided having the structure of any one of Formulas (I) through (XXII-B) wherein $R^2$ is —S(=O)$_2R^5$ or —C(=O)$R^5$ and $R^5$ is heterocyclyl or cycloalkyl. In more specific embodiments, compounds are provided wherein $R^5$ is:

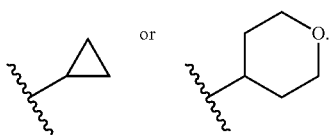

In further embodiments, compounds are provided having the structure of any one of Formulas (I) through (XXII-B) wherein $R^2$ is —S(=O)$_2$R$^5$ or —C(=O)R$^5$ and R$^5$ is —O-heterocyclyl. In more specific embodiments, compounds are provided wherein R$^5$ is:

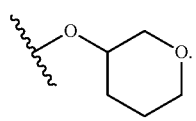

In further embodiments, compounds are provided having the structure of any one of Formulas (I) through (XXII-B) wherein $R^2$ is —S(=O)$_2$R$^5$ or —C(=O)R$^5$ and R$^5$ is heteroaryl. In more specific embodiments, compounds are provided wherein R$^5$ is pyridinyl.

In further embodiments, compounds are provided having the structure of any one of Formulas (I) through (XXII-B) wherein $R^2$ is —S(=O)$_2$R$^5$ or —C(=O)R$^5$ and R$^5$ is cycloalkylalkyl. In more specific embodiments, compounds are provided wherein R$^5$ is:

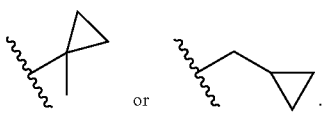

In further embodiments, compounds are provided having the structure of any one of Formulas (I) through (XXII-B) wherein $R^1$ is alkyl, cycloalkyl, lower haloalkyl; $R^4$ is H, halo, lower alkyl, lower haloalkyl, lower alkoxy, lower alkoxyalkyl, lower haloalkoxyalkyl, cyano; and X is halo or lower alkoxy. In further embodiments, $R^1$ is methyl, cyclopropyl, or CF$_3$, $R^4$ is H, F, methyl, —CF$_3$, —O—CH$_3$, or —O-isopropyl; and X is Cl or —O—CH$_3$.

In further embodiments, compounds are provided having the structure of any one of Formulas (I) through (XXII-B) wherein $R^3$ is alkyl, cycloalkyl, lower haloalkyl; $R^4$ is H, halo, lower alkyl, lower haloalkyl, lower alkoxyalkyl, lower alkoxhaloyalkyl, cyano; and X is halo, lower alkoxy. In further embodiments, $R^3$ is methyl, cyclopropyl, or CF$_3$, $R^4$ is H, F, methyl, —CF$_3$, —O—CH$_3$, or —O-isopropyl; and X is Cl or —O—CH$_3$.

In further embodiments, compounds are provided having the structure of any one of Formulas (I) through (XXII-B) wherein $R^1$ is alkyl, haloalkyl, cycloalkyl; $R^5$ is cycloalkyl, lower alkyl, heterocyclyl and X is halo. In further embodiments, $R^1$ is cyclopropyl or —CH$_2$—CF$_2$-cyclopropyl.

In further embodiments, compounds are provided having the structure of any one of Formulas (I) through (XXII-B) wherein $R^3$ is alkyl, cycloalkyl, lower haloalkyl; $R^5$ is cycloalkyl, lower alkyl, heterocyclyl and X is halo. In further embodiments, $R^3$ is methyl or cyclopropyl.

In further embodiments, compounds are provided having the structure of any one of Formulas (I) through (XXII-B) wherein $R^1$ is

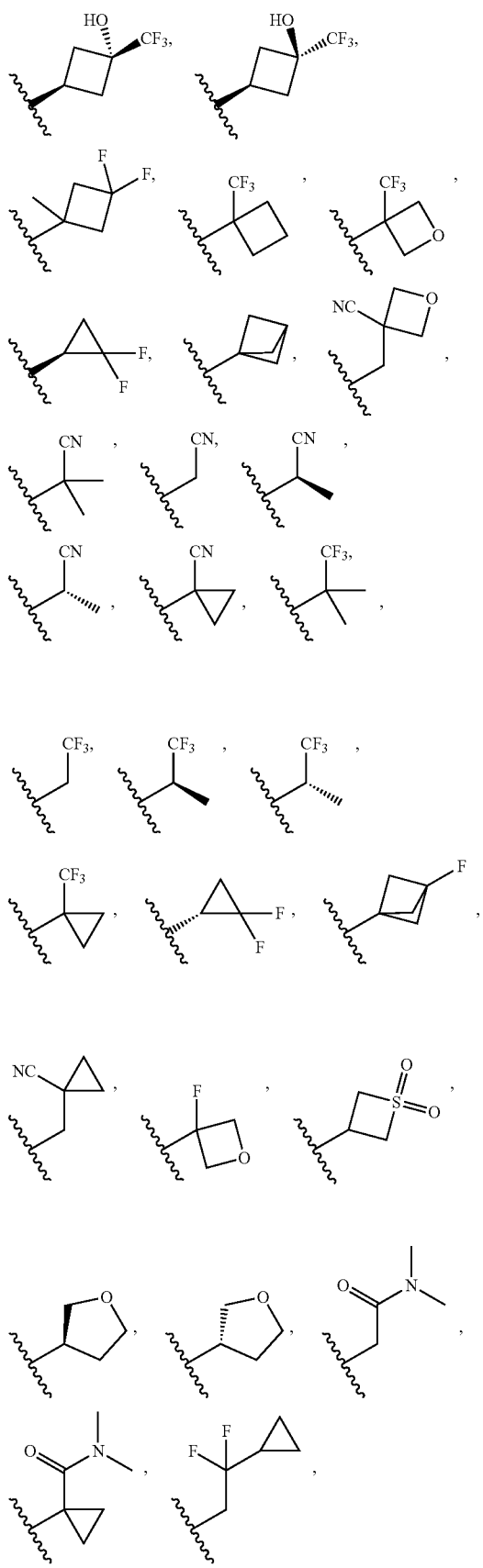

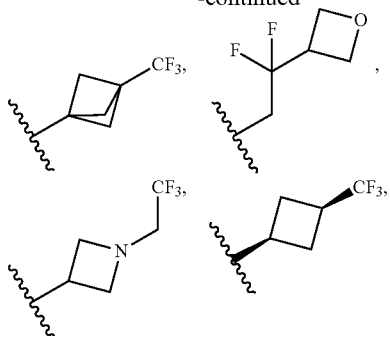
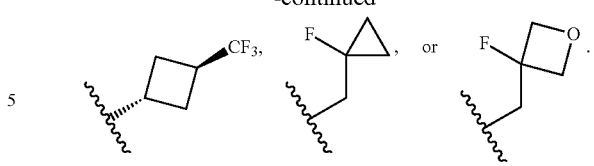
Representative compounds of Formula (I), and Formulas (II) through (XXII-B) as applicable, include the compounds listed in Table 1 below, as well as pharmaceutically acceptable isomers, racemates, hydrates, solvates, isotopes, and salts thereof.
TABLE 1
Representative Compounds
| Cmpd. No. | Structure |
|---|---|
| 1 | 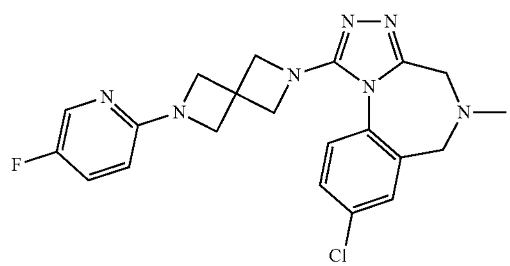 [SMILES: CN1Cc2cc(Cl)ccc2-n2c(nnc2N2CC3(CN(c4ccc(F)cn4)C3)C2)C1] |
| 2 | 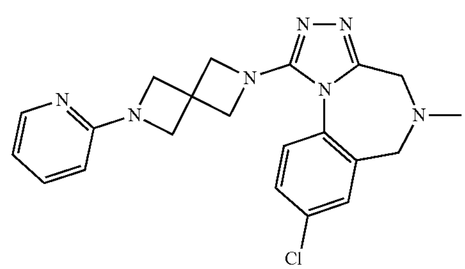 [SMILES: CN1Cc2cc(Cl)ccc2-n2c(nnc2N2CC3(CN(c4ccccn4)C3)C2)C1] |
| 3 | 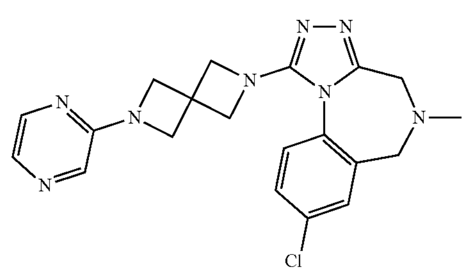 [SMILES: CN1Cc2cc(Cl)ccc2-n2c(nnc2N2CC3(CN(c4cnccn4)C3)C2)C1] |
| 4 | 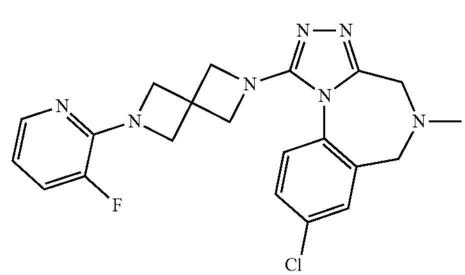 [SMILES: CN1Cc2cc(Cl)ccc2-n2c(nnc2N2CC3(CN(c4ncccc4F)C3)C2)C1] |

TABLE 1-continued
Representative Compounds
| Cmpd. No. | Structure |
|---|---|
| 5 | 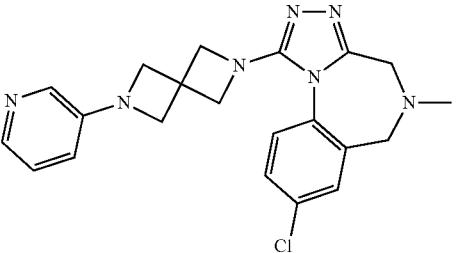 [SMILES: CN1Cc2cc(Cl)ccc2-n2c(nnc2N2CC3(CN(c4cccnc4)C3)C2)C1] |
| 6 | 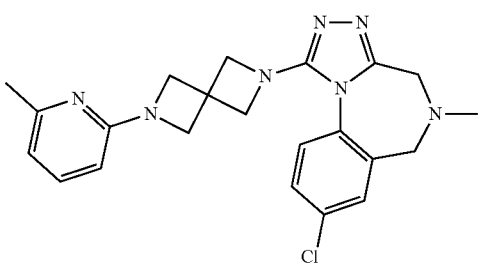 |
| 7 | 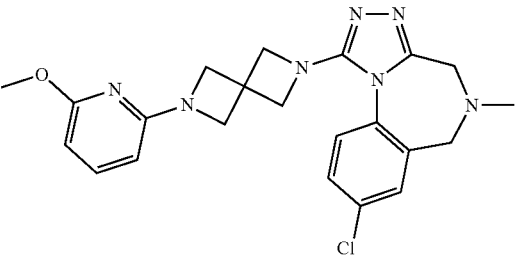 |
| 8 | 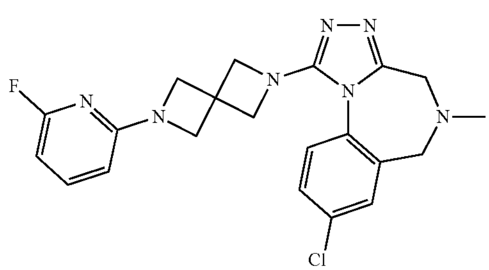 [SMILES: CN1Cc2cc(Cl)ccc2-n2c(nnc2N2CC3(CN(c4cccc(F)n4)C3)C2)C1] |
| 9 | 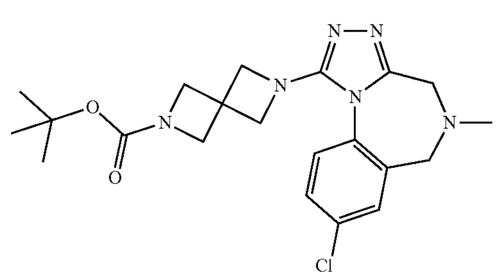 [SMILES: CN1Cc2cc(Cl)ccc2-n2c(nnc2N2CC3(CN(C(=O)OC(C)(C)C)C3)C2)C1] |

TABLE 1-continued

Representative Compounds

| Cmpd. No. | Structure |
|---|---|
| 10 | 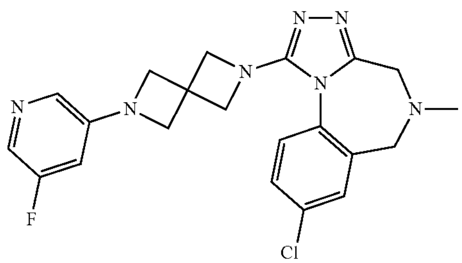 [SMILES: CN1Cc2cc(Cl)ccc2-n2c(nnc2N2CC3(CN(c4cncc(F)c4)C3)C2)C1] |
| 11 | 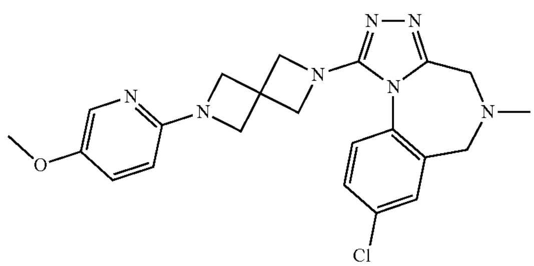 |
| 12 | 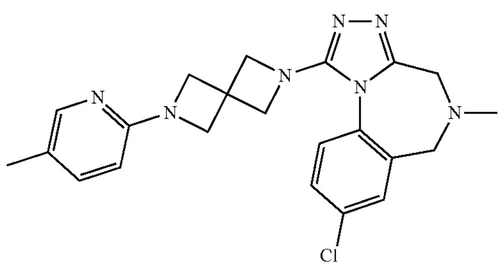 |
| 13 | 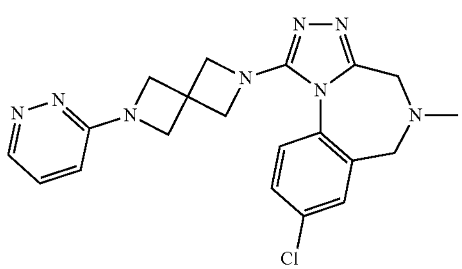 |
| 14 | 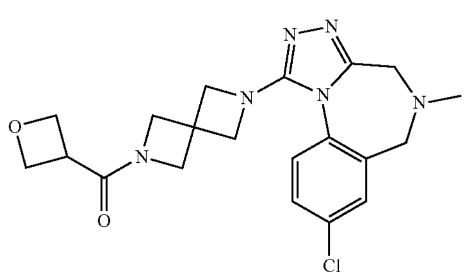 [SMILES: CN1Cc2cc(Cl)ccc2-n2c(nnc2N2CC3(CN(C(=O)C4COC4)C3)C2)C1] |

TABLE 1-continued

Representative Compounds

| Cmpd. No. | Structure |
|---|---|
| 15 | 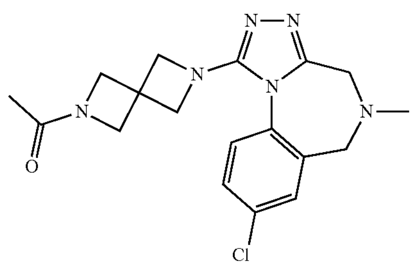 [SMILES: CC(=O)N1CC2(C1)CN(c1nnc3n1-c1ccc(Cl)cc1CN(C)C3)C2] |
| 16 | 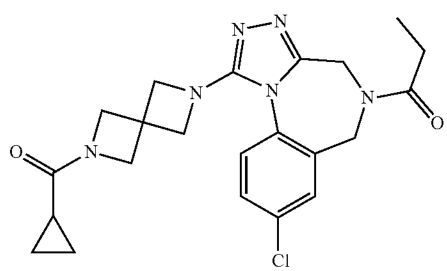 [SMILES: CCC(=O)N1Cc2cc(Cl)ccc2-n2c(nnc2N2CC3(CN(C(=O)C4CC4)C3)C2)C1] |
| 17 | 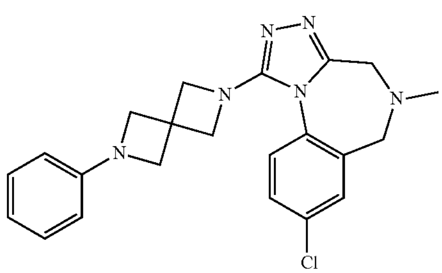 [SMILES: CN1Cc2cc(Cl)ccc2-n2c(nnc2N2CC3(CN(c4ccccc4)C3)C2)C1] |
| 18 | 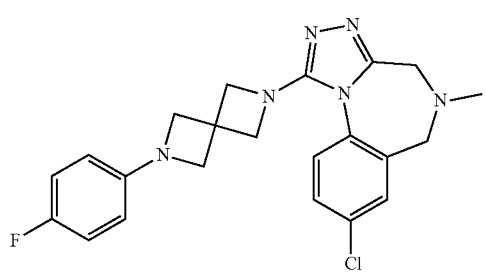 [SMILES: CN1Cc2cc(Cl)ccc2-n2c(nnc2N2CC3(CN(c4ccc(F)cc4)C3)C2)C1] |
| 19 | 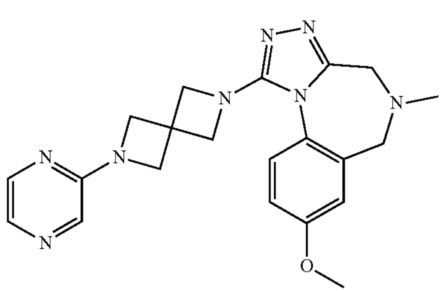 [SMILES: COc1ccc2c(c1)CN(C)Cc1nnc(N3CC4(CN(c5cnccn5)C4)C3)n1-2] |

TABLE 1-continued

Representative Compounds

| Cmpd. No. | Structure |
|---|---|
| 20 | 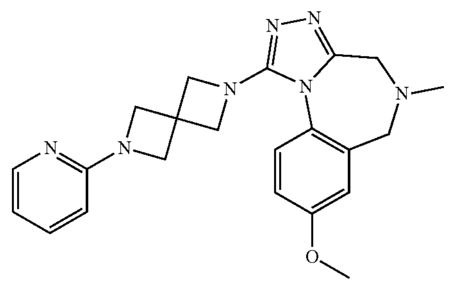 [SMILES: COc1ccc2c(c1)CN(C)Cc1nnc(N3CC4(CN(c5ccccn5)C4)C3)n1-2] |
| 21 | 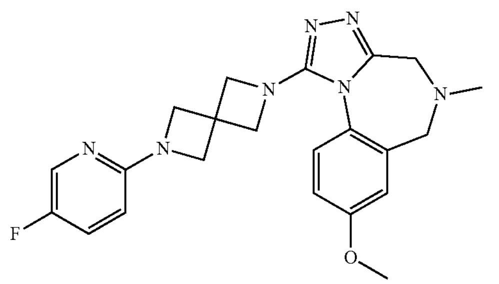 [SMILES: COc1ccc2c(c1)CN(C)Cc1nnc(N3CC4(CN(c5ccc(F)cn5)C4)C3)n1-2] |
| 22 | 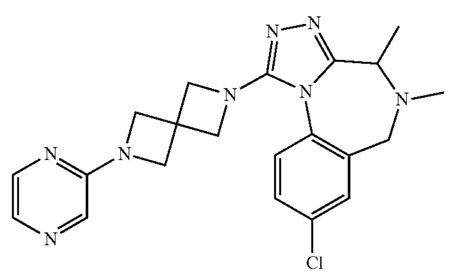 [SMILES: CC1c2nnc(N3CC4(CN(c5cnccn5)C4)C3)n2-c2ccc(Cl)cc2CN1C] |
| 23 | 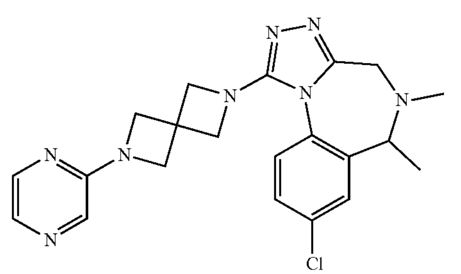 [SMILES: CC1c2cc(Cl)ccc2-n2c(nnc2N2CC3(CN(c4cnccn4)C3)C2)CN1C] |
| 24 | 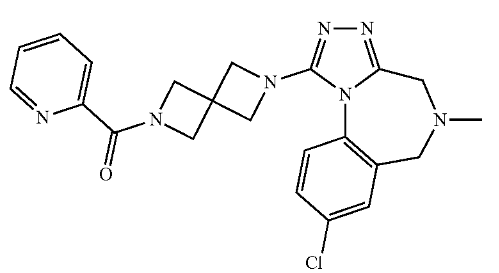 [SMILES: CN1Cc2cc(Cl)ccc2-n2c(nnc2N2CC3(CN(C(=O)c4ccccn4)C3)C2)C1] |

TABLE 1-continued

Representative Compounds

| Cmpd. No. | Structure |
|---|---|
| 25 | 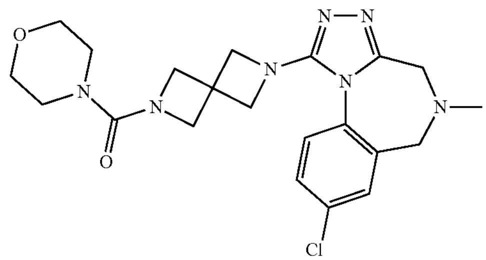 [SMILES: CN1Cc2cc(Cl)ccc2-n2c(nnc2N2CC3(CN(C(=O)N4CCOCC4)C3)C2)C1] |
| 26 | 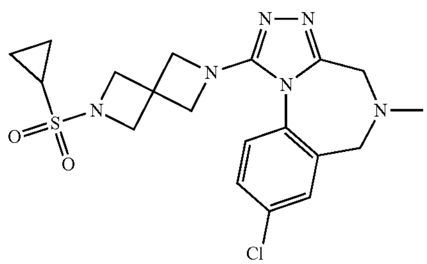 [SMILES: CN1Cc2cc(Cl)ccc2-n2c(nnc2N2CC3(C2)CN(S(=O)(=O)C2CC2)C3)C1] |
| 27 | 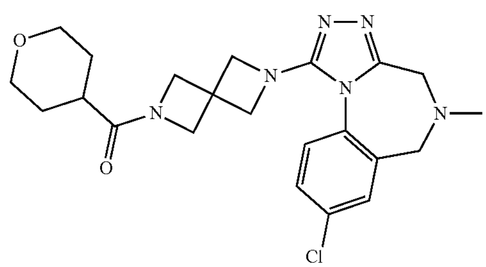 [SMILES: CN1Cc2cc(Cl)ccc2-n2c(nnc2N2CC3(CN(C(=O)C4CCOCC4)C3)C2)C1] |
| 28 | 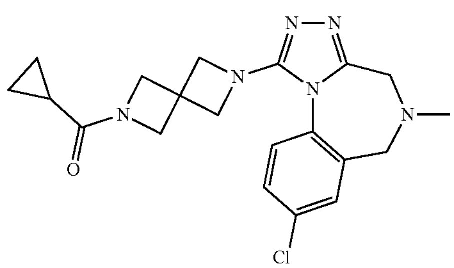 [SMILES: CN1Cc2cc(Cl)ccc2-n2c(nnc2N2CC3(CN(C(=O)C4CC4)C3)C2)C1] |
| 29 | 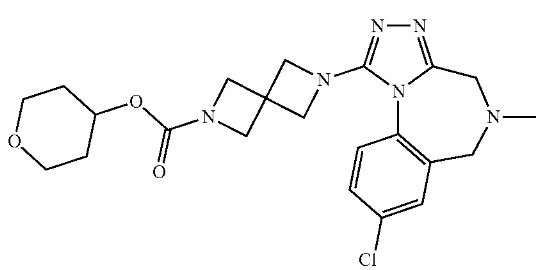 [SMILES: CN1Cc2cc(Cl)ccc2-n2c(nnc2N2CC3(CN(C(=O)OC4CCOCC4)C3)C2)C1] |

TABLE 1-continued

Representative Compounds

| Cmpd. No. | Structure |
|---|---|
| 30 | 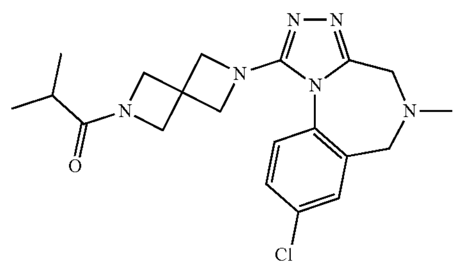 [SMILES: CC(C)C(=O)N1CC2(C1)CN(c1nnc3n1-c1ccc(Cl)cc1CN(C)C3)C2] |
| 31 | 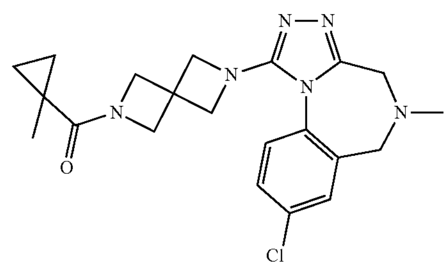 [SMILES: CN1Cc2cc(Cl)ccc2-n2c(nnc2N2CC3(CN(C(=O)C4(C)CC4)C3)C2)C1] |
| 32 | 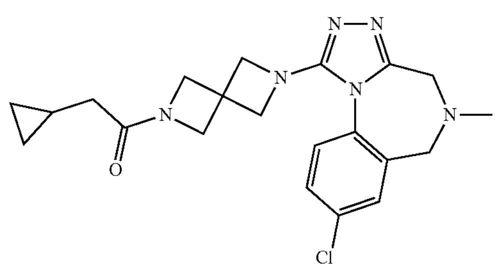 [SMILES: CN1Cc2cc(Cl)ccc2-n2c(nnc2N2CC3(CN(C(=O)CC4CC4)C3)C2)C1] |
| 33 | 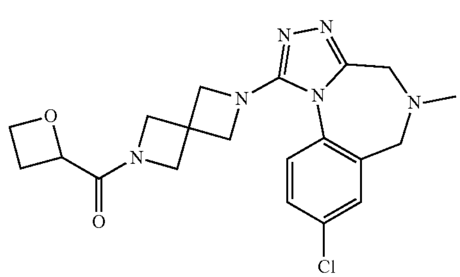 [SMILES: CN1Cc2cc(Cl)ccc2-n2c(nnc2N2CC3(CN(C(=O)C4CCO4)C3)C2)C1] |
| 34 | 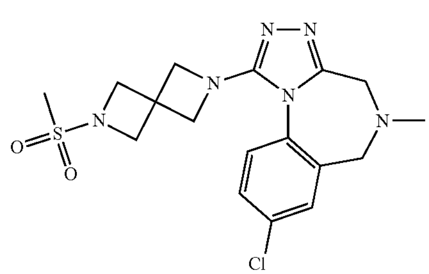 [SMILES: CN1Cc2cc(Cl)ccc2-n2c(nnc2N2CC3(C2)CN(S(C)(=O)=O)C3)C1] |

TABLE 1-continued

Representative Compounds

| Cmpd. No. | Structure |
|---|---|
| 35 | 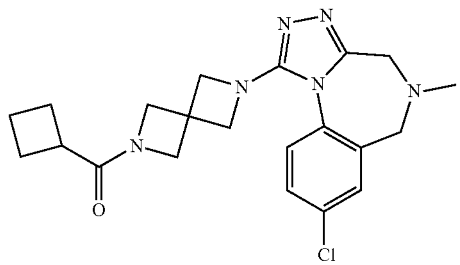 [SMILES: CN1Cc2cc(Cl)ccc2-n2c(nnc2N2CC3(CN(C(=O)C4CCC4)C3)C2)C1] |
| 36 | 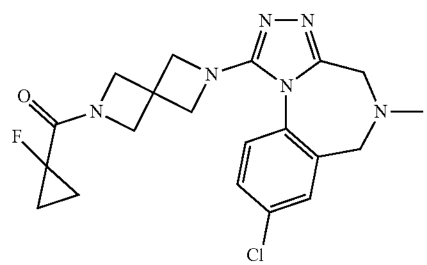 [SMILES: CN1Cc2cc(Cl)ccc2-n2c(nnc2N2CC3(CN(C(=O)C4(F)CC4)C3)C2)C1] |
| 37 | 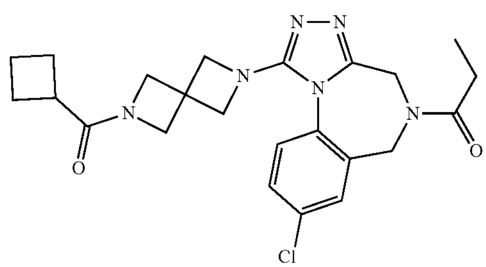 [SMILES: CCC(=O)N1Cc2cc(Cl)ccc2-n2c(nnc2N2CC3(CN(C(=O)C4CCC4)C3)C2)C1] |
| 38 | 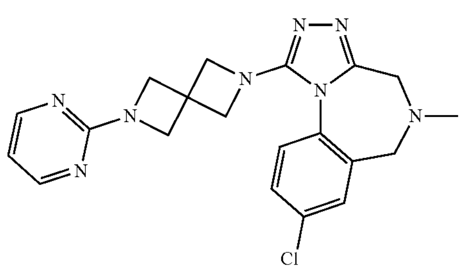 [SMILES: CN1Cc2cc(Cl)ccc2-n2c(nnc2N2CC3(CN(c4ncccn4)C3)C2)C1] |
| 39 | 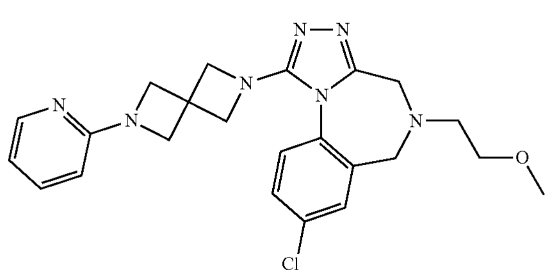 [SMILES: COCCN1Cc2cc(Cl)ccc2-n2c(nnc2N2CC3(CN(c4ccccn4)C3)C2)C1] |

TABLE 1-continued

Representative Compounds

| Cmpd. No. | Structure |
|---|---|
| 40 | 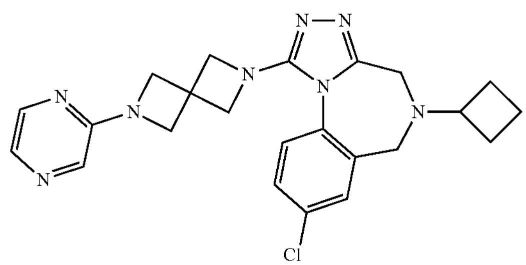 [SMILES: Clc1ccc2c(c1)CN(C1CCC1)Cc1nnc(N3CC4(CN(c5cnccn5)C4)C3)n1-2] |
| 41 | 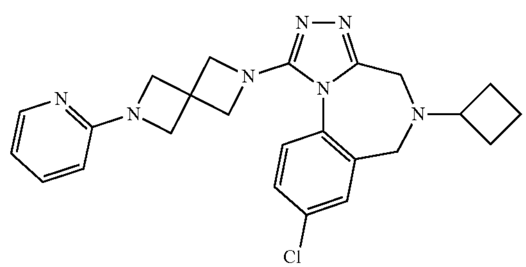 [SMILES: Clc1ccc2c(c1)CN(C1CCC1)Cc1nnc(N3CC4(CN(c5ccccn5)C4)C3)n1-2] |
| 42 | 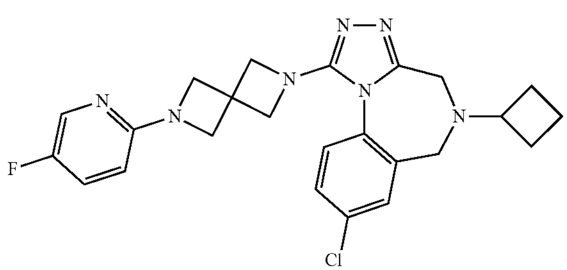 [SMILES: Fc1ccc(N2CC3(C2)CN(c2nnc4n2-c2ccc(Cl)cc2CN(C2CCC2)C4)C3)nc1] |
| 43 | 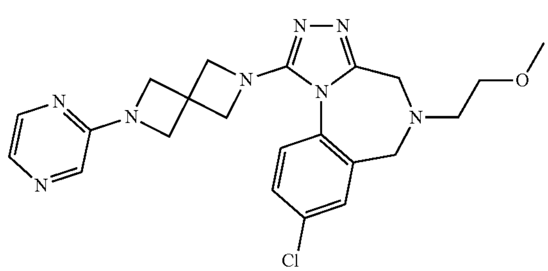 [SMILES: COCCN1Cc2cc(Cl)ccc2-n2c(nnc2N2CC3(CN(c4cnccn4)C3)C2)C1] |
| 44 | 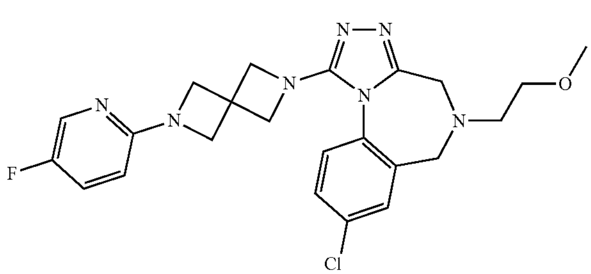 [SMILES: COCCN1Cc2cc(Cl)ccc2-n2c(nnc2N2CC3(CN(c4ccc(F)cn4)C3)C2)C1] |

TABLE 1-continued

Representative Compounds

| Cmpd. No. | Structure |
|---|---|
| 45 | 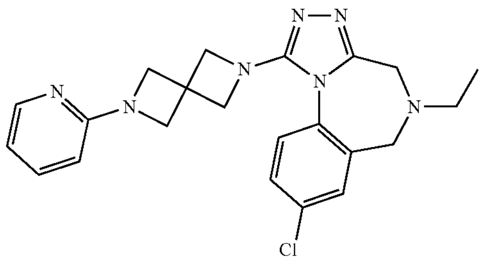 [SMILES: CCN1Cc2cc(Cl)ccc2-n2c(nnc2N2CC3(CN(c4ccccn4)C3)C2)C1] |
| 46 | 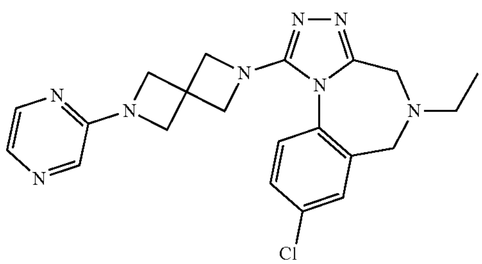 [SMILES: CCN1Cc2cc(Cl)ccc2-n2c(nnc2N2CC3(CN(c4cnccn4)C3)C2)C1] |
| 47 | 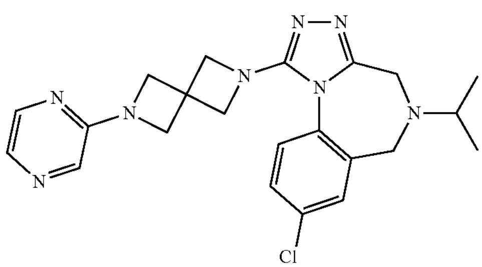 [SMILES: CC(C)N1Cc2cc(Cl)ccc2-n2c(nnc2N2CC3(CN(c4cnccn4)C3)C2)C1] |
| 48 | 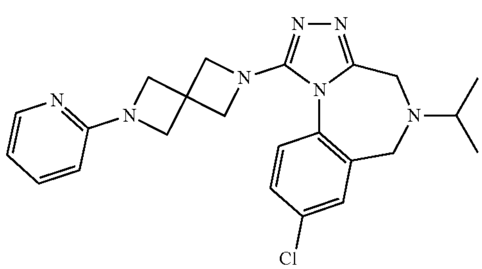 [SMILES: CC(C)N1Cc2cc(Cl)ccc2-n2c(nnc2N2CC3(CN(c4ccccn4)C3)C2)C1] |
| 49 | 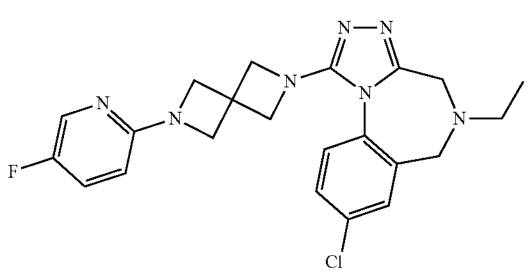 [SMILES: CCN1Cc2cc(Cl)ccc2-n2c(nnc2N2CC3(CN(c4ccc(F)cn4)C3)C2)C1] |

TABLE 1-continued

Representative Compounds

| Cmpd. No. | Structure |
|---|---|
| 50 | 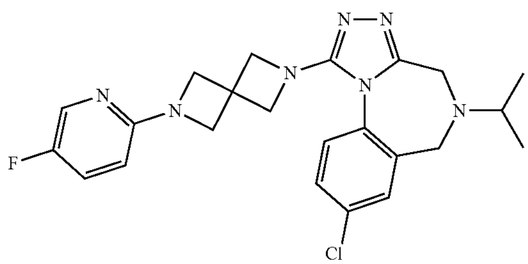 [SMILES: CC(C)N1Cc2cc(Cl)ccc2-n2c(nnc2N2CC3(CN(c4ccc(F)cn4)C3)C2)C1] |
| 51 | 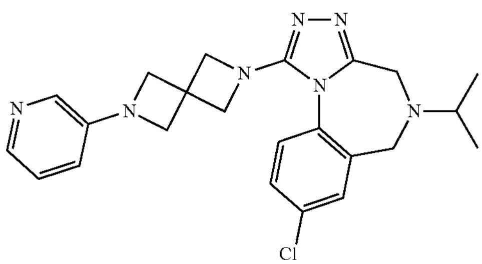 [SMILES: CC(C)N1Cc2cc(Cl)ccc2-n2c(nnc2N2CC3(CN(c4cccnc4)C3)C2)C1] |
| 52 | 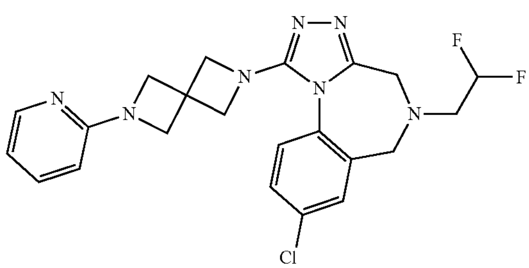 [SMILES: FC(F)CN1Cc2cc(Cl)ccc2-n2c(nnc2N2CC3(CN(c4ccccn4)C3)C2)C1] |
| 53 | 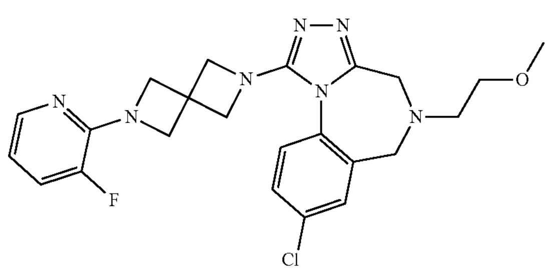 [SMILES: COCCN1Cc2cc(Cl)ccc2-n2c(nnc2N2CC3(CN(c4ncccc4F)C3)C2)C1] |
| 54 | 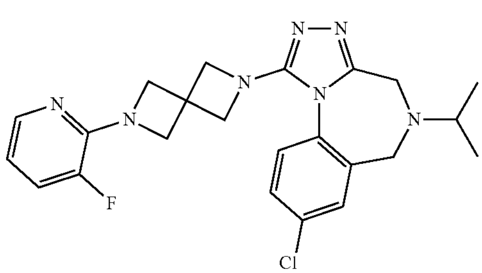 [SMILES: CC(C)N1Cc2cc(Cl)ccc2-n2c(nnc2N2CC3(CN(c4ncccc4F)C3)C2)C1] |

TABLE 1-continued

Representative Compounds

| Cmpd. No. | Structure |
|---|---|
| 55 | 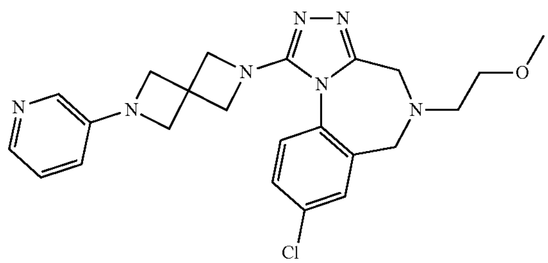 [SMILES: COCCN1Cc2cc(Cl)ccc2-n2c(nnc2N2CC3(CN(c4cccnc4)C3)C2)C1] |
| 56 | 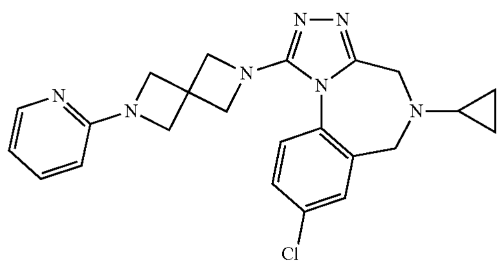 [SMILES: Clc1ccc2c(c1)CN(C1CC1)Cc1nnc(N3CC4(CN(c5ccccn5)C4)C3)n1-2] |
| 57 | 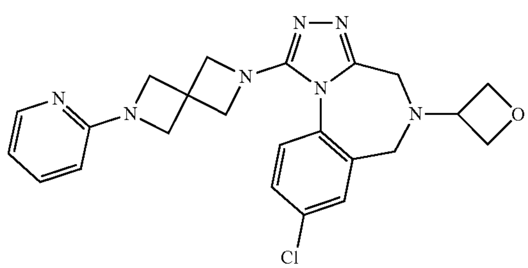 [SMILES: Clc1ccc2c(c1)CN(C1COC1)Cc1nnc(N3CC4(CN(c5ccccn5)C4)C3)n1-2] |
| 58 | 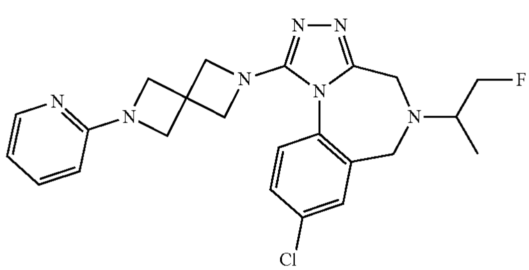 [SMILES: CC(CF)N1Cc2cc(Cl)ccc2-n2c(nnc2N2CC3(CN(c4ccccn4)C3)C2)C1] |
| 59 | 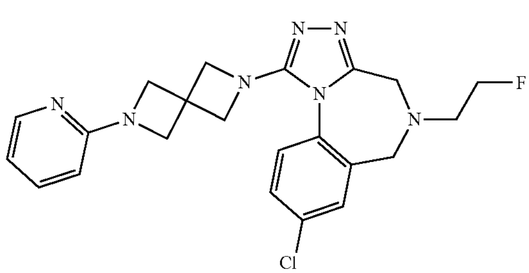 [SMILES: FCCN1Cc2cc(Cl)ccc2-n2c(nnc2N2CC3(CN(c4ccccn4)C3)C2)C1] |

TABLE 1-continued

Representative Compounds

| Cmpd. No. | Structure |
|---|---|
| 60 | 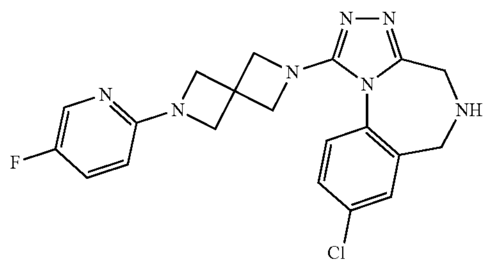 [SMILES: Fc1ccc(N2CC3(C2)CN(c2nnc4n2-c2ccc(Cl)cc2CNC4)C3)nc1] |
| 61 | 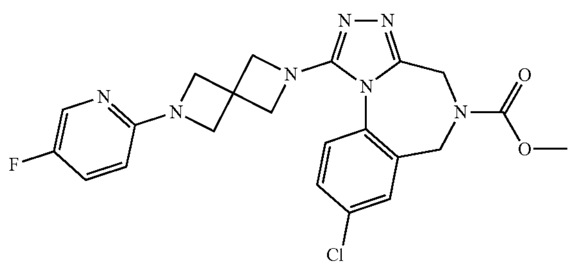 |
| 62 | |
| 63 | 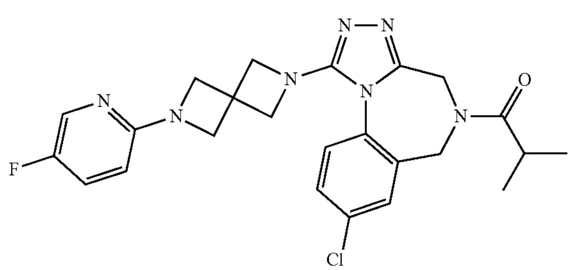 [SMILES: CC(C)C(=O)N1Cc2cc(Cl)ccc2-n2c(nnc2N2CC3(CN(c4ccc(F)cn4)C3)C2)C1] |
| 64 | 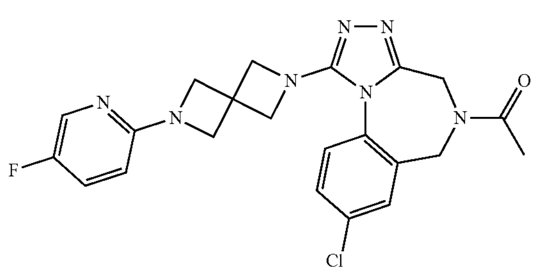 [SMILES: CC(=O)N1Cc2cc(Cl)ccc2-n2c(nnc2N2CC3(CN(c4ccc(F)cn4)C3)C2)C1] |

TABLE 1-continued

Representative Compounds

| Cmpd. No. | Structure |
|---|---|
| 65 | 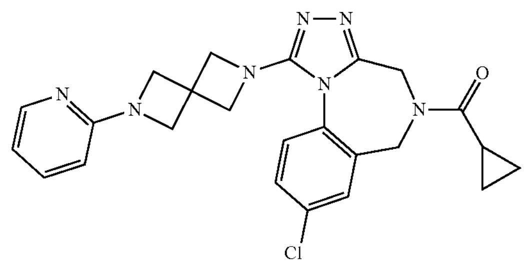 [SMILES: O=C(C1CC1)N1Cc2cc(Cl)ccc2-n2c(nnc2N2CC3(CN(c4ccccn4)C3)C2)C1] |
| 66 | 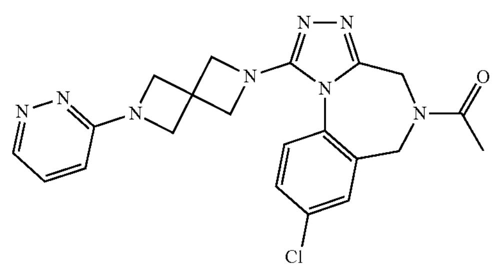 [SMILES: CC(=O)N1Cc2cc(Cl)ccc2-n2c(nnc2N2CC3(CN(c4cccnn4)C3)C2)C1] |
| 67 | 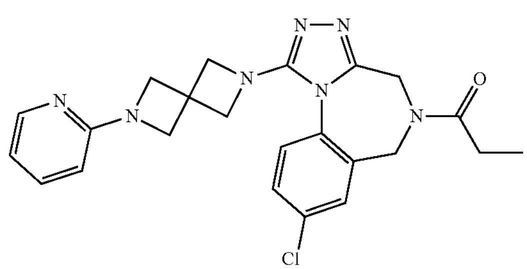 [SMILES: CCC(=O)N1Cc2cc(Cl)ccc2-n2c(nnc2N2CC3(CN(c4ccccn4)C3)C2)C1] |
| 68 | 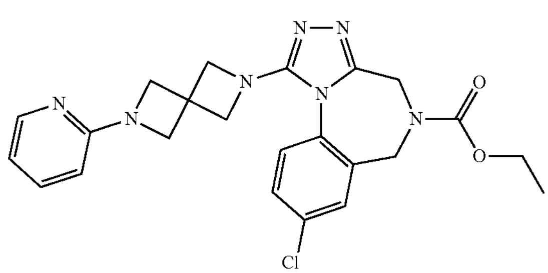 [SMILES: CCOC(=O)N1Cc2cc(Cl)ccc2-n2c(nnc2N2CC3(CN(c4ccccn4)C3)C2)C1] |
| 69 | 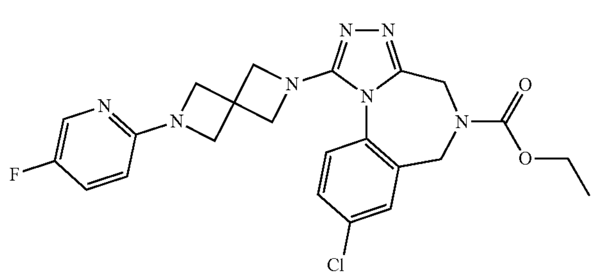 [SMILES: CCOC(=O)N1Cc2cc(Cl)ccc2-n2c(nnc2N2CC3(CN(c4ccc(F)cn4)C3)C2)C1] |

TABLE 1-continued

Representative Compounds

| Cmpd. No. | Structure |
|---|---|
| 70 | 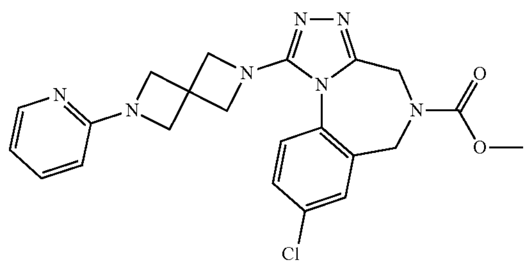 [SMILES: COC(=O)N1Cc2cc(Cl)ccc2-n2c(nnc2N2CC3(CN(c4ccccn4)C3)C2)C1] |
| 71 | 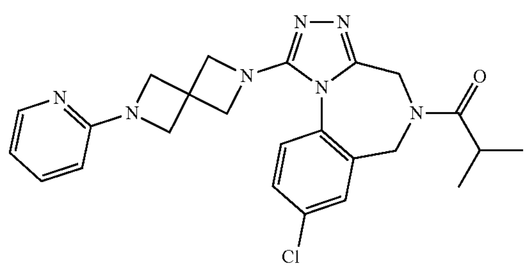 [SMILES: CC(C)C(=O)N1Cc2cc(Cl)ccc2-n2c(nnc2N2CC3(CN(c4ccccn4)C3)C2)C1] |
| 72 | 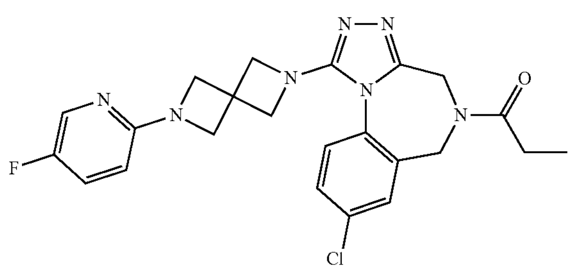 [SMILES: CCC(=O)N1Cc2cc(Cl)ccc2-n2c(nnc2N2CC3(CN(c4ccc(F)cn4)C3)C2)C1] |
| 73 | 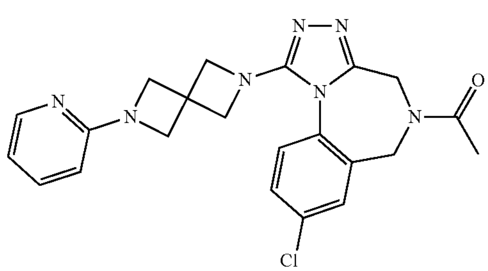 [SMILES: CC(=O)N1Cc2cc(Cl)ccc2-n2c(nnc2N2CC3(CN(c4ccccn4)C3)C2)C1] |
| 74 | 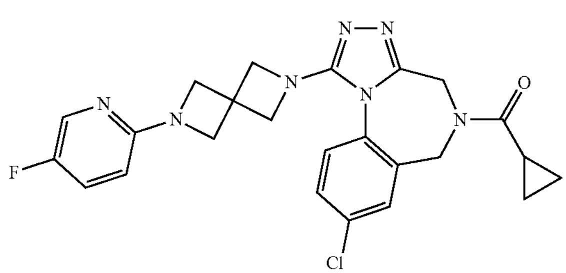 [SMILES: O=C(C1CC1)N1Cc2cc(Cl)ccc2-n2c(nnc2N2CC3(CN(c4ccc(F)cn4)C3)C2)C1] |

TABLE 1-continued

Representative Compounds

| Cmpd. No. | Structure |
|---|---|
| 75 | 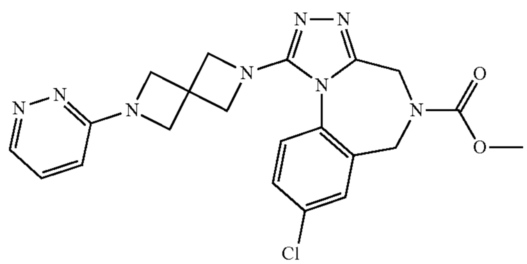 [SMILES: COC(=O)N1Cc2cc(Cl)ccc2-n2c(nnc2N2CC3(CN(c4cccnn4)C3)C2)C1] |
| 76 | 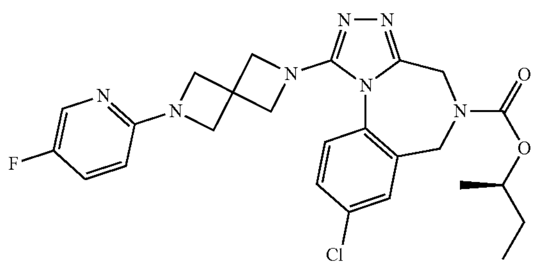 [SMILES: CC[C@@H](C)OC(=O)N1Cc2cc(Cl)ccc2-n2c(nnc2N2CC3(CN(c4ccc(F)cn4)C3)C2)C1] |
| 77 | 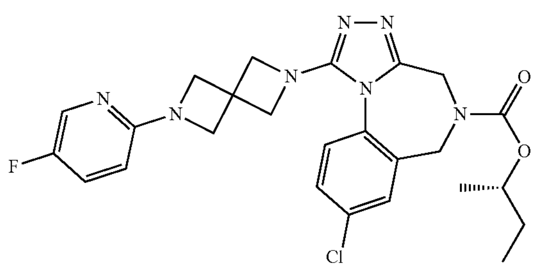 [SMILES: CC[C@H](C)OC(=O)N1Cc2cc(Cl)ccc2-n2c(nnc2N2CC3(CN(c4ccc(F)cn4)C3)C2)C1] |
| 78 | 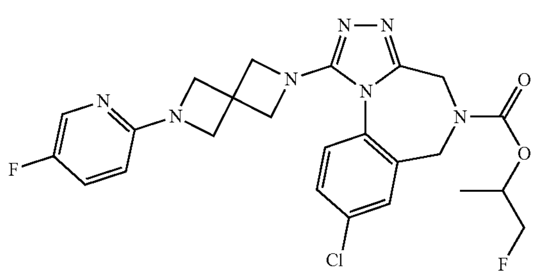 [SMILES: CC(CF)OC(=O)N1Cc2cc(Cl)ccc2-n2c(nnc2N2CC3(CN(c4ccc(F)cn4)C3)C2)C1] |
| 79 | 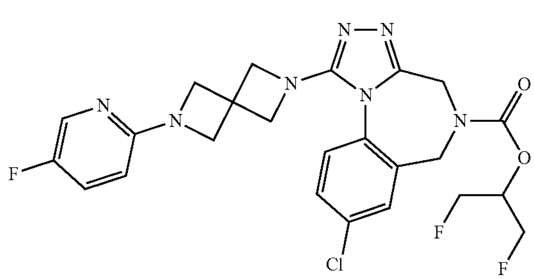 [SMILES: O=C(OC(CF)CF)N1Cc2cc(Cl)ccc2-n2c(nnc2N2CC3(CN(c4ccc(F)cn4)C3)C2)C1] |

TABLE 1-continued

Representative Compounds

| Cmpd. No. | Structure |
|---|---|
| 80 | *(chemical structure)* |
| 81 | *(chemical structure)* |
| 82 | *(chemical structure)* |
| 83 | *(chemical structure)* |
| 84 | *(chemical structure)* |

TABLE 1-continued

Representative Compounds

| Cmpd. No. | Structure |
|---|---|
| 85 | 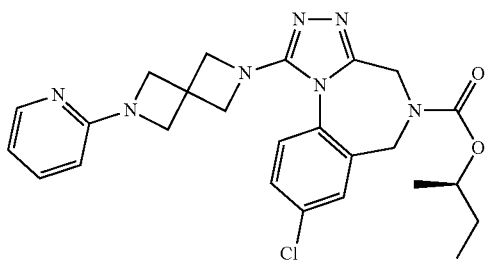 [SMILES: CC[C@@H](C)OC(=O)N1Cc2cc(Cl)ccc2-n2c(nnc2N2CC3(CN(c4ccccn4)C3)C2)C1] |
| 86 | 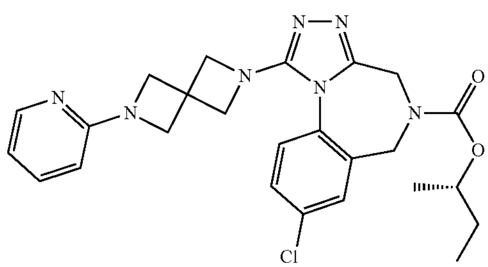 [SMILES: CC[C@H](C)OC(=O)N1Cc2cc(Cl)ccc2-n2c(nnc2N2CC3(CN(c4ccccn4)C3)C2)C1] |
| 87 | 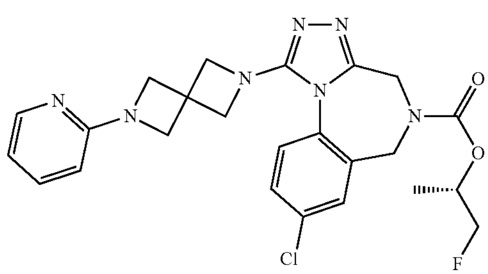 [SMILES: C[C@@H](CF)OC(=O)N1Cc2cc(Cl)ccc2-n2c(nnc2N2CC3(CN(c4ccccn4)C3)C2)C1] |
| 88 | 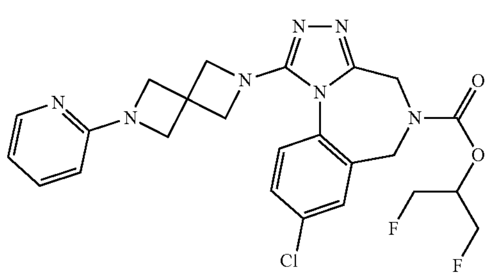 [SMILES: O=C(OC(CF)CF)N1Cc2cc(Cl)ccc2-n2c(nnc2N2CC3(CN(c4ccccn4)C3)C2)C1] |
| 89 | 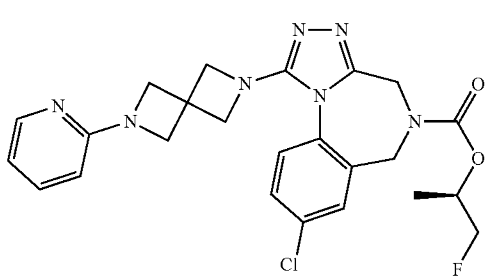 [SMILES: C[C@H](CF)OC(=O)N1Cc2cc(Cl)ccc2-n2c(nnc2N2CC3(CN(c4ccccn4)C3)C2)C1] |

TABLE 1-continued

Representative Compounds

| Cmpd. No. | Structure |
|---|---|
| 90 | 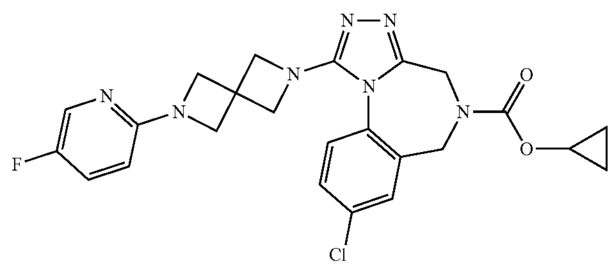 [SMILES: O=C(OC1CC1)N1Cc2cc(Cl)ccc2-n2c(nnc2N2CC3(CN(c4ccc(F)cn4)C3)C2)C1] |
| 91 | 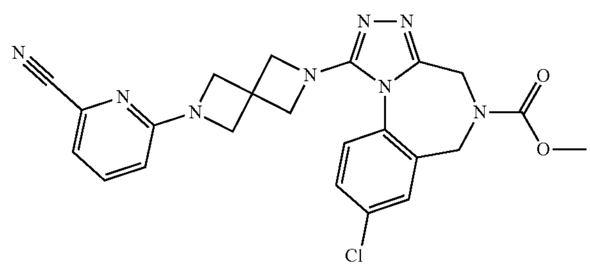 [SMILES: COC(=O)N1Cc2cc(Cl)ccc2-n2c(nnc2N2CC3(CN(c4cccc(C#N)n4)C3)C2)C1] |
| 92 | 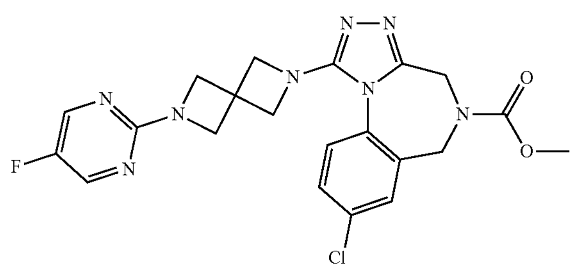 [SMILES: COC(=O)N1Cc2cc(Cl)ccc2-n2c(nnc2N2CC3(CN(c4ncc(F)cn4)C3)C2)C1] |
| 93 | 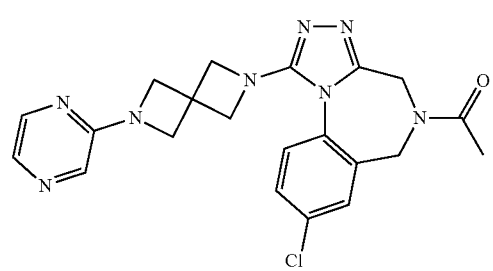 [SMILES: CC(=O)N1Cc2cc(Cl)ccc2-n2c(nnc2N2CC3(CN(c4cnccn4)C3)C2)C1] |
| 94 | 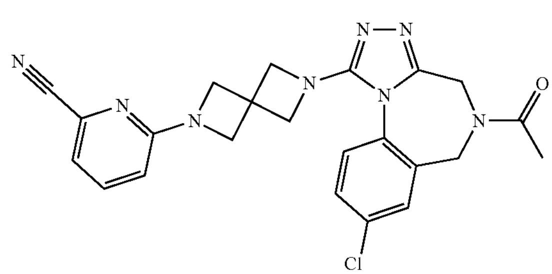 [SMILES: CC(=O)N1Cc2cc(Cl)ccc2-n2c(nnc2N2CC3(CN(c4cccc(C#N)n4)C3)C2)C1] |

TABLE 1-continued

Representative Compounds

| Cmpd. No. | Structure |
|---|---|
| 95 | 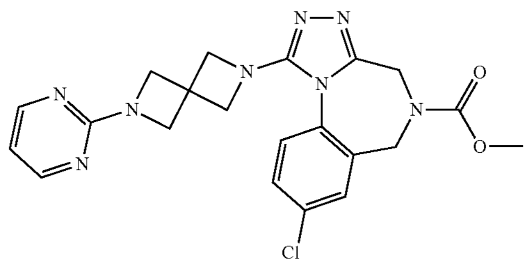 [SMILES: COC(=O)N1Cc2cc(Cl)ccc2-n2c(nnc2N2CC3(CN(c4ncccn4)C3)C2)C1] |
| 96 | 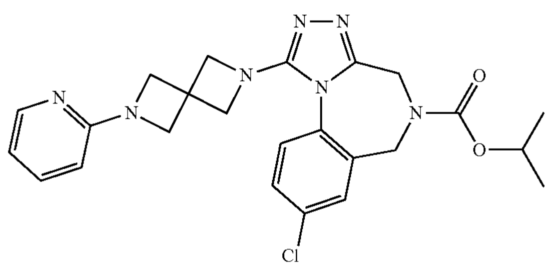 [SMILES: CC(C)OC(=O)N1Cc2cc(Cl)ccc2-n2c(nnc2N2CC3(CN(c4ccccn4)C3)C2)C1] |
| 97 | 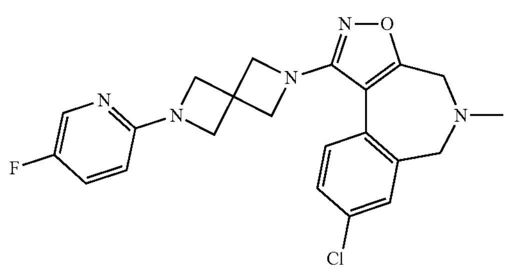 [SMILES: CN1Cc2cc(Cl)ccc2-c2c(N3CC4(CN(c5ccc(F)cn5)C4)C3)noc2C1] |
| 98 | 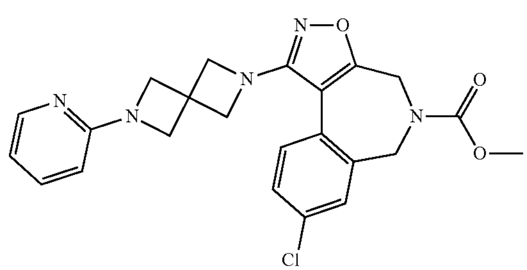 [SMILES: COC(=O)N1Cc2cc(Cl)ccc2-c2c(N3CC4(CN(c5ccccn5)C4)C3)noc2C1] |
| 99 | 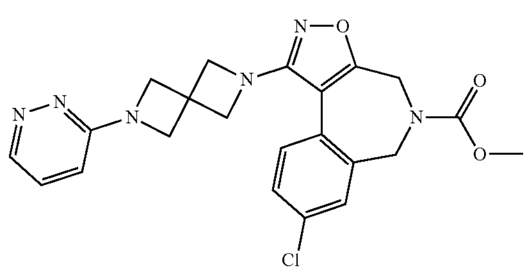 [SMILES: COC(=O)N1Cc2cc(Cl)ccc2-c2c(N3CC4(CN(c5cccnn5)C4)C3)noc2C1] |

TABLE 1-continued

Representative Compounds

| Cmpd. No. | Structure |
|---|---|
| 100 | 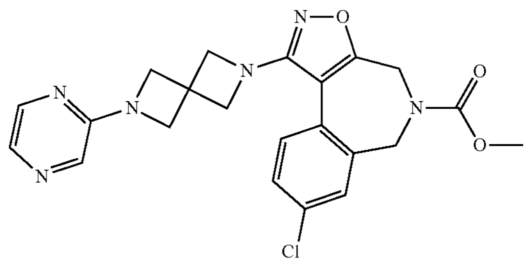 [SMILES: COC(=O)N1Cc2cc(Cl)ccc2-c2c(N3CC4(CN(c5cnccn5)C4)C3)noc2C1] |
| 101 | 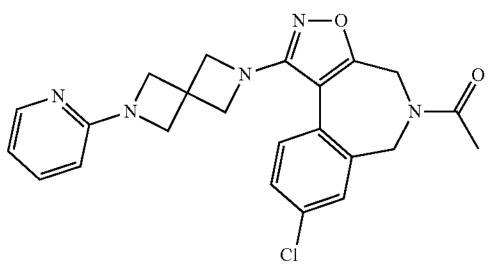 [SMILES: CC(=O)N1Cc2cc(Cl)ccc2-c2c(N3CC4(CN(c5ccccn5)C4)C3)noc2C1] |
| 102 | 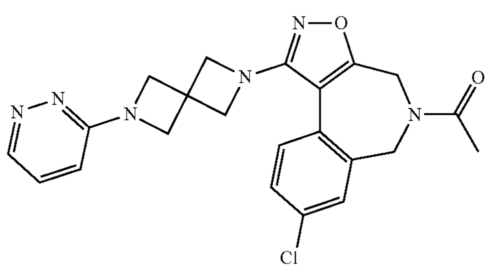 |
| 103 | 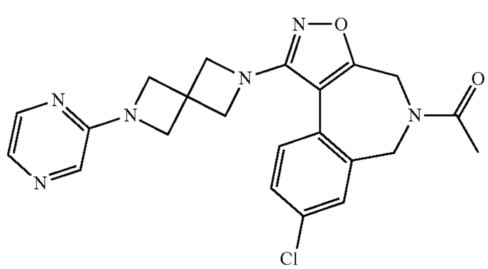 |
| 104 | 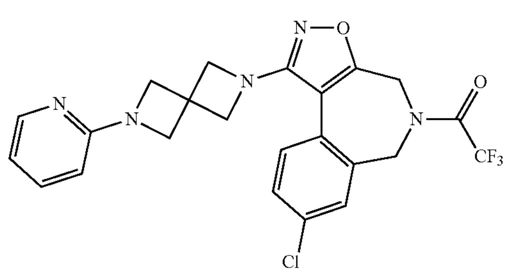 [SMILES: O=C(N1Cc2cc(Cl)ccc2-c2c(N3CC4(CN(c5ccccn5)C4)C3)noc2C1)C(F)(F)F] |

TABLE 1-continued

Representative Compounds

| Cmpd. No. | Structure |
|---|---|
| 105 | 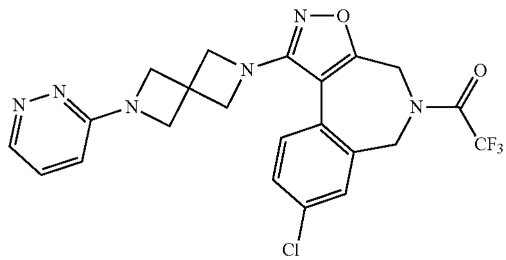 [SMILES: O=C(N1Cc2cc(Cl)ccc2-c2c(N3CC4(CN(c5cccnn5)C4)C3)noc2C1)C(F)(F)F] |
| 106 | 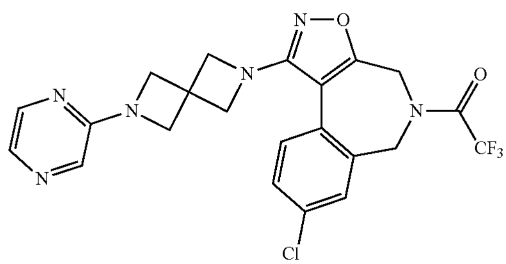 [SMILES: O=C(N1Cc2cc(Cl)ccc2-c2c(N3CC4(CN(c5cnccn5)C4)C3)noc2C1)C(F)(F)F] |
| 107 | 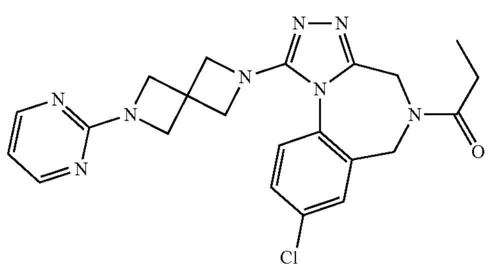 [SMILES: CCC(=O)N1Cc2cc(Cl)ccc2-n2c(nnc2N2CC3(CN(c4ncccn4)C3)C2)C1] |
| 108 | 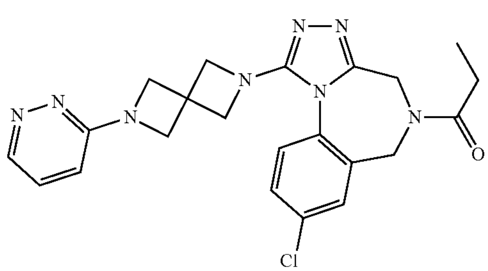 |
| 109 | 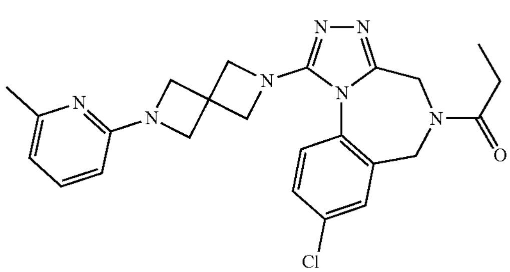 [SMILES: CCC(=O)N1Cc2cc(Cl)ccc2-n2c(nnc2N2CC3(CN(c4cccc(C)n4)C3)C2)C1] |

TABLE 1-continued

Representative Compounds

| Cmpd. No. | Structure |
|---|---|
| 110 | 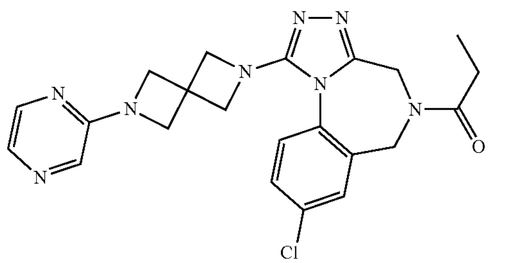 [SMILES: CCC(=O)N1Cc2cc(Cl)ccc2-n2c(nnc2N2CC3(CN(c4cnccn4)C3)C2)C1] |
| 111 | 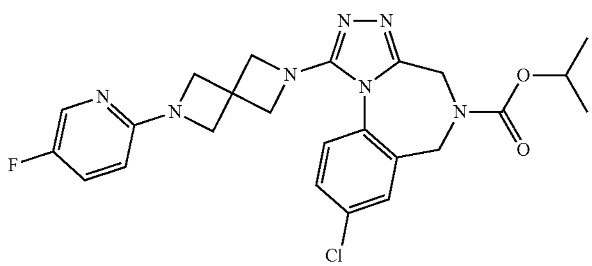 [SMILES: CC(C)OC(=O)N1Cc2cc(Cl)ccc2-n2c(nnc2N2CC3(CN(c4ccc(F)cn4)C3)C2)C1] |
| 112 | 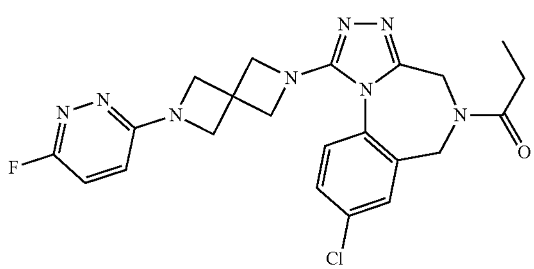 [SMILES: CCC(=O)N1Cc2cc(Cl)ccc2-n2c(nnc2N2CC3(CN(c4ccc(F)nn4)C3)C2)C1] |
| 113 | 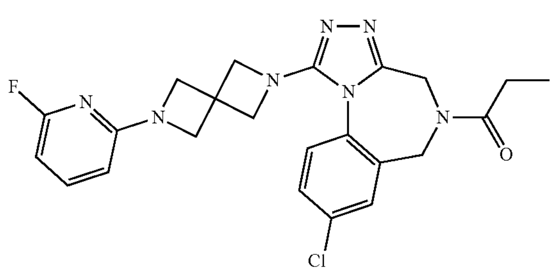 [SMILES: CCC(=O)N1Cc2cc(Cl)ccc2-n2c(nnc2N2CC3(CN(c4cccc(F)n4)C3)C2)C1] |
| 114 | 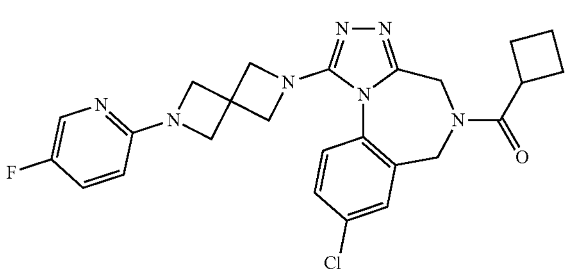 [SMILES: O=C(C1CCC1)N1Cc2cc(Cl)ccc2-n2c(nnc2N2CC3(CN(c4ccc(F)cn4)C3)C2)C1] |

TABLE 1-continued

Representative Compounds

| Cmpd. No. | Structure |
|---|---|
| 115 | 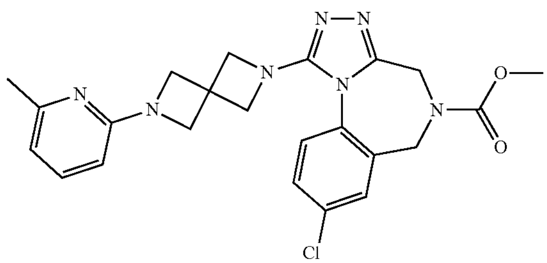 |
| 116 | 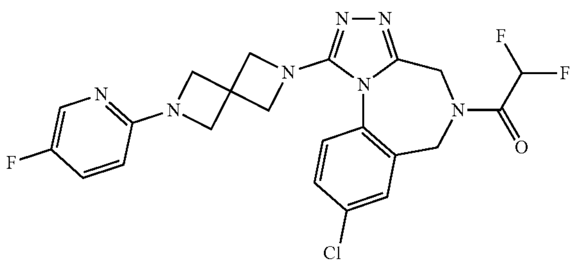 [SMILES: O=C(C(F)F)N1Cc2cc(Cl)ccc2-n2c(nnc2N2CC3(CN(c4ccc(F)cn4)C3)C2)C1] |
| 117 | 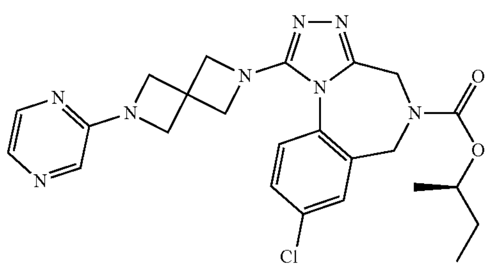 [SMILES: CC[C@@H](C)OC(=O)N1Cc2cc(Cl)ccc2-n2c(nnc2N2CC3(CN(c4cnccn4)C3)C2)C1] |
| 118 | 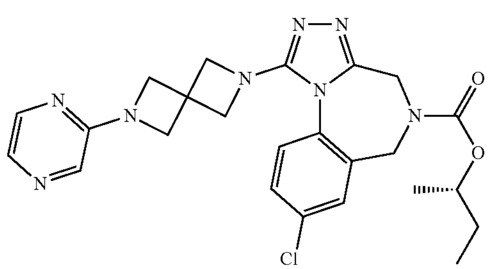 [SMILES: CC[C@H](C)OC(=O)N1Cc2cc(Cl)ccc2-n2c(nnc2N2CC3(CN(c4cnccn4)C3)C2)C1] |
| 119 | 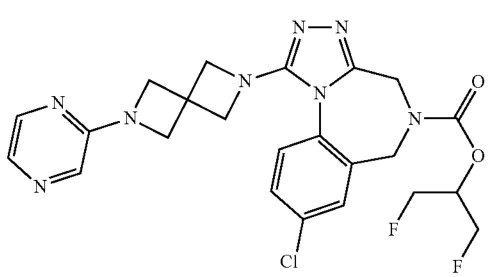 [SMILES: O=C(OC(CF)CF)N1Cc2cc(Cl)ccc2-n2c(nnc2N2CC3(CN(c4cnccn4)C3)C2)C1] |

TABLE 1-continued

Representative Compounds

| Cmpd. No. | Structure |
|---|---|
| 120 | 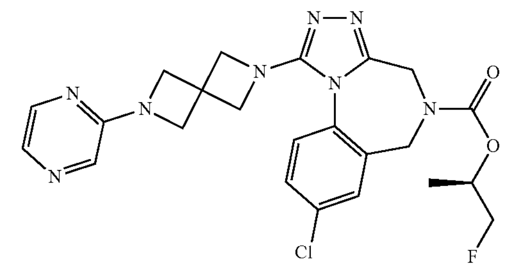 [SMILES: C[C@H](CF)OC(=O)N1Cc2cc(Cl)ccc2-n2c(nnc2N2CC3(CN(c4cnccn4)C3)C2)C1] |
| 121 | 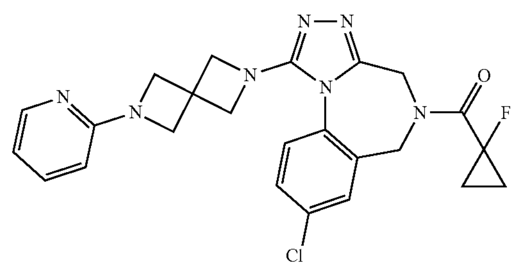 [SMILES: O=C(N1Cc2cc(Cl)ccc2-n2c(nnc2N2CC3(CN(c4ccccn4)C3)C2)C1)C1(F)CC1] |
| 122 | 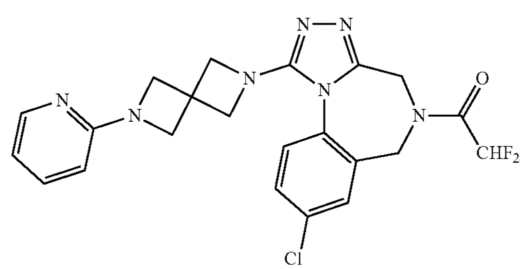 [SMILES: O=C(C(F)F)N1Cc2cc(Cl)ccc2-n2c(nnc2N2CC3(CN(c4ccccn4)C3)C2)C1] |
| 123 | 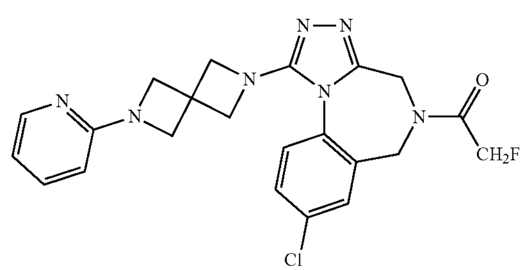 |
| 124 | 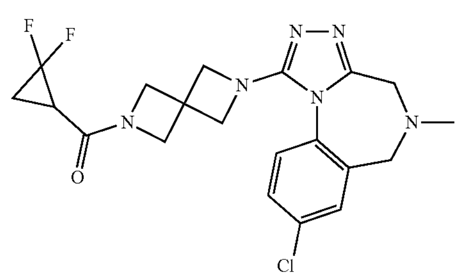 [SMILES: CN1Cc2cc(Cl)ccc2-n2c(nnc2N2CC3(CN(C(=O)C4CC4(F)F)C3)C2)C1] |

TABLE 1-continued

Representative Compounds

| Cmpd. No. | Structure |
|---|---|
| 125 | 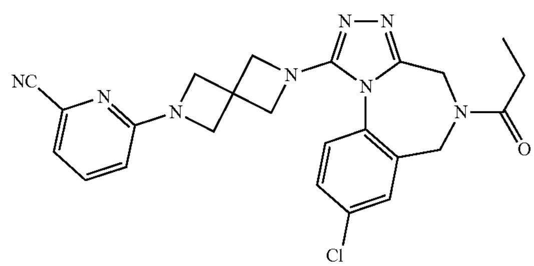 [SMILES: CCC(=O)N1Cc2cc(Cl)ccc2-n2c(nnc2N2CC3(CN(c4cccc(C#N)n4)C3)C2)C1] |
| 126 | 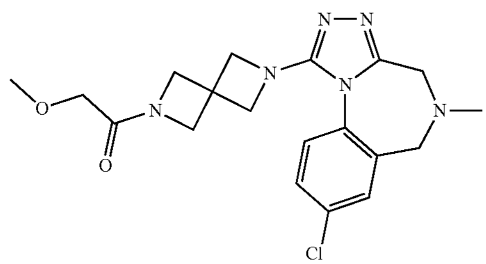 |
| 127 | 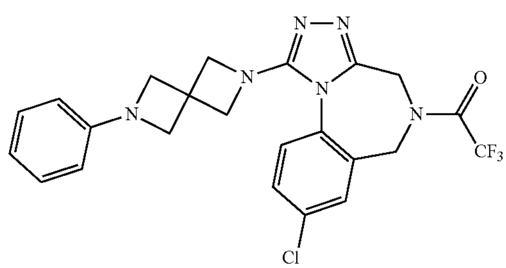 [SMILES: O=C(N1Cc2cc(Cl)ccc2-n2c(nnc2N2CC3(CN(c4ccccc4)C3)C2)C1)C(F)(F)F] |
| 128 | 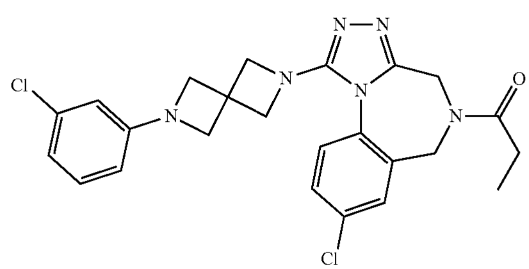 [SMILES: CCC(=O)N1Cc2cc(Cl)ccc2-n2c(nnc2N2CC3(CN(c4cccc(Cl)c4)C3)C2)C1] |
| 129 | 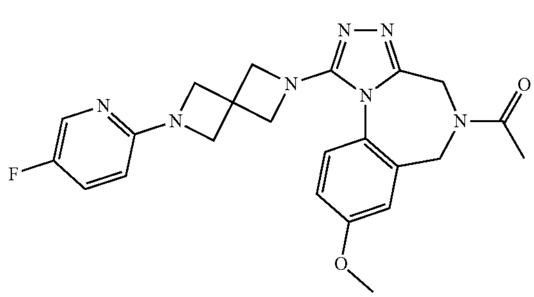 [SMILES: COc1ccc2c(c1)CN(C(C)=O)Cc1nnc(N3CC4(CN(c5ccc(F)cn5)C4)C3)n1-2] |

TABLE 1-continued

Representative Compounds

| Cmpd. No. | Structure |
|---|---|
| 130 | 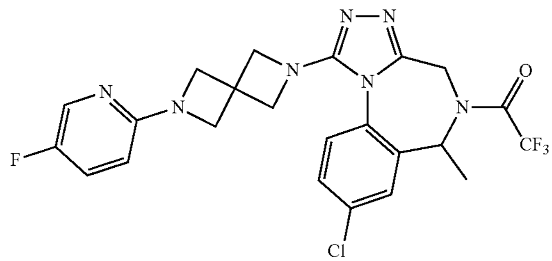 [SMILES: CC1c2cc(Cl)ccc2-n2c(nnc2N2CC3(CN(c4ccc(F)cn4)C3)C2)CN1C(=O)C(F)(F)F] |
| 131 | 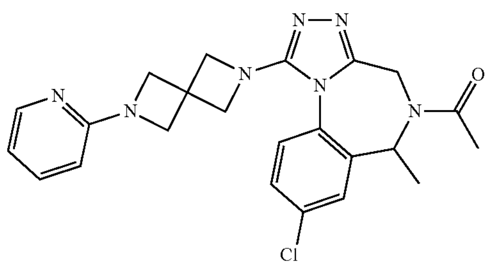 [SMILES: CC(=O)N1Cc2nnc(N3CC4(CN(c5ccccn5)C4)C3)n2-c2ccc(Cl)cc2C1C] |
| 132 | 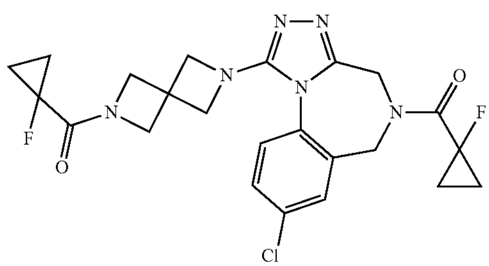 [SMILES: O=C(N1Cc2cc(Cl)ccc2-n2c(nnc2N2CC3(CN(C(=O)C4(F)CC4)C3)C2)C1)C1(F)CC1] |
| 133 | 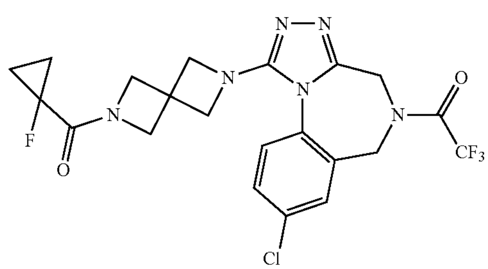 [SMILES: O=C(N1Cc2cc(Cl)ccc2-n2c(nnc2N2CC3(CN(C(=O)C4(F)CC4)C3)C2)C1)C(F)(F)F] |
| 134 | 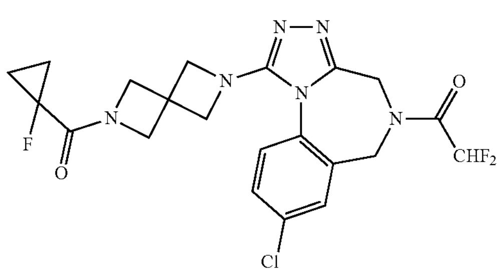 [SMILES: O=C(C(F)F)N1Cc2cc(Cl)ccc2-n2c(nnc2N2CC3(CN(C(=O)C4(F)CC4)C3)C2)C1] |

TABLE 1-continued
Representative Compounds
| Cmpd. No. | Structure |
|---|---|
| 135 | 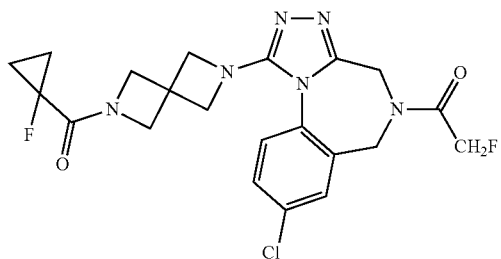 |
| 136 | 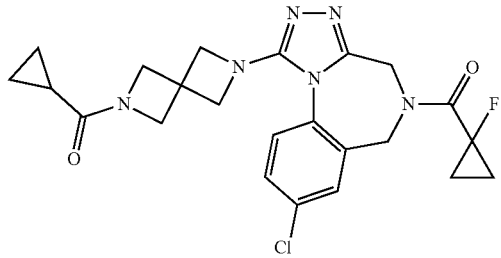 [SMILES: O=C(C1CC1)N1CC2(C1)CN(c1nnc3n1-c1ccc(Cl)cc1CN(C(=O)C1(F)CC1)C3)C2] |
| 137 | 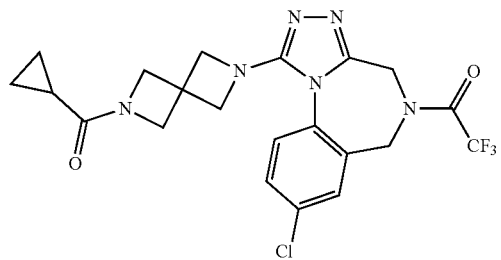 [SMILES: O=C(C1CC1)N1CC2(C1)CN(c1nnc3n1-c1ccc(Cl)cc1CN(C(=O)C(F)(F)F)C3)C2] |
| 138 | 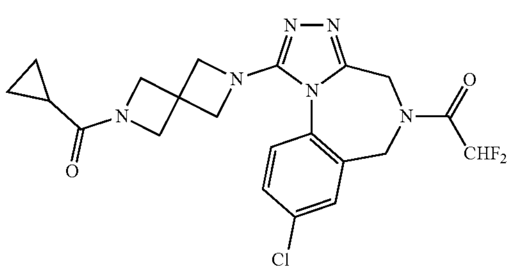 [SMILES: O=C(C(F)F)N1Cc2cc(Cl)ccc2-n2c(nnc2N2CC3(CN(C(=O)C4CC4)C3)C2)C1] |
| 139 | 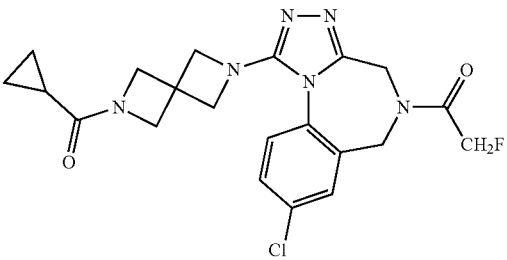 |

TABLE 1-continued

Representative Compounds

| Cmpd. No. | Structure |
|---|---|
| 140 | 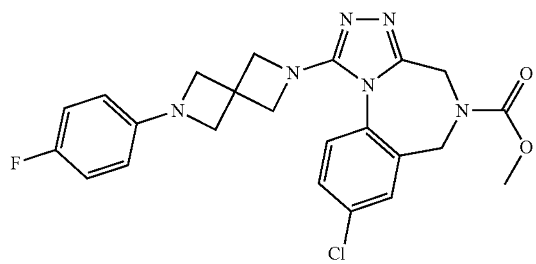 [SMILES: COC(=O)N1Cc2cc(Cl)ccc2-n2c(nnc2N2CC3(CN(c4ccc(F)cc4)C3)C2)C1] |
| 141 | 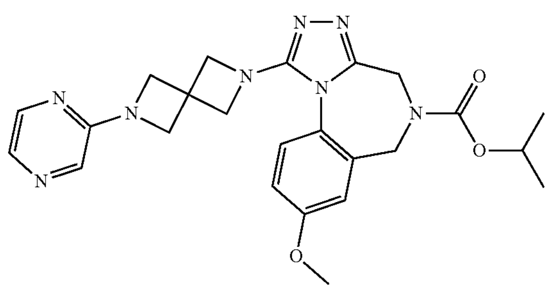 [SMILES: COc1ccc2c(c1)CN(C(=O)OC(C)C)Cc1nnc(N3CC4(CN(c5cnccn5)C4)C3)n1-2] |
| 142 | 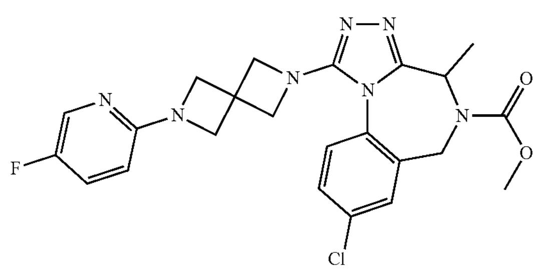 [SMILES: COC(=O)N1Cc2cc(Cl)ccc2-n2c(nnc2N2CC3(CN(c4ccc(F)cn4)C3)C2)C1C] |
| 143 | 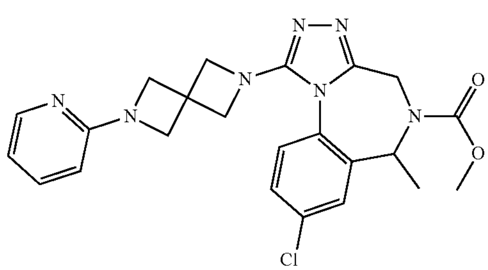 [SMILES: COC(=O)N1Cc2nnc(N3CC4(CN(c5ccccn5)C4)C3)n2-c2ccc(Cl)cc2C1C] |
| 144 | 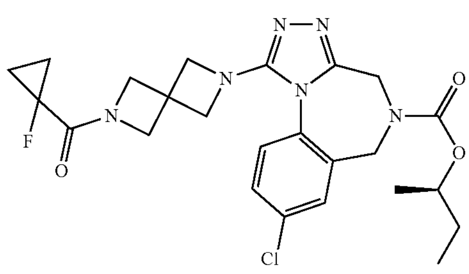 [SMILES: CC[C@@H](C)OC(=O)N1Cc2cc(Cl)ccc2-n2c(nnc2N2CC3(CN(C(=O)C4(F)CC4)C3)C2)C1] |

TABLE 1-continued

Representative Compounds

| Cmpd. No. | Structure |
|---|---|
| 145 | 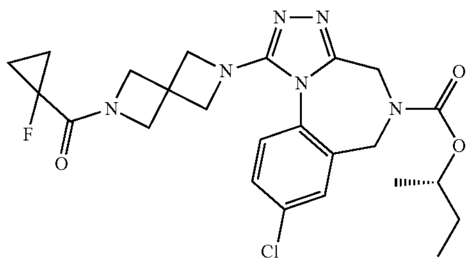 [SMILES: CC[C@H](C)OC(=O)N1Cc2cc(Cl)ccc2-n2c(nnc2N2CC3(CN(C(=O)C4(F)CC4)C3)C2)C1] |
| 146 | 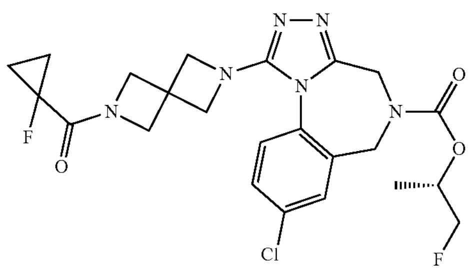 [SMILES: C[C@@H](CF)OC(=O)N1Cc2cc(Cl)ccc2-n2c(nnc2N2CC3(CN(C(=O)C4(F)CC4)C3)C2)C1] |
| 147 | 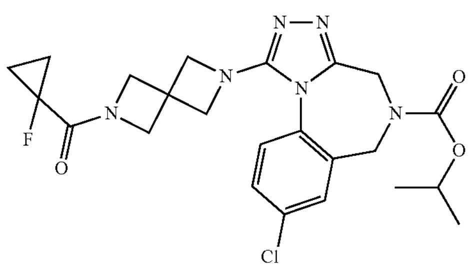 [SMILES: CC(C)OC(=O)N1Cc2cc(Cl)ccc2-n2c(nnc2N2CC3(CN(C(=O)C4(F)CC4)C3)C2)C1] |
| 148 | 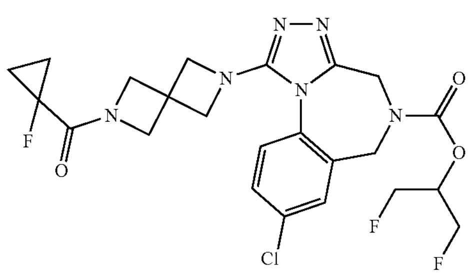 [SMILES: O=C(OC(CF)CF)N1Cc2cc(Cl)ccc2-n2c(nnc2N2CC3(CN(C(=O)C4(F)CC4)C3)C2)C1] |
| 149 | 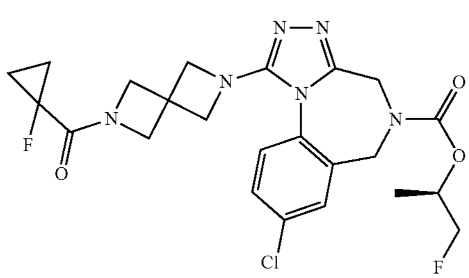 [SMILES: C[C@H](CF)OC(=O)N1Cc2cc(Cl)ccc2-n2c(nnc2N2CC3(CN(C(=O)C4(F)CC4)C3)C2)C1] |

TABLE 1-continued

Representative Compounds

| Cmpd. No. | Structure |
|---|---|
| 150 | 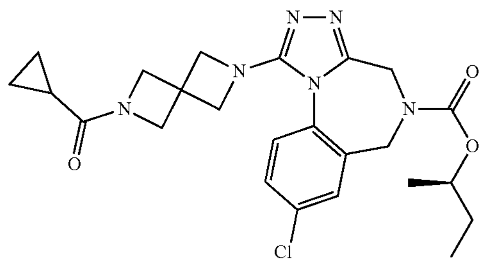 [SMILES: CC[C@@H](C)OC(=O)N1Cc2cc(Cl)ccc2-n2c(nnc2N2CC3(CN(C(=O)C4CC4)C3)C2)C1] |
| 151 | 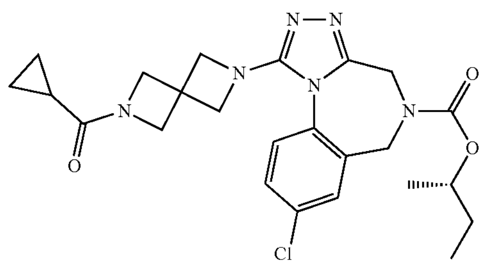 [SMILES: CC[C@H](C)OC(=O)N1Cc2cc(Cl)ccc2-n2c(nnc2N2CC3(CN(C(=O)C4CC4)C3)C2)C1] |
| 152 | 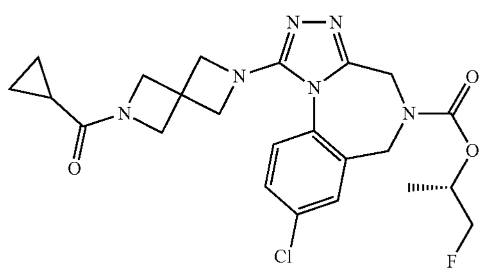 [SMILES: C[C@@H](CF)OC(=O)N1Cc2cc(Cl)ccc2-n2c(nnc2N2CC3(CN(C(=O)C4CC4)C3)C2)C1] |
| 153 | 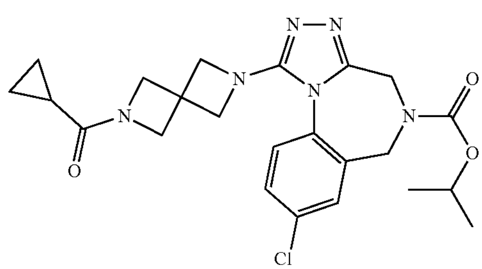 [SMILES: CC(C)OC(=O)N1Cc2cc(Cl)ccc2-n2c(nnc2N2CC3(CN(C(=O)C4CC4)C3)C2)C1] |
| 154 | 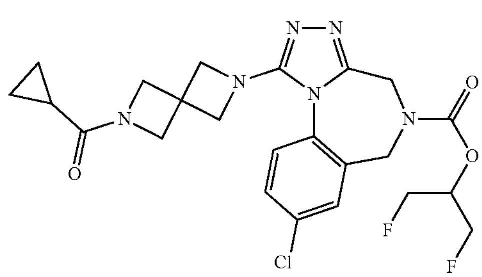 [SMILES: O=C(OC(CF)CF)N1Cc2cc(Cl)ccc2-n2c(nnc2N2CC3(CN(C(=O)C4CC4)C3)C2)C1] |

TABLE 1-continued
Representative Compounds
| Cmpd. No. | Structure |
|---|---|
| 155 | 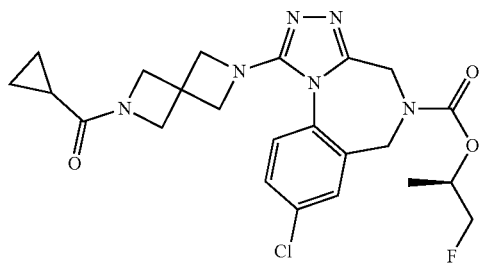 [SMILES: C[C@H](CF)OC(=O)N1Cc2cc(Cl)ccc2-n2c(nnc2N2CC3(CN(C(=O)C4CC4)C3)C2)C1] |
| 156 | 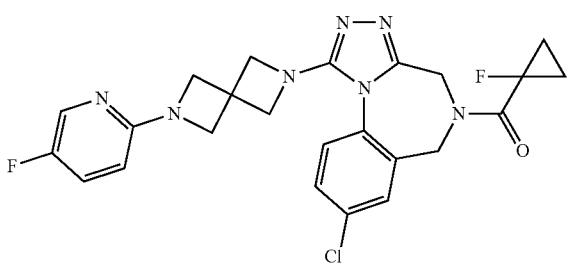 [SMILES: O=C(N1Cc2cc(Cl)ccc2-n2c(nnc2N2CC3(CN(c4ccc(F)cn4)C3)C2)C1)C1(F)CC1] |
| 157 | 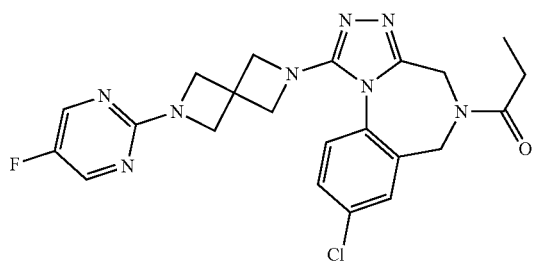 [SMILES: CCC(=O)N1Cc2cc(Cl)ccc2-n2c(nnc2N2CC3(CN(c4ncc(F)cn4)C3)C2)C1] |
| 158 | 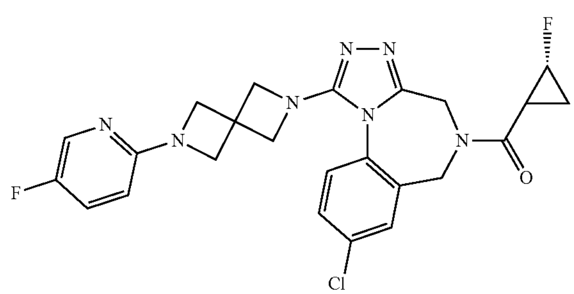 [SMILES: O=C(C1C[C@H]1F)N1Cc2cc(Cl)ccc2-n2c(nnc2N2CC3(CN(c4ccc(F)cn4)C3)C2)C1] |
| 159 | 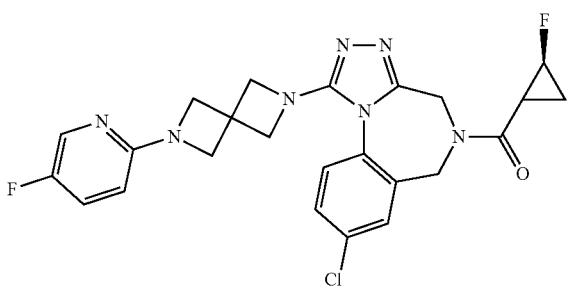 [SMILES: O=C(C1C[C@@H]1F)N1Cc2cc(Cl)ccc2-n2c(nnc2N2CC3(CN(c4ccc(F)cn4)C3)C2)C1] |

TABLE 1-continued
Representative Compounds
| Cmpd. No. | Structure |
|---|---|
| 160 | 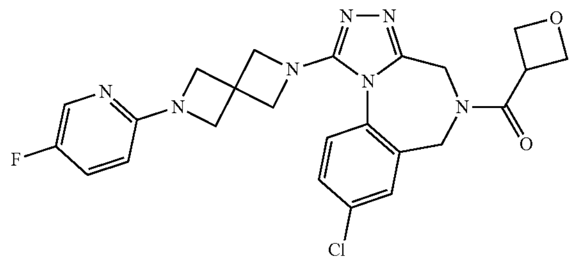 [SMILES: O=C(C1COC1)N1Cc2cc(Cl)ccc2-n2c(nnc2N2CC3(CN(c4ccc(F)cn4)C3)C2)C1] |
| 161 | 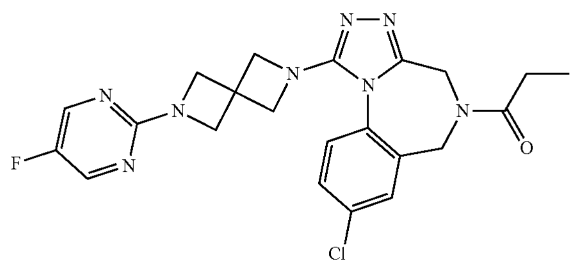 [SMILES: CCC(=O)N1Cc2cc(Cl)ccc2-n2c(nnc2N2CC3(CN(c4ncc(F)cn4)C3)C2)C1] |
| 162 | 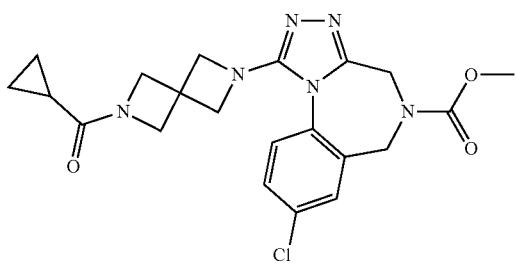 [SMILES: COC(=O)N1Cc2cc(Cl)ccc2-n2c(nnc2N2CC3(CN(C(=O)C4CC4)C3)C2)C1] |
| 163 | 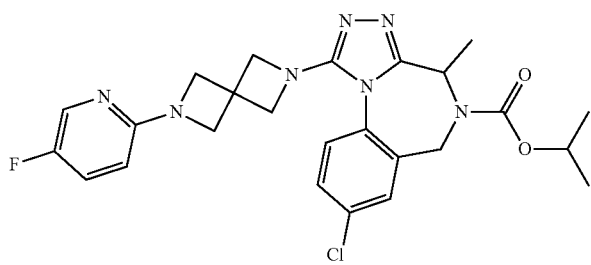 [SMILES: CC(C)OC(=O)N1Cc2cc(Cl)ccc2-n2c(nnc2N2CC3(CN(c4ccc(F)cn4)C3)C2)C1C] |
| 164 | 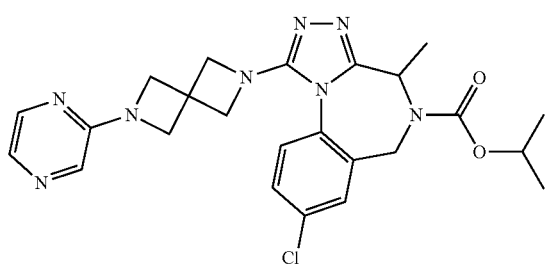 [SMILES: CC(C)OC(=O)N1Cc2cc(Cl)ccc2-n2c(nnc2N2CC3(CN(c4cnccn4)C3)C2)C1C] |

TABLE 1-continued
Representative Compounds
| Cmpd. No. | Structure |
|---|---|
| 165 | 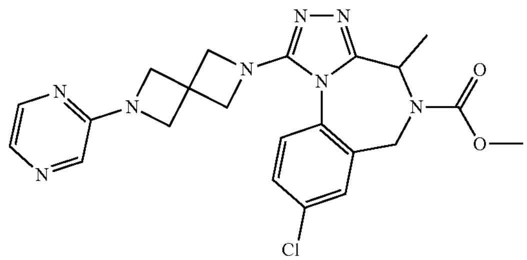 [SMILES: COC(=O)N1Cc2cc(Cl)ccc2-n2c(nnc2N2CC3(CN(c4cnccn4)C3)C2)C1C] |
| 166 | 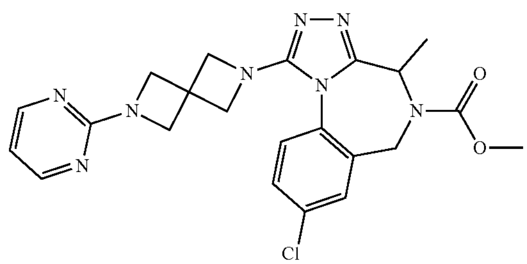 [SMILES: COC(=O)N1Cc2cc(Cl)ccc2-n2c(nnc2N2CC3(CN(c4ncccn4)C3)C2)C1C] |
| 167 | 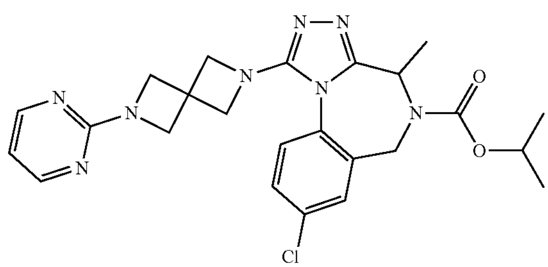 [SMILES: CC(C)OC(=O)N1Cc2cc(Cl)ccc2-n2c(nnc2N2CC3(CN(c4ncccn4)C3)C2)C1C] |
| 168 | 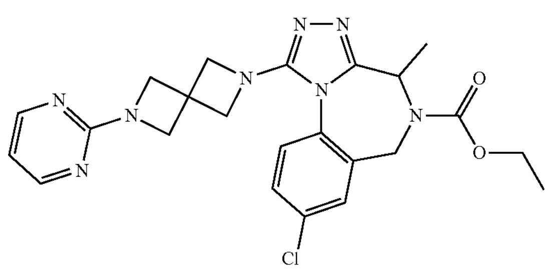 [SMILES: CCOC(=O)N1Cc2cc(Cl)ccc2-n2c(nnc2N2CC3(CN(c4ncccn4)C3)C2)C1C] |
| 169 | 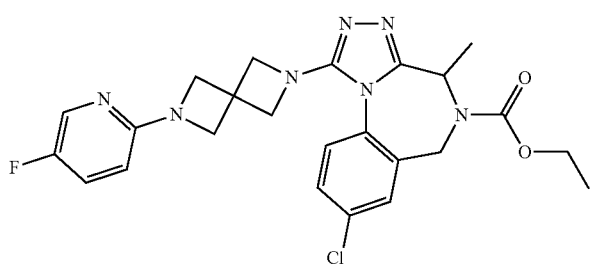 [SMILES: CCOC(=O)N1Cc2cc(Cl)ccc2-n2c(nnc2N2CC3(CN(c4ccc(F)cn4)C3)C2)C1C] |

TABLE 1-continued
Representative Compounds
| Cmpd. No. | Structure |
|---|---|
| 170 | 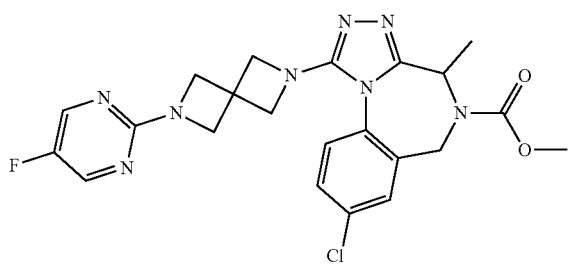 [SMILES: COC(=O)N1Cc2cc(Cl)ccc2-n2c(nnc2N2CC3(CN(c4ncc(F)cn4)C3)C2)C1C] |
| 171 | 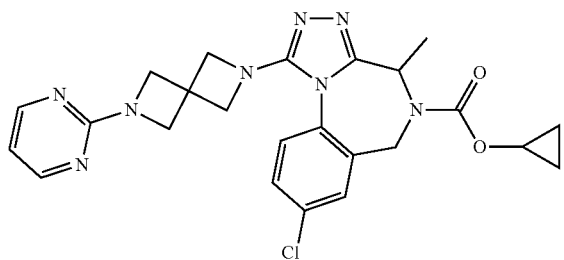 [SMILES: CC1c2nnc(N3CC4(CN(c5ncccn5)C4)C3)n2-c2ccc(Cl)cc2CN1C(=O)OC1CC1] |
| 172 | 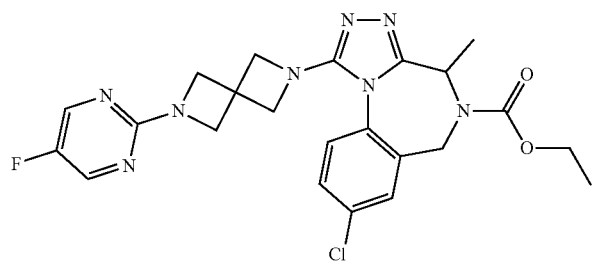 [SMILES: CCOC(=O)N1Cc2cc(Cl)ccc2-n2c(nnc2N2CC3(CN(c4ncc(F)cn4)C3)C2)C1C] |
| 173 | 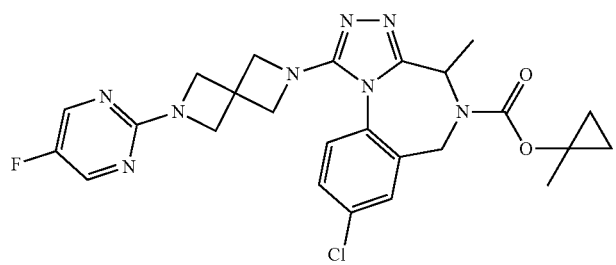 [SMILES: CC1c2nnc(N3CC4(CN(c5ncc(F)cn5)C4)C3)n2-c2ccc(Cl)cc2CN1C(=O)OC1(C)CC1] |
| 174 | 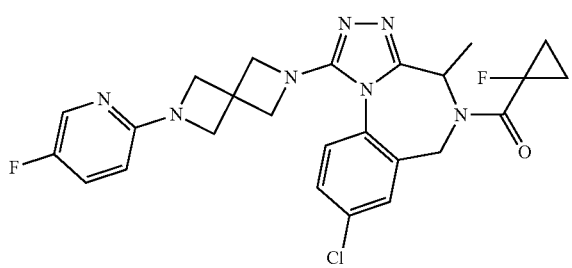 [SMILES: CC1c2nnc(N3CC4(CN(c5ccc(F)cn5)C4)C3)n2-c2ccc(Cl)cc2CN1C(=O)C1(F)CC1] |

TABLE 1-continued
Representative Compounds
| Cmpd. No. | Structure |
|---|---|
| 175 | 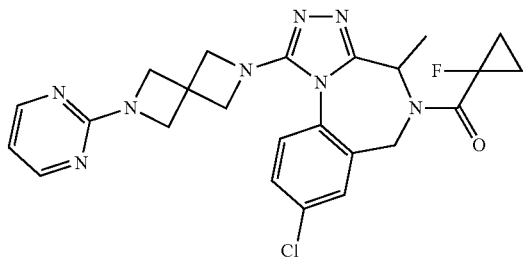 [SMILES: CC1c2nnc(N3CC4(CN(c5ncccn5)C4)C3)n2-c2ccc(Cl)cc2CN1C(=O)C1(F)CC1] |
| 176 | 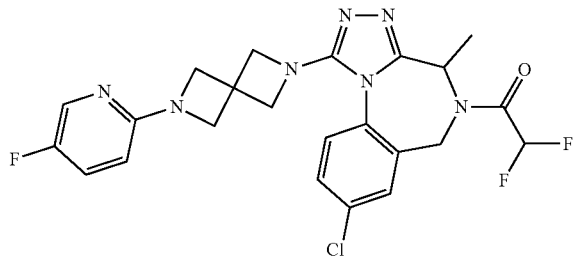 [SMILES: CC1c2nnc(N3CC4(CN(c5ccc(F)cn5)C4)C3)n2-c2ccc(Cl)cc2CN1C(=O)C(F)F] |
| 177 | 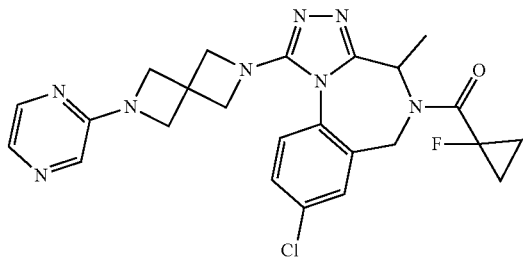 [SMILES: CC1c2nnc(N3CC4(CN(c5cnccn5)C4)C3)n2-c2ccc(Cl)cc2CN1C(=O)C1(F)CC1] |
| 178 | 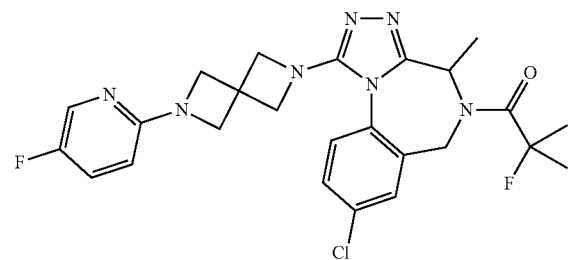 [SMILES: CC1c2nnc(N3CC4(CN(c5ccc(F)cn5)C4)C3)n2-c2ccc(Cl)cc2CN1C(=O)C(C)(C)F] |
| 179 | 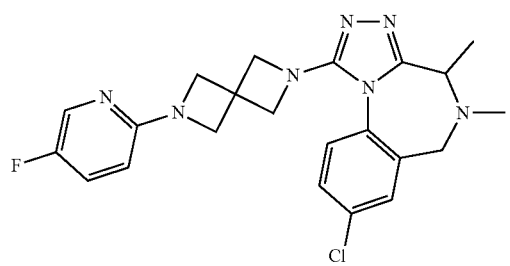 [SMILES: CC1c2nnc(N3CC4(CN(c5ccc(F)cn5)C4)C3)n2-c2ccc(Cl)cc2CN1C] |

125
126
TABLE 1-continued
Representative Compounds
| Cmpd. No. | Structure |
|---|---|
| 180 | 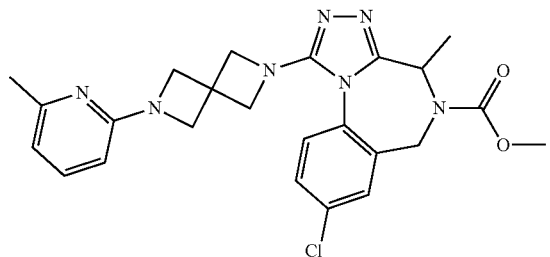 |
| 181 | 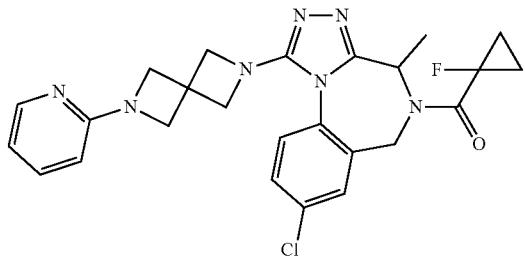 [SMILES: CC1c2nnc(N3CC4(CN(c5ccccn5)C4)C3)n2-c2ccc(Cl)cc2CN1C(=O)C1(F)CC1] |
| 182 | 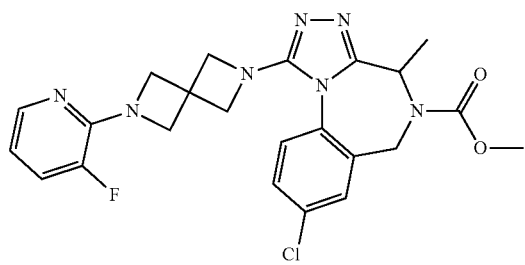 [SMILES: COC(=O)N1Cc2cc(Cl)ccc2-n2c(nnc2N2CC3(CN(c4ncccc4F)C3)C2)C1C] |
| 183 | 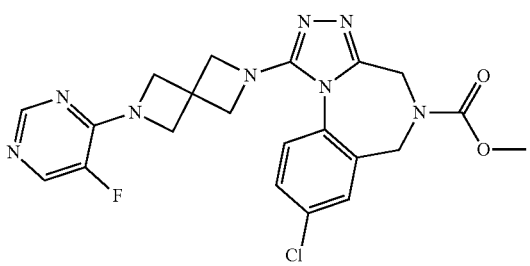 [SMILES: COC(=O)N1Cc2cc(Cl)ccc2-n2c(nnc2N2CC3(CN(c4ncncc4F)C3)C2)C1] |
| 184 | 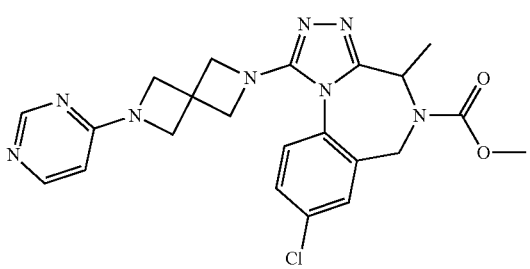 [SMILES: COC(=O)N1Cc2cc(Cl)ccc2-n2c(nnc2N2CC3(CN(c4ccncn4)C3)C2)C1C] |

TABLE 1-continued
Representative Compounds
| Cmpd. No. | Structure |
|---|---|
| 185 | 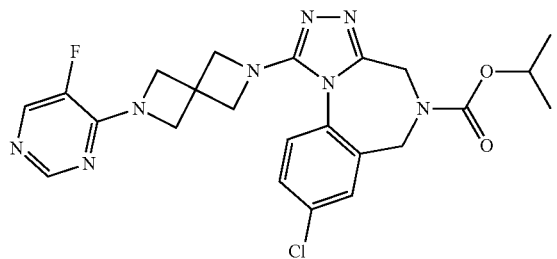 [SMILES: CC(C)OC(=O)N1Cc2cc(Cl)ccc2-n2c(nnc2N2CC3(CN(c4ncncc4F)C3)C2)C1] |
| 186 | 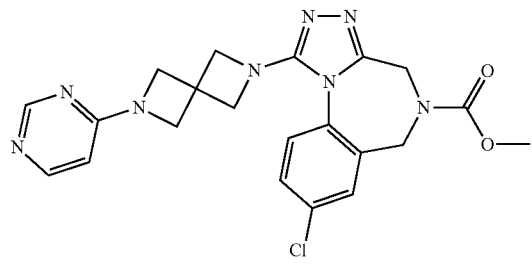 [SMILES: COC(=O)N1Cc2cc(Cl)ccc2-n2c(nnc2N2CC3(CN(c4ccncn4)C3)C2)C1] |
| 187 | 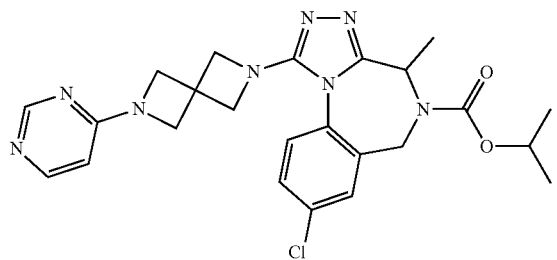 [SMILES: CC(C)OC(=O)N1Cc2cc(Cl)ccc2-n2c(nnc2N2CC3(CN(c4ccncn4)C3)C2)C1C] |
| 188 | 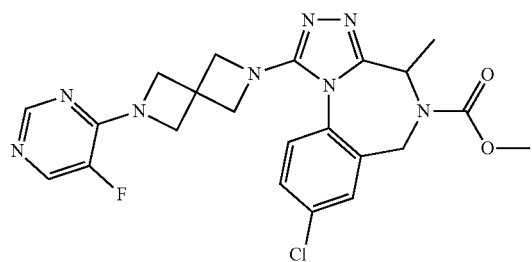 [SMILES: COC(=O)N1Cc2cc(Cl)ccc2-n2c(nnc2N2CC3(CN(c4ncncc4F)C3)C2)C1C] |
| 189 | 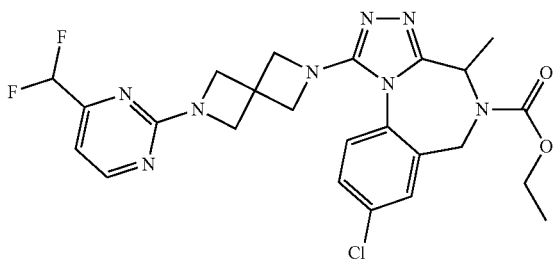 [SMILES: CCOC(=O)N1Cc2cc(Cl)ccc2-n2c(nnc2N2CC3(CN(c4nccc(C(F)F)n4)C3)C2)C1C] |

TABLE 1-continued

Representative Compounds

| Cmpd. No. | Structure |
|---|---|
| 190 | *(structure image)* |
| 191 | *(structure image)* |
| 192 | *(structure image)* |
| 193 | *(structure image)* |
| 194 | *(structure image)* |

TABLE 1-continued
Representative Compounds
| Cmpd. No. | Structure |
|---|---|
| 195 | 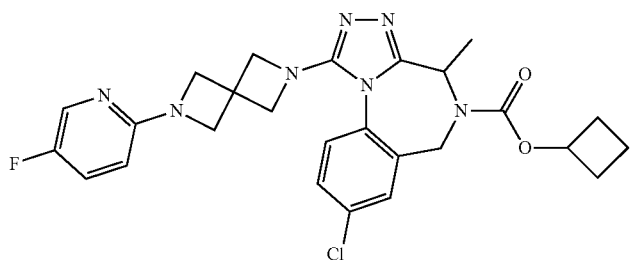 [SMILES: CC1c2nnc(N3CC4(CN(c5ccc(F)cn5)C4)C3)n2-c2ccc(Cl)cc2CN1C(=O)OC1CCC1] |
| 196 | 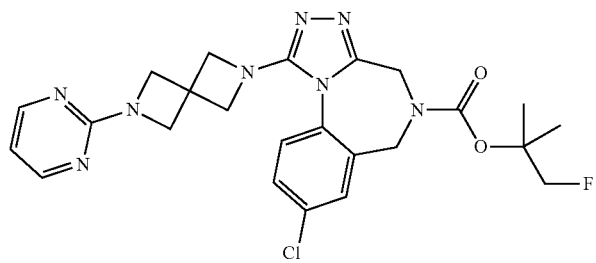 [SMILES: CC(C)(CF)OC(=O)N1Cc2cc(Cl)ccc2-n2c(nnc2N2CC3(CN(c4ncccn4)C3)C2)C1] |
| 197 | 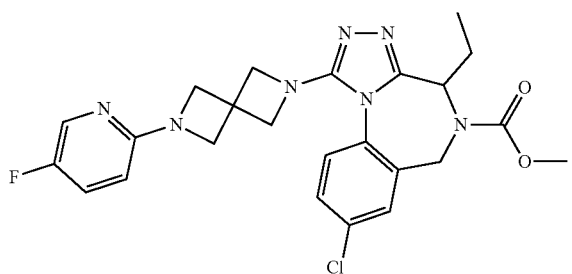 [SMILES: CCC1c2nnc(N3CC4(CN(c5ccc(F)cn5)C4)C3)n2-c2ccc(Cl)cc2CN1C(=O)OC] |
| 198 | 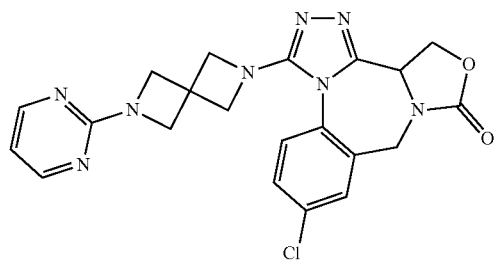 [SMILES: O=C1OCC2c3nnc(N4CC5(CN(c6ncccn6)C5)C4)n3-c3ccc(Cl)cc3CN12] |
| 199 | 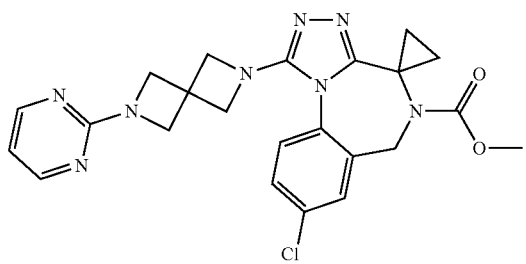 [SMILES: COC(=O)N1Cc2cc(Cl)ccc2-n2c(N3CC4(CN(c5ncccn5)C4)C3)nnc2C12CC2] |

TABLE 1-continued
Representative Compounds
| Cmpd. No. | Structure |
|---|---|
| 200 | 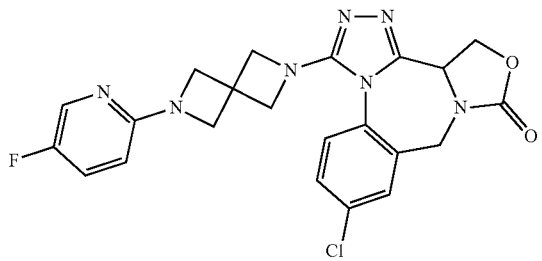 [SMILES: O=C1OCC2c3nnc(N4CC5(CN(c6ccc(F)cn6)C5)C4)n3-c3ccc(Cl)cc3CN12] |
| 201 | 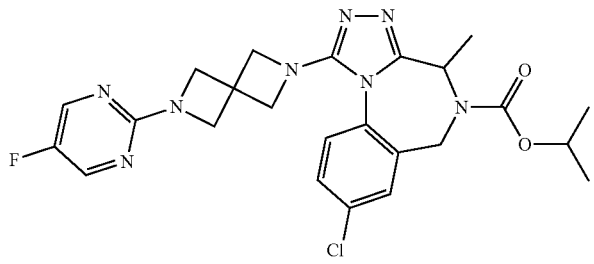 |
| 202 | 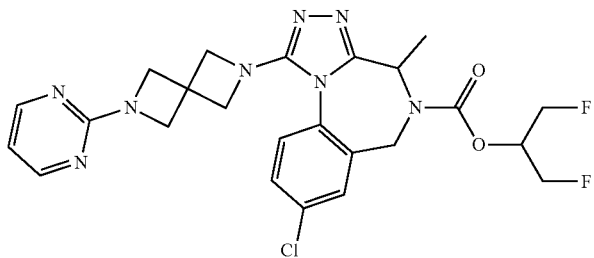 [SMILES: CC1c2nnc(N3CC4(CN(c5ncccn5)C4)C3)n2-c2ccc(Cl)cc2CN1C(=O)OC(CF)CF] |
| 203 | 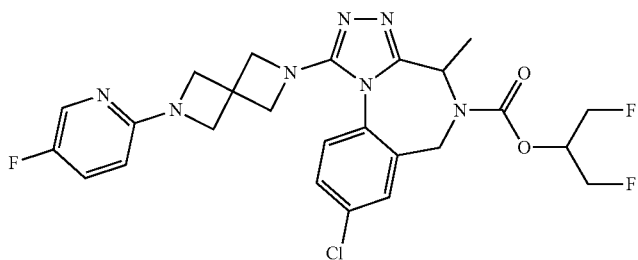 [SMILES: CC1c2nnc(N3CC4(CN(c5ccc(F)cn5)C4)C3)n2-c2ccc(Cl)cc2CN1C(=O)OC(CF)CF] |
| 204 | 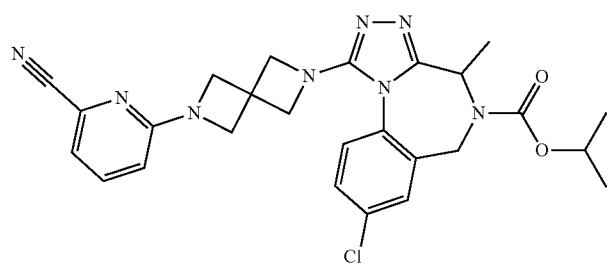 [SMILES: CC(C)OC(=O)N1Cc2cc(Cl)ccc2-n2c(nnc2N2CC3(CN(c4cccc(C#N)n4)C3)C2)C1C] |

TABLE 1-continued
Representative Compounds
| Cmpd. No. | Structure |
|---|---|
| 205 | 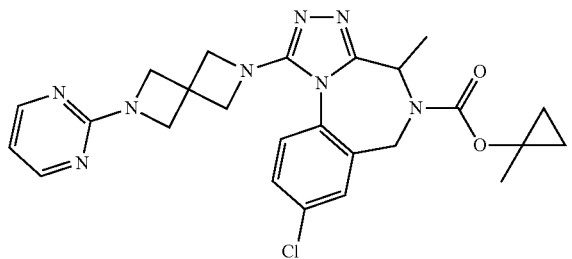 [SMILES: CC1c2nnc(N3CC4(CN(c5ncccn5)C4)C3)n2-c2ccc(Cl)cc2CN1C(=O)OC1(C)CC1] |
| 206 | 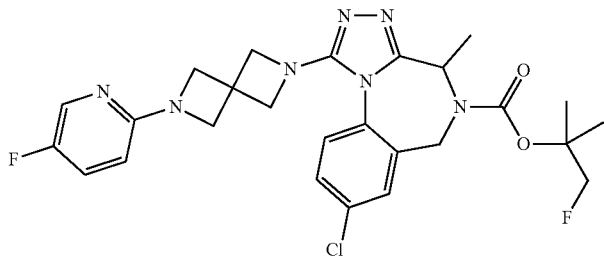 [SMILES: CC1c2nnc(N3CC4(CN(c5ccc(F)cn5)C4)C3)n2-c2ccc(Cl)cc2CN1C(=O)OC(C)(C)CF] |
| 207 | 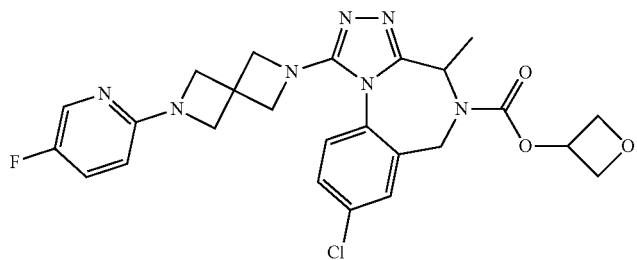 [SMILES: CC1c2nnc(N3CC4(CN(c5ccc(F)cn5)C4)C3)n2-c2ccc(Cl)cc2CN1C(=O)OC1COC1] |
| 208 | 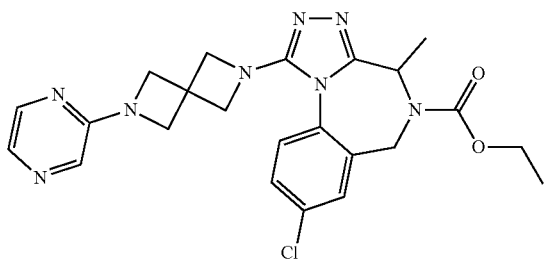 [SMILES: CCOC(=O)N1Cc2cc(Cl)ccc2-n2c(nnc2N2CC3(CN(c4cnccn4)C3)C2)C1C] |
| 209 | 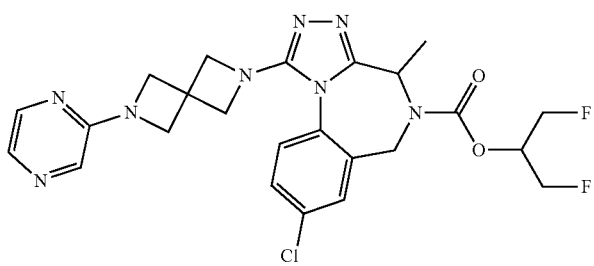 [SMILES: CC1c2nnc(N3CC4(CN(c5cnccn5)C4)C3)n2-c2ccc(Cl)cc2CN1C(=O)OC(CF)CF] |

TABLE 1-continued

Representative Compounds

| Cmpd. No. | Structure |
|---|---|
| 210 | 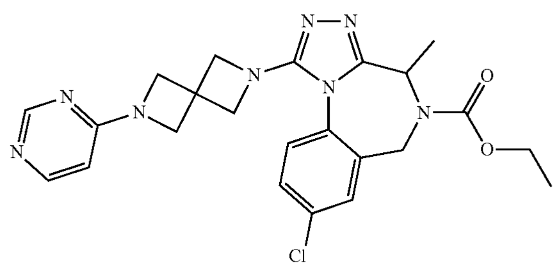 [SMILES: CCOC(=O)N1Cc2cc(Cl)ccc2-n2c(nnc2N2CC3(CN(c4ccncn4)C3)C2)C1C] |
| 211 | 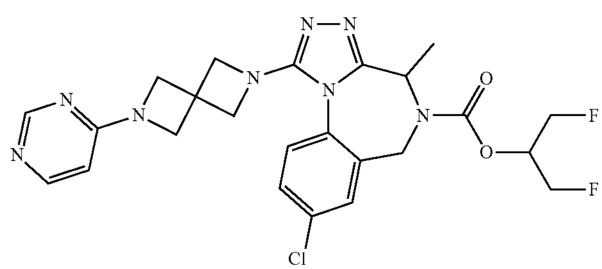 [SMILES: CC1c2nnc(N3CC4(CN(c5ccncn5)C4)C3)n2-c2ccc(Cl)cc2CN1C(=O)OC(CF)CF] |
| 212 | 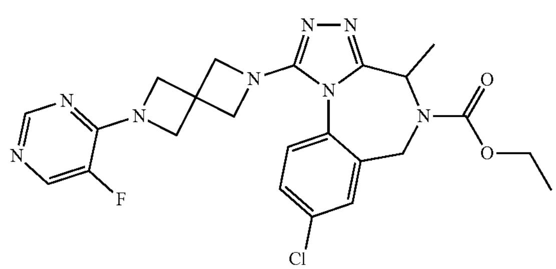 [SMILES: CCOC(=O)N1Cc2cc(Cl)ccc2-n2c(nnc2N2CC3(CN(c4ncncc4F)C3)C2)C1C] |
| 213 | 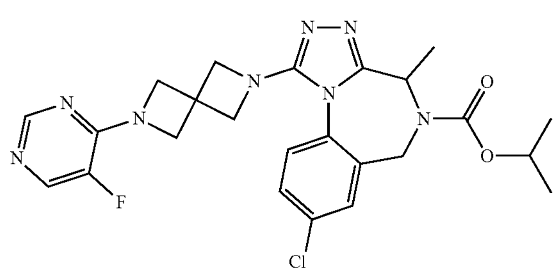 [SMILES: CC(C)OC(=O)N1Cc2cc(Cl)ccc2-n2c(nnc2N2CC3(CN(c4ncncc4F)C3)C2)C1C] |
| 214 | 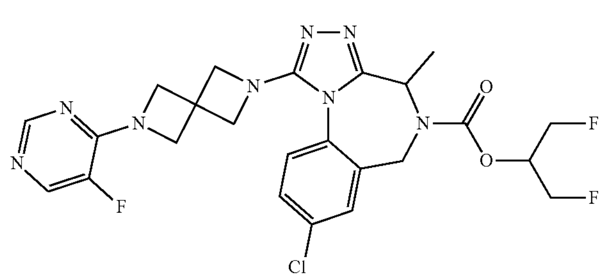 [SMILES: CC1c2nnc(N3CC4(CN(c5ncncc5F)C4)C3)n2-c2ccc(Cl)cc2CN1C(=O)OC(CF)CF] |

TABLE 1-continued

Representative Compounds

| Cmpd. No. | Structure |
|---|---|
| 215 | 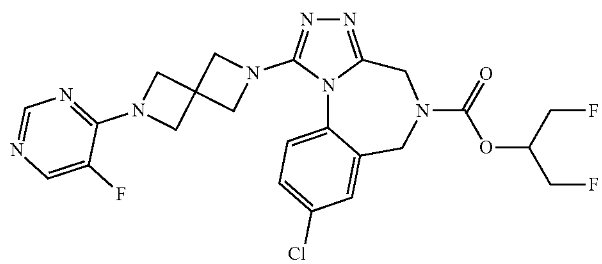 [SMILES: O=C(OC(CF)CF)N1Cc2cc(Cl)ccc2-n2c(nnc2N2CC3(CN(c4ncncc4F)C3)C2)C1] |
| 216 | 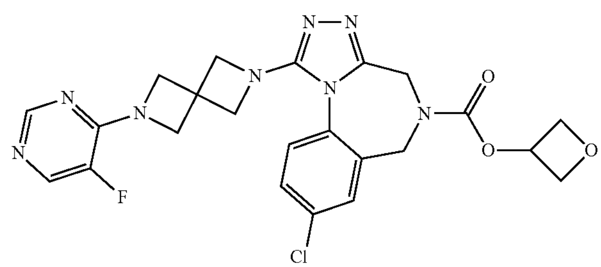 [SMILES: O=C(OC1COC1)N1Cc2cc(Cl)ccc2-n2c(nnc2N2CC3(CN(c4ncncc4F)C3)C2)C1] |
| 217 | 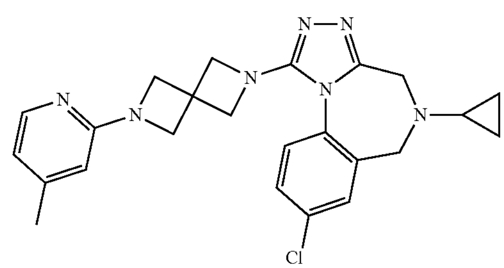 [SMILES: Cc1ccnc(N2CC3(C2)CN(c2nnc4n2-c2ccc(Cl)cc2CN(C2CC2)C4)C3)c1] |
| 218 | 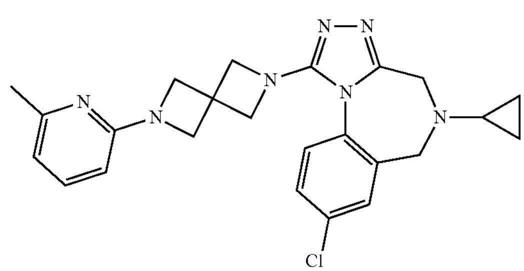 [SMILES: Cc1cccc(N2CC3(C2)CN(c2nnc4n2-c2ccc(Cl)cc2CN(C2CC2)C4)C3)n1] |
| 219 | 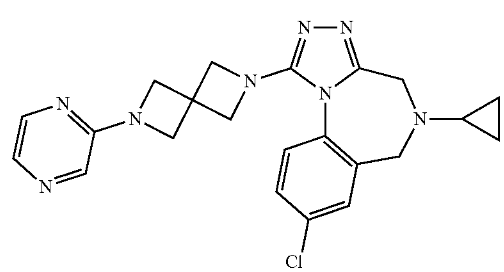 [SMILES: Clc1ccc2c(c1)CN(C1CC1)Cc1nnc(N3CC4(CN(c5cnccn5)C4)C3)n1-2] |

TABLE 1-continued
Representative Compounds
| Cmpd. No. | Structure |
|---|---|
| 220 | 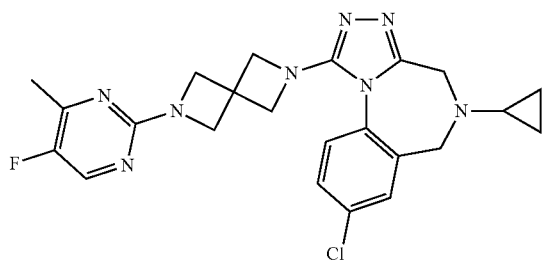 |
| 221 | 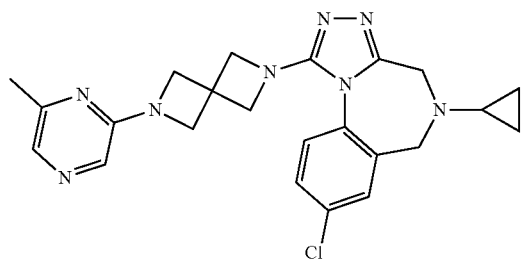 [SMILES: Cc1cncc(N2CC3(C2)CN(c2nnc4n2-c2ccc(Cl)cc2CN(C2CC2)C4)C3)n1] |
| 222 | 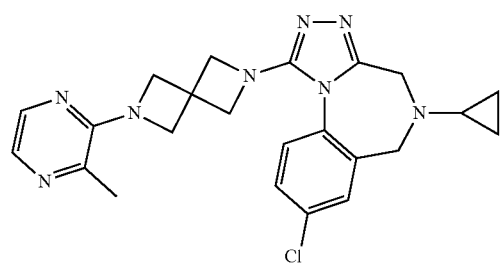 [SMILES: Cc1nccnc1N1CC2(C1)CN(c1nnc3n1-c1ccc(Cl)cc1CN(C1CC1)C3)C2] |
| 223 | 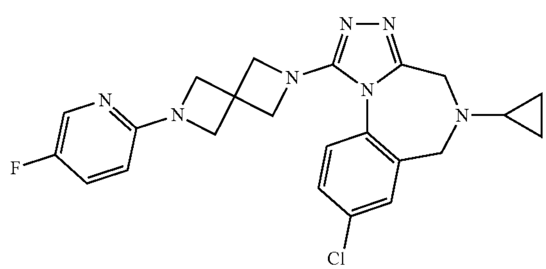 [SMILES: Fc1ccc(N2CC3(C2)CN(c2nnc4n2-c2ccc(Cl)cc2CN(C2CC2)C4)C3)nc1] |
| 224 | 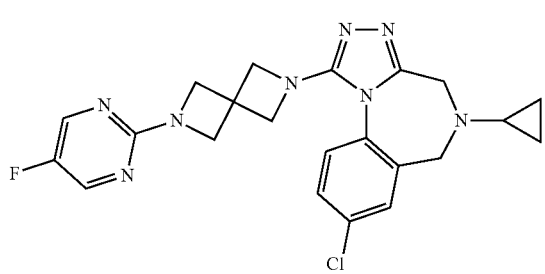 |

TABLE 1-continued
Representative Compounds
| Cmpd. No. | Structure |
|---|---|
| 225 | 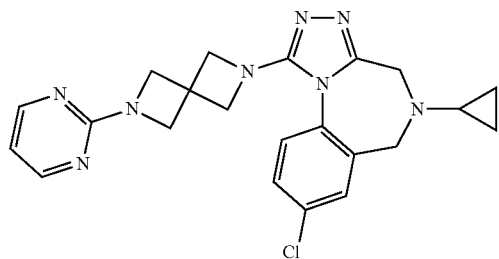 [SMILES: Clc1ccc2c(c1)CN(C1CC1)Cc1nnc(N3CC4(CN(c5ncccn5)C4)C3)n1-2] |
| 226 | 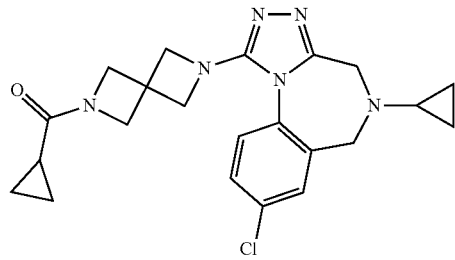 [SMILES: O=C(C1CC1)N1CC2(C1)CN(c1nnc3n1-c1ccc(Cl)cc1CN(C1CC1)C3)C2] |
| 227 | 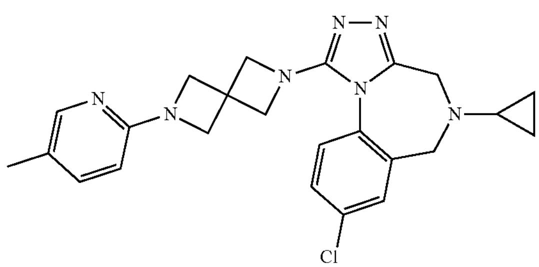 |
| 228 | 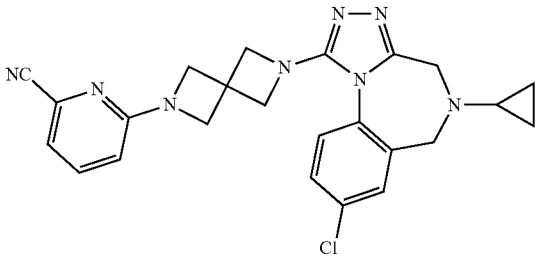 [SMILES: N#Cc1cccc(N2CC3(C2)CN(c2nnc4n2-c2ccc(Cl)cc2CN(C2CC2)C4)C3)n1] |
| 229 | 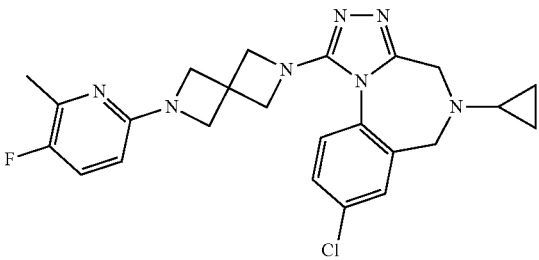 [SMILES: Cc1nc(N2CC3(C2)CN(c2nnc4n2-c2ccc(Cl)cc2CN(C2CC2)C4)C3)ccc1F] |

TABLE 1-continued
Representative Compounds
| Cmpd. No. | Structure |
|---|---|
| 230 | 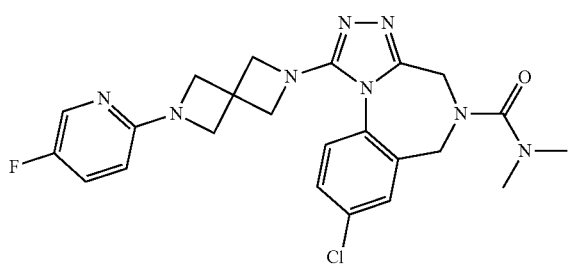 [SMILES: CN(C)C(=O)N1Cc2cc(Cl)ccc2-n2c(nnc2N2CC3(CN(c4ccc(F)cn4)C3)C2)C1] |
| 231 | 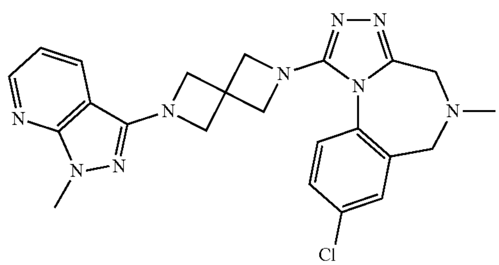 [SMILES: CN1Cc2cc(Cl)ccc2-n2c(nnc2N2CC3(CN(c4nn(C)c5ncccc45)C3)C2)C1] |
| 232 | 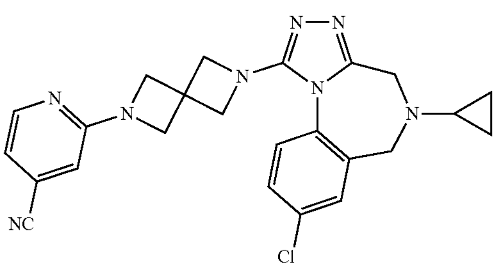 [SMILES: N#Cc1ccnc(N2CC3(C2)CN(c2nnc4n2-c2ccc(Cl)cc2CN(C2CC2)C4)C3)c1] |
| 233 | 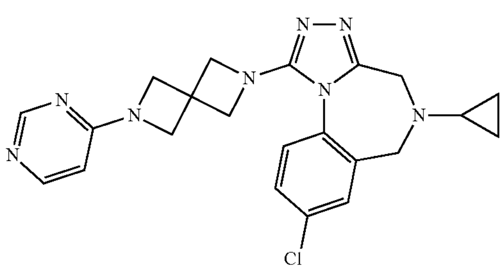 [SMILES: Clc1ccc2c(c1)CN(C1CC1)Cc1nnc(N3CC4(CN(c5ccncn5)C4)C3)n1-2] |
| 234 | 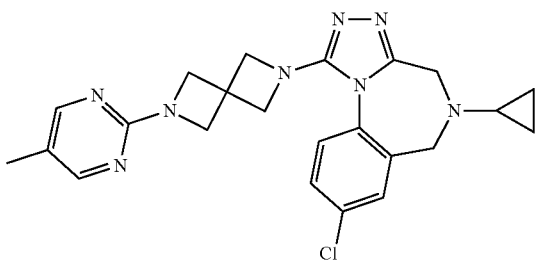 [SMILES: Cc1cnc(N2CC3(C2)CN(c2nnc4n2-c2ccc(Cl)cc2CN(C2CC2)C4)C3)nc1] |

TABLE 1-continued

Representative Compounds

| Cmpd. No. | Structure |
|---|---|
| 235 | 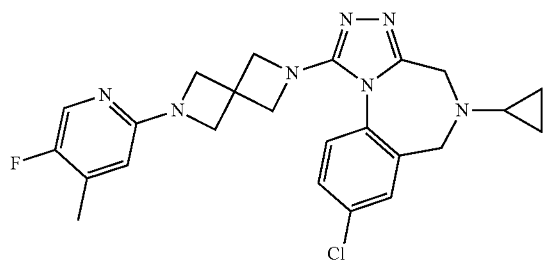 [SMILES: Cc1cc(N2CC3(C2)CN(c2nnc4n2-c2ccc(Cl)cc2CN(C2CC2)C4)C3)ncc1F] |
| 236 | 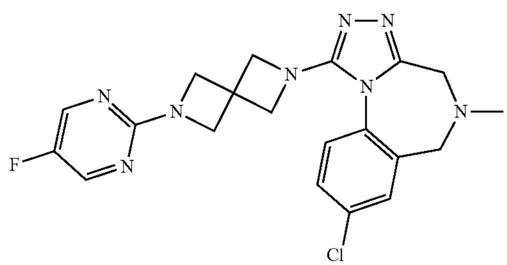 |
| 237 | 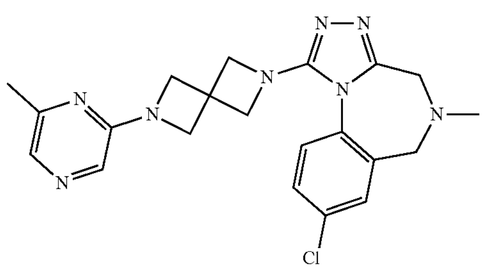 |
| 238 | 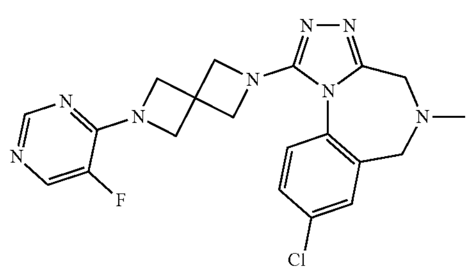 [SMILES: CN1Cc2cc(Cl)ccc2-n2c(nnc2N2CC3(CN(c4ncncc4F)C3)C2)C1] |
| 239 | 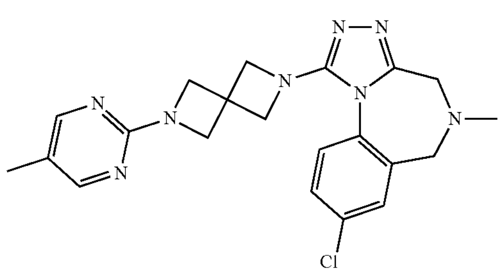 |

TABLE 1-continued
Representative Compounds
| Cmpd. No. | Structure |
|---|---|
| 240 | 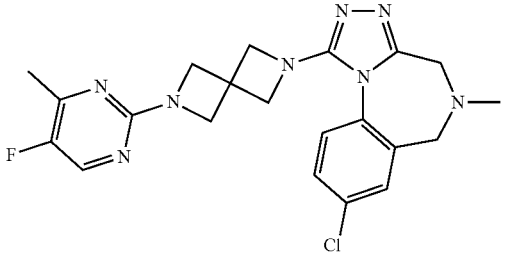 [SMILES: Cc1nc(N2CC3(C2)CN(c2nnc4n2-c2ccc(Cl)cc2CN(C)C4)C3)ncc1F] |
| 241 | 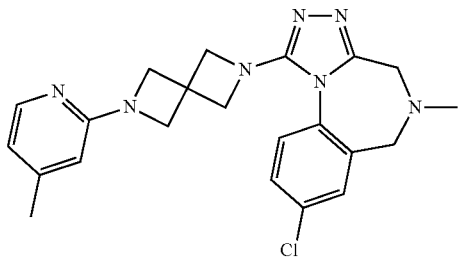 [SMILES: Cc1ccnc(N2CC3(C2)CN(c2nnc4n2-c2ccc(Cl)cc2CN(C)C4)C3)c1] |
| 242 | 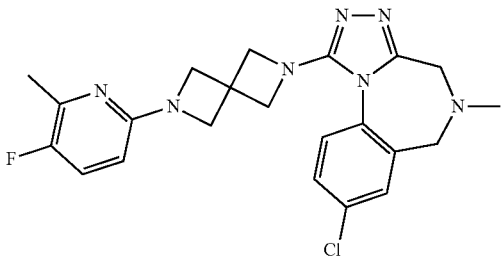 |
| 243 | 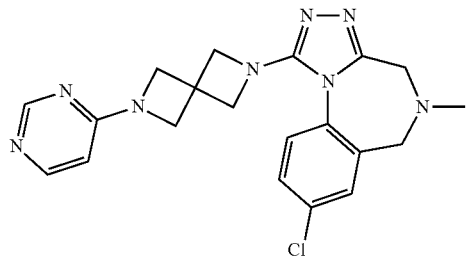 [SMILES: CN1Cc2cc(Cl)ccc2-n2c(nnc2N2CC3(CN(c4ccncn4)C3)C2)C1] |
| 244 | 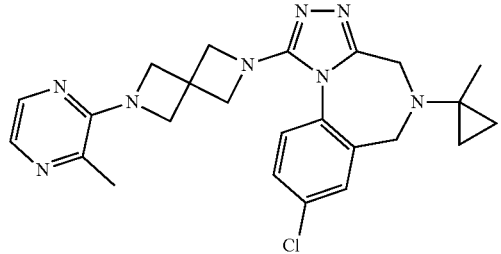 [SMILES: Cc1nccnc1N1CC2(C1)CN(c1nnc3n1-c1ccc(Cl)cc1CN(C1(C)CC1)C3)C2] |

TABLE 1-continued
Representative Compounds
| Cmpd. No. | Structure |
|---|---|
| 245 | 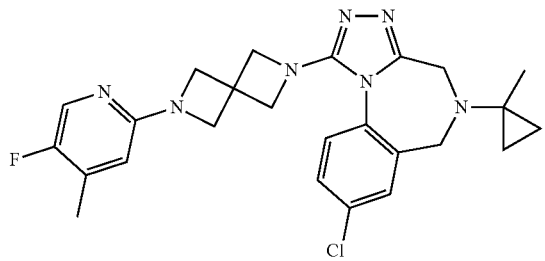 [SMILES: Cc1cc(N2CC3(C2)CN(c2nnc4n2-c2ccc(Cl)cc2CN(C2(C)CC2)C4)C3)ncc1F] |
| 246 | 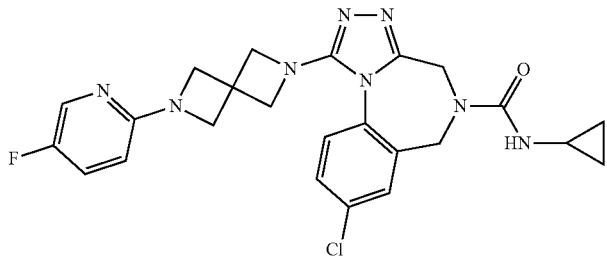 [SMILES: O=C(NC1CC1)N1Cc2cc(Cl)ccc2-n2c(nnc2N2CC3(CN(c4ccc(F)cn4)C3)C2)C1] |
| 247 | 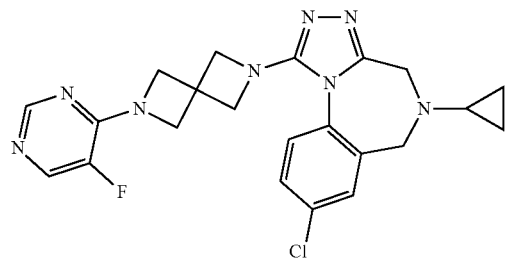 [SMILES: Fc1cncnc1N1CC2(C1)CN(c1nnc3n1-c1ccc(Cl)cc1CN(C1CC1)C3)C2] |
| 248 | 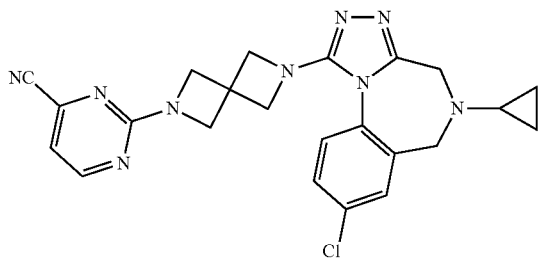 |
| 249 | 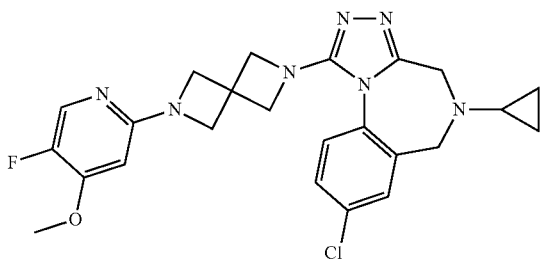 [SMILES: COc1cc(N2CC3(C2)CN(c2nnc4n2-c2ccc(Cl)cc2CN(C2CC2)C4)C3)ncc1F] |

TABLE 1-continued
Representative Compounds
| Cmpd. No. | Structure |
|---|---|
| 250 | 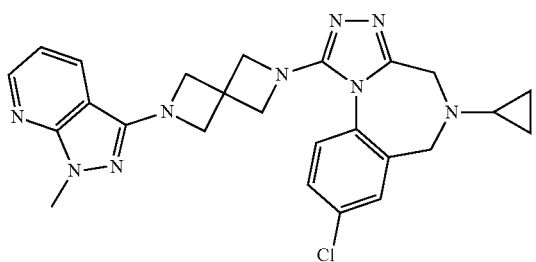 [SMILES: Cn1nc(N2CC3(C2)CN(c2nnc4n2-c2ccc(Cl)cc2CN(C2CC2)C4)C3)c2cccnc21] |
| 251 | 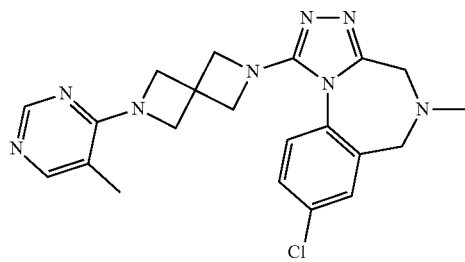 [SMILES: Cc1cncnc1N1CC2(C1)CN(c1nnc3n1-c1ccc(Cl)cc1CN(C)C3)C2] |
| 252 | 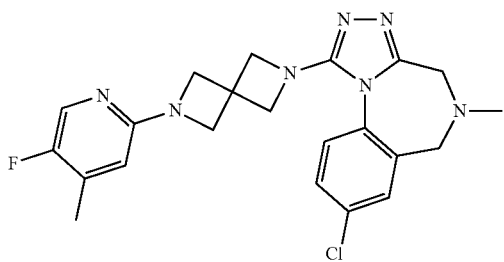 [SMILES: Cc1cc(N2CC3(C2)CN(c2nnc4n2-c2ccc(Cl)cc2CN(C)C4)C3)ncc1F] |
| 253 | 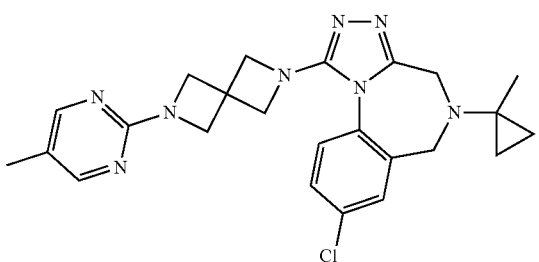 [SMILES: Cc1cnc(N2CC3(C2)CN(c2nnc4n2-c2ccc(Cl)cc2CN(C2(C)CC2)C4)C3)nc1] |
| 254 | 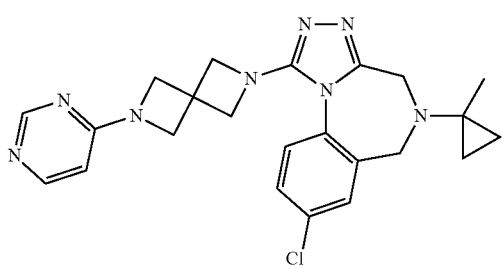 [SMILES: CC1(N2Cc3cc(Cl)ccc3-n3c(nnc3N3CC4(CN(c5ccncn5)C4)C3)C2)CC1] |

TABLE 1-continued
Representative Compounds
| Cmpd. No. | Structure |
|---|---|
| 255 | 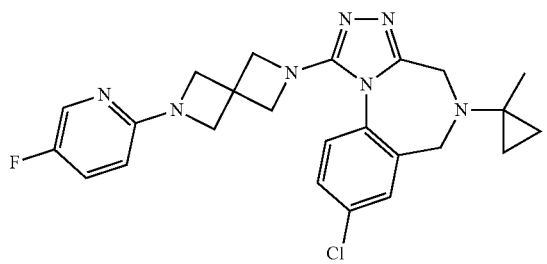 [SMILES: CC1(N2Cc3cc(Cl)ccc3-n3c(nnc3N3CC4(CN(c5ccc(F)cn5)C4)C3)C2)CC1] |
| 256 | 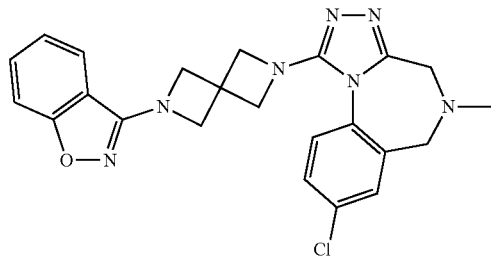 [SMILES: CN1Cc2cc(Cl)ccc2-n2c(nnc2N2CC3(CN(c4noc5ccccc45)C3)C2)C1] |
| 257 | 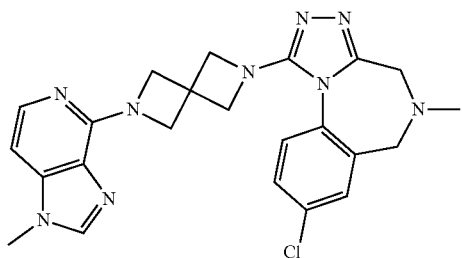 |
| 258 | 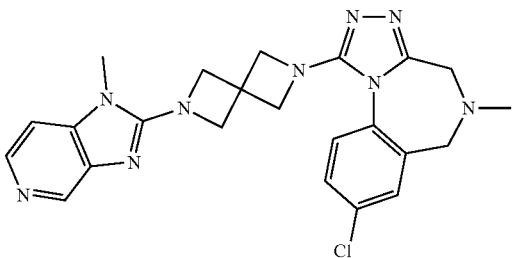 [SMILES: CN1Cc2cc(Cl)ccc2-n2c(nnc2N2CC3(C2)CN(c2nc4cnccc4n2C)C3)C1] |
| 259 | 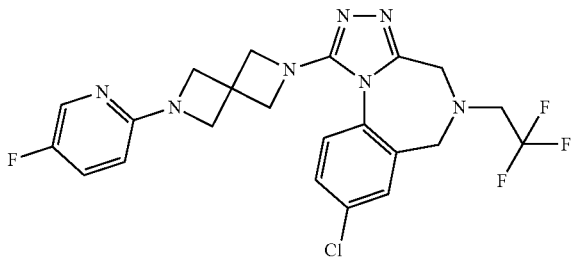 [SMILES: Fc1ccc(N2CC3(C2)CN(c2nnc4n2-c2ccc(Cl)cc2CN(CC(F)(F)F)C4)C3)nc1] |

TABLE 1-continued
Representative Compounds
| Cmpd. No. | Structure |
|---|---|
| 260 | 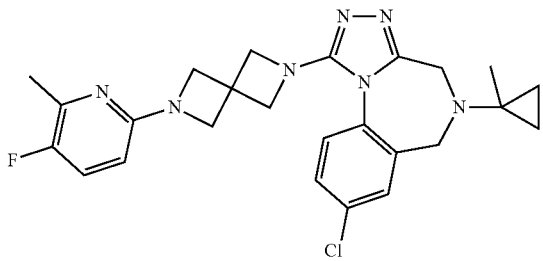 [SMILES: Cc1nc(N2CC3(C2)CN(c2nnc4n2-c2ccc(Cl)cc2CN(C2(C)CC2)C4)C3)ccc1F] |
| 261 | 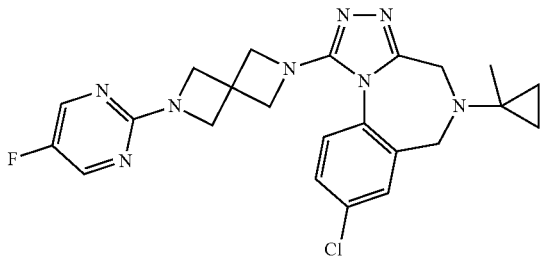 [SMILES: CC1(N2Cc3cc(Cl)ccc3-n3c(nnc3N3CC4(CN(c5ncc(F)cn5)C4)C3)C2)CC1] |
| 262 | 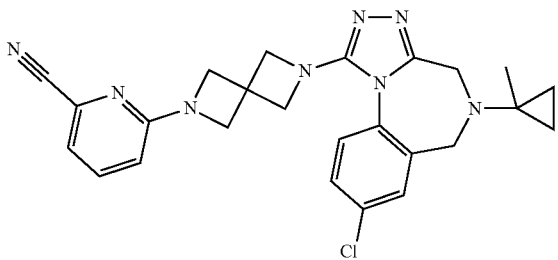 [SMILES: CC1(N2Cc3cc(Cl)ccc3-n3c(nnc3N3CC4(CN(c5cccc(C#N)n5)C4)C3)C2)CC1] |
| 263 | 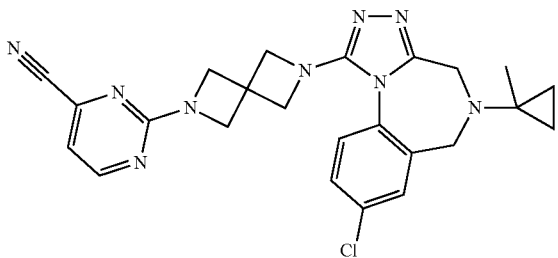 [SMILES: CC1(N2Cc3cc(Cl)ccc3-n3c(nnc3N3CC4(CN(c5nccc(C#N)n5)C4)C3)C2)CC1] |
| 264 | 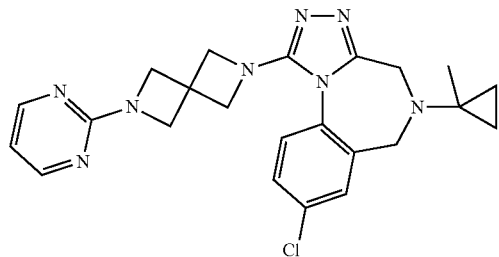 [SMILES: CC1(N2Cc3cc(Cl)ccc3-n3c(nnc3N3CC4(CN(c5ncccn5)C4)C3)C2)CC1] |

TABLE 1-continued

Representative Compounds

| Cmpd. No. | Structure |
|---|---|
| 265 | 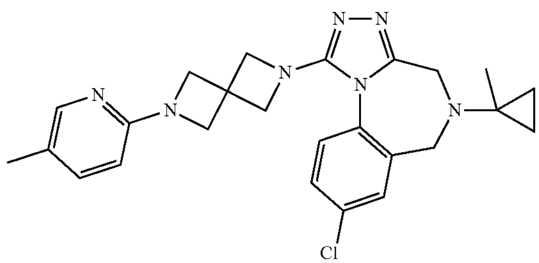 [SMILES: Cc1ccc(N2CC3(C2)CN(c2nnc4n2-c2ccc(Cl)cc2CN(C2(C)CC2)C4)C3)nc1] |
| 266 | 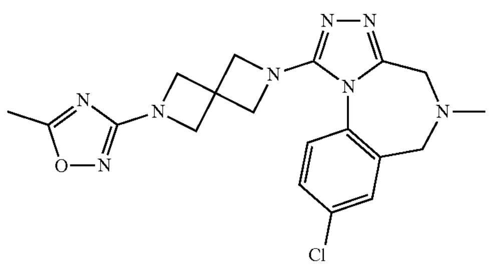 |
| 267 | 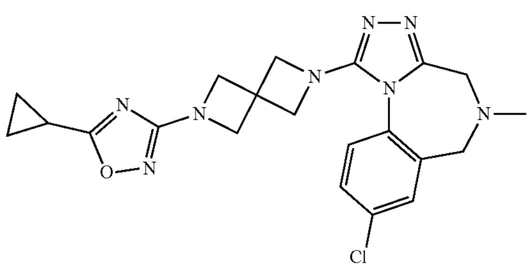 [SMILES: CN1Cc2cc(Cl)ccc2-n2c(nnc2N2CC3(CN(c4noc(C5CC5)n4)C3)C2)C1] |
| 268 | 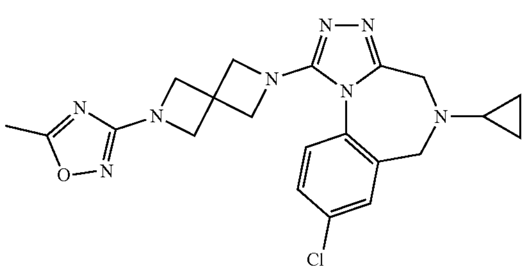 [SMILES: Cc1nc(N2CC3(C2)CN(c2nnc4n2-c2ccc(Cl)cc2CN(C2CC2)C4)C3)no1] |
| 269 | 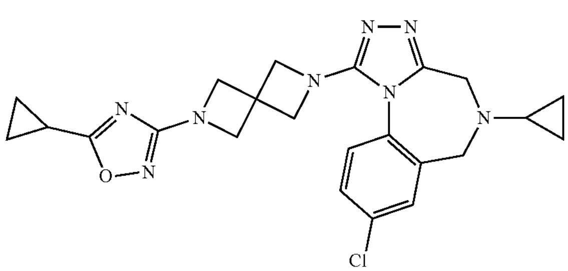 [SMILES: Clc1ccc2c(c1)CN(C1CC1)Cc1nnc(N3CC4(CN(c5noc(C6CC6)n5)C4)C3)n1-2] |

TABLE 1-continued
Representative Compounds
| Cmpd. No. | Structure |
|---|---|
| 270 | 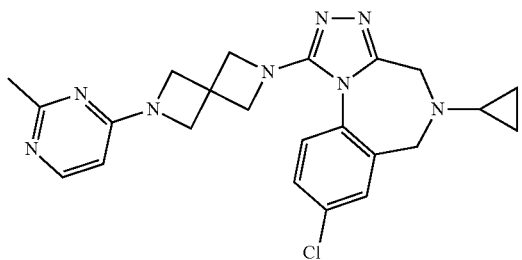 |
| 271 | 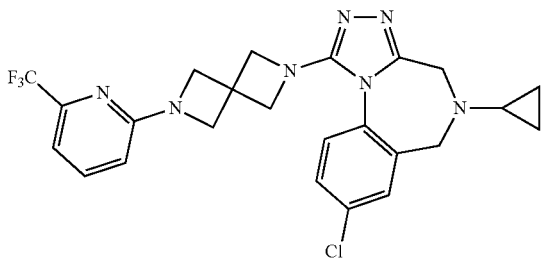 |
| 272 | 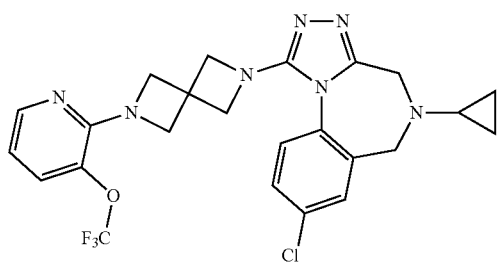 [SMILES: FC(F)(F)Oc1cccnc1N1CC2(C1)CN(c1nnc3n1-c1ccc(Cl)cc1CN(C1CC1)C3)C2] |
| 273 | 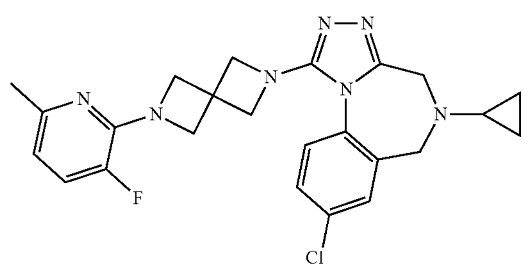 [SMILES: Cc1ccc(F)c(N2CC3(C2)CN(c2nnc4n2-c2ccc(Cl)cc2CN(C2CC2)C4)C3)n1] |
| 274 | 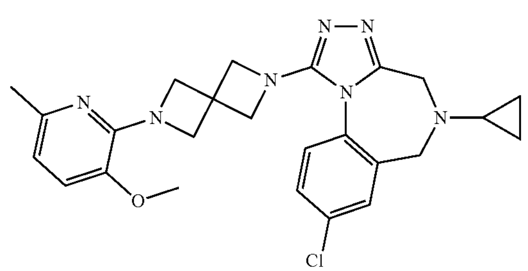 [SMILES: COc1ccc(C)nc1N1CC2(C1)CN(c1nnc3n1-c1ccc(Cl)cc1CN(C1CC1)C3)C2] |

TABLE 1-continued
Representative Compounds
| Cmpd. No. | Structure |
|---|---|
| 275 | 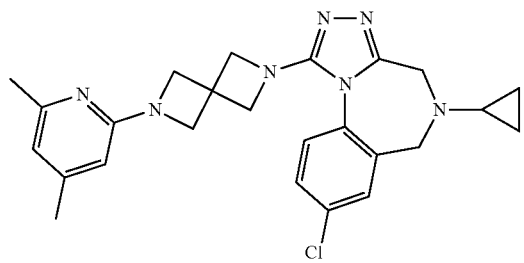 [SMILES: Cc1cc(C)nc(N2CC3(C2)CN(c2nnc4n2-c2ccc(Cl)cc2CN(C2CC2)C4)C3)c1] |
| 276 | 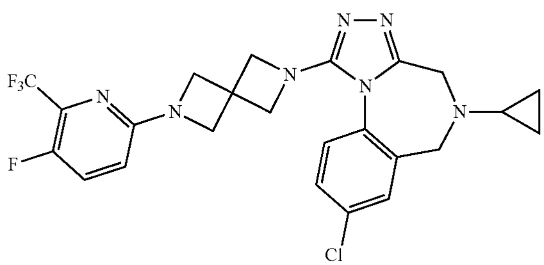 |
| 277 | 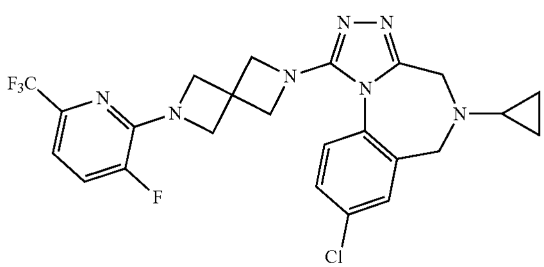 [SMILES: Fc1ccc(C(F)(F)F)nc1N1CC2(C1)CN(c1nnc3n1-c1ccc(Cl)cc1CN(C1CC1)C3)C2] |
| 278 | 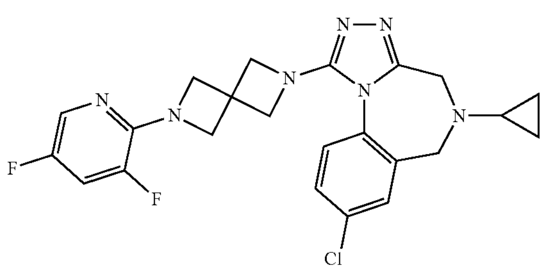 [SMILES: Fc1cnc(N2CC3(C2)CN(c2nnc4n2-c2ccc(Cl)cc2CN(C2CC2)C4)C3)c(F)c1] |
| 279 | 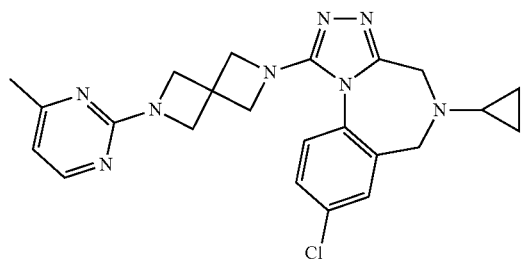 [SMILES: Cc1ccnc(N2CC3(C2)CN(c2nnc4n2-c2ccc(Cl)cc2CN(C2CC2)C4)C3)n1] |

US 12,247,037 B2
165
166
TABLE 1-continued
Representative Compounds
| Cmpd. No. | Structure |
|---|---|
| 280 | 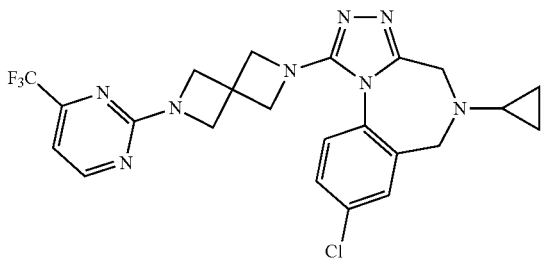 [SMILES: FC(F)(F)c1ccnc(N2CC3(C2)CN(c2nnc4n2-c2ccc(Cl)cc2CN(C2CC2)C4)C3)n1] |
| 281 | 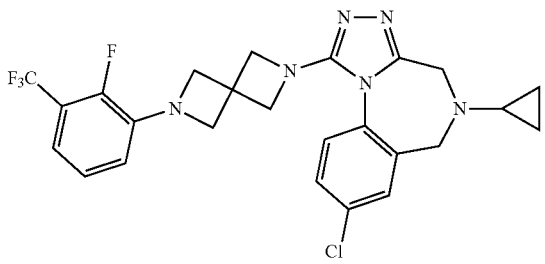 [SMILES: Fc1c(N2CC3(C2)CN(c2nnc4n2-c2ccc(Cl)cc2CN(C2CC2)C4)C3)cccc1C(F)(F)F] |
| 282 | 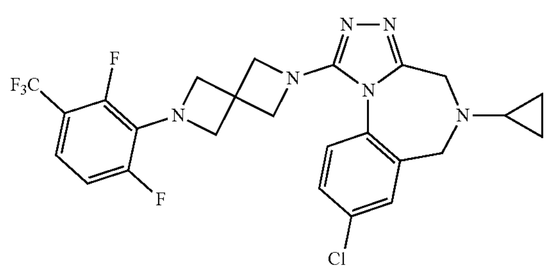 [SMILES: Fc1ccc(C(F)(F)F)c(F)c1N1CC2(C1)CN(c1nnc3n1-c1ccc(Cl)cc1CN(C1CC1)C3)C2] |
| 283 | 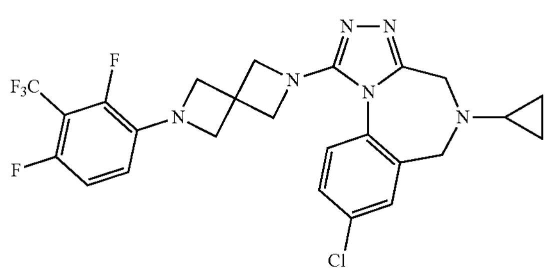 |
| 284 | 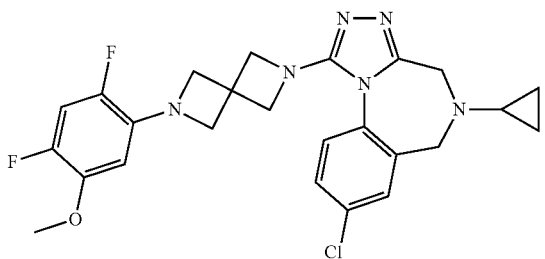 [SMILES: COc1cc(N2CC3(C2)CN(c2nnc4n2-c2ccc(Cl)cc2CN(C2CC2)C4)C3)c(F)cc1F] |

TABLE 1-continued
Representative Compounds
| Cmpd. No. | Structure |
|---|---|
| 285 | 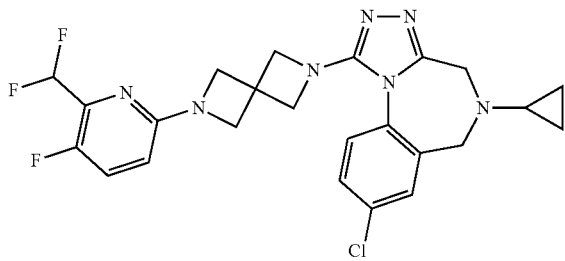 [SMILES: Fc1ccc(N2CC3(C2)CN(c2nnc4n2-c2ccc(Cl)cc2CN(C2CC2)C4)C3)nc1C(F)F] |
| 286 | 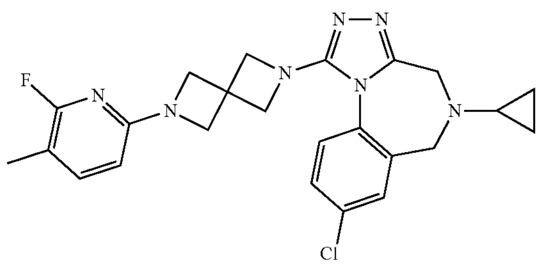 [SMILES: Cc1ccc(N2CC3(C2)CN(c2nnc4n2-c2ccc(Cl)cc2CN(C2CC2)C4)C3)nc1F] |
| 287 | 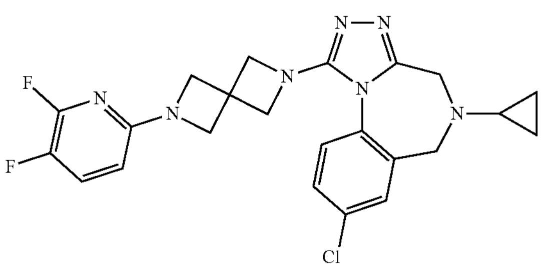 |
| 288 | 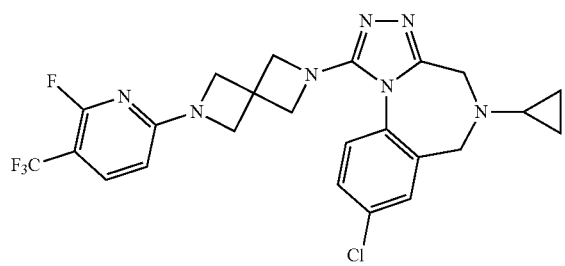 [SMILES: Fc1nc(N2CC3(C2)CN(c2nnc4n2-c2ccc(Cl)cc2CN(C2CC2)C4)C3)ccc1C(F)(F)F] |
| 289 | 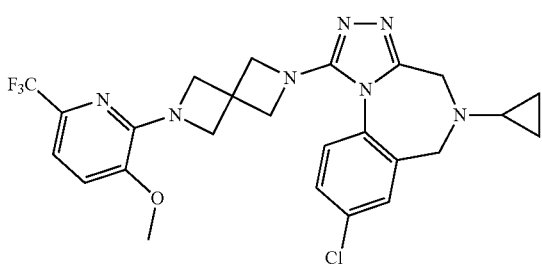 [SMILES: COc1ccc(C(F)(F)F)nc1N1CC2(C1)CN(c1nnc3n1-c1ccc(Cl)cc1CN(C1CC1)C3)C2] |

TABLE 1-continued

Representative Compounds

| Cmpd. No. | Structure |
|---|---|
| 290 | 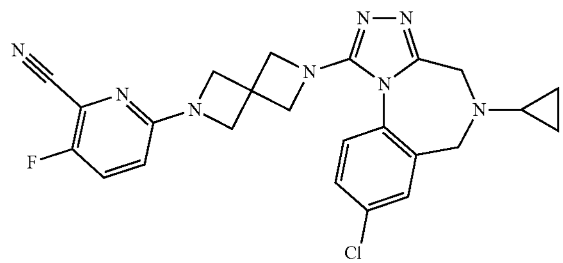 [SMILES: N#Cc1nc(N2CC3(C2)CN(c2nnc4n2-c2ccc(Cl)cc2CN(C2CC2)C4)C3)ccc1F] |
| 291 | 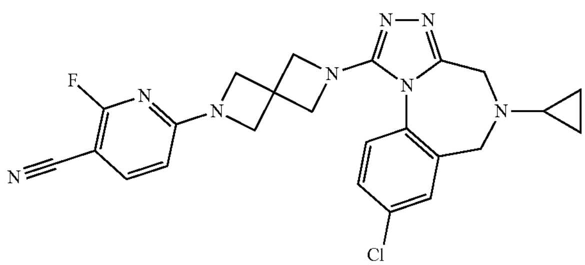 [SMILES: N#Cc1ccc(N2CC3(C2)CN(c2nnc4n2-c2ccc(Cl)cc2CN(C2CC2)C4)C3)nc1F] |
| 292 | 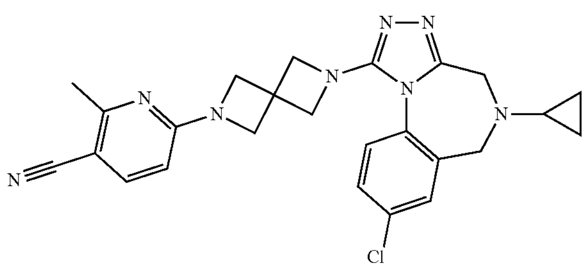 [SMILES: Cc1nc(N2CC3(C2)CN(c2nnc4n2-c2ccc(Cl)cc2CN(C2CC2)C4)C3)ccc1C#N] |
| 293 | 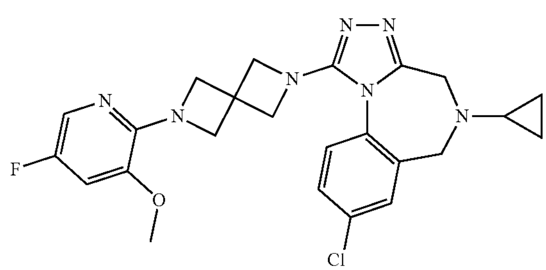 [SMILES: COc1cc(F)cnc1N1CC2(C1)CN(c1nnc3n1-c1ccc(Cl)cc1CN(C1CC1)C3)C2] |
| 294 | 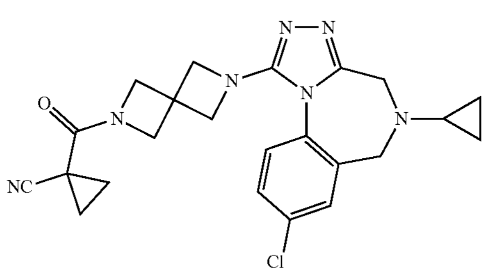 [SMILES: N#CC1(C(=O)N2CC3(C2)CN(c2nnc4n2-c2ccc(Cl)cc2CN(C2CC2)C4)C3)CC1] |

171
TABLE 1-continued
Representative Compounds
| Cmpd. No. | Structure |
|---|---|
| 295 | 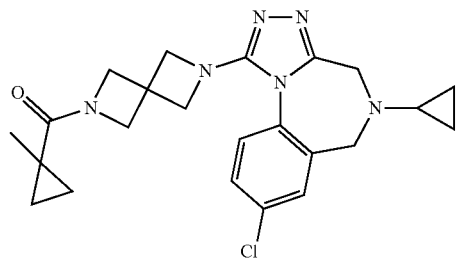 [SMILES: CC1(C(=O)N2CC3(C2)CN(c2nnc4n2-c2ccc(Cl)cc2CN(C2CC2)C4)C3)CC1] |
| 296 | 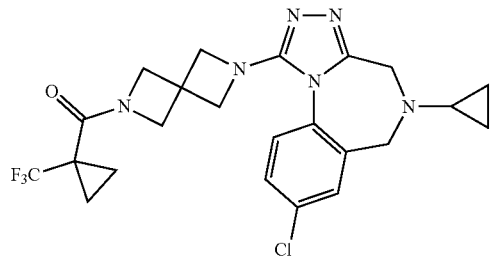 [SMILES: O=C(N1CC2(C1)CN(c1nnc3n1-c1ccc(Cl)cc1CN(C1CC1)C3)C2)C1(C(F)(F)F)CC1] |
| 297 | 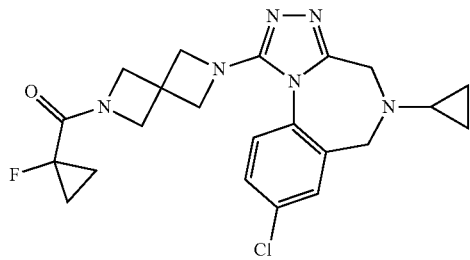 [SMILES: O=C(N1CC2(C1)CN(c1nnc3n1-c1ccc(Cl)cc1CN(C1CC1)C3)C2)C1(F)CC1] |
| 298 | 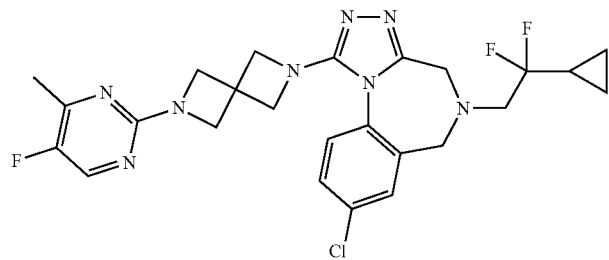 [SMILES: Cc1nc(N2CC3(C2)CN(c2nnc4n2-c2ccc(Cl)cc2CN(CC(F)(F)C2CC2)C4)C3)ncc1F] |
| 299 | 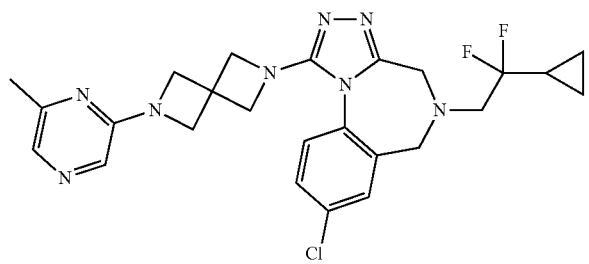 [SMILES: Cc1cncc(N2CC3(C2)CN(c2nnc4n2-c2ccc(Cl)cc2CN(CC(F)(F)C2CC2)C4)C3)n1] |

TABLE 1-continued

Representative Compounds

| Cmpd. No. | Structure |
|---|---|
| 300 | 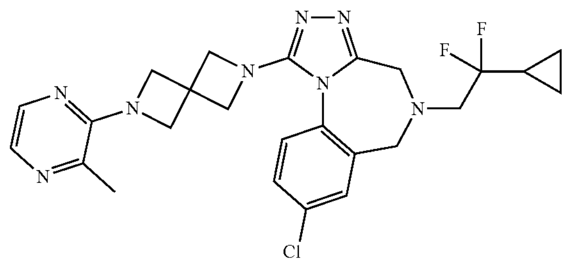 [SMILES: Cc1nccnc1N1CC2(C1)CN(c1nnc3n1-c1ccc(Cl)cc1CN(CC(F)(F)C1CC1)C3)C2] |
| 301 | 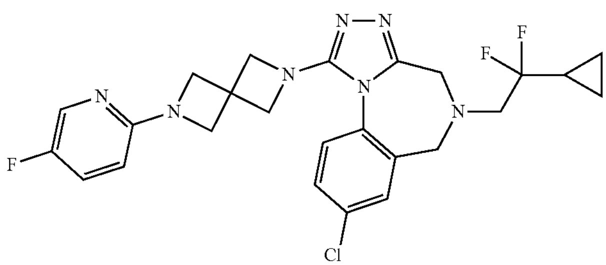 [SMILES: Fc1ccc(N2CC3(C2)CN(c2nnc4n2-c2ccc(Cl)cc2CN(CC(F)(F)C2CC2)C4)C3)nc1] |
| 302 | 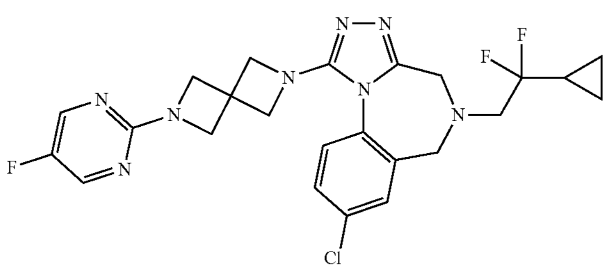 [SMILES: Fc1cnc(N2CC3(C2)CN(c2nnc4n2-c2ccc(Cl)cc2CN(CC(F)(F)C2CC2)C4)C3)nc1] |
| 303 | 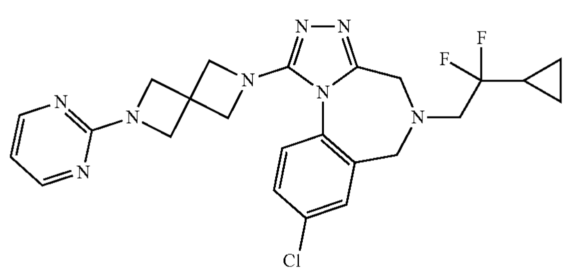 [SMILES: FC(F)(CN1Cc2cc(Cl)ccc2-n2c(nnc2N2CC3(CN(c4ncccn4)C3)C2)C1)C1CC1] |
| 304 | 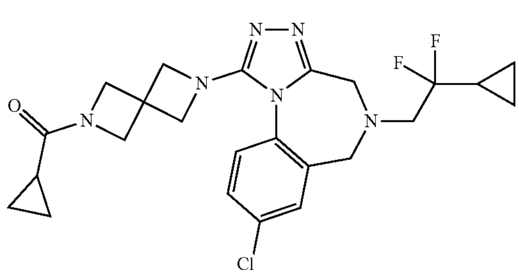 [SMILES: O=C(C1CC1)N1CC2(C1)CN(c1nnc3n1-c1ccc(Cl)cc1CN(CC(F)(F)C1CC1)C3)C2] |

TABLE 1-continued
Representative Compounds
| Cmpd. No. | Structure |
|---|---|
| 305 | 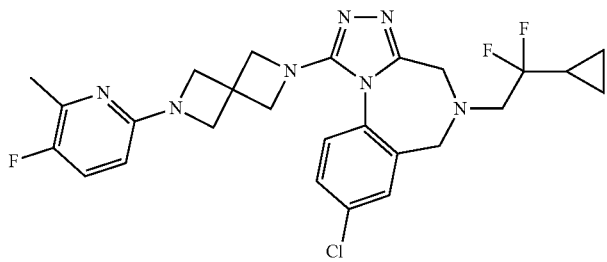 |
| 306 | 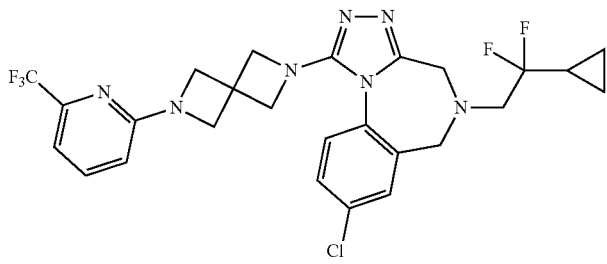 [SMILES: FC(F)(F)c1cccc(N2CC3(C2)CN(c2nnc4n2-c2ccc(Cl)cc2CN(CC(F)(F)C2CC2)C4)C3)n1] |
| 307 | 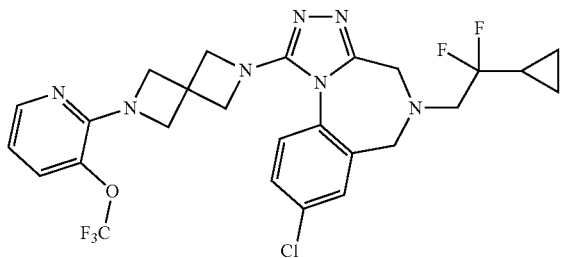 [SMILES: FC(F)(F)Oc1cccnc1N1CC2(C1)CN(c1nnc3n1-c1ccc(Cl)cc1CN(CC(F)(F)C1CC1)C3)C2] |
| 308 | 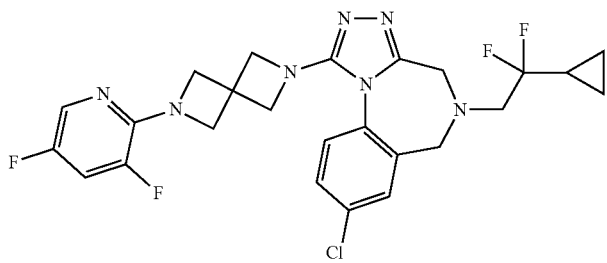 [SMILES: Fc1cnc(N2CC3(C2)CN(c2nnc4n2-c2ccc(Cl)cc2CN(CC(F)(F)C2CC2)C4)C3)c(F)c1] |
| 309 | 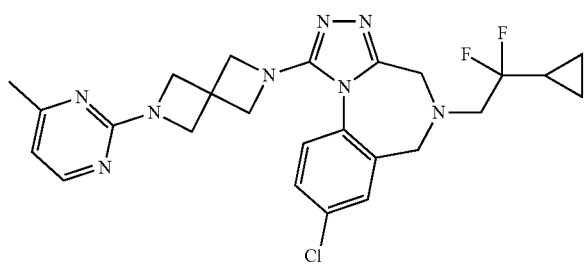 [SMILES: Cc1ccnc(N2CC3(C2)CN(c2nnc4n2-c2ccc(Cl)cc2CN(CC(F)(F)C2CC2)C4)C3)n1] |

TABLE 1-continued
Representative Compounds
| Cmpd. No. | Structure |
|---|---|
| 310 | 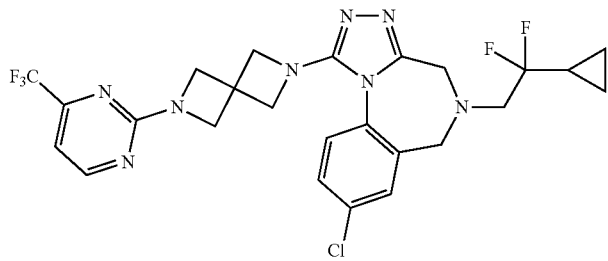 [SMILES: FC(F)(F)c1ccnc(N2CC3(C2)CN(c2nnc4n2-c2ccc(Cl)cc2CN(CC(F)(F)C2CC2)C4)C3)n1] |
| 311 | 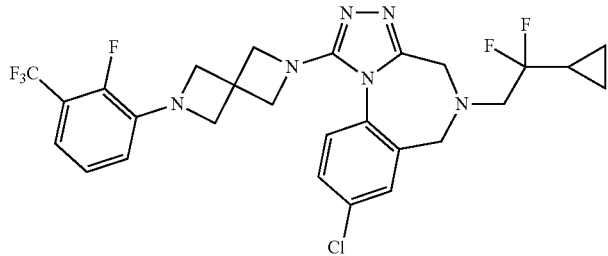 [SMILES: Fc1c(N2CC3(C2)CN(c2nnc4n2-c2ccc(Cl)cc2CN(CC(F)(F)C2CC2)C4)C3)cccc1C(F)(F)F] |
| 312 | 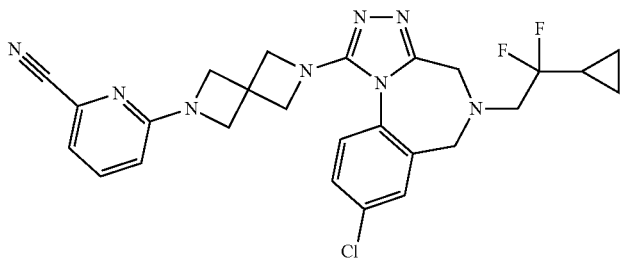 [SMILES: N#Cc1cccc(N2CC3(C2)CN(c2nnc4n2-c2ccc(Cl)cc2CN(CC(F)(F)C2CC2)C4)C3)n1] |
| 313 | 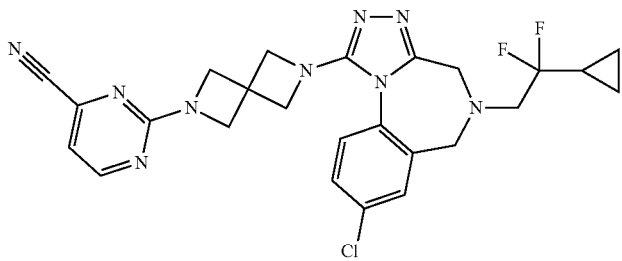 [SMILES: N#Cc1ccnc(N2CC3(C2)CN(c2nnc4n2-c2ccc(Cl)cc2CN(CC(F)(F)C2CC2)C4)C3)n1] |
| 314 | 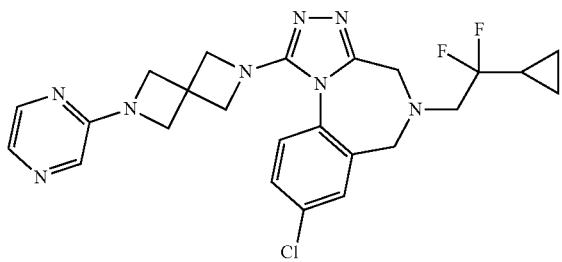 [SMILES: FC(F)(CN1Cc2cc(Cl)ccc2-n2c(nnc2N2CC3(CN(c4cnccn4)C3)C2)C1)C1CC1] |

TABLE 1-continued

Representative Compounds

| Cmpd. No. | Structure |
|---|---|
| 315 | 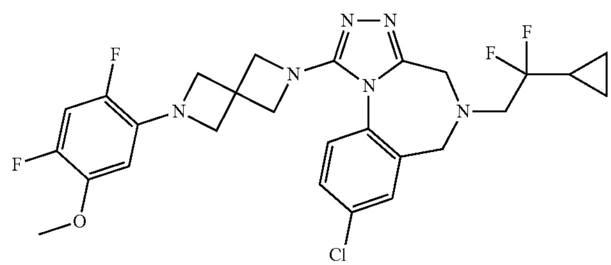 [SMILES: COc1cc(N2CC3(C2)CN(c2nnc4n2-c2ccc(Cl)cc2CN(CC(F)(F)C2CC2)C4)C3)c(F)cc1F] |
| 316 | 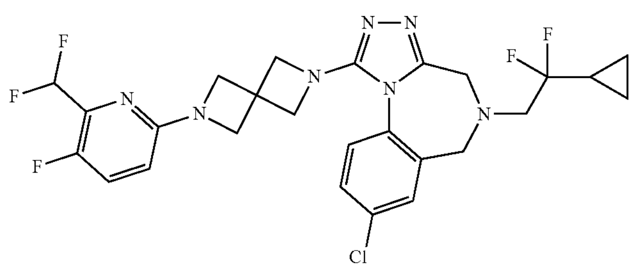 [SMILES: Fc1ccc(N2CC3(C2)CN(c2nnc4n2-c2ccc(Cl)cc2CN(CC(F)(F)C2CC2)C4)C3)nc1C(F)F] |
| 317 | 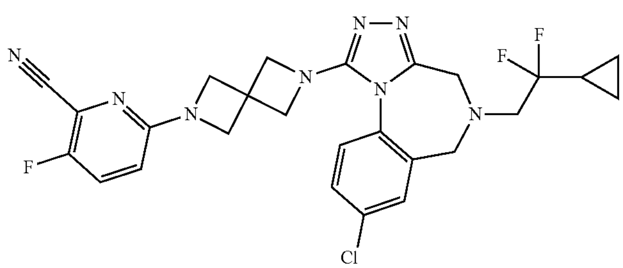 [SMILES: N#Cc1nc(N2CC3(C2)CN(c2nnc4n2-c2ccc(Cl)cc2CN(CC(F)(F)C2CC2)C4)C3)ccc1F] |
| 318 | 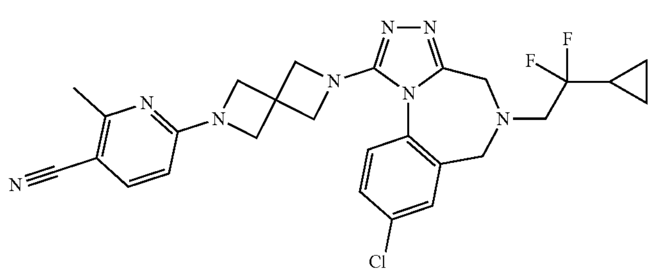 [SMILES: Cc1nc(N2CC3(C2)CN(c2nnc4n2-c2ccc(Cl)cc2CN(CC(F)(F)C2CC2)C4)C3)ccc1C#N] |
| 319 | 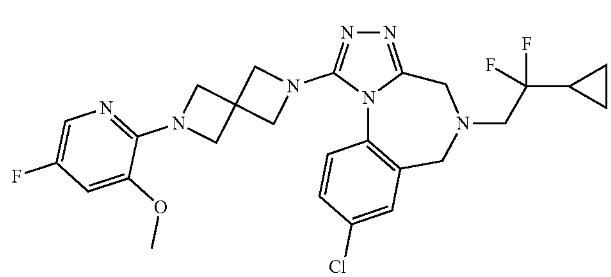 |

TABLE 1-continued

Representative Compounds

| Cmpd. No. | Structure |
|---|---|
| 320 | 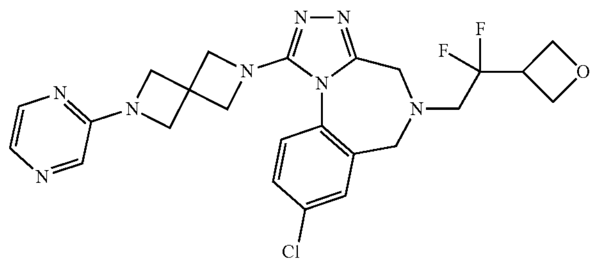 [SMILES: FC(F)(CN1Cc2cc(Cl)ccc2-n2c(nnc2N2CC3(CN(c4cnccn4)C3)C2)C1)C1COC1] |
| 321 | 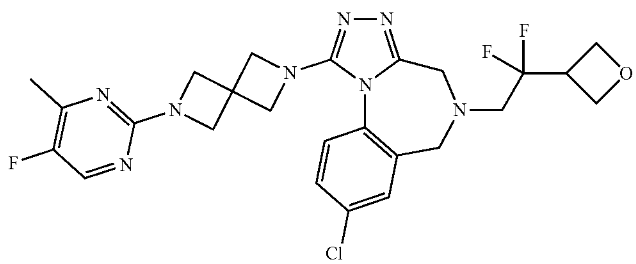 [SMILES: Cc1nc(N2CC3(C2)CN(c2nnc4n2-c2ccc(Cl)cc2CN(CC(F)(F)C2COC2)C4)C3)ncc1F] |
| 322 | 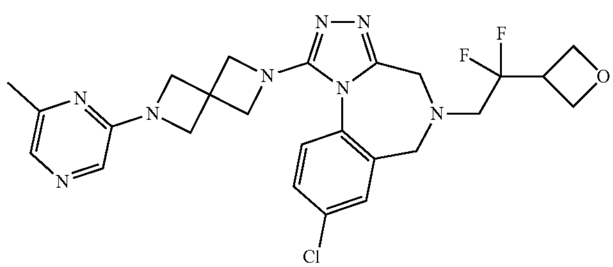 [SMILES: Cc1cncc(N2CC3(C2)CN(c2nnc4n2-c2ccc(Cl)cc2CN(CC(F)(F)C2COC2)C4)C3)n1] |
| 323 | 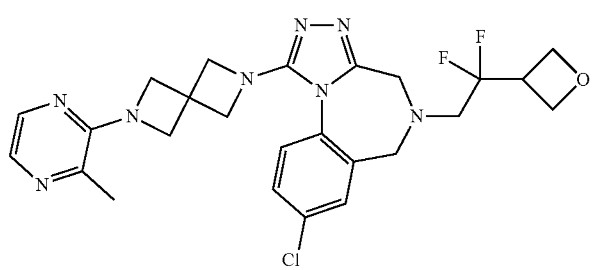 [SMILES: Cc1nccnc1N1CC2(C1)CN(c1nnc3n1-c1ccc(Cl)cc1CN(CC(F)(F)C1COC1)C3)C2] |
| 324 | 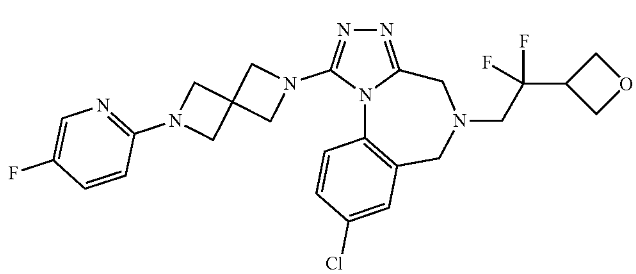 [SMILES: Fc1ccc(N2CC3(C2)CN(c2nnc4n2-c2ccc(Cl)cc2CN(CC(F)(F)C2COC2)C4)C3)nc1] |

TABLE 1-continued

Representative Compounds

| Cmpd. No. | Structure |
|---|---|
| 325 | 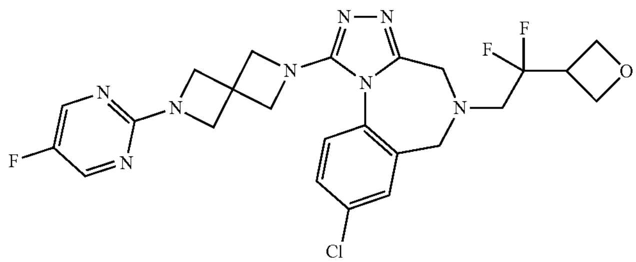 [SMILES: Fc1cnc(N2CC3(C2)CN(c2nnc4n2-c2ccc(Cl)cc2CN(CC(F)(F)C2COC2)C4)C3)nc1] |
| 326 | 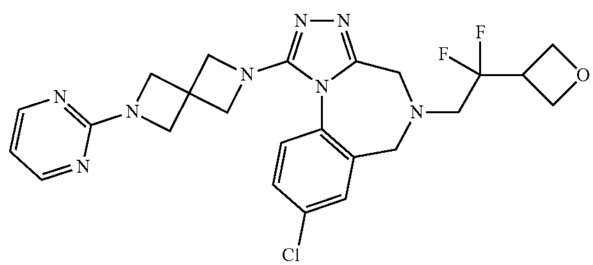 [SMILES: FC(F)(CN1Cc2cc(Cl)ccc2-n2c(nnc2N2CC3(CN(c4ncccn4)C3)C2)C1)C1COC1] |
| 327 | 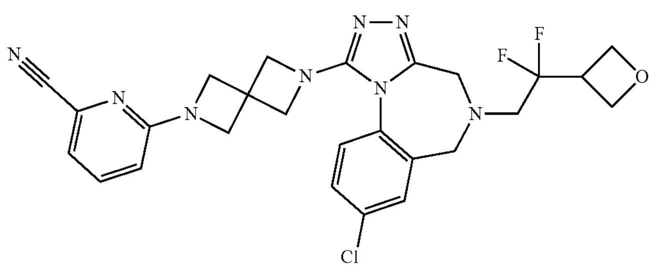 [SMILES: N#Cc1cccc(N2CC3(C2)CN(c2nnc4n2-c2ccc(Cl)cc2CN(CC(F)(F)C2COC2)C4)C3)n1] |
| 328 | 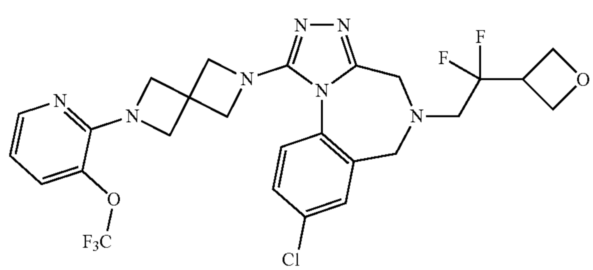 [SMILES: FC(F)(F)Oc1cccnc1N1CC2(C1)CN(c1nnc3n1-c1ccc(Cl)cc1CN(CC(F)(F)C1COC1)C3)C2] |
| 329 | 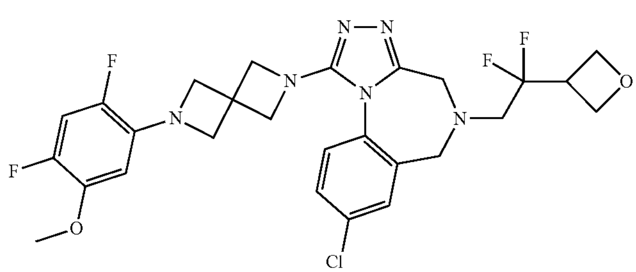 [SMILES: COc1cc(N2CC3(C2)CN(c2nnc4n2-c2ccc(Cl)cc2CN(CC(F)(F)C2COC2)C4)C3)c(F)cc1F] |

TABLE 1-continued
Representative Compounds
| Cmpd. No. | Structure |
|---|---|
| 330 | 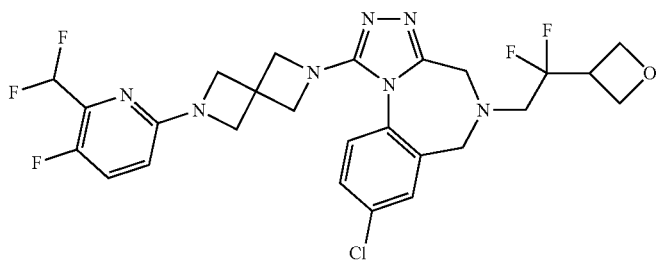 [SMILES: Fc1ccc(N2CC3(C2)CN(c2nnc4n2-c2ccc(Cl)cc2CN(CC(F)(F)C2COC2)C4)C3)nc1C(F)F] |
| 331 | 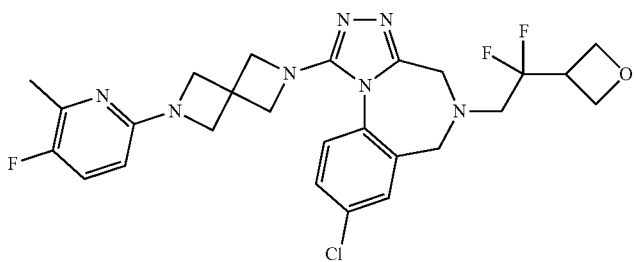 |
| 332 | 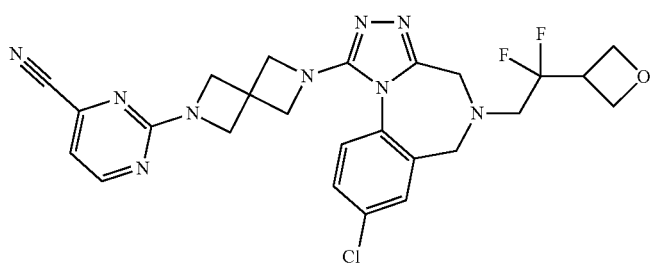 [SMILES: N#Cc1ccnc(N2CC3(C2)CN(c2nnc4n2-c2ccc(Cl)cc2CN(CC(F)(F)C2COC2)C4)C3)n1] |
| 333 | 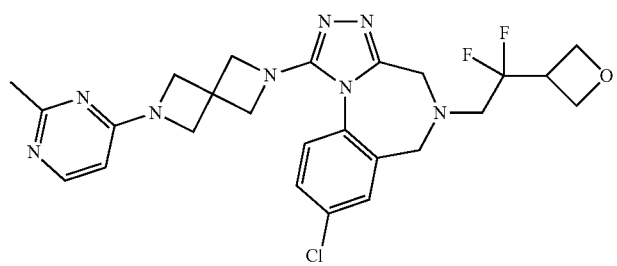 [SMILES: Cc1nccc(N2CC3(C2)CN(c2nnc4n2-c2ccc(Cl)cc2CN(CC(F)(F)C2COC2)C4)C3)n1] |
| 334 | 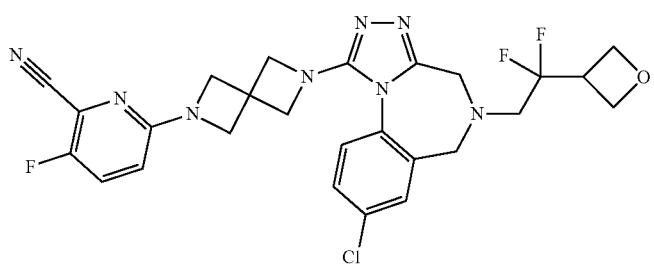 [SMILES: N#Cc1nc(N2CC3(C2)CN(c2nnc4n2-c2ccc(Cl)cc2CN(CC(F)(F)C2COC2)C4)C3)ccc1F] |

TABLE 1-continued
Representative Compounds
| Cmpd. No. | Structure |
|---|---|
| 335 | 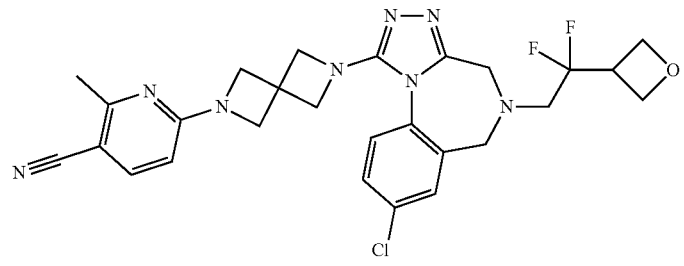 [SMILES: Cc1nc(N2CC3(C2)CN(c2nnc4n2-c2ccc(Cl)cc2CN(CC(F)(F)C2COC2)C4)C3)ccc1C#N] |
| 336 | 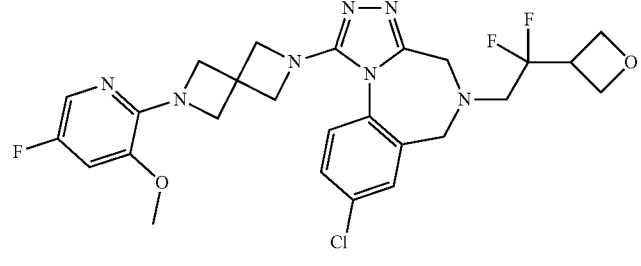 [SMILES: COc1cc(F)cnc1N1CC2(C1)CN(c1nnc3n1-c1ccc(Cl)cc1CN(CC(F)(F)C1COC1)C3)C2] |
| 337 | 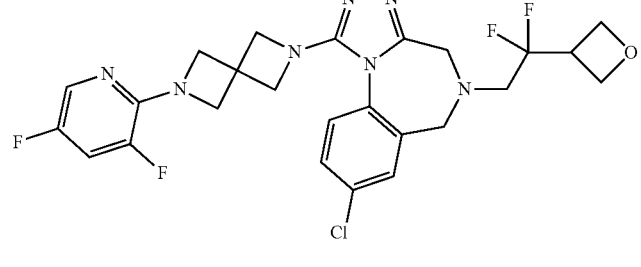 |
| 338 | 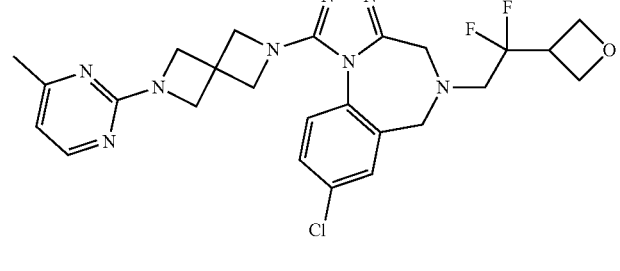 |
| 339 | 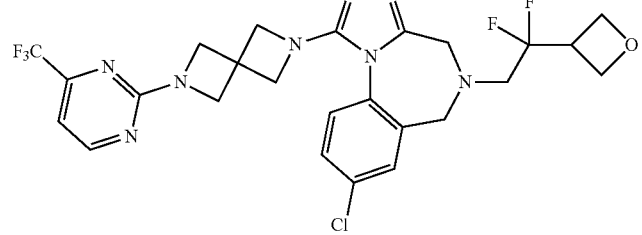 |

TABLE 1-continued

Representative Compounds

| Cmpd. No. | Structure |
|---|---|
| 340 | 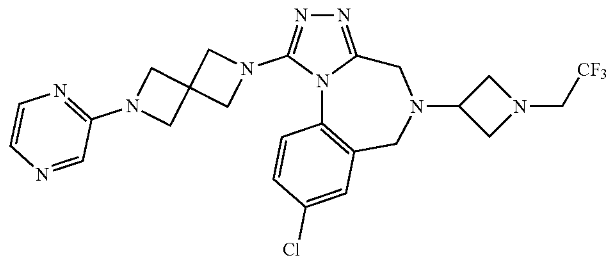 [SMILES: FC(F)(F)CN1CC(N2Cc3cc(Cl)ccc3-n3c(nnc3N3CC4(CN(c5cnccn5)C4)C3)C2)C1] |
| 341 | 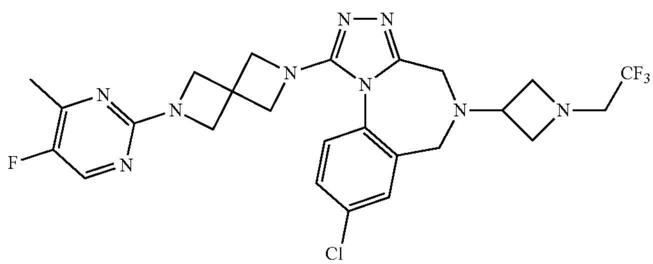 |
| 342 | 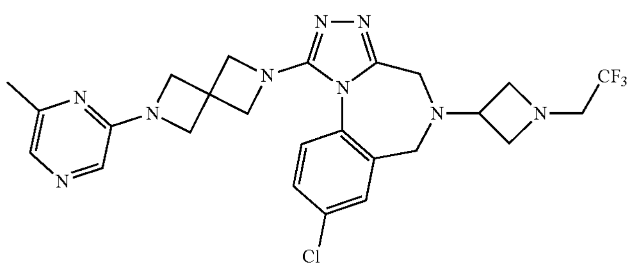 [SMILES: Cc1cncc(N2CC3(C2)CN(c2nnc4n2-c2ccc(Cl)cc2CN(C2CN(CC(F)(F)F)C2)C4)C3)n1] |
| 343 | 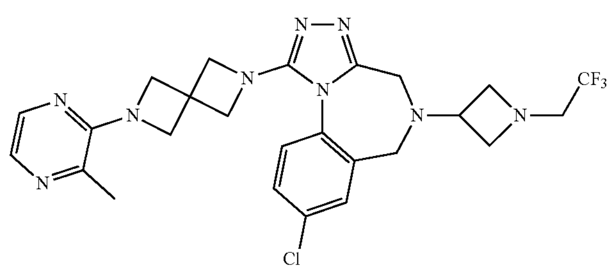 [SMILES: Cc1nccnc1N1CC2(C1)CN(c1nnc3n1-c1ccc(Cl)cc1CN(C1CN(CC(F)(F)F)C1)C3)C2] |
| 344 | 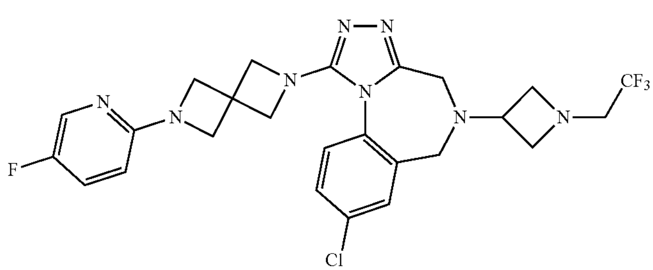 [SMILES: Fc1ccc(N2CC3(C2)CN(c2nnc4n2-c2ccc(Cl)cc2CN(C2CN(CC(F)(F)F)C2)C4)C3)nc1] |

TABLE 1-continued
Representative Compounds
| Cmpd. No. | Structure |
|---|---|
| 345 | 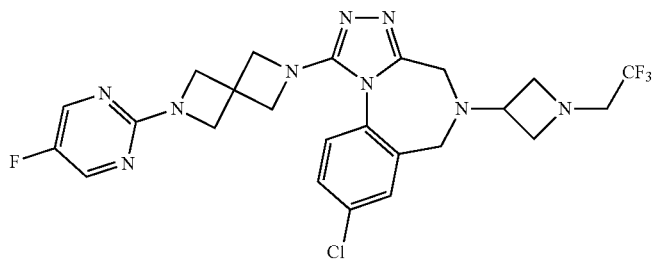 [SMILES: Fc1cnc(N2CC3(C2)CN(c2nnc4n2-c2ccc(Cl)cc2CN(C2CN(CC(F)(F)F)C2)C4)C3)nc1] |
| 346 | 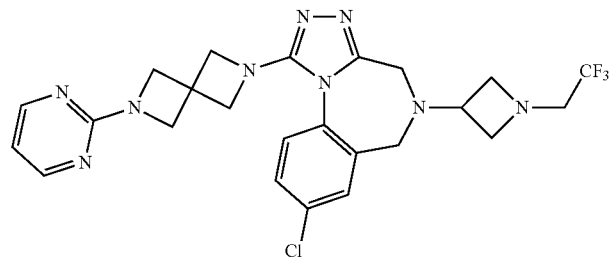 [SMILES: FC(F)(F)CN1CC(N2Cc3cc(Cl)ccc3-n3c(nnc3N3CC4(CN(c5ncccn5)C4)C3)C2)C1] |
| 347 | 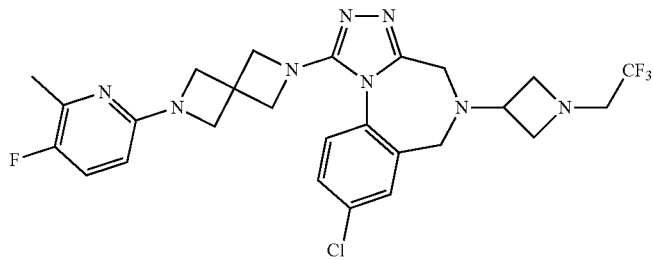 [SMILES: Cc1nc(N2CC3(C2)CN(c2nnc4n2-c2ccc(Cl)cc2CN(C2CN(CC(F)(F)F)C2)C4)C3)ccc1F] |
| 348 | 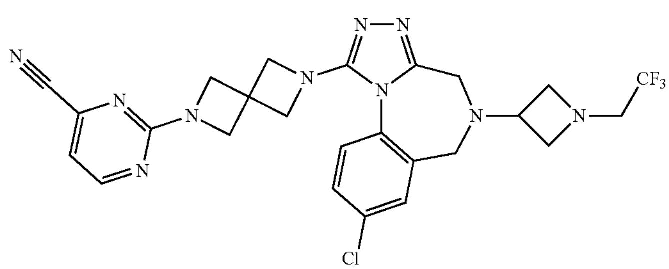 [SMILES: N#Cc1ccnc(N2CC3(C2)CN(c2nnc4n2-c2ccc(Cl)cc2CN(C2CN(CC(F)(F)F)C2)C4)C3)n1] |
| 349 | 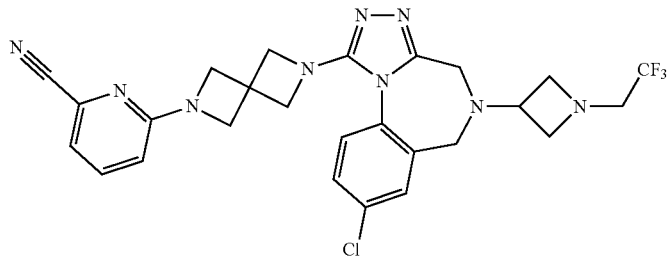 [SMILES: N#Cc1cccc(N2CC3(C2)CN(c2nnc4n2-c2ccc(Cl)cc2CN(C2CN(CC(F)(F)F)C2)C4)C3)n1] |

TABLE 1-continued
Representative Compounds
| Cmpd. No. | Structure |
|---|---|
| 350 | 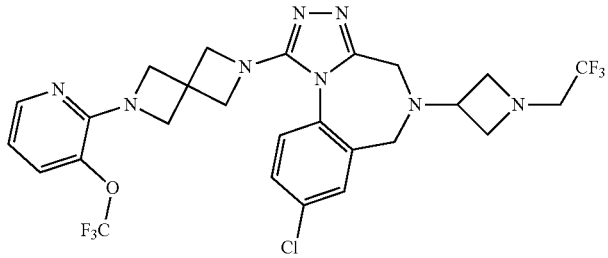 [SMILES: FC(F)(F)CN1CC(N2Cc3cc(Cl)ccc3-n3c(nnc3N3CC4(CN(c5ncccc5OC(F)(F)F)C4)C3)C2)C1] |
| 351 | 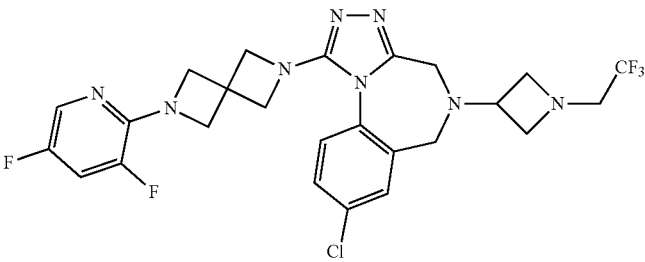 [SMILES: Fc1cnc(N2CC3(C2)CN(c2nnc4n2-c2ccc(Cl)cc2CN(C2CN(CC(F)(F)F)C2)C4)C3)c(F)c1] |
| 352 | 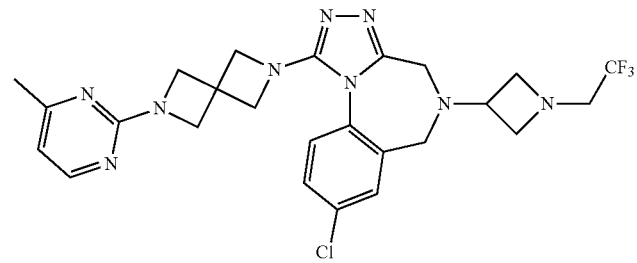 [SMILES: Cc1ccnc(N2CC3(C2)CN(c2nnc4n2-c2ccc(Cl)cc2CN(C2CN(CC(F)(F)F)C2)C4)C3)n1] |
| 353 | 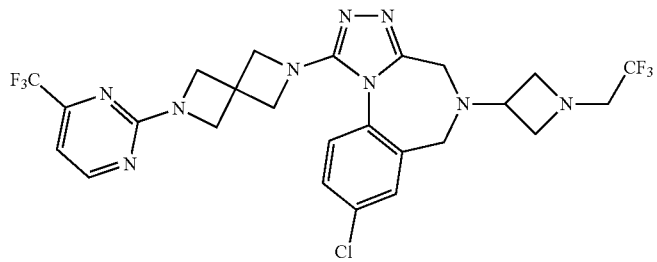 [SMILES: FC(F)(F)CN1CC(N2Cc3cc(Cl)ccc3-n3c(nnc3N3CC4(CN(c5nccc(C(F)(F)F)n5)C4)C3)C2)C1] |
| 354 | 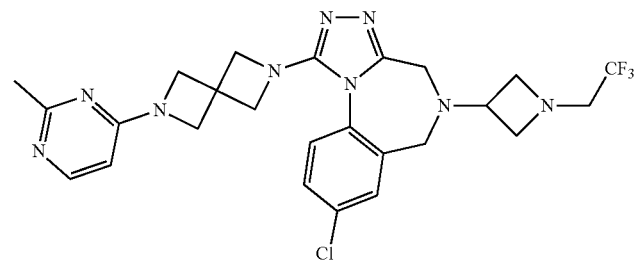 [SMILES: Cc1nccc(N2CC3(C2)CN(c2nnc4n2-c2ccc(Cl)cc2CN(C2CN(CC(F)(F)F)C2)C4)C3)n1] |

TABLE 1-continued
Representative Compounds
| Cmpd. No. | Structure |
|---|---|
| 355 | 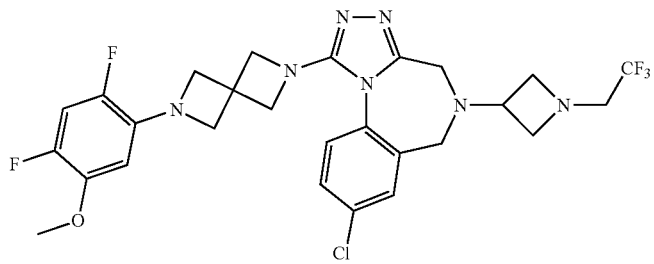 [SMILES: COc1cc(N2CC3(C2)CN(c2nnc4n2-c2ccc(Cl)cc2CN(C2CN(CC(F)(F)F)C2)C4)C3)c(F)cc1F] |
| 356 | 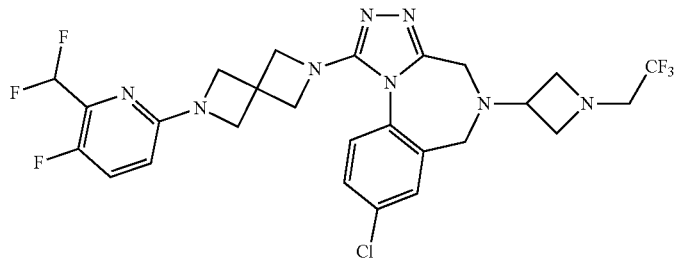 [SMILES: Fc1ccc(N2CC3(C2)CN(c2nnc4n2-c2ccc(Cl)cc2CN(C2CN(CC(F)(F)F)C2)C4)C3)nc1C(F)F] |
| 357 | 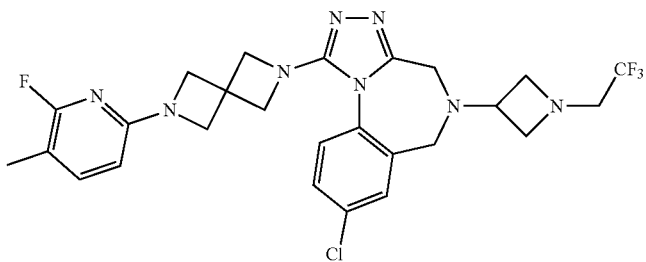 [SMILES: Cc1ccc(N2CC3(C2)CN(c2nnc4n2-c2ccc(Cl)cc2CN(C2CN(CC(F)(F)F)C2)C4)C3)nc1F] |
| 358 | 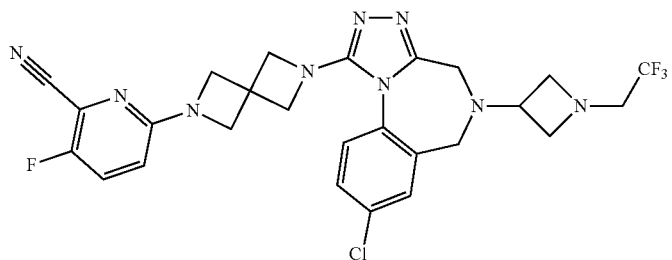 [SMILES: N#Cc1nc(N2CC3(C2)CN(c2nnc4n2-c2ccc(Cl)cc2CN(C2CN(CC(F)(F)F)C2)C4)C3)ccc1F] |
| 359 | 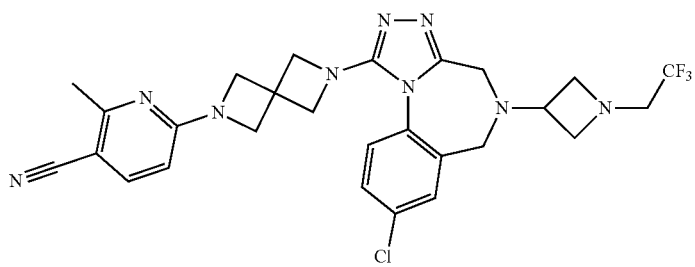 [SMILES: Cc1nc(N2CC3(C2)CN(c2nnc4n2-c2ccc(Cl)cc2CN(C2CN(CC(F)(F)F)C2)C4)C3)ccc1C#N] |

TABLE 1-continued

Representative Compounds

| Cmpd. No. | Structure |
|---|---|
| 360 | 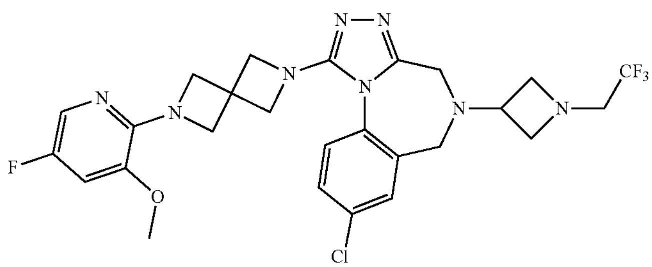 [SMILES: COc1cc(F)cnc1N1CC2(C1)CN(c1nnc3n1-c1ccc(Cl)cc1CN(C1CN(CC(F)(F)F)C1)C3)C2] |
| 361 | 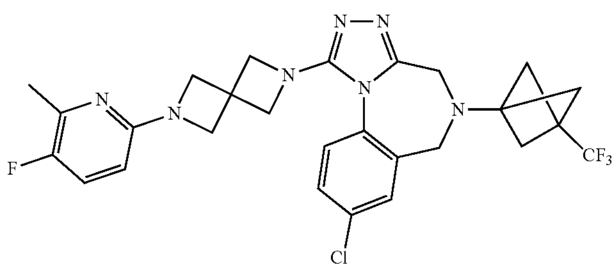 |
| 362 | 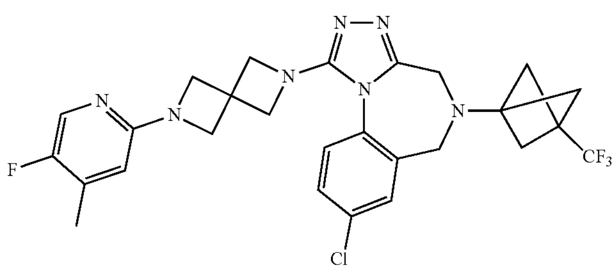 [SMILES: Cc1cc(N2CC3(C2)CN(c2nnc4n2-c2ccc(Cl)cc2CN(C25CC(C(F)(F)F)(C2)C5)C4)C3)ncc1F] |
| 363 | 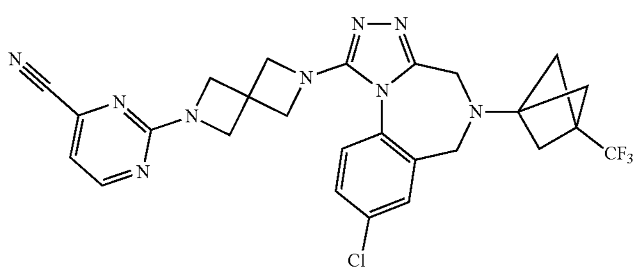 [SMILES: N#Cc1ccnc(N2CC3(C2)CN(c2nnc4n2-c2ccc(Cl)cc2CN(C25CC(C(F)(F)F)(C2)C5)C4)C3)n1] |
| 364 | 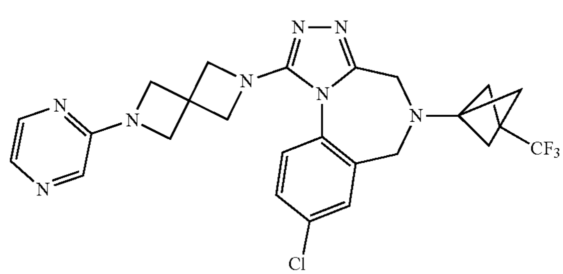 [SMILES: FC(F)(F)C12CC(N3Cc4cc(Cl)ccc4-n4c(nnc4N4CC5(CN(c6cnccn6)C5)C4)C3)(C1)C2] |

TABLE 1-continued

Representative Compounds

| Cmpd. No. | Structure |
|---|---|
| 365 | 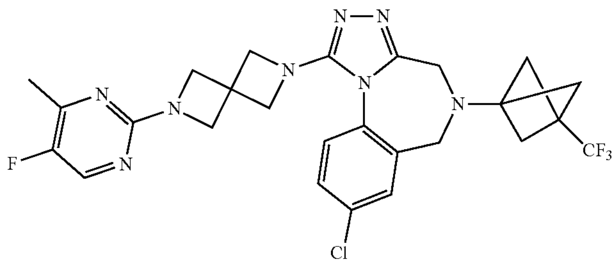 [SMILES: Cc1nc(N2CC3(C2)CN(c2nnc4n2-c2ccc(Cl)cc2CN(C25CC(C(F)(F)F)(C2)C5)C4)C3)ncc1F] |
| 366 | 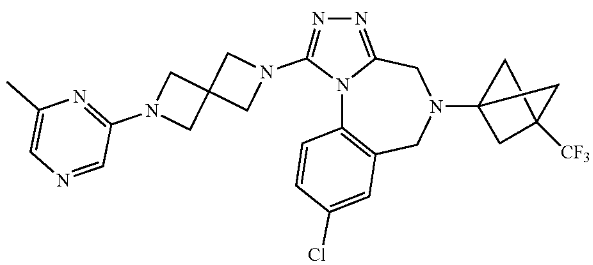 [SMILES: Cc1cncc(N2CC3(C2)CN(c2nnc4n2-c2ccc(Cl)cc2CN(C25CC(C(F)(F)F)(C2)C5)C4)C3)n1] |
| 367 | 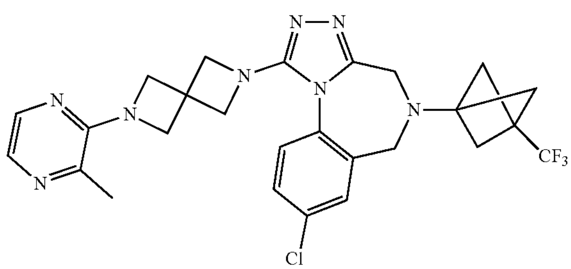 [SMILES: Cc1nccnc1N1CC2(C1)CN(c1nnc3n1-c1ccc(Cl)cc1CN(C14CC(C(F)(F)F)(C1)C4)C3)C2] |
| 368 | 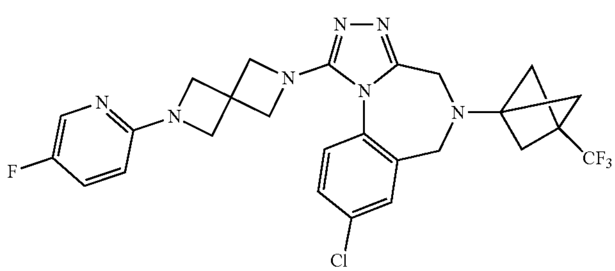 [SMILES: Fc1ccc(N2CC3(C2)CN(c2nnc4n2-c2ccc(Cl)cc2CN(C25CC(C(F)(F)F)(C2)C5)C4)C3)nc1] |
| 369 | 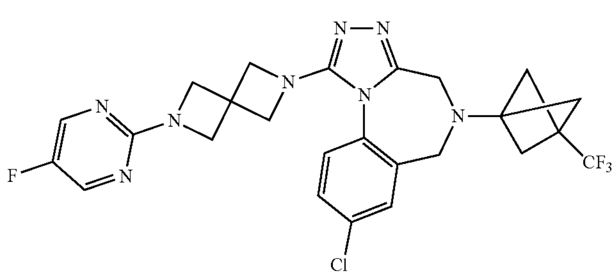 [SMILES: Fc1cnc(N2CC3(C2)CN(c2nnc4n2-c2ccc(Cl)cc2CN(C25CC(C(F)(F)F)(C2)C5)C4)C3)nc1] |

TABLE 1-continued
Representative Compounds
| Cmpd. No. | Structure |
|---|---|
| 370 | 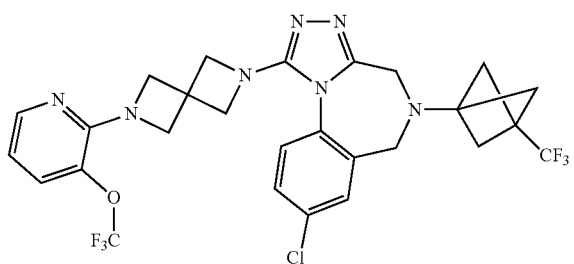 [SMILES: FC(F)(F)Oc1cccnc1N1CC2(C1)CN(c1nnc3n1-c1ccc(Cl)cc1CN(C14CC(C(F)(F)F)(C1)C4)C3)C2] |
| 371 | 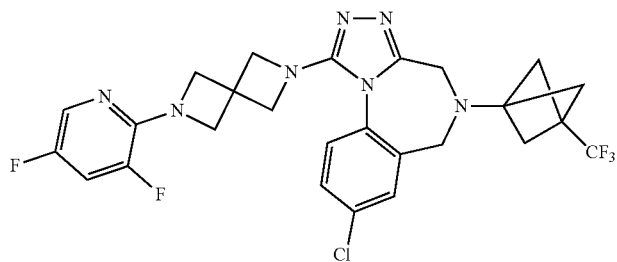 [SMILES: Fc1cnc(N2CC3(C2)CN(c2nnc4n2-c2ccc(Cl)cc2CN(C25CC(C(F)(F)F)(C2)C5)C4)C3)c(F)c1] |
| 372 | 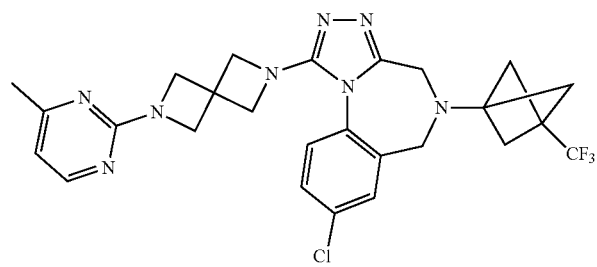 [SMILES: Cc1ccnc(N2CC3(C2)CN(c2nnc4n2-c2ccc(Cl)cc2CN(C25CC(C(F)(F)F)(C2)C5)C4)C3)n1] |
| 373 | 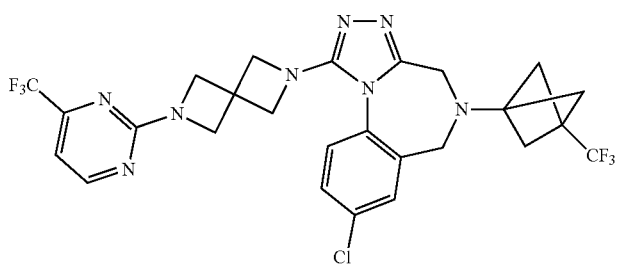 [SMILES: FC(F)(F)c1ccnc(N2CC3(C2)CN(c2nnc4n2-c2ccc(Cl)cc2CN(C25CC(C(F)(F)F)(C2)C5)C4)C3)n1] |
| 374 | 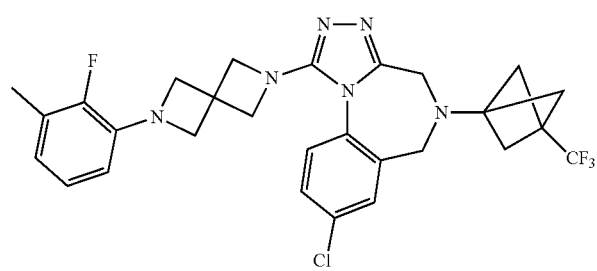 [SMILES: Cc1cccc(N2CC3(C2)CN(c2nnc4n2-c2ccc(Cl)cc2CN(C25CC(C(F)(F)F)(C2)C5)C4)C3)c1F] |

TABLE 1-continued

Representative Compounds

| Cmpd. No. | Structure |
|---|---|
| 375 | 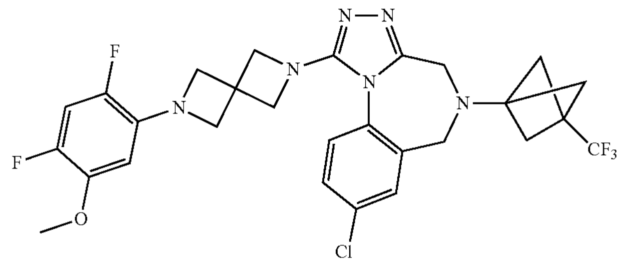 [SMILES: COc1cc(N2CC3(C2)CN(c2nnc4n2-c2ccc(Cl)cc2CN(C25CC(C(F)(F)F)(C2)C5)C4)C3)c(F)cc1F] |
| 376 | 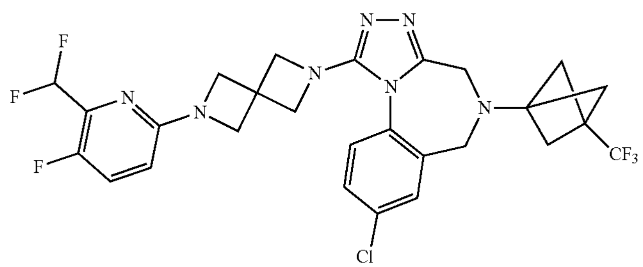 [SMILES: Fc1ccc(N2CC3(C2)CN(c2nnc4n2-c2ccc(Cl)cc2CN(C25CC(C(F)(F)F)(C2)C5)C4)C3)nc1C(F)F] |
| 377 | 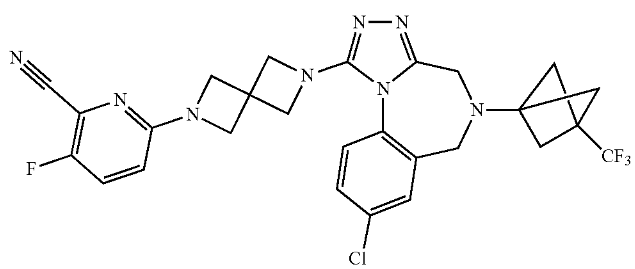 [SMILES: N#Cc1nc(N2CC3(C2)CN(c2nnc4n2-c2ccc(Cl)cc2CN(C25CC(C(F)(F)F)(C2)C5)C4)C3)ccc1F] |
| 378 | 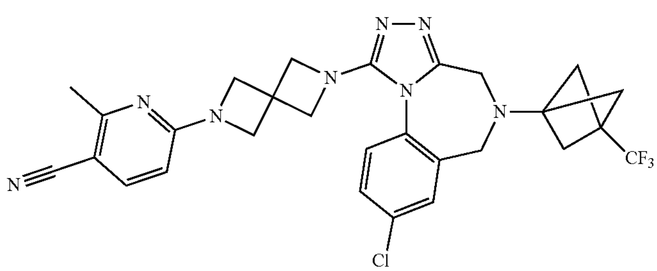 [SMILES: Cc1nc(N2CC3(C2)CN(c2nnc4n2-c2ccc(Cl)cc2CN(C25CC(C(F)(F)F)(C2)C5)C4)C3)ccc1C#N] |
| 379 | 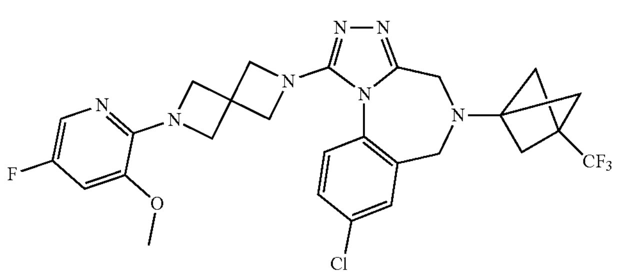 [SMILES: COc1cc(F)cnc1N1CC2(C1)CN(c1nnc3n1-c1ccc(Cl)cc1CN(C14CC(C(F)(F)F)(C1)C4)C3)C2] |

TABLE 1-continued

Representative Compounds

| Cmpd. No. | Structure |
|---|---|
| 380 | 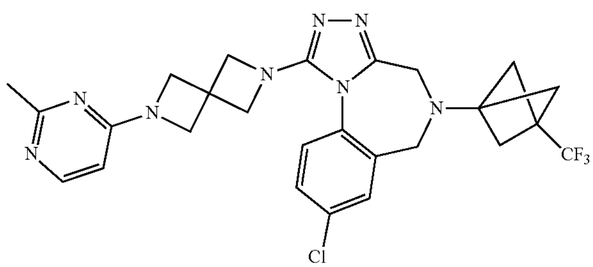 [SMILES: Cc1nccc(N2CC3(C2)CN(c2nnc4n2-c2ccc(Cl)cc2CN(C25CC(C(F)(F)F)(C2)C5)C4)C3)n1] |
| 381 | 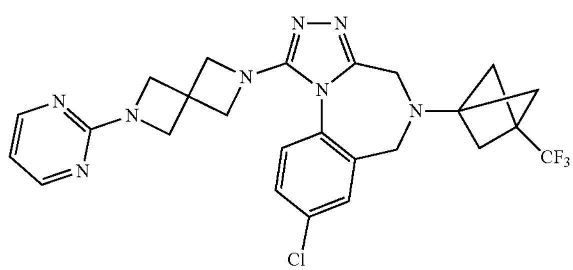 [SMILES: FC(F)(F)C12CC(N3Cc4cc(Cl)ccc4-n4c(nnc4N4CC5(CN(c6ncccn6)C5)C4)C3)(C1)C2] |
| 382 | 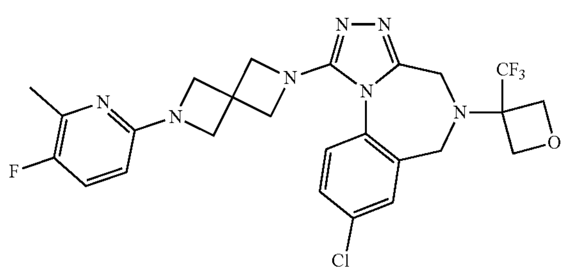 [SMILES: Cc1nc(N2CC3(C2)CN(c2nnc4n2-c2ccc(Cl)cc2CN(C2(C(F)(F)F)COC2)C4)C3)ccc1F] |
| 383 | 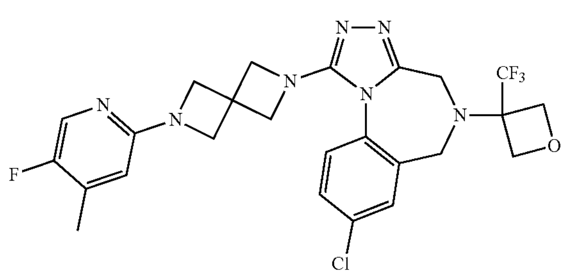 [SMILES: Cc1cc(N2CC3(C2)CN(c2nnc4n2-c2ccc(Cl)cc2CN(C2(C(F)(F)F)COC2)C4)C3)ncc1F] |
| 384 | 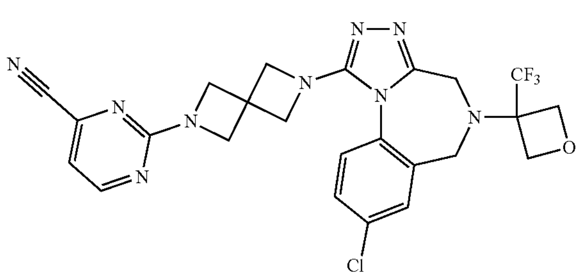 [SMILES: N#Cc1ccnc(N2CC3(C2)CN(c2nnc4n2-c2ccc(Cl)cc2CN(C2(C(F)(F)F)COC2)C4)C3)n1] |

TABLE 1-continued
Representative Compounds
| Cmpd. No. | Structure |
|---|---|
| 385 | 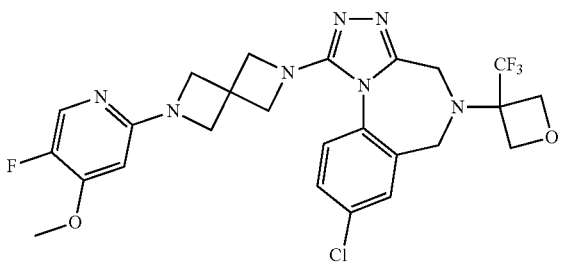 [SMILES: COc1cc(N2CC3(C2)CN(c2nnc4n2-c2ccc(Cl)cc2CN(C2(C(F)(F)F)COC2)C4)C3)ncc1F] |
| 386 | 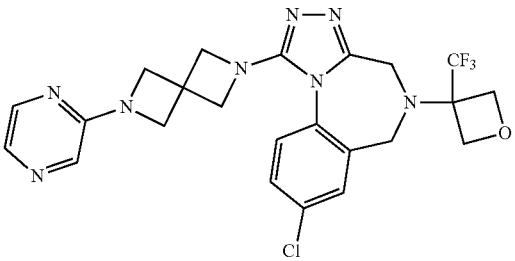 [SMILES: FC(F)(F)C1(N2Cc3cc(Cl)ccc3-n3c(nnc3N3CC4(CN(c5cnccn5)C4)C3)C2)COC1] |
| 387 | 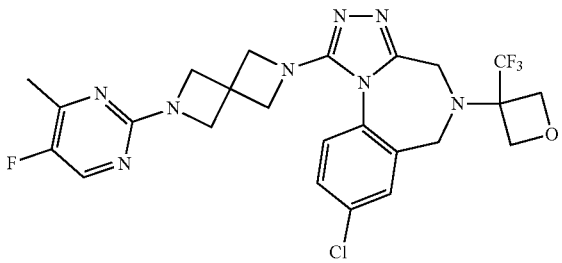 [SMILES: Cc1nc(N2CC3(C2)CN(c2nnc4n2-c2ccc(Cl)cc2CN(C2(C(F)(F)F)COC2)C4)C3)ncc1F] |
| 388 | 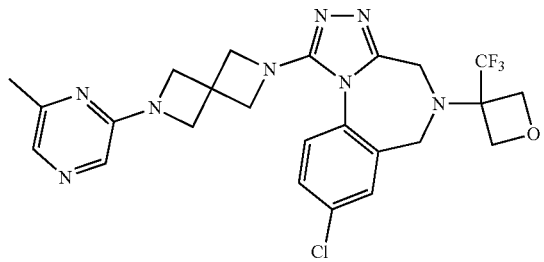 [SMILES: Cc1cncc(N2CC3(C2)CN(c2nnc4n2-c2ccc(Cl)cc2CN(C2(C(F)(F)F)COC2)C4)C3)n1] |
| 389 | 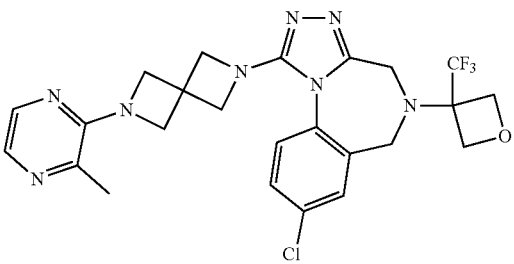 [SMILES: Cc1nccnc1N1CC2(C1)CN(c1nnc3n1-c1ccc(Cl)cc1CN(C1(C(F)(F)F)COC1)C3)C2] |

TABLE 1-continued
Representative Compounds
| Cmpd. No. | Structure |
|---|---|
| 390 | 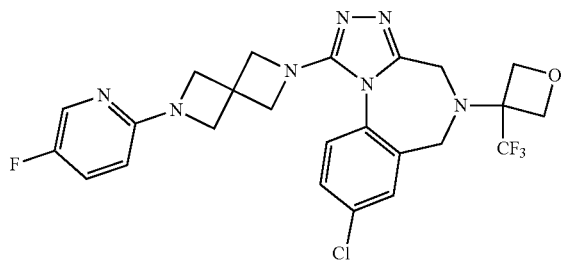 [SMILES: Fc1ccc(N2CC3(C2)CN(c2nnc4n2-c2ccc(Cl)cc2CN(C2(C(F)(F)F)COC2)C4)C3)nc1] |
| 391 | 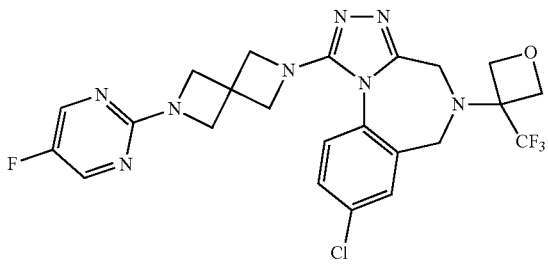 [SMILES: Fc1cnc(N2CC3(C2)CN(c2nnc4n2-c2ccc(Cl)cc2CN(C2(C(F)(F)F)COC2)C4)C3)nc1] |
| 392 | 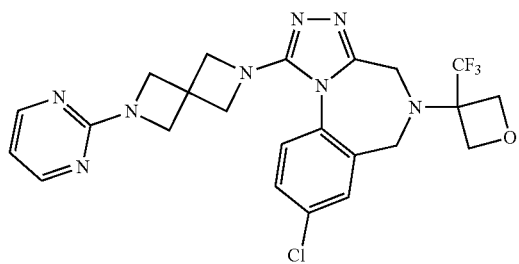 [SMILES: FC(F)(F)C1(N2Cc3cc(Cl)ccc3-n3c(nnc3N3CC4(CN(c5ncccn5)C4)C3)C2)COC1] |
| 393 | 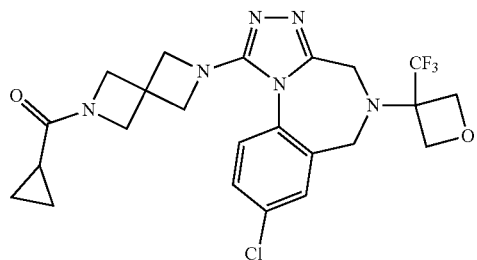 [SMILES: O=C(C1CC1)N1CC2(C1)CN(c1nnc3n1-c1ccc(Cl)cc1CN(C1(C(F)(F)F)COC1)C3)C2] |
| 394 | 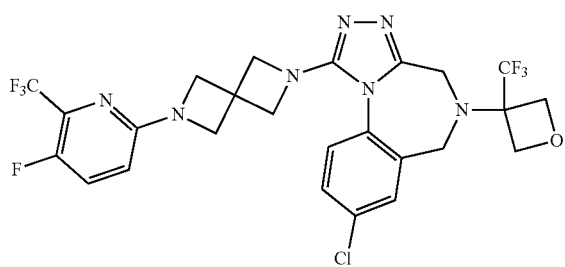 |

TABLE 1-continued
Representative Compounds
| Cmpd. No. | Structure |
|---|---|
| 395 | 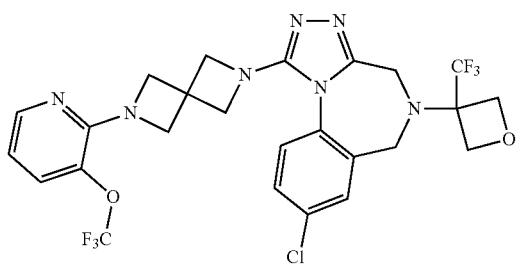 [SMILES: FC(F)(F)Oc1cccnc1N1CC2(C1)CN(c1nnc3n1-c1ccc(Cl)cc1CN(C1(C(F)(F)F)COC1)C3)C2] |
| 396 | 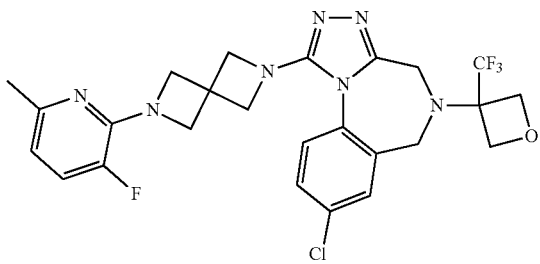 [SMILES: Cc1ccc(F)c(N2CC3(C2)CN(c2nnc4n2-c2ccc(Cl)cc2CN(C2(C(F)(F)F)COC2)C4)C3)n1] |
| 397 | 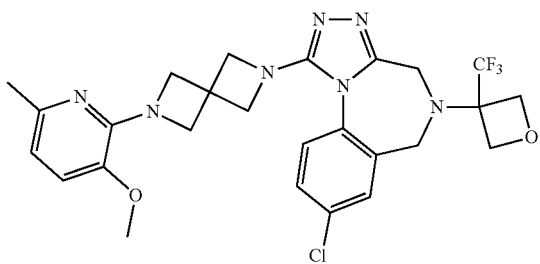 [SMILES: COc1ccc(C)nc1N1CC2(C1)CN(c1nnc3n1-c1ccc(Cl)cc1CN(C1(C(F)(F)F)COC1)C3)C2] |
| 398 | 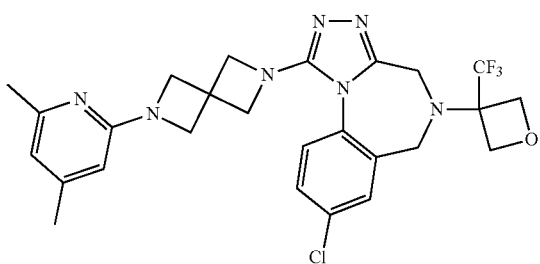 [SMILES: Cc1cc(C)nc(N2CC3(C2)CN(c2nnc4n2-c2ccc(Cl)cc2CN(C2(C(F)(F)F)COC2)C4)C3)c1] |
| 399 | 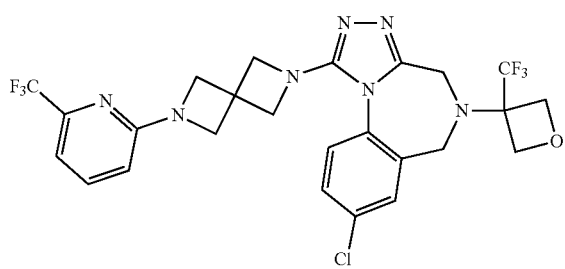 |

TABLE 1-continued

Representative Compounds

| Cmpd. No. | Structure |
|---|---|
| 400 | 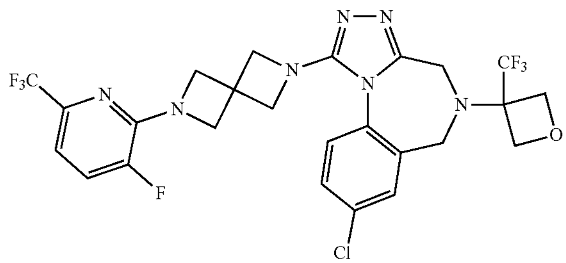 [SMILES: Fc1ccc(C(F)(F)F)nc1N1CC2(C1)CN(c1nnc3n1-c1ccc(Cl)cc1CN(C1(C(F)(F)F)COC1)C3)C2] |
| 401 | 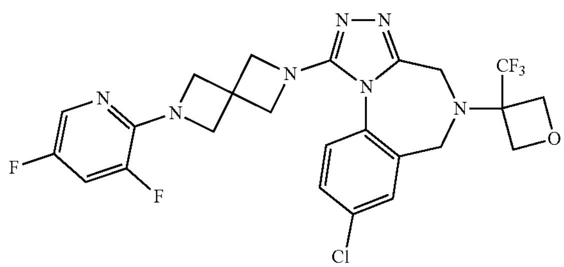 [SMILES: Fc1cnc(N2CC3(C2)CN(c2nnc4n2-c2ccc(Cl)cc2CN(C2(C(F)(F)F)COC2)C4)C3)c(F)c1] |
| 402 | 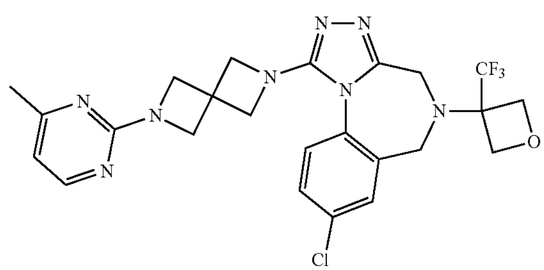 [SMILES: Cc1ccnc(N2CC3(C2)CN(c2nnc4n2-c2ccc(Cl)cc2CN(C2(C(F)(F)F)COC2)C4)C3)n1] |
| 403 | 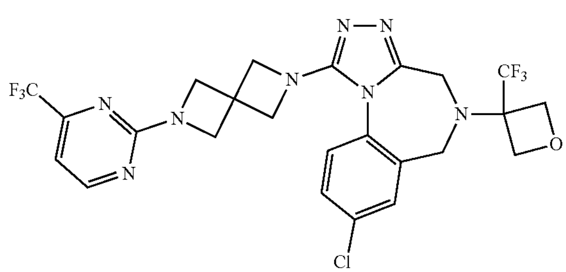 |
| 404 | 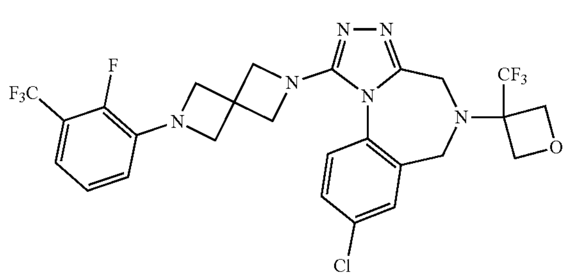 [SMILES: Fc1c(N2CC3(C2)CN(c2nnc4n2-c2ccc(Cl)cc2CN(C2(C(F)(F)F)COC2)C4)C3)cccc1C(F)(F)F] |

TABLE 1-continued
Representative Compounds
| Cmpd. No. | Structure |
|---|---|
| 405 | 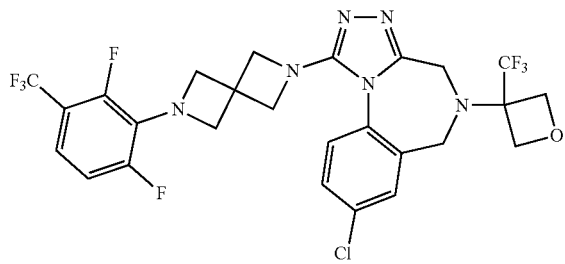 [SMILES: Fc1ccc(C(F)(F)F)c(F)c1N1CC2(C1)CN(c1nnc3n1-c1ccc(Cl)cc1CN(C1(C(F)(F)F)COC1)C3)C2] |
| 406 | 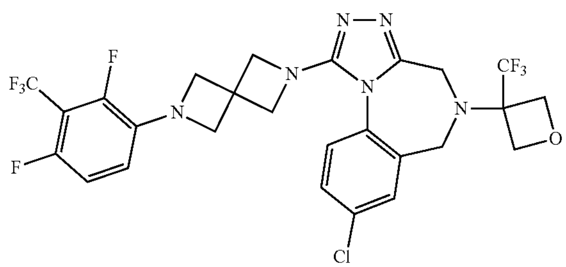 |
| 407 | 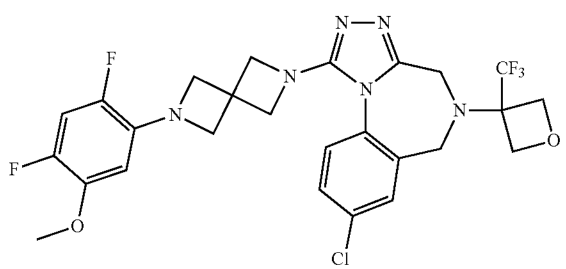 [SMILES: COc1cc(N2CC3(C2)CN(c2nnc4n2-c2ccc(Cl)cc2CN(C2(C(F)(F)F)COC2)C4)C3)c(F)cc1F] |
| 408 | 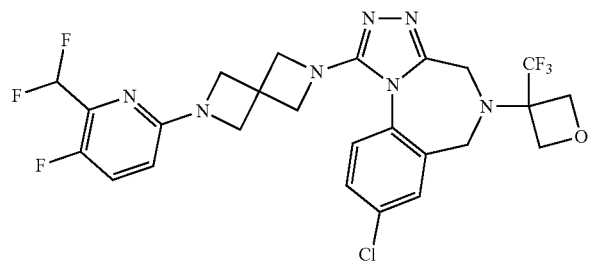 [SMILES: Fc1ccc(N2CC3(C2)CN(c2nnc4n2-c2ccc(Cl)cc2CN(C2(C(F)(F)F)COC2)C4)C3)nc1C(F)F] |
| 409 | 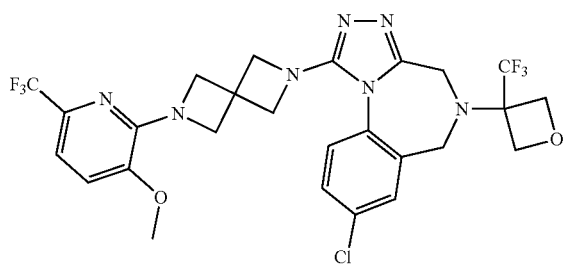 |

TABLE 1-continued
Representative Compounds
| Cmpd. No. | Structure |
|---|---|
| 410 | 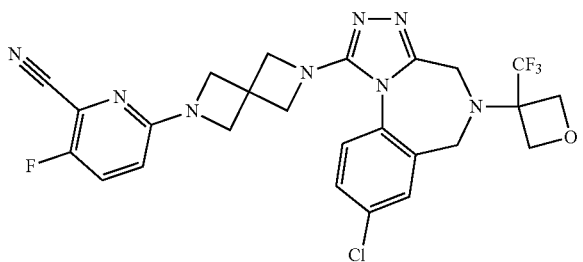 [SMILES: N#Cc1nc(N2CC3(C2)CN(c2nnc4n2-c2ccc(Cl)cc2CN(C2(C(F)(F)F)COC2)C4)C3)ccc1F] |
| 411 | 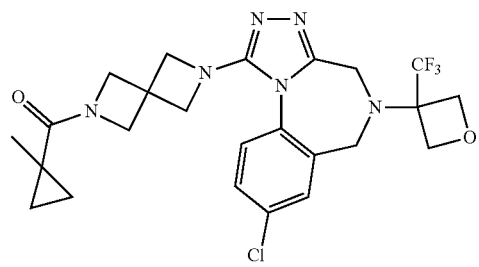 [SMILES: CC1(C(=O)N2CC3(C2)CN(c2nnc4n2-c2ccc(Cl)cc2CN(C2(C(F)(F)F)COC2)C4)C3)CC1] |
| 412 | 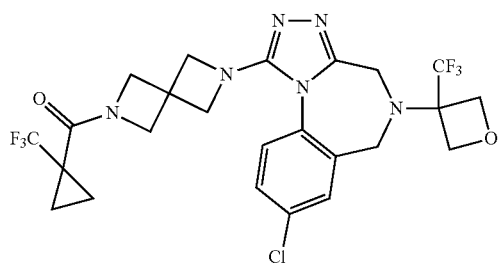 [SMILES: O=C(N1CC2(C1)CN(c1nnc3n1-c1ccc(Cl)cc1CN(C1(C(F)(F)F)COC1)C3)C2)C1(C(F)(F)F)CC1] |
| 413 | 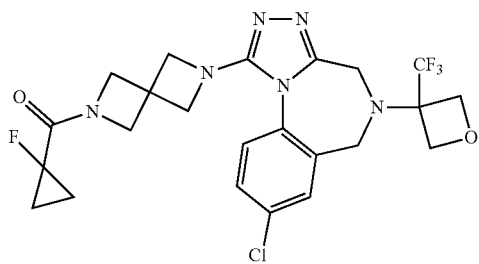 [SMILES: O=C(N1CC2(C1)CN(c1nnc3n1-c1ccc(Cl)cc1CN(C1(C(F)(F)F)COC1)C3)C2)C1(F)CC1] |
| 414 | 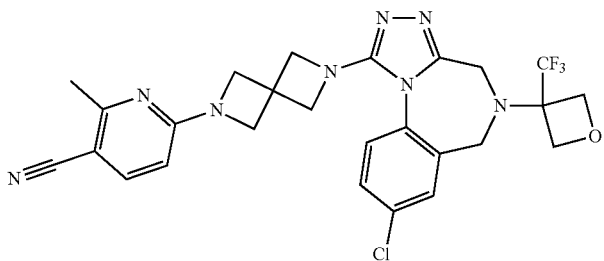 [SMILES: Cc1nc(N2CC3(C2)CN(c2nnc4n2-c2ccc(Cl)cc2CN(C2(C(F)(F)F)COC2)C4)C3)ccc1C#N] |

TABLE 1-continued

Representative Compounds

| Cmpd. No. | Structure |
|---|---|
| 415 | 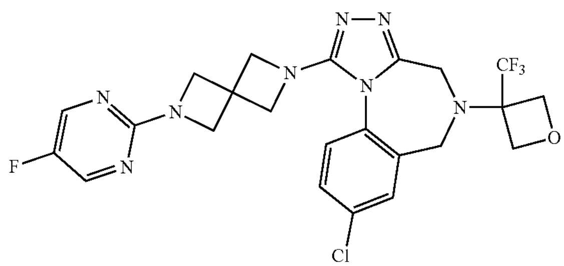 [SMILES: Fc1cnc(N2CC3(C2)CN(c2nnc4n2-c2ccc(Cl)cc2CN(C2(C(F)(F)F)COC2)C4)C3)nc1] |
| 416 | 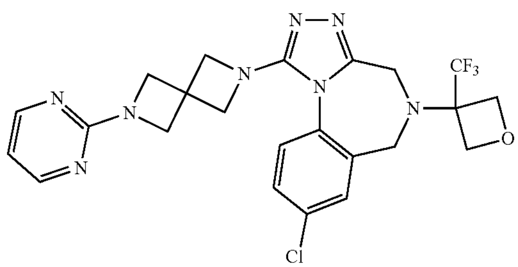 [SMILES: FC(F)(F)C1(N2Cc3cc(Cl)ccc3-n3c(nnc3N3CC4(CN(c5ncccn5)C4)C3)C2)COC1] |
| 417 | 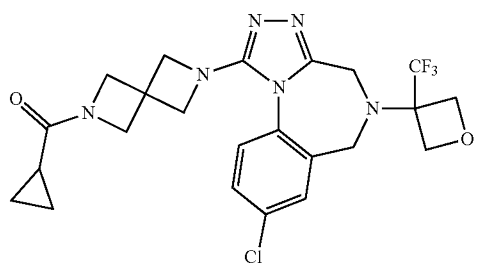 [SMILES: O=C(C1CC1)N1CC2(C1)CN(c1nnc3n1-c1ccc(Cl)cc1CN(C1(C(F)(F)F)COC1)C3)C2] |
| 418 | 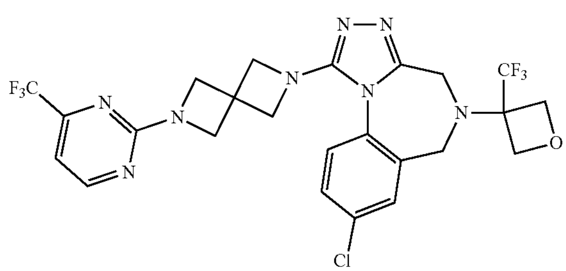 |
| 419 | 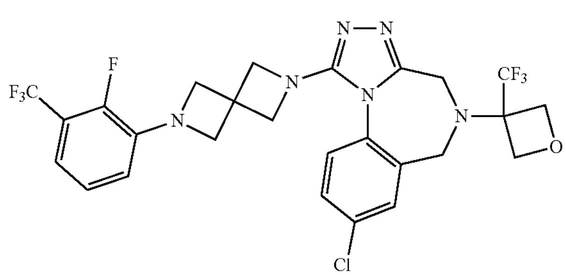 [SMILES: Fc1c(N2CC3(C2)CN(c2nnc4n2-c2ccc(Cl)cc2CN(C2(C(F)(F)F)COC2)C4)C3)cccc1C(F)(F)F] |

TABLE 1-continued

Representative Compounds

| Cmpd. No. | Structure |
|---|---|
| 420 | 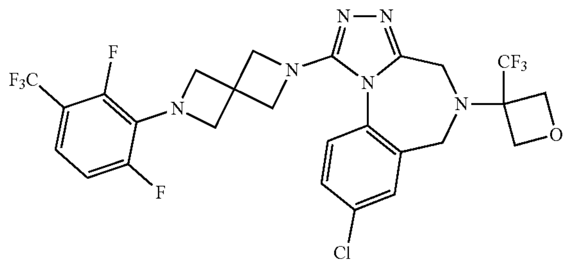 [SMILES: Fc1ccc(C(F)(F)F)c(F)c1N1CC2(C1)CN(c1nnc3n1-c1ccc(Cl)cc1CN(C1(C(F)(F)F)COC1)C3)C2] |
| 421 | 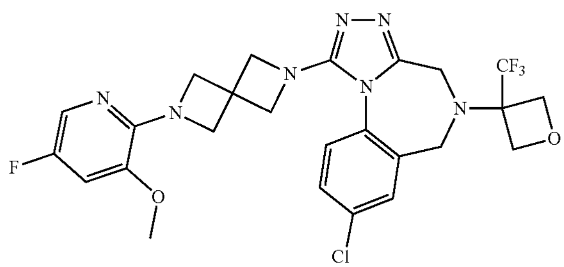 [SMILES: COc1cc(F)cnc1N1CC2(C1)CN(c1nnc3n1-c1ccc(Cl)cc1CN(C1(C(F)(F)F)COC1)C3)C2] |
| 422 | 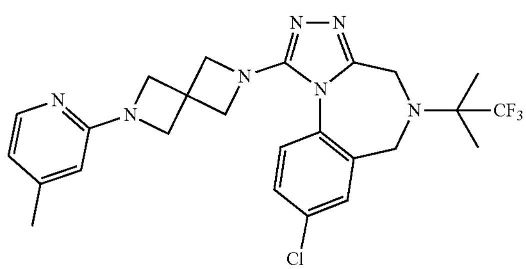 [SMILES: Cc1ccnc(N2CC3(C2)CN(c2nnc4n2-c2ccc(Cl)cc2CN(C(C)(C)C(F)(F)F)C4)C3)c1] |
| 423 | 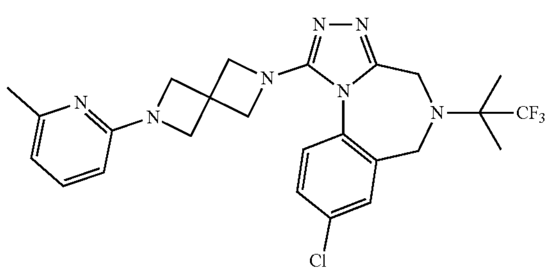 [SMILES: Cc1cccc(N2CC3(C2)CN(c2nnc4n2-c2ccc(Cl)cc2CN(C(C)(C)C(F)(F)F)C4)C3)n1] |
| 424 | 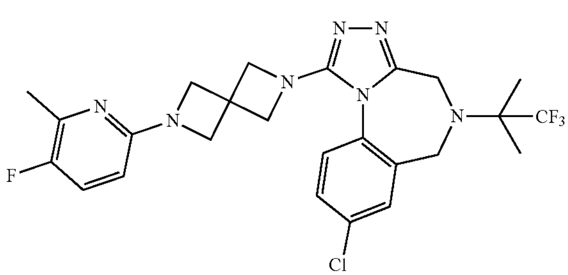 [SMILES: Cc1nc(N2CC3(C2)CN(c2nnc4n2-c2ccc(Cl)cc2CN(C(C)(C)C(F)(F)F)C4)C3)ccc1F] |

TABLE 1-continued

Representative Compounds

| Cmpd. No. | Structure |
|---|---|
| 425 | 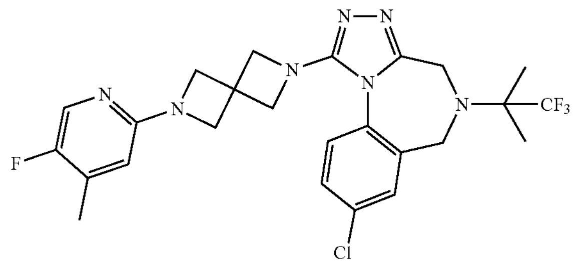 [SMILES: Cc1cc(N2CC3(C2)CN(c2nnc4n2-c2ccc(Cl)cc2CN(C(C)(C)C(F)(F)F)C4)C3)ncc1F] |
| 426 | 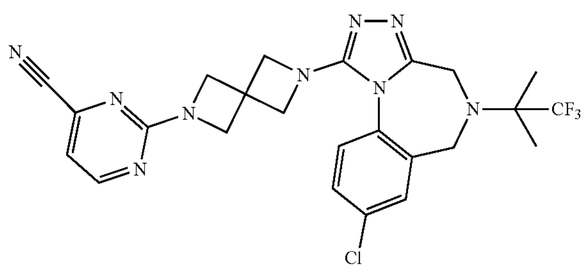 [SMILES: CC(C)(N1Cc2cc(Cl)ccc2-n2c(nnc2N2CC3(CN(c4nccc(C#N)n4)C3)C2)C1)C(F)(F)F] |
| 427 | 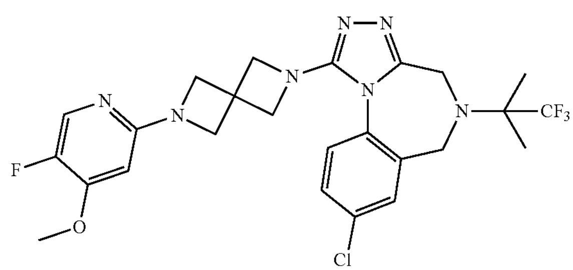 [SMILES: COc1cc(N2CC3(C2)CN(c2nnc4n2-c2ccc(Cl)cc2CN(C(C)(C)C(F)(F)F)C4)C3)ncc1F] |
| 428 | 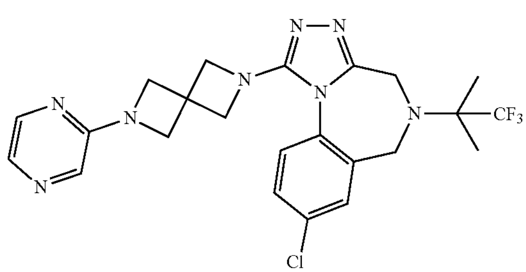 [SMILES: CC(C)(N1Cc2cc(Cl)ccc2-n2c(nnc2N2CC3(CN(c4cnccn4)C3)C2)C1)C(F)(F)F] |
| 429 | 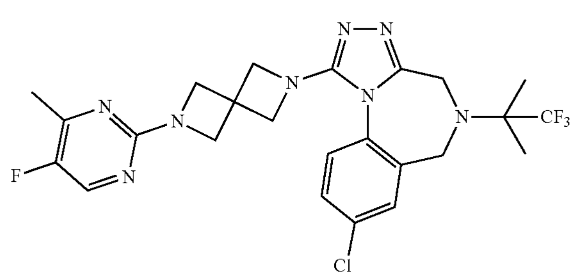 [SMILES: Cc1nc(N2CC3(C2)CN(c2nnc4n2-c2ccc(Cl)cc2CN(C(C)(C)C(F)(F)F)C4)C3)ncc1F] |

TABLE 1-continued
Representative Compounds
| Cmpd. No. | Structure |
|---|---|
| 430 | 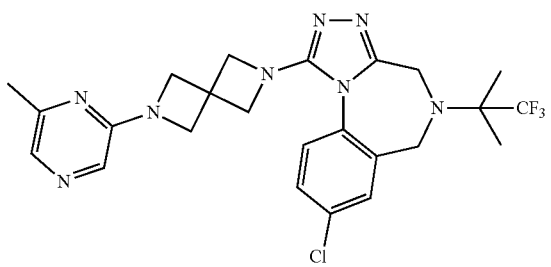 [SMILES: Cc1cncc(N2CC3(C2)CN(c2nnc4n2-c2ccc(Cl)cc2CN(C(C)(C)C(F)(F)F)C4)C3)n1] |
| 431 | 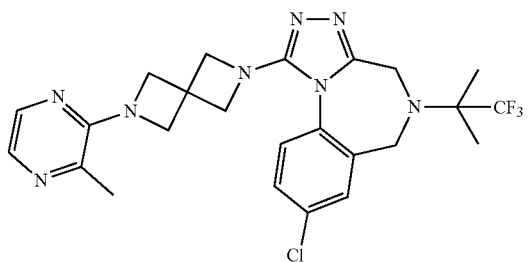 [SMILES: Cc1nccnc1N1CC2(C1)CN(c1nnc3n1-c1ccc(Cl)cc1CN(C(C)(C)C(F)(F)F)C3)C2] |
| 432 | 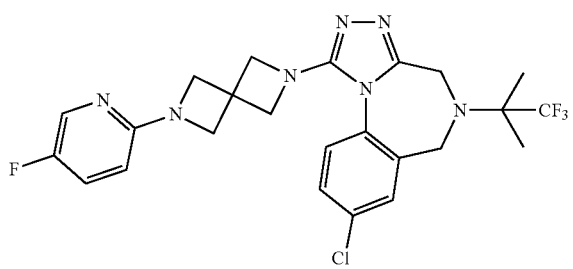 [SMILES: CC(C)(N1Cc2cc(Cl)ccc2-n2c(nnc2N2CC3(CN(c4ccc(F)cn4)C3)C2)C1)C(F)(F)F] |
| 433 | 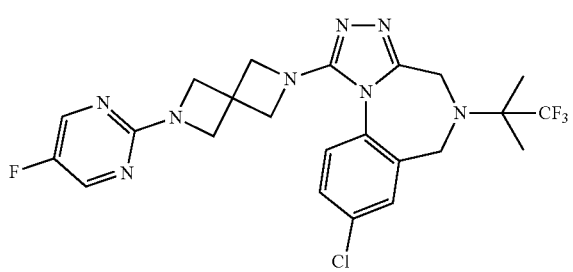 |
| 434 | 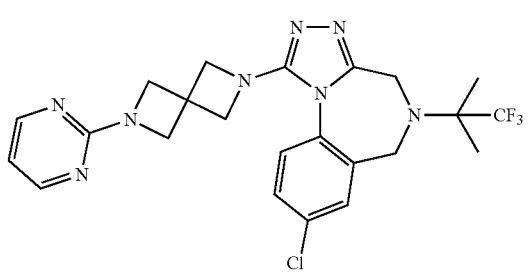 |

TABLE 1-continued

Representative Compounds

| Cmpd. No. | Structure |
|---|---|
| 435 | 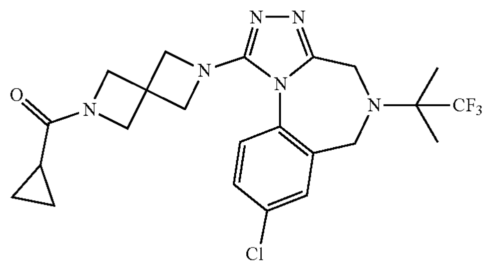 [SMILES: CC(C)(N1Cc2cc(Cl)ccc2-n2c(nnc2N2CC3(CN(C(=O)C4CC4)C3)C2)C1)C(F)(F)F] |
| 436 | 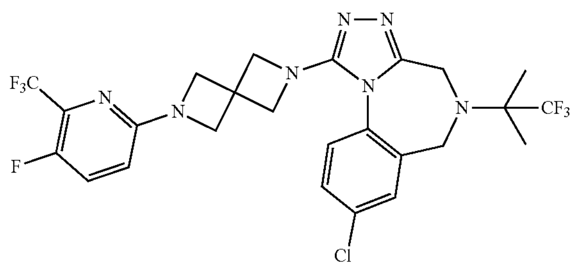 [SMILES: CC(C)(N1Cc2cc(Cl)ccc2-n2c(nnc2N2CC3(CN(c4ccc(F)c(C(F)(F)F)n4)C3)C2)C1)C(F)(F)F] |
| 437 | 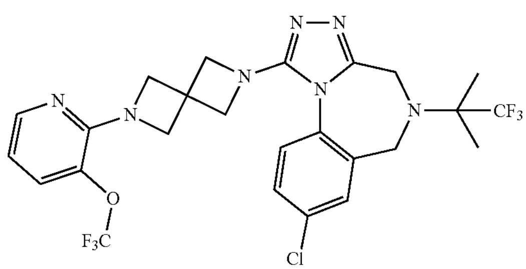 [SMILES: CC(C)(N1Cc2cc(Cl)ccc2-n2c(nnc2N2CC3(CN(c4ncccc4OC(F)(F)F)C3)C2)C1)C(F)(F)F] |
| 438 | 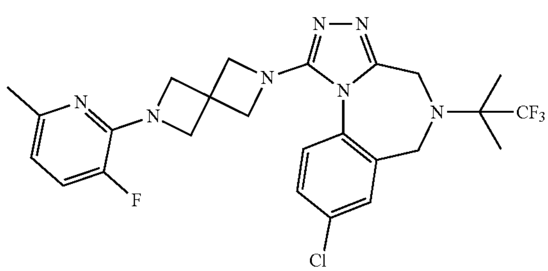 [SMILES: Cc1ccc(F)c(N2CC3(C2)CN(c2nnc4n2-c2ccc(Cl)cc2CN(C(C)(C)C(F)(F)F)C4)C3)n1] |
| 439 | 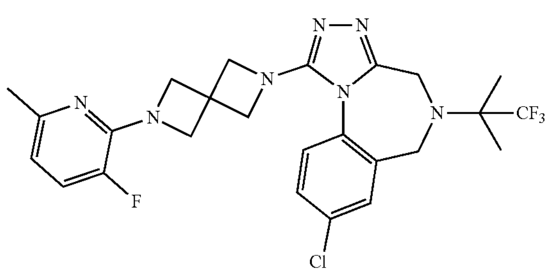 [SMILES: Cc1ccc(F)c(N2CC3(C2)CN(c2nnc4n2-c2ccc(Cl)cc2CN(C(C)(C)C(F)(F)F)C4)C3)n1] |

TABLE 1-continued
Representative Compounds
| Cmpd. No. | Structure |
|---|---|
| 440 | 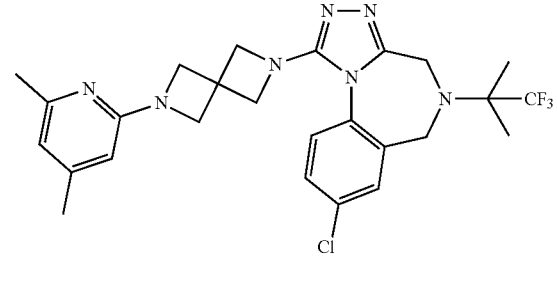 [SMILES: Cc1cc(C)nc(N2CC3(C2)CN(c2nnc4n2-c2ccc(Cl)cc2CN(C(C)(C)C(F)(F)F)C4)C3)c1] |
| 441 | 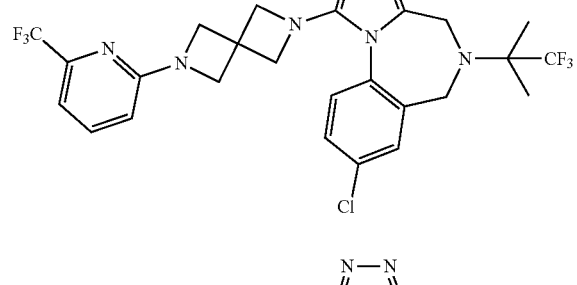 |
| 442 | 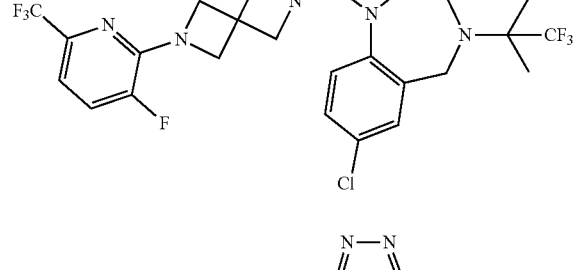 |
| 443 | 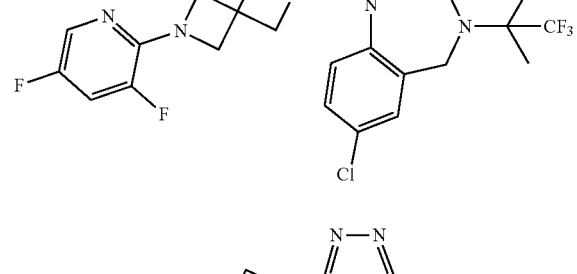 |
| 444 | 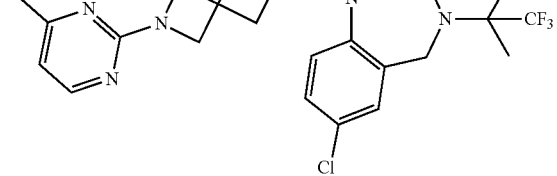 |

TABLE 1-continued

Representative Compounds

| Cmpd. No. | Structure |
|---|---|
| 445 | 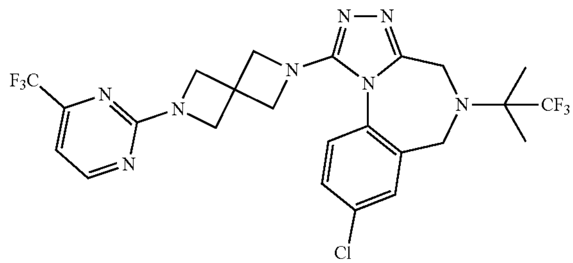 [SMILES: CC(C)(N1Cc2cc(Cl)ccc2-n2c(nnc2N2CC3(CN(c4nccc(C(F)(F)F)n4)C3)C2)C1)C(F)(F)F] |
| 446 | 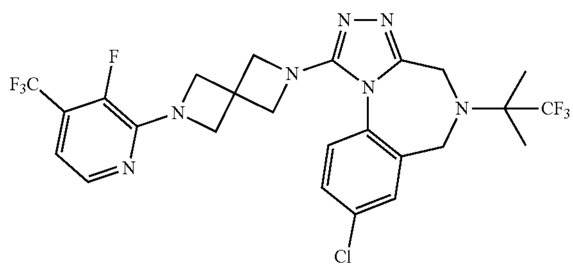 [SMILES: CC(C)(N1Cc2cc(Cl)ccc2-n2c(nnc2N2CC3(CN(c4nccc(C(F)(F)F)c4F)C3)C2)C1)C(F)(F)F] |
| 447 | 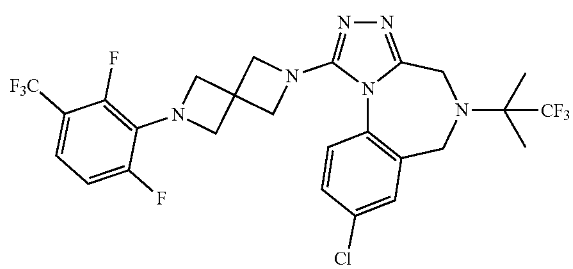 [SMILES: CC(C)(N1Cc2cc(Cl)ccc2-n2c(nnc2N2CC3(CN(c4c(F)ccc(C(F)(F)F)c4F)C3)C2)C1)C(F)(F)F] |
| 448 | 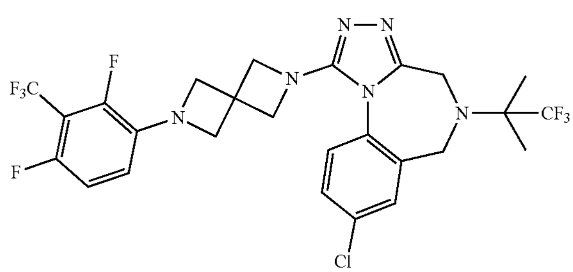 [SMILES: CC(C)(N1Cc2cc(Cl)ccc2-n2c(nnc2N2CC3(CN(c4ccc(F)c(C(F)(F)F)c4F)C3)C2)C1)C(F)(F)F] |
| 449 | 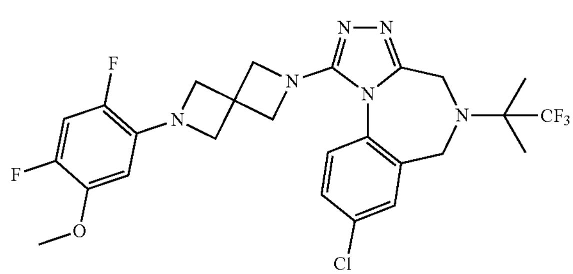 [SMILES: COc1cc(N2CC3(C2)CN(c2nnc4n2-c2ccc(Cl)cc2CN(C(C)(C)C(F)(F)F)C4)C3)c(F)cc1F] |

TABLE 1-continued

Representative Compounds

| Cmpd. No. | Structure |
|---|---|
| 450 | 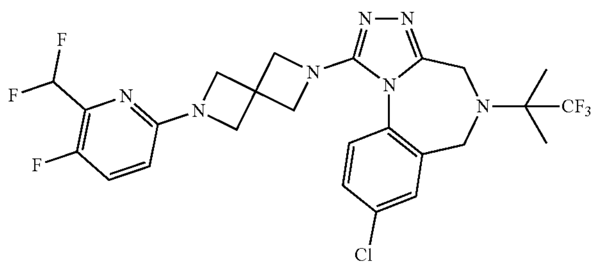 [SMILES: CC(C)(N1Cc2cc(Cl)ccc2-n2c(nnc2N2CC3(CN(c4ccc(F)c(C(F)F)n4)C3)C2)C1)C(F)(F)F] |
| 451 | 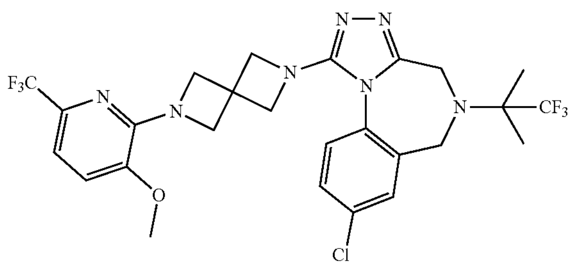 [SMILES: COc1ccc(C(F)(F)F)nc1N1CC2(C1)CN(c1nnc3n1-c1ccc(Cl)cc1CN(C(C)(C)C(F)(F)F)C3)C2] |
| 452 | 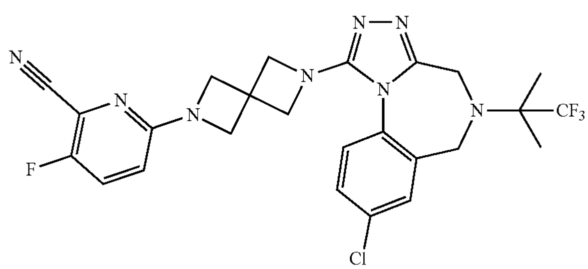 [SMILES: CC(C)(N1Cc2cc(Cl)ccc2-n2c(nnc2N2CC3(CN(c4ccc(F)c(C#N)n4)C3)C2)C1)C(F)(F)F] |
| 453 | 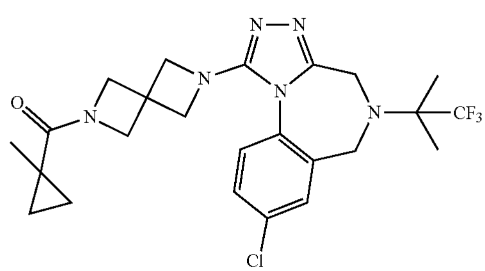 [SMILES: CC1(C(=O)N2CC3(C2)CN(c2nnc4n2-c2ccc(Cl)cc2CN(C(C)(C)C(F)(F)F)C4)C3)CC1] |
| 454 | 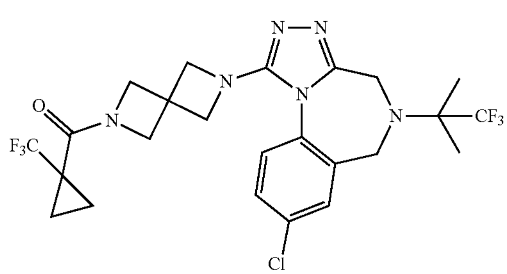 [SMILES: CC(C)(N1Cc2cc(Cl)ccc2-n2c(nnc2N2CC3(CN(C(=O)C4(C(F)(F)F)CC4)C3)C2)C1)C(F)(F)F] |

TABLE 1-continued

Representative Compounds

| Cmpd. No. | Structure |
|---|---|
| 455 | 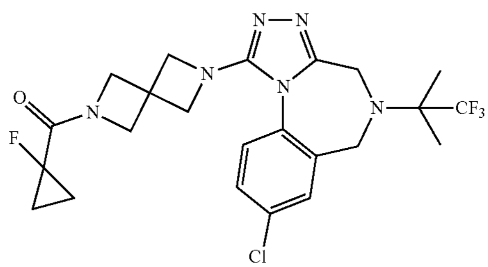 [SMILES: CC(C)(N1Cc2cc(Cl)ccc2-n2c(nnc2N2CC3(CN(C(=O)C4(F)CC4)C3)C2)C1)C(F)(F)F] |
| 456 | 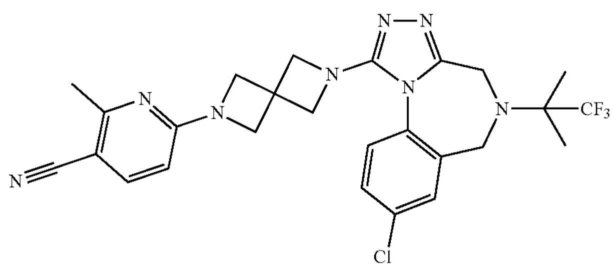 [SMILES: Cc1nc(N2CC3(C2)CN(c2nnc4n2-c2ccc(Cl)cc2CN(C(C)(C)C(F)(F)F)C4)C3)ccc1C#N] |
| 457 | 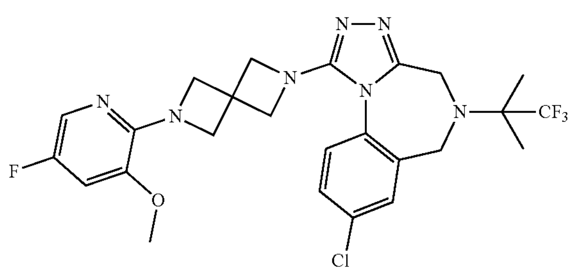 |
| 458 | 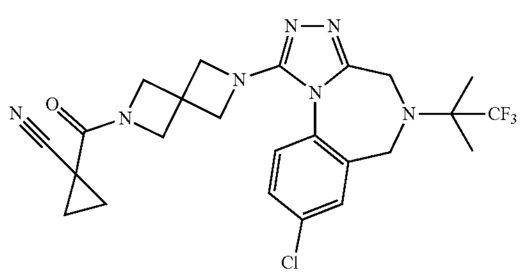 [SMILES: CC(C)(N1Cc2cc(Cl)ccc2-n2c(nnc2N2CC3(CN(C(=O)C4(C#N)CC4)C3)C2)C1)C(F)(F)F] |
| 459 | 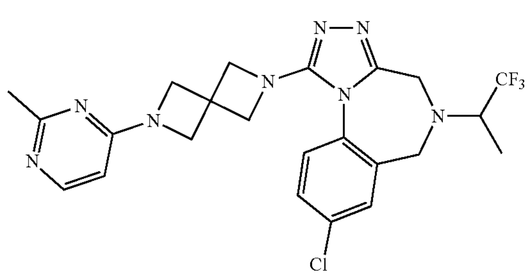 [SMILES: Cc1nccc(N2CC3(C2)CN(c2nnc4n2-c2ccc(Cl)cc2CN(C(C)C(F)(F)F)C4)C3)n1] |

TABLE 1-continued

Representative Compounds

| Cmpd. No. | Structure |
|---|---|
| 460 | 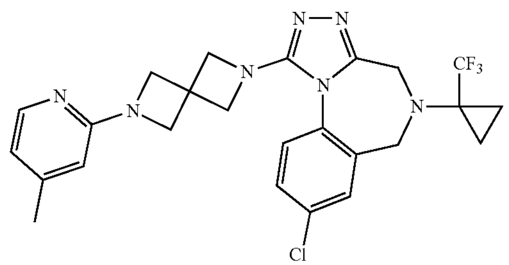 |
| 461 | 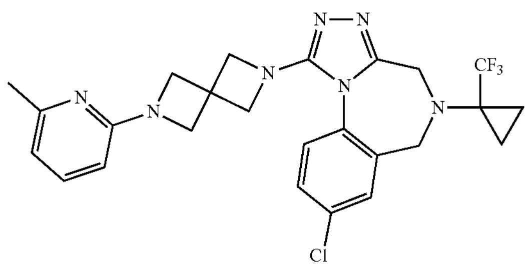 |
| 462 | 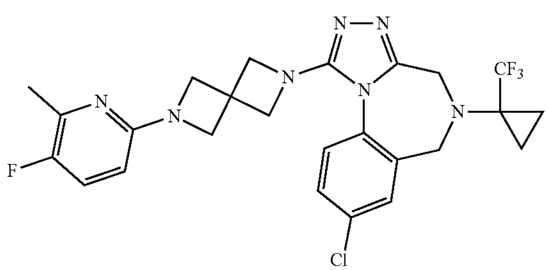 |
| 463 | 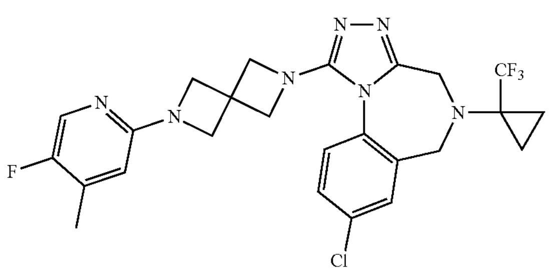 [SMILES: Cc1cc(N2CC3(C2)CN(c2nnc4n2-c2ccc(Cl)cc2CN(C2(C(F)(F)F)CC2)C4)C3)ncc1F] |
| 464 | 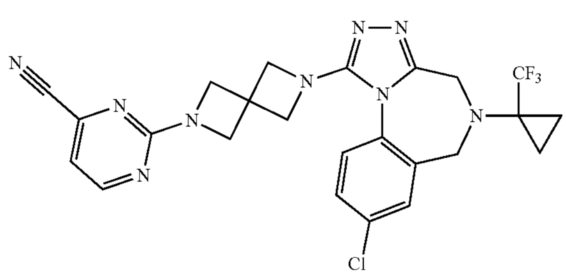 [SMILES: N#Cc1ccnc(N2CC3(C2)CN(c2nnc4n2-c2ccc(Cl)cc2CN(C2(C(F)(F)F)CC2)C4)C3)n1] |

TABLE 1-continued

Representative Compounds

| Cmpd. No. | Structure |
|---|---|
| 465 | 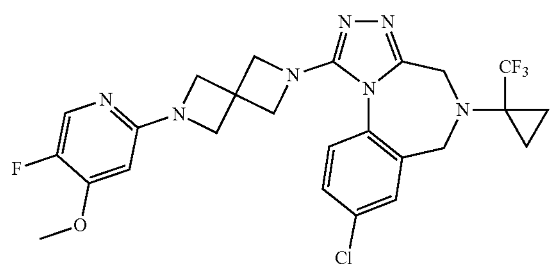 [SMILES: COc1cc(N2CC3(C2)CN(c2nnc4n2-c2ccc(Cl)cc2CN(C2(C(F)(F)F)CC2)C4)C3)ncc1F] |
| 466 | 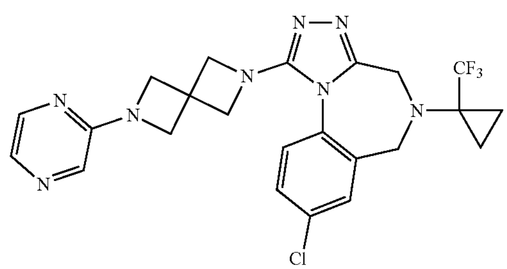 [SMILES: FC(F)(F)C1(N2Cc3cc(Cl)ccc3-n3c(nnc3N3CC4(CN(c5cnccn5)C4)C3)C2)CC1] |
| 467 | 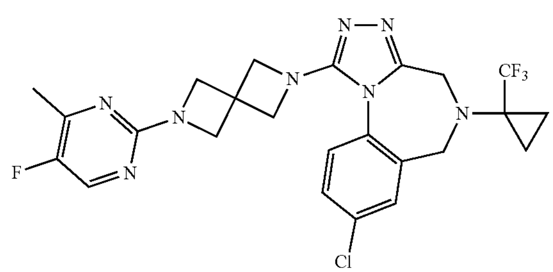 [SMILES: Cc1nc(N2CC3(C2)CN(c2nnc4n2-c2ccc(Cl)cc2CN(C2(C(F)(F)F)CC2)C4)C3)ncc1F] |
| 468 | 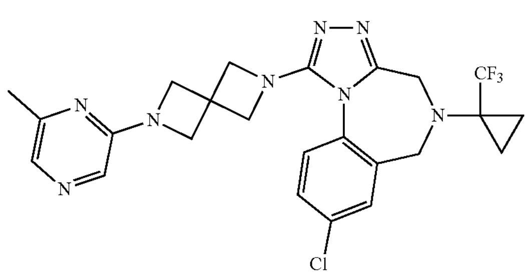 [SMILES: Cc1cncc(N2CC3(C2)CN(c2nnc4n2-c2ccc(Cl)cc2CN(C2(C(F)(F)F)CC2)C4)C3)n1] |
| 469 | 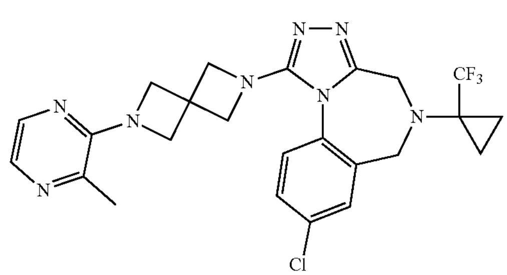 [SMILES: Cc1nccnc1N1CC2(C1)CN(c1nnc3n1-c1ccc(Cl)cc1CN(C1(C(F)(F)F)CC1)C3)C2] |

TABLE 1-continued

Representative Compounds

| Cmpd. No. | Structure |
|---|---|
| 470 | 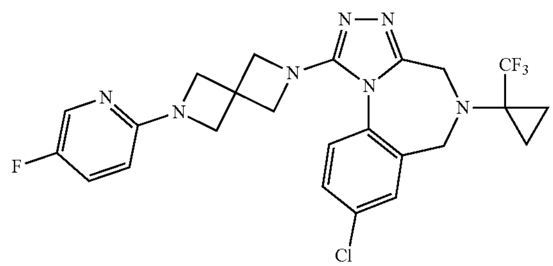 [SMILES: Fc1ccc(N2CC3(C2)CN(c2nnc4n2-c2ccc(Cl)cc2CN(C2(C(F)(F)F)CC2)C4)C3)nc1] |
| 471 | 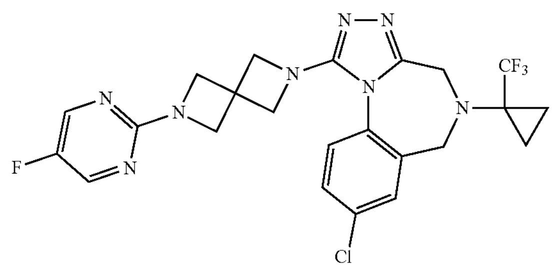 [SMILES: Fc1cnc(N2CC3(C2)CN(c2nnc4n2-c2ccc(Cl)cc2CN(C2(C(F)(F)F)CC2)C4)C3)nc1] |
| 472 | 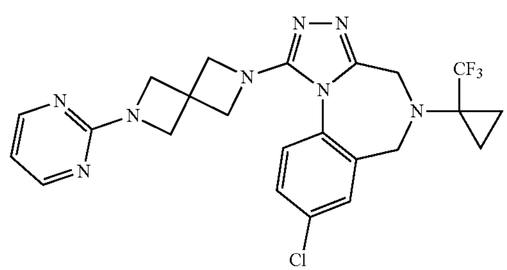 [SMILES: FC(F)(F)C1(N2Cc3cc(Cl)ccc3-n3c(nnc3N3CC4(CN(c5ncccn5)C4)C3)C2)CC1] |
| 473 | 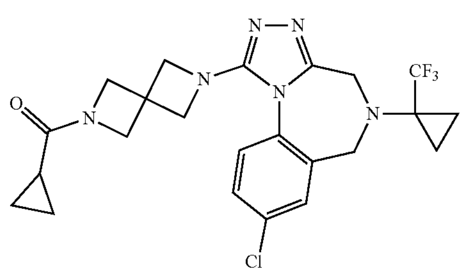 [SMILES: O=C(C1CC1)N1CC2(C1)CN(c1nnc3n1-c1ccc(Cl)cc1CN(C1(C(F)(F)F)CC1)C3)C2] |
| 474 | 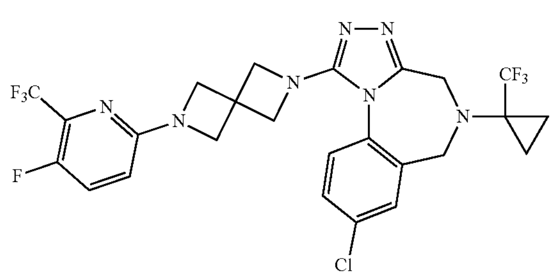 |

TABLE 1-continued

Representative Compounds

| Cmpd. No. | Structure |
|---|---|
| 475 | 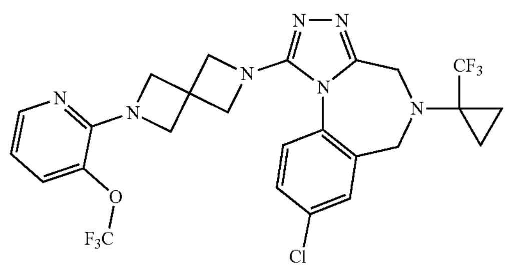 [SMILES: FC(F)(F)Oc1cccnc1N1CC2(C1)CN(c1nnc3n1-c1ccc(Cl)cc1CN(C1(C(F)(F)F)CC1)C3)C2] |
| 476 | 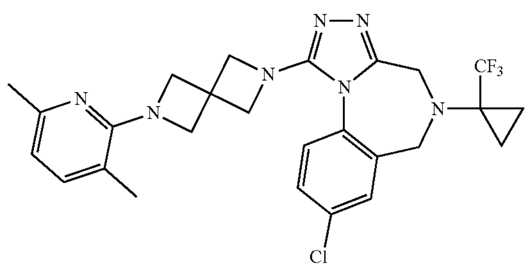 [SMILES: Cc1ccc(C)c(N2CC3(C2)CN(c2nnc4n2-c2ccc(Cl)cc2CN(C2(C(F)(F)F)CC2)C4)C3)n1] |
| 477 | 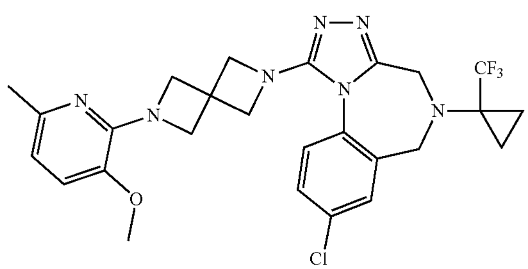 [SMILES: COc1ccc(C)nc1N1CC2(C1)CN(c1nnc3n1-c1ccc(Cl)cc1CN(C1(C(F)(F)F)CC1)C3)C2] |
| 478 | 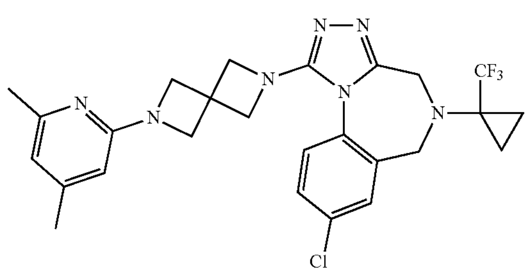 [SMILES: Cc1cc(C)nc(N2CC3(C2)CN(c2nnc4n2-c2ccc(Cl)cc2CN(C2(C(F)(F)F)CC2)C4)C3)c1] |
| 479 | 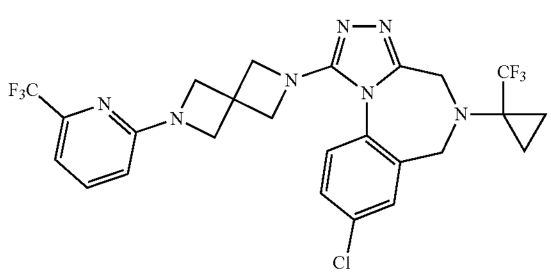 [SMILES: FC(F)(F)c1cccc(N2CC3(C2)CN(c2nnc4n2-c2ccc(Cl)cc2CN(C2(C(F)(F)F)CC2)C4)C3)n1] |

TABLE 1-continued
Representative Compounds
| Cmpd. No. | Structure |
|---|---|
| 480 | 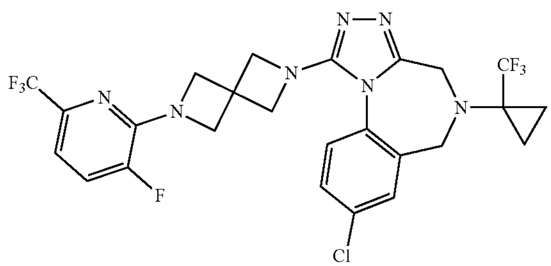 [SMILES: Fc1ccc(C(F)(F)F)nc1N1CC2(C1)CN(c1nnc3n1-c1ccc(Cl)cc1CN(C1(C(F)(F)F)CC1)C3)C2] |
| 481 | 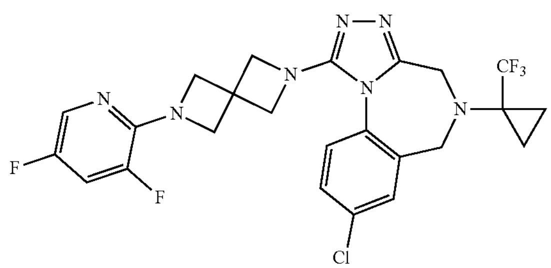 [SMILES: Fc1cnc(N2CC3(C2)CN(c2nnc4n2-c2ccc(Cl)cc2CN(C2(C(F)(F)F)CC2)C4)C3)c(F)c1] |
| 482 | 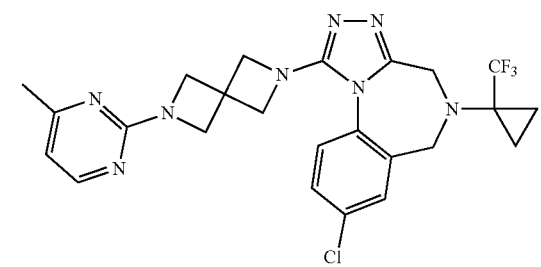 [SMILES: Cc1ccnc(N2CC3(C2)CN(c2nnc4n2-c2ccc(Cl)cc2CN(C2(C(F)(F)F)CC2)C4)C3)n1] |
| 483 | 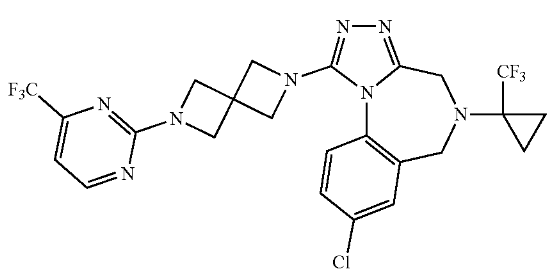 [SMILES: FC(F)(F)c1ccnc(N2CC3(C2)CN(c2nnc4n2-c2ccc(Cl)cc2CN(C2(C(F)(F)F)CC2)C4)C3)n1] |
| 484 | 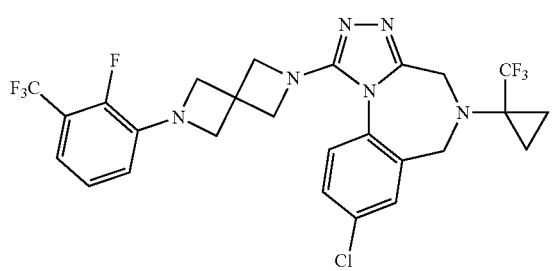 [SMILES: Fc1c(N2CC3(C2)CN(c2nnc4n2-c2ccc(Cl)cc2CN(C2(C(F)(F)F)CC2)C4)C3)cccc1C(F)(F)F] |

TABLE 1-continued
Representative Compounds
| Cmpd. No. | Structure |
|---|---|
| 485 | 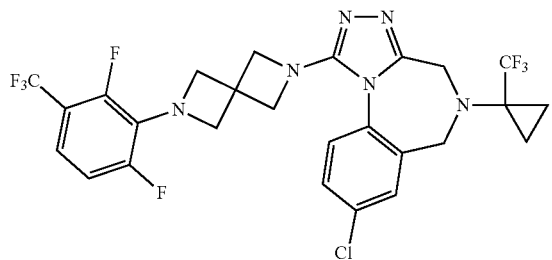 [SMILES: Fc1ccc(C(F)(F)F)c(F)c1N1CC2(C1)CN(c1nnc3n1-c1ccc(Cl)cc1CN(C1(C(F)(F)F)CC1)C3)C2] |
| 486 | 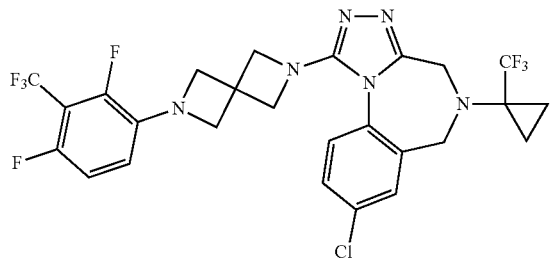 [SMILES: Fc1ccc(N2CC3(C2)CN(c2nnc4n2-c2ccc(Cl)cc2CN(C2(C(F)(F)F)CC2)C4)C3)c(F)c1C(F)(F)F] |
| 487 | 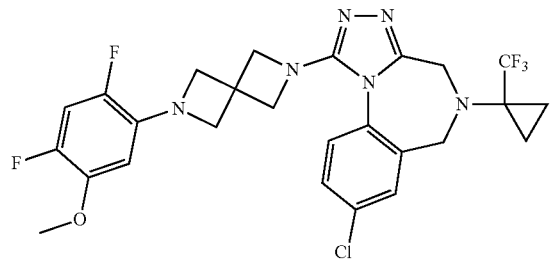 [SMILES: COc1cc(N2CC3(C2)CN(c2nnc4n2-c2ccc(Cl)cc2CN(C2(C(F)(F)F)CC2)C4)C3)c(F)cc1F] |
| 488 | 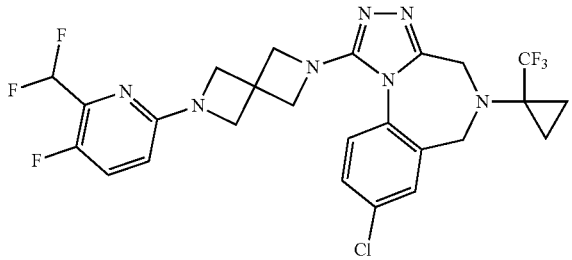 [SMILES: Fc1ccc(N2CC3(C2)CN(c2nnc4n2-c2ccc(Cl)cc2CN(C2(C(F)(F)F)CC2)C4)C3)nc1C(F)F] |
| 489 | 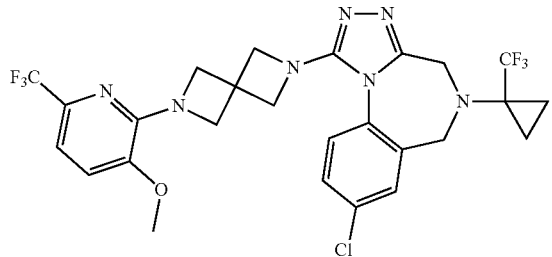 |

TABLE 1-continued

Representative Compounds

| Cmpd. No. | Structure |
|---|---|
| 490 | 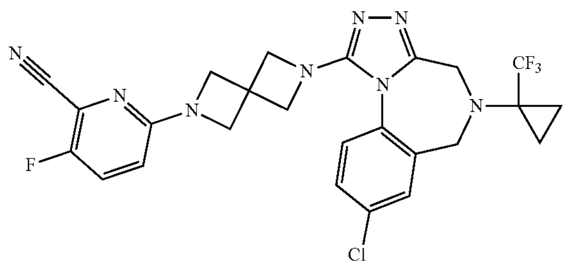 [SMILES: N#Cc1nc(N2CC3(C2)CN(c2nnc4n2-c2ccc(Cl)cc2CN(C2(C(F)(F)F)CC2)C4)C3)ccc1F] |
| 491 | 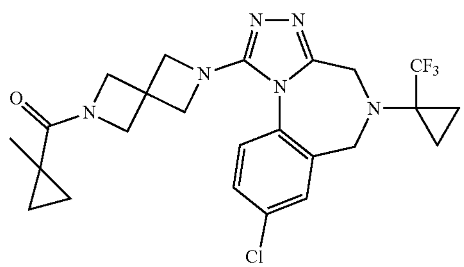 [SMILES: CC1(C(=O)N2CC3(C2)CN(c2nnc4n2-c2ccc(Cl)cc2CN(C2(C(F)(F)F)CC2)C4)C3)CC1] |
| 492 | 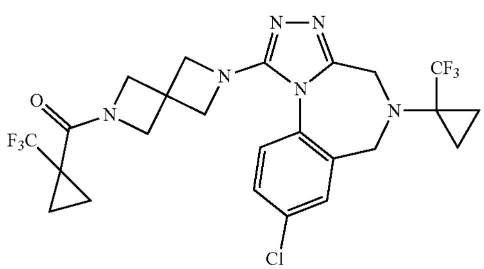 [SMILES: O=C(N1CC2(C1)CN(c1nnc3n1-c1ccc(Cl)cc1CN(C1(C(F)(F)F)CC1)C3)C2)C1(C(F)(F)F)CC1] |
| 493 | 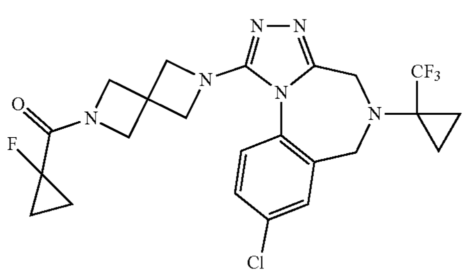 [SMILES: O=C(N1CC2(C1)CN(c1nnc3n1-c1ccc(Cl)cc1CN(C1(C(F)(F)F)CC1)C3)C2)C1(F)CC1] |
| 494 | 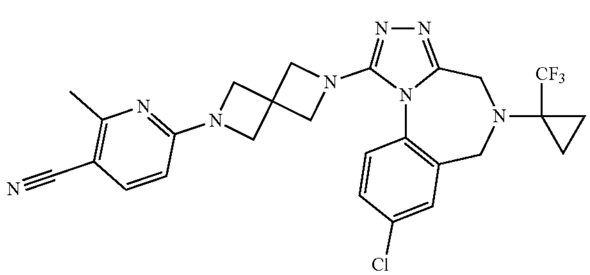 [SMILES: Cc1nc(N2CC3(C2)CN(c2nnc4n2-c2ccc(Cl)cc2CN(C2(C(F)(F)F)CC2)C4)C3)ccc1C#N] |

TABLE 1-continued
Representative Compounds
| Cmpd. No. | Structure |
|---|---|
| 495 | 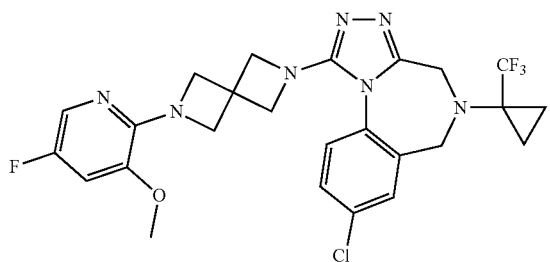 [SMILES: COc1cc(F)cnc1N1CC2(C1)CN(c1nnc3n1-c1ccc(Cl)cc1CN(C1(C(F)(F)F)CC1)C3)C2] |
| 496 | 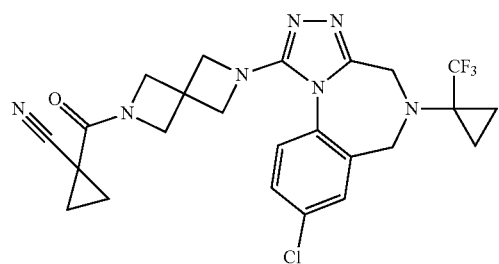 [SMILES: N#CC1(C(=O)N2CC3(C2)CN(c2nnc4n2-c2ccc(Cl)cc2CN(C2(C(F)(F)F)CC2)C4)C3)CC1] |
| 497 | 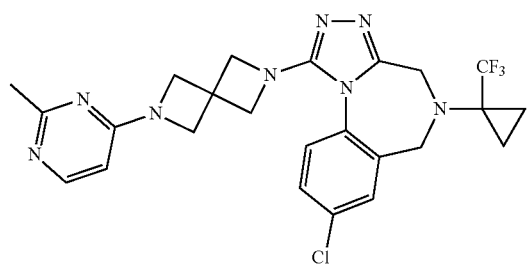 [SMILES: Cc1nccc(N2CC3(C2)CN(c2nnc4n2-c2ccc(Cl)cc2CN(C2(C(F)(F)F)CC2)C4)C3)n1] |
| 498 | 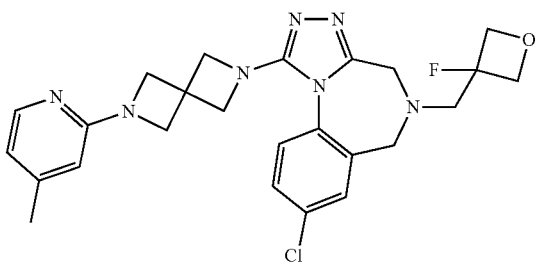 [SMILES: Cc1ccnc(N2CC3(C2)CN(c2nnc4n2-c2ccc(Cl)cc2CN(CC2(F)COC2)C4)C3)c1] |
| 499 | 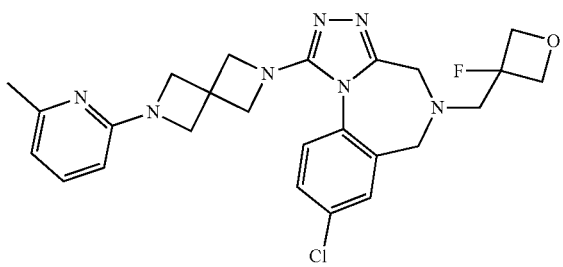 |

TABLE 1-continued
Representative Compounds
| Cmpd. No. | Structure |
|---|---|
| 500 | 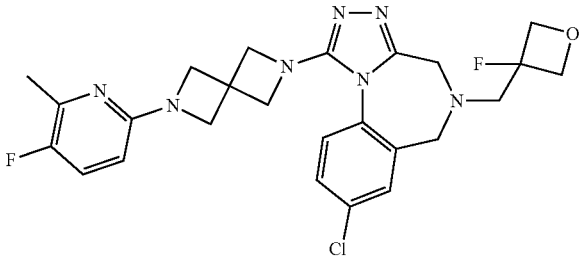 [SMILES: Cc1nc(N2CC3(C2)CN(c2nnc4n2-c2ccc(Cl)cc2CN(CC2(F)COC2)C4)C3)ccc1F] |
| 501 | 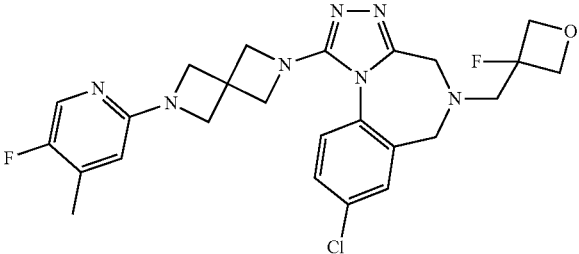 [SMILES: Cc1cc(N2CC3(C2)CN(c2nnc4n2-c2ccc(Cl)cc2CN(CC2(F)COC2)C4)C3)ncc1F] |
| 502 | 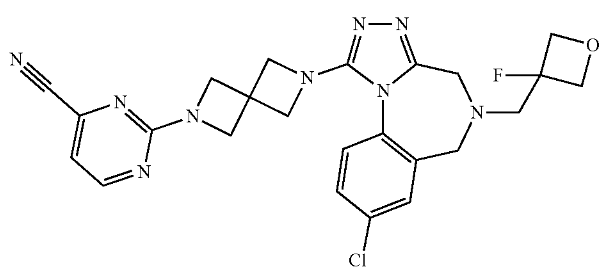 [SMILES: N#Cc1ccnc(N2CC3(C2)CN(c2nnc4n2-c2ccc(Cl)cc2CN(CC2(F)COC2)C4)C3)n1] |
| 503 | 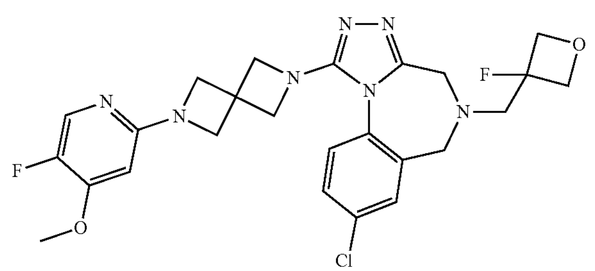 [SMILES: COc1cc(N2CC3(C2)CN(c2nnc4n2-c2ccc(Cl)cc2CN(CC2(F)COC2)C4)C3)ncc1F] |
| 504 | 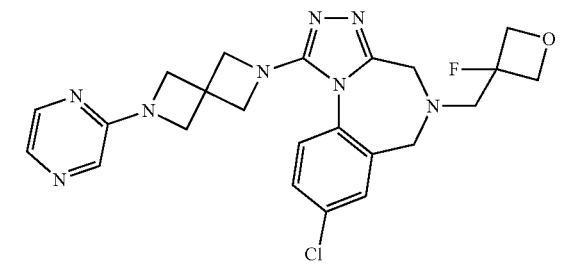 |

TABLE 1-continued
Representative Compounds
| Cmpd. No. | Structure |
|---|---|
| 505 | 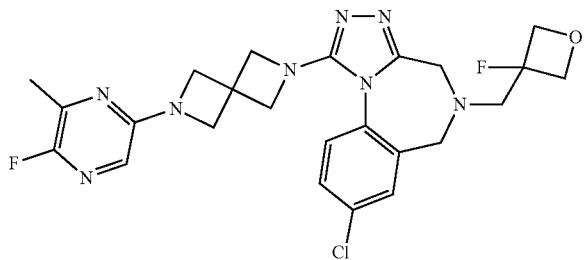 [SMILES: Cc1nc(N2CC3(C2)CN(c2nnc4n2-c2ccc(Cl)cc2CN(CC2(F)COC2)C4)C3)cnc1F] |
| 506 | 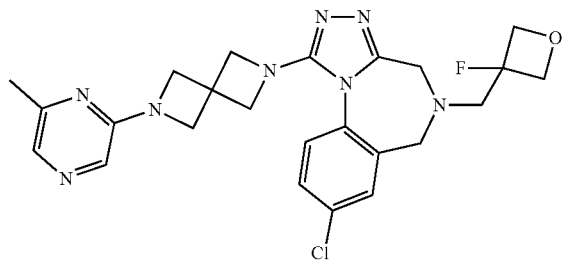 [SMILES: Cc1cncc(N2CC3(C2)CN(c2nnc4n2-c2ccc(Cl)cc2CN(CC2(F)COC2)C4)C3)n1] |
| 507 | 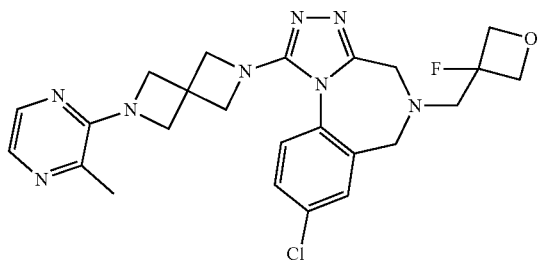 [SMILES: Cc1nccnc1N1CC2(C1)CN(c1nnc3n1-c1ccc(Cl)cc1CN(CC1(F)COC1)C3)C2] |
| 508 | 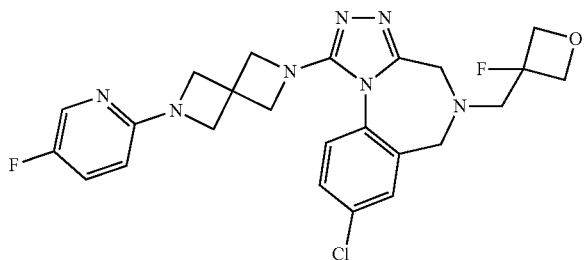 [SMILES: Fc1ccc(N2CC3(C2)CN(c2nnc4n2-c2ccc(Cl)cc2CN(CC2(F)COC2)C4)C3)nc1] |
| 509 | 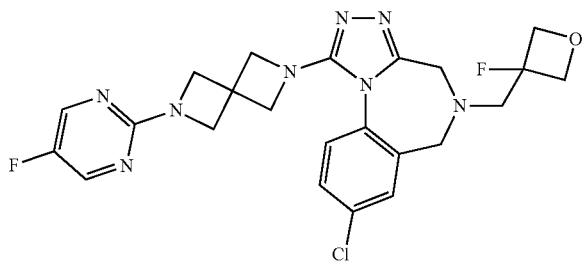 [SMILES: Fc1cnc(N2CC3(C2)CN(c2nnc4n2-c2ccc(Cl)cc2CN(CC2(F)COC2)C4)C3)nc1] |

TABLE 1-continued

Representative Compounds

| Cmpd. No. | Structure |
|---|---|
| 510 | 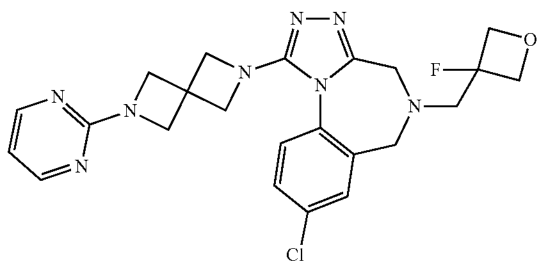 [SMILES: FC1(CN2Cc3cc(Cl)ccc3-n3c(nnc3N3CC4(CN(c5ncccn5)C4)C3)C2)COC1] |
| 511 | 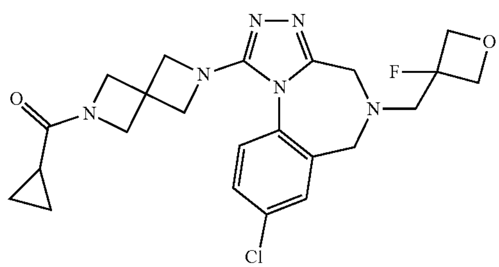 [SMILES: O=C(C1CC1)N1CC2(C1)CN(c1nnc3n1-c1ccc(Cl)cc1CN(CC1(F)COC1)C3)C2] |
| 512 | 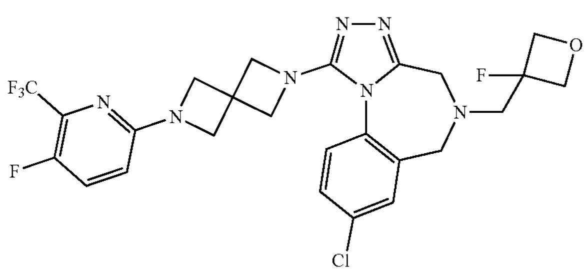 |
| 513 | 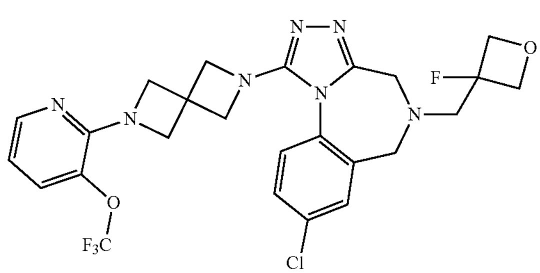 [SMILES: FC1(CN2Cc3cc(Cl)ccc3-n3c(nnc3N3CC4(CN(c5ncccc5OC(F)(F)F)C4)C3)C2)COC1] |
| 514 | 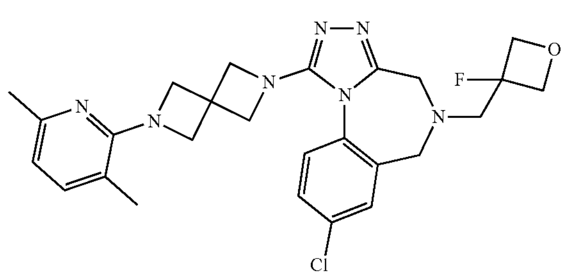 [SMILES: Cc1ccc(C)c(N2CC3(C2)CN(c2nnc4n2-c2ccc(Cl)cc2CN(CC2(F)COC2)C4)C3)n1] |

TABLE 1-continued

Representative Compounds

| Cmpd. No. | Structure |
|---|---|
| 515 | 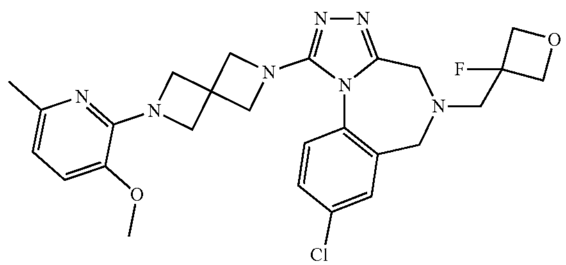 [SMILES: COc1ccc(C)nc1N1CC2(C1)CN(c1nnc3n1-c1ccc(Cl)cc1CN(CC1(F)COC1)C3)C2] |
| 516 | 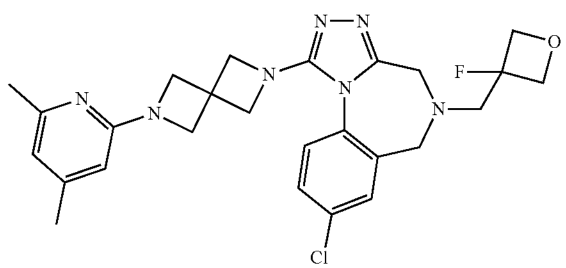 [SMILES: Cc1cc(C)nc(N2CC3(C2)CN(c2nnc4n2-c2ccc(Cl)cc2CN(CC2(F)COC2)C4)C3)c1] |
| 517 | 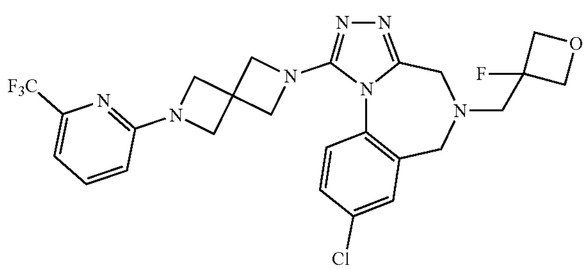 [SMILES: FC1(CN2Cc3cc(Cl)ccc3-n3c(nnc3N3CC4(CN(c5cccc(C(F)(F)F)n5)C4)C3)C2)COC1] |
| 518 | 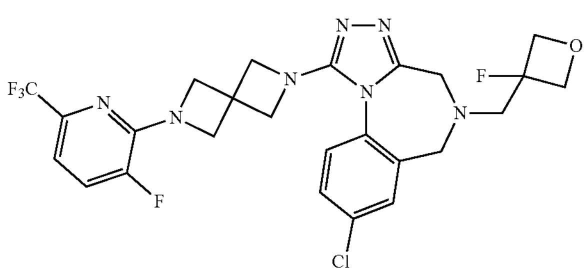 [SMILES: Fc1ccc(C(F)(F)F)nc1N1CC2(C1)CN(c1nnc3n1-c1ccc(Cl)cc1CN(CC1(F)COC1)C3)C2] |
| 519 | 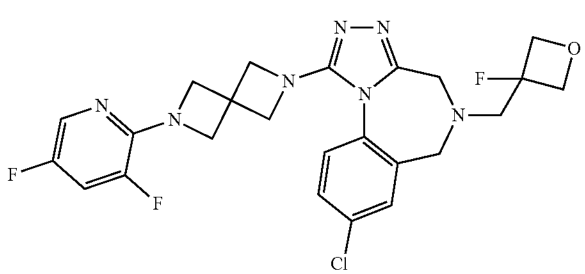 [SMILES: Fc1cnc(N2CC3(C2)CN(c2nnc4n2-c2ccc(Cl)cc2CN(CC2(F)COC2)C4)C3)c(F)c1] |

TABLE 1-continued
Representative Compounds
| Cmpd. No. | Structure |
|---|---|
| 520 | 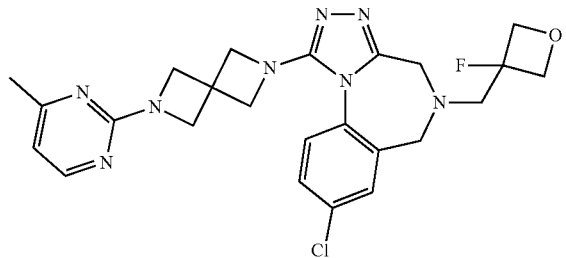 [SMILES: Cc1ccnc(N2CC3(C2)CN(c2nnc4n2-c2ccc(Cl)cc2CN(CC2(F)COC2)C4)C3)n1] |
| 521 | 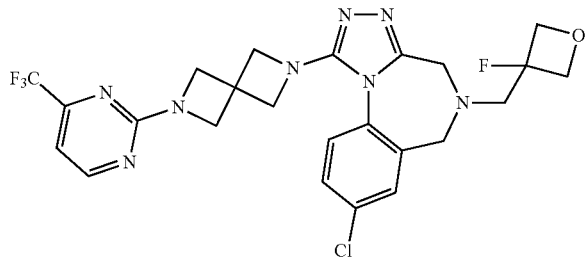 [SMILES: FC1(CN2Cc3cc(Cl)ccc3-n3c(nnc3N3CC4(CN(c5nccc(C(F)(F)F)n5)C4)C3)C2)COC1] |
| 522 | 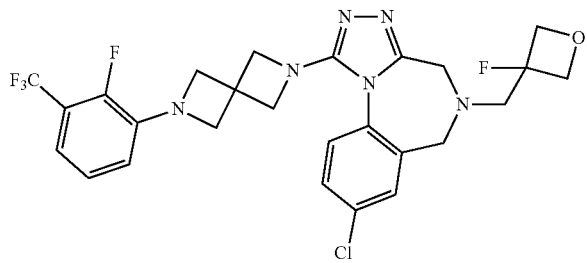 [SMILES: Fc1c(N2CC3(C2)CN(c2nnc4n2-c2ccc(Cl)cc2CN(CC2(F)COC2)C4)C3)cccc1C(F)(F)F] |
| 523 | 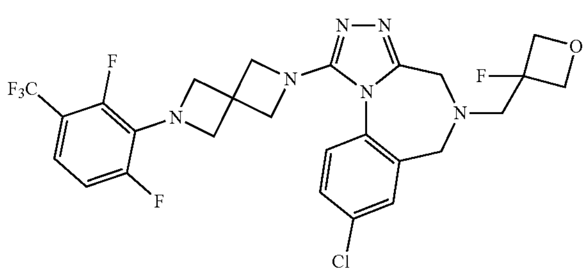 [SMILES: Fc1ccc(C(F)(F)F)c(F)c1N1CC2(C1)CN(c1nnc3n1-c1ccc(Cl)cc1CN(CC1(F)COC1)C3)C2] |
| 524 | 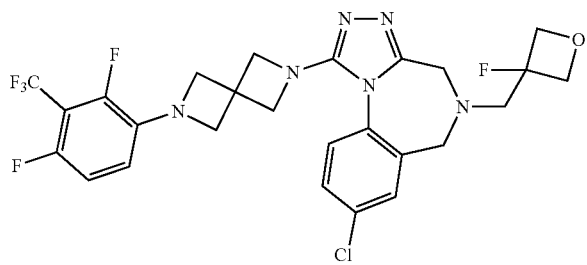 [SMILES: Fc1ccc(N2CC3(C2)CN(c2nnc4n2-c2ccc(Cl)cc2CN(CC2(F)COC2)C4)C3)c(F)c1C(F)(F)F] |

TABLE 1-continued

Representative Compounds

| Cmpd. No. | Structure |
|---|---|
| 525 | 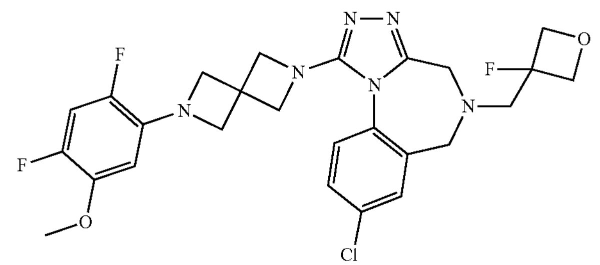 [SMILES: COc1cc(N2CC3(C2)CN(c2nnc4n2-c2ccc(Cl)cc2CN(CC2(F)COC2)C4)C3)c(F)cc1F] |
| 526 | 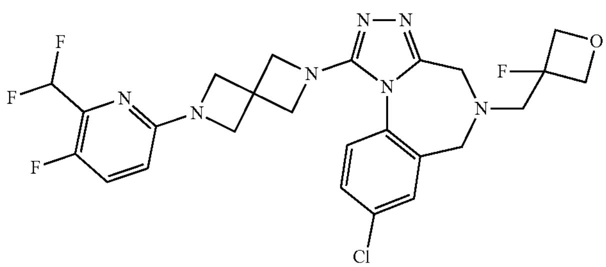 [SMILES: Fc1ccc(N2CC3(C2)CN(c2nnc4n2-c2ccc(Cl)cc2CN(CC2(F)COC2)C4)C3)nc1C(F)F] |
| 527 | 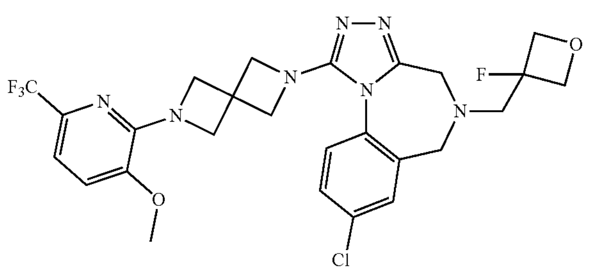 [SMILES: COc1ccc(C(F)(F)F)nc1N1CC2(C1)CN(c1nnc3n1-c1ccc(Cl)cc1CN(CC1(F)COC1)C3)C2] |
| 528 | 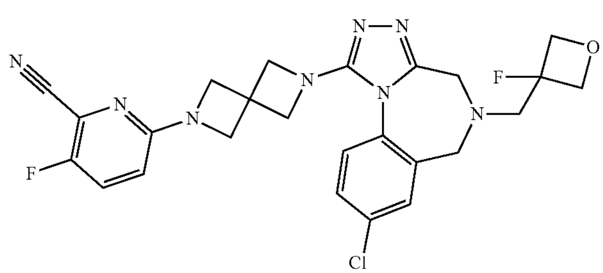 [SMILES: N#Cc1nc(N2CC3(C2)CN(c2nnc4n2-c2ccc(Cl)cc2CN(CC2(F)COC2)C4)C3)ccc1F] |
| 529 | 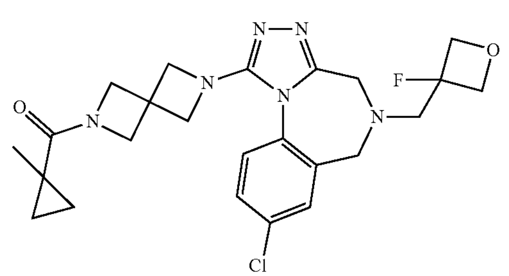 [SMILES: CC1(C(=O)N2CC3(C2)CN(c2nnc4n2-c2ccc(Cl)cc2CN(CC2(F)COC2)C4)C3)CC1] |

TABLE 1-continued
Representative Compounds
| Cmpd. No. | Structure |
|---|---|
| 530 | 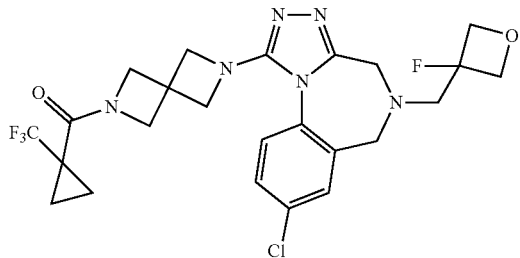 [SMILES: O=C(N1CC2(C1)CN(c1nnc3n1-c1ccc(Cl)cc1CN(CC1(F)COC1)C3)C2)C1(C(F)(F)F)CC1] |
| 531 | 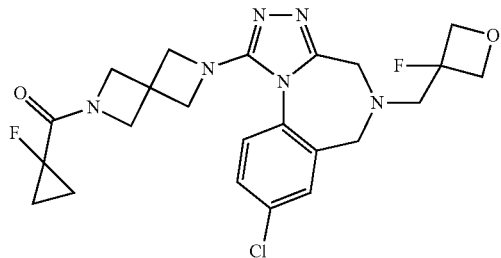 [SMILES: O=C(N1CC2(C1)CN(c1nnc3n1-c1ccc(Cl)cc1CN(CC1(F)COC1)C3)C2)C1(F)CC1] |
| 532 | 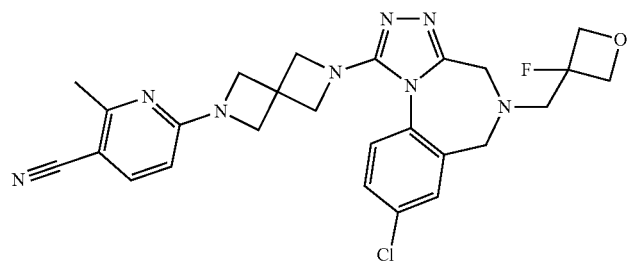 [SMILES: Cc1nc(N2CC3(C2)CN(c2nnc4n2-c2ccc(Cl)cc2CN(CC2(F)COC2)C4)C3)ccc1C#N] |
| 533 | 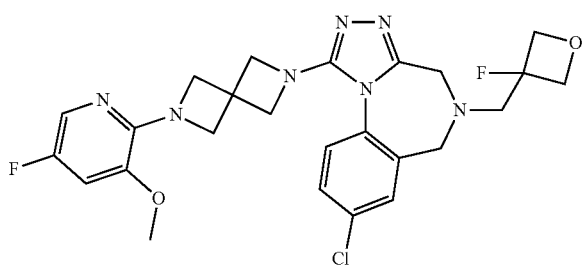 [SMILES: COc1cc(F)cnc1N1CC2(C1)CN(c1nnc3n1-c1ccc(Cl)cc1CN(CC1(F)COC1)C3)C2] |
| 534 | 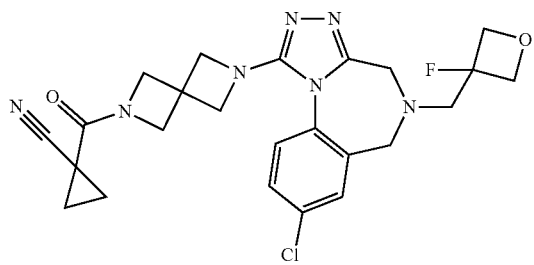 [SMILES: N#CC1(C(=O)N2CC3(C2)CN(c2nnc4n2-c2ccc(Cl)cc2CN(CC2(F)COC2)C4)C3)CC1] |

TABLE 1-continued

Representative Compounds

| Cmpd. No. | Structure |
|---|---|
| 535 | 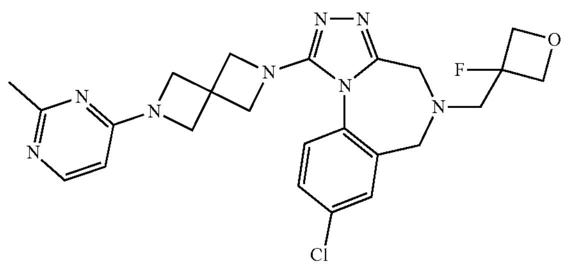 [SMILES: Cc1nccc(N2CC3(C2)CN(c2nnc4n2-c2ccc(Cl)cc2CN(CC2(F)COC2)C4)C3)n1] |
| 536 | 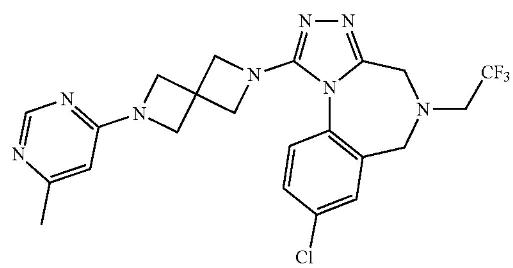 [SMILES: Cc1cc(N2CC3(C2)CN(c2nnc4n2-c2ccc(Cl)cc2CN(CC(F)(F)F)C4)C3)ncn1] |
| 537 | 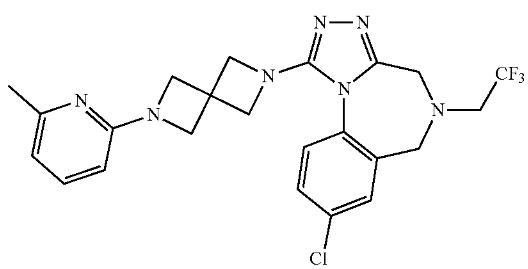 [SMILES: Cc1cccc(N2CC3(C2)CN(c2nnc4n2-c2ccc(Cl)cc2CN(CC(F)(F)F)C4)C3)n1] |
| 538 | 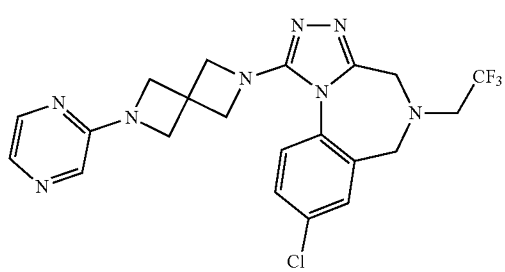 [SMILES: FC(F)(F)CN1Cc2cc(Cl)ccc2-n2c(nnc2N2CC3(CN(c4cnccn4)C3)C2)C1] |
| 539 | 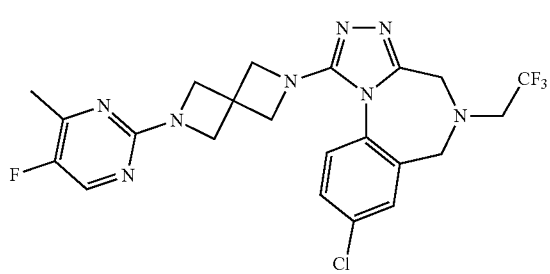 [SMILES: Cc1nc(N2CC3(C2)CN(c2nnc4n2-c2ccc(Cl)cc2CN(CC(F)(F)F)C4)C3)ncc1F] |

TABLE 1-continued

Representative Compounds

| Cmpd. No. | Structure |
|---|---|
| 540 | 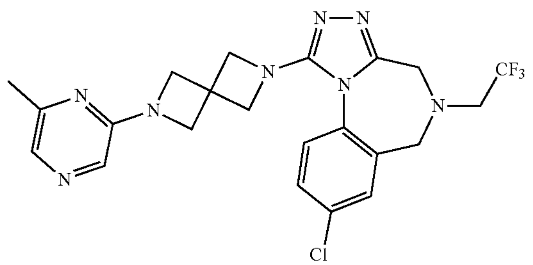 [SMILES: Cc1cncc(N2CC3(C2)CN(c2nnc4n2-c2ccc(Cl)cc2CN(CC(F)(F)F)C4)C3)n1] |
| 541 | 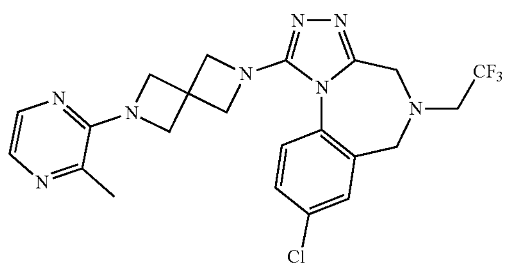 [SMILES: Cc1nccnc1N1CC2(C1)CN(c1nnc3n1-c1ccc(Cl)cc1CN(CC(F)(F)F)C3)C2] |
| 542 | 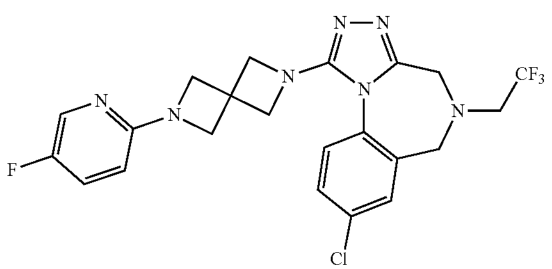 [SMILES: Fc1ccc(N2CC3(C2)CN(c2nnc4n2-c2ccc(Cl)cc2CN(CC(F)(F)F)C4)C3)nc1] |
| 543 | 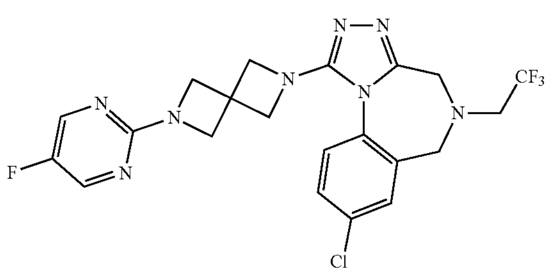 [SMILES: Fc1cnc(N2CC3(C2)CN(c2nnc4n2-c2ccc(Cl)cc2CN(CC(F)(F)F)C4)C3)nc1] |
| 544 | 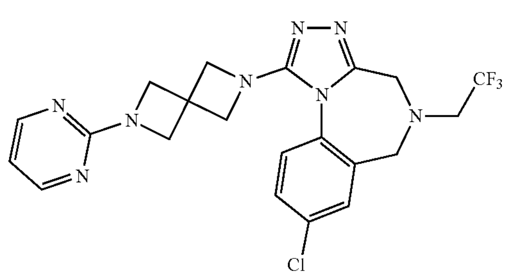 [SMILES: FC(F)(F)CN1Cc2cc(Cl)ccc2-n2c(nnc2N2CC3(CN(c4ncccn4)C3)C2)C1] |

TABLE 1-continued

Representative Compounds

| Cmpd. No. | Structure |
|---|---|
| 545 | 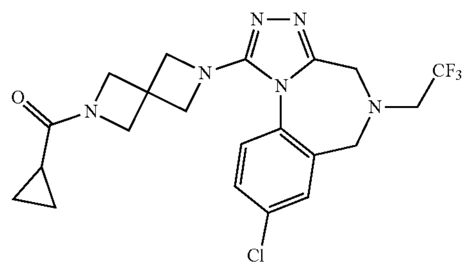 [SMILES: O=C(C1CC1)N1CC2(C1)CN(c1nnc3n1-c1ccc(Cl)cc1CN(CC(F)(F)F)C3)C2] |
| 546 | 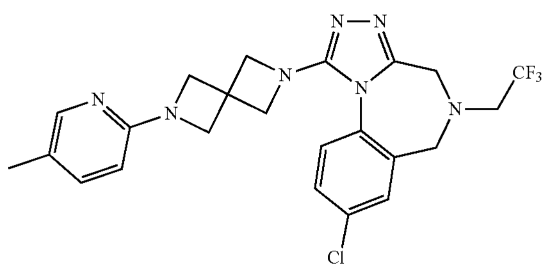 [SMILES: Cc1ccc(N2CC3(C2)CN(c2nnc4n2-c2ccc(Cl)cc2CN(CC(F)(F)F)C4)C3)nc1] |
| 547 | 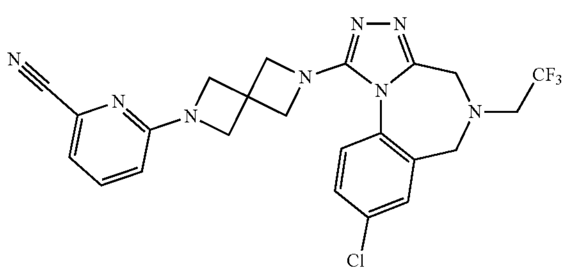 [SMILES: N#Cc1cccc(N2CC3(C2)CN(c2nnc4n2-c2ccc(Cl)cc2CN(CC(F)(F)F)C4)C3)n1] |
| 548 | 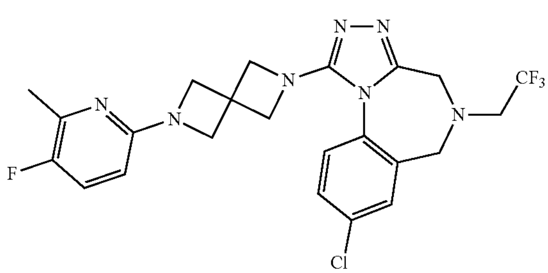 |
| 549 | 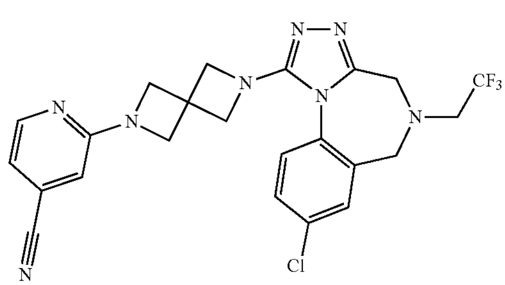 [SMILES: N#Cc1ccnc(N2CC3(C2)CN(c2nnc4n2-c2ccc(Cl)cc2CN(CC(F)(F)F)C4)C3)c1] |

TABLE 1-continued

Representative Compounds

| Cmpd. No. | Structure |
|---|---|
| 550 | 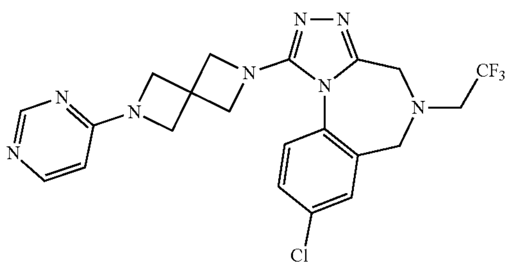 [SMILES: FC(F)(F)CN1Cc2cc(Cl)ccc2-n2c(nnc2N2CC3(CN(c4ccncn4)C3)C2)C1] |
| 552 | 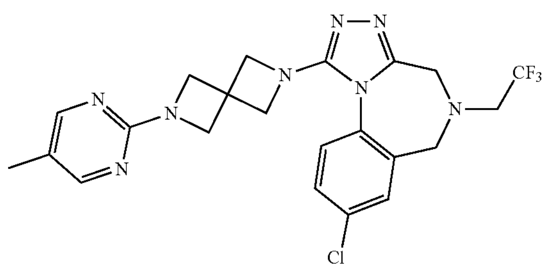 [SMILES: Cc1cnc(N2CC3(C2)CN(c2nnc4n2-c2ccc(Cl)cc2CN(CC(F)(F)F)C4)C3)nc1] |
| 553 | 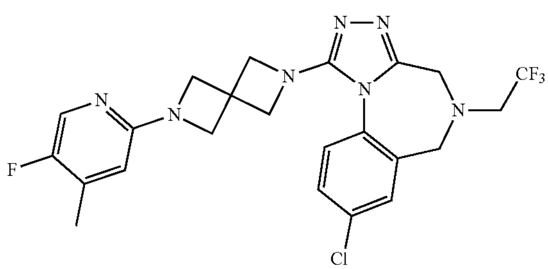 [SMILES: Cc1cc(N2CC3(C2)CN(c2nnc4n2-c2ccc(Cl)cc2CN(CC(F)(F)F)C4)C3)ncc1F] |
| 554 | 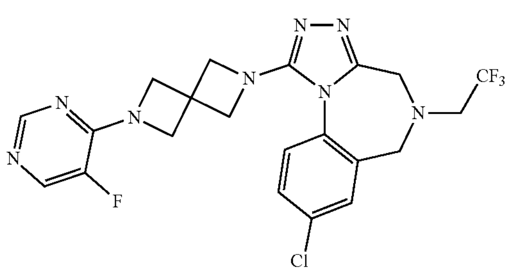 [SMILES: Fc1cncnc1N1CC2(C1)CN(c1nnc3n1-c1ccc(Cl)cc1CN(CC(F)(F)F)C3)C2] |
| 555 | 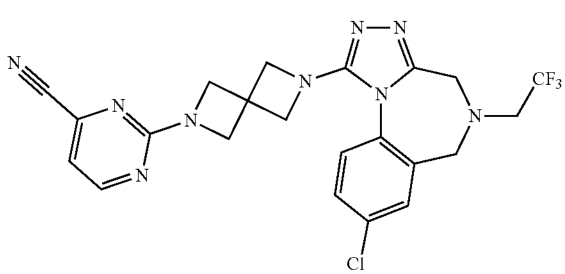 [SMILES: N#Cc1ccnc(N2CC3(C2)CN(c2nnc4n2-c2ccc(Cl)cc2CN(CC(F)(F)F)C4)C3)n1] |

TABLE 1-continued

Representative Compounds

| Cmpd. No. | Structure |
|---|---|
| 556 | 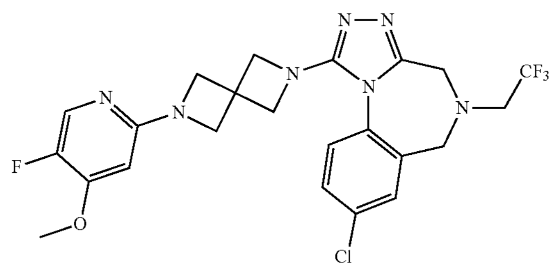 [SMILES: COc1cc(N2CC3(C2)CN(c2nnc4n2-c2ccc(Cl)cc2CN(CC(F)(F)F)C4)C3)ncc1F] |
| 557 | 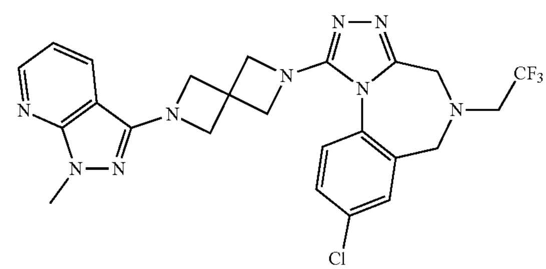 [SMILES: Cn1nc(N2CC3(C2)CN(c2nnc4n2-c2ccc(Cl)cc2CN(CC(F)(F)F)C4)C3)c2cccnc21] |
| 558 | 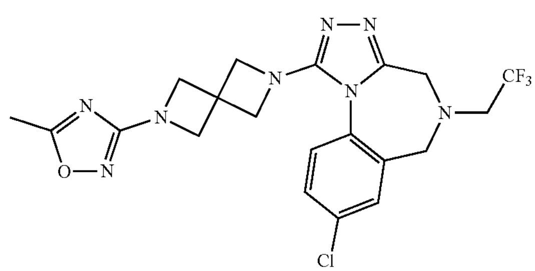 [SMILES: Cc1nc(N2CC3(C2)CN(c2nnc4n2-c2ccc(Cl)cc2CN(CC(F)(F)F)C4)C3)no1] |
| 559 | 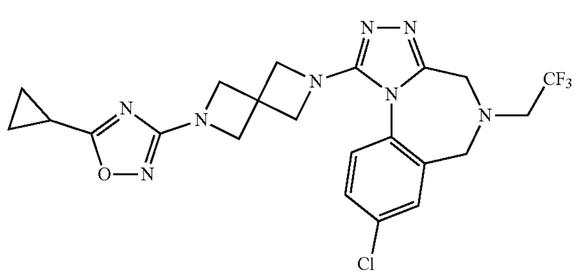 [SMILES: FC(F)(F)CN1Cc2cc(Cl)ccc2-n2c(nnc2N2CC3(CN(c4noc(C5CC5)n4)C3)C2)C1] |
| 560 | 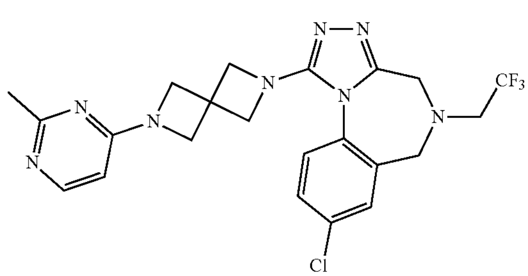 [SMILES: Cc1nccc(N2CC3(C2)CN(c2nnc4n2-c2ccc(Cl)cc2CN(CC(F)(F)F)C4)C3)n1] |

TABLE 1-continued

Representative Compounds

| Cmpd. No. | Structure |
|---|---|
| 561 | 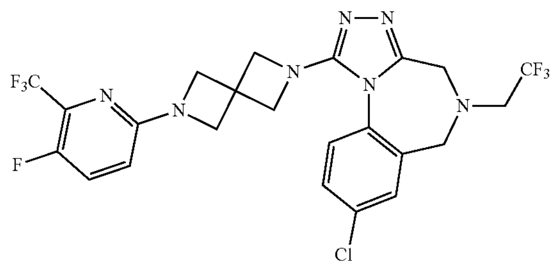 [SMILES: Fc1ccc(N2CC3(C2)CN(c2nnc4n2-c2ccc(Cl)cc2CN(CC(F)(F)F)C4)C3)nc1C(F)(F)F] |
| 562 | 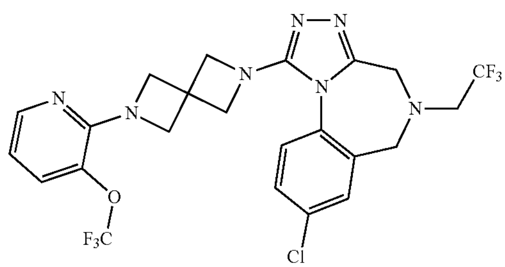 [SMILES: FC(F)(F)CN1Cc2cc(Cl)ccc2-n2c(nnc2N2CC3(CN(c4ncccc4OC(F)(F)F)C3)C2)C1] |
| 563 | 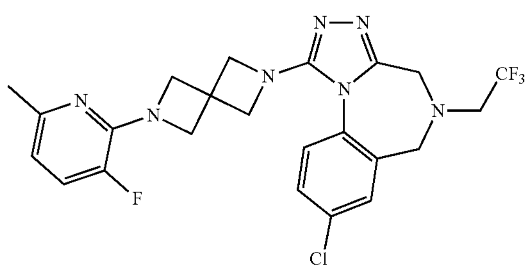 [SMILES: Cc1ccc(F)c(N2CC3(C2)CN(c2nnc4n2-c2ccc(Cl)cc2CN(CC(F)(F)F)C4)C3)n1] |
| 564 | 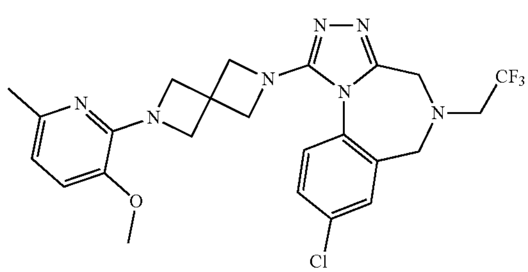 [SMILES: COc1ccc(C)nc1N1CC2(C1)CN(c1nnc3n1-c1ccc(Cl)cc1CN(CC(F)(F)F)C3)C2] |
| 565 | 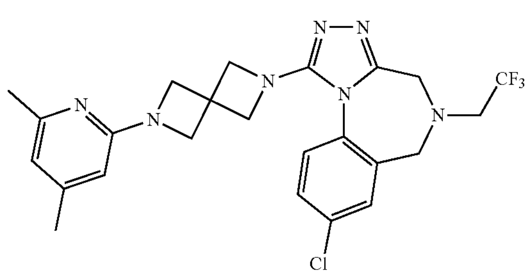 [SMILES: Cc1cc(C)nc(N2CC3(C2)CN(c2nnc4n2-c2ccc(Cl)cc2CN(CC(F)(F)F)C4)C3)c1] |

TABLE 1-continued
Representative Compounds
| Cmpd. No. | Structure |
|---|---|
| 566 | 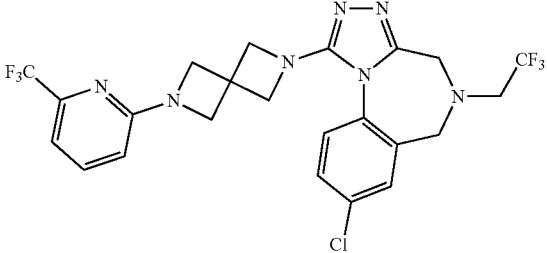 |
| 567 | 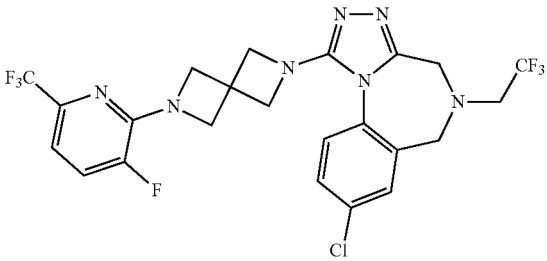 |
| 568 | 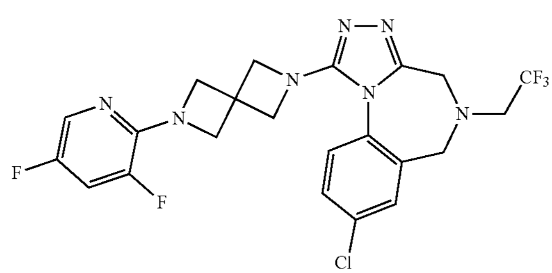 [SMILES: Fc1cnc(N2CC3(C2)CN(c2nnc4n2-c2ccc(Cl)cc2CN(CC(F)(F)F)C4)C3)c(F)c1] |
| 569 | 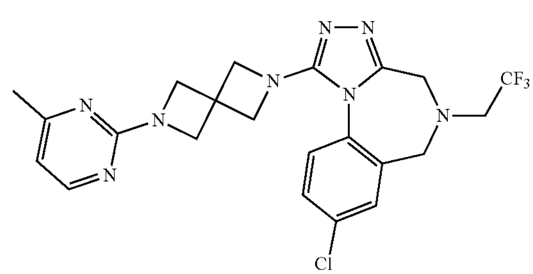 [SMILES: Cc1ccnc(N2CC3(C2)CN(c2nnc4n2-c2ccc(Cl)cc2CN(CC(F)(F)F)C4)C3)n1] |
| 570 | 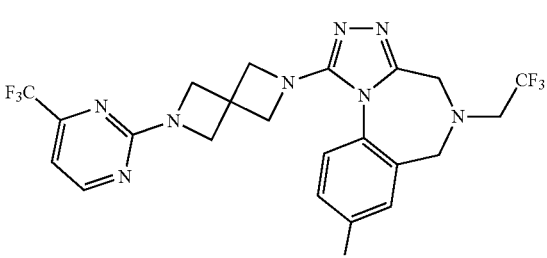 |

TABLE 1-continued
Representative Compounds
| Cmpd. No. | Structure |
|---|---|
| 571 | 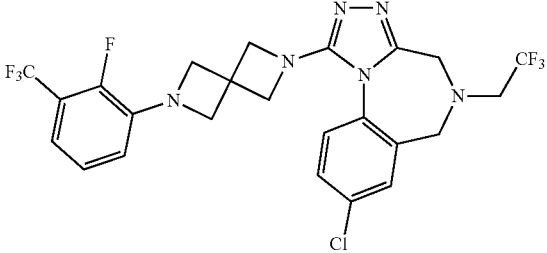 [SMILES: Fc1c(N2CC3(C2)CN(c2nnc4n2-c2ccc(Cl)cc2CN(CC(F)(F)F)C4)C3)cccc1C(F)(F)F] |
| 572 | 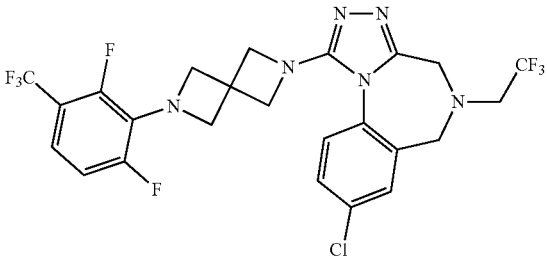 [SMILES: Fc1ccc(C(F)(F)F)c(F)c1N1CC2(C1)CN(c1nnc3n1-c1ccc(Cl)cc1CN(CC(F)(F)F)C3)C2] |
| 573 | 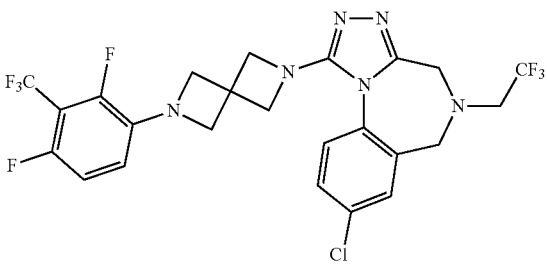 |
| 574 | 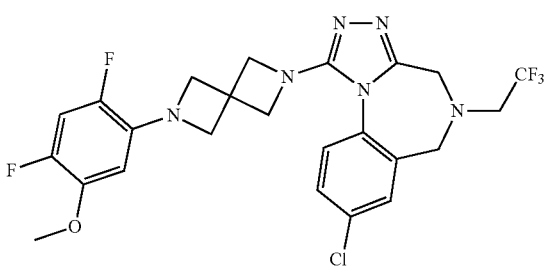 [SMILES: COc1cc(N2CC3(C2)CN(c2nnc4n2-c2ccc(Cl)cc2CN(CC(F)(F)F)C4)C3)c(F)cc1F] |
| 575 | 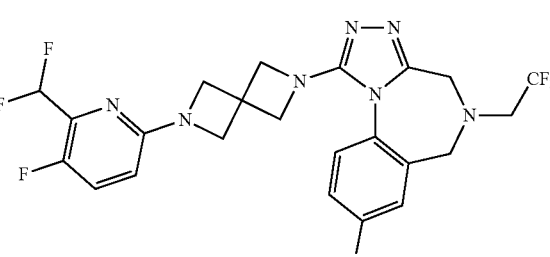 |

TABLE 1-continued
Representative Compounds
| Cmpd. No. | Structure |
|---|---|
| 576 | 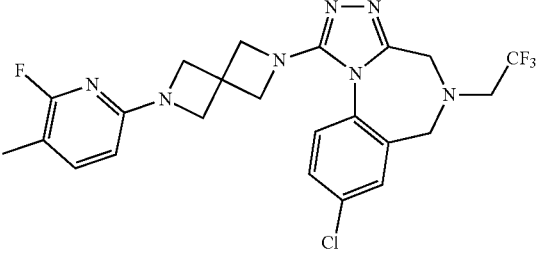 [SMILES: Cc1ccc(N2CC3(C2)CN(c2nnc4n2-c2ccc(Cl)cc2CN(CC(F)(F)F)C4)C3)nc1F] |
| 577 | 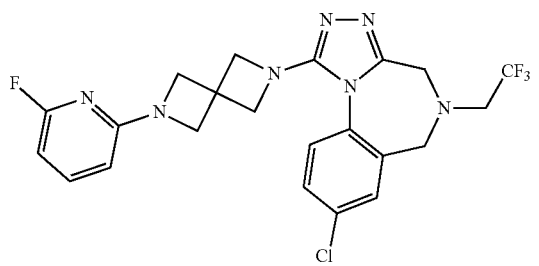 [SMILES: Fc1cccc(N2CC3(C2)CN(c2nnc4n2-c2ccc(Cl)cc2CN(CC(F)(F)F)C4)C3)n1] |
| 578 | 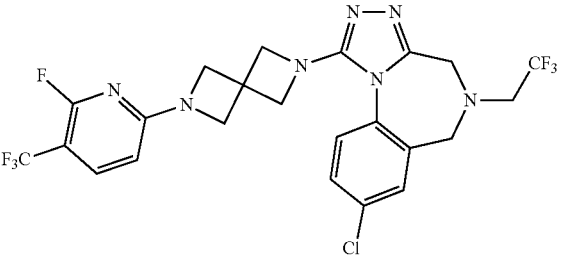 [SMILES: Fc1nc(N2CC3(C2)CN(c2nnc4n2-c2ccc(Cl)cc2CN(CC(F)(F)F)C4)C3)ccc1C(F)(F)F] |
| 579 | 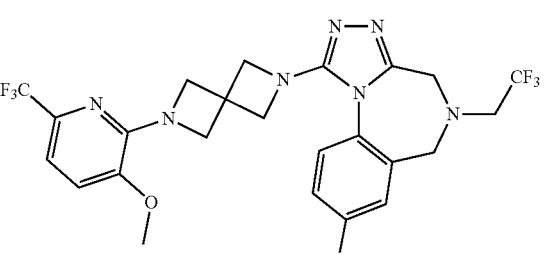 |
| 580 | 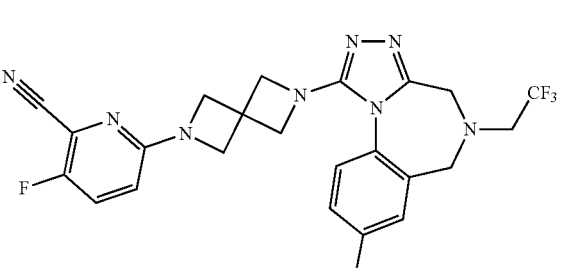 |

TABLE 1-continued

Representative Compounds

| Cmpd. No. | Structure |
|---|---|
| 581 | 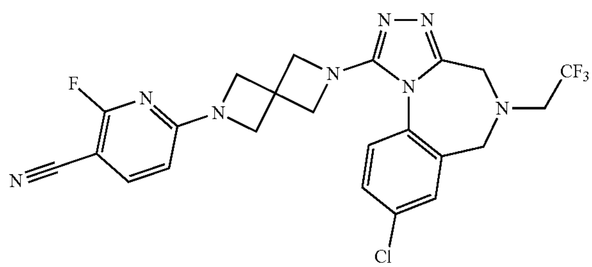 [SMILES: N#Cc1ccc(N2CC3(C2)CN(c2nnc4n2-c2ccc(Cl)cc2CN(CC(F)(F)F)C4)C3)nc1F] |
| 582 | 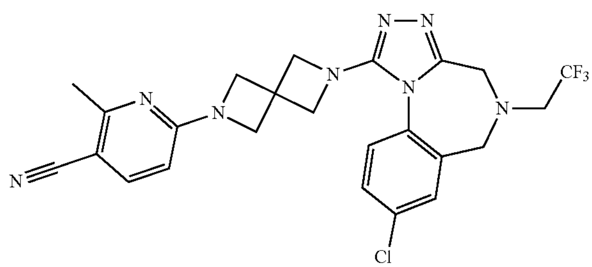 [SMILES: Cc1nc(N2CC3(C2)CN(c2nnc4n2-c2ccc(Cl)cc2CN(CC(F)(F)F)C4)C3)ccc1C#N] |
| 583 | 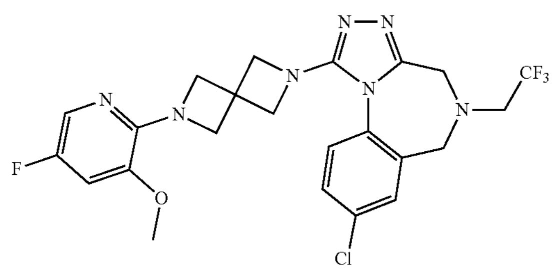 [SMILES: COc1cc(F)cnc1N1CC2(C1)CN(c1nnc3n1-c1ccc(Cl)cc1CN(CC(F)(F)F)C3)C2] |
| 584 | 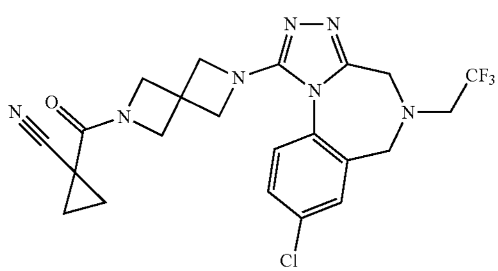 [SMILES: N#CC1(C(=O)N2CC3(C2)CN(c2nnc4n2-c2ccc(Cl)cc2CN(CC(F)(F)F)C4)C3)CC1] |
| 585 | 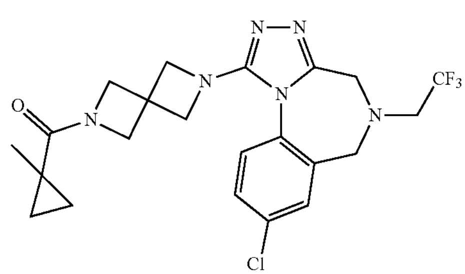 [SMILES: CC1(C(=O)N2CC3(C2)CN(c2nnc4n2-c2ccc(Cl)cc2CN(CC(F)(F)F)C4)C3)CC1] |

TABLE 1-continued

Representative Compounds

| Cmpd. No. | Structure |
|---|---|
| 586 | 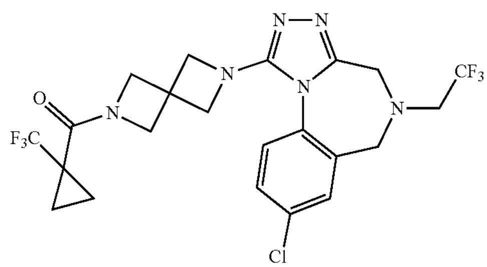 [SMILES: O=C(N1CC2(C1)CN(c1nnc3n1-c1ccc(Cl)cc1CN(CC(F)(F)F)C3)C2)C1(C(F)(F)F)CC1] |
| 587 | 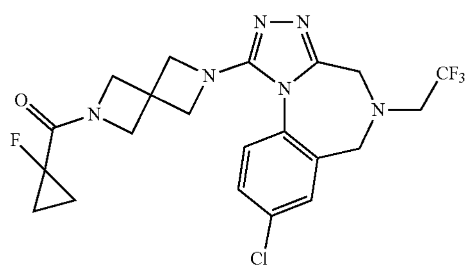 [SMILES: O=C(N1CC2(C1)CN(c1nnc3n1-c1ccc(Cl)cc1CN(CC(F)(F)F)C3)C2)C1(F)CC1] |
| 588 | 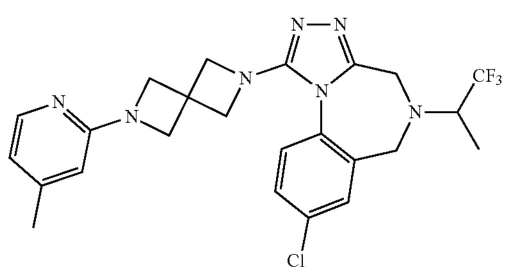 [SMILES: Cc1ccnc(N2CC3(C2)CN(c2nnc4n2-c2ccc(Cl)cc2CN(C(C)C(F)(F)F)C4)C3)c1] |
| 589 | 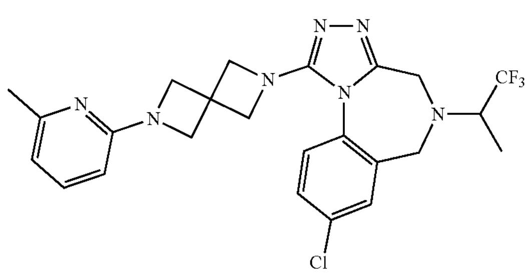 |
| 590 | 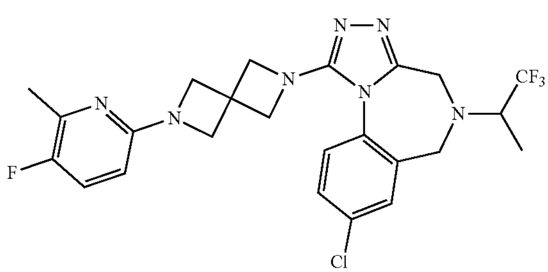 [SMILES: Cc1nc(N2CC3(C2)CN(c2nnc4n2-c2ccc(Cl)cc2CN(C(C)C(F)(F)F)C4)C3)ccc1F] |

TABLE 1-continued

Representative Compounds

| Cmpd. No. | Structure |
|---|---|
| 591 | 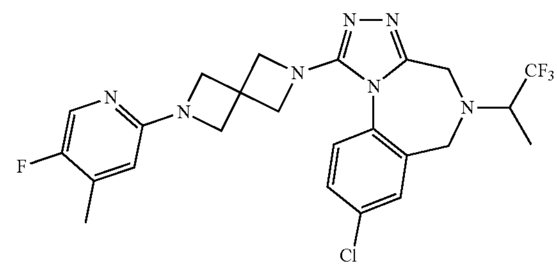 [SMILES: Cc1cc(N2CC3(C2)CN(c2nnc4n2-c2ccc(Cl)cc2CN(C(C)C(F)(F)F)C4)C3)ncc1F] |
| 592 | 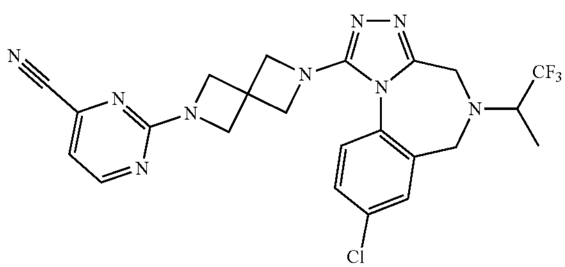 [SMILES: CC(N1Cc2cc(Cl)ccc2-n2c(nnc2N2CC3(CN(c4nccc(C#N)n4)C3)C2)C1)C(F)(F)F] |
| 593 | 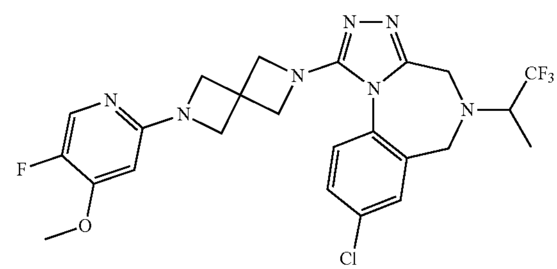 [SMILES: COc1cc(N2CC3(C2)CN(c2nnc4n2-c2ccc(Cl)cc2CN(C(C)C(F)(F)F)C4)C3)ncc1F] |
| 594 | 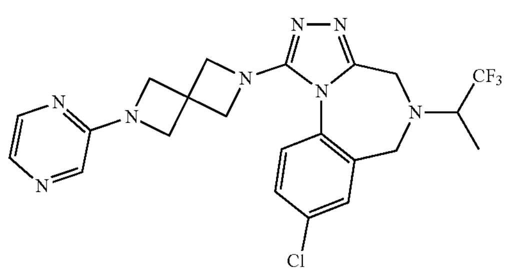 [SMILES: CC(N1Cc2cc(Cl)ccc2-n2c(nnc2N2CC3(CN(c4cnccn4)C3)C2)C1)C(F)(F)F] |
| 595 | 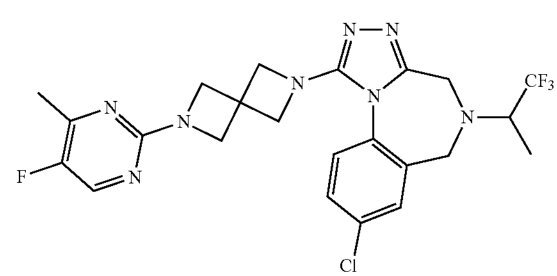 [SMILES: Cc1nc(N2CC3(C2)CN(c2nnc4n2-c2ccc(Cl)cc2CN(C(C)C(F)(F)F)C4)C3)ncc1F] |

TABLE 1-continued
Representative Compounds
| Cmpd. No. | Structure |
|---|---|
| 596 | 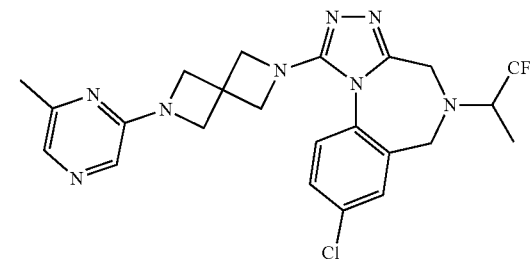 |
| 597 | 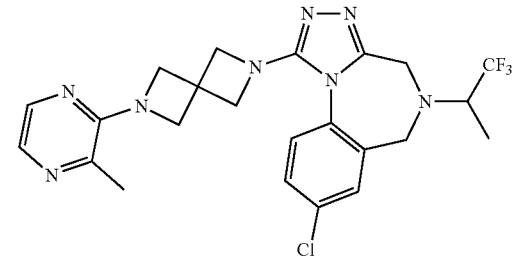 [SMILES: Cc1nccnc1N1CC2(C1)CN(c1nnc3n1-c1ccc(Cl)cc1CN(C(C)C(F)(F)F)C3)C2] |
| 598 | 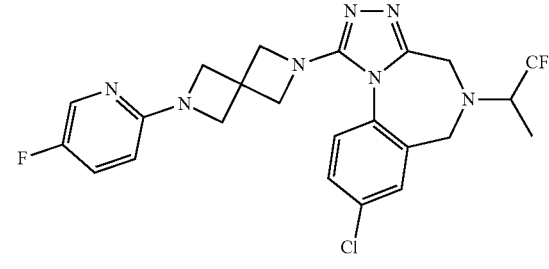 |
| 599 | 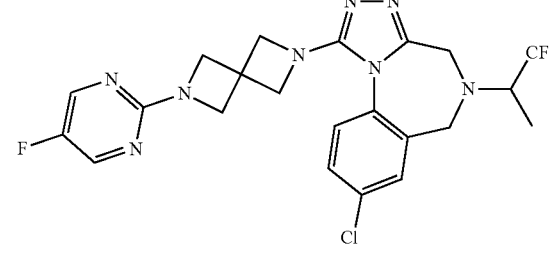 |
| 600 | 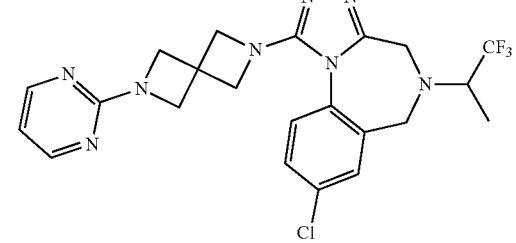 |

TABLE 1-continued

Representative Compounds

| Cmpd. No. | Structure |
|---|---|
| 601 | 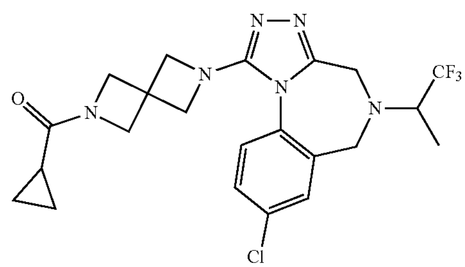 [SMILES: CC(N1Cc2cc(Cl)ccc2-n2c(nnc2N2CC3(CN(C(=O)C4CC4)C3)C2)C1)C(F)(F)F] |
| 602 | 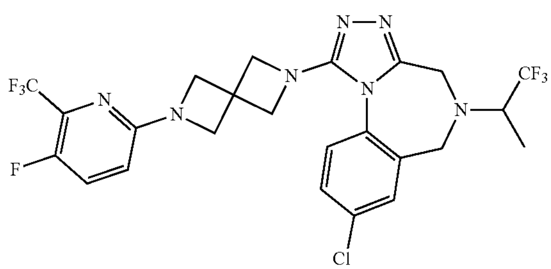 |
| 603 | 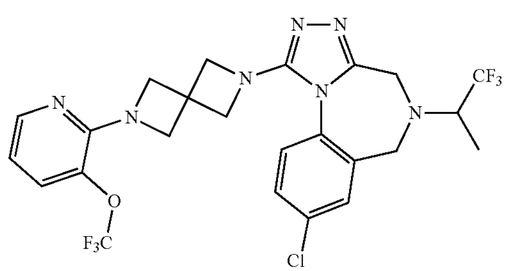 [SMILES: CC(N1Cc2cc(Cl)ccc2-n2c(nnc2N2CC3(CN(c4ncccc4OC(F)(F)F)C3)C2)C1)C(F)(F)F] |
| 604 | 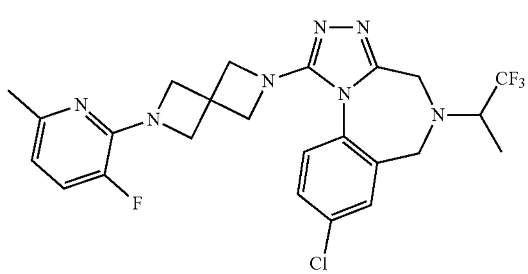 [SMILES: Cc1ccc(F)c(N2CC3(C2)CN(c2nnc4n2-c2ccc(Cl)cc2CN(C(C)C(F)(F)F)C4)C3)n1] |
| 605 | 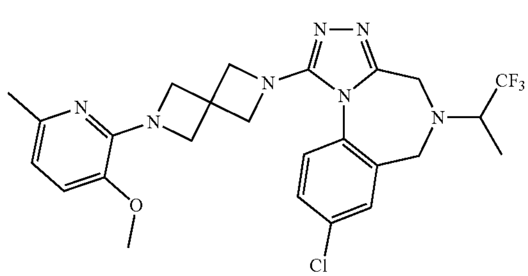 [SMILES: COc1ccc(C)nc1N1CC2(C1)CN(c1nnc3n1-c1ccc(Cl)cc1CN(C(C)C(F)(F)F)C3)C2] |

TABLE 1-continued

Representative Compounds

| Cmpd. No. | Structure |
|---|---|
| 606 | 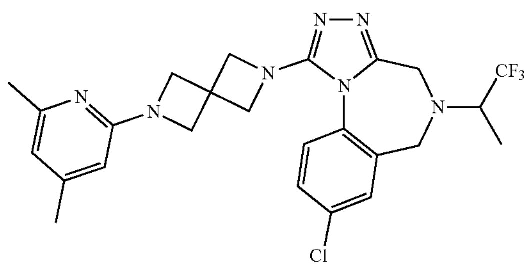 [SMILES: Cc1cc(C)nc(N2CC3(C2)CN(c2nnc4n2-c2ccc(Cl)cc2CN(C(C)C(F)(F)F)C4)C3)c1] |
| 607 | 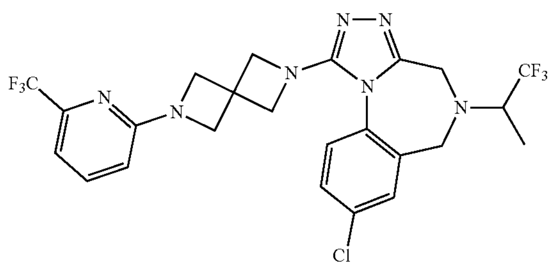 [SMILES: CC(N1Cc2cc(Cl)ccc2-n2c(nnc2N2CC3(CN(c4cccc(C(F)(F)F)n4)C3)C2)C1)C(F)(F)F] |
| 608 | 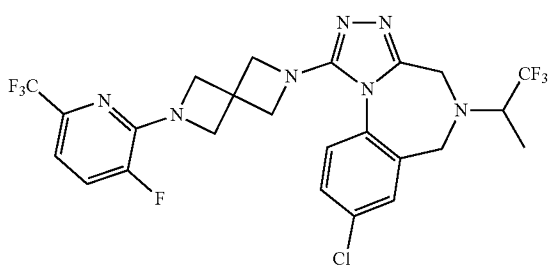 [SMILES: CC(N1Cc2cc(Cl)ccc2-n2c(nnc2N2CC3(CN(c4nc(C(F)(F)F)ccc4F)C3)C2)C1)C(F)(F)F] |
| 609 | 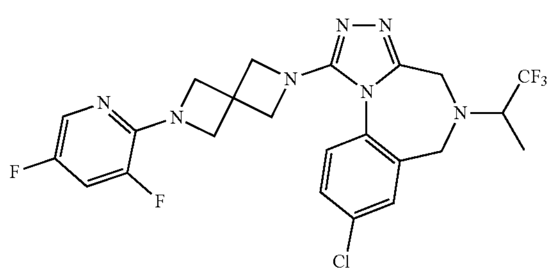 [SMILES: CC(N1Cc2cc(Cl)ccc2-n2c(nnc2N2CC3(CN(c4ncc(F)cc4F)C3)C2)C1)C(F)(F)F] |
| 610 | 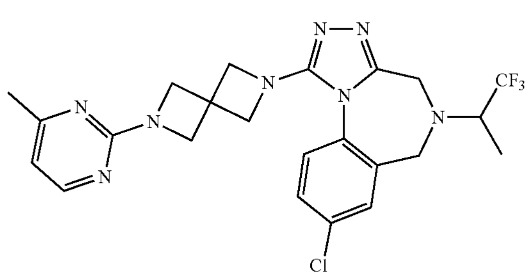 [SMILES: Cc1ccnc(N2CC3(C2)CN(c2nnc4n2-c2ccc(Cl)cc2CN(C(C)C(F)(F)F)C4)C3)n1] |

TABLE 1-continued
Representative Compounds
| Cmpd. No. | Structure |
|---|---|
| 611 | 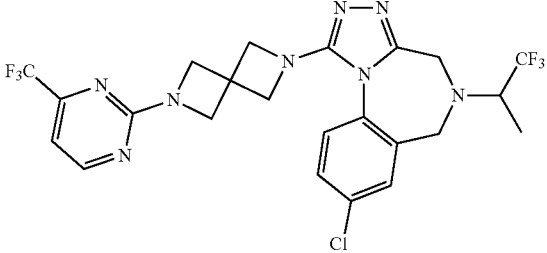 [SMILES: CC(N1Cc2cc(Cl)ccc2-n2c(nnc2N2CC3(CN(c4nccc(C(F)(F)F)n4)C3)C2)C1)C(F)(F)F] |
| 612 | 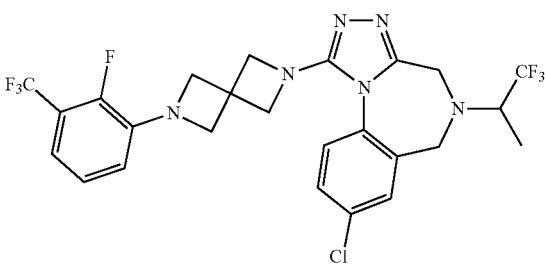 [SMILES: CC(N1Cc2cc(Cl)ccc2-n2c(nnc2N2CC3(CN(c4cccc(C(F)(F)F)c4F)C3)C2)C1)C(F)(F)F] |
| 613 | 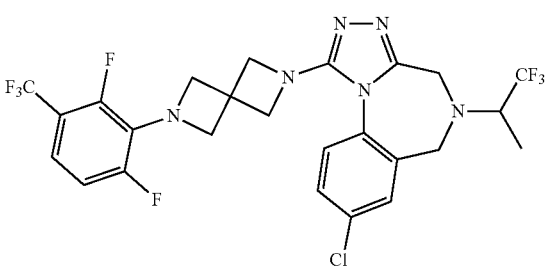 [SMILES: CC(N1Cc2cc(Cl)ccc2-n2c(nnc2N2CC3(CN(c4c(F)ccc(C(F)(F)F)c4F)C3)C2)C1)C(F)(F)F] |
| 614 | 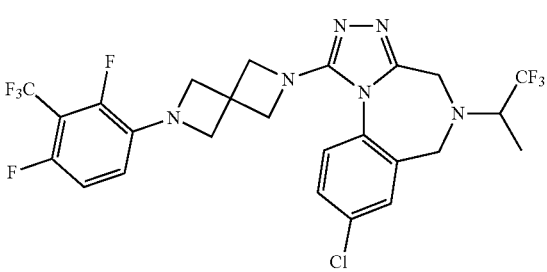 [SMILES: CC(N1Cc2cc(Cl)ccc2-n2c(nnc2N2CC3(CN(c4ccc(F)c(C(F)(F)F)c4F)C3)C2)C1)C(F)(F)F] |
| 615 | 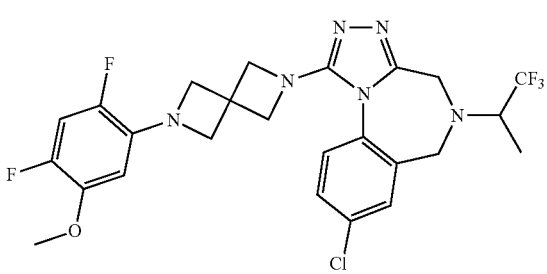 [SMILES: COc1cc(N2CC3(C2)CN(c2nnc4n2-c2ccc(Cl)cc2CN(C(C)C(F)(F)F)C4)C3)c(F)cc1F] |

TABLE 1-continued

Representative Compounds

| Cmpd. No. | Structure |
|---|---|
| 616 | 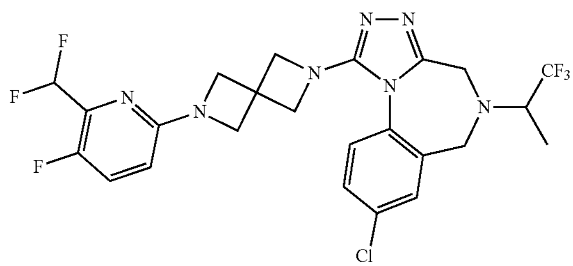 [SMILES: CC(N1Cc2cc(Cl)ccc2-n2c(nnc2N2CC3(CN(c4ccc(F)c(C(F)F)n4)C3)C2)C1)C(F)(F)F] |
| 617 | 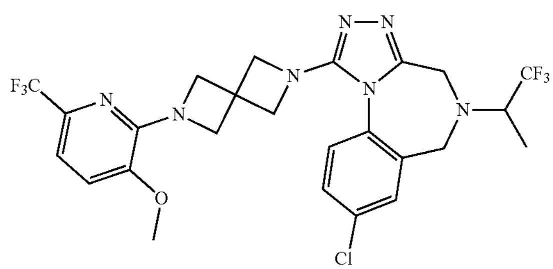 [SMILES: COc1ccc(C(F)(F)F)nc1N1CC2(C1)CN(c1nnc3n1-c1ccc(Cl)cc1CN(C(C)C(F)(F)F)C3)C2] |
| 618 | 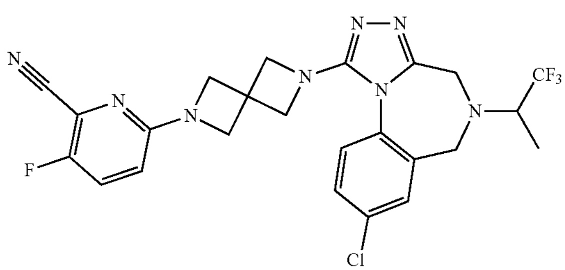 [SMILES: CC(N1Cc2cc(Cl)ccc2-n2c(nnc2N2CC3(CN(c4ccc(F)c(C#N)n4)C3)C2)C1)C(F)(F)F] |
| 619 | 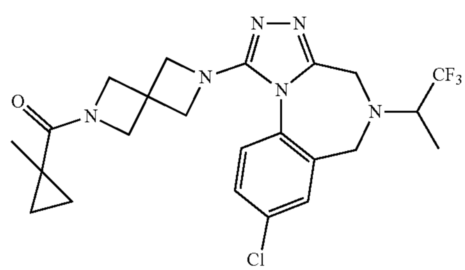 [SMILES: CC(N1Cc2cc(Cl)ccc2-n2c(nnc2N2CC3(CN(C(=O)C4(C)CC4)C3)C2)C1)C(F)(F)F] |
| 620 | 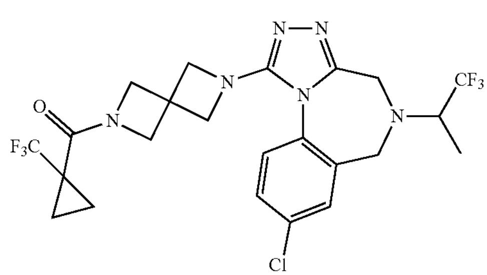 [SMILES: CC(N1Cc2cc(Cl)ccc2-n2c(nnc2N2CC3(CN(C(=O)C4(C(F)(F)F)CC4)C3)C2)C1)C(F)(F)F] |

TABLE 1-continued
Representative Compounds
| Cmpd. No. | Structure |
|---|---|
| 621 | 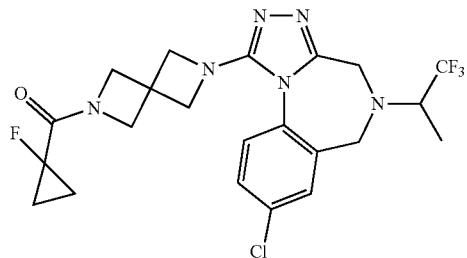 [SMILES: CC(N1Cc2cc(Cl)ccc2-n2c(nnc2N2CC3(CN(C(=O)C4(F)CC4)C3)C2)C1)C(F)(F)F] |
| 622 | 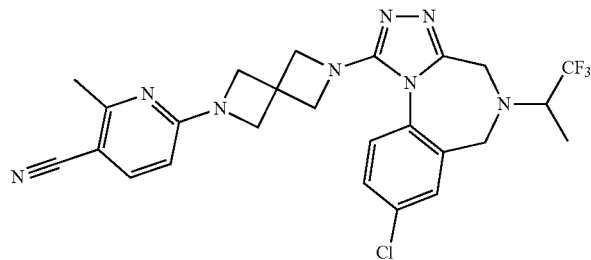 |
| 623 | 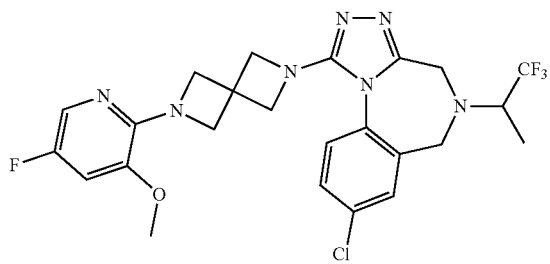 [SMILES: COc1cc(F)cnc1N1CC2(C1)CN(c1nnc3n1-c1ccc(Cl)cc1CN(C(C)C(F)(F)F)C3)C2] |
| 624 | 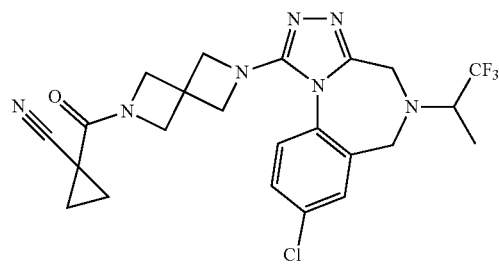 [SMILES: CC(N1Cc2cc(Cl)ccc2-n2c(nnc2N2CC3(CN(C(=O)C4(C#N)CC4)C3)C2)C1)C(F)(F)F] |
| 625 | 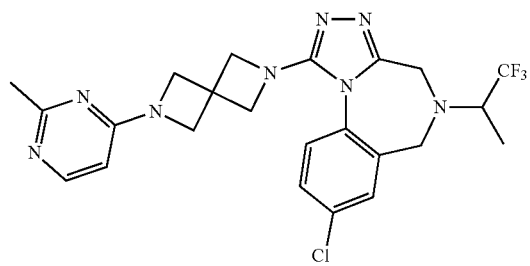 |

TABLE 1-continued
Representative Compounds
| Cmpd. No. | Structure |
|---|---|
| 626 | 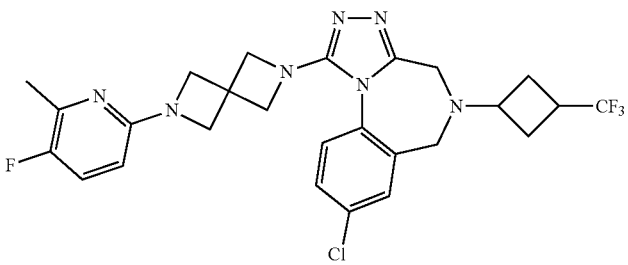 |
| 627 | 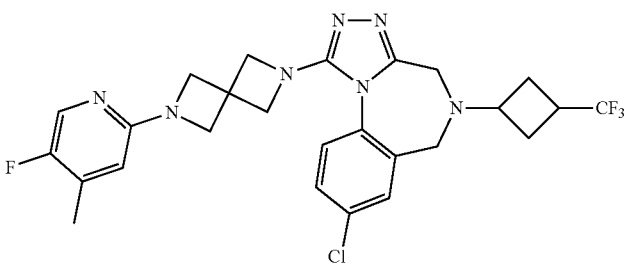 |
| 628 | 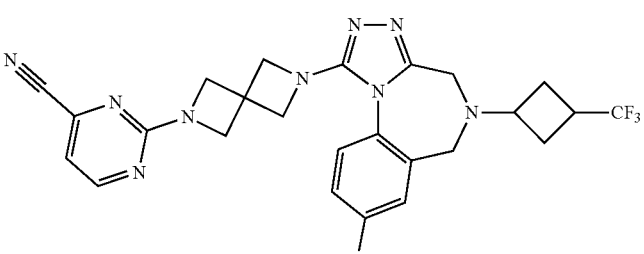 |
| 629 | 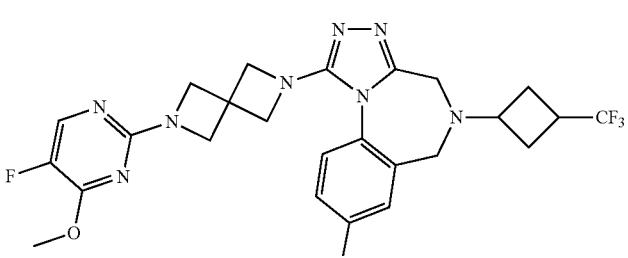 |
| 630 | 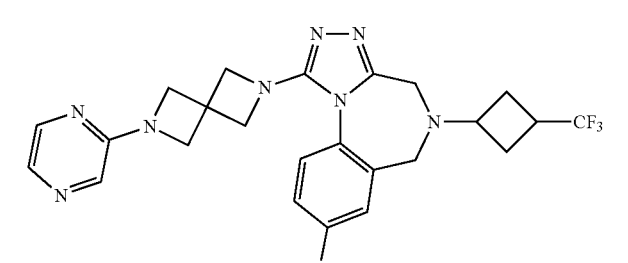 |

TABLE 1-continued

Representative Compounds

| Cmpd. No. | Structure |
|---|---|
| 631 | 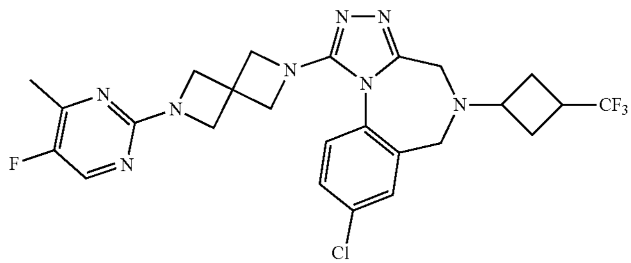 [SMILES: Cc1nc(N2CC3(C2)CN(c2nnc4n2-c2ccc(Cl)cc2CN(C2CC(C(F)(F)F)C2)C4)C3)ncc1F] |
| 632 | 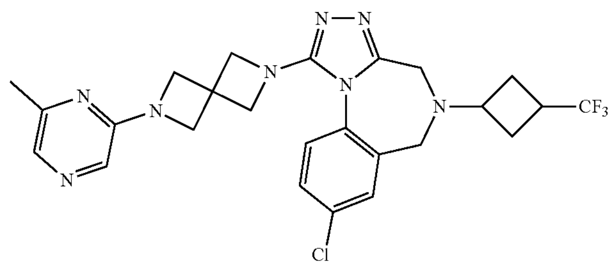 [SMILES: Cc1cncc(N2CC3(C2)CN(c2nnc4n2-c2ccc(Cl)cc2CN(C2CC(C(F)(F)F)C2)C4)C3)n1] |
| 633 | 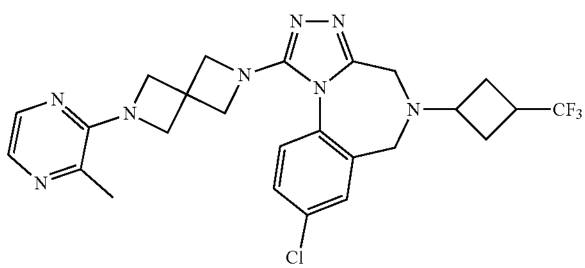 [SMILES: Cc1nccnc1N1CC2(C1)CN(c1nnc3n1-c1ccc(Cl)cc1CN(C1CC(C(F)(F)F)C1)C3)C2] |
| 634 | 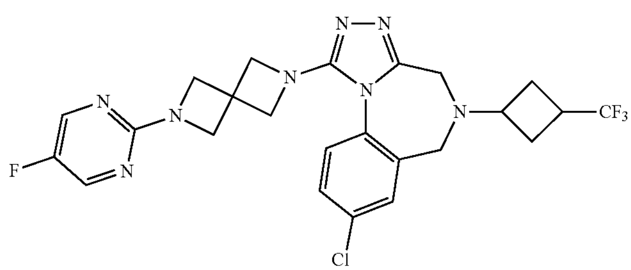 [SMILES: Fc1cnc(N2CC3(C2)CN(c2nnc4n2-c2ccc(Cl)cc2CN(C2CC(C(F)(F)F)C2)C4)C3)nc1] |
| 635 | 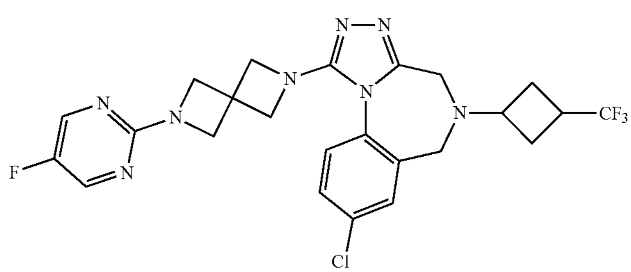 [SMILES: Fc1cnc(N2CC3(C2)CN(c2nnc4n2-c2ccc(Cl)cc2CN(C2CC(C(F)(F)F)C2)C4)C3)nc1] |

TABLE 1-continued

Representative Compounds

| Cmpd. No. | Structure |
|---|---|
| 636 | 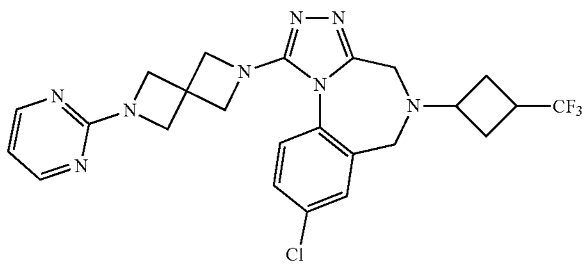 [SMILES: FC(F)(F)C1CC(N2Cc3cc(Cl)ccc3-n3c(nnc3N3CC4(CN(c5ncccn5)C4)C3)C2)C1] |
| 637 | 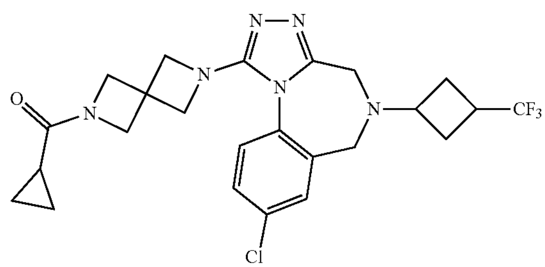 [SMILES: O=C(C1CC1)N1CC2(C1)CN(c1nnc3n1-c1ccc(Cl)cc1CN(C1CC(C(F)(F)F)C1)C3)C2] |
| 638 | 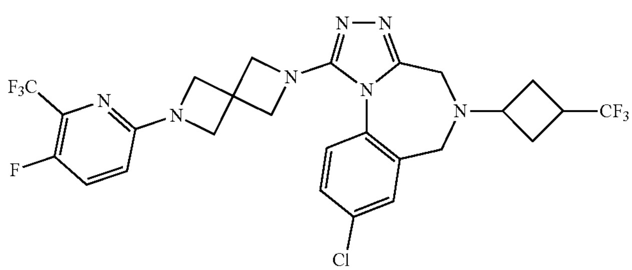 [SMILES: Fc1ccc(N2CC3(C2)CN(c2nnc4n2-c2ccc(Cl)cc2CN(C2CC(C(F)(F)F)C2)C4)C3)nc1C(F)(F)F] |
| 639 | 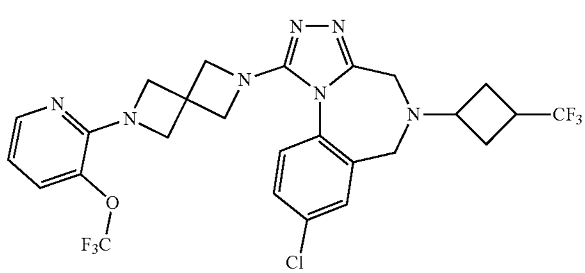 [SMILES: FC(F)(F)Oc1cccnc1N1CC2(C1)CN(c1nnc3n1-c1ccc(Cl)cc1CN(C1CC(C(F)(F)F)C1)C3)C2] |
| 640 | 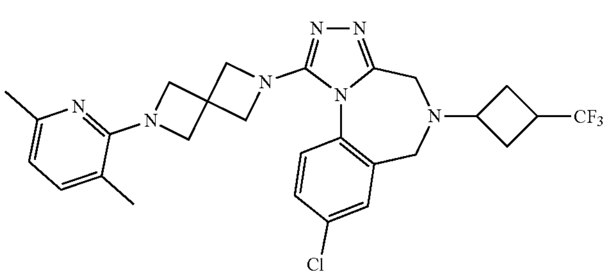 [SMILES: Cc1ccc(C)c(N2CC3(C2)CN(c2nnc4n2-c2ccc(Cl)cc2CN(C2CC(C(F)(F)F)C2)C4)C3)n1] |

TABLE 1-continued

Representative Compounds

| Cmpd. No. | Structure |
|---|---|
| 641 | 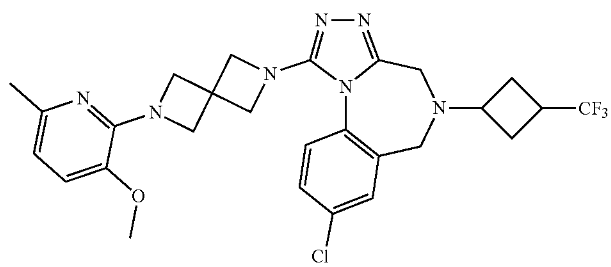 [SMILES: COc1ccc(C)nc1N1CC2(C1)CN(c1nnc3n1-c1ccc(Cl)cc1CN(C1CC(C(F)(F)F)C1)C3)C2] |
| 642 | 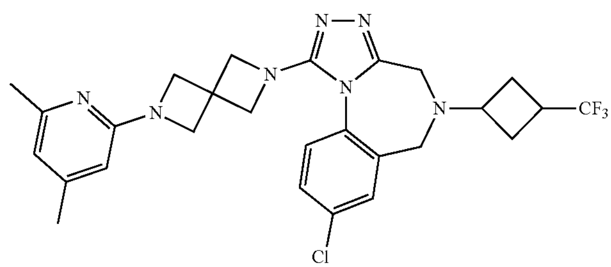 [SMILES: Cc1cc(C)nc(N2CC3(C2)CN(c2nnc4n2-c2ccc(Cl)cc2CN(C2CC(C(F)(F)F)C2)C4)C3)c1] |
| 643 | 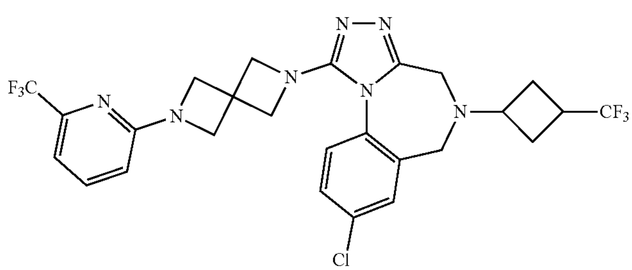 [SMILES: FC(F)(F)c1cccc(N2CC3(C2)CN(c2nnc4n2-c2ccc(Cl)cc2CN(C2CC(C(F)(F)F)C2)C4)C3)n1] |
| 644 | 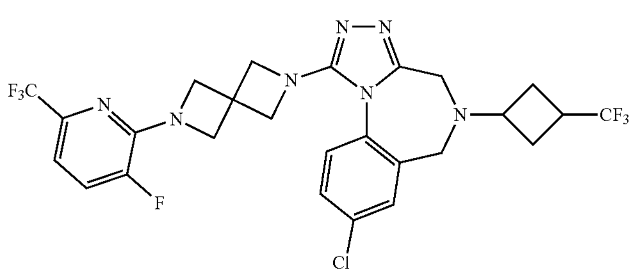 [SMILES: Fc1ccc(C(F)(F)F)nc1N1CC2(C1)CN(c1nnc3n1-c1ccc(Cl)cc1CN(C1CC(C(F)(F)F)C1)C3)C2] |
| 645 | 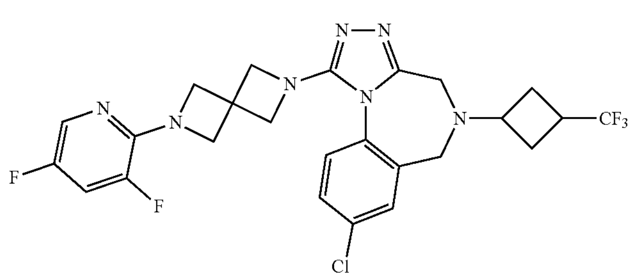 [SMILES: Fc1cnc(N2CC3(C2)CN(c2nnc4n2-c2ccc(Cl)cc2CN(C2CC(C(F)(F)F)C2)C4)C3)c(F)c1] |

TABLE 1-continued

Representative Compounds

| Cmpd. No. | Structure |
|---|---|
| 646 | 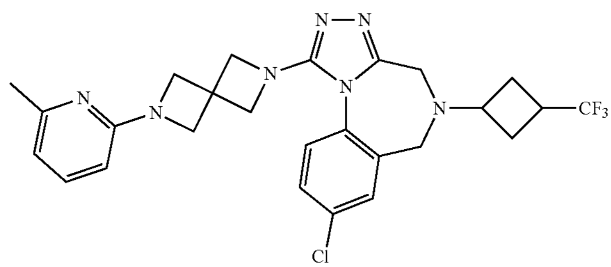 [SMILES: Cc1cccc(N2CC3(C2)CN(c2nnc4n2-c2ccc(Cl)cc2CN(C2CC(C(F)(F)F)C2)C4)C3)n1] |
| 647 | 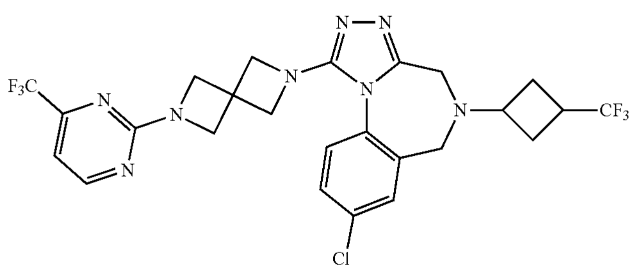 [SMILES: FC(F)(F)c1ccnc(N2CC3(C2)CN(c2nnc4n2-c2ccc(Cl)cc2CN(C2CC(C(F)(F)F)C2)C4)C3)n1] |
| 648 | 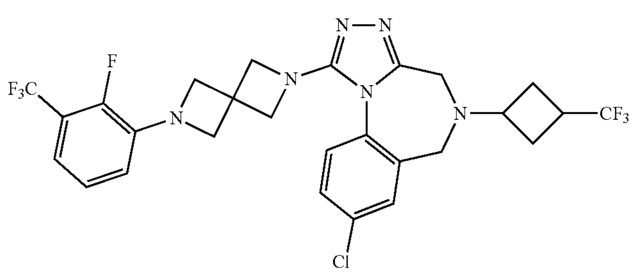 [SMILES: Fc1c(N2CC3(C2)CN(c2nnc4n2-c2ccc(Cl)cc2CN(C2CC(C(F)(F)F)C2)C4)C3)cccc1C(F)(F)F] |
| 649 | 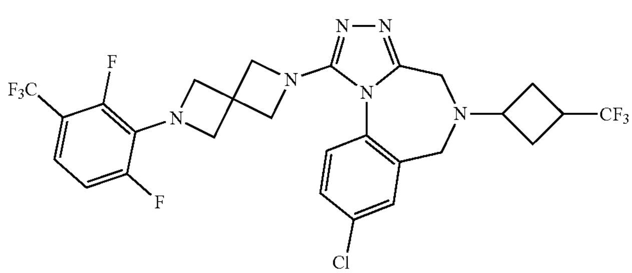 [SMILES: Fc1ccc(C(F)(F)F)c(F)c1N1CC2(C1)CN(c1nnc3n1-c1ccc(Cl)cc1CN(C1CC(C(F)(F)F)C1)C3)C2] |
| 650 | 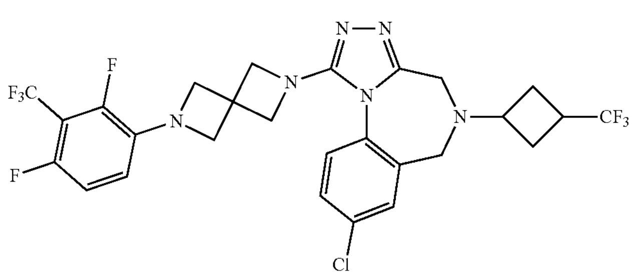 [SMILES: Fc1ccc(N2CC3(C2)CN(c2nnc4n2-c2ccc(Cl)cc2CN(C2CC(C(F)(F)F)C2)C4)C3)c(F)c1C(F)(F)F] |

TABLE 1-continued

Representative Compounds

| Cmpd. No. | Structure |
|---|---|
| 651 | 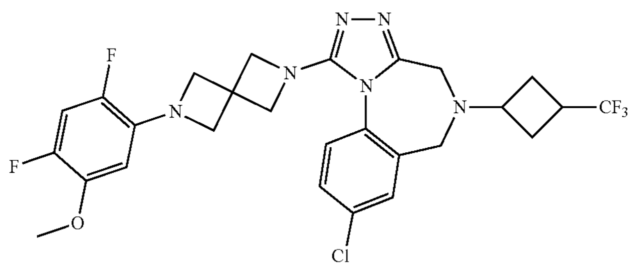 [SMILES: COc1cc(N2CC3(C2)CN(c2nnc4n2-c2ccc(Cl)cc2CN(C2CC(C(F)(F)F)C2)C4)C3)c(F)cc1F] |
| 652 | 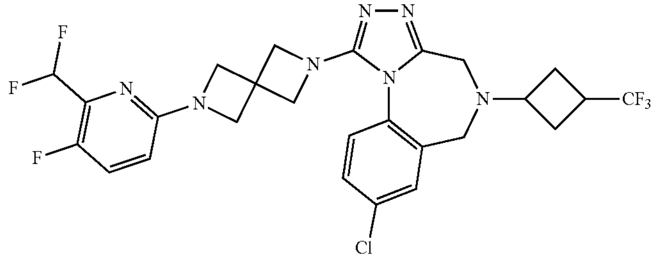 [SMILES: Fc1ccc(N2CC3(C2)CN(c2nnc4n2-c2ccc(Cl)cc2CN(C2CC(C(F)(F)F)C2)C4)C3)nc1C(F)F] |
| 653 | 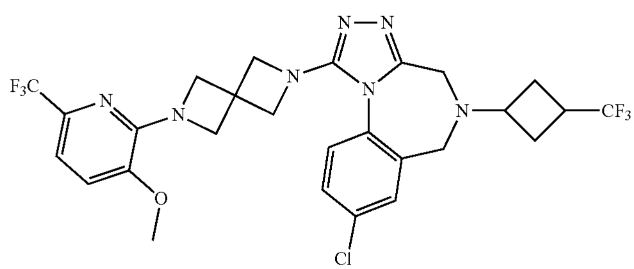 [SMILES: COc1ccc(C(F)(F)F)nc1N1CC2(C1)CN(c1nnc3n1-c1ccc(Cl)cc1CN(C1CC(C(F)(F)F)C1)C3)C2] |
| 654 | 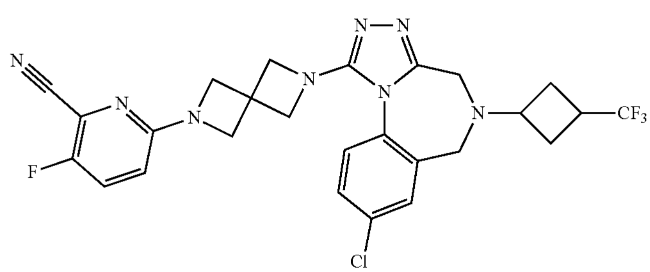 [SMILES: N#Cc1nc(N2CC3(C2)CN(c2nnc4n2-c2ccc(Cl)cc2CN(C2CC(C(F)(F)F)C2)C4)C3)ccc1F] |
| 655 | 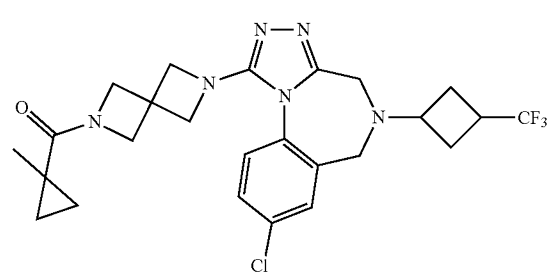 [SMILES: CC1(C(=O)N2CC3(C2)CN(c2nnc4n2-c2ccc(Cl)cc2CN(C2CC(C(F)(F)F)C2)C4)C3)CC1] |

TABLE 1-continued

Representative Compounds

| Cmpd. No. | Structure |
|---|---|
| 656 | 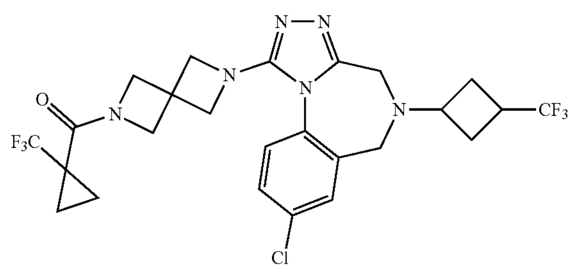 [SMILES: O=C(N1CC2(C1)CN(c1nnc3n1-c1ccc(Cl)cc1CN(C1CC(C(F)(F)F)C1)C3)C2)C1(C(F)(F)F)CC1] |
| 657 | 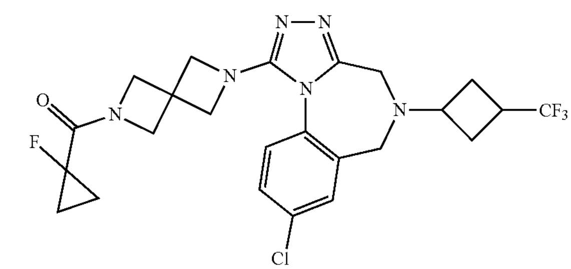 [SMILES: O=C(N1CC2(C1)CN(c1nnc3n1-c1ccc(Cl)cc1CN(C1CC(C(F)(F)F)C1)C3)C2)C1(F)CC1] |
| 658 | 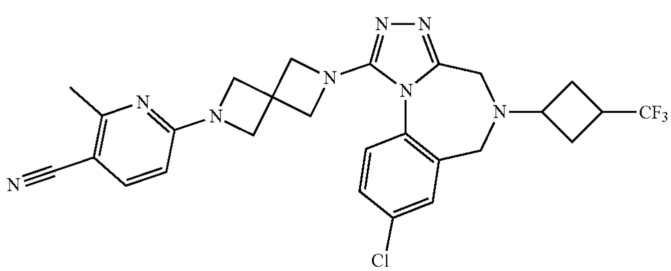 [SMILES: Cc1nc(N2CC3(C2)CN(c2nnc4n2-c2ccc(Cl)cc2CN(C2CC(C(F)(F)F)C2)C4)C3)ccc1C#N] |
| 659 | 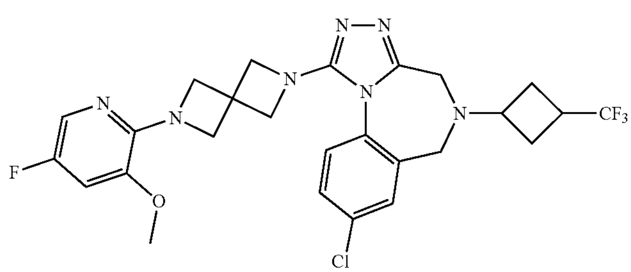 [SMILES: COc1cc(F)cnc1N1CC2(C1)CN(c1nnc3n1-c1ccc(Cl)cc1CN(C1CC(C(F)(F)F)C1)C3)C2] |
| 660 | 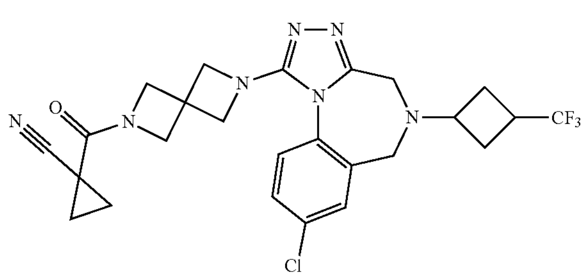 [SMILES: N#CC1(C(=O)N2CC3(C2)CN(c2nnc4n2-c2ccc(Cl)cc2CN(C2CC(C(F)(F)F)C2)C4)C3)CC1] |

TABLE 1-continued

Representative Compounds

| Cmpd. No. | Structure |
|---|---|
| 661 | 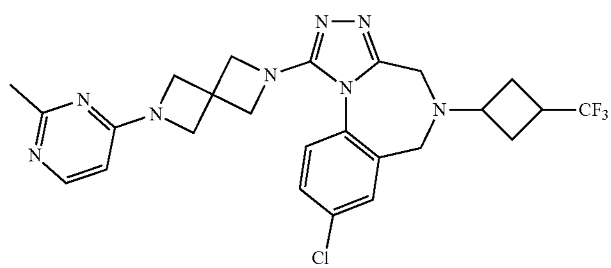 [SMILES: Cc1nccc(N2CC3(C2)CN(c2nnc4n2-c2ccc(Cl)cc2CN(C2CC(C(F)(F)F)C2)C4)C3)n1] |
| 662 | 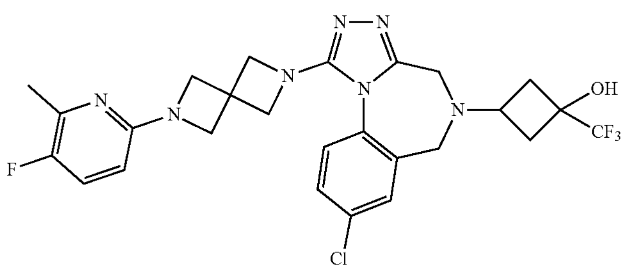 [SMILES: Cc1nc(N2CC3(C2)CN(c2nnc4n2-c2ccc(Cl)cc2CN(C2CC(O)(C(F)(F)F)C2)C4)C3)ccc1F] |
| 663 | 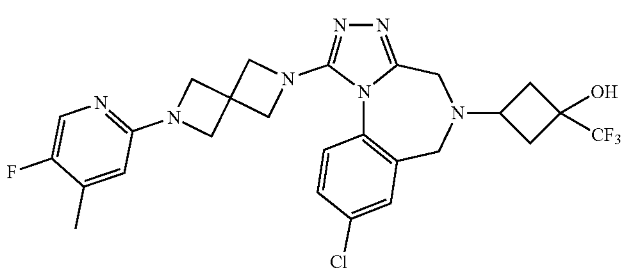 [SMILES: Cc1cc(N2CC3(C2)CN(c2nnc4n2-c2ccc(Cl)cc2CN(C2CC(O)(C(F)(F)F)C2)C4)C3)ncc1F] |
| 664 | 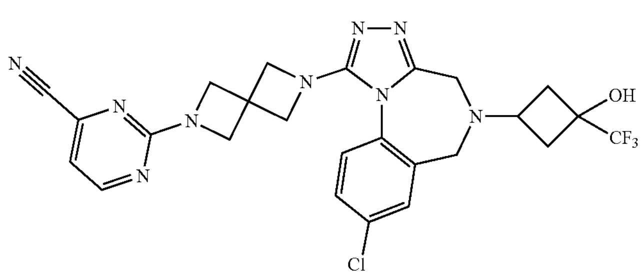 [SMILES: N#Cc1ccnc(N2CC3(C2)CN(c2nnc4n2-c2ccc(Cl)cc2CN(C2CC(O)(C(F)(F)F)C2)C4)C3)n1] |
| 665 | 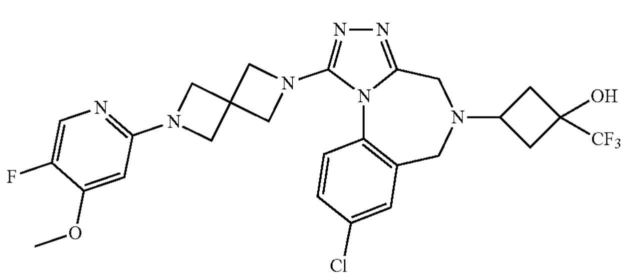 [SMILES: COc1cc(N2CC3(C2)CN(c2nnc4n2-c2ccc(Cl)cc2CN(C2CC(O)(C(F)(F)F)C2)C4)C3)ncc1F] |

TABLE 1-continued

Representative Compounds

| Cmpd. No. | Structure |
|---|---|
| 667 | 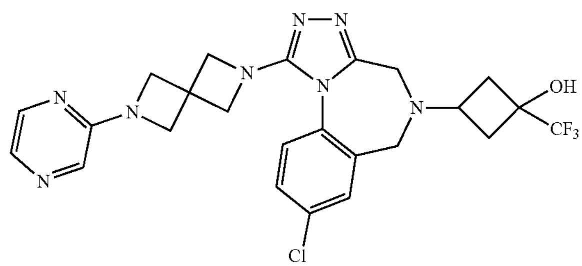 [SMILES: OC1(C(F)(F)F)CC(N2Cc3cc(Cl)ccc3-n3c(nnc3N3CC4(CN(c5cnccn5)C4)C3)C2)C1] |
| 668 | 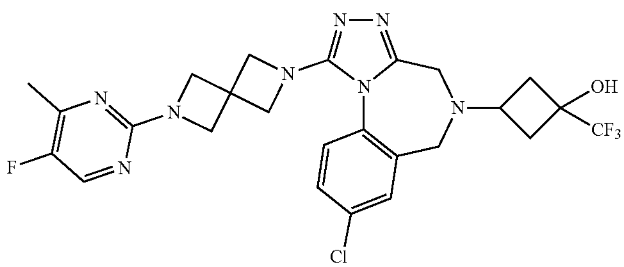 [SMILES: Cc1nc(N2CC3(C2)CN(c2nnc4n2-c2ccc(Cl)cc2CN(C2CC(O)(C(F)(F)F)C2)C4)C3)ncc1F] |
| 669 | 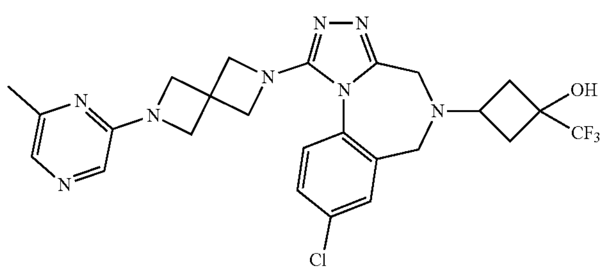 [SMILES: Cc1cncc(N2CC3(C2)CN(c2nnc4n2-c2ccc(Cl)cc2CN(C2CC(O)(C(F)(F)F)C2)C4)C3)n1] |
| 670 | 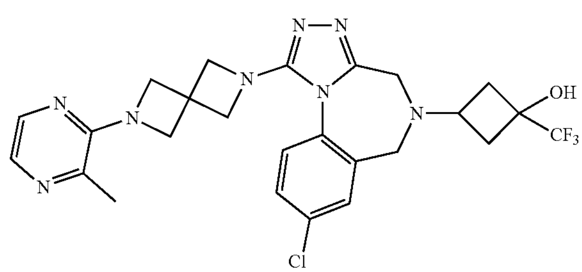 [SMILES: Cc1nccnc1N1CC2(C1)CN(c1nnc3n1-c1ccc(Cl)cc1CN(C1CC(O)(C(F)(F)F)C1)C3)C2] |
| 671 | 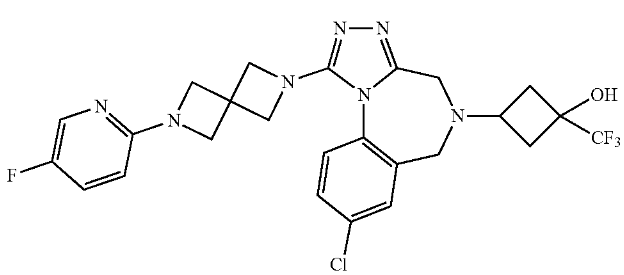 [SMILES: OC1(C(F)(F)F)CC(N2Cc3cc(Cl)ccc3-n3c(nnc3N3CC4(CN(c5ccc(F)cn5)C4)C3)C2)C1] |

TABLE 1-continued

Representative Compounds

| Cmpd. No. | Structure |
|---|---|
| 672 | 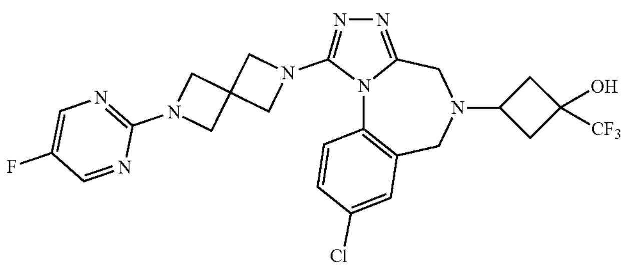 [SMILES: OC1(C(F)(F)F)CC(N2Cc3cc(Cl)ccc3-n3c(nnc3N3CC4(CN(c5ncc(F)cn5)C4)C3)C2)C1] |
| 673 | 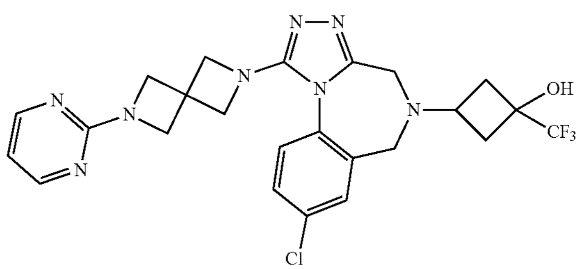 [SMILES: OC1(C(F)(F)F)CC(N2Cc3cc(Cl)ccc3-n3c(nnc3N3CC4(CN(c5ncccn5)C4)C3)C2)C1] |
| 674 | 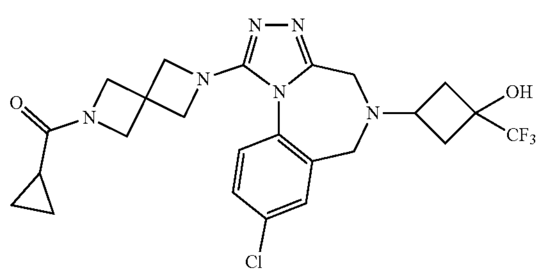 [SMILES: O=C(C1CC1)N1CC2(C1)CN(c1nnc3n1-c1ccc(Cl)cc1CN(C1CC(O)(C(F)(F)F)C1)C3)C2] |
| 675 | 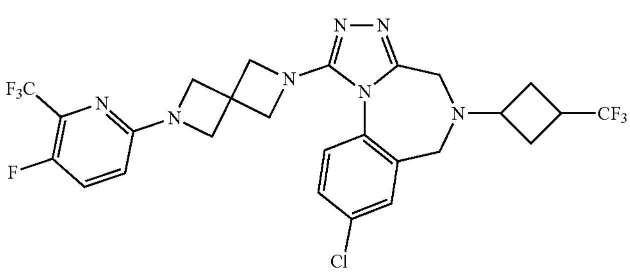 [SMILES: Fc1ccc(N2CC3(C2)CN(c2nnc4n2-c2ccc(Cl)cc2CN(C2CC(C(F)(F)F)C2)C4)C3)nc1C(F)(F)F] |
| 676 | 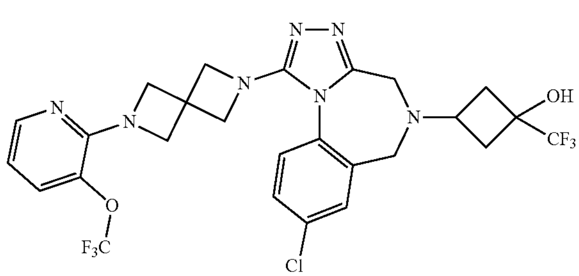 [SMILES: OC1(C(F)(F)F)CC(N2Cc3cc(Cl)ccc3-n3c(nnc3N3CC4(CN(c5ncccc5OC(F)(F)F)C4)C3)C2)C1] |

TABLE 1-continued

Representative Compounds

| Cmpd. No. | Structure |
|---|---|
| 677 | 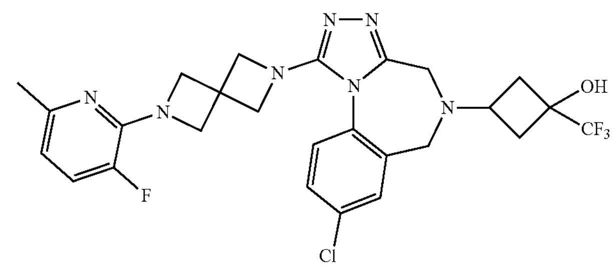 [SMILES: Cc1ccc(F)c(N2CC3(C2)CN(c2nnc4n2-c2ccc(Cl)cc2CN(C2CC(O)(C(F)(F)F)C2)C4)C3)n1] |
| 678 | 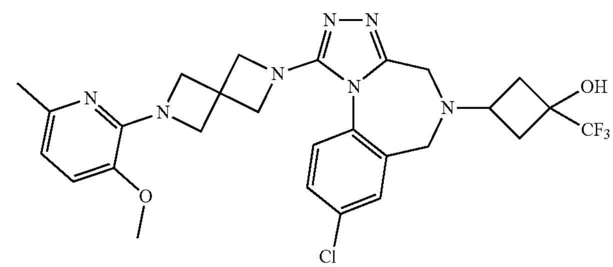 [SMILES: COc1ccc(C)nc1N1CC2(C1)CN(c1nnc3n1-c1ccc(Cl)cc1CN(C1CC(O)(C(F)(F)F)C1)C3)C2] |
| 679 | 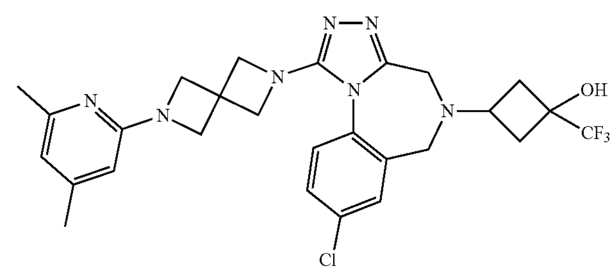 [SMILES: Cc1cc(C)nc(N2CC3(C2)CN(c2nnc4n2-c2ccc(Cl)cc2CN(C2CC(O)(C(F)(F)F)C2)C4)C3)c1] |
| 680 | 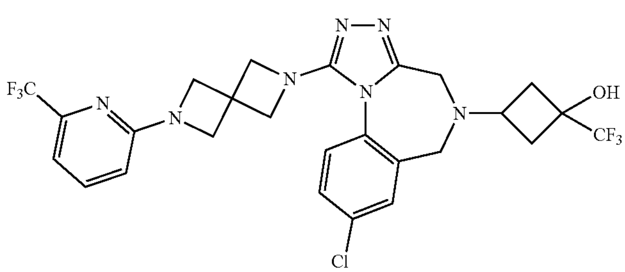 [SMILES: OC1(C(F)(F)F)CC(N2Cc3cc(Cl)ccc3-n3c(nnc3N3CC4(CN(c5cccc(C(F)(F)F)n5)C4)C3)C2)C1] |
| 681 | 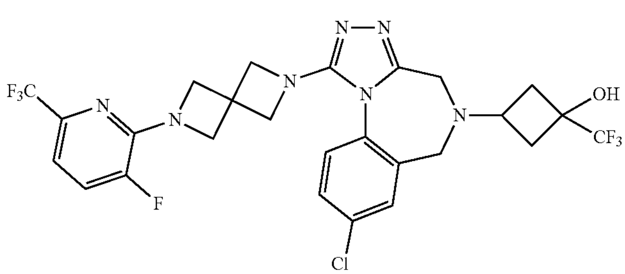 [SMILES: OC1(C(F)(F)F)CC(N2Cc3cc(Cl)ccc3-n3c(nnc3N3CC4(CN(c5nc(C(F)(F)F)ccc5F)C4)C3)C2)C1] |

TABLE 1-continued

Representative Compounds

| Cmpd. No. | Structure |
|---|---|
| 682 | 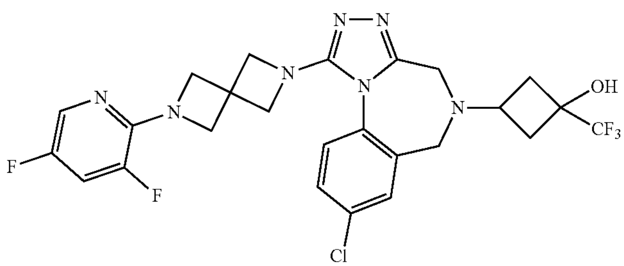 [SMILES: OC1(C(F)(F)F)CC(N2Cc3cc(Cl)ccc3-n3c(nnc3N3CC4(CN(c5ncc(F)cc5F)C4)C3)C2)C1] |
| 683 | 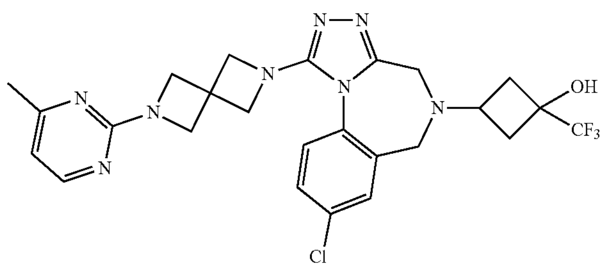 [SMILES: Cc1ccnc(N2CC3(C2)CN(c2nnc4n2-c2ccc(Cl)cc2CN(C2CC(O)(C(F)(F)F)C2)C4)C3)n1] |
| 684 | 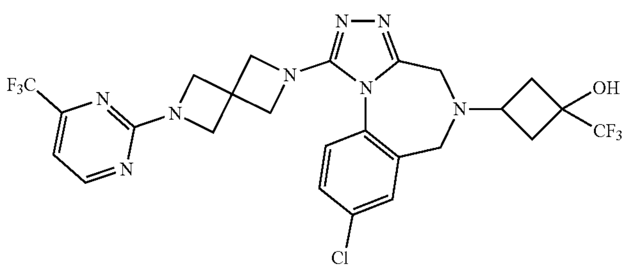 [SMILES: OC1(C(F)(F)F)CC(N2Cc3cc(Cl)ccc3-n3c(nnc3N3CC4(CN(c5nccc(C(F)(F)F)n5)C4)C3)C2)C1] |
| 685 | 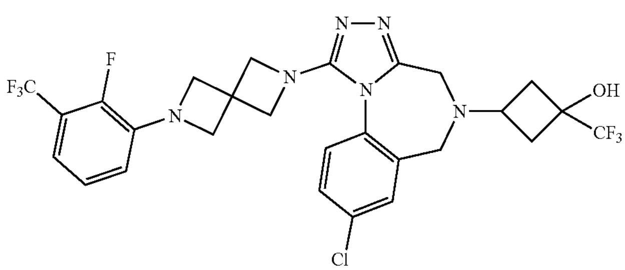 [SMILES: OC1(C(F)(F)F)CC(N2Cc3cc(Cl)ccc3-n3c(nnc3N3CC4(CN(c5cccc(C(F)(F)F)c5F)C4)C3)C2)C1] |
| 686 | 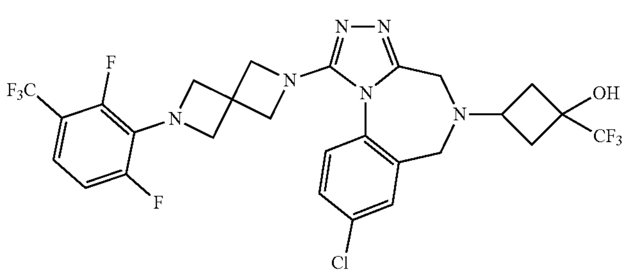 [SMILES: OC1(C(F)(F)F)CC(N2Cc3cc(Cl)ccc3-n3c(nnc3N3CC4(CN(c5c(F)ccc(C(F)(F)F)c5F)C4)C3)C2)C1] |

TABLE 1-continued
Representative Compounds
| Cmpd. No. | Structure |
|---|---|
| 687 | 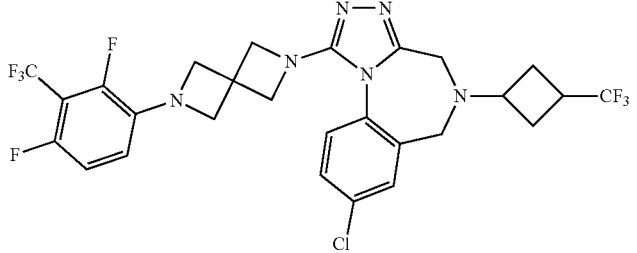 [SMILES: Fc1ccc(N2CC3(C2)CN(c2nnc4n2-c2ccc(Cl)cc2CN(C2CC(C(F)(F)F)C2)C4)C3)c(F)c1C(F)(F)F] |
| 688 | 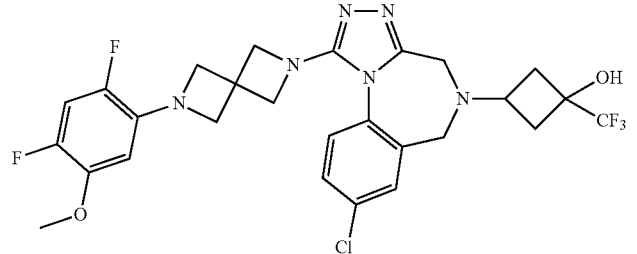 [SMILES: COc1cc(N2CC3(C2)CN(c2nnc4n2-c2ccc(Cl)cc2CN(C2CC(O)(C(F)(F)F)C2)C4)C3)c(F)cc1F] |
| 689 | 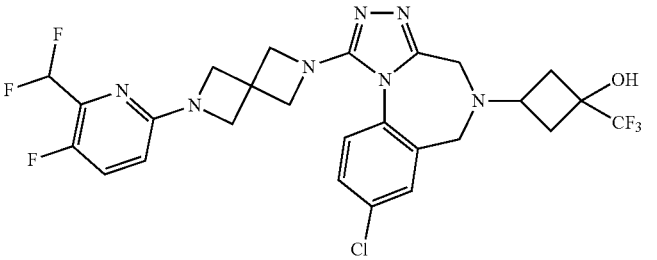 [SMILES: OC1(C(F)(F)F)CC(N2Cc3cc(Cl)ccc3-n3c(nnc3N3CC4(CN(c5ccc(F)c(C(F)F)n5)C4)C3)C2)C1] |
| 690 | 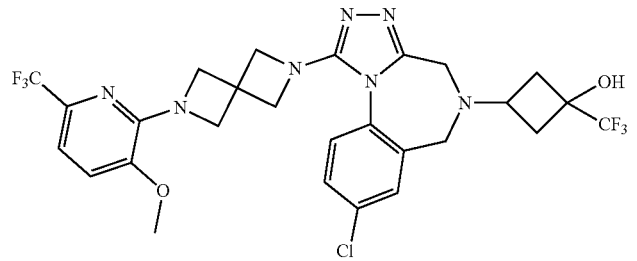 [SMILES: COc1ccc(C(F)(F)F)nc1N1CC2(C1)CN(c1nnc3n1-c1ccc(Cl)cc1CN(C1CC(O)(C(F)(F)F)C1)C3)C2] |
| 691 | 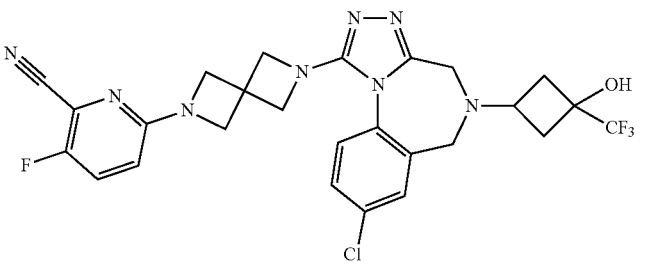 [SMILES: N#Cc1nc(N2CC3(C2)CN(c2nnc4n2-c2ccc(Cl)cc2CN(C2CC(O)(C(F)(F)F)C2)C4)C3)ccc1F] |

TABLE 1-continued

Representative Compounds

| Cmpd. No. | Structure |
|---|---|
| 692 | 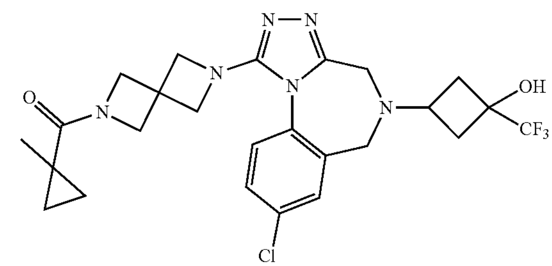 [SMILES: CC1(C(=O)N2CC3(C2)CN(c2nnc4n2-c2ccc(Cl)cc2CN(C2CC(O)(C(F)(F)F)C2)C4)C3)CC1] |
| 693 | 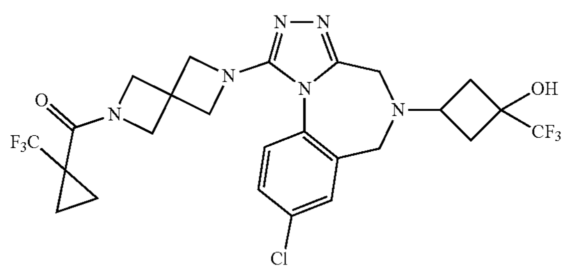 [SMILES: O=C(N1CC2(C1)CN(c1nnc3n1-c1ccc(Cl)cc1CN(C1CC(O)(C(F)(F)F)C1)C3)C2)C1(C(F)(F)F)CC1] |
| 694 | 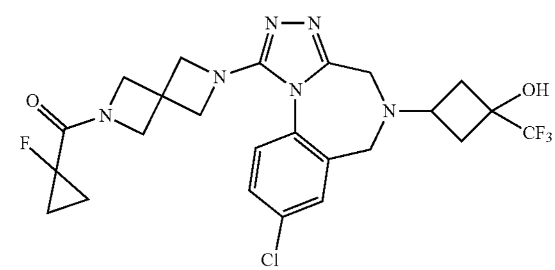 [SMILES: O=C(N1CC2(C1)CN(c1nnc3n1-c1ccc(Cl)cc1CN(C1CC(O)(C(F)(F)F)C1)C3)C2)C1(F)CC1] |
| 695 | 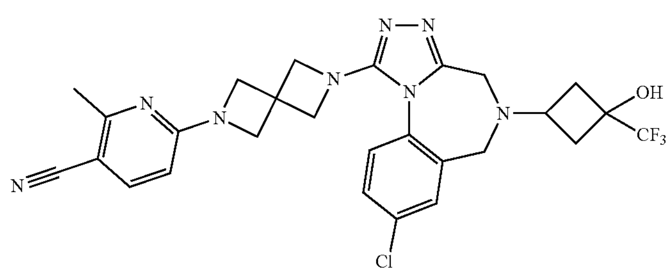 [SMILES: Cc1nc(N2CC3(C2)CN(c2nnc4n2-c2ccc(Cl)cc2CN(C2CC(O)(C(F)(F)F)C2)C4)C3)ccc1C#N] |
| 696 | 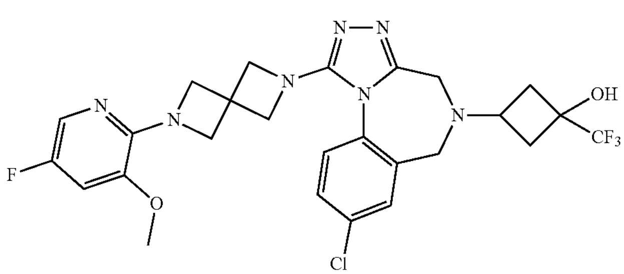 [SMILES: COc1cc(F)cnc1N1CC2(C1)CN(c1nnc3n1-c1ccc(Cl)cc1CN(C1CC(O)(C(F)(F)F)C1)C3)C2] |

TABLE 1-continued

Representative Compounds

| Cmpd. No. | Structure |
|---|---|
| 697 | 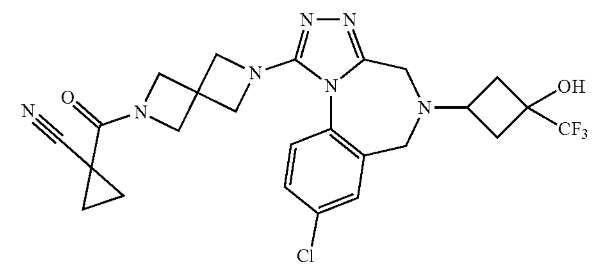 [SMILES: N#CC1(C(=O)N2CC3(C2)CN(c2nnc4n2-c2ccc(Cl)cc2CN(C2CC(O)(C(F)(F)F)C2)C4)C3)CC1] |
| 698 | 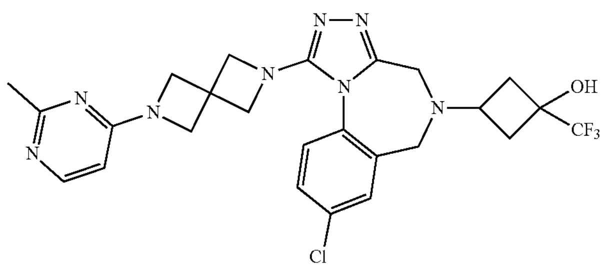 [SMILES: Cc1nccc(N2CC3(C2)CN(c2nnc4n2-c2ccc(Cl)cc2CN(C2CC(O)(C(F)(F)F)C2)C4)C3)n1] |
| 699 | 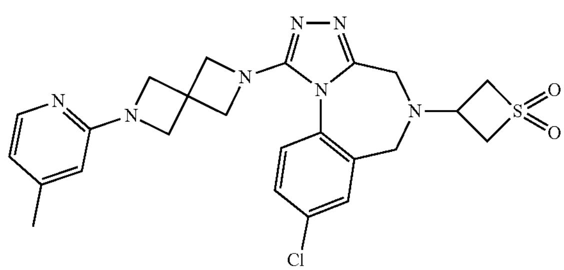 [SMILES: Cc1ccnc(N2CC3(C2)CN(c2nnc4n2-c2ccc(Cl)cc2CN(C2CS(=O)(=O)C2)C4)C3)c1] |
| 700 | 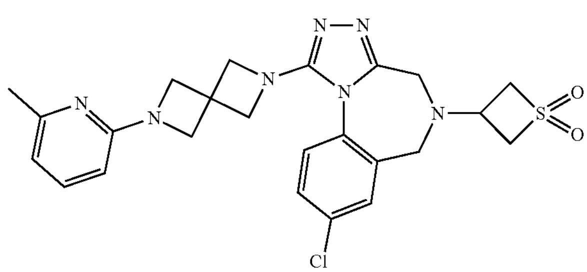 [SMILES: Cc1cccc(N2CC3(C2)CN(c2nnc4n2-c2ccc(Cl)cc2CN(C2CS(=O)(=O)C2)C4)C3)n1] |
| 701 | 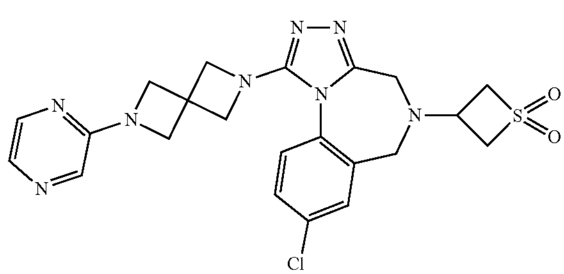 [SMILES: O=S1(=O)CC(N2Cc3cc(Cl)ccc3-n3c(nnc3N3CC4(CN(c5cnccn5)C4)C3)C2)C1] |

TABLE 1-continued

Representative Compounds

| Cmpd. No. | Structure |
|---|---|
| 702 | 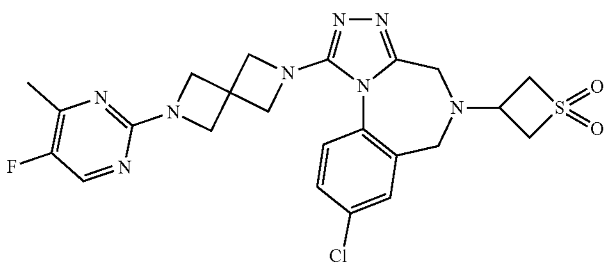 [SMILES: Cc1nc(N2CC3(C2)CN(c2nnc4n2-c2ccc(Cl)cc2CN(C2CS(=O)(=O)C2)C4)C3)ncc1F] |
| 703 | 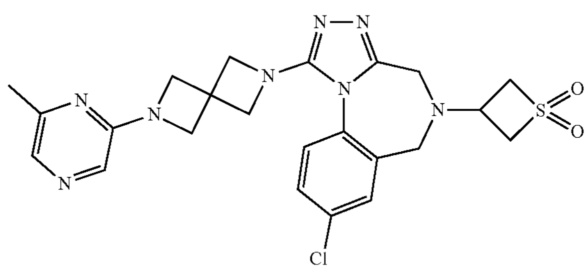 [SMILES: Cc1cncc(N2CC3(C2)CN(c2nnc4n2-c2ccc(Cl)cc2CN(C2CS(=O)(=O)C2)C4)C3)n1] |
| 704 | 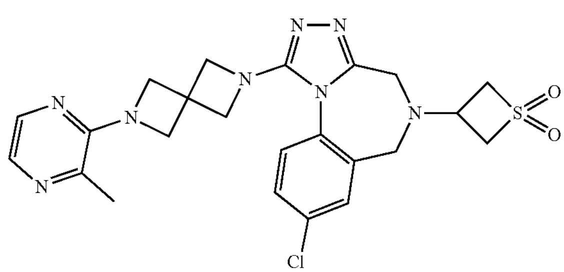 [SMILES: Cc1nccnc1N1CC2(C1)CN(c1nnc3n1-c1ccc(Cl)cc1CN(C1CS(=O)(=O)C1)C3)C2] |
| 705 | 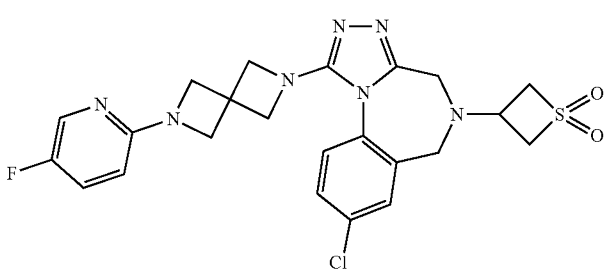 [SMILES: O=S1(=O)CC(N2Cc3cc(Cl)ccc3-n3c(nnc3N3CC4(CN(c5ccc(F)cn5)C4)C3)C2)C1] |
| 706 | 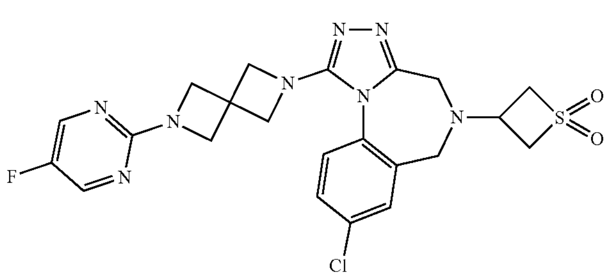 [SMILES: O=S1(=O)CC(N2Cc3cc(Cl)ccc3-n3c(nnc3N3CC4(CN(c5ncc(F)cn5)C4)C3)C2)C1] |

TABLE 1-continued

Representative Compounds

| Cmpd. No. | Structure |
|---|---|
| 707 | 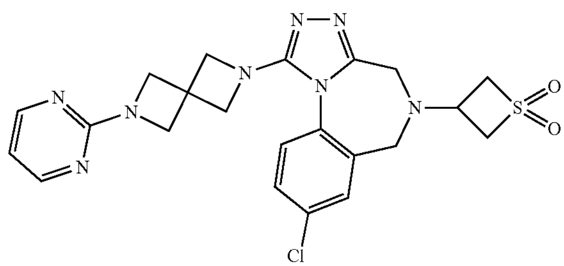 [SMILES: O=S1(=O)CC(N2Cc3cc(Cl)ccc3-n3c(nnc3N3CC4(CN(c5ncccn5)C4)C3)C2)C1] |
| 708 | 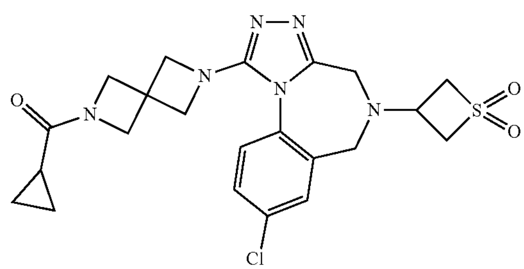 [SMILES: O=C(C1CC1)N1CC2(C1)CN(c1nnc3n1-c1ccc(Cl)cc1CN(C1CS(=O)(=O)C1)C3)C2] |
| 709 | 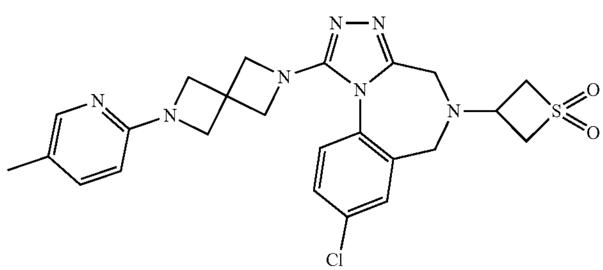 [SMILES: Cc1ccc(N2CC3(C2)CN(c2nnc4n2-c2ccc(Cl)cc2CN(C2CS(=O)(=O)C2)C4)C3)nc1] |
| 710 | 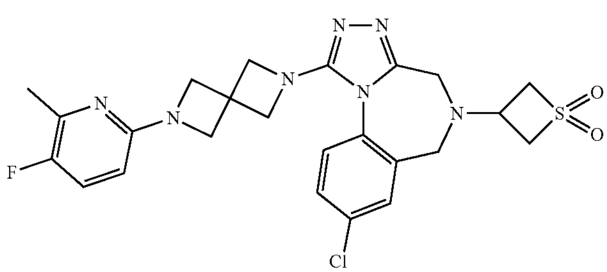 [SMILES: Cc1nc(N2CC3(C2)CN(c2nnc4n2-c2ccc(Cl)cc2CN(C2CS(=O)(=O)C2)C4)C3)ccc1F] |
| 711 | 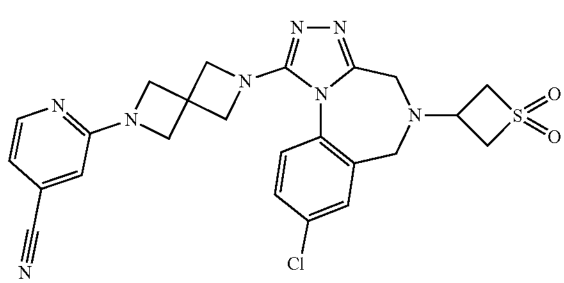 [SMILES: N#Cc1ccnc(N2CC3(C2)CN(c2nnc4n2-c2ccc(Cl)cc2CN(C2CS(=O)(=O)C2)C4)C3)c1] |

TABLE 1-continued
Representative Compounds
| Cmpd. No. | Structure |
|---|---|
| 712 | 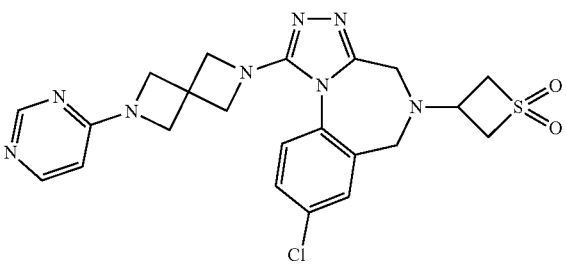 [SMILES: O=S1(=O)CC(N2Cc3cc(Cl)ccc3-n3c(nnc3N3CC4(CN(c5ccncn5)C4)C3)C2)C1] |
| 713 | 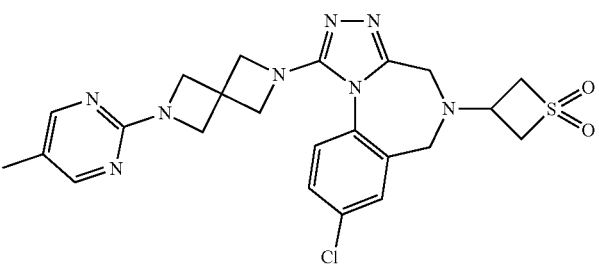 [SMILES: Cc1cnc(N2CC3(C2)CN(c2nnc4n2-c2ccc(Cl)cc2CN(C2CS(=O)(=O)C2)C4)C3)nc1] |
| 714 | 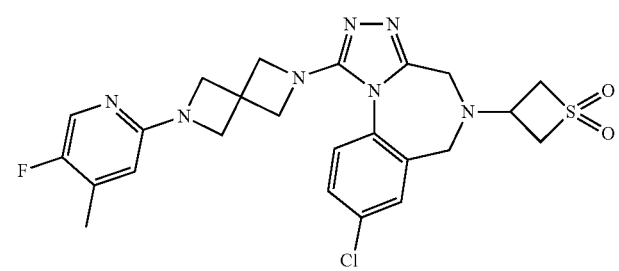 [SMILES: Cc1cc(N2CC3(C2)CN(c2nnc4n2-c2ccc(Cl)cc2CN(C2CS(=O)(=O)C2)C4)C3)ncc1F] |
| 715 | 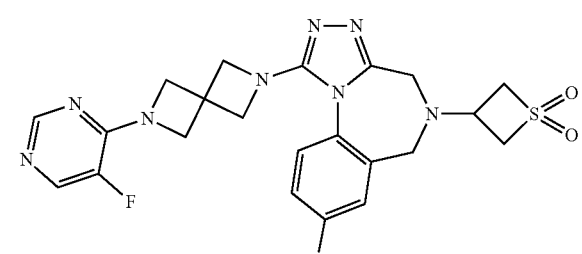 |
| 716 | 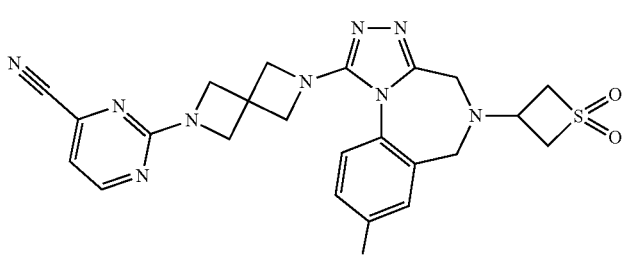 |

TABLE 1-continued

Representative Compounds

| Cmpd. No. | Structure |
|---|---|
| 717 | 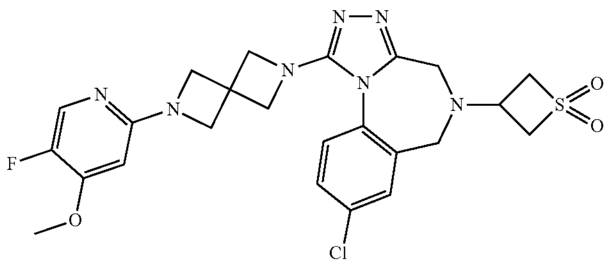 [SMILES: COc1cc(N2CC3(C2)CN(c2nnc4n2-c2ccc(Cl)cc2CN(C2CS(=O)(=O)C2)C4)C3)ncc1F] |
| 718 | 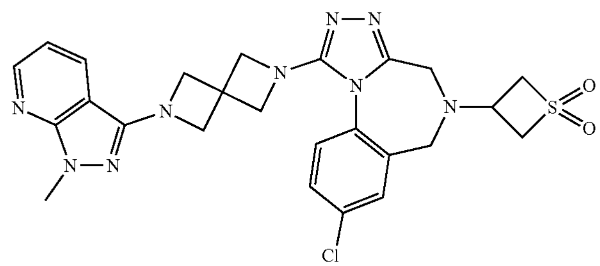 [SMILES: Cn1nc(N2CC3(C2)CN(c2nnc4n2-c2ccc(Cl)cc2CN(C2CS(=O)(=O)C2)C4)C3)c2cccnc21] |
| 719 | 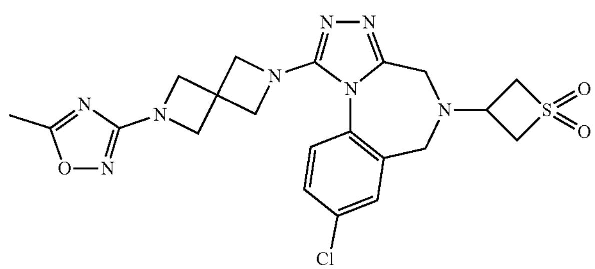 [SMILES: Cc1nc(N2CC3(C2)CN(c2nnc4n2-c2ccc(Cl)cc2CN(C2CS(=O)(=O)C2)C4)C3)no1] |
| 720 | 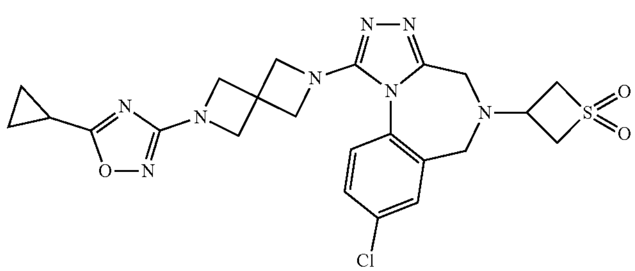 [SMILES: O=S1(=O)CC(N2Cc3cc(Cl)ccc3-n3c(nnc3N3CC4(CN(c5noc(C6CC6)n5)C4)C3)C2)C1] |
| 721 | 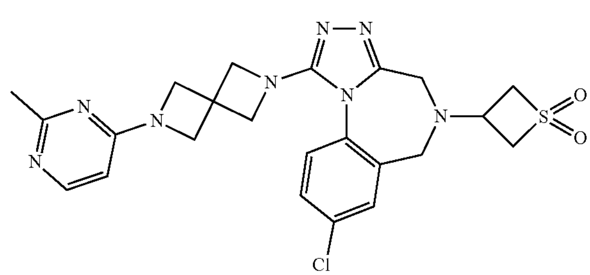 [SMILES: Cc1nccc(N2CC3(C2)CN(c2nnc4n2-c2ccc(Cl)cc2CN(C2CS(=O)(=O)C2)C4)C3)n1] |

TABLE 1-continued

Representative Compounds

| Cmpd. No. | Structure |
|---|---|
| 722 | 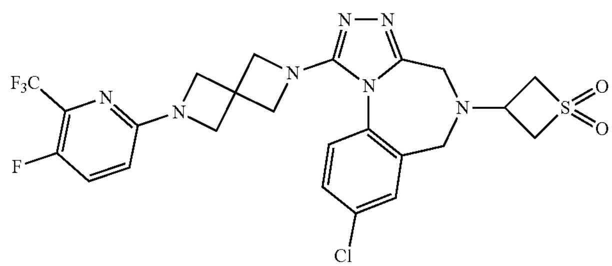 |
| 723 | 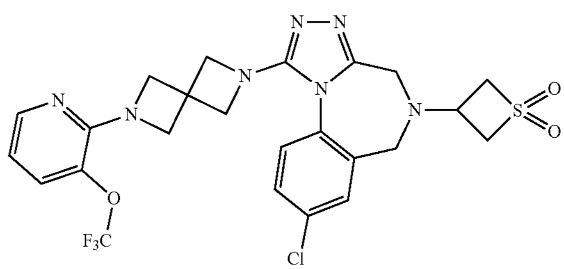 [SMILES: O=S1(=O)CC(N2Cc3cc(Cl)ccc3-n3c(nnc3N3CC4(CN(c5ncccc5OC(F)(F)F)C4)C3)C2)C1] |
| 724 | 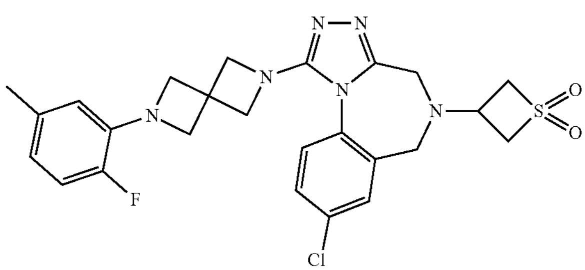 [SMILES: Cc1ccc(F)c(N2CC3(C2)CN(c2nnc4n2-c2ccc(Cl)cc2CN(C2CS(=O)(=O)C2)C4)C3)c1] |
| 725 | 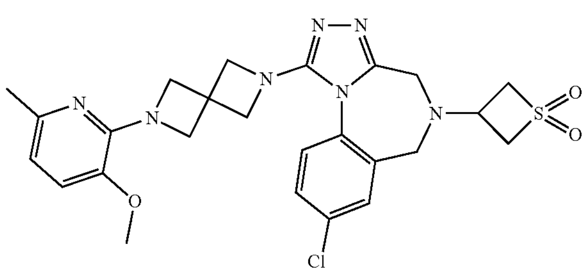 [SMILES: COc1ccc(C)nc1N1CC2(C1)CN(c1nnc3n1-c1ccc(Cl)cc1CN(C1CS(=O)(=O)C1)C3)C2] |
| 726 | 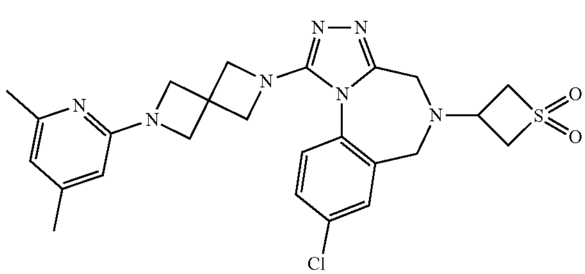 [SMILES: Cc1cc(C)nc(N2CC3(C2)CN(c2nnc4n2-c2ccc(Cl)cc2CN(C2CS(=O)(=O)C2)C4)C3)c1] |

TABLE 1-continued

Representative Compounds

| Cmpd. No. | Structure |
|---|---|
| 727 | 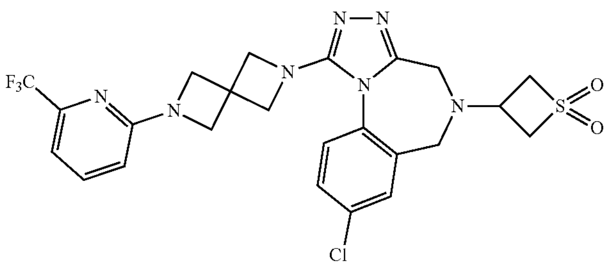 [SMILES: O=S1(=O)CC(N2Cc3cc(Cl)ccc3-n3c(nnc3N3CC4(CN(c5cccc(C(F)(F)F)n5)C4)C3)C2)C1] |
| 728 | 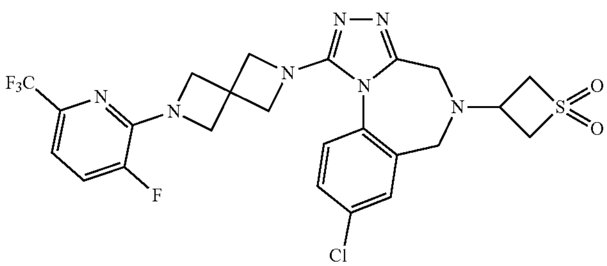 [SMILES: O=S1(=O)CC(N2Cc3cc(Cl)ccc3-n3c(nnc3N3CC4(CN(c5nc(C(F)(F)F)ccc5F)C4)C3)C2)C1] |
| 729 | 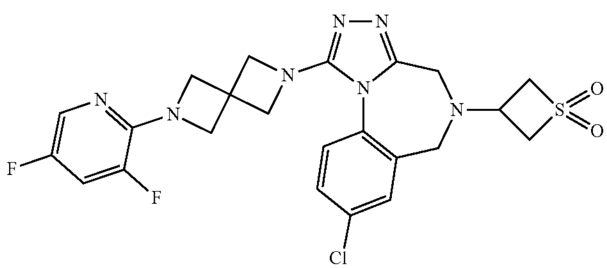 [SMILES: O=S1(=O)CC(N2Cc3cc(Cl)ccc3-n3c(nnc3N3CC4(CN(c5ncc(F)cc5F)C4)C3)C2)C1] |
| 730 | 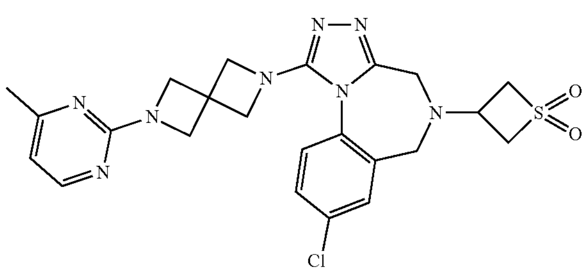 [SMILES: Cc1ccnc(N2CC3(C2)CN(c2nnc4n2-c2ccc(Cl)cc2CN(C2CS(=O)(=O)C2)C4)C3)n1] |
| 731 | 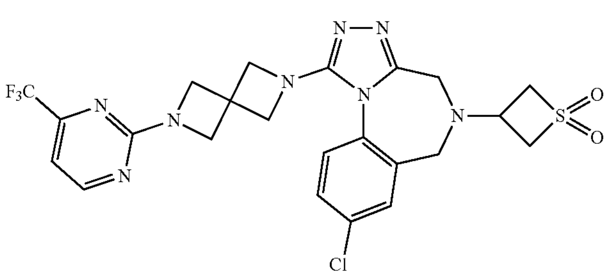 [SMILES: O=S1(=O)CC(N2Cc3cc(Cl)ccc3-n3c(nnc3N3CC4(CN(c5nccc(C(F)(F)F)n5)C4)C3)C2)C1] |

TABLE 1-continued

Representative Compounds

| Cmpd. No. | Structure |
|---|---|
| 732 | 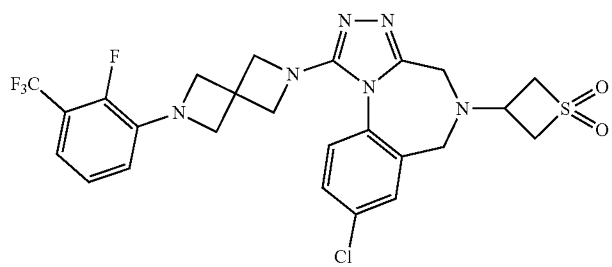 [SMILES: O=S1(=O)CC(N2Cc3cc(Cl)ccc3-n3c(nnc3N3CC4(CN(c5cccc(C(F)(F)F)c5F)C4)C3)C2)C1] |
| 733 | 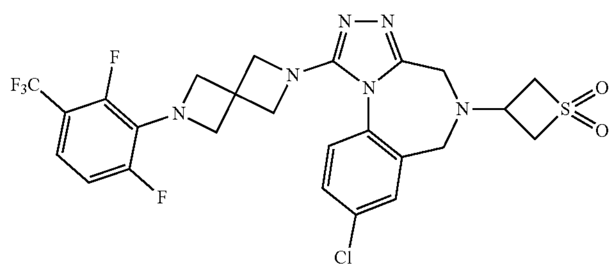 [SMILES: O=S1(=O)CC(N2Cc3cc(Cl)ccc3-n3c(nnc3N3CC4(CN(c5c(F)ccc(C(F)(F)F)c5F)C4)C3)C2)C1] |
| 734 | 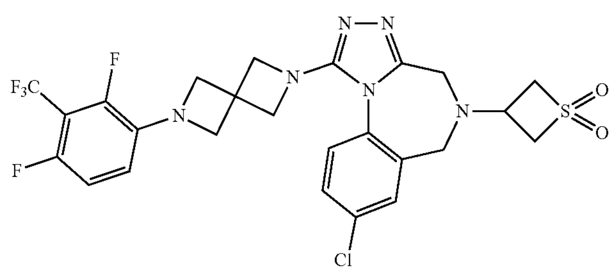 |
| 735 | 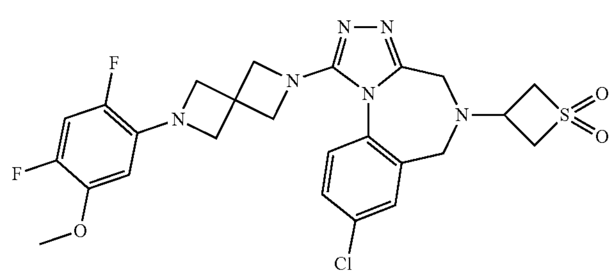 [SMILES: COc1cc(N2CC3(C2)CN(c2nnc4n2-c2ccc(Cl)cc2CN(C2CS(=O)(=O)C2)C4)C3)c(F)cc1F] |
| 736 | 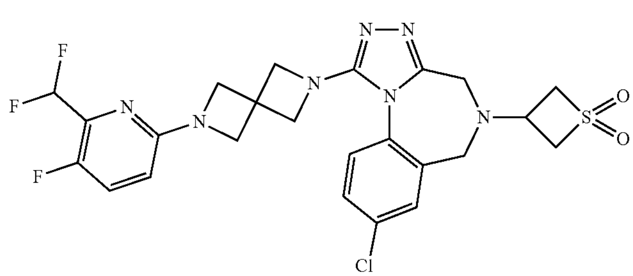 [SMILES: O=S1(=O)CC(N2Cc3cc(Cl)ccc3-n3c(nnc3N3CC4(CN(c5ccc(F)c(C(F)F)n5)C4)C3)C2)C1] |

TABLE 1-continued

Representative Compounds

| Cmpd. No. | Structure |
|---|---|
| 737 | 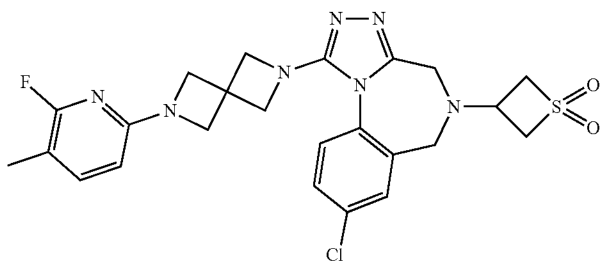 [SMILES: Cc1ccc(N2CC3(C2)CN(c2nnc4n2-c2ccc(Cl)cc2CN(C2CS(=O)(=O)C2)C4)C3)nc1F] |
| 738 | 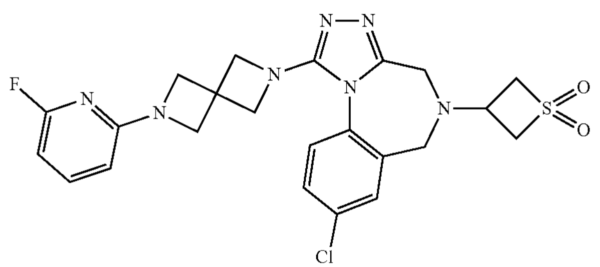 [SMILES: O=S1(=O)CC(N2Cc3cc(Cl)ccc3-n3c(nnc3N3CC4(CN(c5cccc(F)n5)C4)C3)C2)C1] |
| 739 | 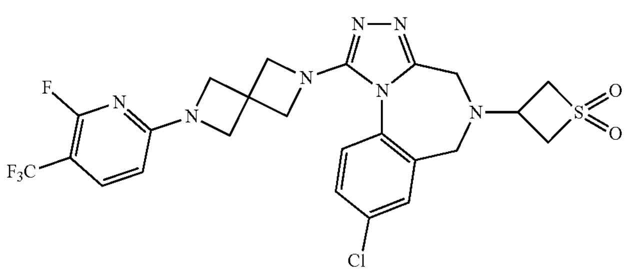 [SMILES: O=S1(=O)CC(N2Cc3cc(Cl)ccc3-n3c(nnc3N3CC4(CN(c5ccc(C(F)(F)F)c(F)n5)C4)C3)C2)C1] |
| 740 | 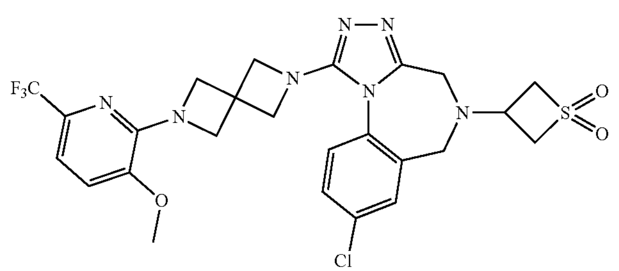 [SMILES: COc1ccc(C(F)(F)F)nc1N1CC2(C1)CN(c1nnc3n1-c1ccc(Cl)cc1CN(C1CS(=O)(=O)C1)C3)C2] |
| 741 | 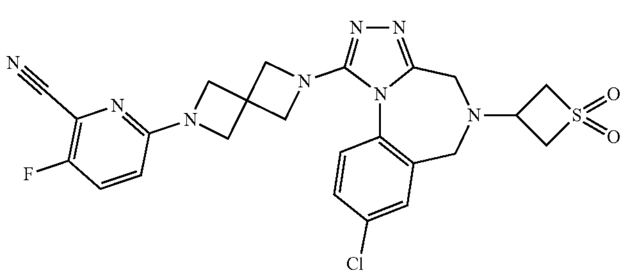 [SMILES: N#Cc1nc(N2CC3(C2)CN(c2nnc4n2-c2ccc(Cl)cc2CN(C2CS(=O)(=O)C2)C4)C3)ccc1F] |

TABLE 1-continued

Representative Compounds

| Cmpd. No. | Structure |
|---|---|
| 742 | 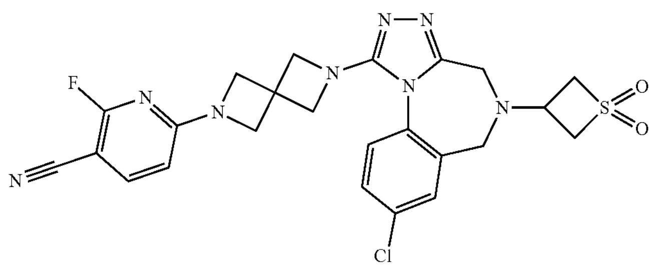 |
| 743 | 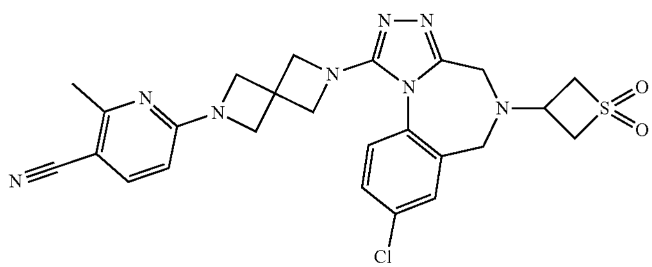 [SMILES: Cc1nc(N2CC3(C2)CN(c2nnc4n2-c2ccc(Cl)cc2CN(C2CS(=O)(=O)C2)C4)C3)ccc1C#N] |
| 744 | 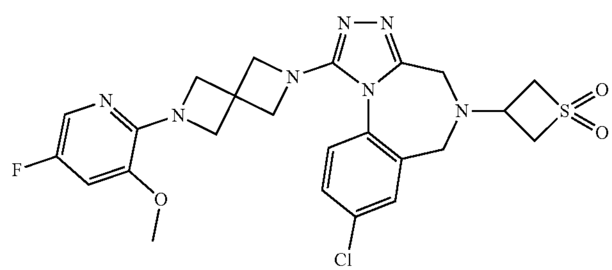 [SMILES: COc1cc(F)cnc1N1CC2(C1)CN(c1nnc3n1-c1ccc(Cl)cc1CN(C1CS(=O)(=O)C1)C3)C2] |
| 745 | 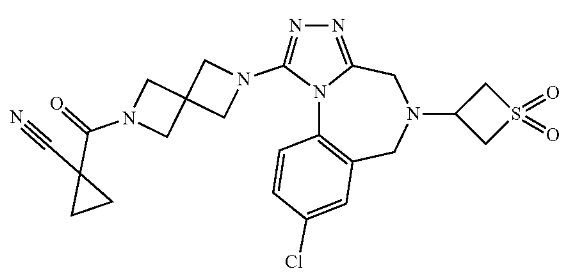 [SMILES: N#CC1(C(=O)N2CC3(C2)CN(c2nnc4n2-c2ccc(Cl)cc2CN(C2CS(=O)(=O)C2)C4)C3)CC1] |
| 746 | 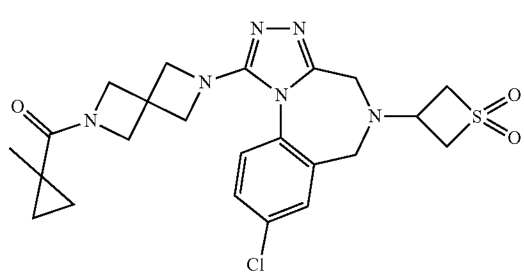 [SMILES: CC1(C(=O)N2CC3(C2)CN(c2nnc4n2-c2ccc(Cl)cc2CN(C2CS(=O)(=O)C2)C4)C3)CC1] |

TABLE 1-continued
Representative Compounds
| Cmpd. No. | Structure |
|---|---|
| 747 | 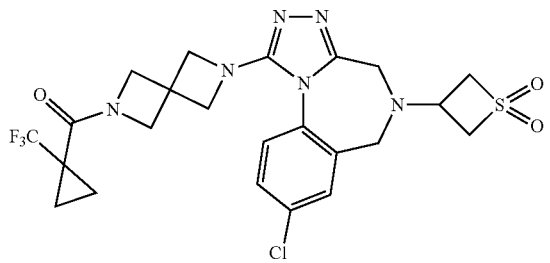 [SMILES: O=C(N1CC2(C1)CN(c1nnc3n1-c1ccc(Cl)cc1CN(C1CS(=O)(=O)C1)C3)C2)C1(C(F)(F)F)CC1] |
| 748 | 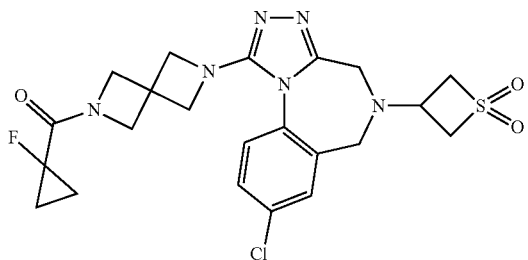 [SMILES: O=C(N1CC2(C1)CN(c1nnc3n1-c1ccc(Cl)cc1CN(C1CS(=O)(=O)C1)C3)C2)C1(F)CC1] |
| 749 | 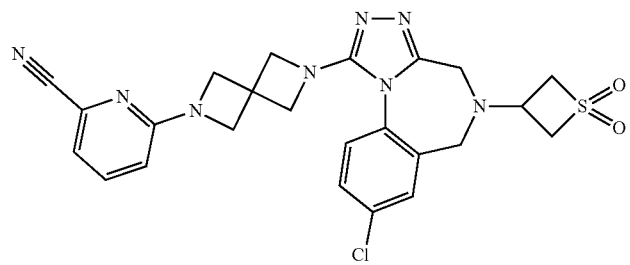 |
| 750 | 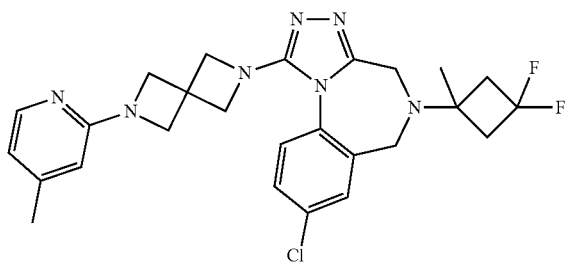 [SMILES: Cc1ccnc(N2CC3(C2)CN(c2nnc4n2-c2ccc(Cl)cc2CN(C2(C)CC(F)(F)C2)C4)C3)c1] |
| 751 | 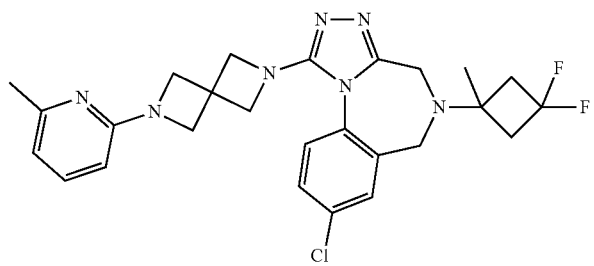 [SMILES: Cc1cccc(N2CC3(C2)CN(c2nnc4n2-c2ccc(Cl)cc2CN(C2(C)CC(F)(F)C2)C4)C3)n1] |

TABLE 1-continued
Representative Compounds
| Cmpd. No. | Structure |
|---|---|
| 752 | 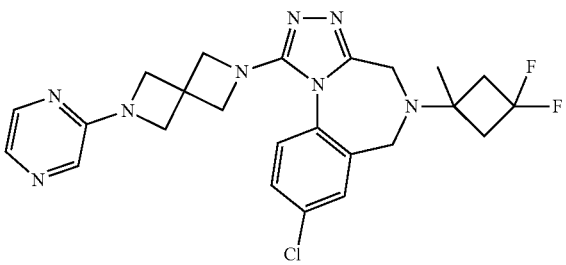 [SMILES: CC1(N2Cc3cc(Cl)ccc3-n3c(nnc3N3CC4(CN(c5cnccn5)C4)C3)C2)CC(F)(F)C1] |
| 753 | 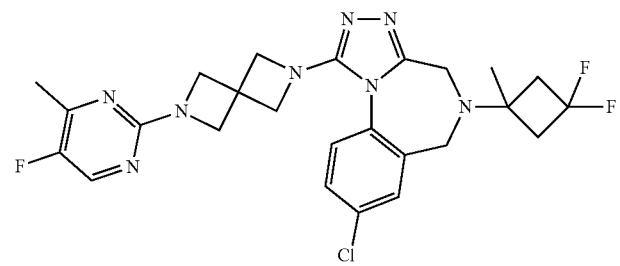 |
| 754 | 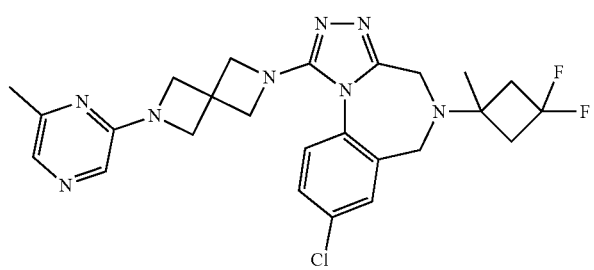 [SMILES: Cc1cncc(N2CC3(C2)CN(c2nnc4n2-c2ccc(Cl)cc2CN(C2(C)CC(F)(F)C2)C4)C3)n1] |
| 755 | 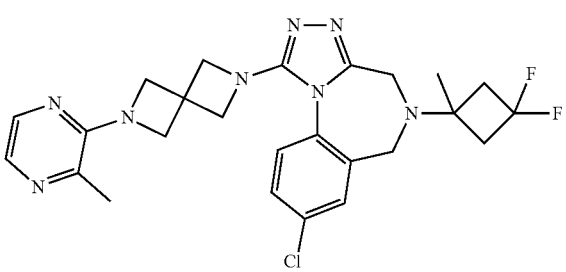 [SMILES: Cc1nccnc1N1CC2(C1)CN(c1nnc3n1-c1ccc(Cl)cc1CN(C1(C)CC(F)(F)C1)C3)C2] |
| 756 | 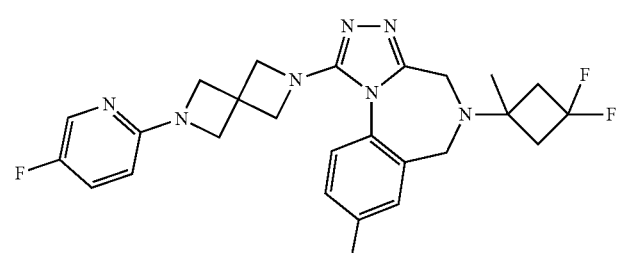 |

TABLE 1-continued

Representative Compounds

| Cmpd. No. | Structure |
|---|---|
| 757 | 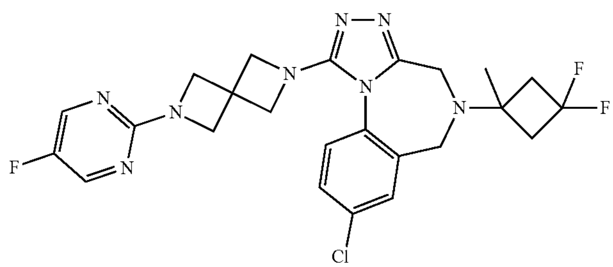 [SMILES: CC1(N2Cc3cc(Cl)ccc3-n3c(nnc3N3CC4(CN(c5ncc(F)cn5)C4)C3)C2)CC(F)(F)C1] |
| 758 | 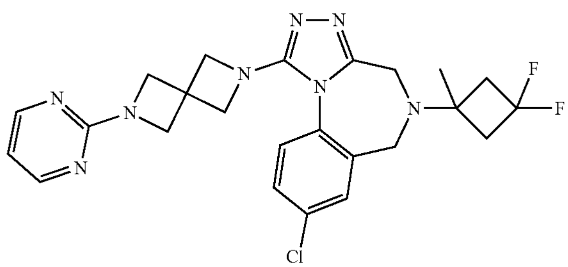 [SMILES: CC1(N2Cc3cc(Cl)ccc3-n3c(nnc3N3CC4(CN(c5ncccn5)C4)C3)C2)CC(F)(F)C1] |
| 759 | 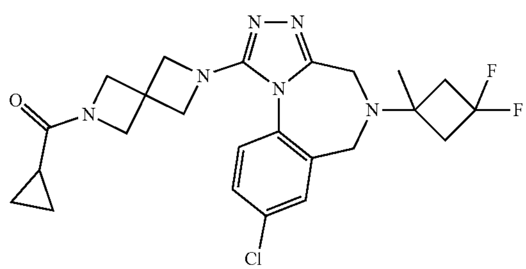 [SMILES: CC1(N2Cc3cc(Cl)ccc3-n3c(nnc3N3CC4(CN(C(=O)C5CC5)C4)C3)C2)CC(F)(F)C1] |
| 760 | 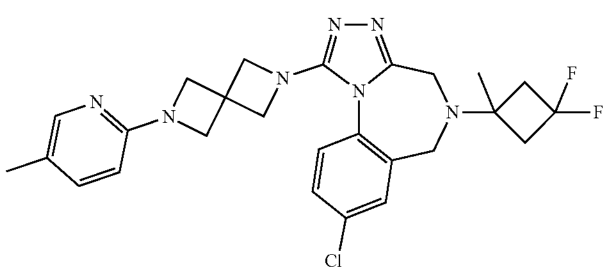 [SMILES: Cc1ccc(N2CC3(C2)CN(c2nnc4n2-c2ccc(Cl)cc2CN(C2(C)CC(F)(F)C2)C4)C3)nc1] |
| 761 | 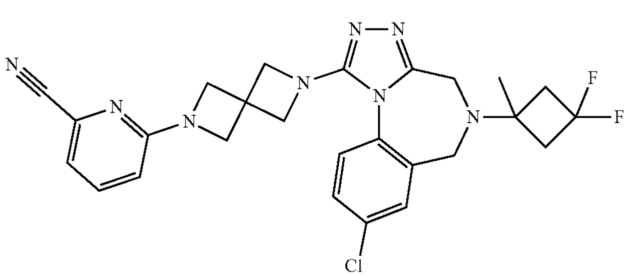 [SMILES: CC1(N2Cc3cc(Cl)ccc3-n3c(nnc3N3CC4(CN(c5cccc(C#N)n5)C4)C3)C2)CC(F)(F)C1] |

TABLE 1-continued

Representative Compounds

| Cmpd. No. | Structure |
|---|---|
| 762 | 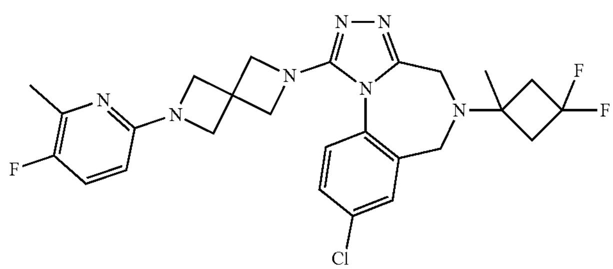 |
| 763 | 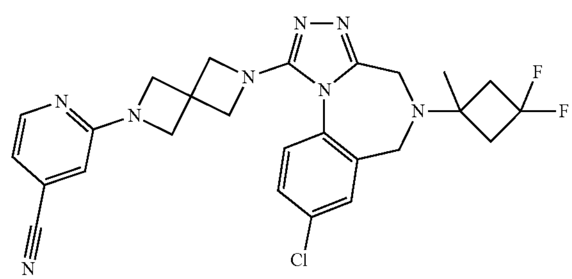 [SMILES: CC1(N2Cc3cc(Cl)ccc3-n3c(nnc3N3CC4(CN(c5cc(C#N)ccn5)C4)C3)C2)CC(F)(F)C1] |
| 764 | 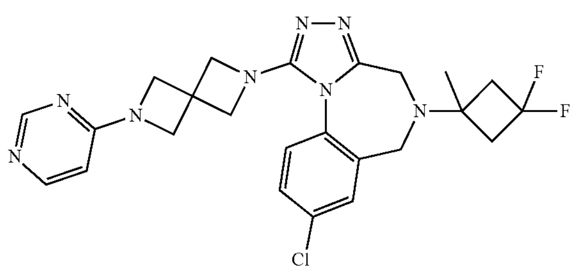 [SMILES: CC1(N2Cc3cc(Cl)ccc3-n3c(nnc3N3CC4(CN(c5ccncn5)C4)C3)C2)CC(F)(F)C1] |
| 765 | 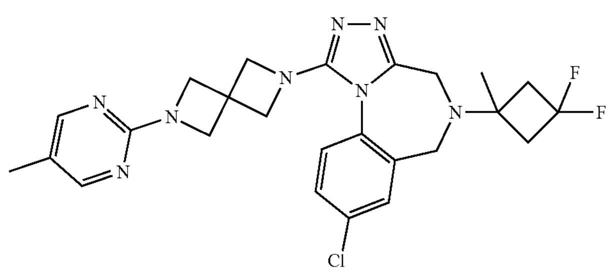 [SMILES: Cc1cnc(N2CC3(C2)CN(c2nnc4n2-c2ccc(Cl)cc2CN(C2(C)CC(F)(F)C2)C4)C3)nc1] |
| 766 | 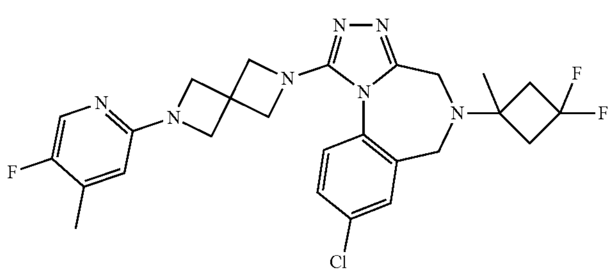 [SMILES: Cc1cc(N2CC3(C2)CN(c2nnc4n2-c2ccc(Cl)cc2CN(C2(C)CC(F)(F)C2)C4)C3)ncc1F] |

TABLE 1-continued

Representative Compounds

| Cmpd. No. | Structure |
|---|---|
| 767 | 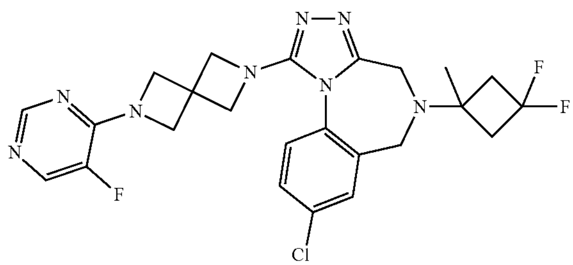 [SMILES: CC1(N2Cc3cc(Cl)ccc3-n3c(nnc3N3CC4(CN(c5ncncc5F)C4)C3)C2)CC(F)(F)C1] |
| 768 | 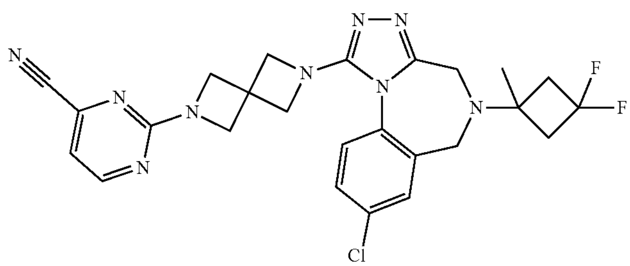 [SMILES: CC1(N2Cc3cc(Cl)ccc3-n3c(nnc3N3CC4(CN(c5nccc(C#N)n5)C4)C3)C2)CC(F)(F)C1] |
| 769 | 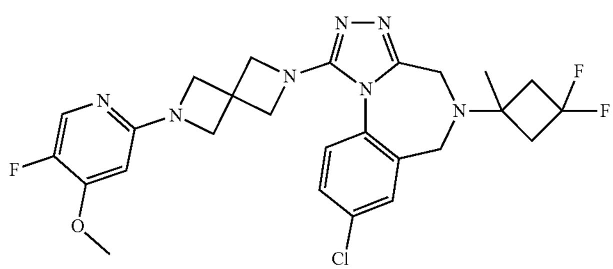 [SMILES: COc1cc(N2CC3(C2)CN(c2nnc4n2-c2ccc(Cl)cc2CN(C2(C)CC(F)(F)C2)C4)C3)ncc1F] |
| 770 | 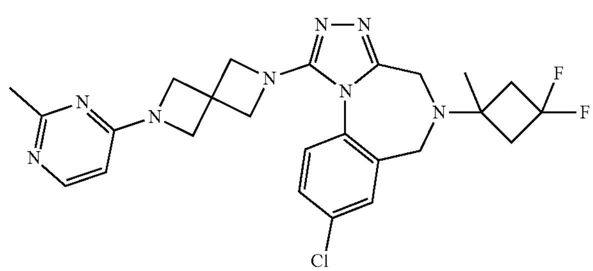 [SMILES: Cc1nccc(N2CC3(C2)CN(c2nnc4n2-c2ccc(Cl)cc2CN(C2(C)CC(F)(F)C2)C4)C3)n1] |
| 771 | 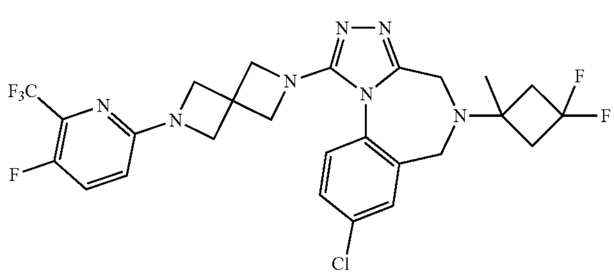 |

TABLE 1-continued
Representative Compounds
| Cmpd. No. | Structure |
|---|---|
| 772 | 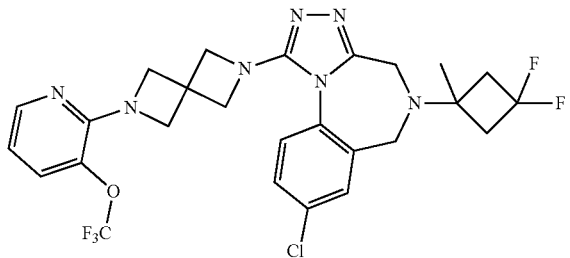 [SMILES: CC1(N2Cc3cc(Cl)ccc3-n3c(nnc3N3CC4(CN(c5ncccc5OC(F)(F)F)C4)C3)C2)CC(F)(F)C1] |
| 773 | 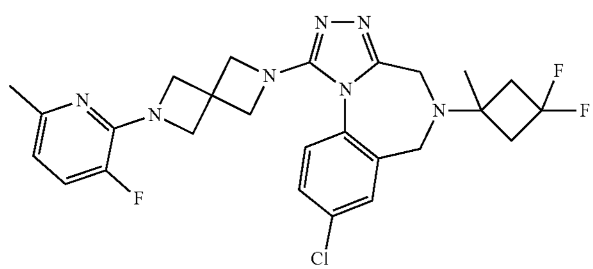 [SMILES: Cc1ccc(F)c(N2CC3(C2)CN(c2nnc4n2-c2ccc(Cl)cc2CN(C2(C)CC(F)(F)C2)C4)C3)n1] |
| 774 | 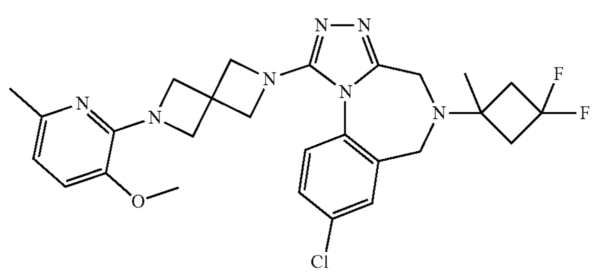 [SMILES: COc1ccc(C)nc1N1CC2(C1)CN(c1nnc3n1-c1ccc(Cl)cc1CN(C1(C)CC(F)(F)C1)C3)C2] |
| 775 | 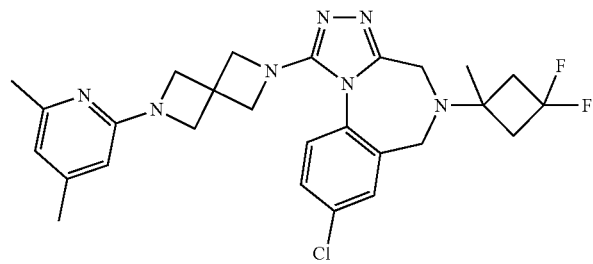 [SMILES: Cc1cc(C)nc(N2CC3(C2)CN(c2nnc4n2-c2ccc(Cl)cc2CN(C2(C)CC(F)(F)C2)C4)C3)c1] |
| 776 | 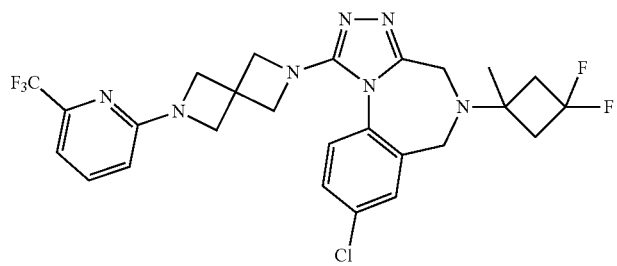 [SMILES: CC1(N2Cc3cc(Cl)ccc3-n3c(nnc3N3CC4(CN(c5cccc(C(F)(F)F)n5)C4)C3)C2)CC(F)(F)C1] |

TABLE 1-continued
Representative Compounds
| Cmpd. No. | Structure |
|---|---|
| 777 | 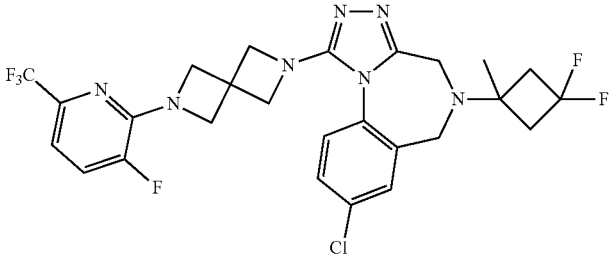 |
| 778 | 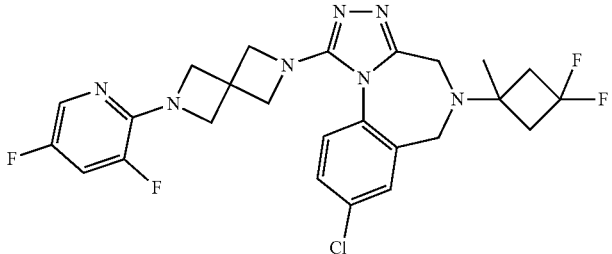 [SMILES: CC1(N2Cc3cc(Cl)ccc3-n3c(nnc3N3CC4(CN(c5ncc(F)cc5F)C4)C3)C2)CC(F)(F)C1] |
| 779 | 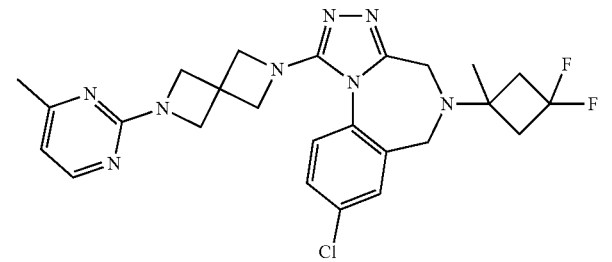 |
| 780 | 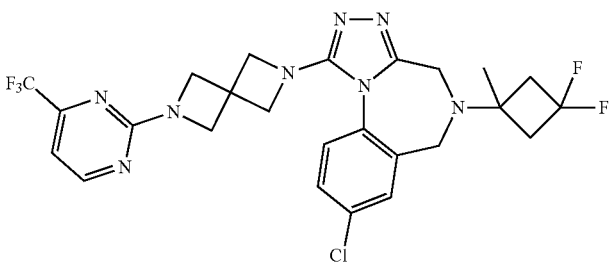 |
| 781 | 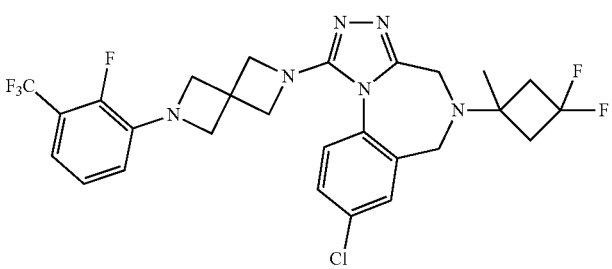 [SMILES: CC1(N2Cc3cc(Cl)ccc3-n3c(nnc3N3CC4(CN(c5cccc(C(F)(F)F)c5F)C4)C3)C2)CC(F)(F)C1] |

TABLE 1-continued

Representative Compounds

| Cmpd. No. | Structure |
|---|---|
| 782 | 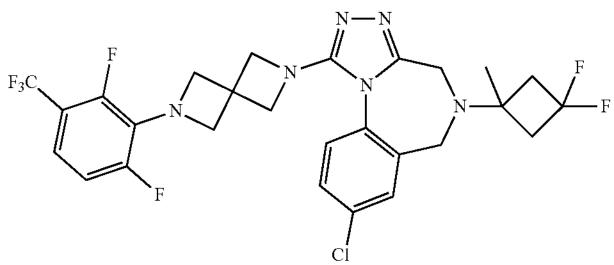 [SMILES: CC1(N2Cc3cc(Cl)ccc3-n3c(nnc3N3CC4(CN(c5c(F)ccc(C(F)(F)F)c5F)C4)C3)C2)CC(F)(F)C1] |
| 783 | 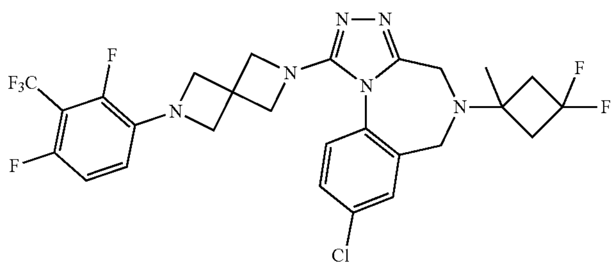 |
| 784 | 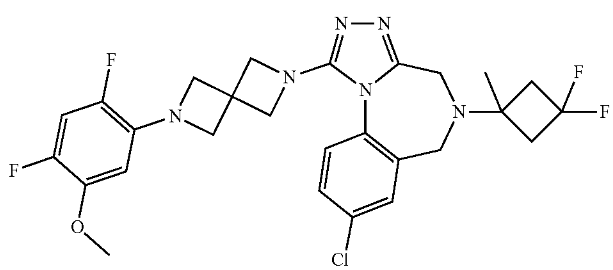 [SMILES: COc1cc(N2CC3(C2)CN(c2nnc4n2-c2ccc(Cl)cc2CN(C2(C)CC(F)(F)C2)C4)C3)c(F)cc1F] |
| 785 | 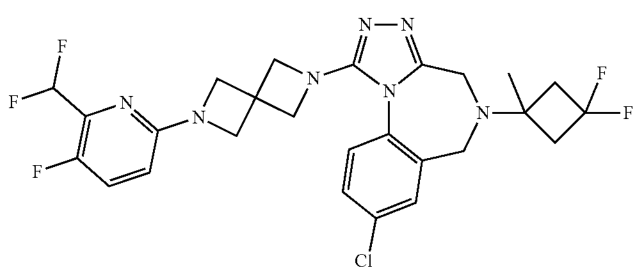 [SMILES: CC1(N2Cc3cc(Cl)ccc3-n3c(nnc3N3CC4(CN(c5ccc(F)c(C(F)F)n5)C4)C3)C2)CC(F)(F)C1] |
| 786 | 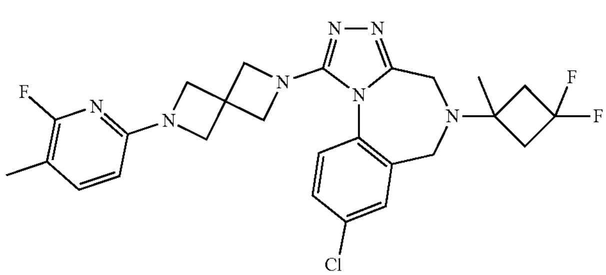 [SMILES: Cc1ccc(N2CC3(C2)CN(c2nnc4n2-c2ccc(Cl)cc2CN(C2(C)CC(F)(F)C2)C4)C3)nc1F] |

TABLE 1-continued

Representative Compounds

| Cmpd. No. | Structure |
|---|---|
| 787 | 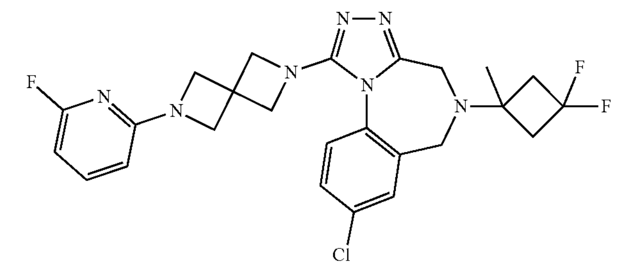 [SMILES: CC1(N2Cc3cc(Cl)ccc3-n3c(nnc3N3CC4(CN(c5cccc(F)n5)C4)C3)C2)CC(F)(F)C1] |
| 788 | 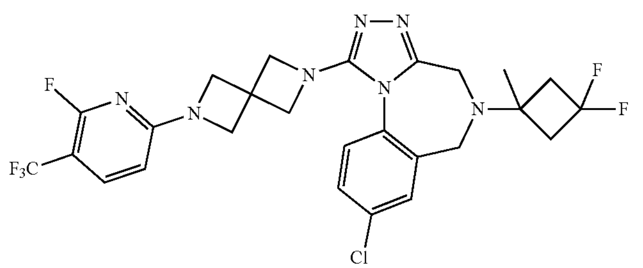 [SMILES: CC1(N2Cc3cc(Cl)ccc3-n3c(nnc3N3CC4(CN(c5ccc(C(F)(F)F)c(F)n5)C4)C3)C2)CC(F)(F)C1] |
| 789 | 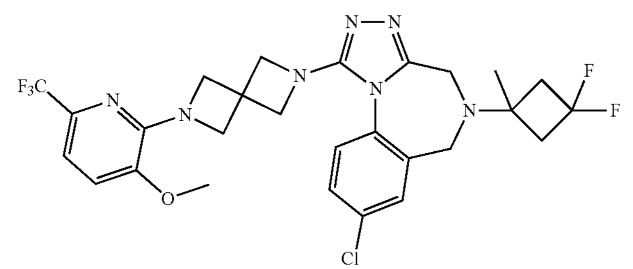 [SMILES: COc1ccc(C(F)(F)F)nc1N1CC2(C1)CN(c1nnc3n1-c1ccc(Cl)cc1CN(C1(C)CC(F)(F)C1)C3)C2] |
| 790 | 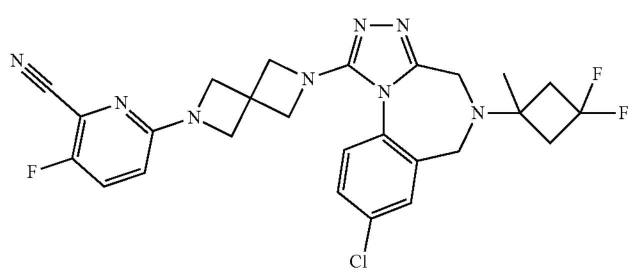 [SMILES: CC1(N2Cc3cc(Cl)ccc3-n3c(nnc3N3CC4(CN(c5ccc(F)c(C#N)n5)C4)C3)C2)CC(F)(F)C1] |
| 791 | 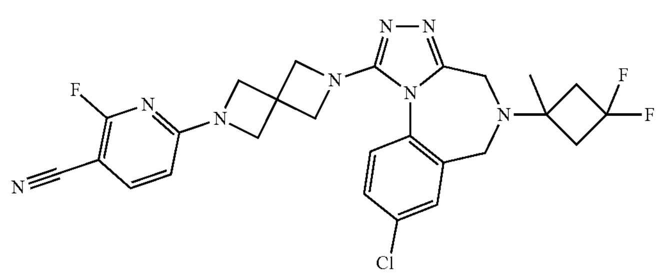 [SMILES: CC1(N2Cc3cc(Cl)ccc3-n3c(nnc3N3CC4(CN(c5ccc(C#N)c(F)n5)C4)C3)C2)CC(F)(F)C1] |

TABLE 1-continued

Representative Compounds

| Cmpd. No. | Structure |
|---|---|
| 792 | 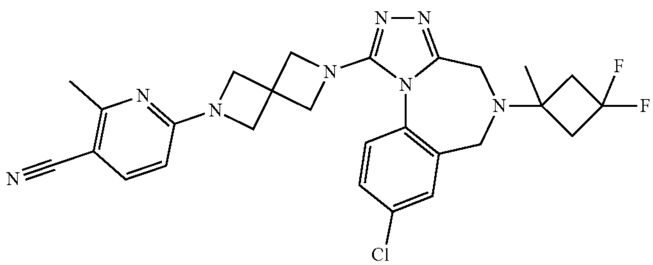 [SMILES: Cc1nc(N2CC3(C2)CN(c2nnc4n2-c2ccc(Cl)cc2CN(C2(C)CC(F)(F)C2)C4)C3)ccc1C#N] |
| 793 | 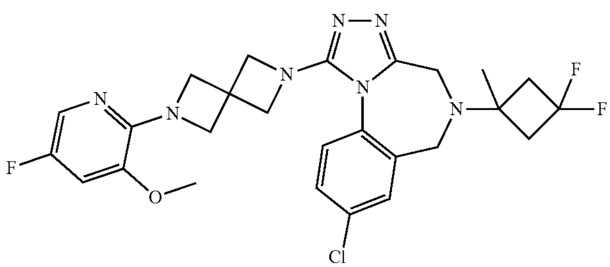 [SMILES: COc1cc(F)cnc1N1CC2(C1)CN(c1nnc3n1-c1ccc(Cl)cc1CN(C1(C)CC(F)(F)C1)C3)C2] |
| 794 | 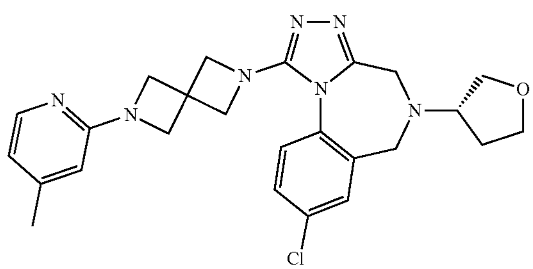 [SMILES: Cc1ccnc(N2CC3(C2)CN(c2nnc4n2-c2ccc(Cl)cc2CN([C@H]2CCOC2)C4)C3)c1] |
| 795 | 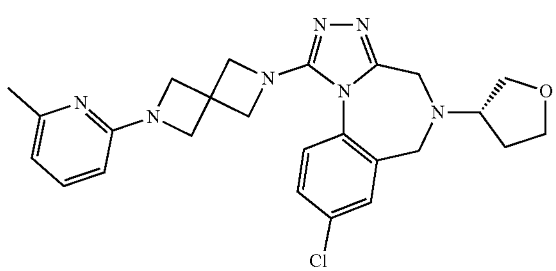 [SMILES: Cc1cccc(N2CC3(C2)CN(c2nnc4n2-c2ccc(Cl)cc2CN([C@H]2CCOC2)C4)C3)n1] |
| 796 | 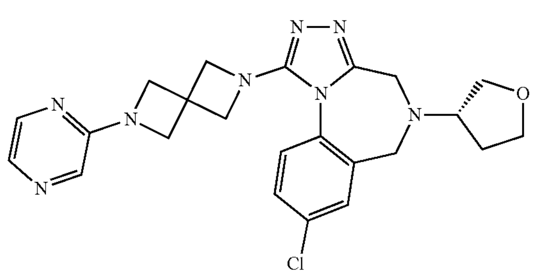 [SMILES: Clc1ccc2c(c1)CN([C@H]1CCOC1)Cc1nnc(N3CC4(CN(c5cnccn5)C4)C3)n1-2] |

TABLE 1-continued

Representative Compounds

| Cmpd. No. | Structure |
|---|---|
| 797 | 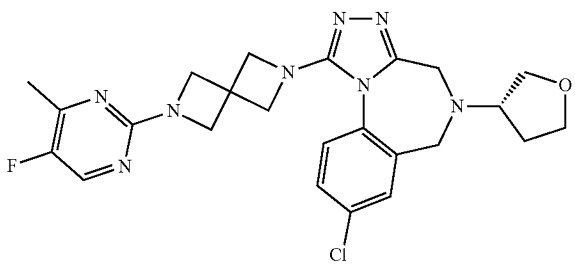 [SMILES: Cc1nc(N2CC3(C2)CN(c2nnc4n2-c2ccc(Cl)cc2CN([C@H]2CCOC2)C4)C3)ncc1F] |
| 798 | 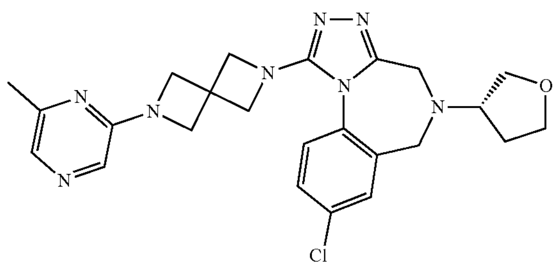 [SMILES: Cc1cncc(N2CC3(C2)CN(c2nnc4n2-c2ccc(Cl)cc2CN([C@H]2CCOC2)C4)C3)n1] |
| 799 | 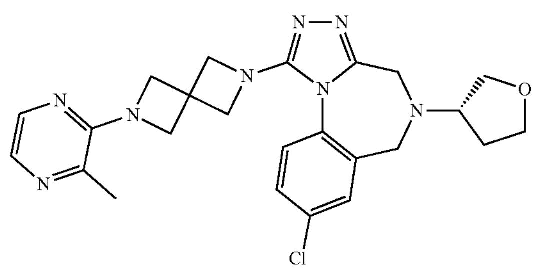 [SMILES: Cc1nccnc1N1CC2(C1)CN(c1nnc3n1-c1ccc(Cl)cc1CN([C@H]1CCOC1)C3)C2] |
| 800 | 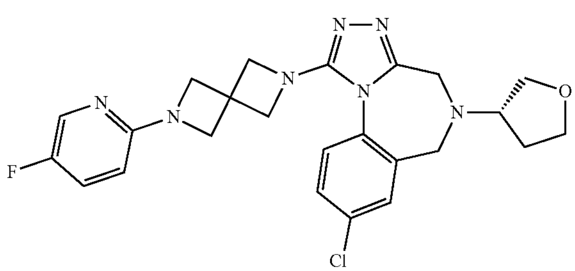 [SMILES: Fc1ccc(N2CC3(C2)CN(c2nnc4n2-c2ccc(Cl)cc2CN([C@H]2CCOC2)C4)C3)nc1] |
| 801 | 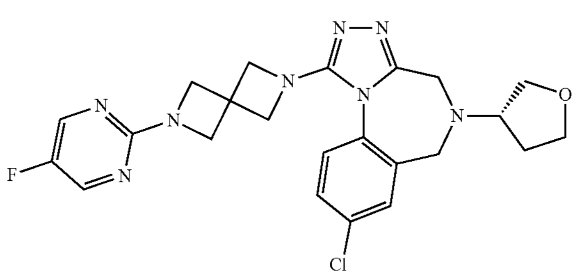 [SMILES: Fc1cnc(N2CC3(C2)CN(c2nnc4n2-c2ccc(Cl)cc2CN([C@H]2CCOC2)C4)C3)nc1] |

TABLE 1-continued

Representative Compounds

| Cmpd. No. | Structure |
|---|---|
| 802 | 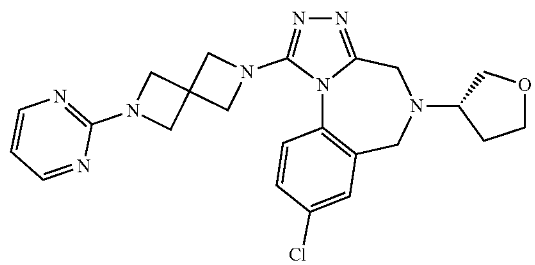 [SMILES: Clc1ccc2c(c1)CN([C@H]1CCOC1)Cc1nnc(N3CC4(CN(c5ncccn5)C4)C3)n1-2] |
| 803 | 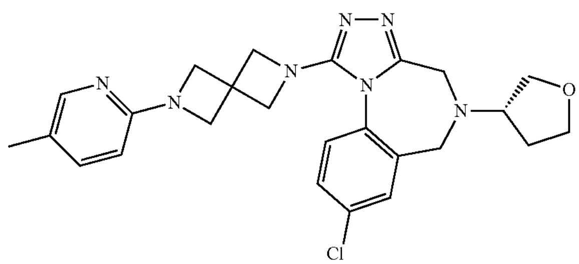 [SMILES: Cc1ccc(N2CC3(C2)CN(c2nnc4n2-c2ccc(Cl)cc2CN([C@H]2CCOC2)C4)C3)nc1] |
| 804 | 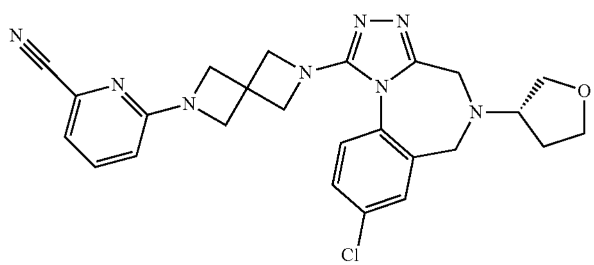 [SMILES: N#Cc1cccc(N2CC3(C2)CN(c2nnc4n2-c2ccc(Cl)cc2CN([C@H]2CCOC2)C4)C3)n1] |
| 805 | 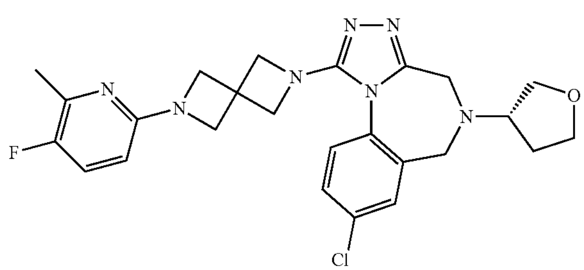 [SMILES: Cc1nc(N2CC3(C2)CN(c2nnc4n2-c2ccc(Cl)cc2CN([C@H]2CCOC2)C4)C3)ccc1F] |
| 806 | 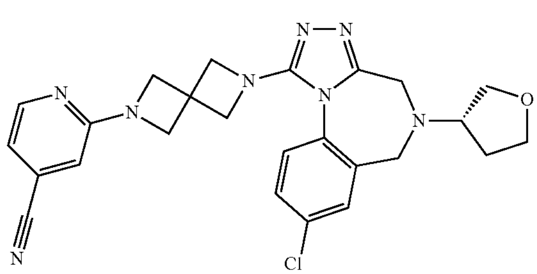 [SMILES: N#Cc1ccnc(N2CC3(C2)CN(c2nnc4n2-c2ccc(Cl)cc2CN([C@H]2CCOC2)C4)C3)c1] |

TABLE 1-continued

Representative Compounds

| Cmpd. No. | Structure |
|---|---|
| 807 | 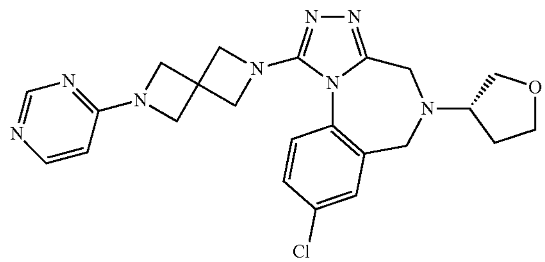 [SMILES: Clc1ccc2c(c1)CN([C@H]1CCOC1)Cc1nnc(N3CC4(CN(c5ccncn5)C4)C3)n1-2] |
| 808 | 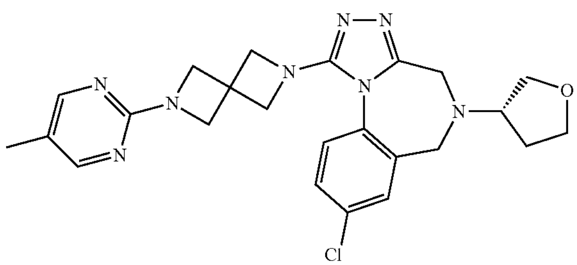 [SMILES: Cc1cnc(N2CC3(C2)CN(c2nnc4n2-c2ccc(Cl)cc2CN([C@H]2CCOC2)C4)C3)nc1] |
| 809 | 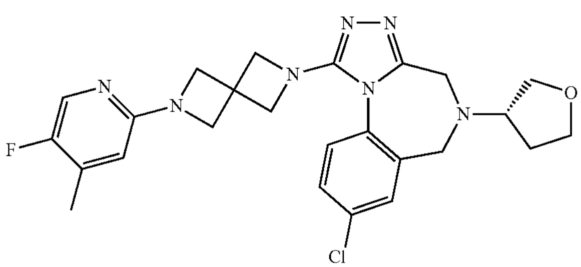 [SMILES: Cc1cc(N2CC3(C2)CN(c2nnc4n2-c2ccc(Cl)cc2CN([C@H]2CCOC2)C4)C3)ncc1F] |
| 810 | 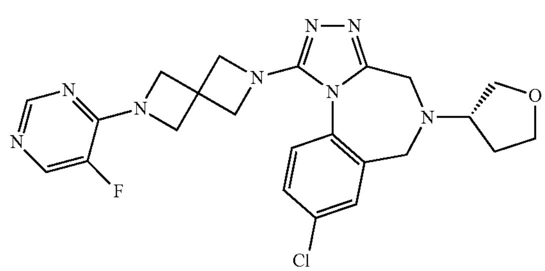 [SMILES: Fc1cncnc1N1CC2(C1)CN(c1nnc3n1-c1ccc(Cl)cc1CN([C@H]1CCOC1)C3)C2] |
| 811 | 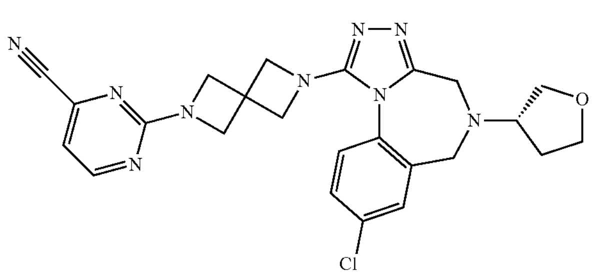 |

TABLE 1-continued

Representative Compounds

| Cmpd. No. | Structure |
|---|---|
| 812 | 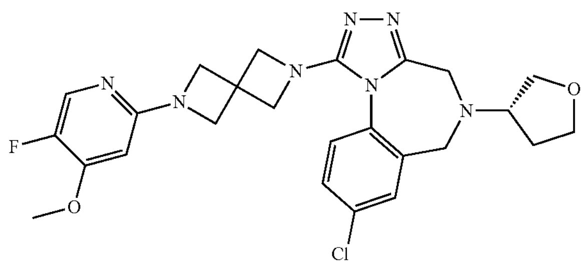 [SMILES: COc1cc(N2CC3(C2)CN(c2nnc4n2-c2ccc(Cl)cc2CN([C@H]2CCOC2)C4)C3)ncc1F] |
| 813 | 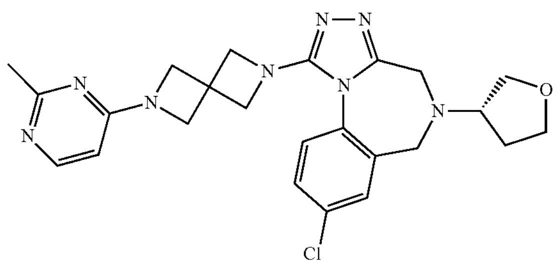 [SMILES: Cc1nccc(N2CC3(C2)CN(c2nnc4n2-c2ccc(Cl)cc2CN([C@H]2CCOC2)C4)C3)n1] |
| 814 | 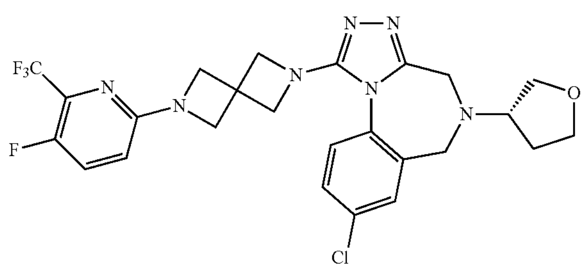 [SMILES: Fc1ccc(N2CC3(C2)CN(c2nnc4n2-c2ccc(Cl)cc2CN([C@H]2CCOC2)C4)C3)nc1C(F)(F)F] |
| 815 | 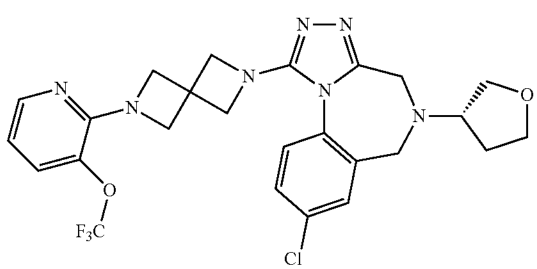 [SMILES: FC(F)(F)Oc1cccnc1N1CC2(C1)CN(c1nnc3n1-c1ccc(Cl)cc1CN([C@H]1CCOC1)C3)C2] |
| 816 | 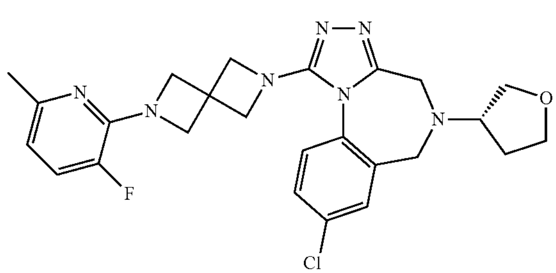 [SMILES: Cc1ccc(F)c(N2CC3(C2)CN(c2nnc4n2-c2ccc(Cl)cc2CN([C@H]2CCOC2)C4)C3)n1] |

TABLE 1-continued

Representative Compounds

| Cmpd. No. | Structure |
|---|---|
| 817 | 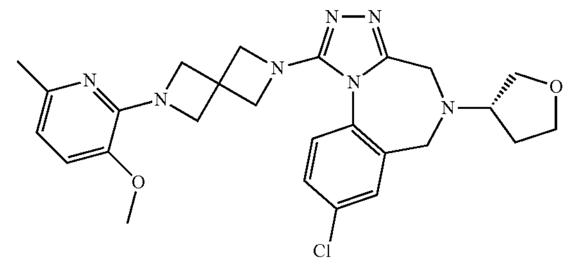 [SMILES: COc1ccc(C)nc1N1CC2(C1)CN(c1nnc3n1-c1ccc(Cl)cc1CN([C@H]1CCOC1)C3)C2] |
| 818 | 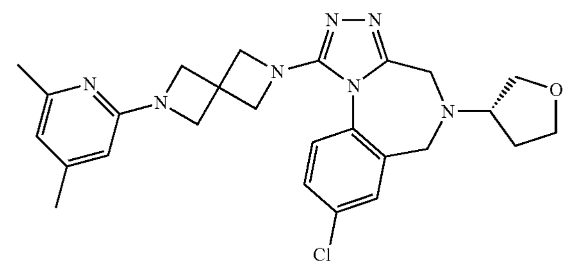 [SMILES: Cc1cc(C)nc(N2CC3(C2)CN(c2nnc4n2-c2ccc(Cl)cc2CN([C@H]2CCOC2)C4)C3)c1] |
| 819 | 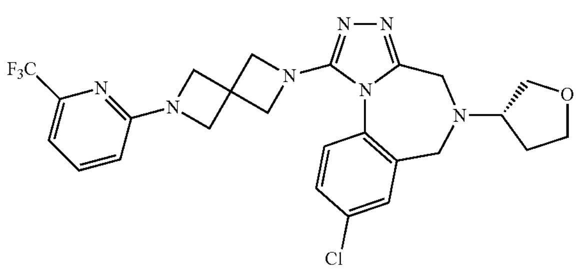 [SMILES: FC(F)(F)c1cccc(N2CC3(C2)CN(c2nnc4n2-c2ccc(Cl)cc2CN([C@H]2CCOC2)C4)C3)n1] |
| 820 | 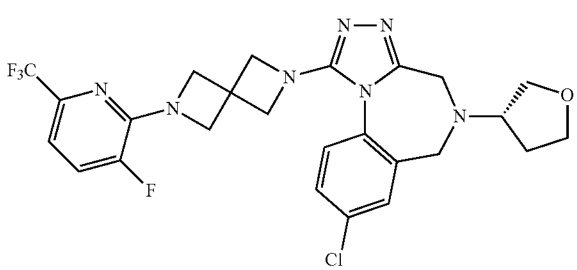 [SMILES: Fc1ccc(C(F)(F)F)nc1N1CC2(C1)CN(c1nnc3n1-c1ccc(Cl)cc1CN([C@H]1CCOC1)C3)C2] |
| 821 | 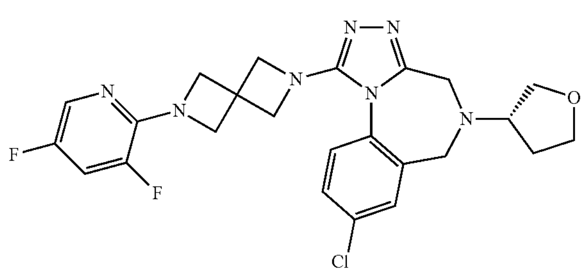 [SMILES: Fc1cnc(N2CC3(C2)CN(c2nnc4n2-c2ccc(Cl)cc2CN([C@H]2CCOC2)C4)C3)c(F)c1] |

TABLE 1-continued

Representative Compounds

| Cmpd. No. | Structure |
|---|---|
| 822 | 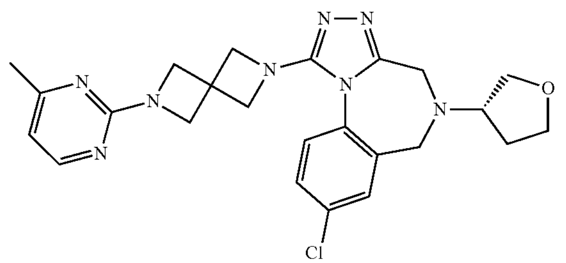 |
| 823 | 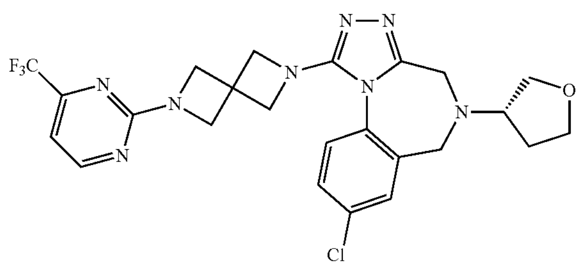 [SMILES: FC(F)(F)c1ccnc(N2CC3(C2)CN(c2nnc4n2-c2ccc(Cl)cc2CN([C@H]2CCOC2)C4)C3)n1] |
| 824 | 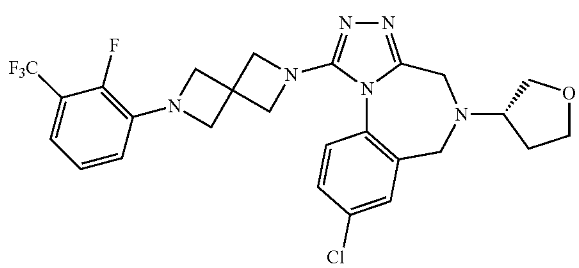 [SMILES: Fc1c(N2CC3(C2)CN(c2nnc4n2-c2ccc(Cl)cc2CN([C@H]2CCOC2)C4)C3)cccc1C(F)(F)F] |
| 825 | 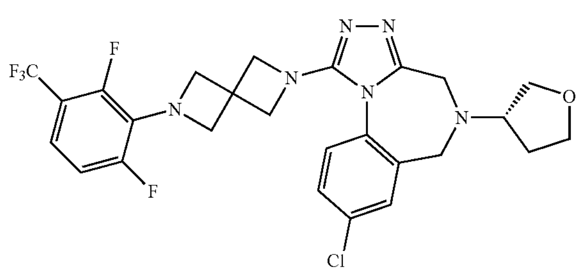 [SMILES: Fc1ccc(C(F)(F)F)c(F)c1N1CC2(C1)CN(c1nnc3n1-c1ccc(Cl)cc1CN([C@H]1CCOC1)C3)C2] |
| 826 | 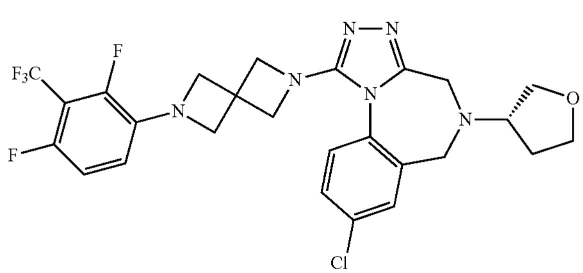 [SMILES: Fc1ccc(N2CC3(C2)CN(c2nnc4n2-c2ccc(Cl)cc2CN([C@H]2CCOC2)C4)C3)c(F)c1C(F)(F)F] |

TABLE 1-continued

Representative Compounds

| Cmpd. No. | Structure |
|---|---|
| 827 | 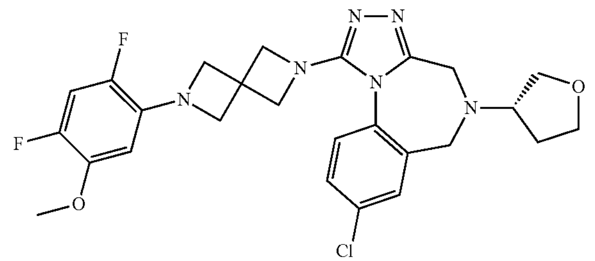 [SMILES: COc1cc(N2CC3(C2)CN(c2nnc4n2-c2ccc(Cl)cc2CN([C@H]2CCOC2)C4)C3)c(F)cc1F] |
| 828 | 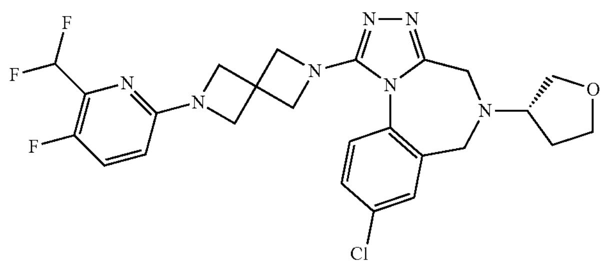 [SMILES: Fc1ccc(N2CC3(C2)CN(c2nnc4n2-c2ccc(Cl)cc2CN([C@H]2CCOC2)C4)C3)nc1C(F)F] |
| 829 | 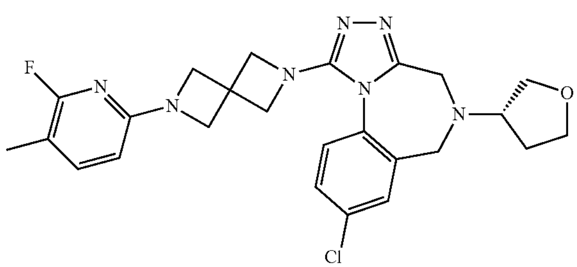 [SMILES: Cc1ccc(N2CC3(C2)CN(c2nnc4n2-c2ccc(Cl)cc2CN([C@H]2CCOC2)C4)C3)nc1F] |
| 830 | 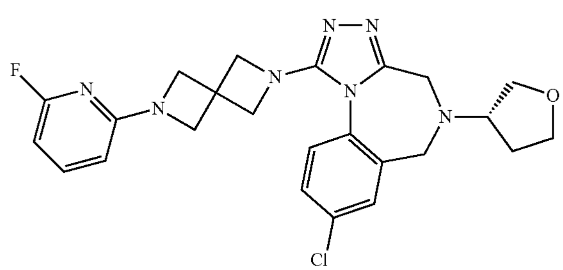 [SMILES: Fc1cccc(N2CC3(C2)CN(c2nnc4n2-c2ccc(Cl)cc2CN([C@H]2CCOC2)C4)C3)n1] |
| 831 | 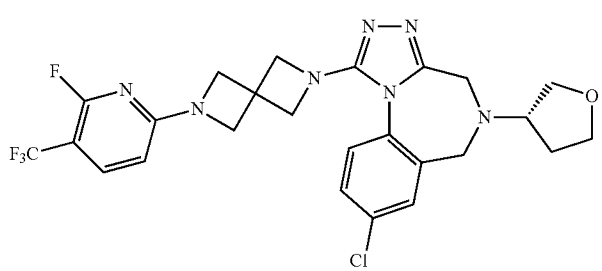 [SMILES: Fc1nc(N2CC3(C2)CN(c2nnc4n2-c2ccc(Cl)cc2CN([C@H]2CCOC2)C4)C3)ccc1C(F)(F)F] |

TABLE 1-continued
Representative Compounds
| Cmpd. No. | Structure |
|---|---|
| 832 | 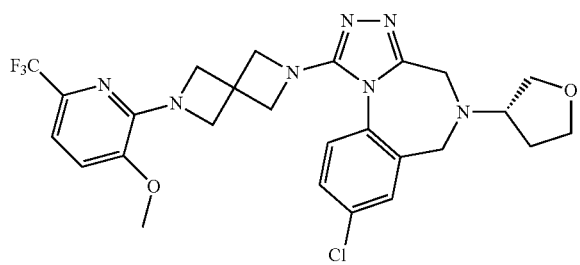 [SMILES: COc1ccc(C(F)(F)F)nc1N1CC2(C1)CN(c1nnc3n1-c1ccc(Cl)cc1CN([C@H]1CCOC1)C3)C2] |
| 833 | 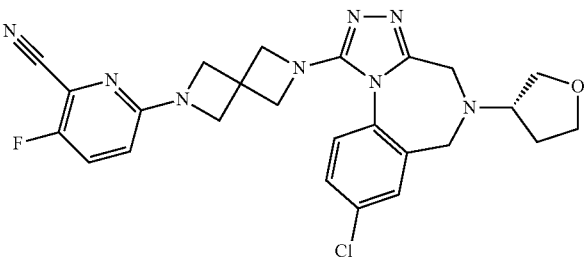 [SMILES: N#Cc1nc(N2CC3(C2)CN(c2nnc4n2-c2ccc(Cl)cc2CN([C@H]2CCOC2)C4)C3)ccc1F] |
| 834 | 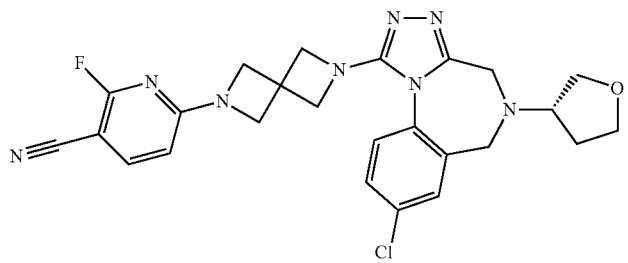 |
| 835 | 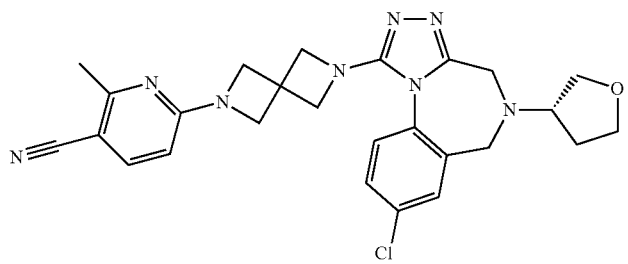 [SMILES: Cc1nc(N2CC3(C2)CN(c2nnc4n2-c2ccc(Cl)cc2CN([C@H]2CCOC2)C4)C3)ccc1C#N] |
| 836 | 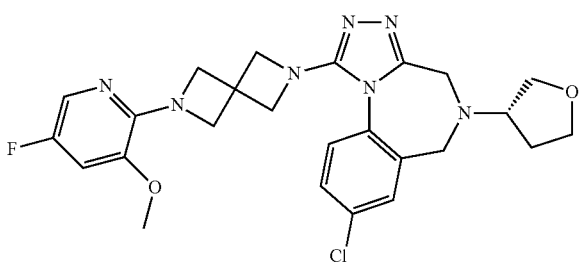 [SMILES: COc1cc(F)cnc1N1CC2(C1)CN(c1nnc3n1-c1ccc(Cl)cc1CN([C@H]1CCOC1)C3)C2] |

TABLE 1-continued
Representative Compounds
| Cmpd. No. | Structure |
|---|---|
| 837 | 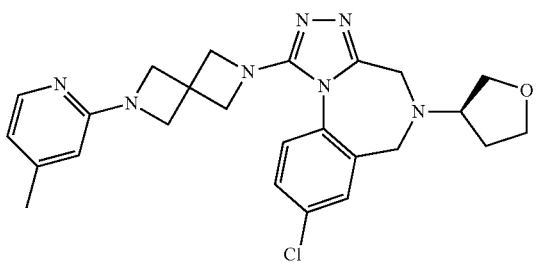 [SMILES: Cc1ccnc(N2CC3(C2)CN(c2nnc4n2-c2ccc(Cl)cc2CN([C@@H]2CCOC2)C4)C3)c1] |
| 838 | 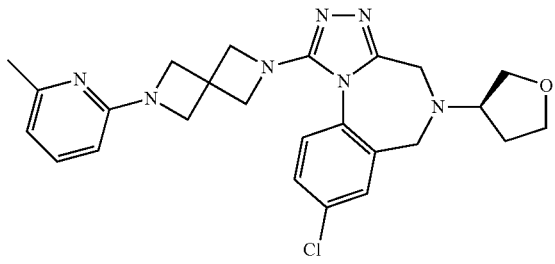 [SMILES: Cc1cccc(N2CC3(C2)CN(c2nnc4n2-c2ccc(Cl)cc2CN([C@@H]2CCOC2)C4)C3)n1] |
| 839 | 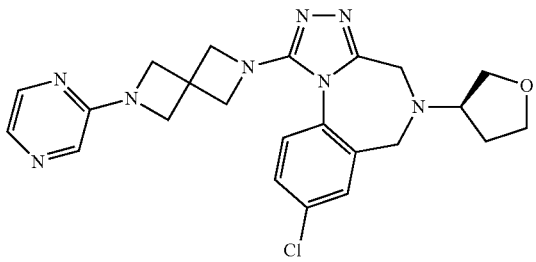 [SMILES: Clc1ccc2c(c1)CN([C@@H]1CCOC1)Cc1nnc(N3CC4(CN(c5cnccn5)C4)C3)n1-2] |
| 840 | 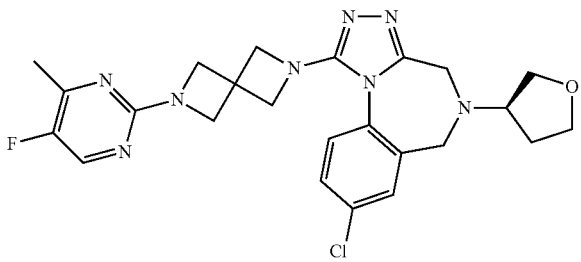 [SMILES: Cc1nc(N2CC3(C2)CN(c2nnc4n2-c2ccc(Cl)cc2CN([C@@H]2CCOC2)C4)C3)ncc1F] |
| 841 | 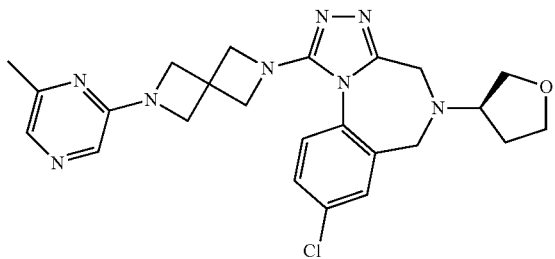 [SMILES: Cc1cncc(N2CC3(C2)CN(c2nnc4n2-c2ccc(Cl)cc2CN([C@@H]2CCOC2)C4)C3)n1] |

TABLE 1-continued

Representative Compounds

| Cmpd. No. | Structure |
|---|---|
| 842 | 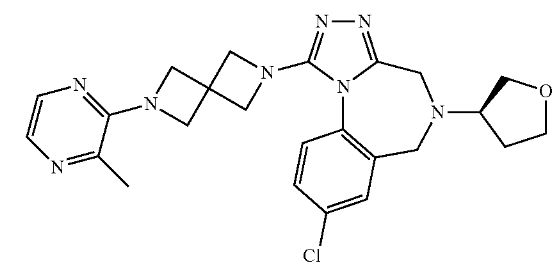 [SMILES: Cc1nccnc1N1CC2(C1)CN(c1nnc3n1-c1ccc(Cl)cc1CN([C@@H]1CCOC1)C3)C2] |
| 843 | 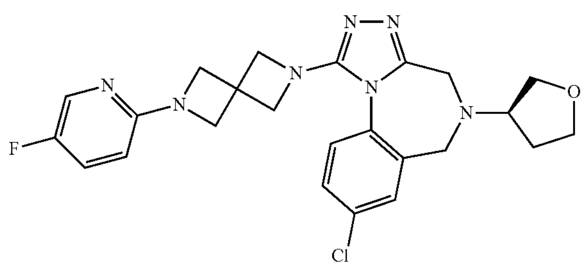 [SMILES: Fc1ccc(N2CC3(C2)CN(c2nnc4n2-c2ccc(Cl)cc2CN([C@@H]2CCOC2)C4)C3)nc1] |
| 844 | 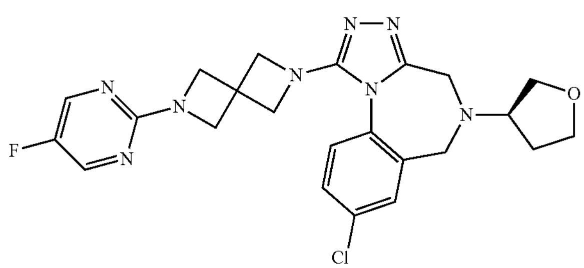 [SMILES: Fc1cnc(N2CC3(C2)CN(c2nnc4n2-c2ccc(Cl)cc2CN([C@@H]2CCOC2)C4)C3)nc1] |
| 845 | 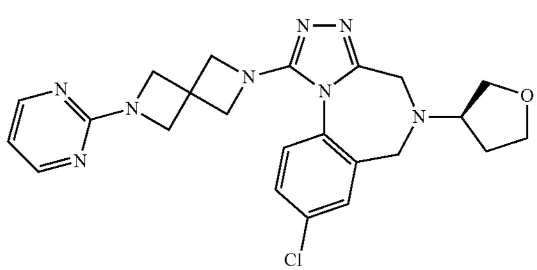 [SMILES: Clc1ccc2c(c1)CN([C@@H]1CCOC1)Cc1nnc(N3CC4(CN(c5ncccn5)C4)C3)n1-2] |
| 846 | 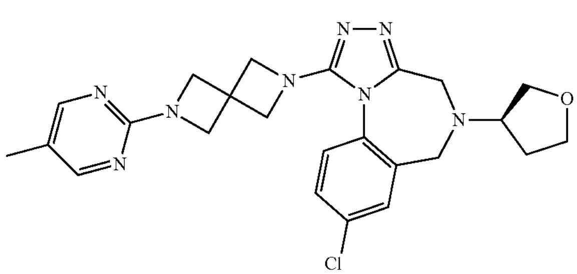 [SMILES: Cc1cnc(N2CC3(C2)CN(c2nnc4n2-c2ccc(Cl)cc2CN([C@@H]2CCOC2)C4)C3)nc1] |

TABLE 1-continued

Representative Compounds

| Cmpd. No. | Structure |
|---|---|
| 847 | 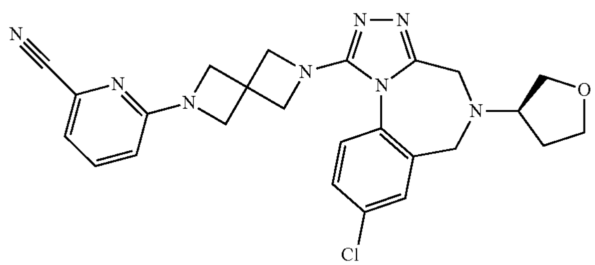 |
| 848 | 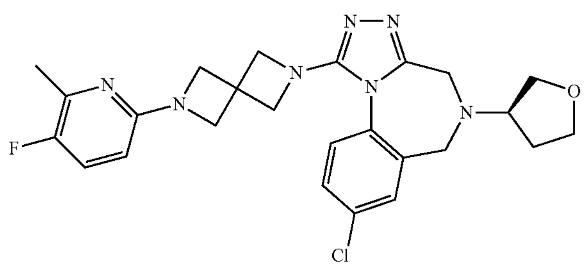 [SMILES: Cc1nc(N2CC3(C2)CN(c2nnc4n2-c2ccc(Cl)cc2CN([C@@H]2CCOC2)C4)C3)ccc1F] |
| 849 | 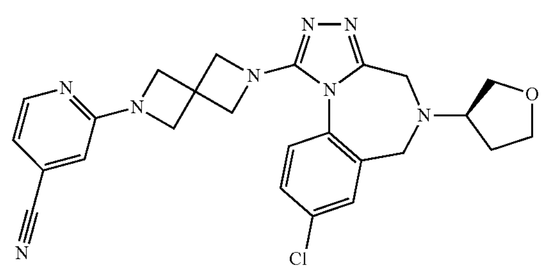 [SMILES: N#Cc1ccnc(N2CC3(C2)CN(c2nnc4n2-c2ccc(Cl)cc2CN([C@@H]2CCOC2)C4)C3)c1] |
| 850 | 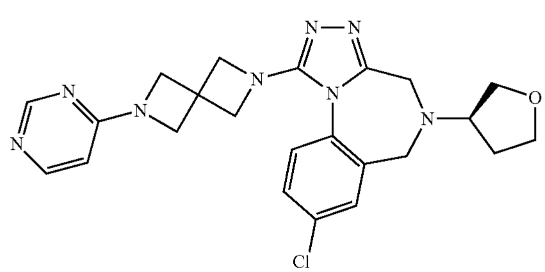 [SMILES: Clc1ccc2c(c1)CN([C@@H]1CCOC1)Cc1nnc(N3CC4(CN(c5ccncn5)C4)C3)n1-2] |
| 851 | 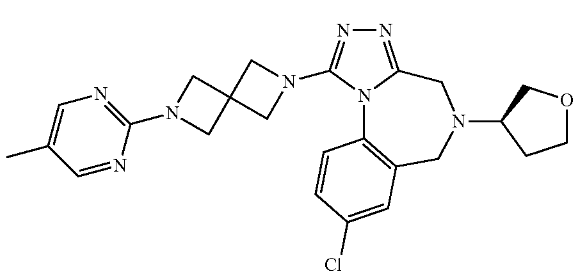 [SMILES: Cc1cnc(N2CC3(C2)CN(c2nnc4n2-c2ccc(Cl)cc2CN([C@@H]2CCOC2)C4)C3)nc1] |

TABLE 1-continued

Representative Compounds

| Cmpd. No. | Structure |
|---|---|
| 852 | 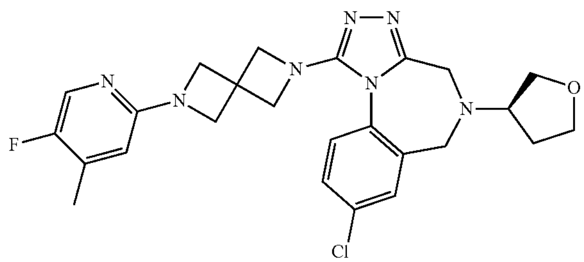 [SMILES: Cc1cc(N2CC3(C2)CN(c2nnc4n2-c2ccc(Cl)cc2CN([C@@H]2CCOC2)C4)C3)ncc1F] |
| 853 | 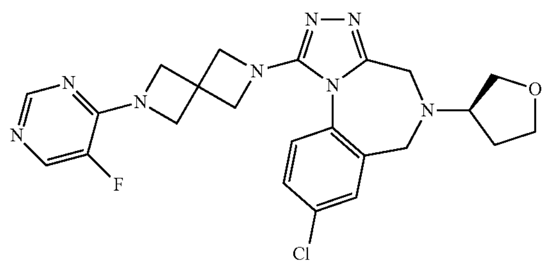 [SMILES: Fc1cncnc1N1CC2(C1)CN(c1nnc3n1-c1ccc(Cl)cc1CN([C@@H]1CCOC1)C3)C2] |
| 854 | 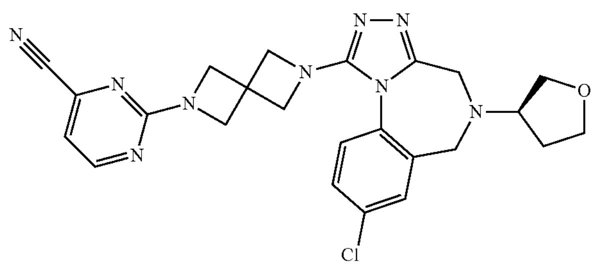 |
| 855 | 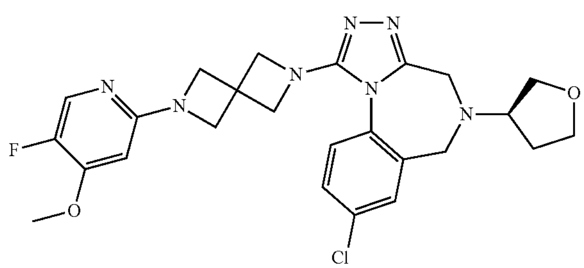 [SMILES: COc1cc(N2CC3(C2)CN(c2nnc4n2-c2ccc(Cl)cc2CN([C@@H]2CCOC2)C4)C3)ncc1F] |
| 856 | 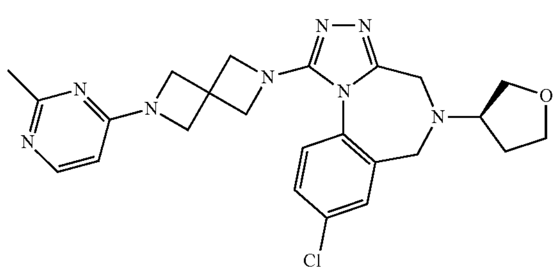 |

TABLE 1-continued

Representative Compounds

| Cmpd. No. | Structure |
|---|---|
| 857 | 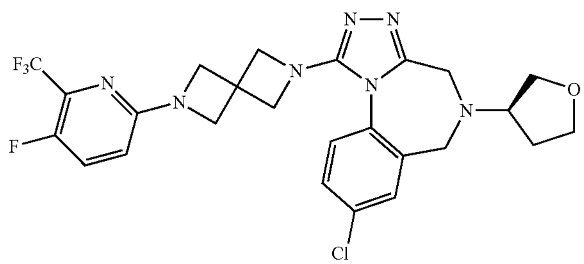 [SMILES: Fc1ccc(N2CC3(C2)CN(c2nnc4n2-c2ccc(Cl)cc2CN([C@@H]2CCOC2)C4)C3)nc1C(F)(F)F] |
| 858 | 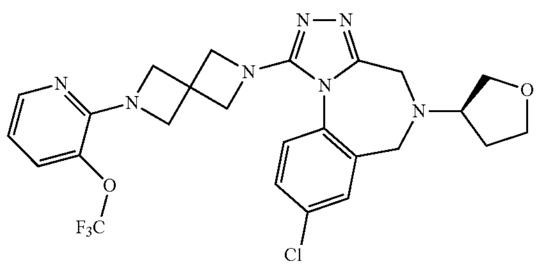 [SMILES: FC(F)(F)Oc1cccnc1N1CC2(C1)CN(c1nnc3n1-c1ccc(Cl)cc1CN([C@@H]1CCOC1)C3)C2] |
| 859 | 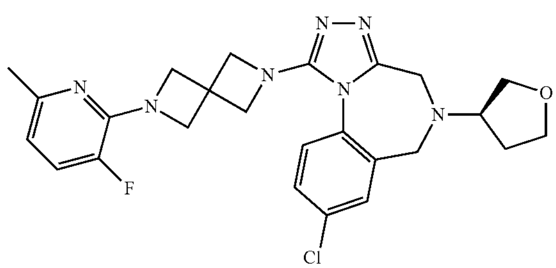 [SMILES: Cc1ccc(F)c(N2CC3(C2)CN(c2nnc4n2-c2ccc(Cl)cc2CN([C@@H]2CCOC2)C4)C3)n1] |
| 860 | 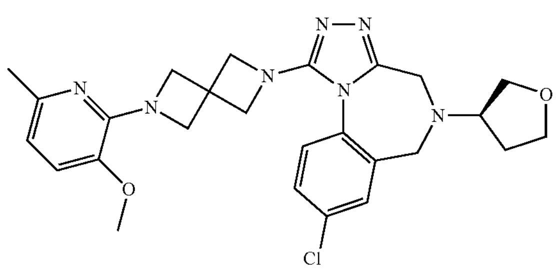 [SMILES: COc1ccc(C)nc1N1CC2(C1)CN(c1nnc3n1-c1ccc(Cl)cc1CN([C@@H]1CCOC1)C3)C2] |
| 861 | 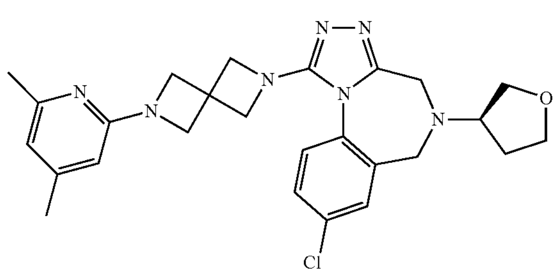 [SMILES: Cc1cc(C)nc(N2CC3(C2)CN(c2nnc4n2-c2ccc(Cl)cc2CN([C@@H]2CCOC2)C4)C3)c1] |

TABLE 1-continued

Representative Compounds

| Cmpd. No. | Structure |
|---|---|
| 862 | 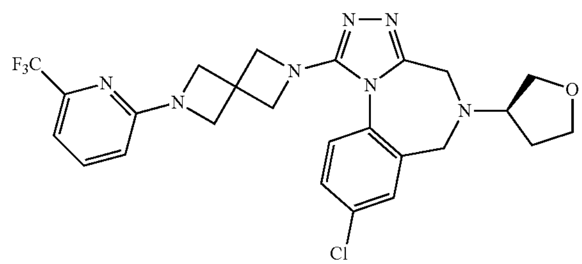 [SMILES: FC(F)(F)c1cccc(N2CC3(C2)CN(c2nnc4n2-c2ccc(Cl)cc2CN([C@@H]2CCOC2)C4)C3)n1] |
| 863 | 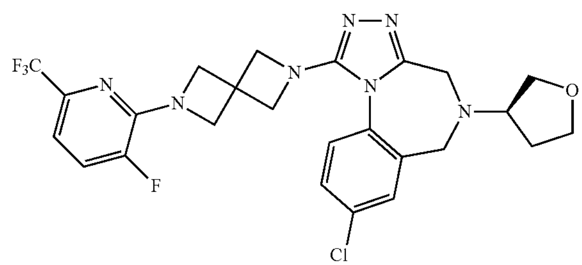 [SMILES: Fc1ccc(C(F)(F)F)nc1N1CC2(C1)CN(c1nnc3n1-c1ccc(Cl)cc1CN([C@@H]1CCOC1)C3)C2] |
| 864 | 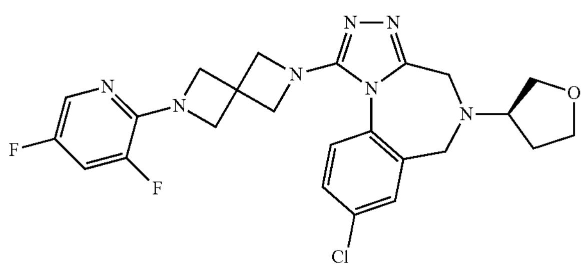 [SMILES: Fc1cnc(N2CC3(C2)CN(c2nnc4n2-c2ccc(Cl)cc2CN([C@@H]2CCOC2)C4)C3)c(F)c1] |
| 865 | 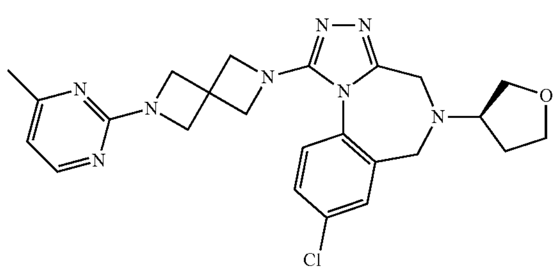 [SMILES: Cc1ccnc(N2CC3(C2)CN(c2nnc4n2-c2ccc(Cl)cc2CN([C@@H]2CCOC2)C4)C3)n1] |
| 866 | 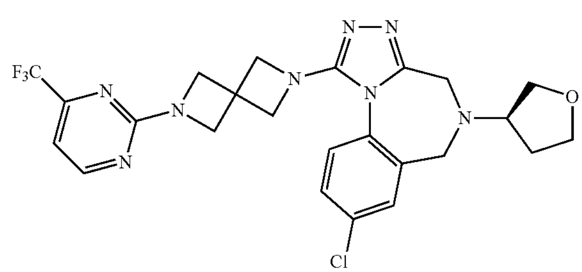 |

TABLE 1-continued
Representative Compounds
| Cmpd. No. | Structure |
|---|---|
| 867 | 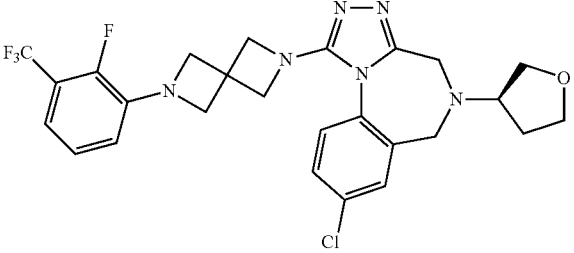 [SMILES: Fc1c(N2CC3(C2)CN(c2nnc4n2-c2ccc(Cl)cc2CN([C@@H]2CCOC2)C4)C3)cccc1C(F)(F)F] |
| 868 | 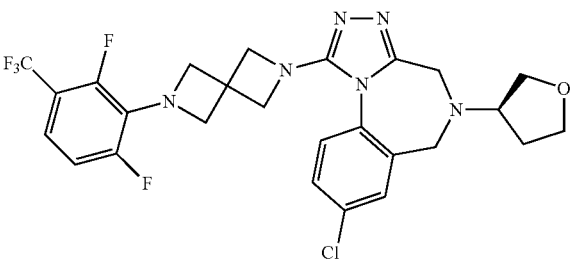 [SMILES: Fc1ccc(C(F)(F)F)c(F)c1N1CC2(C1)CN(c1nnc3n1-c1ccc(Cl)cc1CN([C@@H]1CCOC1)C3)C2] |
| 869 | 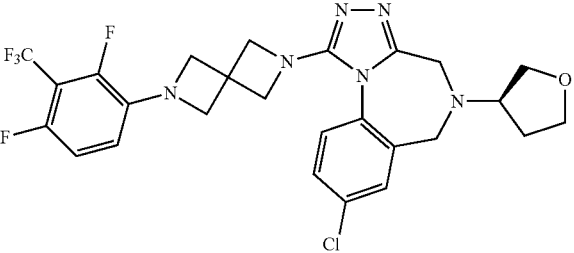 [SMILES: Fc1ccc(N2CC3(C2)CN(c2nnc4n2-c2ccc(Cl)cc2CN([C@@H]2CCOC2)C4)C3)c(F)c1C(F)(F)F] |
| 870 | 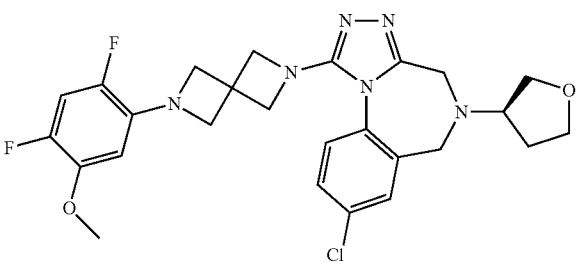 [SMILES: COc1cc(N2CC3(C2)CN(c2nnc4n2-c2ccc(Cl)cc2CN([C@@H]2CCOC2)C4)C3)c(F)cc1F] |
| 871 | 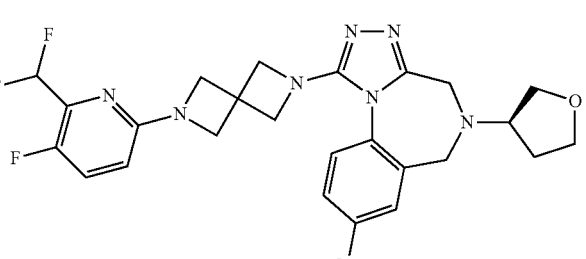 |

TABLE 1-continued

Representative Compounds

| Cmpd. No. | Structure |
|---|---|
| 872 | 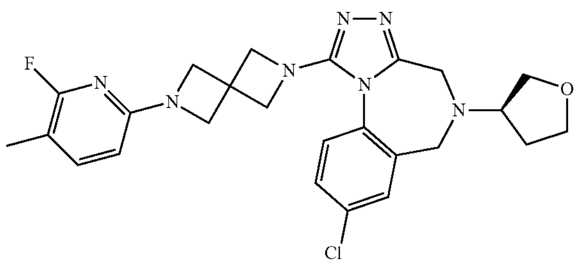 [SMILES: Cc1ccc(N2CC3(C2)CN(c2nnc4n2-c2ccc(Cl)cc2CN([C@@H]2CCOC2)C4)C3)nc1F] |
| 873 | 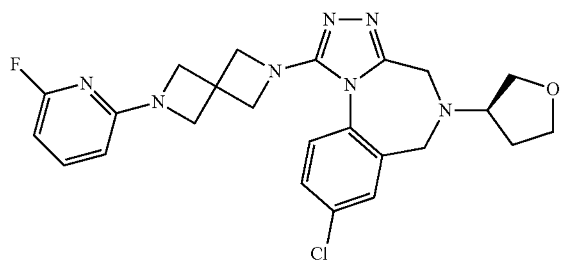 [SMILES: Fc1cccc(N2CC3(C2)CN(c2nnc4n2-c2ccc(Cl)cc2CN([C@@H]2CCOC2)C4)C3)n1] |
| 874 | 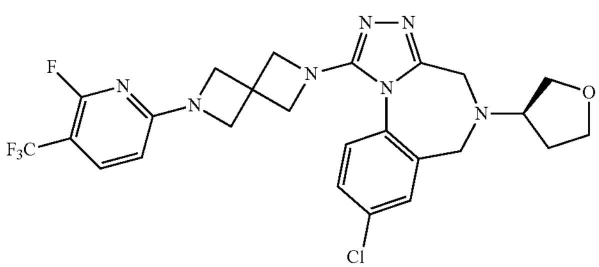 [SMILES: Fc1nc(N2CC3(C2)CN(c2nnc4n2-c2ccc(Cl)cc2CN([C@@H]2CCOC2)C4)C3)ccc1C(F)(F)F] |
| 875 | 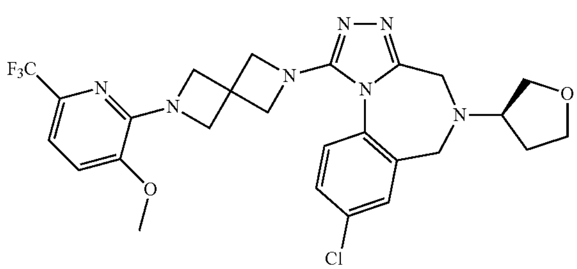 [SMILES: COc1ccc(C(F)(F)F)nc1N1CC2(C1)CN(c1nnc3n1-c1ccc(Cl)cc1CN([C@@H]1CCOC1)C3)C2] |
| 876 | 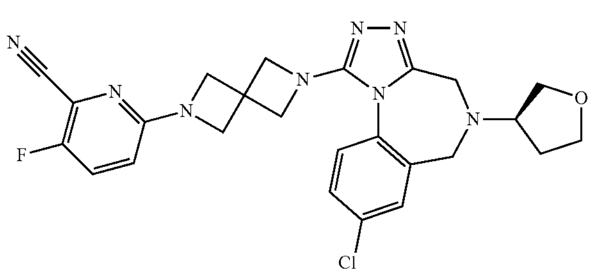 [SMILES: N#Cc1nc(N2CC3(C2)CN(c2nnc4n2-c2ccc(Cl)cc2CN([C@@H]2CCOC2)C4)C3)ccc1F] |

TABLE 1-continued

Representative Compounds

| Cmpd. No. | Structure |
|---|---|
| 877 | 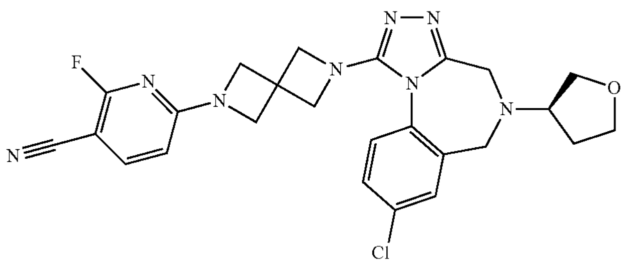 [SMILES: N#Cc1ccc(N2CC3(C2)CN(c2nnc4n2-c2ccc(Cl)cc2CN([C@@H]2CCOC2)C4)C3)nc1F] |
| 878 | 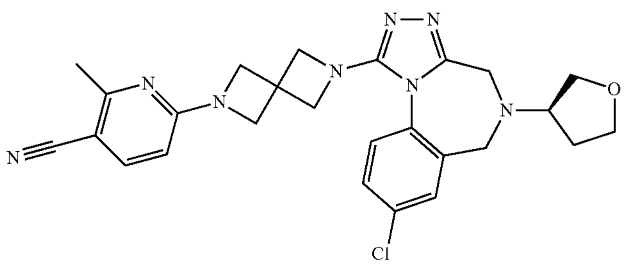 [SMILES: Cc1nc(N2CC3(C2)CN(c2nnc4n2-c2ccc(Cl)cc2CN([C@@H]2CCOC2)C4)C3)ccc1C#N] |
| 879 | 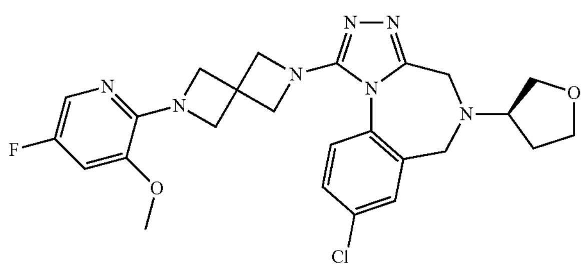 [SMILES: COc1cc(F)cnc1N1CC2(C1)CN(c1nnc3n1-c1ccc(Cl)cc1CN([C@@H]1CCOC1)C3)C2] |
| 880 | 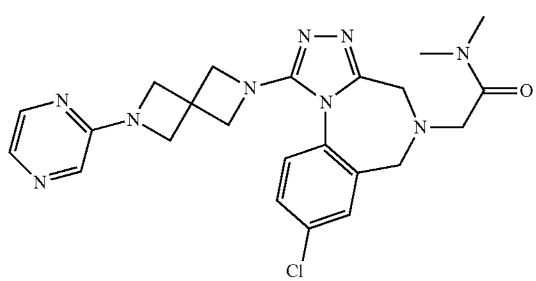 [SMILES: CN(C)C(=O)CN1Cc2cc(Cl)ccc2-n2c(nnc2N2CC3(CN(c4cnccn4)C3)C2)C1] |
| 881 | 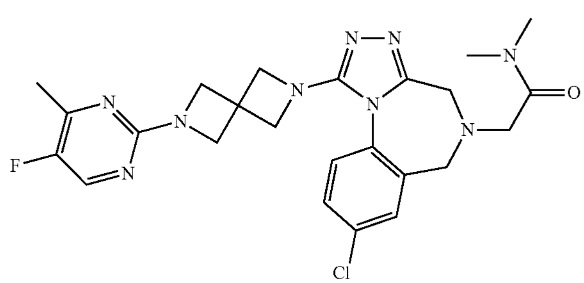 [SMILES: Cc1nc(N2CC3(C2)CN(c2nnc4n2-c2ccc(Cl)cc2CN(CC(=O)N(C)C)C4)C3)ncc1F] |

TABLE 1-continued
Representative Compounds
| Cmpd. No. | Structure |
|---|---|
| 882 | 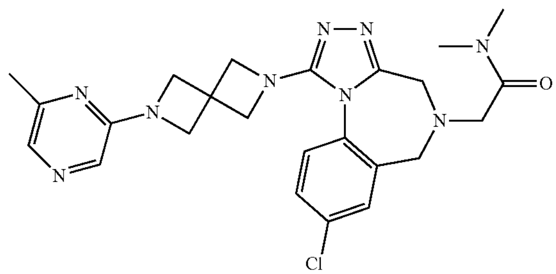 [SMILES: Cc1cncc(N2CC3(C2)CN(c2nnc4n2-c2ccc(Cl)cc2CN(CC(=O)N(C)C)C4)C3)n1] |
| 883 | 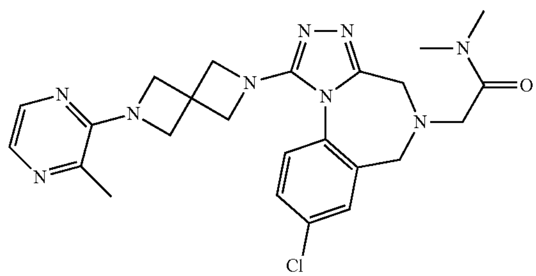 [SMILES: Cc1nccnc1N1CC2(C1)CN(c1nnc3n1-c1ccc(Cl)cc1CN(CC(=O)N(C)C)C3)C2] |
| 884 | 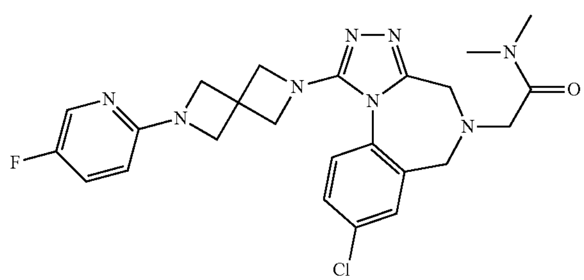 [SMILES: CN(C)C(=O)CN1Cc2cc(Cl)ccc2-n2c(nnc2N2CC3(CN(c4ccc(F)cn4)C3)C2)C1] |
| 885 | 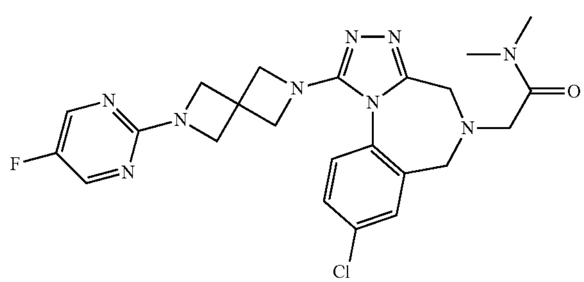 [SMILES: CN(C)C(=O)CN1Cc2cc(Cl)ccc2-n2c(nnc2N2CC3(CN(c4ncc(F)cn4)C3)C2)C1] |
| 886 | 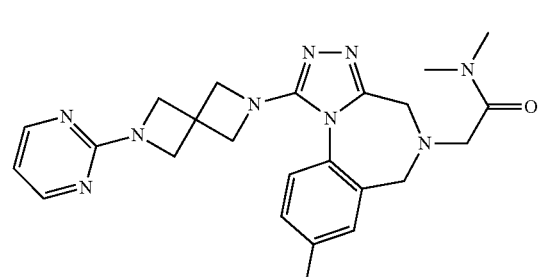 |

TABLE 1-continued

Representative Compounds

| Cmpd. No. | Structure |
|---|---|
| 887 | 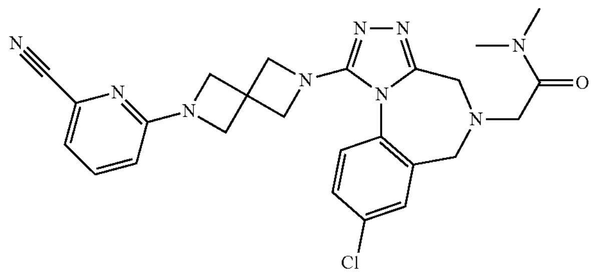 [SMILES: CN(C)C(=O)CN1Cc2cc(Cl)ccc2-n2c(nnc2N2CC3(CN(c4cccc(C#N)n4)C3)C2)C1] |
| 888 | 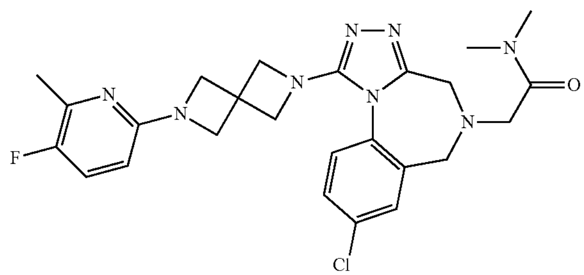 |
| 889 | 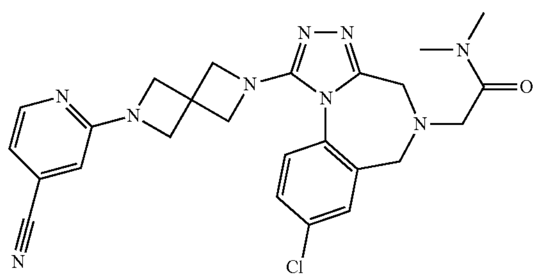 [SMILES: CN(C)C(=O)CN1Cc2cc(Cl)ccc2-n2c(nnc2N2CC3(CN(c4cc(C#N)ccn4)C3)C2)C1] |
| 890 | 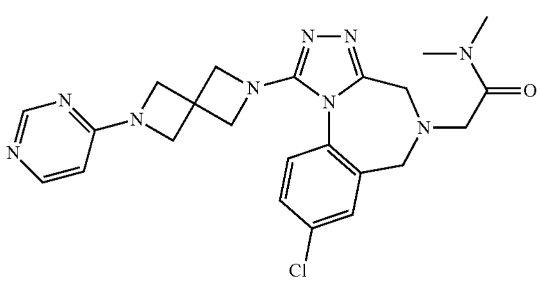 [SMILES: CN(C)C(=O)CN1Cc2cc(Cl)ccc2-n2c(nnc2N2CC3(CN(c4ccncn4)C3)C2)C1] |
| 891 | 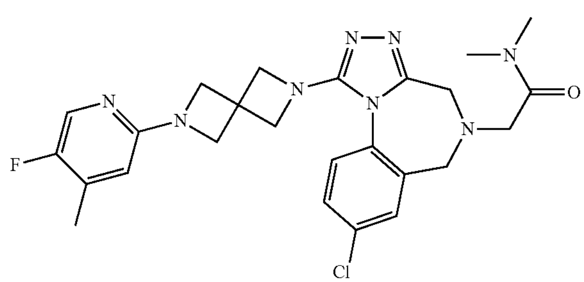 [SMILES: Cc1cc(N2CC3(C2)CN(c2nnc4n2-c2ccc(Cl)cc2CN(CC(=O)N(C)C)C4)C3)ncc1F] |

TABLE 1-continued

Representative Compounds

| Cmpd. No. | Structure |
|---|---|
| 892 | 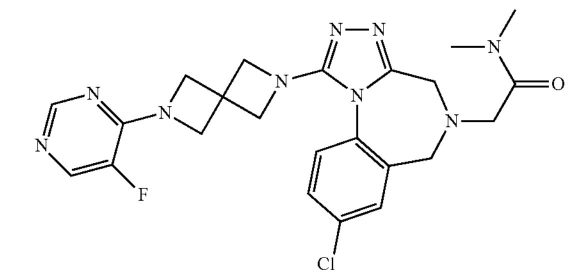 [SMILES: CN(C)C(=O)CN1Cc2cc(Cl)ccc2-n2c(nnc2N2CC3(CN(c4ncncc4F)C3)C2)C1] |
| 893 | 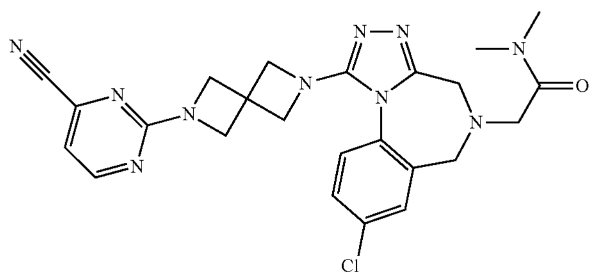 |
| 894 | 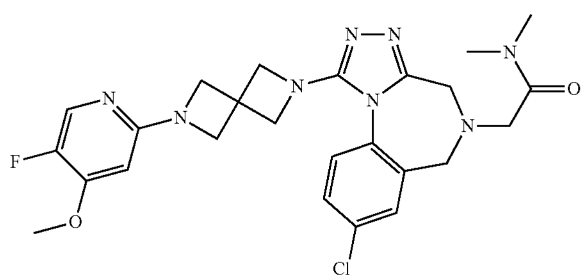 [SMILES: COc1cc(N2CC3(C2)CN(c2nnc4n2-c2ccc(Cl)cc2CN(CC(=O)N(C)C)C4)C3)ncc1F] |
| 895 | 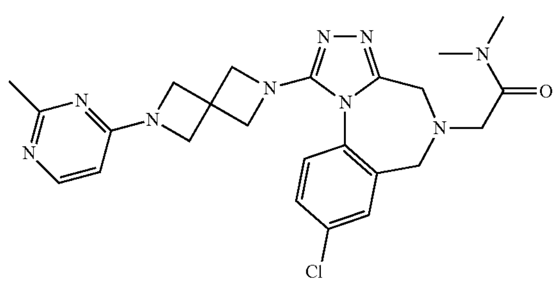 [SMILES: Cc1nccc(N2CC3(C2)CN(c2nnc4n2-c2ccc(Cl)cc2CN(CC(=O)N(C)C)C4)C3)n1] |
| 896 | 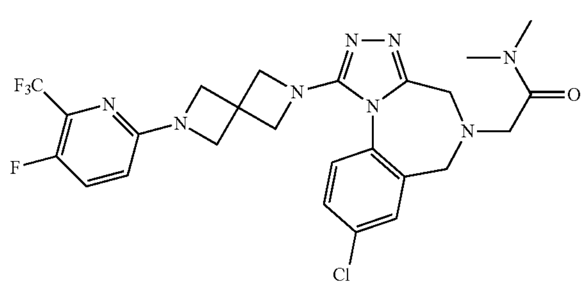 [SMILES: CN(C)C(=O)CN1Cc2cc(Cl)ccc2-n2c(nnc2N2CC3(CN(c4ccc(F)c(C(F)(F)F)n4)C3)C2)C1] |

TABLE 1-continued

Representative Compounds

| Cmpd. No. | Structure |
|---|---|
| 897 | 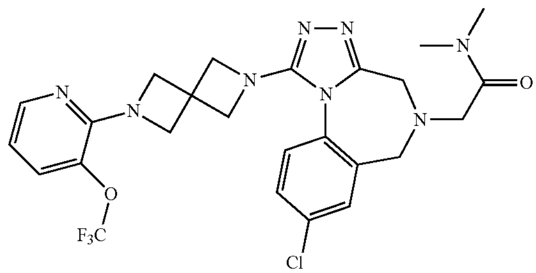 [SMILES: CN(C)C(=O)CN1Cc2cc(Cl)ccc2-n2c(nnc2N2CC3(CN(c4ncccc4OC(F)(F)F)C3)C2)C1] |
| 898 | 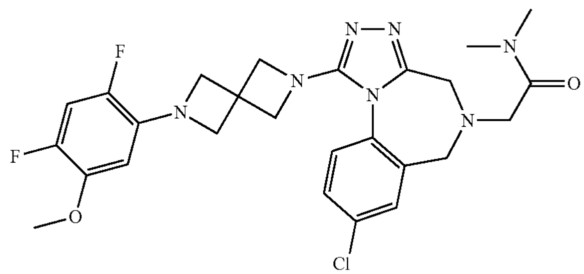 [SMILES: COc1cc(N2CC3(C2)CN(c2nnc4n2-c2ccc(Cl)cc2CN(CC(=O)N(C)C)C4)C3)c(F)cc1F] |
| 899 | 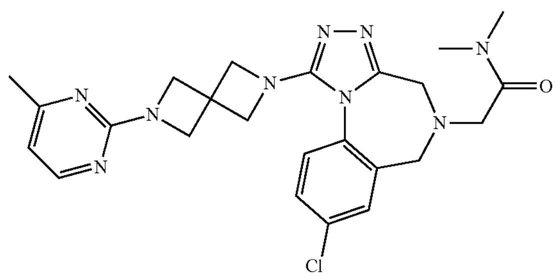 [SMILES: Cc1ccnc(N2CC3(C2)CN(c2nnc4n2-c2ccc(Cl)cc2CN(CC(=O)N(C)C)C4)C3)n1] |
| 900 | 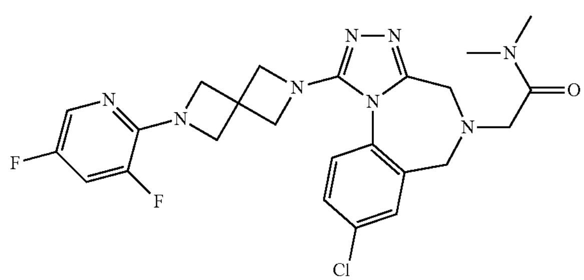 [SMILES: CN(C)C(=O)CN1Cc2cc(Cl)ccc2-n2c(nnc2N2CC3(CN(c4ncc(F)cc4F)C3)C2)C1] |
| 901 | 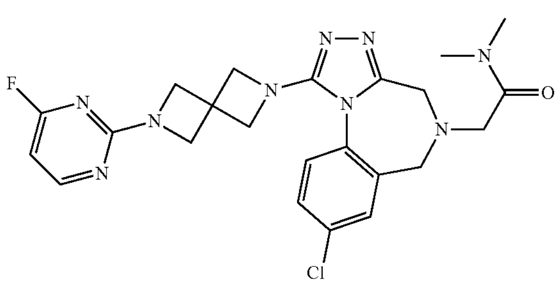 [SMILES: CN(C)C(=O)CN1Cc2cc(Cl)ccc2-n2c(nnc2N2CC3(CN(c4nccc(F)n4)C3)C2)C1] |

TABLE 1-continued

Representative Compounds

| Cmpd. No. | Structure |
|---|---|
| 902 | 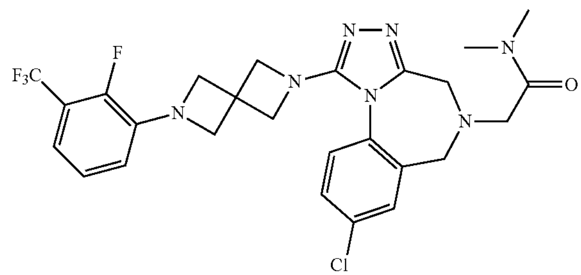 [SMILES: CN(C)C(=O)CN1Cc2cc(Cl)ccc2-n2c(nnc2N2CC3(CN(c4cccc(C(F)(F)F)c4F)C3)C2)C1] |
| 903 | 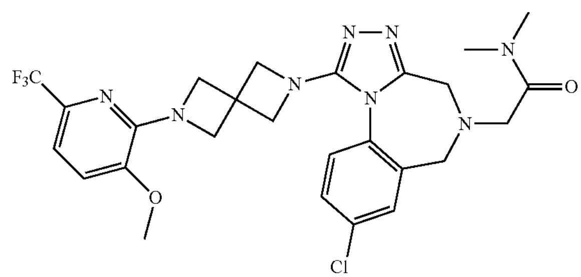 [SMILES: COc1ccc(C(F)(F)F)nc1N1CC2(C1)CN(c1nnc3n1-c1ccc(Cl)cc1CN(CC(=O)N(C)C)C3)C2] |
| 904 | 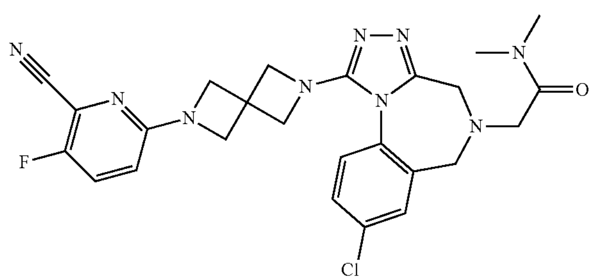 [SMILES: CN(C)C(=O)CN1Cc2cc(Cl)ccc2-n2c(nnc2N2CC3(CN(c4ccc(F)c(C#N)n4)C3)C2)C1] |
| 905 | 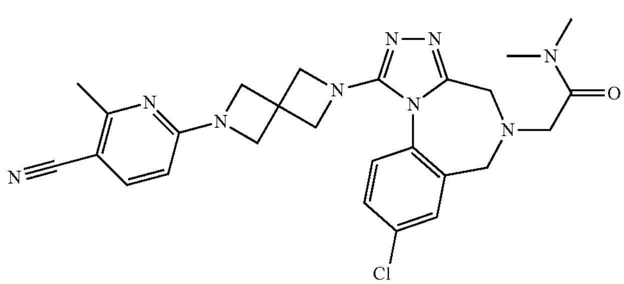 [SMILES: Cc1nc(N2CC3(C2)CN(c2nnc4n2-c2ccc(Cl)cc2CN(CC(=O)N(C)C)C4)C3)ccc1C#N] |
| 906 | 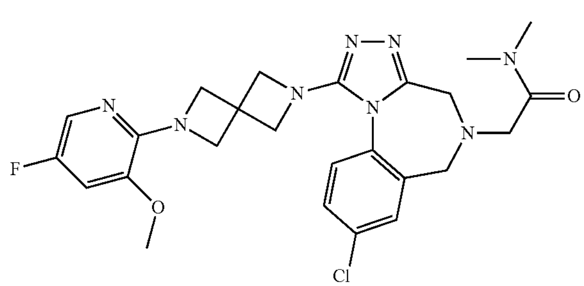 [SMILES: COc1cc(F)cnc1N1CC2(C1)CN(c1nnc3n1-c1ccc(Cl)cc1CN(CC(=O)N(C)C)C3)C2] |

TABLE 1-continued

Representative Compounds

| Cmpd. No. | Structure |
|---|---|
| 907 | 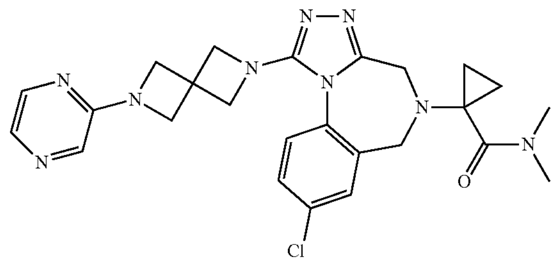 [SMILES: CN(C)C(=O)C1(N2Cc3cc(Cl)ccc3-n3c(nnc3N3CC4(CN(c5cnccn5)C4)C3)C2)CC1] |
| 908 | 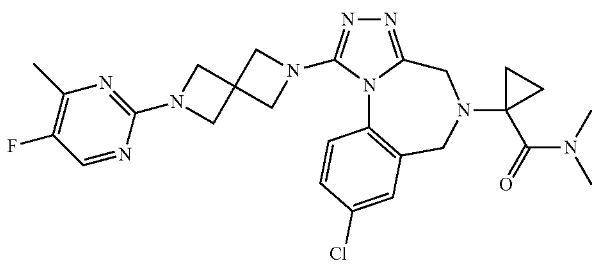 [SMILES: Cc1nc(N2CC3(C2)CN(c2nnc4n2-c2ccc(Cl)cc2CN(C2(C(=O)N(C)C)CC2)C4)C3)ncc1F] |
| 909 | 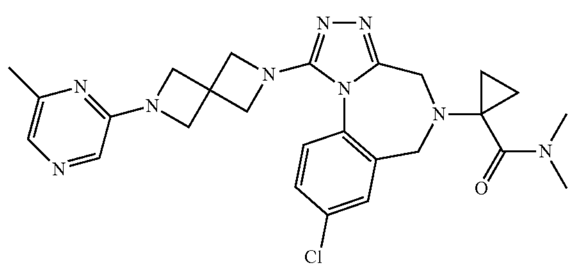 |
| 910 | 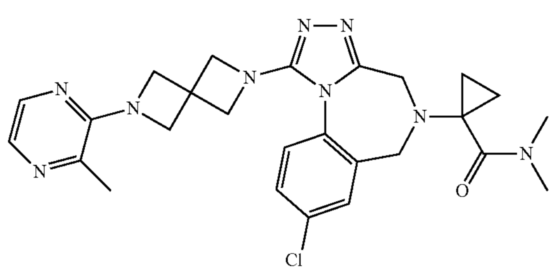 [SMILES: Cc1nccnc1N1CC2(C1)CN(c1nnc3n1-c1ccc(Cl)cc1CN(C1(C(=O)N(C)C)CC1)C3)C2] |
| 911 | 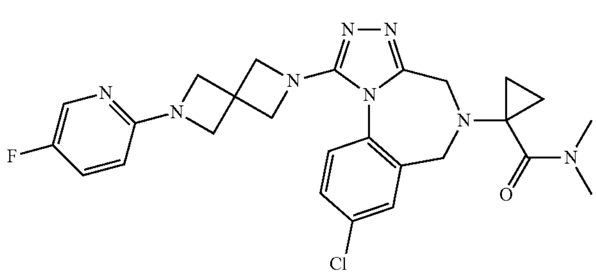 [SMILES: CN(C)C(=O)C1(N2Cc3cc(Cl)ccc3-n3c(nnc3N3CC4(CN(c5ccc(F)cn5)C4)C3)C2)CC1] |

TABLE 1-continued

Representative Compounds

| Cmpd. No. | Structure |
|---|---|
| 912 | 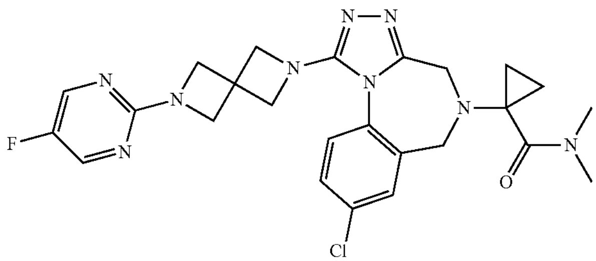 |
| 913 | 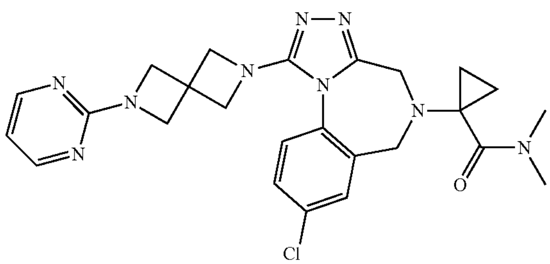 [SMILES: CN(C)C(=O)C1(N2Cc3cc(Cl)ccc3-n3c(nnc3N3CC4(CN(c5ncccn5)C4)C3)C2)CC1] |
| 914 | 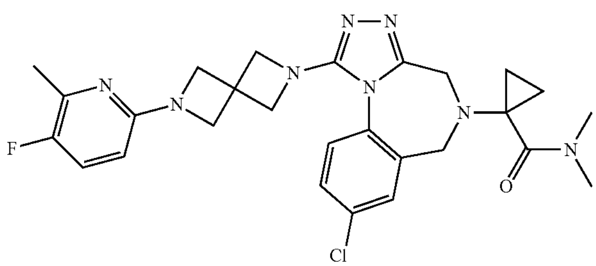 |
| 915 | 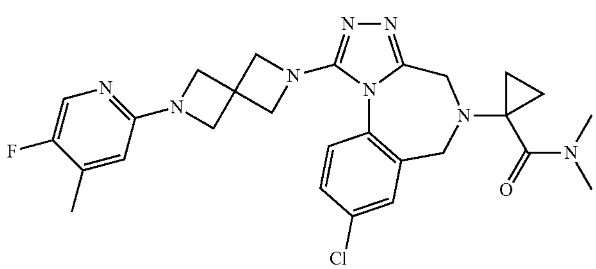 |
| 916 | 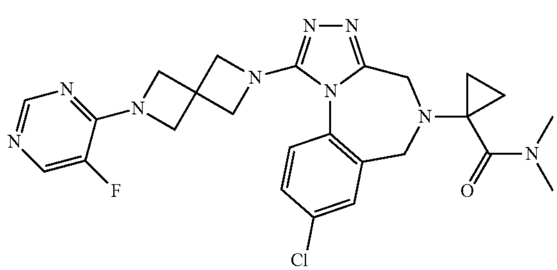 [SMILES: CN(C)C(=O)C1(N2Cc3cc(Cl)ccc3-n3c(nnc3N3CC4(CN(c5ncncc5F)C4)C3)C2)CC1] |

TABLE 1-continued

Representative Compounds

| Cmpd. No. | Structure |
|---|---|
| 917 | 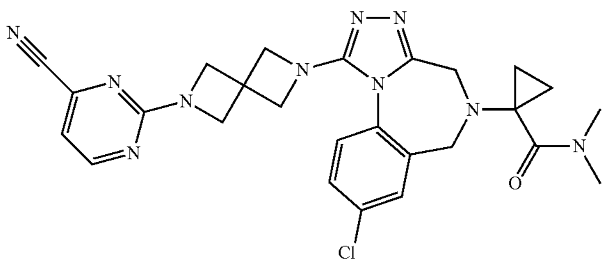 [SMILES: CN(C)C(=O)C1(N2Cc3cc(Cl)ccc3-n3c(nnc3N3CC4(CN(c5nccc(C#N)n5)C4)C3)C2)CC1] |
| 918 | 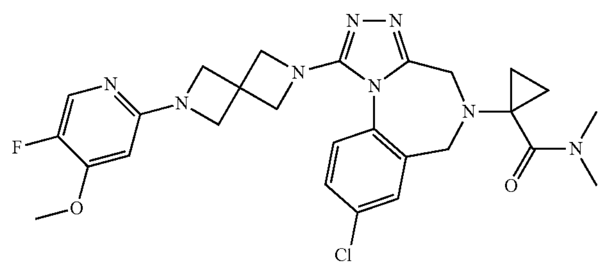 [SMILES: COc1cc(N2CC3(C2)CN(c2nnc4n2-c2ccc(Cl)cc2CN(C2(C(=O)N(C)C)CC2)C4)C3)ncc1F] |
| 919 | 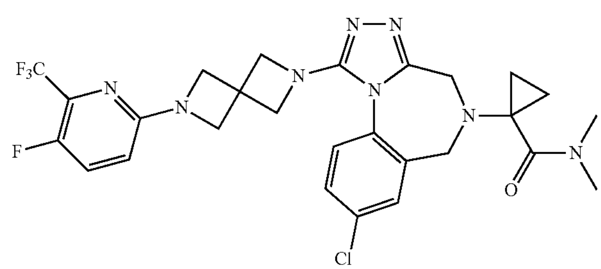 [SMILES: CN(C)C(=O)C1(N2Cc3cc(Cl)ccc3-n3c(nnc3N3CC4(CN(c5ccc(F)c(C(F)(F)F)n5)C4)C3)C2)CC1] |
| 920 | 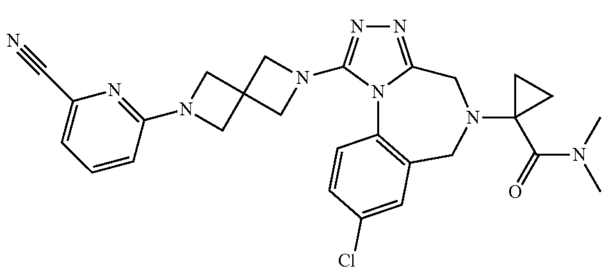 [SMILES: CN(C)C(=O)C1(N2Cc3cc(Cl)ccc3-n3c(nnc3N3CC4(CN(c5cccc(C#N)n5)C4)C3)C2)CC1] |
| 921 | 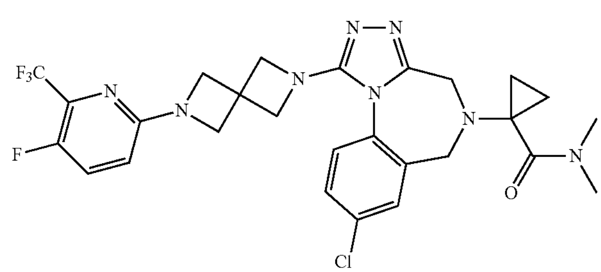 |

TABLE 1-continued

Representative Compounds

| Cmpd. No. | Structure |
|---|---|
| 922 | 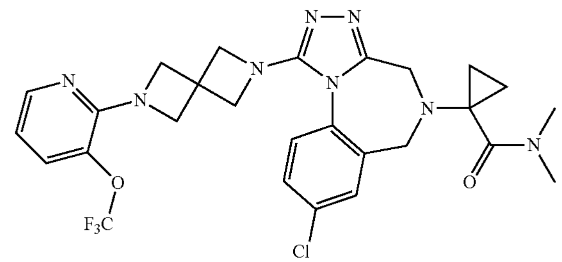 [SMILES: CN(C)C(=O)C1(N2Cc3cc(Cl)ccc3-n3c(nnc3N3CC4(CN(c5ncccc5OC(F)(F)F)C4)C3)C2)CC1] |
| 923 | 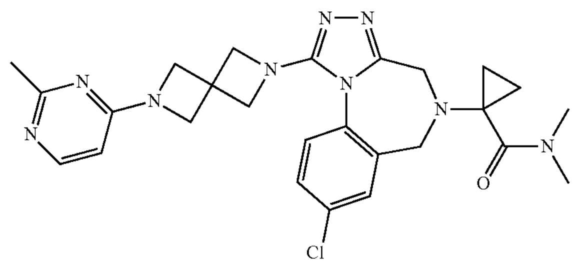 |
| 924 | 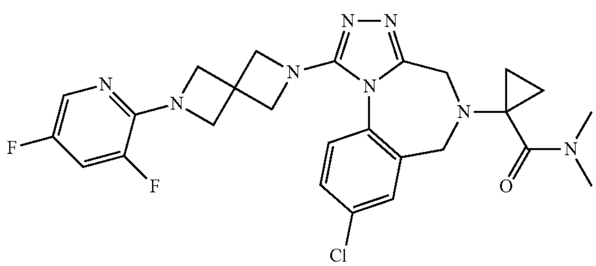 [SMILES: CN(C)C(=O)C1(N2Cc3cc(Cl)ccc3-n3c(nnc3N3CC4(CN(c5ncc(F)cc5F)C4)C3)C2)CC1] |
| 925 | 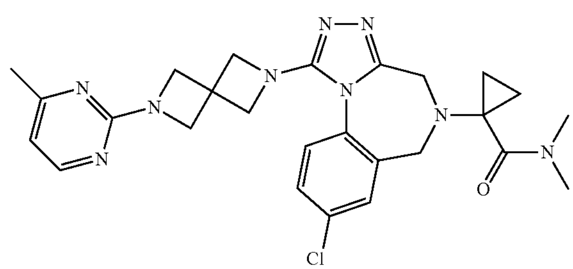 |
| 926 | 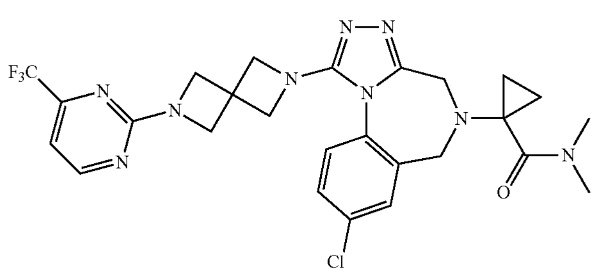 [SMILES: CN(C)C(=O)C1(N2Cc3cc(Cl)ccc3-n3c(nnc3N3CC4(CN(c5nccc(C(F)(F)F)n5)C4)C3)C2)CC1] |

TABLE 1-continued

Representative Compounds

| Cmpd. No. | Structure |
|---|---|
| 927 | 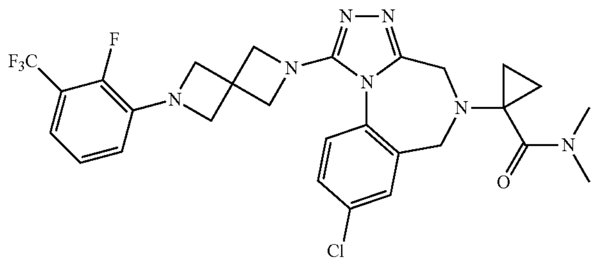 [SMILES: CN(C)C(=O)C1(N2Cc3cc(Cl)ccc3-n3c(nnc3N3CC4(CN(c5cccc(C(F)(F)F)c5F)C4)C3)C2)CC1] |
| 928 | 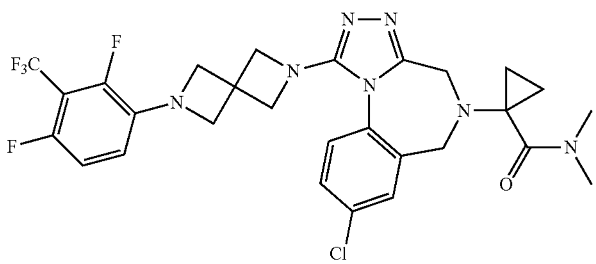 [SMILES: CN(C)C(=O)C1(N2Cc3cc(Cl)ccc3-n3c(nnc3N3CC4(CN(c5ccc(F)c(C(F)(F)F)c5F)C4)C3)C2)CC1] |
| 929 | 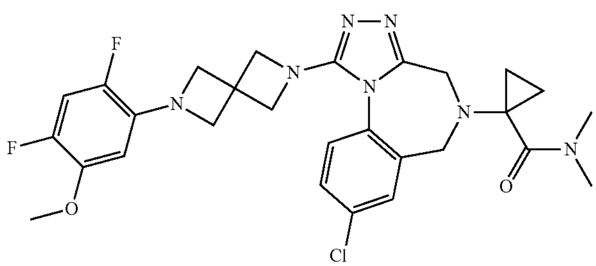 [SMILES: COc1cc(N2CC3(C2)CN(c2nnc4n2-c2ccc(Cl)cc2CN(C2(C(=O)N(C)C)CC2)C4)C3)c(F)cc1F] |
| 930 | 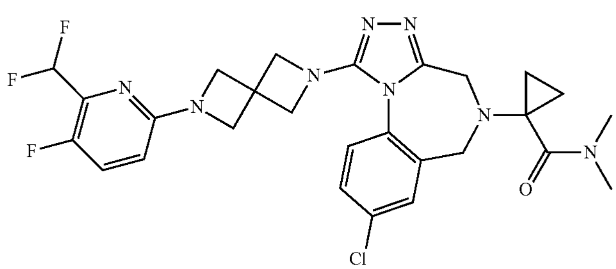 [SMILES: CN(C)C(=O)C1(N2Cc3cc(Cl)ccc3-n3c(nnc3N3CC4(CN(c5ccc(F)c(C(F)F)n5)C4)C3)C2)CC1] |
| 931 | 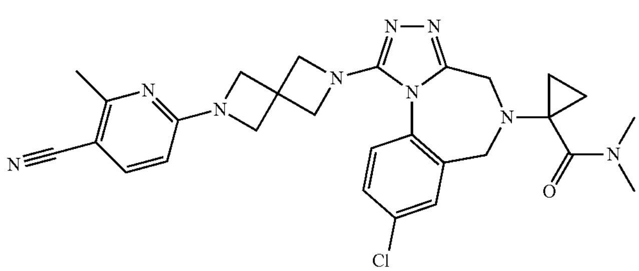 [SMILES: Cc1nc(N2CC3(C2)CN(c2nnc4n2-c2ccc(Cl)cc2CN(C2(C(=O)N(C)C)CC2)C4)C3)ccc1C#N] |

TABLE 1-continued

Representative Compounds

| Cmpd. No. | Structure |
|---|---|
| 932 | 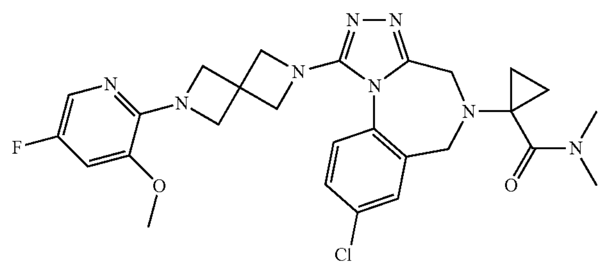 [SMILES: COc1cc(F)cnc1N1CC2(C1)CN(c1nnc3n1-c1ccc(Cl)cc1CN(C1(C(=O)N(C)C)CC1)C3)C2] |
| 933 | 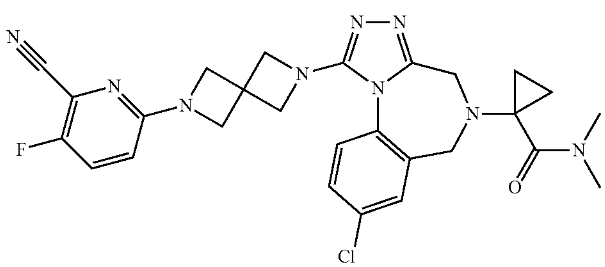 [SMILES: CN(C)C(=O)C1(N2Cc3cc(Cl)ccc3-n3c(nnc3N3CC4(CN(c5ccc(F)c(C#N)n5)C4)C3)C2)CC1] |
| 934 | 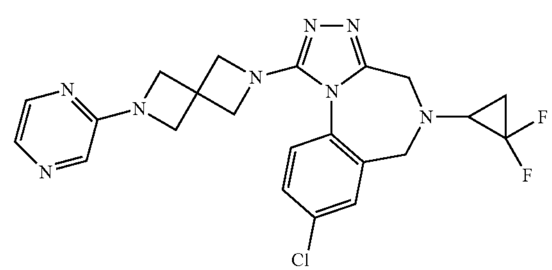 [SMILES: FC1(F)CC1N1Cc2cc(Cl)ccc2-n2c(nnc2N2CC3(CN(c4cnccn4)C3)C2)C1] |
| 935 | 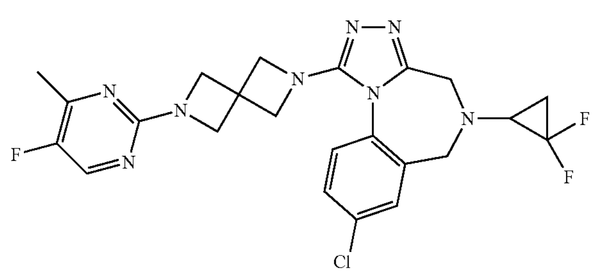 |
| 936 | 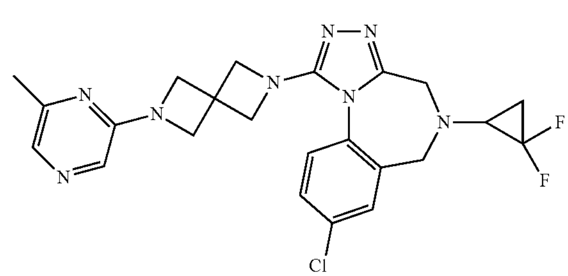 |

TABLE 1-continued

Representative Compounds

| Cmpd. No. | Structure |
|---|---|
| 937 | 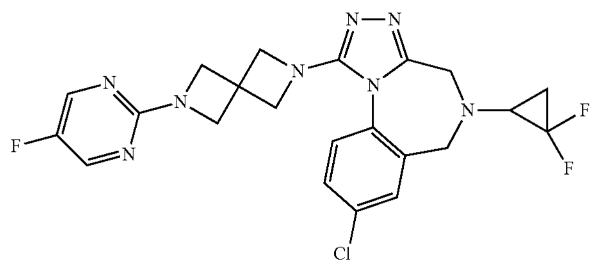 [SMILES: Fc1cnc(N2CC3(C2)CN(c2nnc4n2-c2ccc(Cl)cc2CN(C2CC2(F)F)C4)C3)nc1] |
| 938 | 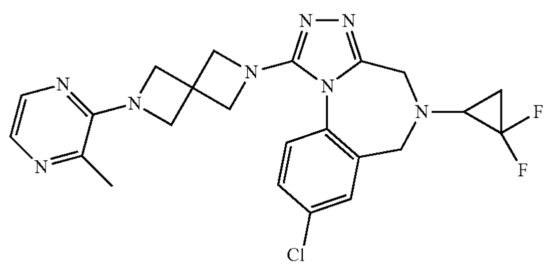 [SMILES: Cc1nccnc1N1CC2(C1)CN(c1nnc3n1-c1ccc(Cl)cc1CN(C1CC1(F)F)C3)C2] |
| 939 | 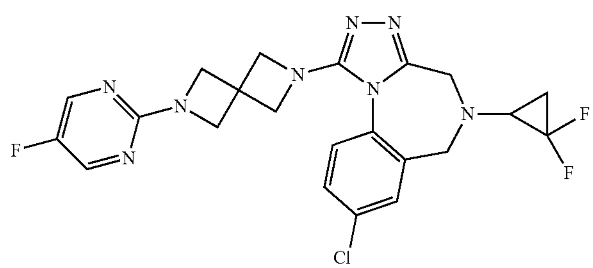 [SMILES: Fc1cnc(N2CC3(C2)CN(c2nnc4n2-c2ccc(Cl)cc2CN(C2CC2(F)F)C4)C3)nc1] |
| 940 | 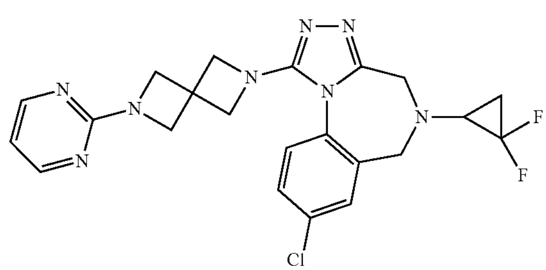 [SMILES: FC1(F)CC1N1Cc2cc(Cl)ccc2-n2c(nnc2N2CC3(CN(c4ncccn4)C3)C2)C1] |
| 941 | 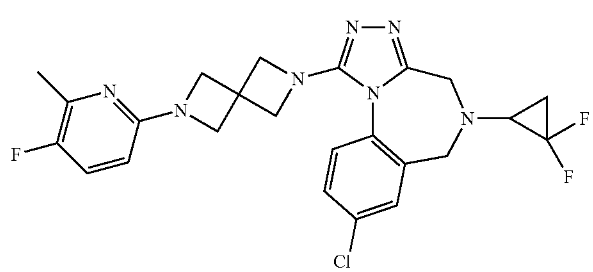 [SMILES: Cc1nc(N2CC3(C2)CN(c2nnc4n2-c2ccc(Cl)cc2CN(C2CC2(F)F)C4)C3)ccc1F] |

TABLE 1-continued

Representative Compounds

| Cmpd. No. | Structure |
|---|---|
| 942 | 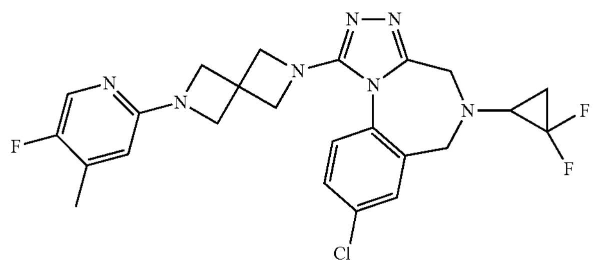 [SMILES: Cc1cc(N2CC3(C2)CN(c2nnc4n2-c2ccc(Cl)cc2CN(C2CC2(F)F)C4)C3)ncc1F] |
| 943 | 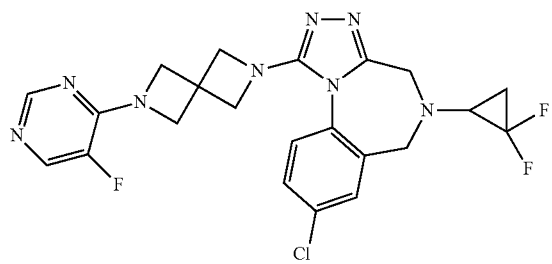 [SMILES: Fc1cncnc1N1CC2(C1)CN(c1nnc3n1-c1ccc(Cl)cc1CN(C1CC1(F)F)C3)C2] |
| 944 | 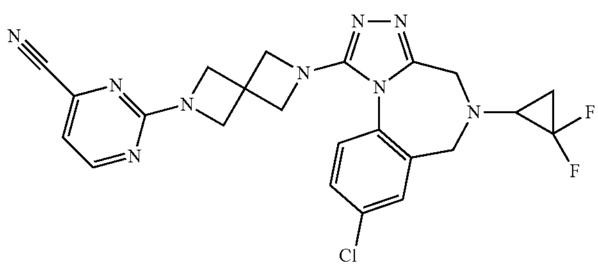 [SMILES: N#Cc1ccnc(N2CC3(C2)CN(c2nnc4n2-c2ccc(Cl)cc2CN(C2CC2(F)F)C4)C3)n1] |
| 945 | 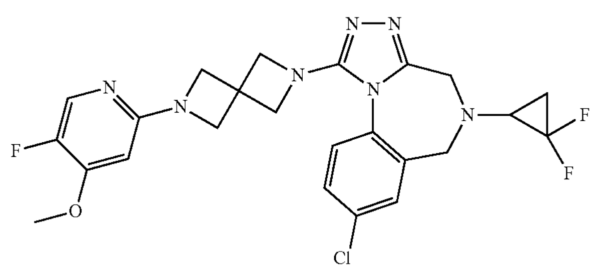 [SMILES: COc1cc(N2CC3(C2)CN(c2nnc4n2-c2ccc(Cl)cc2CN(C2CC2(F)F)C4)C3)ncc1F] |
| 946 | 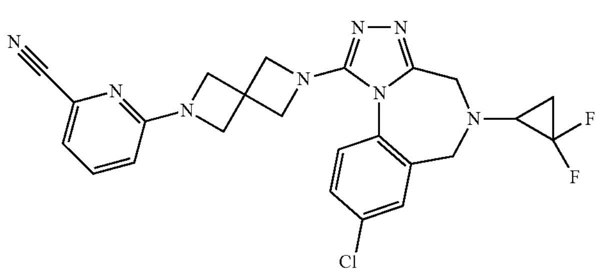 [SMILES: N#Cc1cccc(N2CC3(C2)CN(c2nnc4n2-c2ccc(Cl)cc2CN(C2CC2(F)F)C4)C3)n1] |

TABLE 1-continued

Representative Compounds

| Cmpd. No. | Structure |
|---|---|
| 947 | 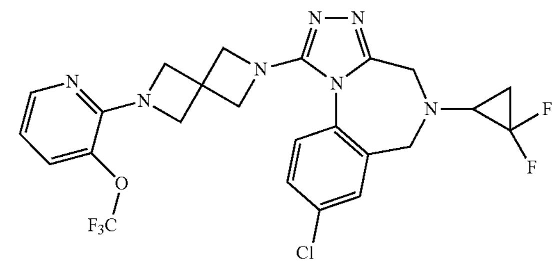 [SMILES: FC(F)(F)Oc1cccnc1N1CC2(C1)CN(c1nnc3n1-c1ccc(Cl)cc1CN(C1CC1(F)F)C3)C2] |
| 948 | 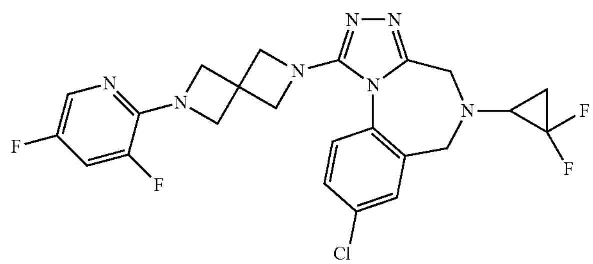 [SMILES: Fc1cnc(N2CC3(C2)CN(c2nnc4n2-c2ccc(Cl)cc2CN(C2CC2(F)F)C4)C3)c(F)c1] |
| 949 | 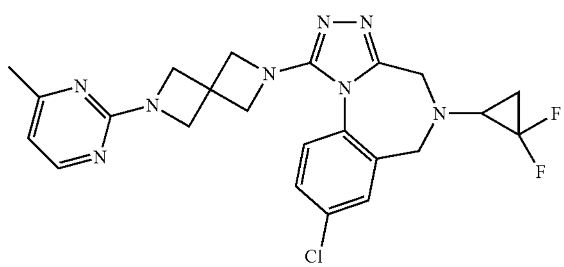 [SMILES: Cc1ccnc(N2CC3(C2)CN(c2nnc4n2-c2ccc(Cl)cc2CN(C2CC2(F)F)C4)C3)n1] |
| 950 | 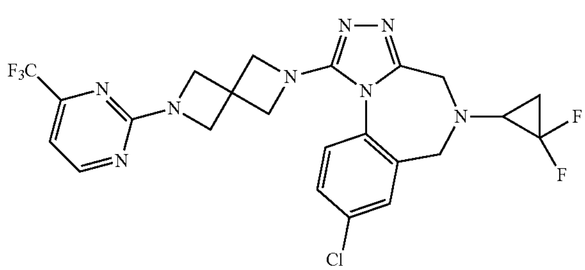 [SMILES: FC(F)(F)c1ccnc(N2CC3(C2)CN(c2nnc4n2-c2ccc(Cl)cc2CN(C2CC2(F)F)C4)C3)n1] |
| 951 | 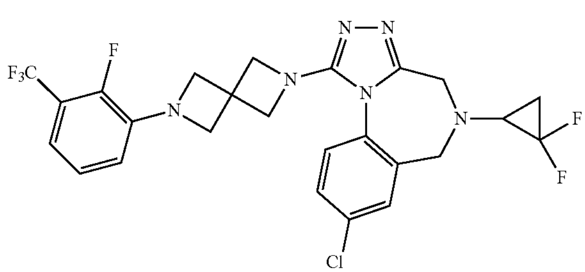 [SMILES: Fc1c(N2CC3(C2)CN(c2nnc4n2-c2ccc(Cl)cc2CN(C2CC2(F)F)C4)C3)cccc1C(F)(F)F] |

TABLE 1-continued

Representative Compounds

| Cmpd. No. | Structure |
|---|---|
| 952 | 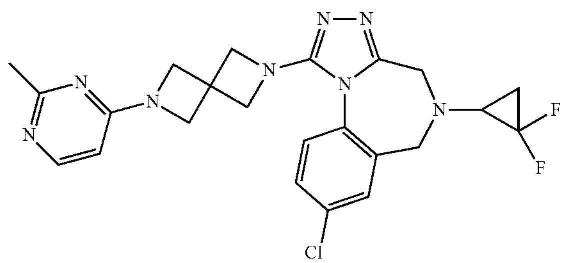 [SMILES: Cc1nccc(N2CC3(C2)CN(c2nnc4n2-c2ccc(Cl)cc2CN(C2CC2(F)F)C4)C3)n1] |
| 953 | 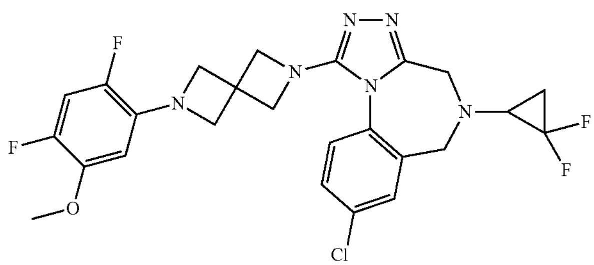 [SMILES: COc1cc(N2CC3(C2)CN(c2nnc4n2-c2ccc(Cl)cc2CN(C2CC2(F)F)C4)C3)c(F)cc1F] |
| 954 | 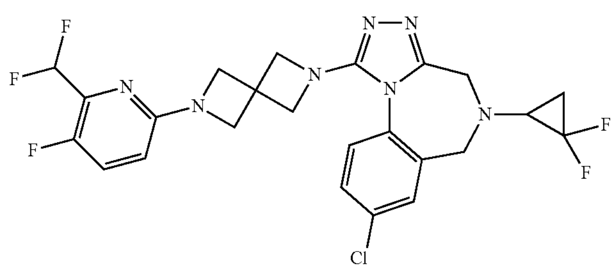 [SMILES: Fc1ccc(N2CC3(C2)CN(c2nnc4n2-c2ccc(Cl)cc2CN(C2CC2(F)F)C4)C3)nc1C(F)F] |
| 955 | 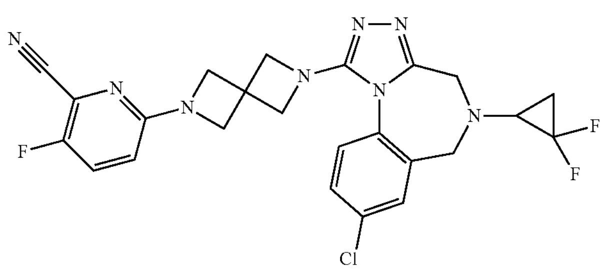 [SMILES: N#Cc1nc(N2CC3(C2)CN(c2nnc4n2-c2ccc(Cl)cc2CN(C2CC2(F)F)C4)C3)ccc1F] |
| 956 | 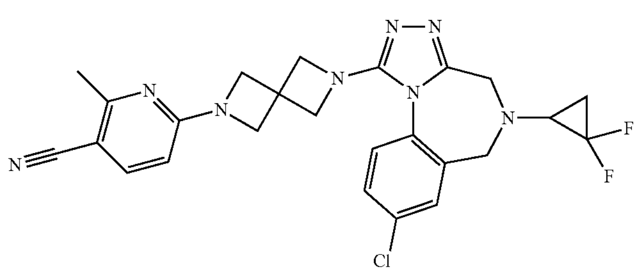 [SMILES: Cc1nc(N2CC3(C2)CN(c2nnc4n2-c2ccc(Cl)cc2CN(C2CC2(F)F)C4)C3)ccc1C#N] |

TABLE 1-continued

Representative Compounds

| Cmpd. No. | Structure |
|---|---|
| 957 | 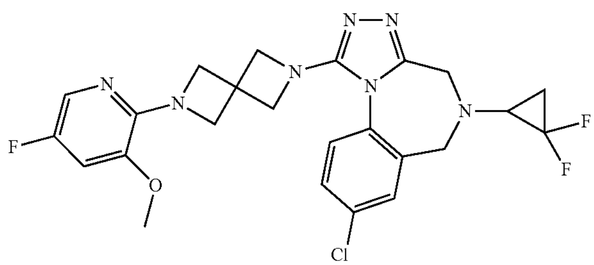 [SMILES: COc1cc(F)cnc1N1CC2(C1)CN(c1nnc3n1-c1ccc(Cl)cc1CN(C1CC1(F)F)C3)C2] |
| 958 | 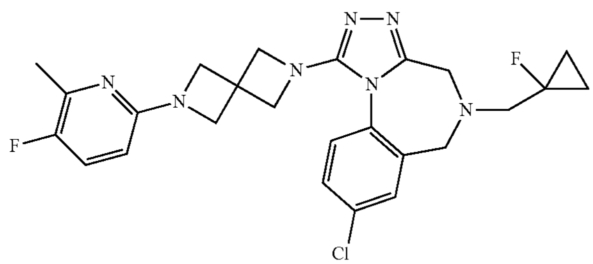 [SMILES: Cc1nc(N2CC3(C2)CN(c2nnc4n2-c2ccc(Cl)cc2CN(CC2(F)CC2)C4)C3)ccc1F] |
| 959 | 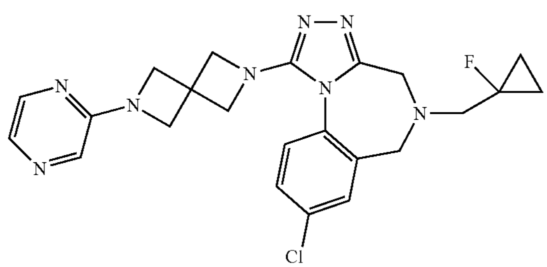 [SMILES: FC1(CN2Cc3cc(Cl)ccc3-n3c(nnc3N3CC4(CN(c5cnccn5)C4)C3)C2)CC1] |
| 960 | 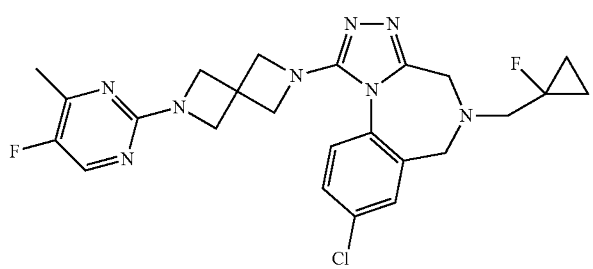 |
| 961 | 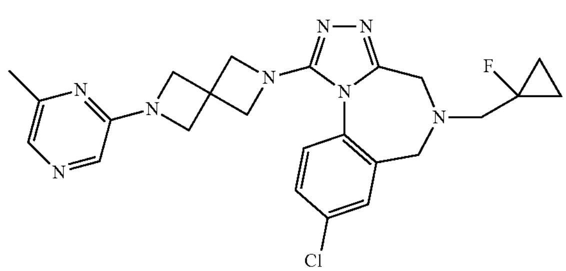 |

TABLE 1-continued

Representative Compounds

| Cmpd. No. | Structure |
|---|---|
| 962 | 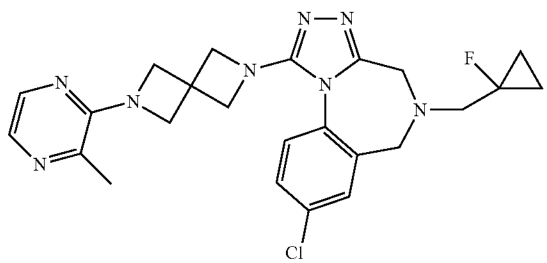 [SMILES: Cc1nccnc1N1CC2(C1)CN(c1nnc3n1-c1ccc(Cl)cc1CN(CC1(F)CC1)C3)C2] |
| 963 | 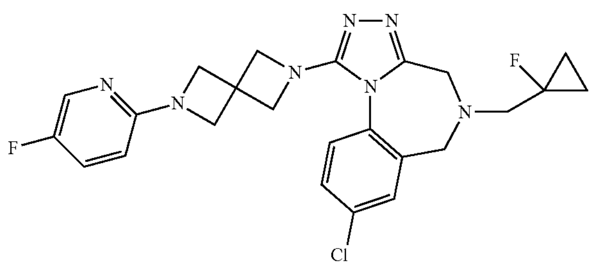 |
| 964 | 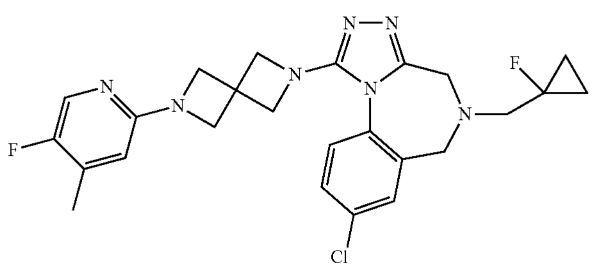 [SMILES: Cc1cc(N2CC3(C2)CN(c2nnc4n2-c2ccc(Cl)cc2CN(CC2(F)CC2)C4)C3)ncc1F] |
| 965 | 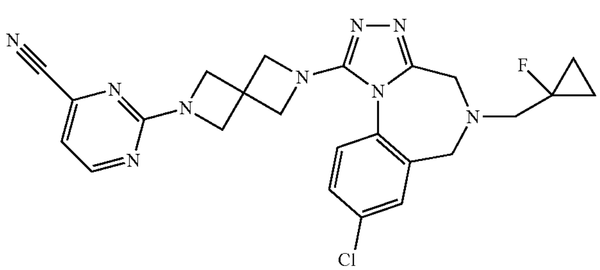 [SMILES: N#Cc1ccnc(N2CC3(C2)CN(c2nnc4n2-c2ccc(Cl)cc2CN(CC2(F)CC2)C4)C3)n1] |
| 966 | 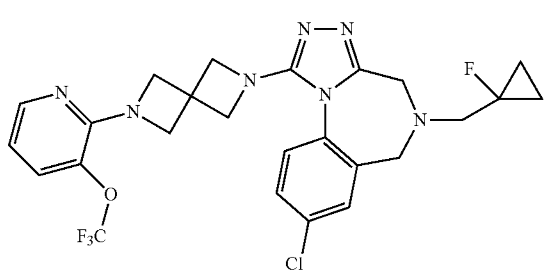 [SMILES: FC1(CN2Cc3cc(Cl)ccc3-n3c(nnc3N3CC4(CN(c5ncccc5OC(F)(F)F)C4)C3)C2)CC1] |

TABLE 1-continued

Representative Compounds

| Cmpd. No. | Structure |
|---|---|
| 967 | 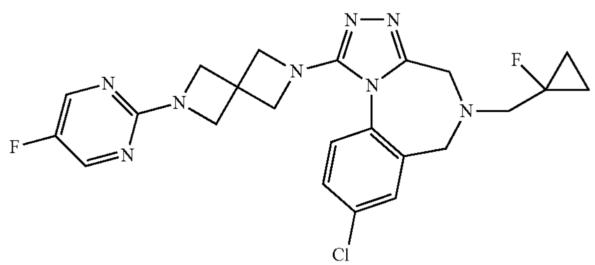 [SMILES: Fc1cnc(N2CC3(C2)CN(c2nnc4n2-c2ccc(Cl)cc2CN(CC2(F)CC2)C4)C3)nc1] |
| 968 | 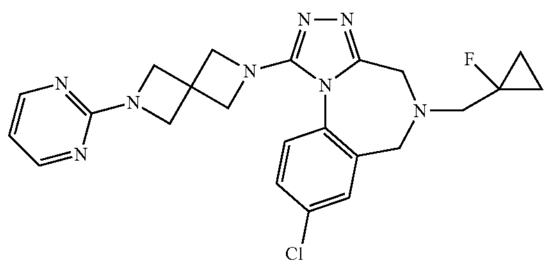 [SMILES: FC1(CN2Cc3cc(Cl)ccc3-n3c(nnc3N3CC4(CN(c5ncccn5)C4)C3)C2)CC1] |
| 969 | 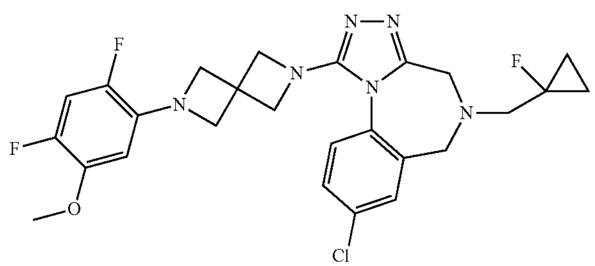 [SMILES: COc1cc(N2CC3(C2)CN(c2nnc4n2-c2ccc(Cl)cc2CN(CC2(F)CC2)C4)C3)c(F)cc1F] |
| 970 | 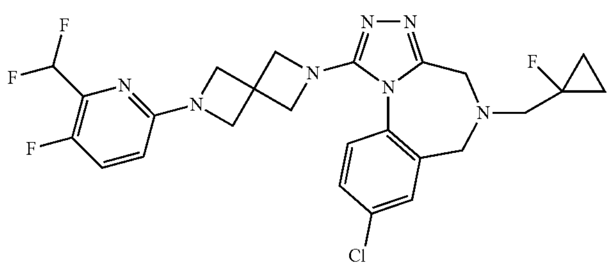 [SMILES: Fc1ccc(N2CC3(C2)CN(c2nnc4n2-c2ccc(Cl)cc2CN(CC2(F)CC2)C4)C3)nc1C(F)F] |
| 971 | 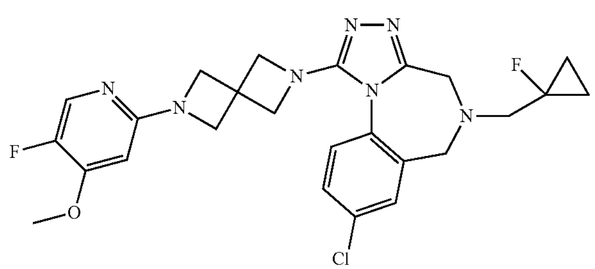 [SMILES: COc1cc(N2CC3(C2)CN(c2nnc4n2-c2ccc(Cl)cc2CN(CC2(F)CC2)C4)C3)ncc1F] |

TABLE 1-continued

Representative Compounds

| Cmpd. No. | Structure |
|---|---|
| 972 | 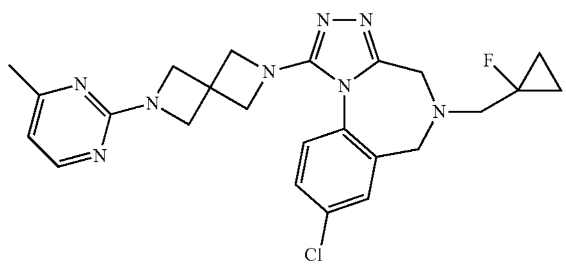 |
| 973 | 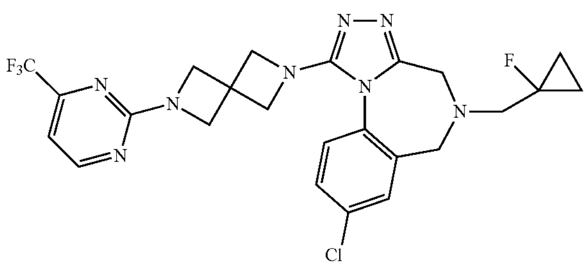 [SMILES: FC1(CN2Cc3cc(Cl)ccc3-n3c(nnc3N3CC4(CN(c5nccc(C(F)(F)F)n5)C4)C3)C2)CC1] |
| 974 | 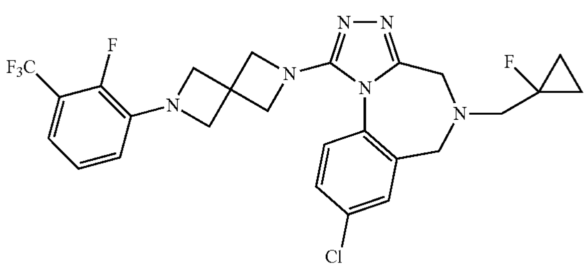 [SMILES: Fc1c(N2CC3(C2)CN(c2nnc4n2-c2ccc(Cl)cc2CN(CC2(F)CC2)C4)C3)cccc1C(F)(F)F] |
| 975 | 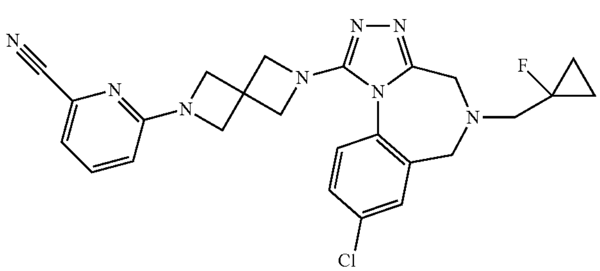 [SMILES: N#Cc1cccc(N2CC3(C2)CN(c2nnc4n2-c2ccc(Cl)cc2CN(CC2(F)CC2)C4)C3)n1] |
| 976 | 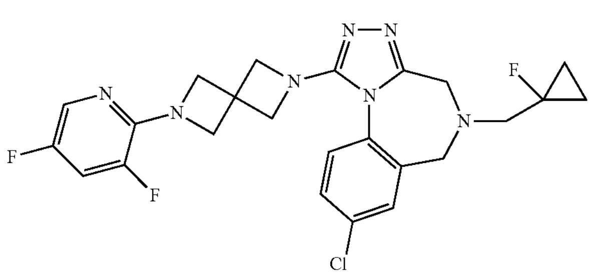 [SMILES: Fc1cnc(N2CC3(C2)CN(c2nnc4n2-c2ccc(Cl)cc2CN(CC2(F)CC2)C4)C3)c(F)c1] |

TABLE 1-continued

Representative Compounds

| Cmpd. No. | Structure |
|---|---|
| 977 | 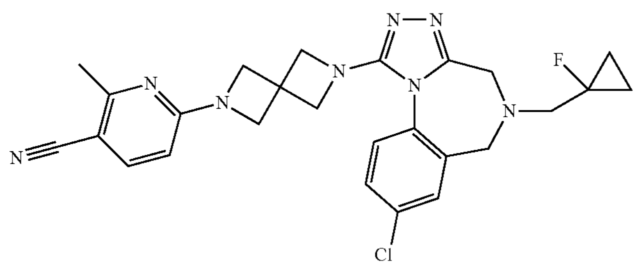 [SMILES: Cc1nc(N2CC3(C2)CN(c2nnc4n2-c2ccc(Cl)cc2CN(CC2(F)CC2)C4)C3)ccc1C#N] |
| 978 | 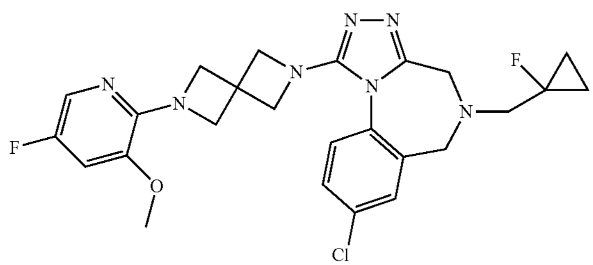 [SMILES: COc1cc(F)cnc1N1CC2(C1)CN(c1nnc3n1-c1ccc(Cl)cc1CN(CC1(F)CC1)C3)C2] |
| 979 | 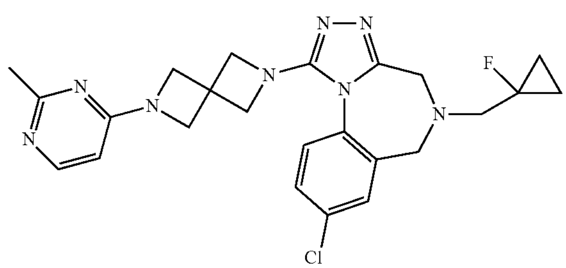 [SMILES: Cc1nccc(N2CC3(C2)CN(c2nnc4n2-c2ccc(Cl)cc2CN(CC2(F)CC2)C4)C3)n1] |
| 980 | 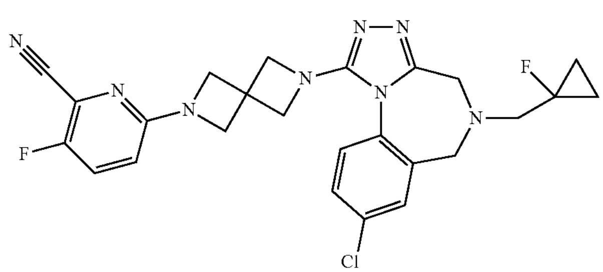 [SMILES: N#Cc1nc(N2CC3(C2)CN(c2nnc4n2-c2ccc(Cl)cc2CN(CC2(F)CC2)C4)C3)ccc1F] |
| 981 | 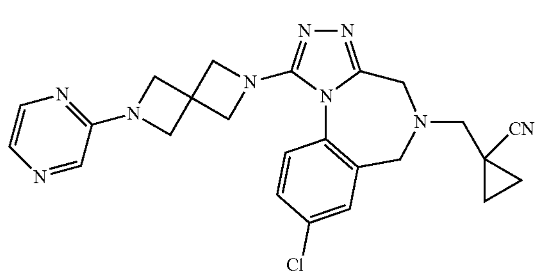 [SMILES: N#CC1(CN2Cc3cc(Cl)ccc3-n3c(nnc3N3CC4(CN(c5cnccn5)C4)C3)C2)CC1] |

TABLE 1-continued

Representative Compounds

| Cmpd. No. | Structure |
|---|---|
| 982 | 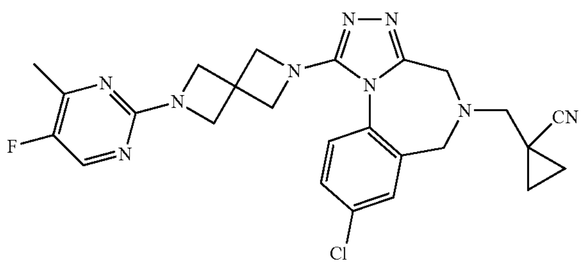 [SMILES: Cc1nc(N2CC3(C2)CN(c2nnc4n2-c2ccc(Cl)cc2CN(CC2(C#N)CC2)C4)C3)ncc1F] |
| 983 | 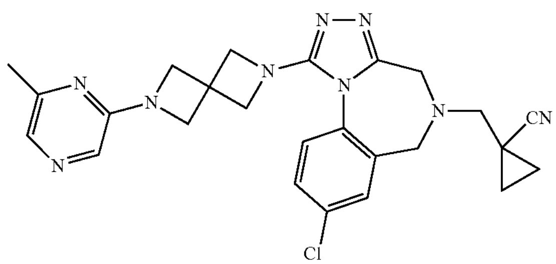 [SMILES: Cc1cncc(N2CC3(C2)CN(c2nnc4n2-c2ccc(Cl)cc2CN(CC2(C#N)CC2)C4)C3)n1] |
| 984 | 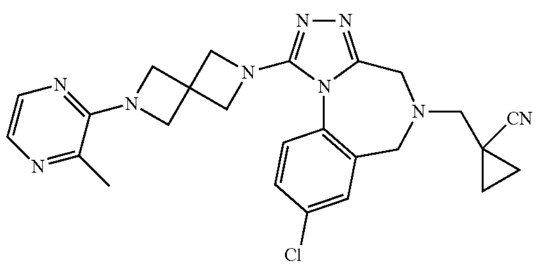 [SMILES: Cc1nccnc1N1CC2(C1)CN(c1nnc3n1-c1ccc(Cl)cc1CN(CC1(C#N)CC1)C3)C2] |
| 985 | 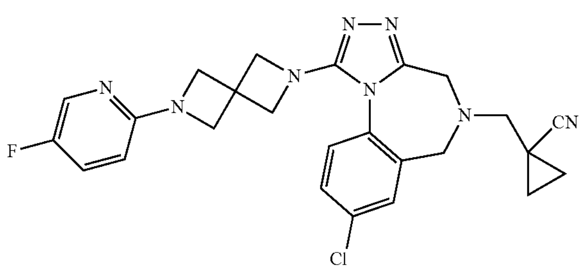 [SMILES: N#CC1(CN2Cc3cc(Cl)ccc3-n3c(nnc3N3CC4(CN(c5ccc(F)cn5)C4)C3)C2)CC1] |
| 986 | 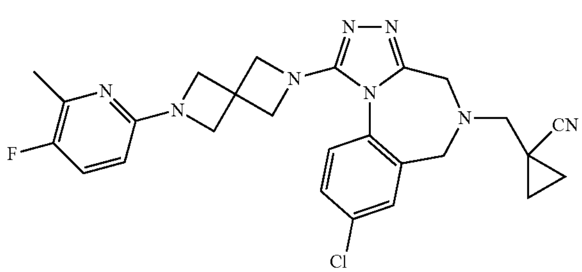 [SMILES: Cc1nc(N2CC3(C2)CN(c2nnc4n2-c2ccc(Cl)cc2CN(CC2(C#N)CC2)C4)C3)ccc1F] |

TABLE 1-continued

Representative Compounds

| Cmpd. No. | Structure |
|---|---|
| 987 | 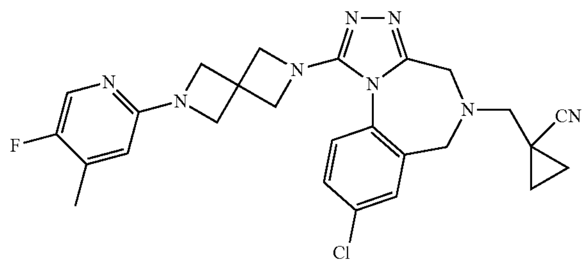 [SMILES: Cc1cc(N2CC3(C2)CN(c2nnc4n2-c2ccc(Cl)cc2CN(CC2(C#N)CC2)C4)C3)ncc1F] |
| 988 | 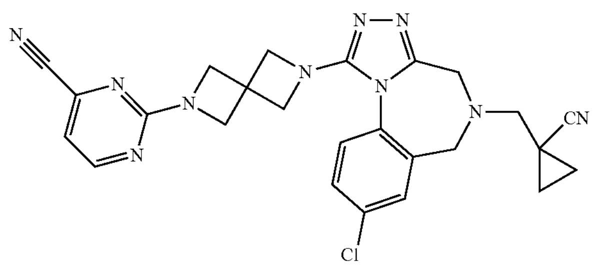 [SMILES: N#Cc1ccnc(N2CC3(C2)CN(c2nnc4n2-c2ccc(Cl)cc2CN(CC2(C#N)CC2)C4)C3)n1] |
| 989 | 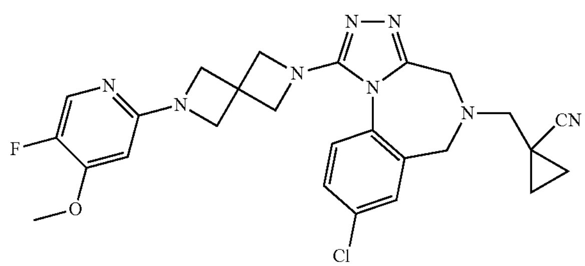 [SMILES: COc1cc(N2CC3(C2)CN(c2nnc4n2-c2ccc(Cl)cc2CN(CC2(C#N)CC2)C4)C3)ncc1F] |
| 990 | 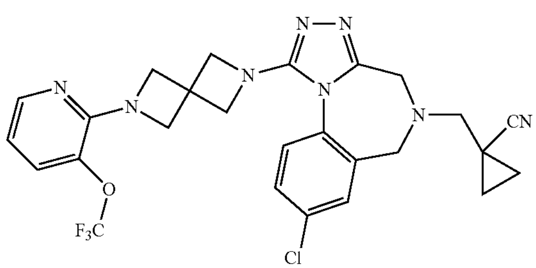 [SMILES: N#CC1(CN2Cc3cc(Cl)ccc3-n3c(nnc3N3CC4(CN(c5ncccc5OC(F)(F)F)C4)C3)C2)CC1] |
| 991 | 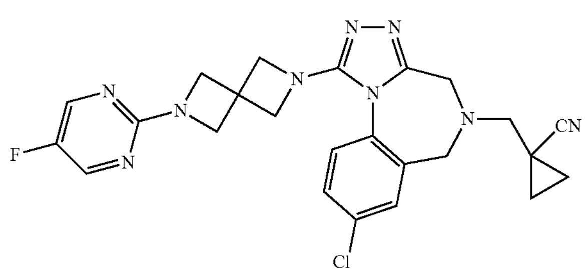 [SMILES: N#CC1(CN2Cc3cc(Cl)ccc3-n3c(nnc3N3CC4(CN(c5ncc(F)cn5)C4)C3)C2)CC1] |

TABLE 1-continued

Representative Compounds

| Cmpd. No. | Structure |
|---|---|
| 992 | 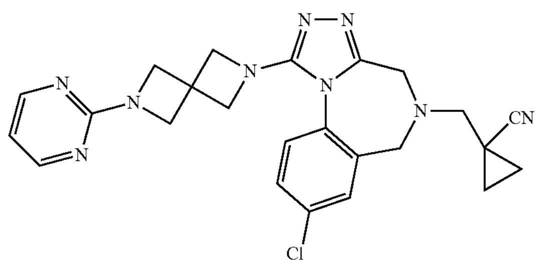 [SMILES: N#CC1(CN2Cc3cc(Cl)ccc3-n3c(nnc3N3CC4(CN(c5ncccn5)C4)C3)C2)CC1] |
| 993 | 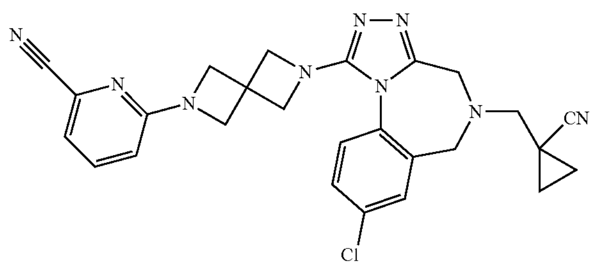 |
| 994 | 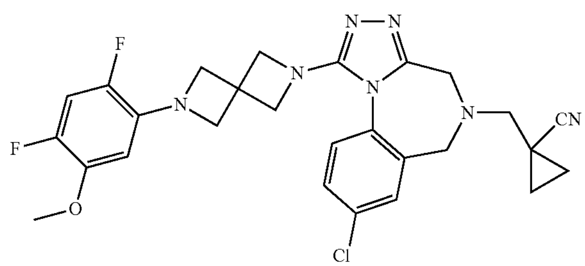 [SMILES: COc1cc(N2CC3(C2)CN(c2nnc4n2-c2ccc(Cl)cc2CN(CC2(C#N)CC2)C4)C3)c(F)cc1F] |
| 995 | 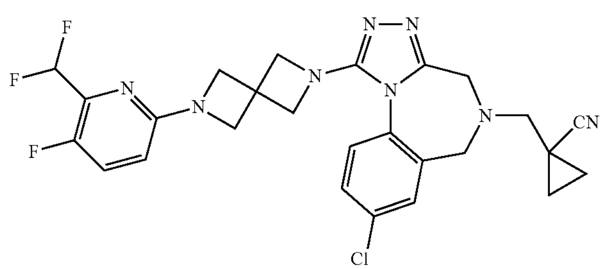 [SMILES: N#CC1(CN2Cc3cc(Cl)ccc3-n3c(nnc3N3CC4(CN(c5ccc(F)c(C(F)F)n5)C4)C3)C2)CC1] |
| 996 | 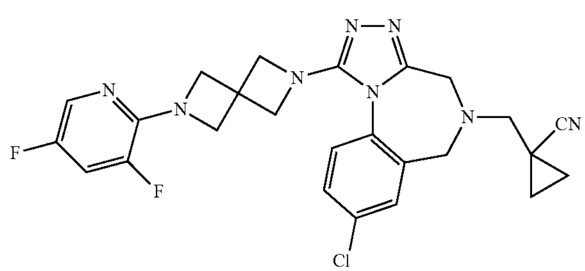 [SMILES: N#CC1(CN2Cc3cc(Cl)ccc3-n3c(nnc3N3CC4(CN(c5ncc(F)cc5F)C4)C3)C2)CC1] |

TABLE 1-continued

Representative Compounds

| Cmpd. No. | Structure |
|---|---|
| 997 | 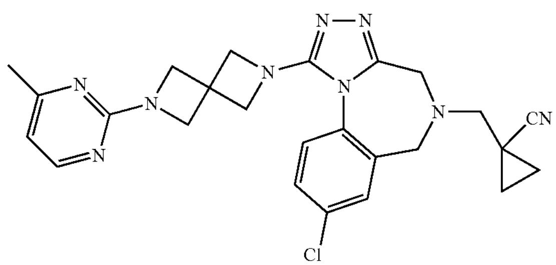 [SMILES: Cc1ccnc(N2CC3(C2)CN(c2nnc4n2-c2ccc(Cl)cc2CN(CC2(C#N)CC2)C4)C3)n1] |
| 998 | 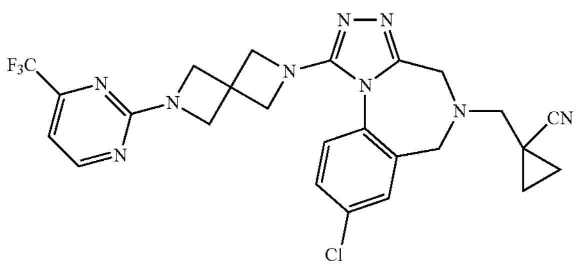 [SMILES: N#CC1(CN2Cc3cc(Cl)ccc3-n3c(nnc3N3CC4(CN(c5nccc(C(F)(F)F)n5)C4)C3)C2)CC1] |
| 999 | 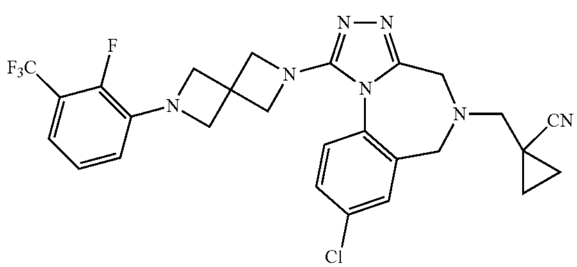 [SMILES: N#CC1(CN2Cc3cc(Cl)ccc3-n3c(nnc3N3CC4(CN(c5cccc(C(F)(F)F)c5F)C4)C3)C2)CC1] |
| 1000 | 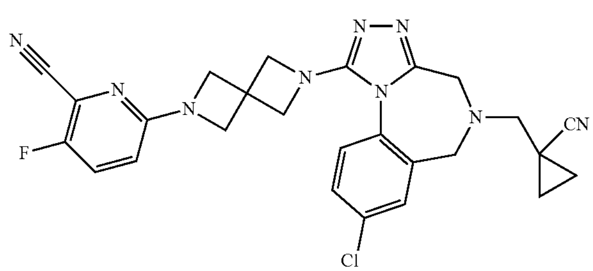 [SMILES: N#Cc1nc(N2CC3(C2)CN(c2nnc4n2-c2ccc(Cl)cc2CN(CC2(C#N)CC2)C4)C3)ccc1F] |
| 1001 | 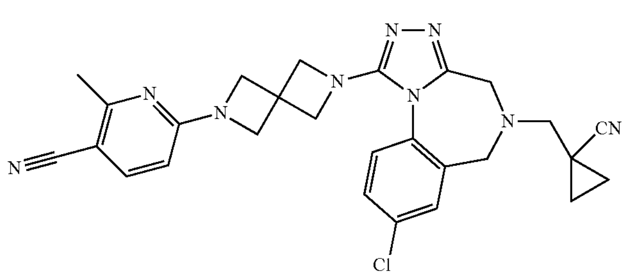 [SMILES: Cc1nc(N2CC3(C2)CN(c2nnc4n2-c2ccc(Cl)cc2CN(CC2(C#N)CC2)C4)C3)ccc1C#N] |

TABLE 1-continued
Representative Compounds
| Cmpd. No. | Structure |
|---|---|
| 1002 | 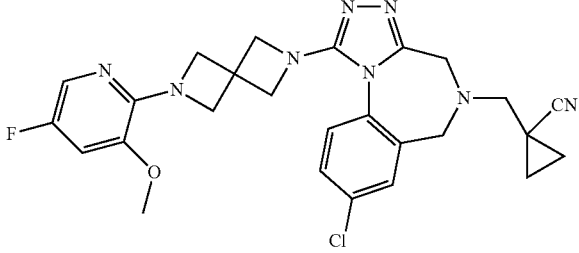 [SMILES: COc1cc(F)cnc1N1CC2(C1)CN(c1nnc3n1-c1ccc(Cl)cc1CN(CC1(C#N)CC1)C3)C2] |
| 1003 | 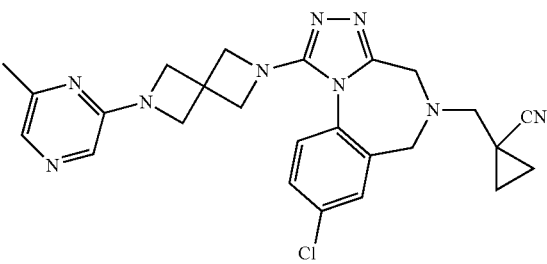 [SMILES: Cc1cncc(N2CC3(C2)CN(c2nnc4n2-c2ccc(Cl)cc2CN(CC2(C#N)CC2)C4)C3)n1] |
| 1004 | 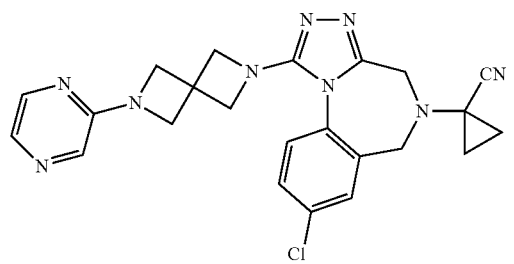 [SMILES: N#CC1(N2Cc3cc(Cl)ccc3-n3c(nnc3N3CC4(CN(c5cnccn5)C4)C3)C2)CC1] |
| 1005 | 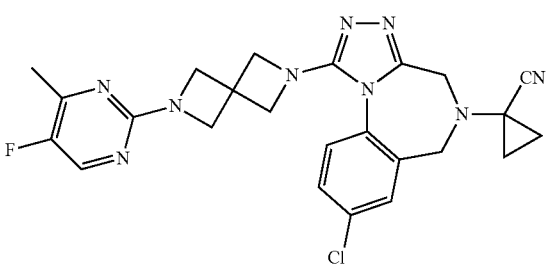 [SMILES: Cc1nc(N2CC3(C2)CN(c2nnc4n2-c2ccc(Cl)cc2CN(C2(C#N)CC2)C4)C3)ncc1F] |
| 1006 | 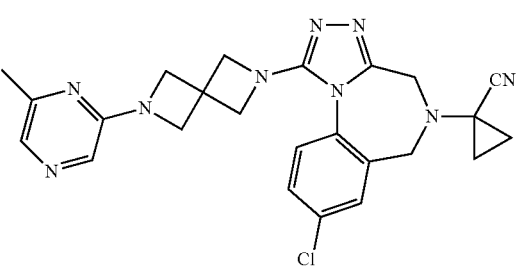 [SMILES: Cc1cncc(N2CC3(C2)CN(c2nnc4n2-c2ccc(Cl)cc2CN(C2(C#N)CC2)C4)C3)n1] |

TABLE 1-continued

Representative Compounds

| Cmpd. No. | Structure |
|---|---|
| 1007 | 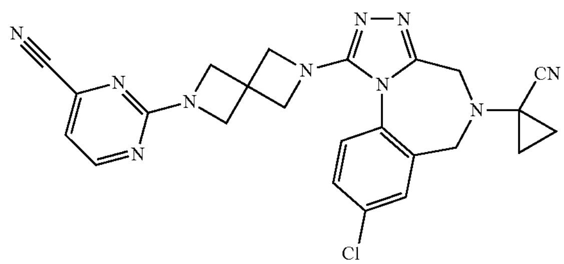 |
| 1008 | 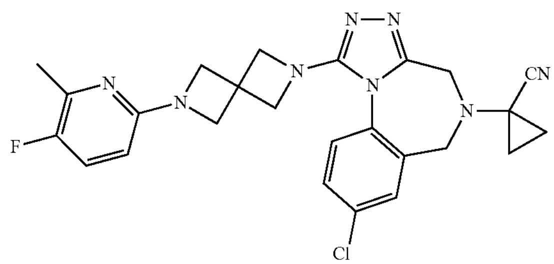 [SMILES: Cc1nc(N2CC3(C2)CN(c2nnc4n2-c2ccc(Cl)cc2CN(C2(C#N)CC2)C4)C3)ccc1F] |
| 1009 | 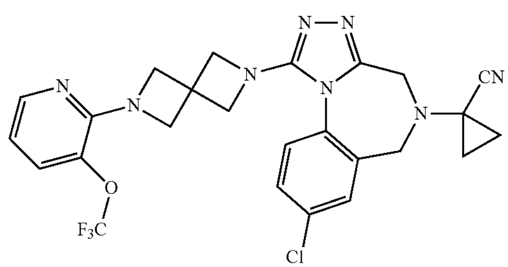 [SMILES: N#CC1(N2Cc3cc(Cl)ccc3-n3c(nnc3N3CC4(CN(c5ncccc5OC(F)(F)F)C4)C3)C2)CC1] |
| 1010 | 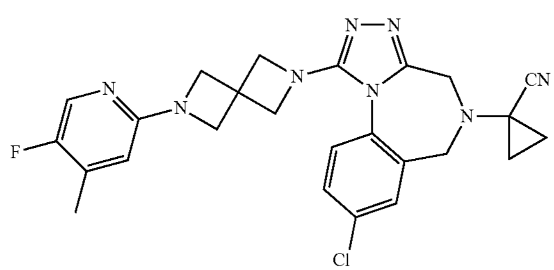 [SMILES: Cc1cc(N2CC3(C2)CN(c2nnc4n2-c2ccc(Cl)cc2CN(C2(C#N)CC2)C4)C3)ncc1F] |
| 1011 | 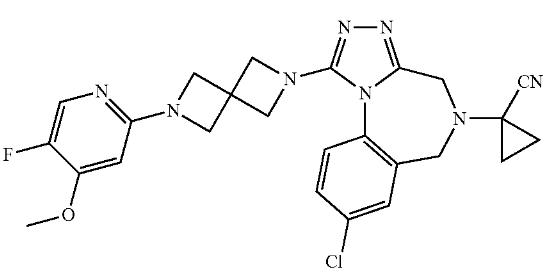 [SMILES: COc1cc(N2CC3(C2)CN(c2nnc4n2-c2ccc(Cl)cc2CN(C2(C#N)CC2)C4)C3)ncc1F] |

TABLE 1-continued

Representative Compounds

| Cmpd. No. | Structure |
|---|---|
| 1012 | 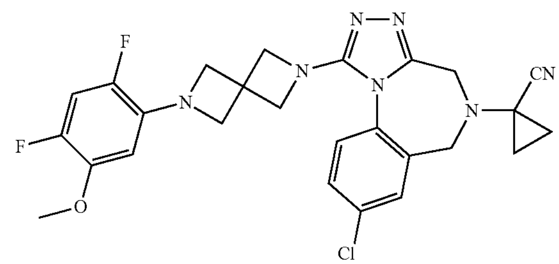 [SMILES: COc1cc(N2CC3(C2)CN(c2nnc4n2-c2ccc(Cl)cc2CN(C2(C#N)CC2)C4)C3)c(F)cc1F] |
| 1013 | 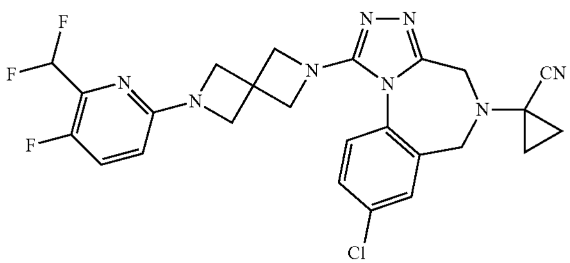 [SMILES: N#CC1(N2Cc3cc(Cl)ccc3-n3c(nnc3N3CC4(CN(c5ccc(F)c(C(F)F)n5)C4)C3)C2)CC1] |
| 1014 | 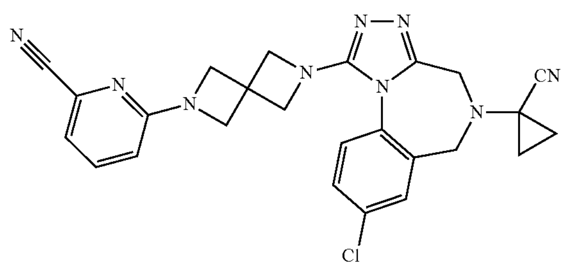 [SMILES: N#Cc1cccc(N2CC3(C2)CN(c2nnc4n2-c2ccc(Cl)cc2CN(C2(C#N)CC2)C4)C3)n1] |
| 1015 | 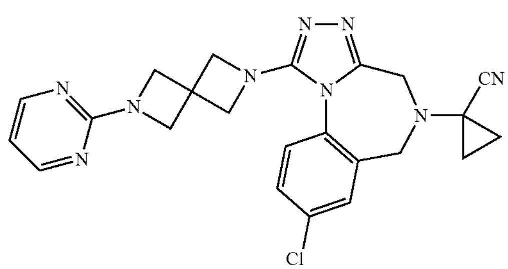 |
| 1016 | 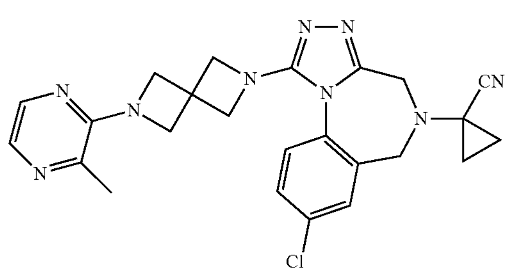 [SMILES: Cc1nccnc1N1CC2(C1)CN(c1nnc3n1-c1ccc(Cl)cc1CN(C1(C#N)CC1)C3)C2] |

TABLE 1-continued

Representative Compounds

| Cmpd. No. | Structure |
|---|---|
| 1017 | 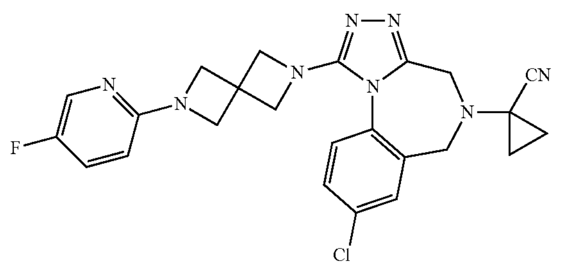 [SMILES: N#CC1(N2Cc3cc(Cl)ccc3-n3c(nnc3N3CC4(CN(c5ccc(F)cn5)C4)C3)C2)CC1] |
| 1018 | 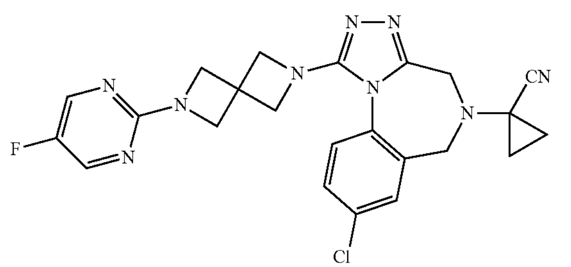 [SMILES: N#CC1(N2Cc3cc(Cl)ccc3-n3c(nnc3N3CC4(CN(c5ncc(F)cn5)C4)C3)C2)CC1] |
| 1019 | 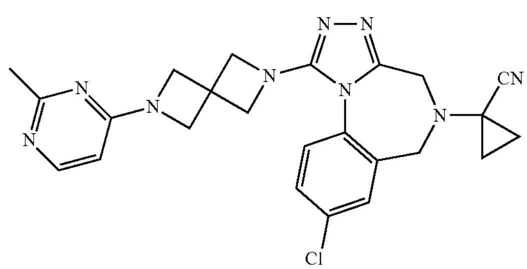 [SMILES: Cc1nccc(N2CC3(C2)CN(c2nnc4n2-c2ccc(Cl)cc2CN(C2(C#N)CC2)C4)C3)n1] |
| 1020 | 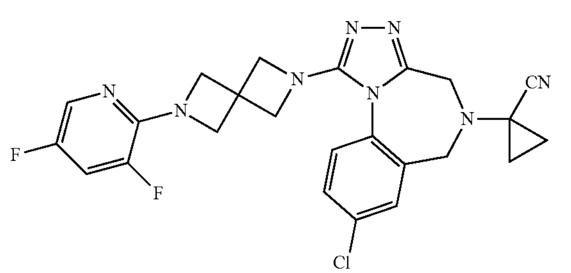 [SMILES: N#CC1(N2Cc3cc(Cl)ccc3-n3c(nnc3N3CC4(CN(c5ncc(F)cc5F)C4)C3)C2)CC1] |
| 1021 | 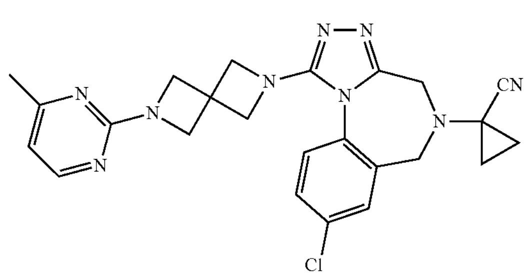 [SMILES: Cc1ccnc(N2CC3(C2)CN(c2nnc4n2-c2ccc(Cl)cc2CN(C2(C#N)CC2)C4)C3)n1] |

TABLE 1-continued
Representative Compounds
| Cmpd. No. | Structure |
|---|---|
| 1022 | 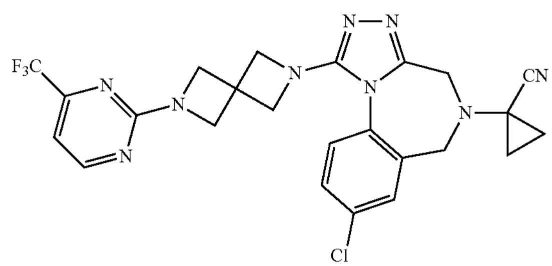 [SMILES: N#CC1(N2Cc3cc(Cl)ccc3-n3c(nnc3N3CC4(CN(c5nccc(C(F)(F)F)n5)C4)C3)C2)CC1] |
| 1023 | 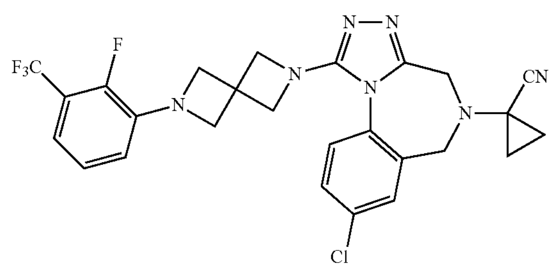 [SMILES: N#CC1(N2Cc3cc(Cl)ccc3-n3c(nnc3N3CC4(CN(c5cccc(C(F)(F)F)c5F)C4)C3)C2)CC1] |
| 1024 | 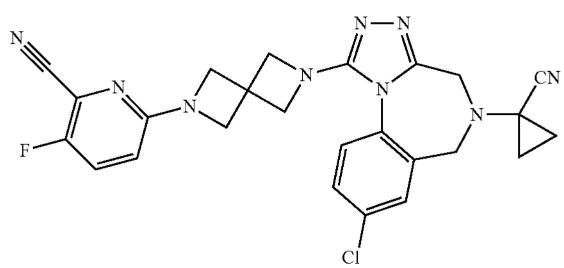 [SMILES: N#Cc1nc(N2CC3(C2)CN(c2nnc4n2-c2ccc(Cl)cc2CN(C2(C#N)CC2)C4)C3)ccc1F] |
| 1025 | 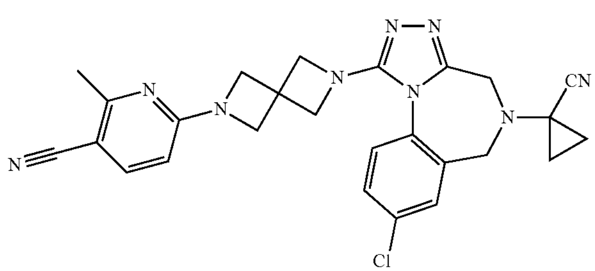 [SMILES: Cc1nc(N2CC3(C2)CN(c2nnc4n2-c2ccc(Cl)cc2CN(C2(C#N)CC2)C4)C3)ccc1C#N] |
| 1026 | 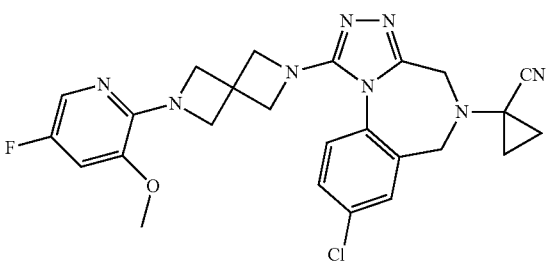 [SMILES: COc1cc(F)cnc1N1CC2(C1)CN(c1nnc3n1-c1ccc(Cl)cc1CN(C1(C#N)CC1)C3)C2] |

TABLE 1-continued
Representative Compounds
| Cmpd. No. | Structure |
|---|---|
| 1027 | 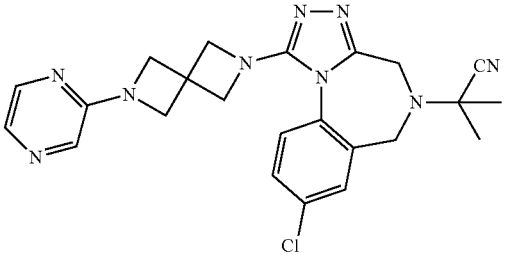 [SMILES: CC(C)(C#N)N1Cc2cc(Cl)ccc2-n2c(nnc2N2CC3(CN(c4cnccn4)C3)C2)C1] |
| 1028 | 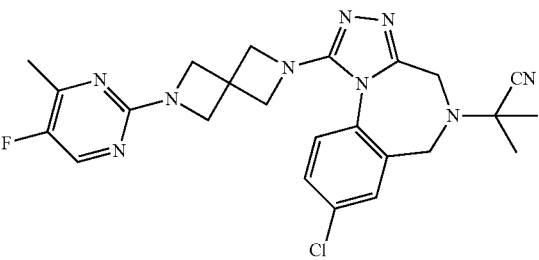 [SMILES: Cc1nc(N2CC3(C2)CN(c2nnc4n2-c2ccc(Cl)cc2CN(C(C)(C)C#N)C4)C3)ncc1F] |
| 1029 | 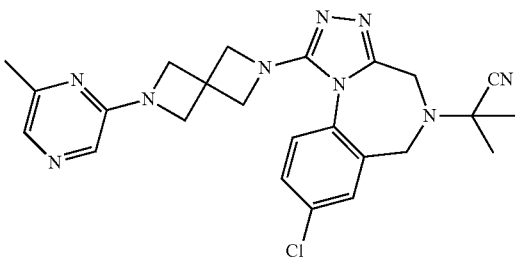 [SMILES: Cc1cncc(N2CC3(C2)CN(c2nnc4n2-c2ccc(Cl)cc2CN(C(C)(C)C#N)C4)C3)n1] |
| 1030 | 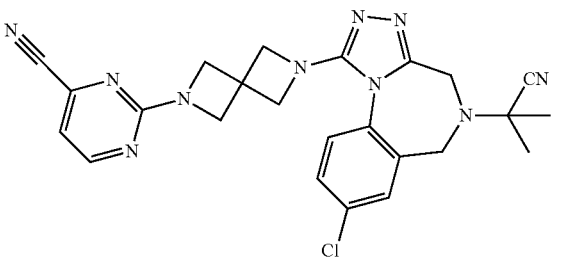 [SMILES: CC(C)(C#N)N1Cc2cc(Cl)ccc2-n2c(nnc2N2CC3(CN(c4nccc(C#N)n4)C3)C2)C1] |
| 1031 | 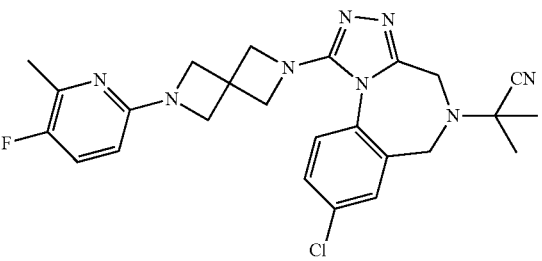 |

TABLE 1-continued

Representative Compounds

| Cmpd. No. | Structure |
|---|---|
| 1032 | 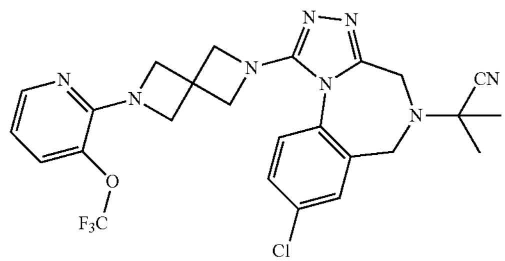 [SMILES: CC(C)(C#N)N1Cc2cc(Cl)ccc2-n2c(nnc2N2CC3(CN(c4ncccc4OC(F)(F)F)C3)C2)C1] |
| 1033 | 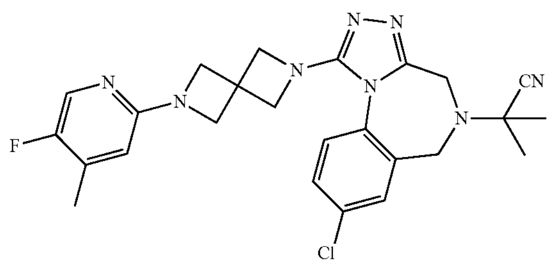 |
| 1034 | 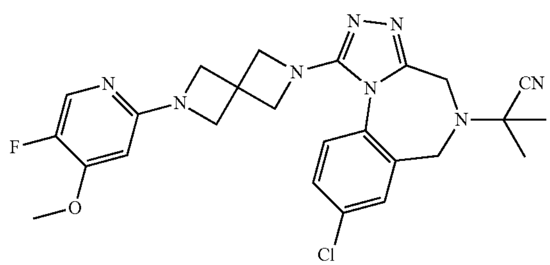 [SMILES: COc1cc(N2CC3(C2)CN(c2nnc4n2-c2ccc(Cl)cc2CN(C(C)(C)C#N)C4)C3)ncc1F] |
| 1035 | 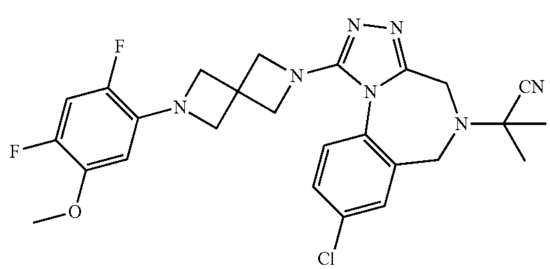 [SMILES: COc1cc(N2CC3(C2)CN(c2nnc4n2-c2ccc(Cl)cc2CN(C(C)(C)C#N)C4)C3)c(F)cc1F] |
| 1036 | 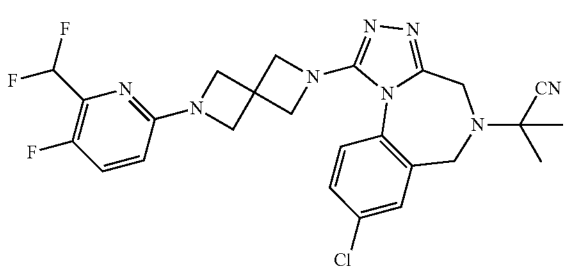 [SMILES: CC(C)(C#N)N1Cc2cc(Cl)ccc2-n2c(nnc2N2CC3(CN(c4ccc(F)c(C(F)F)n4)C3)C2)C1] |

TABLE 1-continued

Representative Compounds

| Cmpd. No. | Structure |
|---|---|
| 1037 | 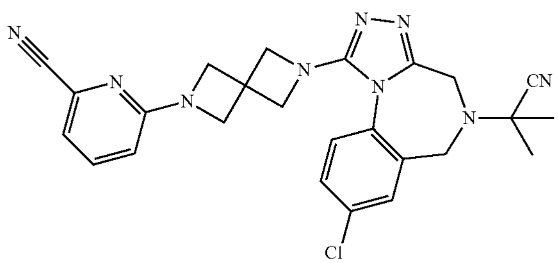 [SMILES: CC(C)(C#N)N1Cc2cc(Cl)ccc2-n2c(nnc2N2CC3(CN(c4cccc(C#N)n4)C3)C2)C1] |
| 1038 | 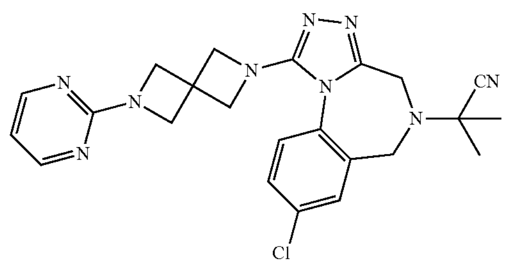 [SMILES: CC(C)(C#N)N1Cc2cc(Cl)ccc2-n2c(nnc2N2CC3(CN(c4ncccn4)C3)C2)C1] |
| 1039 | 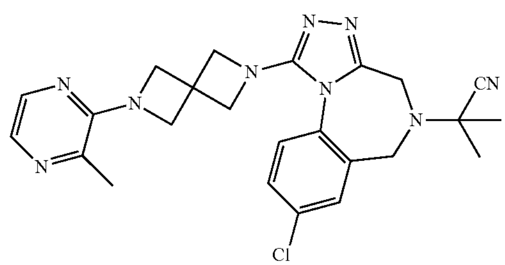 |
| 1040 | 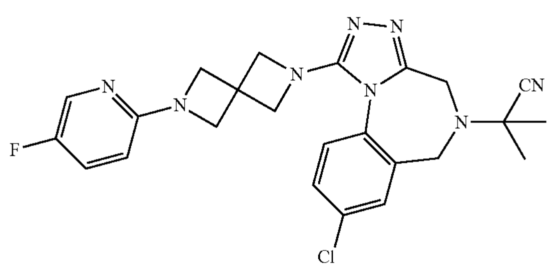 [SMILES: CC(C)(C#N)N1Cc2cc(Cl)ccc2-n2c(nnc2N2CC3(CN(c4ccc(F)cn4)C3)C2)C1] |
| 1041 | 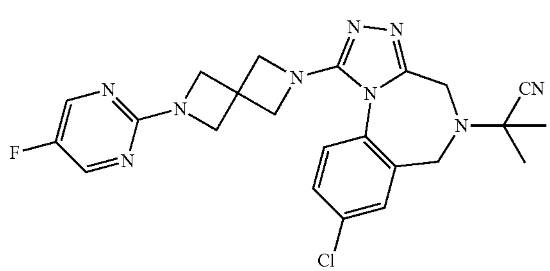 [SMILES: CC(C)(C#N)N1Cc2cc(Cl)ccc2-n2c(nnc2N2CC3(CN(c4ncc(F)cn4)C3)C2)C1] |

TABLE 1-continued

Representative Compounds

| Cmpd. No. | Structure |
|---|---|
| 1042 | 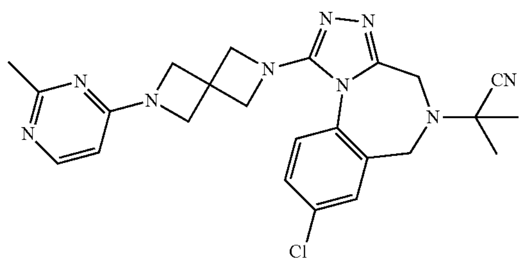 [SMILES: Cc1nccc(N2CC3(C2)CN(c2nnc4n2-c2ccc(Cl)cc2CN(C(C)(C)C#N)C4)C3)n1] |
| 1043 | 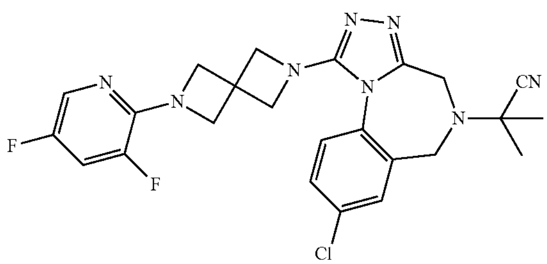 [SMILES: CC(C)(C#N)N1Cc2cc(Cl)ccc2-n2c(nnc2N2CC3(CN(c4ncc(F)cc4F)C3)C2)C1] |
| 1044 | 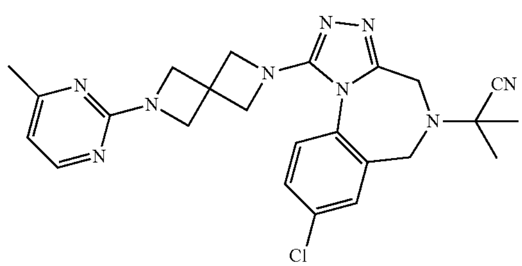 |
| 1045 | 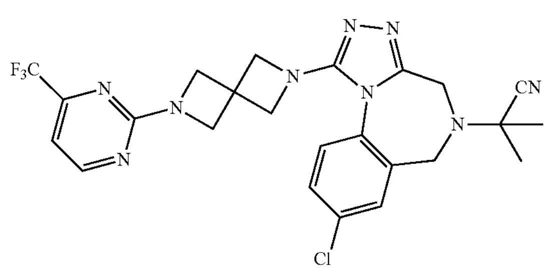 [SMILES: CC(C)(C#N)N1Cc2cc(Cl)ccc2-n2c(nnc2N2CC3(CN(c4nccc(C(F)(F)F)n4)C3)C2)C1] |
| 1046 | 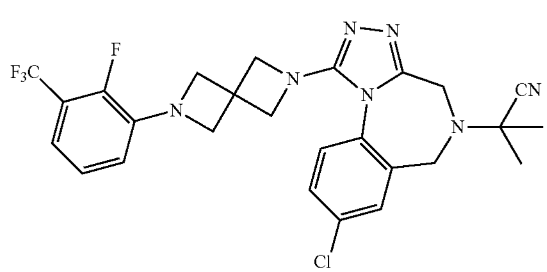 [SMILES: CC(C)(C#N)N1Cc2cc(Cl)ccc2-n2c(nnc2N2CC3(CN(c4cccc(C(F)(F)F)c4F)C3)C2)C1] |

TABLE 1-continued

Representative Compounds

| Cmpd. No. | Structure |
|---|---|
| 1047 | 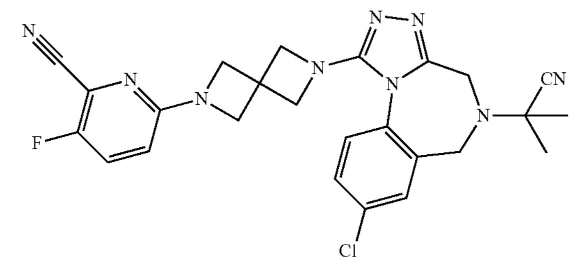 [SMILES: CC(C)(C#N)N1Cc2cc(Cl)ccc2-n2c(nnc2N2CC3(CN(c4ccc(F)c(C#N)n4)C3)C2)C1] |
| 1048 | 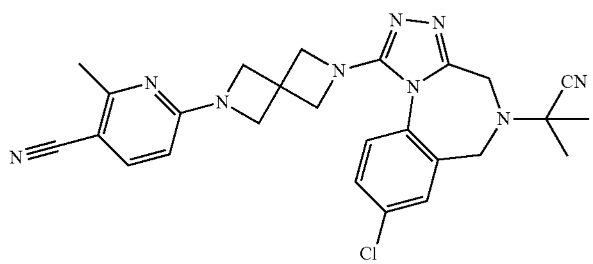 [SMILES: Cc1nc(N2CC3(C2)CN(c2nnc4n2-c2ccc(Cl)cc2CN(C(C)(C)C#N)C4)C3)ccc1C#N] |
| 1049 | 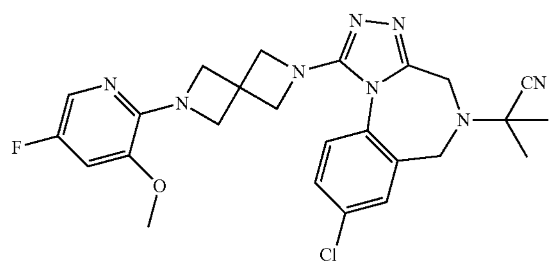 [SMILES: COc1cc(F)cnc1N1CC2(C1)CN(c1nnc3n1-c1ccc(Cl)cc1CN(C(C)(C)C#N)C3)C2] |
| 1050 | 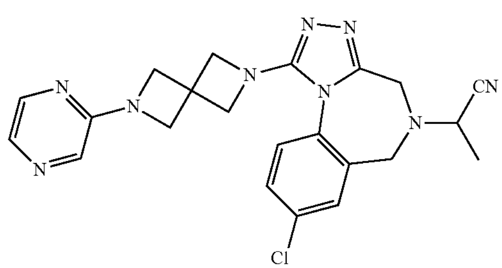 [SMILES: CC(C#N)N1Cc2cc(Cl)ccc2-n2c(nnc2N2CC3(CN(c4cnccn4)C3)C2)C1] |
| 1051 | 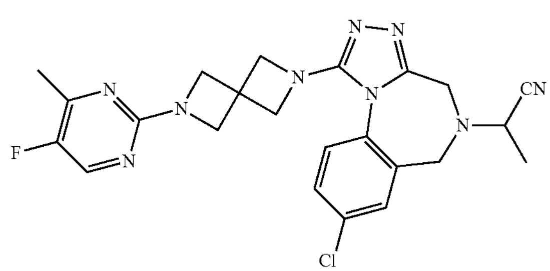 [SMILES: Cc1nc(N2CC3(C2)CN(c2nnc4n2-c2ccc(Cl)cc2CN(C(C)C#N)C4)C3)ncc1F] |

TABLE 1-continued

Representative Compounds

| Cmpd. No. | Structure |
|---|---|
| 1052 | 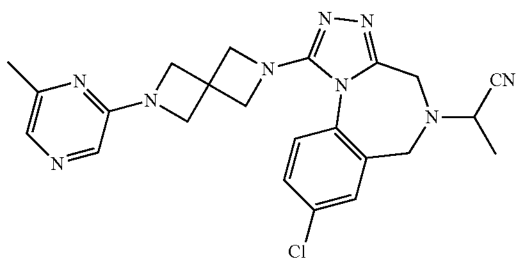 [SMILES: Cc1cncc(N2CC3(C2)CN(c2nnc4n2-c2ccc(Cl)cc2CN(C(C)C#N)C4)C3)n1] |
| 1053 | 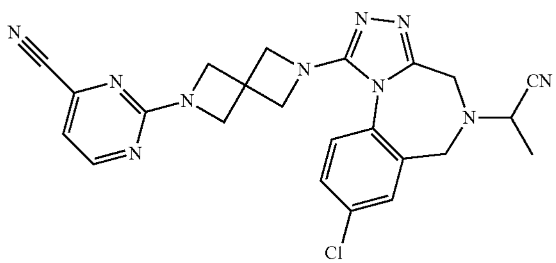 [SMILES: CC(C#N)N1Cc2cc(Cl)ccc2-n2c(nnc2N2CC3(CN(c4nccc(C#N)n4)C3)C2)C1] |
| 1054 | 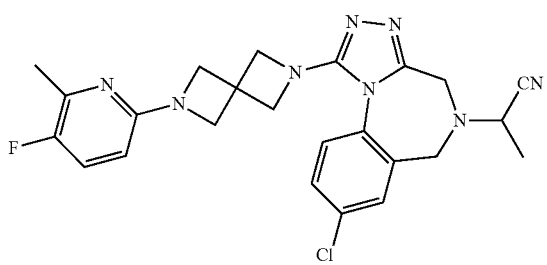 [SMILES: Cc1nc(N2CC3(C2)CN(c2nnc4n2-c2ccc(Cl)cc2CN(C(C)C#N)C4)C3)ccc1F] |
| 1055 | 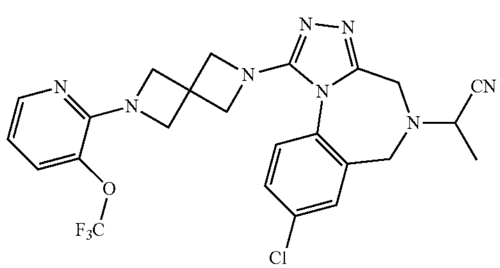 [SMILES: CC(C#N)N1Cc2cc(Cl)ccc2-n2c(nnc2N2CC3(CN(c4ncccc4OC(F)(F)F)C3)C2)C1] |
| 1056 | 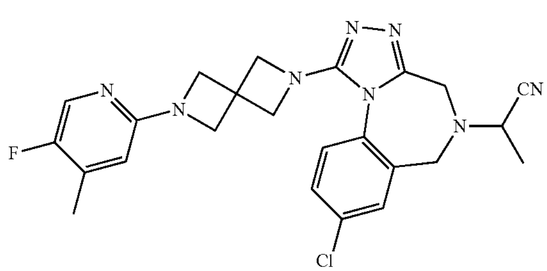 [SMILES: Cc1cc(N2CC3(C2)CN(c2nnc4n2-c2ccc(Cl)cc2CN(C(C)C#N)C4)C3)ncc1F] |

TABLE 1-continued

Representative Compounds

| Cmpd. No. | Structure |
|---|---|
| 1057 | 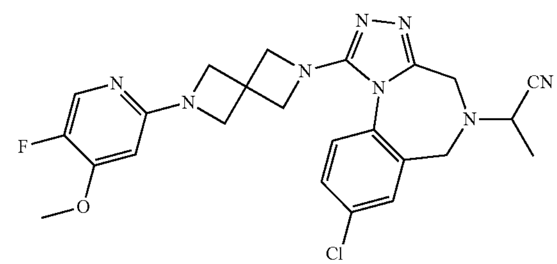 [SMILES: COc1cc(N2CC3(C2)CN(c2nnc4n2-c2ccc(Cl)cc2CN(C(C)C#N)C4)C3)ncc1F] |
| 1058 | 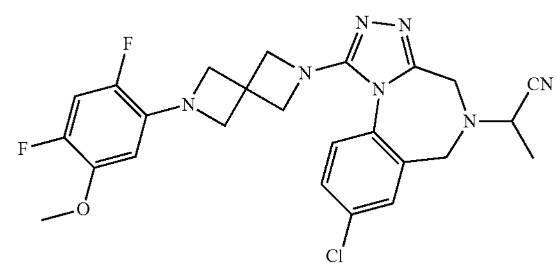 [SMILES: COc1cc(N2CC3(C2)CN(c2nnc4n2-c2ccc(Cl)cc2CN(C(C)C#N)C4)C3)c(F)cc1F] |
| 1059 | 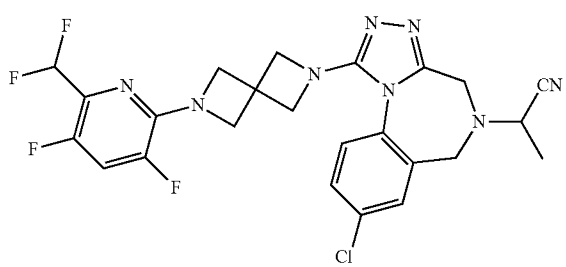 [SMILES: CC(C#N)N1Cc2cc(Cl)ccc2-n2c(nnc2N2CC3(CN(c4nc(C(F)F)c(F)cc4F)C3)C2)C1] |
| 1060 | 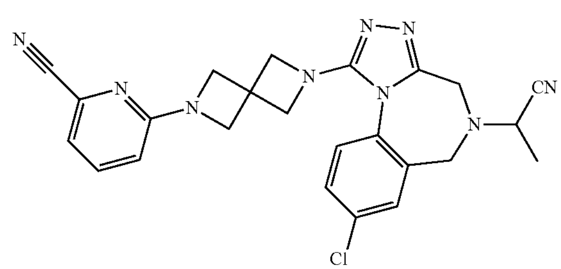 [SMILES: CC(C#N)N1Cc2cc(Cl)ccc2-n2c(nnc2N2CC3(CN(c4cccc(C#N)n4)C3)C2)C1] |
| 1061 | 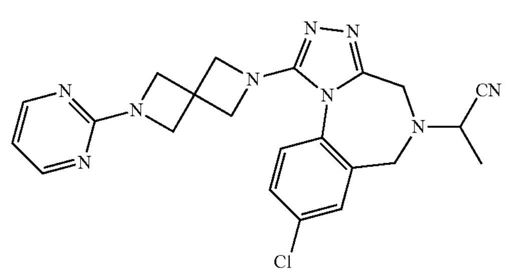 [SMILES: CC(C#N)N1Cc2cc(Cl)ccc2-n2c(nnc2N2CC3(CN(c4ncccn4)C3)C2)C1] |

TABLE 1-continued
| Cmpd. No. | Structure |
|---|---|
| 1062 | 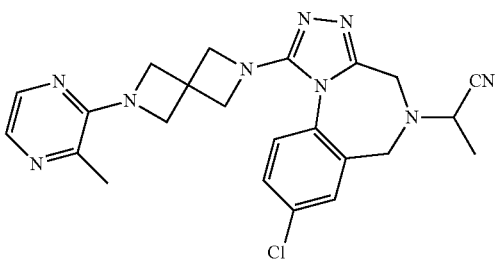 [SMILES: Cc1nccnc1N1CC2(C1)CN(c1nnc3n1-c1ccc(Cl)cc1CN(C(C)C#N)C3)C2] |
| 1063 | 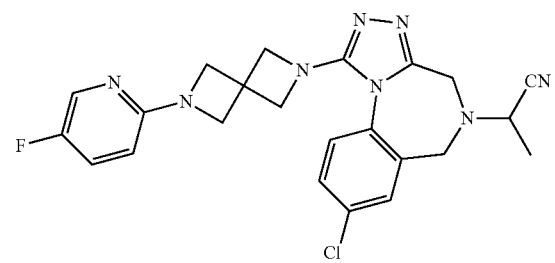 [SMILES: CC(C#N)N1Cc2cc(Cl)ccc2-n2c(nnc2N2CC3(CN(c4ccc(F)cn4)C3)C2)C1] |
| 1064 | 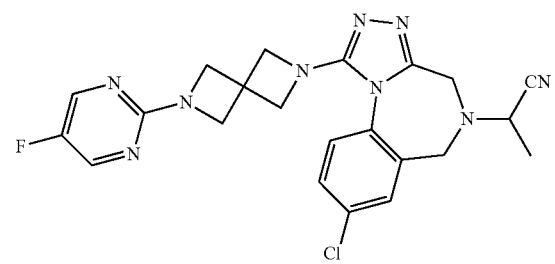 |
| 1065 | 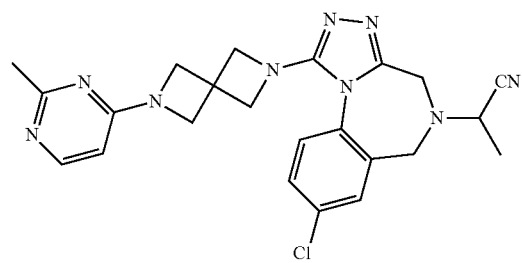 [SMILES: Cc1nccc(N2CC3(C2)CN(c2nnc4n2-c2ccc(Cl)cc2CN(C(C)C#N)C4)C3)n1] |
| 1066 | 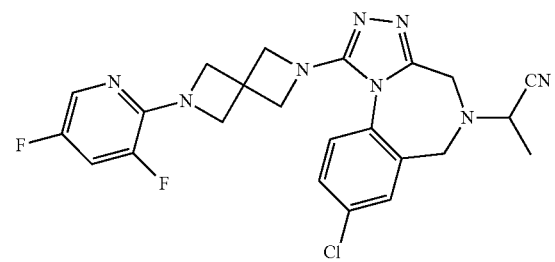 [SMILES: CC(C#N)N1Cc2cc(Cl)ccc2-n2c(nnc2N2CC3(CN(c4ncc(F)cc4F)C3)C2)C1] |

TABLE 1-continued

Representative Compounds

| Cmpd. No. | Structure |
|---|---|
| 1067 | 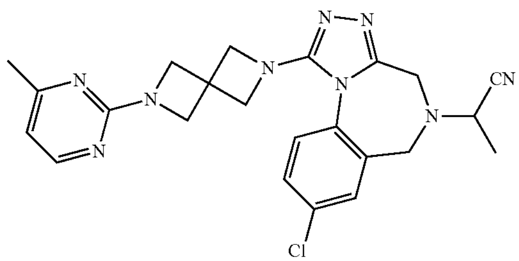 [SMILES: Cc1ccnc(N2CC3(C2)CN(c2nnc4n2-c2ccc(Cl)cc2CN(C(C)C#N)C4)C3)n1] |
| 1068 | 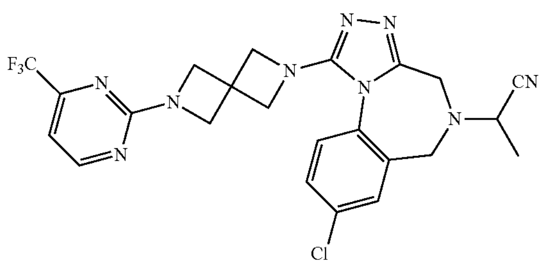 |
| 1069 | 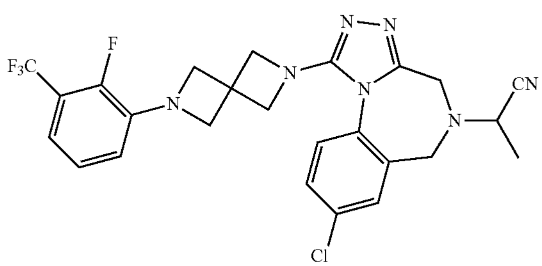 |
| 1070 | 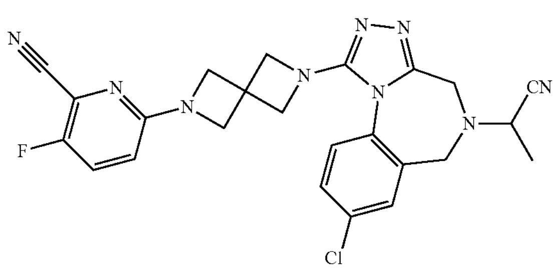 [SMILES: CC(C#N)N1Cc2cc(Cl)ccc2-n2c(nnc2N2CC3(CN(c4ccc(F)c(C#N)n4)C3)C2)C1] |
| 1071 | 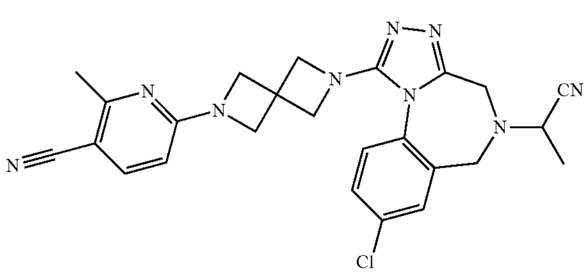 [SMILES: Cc1nc(N2CC3(C2)CN(c2nnc4n2-c2ccc(Cl)cc2CN(C(C)C#N)C4)C3)ccc1C#N] |

481

TABLE 1-continued

Representative Compounds

| Cmpd. No. | Structure |
|---|---|
| 1072 | 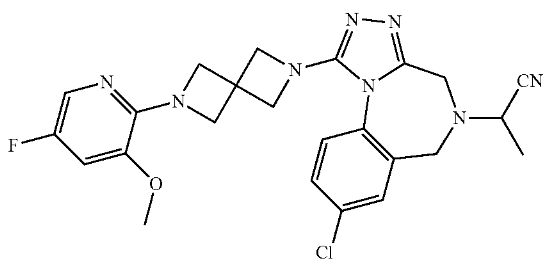 [SMILES: COc1cc(F)cnc1N1CC2(C1)CN(c1nnc3n1-c1ccc(Cl)cc1CN(C(C)C#N)C3)C2] |
| 1073 | 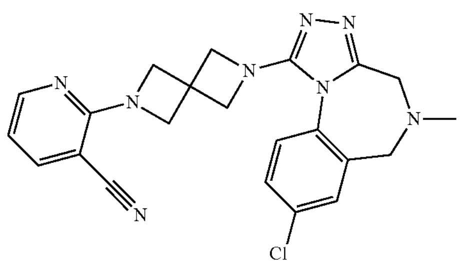 [SMILES: CN1Cc2cc(Cl)ccc2-n2c(nnc2N2CC3(CN(c4ncccc4C#N)C3)C2)C1] |
| 1074 | 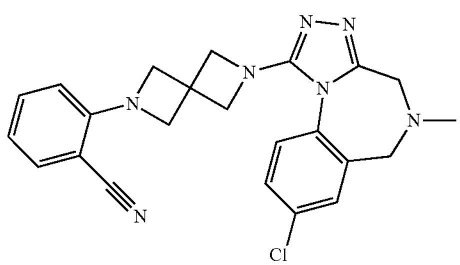 |
| 1075 | 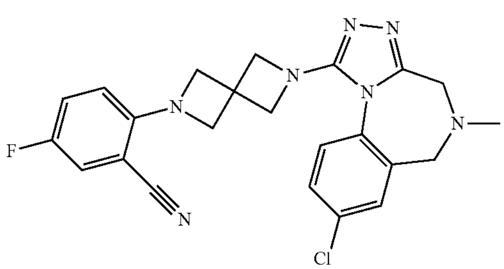 [SMILES: CN1Cc2cc(Cl)ccc2-n2c(nnc2N2CC3(CN(c4ccc(F)cc4C#N)C3)C2)C1] |
| 1076 | 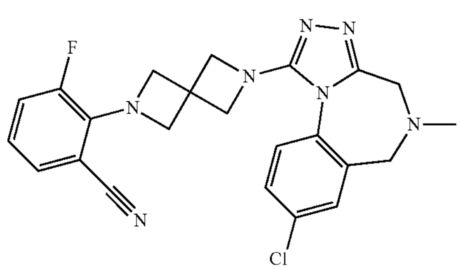 [SMILES: CN1Cc2cc(Cl)ccc2-n2c(nnc2N2CC3(CN(c4c(F)cccc4C#N)C3)C2)C1] |

TABLE 1-continued

Representative Compounds

| Cmpd. No. | Structure |
|---|---|
| 1077 | 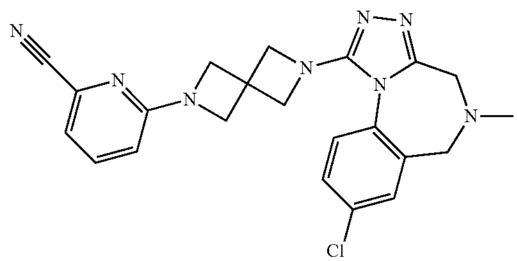 [SMILES: CN1Cc2cc(Cl)ccc2-n2c(nnc2N2CC3(CN(c4cccc(C#N)n4)C3)C2)C1] |
| 1078 | 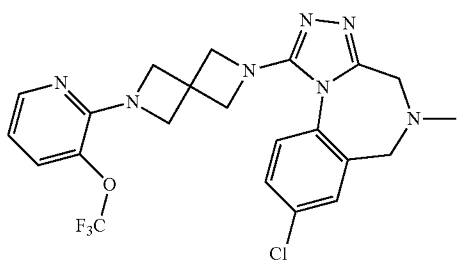 [SMILES: CN1Cc2cc(Cl)ccc2-n2c(nnc2N2CC3(CN(c4ncccc4OC(F)(F)F)C3)C2)C1] |
| 1079 | 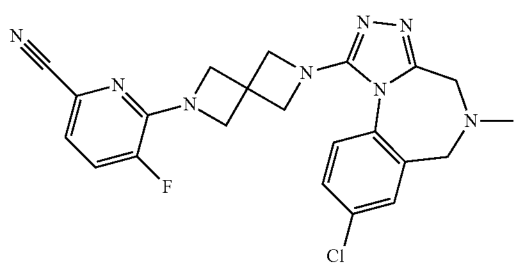 [SMILES: CN1Cc2cc(Cl)ccc2-n2c(nnc2N2CC3(CN(c4nc(C#N)ccc4F)C3)C2)C1] |
| 1080 | 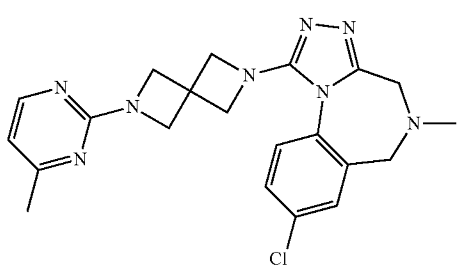 [SMILES: Cc1ccnc(N2CC3(C2)CN(c2nnc4n2-c2ccc(Cl)cc2CN(C)C4)C3)n1] |
| 1081 | 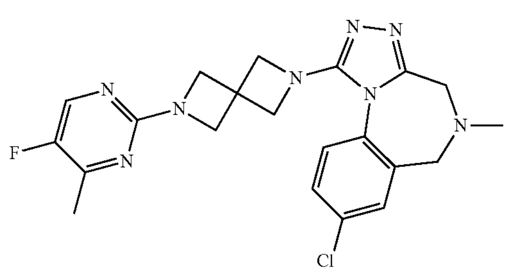 [SMILES: Cc1nc(N2CC3(C2)CN(c2nnc4n2-c2ccc(Cl)cc2CN(C)C4)C3)ncc1F] |

TABLE 1-continued
Representative Compounds
| Cmpd. No. | Structure |
|---|---|
| 1082 | 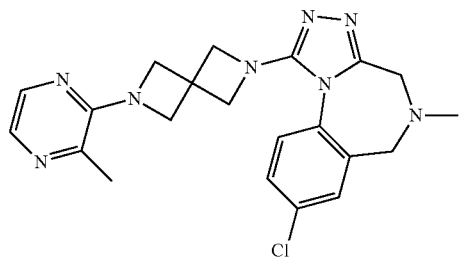 [SMILES: Cc1nccnc1N1CC2(C1)CN(c1nnc3n1-c1ccc(Cl)cc1CN(C)C3)C2] |
| 1083 | 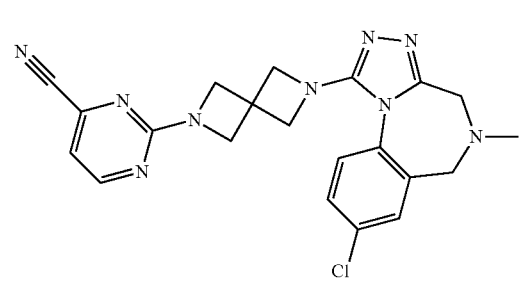 |
| 1084 | 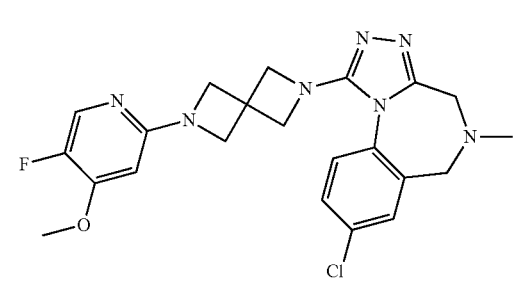 [SMILES: COc1cc(N2CC3(C2)CN(c2nnc4n2-c2ccc(Cl)cc2CN(C)C4)C3)ncc1F] |
| 1085 | 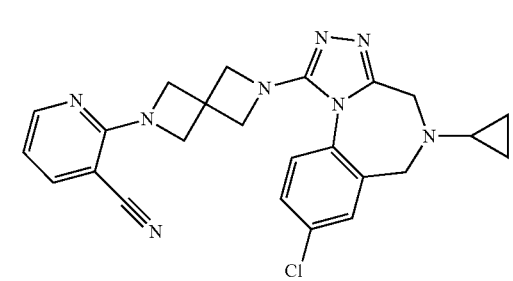 [SMILES: N#Cc1cccnc1N1CC2(C1)CN(c1nnc3n1-c1ccc(Cl)cc1CN(C1CC1)C3)C2] |
| 1086 | 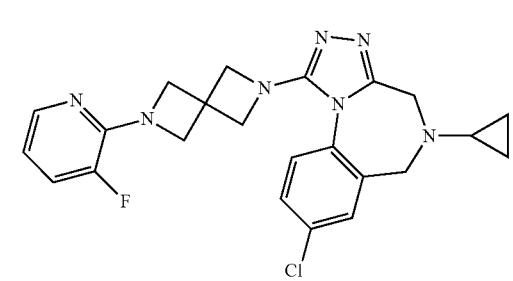 [SMILES: Fc1cccnc1N1CC2(C1)CN(c1nnc3n1-c1ccc(Cl)cc1CN(C1CC1)C3)C2] |

TABLE 1-continued

Representative Compounds

| Cmpd. No. | Structure |
|---|---|
| 1087 | 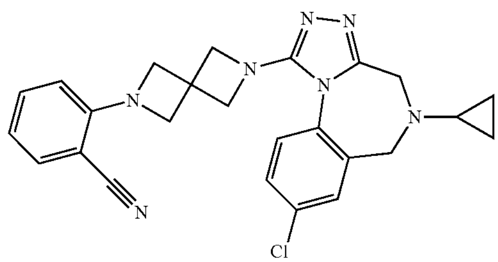 [SMILES: N#Cc1ccccc1N1CC2(C1)CN(c1nnc3n1-c1ccc(Cl)cc1CN(C1CC1)C3)C2] |
| 1088 | 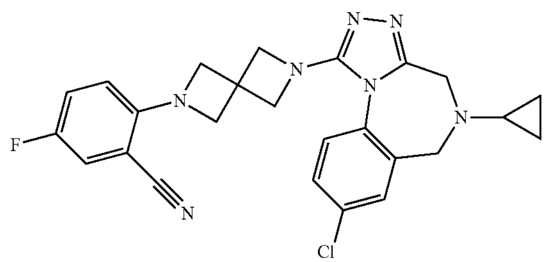 [SMILES: N#Cc1cc(F)ccc1N1CC2(C1)CN(c1nnc3n1-c1ccc(Cl)cc1CN(C1CC1)C3)C2] |
| 1089 | 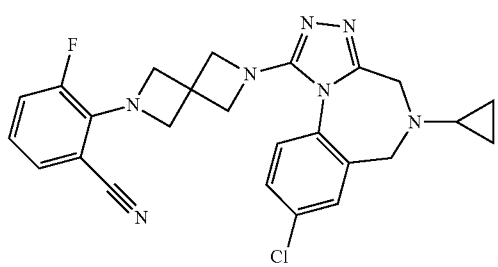 [SMILES: N#Cc1cccc(F)c1N1CC2(C1)CN(c1nnc3n1-c1ccc(Cl)cc1CN(C1CC1)C3)C2] |
| 1090 | 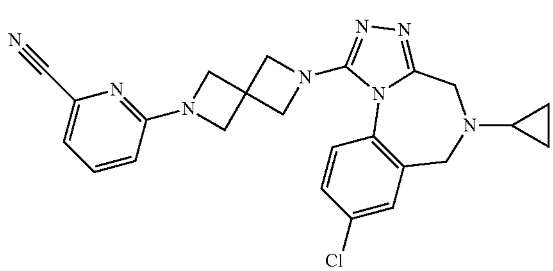 [SMILES: N#Cc1cccc(N2CC3(C2)CN(c2nnc4n2-c2ccc(Cl)cc2CN(C2CC2)C4)C3)n1] |
| 1091 | 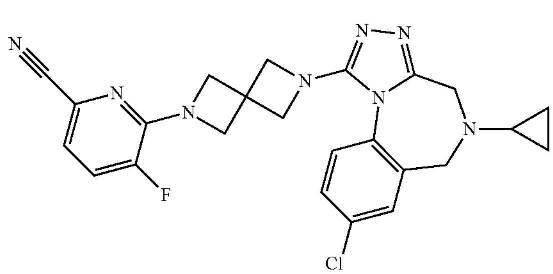 [SMILES: N#Cc1ccc(F)c(N2CC3(C2)CN(c2nnc4n2-c2ccc(Cl)cc2CN(C2CC2)C4)C3)n1] |

TABLE 1-continued

Representative Compounds

| Cmpd. No. | Structure |
|---|---|
| 1092 | 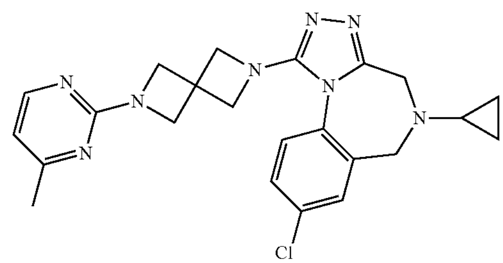 [SMILES: Cc1ccnc(N2CC3(C2)CN(c2nnc4n2-c2ccc(Cl)cc2CN(C2CC2)C4)C3)n1] |
| 1093 | 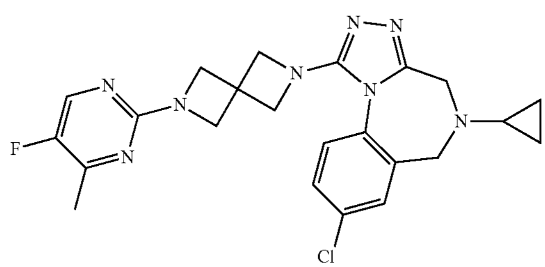 [SMILES: Cc1nc(N2CC3(C2)CN(c2nnc4n2-c2ccc(Cl)cc2CN(C2CC2)C4)C3)ncc1F] |
| 1094 | 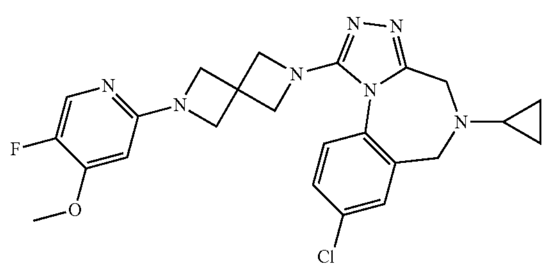 [SMILES: COc1cc(N2CC3(C2)CN(c2nnc4n2-c2ccc(Cl)cc2CN(C2CC2)C4)C3)ncc1F] |
| 1095 | 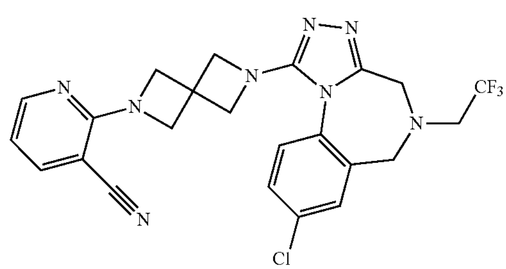 [SMILES: N#Cc1cccnc1N1CC2(C1)CN(c1nnc3n1-c1ccc(Cl)cc1CN(CC(F)(F)F)C3)C2] |
| 1096 | 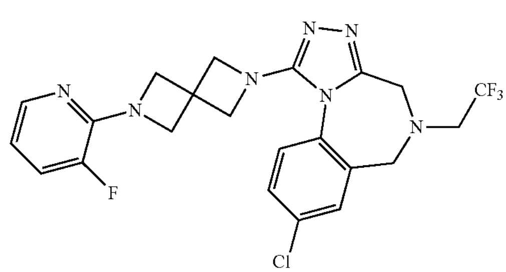 [SMILES: Fc1cccnc1N1CC2(C1)CN(c1nnc3n1-c1ccc(Cl)cc1CN(CC(F)(F)F)C3)C2] |

TABLE 1-continued

Representative Compounds

| Cmpd. No. | Structure |
|---|---|
| 1097 | 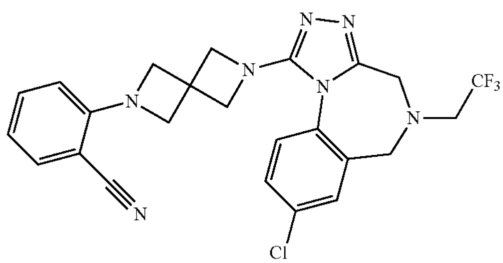 |
| 1098 | 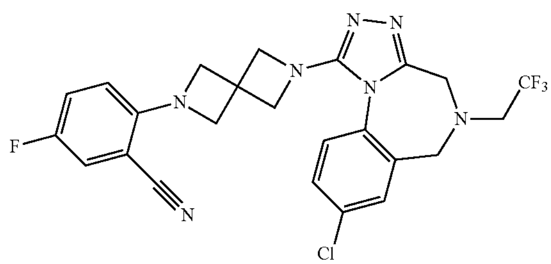 [SMILES: N#Cc1cc(F)ccc1N1CC2(C1)CN(c1nnc3n1-c1ccc(Cl)cc1CN(CC(F)(F)F)C3)C2] |
| 1099 | 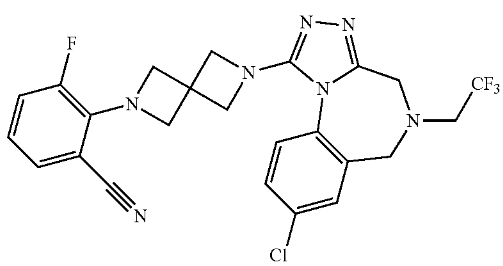 [SMILES: N#Cc1cccc(F)c1N1CC2(C1)CN(c1nnc3n1-c1ccc(Cl)cc1CN(CC(F)(F)F)C3)C2] |
| 1100 | 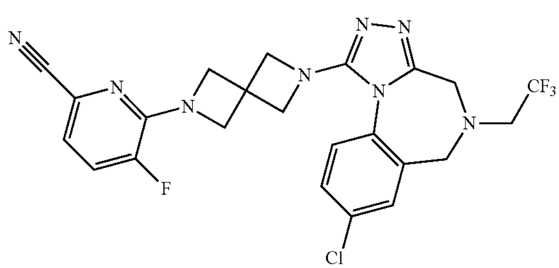 [SMILES: N#Cc1ccc(F)c(N2CC3(C2)CN(c2nnc4n2-c2ccc(Cl)cc2CN(CC(F)(F)F)C4)C3)n1] |
| 1101 | 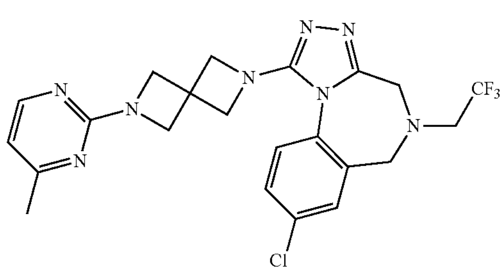 [SMILES: Cc1ccnc(N2CC3(C2)CN(c2nnc4n2-c2ccc(Cl)cc2CN(CC(F)(F)F)C4)C3)n1] |

TABLE 1-continued

Representative Compounds

| Cmpd. No. | Structure |
|---|---|
| 1102 | 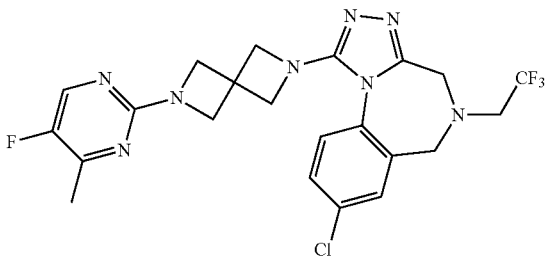 [SMILES: Cc1nc(N2CC3(C2)CN(c2nnc4n2-c2ccc(Cl)cc2CN(CC(F)(F)F)C4)C3)ncc1F] |

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents, and the like can be employed.

For topical administration, the compounds of the present invention can be formulated using bland, moisturizing bases such as ointments or creams.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule, or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di-, or tri-glycerides.

For injection, the formulation can also be a powder suitable for reconstitution with an appropriate solution as described above. Examples of these include, but are not limited to, freeze dried, rotary dried, or spray dried powders, amorphous powders, granules, precipitates, or particulates. For injection, the formulations can optionally contain stabilizers, pH modifiers, surfactants, bioavailability modifiers, and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the *Physicians' Desk Reference*, incorporated herein by reference.

When used to prevent the onset of a malcondition, the compounds provided herein will be administered to a subject at risk for developing the same, typically on the advice and under the supervision of a physician, at the dosage levels described above. Subjects at risk for developing a particular malcondition generally include those that have a family history of the same, or those who have been identified by genetic testing or screening to be particularly susceptible to developing the malcondition.

Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method is provided for antagonizing the V1a receptor, the method comprising contacting the receptor with an effective amount of a compound having the structure of Formula (I) through (XXII-B), or a pharmaceutically acceptable isomer, racemate, hydrate, solvate, isotope, or salt thereof, or a pharmaceutical composition comprising the same.

The term "antagonism" is used herein to encompass molecules that interact in some way with a receptor and thereby function as an antagonist, either by binding to the receptor at the binding site of its natural ligand or at locations other than the binding site. The phrase to "V1a antagonism" is used herein to encompass molecules that interact in some way with the V1a receptor and thereby function as an antagonist, either by binding to the V1a receptor at the binding site of its natural ligand, or at a location other than the binding site (i.e., allosteric binding).

In an embodiment, a method is provided for treatment of a malcondition in a subject for which antagonism of the V1a receptor is medically indicated. Such method comprises administering to the subject an effective amount of a compound having the structure of Formula (I) through (XXII-B), or a pharmaceutically acceptable isomer, racemate, hydrate, solvate, isotope, or salt thereof, or a pharmaceutical composition comprising the same, at a frequency and for duration sufficient to provide a beneficial effect to the subject.

As used herein, a "subject" means both mammals and non-mammals. Mammals include, for example: humans; non-human primates (e.g., apes and monkeys); cattle; horses; sheep; and goats. Non-mammals include, for example, fish and birds.

"Treating" or "treatment" within the meaning herein refers to an alleviation of symptoms associated with a malcondition, or inhibition of further progression or worsening of those symptoms, or prevention or prophylaxis of the malcondition in certain instances.

The expression "effective amount", when used to describe use of a compound for treating a subject suffering from a malcondition for which antagonism of the V1a receptor is medically indicated, refers to an the amount of the compound sufficient to produce a beneficial therapeutic effect for the subject.

The phrase "malcondition" is intended to broadly encompass any and all diseases, disorders, syndromes and/or symptoms wherein the V1a receptor plays a role in the same, such that a therapeutically beneficial effect can be achieved by antagonism of the V1a receptor.

In certain embodiments, the present invention provides a method for antagonizing the V1a receptor with a compound of Formula (I) through (XXII-B), or a pharmaceutically acceptable isomer, racemate, hydrate, solvate, isotope, or salt thereof, by contacting the receptor with a suitable amount of the compound to antagonize the receptor. Such contacting can take place in vitro, for example in carrying out an assay to determine the V1a inhibition activity of a compound undergoing experimentation related to a submission for regulatory approval.

In certain embodiments, the method for antagonizing the V1a receptor can also be carried out in vivo, that is, within the living body of the subject. The compound of Formula (I) through (XXII-B), or a pharmaceutically acceptable isomer, racemate, hydrate, solvate, isotope, or salt thereof, can be supplied to the living organism via one of the routes as described above (e.g., orally) or can be provided locally within the body tissues. In the presence of the inventive compound, inhibition of the receptor takes place, and the effect thereof can be studied.

In another embodiment, a compound of Formula (I) through (XXII-B) is an imaging agent, wherein the compound contains an isotope, such as isotopes of F, O, N and C. In certain embodiments, the isotope is a fluorine isotope. The compounds may be used for therapeutic purposes, or to diagnose or assess the progression of a malcondition (a vasopressin-dependent condition) in a subject for which antagonism of the V1a receptor is medically indicated.

In some embodiments, imaging and/or diagnostic methods are provided comprising administering to a subject in need thereof the imaging agent described herein and detecting the compound comprised in the imaging agent in the subject. In some aspects, the amount of the compound in the subject is quantified. In further aspects, a vasopressin-dependent condition in the subject is detected via a detection of the compound in the subject. In certain embodiments, the imaging is effected by a radiodiagnostic method. The radiodiagnostic method may be performed by any instrument capable of detecting radiation by the compounds. Exemplary radiodiagnostic methods include, but not limited to, Positron Emission Tomography (PET), PET-Time-Activity Curve (TAC) or PET-Magnetic Resonance Imaging (MRI). In particular aspect, the radiodiagnostic method is PET. In one embodiment, methods of treatment are provided comprising administering a compound of Formula (I) through (XXII-B), or a pharmaceutically acceptable isomer, racemate, hydrate, solvate, isotope, or salt thereof, alone or in combination with another pharmacologically active agent or second medicament, to a subject having a malcondition for which antagonizing the V1a receptor is medically indicated.

As mentioned above, V1a receptor antagonists provide significant promise for the treatment of malconditions which benefit from antagonism of the V1a receptor. As summarized in the review article by Szczepanska-Sadowaska et al., *Current Drug Metabolism* 18:306-345, 2017 (incorporated by reference herein in its entirety), vasopressin has been associated with a wide range of regulatory functions in numerous organs and/or tissues and implicated in or with: (1) the cardiovascular system, (2) renal effects, (3) circadian rhythm, (4) food intake and metabolic and endocrine regulation, (5) uterus, (6) endotoxemia, and (7) stress, depression and psychiatric disorders. AVP is also involved in the regulation of several functions, such as, hepatic, pancreatic, and platelet-aggregating effects, and effects on the central and peripheral nervous system. The effects of the AVP receptors depends on where they are located.

In the cardiovascular system, vasopressin is associated with: (a) peripheral effects (e.g., it acts as a potent vasoconstrictor and plays a role in the regulation of carioca muscle differentiation, growth and contractility); (b) central cardiovascular control (e.g., buffering excessive increases and decreases in blood pressure); (c) regulation of cardiovascular reflexes (e.g., in the regulation of the baroreceptor reflex); (d) interaction with other factors (e.g., factors regulating blood pressure such as Ang II); (e) adaption to hemorrhage; and (f) cardiovascular diseases (e.g., hypertension and heart failure, intracranial hemorrhage and stroke).

As for renal effects, vasopressin has antidiuretic action, and interacts with AngII in the regulation of urine excretion. Vasopressin also exerts a diposgenic action, manifested by reduction of the osmotic thirst threshold.

In the context of circadian rhythm, vasopressin neurons in the suprachiasmatic nuclei (SCN) of the hypothalamus manifest a distinct circadian rhythmicity, and studies have shown distinct circadian rhythmicity of vasopressin concentration in the cerebrospinal fluid (CSF). It has been suggested that SCN vasopressin neurons belong to the group of autonomous pacemakers and play a role in the regulation of the circadian rhythm, and studies have shown that circadian rhythmicity of vasopressin release has repercussions in the diurnal rhythmicity of other functions, such as corticosterone release, locomotor activity and body temperature.

With regard to food intake and metabolic and endocrine regulation, vasopressin has been associated with regulation of food intake and glucose homeostasis, and animal studies with V1a receptor knockout mice consuming high fat diet show that vasopressin acting on V1a receptor improves glucose tolerance and protects from the development of obesity. Studies have also shown that vasopressin plays a direct role in the regulation of glucagon and insulin release from the pancreatic cells. In the adrenal gland, vasopressin causes hypertrophy and hyperplasia of the adrenal cortex and stimulates secretion of aldosterone and glucocorticoids through stimulation of V1a receptors. Stimulation of the V1a receptor by vasopressin also influences release of luteinizing hormone releasing hormone (LHRL) and is believed to play a role in initiating the preovulatory LH surge.

The presence of V1a receptors has also been reported in the uterus, with the density of such receptors higher in the myometrium than in the endometrium, and they react with oxytocin (OT) receptors.

Endotoxemia is associated with the increased expression of the vasopressin gene in the hypothalamic nuclei and elevated concentration of vasopressin in the blood. Vasopressin exerts various effects on the cardiovascular system during endotoxemia, including reducing renal medullary blood flow where aortic contractility is reduced. There is also evidence that vasopressin plays a role in the regulation of immunologic processes, and that it may play a role in the regeneration of the liver.

With regard to stress, depression and psychiatric disorders, the role of vasopressin in the regulation of behavior has been studied for many decades, with early studies showing that it facilitates conditioned avoidance responses in rats. Experimental studies have shown that vasopressin has long-lasting effects on learning and new memory acquisition as well as emotional and social behaviors, and clinical observations have shown that depression and other psychiatric disorders are associated with significant changes in vasopressin secretion. Neurogenic stress has also been shown to stimulate vasopressin release in the blood and CSF. A strong association has been shown between chronic stress, inappropriate activation of the vasopressinergic system and depression. Studies in humans have shown that patients with major depression manifested an elevated plasma vasopressin level, and in patients with unipolar depression there was a significant positive correlation between peripheral plasma vasopressin and hypercortisolemia. There is also evidence that vasopressin is an anxiogenic agent, and direct administration of V1a receptor antagonist into the paraventricular nucleus (PVN) of rats attenuated anxiety and depression behavior. Aggression has also been associated with an increased release of vasopression into the CSF. Vasopressin plays a role in the regulation of pain, and its antinociceptive action has been shown in a number of studies. Inappropriate secretion of vasopressin has also been suggested in the disordered processing of psychosomatic stress which occurs in schizophrenia.

Due to its wide and pivotal role for maintaining body homeostatis under a variety of conditions, vasopressin and its receptors, including V1a, have been recognized as an important target for diagnostic and therapeutic applications. To this end, vasopressin antagonists have shown efficacy in easing congestion symptoms and edema and increasing plasma sodium ion concentration in clinical trials. In addition, the compounds of the present invention have utility across a broad spectrum of malconditions, including the following: heart failure, hepatic cirrhosis, psychiatric disorders (e.g., major depressive disorder or generalized anxiety disorder), brain injury, circadian rhythm disorders (e.g., associated with shift work or jet lag, resulting in sleep drifting later each day, abnormal night sleep patterns, and/or difficulty staying awake during the day), bone growth, diabetes mellitus, ovarian function, septic shock (e.g., maintaining haemodynamic parameters and preventing organ damage), and cancer and metastisis (e.g., decreasing dissemination of tumor cells and the spread of metasteses by improving haemostasis and slowing of proliferation of carcinoma cells).

The compounds of the present invention selectively block the effects of V1a receptors, are orally bioavailable/effective, and demonstrate central nervous system (CNS)-penetrating effects. These compounds, (when acting peripherally and/or centrally) are useful in the treatment of vasopressin-dependent conditions or in the conditions related to inappropriate secretion of vasopressin, particularly in the response to chronic stress and in circuits that are dysregulated in affective disorders. These compounds reduce measures of stress, fear, aggression, depression, and anxiety.

In an embodiment, a method is provided for treatment or prevention of vasopressin-dependent conditions or in the conditions related to inappropriate secretion of vasopressin, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject.

In an embodiment, a method is provided for treatment of a vasopressin-dependent condition, whether organic, stress-induced or iatrogenic.

As used herein a "vasopressin-dependent condition" is defined as conditions related to inappropriate secretion of vasopressin, particularly in the response to chronic stress and in circuits that are dysregulated in affective disorders, such as disorders of stress, mood, and behavioral disorders, including stress-related affective disorders. Vasopressin-dependent conditions, include conditions such as cardiovascular conditions, for example hypertension, pulmonary hypertension, cardiac insufficiency, myocardial infarction or coronary vasospasm, in particular in smokers, Raynaud's syndrome, unstable angina and PTCA (percutaneous transluminal coronary angioplasty), cardiac ischemia, hemostasis disturbances or thrombosis; conditions of the central nervous system, such as migraine, cerebral vasospasm, cerebral hemorrhage, trauma and cerebral edema, depression, anxiety, stress, emotional disorders, obsessive-compulsive disorder, panic attacks, psychotic states, aggression, memory or sleep disorders, or cognitive disorders, for example disorders associated with impaired social cognition (e.g., schizophrenia, autism spectrum disorder); conditions of the renal system, such as renal vasospasm, necrosis of the renal cortex, nephrogenic diabetes insipidus or diabetic nephropathy; or conditions of the gastric system, such as gastric vasospasm, cirrhosis of the liver, ulcers or the pathology of vomiting, for example nausea, including nausea due to chemotherapy, or travel sickness; circadian rhythm-related disorders such as phase shift sleep disorders, jet-lag, sleep disorders and other chronobiological disorders. Additional examples of vasopressin-dependent conditions include but are not limited to neuropsychiatric disorders, neuropsychiatric symptoms in neurodegenerative diseases, PTSD, inappropriate aggression, anxiety, depressive disorders, major depression, obsessive compulsive disorder, autistic spectrum disorders, schizophrenia, and aggressive behavior, and other affective disorders.

In an embodiment, a method is provided for treatment of an autism spectrum disorder, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject.

Autism spectrum disorder (ASD), also referred to herein as autistic spectrum disorders, is a blanket term describing a complex developmental disorder that affects the brain's normal development of social and communication skills. Core symptoms of ASD include impaired social interactions such as social interaction difficulties, communication challenges including impaired verbal and nonverbal communication, problems processing information from the senses, and a tendency to engage in restricted and repetitive patterns of behavior. In one embodiment, the core symptoms of the autism spectrum disorder are impaired social interactions and communication challenges. In one embodiment, the core symptom of the autism spectrum disorder is impaired social interactions. In one embodiment, the core symptom of the autism spectrum disorder is impaired communication challenges. In one embodiment, the core symptom of the autism spectrum disorder is the tendency to engage in restricted and repetitive patterns of behavior.

In an embodiment, a method is provided for treatment of an anxiety disorder, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject.

Anxiety disorder is a blanket term covering several different forms of abnormal and pathological fear and anxiety. Current psychiatric diagnostic criteria recognize a wide variety of anxiety disorders, including generalized anxiety disorder, panic disorder, stress-related disorders, obsessive compulsive disorder, phobia, social anxiety disorder, separation anxiety disorder and post-traumatic stress disorder (PTSD). In one embodiment, the anxiety disorder is a social anxiety disorder. In one embodiment, the anxiety disorder is phobia. In one embodiment, the anxiety disorder is a stress-related disorder. In one embodiment, the anxiety related disorder is PTSD.

Generalized anxiety disorder is a common chronic disorder characterized by long-lasting anxiety that is not focused on any one object or situation. A person suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attack's potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from social phobia, specific phobia, agoraphobia, phobia of an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

In an embodiment, a method is provided for treatment of a depressive disorder, depression, or depressive illness, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject. Examples of such disorders include major depression, MDD, drug-resistant depression, dysthymia and bipolar disorder.

In an embodiment, a method is provided for treatment of a mood disorder, or an affective disorder comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject.

Examples of a mood disorder or a affective disorder include major depressive disorder (MDD); bipolar disorder; anhedonia; dysthymia; major depression, Psychotic major depression (PMD), or psychotic depression; postpartum depression; seasonal affective disorder (SAD); and catatonic depression is a rare and severe form of major depression involving disturbances of motor behavior and other symptoms.

The terms "anhedonia" and "anhedonic symptom" are used interchangeably and is defined as the inability to experience pleasure from activities usually found enjoyable, e.g. exercise, hobbies, music, sexual activities or social interactions. The terms "anhedonia" and "anhedonic symptom" are closely related to criterion of "depressive disorder with melancholic features" which is defined in DSM-5 as melancholic depression characterized by a loss of pleasure in most or all activities, a failure of reactivity to pleasurable stimuli, a quality of depressed mood more pronounced than that of grief or loss, a worsening of symptoms in the morning hours, early morning waking, psychomotor retardation, excessive weight loss, or excessive guilt. The term "treatment of depressive disorder with melancholic features" comprises treatment of both the depressive disorder and melancholic features associated herewith. In one embodiment, the mood disorder is anhedonia. In one embodiment, the mood disorder is major depression. In one embodiment, the mood disorder is seasonal affective disorder (SAD).

In an embodiment, a method is provided for treatment of an affective disorder, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject. Affective disorders such as disorders of stress, mood, and behavioral disorders, including stress-related affective disorders, obsessive compulsive disorder, autistic spectrum disorders, Personality disorders, ADHD, panic attacks and the like. As used herein, "autistic spectrum disorders" and "Autism spectrum disorders" are used interchangeably and refer to autism, monogenetic causes of autism such as synaptophathies, e.g., Rett syndrome, Fragile X syndrome, Angelman syndrome and the like.

In an embodiment, a method is provided for treatment of Anger, Aggression or Aggressive Disorder, or Impulse Control Disorders comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject. Examples of Anger, Aggression or Aggressive Disorder, or Impulse Control Disorders include, but are not limited to, inappropriate aggression, aggressive behavior, aggression related to social isolation, for treatment of interpersonal violence co-occurring with such illness as ADHD, autism, bipolar disorder, emotional disorders, disorders of memory and/or cognition and cognitive disorders (such as Alzheimer's disease, Parkinson's disease, Huntington's disease and the like), and addictive disorder/substance abuse.

In an embodiment, a method is provided for treatment of Intermittent Explosive Disorder (sometimes abbreviated as IED) comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject. Intermittent explosive disorder is a behavioral disorder characterized by explosive outbursts of anger and violence, often to the point of rage, that are disproportionate to the situation at hand (e.g., impulsive screaming triggered by relatively inconsequential events). Impulsive aggression is unpremeditated, and is defined by a disproportionate reaction to any provocation, real or perceived. Some individuals have reported affective changes prior to an outburst (e.g., tension, mood changes, energy changes, etc.). The disorder is currently categorized in the *Diagnostic and Statistical Manual of Mental Disorders* (DSM-5) under the "Disruptive, Impulse-Control, and Conduct Disorders" category. The disorder itself is not easily characterized and often exhibits comorbidity with other mood disorders, particularly bipolar disorder. Individuals diagnosed with IED report their outbursts as being brief (lasting less than an hour), with a variety of bodily symptoms (sweating, stuttering, chest tightness, twitching, palpitations) reported by a third of one sample. Aggressive acts are frequently reported accompanied by a sensation of relief and in some cases pleasure, but often followed by later remorse.

In other embodiments, a method is provided for treatment of a Schizophrenia spectrum disorders, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject. Examples of Schizophrenia spectrum disorders include schizophrenia, schizoaffective disorder, psychotic states and memory disorders.

In other embodiments, a method is provided for treatment of a circadian rhythm related disorders, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject. Circadian rhythm sleep disorders are caused by desynchronization or misalignment between internal sleep-wake rhythms (body clock) and the external light-darkness cycle. Circadian rhythm disorders (sometimes also referred to as phase shift disorders) include sleep disorders associated with jet lag, shift work, or altered sleep phase types, resulting in sleep drifting later each day, abnormal nigh sleep patterns, and/or difficulty staying awake during the day. The cause may be internal (e.g., delayed or advanced sleep phase syndrome, or Non-24-h sleep-wake syndrome) or external (e.g., jet lag, shift work). If the cause is external, other circadian body rhythms, including temperature and hormone secretion, can become out of sync with the light-darkness cycle (external desynchronization) and with one another (internal desynchronization); in addition to insomnia and excessive sleepiness, these alterations may cause nausea, malaise, irritability, and depression. Risk of cardiovascular and metabolic disorders may also be increased. Compounds of the invention are useful for treating circadian rhythm-related disorders, such as depression, jet-lag, work-shift syndrome, sleep disorders, glaucoma, reproduction, cancer, premenstrual syndrome, immune disorders, inflammatory articular diseases and neuroendocrine disorders, Non-24 Hour Disorder.

The compounds according to the invention may also be used in the treatment or prevention of Neuropsychiatric Disorders such as anorexia nervosa, bulimia, mood disorders, depression, anxiety, sleeping disorders, addictive disorders, panic attacks, phobias, obsession, pain-perception disorders (fibromyalgia), dependency on a substance, hemorrhagic stress, muscular spasms and hypoglycemia. Addictive disorder, including disorders related to substance abuse or addiction, and compulsive behavior.

The compounds according to the invention may also be used in the treatment or prevention of chronic stress states such as immunodepression, fertility disorders and dysfunctions of the hypothalamopituitaryadrenal axis.

The compounds according to the invention can also be used in the treatment of disorders such as primary or secondary dysmenorrhea, premature labor or endometriosis, male or female sexual dysfunction, hypertension, chronic heart failure, inappropriate secretion of vasopressin, liver cirrhosis and nephrotic syndrome.

The compounds according to the invention can also be used in the treatment or prevention of any pathology resulting from stress, such as fatigue and its syndromes, ACTH-dependent disorders, cardiac disorders, pain, modifications in gastric emptying, in fecal excretion (colitis, irritable bowel syndrome or Crohn's disease) or in acid secretion, hyperglycemia, immunosuppression, inflammatory processes (rheumatoid arthritis and osteoarthritis), multiple infections, septic shock, cancers, asthma, psoriasis and allergies.

The compounds according to the invention may also be used as psychostimulants, bringing about an increase in consciousness/alertness and/or in emotional reactivity towards the environment and making adaptation easier.

The compounds according to the present invention can be used in healing, in analgesia, in anxiolysis, in the prevention of pain, in the prevention of anxiety, depression, schizophrenia, autism or obsessive-compulsive syndrome, in maternal behavior (facilitation of recognition and acceptance of the mother by the child) and social behavior, memory; regulation of food and drink intake, dependence on drugs, withdrawal and sexual motivation; hypertension, hyponatremia, cardiac insufficiency, atherosclerosis, angiogenesis, the proliferation of tumors, Kaposi's sarcoma, to regulate the storage of fat by the adipocyte, to control hyperlipidemia, triglyceridemia and metabolic syndrome.

The compounds according to the invention can also be used in the treatment of cancers, such as small cell lung cancers or breast cancers; hyponatremic encephalopathy; pulmonary syndrome; Meniere's disease; ocular hypertension; glaucoma; cataracts; obesity; type-I and type-II diabetes; atherosclerosis; metabolic syndrome; hyperlipidemia; insulin resistance; or hypertriglyceridemia; in post-operative treatments, in particular after abdominal surgery; autism; hypercortisolemia; hyperaldosteronemia; pheochromocytoma; Cushing's syndrome; preeclampsia; disorders of micturition; or premature ejaculation.

Compounds having the structure of Formula (I), as well as the sub-structures for Formulas (II) through (XXII-B), can be synthesized using standard synthetic techniques known to those of skill in the art. For examples, compounds of the present invention can be synthesized using the general synthetic procedures set forth in Schemes 1 to 4.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

505
Scheme 1
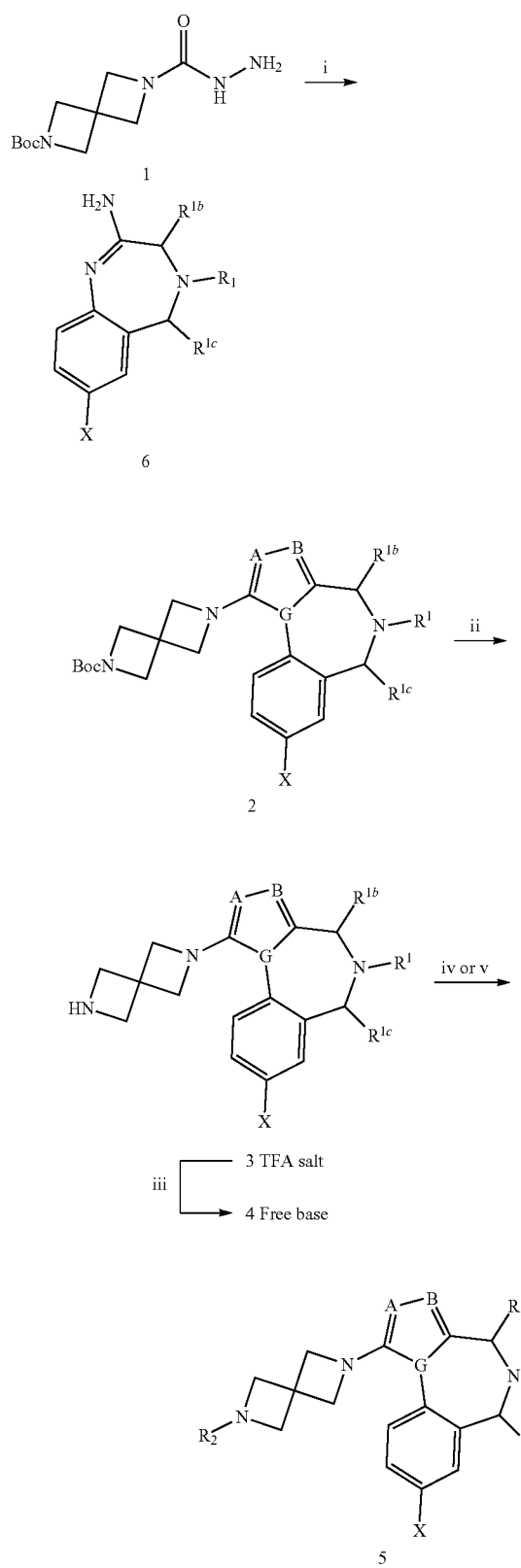
506
Scheme 2
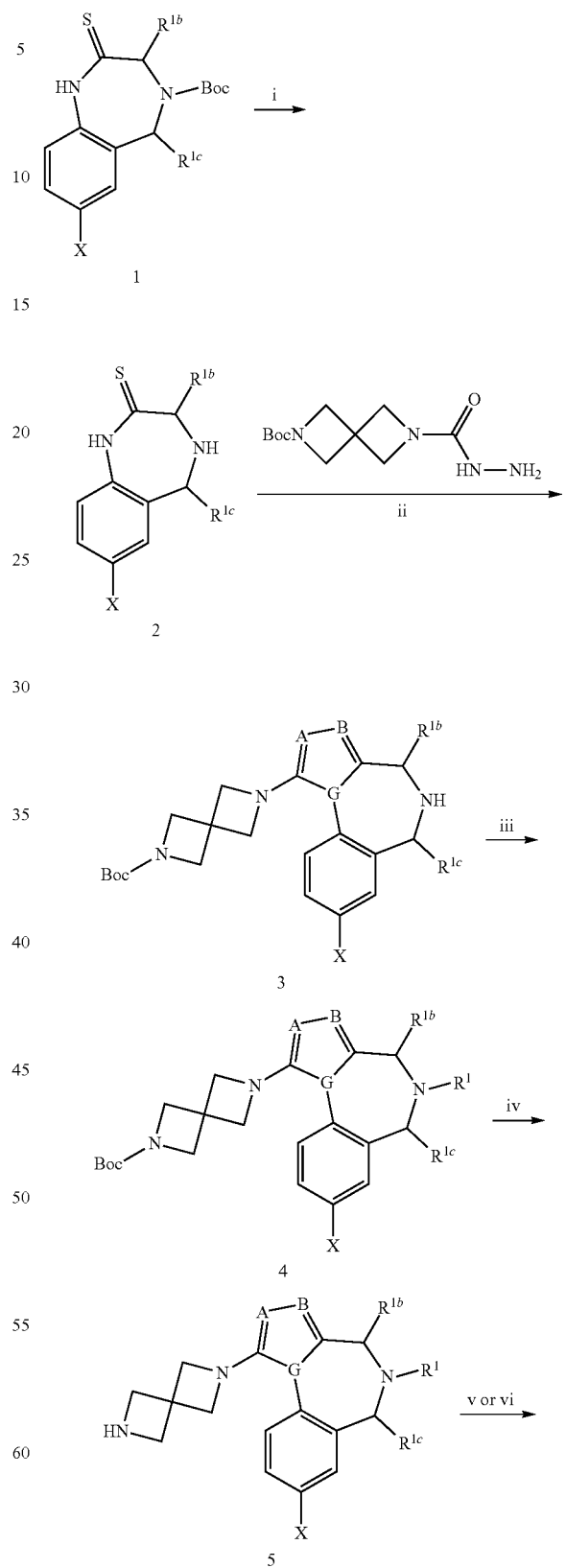
Reagents and conditions: i) iPrOH; ii) TFA; iii) MP-carbonate, MeOH; iv) R²Br, RuPhos, Pd(OAc)₂, Cs₂CO₃ dioxane; v) R²Cl, Cs₂CO₃, DMF.

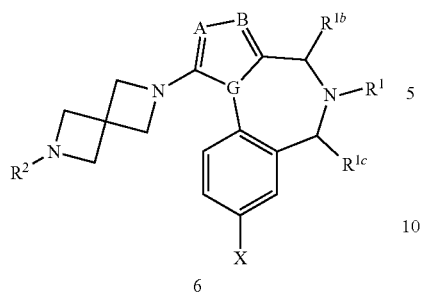
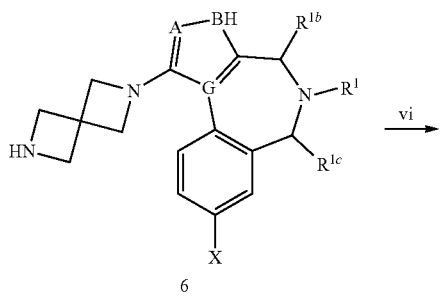
Reagents and conditions: i) TFA, DCM; ii) dioxane; iii) R₁Cl; iv) TFA, DCM; v) R²Br, RuPhos, Pd(OAc)₂, Cs₂CO₃ dioxane; vi) R²Cl, Cs₂CO₃, DMF.
Reagents and conditions: i) NH₂OH·HCl, Na₂CO₃, MeOH then N-chlorosuccinimide, DMF; ii) NEt₃, DCM; iii) K₂CO₃, THF; iv) Pd(OAc)₂, pivalic acid, K₂CO₃, DMA; v) TFA, DCM; vi) R²Br, RuPhos, Pd(OAc)₂, Cs₂CO₃, dioxane.
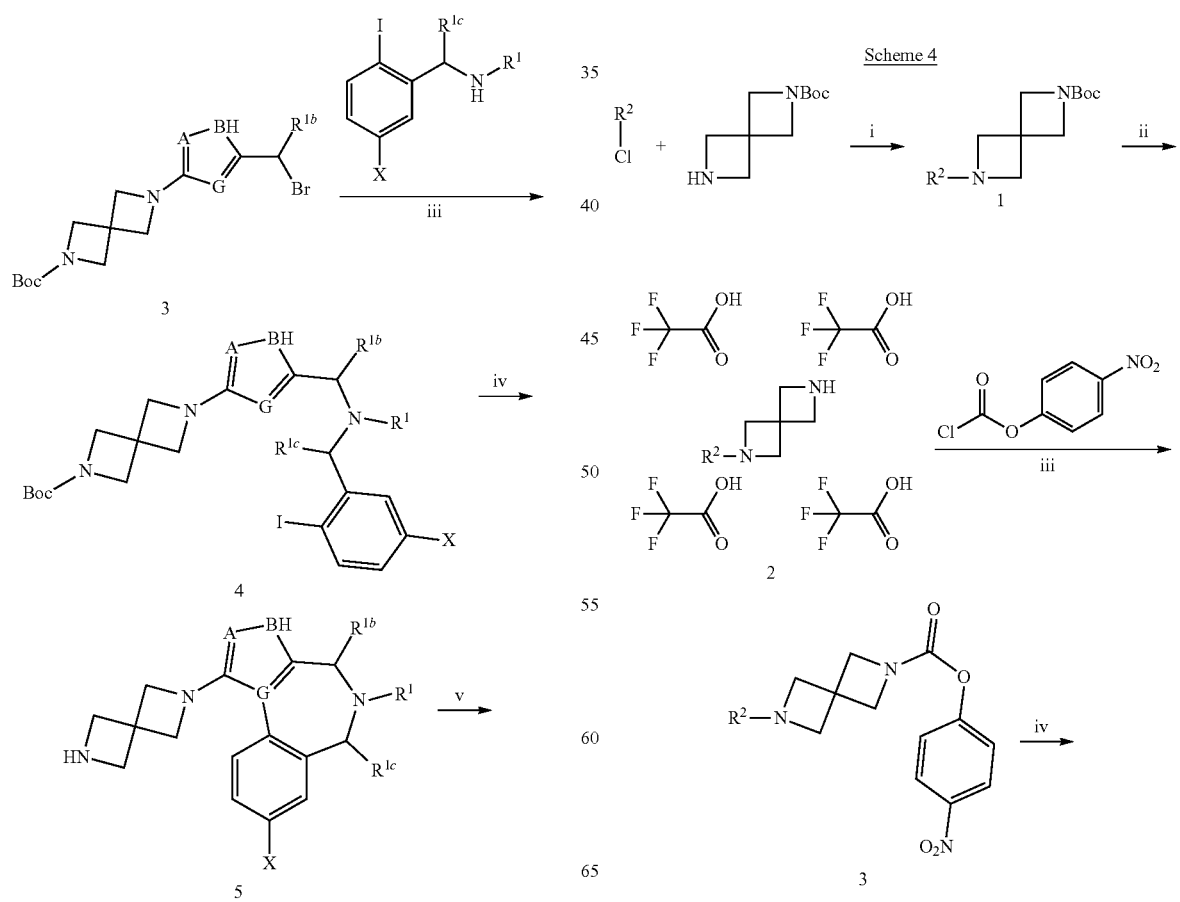

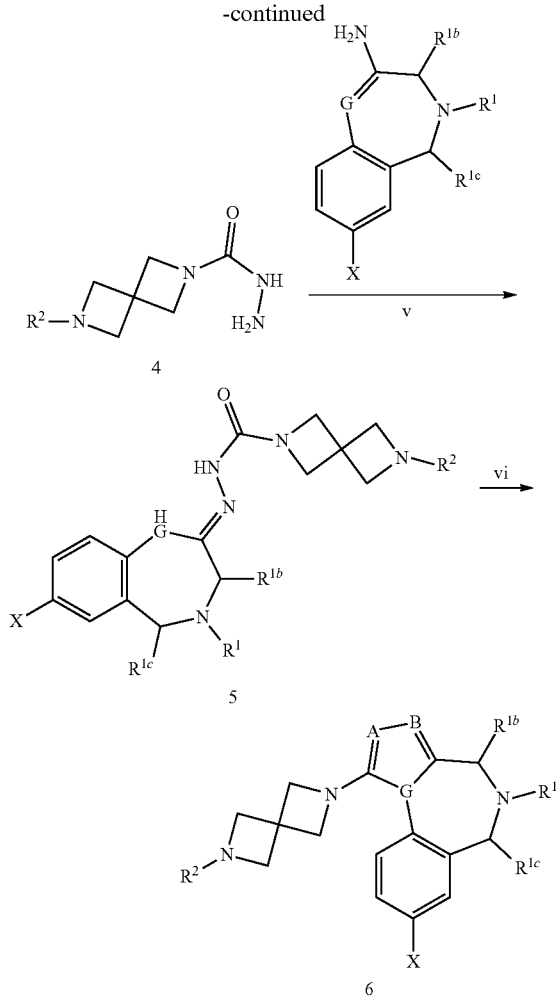

Reagent and conditions: i) dioxane, RuPhos and (CH$_3$)$_3$CONa; ii) DCM, CF$_3$CO$_2$H; iii) CF$_3$CO$_2$H, DCM, NEt$_3$; iv) THF, N$_2$H$_4$; v) IPA, CH$_3$COOH, then EtOH; and vi) NEt$_3$, Ph$_3$PCl$_2$, ACN.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All the starting materials and reagents are commercially available and are used as is. $^1$H Nuclear magnetic resonance (NMR) spectroscopy may be carried out using a Bruker instrument operating at 400 MHz using the stated solvent at around room temperature unless otherwise stated. In all cases, NMR data are consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad. Preparative HPLC purification may be performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds are a Waters Sunfire OBD Phenomenex Luna Phenyl Hexyl (10 μm 21.2×150 mm, 10 μm) or Waters Xbridge Phenyl (10 μm 19×150 mm, 5 μm). Appropriate focused gradients are selected based on acetonitrile and methanol solvent systems under either acidic or basic conditions. The modifiers used under acidic/basic conditions are formic acid (0.1% V/V) and ammonium bicarbonate (10 mM) respectively. The purification may be controlled by Waters Fractionlynx software through monitoring at 210-400 nm, and triggered a threshold collection value at 260 nm and, when using the Fractionlynx, the presence of target molecular ion as observed under APi conditions. Collected fractions are analysed by LCMS (Waters Acquity systems with Waters SQD). Normal phase flash column chromatography may be performed utilizing a Biotage Isolera system. The silica gel columns are purchased from either Interchim or Biotage. The mobile phase may be either ethyl acetate in hexanes or methanol in dichloromethane with various ratios, and the fraction collection may be triggered by UV absorbance at 254 nm. Analytical high-performance liquid chromatography-mass spectrometry (HPLC-MS) may be performed utilizing HP or Waters DAD+Micromass ZQ, single quadrupole LC-MS or Quattro Micro LC-MS-MS. Method 1: The RP-HPLC column may be Phenomenex Luna 5 μm C18 (2), (100×4.6 mm). Mobile phase 5-95% acetonitrile in water (0.1% formic acid) gradient, flow rate 2.0 mL/min, and 6.5 min run time; Method 2: The RP-HPLC column may be Waters Xterra MS 5 μm C18, 100×4.6 mm. Mobile phase 5-95% acetonitrile in water (10 mM ammonium bicarbonate (ammonium hydrogen carbonate); Method 3: method 1 with mobile phase 50-100% acetonitrile in water (0.1% formic acid) gradient, and 5 min run time; Method 4: method 1 with mobile phase 10-100% acetonitrile in water (0.1% formic acid) gradient, and 10 min run time; Method 5: method 1 with 20 min run time.

Abbreviations

The following abbreviations are used in the examples:
ACN: acetonitrile
Aq. Aqueous solution
BrettPhos: 2-(dicyclohexylphosphino)3,6-dimethoxy-2', 4',6'-triisopropyl-1,1'-biphenyl
CDCl$_3$: deuterochloroform
CF$_3$CO$_2$H: trifluoroacetic acid
(CH$_3$)$_3$CONa: sodium tert-butoxide
CH$_3$COOH: acetic acid
DCM: dichloromethane
DMF: dimethylformamide
DMSO: dimethyl sulfoxide
DMA: N,N-Dimethylacetamide
ESI electrospray Ionisation
EtOAc: ethyl acetate
EtOH: ethyl alcohol
eq.: equivalent
g: gram
HATU: (1-[bis(dimethylamino)methylene]-1H-1,2,3-triazolo[4,5-b]pyridinium-3-oxidhexafluoro-phosphate
HPLC: high performance liquid chromatography
IPA: isopropyl alcohol
LiCl: lithium chloride
M: molar
MeOH: methanol
mg: milligram
MHz: megahertz
Ml: milliliter
Mmol: millimole MP: macroporous
MS: mass spectrometry
NaHCO$_3$: sodium hydrogencarbonate
NEt$_3$: trimethylamine
N$_2$H$_4$: hydrazine monohydrate
NMP: N-methyl-2-pyrrolidone
NMR: nuclear magnetic resonance
Ph$_3$PCl$_2$: dichloro-triphenylphosphorane
RuPhos: 2-dicyclohexylphosphino-2',6'-diisopropoxybiphenyl
SFC: supercritical fluid chromatography
THF: tetrahydrofuran
µL: microliters Example 1

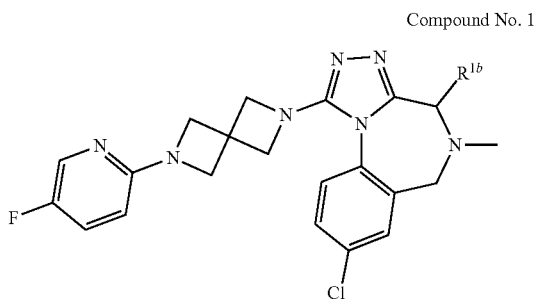

Compound No. 1

Step 1: Synthesis of tert-butyl 6-(hydrazinecarbonyl)-2,6-diazaspiro[3.3]heptane-2-carboxylate

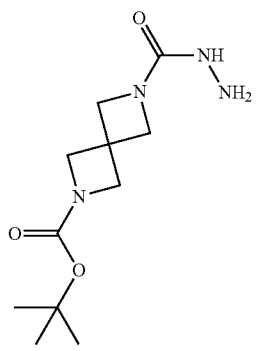 [SMILES: CC(C)(C)OC(=O)N1CC2(CN(C(=O)NN)C2)C1]

To a stirred solution of 2-(tert-butoxycarbonyl)-2,6-diazaspiro[3.3]heptane-6-carboxylic acid (1 mmol, 1 eq.) in THF (5 mL) is added 1-1'-carbonyldiimidazole (0.19 g, 1.2 mmol, 1.2 eq.) and the mixture is stirred at RT overnight. The resulting mixture is added to a solution of hydrazine monohydrate (0.07 mL, 1.4 mmol, 1.4 eq.) in THF (10 mL) and stirred at RT overnight. The mixture is diluted with brine and extracted with ethyl acetate. The organic phase is separated, washed with brine, dried (MgSO$_4$), filtered and concentrated in vacuo to afford the title compound.

Step 2: Synthesis of terttert-butyl 6-(8-chloro-5-methyl-5,6-dihydro-4H-benzo[f][1,2,4]triazolo[4,3-a][1,4]diazepin-1-yl)-2,6-diazaspiro[3.3]heptane-2-carboxylate

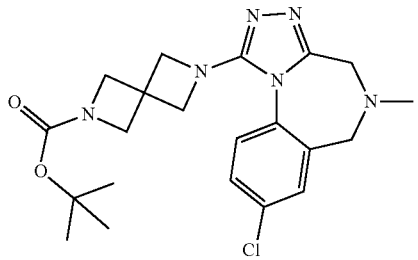 [SMILES: CN1Cc2cc(Cl)ccc2-n2c(nnc2N2CC3(CN(C(=O)OC(C)(C)C)C3)C2)C1]

To a solution of tert-butyl 6-(hydrazinecarbonyl)-2,6-diazaspiro[3.3]heptane-2-carboxylate (1.06 mmol, 1 eq.) in 2-propanol (20 mL) is added 7-chloro-4-methyl-1,3,4,5-tetrahydro-2H-benzo[e][1,4]diazepin-2-imine (0.22 g, 1.06 mmol, 1 eq.) and the mixture is stirred at 80° C. over the weekend. The reaction mixture is concentrated under reduced pressure, extracted, and purified by silica gel chromatography eluting with 0-10% methanol in DCM to afford the title compound.

Step 3: Synthesis of 8-chloro-5-methyl-1-(2,6-diazaspiro[3.3]heptan-6-yl)-5,6-dihydro-4H-benzo[f][1,2,4]triazolo[4,3-a][1,4]diazepine bis(2,2,2-trifluoroacetate)

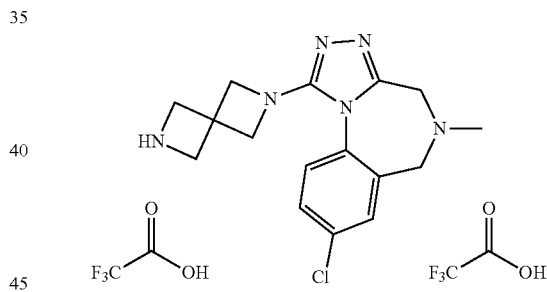

TFA (0.33 mL, 4.32 mmol, 74.4 eq.) is added dropwise to a solution of tert-butyl 6-(8-chloro-5-methyl-5,6-dihydro-4H-benzo[f][1,2,4]triazolo[4,3-a][1,4]diazepin-1-yl)-2,6-diazaspiro[3.3]heptane-2-carboxylate (0.058 mmol, 1.0 eq.) in DCM (1 mL) at RT and mixture is stirred at RT for 20 min. The mixture is concentrated in vacuo to give a product which is used without further purification.

Step 4: Synthesis of 8-chloro-1-(2-(5-fluoropyridin-2-yl)-2,6-diazaspiro[3.3]heptan-6-yl)-5-methyl-5,6-dihydro-4H-benzo[f][1,2,4]triazolo[4,3-a][1,4]diazepine (Compound No. 1)

A mixture of 8-chloro-5-methyl-1-(2,6-diazaspiro[3.3]heptan-6-yl)-5,6-dihydro-4H-benzo[f][1,2,4]triazolo[4,3-a][1,4]diazepine bis(2,2,2-trifluoroacetate) (0.08 mmol, 1 eq.), 2-bromo-5-fluoropyridine (0.029 g, 0.16 mmol, 2.04 eq.), RuPhos (0.013 g, 0.03 mmol, 0.345 eq.), palladium acetate (0.003 g, 0.01 mmol, 0.165 eq.), cesium carbonate (0.133 g, 0.41 mmol, 5.06 eq.) in NMP (1 mL) is degassed using N$_2$, for 10 minutes and then heated to 80° C. for 20 minutes. The reaction is allowed to cool and allowed to stand at RT over the weekend. The mixture is diluted with EtOAc, 4% aq. sol. of LiCl and filtered through a layer of celite. The organic phase is separated, washed with aq. sol. of LiCl, dried (MgSO$_4$), filtered and concentrated in vacuo to give a yellow oil. The crude material is purified by column chromatography on a Biotage® KP—NH cartridge eluting with 0-100% EtOAc in isohexane followed by 0-5% methanol in ethyl acetate to give a product. This is lyophilized to afford the title compound.

Compound Nos. 2 to 13 and 17 to 21

Compound Nos. 2 to 13 and 17 to 21 are prepared according to the procedure of Example 1 using appropriately substituted intermediates.

Example 2

Compound No. 15

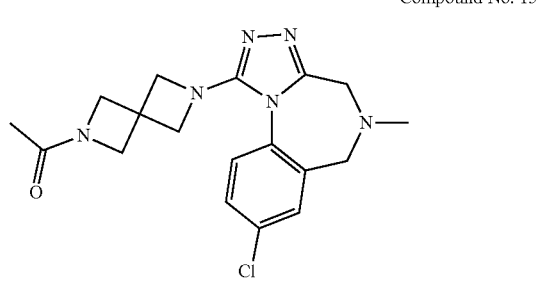

Step 1: Synthesis of 1-(6-(8-chloro-5-methyl-5,6-dihydro-4H-benzo[f][1,2,4]triazolo[4,3-a][1,4]diazepin-1-yl)-2,6-diazaspiro[3.3]heptan-2-yl)-2,2,2-trifluoroethan-1-one

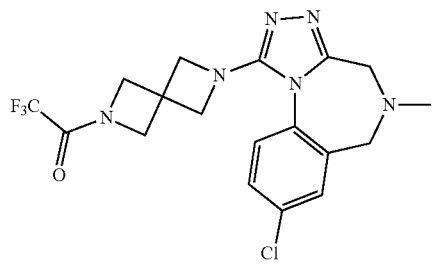 [SMILES: CN1Cc2cc(Cl)ccc2-n2c(nnc2N2CC3(CN(C(=O)C(F)(F)F)C3)C2)C1]

To a solution of 8-chloro-5-methyl-1-(2,6-diazaspiro[3.3]heptan-6-yl)-5,6-dihydro-4H-benzo[f][1,2,4]triazolo[4,3-a][1,4]diazepine bis(2,2,2-trifluoroacetate) from Example 1 step 3 (0.1 mmol, 1 eq.), NEt$_3$ (69 μL, 0.49 mmol, 5.0 eq.) in DCM (2 mL) is added trifluoroacetic anhydride (21 μL, 0.15 mmol, 1.5 eq.) and the mixture is stirred at RT for 1 hour. The mixture is diluted with DCM/water and the organic layer is separated by passing through a hydrophobic phase separator. The organic phase is concentrated in vacuo to give the title compound. This material is used without further purification (32 mg).

Step 2: Synthesis of 1-(6-(8-chloro-5,6-dihydro-4H-benzo[f][1,2,4]triazolo[4,3-a][1,4]diazepin-1-yl)-2,6-diazaspiro[3.3]heptan-2-yl)ethan-1-one (Compound No. 15)

A suspension of 1-(6-(8-chloro-5,6-dihydro-4H-benzo[f][1,2,4]triazolo[4,3-a][1,4] diazepin-1-yl)-2,6-diazaspiro [3.3]heptan-2-yl)-2,2,2-trifluoroethan-1-one (0.1 mmol, 1 eq.) from step 1, K$_2$CO$_3$ (0.056 g, 0.4 mmol, 4.0 eq.) and MeOH (2 mL) is stirred at RT for 1 hour. The mixture is concentrated under reduced pressure and the residue is treated with 20% MeOH in DCM, filtered and the filtrate is concentrated under reduced pressure to give a product. To a solution of the product in DCM (2 mL) is added NEt$_3$ (21.11 μL, 1.50 eq.), AcCl (10.81 μL, 0.15 mmol, 1.50 eq.) and the mixture is stirred at RT for 45 minutes. The mixture is concentrated under reduced pressure and the residue is treated with EtAc, sat. sol. of NaHCO$_3$. The organic phase is separated, the aqueous phase is extracted with EtOAc. The organic phases are combined, dried (MgSO$_4$), filtered and concentrated in vacuo to give a product. This is purified using reverse phase column chromatography on a C18 cartridge, eluting with 5-50% MeCN/H$_2$O/0.1% formic acid. After lyophilisation this give the title compound.

Compound 16

Compound No. 16 is prepared according to the methods set forth in Example 2. using appropriately substituted intermediates.

Example 3

Compound No. 24

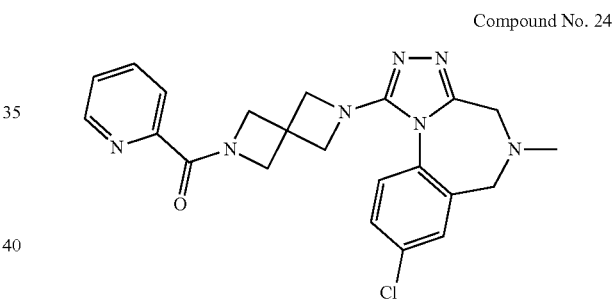

To a solution of 8-chloro-5-methyl-1-(2,6-diazaspiro[3.3]heptan-6-yl)-5,6-dihydro-4H-benzo[f][1,2,4]triazolo[4,3-a][1,4]diazepine bis(2,2,2-trifluoroacetate) from Example 1 Step 3 (0.47 mmol, 1 eq.) in MeOH (10 mL) is added MP-carbonate (2.43 g, 7.05 mmol, 15.0 eq.) and the mixture is stirred at RT for 2 hours. The mixture is filtered and concentrated in vacuo to give a product. To a solution of the product (0.03 g, 0.09 mmol, 1.0 eq.) in DCM (1 mL) is added DIPEA (40 μL, 0.23 mmol, 2.5 eq.), picolinoyl chloride hydrochloride (0.19 g, 0.11 mmol, 1.2 eq.) and the mixture is stirred at RT for 15 minutes. The mixture is diluted with DCM, passed through a hydrophobic phase separator and concentrated in vacuo to give a residue. The residue is purified by preparative HPLC to give the title compound.

Compounds 14 and 25 to 33

Compound Nos. 14 and 25 to 33 are prepared according to the methods set forth in Example 3 using appropriately substituted intermediates.

Example 4

Compound No. 34

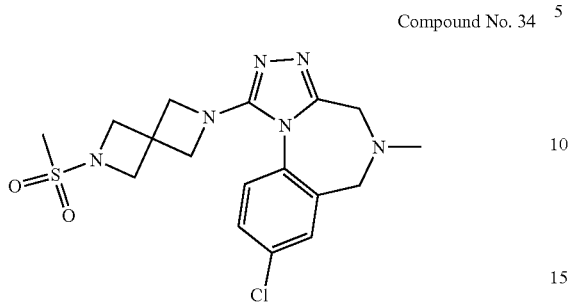

Step 1: Synthesis of 8-chloro-5-methyl-1-(2,6-diazaspiro[3.3]heptan-6-yl)-5,6-dihydro-4H-benzo[f][1,2,4]triazolo[4,3-a][1,4]diazepine

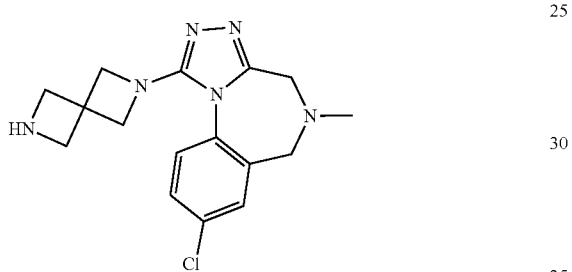

To a solution of tert-butyl 6-(8-chloro-5-methyl-5,6-dihydro-4H-benzo[f][1,2,4]triazolo[4,3-a][1,4]diazepin-1-yl)-2,6-diazaspiro[3.3]heptane-2-carboxylate form Example 1 Step 2 (0.965 mmol, 1 eq.) in DCM (17 mL) is added TFA (6 mL) dropwise at RT. Mixture is stirred at RT for 15 minutes and concentrated in vacuo to give a product. MeOH is added and the mixture is passed through an SCX (10 g, cartridge) eluting with MeOH followed by 2.3M ammonia solution in MeOH to give the title compound.

Step 2: Synthesis of 8-chloro-5-methyl-1-(2-(methylsulfonyl)-2,6-diazaspiro[3.3]heptan-6-yl)-5,6-dihydro-4H-benzo[f][1,2,4]triazolo[4,3-a][1,4]diazepine (Compound No. 34)

To a solution of 8-chloro-5-methyl-1-(2,6-diazaspiro[3.3]heptan-6-yl)-5,6-dihydro-4H-benzo[f][1,2,4]triazolo[4,3-a][1,4]diazepine (0.091 mmol, 1 eq.), DIPEA (19 µL, 0.109 mmol, 1.2 eq.) in DCM 91 mL) is added methanesulfonyl chloride (8 µL, 0.10 mmol, 1.1 eq.) and the mixture is stirred at RT for 15 minutes. The mixture is diluted with DCM/H$_2$O and passed through a phase separator. The organics are concentrated in vacuo and the residue purified by preparative HPLC to give the title compound.

Compounds 35 to 37

Compound Nos. 35 to 37 are prepared according to the methods set forth in Example 4, using appropriately substituted intermediates.

Example 5

Compound No. 38

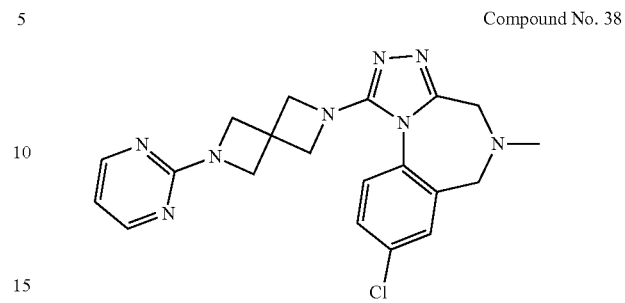

To a solution of 8-chloro-5-methyl-1-(2,6-diazaspiro[3.3]heptan-6-yl)-5,6-dihydro-4H-benzo[f][1,2,4]triazolo[4,3-a][1,4]diazepine from Example 4 Step 1 (0.091 mmol, 1 eq.) in DMF (1 mL) is added Cs$_2$CO$_3$ (36 mg, 0.19 mmol, 1.2 eq.), 2-chloropyrimidine (10 mg, 0.091 mmol, 1 eq.) and the mixture is heated to 80° C. overnight. The mixture is diluted with water and extracted with EtOAc (3×). The organic fractions are combined, washed with brine, dried (MgSO4), filtered, concentrated in vacuo to give a product and purified using preparative HPLC to give the title compound.

Example 6

Compound No. 39

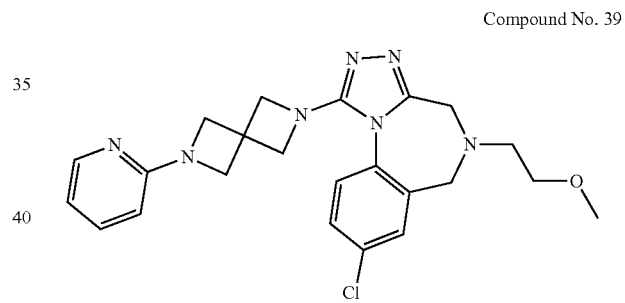

Step 1: Synthesis of tert-butyl (4-chloro-2-(((2-methoxyethyl)amino)methyl)phenyl)carbamate

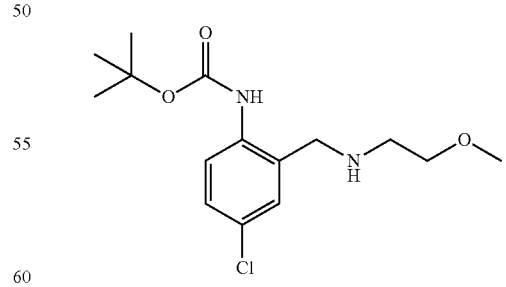

To a solution of tert-butyl (4-chloro-2-formylphenyl)carbamate (0.4 g, 1.56 mmol, 1.0 eq.) in MeOH (10 mL) is added 2-methoxyethylamine (273 µL, 3.13 mmol, 2.0 eq.) and the mixture is heated to 65° C. for 45 minutes. The mixture is cooled in ice and sodium borohydride (0.12 g, 3.13 mmol, 2.0 eq.) is added portionwise. An additional amount of sodium borohydride (0.06 g, 1.56 mmol, 1 eq.) is added after 1 hour at RT. The mixture is stirred at RT for 16 hours, diluted with EtOAc/sat. NaHCO₃ and the organic layer separated. The aqueous phase is extracted with fresh EtOAc (×2), the organic phases are combined, washed with brine, dried (MgSO4), filtered and concentrated in vacuo to give the title compound.

Step 2: Synthesis of tert-butyl (4-chloro-2-(((cyanomethyl)(2-methoxyethyl)amino)methyl)phenyl) carbamate

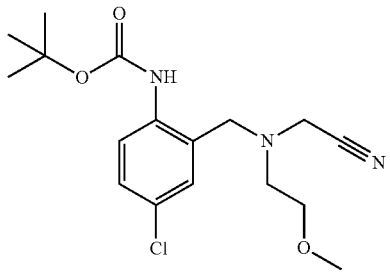 [SMILES: COCCN(CC#N)Cc1cc(Cl)ccc1NC(=O)OC(C)(C)C]

A mixture of tert-butyl (4-chloro-2-(((2-methoxyethyl)amino)methyl)phenyl) carbamate (0.49 g, 1.56 mmol, 1 eq.), sodium bicarbonate (0.14 g, 1.72 mmol, 1.10 eq.), potassium iodide (0.05 g, 0.31 mmol, 0.20 eq.), chloroacetonitrile (0.109 mL, 1.72 mmol, 1.10 eq.) in EtOAc (5 mL) is heated to 75° C. overnight. The mixture is allowed to cool, diluted with EtOAc/NaHCO₃ (1:1) and the organic layer is separated, washed with brine, dried (MgSO₄), filtered and concentrated in vacuo. The residue is triturated with MeOH to give the title compound.

Step 3: Synthesis of 7-chloro-4-(2-methoxyethyl)-4,5-dihydro-3H-benzo[e][1,4]diazepin-2-amine

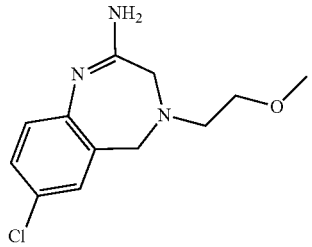 [SMILES: COCCN1CC(N)=Nc2ccc(Cl)cc2C1]

Acetyl chloride (1.21 mL, 16.96 mmol, 20.0 eq.) is added to 2-propanol (7 mL) at RT over 20 minutes (reaction is exothermic) to give a suspension. This suspension is added to a solution of tert-butyl (4-chloro-2-(((cyanomethyl)(2-methoxyethyl)amino)methyl)phenyl) carbamate (0.30 g, 0.85 mmol, 1.0 eq.) in 2-propanol (8 mL) and the mixture is heated to 40° C. overnight. The mixture is allowed to cool, concentrated in vacuo, EtOAc/NaHCO₃ is added, and the organic phase is separated. The aqueous layer is extracted with further EtOAc (×2), the organics are combined, washed with brine and concentrated in vacuo to give a product. This is purified using flash column chromatography (Biotage® KP—NH) eluting with 0-100% EtOAc in isohexane followed by 0-10% methanol in ethyl acetate to give the title compound.

Step 4: Synthesis of methyl 2-(pyridin-2-yl)-2,6-diazaspiro[3.3]heptane-6-carboxylate

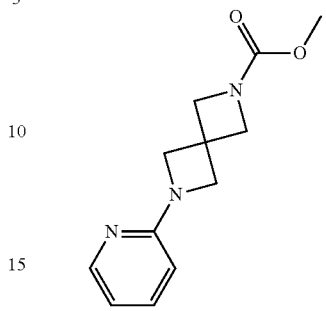

To a solution of 2-(tert-butyl) 6-methyl 2,6-diazaspiro[3.3]heptane-2,6-dicarboxylate (4.31 mmol, 1.0 eq.) in DCM (15 mL) is added TFA (5 mL) and the mixture is stirred at RT for 1 hour. Toluene is added and the mixture is concentrated in vacuo to give a product. A mixture of the product (0.58 g, 2.15 mmol, 1.0 eq.), 2-bromopyridine (247 µL, 2.59 mmol, 1.2 eq.), RuPhos (0.201 g, 0.43 mmol, 0.20 eq.), palladium acetate (0.048 g, 0.22 mmol, 0.1 eq.), cesium carbonate (2.106 g, 6.46 mmol, 3.0 eq.) in dioxane (10 mL) is de-gassed using nitrogen for 10 minutes and heated to 80° C. overnight. The mixture is diluted with EtOAc, filtered through a layer of celite and the filtrate is concentrated in vacuo. The residue is purified by flash column chromatography (Biotage® KP—NH) eluting with 0-50% EtOAc in Isohexane to give the title compound.

Step 5: Synthesis of 2-(pyridin-2-yl)-2,6-diazaspiro[3.3]heptane-6-carbohydrazide

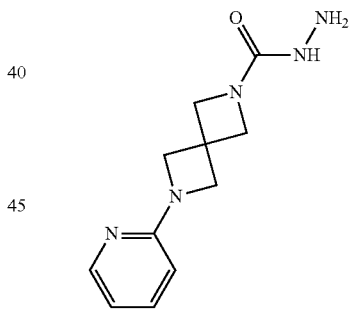

To a solution of methyl 2-(pyridin-2-yl)-2,6-diazaspiro[3.3]heptane-6-carboxylate (1.72 mmol, 1.0 eq.) in MeOH (5 mL) is added hydrazine hydrate (501 µL, 10.33 mmol, 6.0 eq.) over 3 minutes. The mixture is stirred at RT overnight. The mixture is diluted with EtOAc, filtered through a layer of celite, the filtrate is washed with brine and the organic layer is separated. The aqueous phase is further extracted with fresh EtOAc (×2), DCM (×2), the organic phases are combine and concentrated in vacuo to give the title compound.

Step 6: Synthesis of 8-chloro-5-(2-methoxyethyl)-1-(2-(pyridin-2-yl)-2,6-diazaspiro[3.3]heptan-6-yl)-5,6-dihydro-4H-benzo[f][1,2,4]triazolo[4,3-a][1,4]diazepine (Compound No. 39)

A mixture of 7-chloro-4-(2-methoxyethyl)-4,5-dihydro-3H-benzo[e][1,4]diazepin-2-amine from step 3 (0.036 g, 0.14 mmol, 1.0 eq.), 2-(pyridin-2-yl)-2,6-diazaspiro[3.3]heptane-6-carbohydrazide from step 4 (0.15 mmol, 1.05 eq.), AcOH (2 drops) in 2-propanol (1 mL) is heated to 80° C. for 90 minutes. The mixture is concentrated in vacuo, diluted with DCM/NaHCO₃ and passed through a through a phase separator and concentrated in vacuo. The residue is purified using preparative HPLC to give the title compound.

Compounds 40 to 56

Compound Nos. 40 to 56 are prepared according to the methods set forth in Example 6 using appropriately substituted intermediates.

Example 7

Compound No. 57

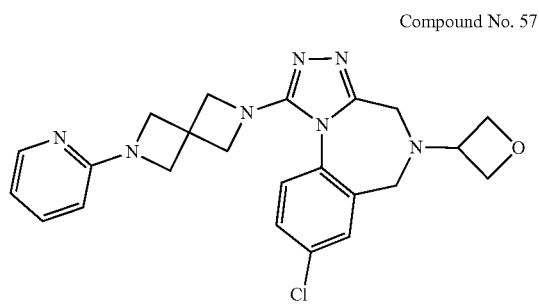 [SMILES: Clc1ccc2c(c1)CN(C1COC1)Cc1nnc(N3CC4(CN(c5ccccn5)C4)C3)n1-2]

Step 1: Synthesis of tert-butyl 8-chloro-1-(2-(pyridin-2-yl)-2,6-diazaspiro[3.3]heptan-6-yl)-4H-benzo[f][1,2,4]triazolo[4,3-a][1,4]diazepine-5(6H)-carboxylate

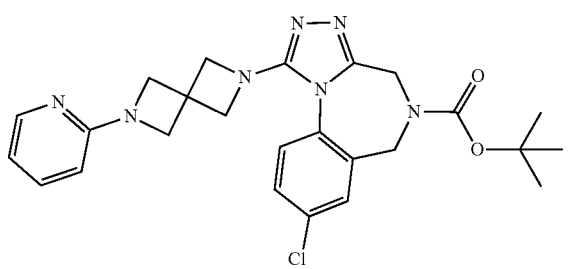 [SMILES: CC(C)(C)OC(=O)N1Cc2cc(Cl)ccc2-n2c(nnc2N2CC3(CN(c4ccccn4)C3)C2)C1]

To a solution of tert-butyl 7-chloro-2-thioxo-1,2,3,5-tetrahydro-4H-benzo[e][1,4]diazepine-4-carboxylate (0.4 g, 1.28 mmol, 1.0 eq.), is added 2-(pyridin-2-yl)-2,6-diazaspiro[3.3]heptane-6-carbohydrazide from Ex6 step 4 (1.28 mmol, 1.0 eq.) in dioxane (10 mL) and the mixture is heated to 90° C. for 36 hours. The mixture is allowed to cool, saturated with nitrogen gas and is concentrated in vacuo. The residue is purified by flash column chromatography eluting with 50-100 EtOAc in isohexane then 0-10% MeOH in DCM to give the title product.

Step 2: Synthesis of 8-chloro-1-(2-(pyridin-2-yl)-2,6-diazaspiro[3.3]heptan-6-yl)-5,6-dihydro-4H-benzo[f][1,2,4]triazolo[4,3-a][1,4]diazepine hydrochloride

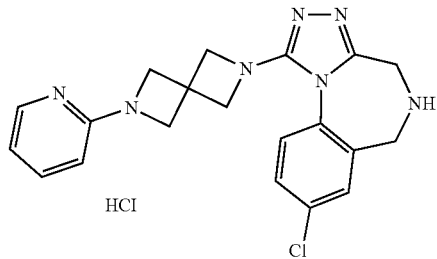

To a solution of tert-butyl 8-chloro-1-(2-(pyridin-2-yl)-2,6-diazaspiro[3.3]heptan-6-yl)-4H-benzo[f][1,2,4]triazolo[4,3-a][1,4]diazepine-5(6H)-carboxylate (0.20 mmol, 1.0 eq.) in MeOH is added 4N HCl solution in dioxane (0.5 mL, 2.03 mmol, 10.0 eq.) and the mixture is stirred at RT for 6 hours. The mixture is concentrated in vacuo, EtOAc is added and the solution is washed with Sat. NaHCO₃, the aqueous layer is re-extracted with EtOAc (×2). The organic phases are combined, dried (MgSO4), filtered and concentrated in vacuo to give the title compound.

Step 3: Synthesis of 8-chloro-5-(oxetan-3-yl)-1-(2-(pyridin-2-yl)-2,6-diazaspiro[3.3]heptan-6-yl)-5,6-dihydro-4H-benzo[f][1,2,4]triazolo[4,3-a][1,4]diazepine (Compound No. 57)

A solution of 8-chloro-1-(2-(pyridin-2-yl)-2,6-diazaspiro[3.3]heptan-6-yl)-5,6-dihydro-4H-benzo[f][1,2,4]triazolo[4,3-a][1,4]diazepine (0.06 mmol, 1.0 eq.), 3-oxetanone (35 μL, 0.51 mmol, 8.0 eq.) in MeOH (0.5 mL) is heated to 70° C. for 6 hours. The mixture is cooled to 0° C. and sodium cyanoborohydride (0.012 g, 0.19 mmol, 3.0 eq.) is added and the mixture stirred at RT overnight. The mixture is concentrated in vacuo, diluted with DCM, passed through a phase separator and concentrated in vacuo. The residue is purified by preparative HPLC.

Example 8

Compound No. 58

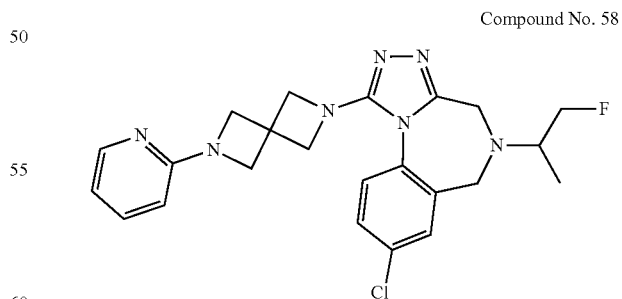

A mixture of 8-chloro-1-(2-(pyridin-2-yl)-2,6-diazaspiro[3.3]heptan-6-yl)-5,6-dihydro-4H-benzo[f][1,2,4]triazolo[4,3-a][1,4]diazepine dihydrochloride (0.11 mmol, 1.0 eq.), Et₃N (30 μL, 0.21 mmol, 2.0 eq.), fluoroacetone (62 μL, 0.86 mmol, 8.0 eq.) in MeOH (1 mL) is heated to 70° C. for 2.5 hours. Mixture is cooled to 0° C. and sodium borohydride (0.02 g, 0.32 mmol, 3 eq.) is added, mixture is stirred at RT for 2 hours. Additional sodium borohydride (0.02 g, 0.32 mmol, 3 eq.), Et₃N (30 µL, 0.21 mmol, 2.0 eq.), fluoroacetone (62 µL, 0.86 mmol, 8.0 eq.) are added and the mixture is stirred at RT for 3 days. The mixture is concentrated in vacuo, diluted with DCM, passed through a phase separator and concentrated in vacuo. The residue is purified by preparative HPLC to give the title compound.

Example 9

Compound No. 59

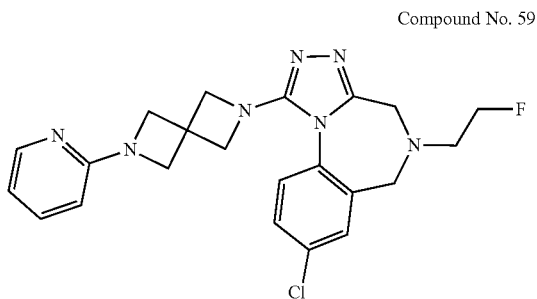 [SMILES: FCCN1Cc2cc(Cl)ccc2-n2c(nnc2N2CC3(CN(c4ccccn4)C3)C2)C1]

A mixture of 8-chloro-1-(2-(pyridin-2-yl)-2,6-diazaspiro[3.3]heptan-6-yl)-5,6-dihydro-4H-benzo[f][1,2,4]triazolo[4,3-a][1,4]diazepine in MeCN (1 mL) is added K₂CO₃ (0.13 mmol, 2.0 eq.) followed by fluoro-2-iodoethane (6 µL, 0.08 mmol, 2.0 eq.) and stirred at RT for 2 hours. The mixture is then heated to 80° C. overnight. The mixture is diluted with NaHCO₃/DCM, passed through a phase separator and concentrated in vacuo. The residue is purified by preparative HPLC. to give the title compound.

Example 10

Compound No. 60

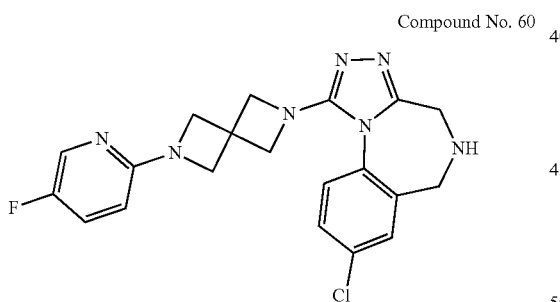

Step 1: Synthesis of 2-(4-fluoropyridin-2-yl)-2,6-diazaspiro[3.3]heptane-6-carbohydrazide

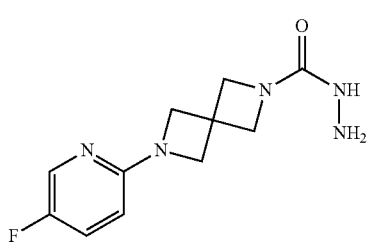 [SMILES: NNC(=O)N1CC2(C1)CN(c1ccc(F)cn1)C2]

A solution of methyl 2-(4-fluoropyridin-2-yl)-2,6-diazaspiro[3.3]heptane-6-carboxylate [prepared in a similar manner as Example 6 Step 4 using 2-bromo-5-fluoropyridine instead of 2-bromopyridine] (2.11 mmol, 1.0 eq.) in EtOH (10 mL) is added dropwise to a mixture of hydrazine monohydrate (0.62 mL, 12.7 mmol, 6.0 eq.) in EtOH. The mixture is heated to 50° C. for 1 hours, diluted with EtOAc, washed with brine and concentrated in vacuo to give the title compound.

Step 2: Synthesis of tert-butyl 8-chloro-1-(2-(5-fluoropyridin-2-yl)-2,6-diazaspiro[3.3]heptan-6-yl)-4H-benzo[f][1,2,4]triazolo[4,3-a][1,4]diazepine-5 (6H)-carboxylate

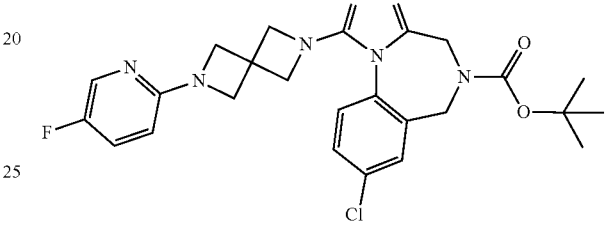

The title compound is prepared in the manner of Example 7 Step 1.

Step 3: Synthesis of 8-chloro-1-(2-(5-fluoropyridin-2-yl)-2,6-diazaspiro[3.3]heptan-6-yl)-5,6-dihydro-4H-benzo[f][1,2,4]triazolo[4,3-a][1,4]diazepine (Compound No. 60)

The title compound is prepared in the manner of Example 7 Step 2.

Example 11

Compound No. 61

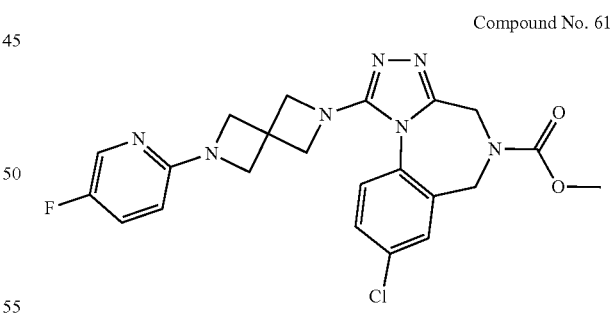

To a cooled suspension of 8-chloro-1-(2-(5-fluoropyridin-2-yl)-2,6-diazaspiro[3.3]heptan-6-yl)-4,5-dihydro-6H-benzo[f][1,2,4]triazolo[4,3-a][1,4]diazepin-6-one (prepared as in Example 7, Step 2) (0.19 mmol, 1.0 eq.), Et₃N (0.091 mL, 0.65 mmol, 3.5 eq.), at 0° C. in THF (5 mL) is added methyl chloroformate (0.022 mL, 0.28 mMol, 1.5 eq.) dropwise. The resulting suspension is stirred at RT for 1 hour, diluted with EtOAc, washed with an aq. sol. of sat. NaHCO₃, dried, concentrated in vacuo and the residue is purified by preparative HPLC to give the title compound. Compounds 62 to 90

Compound Nos. 62 to 90 are prepared according to the methods set forth in Example 11 using appropriately substituted intermediates.

Example 12

Compound No. 91

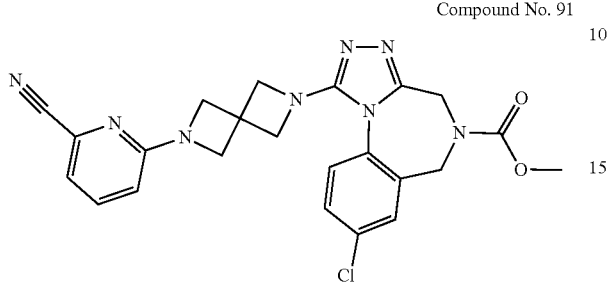

Step 1: Synthesis of tert-butyl (2-amino-5-chlorobenzyl)glycinate

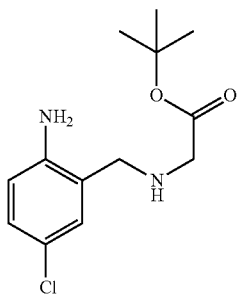 [SMILES: CC(C)(C)OC(=O)CNCc1cc(Cl)ccc1N]

To a solution of 2-amino-5-chlorobenzylamine (3.0 g, 19.16 mmol, 1.0 eq.), tert-butylbromoacetate (2.97 mL, 20.11 mmol, 1.05 eq.) in THF (60 mL) is added Et₃N (3.20 mL, 22.99 mmol, 1.2 eq.) and the mixture is stirred at room temperature overnight. The mixture is diluted with EtOAc, water and the layers separated. The aq. phase is extracted with EtOAc, the organic phases are combined, dried (MgSO₄), filtered and concentrated in vacuo to afford the title compound.

Step 2: Synthesis of 7-chloro-1,3,4,5-tetrahydro-2H-benzo[e][1,4]diazepin-2-one

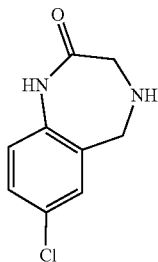 [SMILES: O=C1CNCc2cc(Cl)ccc2N1]

To a solution of tert-butyl (2-amino-5-chlorobenzyl)glycinate in THF (90 mL) is slowly added a solution of KOtBu (2.53 g, 22.56 mmol, 1.2 eq.) in THF (60 mL). The mixture is stirred at RT for 90 minutes, diluted with sat. sol. of NH₄Cl and extracted with EtOAc (×3). The organic phases are combined, dried (MgSO₄), filtered and concentrated in vacuo to afford the title compound.

Step 3: Synthesis of tert-butyl 7-chloro-2-oxo-1,2,3,5-tetrahydro-4H-benzo[e][1,4]diazepine-4-carboxylate

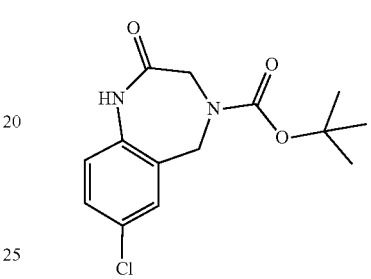

To a cooled suspension of 7-chloro-1,3,4,5-tetrahydro-2H-benzo[e][1,4]diazepin-2-one (3.11 g, 15.82 mmol, 1.0 eq.) in THF (75 mL) at 0° C. is added a solution of di-tert-butyl dicarbonate (4.14 g, 18.98 mmol, 1.2 eq.) in THF (35 mL) dropwise over 10 minutes. The mixture is allowed to warm to RT and stirred overnight. The mixture is concentrated in vacuo and triturated with diethyl ether to afford the title compound.

Step 4: Synthesis of tert-butyl 7-chloro-2-thioxo-1,2,3,5-tetrahydro-4H-benzo[e][1,4]diazepine-4-carboxylate

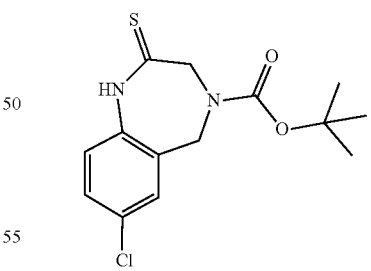

To a suspension of tert-butyl 7-chloro-2-oxo-1,2,3,5-tetrahydro-4H-benzo[e][1,4]diazepine-4-carboxylate (3.36 g, 11.32 mmol, 1.0 eq.) in THF (80 mL) is added 2,4-bis(4-methoxyphenyl)-2,4-dithioxo-1,3,2,4-dithiadiphosphetane (2.75 g, 6.79 mmol, 0.60 eq.) and the mixture is heated to reflux for 90 minutes. The mixture is allowed to cool, concentrated in vacuo, triturated with TBME and filtered. The solid is discarded and the filtrate is concentrated in vacuo to afford the title compound.

Step 5: Synthesis of 7-chloro-1,3,4,5-tetrahydro-2H-benzo[e][1,4]diazepine-2-thione

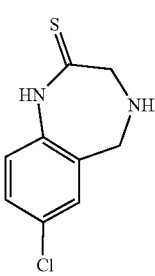 [SMILES: S=C1CNCc2cc(Cl)ccc2N1]

To a solution of tert-butyl 7-chloro-2-thioxo-1,2,3,5-tetrahydro-4H-benzo[e][1,4]diazepine-4-carboxylate (1.08 g, 3.45 mmol, 1.0 eq.) in DCM (30 mL) is added TFA (10 mL) and the mixture is stirred at RT for 1 hour and concentrated in vacuo to afford the title compound.

Step 6: Synthesis of tert-butyl 6-(8-chloro-5,6-dihydro-4H-benzo[f][1,2,4]triazolo[4,3-a][1,4]diazepin-1-yl)-2,6-diazaspiro[3.3]heptane-2-carboxylate

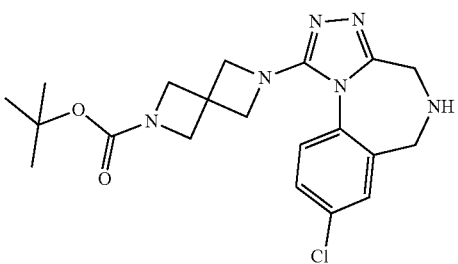 [SMILES: CC(C)(C)OC(=O)N1CC2(C1)CN(c1nnc3n1-c1ccc(Cl)cc1CNC3)C2]

The procedure of Example 1, Step 2 is employed to afford the title compound.

Step 7: Synthesis of methyl 1-(2-(tert-butoxycarbonyl)-2,6-diazaspiro[3.3]heptan-6-yl)-8-chloro-4H-benzo[f][1,2,4]triazolo[4,3-a][1,4]diazepine-5(6H)-carboxylate

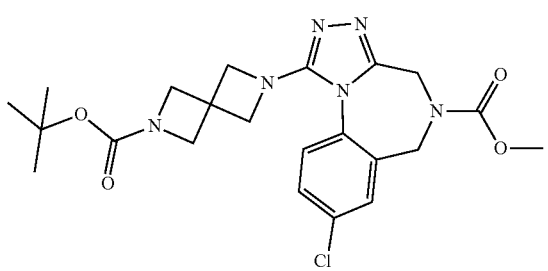 [SMILES: COC(=O)N1Cc2cc(Cl)ccc2-n2c(nnc2N2CC3(CN(C(=O)OC(C)(C)C)C3)C2)C1]

The procedure of Example 11 is employed to afford the title compound.

Step 8: Synthesis of methyl 8-chloro-1-(2,6-diazaspiro[3.3]heptan-6-yl)-4H-benzo[f][1,2,4]-triazolo[4,3-a][1,4]diazepine-5(6H)-carboxylate

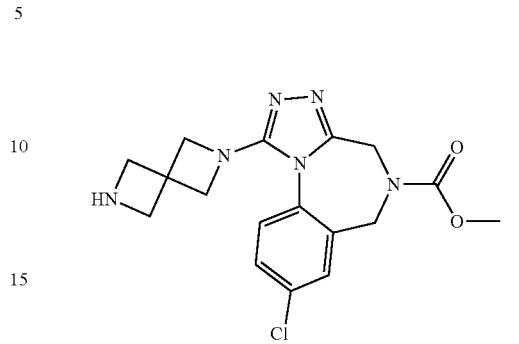

The procedure of Example 1, Step 3, is employed to afford the title compound.

Step 9: Synthesis of methyl 8-chloro-1-(2-(6-cyanopyridin-2-yl)-2,6-diazaspiro[3.3]heptan-6-yl)-4H-benzo[f][1,2,4]triazolo[4,3-a][1,4]diazepine-5(6H)-carboxylate (Compound No. 91)

The procedure of Example 1, Step 4 using 6-bromo-2-pyridinecarbonitrile is employed to afford the title compound.

Compound Nos. 92 to 94

Compound Nos. 92 to 94 are prepared according to the methods set forth in Example 12 using appropriately substituted intermediates.

Example 13

Compound No. 95

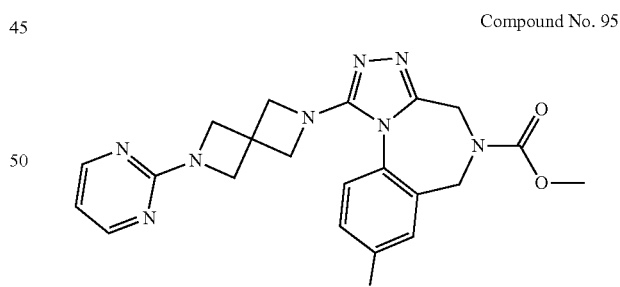

A mixture of methyl 8-chloro-1-(2,6-diazaspiro[3.3]heptan-6-yl)-4Hbenzo[f][1,2,4]triazolo[4,3-a][1,4]diazepine-5(6H)-carboxylate (Example 2 Step 8) (0.0802 mmol, 1.0 eq.), 2-chloropyrimidine (0.0092 g, 0.0802 mmol, 1.0 eq.), cesium carbonate (0.031 g, 0.0963 mmol, 1.2 eq.) in DMF is heated 80° C. in a reaction tube for 4 hours. The mixture is diluted with water and extracted with EtOAc (×3). The organic phases are combined washed with brine, dried (MgSO4), filtered and concentrated in vacuo to afford the title compound.

527

Example 14

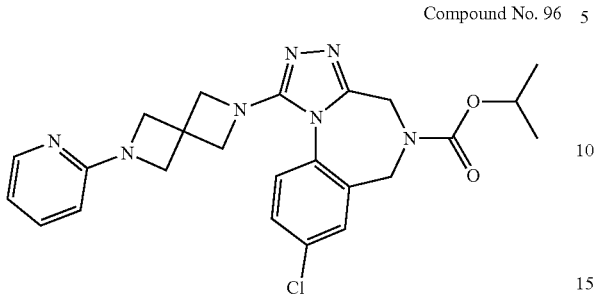

Compound No. 96

Step 1: Synthesis of isopropyl 7-chloro-2-thioxo-1,2,3,5-tetrahydro-4H-benzo[e][1,4]diazepine-4-carboxylate

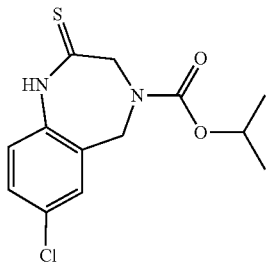 [SMILES: CC(C)OC(=O)N1CC(=S)Nc2ccc(Cl)cc2C1]

To a cooled mixture of 7-chloro-1,3,4,5-tetrahydro-2H-benzo[e][1,4]diazepine-2-thione as prepared by Example 12, Step 5 (0.06 g, 0.28 mmol, 1.0 eq.), Et₃N (59 μL, 0.42 mmol, 1.5 eq.) at 0° C. in DCM is added isopropyl chloroformate (0.31 mL, 0.31 mmol, 1.10 eq.) and the mixture is stirred at RT overnight. The mixture is diluted with DCM, Sat. NaHCO₃ and passed through a phase separator and concentrated in vacuo to afford the title compound.

Step 2: Synthesis of isopropyl 8-chloro-1-(2-(pyridin-2-yl)-2,6-diazaspiro[3.3]heptan-6-yl)-4H-benzo[f][1,2,4]triazolo[4,3-a][1,4]diazepine-5(6H)-carboxylate (Compound No. 96

The procedure of Example 7, Step 2 is employed to afford the title compound.

Example 15

Compound No. 97

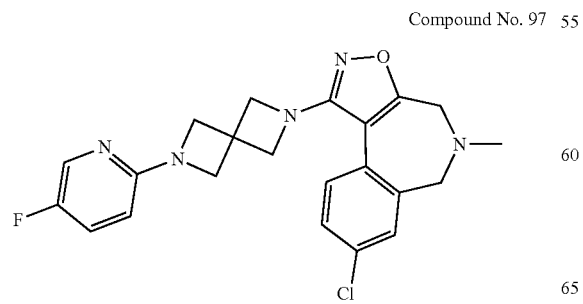

528

Step 1: Synthesis of tert-butyl (E)-6-(chloro(hydroxyimino)methyl)-2,6-diazaspiro[3.3]heptane-2-carboxylate

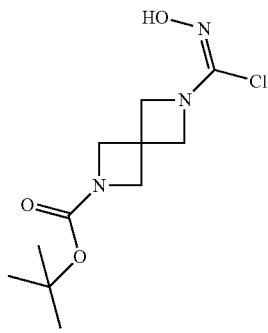 [SMILES: CC(C)(C)OC(=O)N1CC2(C1)CN(/C(Cl)=N\O)C2]

To a cooled solution of tert-butyl 6-formyl-2,6-diazaspiro[3.3]heptane-2-carboxylate (3.6 mmol, 1.0 eq.) in MeOH (4 mL), water (4 mL) at 0° C. is added Na₂CO₃ (0.188 g, 1.8 mmol, 0.5 eq.) followed by hydroxylamine hydrochloride (0.283 mg, 4.1 mmol, 1.15 eq.) and stirred at 0° C. for 2 hours. The mixture is then stirred at RT for 3 days, concentrated in vacuo, partitioned between EtOAc and H₂O. The organic phase is isolated, concentrated in vacuo the residue dissolved in DMF (8 mL), NCS (0.474 g, 3.6 mmol, 1.0 eq) is added and the mixture is stirred at RT overnight. The mixture is diluted with EtOAc and 4% aq. sol. of LiCl and stirred at RT overnight. The organic layer is separated and concentrated in vacuo to afford the title compound.

Step 2: Synthesis of tert-butyl 6-(5-(bromomethyl) isoxazol-3-yl)-2,6-diazaspiro[3.3]heptane-2-carboxylate

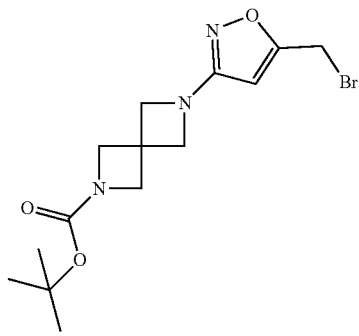 [SMILES: CC(C)(C)OC(=O)N1CC2(C1)CN(c1cc(CBr)on1)C2]

To a cooled mixture of tert-butyl (E)-6-(chloro(hydroxyimino)methyl)-2,6-diazaspiro[3.3]heptane-2-carboxylate (3.6 mmol, 1.0 eq.), propargyl bromide (80% sol. in toluene, 481.2 μL, 4.3 mmol, 1.2 eq) at 0° C. in DCM (10 mL) is added Et₃N (607.1 μL, 4.3 mmol, 1.2 eq.) in DCM dropwise. The mixture is allowed to warm to RT and stirred overnight. Mixture is diluted with DCM, washed with water and concentrated in vacuo to afford the title compound.

Step 3: Synthesis of 1-(5-chloro-2-iodophenyl)-N-methylmethanamine

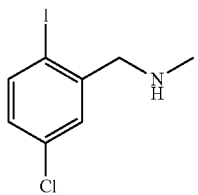

To a solution of 5-chloro-2-iodobenzaldehyde (1.0 g, 3.8 mmol, 1.0 eq.) in anhydrous MeOH (20 mL) is added NaHCO$_3$ (0.95 g, 11.3 mmol, 3.0 eq.), methylamine (33% sol. in EtOH) (0.93 mL, 7.5 mmol, 2.0 eq.) and the mixture is refluxed for 4 hours. The mixture is cooled to 0° C., sodium borohydride (0.17 g, 4.5 mmol, 1.20 eq.) is added portion wise, the mixture is allowed to warm to RT and stirred at RT overnight. The reaction is quenched with H$_2$O (2 mL) and concentrated in vacuo to give a residue. This is partitioned between DCM and brine. The organic phase is separated and the aq. layer is extracted with DCM (×2). The organic phases are combined, dried (MgSO$_4$), concentrated in vacuo to afford the title compound.

Step 4: Synthesis of tert-butyl 6-(5-(((5-chloro-2-iodobenzyl)(methyl)amino)methyl)isoxazol-3-yl)-2,6-diazaspiro[3.3]heptane-2-carboxylate

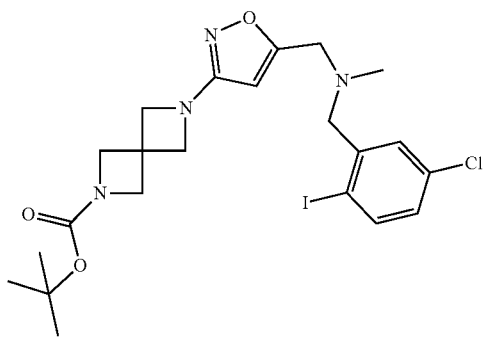 [SMILES: CN(Cc1cc(N2CC3(CN(C(=O)OC(C)(C)C)C3)C2)no1)Cc1cc(Cl)ccc1I]

To a solution of tert-butyl 6-(5-(bromomethyl)isoxazol-3-yl)-2,6-diazaspiro[3.3]heptane-2-carboxylate (1.4 mmol, 1.0 eq) in THF (5 mL) is added 1-(5-chloro-2-iodophenyl)-N-methylmethanamine (0.433 g, 2.1 mmol, 1.1 eq.), potassium carbonate (0.29 g, 2.1 mmol, 1.5 eq.) and stirred at RT for 48 hours. The mixture is diluted with DCM, washed with brine and concentrated in vacuo. The residue is purified using a Biotage® KP—NH cartridge, eluting with isohexane, isohexane:EtOAc (75%:25%) followed by 100% EtOAc, to afford the title compound.

Step 5: Synthesis of tert-butyl 6-(8-chloro-5-methyl-5,6-dihydro-4H-benzo[c]isoxazolo[4,5-e]azepin-1-yl)-2,6-diazaspiro[3.3]heptane-2-carboxylate

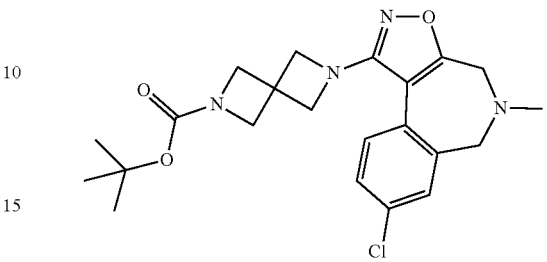

A mixture of tert-butyl 6-(5-(((5-chloro-2-iodobenzyl)(methyl)amino)-methyl)isoxazol-3-yl)-2,6-diazaspiro[3.3]heptane-2-carboxylate (0.3 mmol, 1.0 eq.), potassium carbonate (0.178 g, 1.3 mmol, 4.0 eq.), pivalic acid (0.0098 g, 0.1 mmol, 0.3 eq.), triphenylphosphine (0.0253 mg, 0.1 mmol, 0.3 eq.) in DMA (2 mL) is degassed using N$_2$ for 2 hours. Palladium acetate (0.0072 g, 0.0032 mmol, 0.1 eq.) is added and the reaction is heated to 80° C. for 2 hours, 100° C. for 2 hour, and 110° C. for 2 hours. The mixture is allowed to cool overnight. The mixture is filtered through a pad of celite, the filtrate is diluted with EtOAc, washed with 4% aq. sol. of LiCl (×4). The organic phase is concentrated in vacuo, the residue is purified using a Biotage® KP—NH cartridge, eluting with isohexane, isohexane:EtOAc (70%:30%) to afford the title compound.

Step 6: Synthesis of 8-chloro-1-(2-(5-fluoropyridin-2-yl)-2,6-diazaspiro[3.3]heptan-6-yl)-5-methyl-5,6-dihydro-4H-benzo[c]isoxazolo[4,5-e]azepine (Compound No. 97)

To a solution of tert-butyl 6-(8-chloro-5-methyl-5,6-dihydro-4H-benzo[c]isoxazolo[4,5-e]azepin-1-yl)-2,6-diazaspiro[3.3]heptane-2-carboxylate (0.2 mmol, 1.0 eq.) in DCM (1 mL) is added TFA (0.3 mL, 3.30 mmol, 20.0 eq.), the mixture is stirred at RT for 30 minutes and concentrated in vacuo. The procedure of Example 1, Step 4 is employed to afford the title compound.

Compound Nos 98 to 106

Compound Nos. 98 to 106 are prepared according to the methods set forth in Table 2 below. In particular, such compound may be prepared according to the procedures of Examples 1, 11, 15, and 16 using appropriately substituted intermediates.

TABLE 2

Compound Nos. 98 to 106

| Cpd. No. | Synthesis Method |
|---|---|
| 98 | Examples 15 and 1 |
| 99 | Examples 15 and 11 |
| 100 | Examples 15 and 11 |
| 101 | Examples 15 and 11 |
| 102 | Examples 15 and 16 |
| 103 | Examples 15 and 16 |
| 104 | Examples 15 and 16 |
| 105 | Examples 15 and 16 |
| 106 | Examples 15 and 16 |

Example 16

Compound No. 107

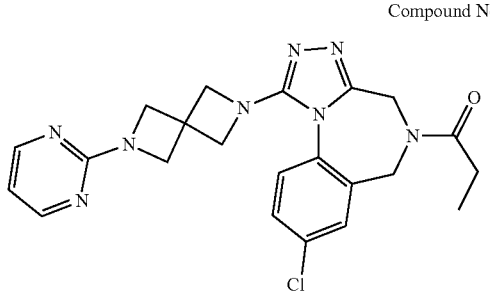

Step 1: Synthesis of tert-butyl 6-(8-chloro-5-propionyl-5,6-dihydro-4H-benzo[f][1,2,4]triazolo[4,3-a][1,4]diazepin-1-yl)-2,6-diazaspiro[3.3]heptane-2-carboxylate

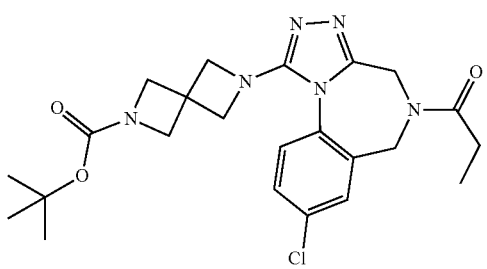 [SMILES: CCC(=O)N1Cc2cc(Cl)ccc2-n2c(nnc2N2CC3(CN(C(=O)OC(C)(C)C)C3)C2)C1]

To a cooled solution of tert-butyl 6-(8-chloro-5,6-dihydro-4H-benzo[f][1,2,4]triazolo[4,3-a][1,4]diazepin-1-yl)-2,6-diazaspiro[3.3]heptane-2-carboxylate (2.4 mmol, 1.0 eq.), prepared in Example 12, Step 6, in DCM (20 mL) at 0° C. is added Et₃N (503 µL, 3.61 mmol, 1.5 eq.), propionyl chloride (231 µL, 2.64 mmol, 1.1 eq.) and the mixture is stirred at 0° C. for 30 minutes. The mixture is diluted with DCM and washed with sat.NaHCO₃, the organic layer is isolated and concentrated in vacuo. The residue is purified using flash column chromatography, eluting with 0-10 MeOH in EtOAc to give the title compound.

Step 2: Synthesis of 1-(8-chloro-1-(2-(pyrimidin-2-yl)-2,6-diazaspiro[3.3]heptan-6-yl)-4H-benzo[f][1,2,4]triazolo[4,3-a][1,4]diazepin-5(6H)-yl)propan-1-one (Compound No. 107)

A solution of tert-butyl 6-(8-chloro-5-propionyl-5,6-dihydro-4H-benzo[f][1,2,4]triazolo[4,3-a][1,4]diazepin-1-yl)-2,6-diazaspiro[3.3]heptane-2-carboxylate (0.11 mmol, 1.0 eq.), 2-chloropyrimidine (15 mg, 0.13 mmol, 1.2 eq.), cesium carbonate (53 mg, 0.16 mmol, 1.5 eq.) in DMF (1 mL) is heated to 80° C. for 3 hours. The mixture is diluted with DCM and concentrated in vacuo. The residue is purified by preparative HPLC to yield the title compound. Compound Nos 108 to 123, 125, and 127 to 131

Compound Nos. 108 to 123, 125, and 127 to 131 are prepared according to the procedure of Example 16 using appropriately substituted intermediates.

Example 17

Compound No. 124

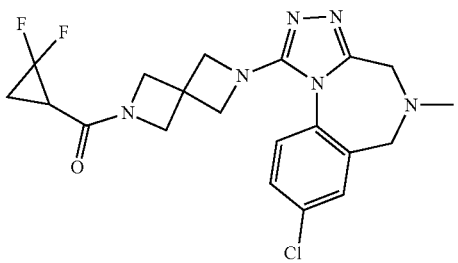

To a solution of 8-chloro-5-methyl-1-(2,6-diazaspiro[3.3]heptan-6-yl)-5,6-dihydro-4H-benzo[f][1,2,4]triazolo[4,3-a][1,4]diazepine bis(2,2,2-trifluoroacetate) (0.09 mmol, 1.0 eq.) in DMF (1.5 mL) is added 2,2-difluorocyclopropane carboxylic acid (13 mg, 0.11 mmol, 1.2 eq.), HOBt (3 mg, 0102 mmol, 0.2 eq.), EDCl·HCl (23 mg, 0.12 mmol, 1.3 eq.), DIPEA (32 µL, 0.14 mmol, 1.5 eq.) and the mixture is stirred at RT overnight. The mixture is diluted with DCM, passed through a phase separator and concentrated in vacuo. The residue is purified by preparative HPLC to give the title compound.

Compound Nos 126, 132 to 139, 144 to 155

Compound Nos. 126, 134, 136 to 138, 147, and 153 are prepared according to the methods set forth in Example 17. For example, Compound No. 126 of Table 3 lists the method of "Example 17", indicating that this compound is prepared according to the procedure of Example 17 using appropriately substituted intermediates.

Compound Nos. to 132 to 133, 135, and 139 are prepared according to the methods set forth in Table 3 below. In particular, such compound may be prepared according to the procedures of Examples 11 and 17 using appropriately substituted intermediates.

TABLE 3

Compound Nos, to 132, 133, 135, 139, 144 to 146, 148 to 152, 154 and 155

| Cpd. No. | Synthesis Method | Cpd. No. | Synthesis Method |
|---|---|---|---|
| 132 | Example 17 | 149 | Examples 17 and 11 |
| 133 | Example 17 | 150 | Examples 17 and 11 |
| 135 | Example 17 | 151 | Examples 17 and 11 |
| 139 | Example 17 | 152 | Examples 17 and 11 |
| 144 | Examples 17 and 11 | 154 | Examples 17 and 11 |
| 145 | Examples 17 and 11 | 155 | Examples 17 and 11 |
| 146 | Examples 17 and 11 | | |
| 148 | Examples 17 and 11 | | |

Example 18

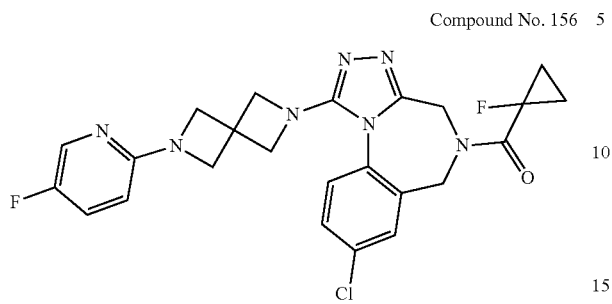

Compound No. 156

The title compound is prepared by using 8-chloro-1-(2-(5-fluoropyridin-2-yl)-2,6-diazaspiro[3.3]heptan-6-yl)-5,6-dihydro-4H-benzo[f][1,2,4]triazolo[4,3-a][1,4]diazepine from Example 10 and treating in the manner of Example 17.

Compounds 157 to 162

Compound Nos. 157 to 162 are prepared according to the methods set forth in Example 18 using appropriately substituted intermediates.

Example 19

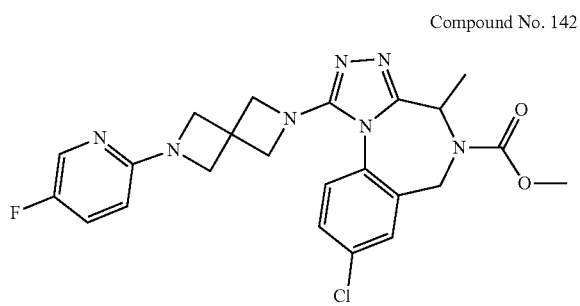 [SMILES: COC(=O)N1Cc2cc(Cl)ccc2-n2c(nnc2N2CC3(CN(c4ccc(F)cn4)C3)C2)C1C]

Compound No. 142

Step 1: Synthesis of methyl (5-chloro-2-nitrobenzyl)alaninate

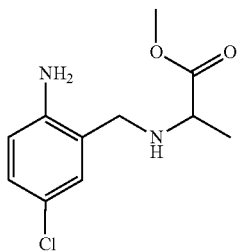 [SMILES: COC(=O)C(C)NCc1cc(Cl)ccc1N]

To a solution of 5-chloro-2-nitrobenzaldehyde (2 g, 10.78 mmol, 1.0 eq.) in DCM (30 mL) is added DL-Alanine methyl ester hydrochloride (1.5 g, 10.78 mmol, 1.0 eq.), trimethylamine (1.1 g, 10.78 mmol, 1.0 eq.) and sodium triacetoxyborohydride (4.6 g, 21.56 mmol, 2.0 eq.). The resulting solution is stirred at RT for 1 hour, diluted with DCM, washed with an aq. sol. of sat. NaHCO₃, dried, concentrated in vacuo. The residue is purified by flash column chromatography eluting with 50-100% EtOAc in isohexane to give the title compound.

Step 2: Synthesis of 7-chloro-3-methyl-1,3,4,5-tetrahydro-2H-benzo[e][1,4]diazepin-2-one

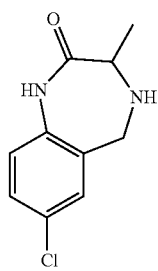

To a solution of methyl (5-chloro-2-nitrobenzyl)alaninate (1.23 g, 4.51 mmol, 1.0 eq.) in acetic acid (30 mL) is added iron (0.63 g, 11.28 mmol, 2.5 eq.). The resulting suspension is heated at 110° C. for 30 minutes, cooled to RT and filtered through celite rinsing with acetic acid. The filtrate is partitioned between aq. sol. of sat. NaHCO₃ and EtOAc and the organic phase is dried and concentrated in vacuo. The residue is triturated with diethyl ether to give the title compound.

Step 3: Synthesis of tert-butyl 7-chloro-3-methyl-2-oxo-1,2,3,5-tetrahydro-4H-benzo[e][1,4]diazepine-4-carboxylate

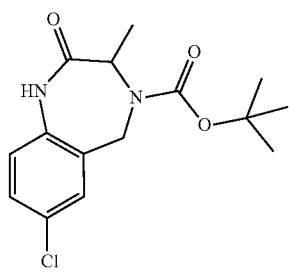 [SMILES: CC1C(=O)Nc2ccc(Cl)cc2CN1C(=O)OC(C)(C)C]

To a cooled suspension of 7-chloro-3-methyl-1,3,4,5-tetrahydro-2H-benzo[e][1,4]diazepin-2-one (2.07 g, 9.82 mmol, 1.0 eq.) in THF (20 mL) at 0° C. is added a solution of di-tert-butyl dicarbonate (3.21 g, 14.73 mmol, 1.5 eq.) in THF (10 mL) dropwise over 10 minutes. The mixture is allowed to warm to RT and stirred overnight. The mixture is concentrated in vacuo and triturated with diisopropyl ether to afford the title compound.

Step 4: Synthesis of tert-butyl 7-chloro-3-methyl-2-thioxo-1,2,3,5-tetrahydro-4H-benzo[e][1,4]diazepine-4-carboxylate

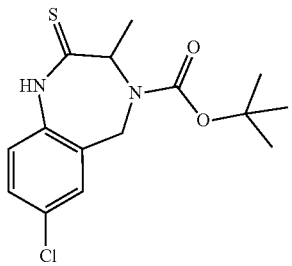 [SMILES: CC1C(=S)Nc2ccc(Cl)cc2CN1C(=O)OC(C)(C)C]

To a suspension of tert-butyl 7-chloro-3-methyl-2-oxo-1,2,3,5-tetrahydro-4H-benzo[e][1,4]diazepine-4-carboxylate (0.95 g, 3.06 mmol, 1.0 eq.) in THF (10 mL) is added 2,4-bis(4-methoxyphenyl)-2,4-dithioxo-1,3,2,4-dithiadiphosphetane (0.74 g, 1.83 mmol, 0.60 eq.) and the mixture is heated to reflux for 90 minutes. The mixture is allowed to cool, concentrated in vacuo. The residue is purified by flash column chromatography eluting with 90-100% EtOAc in isohexane to give the title compound.

Step 5: Synthesis of tert-butyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate

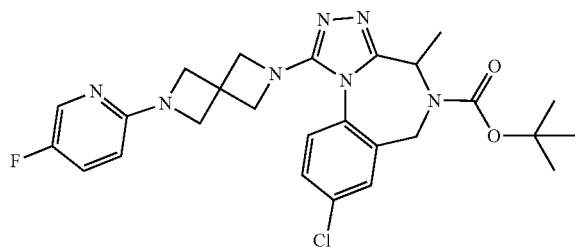 [SMILES: CC1c2nnc(N3CC4(CN(c5ccc(F)cn5)C4)C3)n2-c2ccc(Cl)cc2CN1C(=O)OC(C)(C)C]

To a solution of tert-butyl 7-chloro-3-methyl-2-thioxo-1,2,3,5-tetrahydro-4H-benzo[e][1,4]diazepine-4-carboxylate (0.3 g, 0.92 mmol, 1.0 eq.), is added 2-(4-fluoropyridin-2-yl)-2,6-diazaspiro[3.3]heptane-6-carbohydrazide (1.01 mmol, 1.1 eq.) in dioxane (5 mL) and the mixture is heated to 90° C. for 36 hours. The mixture is allowed to cool and is concentrated in vacuo. The residue is purified by flash column chromatography eluting with 90-100% EtOAc in isohexane then 0-10% MeOH in DCM to give the title product.

Step 6: Synthesis of methyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (Compound No. 142)

To a solution of tert-butyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (4.31 mmol, 1.0 eq.) in MeOH (3 mL) is added 4 M HCl in dioxane (1.5 mL, 5.90 mmol, 10.0 eq.) and the mixture is stirred at RT for 1 hour. The mixture is concentrated in vacuo to give a product. To product (137 mg, 0.29 mmol, 1.0 eq.) and Et₃N (0.15 mL, 1.04 mmol, 3.5 eq.) at 0° C. in THF (3 mL) is added methyl chloroformate (0.034 mL, 0.45 mmol, 1.5 eq.) dropwise. The resulting solution is stirred at RT for 1 hour, diluted with EtOAc, washed with an aq. sol. of sat. NaHCO₃, and dried. The mixture is concentrated in vacuo and the residue is purified by preparative HPLC to give the title compound.

Compounds 140, 141, 143 and 163 to 173

Compound Nos. 163 to 173, and 140, 141, and 143 are prepared according to the procedures of Examples 19 using appropriately substituted intermediates.

Example 20

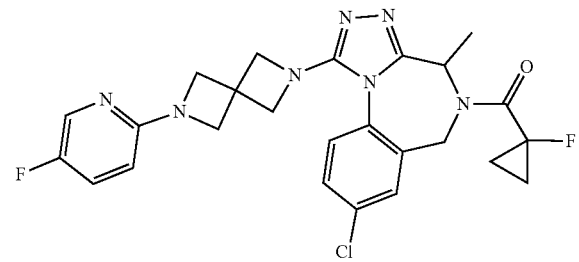

Compound No. 174

To a solution of tert-butyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (4.31 mmol, 1.0 eq.) in MeOH (3 mL) is added 4 M HCl in dioxane (1.5 mL, 5.90 mmol, 10.0 eq.) and the mixture is stirred at RT for 1 hour. The mixture is concentrated in vacuo to give a product. To a solution of the product (137 mg, 0.29 mmol, 1.0 eq.) in DMF (3 mL) is added 1-fluorocyclopropane-1-carboxylic acid (37 mg, 0.36 mmol, 1.2 eq.), HOBt (8 mg, 0.059 mmol, 0.2 eq.), EDCl·HCl (74 mg, 0.39 mmol, 1.3 eq.), DIPEA (181 µL, 1.04 mmol, 3.5 eq.) and the mixture is stirred at RT overnight. The mixture is partitioned between aq. sol. of sat. NaHCO₃ and DCM and the organic phase is dried and concentrated in vacuo. The residue is purified by preparative HPLC to give the title compound.

Compound 175

Compound No. 175 is prepared according to the methods set forth in Example 20 using appropriately substituted intermediates.

Example 21

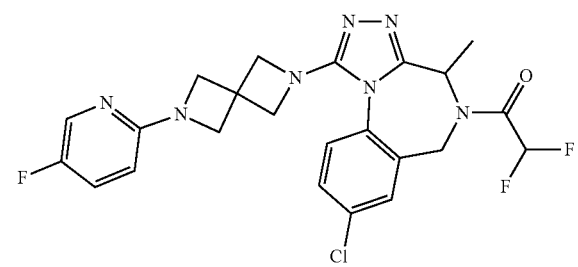

Compound No. 176

To a solution of tert-butyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (4.31 mmol, 1.0 eq.) in MeOH (3 mL) is added 4 M HCl in dioxane (1.5 mL, 5.90 mmol, 10.0 eq.) and the mixture is stirred at RT for 1 hour. The mixture is concentrated in vacuo to give a product. To a solution of the product (60 mg, 0.14 mmol, 1.0 eq.) in DMF (1 mL) is added difluoroacetic acid (13 μL, 0.21 mmol, 1.5 eq.), HATU (80 mg, 0.21 mmol, 1.5 eq.), DIPEA (37 μL, 0.21 mmol, 1.5 eq.) and the mixture is stirred at RT overnight. The mixture is partitioned between aq. sol. of sat. NaHCO$_3$ and DCM and the organic phase is dried and concentrated in vacuo. The residue is purified by preparative HPLC to give the title compound.

Compound Nos. 177 to 178

Compound Nos. 177 to 178 are prepared according to the methods set forth in Example 21 using appropriately substituted intermediates.

Example 22

Compound No. 179

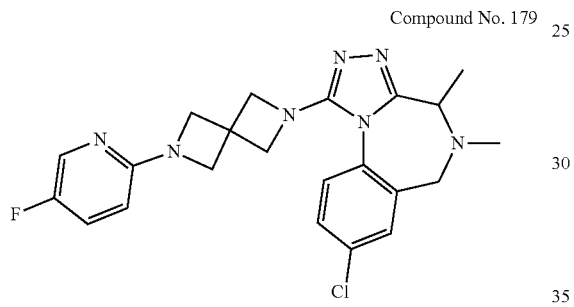

To a solution of 8-chloro-1-(2-(5-fluoropyridin-2-yl)-2,6-diazaspiro[3.3]heptan-6-yl)-4-methyl-5,6-dihydro-4H-benzo[f][1,2,4]triazolo[4,3-a][1,4]diazepine (0.19 mmol, 1.0 eq.) in DCM (2 mL) is added a 37% formaldehyde aq. (0.043 mL, 0.57 mmol, 3.0 eq.), acetic acid (0.1 mL) and sodium triacetoxyborohydride (81 mg, 0.38 mmol, 2.0 eq.). The resulting solution is stirred at RT for 16 hours, diluted with DCM, washed with an aq. sol. of sat. NaHCO$_3$, dried, concentrated in vacuo to give the title compound.

Compound Nos. 22 and 23

Compound Nos. 22 and 23 are prepared according to the procedure of Example 22 using appropriately substituted intermediates.

Example 23

Compound No. 180

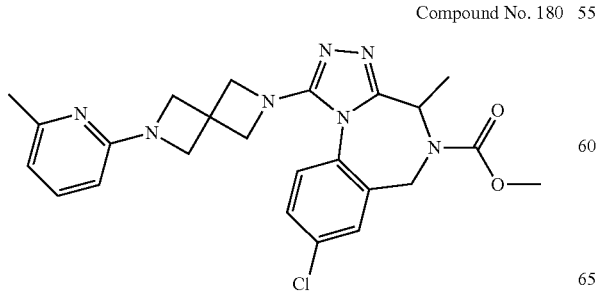

To a solution of methyl 1-(2-(tert-butoxycarbonyl)-2,6-diazaspiro[3.3]heptan-6-yl)-8-chloro-4-methyl-4H-benzo[f][1,2,4]triazolo[4,3-a][1,4]diazepine-5(6H)-carboxylate (0.51 mmol, 1.0 eq.) in DCM (15 mL) is added TFA (1.1 mL, 14.4 mmol, 28.1 eq.) and the mixture is stirred at RT for 1 hour. Toluene is added and the mixture is concentrated in vacuo to give a product. A mixture of the product (50 mg, 0.13 mmol, 1.0 eq.), 2-bromo-6-methylpyridine (0.015 mL, 0.13 mmol, 1.0 eq.), RuPhos (12 mg, 0.03 mmol, 0.20 eq.), palladium acetate (3 mg, 0.01 mmol, 0.10 eq.), cesium carbonate (0.126 g, 0.39 mmol, 3.0 eq.) in dioxane (3 mL) is degassed using N$_2$, for 10 minutes and then heated to 80° C. for 2 hours. The mixture is allowed to cool to RT and partitioned between water and EtOAc. The organic phase is dried and concentrated in vacuo and the residue is purified by preparative HPLC to give the title compound.

Compound Nos 181 to 183

Compound Nos. 181 to 183 are prepared according to the methods set forth in Example 23 using appropriately substituted intermediates.

Example 24

Compound No. 184

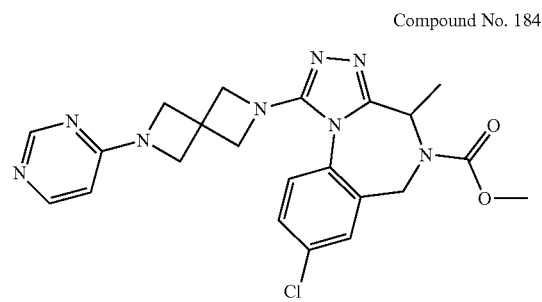 [SMILES: COC(=O)N1Cc2cc(Cl)ccc2-n2c(nnc2N2CC3(CN(c4ccncn4)C3)C2)C1C]

Step 1: Synthesis of methyl 7-chloro-3-methyl-2-oxo-1,2,3,5-tetrahydro-4H-benzo[e][1,4] diazepine-4-carboxylate

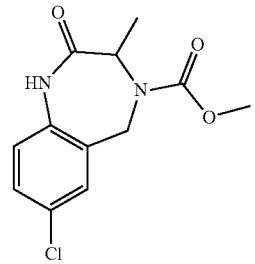 [SMILES: COC(=O)N1Cc2cc(Cl)ccc2NC(=O)C1C]

To a solution 7-chloro-3-methyl-1,3,4,5-tetrahydro-2H-benzo[e][1,4]diazepin-2-one, prepared in Example 1 Step 2, (1.0 g, 4.75 mmol, 1.0 eq.) and Et$_3$N (1.3 mL, 9.49 mmol, 2.0 eq.) at 0° C. in THF (20 mL) is added methyl chloroformate (0.55 mL, 7.12 mmol, 1.5 eq.) dropwise. The resulting solution is stirred at RT for 2 hours, diluted with EtOAc, washed with an aq. sol. of sat. NaHCO$_3$, and dried. The residue is purified by flash column chromatography eluting with 70-100% EtOAc in isohexane to give the title compound.

Step 2: Synthesis of methyl 7-chloro-3-methyl-2-thioxo-1,2,3,5-tetrahydro-4H-benzo[e][1,4]diazepine-4-carboxylate

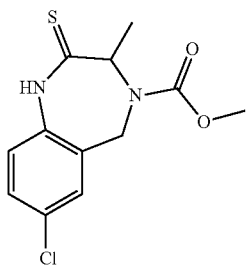

To a suspension of methyl 7-chloro-3-methyl-2-oxo-1,2,3,5-tetrahydro-4H-benzo[e][1,4]diazepine-4-carboxylate (0.82 g, 3.05 mmol, 1.0 eq.) in THF (10 mL) is added 2,4-bis(4-methoxyphenyl)-2,4-dithioxo-1,3,2,4-dithiadiphosphetane (0.74 g, 1.83 mmol, 0.60 eq.) and the mixture is heated to reflux for 1 hour. The mixture is allowed to cool and is concentrated in vacuo. The residue is purified by flash column chromatography eluting with 90-100% EtOAc in isohexane to give the title compound.

Step 3: Synthesis of methyl 1-(2-(tert-butoxycarbonyl)-2,6-diazaspiro[3.3]heptan-6-yl)-8-chloro-4-methyl-4H-benzo[f][1,2,4]triazolo[4,3-a][1,4]diazepine-5(6H)-carboxylate

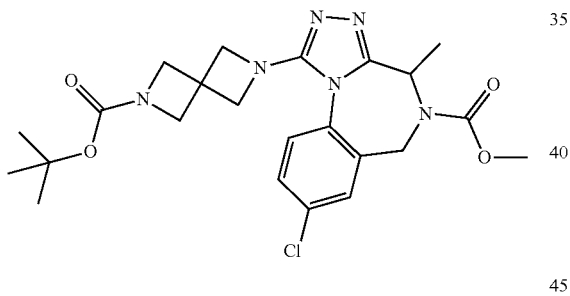

To a solution of methyl 7-chloro-3-methyl-2-thioxo-1,2,3,5-tetrahydro-4H-benzo[e][1,4]diazepine-4-carboxylate (0.3 g, 1.05 mmol, 1.0 eq.), is added tert-butyl 6-(hydrazinecarbonyl)-2,6-diazaspiro[3.3]heptane-2-carboxylate (1.26 mmol, 1.2 eq.) in dioxane (5 mL) and the mixture is heated to 90° C. for 36 hours. The mixture is allowed to cool and is concentrated in vacuo. The residue is purified by flash column chromatography eluting with 50-100% EtOAc in isohexane then 0-10% MeOH in DCM to give the title product.

Step 4: Synthesis of methyl 8-chloro-4-methyl-1-(2-(pyrimidin-4-yl)-2,6-diazaspiro[3.3]heptan-6-yl)-4H-benzo[f][1,2,4]triazolo[4,3-a][1,4]diazepine-5(6H)-carboxylate (Compound No. 184)

To a solution of methyl 1-(2-(tert-butoxycarbonyl)-2,6-diazaspiro[3.3]heptan-6-yl)-8-chloro-4-methyl-4H-benzo[f][1,2,4]triazolo[4,3-a][1,4]diazepine-5(6H)-carboxylate (0.62 mmol, 1.0 eq.) in DCM (4 mL) is added TFA (1.3 mL, 17.3 mmol, 28.1 eq.) and the mixture is stirred at RT for 1 hour. The mixture is concentrated in vacuo and is purified using a 5 g SCX-2 cartridge eluting with MeOH then 2.3 M ammonia in MeOH to give a product. To a solution of the product (20 mg, 0.052 mmol, 1.0 eq.) in N,N-dimethylformamide (1 mL) is added cesium carbonate (50 mg, 0.155 mmol, 3.0 eq.) and 4-chloropyrimidine hydrochloride (12 mg, 0.077 mmol, 1.50 eq.). The mixture is heated to 80° C. for 16 hours, allowed to cool to RT and partitioned between water and EtOAc. The organic phase is dried and concentrated in vacuo and the residue is purified by preparative HPLC to give the title compound.

Compound Nos. 185 to 190

Compound Nos. 185 to 190 are prepared according to the methods set forth in Example 24 using appropriately substituted intermediates.

Example 25

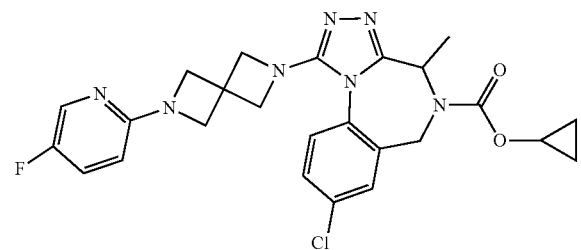

Compound No. 191

Step 1: Synthesis of 8-chloro-1-(2-(5-fluoropyridin-2-yl)-2,6-diazaspiro[3.3]heptan-6-yl)-4-methyl-5,6-dihydro-4H-benzo[f][1,2,4]triazolo[4,3-a][1,4]diazepine

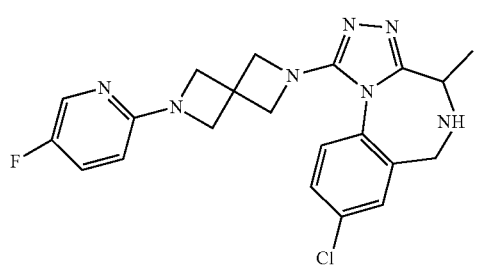 [SMILES: CC1NCc2cc(Cl)ccc2-n2c1nnc2N1CC2(CN(c3ccc(F)cn3)C2)C1]

To a solution of tert-butyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (0.57 mmol, 1.0 eq.) in DCM (4 mL) is added TFA (1.2 mL, 15.4 mmol, 28.1 eq.) and the mixture is stirred at RT for 1 hour. The mixture is concentrated in vacuo and is purified using a 5 g SCX-2 cartridge eluting with MeOH then 2.3 M ammonia in MeOH to give the title compound.

Step 2: Synthesis of cyclopropyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (Compound No. 191)

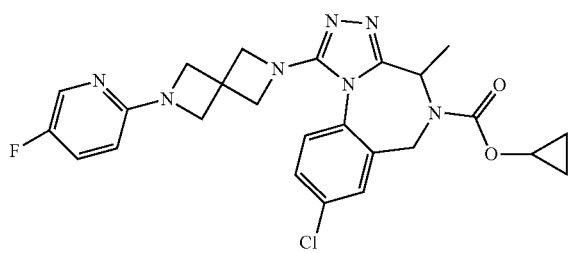 [SMILES: CC1c2nnc(N3CC4(CN(c5ccc(F)cn5)C4)C3)n2-c2ccc(Cl)cc2CN1C(=O)OC1CC1]

To a solution of cyclopropanol (33 mg, 0.57 mmol, 7.0 eq.) in MeCN (1 mL) is added CDI (93 mg, 0.57 mmol, 7.0 eq.) and the mixture stirred for 6 hours. To the mixture is added 8-chloro-1-(2-(5-fluoropyridin-2-yl)-2,6-diazaspiro[3.3]heptan-6-yl)-4-methyl-5,6-dihydro-4H-benzo[f][1,2,4]triazolo[4,3-a][1,4]diazepine (0.082 mmol, 1.0 eq.) and the resulting solution is heated to 80° C. for 16 hours. The mixture is partitioned between aq. sol. of sat. NaHCO₃ and DCM and the organic phase is dried and concentrated in vacuo. The residue is purified by preparative HPLC to give the title compound.

Compound 192

Compound No. 192 is prepared according to the methods set forth in Example 25 using appropriately substituted intermediates.

Example 26

Compound No. 193

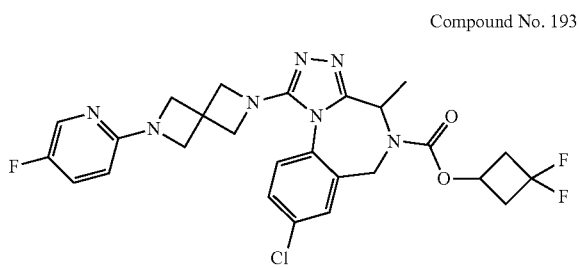 [SMILES: CC1c2nnc(N3CC4(CN(c5ccc(F)cn5)C4)C3)n2-c2ccc(Cl)cc2CN1C(=O)OC1CC(F)(F)C1]

Step 1: Synthesis of 1-((3,3-difluorocyclobutoxy)carbonyl)-3-methyl-1H-imidazol-3-ium

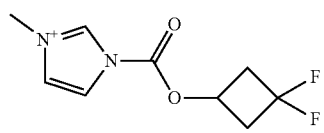

To a solution of 3,3-difluorocyclobutan-1-ol (22 mg, 0.20 mmol, 1.0 eq.) in THF (1 mL) is added CDI (40 mg, 0.24 mmol, 1.20 eq.) and the mixture stirred for 16 hours. The mixture is partitioned between water and EtOAc. The organic phase is dried and concentrated in vacuo. To a solution of the residue in MeCN (1 mL) is added iodomethane (0.038 mL, 0.61 mmol, 3.0 eq.) and the mixture stirred for 16 hours. The mixture is concentrated in vacuo to give the title compound.

Step 2: Synthesis of 3,3-difluorocyclobutyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (Compound No. 193)

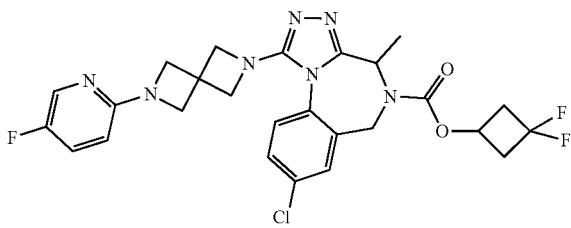 [SMILES: CC1c2nnc(N3CC4(CN(c5ccc(F)cn5)C4)C3)n2-c2ccc(Cl)cc2CN1C(=O)OC1CC(F)(F)C1]

To a solution of tert-butyl 8-chloro-1-(2-(5-fluoropyridin-2-yl)-2,6-diazaspiro[3.3]heptan-6-yl)-4-methyl-4H-benzo[f][1,2,4]triazolo[4,3-a][1,4]diazepine-5(6H)-carboxylate (0.28 g, 0.57 mmol, 1.0 eq.) in DCM (4 mL) is added TFA (1.2 mL, 15.4 mmol, 28.1 eq.) and the mixture is stirred at RT for 1 hour. The mixture is concentrated in vacuo and is purified using a 5 g SCX-2 cartridge eluting with MeOH then 2.3 M ammonia in MeOH to give a product. To a solution of the product (1.0 g, 4.75 mmol, 1.0 eq.) and Et₃N (1.3 mL, 9.49 mmol, 2.0 eq.) in MeCN (3 mL) is added a solution of 1-((3,3-difluorocyclobutoxy)carbonyl)-3-methyl-1H-imidazol-3-ium (71 mg, 0.21 mmol, 1.75 eq.) in MeCN (1 mL). The resulting solution is stirred at RT for 2 hours, filtered through celite and concentrated in vacuo. The residue is purified by preparative HPLC to give the title compound.

Compound Nos. 194 to 196 and 201 to 217

Compound Nos. 194 to 196, 201 to 207 and 215 are prepared according to the methods set forth in Example 26 using appropriately substituted intermediates.

Compound Nos. 208 to 214, 216 and 217 are prepared according to the procedure of Example 19 using appropriately substituted intermediates.

Example 27

Compound No. 197

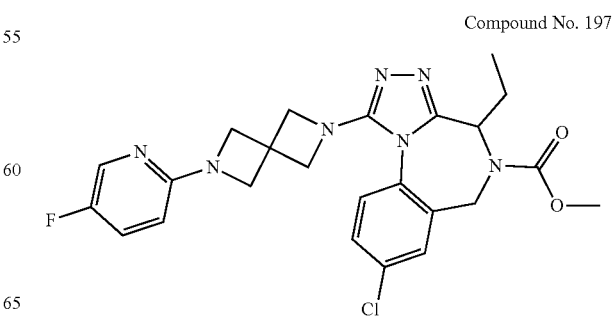

Step 1: Synthesis of methyl 2-((5-chloro-2-nitrobenzyl)amino)butanoate

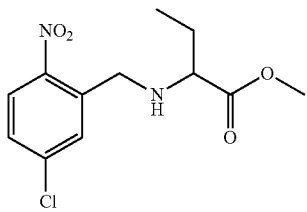 [SMILES: CCC(NCc1cc(Cl)ccc1[N+](=O)[O-])C(=O)OC]

To a solution of 5-chloro-2-nitrobenzaldehyde (0.68 g, 3.66 mmol, 1.0 eq.) in DCM (18 mL) is added methyl-DL-alpha-aminobutyrate hydrochloride (0.69 g, 3.66 mmol, 1.0 eq.), triethylamine (0.51 mL, 3.66 mmol, 1.0 eq.) and sodium triacetoxyborohydride (1.55 g, 7.31 mmol, 2.0 eq.). The resulting solution is stirred at RT for 36 hours, diluted with DCM, washed with an aq. sol. of sat. NaHCO₃, dried, concentrated in vacuo to give the title compound.

Step 2: Synthesis of 7-chloro-3-ethyl-1,3,4,5-tetrahydro-2H-benzo[e][1,4]diazepin-2-one

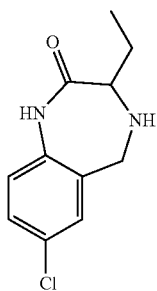

To a solution of methyl 2-((5-chloro-2-nitrobenzyl)amino)butanoate (0.29 g, 1.01 mmol, 1.0 eq.) in acetic acid (10 mL) is added iron (0.14 g, 2.53 mmol, 2.5 eq.). The resulting suspension is heated at 110° C. for 30 minutes, cooled to RT and filtered through celite rinsing with acetic acid. The filtrate is partitioned between aq. sol. of sat. NaHCO₃ and EtOAc and the organic phase is dried and concentrated in vacuo. The residue is triturated with diethyl ether to give the title compound.

Step 3: Synthesis of methyl 7-chloro-3-ethyl-2-oxo-1,2,3,5-tetrahydro-4H-benzo[e][1,4] diazepine-4-carboxylate

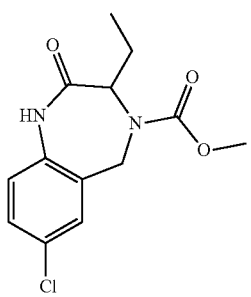 [SMILES: CCC1C(=O)Nc2ccc(Cl)cc2CN1C(=O)OC]

To a solution 7-chloro-3-ethyl-1,3,4,5-tetrahydro-2H-benzo[e][1,4]diazepin-2-one (75 mg, 0.33 mmol, 1.0 eq.) and Et₃N (0.07 mL, 0.50 mmol, 1.5 eq.) at 0° C. in THF (3 mL) is added methyl chloroformate (0.028 mL, 0.36 mmol, 1.1 eq.) dropwise. The resulting solution is stirred at RT for 20 minutes, partitioned between DCM and an aq. sol. of sat. NaHCO₃. The organics are dried, concentrated in vacuo to give the title compound.

Step 4: Synthesis of methyl 7-chloro-3-ethyl-2-thioxo-1,2,3,5-tetrahydro-4H-benzo[e][1,4] diazepine-4-carboxylate

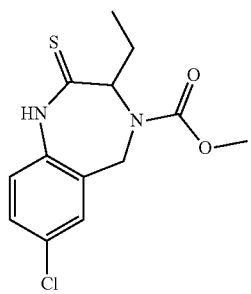 [SMILES: CCC1C(=S)Nc2ccc(Cl)cc2CN1C(=O)OC]

To a suspension of methyl 7-chloro-3-ethyl-2-oxo-1,2,3,5-tetrahydro-4H-benzo[e][1,4]diazepine-4-carboxylate (0.11 g, 0.39 mmol, 1.0 eq.) in THF (4 mL) is added 2,4-bis(4-methoxyphenyl)-2,4-dithioxo-1,3,2,4-dithiadiphosphetane (94 mg, 0.23 mmol, 0.60 eq.) and the mixture is heated to reflux for 1 hour. The mixture is allowed to cool and is concentrated in vacuo to give the title compound.

Step 5: Synthesis of methyl 8-chloro-4-ethyl-1-(2-(5-fluoropyridin-2-yl)-2,6-diazaspiro[3.3]heptan-6-yl)-4H-benzo[f][1,2,4]triazolo[4,3-a][1,4]diazepine-5(6H)-carboxylate (Compound No. 197)

To a solution of methyl 7-chloro-3-ethyl-2-thioxo-1,2,3,5-tetrahydro-4H-benzo[e][1,4]diazepine-4-carboxylate (58 mg, 0.19 mmol, 1.0 eq.), is added 2-(4-fluoropyridin-2-yl)-2,6-diazaspiro[3.3]heptane-6-carbohydrazide (0.21 mmol, 1.1 eq.) in dioxane (1 mL) and the mixture is heated to 100° C. for 16 hours. The mixture is allowed to cool and is concentrated in vacuo. The residue is purified by preparative HPLC to give the title compound.

Compound Nos. 198 to 199

Compound Nos. 198 to 199 are prepared according to the methods set forth in Example 27 using appropriately substituted intermediates.

Example 28

Compound No. 200

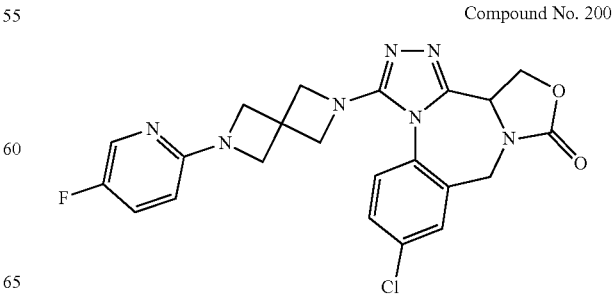

Step 1: Synthesis of methyl (5-chloro-2-nitrobenzyl)serinate

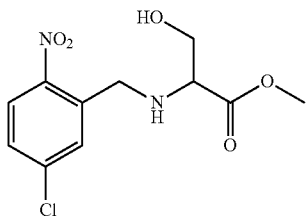 [SMILES: COC(=O)C(CO)NCc1cc(Cl)ccc1[N+](=O)[O-]]

To a solution of 2-(bromomethyl)-4-chloro-1-nitrobenzene (0.97 g, 3.86 mmol, 1.0 eq.) in DMF (10 mL) is added DL-Serine methyl ester hydrochloride (0.6 g, 3.86 mmol, 1.0 eq.) and potassium carbonate (1.07 g, 7.71 mmol, 2.0 eq.). The resulting mixture is stirred at RT for 4 hours, concentrated in vacuo, diluted with EtOAc and washed with an aq. sol. of sat. NaHCO$_3$. The organics are dried, concentrated in vacuo and the residue is purified by flash column chromatography eluting with 5% EtOAc in isohexane to give the title compound.

Step 2: Synthesis of methyl 3-(5-chloro-2-nitrobenzyl)-2-oxooxazolidine-4-carboxylate

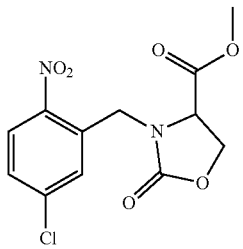 [SMILES: COC(=O)C1COC(=O)N1Cc1cc(Cl)ccc1[N+](=O)[O-]]

To a solution methyl (5-chloro-2-nitrobenzyl)serinate (0.77 g, 2.67 mmol, 1.0 eq.) and Et$_3$N (0.56 mL, 4.0 mmol, 1.5 eq.) at 0° C. in DCM (10 mL) is added triphosgene (0.23 mL, 0.80 mmol, 0.3 eq.) dropwise. The resulting solution is stirred at RT for 30 minutes, partitioned between DCM and an aq. sol. of sat. NaHCO$_3$. The organics are washed with brine, dried and concentrated in vacuo. The residue is purified by flash column chromatography eluting with 20% EtOAc in isohexane to give the title compound.

Step 3: Synthesis of 7-chloro-1,5,10,11a-tetrahydro-3H,11H-benzo[e]oxazolo[3,4-a][1,4] diazepine-3,11-dione

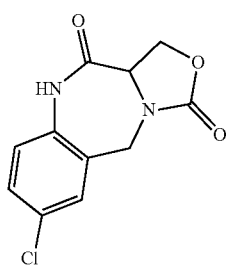

To a solution of methyl 3-(5-chloro-2-nitrobenzyl)-2-oxooxazolidine-4-carboxylate (0.51 g, 1.62 mmol, 1.0 eq.) in acetic acid (15 mL) is added iron (0.23 g, 4.05 mmol, 2.5 eq.). The resulting suspension is heated at 110° C. for 2 hours, cooled to RT and filtered through celite rinsing with acetic acid. The filtrate is partitioned between water and EtOAc and the organic phase is dried and concentrated in vacuo. The residue is triturated with diisopropyl ether to give the title compound.

Step 4: Synthesis of 7-chloro-11-thioxo-5,10,11,11a-tetrahydro-1H,3H-benzo[e]oxazolo[3,4-a][1,4] diazepin-3-one

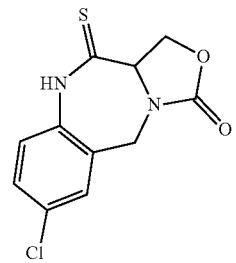 [SMILES: O=C1OCC2C(=S)Nc3ccc(Cl)cc3CN12]

To a suspension of 7-chloro-1,5,10,11a-tetrahydro-3H,11H-benzo[e]oxazolo[3,4-a][1,4]diazepine-3,11-dione (0.27 g, 1.07 mmol, 1.0 eq.) in THF (5 mL) is added 2,4-bis(4-methoxyphenyl)-2,4-dithioxo-1,3,2,4-dithiadiphosphetane (0.26 g, 0.64 mmol, 0.60 eq.) and the mixture is heated to reflux for 2 hours. The mixture is allowed to cool and is concentrated in vacuo. The residue is purified by flash column chromatography eluting with 10-100% EtOAc in isohexane to give the title compound.

Step 5: Synthesis of 7-chloro-3-(2-(5-fluoropyridin-2-yl)-2,6-diazaspiro[3.3]heptan-6-yl)-13,13a-dihydro-9H,11H-benzo[e]oxazolo[3,4-a][1,2,4]triazolo[3,4-c][1,4]diazepin-11-one (Compound No. 200)

To a solution of 7-chloro-11-thioxo-5,10,11,11a-tetrahydro-1H,3H-benzo[e] oxazolo[3,4-a][1,4]diazepin-3-one (40 mg, 0.15 mmol, 1.0 eq.), is added 2-(4-fluoropyridin-2-yl)-2,6-diazaspiro[3.3]heptane-6-carbohydrazide (0.16 mmol, 1.1 eq.) in dioxane (1 mL) and the mixture is heated to 100° C. for 16 hours. The mixture is allowed to cool and is concentrated in vacuo. The residue is purified by preparative HPLC to give the title compound.

Example 29

Isomer Separation

To the extent racemic mixtures are obtained by the synthetic techniques disclosed herein, such mixture can be resolved to homochiral forms using Supercritical Fluid Chromatography (SFC) chiral separation of the corresponding racemates. Either a Waters Thar Prep100 preparative SFC system (P200 CO2 pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module) are used. Where the Waters 2767 liquid handler is used it acted as both autosampler and fraction collector. The compounds are purified using an appropriate column selected from the following: YMC Amylose-C, YMC Cellulose-C, YMC Cellulose-SC, Phenomenex LUX Cellulose-3 or Phenomenex LUX Cellulose-4. Appropriate isocratic methods are selected based on methanol, ethanol or isopropanol solvent systems under un-modified or basic conditions. The standard method used is modifier/CO2, 100 ml/min (or as appropriate), 120 Bar backpressure, 40° C. column temperature. The modifier used under basic conditions is diethyl amine (0.1% V/V). The purification is controlled either by Waters Fractionlynx or Waters Chromscope software through monitoring at 210-400 nm and triggered a threshold collection value at an appropriate wavelength. Collected fractions are analysed by SFC (Waters/Thar SFC systems with Waters SQD or Waters UPCC with Waters QDa). The fractions that contained the desired product are concentrated by vacuum centrifugation.

Example 30

Compound No. 217

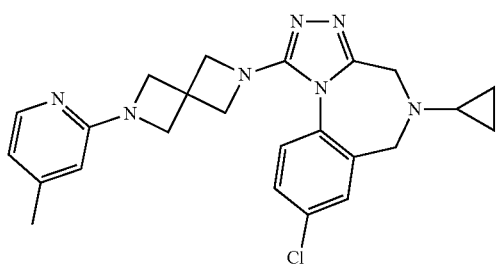

Step 1: Synthesis of tert-butyl 6-(hydrazinecarbonyl)-2,6-diazaspiro[3.3]heptane-2-carboxylate

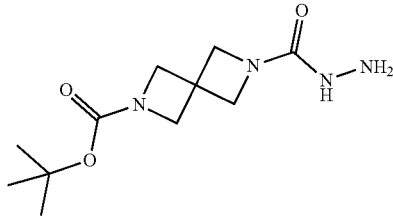 [SMILES: CC(C)(C)OC(=O)N1CC2(CN(C(=O)NN)C2)C1]

To a stirred solution of 2-(tert-butoxycarbonyl)-2,6-diazaspiro[3.3]heptane-6-carboxylic acid (1 mmol, 1 eq.) in THF (5 mL) is added 1-1'-Carbonyldiimidazole (0.19 g, 1.2 mmol, 1.2 eq.) and the mixture is stirred at RT overnight. The resulting mixture is added to a solution of hydrazine monohydrate (0.07 mL, 1.4 mmol, 1.4 eq.) in THF (10 mL) and stirred at RT overnight. The mixture is diluted with brine and extracted with ethyl acetate. The organic phase is separated, washed with brine, dried (MgSO₄), filtered and concentrated under reduced pressure to afford the title compound.

Step 2: Synthesis of tert-butyl (4-chloro-2-((cyclopropylamino)methyl)phenyl)-carbamate

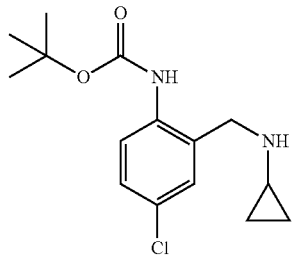 [SMILES: CC(C)(C)OC(=O)Nc1ccc(Cl)cc1CNC1CC1]

A mixture of tert-butyl (4-chloro-2-formylphenyl)carbamate (5.122 g, 20.03 mmol, 1 eq.) and cyclopropanamine (2.08 mL, 30.05 mmol, 1.5 eq.) in MeOH (65.2 mL) is stirred for 5 h at 60° C., allowed to cool to RT, and then stirred 18 h. THF (30 mL) is added to the reaction mixture, followed by solid NaCNBH₃ (2.517 g, 40.06 mmol, 2 eq.). The reaction mixture is stirred at RT for 2 hours. Acetic acid (2.29 mL, 40.06 mmol, 2 eq) is added and stirring is continued for 20 min. The reaction mixture is concentrated under reduced pressure, and the resultant crude residue is diluted with EtOAc (150 mL) and washed with sat. aq. NaHCO₃ (100 mL). The aqueous layer is collected, and the organic layer is further washed with sat. aq. NaHCO₃ (2×50 mL). The combined aqueous washes are back-extracted with EtOAc (1×100 mL) and the combined organic phases are dried over MgSO₄, filtered to remove solid material, and concentrated under reduced pressure. The residue is purified by column chromatography (SiO₂, 0-30% EtOAc/Hex—2% DCM additive) to afford the title compound.

Step 3: Synthesis of tert-butyl (4-chloro-2-(((cyanomethyl)(cyclopropyl)amino)-methyl)phenyl) carbamate

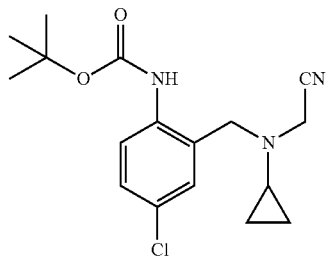 [SMILES: CC(C)(C)OC(=O)Nc1ccc(Cl)cc1CN(CC#N)C1CC1]

A mixture of K₂CO₃ (1.87 g, 13.5 mmol, 2 eq.), KI (0.671 g, 4.04 mmol, 0.6 eq.), 2-chloroacetonitrile (0.855 mL, 13.5 mmol, 2 eq.), and tert-butyl (4-chloro-2-((cyclopropylamino)methyl)phenyl)carbamate (2.00 g, 6.74 mmol, 1 eq.), added in sequence, is stirred in ACN (15 mL) under an atmosphere of N2 for 18 h at 75° C. The reaction mixture is allowed to cool to RT, diluted with EtOAc (100 mL), and washed with sat aq. NaHCO₃ (100 mL). The organic phase is collected, and the aq. phase is extracted with EtOAc (2×100 mL). The combined organic extracts are washed with 15% aq. Na₂S₂O₃ (2×100 mL), brine (1×100 mL), and dried over MgSO4. Solids are removed by vacuum filtration and the filtrate is concentrated under reduced pressure to afford the title compound.

Step 4: Synthesis of 7-chloro-4-cyclopropyl-4,5-dihydro-3H-benzo[e][1,4]diazepin-2-amine

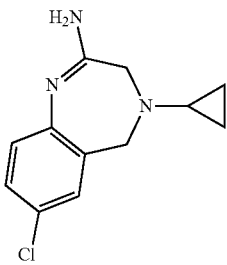 [SMILES: NC1=Nc2ccc(Cl)cc2CN(C2CC2)C1]

A solution of acetyl chloride (9.64 mL, 134.6 mmol, 20 eq.) in isopropanol (55.6 mL) is stirred for 20 min prior to slow addition to a solution of tert-butyl (4-chloro-2-(((cyanomethyl)(cyclopropyl)amino) methyl)phenyl) carbamate (2.26 g, 6.730 mmol, 1 eq.) in isopropanol (67.3 mL) and stirred for 60 h at 50° C. The reaction mixture is concentrated under reduced pressure and the crude residue is diluted with EtOAc (125 mL). The crude mixture is washed with sat aq. NaHCO₃ (1×125 mL). The organic phase is collected, and the aqueous phase is extracted with EtOAc (3×50 mL). The combined organics are washed with brine (1×50 mL), dried over MgSO₄, and solids are removed by vacuum filtration. The filtrate is concentrated under reduced pressure, and the crude residue is purified by column chromatography (SiO₂, 0-100% EtOAc/Hex, 0-100% DCM/EtOAc, 0-12% MeOH/DCM) to afford the title compound.

Step 5: Synthesis of tert-butyl 6-(8-chloro-5-cyclopropyl-5,6-dihydro-4H-benzo[f][1,2,4]triazolo [4,3-a][1,4]diazepin-1-yl)-2,6-diazaspiro[3.3]heptane-2-carboxylate

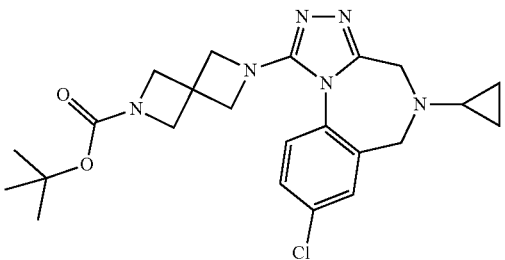 [SMILES: CC(C)(C)OC(=O)N1CC2(C1)CN(c1nnc3n1-c1ccc(Cl)cc1CN(C1CC1)C3)C2]

A mixture of 7-chloro-4-(2-methoxyethyl)-4,5-dihydro-3H-benzo[e][1,4]diazepin-2-amine (0.200 g, 0.848 mmol, 1.0 eq.), tert-butyl 6-(hydrazinecarbonyl)-2,6-diazaspiro[3.3]heptane-2-carboxylate (0.890 mmol, 1.05 eq.) from Example 32, Step 1, and AcOH (0.097 mL, 1.70 mmol, 2.0 eq.) in 2-propanol (10 mL) is heated to 80° C. for 2 h. The reaction mixture is concentrated under reduced pressure, the crude residue is diluted with DCM (10 mL) and washed with sat. aq. NaHCO₃ (10 mL). The organic phase is collected, and the aq. phase is extracted with DCM (3×10 mL). The combined organics are dried over MgSO₄, solids are removed by vacuum filtration, and the filtrate is concentrated under reduced pressure. The crude residue is purified by column chromatography (SiO₂, 0-10% MeOH/DCM) to afford the title compound.

Step 6: Synthesis of 8-chloro-5-cyclopropyl-1-(2,6-diazaspiro[3.3]heptan-2-ium-6-yl)-5,6-dihydro-4H-benzo[f][1,2,4]triazolo[4,3-a][1,4]diazepin-5-ium 2,2,2-trifluoroacetate

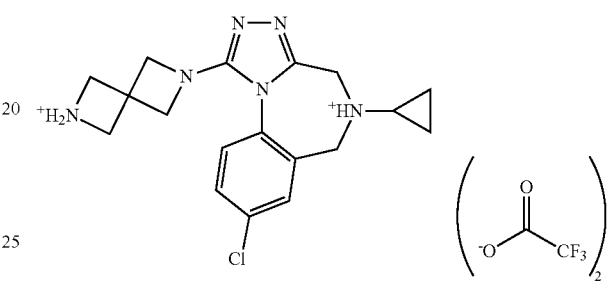

A solution of tert-butyl 6-(8-chloro-5-methyl-5,6-dihydro-4H-benzo[f][1,2,4] triazolo[4,3-a][1,4]diazepin-1-yl)-2,6-diazaspiro[3.3]heptane-2-carboxylate (0.923 mmol, 1.0 eq.) in DCM (10 mL) is stirred at 0° C. Trifluoroacetic acid (2.11 mL, 27.7 mmol, 30 eq.) is added dropwise. The reaction mixture is allowed to warm to RT and stirred for 60 min. The mixture is concentrated under reduced pressure, and the crude residue is azeotroped with toluene (4×20 mL). After 6 h under high vacuum, the title compound is isolated.

Step 7: Synthesis of 8-chloro-5-cyclopropyl-1-(2-(4-methylpyridin-2-yl)-2,6-diazaspiro[3.3]heptan-6-yl)-5,6-dihydro-4H-benzo[f][1,2,4]triazolo[4,3-a][1,4]diazepine (Compound No. 217)

A mixture of 8-chloro-5-cyclopropyl-1-(2,6-diazaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.0771 mmol, 1.0 eq), 2-chloro-4-methylpyridine (0.020 g, 0.157 mmol, 2.0 eq.), NaOᵗBu (0.0371 g, 0.386 mmol, 5.0 eq.), and RuPhos Pd G3 (0.007 g, 0.0077 mmol, 0.1 eq.) is stirred in 1,4-dioxane (1.0 mL) under a N₂ atmosphere for 2.5 h at 155° C. The reaction mixture is diluted with EtOAc (3 mL) and filtered through a pad of celite. The filter cake is washed with EtOAc (2×2 mL) and the combined filtrates are concentrated under reduced pressure. The crude residue is purified by reverse phase chromatography (5-85% ACN/H₂O, 20 min method). The title compound is isolated after lyophilization of pure fractions.

Compound Nos. 218 to 225, 227 to 229, 232 to 235, 247 to 250, and 270 to 1072

Compound Nos. 218 to 225, 227 to 229, 232 to 235, 247 to 250, and 270 to 1072 are prepared according to the procedure of Example 30 using appropriately substituted intermediates.

Example 31

Compound No. 226

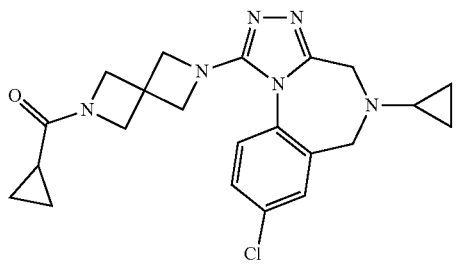

A mixture of 8-chloro-5-cyclopropyl-1-(2,6-diazaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.103 mmol, 1.0 eq) from Example 30, Step 6, DIPEA (0.090 mL, 0.515 mmol, 5 eq.), and cyclopropanecarbonyl chloride (0.014 mL, 0.154 mmol, 1.5 eq.) in DCM (1.0 mL) is stirred for 60 h at RT. The reaction mixture is concentrated under reduced pressure and the crude residue is purified by reverse phase chromatography (5-85% ACN/H$_2$O, 20 min method). The title compound is isolated.

Example 32

Compound No. 268

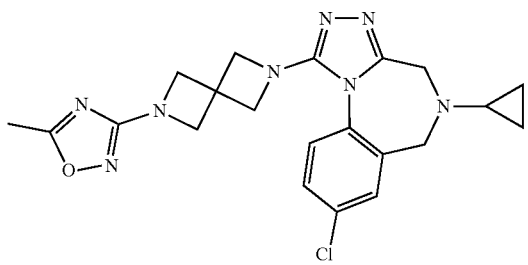

Step 1: Synthesis of 6-(8-chloro-5-cyclopropyl-5,6-dihydro-4H-benzo[f][1,2,4]triazolo[4,3-a][1,4]diazepin-1-yl)-2,6-diazaspiro[3.3]heptane-2-carbonitrile

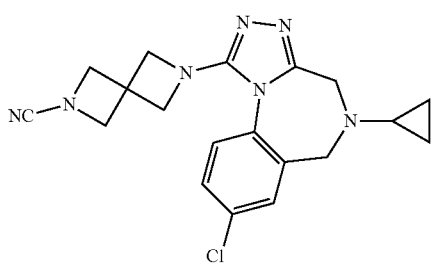 [SMILES: N#CN1CC2(C1)CN(c1nnc3n1-c1ccc(Cl)cc1CN(C1CC1)C3)C2]

A mixture of 8-chloro-5-cyclopropyl-1-(2,6-diazaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.750 mmol, 1.0 eq) from Example 30, Step 7, DIPEA (0.654 mL, 3.76 mmol, 5 eq.), and cyanogen bromide (0.159 g, 1.50 mmol, 2 eq.) is stirred in DCM (2.5 mL) for 60 min at 0° C. The reaction mixture is diluted with EtOAc (10 mL) and washed with sat. aq. NaHCO$_3$ (2×10 mL), brine (1×10 mL) and dried over MgSO$_4$. Solids are removed by vacuum filtration, and the filtrate is concentrated under reduced pressure. The crude residue is purified by column chromatography (SiO$_2$, 0-10% MeOH/DCM) to afford the title compound.

Step 2: Synthesis of (E)-6-(8-chloro-5-cyclopropyl-5,6-dihydro-4H-benzo[f][1,2,4] triazolo[4,3-a][1,4]diazepin-1-yl)-N-hydroxy-2,6-diazaspiro[3.3]heptane-2-carboximidamide

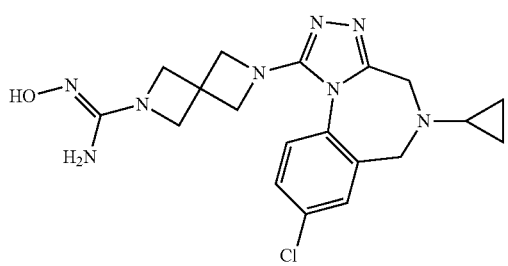 [SMILES: N/C(=N\O)N1CC2(C1)CN(c1nnc3n1-c1ccc(Cl)cc1CN(C1CC1)C3)C2]

A suspension of 6-(7-chloro-3,4-dihydro-2H-benzo[b][1,4]oxazine-4-carbonyl)-2,6-diazaspiro[3.3]heptane-2-carbonitrile (0.263 mmol, 1.0 eq.), TEA (0.0385 mL, 0.276 mmol, 1.05 eq.) and hydroxylamine hydrochloride (19.2 mg, 0.276 mmol, 1.05 eq.) in EtOH (1 mL) is heated at 80° C. for 1 hour. The mixture is concentrated under reduced pressure to afford the title compound.

Step 3: Synthesis of 3-(6-(8-chloro-5-cyclopropyl-5,6-dihydro-4H-benzo[f][1,2,4] triazolo[4,3-a][1,4]diazepin-1-yl)-2,6-diazaspiro[3.3]heptan-2-yl)-5-methyl-1,2,4-oxadiazole (Compound No. 268)

A mixture of (E)-6-(8-chloro-5-cyclopropyl-5,6-dihydro-4H-benzo[f][1,2,4]triazolo[4,3-a][1,4]diazepin-1-yl)-N-hydroxy-2,6-diazaspiro[3.3]heptane-2-carboximidamide (0.133 mmol, 1 eq) and acetic anhydride (0.027 mL, 0.28 mmol, 1.05 eq.) in pyridine (1 mL) is stirred for 1 h at 80° C. The reaction mixture is concentrated under reduced pressure and the crude residue is purified by reverse phase chromatography (5-85% ACN/H$_2$O, 20 min method). The title compound is isolated.

Compound No. 269

Compound No. 269 is prepared according to the methods set forth in Example 32 using appropriately substituted intermediates.

Example 33

Compound No. 241

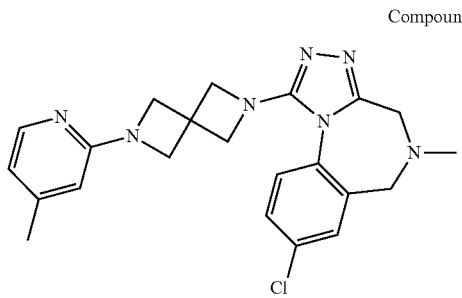

Step 1: Synthesis of tert-butyl (4-chloro-2-(((cyanomethyl)(methyl)amino) methyl)phenyl)carbamate

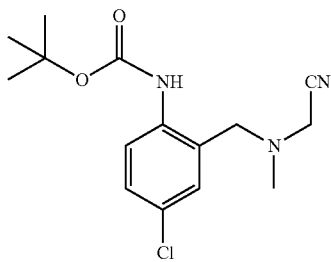 [SMILES: CN(CC#N)Cc1cc(Cl)ccc1NC(=O)OC(C)(C)C]

Tert-butyl (4-chloro-2-formylphenyl)carbamate (3.00 g, 11.7 mmol, 1 eq.), 2-(methylamino)-acetonitrile hydrochloride (3.74 g, 35.1 mmol, 3 eq.), and DIPEA (6.16 g, 35.1 mmol, 3 eq.) are mixed in DCE (76 mL) and stirred for 15 min at 25° C. Acetic acid (2.1 mL, 35.1 mmol, 3 eq.)) and MgSO$_4$ (4.32 g, 35.1 mmol, 3 eq.) are added, and the suspension is stirred for 2 h at 60° C. After the reaction mixture is cooled to 25° C., sodium triacetoxyborohydride (6.21 g, 29.3 mmol, 2.5 eq.) is added in two portions, and the reaction is stirred for 18 h at 25° C. The reaction is quenched with methanol and sodium bicarbonate (sat. aq.) to pH 8, and the aqueous layer is extracted with ethyl acetate twice. The organic layers are combined, dried over MgSO$_4$, and evaporated under reduced pressure. The residue is purified by column chromatography (SiO$_2$, 0-30% EtOAc/Hex) to give the title compound.

Step 2: Synthesis of 7-chloro-4-methyl-4,5-dihydro-3H-benzo[e][1,4]diazepin-2-amine

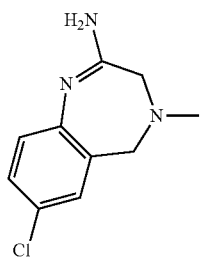

To a solution of tert-butyl (4-chloro-2-(((cyanomethyl)(methyl) amino)methyl)phenyl)carbamate (0.140 g, 0.45 mmol, 1 eq.) in dioxane (1.0 mL) is added hydrogen chloride solution in 1,4-dioxane (4.0 M, 2.25 mL, 9.0 mmol, 9 eq.) dropwise, and the reaction is stirred at 25° C. for 2 h. 2-Propanol (2.0 mL) is added. The solution is stirred for 18 h at 65° C., resulting in a suspension. Na$_2$CO$_3$ (2.0 M, aq.) is added to the suspension, and the final pH is 11. The mixture is extracted with EtOAc three times, and the organic layers are combined, dried over MgSO4, and evaporated under reduced pressure. The title compound.

Step 3: Synthesis of tert-butyl 6-(8-chloro-5-methyl-5,6-dihydro-4H-benzo[f][1,2,4]triazolo[4,3-a][1,4]-diazepin-1-yl)-2,6-diazaspiro[3.3]heptane-2-carboxylate

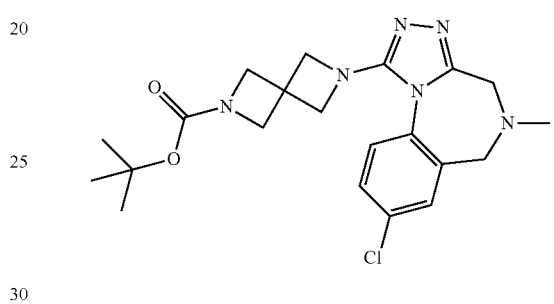

7-chloro-4-methyl-4,5-dihydro-3H-benzo[e][1,4]diazepin-2-amine (1.36 g, 6.5 mmol) and tert-butyl 6-(hydrazinecarbonyl)-2,6-diazaspiro[3.3]heptane-2-carboxylate (6.5 mmol) are mixed in isopropanol (35 mL) and acetic acid (0.38 mL, 6.5 mmol), and the solution is stirred at 80° C. for 2 h. The reaction solution is diluted with EtOAc, washed by Na$_2$CO$_3$ (twice) and brine, dried over MgSO$_4$, and evaporated under reduced pressure. The product is purified by column chromatography (SiO$_2$, 0-15% MeOH/DCM) to afford the title compound.

Step 4: Synthesis of 8-chloro-5-methyl-1-(2,6-diazaspiro[3.3]heptan-6-yl)-5,6-dihydro-4H-benzo[f][1,2,4]-triazolo[4,3-a][1,4]diazepine TFA Salt

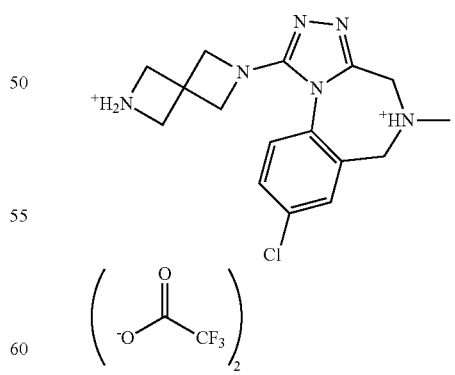

To a solution of tert-butyl 6-(8-chloro-5-methyl-5,6-dihydro-4H-benzo[f][1,2,4]triazolo-[4,3-a][1,4]diazepin-1-yl)-2,6-diazaspiro[3.3]heptane-2-carboxylate (3.56 mmol) in DCM (21 mL) is added trifluoroacetic acid (5.5 mL, 71 mmol) at 0° C., and the solution is stirred at 25° C. for 2 h.

The reaction mixture is evaporated under reduced pressure, and azeotropic evaporation is done with acetonitrile (twice) and toluene (once). The title compound is obtained.

Step 5: Synthesis of 8-chloro-5-methyl-1-(2-(4-methylpyridin-2-yl)-2,6-diazaspiro[3.3]heptan-6-yl)-5,6-dihydro-4H-benzo[f][1,2,4]triazolo[4,3-a][1,4]diazepine (Compound No. 241)

8-Chloro-5-methyl-1-(2,6-diazaspiro[3.3]heptan-6-yl)-5,6-dihydro-4H-benzo[f][1,2,4] triazolo[4,3-a][1,4]diazepine TFA salt (0.090 mmol, crude from Step 4), 2-bromo-4-methylpyridine (31 mg, 0.18 mmol), sodium tert-butoxide (43 mg, 0.45 mmol), RuPhos (4.2 mg, 9.0 umol) and RuPhos-Palladacycle-G3 (7.5 mg, 9.0 umol) are mixed in 1,4-dioxane (1.0 mL) and N-methylpyrrolidine (0.1 mL), and the mixture is stirred at 120° C. for 5 h. The reaction mixture is diluted with EtOAc, washed by NaHCO$_3$ (sat. aq.) and brine, dried over MgSO$_4$, filtered and evaporated under reduced pressure. The residue is purified by RP-HPLC (5-85% ACN/H$_2$O) to give the title compound.
Compound Nos. 231, 237 to 240, 242, 243, 251, 252, 256 to 258 and 1073 to 1084

Compound Nos. 231, 237 to 240, 242, 243, 251, 252, 256 to 258 and 1073 to 1084 are prepared according to the methods set forth in Example 33 using appropriately substituted intermediates.

Example 34

Compound No. 266

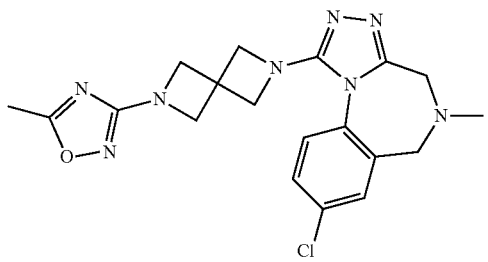

Step 1: Synthesis of 6-(8-chloro-5-methyl-5,6-dihydro-4H-benzo[f][1,2,4]triazolo[4,3-a][1,4]diazepin-1-yl)-2,6-diazaspiro[3.3]heptane-2-carbonitrile

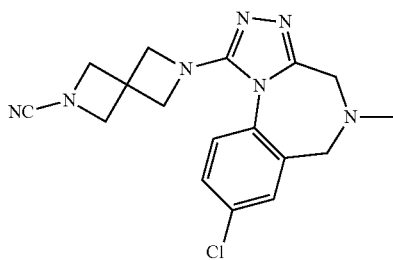 [SMILES: CN1Cc2cc(Cl)ccc2-n2c(nnc2N2CC3(CN(C#N)C3)C2)C1]

To a solution of 8-chloro-5-methyl-1-(2,6-diazaspiro[3.3]heptan-6-yl)-5,6-dihydro-4H-benzo[f][1,2,4]triazolo[4,3-a][1,4]diazepine TFA salt (100 mg, 0.18 mmol) and DIPEA (0.16 mL) in DCM (0.5 mL) is added cyanogen bromide (38 mg) at 0° C., and the reaction is stirred at 0° C. for 1 h. The reaction mixture is diluted with EtOAc, washed by NaHCO$_3$ (sat. aq.) and brine. The organic layer is dried over MgSO$_4$ and evaporated under reduced pressure. The residue is purified by column chromatography (SiO$_2$, 0-10% MeOH/DCM) to give the title compound.

Step 2: Synthesis of 6-(8-chloro-5-methyl-5,6-dihydro-4H-benzo[f][1,2,4]triazolo[4,3-a][1,4]diazepin-1-yl)-N-hydroxy-2,6-diazaspiro[3.3]heptane-2-carboximidamide

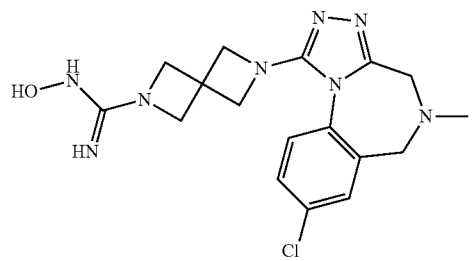 [SMILES: CN1Cc2cc(Cl)ccc2-n2c(nnc2N2CC3(CN(C(=N)NO)C3)C2)C1]

To a suspension of 6-(8-chloro-5-methyl-5,6-dihydro-4H-benzo[f][1,2,4]triazolo-[4,3-a][1,4]diazepin-1-yl)-2,6-diazaspiro[3.3]heptane-2-carbonitrile (0.41 mmol) and hydroxyamine hydrochloride (30 mg, 0.43 mmol) in ethanol (1.5 mL) is added triethylamine (60 uL, 0.43 mmol), and the reaction is stirred at 80° C. for 1 h, resulting in a solution. Ethanol is evaporated under reduced pressure, and the crude title compound is diluted with pyridine (1.2 mL) and used without further treatment.

Step 3: Synthesis of 3-(6-(8-chloro-5-methyl-5,6-dihydro-4H-benzo[f][1,2,4]triazolo[4,3-a][1,4]diazepin-1-yl)-2,6-diazaspiro[3.3]heptan-2-yl)-5-methyl-1,2,4-oxadiazole (Compound No. 266)

To a solution of 6-(8-chloro-5-methyl-5,6-dihydro-4H-benzo[f][1,2,4]triazolo[4,3-a][1,4]diazepin-1-yl)-N-hydroxy-2,6-diazaspiro[3.3]heptane-2-carboximidamide (0.12 mmol) in pyridine (0.4 mL) is added acetic anhydride (13 uL, 0.14 mmol) at 0° C., and the reaction is stirred at 0° C. for 30 min, then at 80° C. for 1 h. The reaction solution is diluted with EtOAc and washed by NaHCO$_3$ (sat. aq.) and brine. The organic layer is dried over MgSO$_4$ and evaporated under reduced pressure. The residue is purified by RP-HPLC (5-85% ACN/H$_2$O) to give The title compound.

Compound No. 267

Compound No. 267 is prepared according to the methods set forth in Example 34 using appropriately substituted intermediates.

Example 35

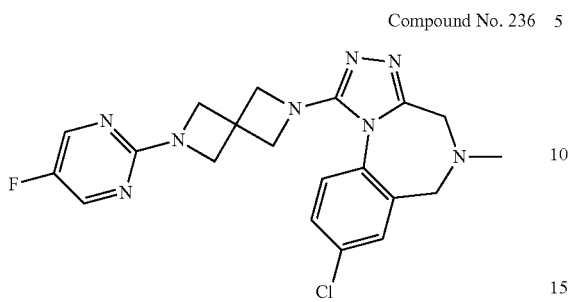

Compound No. 236

8-chloro-5-methyl-1-(2-(pyrimidin-2-yl)-2,6-diaz-aspiro[3.3]heptan-6-yl)-5,6-dihydro-4H-benzo[f][1,2,4]triazolo[4,3-a][1,4]diazepine (Compound No. 236)

To a solution of 7-chloro-4-methyl-4,5-dihydro-3H-benzo[e][1,4]diazepin-2-amine (20 mg, 0.095 mmol) and 2-(5-fluoropyrimidin-2-yl)-2,6-diazaspiro[3.3]heptane-6-carbohydrazide (0.11 mmol) in 2-propanol (1 mL) is added acetic acid (6 uL), and the reaction is stirred at 80° C. for 4 h. The reaction solution is diluted with EtOAc and washed by NaHCO$_3$ (sat. aq.) and brine. The organic layer is dried over MgSO4 and evaporated under reduced pressure. The residue is purified by RP-HPLC (5-85% ACN/H$_2$O) to give the title compound.

Example 36

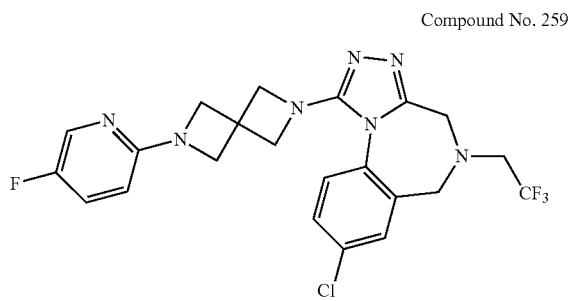 [SMILES: Fc1ccc(N2CC3(C2)CN(c2nnc4n2-c2ccc(Cl)cc2CN(CC(F)(F)F)C4)C3)nc1]

Compound No. 259

8-chloro-1-(2-(5-fluoropyridin-2-yl)-2,6-diazaspiro[3.3]heptan-6-yl)-5-(2,2,2-trifluoroethyl)-5,6-dihydro-4H-benzo[f][1,2,4]triazolo[4,3-a][1,4]diazepine (Compound No. 259

To a mixture of 2,2,2-trifluoroethyl trifluoromethanesulfonate (56 mg, 0.244 mg, 2 eq.) and 8-chloro-1-(2-(5-fluoropyridin-2-yl)-2,6-diazaspiro[3.3]heptan-6-yl)-5,6-dihydro-4H-benzo[f][1,2,4]triazolo[4,3-a][1,4]diazepine from Example 10, Step 3 (0.122 mmol, 1.0 eq.) in anhydrous MeCN (0.75 mL) is added K$_2$CO$_3$ (35 mg, 0.13 mmol, 2.1 eq.) and the resultant mixture is stirred at room temperature for 0.5 hours and then at 75° C. for 3 hours. The mixture is cooled and partitioned between sodium bicarbonate solution and DCM. The organic fraction is collected, concentrated to a residue, and purified by reverse phase HPLC, eluting with a gradient of 5-85% CH$_3$CN in water, to give the title compound.

Compound Nos. 1095 to 1102

Compound Nos. and 1095 to 1102 are prepared according to the procedure of Example 36 using appropriately substituted intermediates.

Example 37

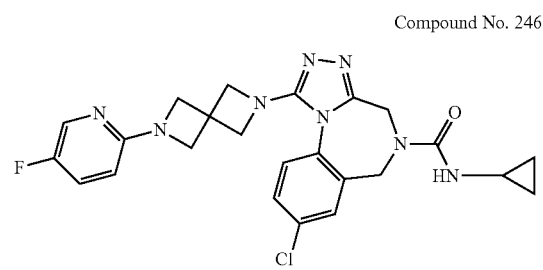 [SMILES: O=C(NC1CC1)N1Cc2cc(Cl)ccc2-n2c(nnc2N2CC3(CN(c4ccc(F)cn4)C3)C2)C1]

Compound No. 246

8-chloro-N-cyclopropyl-1-(2-(5-fluoropyridin-2-yl)-2,6-diazaspiro[3.3]heptan-6-yl)-4H-benzo[f][1,2,4]triazolo[4,3-a][1,4]diazepine-5(6H)-carboxamide (Compound No. 246)

To a solution of 8-chloro-1-(2-(5-fluoropyridin-2-yl)-2,6-diazaspiro[3.3]heptan-6-yl)-5,6-dihydro-4H-benzo[f][1,2,4]triazolo[4,3-a][1,4]-diazepine from Example 10, Step 3 (0.085 mmol, 1.0 eq.) in 0.5 ml anhydrous THF and 30 μL DMF is added isocyanatocyclopropane (9 μL, 0.128 mmol, 1.5 eq.) and the mixture is heated at 45° C. in a sealed tube for 18 hours. The solution is diluted with methanol, concentrated under vacuum, and purified by reverse phase HPLC, eluting with a gradient of 5-85% CH$_3$CN in water to give the title compound.

Example 38

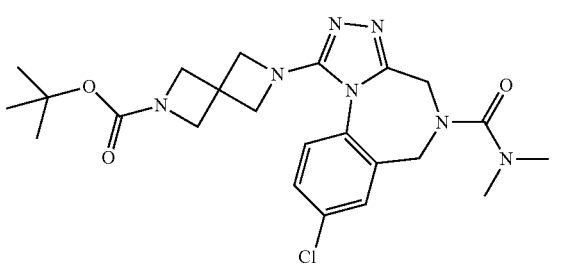 [SMILES: CN(C)C(=O)N1Cc2cc(Cl)ccc2-n2c(nnc2N2CC3(CN(C(=O)OC(C)(C)C)C3)C2)C1]

Compound No. 230

Step 1: Synthesis of tert-butyl 6-(8-chloro-5-(dimethylcarbamoyl)-5,6-dihydro-4H-benzo[f][1,2,4]triazolo[4,3-a][1,4]diazepin-1-yl)-2,6-diazaspiro[3.3]heptane-2-carboxylate

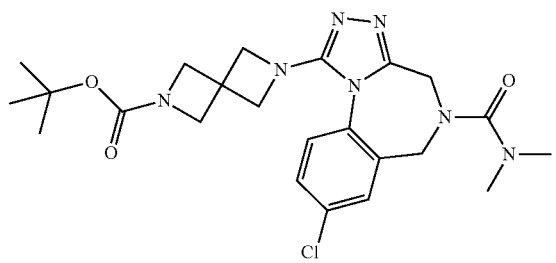

To a cooled 0° C. solution of 4-nitrophenyl chloroformate (29 mg, 0.143 mmol, 1.1 eq.) and triethylamine (36 μL, 0.26 mmol, 2 eq.) in anhydrous DCM (300 μL) is slowly added a solution of tert-butyl 6-(8-chloro-5,6-dihydro-4H-benzo[f][1,2,4]triazolo[4,3-a][1,4]diazepin-1-yl)-2,6-diazaspiro[3.3]heptane-2-carboxylate from Example 12, Step 6 (0.13 mmol, 1.0 eq.) in DCM (1 mL). The mixture is stirred for three hours at 0° C., then allowed to warm to room temperature and stirred for 1 hour. A solution of 2M dimethylamine in THF (500 μL, 1.0 mmol, 7.7 eq) and the mixture is stirred at 45° C. for 72 hours. The reaction mixture is diluted with DCM and successively washed with water, 1M citric acid soln., and brine. The organic fraction is dried over sodium sulfate and concentrated to clear residue, which is used in the next step without further purification.

Step 2: Synthesis of 6-(8-chloro-5-(dimethylcarbamoyl)-5,6-dihydro-4H-benzo[f][1,2,4]triazolo[4,3-a][1,4]diazepin-1-yl)-2,6-diazaspiro[3.3]heptan-2-ium 2,2,2-trifluoroacetate

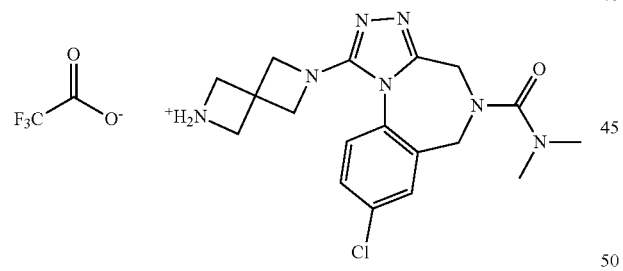

To a solution of tert-butyl 6-(8-chloro-5-(dimethylcarbamoyl)-5,6-dihydro-4H-benzo[f][1,2,4]triazolo[4,3-a][1,4]diazepin-1-yl)-2,6-diazaspiro[3.3]heptane-2-carboxylate (0.10 mmol, 1 eq.) in 3 mL of DCM is added 1 mL of TFA, and the solution is stirred at room temperature for 2 hours. The solution is concentrated under vacuum, and the residue suspended in toluene and concentrated under vacuum to give the title compound.

Step 3: Synthesis of 8-chloro-1-(2-(5-fluoropyridin-2-yl)-2,6-diazaspiro[3.3]heptan-6-yl)-N,N-dimethyl-4H-benzo[f][1,2,4]triazolo[4,3-a][1,4]diazepine-5(6H)-carboxamide (Compound No. 230)

A vial is charged with 6-(8-chloro-5-(dimethylcarbamoyl)-5,6-dihydro-4H-benzo[f][1,2,4]triazolo[4,3-a][1,4]diazepin-1-yl)-2,6-diazaspiro[3.3]heptan-2-ium 2,2,2-trifluoroacetate (0.11 mmol, 1.0 eq.), 2-bromo-5-fluoropyridine (39 mg, 0.22 mmol, 2 eq.), sodium tert-butoxide (53 mg, 0.55 mmol, 5 eq.), and 1 ml of a 9:1 mixture of 1,4-dioxane:NMP. The resultant suspension is degassed, placed under a nitrogen atmosphere, and heated at 85° C. for 5 hours. The mixture is cooled, filtered through celite (washing with DCM and EtOAc) and concentrated to give a product. The crude product is dissolved in methanol and purified by reverse phase chromatography, eluting from a C18 column with a gradient of 5-85% $CH_3CN$ in water to give the title compound.

Example 39

Compound No. 255

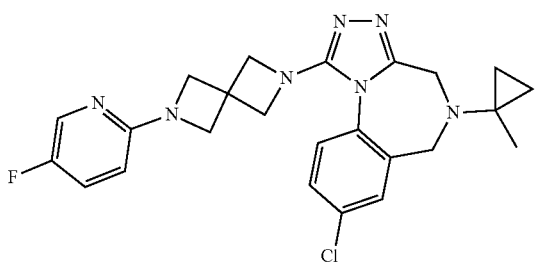

Step 1: Synthesis of tert-butyl (4-chloro-2-(((1-methylcyclopropyl)-amino)methyl)phenyl)-carbamate

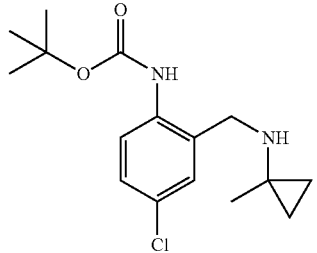 [SMILES: CC1(NCc2cc(Cl)ccc2NC(=O)OC(C)(C)C)CC1]

To a stirred solution of tert-butyl (4-chloro-2-formylphenyl)carbamate (0.5 g, 1.955 mmol, 1.0 eq) in MeOH (10 mL) is added 1-methylcyclopropan-1-amine (0.2781 g, 3.910 mmol, 2.0 eq) and the mixture is stirred at 43° C. for 16 h. THF (6.0 mL) is added to the reaction mixture, followed by the addition of sodium triacetoxyborohydride (2.08 g, 9.80 mmol, 5.0 eq) and acetic acid (0.35 g, 5.89 mmol, 3.0 eq), and stirred at RT for 20 h. The reaction mixture is diluted with EtOAc (20 mL) and sat. aq. $NaHCO_3$ (20 mL). The organic phase is collected, and the aqueous phase is extracted with EtOAc (2×10 mL). Combined organics are washed with brine, dried over $MgSO_4$, filtered, and concentrated under reduced pressure. The residue is purified by column chromatography ($SiO_2$, 0-20% EtOAc/Hex) to afford the title compound.

Step 2: Synthesis of tert-butyl (4-chloro-2-(((cyanomethyl)(1-methylcyclopropyl)-amino)methyl)-phenyl)carbamate

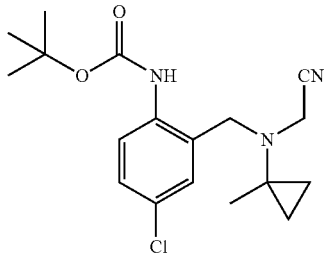 [SMILES: CC(C)(C)OC(=O)Nc1ccc(Cl)cc1CN(CC#N)C1(C)CC1]

To a mixture of tert-butyl (4-chloro-2-(((1-methylcyclopropyl)amino)methyl)-phenyl)carbamate (0.510 g, 1.64 mmol, 1.0 eq), $K_2CO_3$ (0.453 g, 3.28 mmol, 2.0 eq), and KI (0.164 g, 0.988 mmol, 0.6 eq) in ACN (2.0 mL) and 1,4-dioxane (3.0 mL) is added 2-chloroacetonitrile (0.248 g, 3.28 mmol, 2.0 eq). The mixture is stirred at 80° C. for 22 h under an atmosphere of $N_2$. The reaction mixture is then cooled to RT, diluted with (1:1) mixture of EtOAc and sat. aq. $NaHCO_3$ (20 mL). The organic phase is collected, and the aqueous phase is extracted with EtOAc (2×20 mL). The combined organics are washed with sat. aq $Na_2S_2O_3$ solution, brine, dried over $MgSO_4$, filtered, and concentrated under reduced pressure. The residue is purified by column chromatography ($SiO_2$, 0-20% EtOAc/Hex) to afford the title compound.

Step 3: Synthesis of 7-chloro-4-(1-methylcyclopropyl)-4,5-dihydro-3H-benzo[e][1,4]diazepin-2-amine

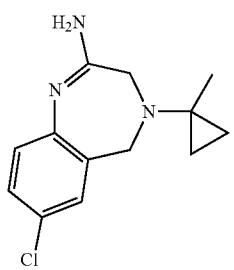 [SMILES: CC1(N2CC(N)=Nc3ccc(Cl)cc3C2)CC1]

A solution of acetyl chloride (3.17 g, 40.4 mmol, 20.0 eq) in isopropanol (15 mL) is stirred for 20 min at RT prior to slow addition to a solution of tert-butyl (4-chloro-2-(((cyanomethyl)(1-methylcyclopropyl)amino)-methyl)-phenyl)carbamate (0.705 g, 2.02 mmol, 1.0 eq) in isopropanol (15 mL) and stirred for 60 h at 50° C. The reaction mixture is concentrated under reduced pressure and the crude is mixed vigorously with a (1:1) mixture of EtOAc/satd aq $NaHCO_3$ (60 mL) The organic phase is collected, and the aqueous phase is extracted with EtOAc (3×15 mL). Combined organics are washed with brine, dried over $MgSO_4$, filtered, and concentrated under reduced pressure. The crude residue is purified by column chromatography ($SiO_2$, 0-100% EtOAc/Hex, 0-100% DCM/EtOAc, 0-12% MeOH/DCM) to afford the title compound.

Step 4: Synthesis of tert-butyl 6-(hydrazinecarbonyl)-2,6-diazaspiro[3.3]heptane-2-carboxylate

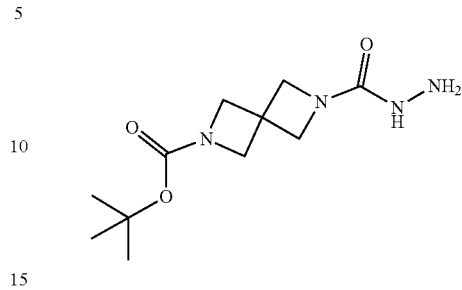

To a stirred solution of 2-(tert-butoxycarbonyl)-2,6-diazaspiro[3.3]heptane-6-carboxylic acid (0.26 g, 1 mmol, 1 eq.) in THF (5 mL) is added 1-1'-carbonyldiimidazole (0.19 g, 1.2 mmol, 1.2 eq.) and the mixture is stirred at RT overnight. The resulting mixture is added to a solution of hydrazine monohydrate (0.07 mL, 1.4 mmol, 1.4 eq.) in THF (10 mL) and stirred at RT overnight. The mixture is diluted with brine and extracted with ethyl acetate. The organic phase is separated, washed with brine, dried ($MgSO_4$), filtered and concentrated in vacuo to afford the title compound.

Step 5: Synthesis of tert-butyl 6-(8-chloro-5-(1-methylcyclopropyl)-5,6-dihydro-4H-benzo[f]-[1,2,4]triazolo[4,3-a][1,4]diazepin-1-yl)-2,6-diazaspiro[3.3]heptane-2-carboxylate

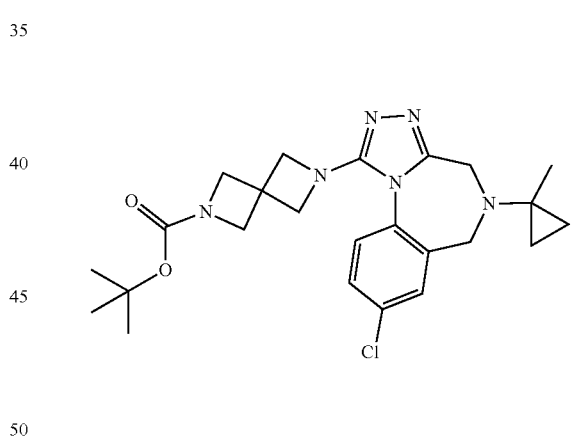

A mixture of 7-chloro-4-(1-methylcyclopropyl)-4,5-dihydro-3H-benzo[e][1,4]-diazepin-2-amine (0.058 g, 0.232 mmol, 1.0 eq), 2-(5-fluoro-4-methylpyridin-2-yl)-2,6-diazaspiro-[3.3]heptane-6-carbohydrazide (0.348 mmol, 1.5 eq), and AcOH (2 drops) in 2-propanol (1 mL) is stirred for 20 h at 80° C. The reaction mixture is then concentrated under reduced pressure, and the crude product is diluted with DCM (5 mL) and satd aq $NaHCO_3$ (5 mL). Organic phase is collected, and the aqueous phase is extracted with DCM (3×5 mL). Combined organics are washed with brine, dried over MgSO4, filtered, and concentrated under reduced pressure. The crude residue is purified by column chromatography ($SiO_2$, 0-10% MeOH/DCM) to afford the title compound.

Step 6: Synthesis of 8-chloro-5-(1-methylcyclopropyl)-1-(2,6-diazaspiro[3.3]heptan-2-ium-6-yl)-5,6-dihydro-4H-benzo[f][1,2,4]triazolo[4,3-a][1,4]diazepin-5-ium-6-ylium 2,2,2-trifluoroacetate

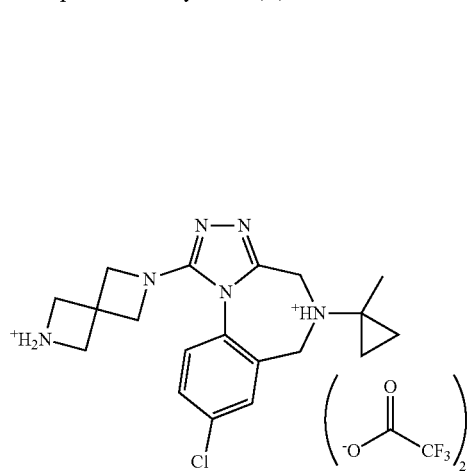

To a solution of tert-butyl 8-chloro-5-(1-methylcyclopropyl)-1-(2,6-diazaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.594 mmol, 1.0 eq) in DCM (20 mL) at 0° C., TFA (6 mL) is added dropwise. The reaction mixture is allowed to warm to RT and stirred 60 min. The mixture is concentrated under reduced pressure, and the crude residue is azeotroped with toluene (4×20 mL). After 6 h under high vacuum, the title compound is isolated.

Step 7: Synthesis of 8-chloro-1-(2-(5-fluoropyridin-2-yl)-2,6-diazaspiro[3.3]heptan-6-yl)-5-(1-methylcyclopropyl)-5,6-dihydro-4H-benzo[/][1,2,4]triazolo[4,3-a][1,4]diazepine (Compound No. 255)

A mixture of 8-chloro-5-(1-methylcyclopropyl)-1-(2,6-diazaspiro[3.3]heptan-2-ium-6-yl)-5,6-dihydro-4H-benzo[f][1,2,4]triazolo[4,3-a][1,4]diazepin-5-ium-6-ylium 2,2,2-trifluoroacetate (0.043 mmol, 1.0 eq), 2-chloro-5-fluoropyridine (0.012 g, 0.087 mmol, 2.0 eq), NaO$^t$Bu (0.021 g, 0.218 mmol, 5.0 eq.), and RuPhos Pd G3 (0.004 g, 0.004 mmol, 0.1 eq) is stirred in 1,4-dioxane (1.0 mL) and few drops of NMP under a N$_2$ atmosphere for 16 h at 90° C. The reaction mixture is diluted with EtOAc (3 mL) and filtered through a pad of celite. The filter cake is washed with EtOAc (2×2 mL) and the combined filtrates are concentrated under reduced pressure. The crude residue is purified by reverse phase chromatography (5-85% ACN/H$_2$O, 20 min method). The title compound is isolated after lyophilization of pure fractions.

Compound Nos. 244, 245, 253, 254 and 260 to 265

Compound Nos. 244, 245, 253, 254 and 260 to 265 are prepared according to the methods set forth in Example 38 using appropriately substituted intermediates.

Example 40

Compound No. 223

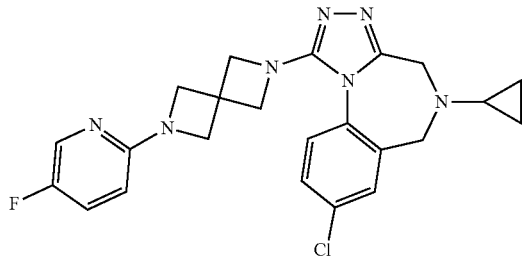

Step 1: Synthesis of tert-butyl 6-(5-fluoropyridin-2-yl)-2,6-diazaspiro[3.3]heptane-2-carboxylate

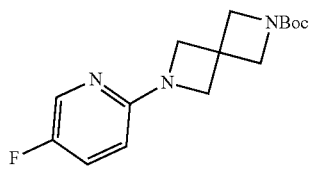 [SMILES: CC(C)(C)OC(=O)N1CC2(C1)CN(c1ccc(F)cn1)C2]

To a solution of tert-butyl 2,6-diazaspiro[3.3]heptane-2-carboxylate (0.250 g, 1.26 mmol, 1 eq.), 2-chloro-5-fluoropyridine (0.255 mL, 2.52 mmol, 2 eq) in 1,4-dioxane (10 mL), RuPhos-Palladacycle G3 (84.5 mg, 0.101 mmol, 0.08 eq) and sodium tert-butoxide (0.242 g, 2.52 mmol, 2 eq) are added. The mixture is stirred at 120° C. for 5 hours. The reaction mixture is diluted with ethyl acetate and washed with water. The aqueous phase is back extracted with ethyl acetate (×1). Combined organic phases are washed with brine, dried using sodium sulfate, filtered, and concentrated under reduced pressure. The crude material is purified by flash chromatography eluting from silica gel with a gradient of ethyl acetate in hexanes to give the title compound as an off-white solid (0.230 g, 62.2% yield). LCMS (ESI): m/z 294 (M+H).

Step 2: Synthesis of 2-(5-fluoropyridin-2-yl)-2,6-diazaspiro[3.3]heptane; tetrakis(trifluoroacetic Acid)

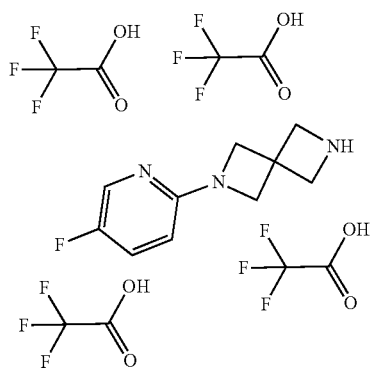

To solution of tert-butyl 6-(5-fluoropyridin-2-yl)-2,6-diazaspiro[3.3]heptane-2-carboxylate (0.370, 1.26 mmol, 1 eq) in DCM (6 mL), trifluoroacetic acid (1.93 mL, 25.2 mmol, 5 eq) is added at 0° C. and the mixture is stirred for one hour at room temperature. The solvent is evaporated under reduced pressure and the residue is azeotroped with toluene three times and is dried under vacuum to obtain the titled compound as a pale yellow solid (0.846 g, quantitative yield). LCMS (ESI): m/z 194 (M+H).

Step 3: Synthesis of 4-nitrophenyl 6-(5-fluoropyridin-2-yl)-2,6-diazaspiro[3.3]heptane-2-carboxylate

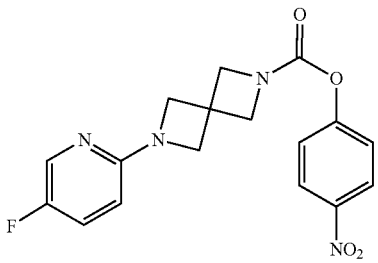 [SMILES: O=C(Oc1ccc([N+](=O)[O-])cc1)N1CC2(C1)CN(c1ccc(F)cn1)C2]

To a solution of 2-(5-fluoropyridin-2-yl)-2,6-diazaspiro[3.3]heptane; tetrakis(trifluoroacetic acid) (0.846 mg, 1.3 mmol, 1 eq.) in anhydrous DCM (10 mL), triethylamine (1.1 mL, 7.8 mmol, 6 eq.) is added followed by 4-nitrophenyl chloroformate (329 mg, 1.63 mmol, 1.25 eq.) at 0° C. and is warmed to room temperature overnight. The reaction mixture is diluted with ethyl acetate, washed with water and the aqueous layer is back extracted with ethyl acetate (×3). Combined organic phases are washed with brine, dried using sodium sulfate, filtered and concentrated under reduced pressure to yield a yellow solid. The crude material is purified by flash chromatography using ethyl acetate and hexanes as gradients to give the titled compound as a pale yellow solid (0.408 g, 65% yield). LCMS (ESI): m/z 359 (M+H).

Step 4: Synthesis of 6-(5-fluoropyridin-2-yl)-2,6-diazaspiro[3.3]heptane-2-carbohydrazide

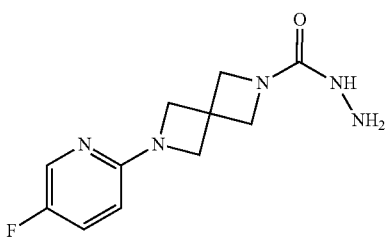 [SMILES: NNC(=O)N1CC2(C1)CN(c1ccc(F)cn1)C2]

To a solution of 4-nitrophenyl 6-(5-fluoropyridin-2-yl)-2,6-diazaspiro[3.3]heptane-2-carboxylate (0.400 g, 1.12 mmol, 1 eq) and THF (10 mL), hydrazine monohydrate (0.272 mL, 5.6 mmol, 5 eq.) is added and the mixture is stirred at 70° C. for 2 hours. The reaction mixture is cooled to room temperature, the solvents are evaporated under reduced pressure, and the residue is placed under vacuum overnight. The obtained residue is re-dissolved in DCM and methanol and MP-carbonate resin (Biotage, 1.25 g, 3.73 mmol, 3.3 eq.) is added and the mixture is stirred for 1.5 hours at room temperature. The solids are filtered off and washed with 10% methanol/DCM and the solvents are evaporated under reduced pressure. The crude material is purified by flash chromatography using a gradient of 0-20% methanol/DCM to elute the titled compound as an off-white solid (0.230 g, 82% yield). LCMS (ESI): m/z 252 (M+H).

Step 5: Synthesis of N'-(7-chloro-4-cyclopropyl-1,3,4,5-tetrahydro-2H-benzo[e][1,4]diazepin-2-ylidene)-6-(5-fluoropyridin-2-yl)-2,6-diazaspiro[3.3]heptane-2-carbohydrazide

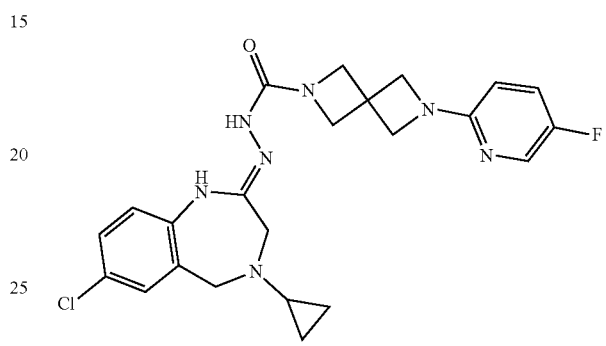

To a suspension of 6-(5-fluoropyridin-2-yl)-2,6-diazaspiro[3.3]heptane-2-carbohydrazide (0.1 g, 0.398 mmol, 1 eq.), 7-chloro-4-cyclopropyl-4,5-dihydro-3H-1,4-benzodiazepin-2-amine (0.0938 g, 0.398 mmol, 1 eq.) in isopropyl alcohol (4 mL), is added acetic acid (68 µL, 1.19 mmol, 3 eq.) and the mixture is stirred at 60° C. for 30 minutes. Ethyl alcohol (1 mL) is added and the reaction mixture is heated to 80 C for 1 hour. The reaction mixture is cooled to room temperature and the solvent is evaporated under reduced pressure. The residue is re-dissolved in DCM, and washed with saturated sodium bicarbonate solution. The aqueous layer is extracted with DCM (×1), and the organic phases are combined, washed with brine, dried using sodium sulfate, filtered, and concentrated under reduced pressure. The crude material is purified by flash chromatography using a gradient of 0-10% methanol/DCM to elute the titled product from silica gel as an off-white solid (0.140 g, 75% yield). LCMS (ESI): m/z 470 (M+H).

Step 6: Synthesis of 8-chloro-5-cyclopropyl-1-(6-(5-fluoropyridin-2-yl)-2,6-diazaspiro[3.3]heptan-2-yl)-5,6-dihydro-4H-benzo[f][1,2,4]triazolo[4,3-a][1,4]diazepine (Compound No. 223)

A suspension of N'-[(2Z)-7-chloro-4-cyclopropyl-2,3,4,5-tetrahydro-1H-1,4-benzodiazepin-2-ylidene]-6-(5-fluoropyridin-2-yl)-2,6-diazaspiro[3.3]heptane-2-carbohydrazide (0.140 g, 0.298 mmol, 1 eq.), triethylamine (250 uL, 1.79 mmol, 6 eq.), dichloro-triphenylphosphorane (0.248 g, 0.748 mmol, 2.5 eq.) and anhydrous acetonitrile (6.7 mL) is heated at 80° C. for 1 hour. The reaction mixture is cooled to room temperature and dichloro-triphenylphosphorane (0.100 g, 0.298 mmol, 1 eq) and ACN (0.8 mL) are added and the mixture is stirred at 80° C. for 1.5 hour, after which additional dichloro-triphenylphosphorane (0.05 g, 0.149 mmol, 0.5 eq) is added and the mixture is stirred at 80° C. for 2 hours. The reaction mixture is cooled to room temperature and diluted with acetonitrile. Solids are filtered off and washed with additional ACN. The filtrate is concentrated under reduced pressure and the crude is purified using flash chromatography using a gradient of 0-10% methanol/DCM to elute from silica gel followed by a second purification by preparative HPLC using a gradient of 0-85% acetonitrile/water to elute from C18 column to give the titled compound as a white solid (41 mg, 30% yield, 99.4% purity). LCMS (ESI): m/z 452.2 (M+H).

Compound Nos. 1092 to 1094

Compound Nos. 1092 to 1094 are prepared according to the methods set forth in Example 40 using appropriately substituted intermediates.

Example 41

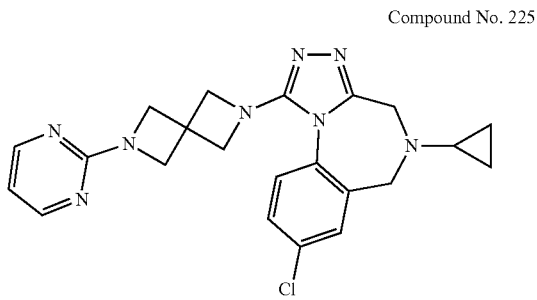 [SMILES: Clc1ccc2c(c1)CN(C1CC1)Cc1nnc(N3CC4(CN(c5ncccn5)C4)C3)n1-2]

Compound No. 225

Step 1: Synthesis of tert-butyl 6-(pyrimidin-2-yl)-2,6-diazaspiro[3.3]heptane-2-carboxylate

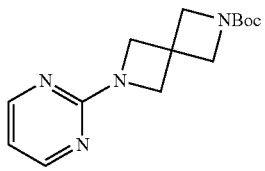 [SMILES: CC(C)(C)OC(=O)N1CC2(C1)CN(c1ncccn1)C2]

A mixture of tert-butyl 2,6-diazaspiro[3.3]heptane-2-carboxylate hemioxalate salt (10.0 g, 3.47 mmol, 1.0 eq), 2-chloropyrimidine (5.9 g, 52 mmol, 1.5 eq.) in 1,4-dioxane (100 mL) and N,N-dimethylformamide (50 mL) is treated with N,N-diisopropylethylamine (24.2 mL, 138.7 mmol, 4.0 eq.) and the mixture is heated to 100° C. and stirred overnight. The mixture is concentrated in vacuo, the residue is dissolved in DCM (100 mL), washed with saturated aqueous sodium bicarbonate soln. and the aqueous layer is extracted with DCM (2×50 mL). The organics are passed through a phase separator cartridge and concentrated in vacuo. The residue is purified by flash column chromatography eluting with 20-100% EtOAc in isohexane to give the title compound an off-white solid (7.91 g, 55% yield). $^1$H NMR (400 MHz, CDCl$_3$) δ 8.32 (d, J=4.8 Hz, 2H), 6.57 (dd, J=4.8, 4.8 Hz, 1H), 4.24 (s, 4H), 4.12 (s, 4H), 1.45 (s, 9H).

Step 2: Synthesis of 2-(pyrimidin-2-yl)-2,6-diazaspiro[3.3]heptane bis(2,2,2-trifluoroacetate)

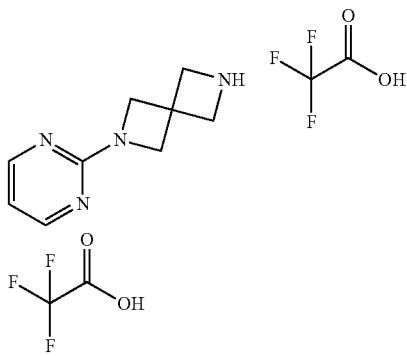

To a solution of tert-butyl 6-(pyrimidin-2-yl)-2,6-diazaspiro[3.3]heptane-2-carboxylate (7.65 g, 27.7 mmol, 1.0 eq.) in DCM (150 mL) is added TFA (63.6 mL, 830.5 mmol, 30 eq.) dropwise. The mixture is stirred at RT for 45 minutes, concentrated in vacuo and the residue is triturated with diethyl ether to afford the titled compound as a white solid. $^1$H NMR (400 MHz, DMSO-d$_6$) δ (9.31 g, 83% yield). 8.64-8.64 (m, 2H), 8.37 (d, J=4.8 Hz, 2H), 6.72 (dd, J=4.8, 4.8 Hz, 1H), 4.21-4.18 (m, 8H).

Step 3: Synthesis of tert-butyl (4-chloro-2-((cyclopropylamino)methyl)-phenyl)carbamate

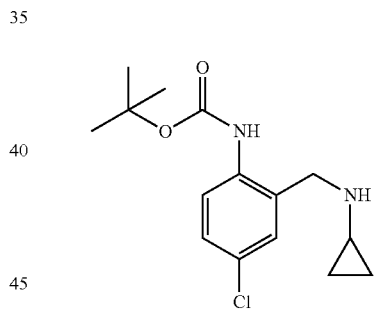

A mixture of tert-butyl N-(4-chloro-2-formylphenyl)carbamate (5.122 g, 20.03 mmol, 1 eq.) and cyclopropanamine (2.08 mL, 30.05 mmol, 1.5 eq.) in MeOH (65.2 mL) is stirred for 5 h at 60° C., allowed to cool to RT, and then stirred 18 h. THF (30 mL) is added to the reaction mixture, followed by solid NaCNBH$_3$ (2.517 g, 40.06 mmol, 2 eq.). The reaction mixture is stirred at RT for 2 hours. Acetic acid (2.29 mL, 40.06 mmol, 2 eq) is added and stirring was continued for 20 min. The reaction mixture is concentrated under reduced pressure, and the resultant crude residue is diluted with EtOAc (150 mL) and washed with sat. aq. NaHCO$_3$ (100 mL). The aqueous later is collected, and the organic layer is further washed with sat. aq. NaHCO$_3$ (2×50 mL). The combined aqueous washes are back-extracted with EtOAc (1×100 mL) and the combined organic phases were dried over MgSO$_4$, filtered to remove solid material, and concentrated under reduced pressure. The residue is purified by column chromatography (SiO$_2$, 0-30% EtOAc/Hex—2% DCM additive) to afford the title compound.

Step 4: Synthesis of tert-butyl (4-chloro-2-(((cyanomethyl)(cyclopropyl)amino)-methyl)phenyl) carbamate

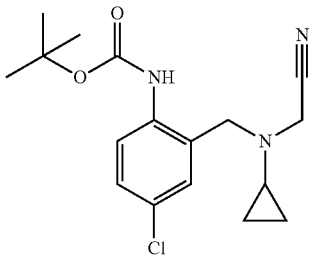 [SMILES: CC(C)(C)OC(=O)Nc1ccc(Cl)cc1CN(CC#N)C1CC1]

A mixture of K₂CO₃ (1.87 g, 13.5 mmol, 2 eq.), KI (0.671 g, 4.04 mmol, 0.6 eq.), 2-chloroacetonitrile (0.855 mL, 13.5 mmol, 2 eq.), and tert-butyl N-{4-chloro-2-[(cyclopropylamino)methyl]phenyl}carbamate (2.00 g, 6.74 mmol, 1 eq.), added in sequence, is stirred in ACN (15 mL) under an atmosphere of N₂ for 18 h at 75° C. The reaction mixture is allowed to cool to RT, diluted with EtOAc (100 mL), and washed with sat aq. NaHCO₃ (100 mL). The organic phase is collected, and the aq. phase is extracted with EtOAc (2×100 mL). The combined organic extracts are washed with 15% aq. Na₂S₂O₃ (2×100 mL), brine (1×100 mL), and dried over MgSO4. Solids are removed by vacuum filtration and the filtrate is concentrated under reduced pressure to afford the title compound (2.548 g, 88% pure, 99% yield) as a brown oil. The crude material was taken on to the next step without further purification. LCMS (ESI): m/z 336.1 (M+H).

Step 5: Synthesis of 7-chloro-4-cyclopropyl-4,5-dihydro-3H-benzo[e][1,4]diazepin-2-amine

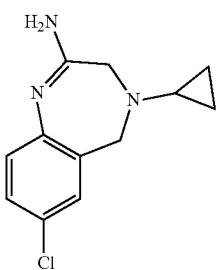 [SMILES: NC1=Nc2ccc(Cl)cc2CN(C2CC2)C1]

A solution of acetyl chloride (9.64 mL, 134.6 mmol, 20 eq.) in isopropanol (55.6 mL) is stirred for 20 min prior to slow addition to a solution of tert-butyl N-(4-chloro-2-{[(cyanomethyl)(cyclopropyl)amino]methyl}phenyl) carbamate (2.26 g, 6.730 mmol, 1 eq.) in isopropanol (67.3 mL) and stirred for 60 h at 50° C. The reaction mixture is concentrated under reduced pressure and the crude residue is diluted with EtOAc (125 mL). The crude mixture is washed with sat aq. NaHCO₃ (1×125 mL). The organic phase is collected, and the aqueous phase is extracted with EtOAc (3×50 mL). The combined organics are washed with brine (1×50 mL), dried over MgSO₄, and solids are removed by vacuum filtration. The filtrate is concentrated under reduced pressure, and the crude residue is purified by column chromatography (SiO₂, 0-100% EtOAc/Hex, 0-100% DCM/EtOAc, 0-12% MeOH/DCM) to afford the title compound (0.721 g, 45.5% yield) as a light brown solid. LCMS (ESI): m/z 236.0 (M+H).

Step 6: Synthesis of 7-chloro-4-cyclopropyl-4,5-dihydro-3H-benzo[e][1,4]diazepin-2-amine, di hydrochloride Salt

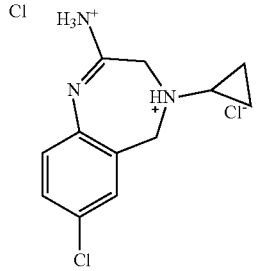

7-chloro-4-cyclopropyl-4,5-dihydro-3H-1,4-benzodiazepin-2-amine (0.500 g, 2.12 mmol) is dissolved in THF (5 mL) and 4M HCl in dioxane (1 mL, 4.42 mmol, 2 eq) is added at 0° C. and the resultant mixture is stirred for 1 hour. The solids are collected on a fritted filter and dried to give the title compound as 563 mg of a hygroscopic solid (85% yield). LCMS (ESI): m/z 236.0 (M+H).

Step 7: Synthesis of 8-chloro-5-cyclopropyl-5,6-dihydro-4H-benzo[f][1,2,4]triazolo-[4,3-a][1,4]diazepine

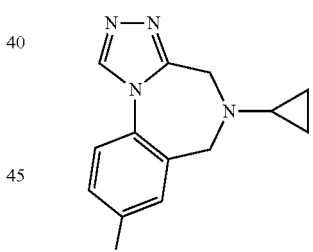

To a suspension of 7-chloro-4-cyclopropyl-4,5-dihydro-3H-benzo[e][1,4]diazepin-2-amine, di-hydrochloride salt (269 mg, 0.871 mmol, 1 eq.) and formic hydrazide (63 mg, 1.05 mmol, 1.2 eq.) in 9 mL of isopropanol is added acetic acid (99 µL, 1.73 mmol, 2 eq.) and the resultant mixture is heated at 80° C. and stirred overnight. The mixture is concentrated to a tan residue, suspended in saturated sodium bicarbonate solution and extracted three times with DCM. The combined organic layers are dried over sodium sulfate and concentrated to 294 mg of tan solid. The crude product is purified by column chromatography eluting from 12 g silica gel with a gradient of 0-10% MeOH/DCM to give 220 mg of the title compound (97% yield); LCMS (ESI): m/z 261 (M+1).

Step 8: Synthesis of 1-bromo-8-chloro-5-cyclopropyl-5,6-dihydro-4H-benzo[f][1,2,4]triazolo[4,3-a][1,4]diazepine

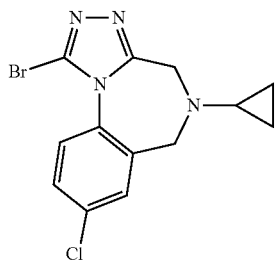 [SMILES: Clc1ccc2c(c1)CN(C1CC1)Cc1nnc(Br)n1-2]

To a suspension of 8-chloro-5-cyclopropyl-5,6-dihydro-4H-benzo[f][1,2,4]triazolo[4,3-a][1,4]diazepine (170 mg, 0.652 mmol, 1 eq.) in 3.5 ml of acetonitrile is added N-bromosuccinimide (160 mg, 0.89 mmol, 1.35 eq.) and the mixture is stirred at room temperature for 22 hours. The mixture is diluted with saturated sodium bicarbonate solution and extracted 3 times with dichloromethane. The combined organic fractions are dried over sodium sulfate and concentrated to a crude residue, which is purified by column chromatography eluting from 12 g of silica gel with a gradient of 0-10% MeOH/DCM to give a white solid containing the title compound contaminated with succinimide (130 mg, 59% yield). LCMS (ESI): m/z 339/341 (M+1)

Step 9: Synthesis of 8-chloro-5-cyclopropyl-1-(6-(pyrimidin-2-yl)-2,6-diazaspiro[3.3]heptan-2-yl)-5,6-dihydro-4H-benzo[f][1,2,4]triazolo[4,3-a][1,4]diazepine (Compound No. 225)

To a solution of 1-bromo-8-chloro-5-cyclopropyl-5,6-dihydro-4H-benzo[f][1,2,4]triazolo[4,3-a][1,4]diazepine (45 mg, 0.133 mmol, 1 eq.) and 2-(pyrimidin-2-yl)-2,6-diazaspiro[3.3]heptane; bis(trifluoroacetic acid) (81 mg, 0.200 mmol, 1.5 eq.) in 1,4-dioxane (0.9 mL) and NMP (0.1 mL) is added sodium tert-butoxide (64 mg, 0.665 mmol, 5 eq) and RuPhos-Palladacycle G3 (12 mg, 0.014 mmol, 0.1 eq), and the reaction is stirred at 110° C. for 4 h. The reaction mixture is cooled, diluted with acetonitrile and methanol, and 175 mg of SiliaMet-DMT (Silicycle, 0.10 mmol) is added. The resultant slurry is stirred at room for one hour. The solids are removed by filtration and the crude product is purified by HPLC (eluting from a C18 column with a gradient of 5-85% acetonitrile/water to give the title compound as a white solid (3 mg, 5% yield). LCMS (ESI): m/z 435.6 (M+1).

Compound Nos. 1085 to 1091

Compound Nos. 1085 to 1091 are prepared according to the methods set forth in Example 41 using appropriately substituted intermediates.

Example 42

Vasopressin V1a Receptor Antagonist Assay

The purpose of this assay is to determine the inhibitory effect of synthesized compounds on the Vasopressin V1a receptor. The assay is performed in Chinese Hamster Ovary (CHO) cells expressing the human Arginine Vasopressin Receptor 1a (AVPR1a). Arginine Vasopressin (AVP) evokes an increase in intracellular calcium in CHO-AVPR1a cells which is measured in a fluorescence assay on the FLIPR$^{TETRA}$ using calcium sensitive dyes. Test compounds are assessed for their ability to affect the magnitude of the response to AVP, with antagonists showing a concentration-dependent reduction in the AVP-mediated fluorescence. Compounds are tested in duplicate in a 10-point, 1:3 dilution series starting at a nominal concentration of 3 µM in the assay.

CHO-AVPR1a cells are maintained in routine culture in T175 Flasks at 37° C., 5% CO2. The growth medium consists of Ham's F12 media supplemented with 10% v/v fetal bovine serum, 1× non-essential amino acids, and 0.4 mg/ml Geneticin G418.

On day one, cells are harvested from T175 flasks when they are 80-90% confluent by first washing the cell monolayer with PBS and then dissociated using trypsin 0.05%/EDTA (3 mL for a T175 Flask). The flasks are incubated at room temperature until the cells detached. To the cell suspension, 10 ml of growth media is added and the cell density determined using the Vi-Cell automated cell counter. The cells are spun at 1000 rpm for 3 minutes, then the supernatant is carefully removed and discarded. The cell pellet is re-suspended at 6.0e$^5$ cells/ml in growth media. 25 µL of cells in growth media is dispensed into each well (15,000 cells per well) of a poly-D-lysine coated black, clear bottomed, 384-well plate. The plates are incubated at 37° C., 5% CO$_2$ overnight.

At the start of each assay day, the potency of AVP is assessed and an EC$_{80}$ concentration determined for subsequent compound profiling. Assays are performed using a two-step addition protocol on the FLIPR$^{TETRA}$; first addition of 5 µl of control or test compound at 10× final in assay buffer with 15 min incubation at 37° C., 5% CO$_2$ followed by 10 µl of AVP at 6× final concentration in assay buffer. Changes in fluorescence are monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the AVP agonist only, 0.1% w/v bovine serum albumin. The assay is initiated by the removal of growth media from the cells and replacement with 45 µl of Calcium-6 dye (Molecular Devices) prepared at 1× in assay buffer. Cells are loaded with dye for 60-90 min at 37° C., 5% CO$_2$ before initiation of the FLIPR$^{TETRA}$ protocol. For the AVP potency determination, the first addition consisted of assay buffer containing 3% v/v DMSO and the second addition, a 10-point dilution series of AVP (1:3 dilutions from 1 µM) in assay buffer supplemented with 0.1% BSA. For compound profiling, test compounds are first serially diluted in DMSO (10-point curve, 1:3 dilutions) then diluted 33.3-fold in assay buffer prior to addition to the dye loaded cells on the FLIPR$^{TETRA}$. At the end of the incubation period, 10 µl of AVP in assay buffer containing 0.1% BSA is added at the previously determined EC$_{80}$ concentration.

In-plate controls for the assay include Ro5028442 and PF-184563 concentration-response curves as reference V1a antagonists and an AVP concentration-response curve to confirm the reproducibility of the EC$_{80}$ used for the compound challenge. MAX-MIN raw data is normalised to in-plate assay controls comprising DMSO matched solutions of 300 nM SR49059 (100% inhibition) and AVP EC$_{80}$ (0% inhibition). Selectivity profiling of certain example compounds is determined against Vasopressin V1b and V2 receptors.

Example 43

Vasopressin V1B Receptor Antagonist Assay

The purpose of the assay is to determine the inhibitory effect of synthesized compounds on the Vasopressin V1b receptor. The assay is performed in Chinese Hamster Ovary (CHO) cells expressing the human Arginine Vasopressin Receptor 1b (AVPR1b). Arginine Vasopressin (AVP) evokes an increase in intracellular calcium in CHO-AVPR1b cells which is measured in a fluorescence assay on the FLIPR$^{TETRA}$ using calcium sensitive dyes. Test compounds are assessed for their ability to affect the magnitude of the response to AVP, with antagonists showing a concentration-dependent reduction in the AVP-mediated fluorescence.

CHO-AVPR1b cells are maintained in routine culture in T175 Flasks at 37° C., 5% CO2. The growth medium consisted of Ham's F12 media supplemented with 10% v/v fetal bovine serum, 1× non-essential amino acids, and 0.4 mg/ml Geneticin G418.

Cells are harvested from T175 flasks when they are 80-90% confluent by first washing the cell monolayer with PBS and then dissociated using trypsin 0.05%/EDTA (3 mL for a T175 Flask). The flasks are incubated at room temperature until the cells detached. To the cell suspension, 10 ml of growth media is added and the cell density determined using the Vi-Cell automated cell counter. The cells are spun at 1000 rpm for 3 minutes, then the supernatant is carefully removed and discarded. The cell pellet is re-suspended at $6.0e^5$ cells/ml in growth media. 25 µL of cells in growth media is dispensed into each well (15,000 cells per well) of a poly-D-lysine coated black, clear bottomed, 384-well plate. The plates are incubated at 37° C., 5% $CO_2$ overnight.

At the start of each assay day, the potency of AVP is assessed and an $EC_{80}$ concentration determined for subsequent compound profiling. Assays are performed using a two-step addition protocol on the FLIPR$^{TETRA}$; first addition of 5 µl of control or test compound at 10× final in assay buffer with 15 min incubation at 37° C., 5% $CO_2$ followed by 10 µl of AVP at 6× final concentration in assay buffer. Changes in fluorescence are monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the AVP agonist only, 0.1% w/v bovine serum albumin. The assay is initiated by the removal of growth media from the cells and replacement with 45 µl of Calcium-6 dye (Molecular Devices) prepared at 1× in assay buffer. Cells are loaded with dye for 60-90 min at 37° C., 5% $CO_2$ before initiation of the FLIPR$^{TETRA}$ protocol. For the AVP potency determination, the first addition consisted of assay buffer containing 3% v/v DMSO and the second addition a 10-point dilution series of AVP (1:3 dilutions from 1 µM) in assay buffer supplemented with 0.1% BSA. For compound profiling, test compounds are first serially diluted in DMSO (10-point curve, 1:3 dilutions) then diluted 33.3-fold in assay buffer prior to addition to the dye loaded cells on the FLIPR$^{TETRA}$. At the end of the incubation period 10 µl of AVP in assay buffer containing 0.1% BSA is added at the previously determined $EC_{80}$ concentration.

In-plate controls for the assay include a Nelivaptan concentration-response curve as the reference V1b antagonist and an AVP concentration-response curve to confirm the reproducibility of the $EC_{80}$ used for the compound challenge. MAX-MIN raw data is normalised to in-plate assay controls comprising DMSO matched solutions of 3 µM nelivaptan (100% inhibition) and AVP $EC_{80}$ (0% inhibition).

Example 44

Vasopressin V2 Receptor Antagonist Assay

The purpose of the assay is to determine the inhibitory effect of synthesized compounds on the Vasopressin receptor 2. The assay is performed in commercially available 1321N1 cells expressing the human Arginine Vasopressin Receptor V2 (AVPR2) (Perkin Elmer #ES-363-CF). Arginine Vasopressin (AVP) evokes an increase in intracellular cAMP in these cells which is measured in a TR-FRET assay using a Europium cAMP tracer and ULight labelled antibody reagents contained in a LANCE Ultra cAMP kit (Perkin Elmer #TRF0263). Increases in cAMP in the assay result in a reduction in TR-FRET as the cAMP produced by the stimulated cells competes with the Eu-cAMP tracer for binding sites on the ULight labelled antibody. Test compounds are assessed for their ability to affect the magnitude of the response to AVP, with antagonists showing a concentration-dependent decrease in the AVP-mediated reduction in TR-FRET signal.

cAMPZen V2 assay ready cells are thawed at 37° C. and resuspended directly from frozen in 9 ml growth medium consisting of DMEM supplemented with 10% v/v fetal bovine serum, 1× non-essential amino acids, and 1 mM sodium pyruvate. Cells are spun at 1000 rpm for 3 minutes and the supernatant is carefully removed and discarded. The pellet is resuspended in 5 ml stimulation buffer and the cell density determined using the Vi-Cell automated cell counter. The cell suspension is diluted to a $0.2×10^6$/ml suspension ready for plating. To all wells of a white 384-well Optiplate (Perkin Elmer #6007299) 5 µL of cells in stimulation buffer are dispensed (1,000 cells per well). Stimulation buffer consisted of HBSS (+Ca/+Mg) supplemented with 5 mM HEPES, 0.1% BSA stabiliser and 0.5 mM IBMX.

At the start of each assay day the potency of AVP is assessed and an $EC_{80}$ concentration determined for subsequent compound profiling. Assays are performed by first an addition of 2.5 µl of control or test compound at 4× final concentration in stimulation buffer followed by 2.5 µl of AVP at 4× final concentration in stimulation buffer. After a 1 hour reaction, detection reagents are added by first an addition of 5 µl EU-cAMP tracer, followed by 5 µl ULight-anti-cAMP both diluted as per the manufacturer's instructions. After a one hour incubation, plates are ready to be read (signals then remained stable for up to 24 hours). Changes in time resolved fluorescence are monitored with excitation via a laser (337 nm) measuring both 615 nm and 665 nm emission wavelengths. For the AVP potency determination the first addition consisted of stimulation buffer containing 3% v/v DMSO and the second addition a 10-point dilution series of AVP (1:3 dilutions from 0.1 nM) in stimulation buffer. For compound profiling, test compounds are dispensed by the Labcyte Echo (10-point curve, 1:3 dilutions) in a target 0.1 µl volume then diluted 750-fold in stimulation buffer containing 3% DMSO prior to addition to the cells. At the end of the incubation period, 2.5 µl of AVP in stimulation buffer is added at the previously determined $EC_{80}$ concentration.

In-plate controls for the assay include a Tolvaptan concentration-response curve as the reference V2 antagonist and an AVP concentration-response curve to confirm the reproducibility of the $EC_{80}$ used for the compound challenge. Data for fluorescence at 665 nm is normalised to in-plate assay controls comprising DMSO matched solutions of assay buffer without agonist (100% inhibition) and AVP $EC_{80}$ (0% inhibition).

Example 45

Oxytocin Receptor Antagonist Assay

This assay is performed in CHEM-1 cells expressing the human Oxytocin Receptor (hOTR) to determine the inhibitory effect of the compounds of the invention on the human Oxytocin receptor. Oxytocin evokes an increase in intracellular calcium in CHEM-1-hOTR cells which is measured in a fluorescence assay on the FLIPR$^{TETRA}$ using calcium sensitive dyes. Test compounds are assessed for their ability to affect the magnitude of the response to oxytocin, with antagonists showing a concentration-dependent reduction in the oxytocin-mediated fluorescence. Compounds displaying potency at the vasopressin V1a receptor of <100 nM are progressed to selectivity testing against hOTR and are tested in triplicate in a 10-point, 1:3 dilution series starting at a nominal concentration of 3 µM in the assay.

CHEM-1-hOTR ready is used to assay frozen cells (Eurofins #HTS090RTA) which are supplied with a proprietary Media Component.

Day 1 of the assay: Cells are thawed in a 37° C. water bath and diluted with the supplied Media Component to a final volume of 10 ml. The cell suspension is centrifuged at 1000 rpm for 3 min at room temperature and the supernatant is discarded. The cell pellet is resuspended in Media Component (10.5 ml) and the cells (25 µL) are dispensed into a poly-D-lysine coated black, clear bottomed, 384-well plate. The plates are incubated overnight at 37° C., 5% $CO_2$.

Day 2: At the start of each assay day the potency of oxytocin is assessed and an $EC_{80}$ concentration is determined for subsequent compound profiling. Assays are performed using a two-step addition protocol on the FLIPR$^{TETRA}$; first addition of 5 µl of control or test compound at 10× final in assay buffer with 15 min incubation at 37° C., 5% $CO_2$ followed by 10 µl of oxytocin at 6× final concentration in assay buffer. Changes in fluorescence are monitored for 3 min after both additions on the FLIPR$^{TETRA}$ using 470-495 nm excitation and 515-575 nm emission wavelengths. The assay buffer consisted of HBSS (+ Ca/+ Mg) supplemented with 20 mM HEPES, and for the preparation of the oxytocin agonist only, 0.1% w/v bovine serum albumin. The assay is initiated by the removal of growth media from the cells and replaced with 45 µl of Calcium-6 dye (Molecular Devices) prepared at 1× in assay buffer. Cells are loaded with dye for 60-90 min at 37° C., 5% $CO_2$ before initiation of the FLIPR$^{TETRA}$ protocol. For the oxytocin potency determination the first addition consisted of assay buffer containing 3% v/v DMSO and the second addition involved a 10-point dilution series of oxytocin (1:3 dilutions from 1 µM) in assay buffer supplemented with 0.1% BSA. For compound profiling, test compounds are first serially diluted in DMSO (10-point curve, 1:3 dilutions) then diluted 33.3-fold in assay buffer prior to addition to the dye loaded cells on the FLIPR$^{TETRA}$. At the end of the incubation period 10 µl of oxytocin in assay buffer containing 0.1% BSA is added at the previously determined $EC_{80}$ concentration.

In-plate controls for the assay include a L-368,899 concentration-response curve as the reference OTR antagonist and an oxytocin concentration-response curve to confirm the reproducibility of the $EC_{80}$ used for the compound challenge. MAX-MIN raw data is normalised to in-plate assay controls comprising DMSO matched solutions of assay buffer without agonist (100% inhibition) and oxytocin $EC_{80}$ (0% inhibition).

Activity expressed as $IC_{50}$ of representative compounds against the V1a, V1b, V2, and OT receptors is provided in Table 4 below. With respect to V1a, V1b, V2, and OT activity: "++++" denotes an $IC_{50}$ of less than 100 nM; "+++" denotes an $IC_{50}$ of from 100 nM to less than 500 nM; "++" denotes an $IC_{50}$ of from 500 nM to less than 1000 nM; and "+" denotes an $IC_{50}$ of 1000 nM or more. Reference compounds were assessed in the in vitro antagonist assay with the following results: balovaptan—V1A (++++), V1B (+), V2 (+), OT (+); relcovaptan—V1A (++++), V1B (−), V2 (−), OT (−); JNJ-17308616—V1A (++++), V1B (+), V2 (+++), OT (+).

TABLE 4

| Activity of Representative Compound | | | | |
|---|---|---|---|---|
| Cpd No. | V1a $IC_{50}$ | V1b $IC_{50}$ | V2 $IC_{50}$ | OT $IC_{50}$ |
| 225 | ++++ | −− | | + |

Example 46

MDCK-MDR1 Effective Efflux Ratio

The MDR1-MDCK effective efflux assay is performed as described in the BioFocus Standard Operating Procedure, ADME-SOP-56. Both wild-type (WT) and MDR1-MDCK cells (Solvo Biotechnology) are seeded onto 24-well Transwell plates at 2.35×105 cells per well and used in confluent monolayers after a 3 day culture at 37° C. under 5% CO2. For both cell types, test and control compounds (propranolol, vinblastine) are added (10 µM, 0.1% DMSO final, n=2) to donor compartments of the Transwell plate assembly in assay buffer (Hanks balanced salt solution supplemented with 25 mM HEPES, adjusted to pH 7.4) for both apical to basolateral (A>B) and basolateral to apical (B>A) measurements. Incubations are performed at 37° C., with samples removed from both donor and acceptor chambers at T=0 and 1 hour and compound analysed by mass spectrometry (LC-MS/MS) including an analytical internal standard.

Apparent permeability (Papp) values are determined from the relationship:

Papp=[Compound Acceptor $T$=end]×$V$ Acceptor/
([Compound Donor $T$=0]×$V$ Donor)/incubation
time×$V$ Donor/Area×60×10-6 cm/s Where V is the volume of each Transwell compartment (apical 125 µL, basolateral 600 µL), and concentrations are the relative MS responses for compound (normalized to internal standard) in the donor chamber before incubation and acceptor chamber at the end of the incubation. Area=area of cells exposed for drug transfer (0.33 cm2).

Efflux ratios (Papp B>A/Papp A>B) are calculated for each compound from the mean Papp values in each direction for both wild-type and MDR1-MDCK cells. The MDR1-MDCK cell line has been engineered to over-express the efflux transporter, MDR1 (P-glycoprotein), and a finding of good permeability B>A, but poor permeability A>B, suggests that a compound is a substrate for this transporter.

In order to confirm the involvement of MDR1 in any efflux seen, an "effective efflux ratio" (EER) is calculated by comparing compound efflux ratios (ER) in the two cell types, i.e.

EER=ER(MDR1-MDCK)/ER(wild-type MDCK)

This ratio illustrates the effect of the over-expressed MDR1 normalised for the background movement of compound through the wild-type cells.

Lucifer Yellow (LY) is added to the apical buffer in all wells to assess viability of the cell layer. Compound recovery from the wells is determined from MS responses (normalized to internal standard) in donor and acceptor chambers at the end of incubation compared to response in the donor chamber pre-incubation.

MDCK II Cell Permeability Assay Procedure

MDCK II cell culture media is prepared using Dulbecco's modified eagle medium (DMEM), fetal bovine serum (FBS) 10%, Glutamax 1% and PenStrep 1% and is sterile-filtered. Transwell 24-well plates of MDCK II_WT or MDCK II-MDR1 cells are prepared and the plates are fed every alternate day until the day of use. Plates are used on 5th day after cell plating. Preparation for changing the media of the basal plate is conducted by filling all wells of a 24 well sterile plate with 900 µl of culture media and placing it in an incubator until use. Then the apical section of plate is lifted out and lowered onto an empty basal plate, followed by aspiration of 200 µl of the culture media from the apical compartment and replacement with 200 µl of fresh culture media. This step is repeated twice for a total of 3 washes followed by removal of the basal plate from the incubator and placement of the plate in the hood. The apical section of plate is then added to the basal plate and returned to incubator.

On the day of the assay, approximately 3 ml of 1000-fold diluted compound solution (required concentration for the assay) is prepared in transport buffer using the following volumes: 200 µl/insert/well (apical application) and 780 µl/insert/well (basal application). The basal assay plate is prepared by adding 750 µl of transport buffer (Hank's Balanced Salt Solution) to A-B wells, and 780 µl of diluted compound solution to B-A wells. Triplicate samples of 10 µl each are collected from basal compartments of B-A wells for T0, and then basal assay plates are placed in the incubator. MDCK plates are placed in the hood and the apical section of the plates are lifted out and lowered onto empty basal plates. 200 µl of the media is removed from the apical wells and replaced with 200 µl of fresh transport media, and this step is repeated twice for a total of 3 washes. 200 µl of the media is removed from the apical wells and replaced with 200 µl of the diluted compound (for A-B wells) or 200 µl of fresh transport buffer (for B-A wells). Triplicate samples are collected (10 µl each) from apical compartments of A-B wells for T0. Basal plates are removed from the incubator and transferred to the apical section of the plate to the basal plate and the assay plates are covered and returned to the incubator. The T0 samples are diluted with 40 µl transport buffer and 100 µl of room temperature quench solution is added to the diluted T0 samples. 50 µl of all T0 samples are mixed and transferred to T0 sample plates and diluted with 100 µl of MilliQ water for bioanalysis. At T-2 hrs, 3 replicate 10 µl samples from all apical compartments and B-A basal compartments are collected; and, 3 replicate 50 µl samples from A-B basal compartments are collected. The 10 µl samples are diluted with 40 µl transport buffer. 100 µl of quench solution is added to all T-2 hrs samples. 50 µl of all T-2 hrs samples are mixed and transferred to sample plates and diluted with 100 µl of MilliQ water for bioanalysis.

Analyte levels (peak area ratios) are measured on apical (A) and basolateral (B) sides at T0 and T2 hrs. A-to-B and B-to-A fluxes are calculated (mean of n=3 measurements). Apparent permeability (Papp, $10^{-6}$ cm/sec) is calculated as dQ (flux)/(dt×Area×Concentration).

The efflux ratio is (B-to-A)/(A-to-B) ratio [i.e., Papp(B-A)/Papp(B-A)]. A ratio>2-3 is determined as evidence of efflux, and compounds that demonstrate efflux ratios in or above this range PGP efflux can be confirmed by testing+/- pgp inhibitor (dosing solutions prepared with and without verapamil at a final assay concentration of 25 µM).

The ability of a test compound to penetrate the blood brain barrier and avoid efflux by transporters expressed in the brain, can be roughly correlated with the Papp(A-B) and the efflux ratio (as defined above), respectively. The results are provided in Table 5. (+) denotes an apparent permeability<7 ($10^{-6}$ cm/sec); (++) denotes >7 ($10^{-6}$ cm/sec) but <10 ($10^{-6}$ cm/sec; (+++) denotes >10 ($10^{-6}$ cm/sec) but <20 ($10^{-6}$ cm/sec); and (++++) denotes >20 ($10^{-6}$ cm/sec).

PGP efflux can be confirmed by testing+/-pgp inhibitor (dosing solutions prepared with and without verapamil at a final assay concentration of 25 µM). Reference compounds were assessed in the in vitro MDCK apparent permeability, efflux ratio, and effective efflux ratio assays (MDR1 and WT) with the following results: balovaptan—MDR1AB (++++), MDR1ER (++), MDR1EER (++), WTAB (+++), WTER (++++); JNJ-17308616—MDR1AB (+), MDR1ER (+), MDR1EER (+), WTAB (+++), WTER (+).

TABLE 5

Papp ($10^{-6}$ cm/sec) and Efflux ratio

| Compound No. | Papp ABMDR1 | MDR1ER |
|---|---|---|
| 225 | ++++ | + |

Example 47

Evaluation of Behavioral, Biochemical and/or Neurophysiological Characteristics in the Valproate Model Valproate (VPA) is an anticonvulsant drug commonly prescribed for patients with epilepsy. During pregnancy, administration of VPA elevates the risk of neurodevelopmental disorders in the offspring and this effect has been modeled similarly in rodents to better understand the mechanisms underlying the VPA-induced neurodevelopmental changes. V1a antagonists are assessed for preventative and/or restorative effects in rodents following the administration of a single injection of valproate acid (600 mg/kg) or vehicle (sham) to pregnant females dams on gestational day 13 (embryonic day 13). Pregnant dams are monitored on a daily basis for changes in weight and health, or in their feeding patterns. After birth, pups are monitored for any signs of physical abnormalities (e.g., weights, food and water intake, postnatal day of eye opening).

Selective studies are conducted to evaluate behavioral, biochemical and/or neurophysiological characteristics of the valproate treated animals as compared to control animals. More specifically, the effects of V1 antagonists administered to VPA treated animals are assessed using standard methodology for behavioral changes such as anxiety (e.g., ultrasonic vocalizations, elevated plus maze), learning and memory (e.g., Morris water maze, novel object recognition), social interactions, sensorimotor gating and locomotor activity. Biochemical changes are measured by assessing synaptic proteins and mRNA (e.g., gamma-aminobutyric acid

[GABA]synthesis, glutamic acid decarboxylase [GAD], brain derived neurotrophic factor [BDNF]). Neurophysiological characteristics are assessed by whole cell recordings of the electrophysiological properties of neurons from VPA- and sham-treated animals to identify differences in neuronal function with and without V1 antagonists.

Activity and/or Telemetry Studies in Rodents and Non-Human Primates to Assess Sleep/Wake Cycles and Circadian Rhythms:

The vasopressin system is important in regulating biological circadian rhythms and re-entrainment following environmental alterations. In these studies, animals are housed on a 12 hour light/dark cycle and activity is monitored using an infrared beam break system or by wheel running (rodents) or by activity monitors attached to the collar of the animal (non-human primates). Activity data is collected for up to 30 days to establish circadian rhythms and changes induced by phase shifting the light/dark cycle by e.g., 4, 8 or 12 hours is recorded and analyzed. V1a antagonist is administered to improve re-entrainment as measured by re-establishment of the regular activity patterns. Additional endpoints may include cognitive assessment (e.g., spatial working memory).

Implantation of a telemetry device with electrodes to record electroencephalography/electromyography/electroculography (EEG/EMG/EOG) for staging sleep/wake cycles is used. In this case, EEG/EMG electrodes and transmitters are implanted in fully anesthetized animals by trained surgeons. The transmitter module is implanted subcutaneously below the scapular region or into the abdomen. Biopotential leads are guided subcutaneously from the back to the head via a midline incision. Using a stereotaxic approach, stainless steel screws are implanted into the skull over areas of interest until the tips are on the surface of the dura mater. The biopotential leads are wrapped around the screws and referenced. The EMG or EOG leads are sutured into the temporalis muscle or intra-ocular muscle, respectively. Animals receive postoperative analgesia and antibiotics and recover for a minimum of 21-days before testing. Receiver boards are placed in close proximity to the animal to facilitate real-time EEG/EMG/EOG recordings during testing.

Physiological Measures

Vasopressin is an important regulator of water conservation and blood pressure in the body and its release into the peripheral blood supply can be induced by an increase in plasma osmolality. In healthy adults, a rise in plasma osmolality of 1-2% above basal level produces thirst that promotes water intake and normalization of osmolality. Intravenous administration of a hyperosmolic solution to rodents or humans increases the plasma vasopressin concentration and other measures (e.g., thirst, urine output and vasoconstriction). V1a antagonist is evaluated for its ability to alter plasma vasopressin concentrations, vasoconstriction and/or urine output following administration of a hyperosmolic solution.

Example 48

Arginine-Vasopressin (AVP) Induced Phospho-Erk Measurement in Native Tissue

When V1a receptors are coupled to phospholipase C (PLC), they increase intracellular Ca2+ concentrations and protein kinase C (PKC) activity, and transactivate the mitogen-activated protein kinases/extracellular signal-regulated kinase (MAPK/Erk) and PI3 kinase/Akt pathways upon activation (Chen et al., J Neuroendocrinol. 2010). Rat choroid plexus (RCP) cell lines express functional V1a receptors measured by increased calcium concentrations in response to V1a receptor agonists (Battle et al., Biochem Biophys Res Comm 2000). In these studies, RCP are stimulated with AVP and V1a receptor antagonists reference compounds relcovaptan and balovaptan and test compound 142A are evaluated.

RCP P9(18) cells are seeded 30K/well, in 100 µl growth medium containing 10% FBS in polystyrene 96-well plates and incubated at 37° C., 5% CO2 and incubated overnight. The following day, the growth medium is replaced with 50 µl pre-warmed HBSS containing 20 mM HEPES and the cells are incubated at 37° C., 5% CO2 for 1.5 hrs. 1 mM AVP (Sigma V9879) is freshly prepared in distilled water in a glass vial, and diluted to 3× concentrations in HBSS containing 20 mM HEPES and 0.1% BSA in glass vials and kept on ice. Cells are treated with 25 µl 3× vehicle, 3× eBioscience Cell Stimulation Cocktail (Thermo Fisher Scientific 00-4970-93) or 3×AVP and incubated at 37° C., 5% CO2 for 5, 10 or 20 min. Final concentrations of AVP: 10, 100 or 1000 nM. Final concentrations of components in Cell Stimulation Cocktail: 81 nM PMA, 1.34 µM ionomycin, 0.2% ethanol. Cells are lysed with 25 µl 4× CST lysis buffer containing protease and phosphatase inhibitors, PMSF and SDS and then stored at −80° C., for 48 h. The lysates are thawed, centrifuged at 2000 g for 30 min at 4° C. and 40 µl supernatants assayed for pERK1/2 (Thr202/Tyr204; Thr185/Tyr187) and total ERK1/2 using MSD kit K15107D. The MSD ECL data for the lysates are corrected for no cell blanks, then phospho-protein levels expressed as a ratio to the total ERK1/2 level. The ratios are expressed as fold-change from the vehicle-treated control at each timepoint.

Example 49

Arginine-Vasopressin (AVP) Induced Behavior in Mouse

Administration of Arginine-Vasopressin (AVP) intracerebroventricularly (i.c.v.) elicits characteristic scratching, digging and grooming behavior in mice that can be measured readily and is sensitive to blockade with vasopressin antagonists (Meisenberg, 1988; Bleickart et al., 2009).

Male CD-1 mice (Charles River Germany) weighing 22-25 g upon the study in-life are used for this study. Animals are housed in groups of 4-5 per cage in standard temperature (22±1° C.) and light-controlled environment (lights on from 7 am to 8 µm), with ad libitum access to food and water. Prior to commencing any procedures to the mice, they are allowed to habituate in the vivarium for a minimum of 7 days.

Anesthesia is induced in a plexiglass chamber for 2-3 min with 5% isoflurane, and maintained through a snout mask with 1-2% isoflurane thereafter. A homeothermic blanket system with a rectal probe is used to monitor and maintain the animal's body temperature at 37.0° C.±1.5° C. during the operation. Anesthetized mice are placed in a stereotaxic apparatus and skin between the ears shaved and disinfected with povidone-iodine solution (Betadine). A 10-µl Hamilton syringe with 28-gauge needle is used for the i.c.v. injections. All animals receive identical AVP injections (3.689 µM) or sterile saline (0.9% sodium chloride solution) into the right lateral ventricle at the following coordinates: AP=+0.5 mm; ML=+1.0 mm; DV=−2.5 mm (approximately from bregma). The actual coordinates are calculated by the distance from the point in midline between the eyes and no skin incision is made. After the needle is placed in the ventricle and the AVP is delivered, the needle is left in place for 3 minutes before withdrawal. Finally, the mouse is detached from the anesthesia mask and immediately placed in a clean cage to commence the observation.

Mice are observed and video-recorded for 15 minutes following AVP/saline administration and behaviors are measured (in seconds) and a cumulative time is calculated. The following behaviors are considered as AVP-related: scratching of limbs or torso, digging, licking and face washing (swiping of face). Using this assay, balovaptan (100 and 300 mg/kg, po) and JNJ-17308616 (30, 100 mg/kg, po) are evaluated for antagonist activity to AVP-induced scratching behaviors.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Application 62/515,473 filed Jun. 5, 2017 and U.S. Provisional Application 62/778,831 filed Dec. 12, 2018 are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure

I claim:

1. A compound having the structure of Formula (I) or a pharmaceutically acceptable isomer, racemate, hydrate, solvate, isotope, or salt thereof:

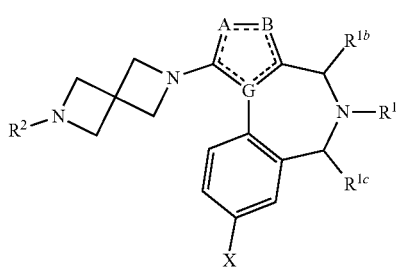

wherein
 $\mathrm{---}$ represents an optional double bond;
 A and B are independently nitrogen or oxygen, with the proviso that A and B are not both oxygen;
 G is nitrogen or carbon;
 X is halogen, lower alkyl, lower haloalkyl, lower alkoxy, or cyano;
 $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
 $R^{1b}$ and $R^{1c}$ are independently hydrogen, lower alkyl, or spiroalkyl;
 $R^2$ is -Q-($R^4$)$_n$, —S(=O)$_2R^5$, or —C(=O)$R^5$;

$R^3$ is lower alkyl, lower haloalkyl, lower alkoxy, lower haloalkoxy, -cycloalkyl-$R^6$, —O-cycloalkyl-$R^6$, —O-heterocyclyl-$R^6$, —NH$R^5$, or —N$R^5R^5$;
or $R^{1b}$ and $R^1$ or $R^{1b}$ and $R^3$, together with the atoms to which they are attached, form a ring;
Q is aryl or heteroaryl;
each $R^4$ is independently halogen, hydroxy, lower alkyl, lower haloalkyl, lower alkoxy, lower haloalkoxyalkyl, or cyano;
each $R^5$ is independently cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and
n is 0, 1, or 2.

2. The compound of claim 1 having the structure of Formula (II), or a pharmaceutically acceptable isomer, racemate, hydrate, solvate, isotope, or salt thereof:

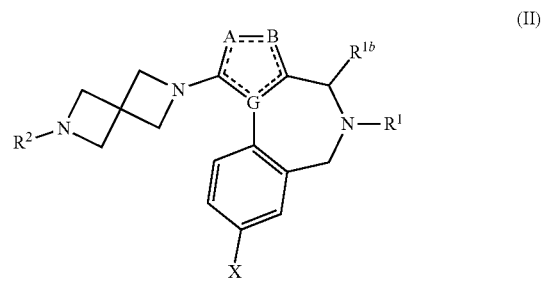

wherein
 $\mathrm{---}$ represents an optional double bond;
 A and B are independently nitrogen or oxygen, with the proviso that A and B are not both oxygen;
 G is nitrogen or carbon;
 X is halogen, lower alkyl, lower haloalkyl, lower alkoxy, or cyano;
 $R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
 $R^{1b}$ is hydrogen or lower alkyl;
 $R^2$ is -Q-($R^4$)$_n$, —S(=O)$_2R^5$, or —C(=O)$R^5$;
 $R^3$ lower alkyl, lower haloalkyl, alkoxy, lower haloalkoxy, -cycloalkyl-$R^6$, —O-cycloalkyl-$R^6$, or —O-heterocyclyl-$R^6$;
or $R^{1b}$ and $R^1$ or $R^{1b}$ and $R^3$, together with the atoms to which they are attached, form a ring
Q is aryl or heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, lower haloalkoxy, heterocyclyl, or —O-heterocyclyl;
$R^6$ is hydrogen, halo, alkyl, lower haloalkyl, or cyano; and
n is 0, 1, or 2.

3. The compound of claim 1 having the structure of Formula (III), or a pharmaceutically acceptable isomer, racemate, hydrate, solvate, isotope, or salt thereof:

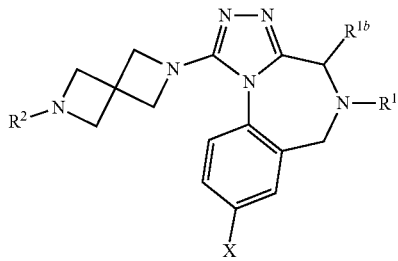

(III)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^2$ is -Q-(R$^4$)$_n$, —S(=O)$_2$R$^5$, or —C(=O)R$^5$;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
Q is heteroaryl;
each R$^4$ is independently halogen, hydroxy, lower alkyl, lower haloalkyl, lower alkoxy, lower haloalkoxyalkyl, or cyano;
R$^5$ is cycloalkyl, lower alkyl, lower haloalkyl, cycloalkylalkyl, lower alkoxy, heterocyclyl, or —O-heterocyclyl;
R$^6$ is hydrogen, halo, alkyl, lower haloalkyl, or cyano; and
n is 0, 1, or 2.

4. The compound of claim 1 having the structure of Formula (IV), or a pharmaceutically acceptable isomer, racemate, hydrate, solvate, isotope, or salt thereof:

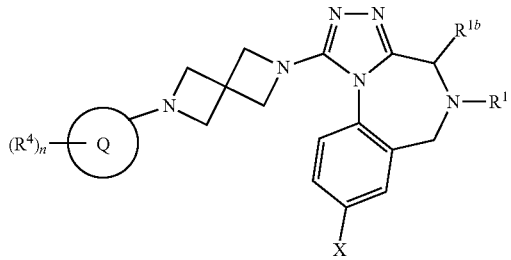

(IV)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;

Q is heteroaryl;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

5. The compound of claim 1 having the structure of Formula (V), or a pharmaceutically acceptable isomer, racemate, hydrate, solvate, isotope, or salt thereof:

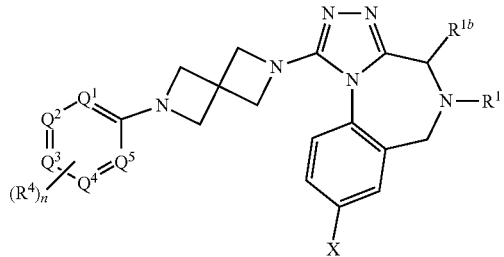

(V)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O-cycloalkyl-R$^6$, or —O-heterocyclyl-R$^6$;
or R$^{1b}$ and R$^1$ or R$^{1b}$ and R$^3$, together with the atoms to which they are attached, form a ring;
Q$^1$, Q$^2$, Q$^3$, Q$^4$, and Q$^5$ are independently N, CH, or CR$^4$,
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and
n is 0, 1, or 2.

6. The compound of claim 1 having the structure of Formula (VI), or a pharmaceutically acceptable isomer, racemate, hydrate, solvate, isotope, or salt thereof:

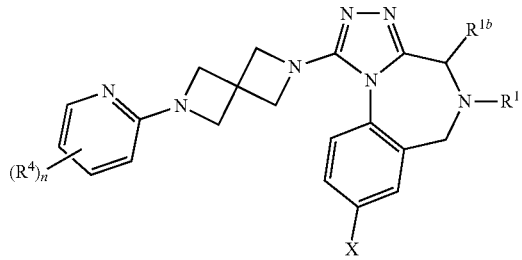

(VI)

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

7. The compound of claim 1 having the structure of Formula (VII), or a pharmaceutically acceptable isomer, racemate, hydrate, solvate, isotope, or salt thereof:

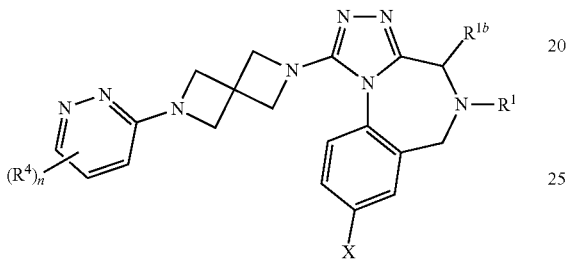

(VII)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

8. The compound of claim 1 having the structure of Formula (VIII), or a pharmaceutically acceptable isomer, racemate, hydrate, solvate, isotope, or salt thereof:

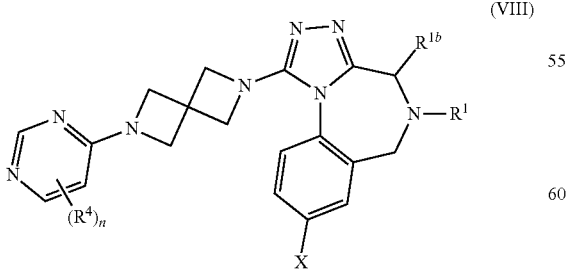

(VIII)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

9. The compound of claim 1 having the structure of Formula (IX), or a pharmaceutically acceptable isomer, racemate, hydrate, solvate, isotope, or salt thereof:

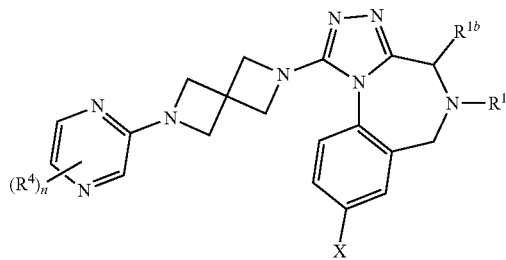

(IX)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

10. The compound of claim 1 having the structure of Formula (X), or a pharmaceutically acceptable isomer, racemate, hydrate, solvate, isotope, or salt thereof:

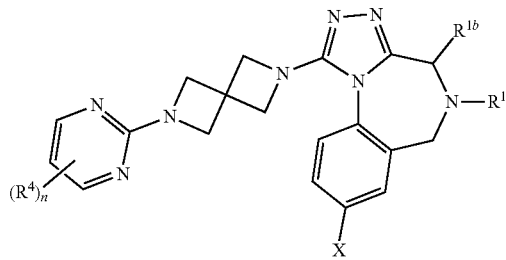

(X)

wherein
X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R¹ᵇ is hydrogen or lower alkyl;

R³ is lower alkyl, lower haloalkyl, alkoxy, lower haloalkoxy, -cycloalkyl-R⁶, —O-cycloalkyl-R⁶, or —O-heterocyclyl-R⁶;

or R¹ᵇ and R¹ or R¹ᵇ and R³, together with the atoms to which they are attached, form a ring;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

11. The compound of claim 1 having the structure of Formula (XI), or a pharmaceutically acceptable isomer, racemate, hydrate, solvate, isotope, or salt thereof:

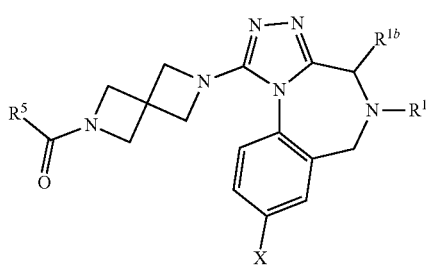

(XI)

wherein
X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R¹ᵇ is hydrogen or lower alkyl;

R³ is lower alkyl, lower haloalkyl, alkoxy, lower haloalkoxy, -cycloalkyl-R⁶, —O-cycloalkyl-R⁶, or —O-heterocyclyl-R⁶;

or R¹ᵇ and R¹ or R¹ᵇ and R³, together with the atoms to which they are attached, form a ring;

R⁵ is cycloalkyl, lower alkyl, lower haloalkyl, cycloalkylalkyl, lower alkoxy, heterocyclyl, or —O-heterocyclyl; and R⁶ is hydrogen, halo, alkyl, lower haloalkyl, or cyano.

12. The compound of claim 1 having the structure of Formula (XII), or a pharmaceutically acceptable isomer, racemate, hydrate, solvate, isotope, or salt thereof:

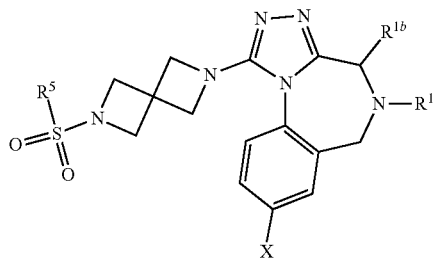

(XII)

wherein
X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R¹ᵇ is hydrogen or lower alkyl;

R³ is lower alkyl, lower haloalkyl, alkoxy, lower haloalkoxy, -cycloalkyl-R⁶, —O-cycloalkyl-R⁶, or —O-heterocyclyl-R⁶;

or R¹ᵇ and R¹ or R¹ᵇ and R³, together with the atoms to which they are attached, form a ring;

R⁵ is cycloalkyl, lower alkyl, lower haloalkyl, cycloalkylalkyl, lower alkoxy, heterocyclyl, or —O-heterocyclyl; and R⁶ is hydrogen, halo, alkyl, lower haloalkyl, or cyano.

13. The compound of claim 1 having the structure of Formula (XIII), or a pharmaceutically acceptable isomer, racemate, hydrate, solvate, isotope, or salt thereof:

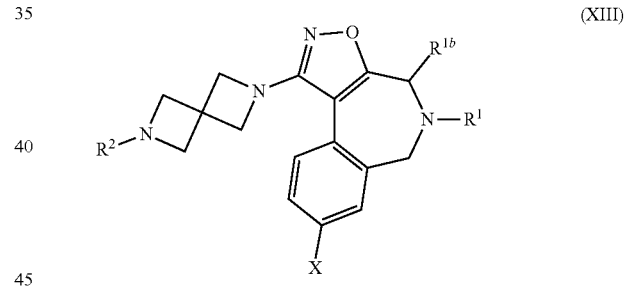

(XIII)

wherein
X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R¹ᵇ is hydrogen or lower alkyl;

R² is -Q-(R⁴)ₙ, —S(=O)₂R⁵, or —C(=O)R⁵;

R³ is lower alkyl, lower haloalkyl, lower alkoxy, lower haloalkoxy, -cycloalkyl-R⁶, —O-cycloalkyl-R⁶, or —O-heterocyclyl-R⁶;

or R¹ᵇ and R¹ or R¹ᵇ and R³, together with the atoms to which they are attached, form a ring;

Q is heteroaryl;

each R⁴ is independently halogen, hydroxy, lower alkyl, lower haloalkyl, lower alkoxy, lower haloalkoxyalkyl, or cyano;

R⁵ is cycloalkyl, lower alkyl, lower haloalkyl, cycloalkylalkyl, lower alkoxy, heterocyclyl, or —O-heterocyclyl;

R⁶ is hydrogen, halo, alkyl, lower haloalkyl, or cyano; and
n is 0, 1, or 2.

14. The compound of claim 1 having the structure of Formula (XIV), or a pharmaceutically acceptable isomer, racemate, hydrate, solvate, isotope, or salt thereof:

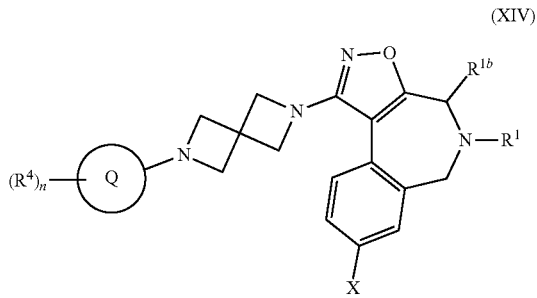

(XIV)

wherein
- X is halogen, lower alkyl, lower haloalkyl, lower alkoxy, or cyano;
- R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;
- R¹ᵇ is hydrogen or lower alkyl;
- R³ is lower alkyl, lower haloalkyl, lower alkoxy, lower haloalkoxy, -cycloalkyl-R⁶, —O-cycloalkyl-R⁶, or —O-heterocyclyl-R⁶;
- or R¹ᵇ and R¹ or R¹ᵇ and R³, together with the atoms to which they are attached, form a ring;
- Q is heteroaryl;
- each R⁴ is independently halogen, hydroxy, lower alkyl, lower haloalkyl, lower alkoxy, lower haloalkoxyalkyl, or cyano;
- R⁶ is hydrogen, halo, alkyl, lower haloalkyl, or cyano; and
- n is 0, 1, or 2.

15. The compound of claim 1 having the structure of Formula (XV), or a pharmaceutically acceptable isomer, racemate, hydrate, solvate, isotope, or salt thereof:

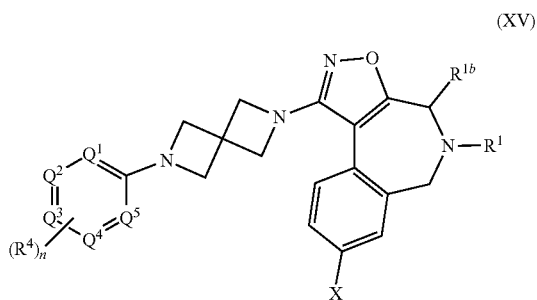

(XV)

wherein
- X is halogen, lower alkyl, lower haloalkyl, lower alkoxy, or cyano;
- R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;
- R¹ᵇ is hydrogen or lower alkyl;
- R³ is lower alkyl, lower haloalkyl, alkoxy, lower haloalkoxy, -cycloalkyl-R⁶, —O-cycloalkyl-R⁶, or —O-heterocyclyl-R⁶;
- or R¹ᵇ and R¹ or R¹ᵇ and R³, together with the atoms to which they are attached, form a ring;
- Q¹, Q², Q³, Q⁴, and Q⁵ are independently N, CH, or CR⁴;
- each R⁴ is independently halogen, hydroxy, lower alkyl, lower haloalkyl, lower alkoxy, lower haloalkoxyalkyl, or cyano;
- R⁶ is hydrogen, halo, alkyl, lower haloalkyl, or cyano; and
- n is 0, 1, or 2.

16. The compound of claim 1 having the structure of Formula (XVI), or a pharmaceutically acceptable isomer, racemate, hydrate, solvate, isotope, or salt thereof:

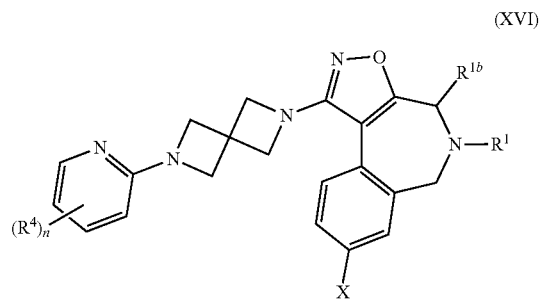

(XVI)

wherein
- X is halogen, lower alkyl, lower haloalkyl, lower alkoxy, or cyano;
- R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;
- R¹ᵇ is hydrogen or lower alkyl;
- R³ is lower alkyl, lower haloalkyl, alkoxy, lower haloalkoxy, -cycloalkyl-R⁶, —O-cycloalkyl-R⁶, or —O-heterocyclyl-R⁶;
- or R¹ᵇ and R¹ or R¹ᵇ and R³, together with the atoms to which they are attached, form a ring;
- each R⁴ is independently halogen, hydroxy, lower alkyl, lower haloalkyl, lower alkoxy, lower haloalkoxyalkyl, or cyano;
- R⁶ is hydrogen, halo, alkyl, lower haloalkyl, or cyano; and
- n is 0, 1, or 2.

17. The compound of claim 1 having the structure of Formula (XVII), or a pharmaceutically acceptable isomer, racemate, hydrate, solvate, isotope, or salt thereof:

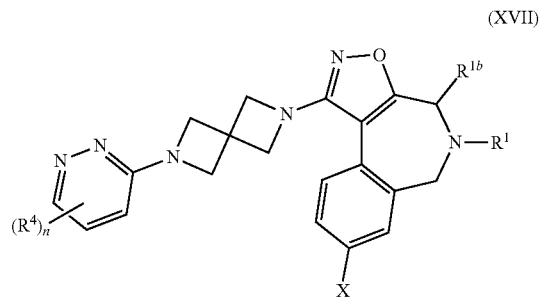

(XVII)

wherein
- X is halogen, lower alkyl, lower haloalkyl, lower alkoxy, or cyano;
- R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

18. The compound of claim 1 having the structure of Formula (XVIII), or a pharmaceutically acceptable isomer, racemate, hydrate, solvate, isotope, or salt thereof:

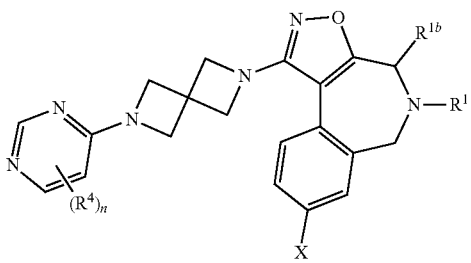

(XVIII)

wherein
X is halogen, lower alkyl, lower haloalkyl, lower alkoxy, or cyano;

$R^1$ is hydrogen, lower alkyl-$R^6$, haloalkyl, lower alkoxy-alkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

19. The compound of claim 1 having the structure of Formula (XIX), or a pharmaceutically acceptable isomer, racemate, hydrate, solvate, isotope, or salt thereof:

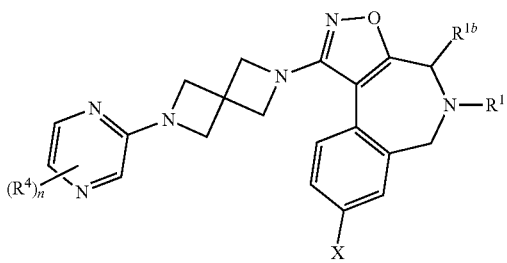

(XIX)

wherein
X is halogen, lower alkyl, lower haloalkyl, lower alkoxy, or cyano;

$R^1$ is hydrogen, lower alkyl-$R^6$, haloalkyl, lower alkoxy-alkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

20. The compound of claim 1 having the structure of Formula (XX), or a pharmaceutically acceptable isomer, racemate, hydrate, solvate, isotope, or salt thereof:

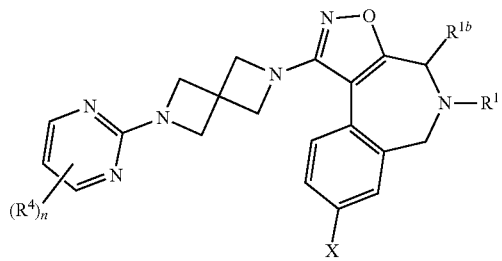

(XX)

wherein
X is halogen, lower alkyl, lower haloalkyl, lower alkoxy, or cyano;

$R^1$ is hydrogen, lower alkyl-$R^6$, haloalkyl, lower alkoxy-alkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O-cycloalkyl-$R^6$, or —O-heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

21. The compound of claim 1 having the structure of Formula (XXI), or a pharmaceutically acceptable isomer, racemate, hydrate, solvate, isotope, or salt thereof:

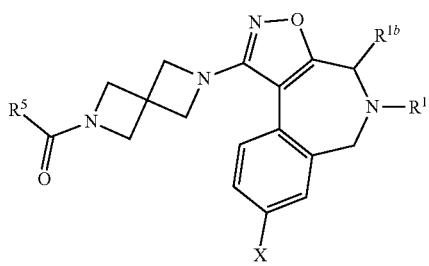 (XXI)

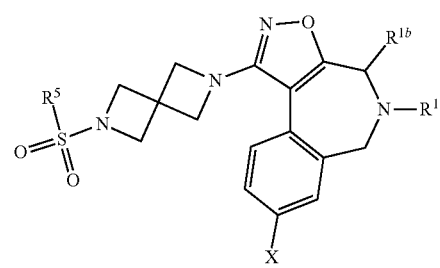 (XXII)

wherein
- X is halogen, lower alkyl, lower haloalkyl, lower alkoxy, or cyano;
- $R^1$ is hydrogen, lower alkyl-$R^6$, haloalkyl, lower alkoxy-alkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

22. The compound of claim 1 having the structure of Formula (XXII), or a pharmaceutically acceptable isomer, racemate, hydrate, solvate, isotope, or salt thereof:

wherein
- X is halogen, lower alkyl, lower haloalkyl, lower alkoxy, or cyano;
- $R^1$ is hydrogen, lower alkyl-$R^6$, haloalkyl, lower alkoxy-alkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
- $R^{1b}$ is hydrogen or lower alkyl;
- $R^3$ is lower alkyl, lower haloalkyl, alkoxy, lower haloalkoxy, -cycloalkyl-$R^6$, —O-cycloalkyl-$R^6$, or —O-heterocyclyl-$R^6$;
- or $R^{1b}$ and $R^1$ or $R^{1b}$ and $R^3$, together with the atoms to which they are attached, form a ring;
- $R^5$ is cycloalkyl, lower alkyl, lower haloalkyl, cycloalkylalkyl, lower alkoxy, heterocyclyl, or —O-heterocyclyl; and
- $R^6$ is hydrogen, halo, alkyl, lower haloalkyl, or cyano.

23. The compound of claim 1 having the structure of any one of the following compounds, or a pharmaceutically acceptable isomer, racemate, hydrate, solvate, isotope, or salt thereof:

| Compound No. | Structure |
|---|---|
| 1 | ![structure 1] |
| 2 | ![structure 2] |

-continued
| Compound No. | Structure |
|---|---|
| 3 | 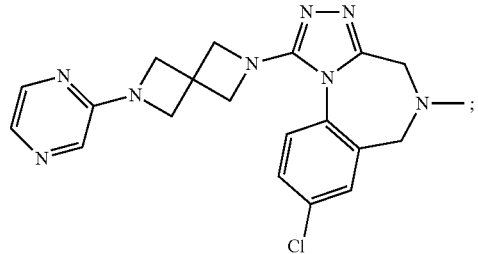 [SMILES: CN1Cc2cc(Cl)ccc2-n2c(nnc2N2CC3(CN(c4cnccn4)C3)C2)C1] |
| 4 | 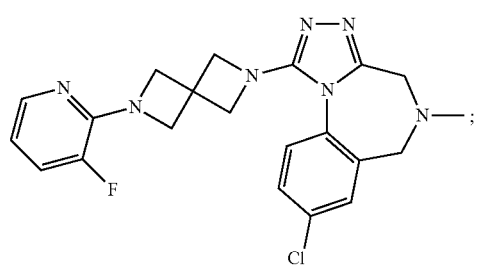 [SMILES: CN1Cc2cc(Cl)ccc2-n2c(nnc2N2CC3(CN(c4ncccc4F)C3)C2)C1] |
| 5 | 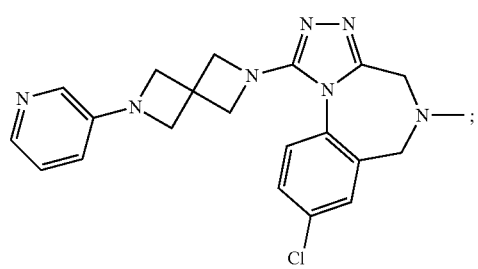 [SMILES: CN1Cc2cc(Cl)ccc2-n2c(nnc2N2CC3(CN(c4cccnc4)C3)C2)C1] |
| 6 | 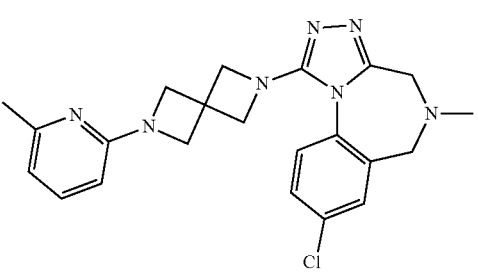 |
| 7 | 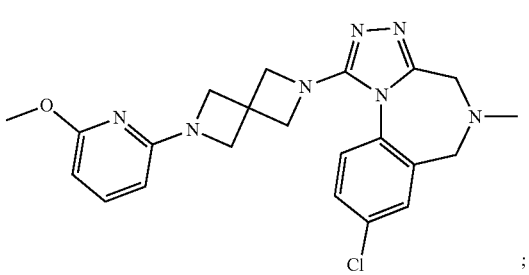 |
| 8 | 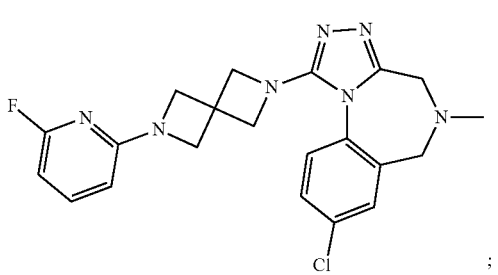 [SMILES: CN1Cc2cc(Cl)ccc2-n2c(nnc2N2CC3(CN(c4cccc(F)n4)C3)C2)C1] |

-continued

| Compound No. | Structure |
|---|---|
| 9 | 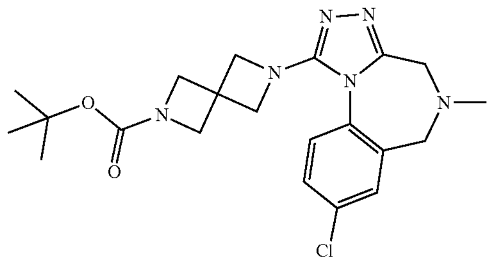 |
| 10 | 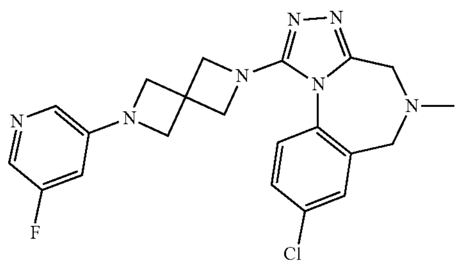 |
| 11 | 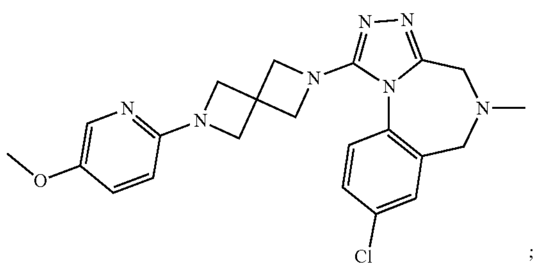 |
| 12 | 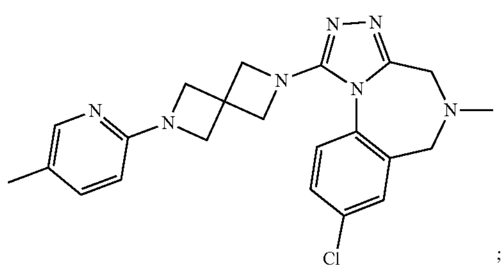 |
| 13 | 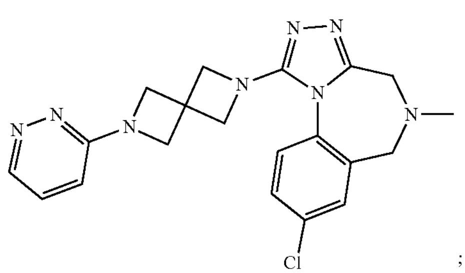 [SMILES: CN1Cc2cc(Cl)ccc2-n2c(nnc2N2CC3(CN(c4cccnn4)C3)C2)C1] |
| 14 | 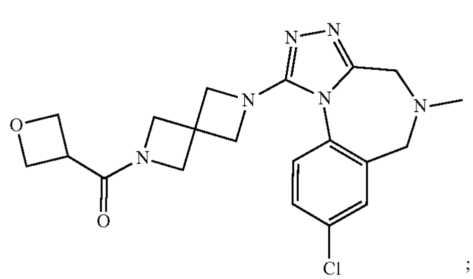 [SMILES: CN1Cc2cc(Cl)ccc2-n2c(nnc2N2CC3(CN(C(=O)C4COC4)C3)C2)C1] |

-continued
| Compound No. | Structure |
|---|---|
| 15 | 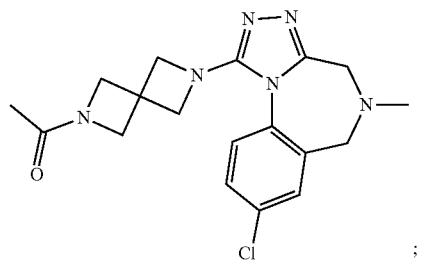 [SMILES: CC(=O)N1CC2(C1)CN(c1nnc3n1-c1ccc(Cl)cc1CN(C)C3)C2] ; |
| 16 | 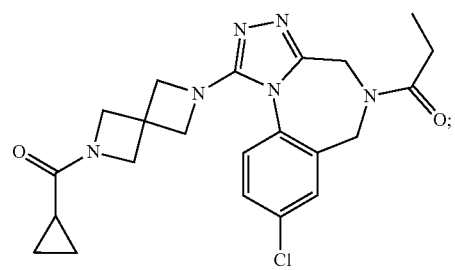 [SMILES: CCC(=O)N1Cc2cc(Cl)ccc2-n2c(nnc2N2CC3(CN(C(=O)C4CC4)C3)C2)C1] ; |
| 17 | 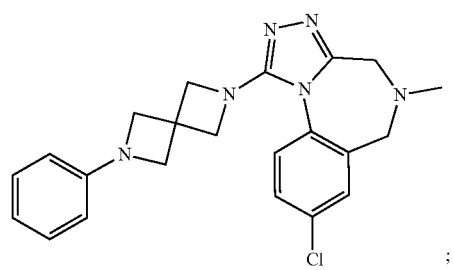 [SMILES: CN1Cc2cc(Cl)ccc2-n2c(nnc2N2CC3(CN(c4ccccc4)C3)C2)C1] ; |
| 18 | 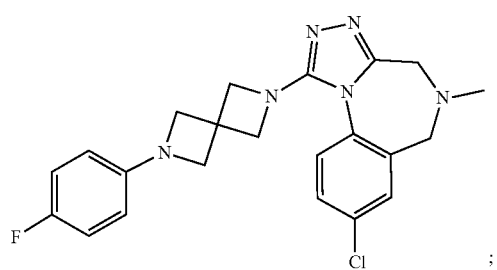 [SMILES: CN1Cc2cc(Cl)ccc2-n2c(nnc2N2CC3(CN(c4ccc(F)cc4)C3)C2)C1] ; |
| 19 | 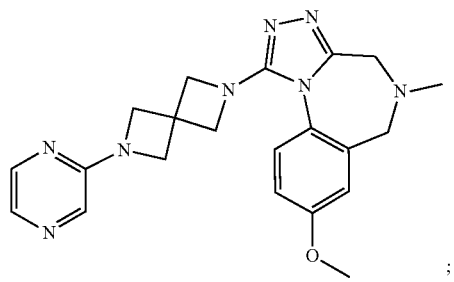 [SMILES: COc1ccc2c(c1)CN(C)Cc1nnc(N3CC4(CN(c5cnccn5)C4)C3)n1-2] ; |

| Compound No. | Structure |
|---|---|
| 20 | 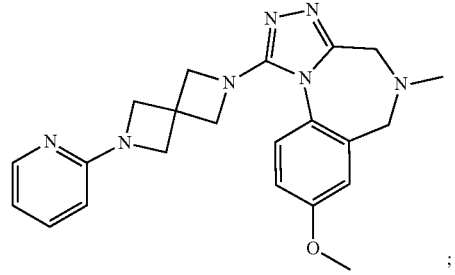 [SMILES: COc1ccc2c(c1)CN(C)Cc1nnc(N3CC4(CN(c5ccccn5)C4)C3)n1-2] |
| 21 | 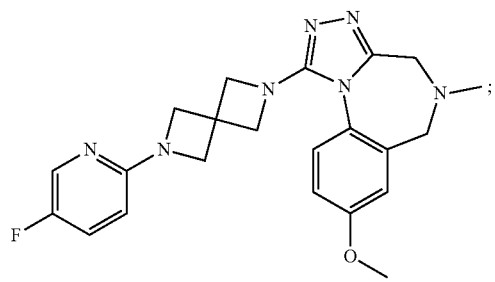 [SMILES: COc1ccc2c(c1)CN(C)Cc1nnc(N3CC4(CN(c5ccc(F)cn5)C4)C3)n1-2] |
| 22 | 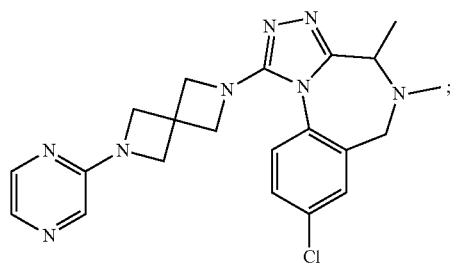 [SMILES: CC1c2nnc(N3CC4(CN(c5cnccn5)C4)C3)n2-c2ccc(Cl)cc2CN1C] |
| 23 | 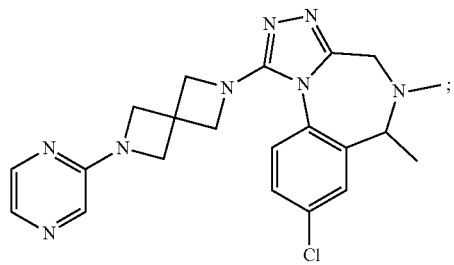 [SMILES: CC1c2cc(Cl)ccc2-n2c(nnc2N2CC3(CN(c4cnccn4)C3)C2)CN1C] |
| 24 | 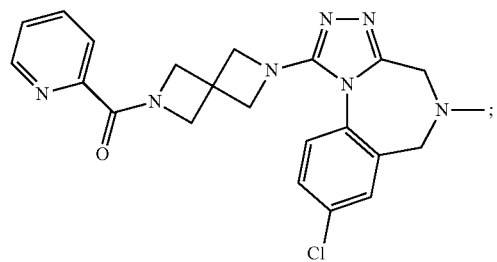 [SMILES: CN1Cc2cc(Cl)ccc2-n2c(nnc2N2CC3(CN(C(=O)c4ccccn4)C3)C2)C1] |

-continued

| Compound No. | Structure |
|---|---|
| 25 | 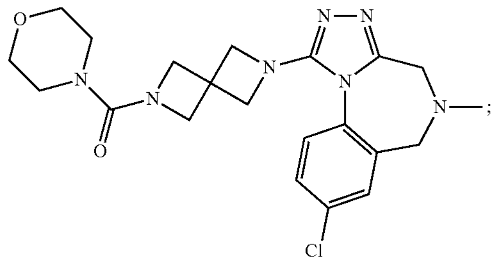 [SMILES: CN1Cc2cc(Cl)ccc2-n2c(nnc2N2CC3(CN(C(=O)N4CCOCC4)C3)C2)C1] |
| 26 | 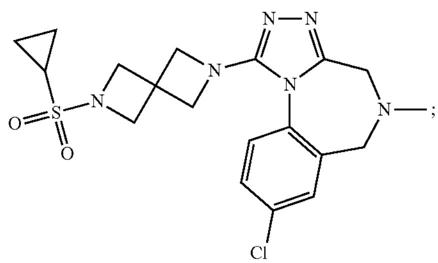 [SMILES: CN1Cc2cc(Cl)ccc2-n2c(nnc2N2CC3(C2)CN(S(=O)(=O)C2CC2)C3)C1] |
| 27 | 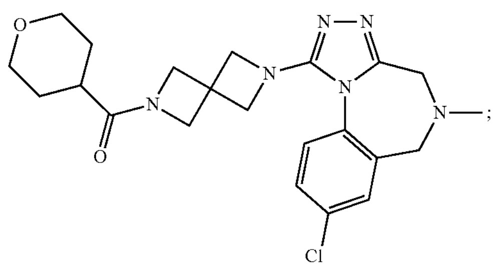 [SMILES: CN1Cc2cc(Cl)ccc2-n2c(nnc2N2CC3(CN(C(=O)C4CCOCC4)C3)C2)C1] |
| 28 | 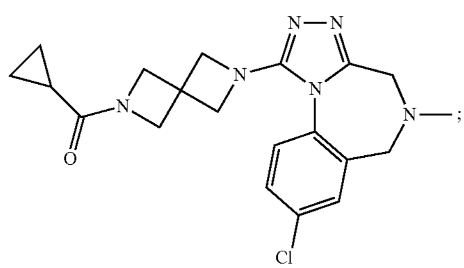 [SMILES: CN1Cc2cc(Cl)ccc2-n2c(nnc2N2CC3(CN(C(=O)C4CC4)C3)C2)C1] |
| 29 | 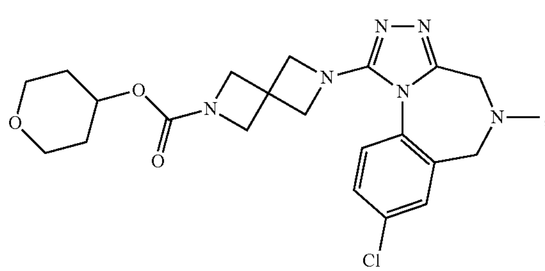 |
| 30 | 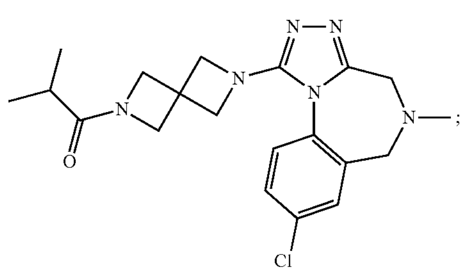 [SMILES: CC(C)C(=O)N1CC2(C1)CN(c1nnc3n1-c1ccc(Cl)cc1CN(C)C3)C2] |

-continued
| Compound No. | Structure |
|---|---|
| 31 | 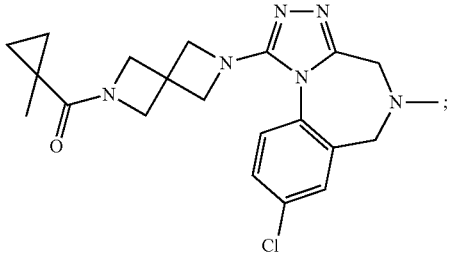 [SMILES: CN1Cc2cc(Cl)ccc2-n2c(nnc2N2CC3(CN(C(=O)C4(C)CC4)C3)C2)C1] |
| 32 | 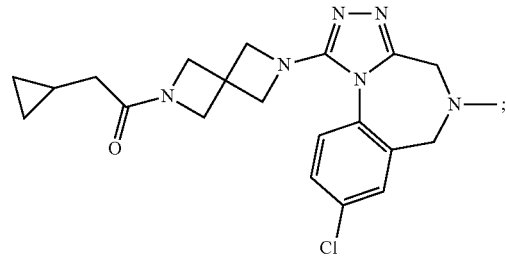 [SMILES: CN1Cc2cc(Cl)ccc2-n2c(nnc2N2CC3(CN(C(=O)CC4CC4)C3)C2)C1] |
| 33 | 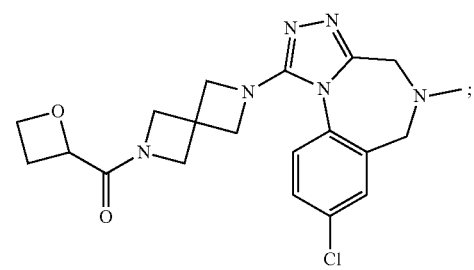 [SMILES: CN1Cc2cc(Cl)ccc2-n2c(nnc2N2CC3(CN(C(=O)C4CCO4)C3)C2)C1] |
| 34 | 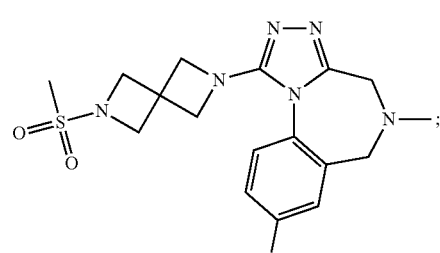 |
| 35 | 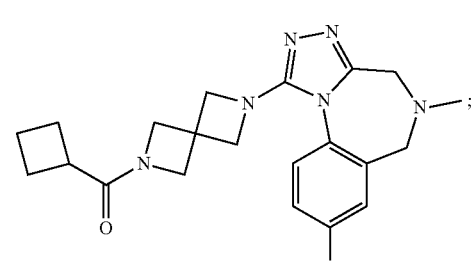 |
| 36 | 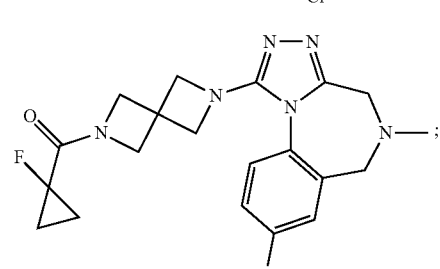 |

| Compound No. | Structure |
|---|---|
| 37 | 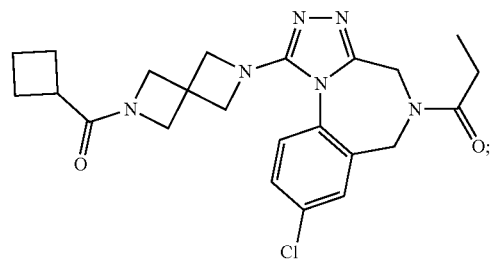 [SMILES: CCC(=O)N1Cc2cc(Cl)ccc2-n2c(nnc2N2CC3(CN(C(=O)C4CCC4)C3)C2)C1] |
| 38 | 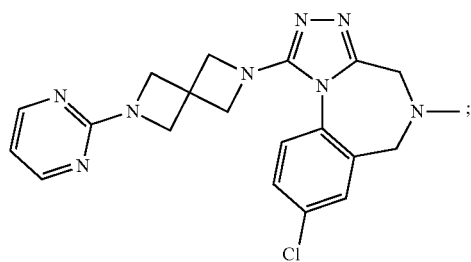 [SMILES: CN1Cc2cc(Cl)ccc2-n2c(nnc2N2CC3(CN(c4ncccn4)C3)C2)C1] |
| 39 | 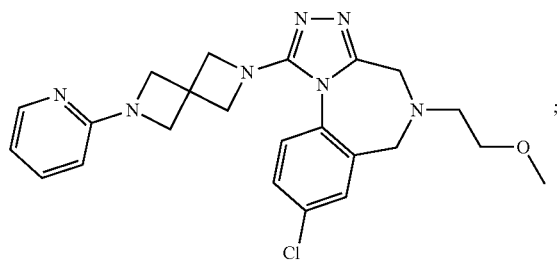 [SMILES: COCCN1Cc2cc(Cl)ccc2-n2c(nnc2N2CC3(CN(c4ccccn4)C3)C2)C1] |
| 40 | 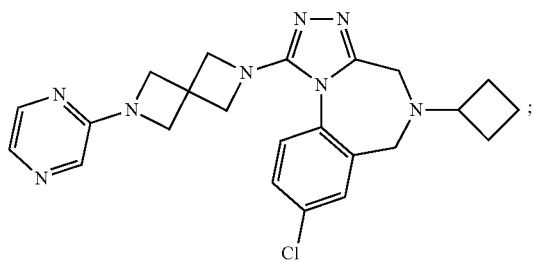 [SMILES: Clc1ccc2c(c1)CN(C1CCC1)Cc1nnc(N3CC4(CN(c5cnccn5)C4)C3)n1-2] |
| 41 | 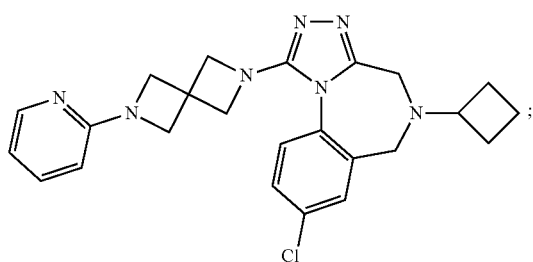 [SMILES: Clc1ccc2c(c1)CN(C1CCC1)Cc1nnc(N3CC4(CN(c5ccccn5)C4)C3)n1-2] |

-continued
| Compound No. | Structure |
|---|---|
| 42 | 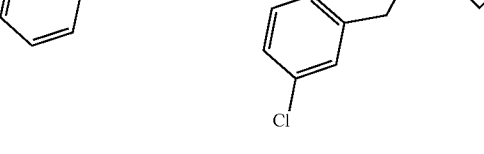 ; |
| 43 | 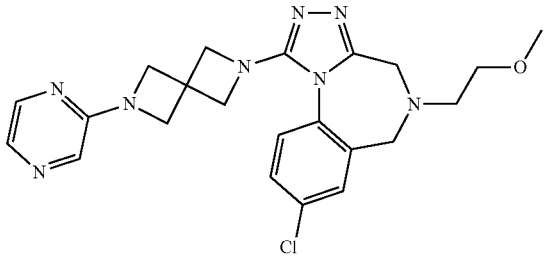 ; |
| 44 |  ; |
| 45 |  ; |
| 46 |  ; |
| 47 | 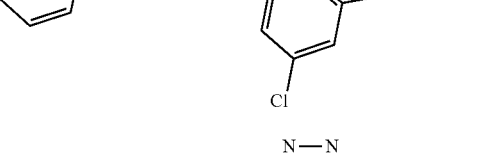 ; |

| Compound No. | Structure |
| --- | --- |
| 48 | 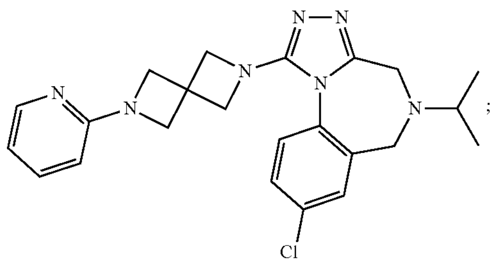 [SMILES: CC(C)N1Cc2cc(Cl)ccc2-n2c(nnc2N2CC3(CN(c4ccccn4)C3)C2)C1] |
| 49 | 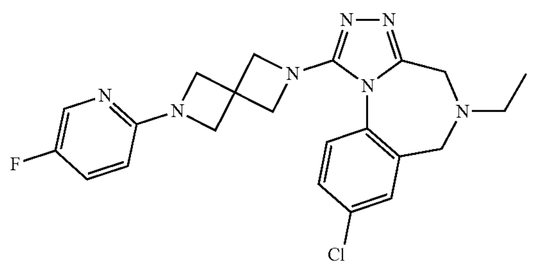 |
| 50 | 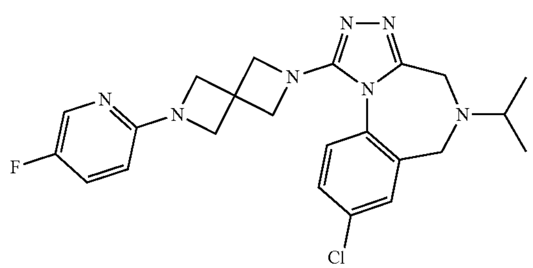 |
| 51 | 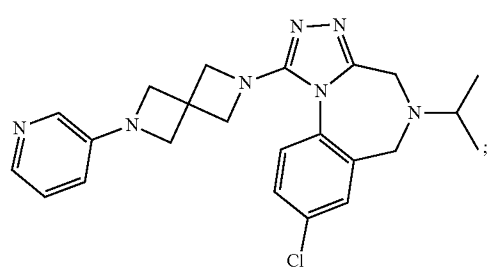 [SMILES: CC(C)N1Cc2cc(Cl)ccc2-n2c(nnc2N2CC3(CN(c4cccnc4)C3)C2)C1] |
| 52 | 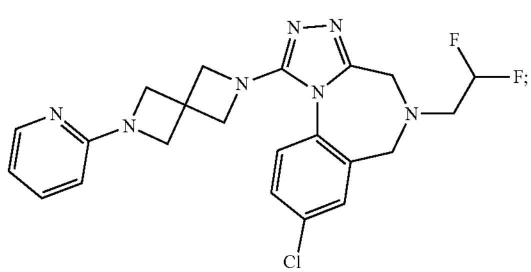 [SMILES: FC(F)CN1Cc2cc(Cl)ccc2-n2c(nnc2N2CC3(CN(c4ccccn4)C3)C2)C1] |

-continued
| Compound No. | Structure |
|---|---|
| 53 | 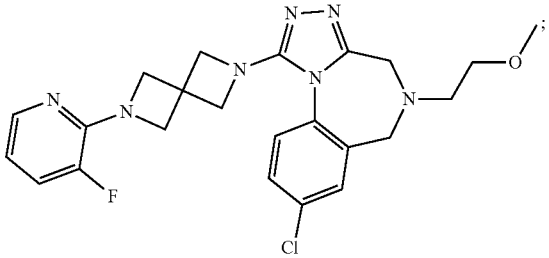 [SMILES: COCCN1Cc2cc(Cl)ccc2-n2c(nnc2N2CC3(CN(c4ncccc4F)C3)C2)C1] |
| 54 | 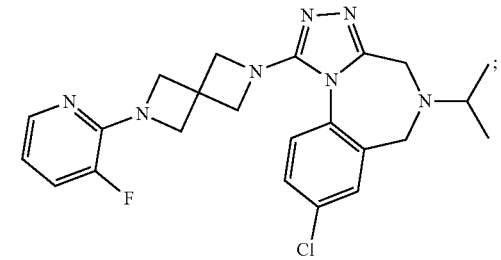 [SMILES: CC(C)N1Cc2cc(Cl)ccc2-n2c(nnc2N2CC3(CN(c4ncccc4F)C3)C2)C1] |
| 55 | 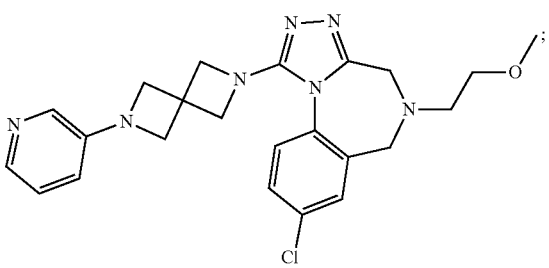 [SMILES: COCCN1Cc2cc(Cl)ccc2-n2c(nnc2N2CC3(CN(c4cccnc4)C3)C2)C1] |
| 56 | 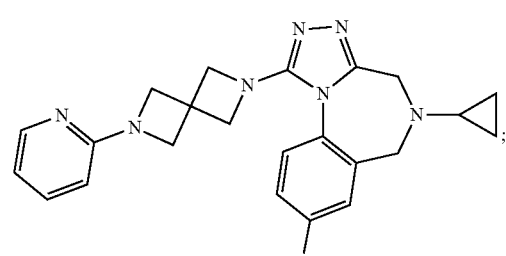 |
| 57 | 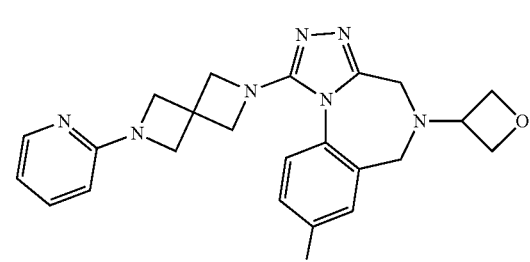 |
| 58 | 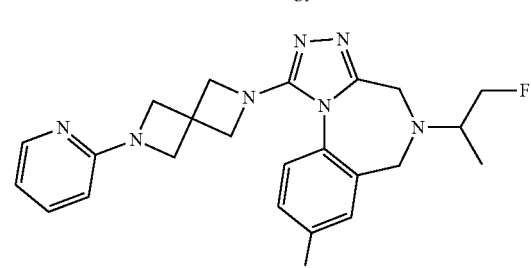 |

| Compound No. | Structure |
|---|---|
| 59 | 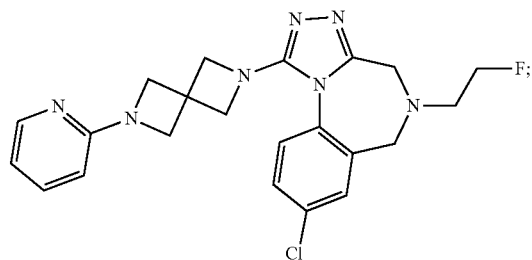 [SMILES: FCCN1Cc2cc(Cl)ccc2-n2c(nnc2N2CC3(CN(c4ccccn4)C3)C2)C1] |
| 60 | 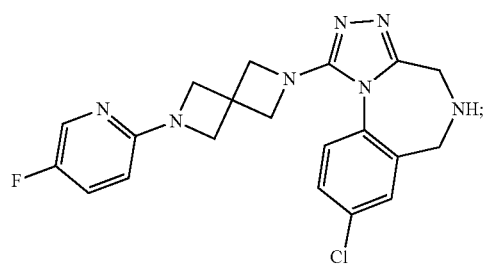 [SMILES: Fc1ccc(N2CC3(C2)CN(c2nnc4n2-c2ccc(Cl)cc2CNC4)C3)nc1] |
| 61 | 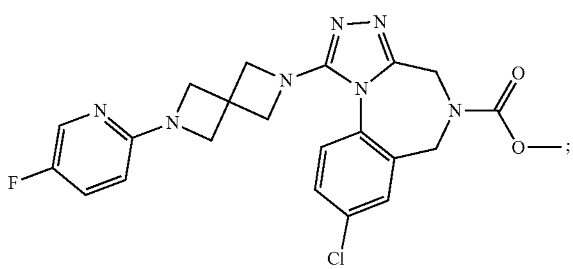 [SMILES: COC(=O)N1Cc2cc(Cl)ccc2-n2c(nnc2N2CC3(CN(c4ccc(F)cn4)C3)C2)C1] |
| 62 | 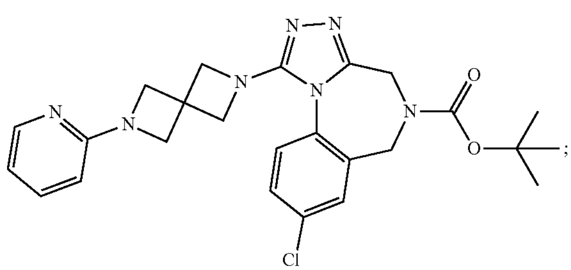 [SMILES: CC(C)(C)OC(=O)N1Cc2cc(Cl)ccc2-n2c(nnc2N2CC3(CN(c4ccccn4)C3)C2)C1] |
| 63 | 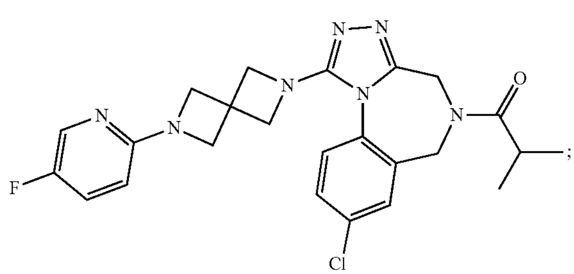 |

-continued

| Compound No. | Structure |
|---|---|
| 64 | [structure] |
| 65 | [structure] |
| 66 | [structure] |
| 67 | [structure] |
| 68 | [structure] |
| 69 | [structure] |

| Compound No. | Structure |
|---|---|
| 70 | 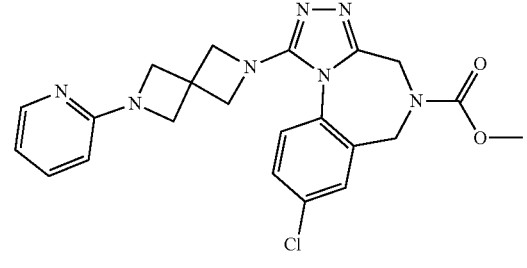 ; |
| 71 | 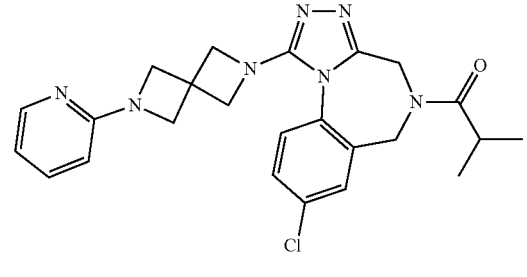 ; |
| 72 | 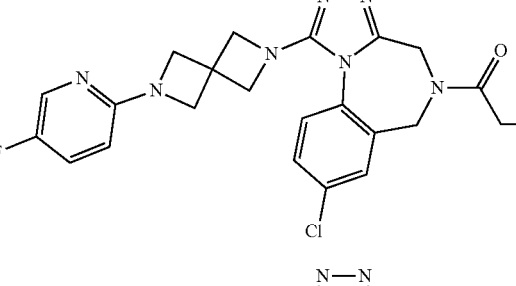 ; |
| 73 | 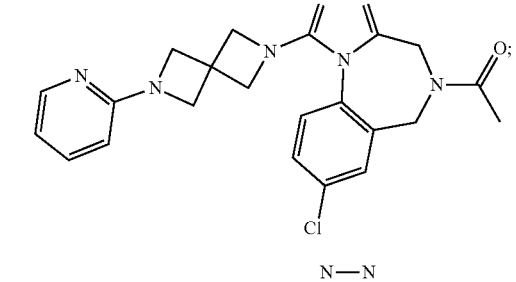 ; |
| 74 | 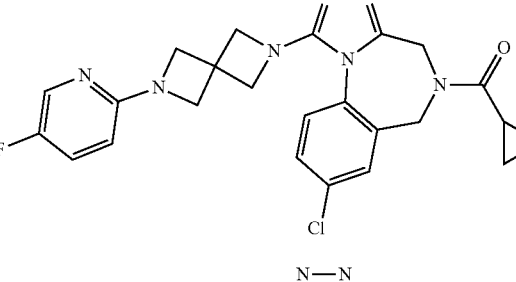 ; |
| 75 | 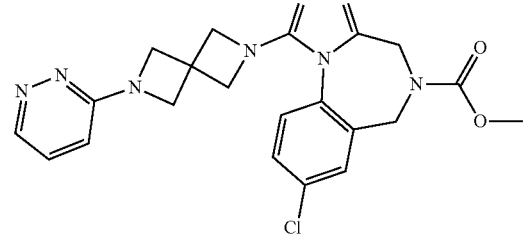 ; |

| Compound No. | Structure |
|---|---|
| 76 | 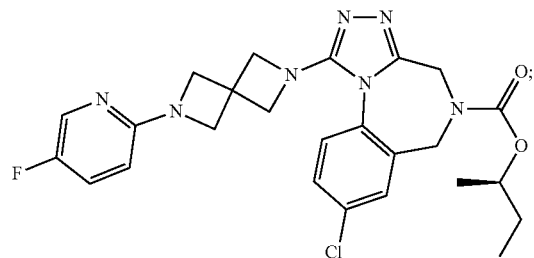 [SMILES: CC[C@@H](C)OC(=O)N1Cc2cc(Cl)ccc2-n2c(nnc2N2CC3(CN(c4ccc(F)cn4)C3)C2)C1] |
| 77 | 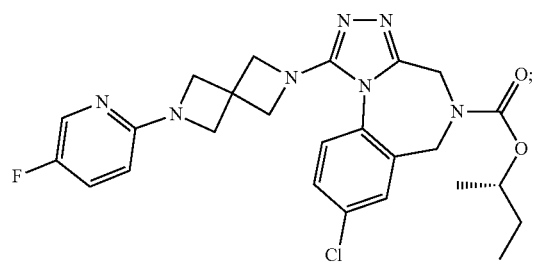 [SMILES: CC[C@H](C)OC(=O)N1Cc2cc(Cl)ccc2-n2c(nnc2N2CC3(CN(c4ccc(F)cn4)C3)C2)C1] |
| 78 | 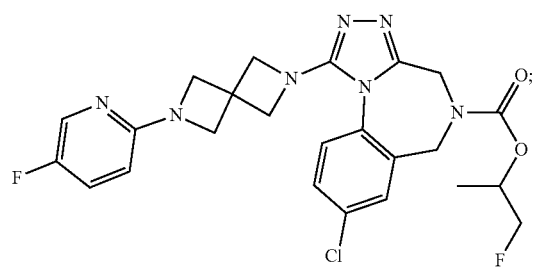 [SMILES: CC(CF)OC(=O)N1Cc2cc(Cl)ccc2-n2c(nnc2N2CC3(CN(c4ccc(F)cn4)C3)C2)C1] |
| 79 | 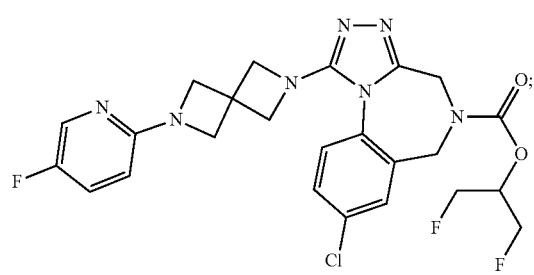 [SMILES: O=C(OC(CF)CF)N1Cc2cc(Cl)ccc2-n2c(nnc2N2CC3(CN(c4ccc(F)cn4)C3)C2)C1] |
| 80 | 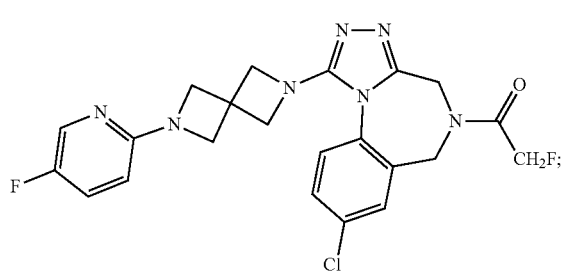 |

-continued
| Compound No. | Structure |
|---|---|
| 81 | 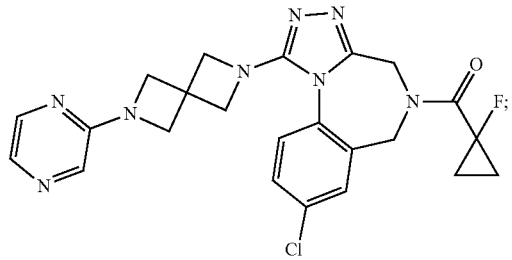 [SMILES: O=C(N1Cc2cc(Cl)ccc2-n2c(nnc2N2CC3(CN(c4cnccn4)C3)C2)C1)C1(F)CC1] |
| 82 | 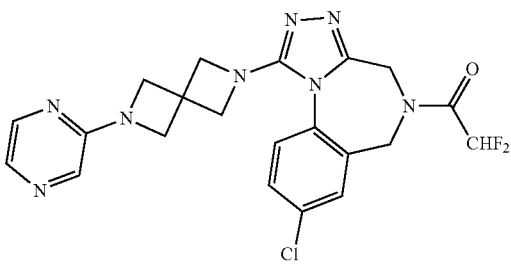 |
| 83 | 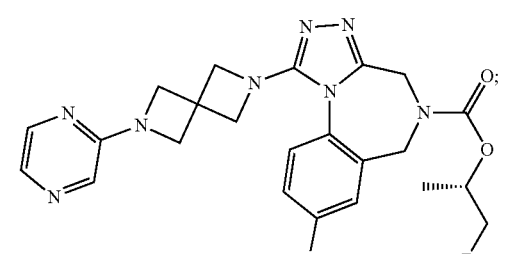 |
| 84 | 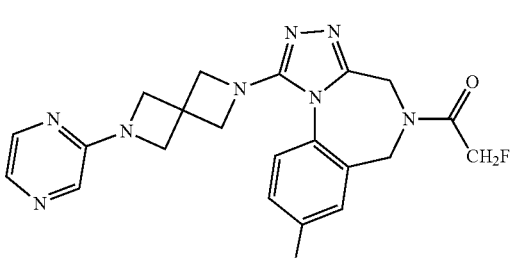 |
| 85 | 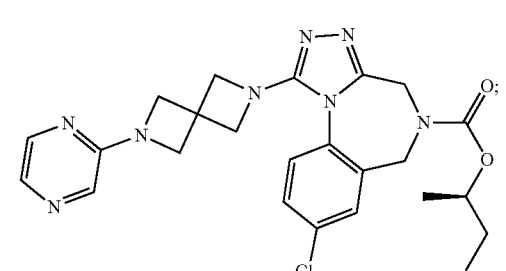 |
| 86 | 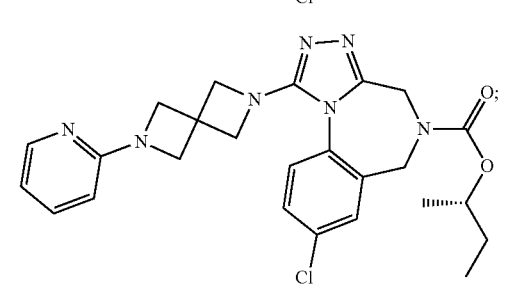 |

| Compound No. | Structure |
| --- | --- |
| 87 | 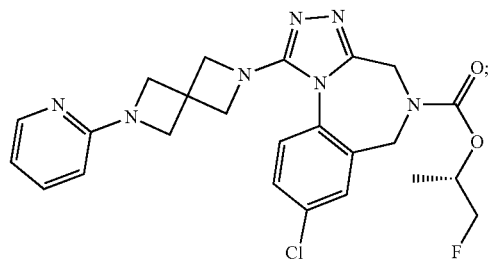 [SMILES: C[C@@H](CF)OC(=O)N1Cc2cc(Cl)ccc2-n2c(nnc2N2CC3(CN(c4ccccn4)C3)C2)C1] |
| 88 | 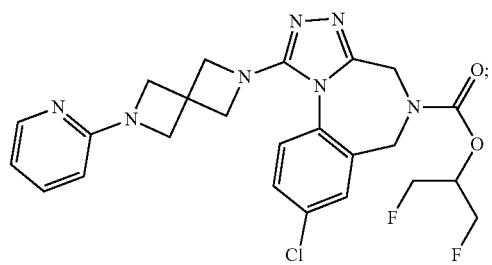 [SMILES: O=C(OC(CF)CF)N1Cc2cc(Cl)ccc2-n2c(nnc2N2CC3(CN(c4ccccn4)C3)C2)C1] |
| 89 | 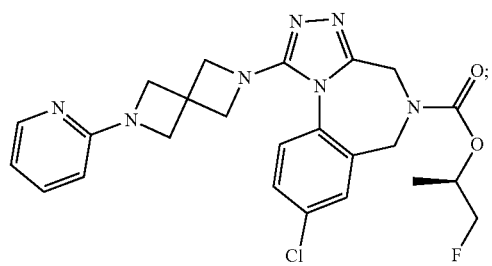 |
| 90 | 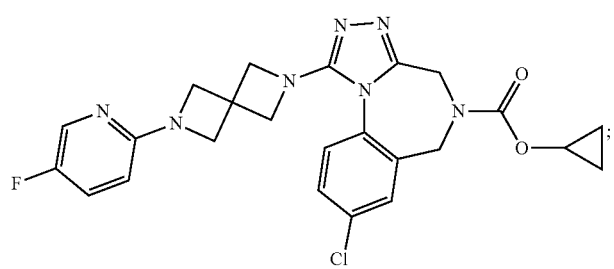 [SMILES: O=C(OC1CC1)N1Cc2cc(Cl)ccc2-n2c(nnc2N2CC3(CN(c4ccc(F)cn4)C3)C2)C1] |
| 91 | 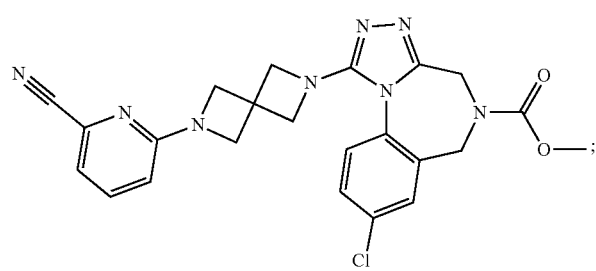 [SMILES: COC(=O)N1Cc2cc(Cl)ccc2-n2c(nnc2N2CC3(CN(c4cccc(C#N)n4)C3)C2)C1] |

-continued

| Compound No. | Structure |
|---|---|
| 92 | (structure) |
| 93 | (structure) |
| 94 | (structure) |
| 95 | (structure) |
| 96 | (structure) |
| 97 | (structure) |

-continued
| Compound No. | Structure |
|---|---|
| 98 | 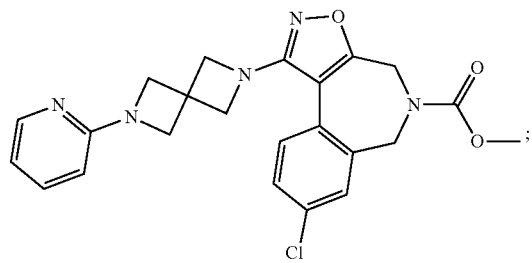 [SMILES: COC(=O)N1Cc2cc(Cl)ccc2-c2c(N3CC4(CN(c5ccccn5)C4)C3)noc2C1] |
| 99 | 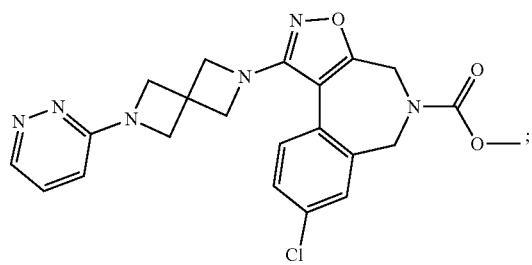 [SMILES: COC(=O)N1Cc2cc(Cl)ccc2-c2c(N3CC4(CN(c5cccnn5)C4)C3)noc2C1] |
| 100 | 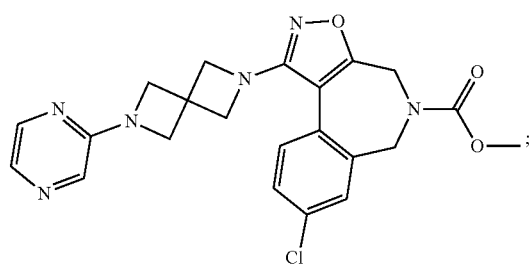 [SMILES: COC(=O)N1Cc2cc(Cl)ccc2-c2c(N3CC4(CN(c5cnccn5)C4)C3)noc2C1] |
| 101 | 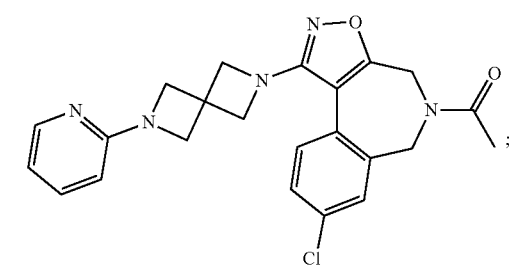 [SMILES: CC(=O)N1Cc2cc(Cl)ccc2-c2c(N3CC4(CN(c5ccccn5)C4)C3)noc2C1] |
| 102 | 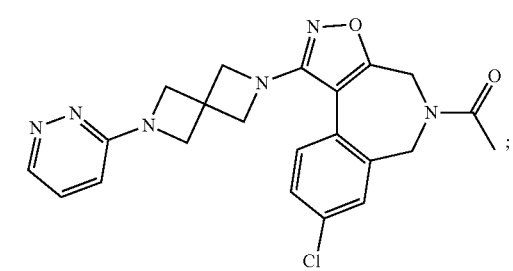 [SMILES: CC(=O)N1Cc2cc(Cl)ccc2-c2c(N3CC4(CN(c5cccnn5)C4)C3)noc2C1] |

-continued

| Compound No. | Structure |
|---|---|
| 103 | [chemical structure] |
| 104 | [chemical structure] |
| 105 | [chemical structure] |
| 106 | [chemical structure] |
| 107 | [chemical structure] |
| 108 | [chemical structure] |

-continued
| Compound No. | Structure |
| --- | --- |
| 109 | 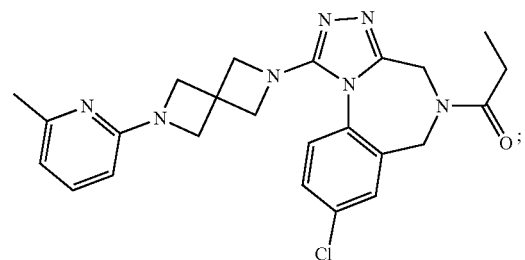 [SMILES: CCC(=O)N1Cc2cc(Cl)ccc2-n2c(nnc2N2CC3(CN(c4cccc(C)n4)C3)C2)C1] |
| 110 | 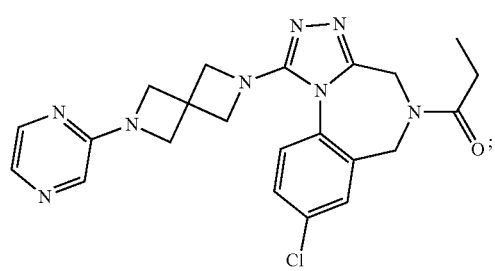 [SMILES: CCC(=O)N1Cc2cc(Cl)ccc2-n2c(nnc2N2CC3(CN(c4cnccn4)C3)C2)C1] |
| 111 | 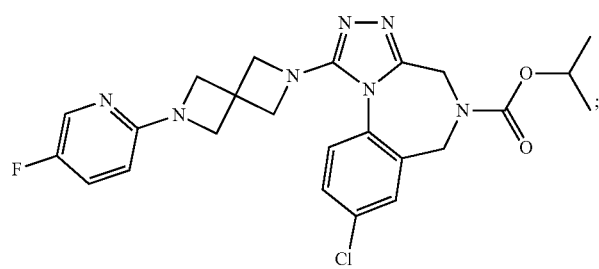 [SMILES: CC(C)OC(=O)N1Cc2cc(Cl)ccc2-n2c(nnc2N2CC3(CN(c4ccc(F)cn4)C3)C2)C1] |
| 112 | 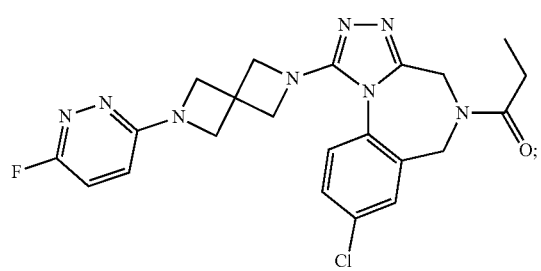 [SMILES: CCC(=O)N1Cc2cc(Cl)ccc2-n2c(nnc2N2CC3(CN(c4ccc(F)nn4)C3)C2)C1] |
| 113 | 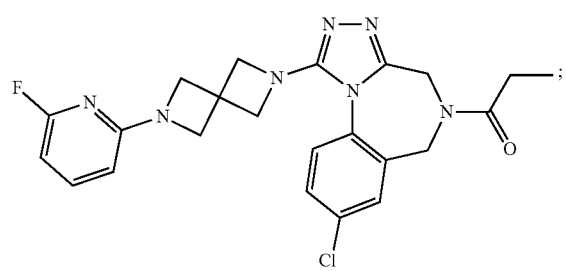 [SMILES: CCC(=O)N1Cc2cc(Cl)ccc2-n2c(nnc2N2CC3(CN(c4cccc(F)n4)C3)C2)C1] |

-continued

| Compound No. | Structure |
|---|---|
| 114 | (structure) |
| 115 | (structure) |
| 116 | (structure) |
| 117 | (structure) |
| 118 | (structure) |
| 119 | (structure) |

-continued
| Compound No. | Structure |
|---|---|
| 120 | 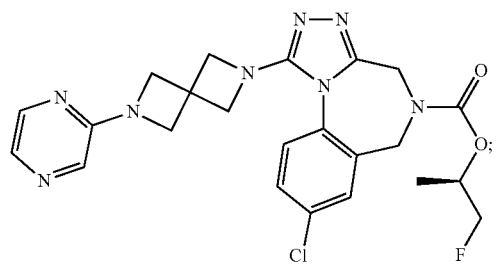 [SMILES: CC[C@@H](C)OC(=O)N1Cc2cc(Cl)ccc2-n2c(nnc2N2CC3(CN(c4cnccn4)C3)C2)C1] |
| 121 | 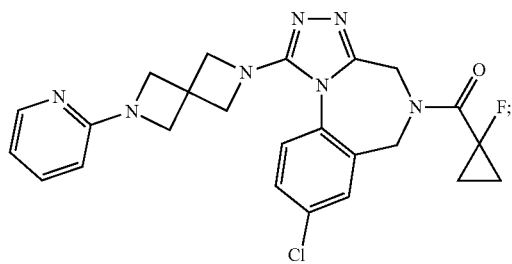 [SMILES: O=C(N1Cc2cc(Cl)ccc2-n2c(nnc2N2CC3(CN(c4ccccn4)C3)C2)C1)C1(F)CC1] |
| 122 | 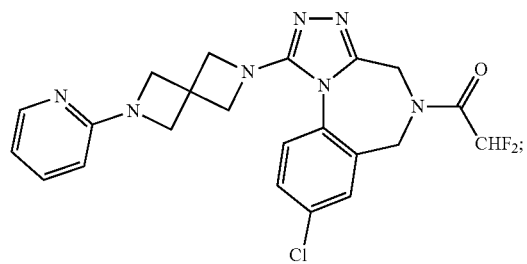 [SMILES: O=C(C(F)F)N1Cc2cc(Cl)ccc2-n2c(nnc2N2CC3(CN(c4ccccn4)C3)C2)C1] |
| 123 | 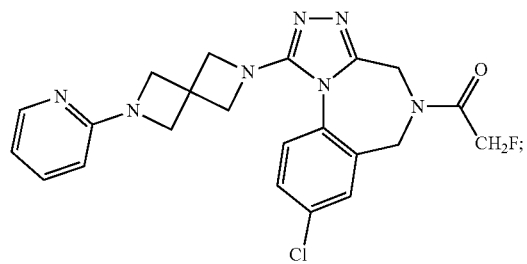 |
| 124 | 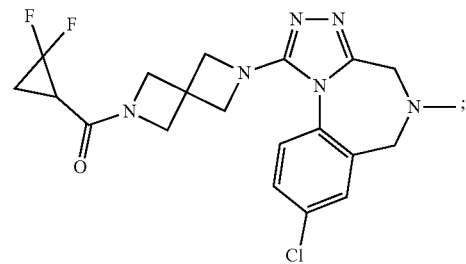 [SMILES: CN1Cc2cc(Cl)ccc2-n2c(nnc2N2CC3(CN(C(=O)C4CC4(F)F)C3)C2)C1] |

-continued

| Compound No. | Structure |
|---|---|
| 125 | 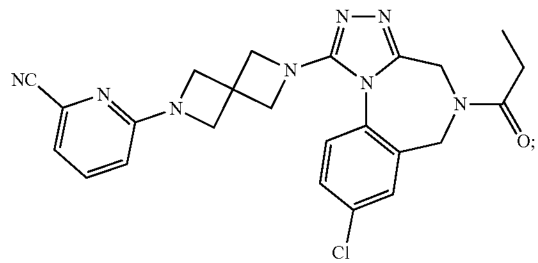 [SMILES: CCC(=O)N1Cc2cc(Cl)ccc2-n2c(nnc2N2CC3(CN(c4cccc(C#N)n4)C3)C2)C1] |
| 126 | 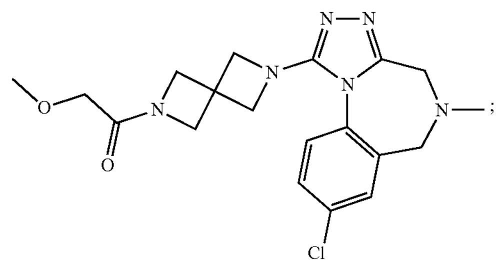 |
| 127 | 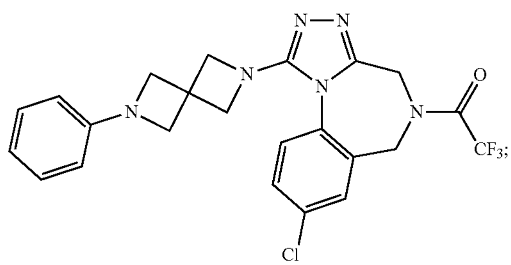 [SMILES: O=C(N1Cc2cc(Cl)ccc2-n2c(nnc2N2CC3(CN(c4ccccc4)C3)C2)C1)C(F)(F)F] |
| 128 | 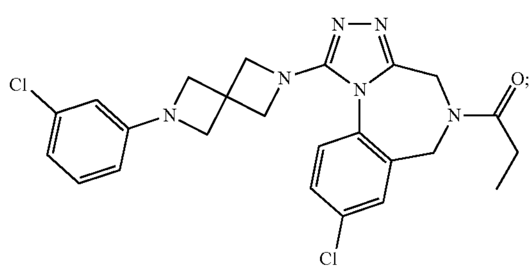 [SMILES: CCC(=O)N1Cc2cc(Cl)ccc2-n2c(nnc2N2CC3(CN(c4cccc(Cl)c4)C3)C2)C1] |
| 129 | 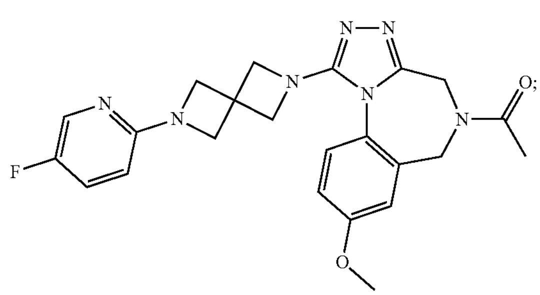 [SMILES: COc1ccc2c(c1)CN(C(C)=O)Cc1nnc(N3CC4(CN(c5ccc(F)cn5)C4)C3)n1-2] |
| 130 | 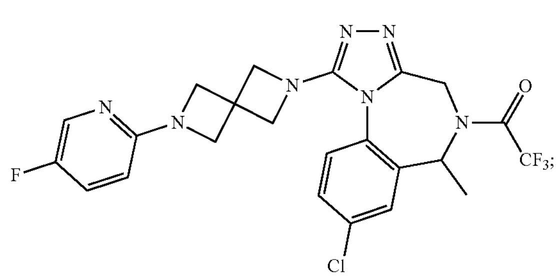 [SMILES: CC1c2cc(Cl)ccc2-n2c(nnc2N2CC3(CN(c4ccc(F)cn4)C3)C2)CN1C(=O)C(F)(F)F] |

| Compound No. | Structure |
|---|---|
| 131 | 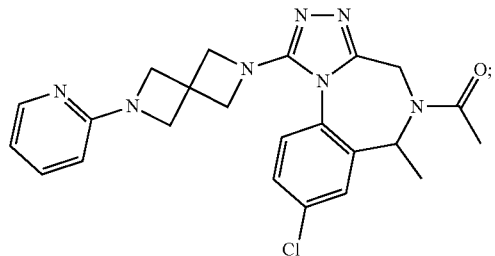 [SMILES: CC(=O)N1Cc2nnc(N3CC4(CN(c5ccccn5)C4)C3)n2-c2ccc(Cl)cc2C1C] |
| 132 | 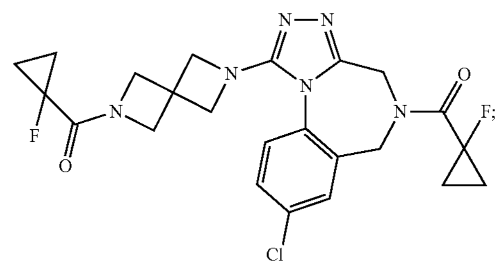 [SMILES: O=C(N1Cc2cc(Cl)ccc2-n2c(nnc2N2CC3(CN(C(=O)C4(F)CC4)C3)C2)C1)C1(F)CC1] |
| 133 | 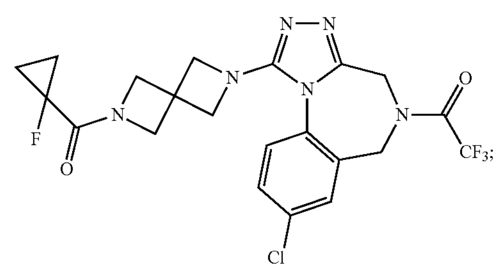 [SMILES: O=C(N1Cc2cc(Cl)ccc2-n2c(nnc2N2CC3(CN(C(=O)C4(F)CC4)C3)C2)C1)C(F)(F)F] |
| 134 | 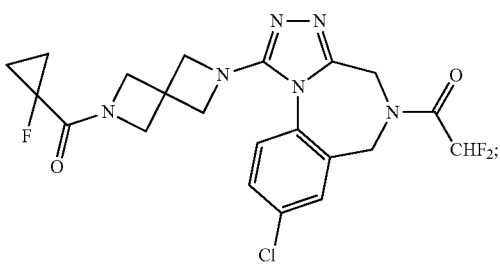 [SMILES: O=C(C(F)F)N1Cc2cc(Cl)ccc2-n2c(nnc2N2CC3(CN(C(=O)C4(F)CC4)C3)C2)C1] |
| 135 | 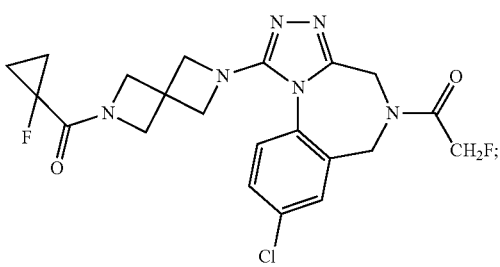 |

| Compound No. | Structure |
|---|---|
| 136 | 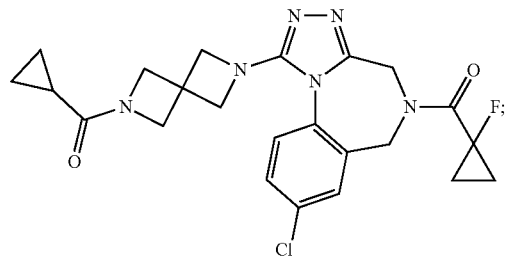 [SMILES: O=C(C1CC1)N1CC2(C1)CN(c1nnc3n1-c1ccc(Cl)cc1CN(C(=O)C1(F)CC1)C3)C2] |
| 137 | 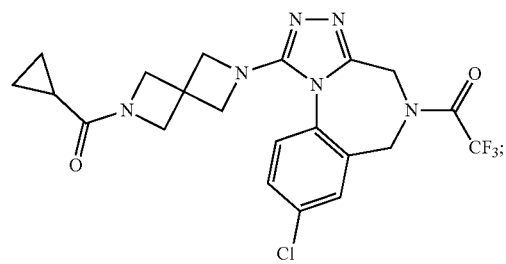 [SMILES: O=C(C1CC1)N1CC2(C1)CN(c1nnc3n1-c1ccc(Cl)cc1CN(C(=O)C(F)(F)F)C3)C2] |
| 138 | 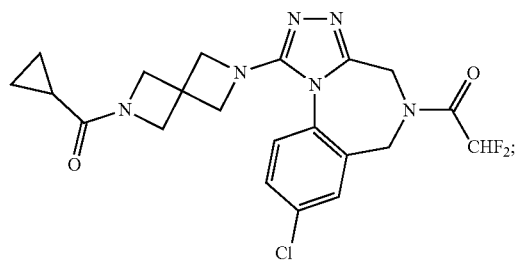 [SMILES: O=C(C(F)F)N1Cc2cc(Cl)ccc2-n2c(nnc2N2CC3(CN(C(=O)C4CC4)C3)C2)C1] |
| 139 | 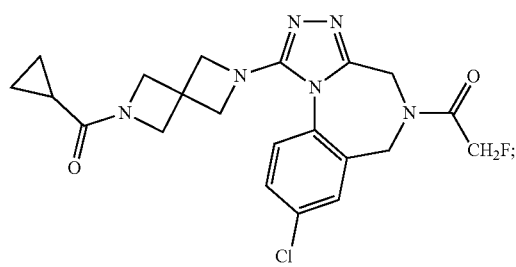 |
| 140 | 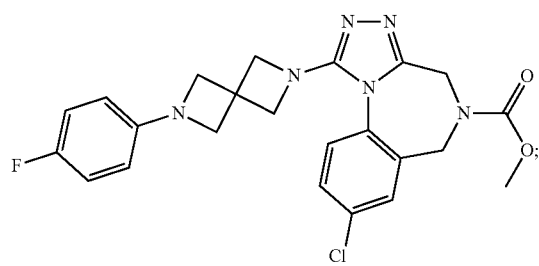 [SMILES: COC(=O)N1Cc2cc(Cl)ccc2-n2c(nnc2N2CC3(CN(c4ccc(F)cc4)C3)C2)C1] |

| Compound No. | Structure |
|---|---|
| 141 | 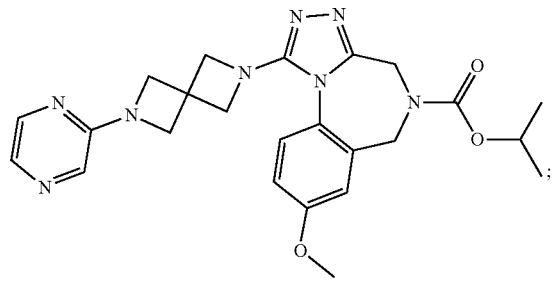 [SMILES: COc1ccc2c(c1)CN(C(=O)OC(C)C)Cc1nnc(N3CC4(CN(c5cnccn5)C4)C3)n1-2] |
| 142 | 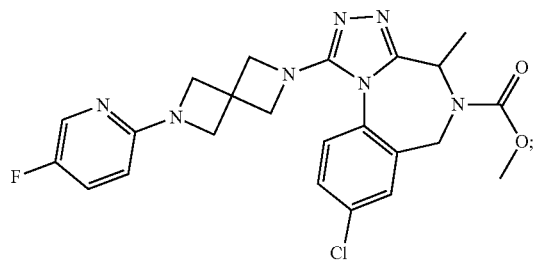 [SMILES: COC(=O)N1Cc2cc(Cl)ccc2-n2c(nnc2N2CC3(CN(c4ccc(F)cn4)C3)C2)C1C] |
| 143 | 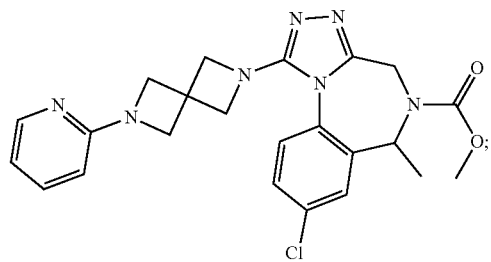 [SMILES: COC(=O)N1Cc2nnc(N3CC4(CN(c5ccccn5)C4)C3)n2-c2ccc(Cl)cc2C1C] |
| 144 | 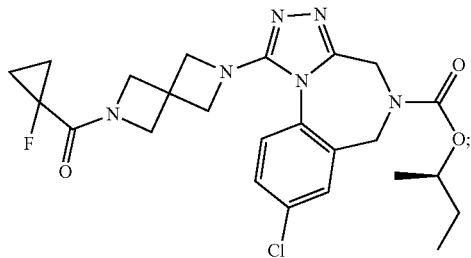 |
| 145 | 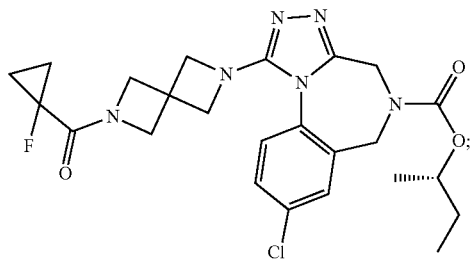 |

-continued

| Compound No. | Structure |
|---|---|
| 146 | 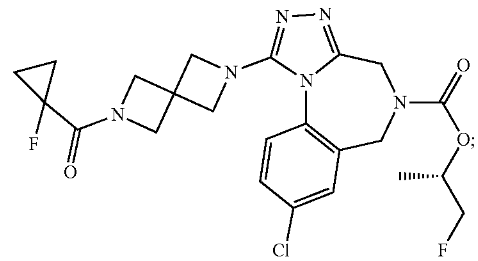 [SMILES: CC[C@H](C)OC(=O)N1Cc2cc(Cl)ccc2-n2c(nnc2N2CC3(CN(C(=O)C4(F)CC4)C3)C2)C1] |
| 147 | 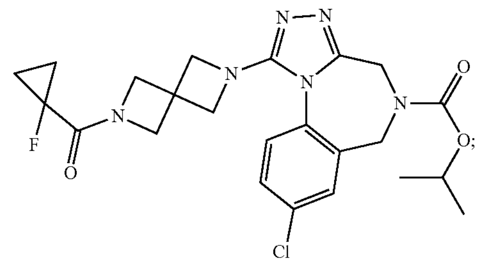 [SMILES: CC(C)OC(=O)N1Cc2cc(Cl)ccc2-n2c(nnc2N2CC3(CN(C(=O)C4(F)CC4)C3)C2)C1] |
| 148 | 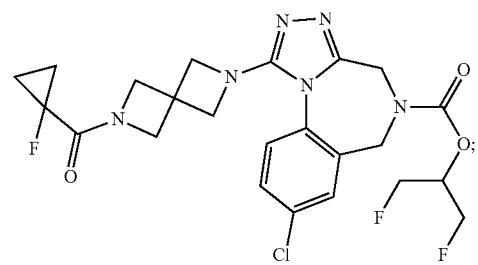 [SMILES: O=C(OC(CF)CF)N1Cc2cc(Cl)ccc2-n2c(nnc2N2CC3(CN(C(=O)C4(F)CC4)C3)C2)C1] |
| 149 | 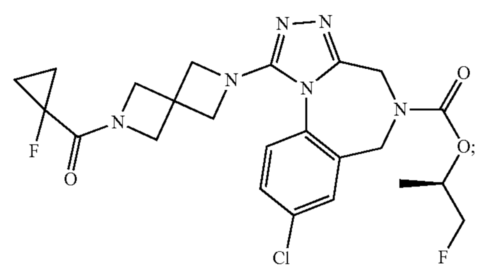 |
| 150 | 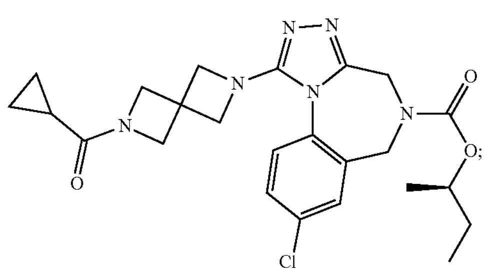 [SMILES: CC[C@@H](C)OC(=O)N1Cc2cc(Cl)ccc2-n2c(nnc2N2CC3(CN(C(=O)C4CC4)C3)C2)C1] |
| 151 | 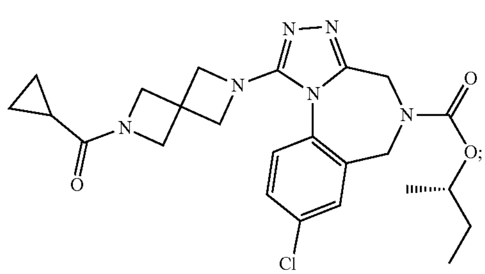 [SMILES: CC[C@H](C)OC(=O)N1Cc2cc(Cl)ccc2-n2c(nnc2N2CC3(CN(C(=O)C4CC4)C3)C2)C1] |

-continued
| Compound No. | Structure |
|---|---|
| 152 | 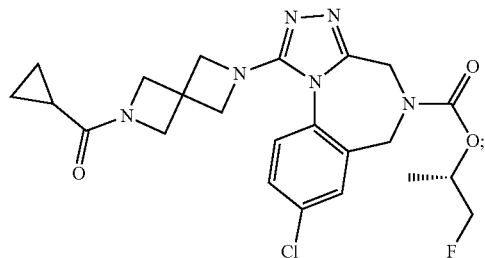 |
| 153 | 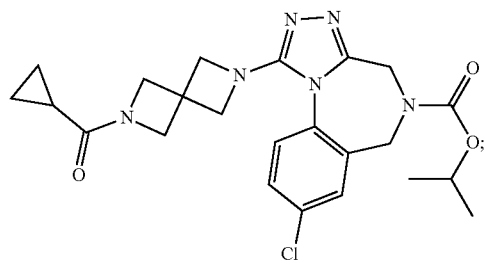 [SMILES: CC(C)OC(=O)N1Cc2cc(Cl)ccc2-n2c(nnc2N2CC3(CN(C(=O)C4CC4)C3)C2)C1] |
| 154 | 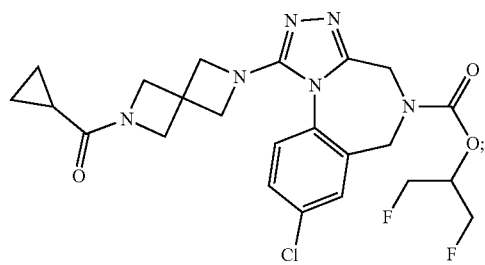 [SMILES: O=C(OC(CF)CF)N1Cc2cc(Cl)ccc2-n2c(nnc2N2CC3(CN(C(=O)C4CC4)C3)C2)C1] |
| 155 | 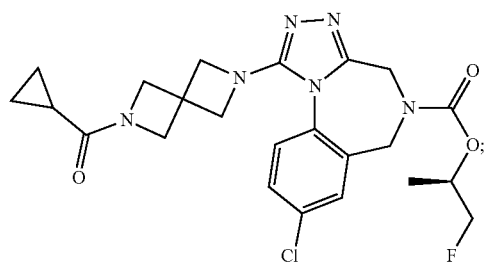 |
| 156 | 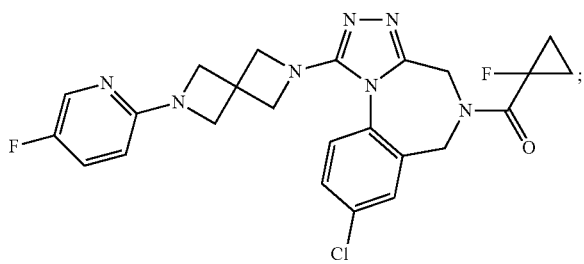 [SMILES: O=C(N1Cc2cc(Cl)ccc2-n2c(nnc2N2CC3(CN(c4ccc(F)cn4)C3)C2)C1)C1(F)CC1] |
| 157 | 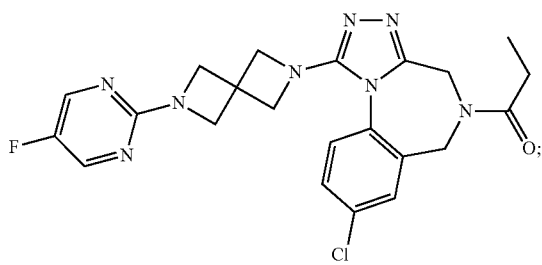 [SMILES: CCC(=O)N1Cc2cc(Cl)ccc2-n2c(nnc2N2CC3(CN(c4ncc(F)cn4)C3)C2)C1] |

US 12,247,037 B2
651                                                                 652
-continued
| Compound No. | Structure |
|---|---|
| 158 | 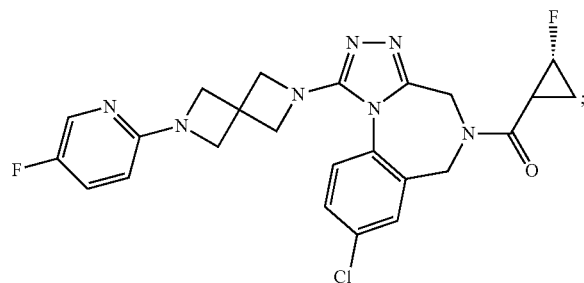 [SMILES: O=C(C1C[C@H]1F)N1Cc2cc(Cl)ccc2-n2c(nnc2N2CC3(CN(c4ccc(F)cn4)C3)C2)C1] |
| 159 | 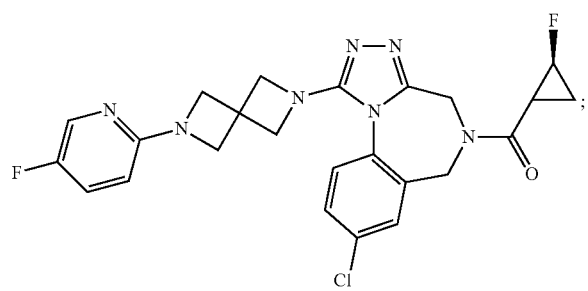 [SMILES: O=C(C1C[C@@H]1F)N1Cc2cc(Cl)ccc2-n2c(nnc2N2CC3(CN(c4ccc(F)cn4)C3)C2)C1] |
| 160 | 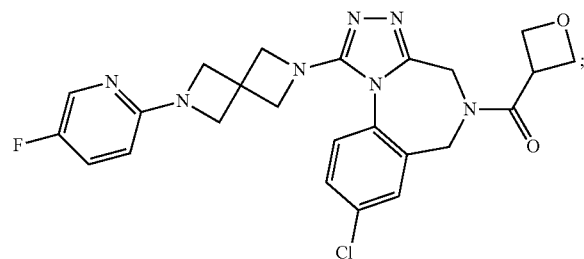 [SMILES: O=C(C1COC1)N1Cc2cc(Cl)ccc2-n2c(nnc2N2CC3(CN(c4ccc(F)cn4)C3)C2)C1] |
| 161 | 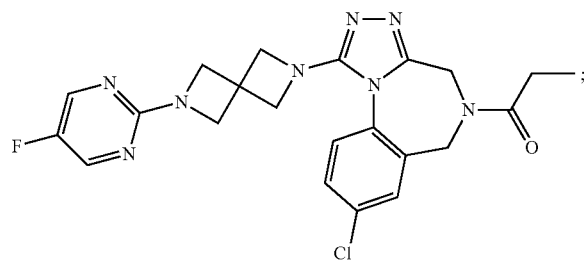 [SMILES: CCC(=O)N1Cc2cc(Cl)ccc2-n2c(nnc2N2CC3(CN(c4ncc(F)cn4)C3)C2)C1] |
| 162 | 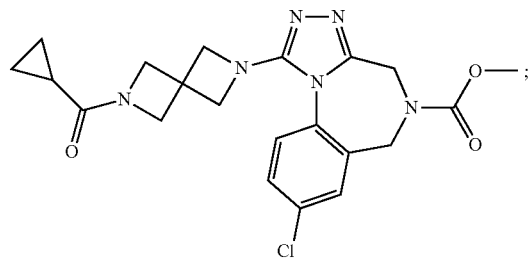 [SMILES: COC(=O)N1Cc2cc(Cl)ccc2-n2c(nnc2N2CC3(CN(C(=O)C4CC4)C3)C2)C1] |

-continued

| Compound No. | Structure |
|---|---|
| 163 | ![structure] |
| 164 | ![structure] |
| 165 | ![structure] |
| 166 | ![structure] |
| 167 | ![structure] |
| 168 | ![structure] |

| Compound No. | Structure |
|---|---|
| 169 | 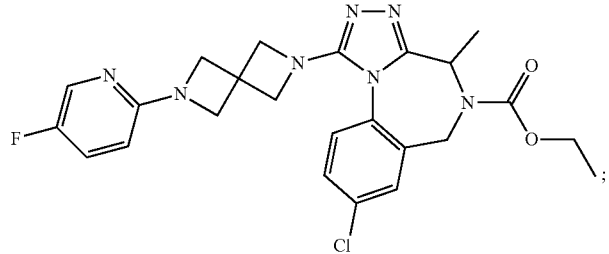 [SMILES: CCOC(=O)N1Cc2cc(Cl)ccc2-n2c(nnc2N2CC3(CN(c4ccc(F)cn4)C3)C2)C1C] |
| 170 | 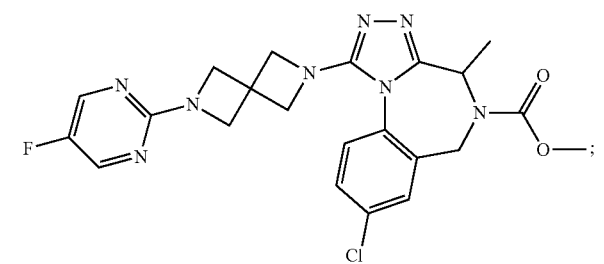 [SMILES: COC(=O)N1Cc2cc(Cl)ccc2-n2c(nnc2N2CC3(CN(c4ncc(F)cn4)C3)C2)C1C] |
| 171 | 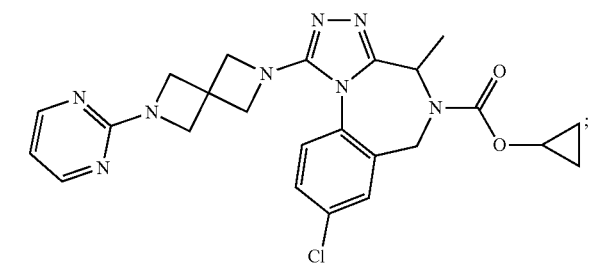 [SMILES: CC1c2nnc(N3CC4(CN(c5ncccn5)C4)C3)n2-c2ccc(Cl)cc2CN1C(=O)OC1CC1] |
| 172 | 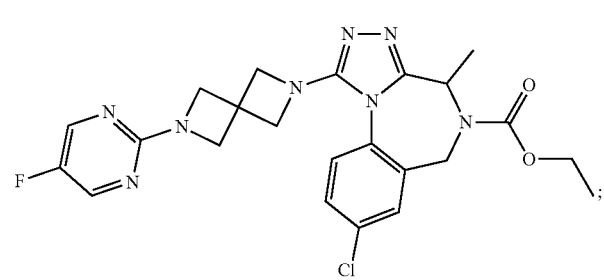 [SMILES: CCOC(=O)N1Cc2cc(Cl)ccc2-n2c(nnc2N2CC3(CN(c4ncc(F)cn4)C3)C2)C1C] |
| 173 | 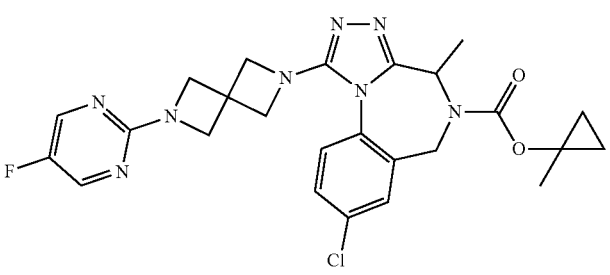 [SMILES: CC1c2nnc(N3CC4(CN(c5ncc(F)cn5)C4)C3)n2-c2ccc(Cl)cc2CN1C(=O)OC1(C)CC1] |
| 174 | 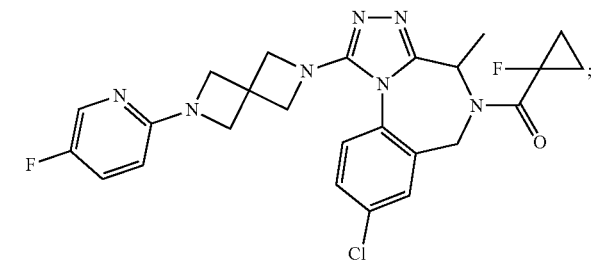 [SMILES: CC1c2nnc(N3CC4(CN(c5ccc(F)cn5)C4)C3)n2-c2ccc(Cl)cc2CN1C(=O)C1(F)CC1] |

-continued

| Compound No. | Structure |
| --- | --- |
| 175 | 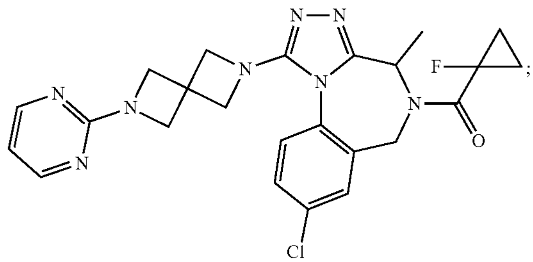 |
| 176 | 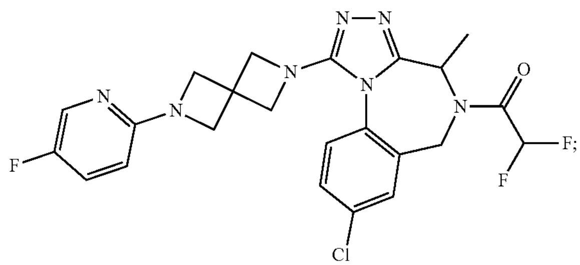 [SMILES: CC1c2nnc(N3CC4(CN(c5ccc(F)cn5)C4)C3)n2-c2ccc(Cl)cc2CN1C(=O)C(F)F] |
| 177 | 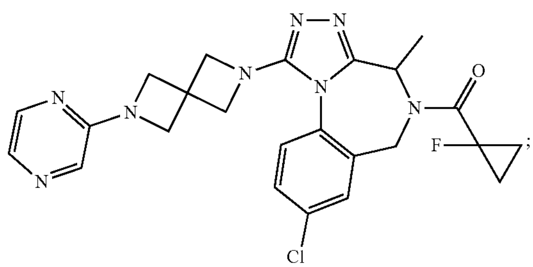 [SMILES: CC1c2nnc(N3CC4(CN(c5cnccn5)C4)C3)n2-c2ccc(Cl)cc2CN1C(=O)C1(F)CC1] |
| 178 | 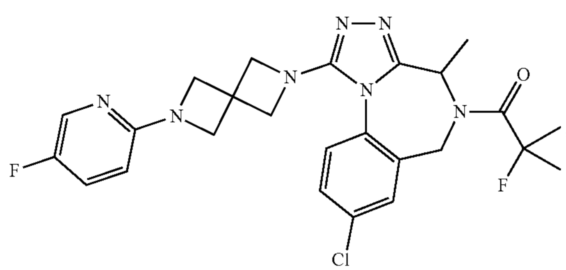 |
| 179 | 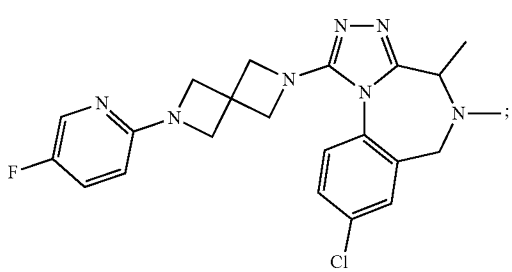 [SMILES: CC1c2nnc(N3CC4(CN(c5ccc(F)cn5)C4)C3)n2-c2ccc(Cl)cc2CN1C] |
| 180 | 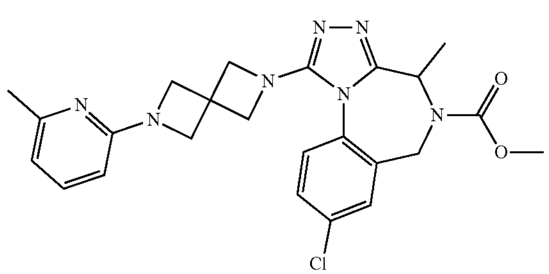 |

-continued
| Compound No. | Structure |
|---|---|
| 181 | 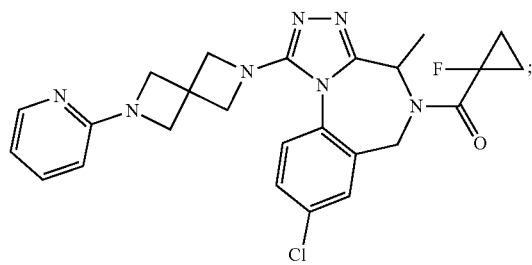 [SMILES: CC1c2nnc(N3CC4(CN(c5ccccn5)C4)C3)n2-c2ccc(Cl)cc2CN1C(=O)C1(F)CC1] |
| 182 | 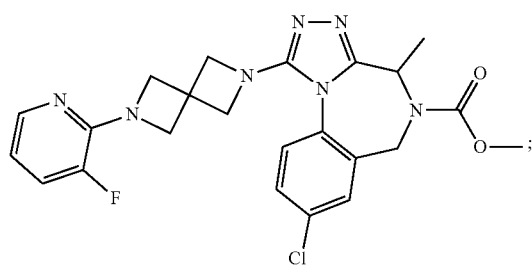 [SMILES: COC(=O)N1Cc2cc(Cl)ccc2-n2c(nnc2N2CC3(CN(c4ncccc4F)C3)C2)C1C] |
| 183 | 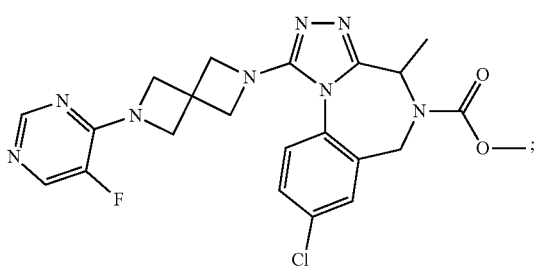 [SMILES: COC(=O)N1Cc2cc(Cl)ccc2-n2c(nnc2N2CC3(CN(c4ncncc4F)C3)C2)C1C] |
| 184 | 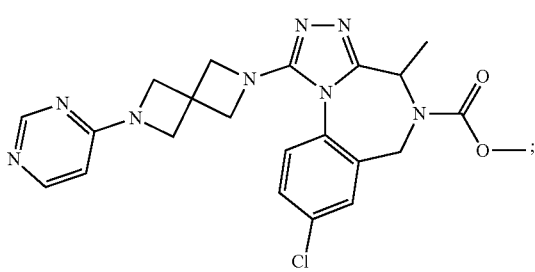 [SMILES: COC(=O)N1Cc2cc(Cl)ccc2-n2c(nnc2N2CC3(CN(c4ccncn4)C3)C2)C1C] |
| 185 | 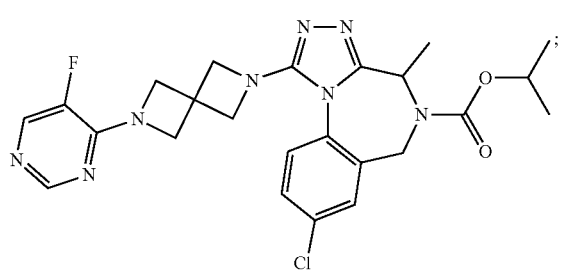 [SMILES: CC(C)OC(=O)N1Cc2cc(Cl)ccc2-n2c(nnc2N2CC3(CN(c4ncncc4F)C3)C2)C1C] |

| Compound No. | Structure |
| --- | --- |
| 186 | 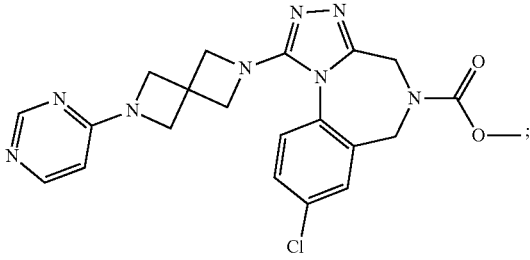 [SMILES: COC(=O)N1Cc2cc(Cl)ccc2-n2c(nnc2N2CC3(CN(c4ccncn4)C3)C2)C1] |
| 187 | 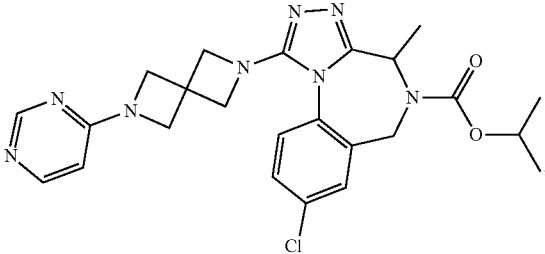 |
| 188 | 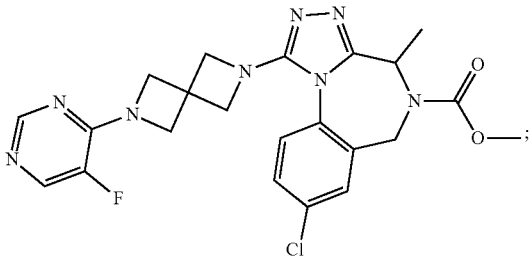 [SMILES: COC(=O)N1Cc2cc(Cl)ccc2-n2c(nnc2N2CC3(CN(c4ncncc4F)C3)C2)C1C] |
| 189 | 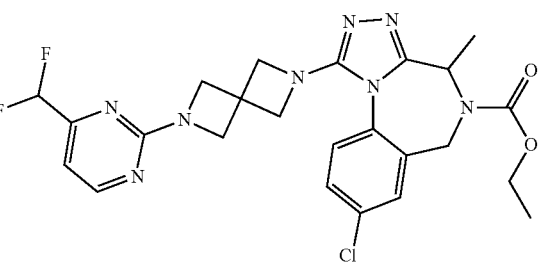 [SMILES: CCOC(=O)N1Cc2cc(Cl)ccc2-n2c(nnc2N2CC3(CN(c4nccc(C(F)F)n4)C3)C2)C1C] |
| 190 | 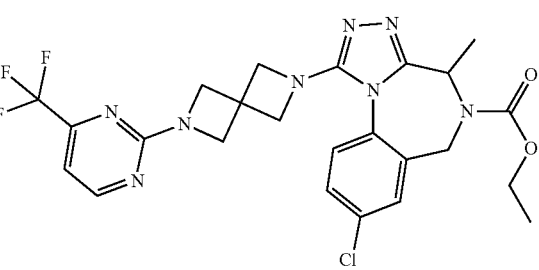 |
| 191 | 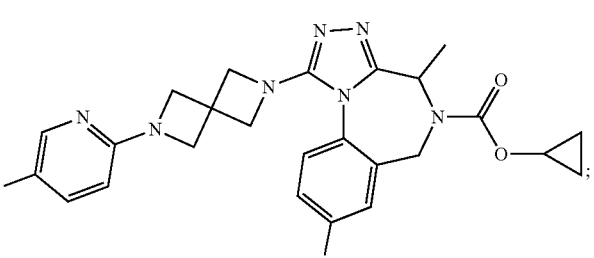 |

US 12,247,037 B2
663                                                                                                                     664
-continued
| Compound No. | Structure |
|---|---|
| 192 | 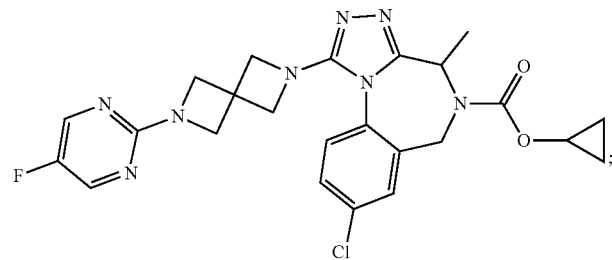 [SMILES: CC1c2nnc(N3CC4(CN(c5ncc(F)cn5)C4)C3)n2-c2ccc(Cl)cc2CN1C(=O)OC1CC1] |
| 193 | 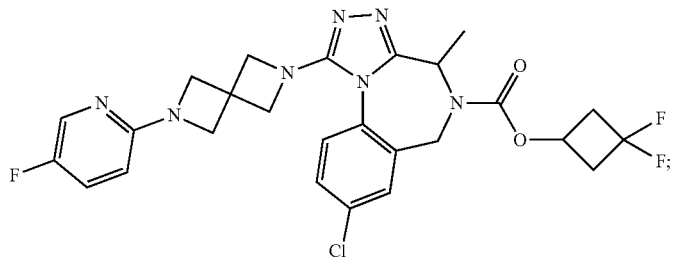 [SMILES: CC1c2nnc(N3CC4(CN(c5ccc(F)cn5)C4)C3)n2-c2ccc(Cl)cc2CN1C(=O)OC1CC(F)(F)C1] |
| 194 | 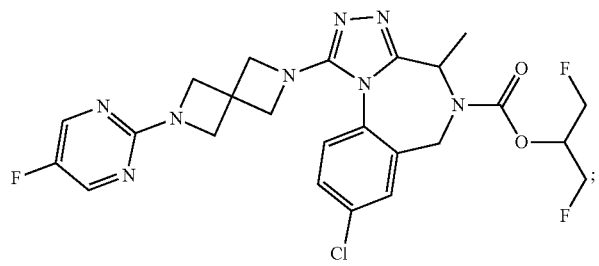 [SMILES: CC1c2nnc(N3CC4(CN(c5ncc(F)cn5)C4)C3)n2-c2ccc(Cl)cc2CN1C(=O)OC(CF)CF] |
| 195 | 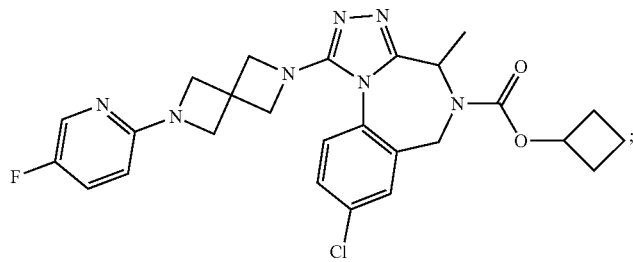 [SMILES: CC1c2nnc(N3CC4(CN(c5ccc(F)cn5)C4)C3)n2-c2ccc(Cl)cc2CN1C(=O)OC1CCC1] |
| 196 | 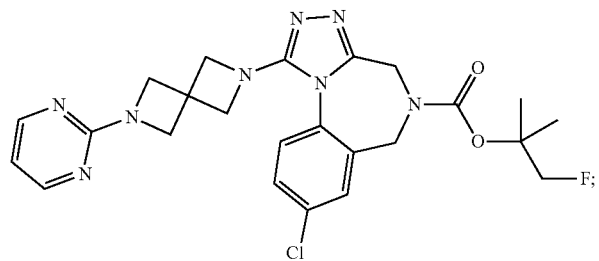 [SMILES: CC(C)(CF)OC(=O)N1Cc2cc(Cl)ccc2-n2c(nnc2N2CC3(CN(c4ncccn4)C3)C2)C1] |

-continued
| Compound No. | Structure |
|---|---|
| 197 | 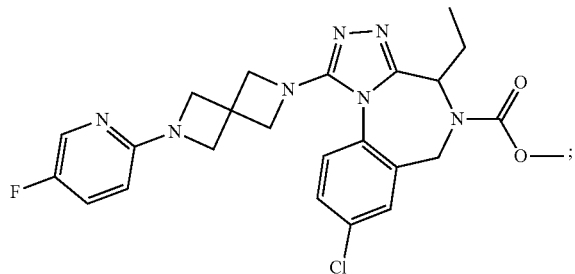 [SMILES: CCC1c2nnc(N3CC4(CN(c5ccc(F)cn5)C4)C3)n2-c2ccc(Cl)cc2CN1C(=O)OC] |
| 198 | 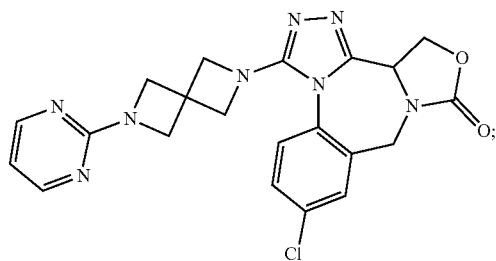 [SMILES: O=C1OCC2c3nnc(N4CC5(CN(c6ncccn6)C5)C4)n3-c3ccc(Cl)cc3CN12] |
| 199 | 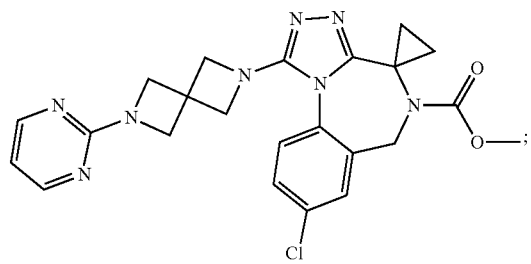 [SMILES: COC(=O)N1Cc2cc(Cl)ccc2-n2c(N3CC4(CN(c5ncccn5)C4)C3)nnc2C12CC2] |
| 200 | 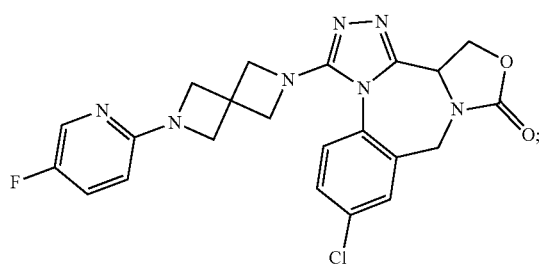 [SMILES: O=C1OCC2c3nnc(N4CC5(CN(c6ccc(F)cn6)C5)C4)n3-c3ccc(Cl)cc3CN12] |
| 201 | 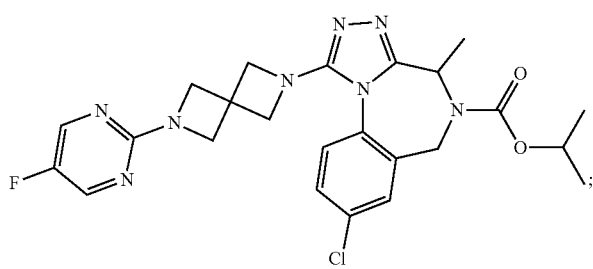 [SMILES: CC(C)OC(=O)N1Cc2cc(Cl)ccc2-n2c(nnc2N2CC3(CN(c4ncc(F)cn4)C3)C2)C1C] |

-continued
| Compound No. | Structure |
|---|---|
| 202 | 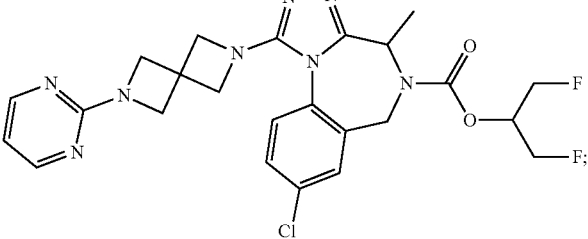 |
| 203 | 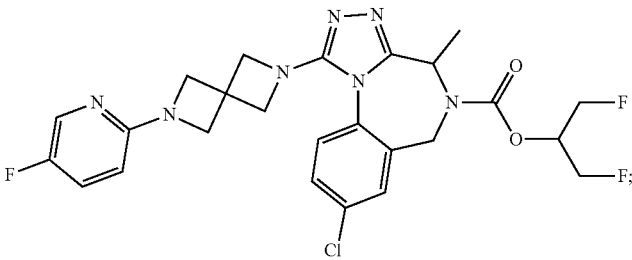 [SMILES: CC1c2nnc(N3CC4(CN(c5ccc(F)cn5)C4)C3)n2-c2ccc(Cl)cc2CN1C(=O)OC(CF)CF] |
| 204 | 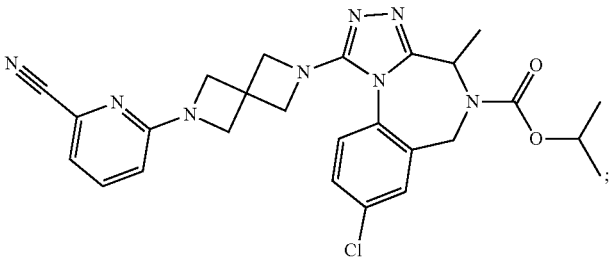 [SMILES: CC(C)OC(=O)N1Cc2cc(Cl)ccc2-n2c(nnc2N2CC3(CN(c4cccc(C#N)n4)C3)C2)C1C] |
| 205 | 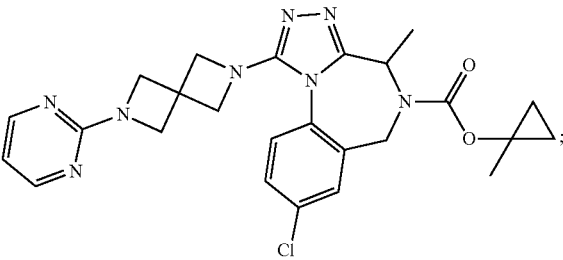 [SMILES: CC1c2nnc(N3CC4(CN(c5ncccn5)C4)C3)n2-c2ccc(Cl)cc2CN1C(=O)OC1(C)CC1] |
| 206 | 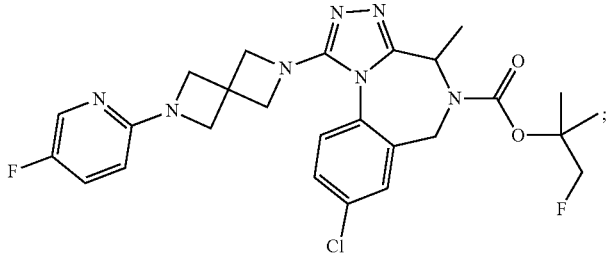 [SMILES: CC1c2nnc(N3CC4(CN(c5ccc(F)cn5)C4)C3)n2-c2ccc(Cl)cc2CN1C(=O)OC(C)(C)CF] |
| 207 | 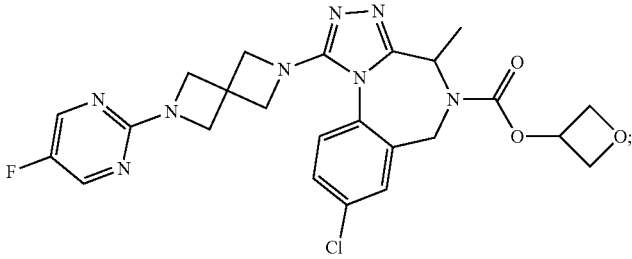 [SMILES: CC1c2nnc(N3CC4(CN(c5ncc(F)cn5)C4)C3)n2-c2ccc(Cl)cc2CN1C(=O)OC1COC1] |

| Compound No. | Structure |
|---|---|
| 208 | 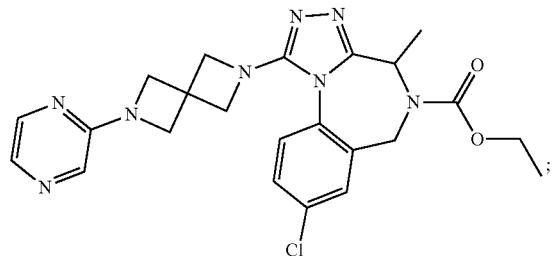 [SMILES: CCOC(=O)N1Cc2cc(Cl)ccc2-n2c(nnc2N2CC3(CN(c4cnccn4)C3)C2)C1C] |
| 209 | 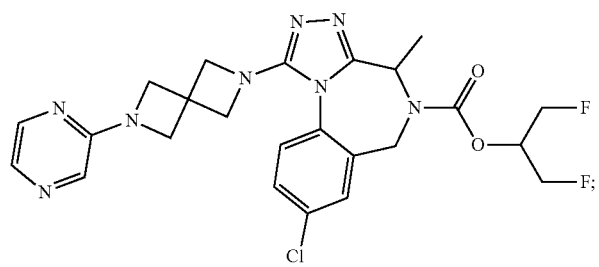 [SMILES: CC1c2nnc(N3CC4(CN(c5cnccn5)C4)C3)n2-c2ccc(Cl)cc2CN1C(=O)OC(CF)CF] |
| 210 | 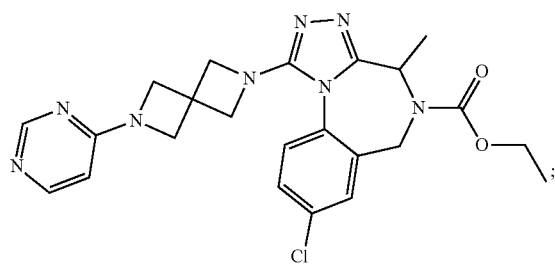 [SMILES: CCOC(=O)N1Cc2cc(Cl)ccc2-n2c(nnc2N2CC3(CN(c4ccncn4)C3)C2)C1C] |
| 211 | 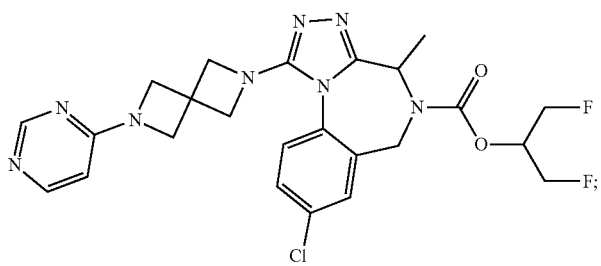 [SMILES: CC1c2nnc(N3CC4(CN(c5ccncn5)C4)C3)n2-c2ccc(Cl)cc2CN1C(=O)OC(CF)CF] |
| 212 | 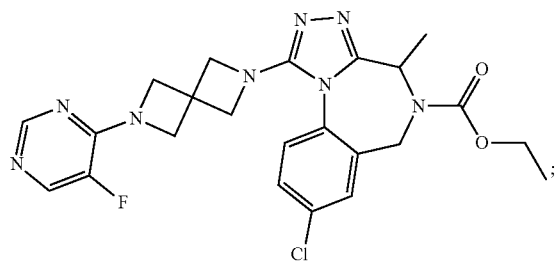 [SMILES: CCOC(=O)N1Cc2cc(Cl)ccc2-n2c(nnc2N2CC3(CN(c4ncncc4F)C3)C2)C1C] |

| Compound No. | Structure |
|---|---|
| 213 | 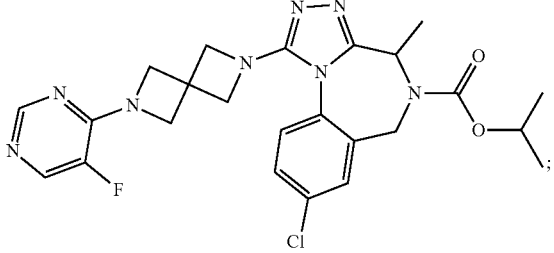 [SMILES: CC(C)OC(=O)N1Cc2cc(Cl)ccc2-n2c(nnc2N2CC3(CN(c4ncncc4F)C3)C2)C1C] |
| 214 | 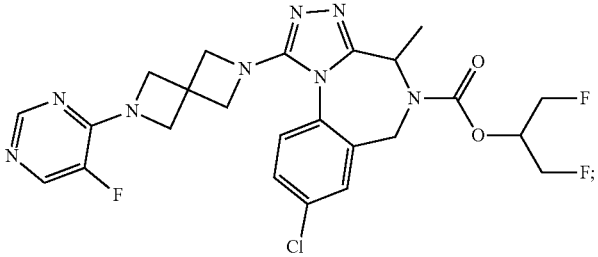 [SMILES: CC1c2nnc(N3CC4(CN(c5ncncc5F)C4)C3)n2-c2ccc(Cl)cc2CN1C(=O)OC(CF)CF] |
| 215 | 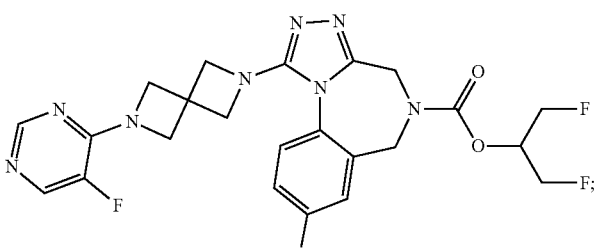 |
| 216 | 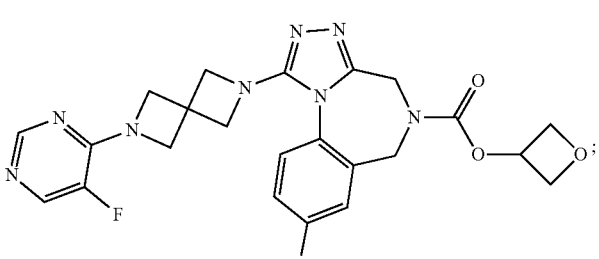 |
| 217 | 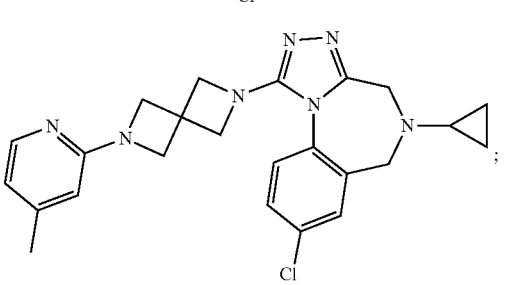 |
| 218 | 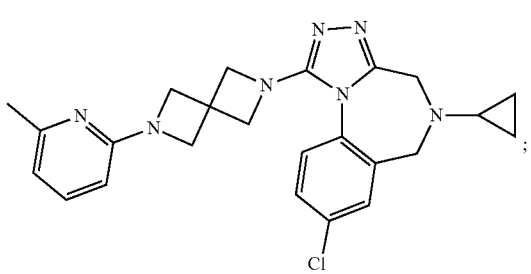 [SMILES: Cc1cccc(N2CC3(C2)CN(c2nnc4n2-c2ccc(Cl)cc2CN(C2CC2)C4)C3)n1] |

| Compound No. | Structure |
|---|---|
| 219 | 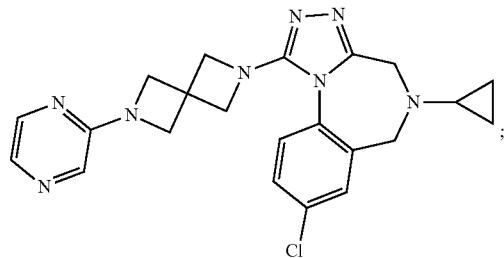 [SMILES: Clc1ccc2c(c1)CN(C1CC1)Cc1nnc(N3CC4(CN(c5cnccn5)C4)C3)n1-2] ; |
| 220 | 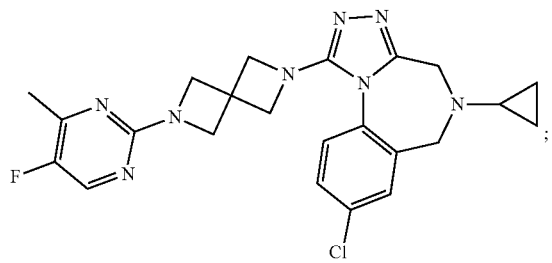 [SMILES: Cc1nc(N2CC3(C2)CN(c2nnc4n2-c2ccc(Cl)cc2CN(C2CC2)C4)C3)ncc1F] ; |
| 221 | 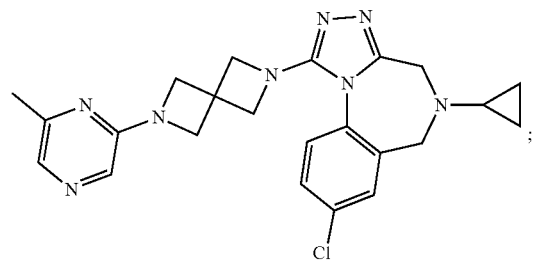 [SMILES: Cc1cncc(N2CC3(C2)CN(c2nnc4n2-c2ccc(Cl)cc2CN(C2CC2)C4)C3)n1] ; |
| 222 | 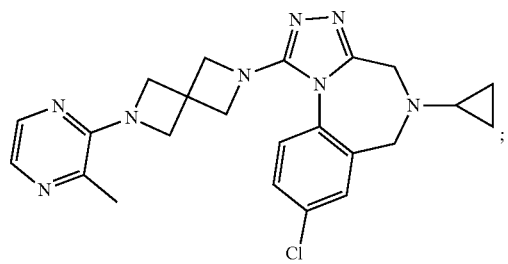 [SMILES: Cc1nccnc1N1CC2(C1)CN(c1nnc3n1-c1ccc(Cl)cc1CN(C1CC1)C3)C2] ; |
| 223 | 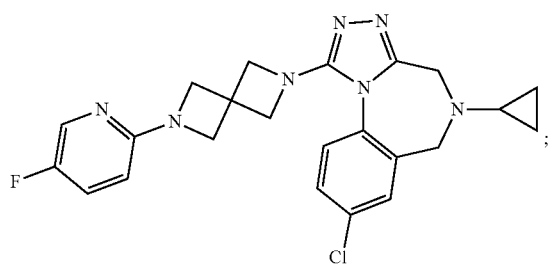 [SMILES: Fc1ccc(N2CC3(C2)CN(c2nnc4n2-c2ccc(Cl)cc2CN(C2CC2)C4)C3)nc1] ; |

-continued
| Compound No. | Structure |
|---|---|
| 224 | 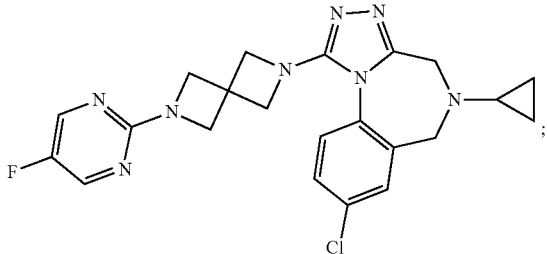 [SMILES: Fc1cnc(N2CC3(C2)CN(c2nnc4n2-c2ccc(Cl)cc2CN(C2CC2)C4)C3)nc1] ; |
| 225 | 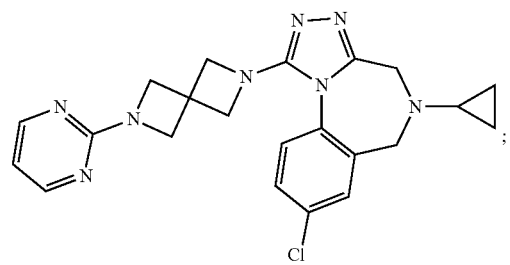 [SMILES: Clc1ccc2c(c1)CN(C1CC1)Cc1nnc(N3CC4(CN(c5ncccn5)C4)C3)n1-2] ; |
| 226 | 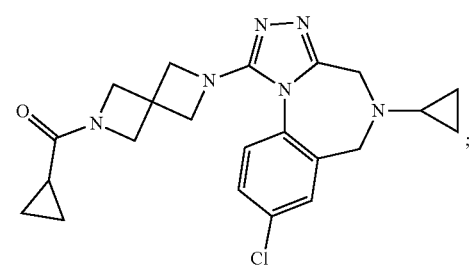 [SMILES: O=C(C1CC1)N1CC2(C1)CN(c1nnc3n1-c1ccc(Cl)cc1CN(C1CC1)C3)C2] ; |
| 227 | 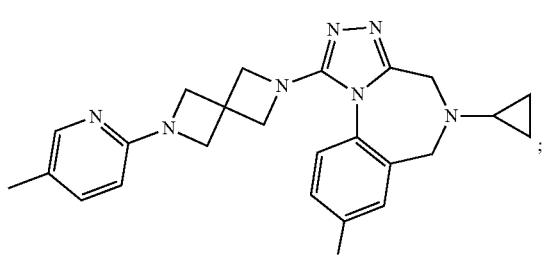 ; |
| 228 | 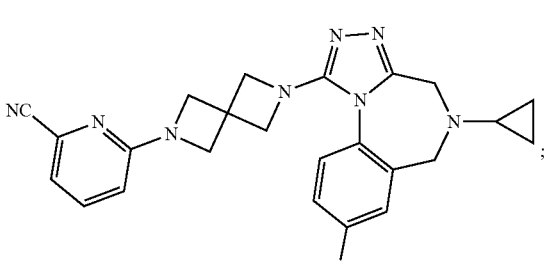 ; |
| 229 | 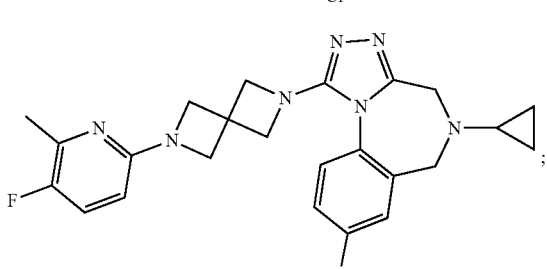 ; |

| Compound No. | Structure |
|---|---|
| 230 | 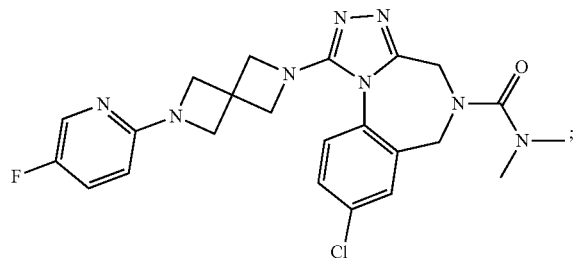 |
| 231 | 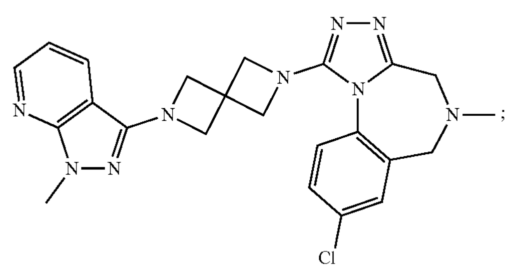 [SMILES: CN1Cc2cc(Cl)ccc2-n2c(nnc2N2CC3(CN(c4nn(C)c5ncccc45)C3)C2)C1] |
| 232 | 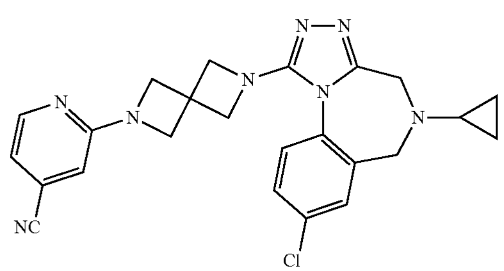 |
| 233 | 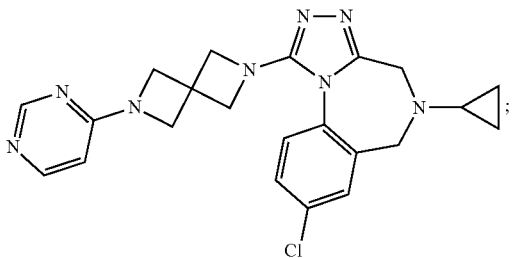 [SMILES: Clc1ccc2c(c1)CN(C1CC1)Cc1nnc(N3CC4(CN(c5ccncn5)C4)C3)n1-2] |
| 234 | 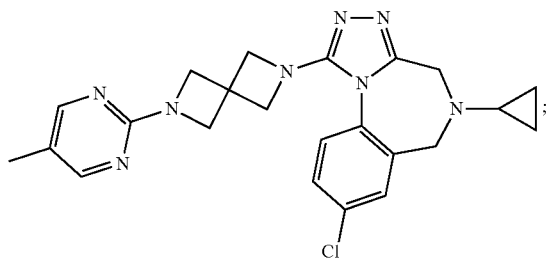 [SMILES: Cc1cnc(N2CC3(C2)CN(c2nnc4n2-c2ccc(Cl)cc2CN(C2CC2)C4)C3)nc1] |

| Compound No. | Structure |
|---|---|
| 235 | 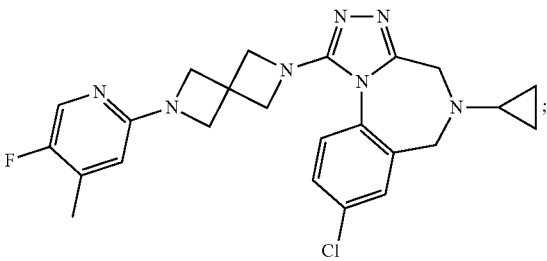 [SMILES: Cc1cc(N2CC3(C2)CN(c2nnc4n2-c2ccc(Cl)cc2CN(C2CC2)C4)C3)ncc1F] |
| 236 | 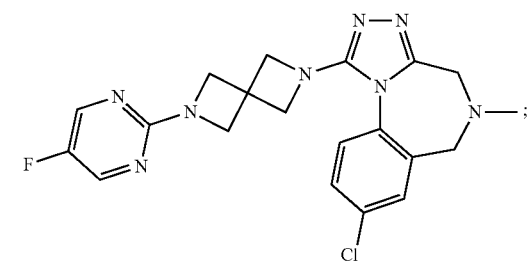 [SMILES: CN1Cc2cc(Cl)ccc2-n2c(nnc2N2CC3(CN(c4ncc(F)cn4)C3)C2)C1] |
| 237 | 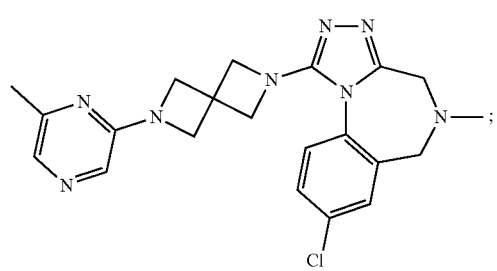 |
| 238 | 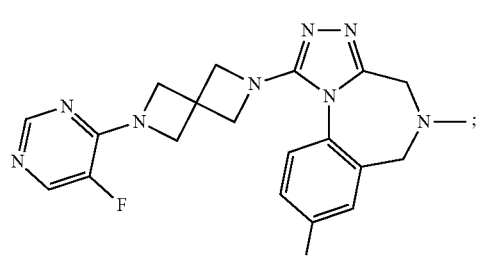 |
| 239 | 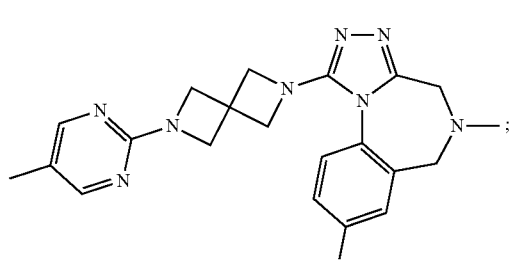 |
| 240 | 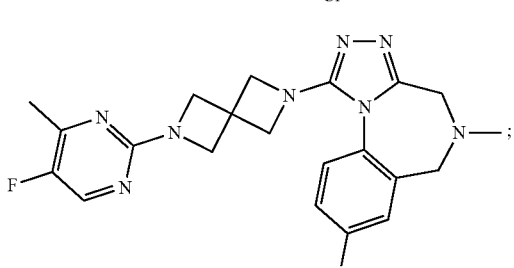 |

-continued
| Compound No. | Structure |
|---|---|
| 241 | 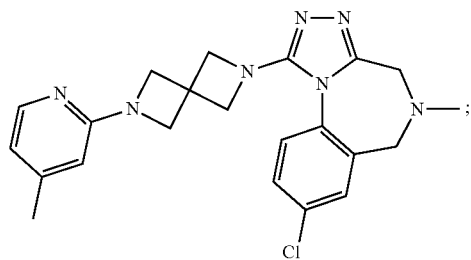 [SMILES: Cc1ccnc(N2CC3(C2)CN(c2nnc4n2-c2ccc(Cl)cc2CN(C)C4)C3)c1] |
| 242 | 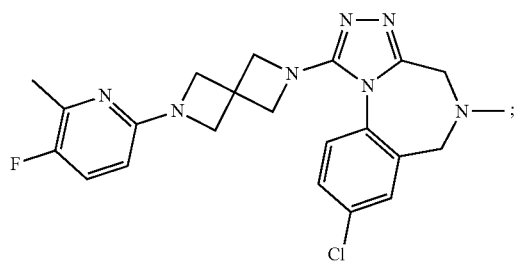 [SMILES: Cc1nc(N2CC3(C2)CN(c2nnc4n2-c2ccc(Cl)cc2CN(C)C4)C3)ccc1F] |
| 243 | 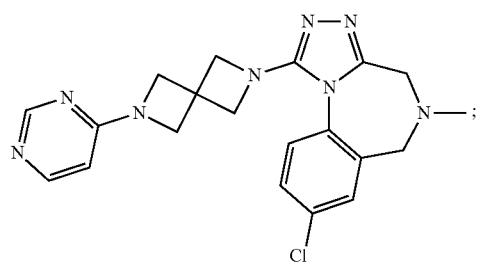 [SMILES: CN1Cc2cc(Cl)ccc2-n2c(nnc2N2CC3(CN(c4ccncn4)C3)C2)C1] |
| 244 | 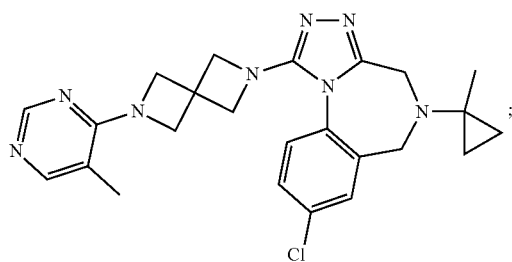 [SMILES: Cc1cncnc1N1CC2(C1)CN(c1nnc3n1-c1ccc(Cl)cc1CN(C1(C)CC1)C3)C2] |
| 245 | 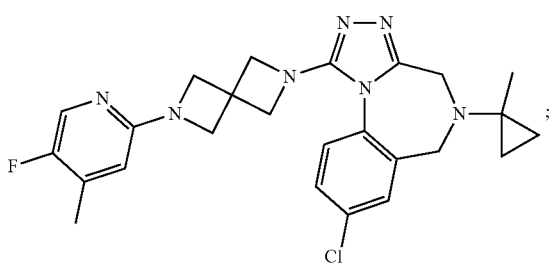 [SMILES: Cc1cc(N2CC3(C2)CN(c2nnc4n2-c2ccc(Cl)cc2CN(C2(C)CC2)C4)C3)ncc1F] |

-continued

| Compound No. | Structure |
|---|---|
| 246 | (structure) |
| 247 | (structure) |
| 248 | (structure) |
| 249 | (structure) |
| 250 | (structure) |
| 251 | (structure) |

| Compound No. | Structure |
|---|---|
| 252 | 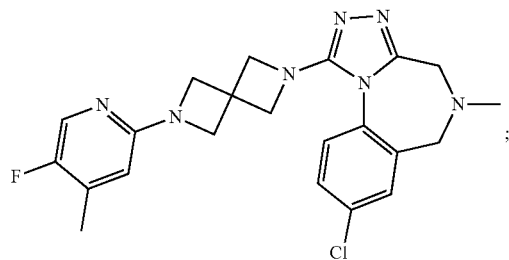 [SMILES: Cc1cc(N2CC3(C2)CN(c2nnc4n2-c2ccc(Cl)cc2CN(C)C4)C3)ncc1F] ; |
| 253 | 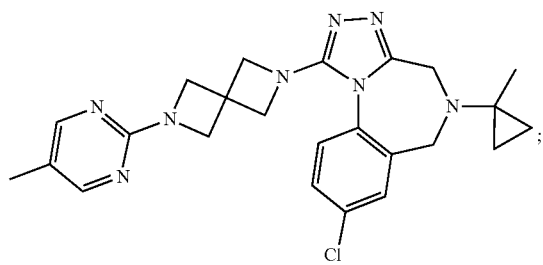 [SMILES: Cc1cnc(N2CC3(C2)CN(c2nnc4n2-c2ccc(Cl)cc2CN(C2(C)CC2)C4)C3)nc1] ; |
| 254 | 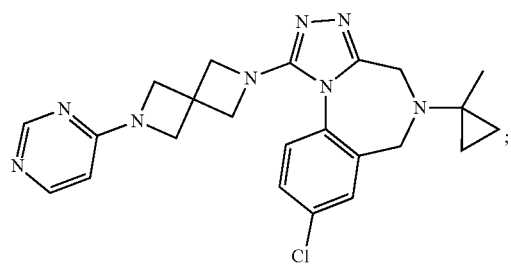 [SMILES: CC1(N2Cc3cc(Cl)ccc3-n3c(nnc3N3CC4(CN(c5ccncn5)C4)C3)C2)CC1] ; |
| 255 | 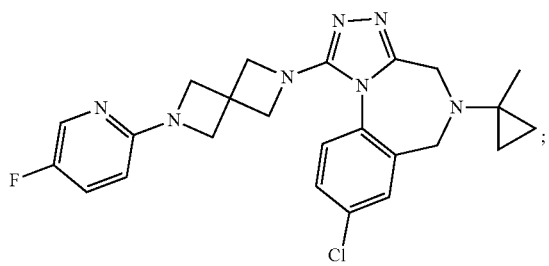 [SMILES: CC1(N2Cc3cc(Cl)ccc3-n3c(nnc3N3CC4(CN(c5ccc(F)cn5)C4)C3)C2)CC1] ; |
| 256 | 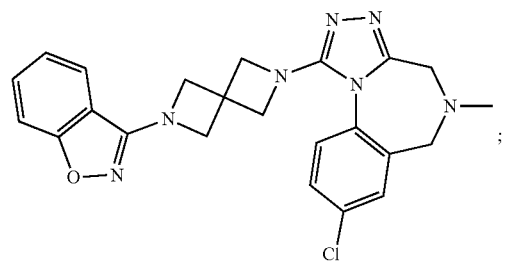 [SMILES: CN1Cc2cc(Cl)ccc2-n2c(nnc2N2CC3(CN(c4noc5ccccc45)C3)C2)C1] ; |

| Compound No. | Structure |
|---|---|
| 257 | 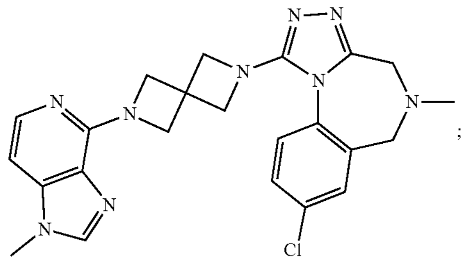 [SMILES: CN1Cc2cc(Cl)ccc2-n2c(nnc2N2CC3(CN(c4nccc5c4ncn5C)C3)C2)C1] |
| 258 | 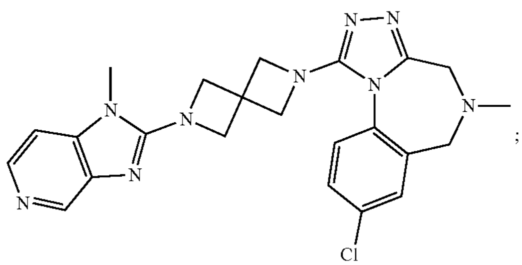 [SMILES: CN1Cc2cc(Cl)ccc2-n2c(nnc2N2CC3(C2)CN(c2nc4cnccc4n2C)C3)C1] |
| 259 | 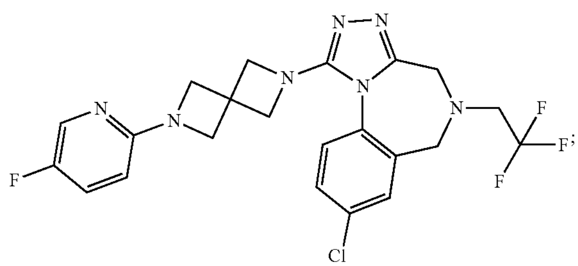 [SMILES: Fc1ccc(N2CC3(C2)CN(c2nnc4n2-c2ccc(Cl)cc2CN(CC(F)(F)F)C4)C3)nc1] |
| 260 | 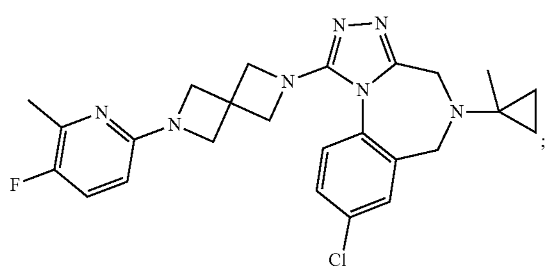 [SMILES: Cc1nc(N2CC3(C2)CN(c2nnc4n2-c2ccc(Cl)cc2CN(C2(C)CC2)C4)C3)ccc1F] |
| 261 | 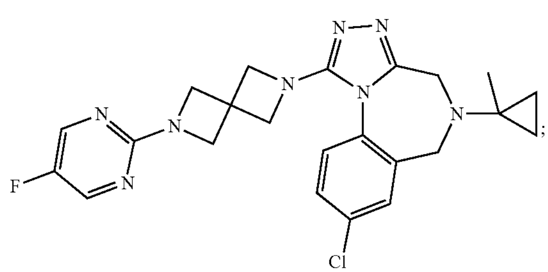 [SMILES: CC1(N2Cc3cc(Cl)ccc3-n3c(nnc3N3CC4(CN(c5ncc(F)cn5)C4)C3)C2)CC1] |
| 262 | 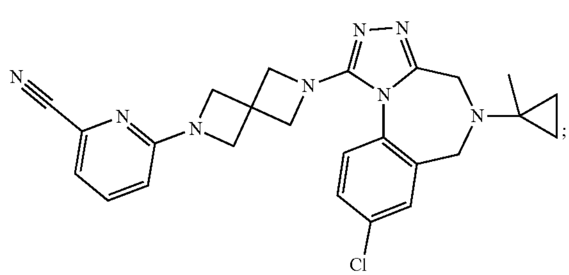 [SMILES: CC1(N2Cc3cc(Cl)ccc3-n3c(nnc3N3CC4(CN(c5cccc(C#N)n5)C4)C3)C2)CC1] |

| Compound No. | Structure |
|---|---|
| 263 | 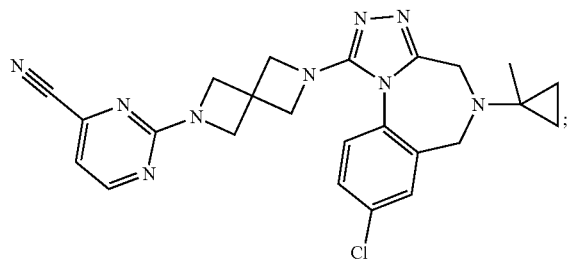 [SMILES: CC1(N2Cc3cc(Cl)ccc3-n3c(nnc3N3CC4(CN(c5nccc(C#N)n5)C4)C3)C2)CC1] |
| 264 | 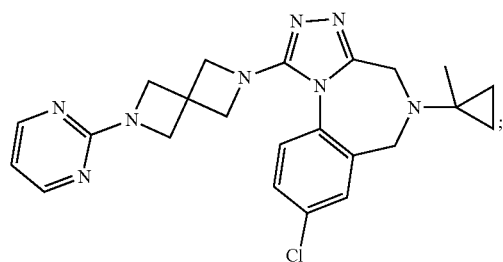 [SMILES: CC1(N2Cc3cc(Cl)ccc3-n3c(nnc3N3CC4(CN(c5ncccn5)C4)C3)C2)CC1] |
| 265 | 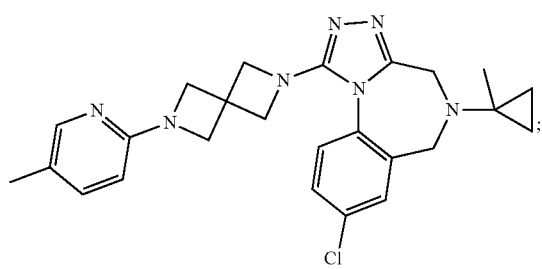 [SMILES: Cc1ccc(N2CC3(C2)CN(c2nnc4n2-c2ccc(Cl)cc2CN(C2(C)CC2)C4)C3)nc1] |
| 266 | 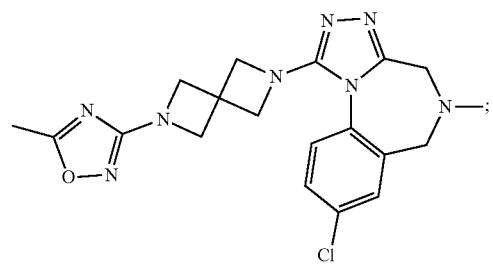 |
| 267 | 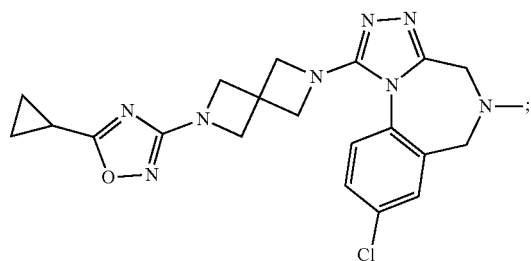 |

-continued

| Compound No. | Structure |
|---|---|
| 268 | 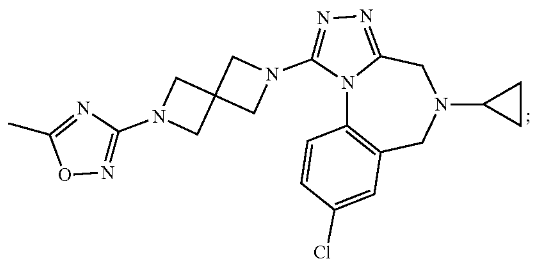 [SMILES: Cc1nc(N2CC3(C2)CN(c2nnc4n2-c2ccc(Cl)cc2CN(C2CC2)C4)C3)no1] |
| 269 | 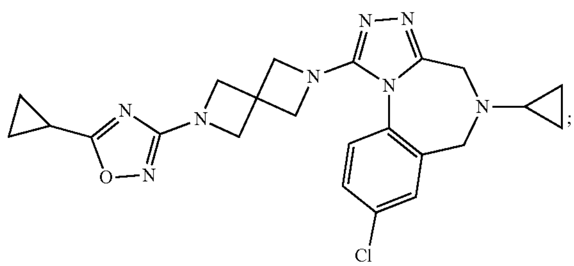 [SMILES: Clc1ccc2c(c1)CN(C1CC1)Cc1nnc(N3CC4(CN(c5noc(C6CC6)n5)C4)C3)n1-2] |
| 270 | 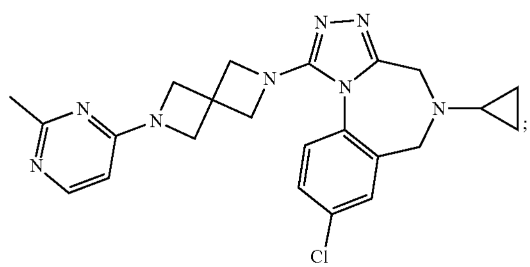 [SMILES: Cc1nccc(N2CC3(C2)CN(c2nnc4n2-c2ccc(Cl)cc2CN(C2CC2)C4)C3)n1] |
| 271 | 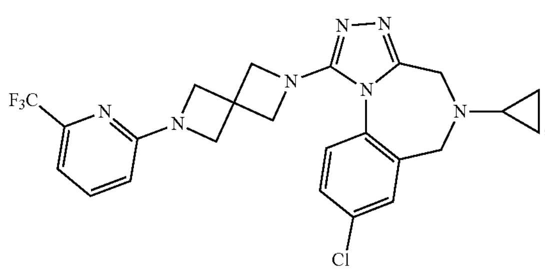 |
| 272 | 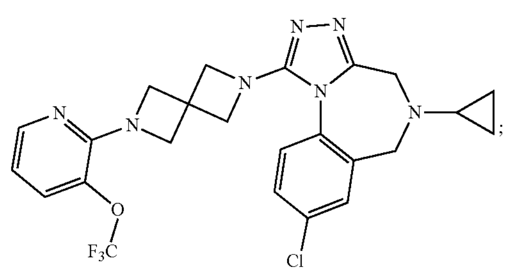 [SMILES: FC(F)(F)Oc1cccnc1N1CC2(C1)CN(c1nnc3n1-c1ccc(Cl)cc1CN(C1CC1)C3)C2] |
| 273 | 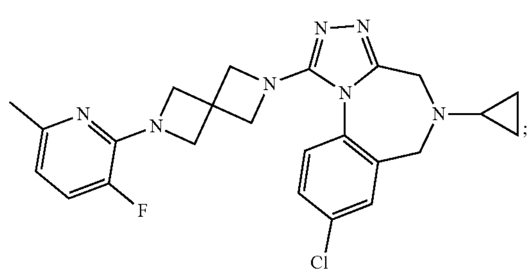 [SMILES: Cc1ccc(F)c(N2CC3(C2)CN(c2nnc4n2-c2ccc(Cl)cc2CN(C2CC2)C4)C3)n1] |

| Compound No. | Structure |
|---|---|
| 274 | 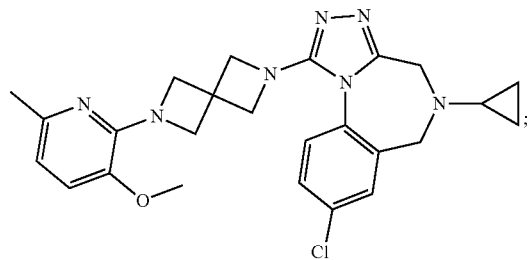 [SMILES: COc1ccc(C)nc1N1CC2(C1)CN(c1nnc3n1-c1ccc(Cl)cc1CN(C1CC1)C3)C2] |
| 275 | 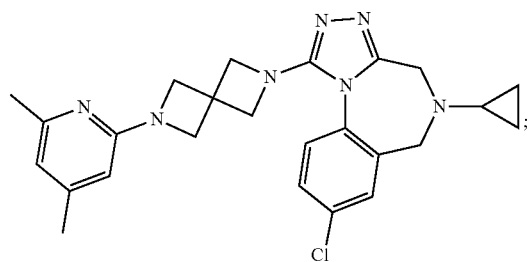 [SMILES: Cc1cc(C)nc(N2CC3(C2)CN(c2nnc4n2-c2ccc(Cl)cc2CN(C2CC2)C4)C3)c1] |
| 276 | 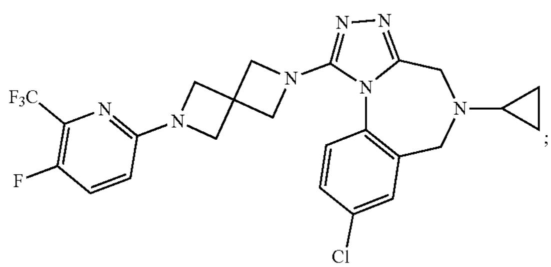 |
| 277 | 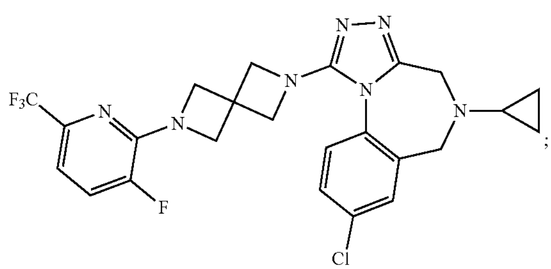 |
| 278 | 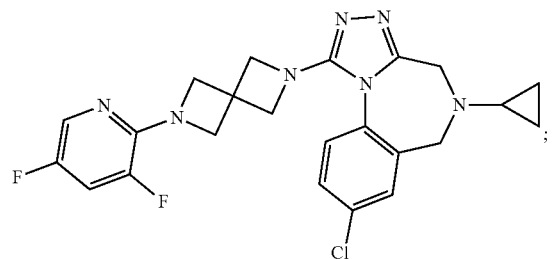 |

-continued
| Compound No. | Structure |
|---|---|
| 279 | 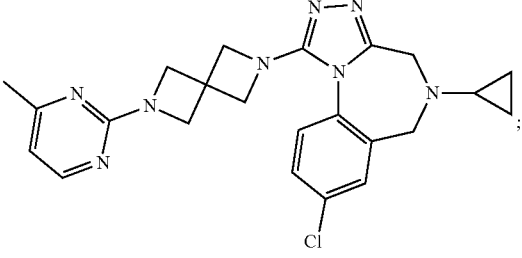 |
| 280 | 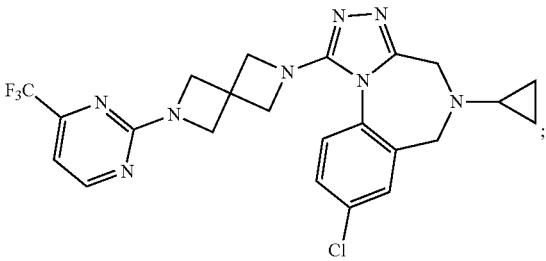 |
| 281 | 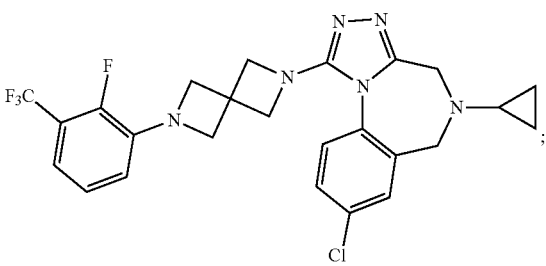 |
| 282 | 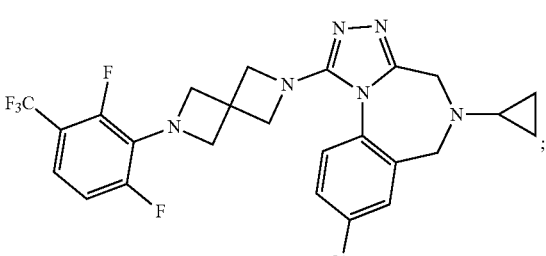 |
| 283 | 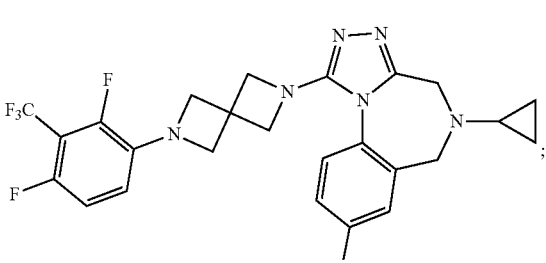 |
| 284 | 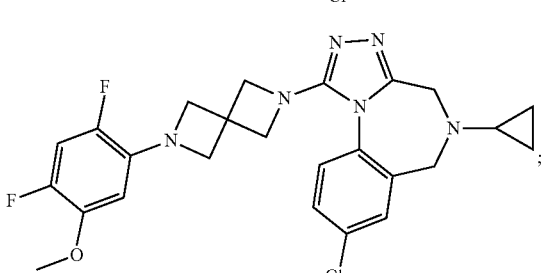 |

| Compound No. | Structure |
|---|---|
| 285 | 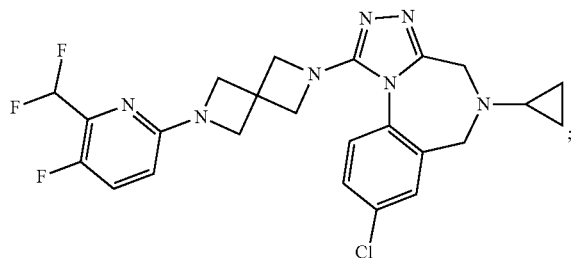 |
| 286 | 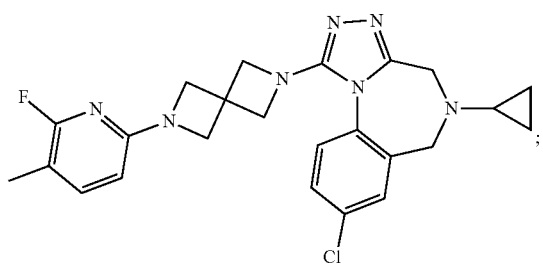 |
| 287 | 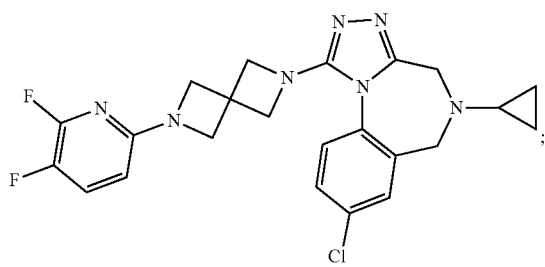 |
| 288 | 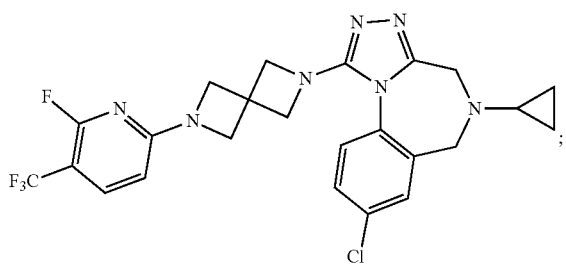 |
| 289 | 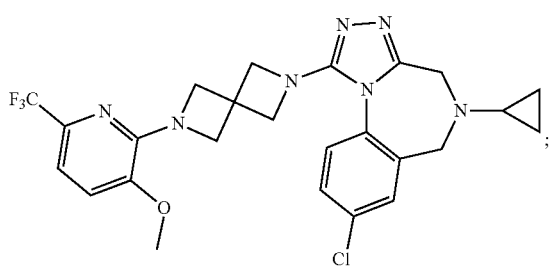 |

| Compound No. | Structure |
|---|---|
| 290 | 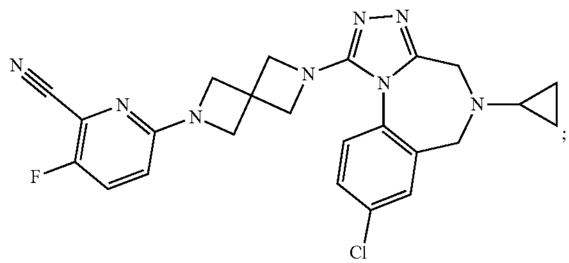 |
| 291 | 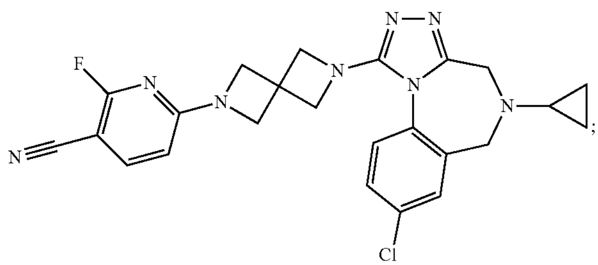 [SMILES: N#Cc1ccc(N2CC3(C2)CN(c2nnc4n2-c2ccc(Cl)cc2CN(C2CC2)C4)C3)nc1F] |
| 292 | 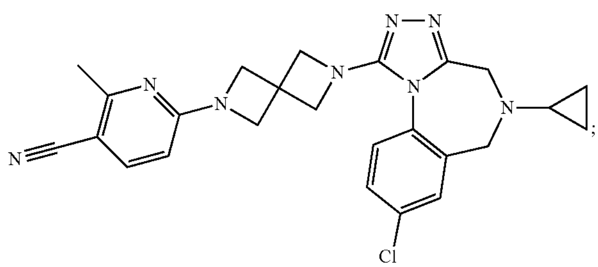 [SMILES: Cc1nc(N2CC3(C2)CN(c2nnc4n2-c2ccc(Cl)cc2CN(C2CC2)C4)C3)ccc1C#N] |
| 293 | 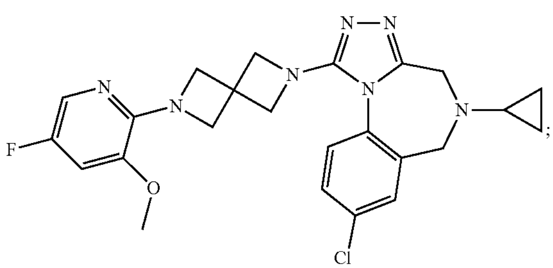 [SMILES: COc1cc(F)cnc1N1CC2(C1)CN(c1nnc3n1-c1ccc(Cl)cc1CN(C1CC1)C3)C2] |
| 294 | 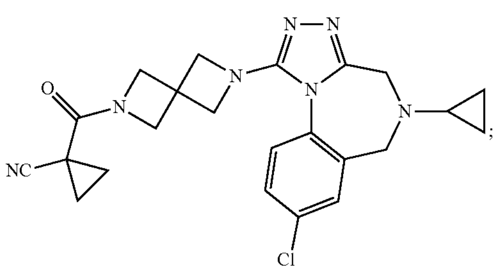 [SMILES: N#CC1(C(=O)N2CC3(C2)CN(c2nnc4n2-c2ccc(Cl)cc2CN(C2CC2)C4)C3)CC1] |
| 295 | 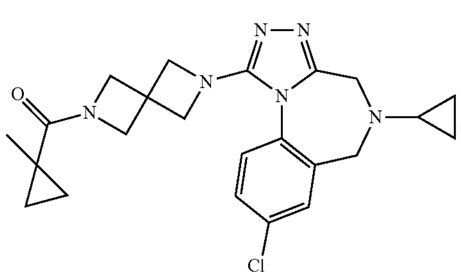 |

| Compound No. | Structure |
|---|---|
| 296 | 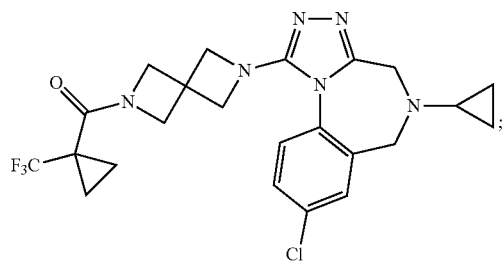 |
| 297 | 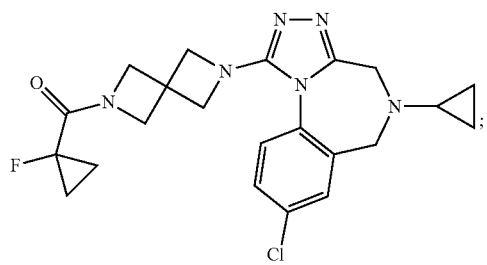 [SMILES: O=C(N1CC2(C1)CN(c1nnc3n1-c1ccc(Cl)cc1CN(C1CC1)C3)C2)C1(F)CC1] |
| 298 | 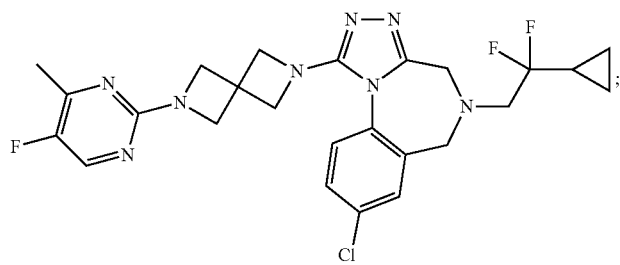 [SMILES: Cc1nc(N2CC3(C2)CN(c2nnc4n2-c2ccc(Cl)cc2CN(CC(F)(F)C2CC2)C4)C3)ncc1F] |
| 299 | 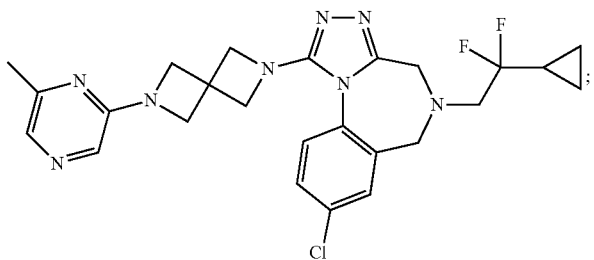 [SMILES: Cc1cncc(N2CC3(C2)CN(c2nnc4n2-c2ccc(Cl)cc2CN(CC(F)(F)C2CC2)C4)C3)n1] |
| 300 | 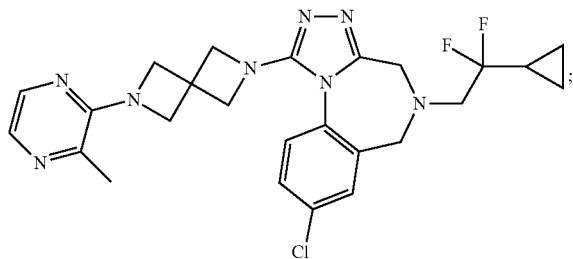 [SMILES: Cc1nccnc1N1CC2(C1)CN(c1nnc3n1-c1ccc(Cl)cc1CN(CC(F)(F)C1CC1)C3)C2] |
| 301 | 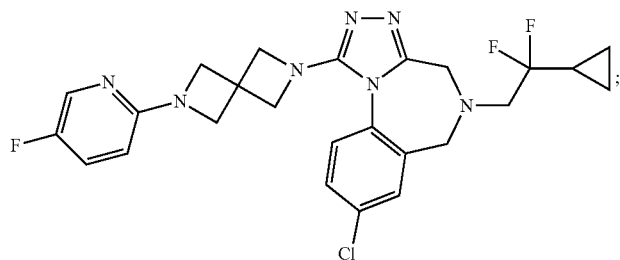 |

-continued
| Compound No. | Structure |
|---|---|
| 302 | 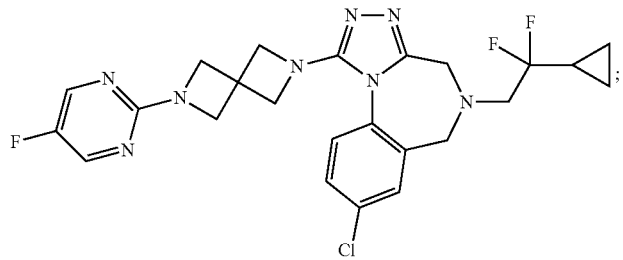 [SMILES: Fc1cnc(N2CC3(C2)CN(c2nnc4n2-c2ccc(Cl)cc2CN(CC(F)(F)C2CC2)C4)C3)nc1] |
| 303 | 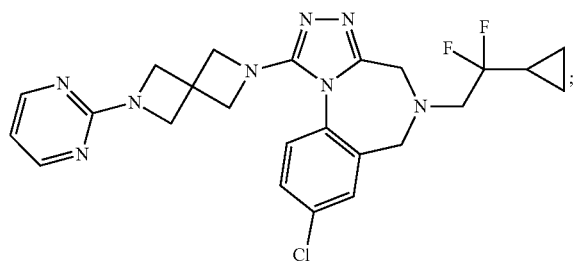 [SMILES: FC(F)(CN1Cc2cc(Cl)ccc2-n2c(nnc2N2CC3(CN(c4ncccn4)C3)C2)C1)C1CC1] |
| 304 | 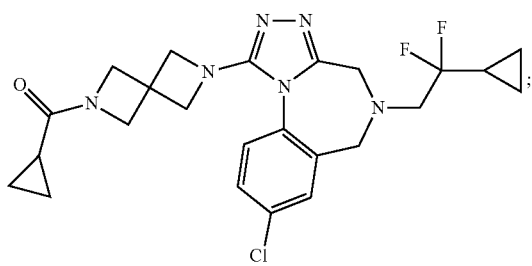 [SMILES: O=C(C1CC1)N1CC2(C1)CN(c1nnc3n1-c1ccc(Cl)cc1CN(CC(F)(F)C1CC1)C3)C2] |
| 305 | 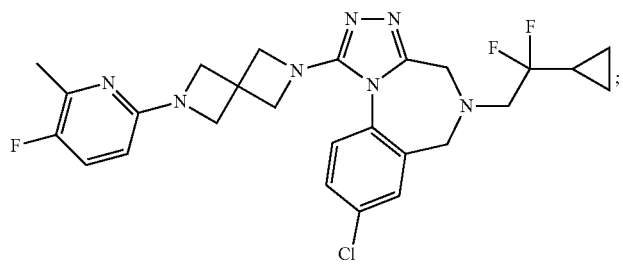 [SMILES: Cc1nc(N2CC3(C2)CN(c2nnc4n2-c2ccc(Cl)cc2CN(CC(F)(F)C2CC2)C4)C3)ccc1F] |
| 306 | 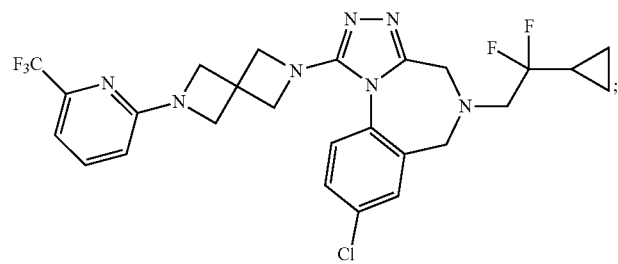 |

-continued

| Compound No. | Structure |
|---|---|
| 307 | 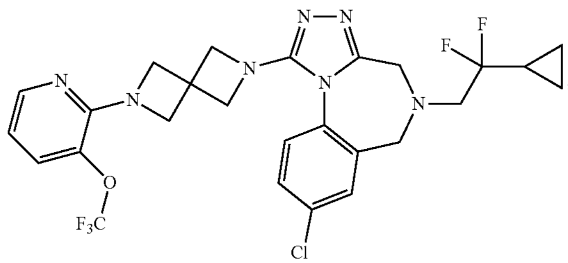 |
| 308 | 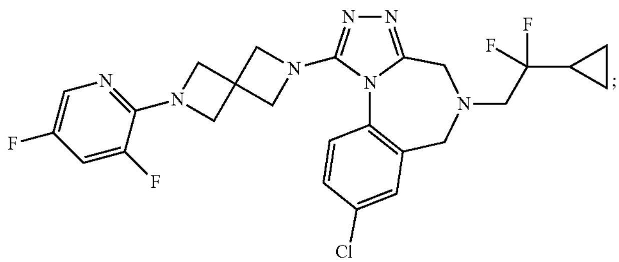 [SMILES: Fc1cnc(N2CC3(C2)CN(c2nnc4n2-c2ccc(Cl)cc2CN(CC(F)(F)C2CC2)C4)C3)c(F)c1] |
| 309 | 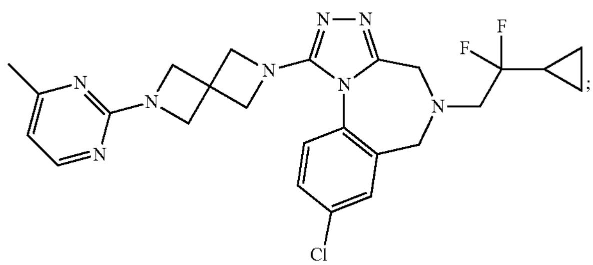 [SMILES: Cc1ccnc(N2CC3(C2)CN(c2nnc4n2-c2ccc(Cl)cc2CN(CC(F)(F)C2CC2)C4)C3)n1] |
| 310 | 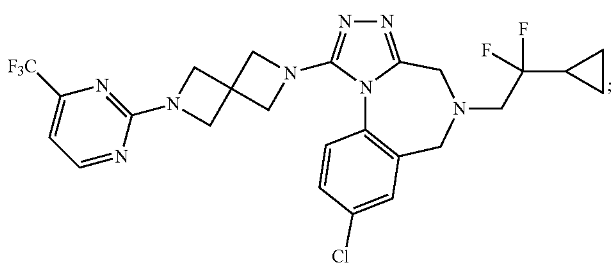 [SMILES: FC(F)(F)c1ccnc(N2CC3(C2)CN(c2nnc4n2-c2ccc(Cl)cc2CN(CC(F)(F)C2CC2)C4)C3)n1] |
| 311 | 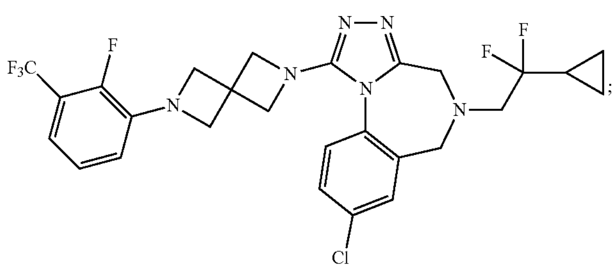 [SMILES: Fc1c(N2CC3(C2)CN(c2nnc4n2-c2ccc(Cl)cc2CN(CC(F)(F)C2CC2)C4)C3)cccc1C(F)(F)F] |
| 312 | 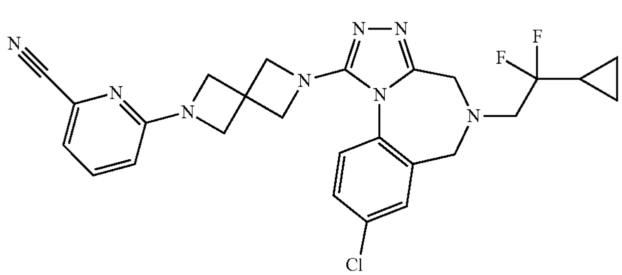 |

-continued
| Compound No. | Structure |
|---|---|
| 313 | 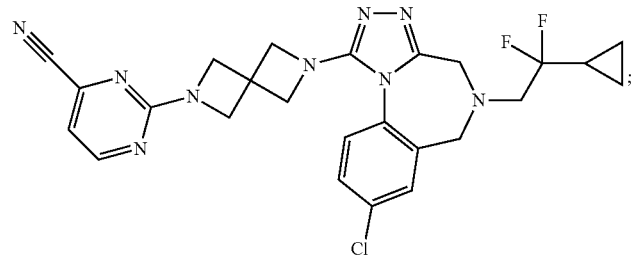 [SMILES: N#Cc1cccc(N2CC3(C2)CN(c2nnc4n2-c2ccc(Cl)cc2CN(CC(F)(F)C2CC2)C4)C3)n1] |
| 314 | 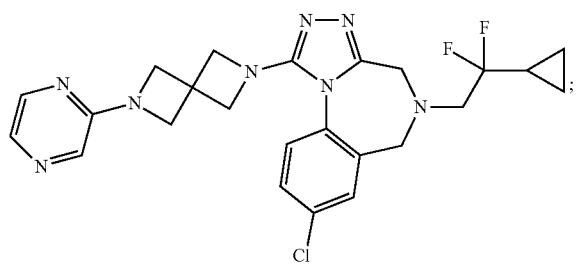 |
| 315 | 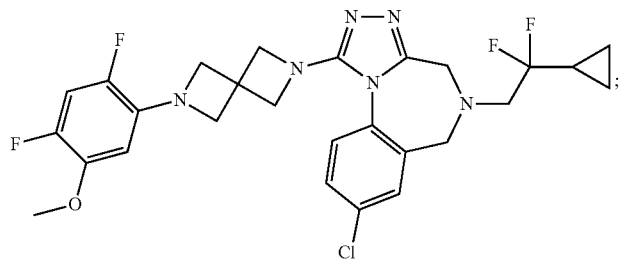 [SMILES: COc1cc(N2CC3(C2)CN(c2nnc4n2-c2ccc(Cl)cc2CN(CC(F)(F)C2CC2)C4)C3)c(F)cc1F] |
| 316 | 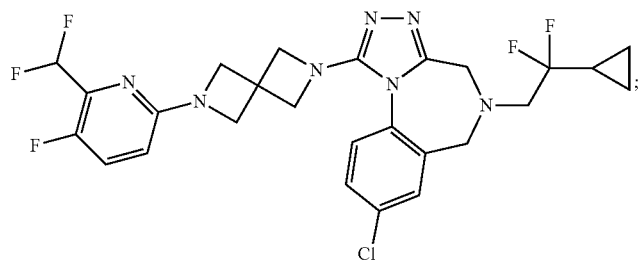 [SMILES: Fc1ccc(N2CC3(C2)CN(c2nnc4n2-c2ccc(Cl)cc2CN(CC(F)(F)C2CC2)C4)C3)nc1C(F)F] |
| 317 | 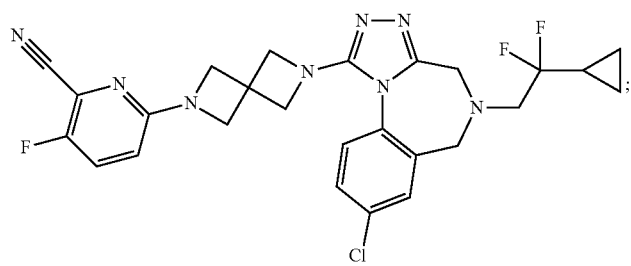 [SMILES: N#Cc1nc(N2CC3(C2)CN(c2nnc4n2-c2ccc(Cl)cc2CN(CC(F)(F)C2CC2)C4)C3)ccc1F] |

| Compound No. | Structure |
|---|---|
| 318 | 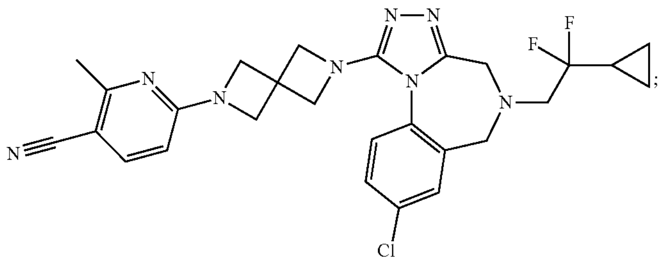 [SMILES: Cc1nc(N2CC3(C2)CN(c2nnc4n2-c2ccc(Cl)cc2CN(CC(F)(F)C2CC2)C4)C3)ccc1C#N] |
| 319 | 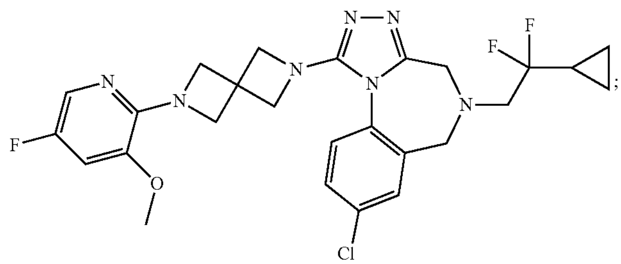 [SMILES: COc1cc(F)cnc1N1CC2(C1)CN(c1nnc3n1-c1ccc(Cl)cc1CN(CC(F)(F)C1CC1)C3)C2] |
| 320 | 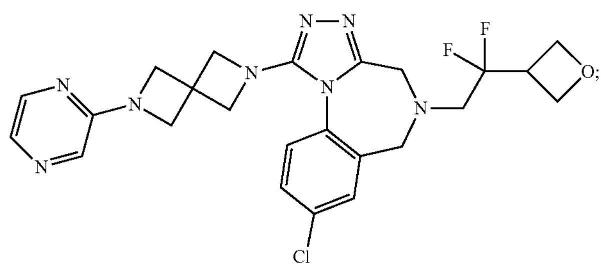 [SMILES: FC(F)(CN1Cc2cc(Cl)ccc2-n2c(nnc2N2CC3(CN(c4cnccn4)C3)C2)C1)C1COC1] |
| 321 | 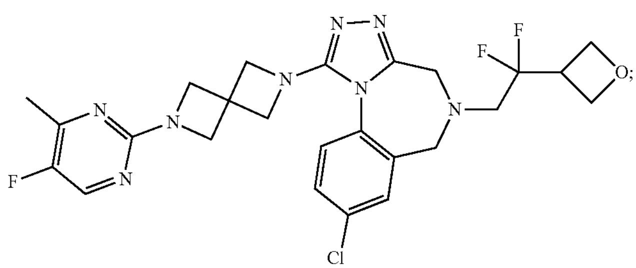 |
| 322 | 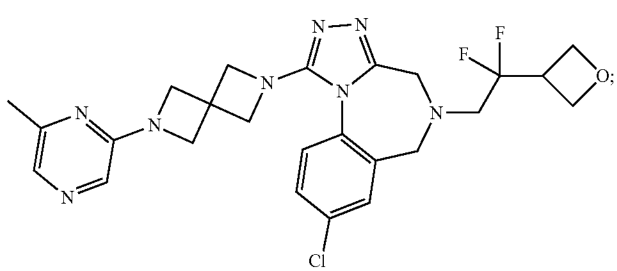 |
| 323 | 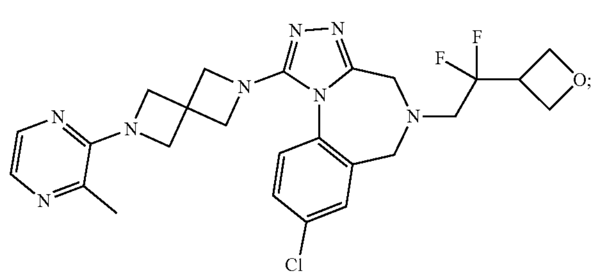 |

| Compound No. | Structure |
|---|---|
| 324 | 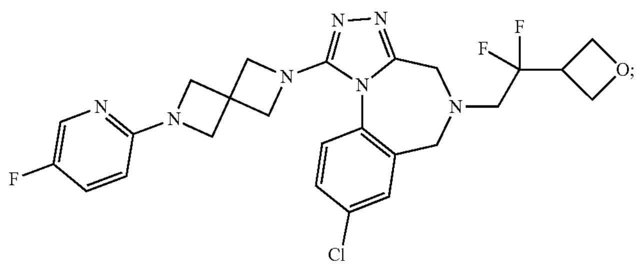 |
| 325 | 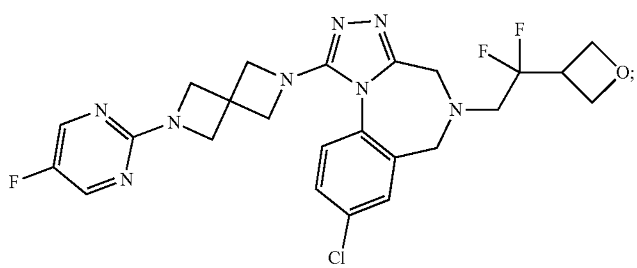 |
| 326 | 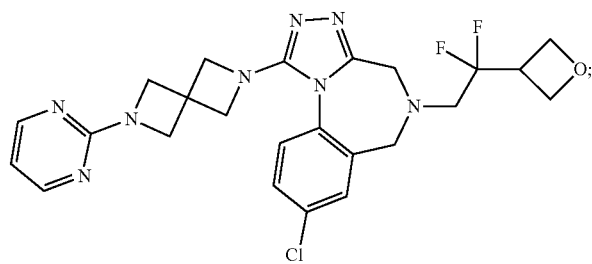 |
| 327 | 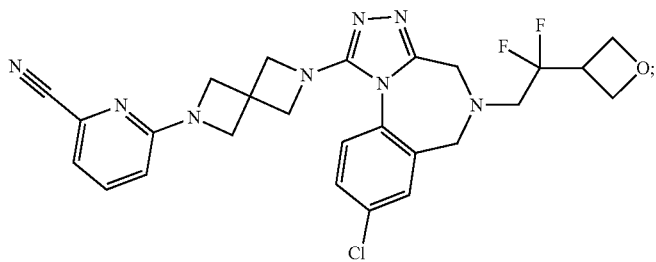 |
| 328 | 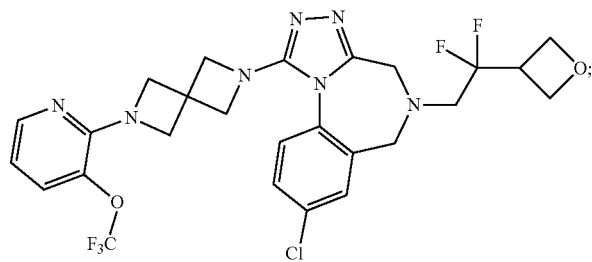 |

| Compound No. | Structure |
|---|---|
| 329 | 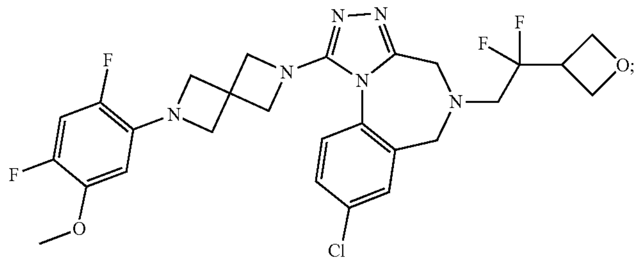 |
| 330 | 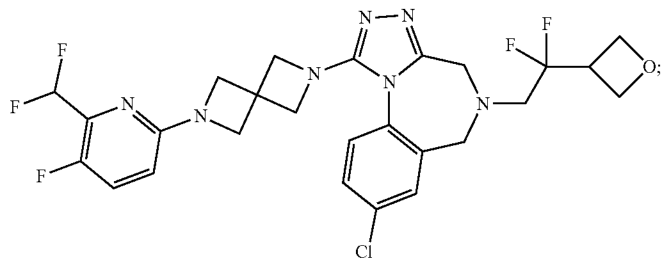 |
| 331 | 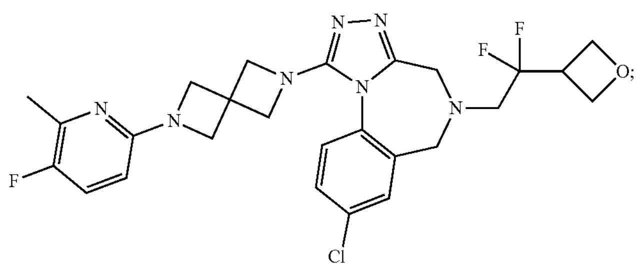 |
| 332 | 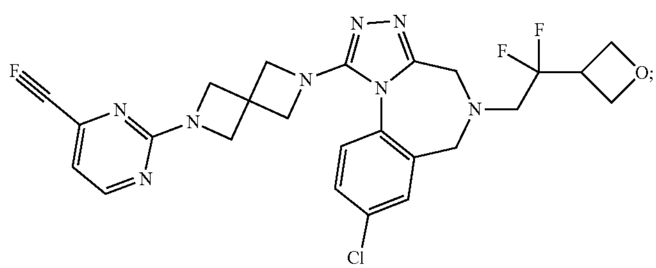 |
| 333 | 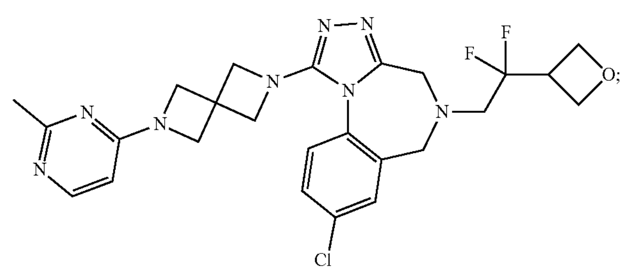 |
| 334 | 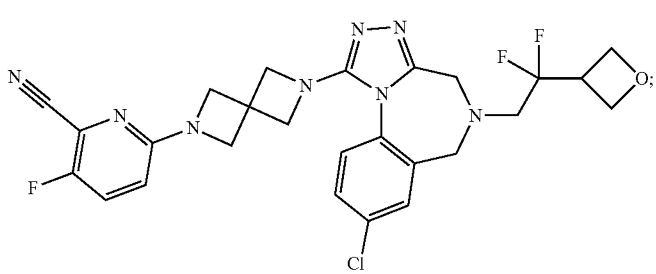 |

-continued
| Compound No. | Structure |
|---|---|
| 335 | 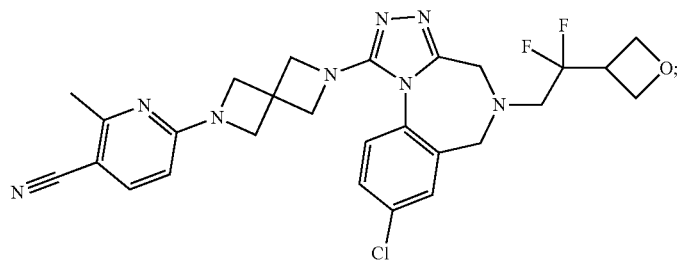 |
| 336 | 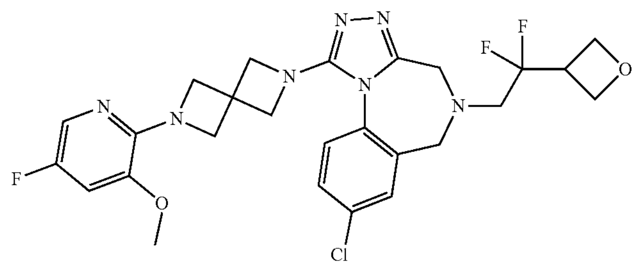 [SMILES: COc1cc(F)cnc1N1CC2(C1)CN(c1nnc3n1-c1ccc(Cl)cc1CN(CC(F)(F)C1COC1)C3)C2] |
| 337 | 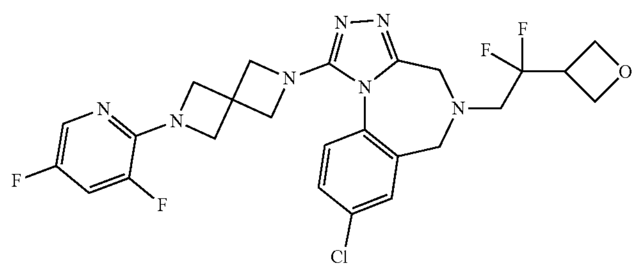 [SMILES: Fc1cnc(N2CC3(C2)CN(c2nnc4n2-c2ccc(Cl)cc2CN(CC(F)(F)C2COC2)C4)C3)c(F)c1] |
| 338 | 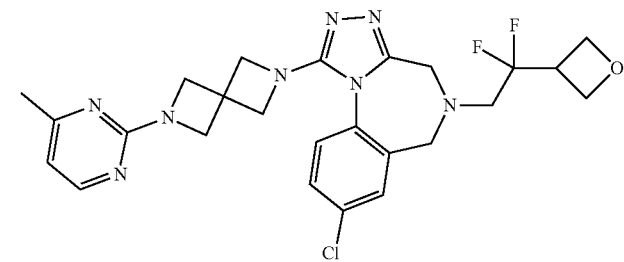 [SMILES: Cc1ccnc(N2CC3(C2)CN(c2nnc4n2-c2ccc(Cl)cc2CN(CC(F)(F)C2COC2)C4)C3)n1] |
| 339 | 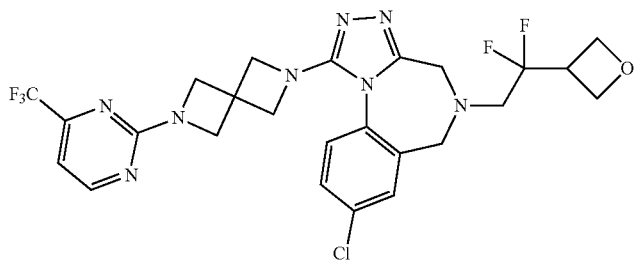 [SMILES: FC(F)(F)c1ccnc(N2CC3(C2)CN(c2nnc4n2-c2ccc(Cl)cc2CN(CC(F)(F)C2COC2)C4)C3)n1] |

-continued

| Compound No. | Structure |
|---|---|
| 340 | 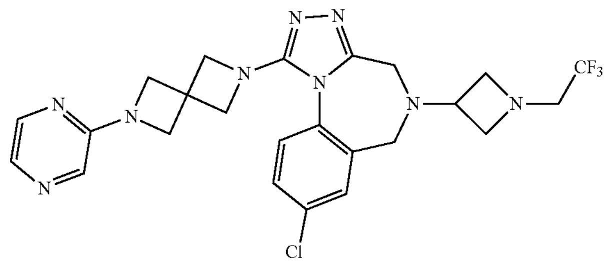 [SMILES: FC(F)(F)CN1CC(N2Cc3cc(Cl)ccc3-n3c(nnc3N3CC4(CN(c5cnccn5)C4)C3)C2)C1] |
| 341 | 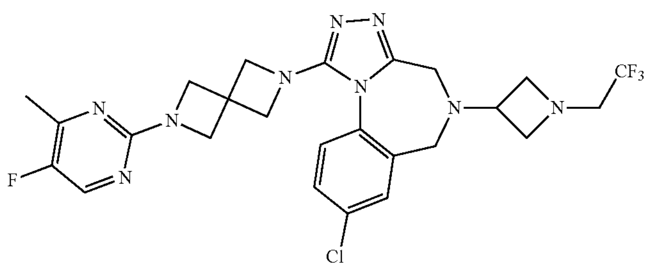 [SMILES: Cc1nc(N2CC3(C2)CN(c2nnc4n2-c2ccc(Cl)cc2CN(C2CN(CC(F)(F)F)C2)C4)C3)ncc1F] |
| 342 | 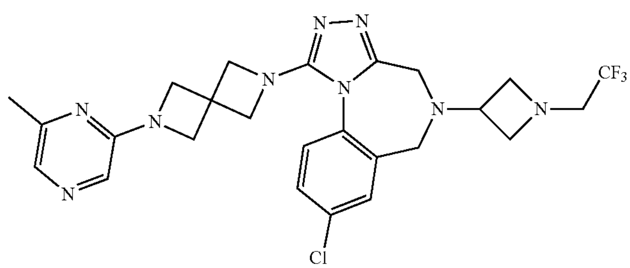 [SMILES: Cc1cncc(N2CC3(C2)CN(c2nnc4n2-c2ccc(Cl)cc2CN(C2CN(CC(F)(F)F)C2)C4)C3)n1] |
| 343 | 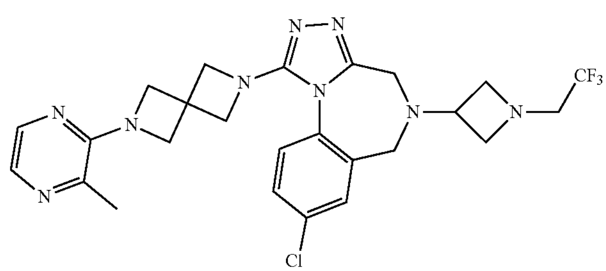 [SMILES: Cc1nccnc1N1CC2(C1)CN(c1nnc3n1-c1ccc(Cl)cc1CN(C1CN(CC(F)(F)F)C1)C3)C2] |
| 344 | 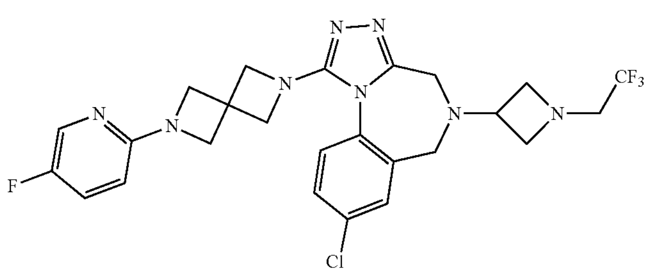 [SMILES: Fc1ccc(N2CC3(C2)CN(c2nnc4n2-c2ccc(Cl)cc2CN(C2CN(CC(F)(F)F)C2)C4)C3)nc1] |
| 345 | 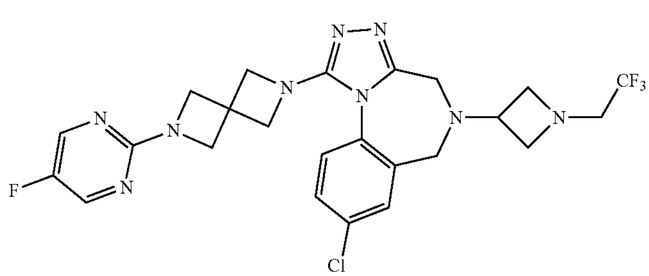 [SMILES: Fc1cnc(N2CC3(C2)CN(c2nnc4n2-c2ccc(Cl)cc2CN(C2CN(CC(F)(F)F)C2)C4)C3)nc1] |

| Compound No. | Structure |
|---|---|
| 346 | 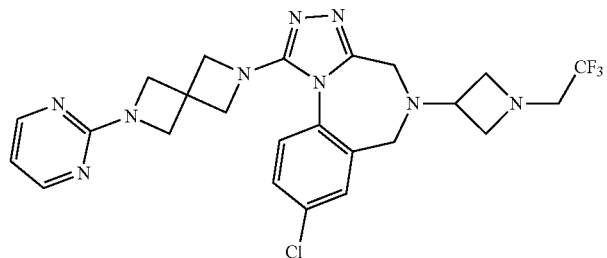 [SMILES: FC(F)(F)CN1CC(N2Cc3cc(Cl)ccc3-n3c(nnc3N3CC4(CN(c5ncccn5)C4)C3)C2)C1] |
| 347 | 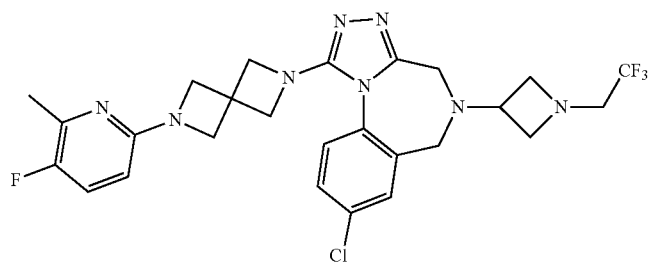 [SMILES: Cc1nc(N2CC3(C2)CN(c2nnc4n2-c2ccc(Cl)cc2CN(C2CN(CC(F)(F)F)C2)C4)C3)ccc1F] |
| 348 | 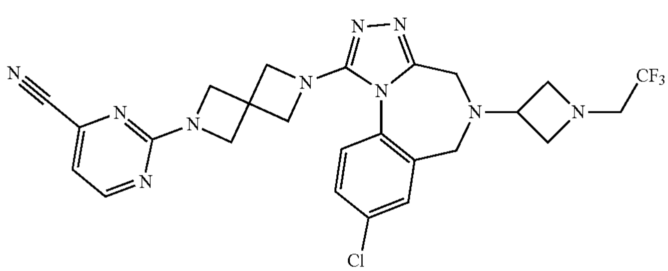 [SMILES: N#Cc1ccnc(N2CC3(C2)CN(c2nnc4n2-c2ccc(Cl)cc2CN(C2CN(CC(F)(F)F)C2)C4)C3)n1] |
| 349 | 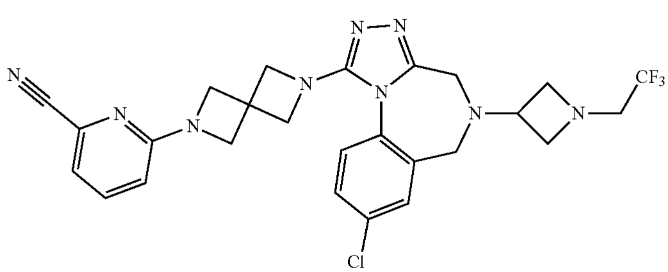 [SMILES: N#Cc1cccc(N2CC3(C2)CN(c2nnc4n2-c2ccc(Cl)cc2CN(C2CN(CC(F)(F)F)C2)C4)C3)n1] |
| 350 | 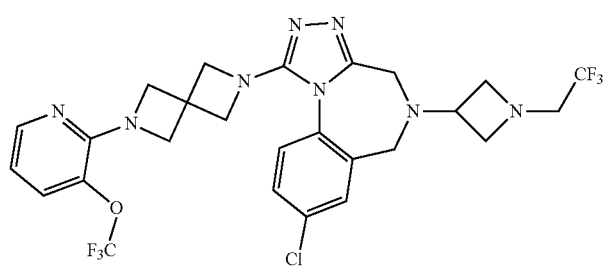 [SMILES: FC(F)(F)CN1CC(N2Cc3cc(Cl)ccc3-n3c(nnc3N3CC4(CN(c5ncccc5OC(F)(F)F)C4)C3)C2)C1] |

| Compound No. | Structure |
|---|---|
| 351 | (structure image) |
| 352 | (structure image) |
| 353 | (structure image) |
| 354 | (structure image) |
| 355 | (structure image) |
| 356 | (structure image) |

-continued
| Compound No. | Structure |
|---|---|
| 357 | 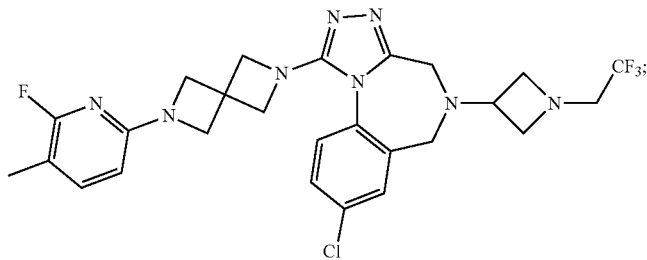 [SMILES: Cc1ccc(N2CC3(C2)CN(c2nnc4n2-c2ccc(Cl)cc2CN(C2CN(CC(F)(F)F)C2)C4)C3)nc1F] |
| 358 | 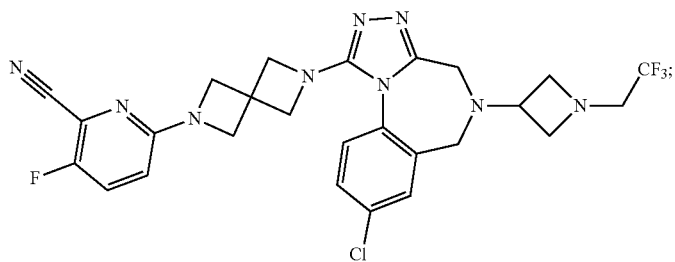 [SMILES: N#Cc1nc(N2CC3(C2)CN(c2nnc4n2-c2ccc(Cl)cc2CN(C2CN(CC(F)(F)F)C2)C4)C3)ccc1F] |
| 359 | 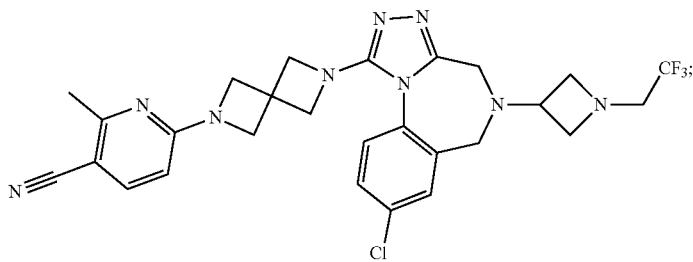 [SMILES: Cc1nc(N2CC3(C2)CN(c2nnc4n2-c2ccc(Cl)cc2CN(C2CN(CC(F)(F)F)C2)C4)C3)ccc1C#N] |
| 360 | 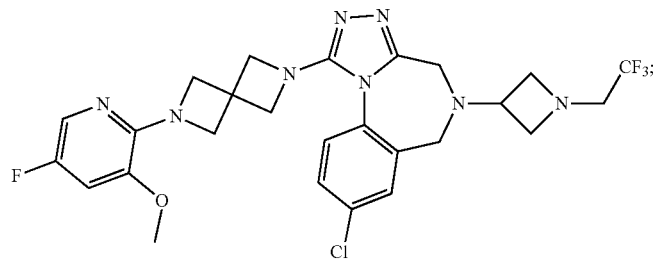 [SMILES: COc1cc(F)cnc1N1CC2(C1)CN(c1nnc3n1-c1ccc(Cl)cc1CN(C1CN(CC(F)(F)F)C1)C3)C2] |
| 361 | 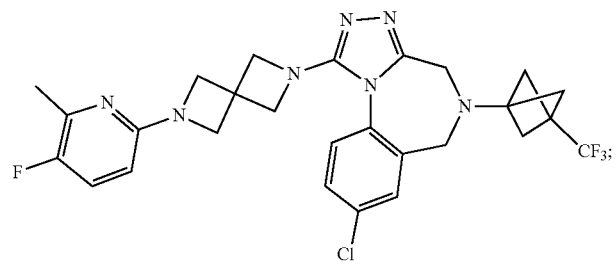 [SMILES: Cc1nc(N2CC3(C2)CN(c2nnc4n2-c2ccc(Cl)cc2CN(C25CC(C(F)(F)F)(C2)C5)C4)C3)ccc1F] |

-continued

| Compound No. | Structure |
|---|---|
| 362 | 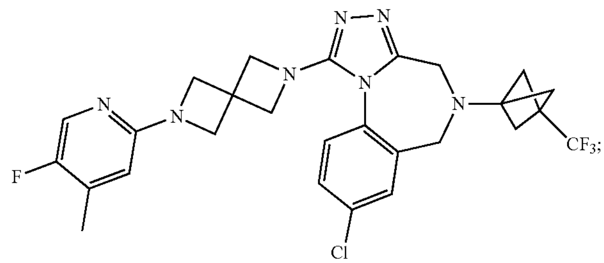 [SMILES: Cc1cc(N2CC3(C2)CN(c2nnc4n2-c2ccc(Cl)cc2CN(C25CC(C(F)(F)F)(C2)C5)C4)C3)ncc1F] |
| 363 | 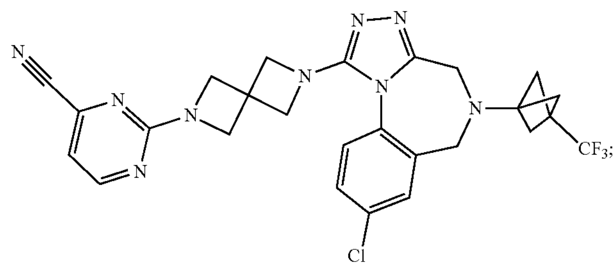 [SMILES: N#Cc1ccnc(N2CC3(C2)CN(c2nnc4n2-c2ccc(Cl)cc2CN(C25CC(C(F)(F)F)(C2)C5)C4)C3)n1] |
| 364 | 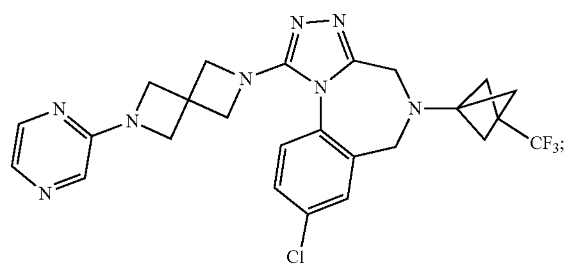 [SMILES: FC(F)(F)C12CC(N3Cc4cc(Cl)ccc4-n4c(nnc4N4CC5(CN(c6cnccn6)C5)C4)C3)(C1)C2] |
| 365 | 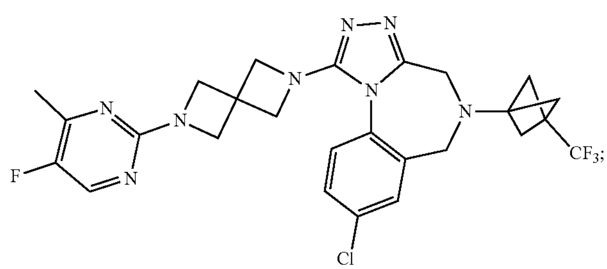 [SMILES: Cc1nc(N2CC3(C2)CN(c2nnc4n2-c2ccc(Cl)cc2CN(C25CC(C(F)(F)F)(C2)C5)C4)C3)ncc1F] |
| 366 | 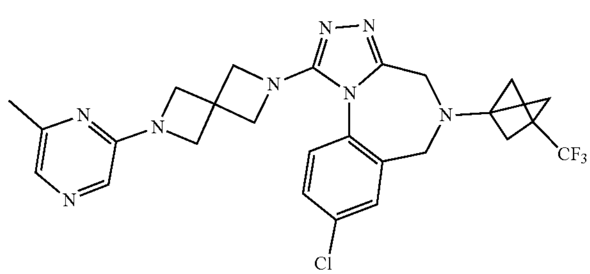 [SMILES: Cc1cncc(N2CC3(C2)CN(c2nnc4n2-c2ccc(Cl)cc2CN(C25CC(C(F)(F)F)(C2)C5)C4)C3)n1] |
| 367 | 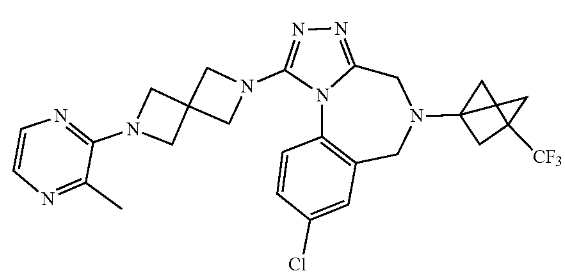 [SMILES: Cc1nccnc1N1CC2(C1)CN(c1nnc3n1-c1ccc(Cl)cc1CN(C14CC(C(F)(F)F)(C1)C4)C3)C2] |

| Compound No. | Structure |
|---|---|
| 368 | 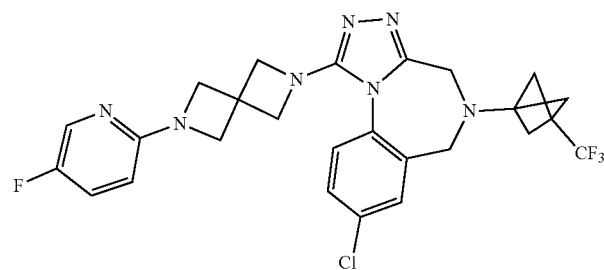 [SMILES: Fc1ccc(N2CC3(C2)CN(c2nnc4n2-c2ccc(Cl)cc2CN(C25CC(C(F)(F)F)(C2)C5)C4)C3)nc1] |
| 369 | 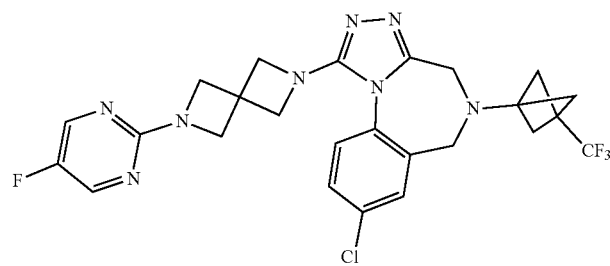 [SMILES: Fc1cnc(N2CC3(C2)CN(c2nnc4n2-c2ccc(Cl)cc2CN(C25CC(C(F)(F)F)(C2)C5)C4)C3)nc1] |
| 370 | 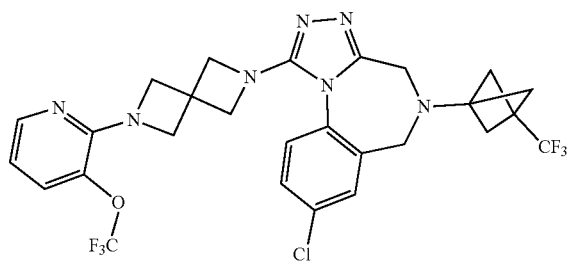 [SMILES: FC(F)(F)Oc1cccnc1N1CC2(C1)CN(c1nnc3n1-c1ccc(Cl)cc1CN(C14CC(C(F)(F)F)(C1)C4)C3)C2] |
| 371 | 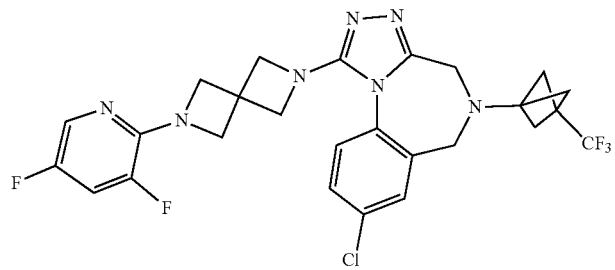 [SMILES: Fc1cnc(N2CC3(C2)CN(c2nnc4n2-c2ccc(Cl)cc2CN(C25CC(C(F)(F)F)(C2)C5)C4)C3)c(F)c1] |
| 372 | 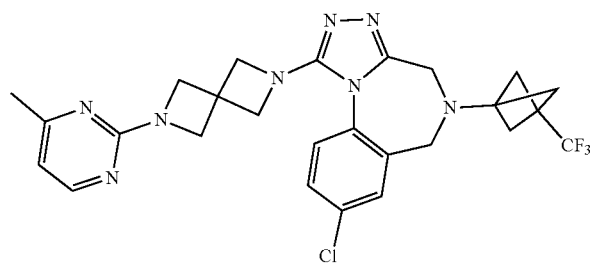 [SMILES: Cc1ccnc(N2CC3(C2)CN(c2nnc4n2-c2ccc(Cl)cc2CN(C25CC(C(F)(F)F)(C2)C5)C4)C3)n1] |

| Compound No. | Structure |
|---|---|
| 373 | 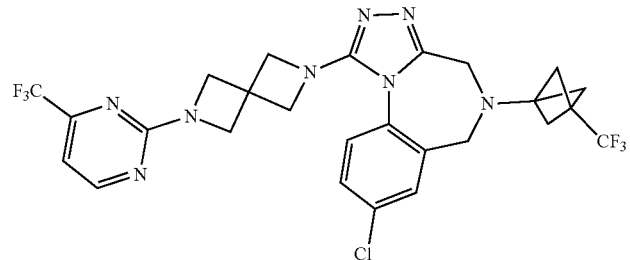 [SMILES: FC(F)(F)c1ccnc(N2CC3(C2)CN(c2nnc4n2-c2ccc(Cl)cc2CN(C25CC(C(F)(F)F)(C2)C5)C4)C3)n1] |
| 374 | 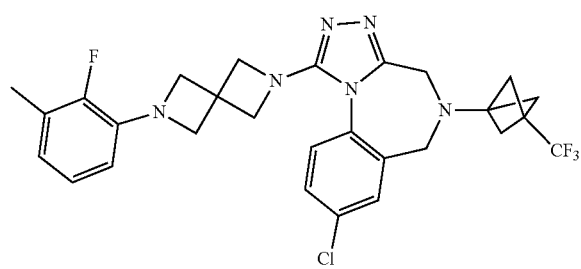 [SMILES: Cc1cccc(N2CC3(C2)CN(c2nnc4n2-c2ccc(Cl)cc2CN(C25CC(C(F)(F)F)(C2)C5)C4)C3)c1F] |
| 375 | 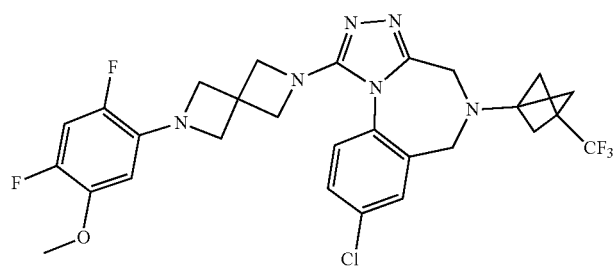 [SMILES: COc1cc(N2CC3(C2)CN(c2nnc4n2-c2ccc(Cl)cc2CN(C25CC(C(F)(F)F)(C2)C5)C4)C3)c(F)cc1F] |
| 376 | 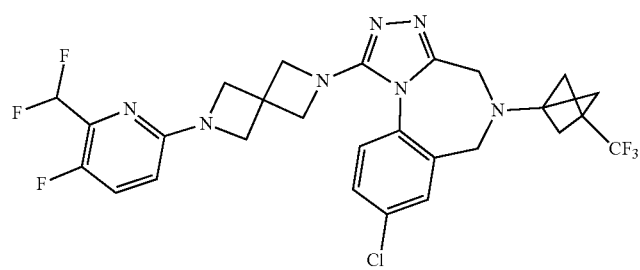 [SMILES: Fc1ccc(N2CC3(C2)CN(c2nnc4n2-c2ccc(Cl)cc2CN(C25CC(C(F)(F)F)(C2)C5)C4)C3)nc1C(F)F] |
| 377 | 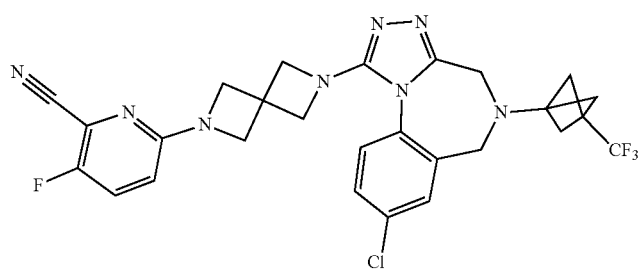 [SMILES: N#Cc1nc(N2CC3(C2)CN(c2nnc4n2-c2ccc(Cl)cc2CN(C25CC(C(F)(F)F)(C2)C5)C4)C3)ccc1F] |

-continued

| Compound No. | Structure |
|---|---|
| 378 | 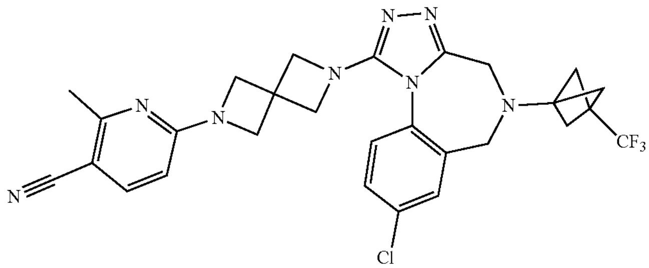 [SMILES: Cc1nc(N2CC3(C2)CN(c2nnc4n2-c2ccc(Cl)cc2CN(C25CC(C(F)(F)F)(C2)C5)C4)C3)ccc1C#N] |
| 379 | 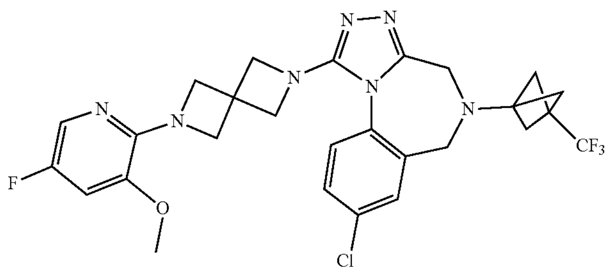 [SMILES: COc1cc(F)cnc1N1CC2(C1)CN(c1nnc3n1-c1ccc(Cl)cc1CN(C14CC(C(F)(F)F)(C1)C4)C3)C2] |
| 380 | 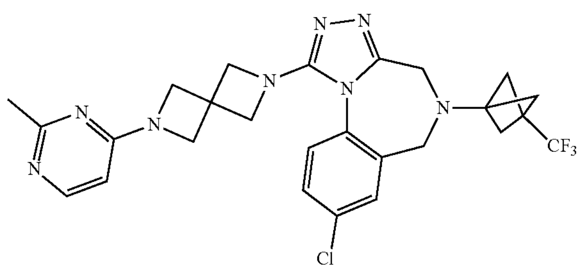 [SMILES: Cc1nccc(N2CC3(C2)CN(c2nnc4n2-c2ccc(Cl)cc2CN(C25CC(C(F)(F)F)(C2)C5)C4)C3)n1] |
| 381 | 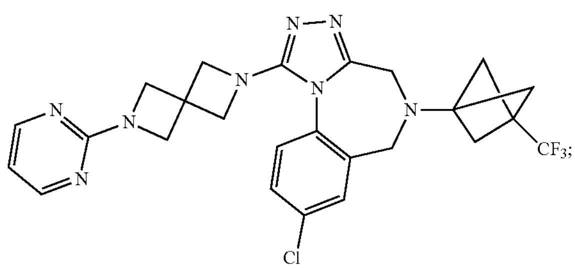 [SMILES: FC(F)(F)C12CCC(N3Cc4cc(Cl)ccc4-n4c(nnc4N4CC5(CN(c6ncccn6)C5)C4)C3)(C1)C2] |
| 382 | 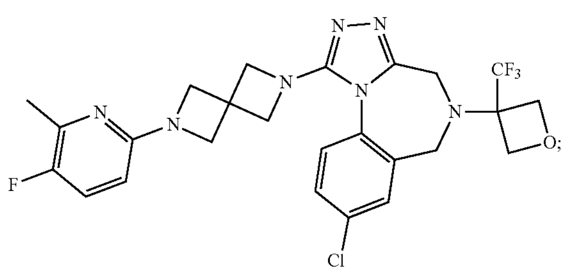 [SMILES: Cc1nc(N2CC3(C2)CN(c2nnc4n2-c2ccc(Cl)cc2CN(C2(C(F)(F)F)COC2)C4)C3)ccc1F] |
| 383 | 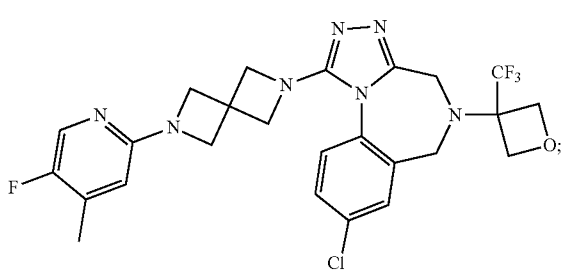 [SMILES: Cc1cc(N2CC3(C2)CN(c2nnc4n2-c2ccc(Cl)cc2CN(C2(C(F)(F)F)COC2)C4)C3)ncc1F] |

| Compound No. | Structure |
|---|---|
| 384 | 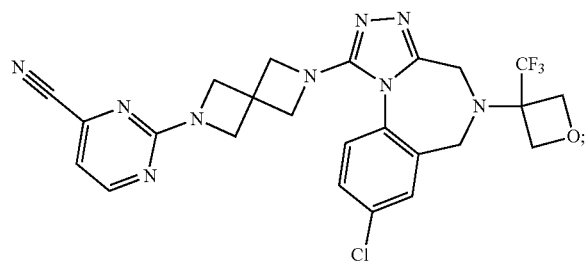 [SMILES: N#Cc1ccnc(N2CC3(C2)CN(c2nnc4n2-c2ccc(Cl)cc2CN(C2(C(F)(F)F)COC2)C4)C3)n1] |
| 385 | 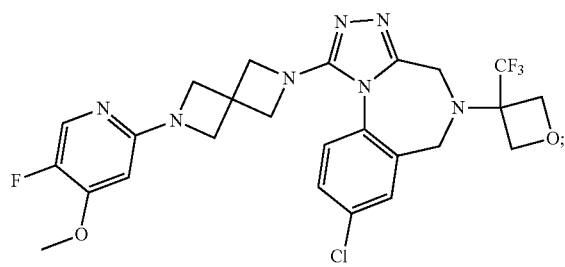 [SMILES: COc1cc(N2CC3(C2)CN(c2nnc4n2-c2ccc(Cl)cc2CN(C2(C(F)(F)F)COC2)C4)C3)ncc1F] |
| 386 | 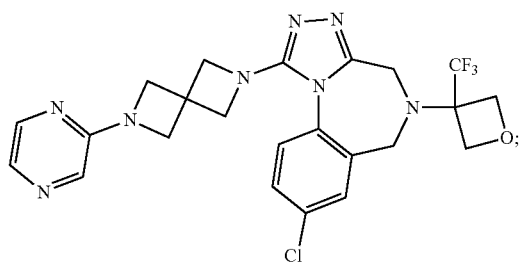 [SMILES: FC(F)(F)C1(N2Cc3cc(Cl)ccc3-n3c(nnc3N3CC4(CN(c5cnccn5)C4)C3)C2)COC1] |
| 387 | 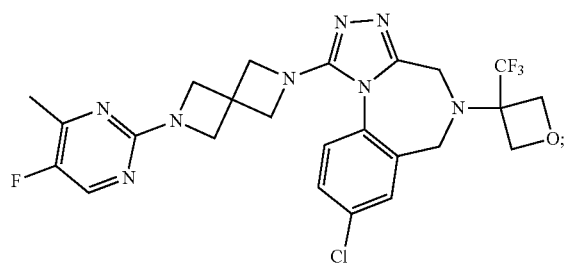 |
| 388 | 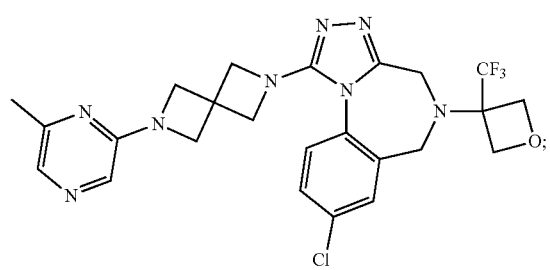 [SMILES: Cc1cncc(N2CC3(C2)CN(c2nnc4n2-c2ccc(Cl)cc2CN(C2(C(F)(F)F)COC2)C4)C3)n1] |

-continued

| Compound No. | Structure |
| --- | --- |
| 389 | 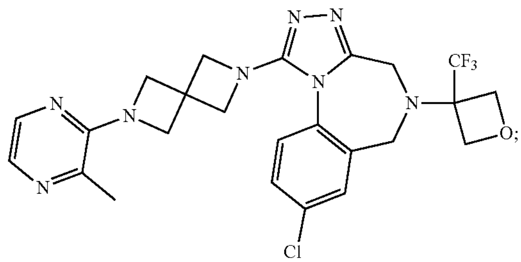 [SMILES: Cc1nccnc1N1CC2(C1)CN(c1nnc3n1-c1ccc(Cl)cc1CN(C1(C(F)(F)F)COC1)C3)C2] |
| 390 | 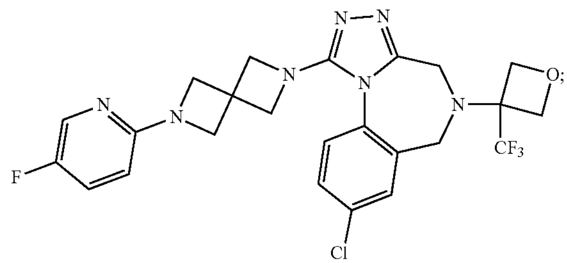 [SMILES: Fc1ccc(N2CC3(C2)CN(c2nnc4n2-c2ccc(Cl)cc2CN(C2(C(F)(F)F)COC2)C4)C3)nc1] |
| 391 | 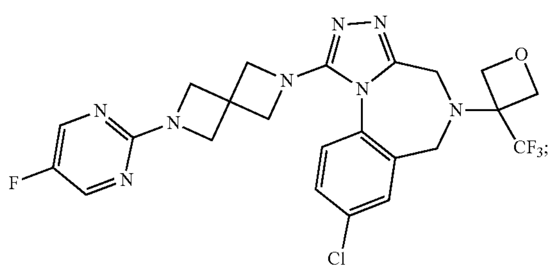 [SMILES: Fc1cnc(N2CC3(C2)CN(c2nnc4n2-c2ccc(Cl)cc2CN(C2(C(F)(F)F)COC2)C4)C3)nc1] |
| 392 | 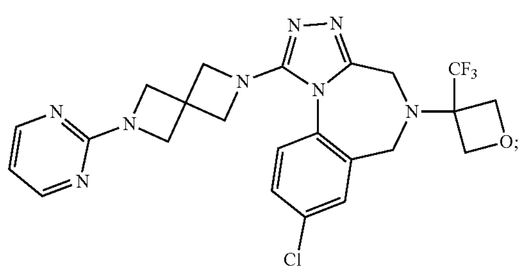 [SMILES: FC(F)(F)C1(N2Cc3cc(Cl)ccc3-n3c(nnc3N3CC4(CN(c5ncccn5)C4)C3)C2)COC1] |
| 393 | 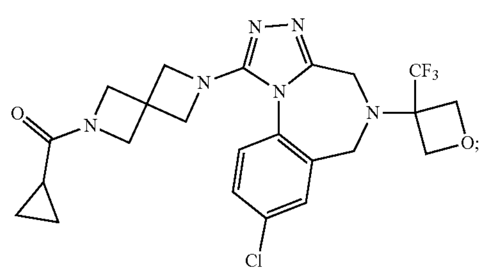 [SMILES: O=C(C1CC1)N1CC2(C1)CN(c1nnc3n1-c1ccc(Cl)cc1CN(C1(C(F)(F)F)COC1)C3)C2] |
| 394 | 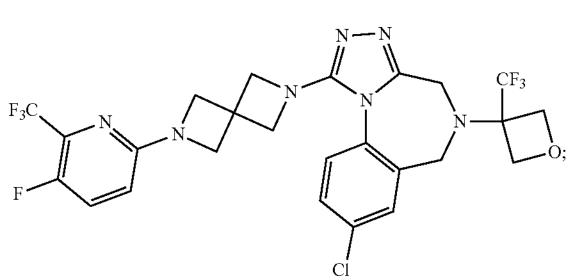 [SMILES: Fc1ccc(N2CC3(C2)CN(c2nnc4n2-c2ccc(Cl)cc2CN(C2(C(F)(F)F)COC2)C4)C3)nc1C(F)(F)F] |

-continued
| Compound No. | Structure |
|---|---|
| 395 | 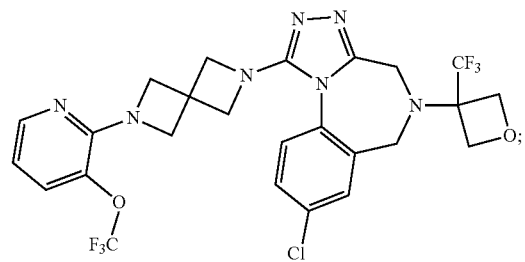 [SMILES: FC(F)(F)Oc1cccnc1N1CC2(C1)CN(c1nnc3n1-c1ccc(Cl)cc1CN(C1(C(F)(F)F)COC1)C3)C2] |
| 396 | 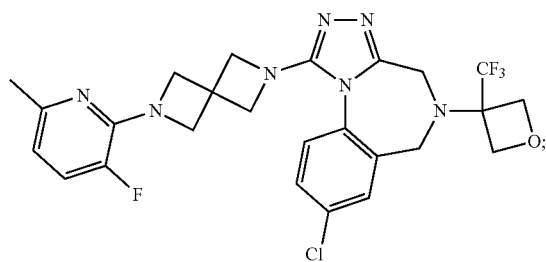 [SMILES: Cc1ccc(F)c(N2CC3(C2)CN(c2nnc4n2-c2ccc(Cl)cc2CN(C2(C(F)(F)F)COC2)C4)C3)n1] |
| 397 | 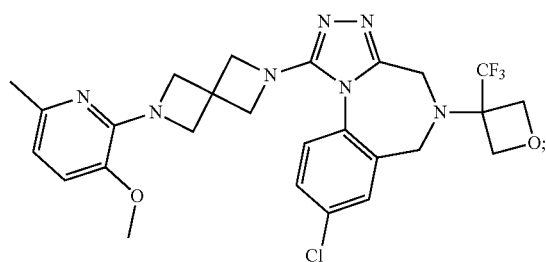 [SMILES: COc1ccc(C)nc1N1CC2(C1)CN(c1nnc3n1-c1ccc(Cl)cc1CN(C1(C(F)(F)F)COC1)C3)C2] |
| 398 | 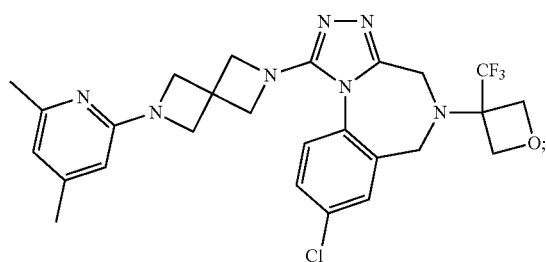 [SMILES: Cc1cc(C)nc(N2CC3(C2)CN(c2nnc4n2-c2ccc(Cl)cc2CN(C2(C(F)(F)F)COC2)C4)C3)c1] |
| 399 | 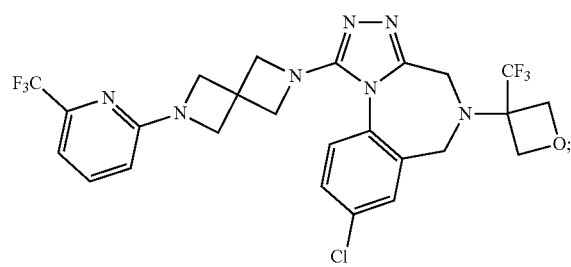 [SMILES: FC(F)(F)c1cccc(N2CC3(C2)CN(c2nnc4n2-c2ccc(Cl)cc2CN(C2(C(F)(F)F)COC2)C4)C3)n1] |

| Compound No. | Structure |
|---|---|
| 400 | (structure) |
| 401 | (structure) |
| 402 | (structure) |
| 403 | (structure) |
| 404 | (structure) |
| 405 | (structure) |

| Compound No. | Structure |
|---|---|
| 406 | 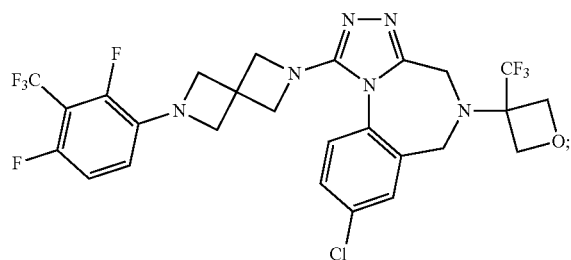 [SMILES: Fc1ccc(N2CC3(C2)CN(c2nnc4n2-c2ccc(Cl)cc2CN(C2(C(F)(F)F)COC2)C4)C3)c(F)c1C(F)(F)F] |
| 407 | 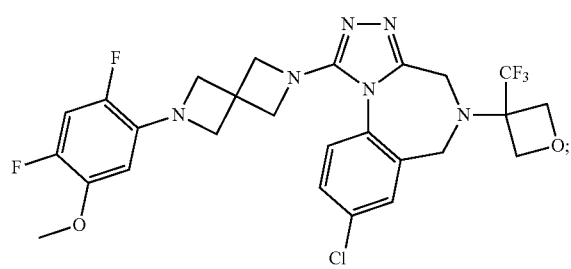 [SMILES: COc1cc(N2CC3(C2)CN(c2nnc4n2-c2ccc(Cl)cc2CN(C2(C(F)(F)F)COC2)C4)C3)c(F)cc1F] |
| 408 | 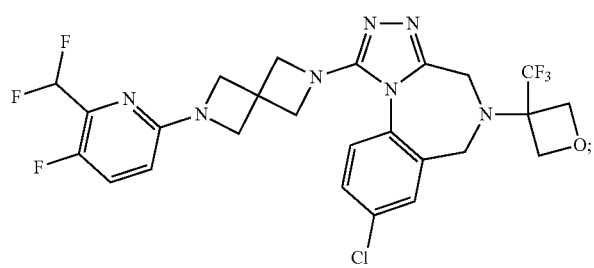 [SMILES: Fc1ccc(N2CC3(C2)CN(c2nnc4n2-c2ccc(Cl)cc2CN(C2(C(F)(F)F)COC2)C4)C3)nc1C(F)F] |
| 409 | 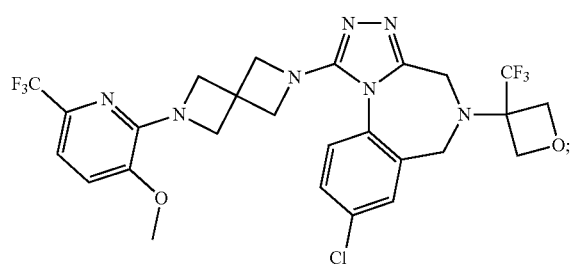 [SMILES: COc1ccc(C(F)(F)F)nc1N1CC2(C1)CN(c1nnc3n1-c1ccc(Cl)cc1CN(C1(C(F)(F)F)COC1)C3)C2] |
| 410 | 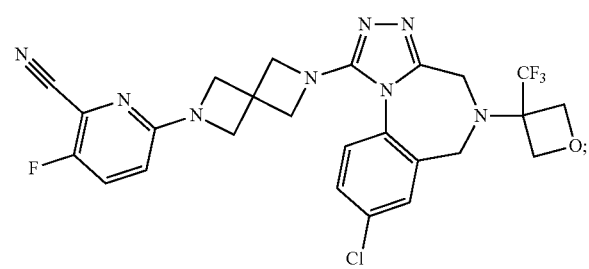 [SMILES: N#Cc1nc(N2CC3(C2)CN(c2nnc4n2-c2ccc(Cl)cc2CN(C2(C(F)(F)F)COC2)C4)C3)ccc1F] |

| Compound No. | Structure |
|---|---|
| 411 | 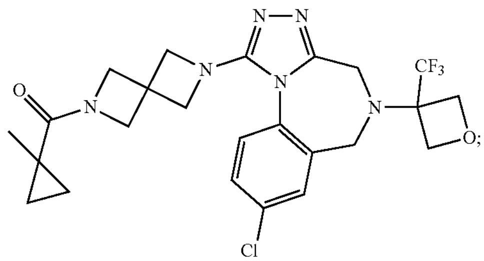 [SMILES: CC1(C(=O)N2CC3(C2)CN(c2nnc4n2-c2ccc(Cl)cc2CN(C2(C(F)(F)F)COC2)C4)C3)CC1] |
| 412 | 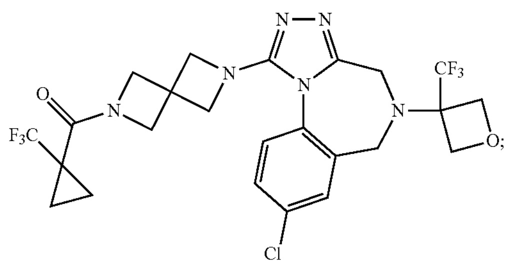 [SMILES: O=C(N1CC2(C1)CN(c1nnc3n1-c1ccc(Cl)cc1CN(C1(C(F)(F)F)COC1)C3)C2)C1(C(F)(F)F)CC1] |
| 413 | 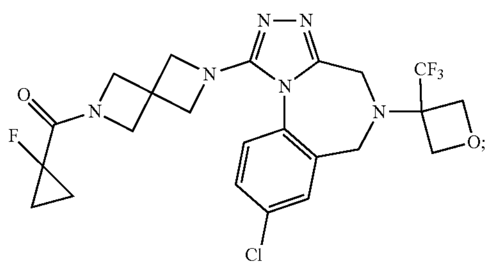 [SMILES: O=C(N1CC2(C1)CN(c1nnc3n1-c1ccc(Cl)cc1CN(C1(C(F)(F)F)COC1)C3)C2)C1(F)CC1] |
| 414 | 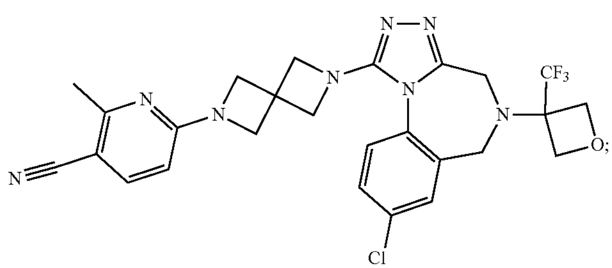 [SMILES: Cc1nc(N2CC3(C2)CN(c2nnc4n2-c2ccc(Cl)cc2CN(C2(C(F)(F)F)COC2)C4)C3)ccc1C#N] |
| 415 | 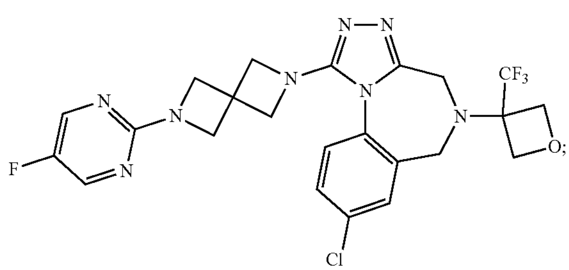 [SMILES: Fc1cnc(N2CC3(C2)CN(c2nnc4n2-c2ccc(Cl)cc2CN(C2(C(F)(F)F)COC2)C4)C3)nc1] |
| 416 | 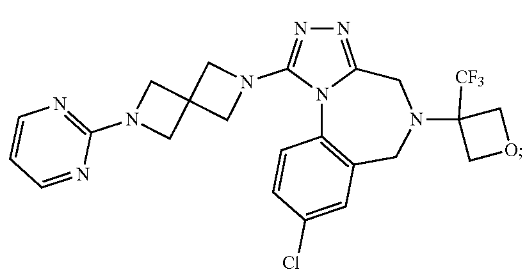 [SMILES: FC(F)(F)C1(N2Cc3cc(Cl)ccc3-n3c(nnc3N3CC4(CN(c5ncccn5)C4)C3)C2)COC1] |

| Compound No. | Structure |
|---|---|
| 417 | 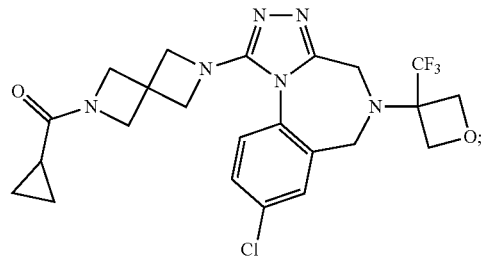 [SMILES: O=C(C1CC1)N1CC2(C1)CN(c1nnc3n1-c1ccc(Cl)cc1CN(C1(C(F)(F)F)COC1)C3)C2] |
| 418 | 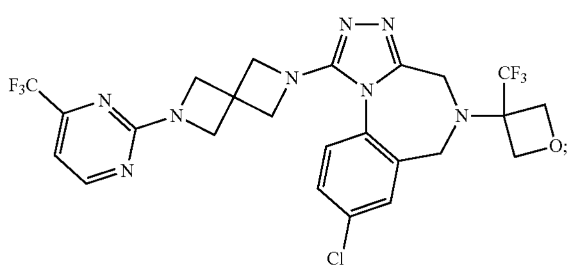 [SMILES: FC(F)(F)c1ccnc(N2CC3(C2)CN(c2nnc4n2-c2ccc(Cl)cc2CN(C2(C(F)(F)F)COC2)C4)C3)n1] |
| 419 | 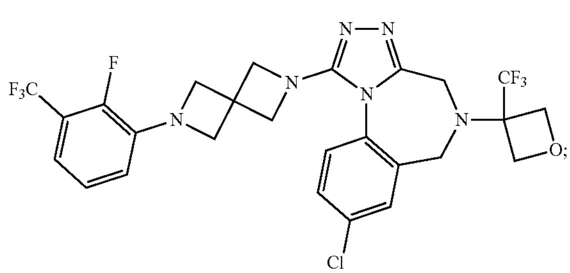 [SMILES: Fc1c(N2CC3(C2)CN(c2nnc4n2-c2ccc(Cl)cc2CN(C2(C(F)(F)F)COC2)C4)C3)cccc1C(F)(F)F] |
| 420 | 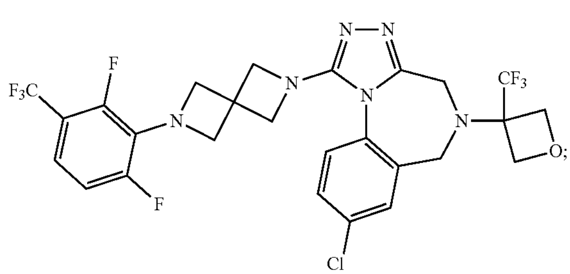 [SMILES: Fc1ccc(C(F)(F)F)c(F)c1N1CC2(C1)CN(c1nnc3n1-c1ccc(Cl)cc1CN(C1(C(F)(F)F)COC1)C3)C2] |
| 421 | 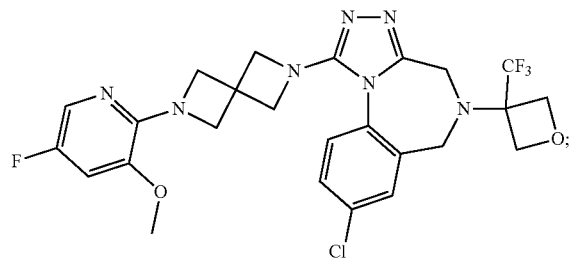 [SMILES: COc1cc(F)cnc1N1CC2(C1)CN(c1nnc3n1-c1ccc(Cl)cc1CN(C1(C(F)(F)F)COC1)C3)C2] |

| Compound No. | Structure |
|---|---|
| 422 | 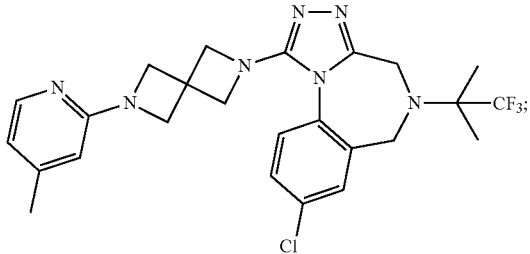 [SMILES: Cc1ccnc(N2CC3(C2)CN(c2nnc4n2-c2ccc(Cl)cc2CN(C(C)(C)C(F)(F)F)C4)C3)c1] |
| 423 | 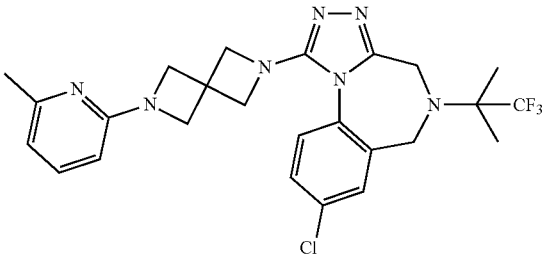 |
| 424 | 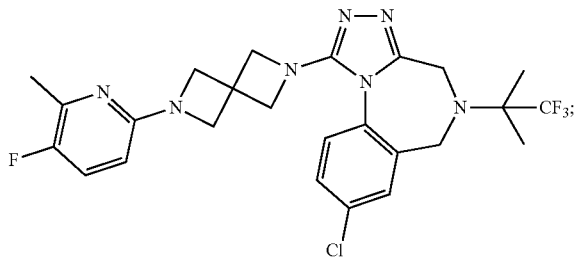 [SMILES: Cc1nc(N2CC3(C2)CN(c2nnc4n2-c2ccc(Cl)cc2CN(C(C)(C)C(F)(F)F)C4)C3)ccc1F] |
| 425 | 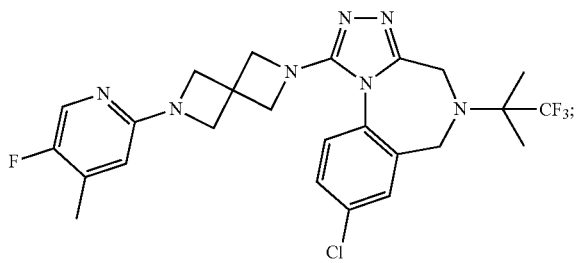 [SMILES: Cc1cc(N2CC3(C2)CN(c2nnc4n2-c2ccc(Cl)cc2CN(C(C)(C)C(F)(F)F)C4)C3)ncc1F] |
| 426 | 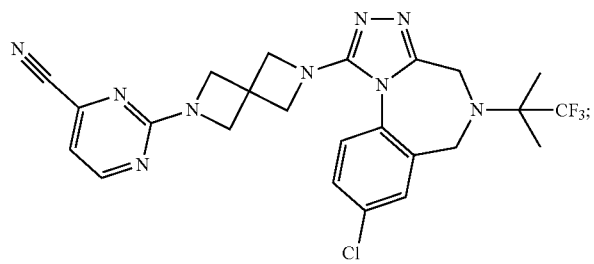 [SMILES: CC(C)(N1Cc2cc(Cl)ccc2-n2c(nnc2N2CC3(CN(c4nccc(C#N)n4)C3)C2)C1)C(F)(F)F] |
| 427 | 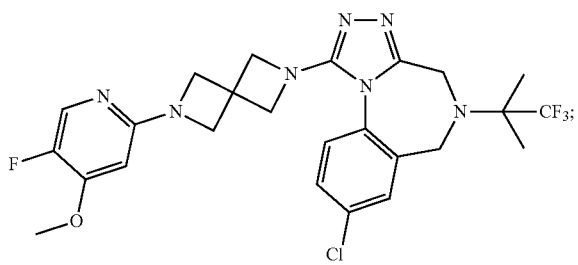 [SMILES: COc1cc(N2CC3(C2)CN(c2nnc4n2-c2ccc(Cl)cc2CN(C(C)(C)C(F)(F)F)C4)C3)ncc1F] |

-continued

| Compound No. | Structure |
|---|---|
| 428 | 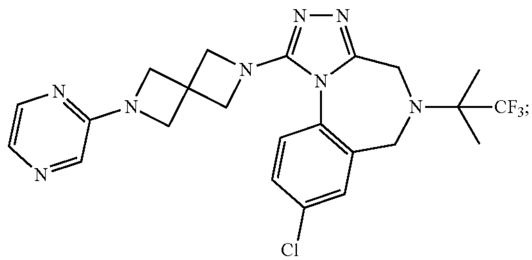 [SMILES: CC(C)(N1Cc2cc(Cl)ccc2-n2c(nnc2N2CC3(CN(c4cnccn4)C3)C2)C1)C(F)(F)F] |
| 429 | 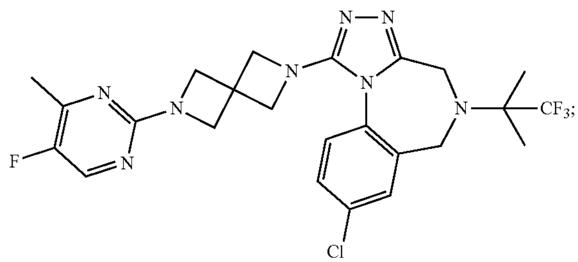 |
| 430 | 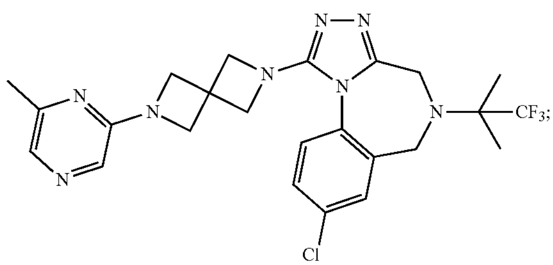 [SMILES: Cc1cncc(N2CC3(C2)CN(c2nnc4n2-c2ccc(Cl)cc2CN(C(C)(C)C(F)(F)F)C4)C3)n1] |
| 431 | 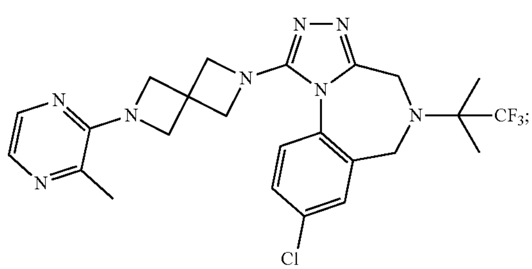 [SMILES: Cc1nccnc1N1CC2(C1)CN(c1nnc3n1-c1ccc(Cl)cc1CN(C(C)(C)C(F)(F)F)C3)C2] |
| 432 | 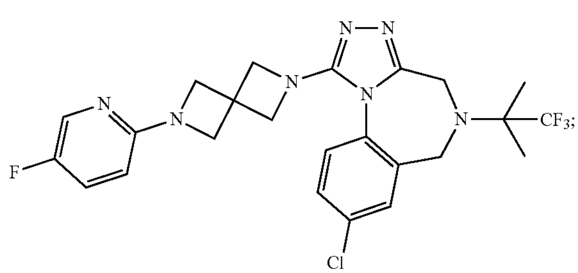 [SMILES: CC(C)(N1Cc2cc(Cl)ccc2-n2c(nnc2N2CC3(CN(c4ccc(F)cn4)C3)C2)C1)C(F)(F)F] |
| 433 | 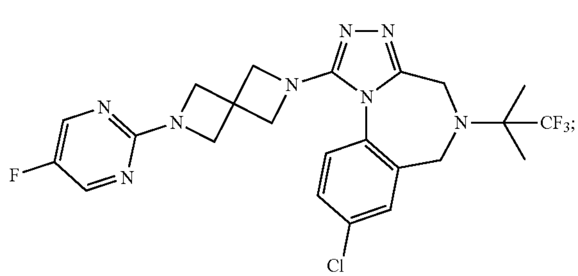 [SMILES: CC(C)(N1Cc2cc(Cl)ccc2-n2c(nnc2N2CC3(CN(c4ncc(F)cn4)C3)C2)C1)C(F)(F)F] |

-continued

| Compound No. | Structure |
|---|---|
| 434 | 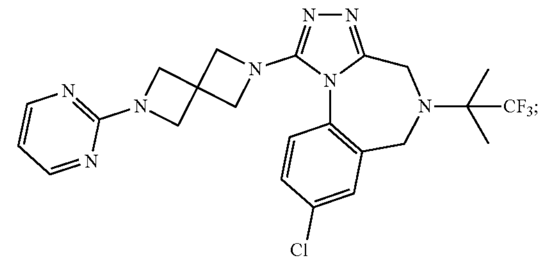 [SMILES: CC(C)(N1Cc2cc(Cl)ccc2-n2c(nnc2N2CC3(CN(c4ncccn4)C3)C2)C1)C(F)(F)F] |
| 435 | 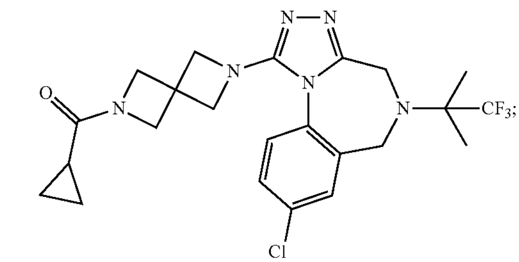 [SMILES: CC(C)(N1Cc2cc(Cl)ccc2-n2c(nnc2N2CC3(CN(C(=O)C4CC4)C3)C2)C1)C(F)(F)F] |
| 436 | 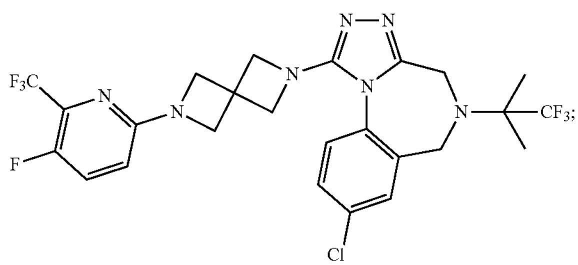 |
| 437 | 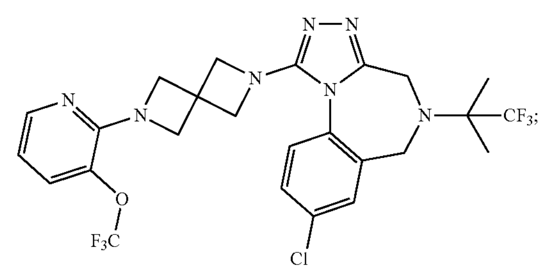 [SMILES: CC(C)(N1Cc2cc(Cl)ccc2-n2c(nnc2N2CC3(CN(c4ncccc4OC(F)(F)F)C3)C2)C1)C(F)(F)F] |
| 438 | 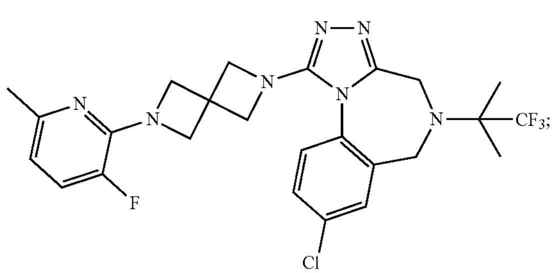 [SMILES: Cc1ccc(F)c(N2CC3(C2)CN(c2nnc4n2-c2ccc(Cl)cc2CN(C(C)(C)C(F)(F)F)C4)C3)n1] |
| 439 | 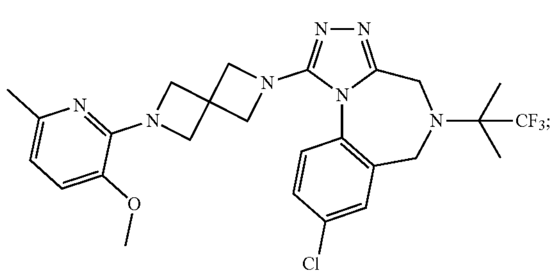 [SMILES: COc1ccc(C)nc1N1CC2(C1)CN(c1nnc3n1-c1ccc(Cl)cc1CN(C(C)(C)C(F)(F)F)C3)C2] |

-continued

| Compound No. | Structure |
|---|---|
| 440 | 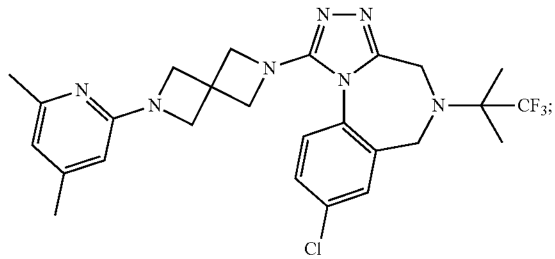 [SMILES: Cc1cc(C)nc(N2CC3(C2)CN(c2nnc4n2-c2ccc(Cl)cc2CN(C(C)(C)C(F)(F)F)C4)C3)c1] |
| 441 | 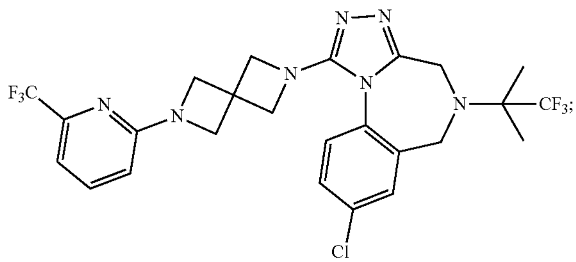 |
| 442 | 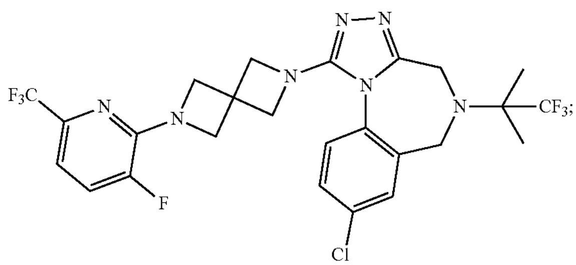 [SMILES: CC(C)(N1Cc2cc(Cl)ccc2-n2c(nnc2N2CC3(CN(c4nc(C(F)(F)F)ccc4F)C3)C2)C1)C(F)(F)F] |
| 443 | 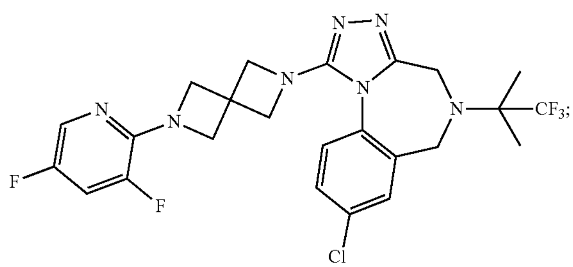 [SMILES: CC(C)(N1Cc2cc(Cl)ccc2-n2c(nnc2N2CC3(CN(c4ncc(F)cc4F)C3)C2)C1)C(F)(F)F] |
| 444 | 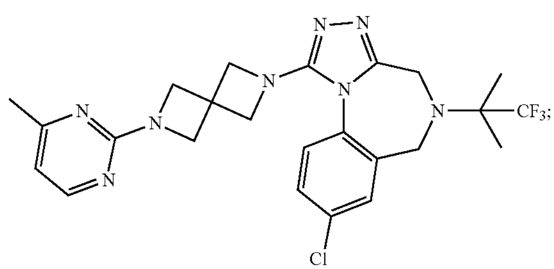 [SMILES: Cc1ccnc(N2CC3(C2)CN(c2nnc4n2-c2ccc(Cl)cc2CN(C(C)(C)C(F)(F)F)C4)C3)n1] |
| 445 | 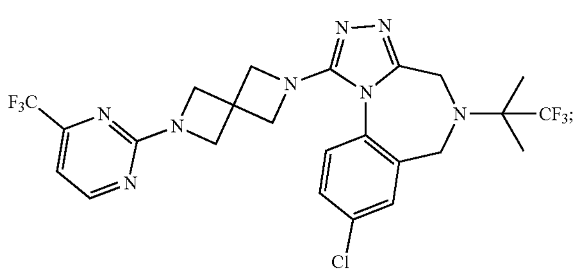 [SMILES: CC(C)(N1Cc2cc(Cl)ccc2-n2c(nnc2N2CC3(CN(c4nccc(C(F)(F)F)n4)C3)C2)C1)C(F)(F)F] |

| Compound No. | Structure |
|---|---|
| 446 | 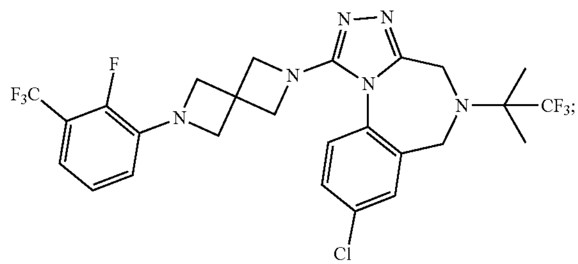 [SMILES: CC(C)(N1Cc2cc(Cl)ccc2-n2c(nnc2N2CC3(CN(c4cccc(C(F)(F)F)c4F)C3)C2)C1)C(F)(F)F] |
| 447 | 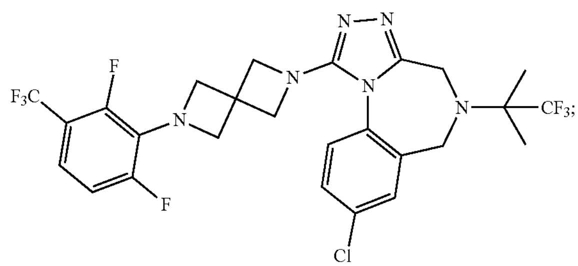 [SMILES: CC(C)(N1Cc2cc(Cl)ccc2-n2c(nnc2N2CC3(CN(c4c(F)ccc(C(F)(F)F)c4F)C3)C2)C1)C(F)(F)F] |
| 448 | 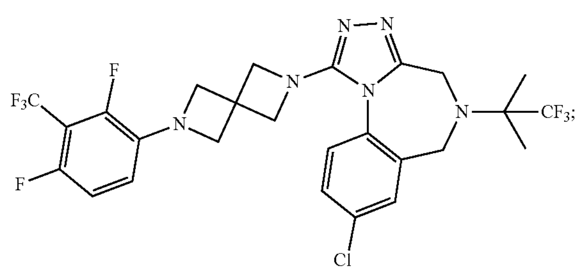 [SMILES: CC(C)(N1Cc2cc(Cl)ccc2-n2c(nnc2N2CC3(CN(c4ccc(F)c(C(F)(F)F)c4F)C3)C2)C1)C(F)(F)F] |
| 449 | 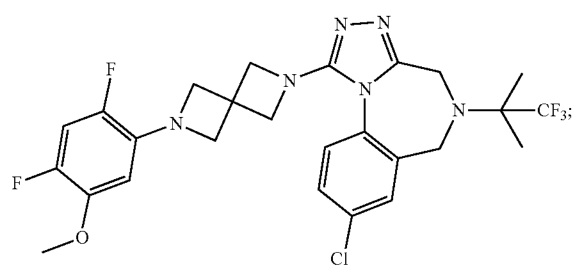 [SMILES: COc1cc(N2CC3(C2)CN(c2nnc4n2-c2ccc(Cl)cc2CN(C(C)(C)C(F)(F)F)C4)C3)c(F)cc1F] |
| 450 | 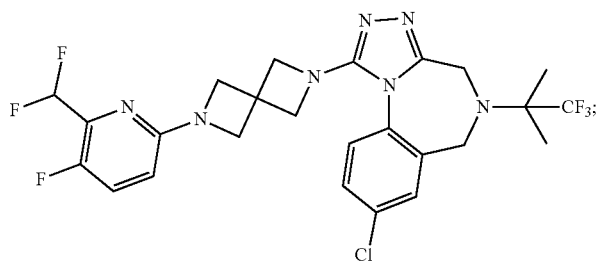 [SMILES: CC(C)(N1Cc2cc(Cl)ccc2-n2c(nnc2N2CC3(CN(c4ccc(F)c(C(F)F)n4)C3)C2)C1)C(F)(F)F] |

| Compound No. | Structure |
|---|---|
| 451 | 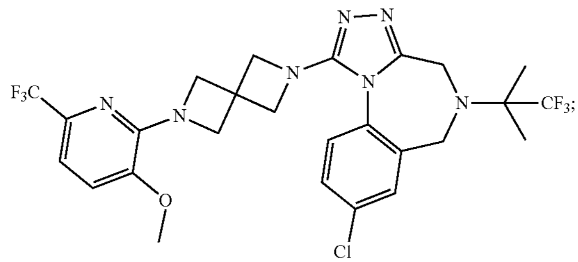 [SMILES: COc1ccc(C(F)(F)F)nc1N1CC2(C1)CN(c1nnc3n1-c1ccc(Cl)cc1CN(C(C)(C)C(F)(F)F)C3)C2] |
| 452 | 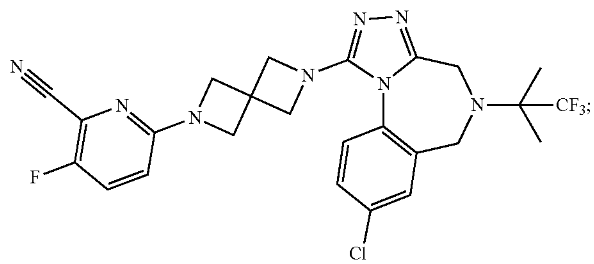 [SMILES: CC(C)(N1Cc2cc(Cl)ccc2-n2c(nnc2N2CC3(CN(c4ccc(F)c(C#N)n4)C3)C2)C1)C(F)(F)F] |
| 453 | 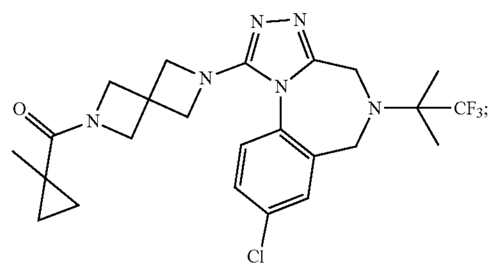 [SMILES: CC1(C(=O)N2CC3(C2)CN(c2nnc4n2-c2ccc(Cl)cc2CN(C(C)(C)C(F)(F)F)C4)C3)CC1] |
| 454 | 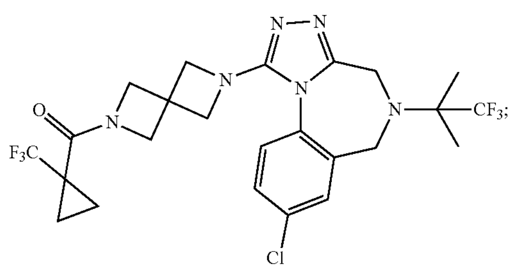 [SMILES: CC(C)(N1Cc2cc(Cl)ccc2-n2c(nnc2N2CC3(CN(C(=O)C4(C(F)(F)F)CC4)C3)C2)C1)C(F)(F)F] |
| 455 | 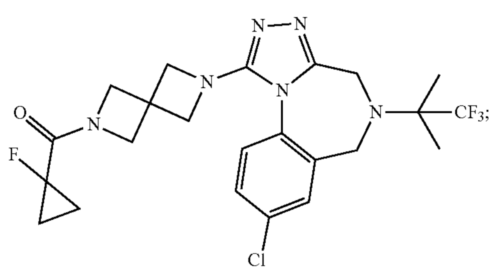 [SMILES: CC(C)(N1Cc2cc(Cl)ccc2-n2c(nnc2N2CC3(CN(C(=O)C4(F)CC4)C3)C2)C1)C(F)(F)F] |
| 456 | 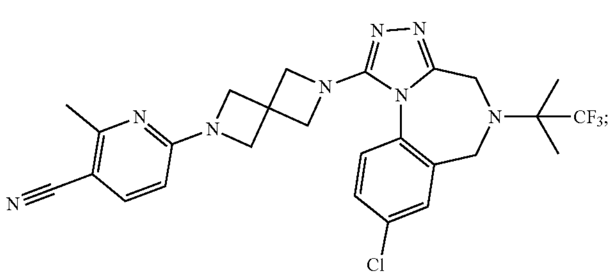 [SMILES: Cc1nc(N2CC3(C2)CN(c2nnc4n2-c2ccc(Cl)cc2CN(C(C)(C)C(F)(F)F)C4)C3)ccc1C#N] |

| Compound No. | Structure |
|---|---|
| 457 | 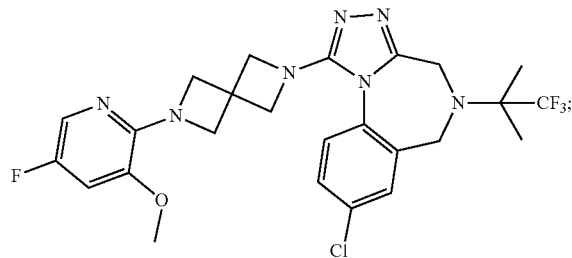 [SMILES: COc1cc(F)cnc1N1CC2(C1)CN(c1nnc3n1-c1ccc(Cl)cc1CN(C(C)(C)C(F)(F)F)C3)C2] |
| 458 | 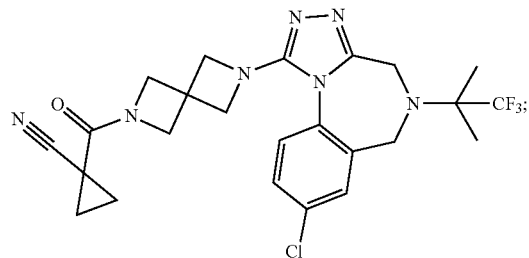 [SMILES: CC(C)(N1Cc2cc(Cl)ccc2-n2c(nnc2N2CC3(CN(C(=O)C4(C#N)CC4)C3)C2)C1)C(F)(F)F] |
| 459 | 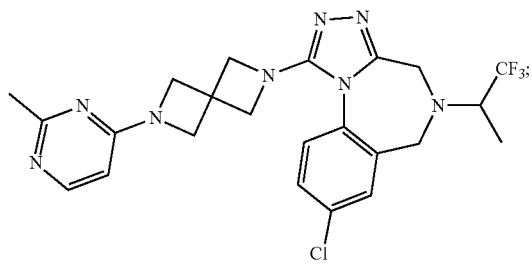 [SMILES: Cc1nccc(N2CC3(C2)CN(c2nnc4n2-c2ccc(Cl)cc2CN(C(C)C(F)(F)F)C4)C3)n1] |
| 460 | 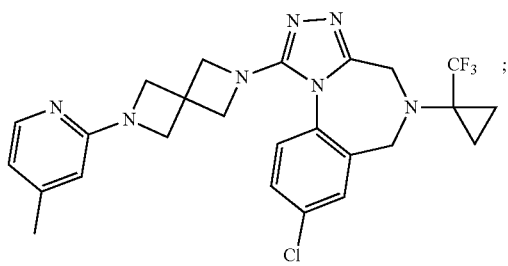 [SMILES: Cc1ccnc(N2CC3(C2)CN(c2nnc4n2-c2ccc(Cl)cc2CN(C2(C(F)(F)F)CC2)C4)C3)c1] |
| 461 | 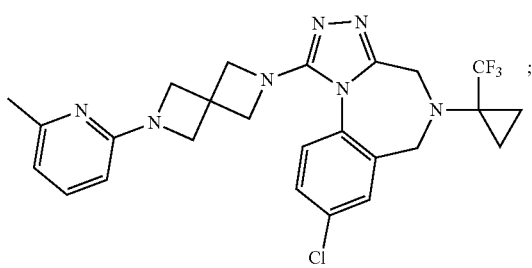 [SMILES: Cc1cccc(N2CC3(C2)CN(c2nnc4n2-c2ccc(Cl)cc2CN(C2(C(F)(F)F)CC2)C4)C3)n1] |

-continued
| Compound No. | Structure |
|---|---|
| 462 | 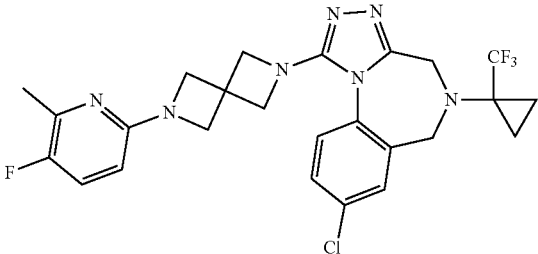 |
| 463 | 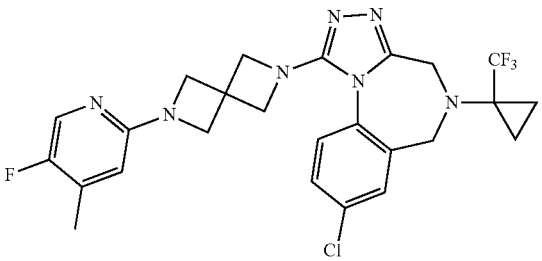 |
| 464 | 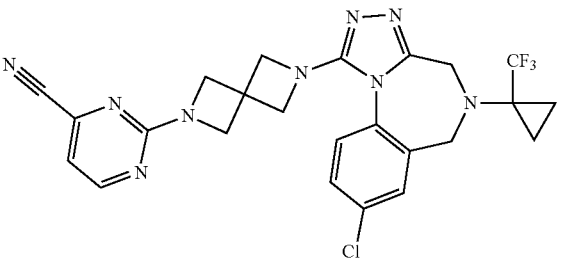 |
| 465 | 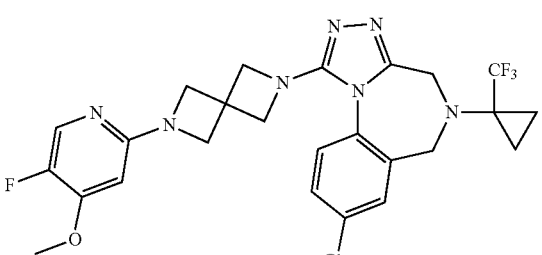 |
| 466 | 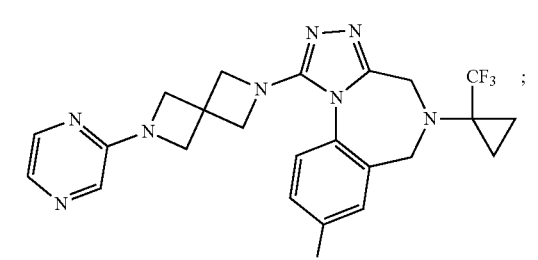 |
| 467 | 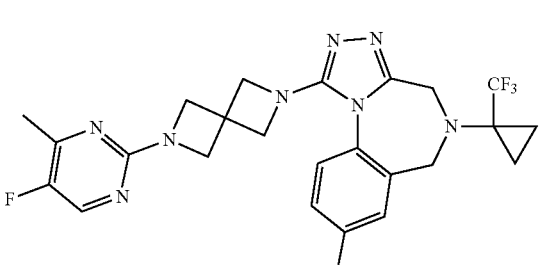 |

| Compound No. | Structure |
|---|---|
| 468 | 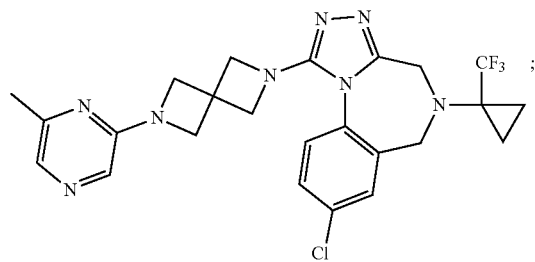 [SMILES: Cc1cncc(N2CC3(C2)CN(c2nnc4n2-c2ccc(Cl)cc2CN(C2(C(F)(F)F)CC2)C4)C3)n1] ; |
| 469 | 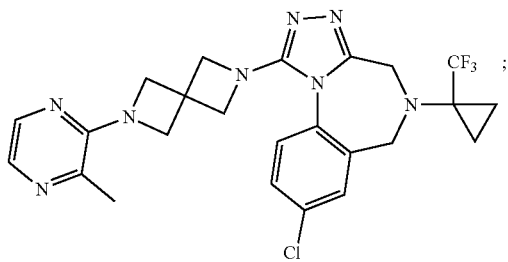 [SMILES: Cc1nccnc1N1CC2(C1)CN(c1nnc3n1-c1ccc(Cl)cc1CN(C1(C(F)(F)F)CC1)C3)C2] ; |
| 470 | 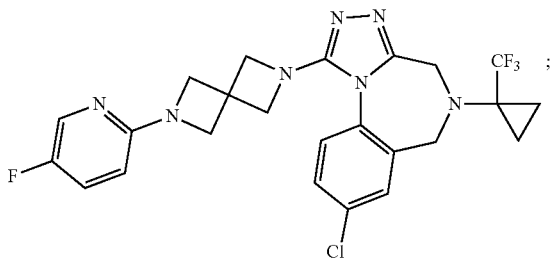 ; |
| 471 | 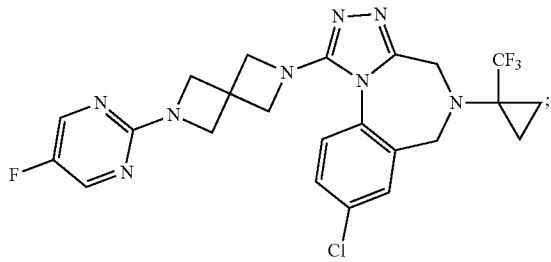 [SMILES: Fc1ccc(N2CC3(C2)CN(c2nnc4n2-c2ccc(Cl)cc2CN(C2(C(F)(F)F)CC2)C4)C3)nc1] ; |
| 472 | 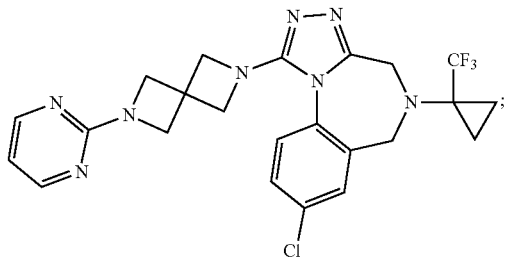 [SMILES: FC(F)(F)C1(N2Cc3cc(Cl)ccc3-n3c(nnc3N3CC4(CN(c5ncccn5)C4)C3)C2)CC1] ; |

| Compound No. | Structure |
|---|---|
| 473 | 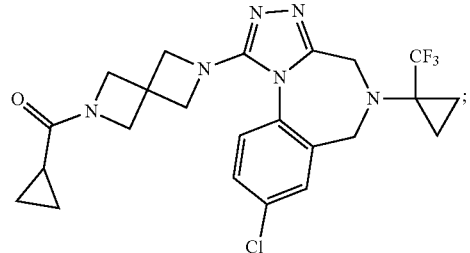 [SMILES: O=C(C1CC1)N1CC2(C1)CN(c1nnc3n1-c1ccc(Cl)cc1CN(C1(C(F)(F)F)CC1)C3)C2] |
| 474 | 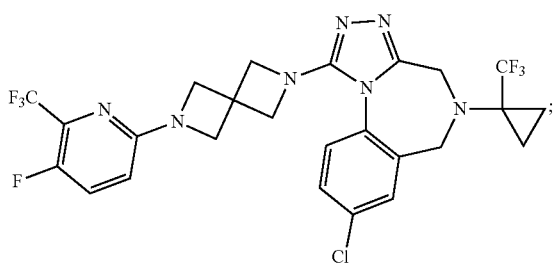 [SMILES: Fc1ccc(N2CC3(C2)CN(c2nnc4n2-c2ccc(Cl)cc2CN(C2(C(F)(F)F)CC2)C4)C3)nc1C(F)(F)F] |
| 475 | 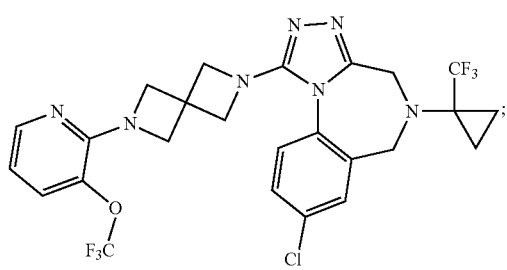 [SMILES: FC(F)(F)Oc1cccnc1N1CC2(C1)CN(c1nnc3n1-c1ccc(Cl)cc1CN(C1(C(F)(F)F)CC1)C3)C2] |
| 476 | 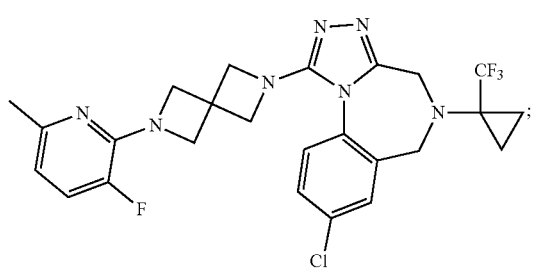 [SMILES: Cc1ccc(F)c(N2CC3(C2)CN(c2nnc4n2-c2ccc(Cl)cc2CN(C2(C(F)(F)F)CC2)C4)C3)n1] |
| 477 | 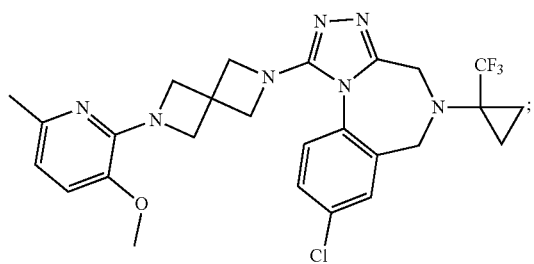 [SMILES: COc1ccc(C)nc1N1CC2(C1)CN(c1nnc3n1-c1ccc(Cl)cc1CN(C1(C(F)(F)F)CC1)C3)C2] |
| 478 | 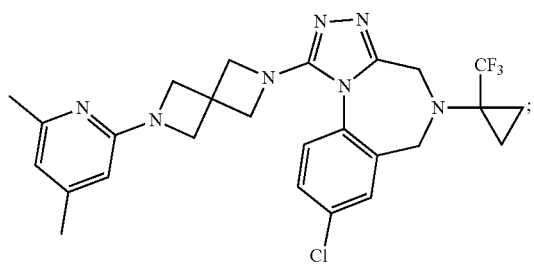 [SMILES: Cc1cc(C)nc(N2CC3(C2)CN(c2nnc4n2-c2ccc(Cl)cc2CN(C2(C(F)(F)F)CC2)C4)C3)c1] |

| Compound No. | Structure |
|---|---|
| 479 | 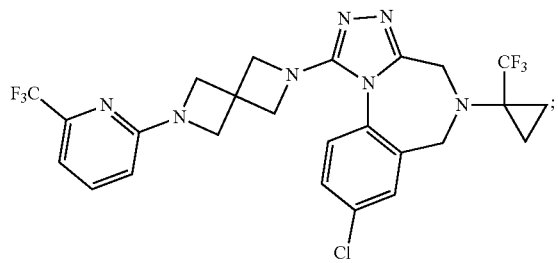 [SMILES: FC(F)(F)c1cccc(N2CC3(C2)CN(c2nnc4n2-c2ccc(Cl)cc2CN(C2(C(F)(F)F)CC2)C4)C3)n1] |
| 480 | 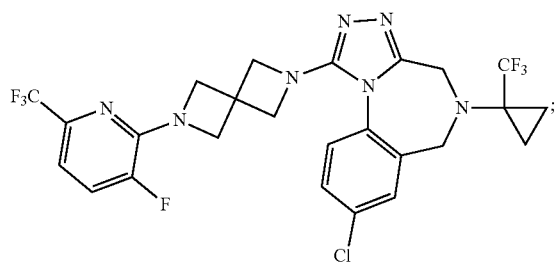 [SMILES: Fc1ccc(C(F)(F)F)nc1N1CC2(C1)CN(c1nnc3n1-c1ccc(Cl)cc1CN(C1(C(F)(F)F)CC1)C3)C2] |
| 481 | 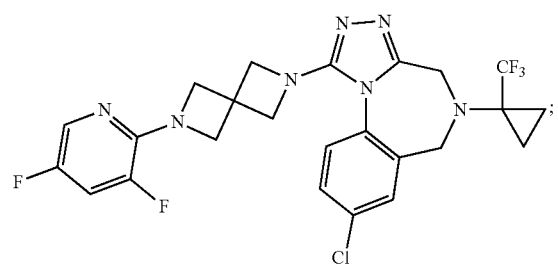 |
| 482 | 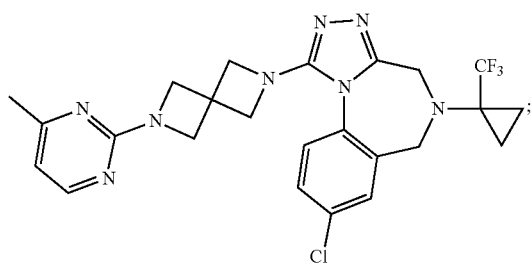 [SMILES: Cc1ccnc(N2CC3(C2)CN(c2nnc4n2-c2ccc(Cl)cc2CN(C2(C(F)(F)F)CC2)C4)C3)n1] |
| 483 | 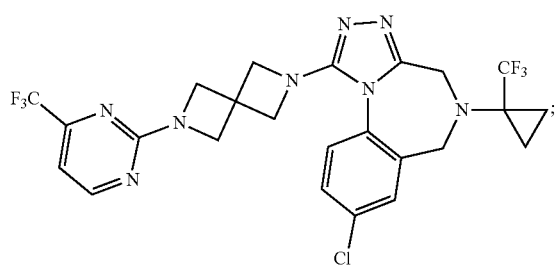 [SMILES: FC(F)(F)c1ccnc(N2CC3(C2)CN(c2nnc4n2-c2ccc(Cl)cc2CN(C2(C(F)(F)F)CC2)C4)C3)n1] |

-continued

| Compound No. | Structure |
|---|---|
| 484 | 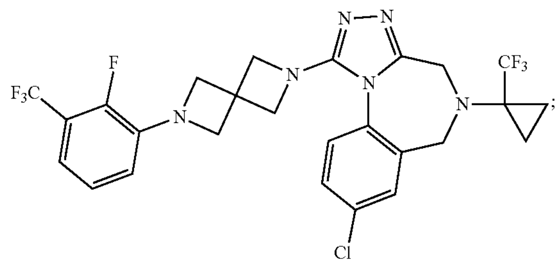 [SMILES: Fc1c(N2CC3(C2)CN(c2nnc4n2-c2ccc(Cl)cc2CN(C2(C(F)(F)F)CC2)C4)C3)cccc1C(F)(F)F] |
| 485 | 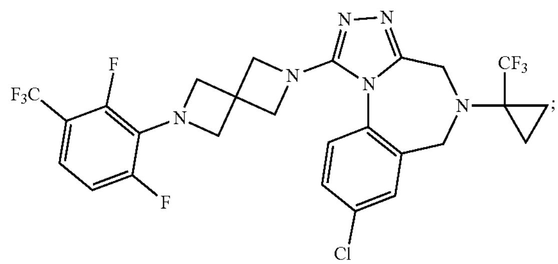 [SMILES: Fc1ccc(C(F)(F)F)c(F)c1N1CC2(C1)CN(c1nnc3n1-c1ccc(Cl)cc1CN(C1(C(F)(F)F)CC1)C3)C2] |
| 486 | 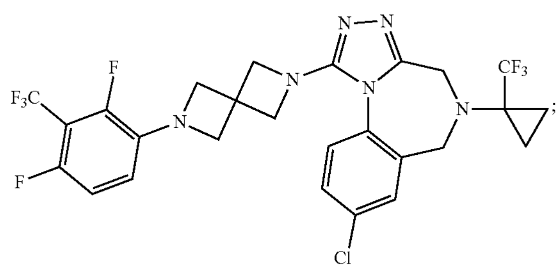 [SMILES: Fc1ccc(N2CC3(C2)CN(c2nnc4n2-c2ccc(Cl)cc2CN(C2(C(F)(F)F)CC2)C4)C3)c(F)c1C(F)(F)F] |
| 487 | 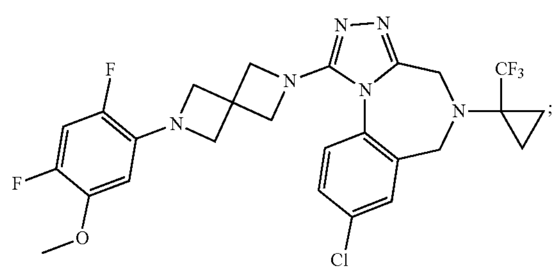 [SMILES: COc1cc(N2CC3(C2)CN(c2nnc4n2-c2ccc(Cl)cc2CN(C2(C(F)(F)F)CC2)C4)C3)c(F)cc1F] |
| 488 | 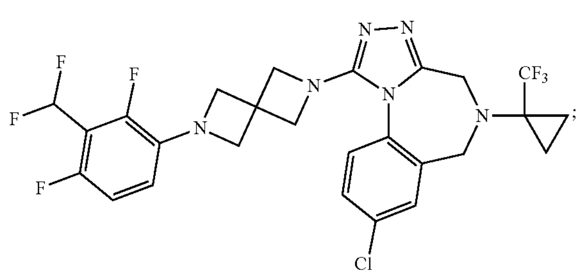 [SMILES: Fc1ccc(N2CC3(C2)CN(c2nnc4n2-c2ccc(Cl)cc2CN(C2(C(F)(F)F)CC2)C4)C3)c(F)c1C(F)F] |
| 489 | 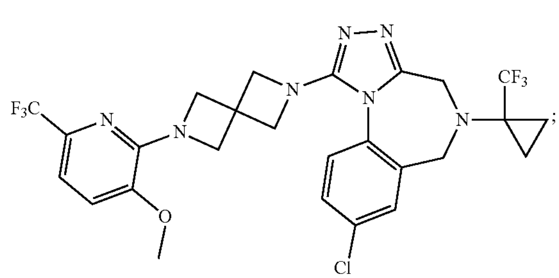 [SMILES: COc1ccc(C(F)(F)F)nc1N1CC2(C1)CN(c1nnc3n1-c1ccc(Cl)cc1CN(C1(C(F)(F)F)CC1)C3)C2] |

| Compound No. | Structure |
| --- | --- |
| 490 | 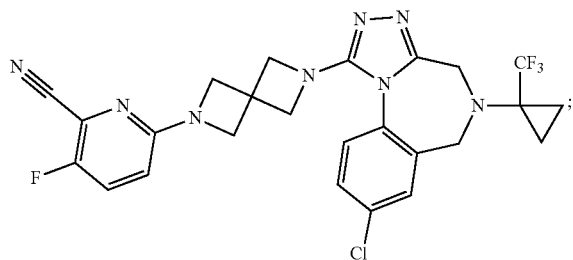 [SMILES: N#Cc1nc(N2CC3(C2)CN(c2nnc4n2-c2ccc(Cl)cc2CN(C2(C(F)(F)F)CC2)C4)C3)ccc1F] |
| 491 | 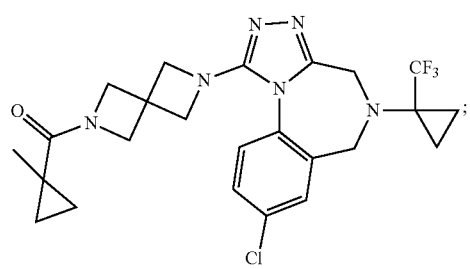 [SMILES: CC1(C(=O)N2CC3(C2)CN(c2nnc4n2-c2ccc(Cl)cc2CN(C2(C(F)(F)F)CC2)C4)C3)CC1] |
| 492 | 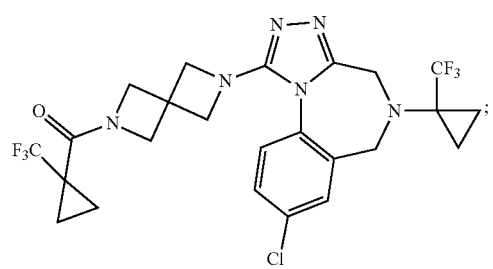 [SMILES: O=C(N1CC2(C1)CN(c1nnc3n1-c1ccc(Cl)cc1CN(C1(C(F)(F)F)CC1)C3)C2)C1(C(F)(F)F)CC1] |
| 493 | 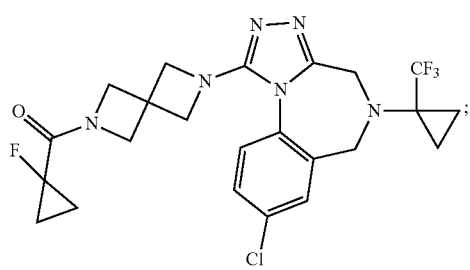 [SMILES: O=C(N1CC2(C1)CN(c1nnc3n1-c1ccc(Cl)cc1CN(C1(C(F)(F)F)CC1)C3)C2)C1(F)CC1] |
| 494 | 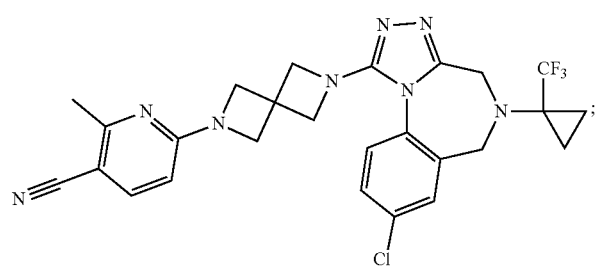 [SMILES: Cc1nc(N2CC3(C2)CN(c2nnc4n2-c2ccc(Cl)cc2CN(C2(C(F)(F)F)CC2)C4)C3)ccc1C#N] |

| Compound No. | Structure |
|---|---|
| 495 | 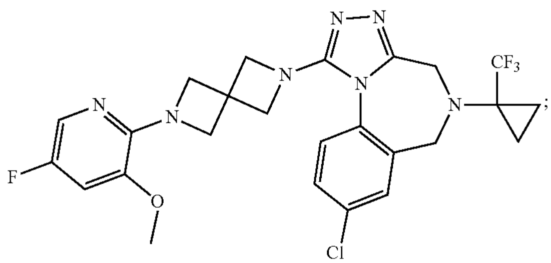 [SMILES: COc1cc(F)cnc1N1CC2(C1)CN(c1nnc3n1-c1ccc(Cl)cc1CN(C1(C(F)(F)F)CC1)C3)C2] |
| 496 | 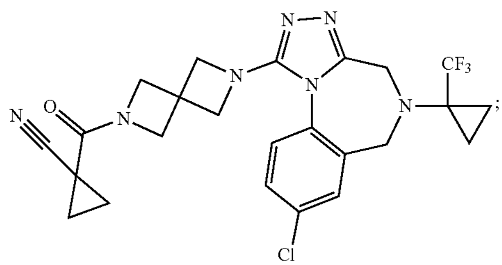 [SMILES: N#CC1(C(=O)N2CC3(C2)CN(c2nnc4n2-c2ccc(Cl)cc2CN(C2(C(F)(F)F)CC2)C4)C3)CC1] |
| 497 | 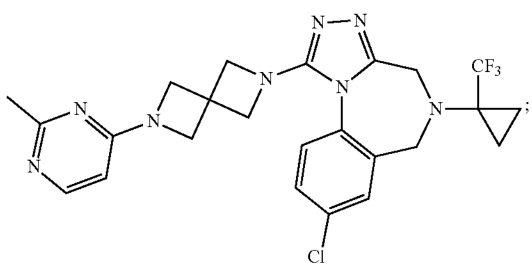 |
| 498 | 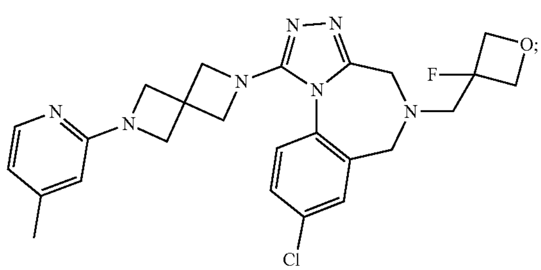 [SMILES: Cc1ccnc(N2CC3(C2)CN(c2nnc4n2-c2ccc(Cl)cc2CN(CC2(F)COC2)C4)C3)c1] |
| 499 | 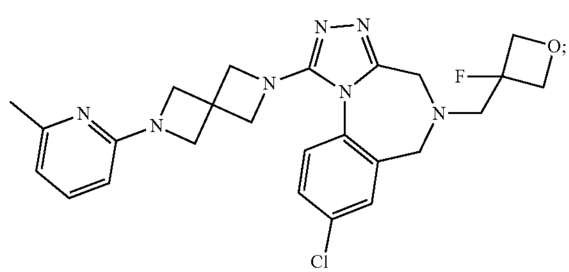 [SMILES: Cc1cccc(N2CC3(C2)CN(c2nnc4n2-c2ccc(Cl)cc2CN(CC2(F)COC2)C4)C3)n1] |
| 500 | 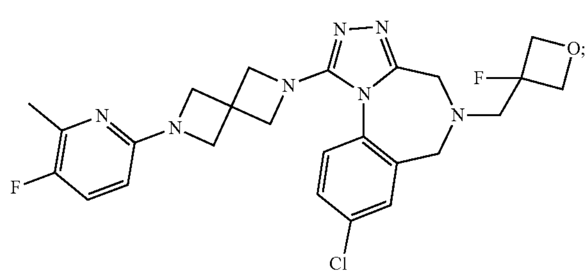 [SMILES: Cc1nc(N2CC3(C2)CN(c2nnc4n2-c2ccc(Cl)cc2CN(CC2(F)COC2)C4)C3)ccc1F] |

-continued
| Compound No. | Structure |
|---|---|
| 501 | 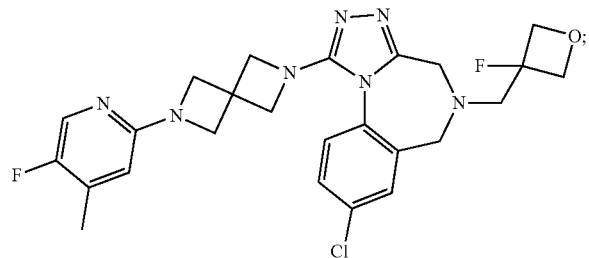 [SMILES: Cc1cc(N2CC3(C2)CN(c2nnc4n2-c2ccc(Cl)cc2CN(CC2(F)COC2)C4)C3)ncc1F] |
| 502 | 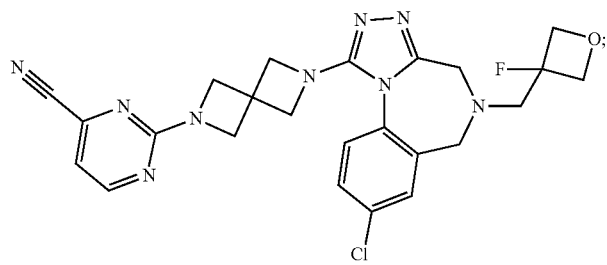 [SMILES: N#Cc1ccnc(N2CC3(C2)CN(c2nnc4n2-c2ccc(Cl)cc2CN(CC2(F)COC2)C4)C3)n1] |
| 503 | 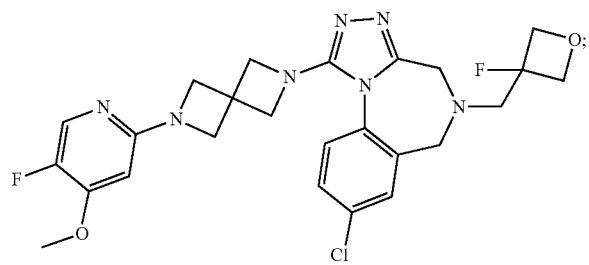 [SMILES: COc1cc(N2CC3(C2)CN(c2nnc4n2-c2ccc(Cl)cc2CN(CC2(F)COC2)C4)C3)ncc1F] |
| 504 | 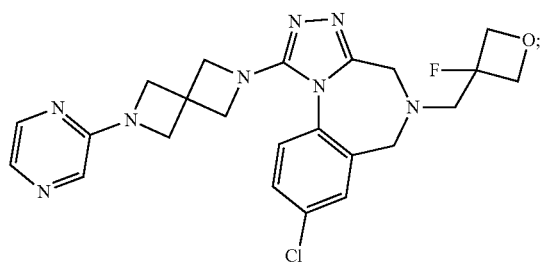 |
| 505 | 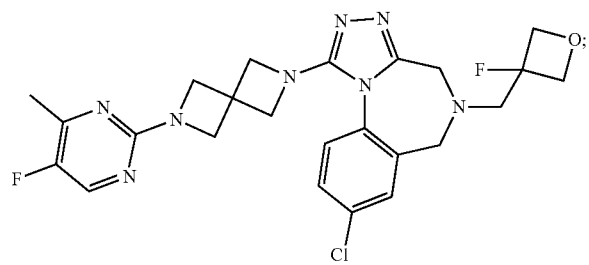 [SMILES: Cc1nc(N2CC3(C2)CN(c2nnc4n2-c2ccc(Cl)cc2CN(CC2(F)COC2)C4)C3)ncc1F] |

| Compound No. | Structure |
|---|---|
| 506 | *(structure)* |
| 507 | *(structure)* |
| 508 | *(structure)* |
| 509 | *(structure)* |
| 510 | *(structure)* |
| 511 | *(structure)* |

-continued
| Compound No. | Structure |
|---|---|
| 512 | 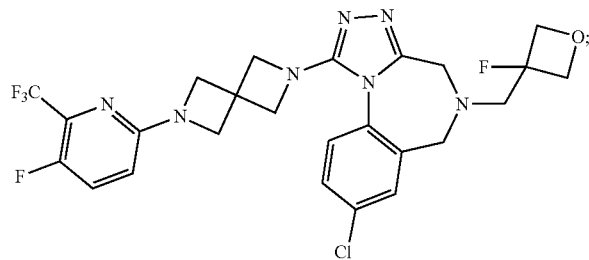 [SMILES: Fc1ccc(N2CC3(C2)CN(c2nnc4n2-c2ccc(Cl)cc2CN(CC2(F)COC2)C4)C3)nc1C(F)(F)F] |
| 513 | 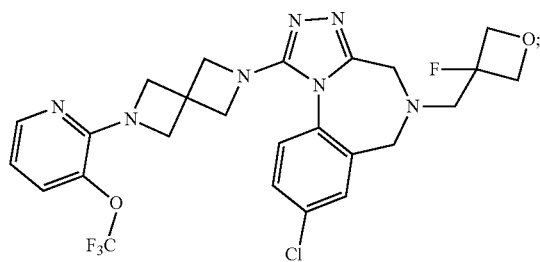 [SMILES: FC1(CN2Cc3cc(Cl)ccc3-n3c(nnc3N3CC4(CN(c5ncccc5OC(F)(F)F)C4)C3)C2)COC1] |
| 514 | 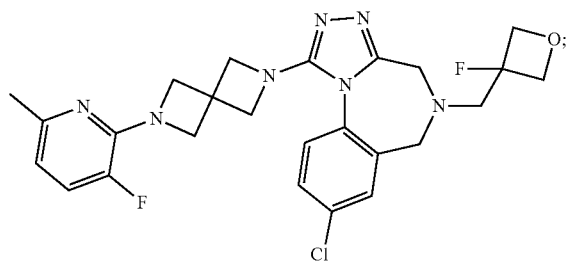 [SMILES: Cc1ccc(F)c(N2CC3(C2)CN(c2nnc4n2-c2ccc(Cl)cc2CN(CC2(F)COC2)C4)C3)n1] |
| 515 | 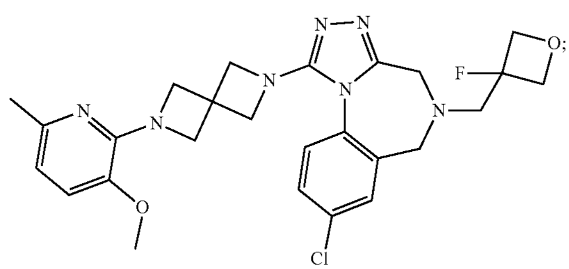 [SMILES: COc1ccc(C)nc1N1CC2(C1)CN(c1nnc3n1-c1ccc(Cl)cc1CN(CC1(F)COC1)C3)C2] |
| 516 | 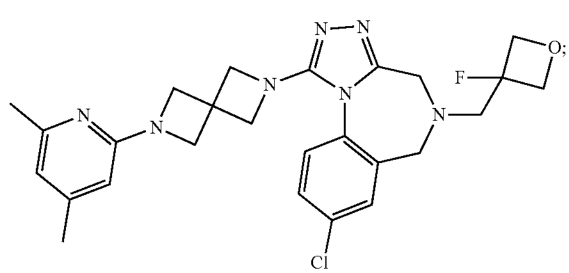 [SMILES: Cc1cc(C)nc(N2CC3(C2)CN(c2nnc4n2-c2ccc(Cl)cc2CN(CC2(F)COC2)C4)C3)c1] |

-continued

| Compound No. | Structure |
|---|---|
| 517 | 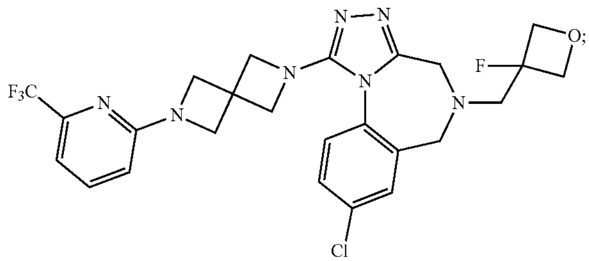 [SMILES: FC1(CN2Cc3cc(Cl)ccc3-n3c(nnc3N3CC4(CN(c5cccc(C(F)(F)F)n5)C4)C3)C2)COC1] |
| 518 | 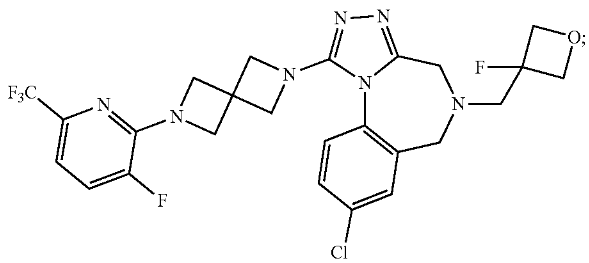 [SMILES: Fc1ccc(C(F)(F)F)nc1N1CC2(C1)CN(c1nnc3n1-c1ccc(Cl)cc1CN(CC1(F)COC1)C3)C2] |
| 519 | 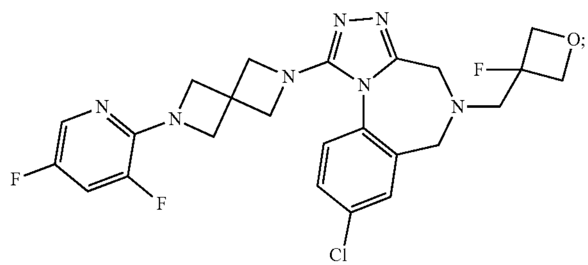 [SMILES: Fc1cnc(N2CC3(C2)CN(c2nnc4n2-c2ccc(Cl)cc2CN(CC2(F)COC2)C4)C3)c(F)c1] |
| 520 | 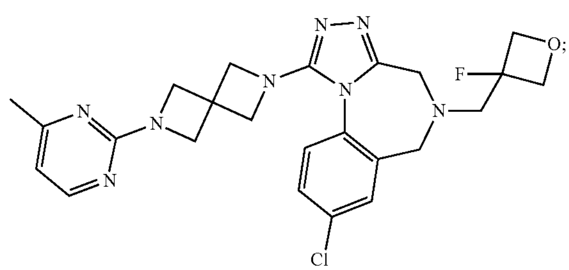 [SMILES: Cc1ccnc(N2CC3(C2)CN(c2nnc4n2-c2ccc(Cl)cc2CN(CC2(F)COC2)C4)C3)n1] |
| 521 | 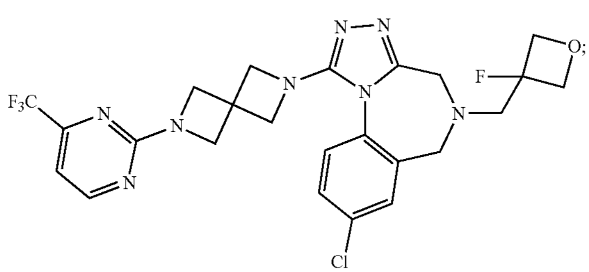 |
| 522 | 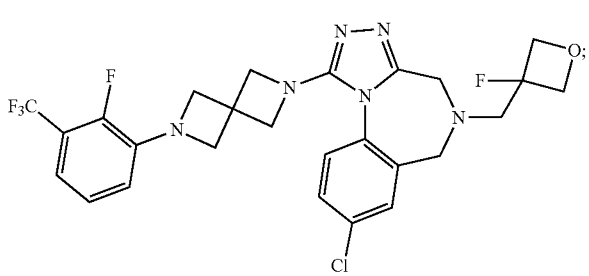 [SMILES: Fc1c(N2CC3(C2)CN(c2nnc4n2-c2ccc(Cl)cc2CN(CC2(F)COC2)C4)C3)cccc1C(F)(F)F] |

-continued
| Compound No. | Structure |
|---|---|
| 523 | 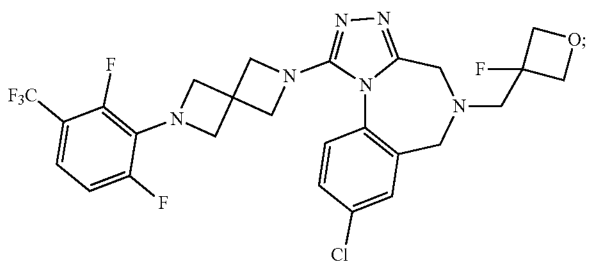 [SMILES: Fc1ccc(C(F)(F)F)c(F)c1N1CC2(C1)CN(c1nnc3n1-c1ccc(Cl)cc1CN(CC1(F)COC1)C3)C2] |
| 524 | 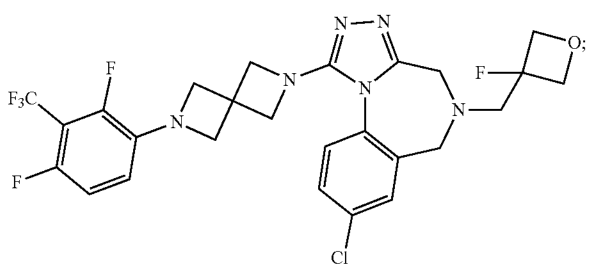 [SMILES: Fc1ccc(N2CC3(C2)CN(c2nnc4n2-c2ccc(Cl)cc2CN(CC2(F)COC2)C4)C3)c(F)c1C(F)(F)F] |
| 525 | 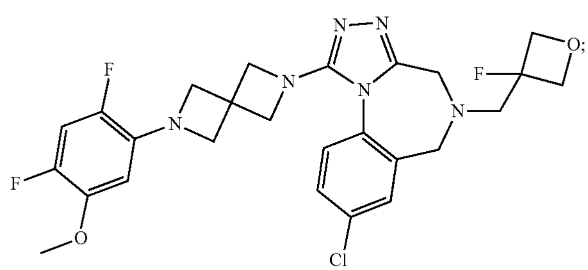 [SMILES: COc1cc(N2CC3(C2)CN(c2nnc4n2-c2ccc(Cl)cc2CN(CC2(F)COC2)C4)C3)c(F)cc1F] |
| 526 | 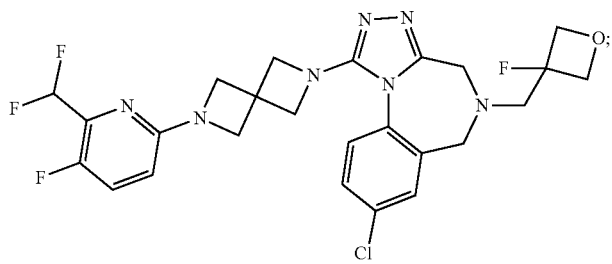 [SMILES: Fc1ccc(N2CC3(C2)CN(c2nnc4n2-c2ccc(Cl)cc2CN(CC2(F)COC2)C4)C3)nc1C(F)F] |
| 527 | 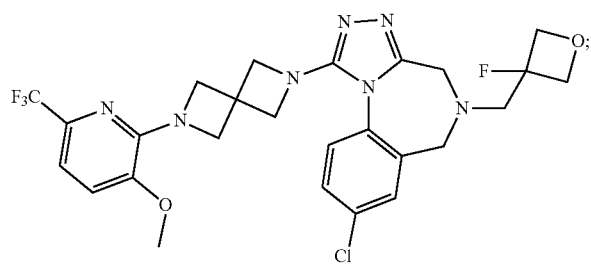 |

| Compound No. | Structure |
|---|---|
| 528 | 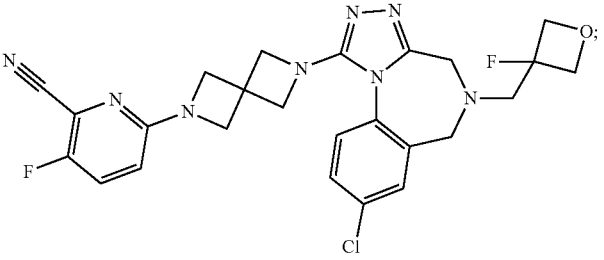 [SMILES: N#Cc1nc(N2CC3(C2)CN(c2nnc4n2-c2ccc(Cl)cc2CN(CC2(F)COC2)C4)C3)ccc1F] |
| 529 | 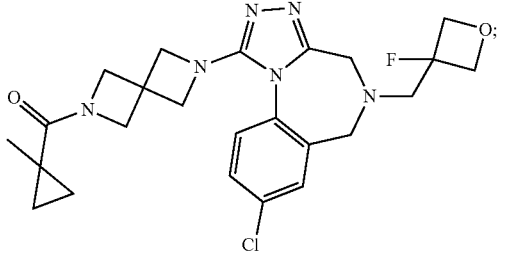 [SMILES: CC1(C(=O)N2CC3(C2)CN(c2nnc4n2-c2ccc(Cl)cc2CN(CC2(F)COC2)C4)C3)CC1] |
| 530 | 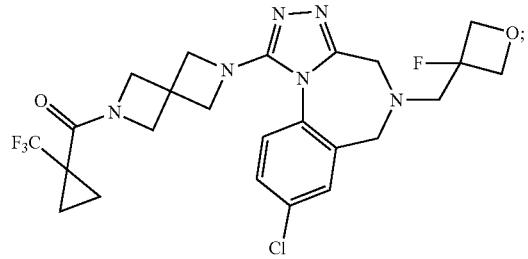 [SMILES: O=C(N1CC2(C1)CN(c1nnc3n1-c1ccc(Cl)cc1CN(CC1(F)COC1)C3)C2)C1(C(F)(F)F)CC1] |
| 531 | 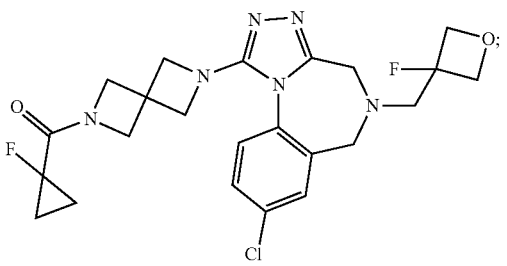 [SMILES: O=C(N1CC2(C1)CN(c1nnc3n1-c1ccc(Cl)cc1CN(CC1(F)COC1)C3)C2)C1(F)CC1] |
| 532 | 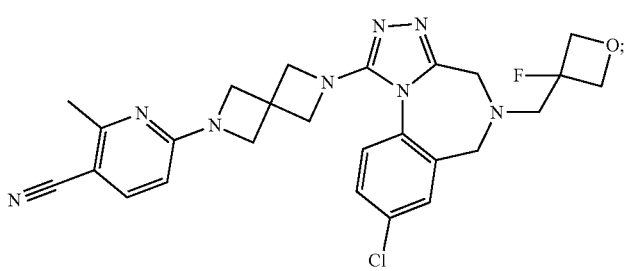 [SMILES: Cc1nc(N2CC3(C2)CN(c2nnc4n2-c2ccc(Cl)cc2CN(CC2(F)COC2)C4)C3)ccc1C#N] |
| 533 | 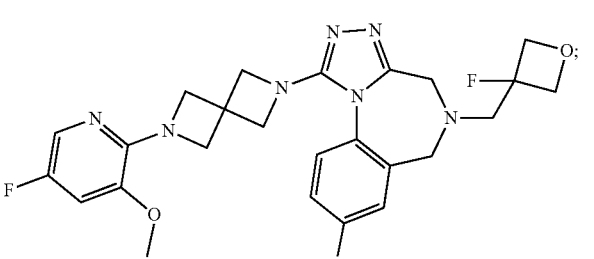 |

| Compound No. | Structure |
|---|---|
| 534 | 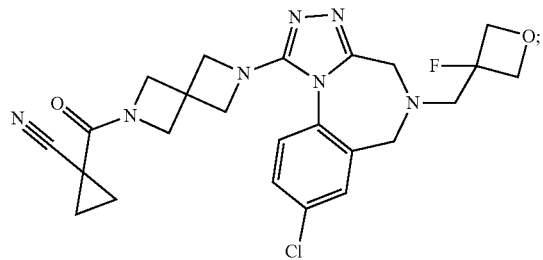 [SMILES: N#CC1(C(=O)N2CC3(C2)CN(c2nnc4n2-c2ccc(Cl)cc2CN(CC2(F)COC2)C4)C3)CC1] |
| 535 | 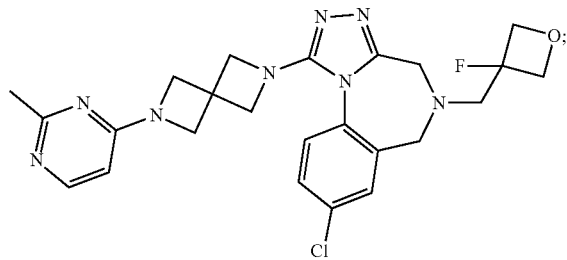 |
| 536 | 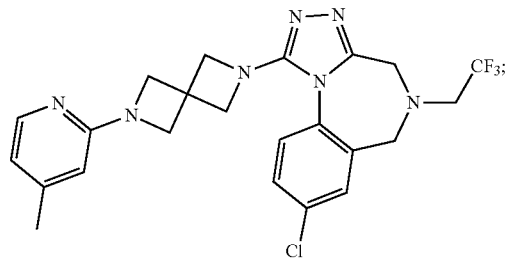 [SMILES: Cc1ccnc(N2CC3(C2)CN(c2nnc4n2-c2ccc(Cl)cc2CN(CC(F)(F)F)C4)C3)c1] |
| 537 | 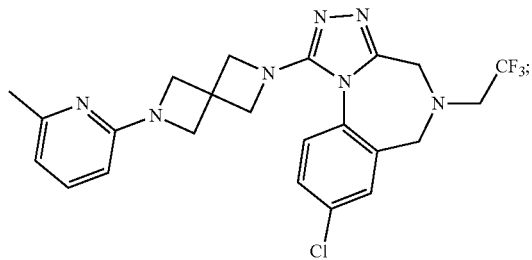 [SMILES: Cc1cccc(N2CC3(C2)CN(c2nnc4n2-c2ccc(Cl)cc2CN(CC(F)(F)F)C4)C3)n1] |
| 538 | 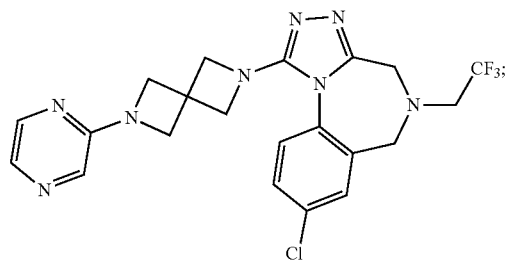 [SMILES: FC(F)(F)CN1Cc2cc(Cl)ccc2-n2c(nnc2N2CC3(CN(c4cnccn4)C3)C2)C1] |

-continued

| Compound No. | Structure |
|---|---|
| 539 | 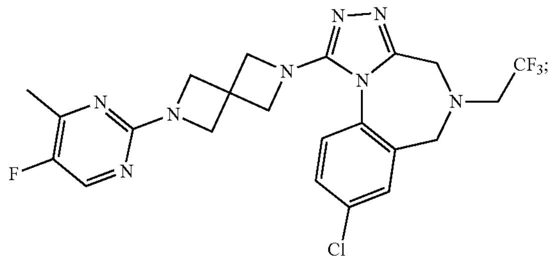 [SMILES: Cc1nc(N2CC3(C2)CN(c2nnc4n2-c2ccc(Cl)cc2CN(CC(F)(F)F)C4)C3)ncc1F] |
| 540 | 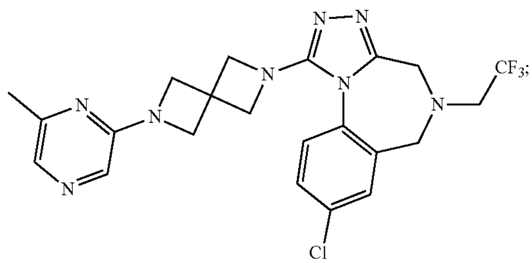 [SMILES: Cc1cncc(N2CC3(C2)CN(c2nnc4n2-c2ccc(Cl)cc2CN(CC(F)(F)F)C4)C3)n1] |
| 541 | 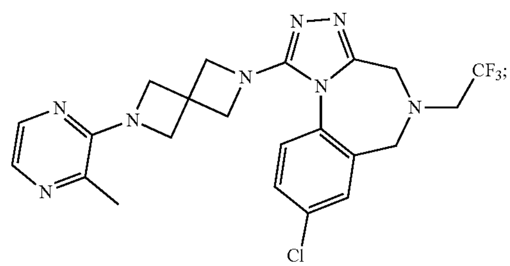 [SMILES: Cc1nccnc1N1CC2(C1)CN(c1nnc3n1-c1ccc(Cl)cc1CN(CC(F)(F)F)C3)C2] |
| 542 | 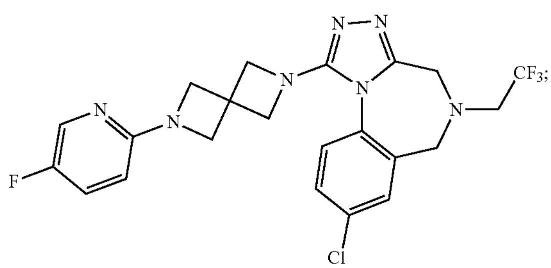 [SMILES: Fc1ccc(N2CC3(C2)CN(c2nnc4n2-c2ccc(Cl)cc2CN(CC(F)(F)F)C4)C3)nc1] |
| 543 | 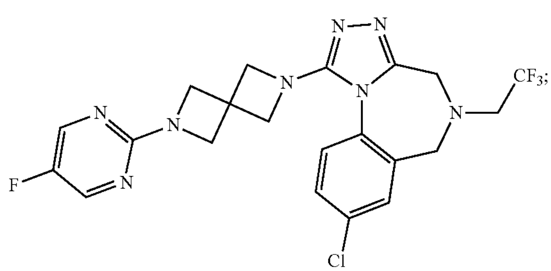 [SMILES: Fc1cnc(N2CC3(C2)CN(c2nnc4n2-c2ccc(Cl)cc2CN(CC(F)(F)F)C4)C3)nc1] |
| 544 | 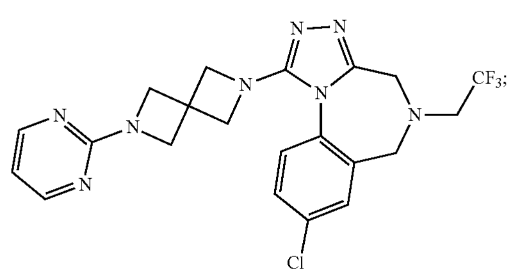 [SMILES: FC(F)(F)CN1Cc2cc(Cl)ccc2-n2c(nnc2N2CC3(CN(c4ncccn4)C3)C2)C1] |

-continued
| Compound No. | Structure |
|---|---|
| 545 | 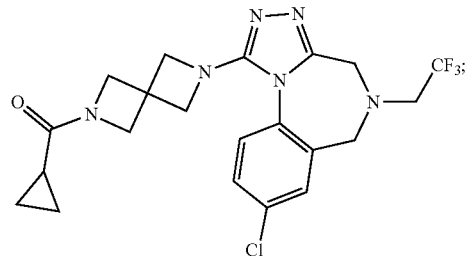 [SMILES: O=C(C1CC1)N1CC2(C1)CN(c1nnc3n1-c1ccc(Cl)cc1CN(CC(F)(F)F)C3)C2] |
| 546 | 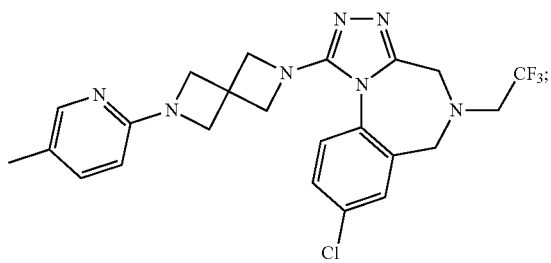 [SMILES: Cc1ccc(N2CC3(C2)CN(c2nnc4n2-c2ccc(Cl)cc2CN(CC(F)(F)F)C4)C3)nc1] |
| 547 | 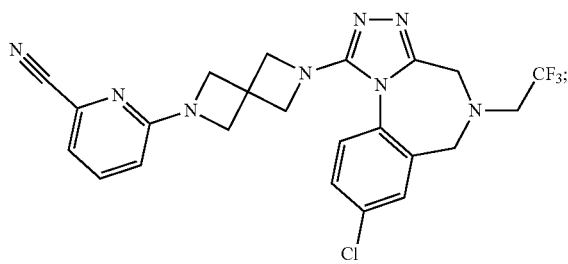 [SMILES: N#Cc1cccc(N2CC3(C2)CN(c2nnc4n2-c2ccc(Cl)cc2CN(CC(F)(F)F)C4)C3)n1] |
| 548 | 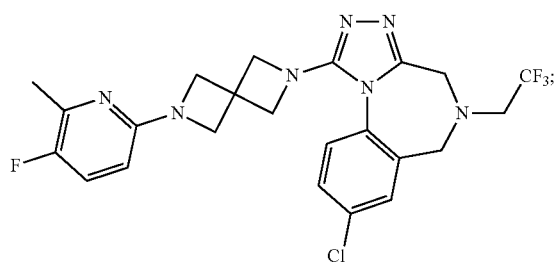 [SMILES: Cc1nc(N2CC3(C2)CN(c2nnc4n2-c2ccc(Cl)cc2CN(CC(F)(F)F)C4)C3)ccc1F] |
| 549 | 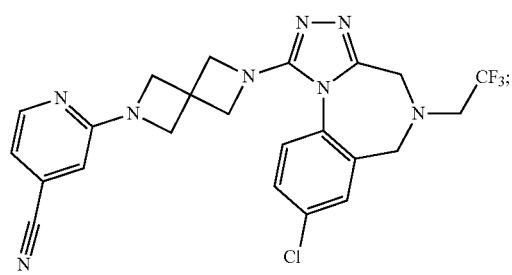 [SMILES: N#Cc1ccnc(N2CC3(C2)CN(c2nnc4n2-c2ccc(Cl)cc2CN(CC(F)(F)F)C4)C3)c1] |

-continued

| Compound No. | Structure |
|---|---|
| 550 | 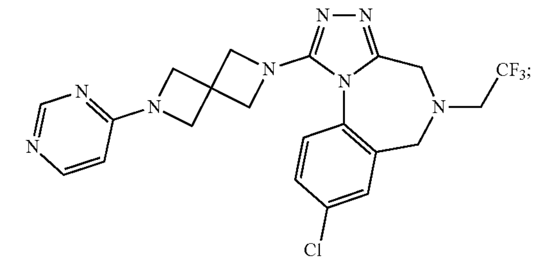 [SMILES: FC(F)(F)CN1Cc2cc(Cl)ccc2-n2c(nnc2N2CC3(CN(c4ccncn4)C3)C2)C1] |
| 552 | 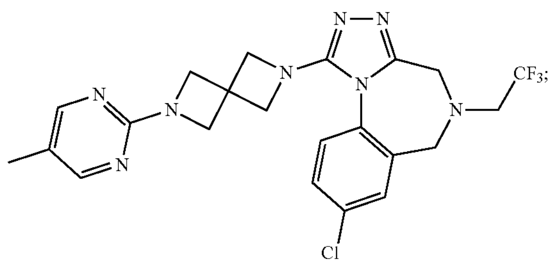 [SMILES: Cc1cnc(N2CC3(C2)CN(c2nnc4n2-c2ccc(Cl)cc2CN(CC(F)(F)F)C4)C3)nc1] |
| 553 | 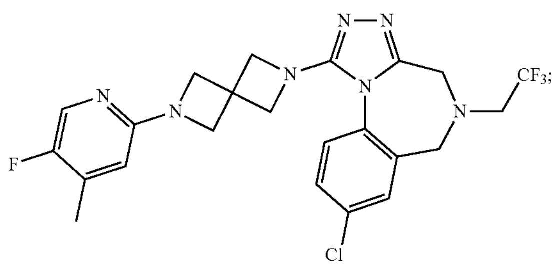 [SMILES: Cc1cc(N2CC3(C2)CN(c2nnc4n2-c2ccc(Cl)cc2CN(CC(F)(F)F)C4)C3)ncc1F] |
| 554 | 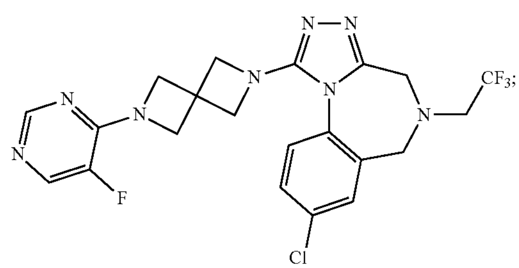 [SMILES: Fc1cncnc1N1CC2(C1)CN(c1nnc3n1-c1ccc(Cl)cc1CN(CC(F)(F)F)C3)C2] |
| 555 | 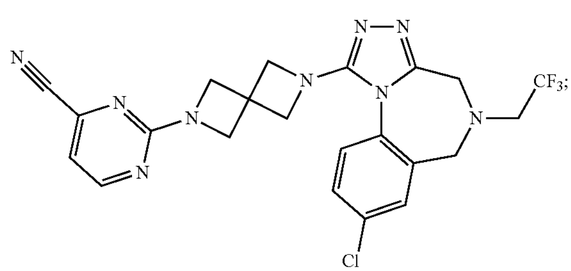 [SMILES: N#Cc1ccnc(N2CC3(C2)CN(c2nnc4n2-c2ccc(Cl)cc2CN(CC(F)(F)F)C4)C3)n1] |
| 556 | 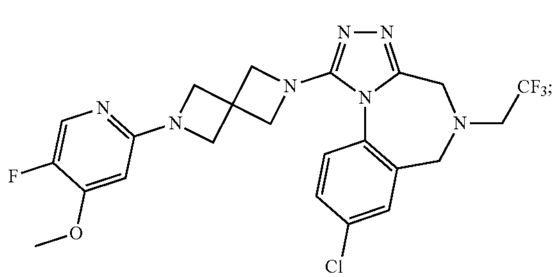 [SMILES: COc1cc(N2CC3(C2)CN(c2nnc4n2-c2ccc(Cl)cc2CN(CC(F)(F)F)C4)C3)ncc1F] |

| Compound No. | Structure |
|---|---|
| 557 | 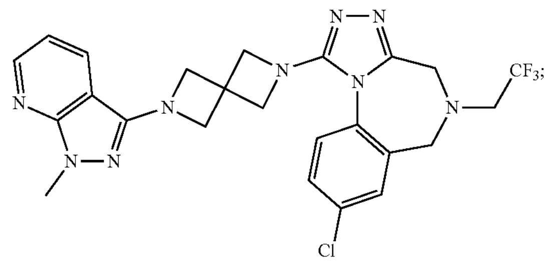 [SMILES: Cn1nc(N2CC3(C2)CN(c2nnc4n2-c2ccc(Cl)cc2CN(CC(F)(F)F)C4)C3)c2cccnc21] |
| 558 | 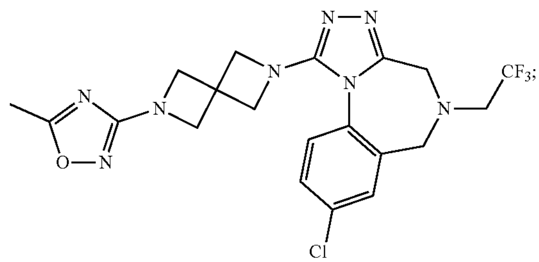 [SMILES: Cc1nc(N2CC3(C2)CN(c2nnc4n2-c2ccc(Cl)cc2CN(CC(F)(F)F)C4)C3)no1] |
| 559 | 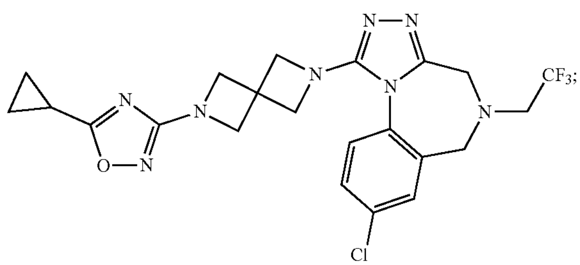 [SMILES: FC(F)(F)CN1Cc2cc(Cl)ccc2-n2c(nnc2N2CC3(CN(c4noc(C5CC5)n4)C3)C2)C1] |
| 560 | 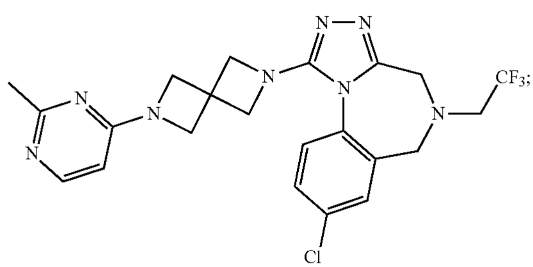 [SMILES: Cc1nccc(N2CC3(C2)CN(c2nnc4n2-c2ccc(Cl)cc2CN(CC(F)(F)F)C4)C3)n1] |
| 561 | 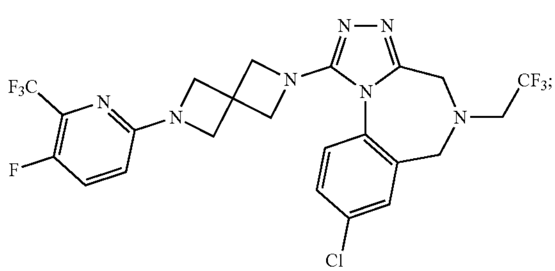 |
| 562 | 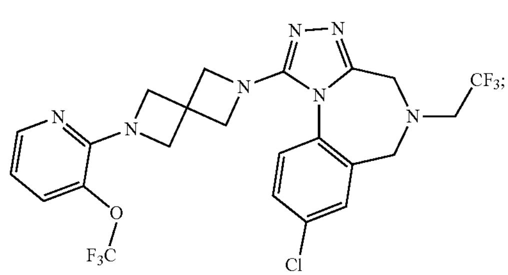 [SMILES: FC(F)(F)CN1Cc2cc(Cl)ccc2-n2c(nnc2N2CC3(CN(c4ncccc4OC(F)(F)F)C3)C2)C1] |

-continued
| Compound No. | Structure |
|---|---|
| 563 | 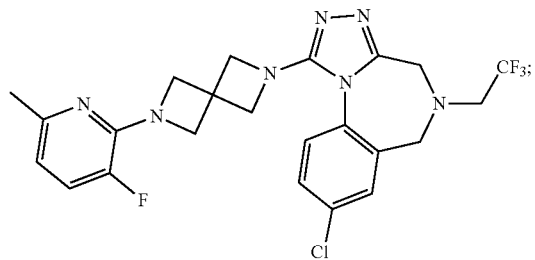 [SMILES: Cc1ccc(F)c(N2CC3(C2)CN(c2nnc4n2-c2ccc(Cl)cc2CN(CC(F)(F)F)C4)C3)n1] |
| 564 | 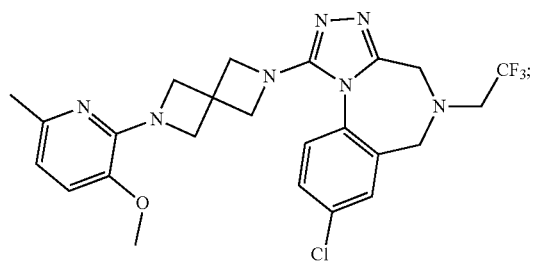 [SMILES: COc1ccc(C)nc1N1CC2(C1)CN(c1nnc3n1-c1ccc(Cl)cc1CN(CC(F)(F)F)C3)C2] |
| 565 | 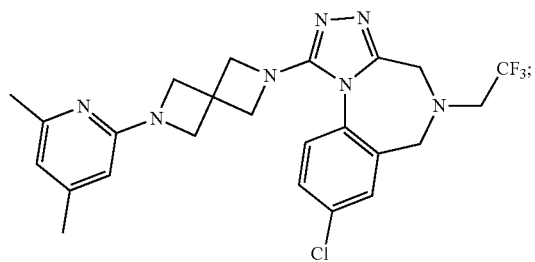 [SMILES: Cc1cc(C)nc(N2CC3(C2)CN(c2nnc4n2-c2ccc(Cl)cc2CN(CC(F)(F)F)C4)C3)c1] |
| 566 | 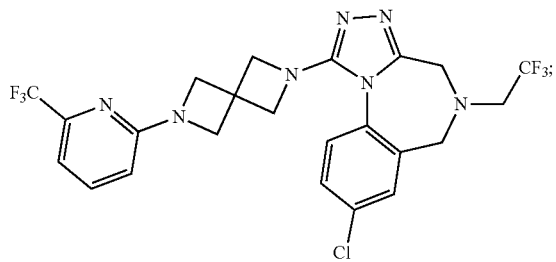 [SMILES: FC(F)(F)CN1Cc2cc(Cl)ccc2-n2c(nnc2N2CC3(CN(c4cccc(C(F)(F)F)n4)C3)C2)C1] |
| 567 | 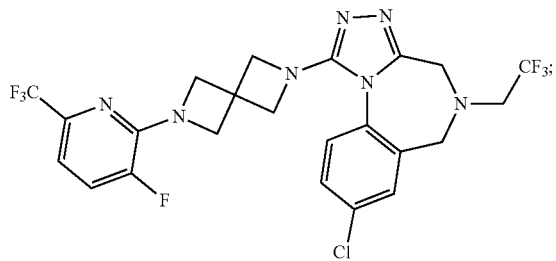 [SMILES: Fc1ccc(C(F)(F)F)nc1N1CC2(C1)CN(c1nnc3n1-c1ccc(Cl)cc1CN(CC(F)(F)F)C3)C2] |

| Compound No. | Structure |
|---|---|
| 568 | (structure) |
| 569 | (structure) |
| 570 | (structure) |
| 571 | (structure) |
| 572 | (structure) |
| 573 | (structure) |

| Compound No. | Structure |
|---|---|
| 574 | 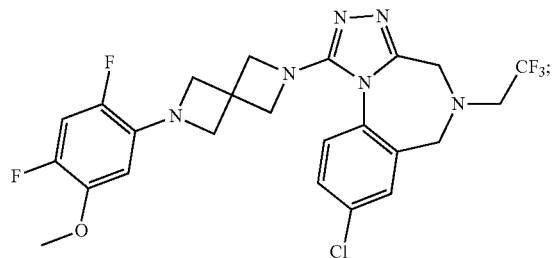 [SMILES: COc1cc(N2CC3(C2)CN(c2nnc4n2-c2ccc(Cl)cc2CN(CC(F)(F)F)C4)C3)c(F)cc1F] |
| 575 | 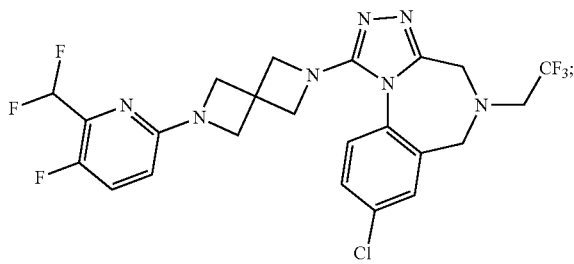 |
| 576 | 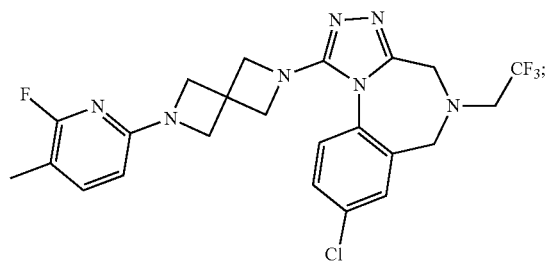 [SMILES: Cc1ccc(N2CC3(C2)CN(c2nnc4n2-c2ccc(Cl)cc2CN(CC(F)(F)F)C4)C3)nc1F] |
| 577 | 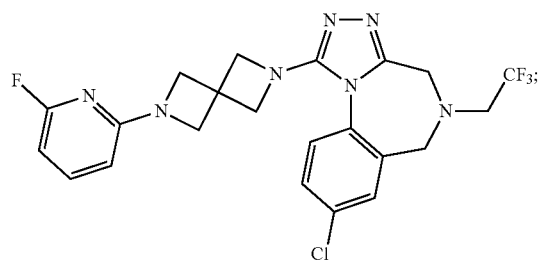 [SMILES: Fc1cccc(N2CC3(C2)CN(c2nnc4n2-c2ccc(Cl)cc2CN(CC(F)(F)F)C4)C3)n1] |
| 578 | 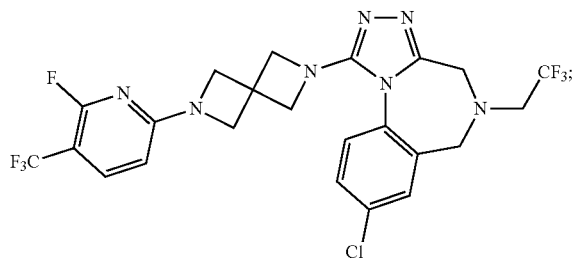 [SMILES: Fc1nc(N2CC3(C2)CN(c2nnc4n2-c2ccc(Cl)cc2CN(CC(F)(F)F)C4)C3)ccc1C(F)(F)F] |
| 579 | 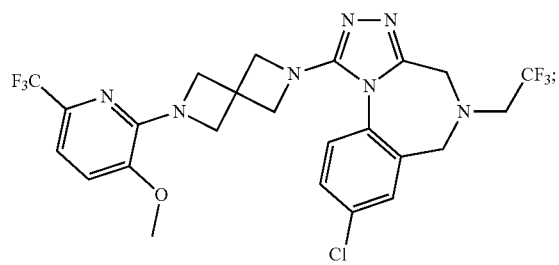 [SMILES: COc1ccc(C(F)(F)F)nc1N1CC2(C1)CN(c1nnc3n1-c1ccc(Cl)cc1CN(CC(F)(F)F)C3)C2] |

-continued

| Compound No. | Structure |
|---|---|
| 580 | 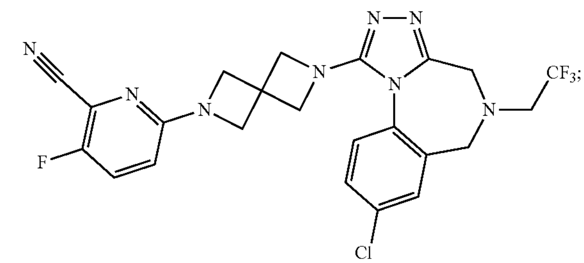 [SMILES: N#Cc1nc(N2CC3(C2)CN(c2nnc4n2-c2ccc(Cl)cc2CN(CC(F)(F)F)C4)C3)ccc1F] |
| 581 | 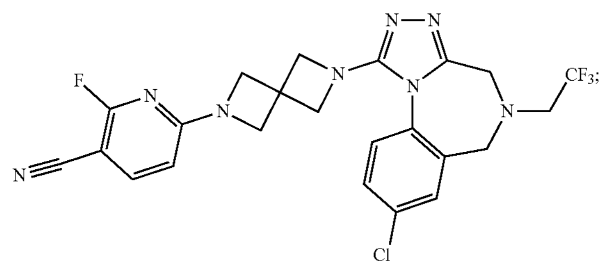 [SMILES: N#Cc1ccc(N2CC3(C2)CN(c2nnc4n2-c2ccc(Cl)cc2CN(CC(F)(F)F)C4)C3)nc1F] |
| 582 | 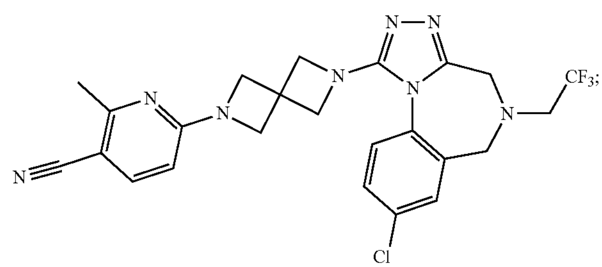 [SMILES: Cc1nc(N2CC3(C2)CN(c2nnc4n2-c2ccc(Cl)cc2CN(CC(F)(F)F)C4)C3)ccc1C#N] |
| 583 | 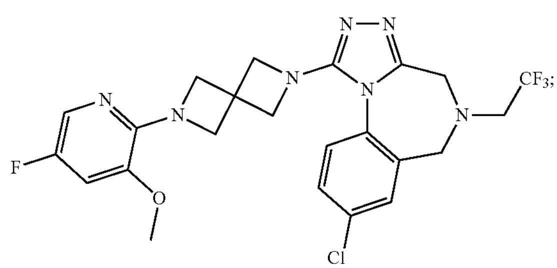 [SMILES: COc1cc(F)cnc1N1CC2(C1)CN(c1nnc3n1-c1ccc(Cl)cc1CN(CC(F)(F)F)C3)C2] |
| 584 | 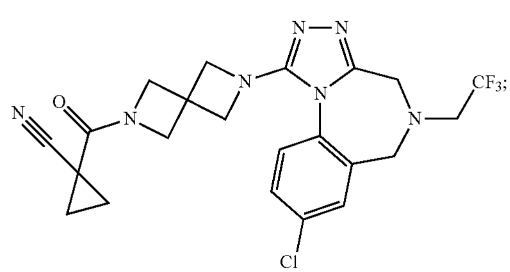 [SMILES: N#CC1(C(=O)N2CC3(C2)CN(c2nnc4n2-c2ccc(Cl)cc2CN(CC(F)(F)F)C4)C3)CC1] |
| 585 | 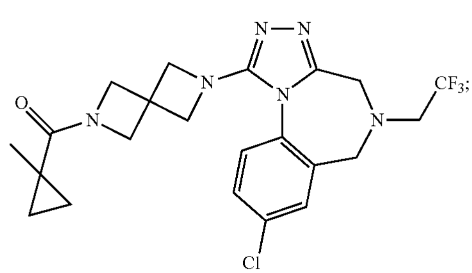 [SMILES: CC1(C(=O)N2CC3(C2)CN(c2nnc4n2-c2ccc(Cl)cc2CN(CC(F)(F)F)C4)C3)CC1] |

-continued
| Compound No. | Structure |
|---|---|
| 586 | 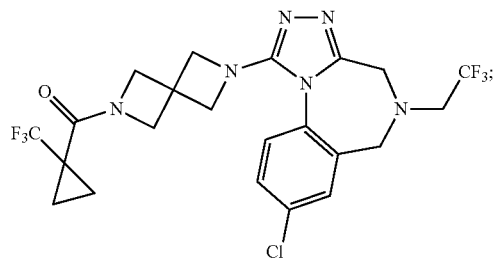 [SMILES: O=C(N1CC2(C1)CN(c1nnc3n1-c1ccc(Cl)cc1CN(CC(F)(F)F)C3)C2)C1(C(F)(F)F)CC1] |
| 587 | 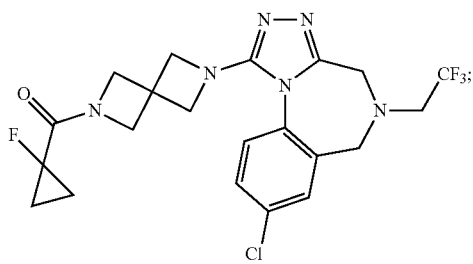 [SMILES: O=C(N1CC2(C1)CN(c1nnc3n1-c1ccc(Cl)cc1CN(CC(F)(F)F)C3)C2)C1(F)CC1] |
| 588 | 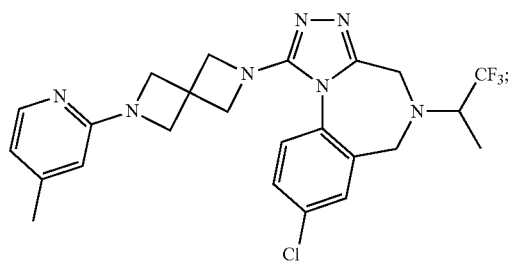 |
| 589 | 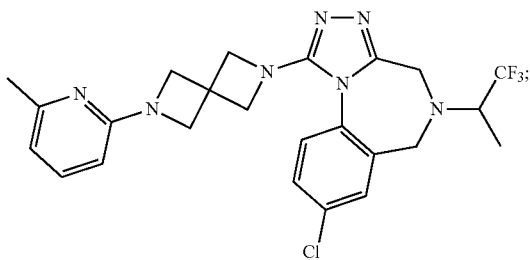 |
| 590 | 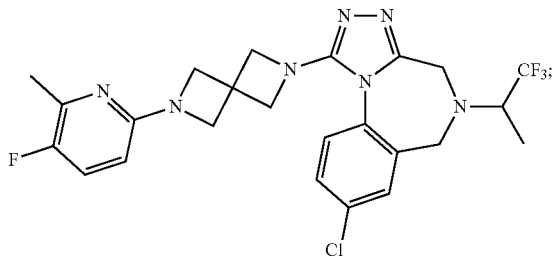 [SMILES: Cc1nc(N2CC3(C2)CN(c2nnc4n2-c2ccc(Cl)cc2CN(C(C)C(F)(F)F)C4)C3)ccc1F] |
| 591 | 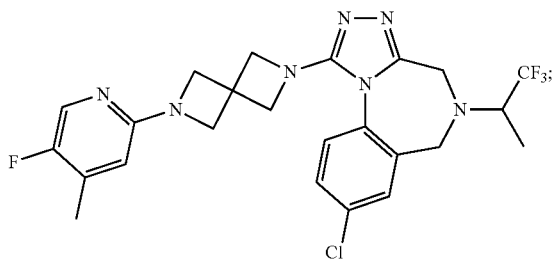 [SMILES: Cc1cc(N2CC3(C2)CN(c2nnc4n2-c2ccc(Cl)cc2CN(C(C)C(F)(F)F)C4)C3)ncc1F] |

-continued
| Compound No. | Structure |
|---|---|
| 592 | 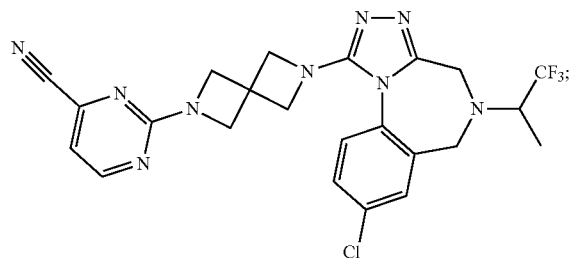 [SMILES: CC(N1Cc2cc(Cl)ccc2-n2c(nnc2N2CC3(CN(c4nccc(C#N)n4)C3)C2)C1)C(F)(F)F] |
| 593 | 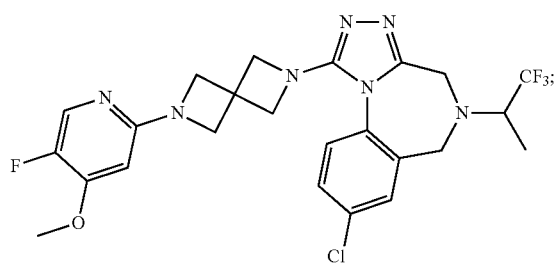 [SMILES: COc1cc(N2CC3(C2)CN(c2nnc4n2-c2ccc(Cl)cc2CN(C(C)C(F)(F)F)C4)C3)ncc1F] |
| 594 | 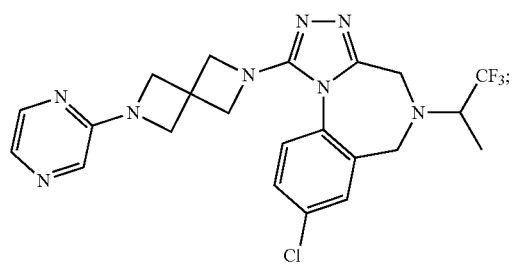 [SMILES: CC(N1Cc2cc(Cl)ccc2-n2c(nnc2N2CC3(CN(c4cnccn4)C3)C2)C1)C(F)(F)F] |
| 595 | 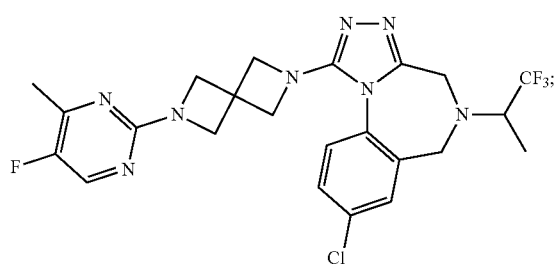 [SMILES: Cc1nc(N2CC3(C2)CN(c2nnc4n2-c2ccc(Cl)cc2CN(C(C)C(F)(F)F)C4)C3)ncc1F] |
| 596 | 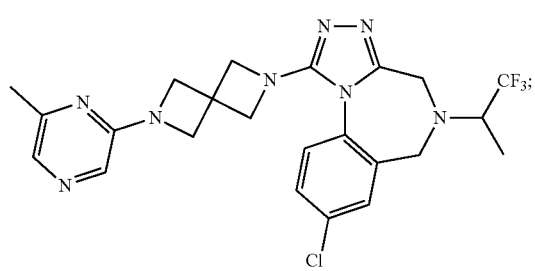 [SMILES: Cc1cncc(N2CC3(C2)CN(c2nnc4n2-c2ccc(Cl)cc2CN(C(C)C(F)(F)F)C4)C3)n1] |

-continued
| Compound No. | Structure |
|---|---|
| 597 | 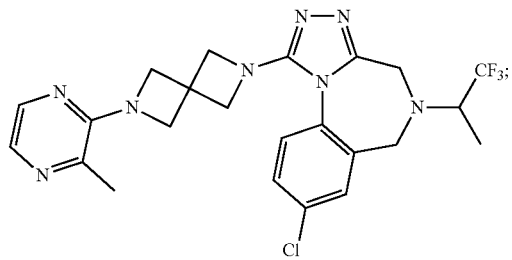 [SMILES: Cc1nccnc1N1CC2(C1)CN(c1nnc3n1-c1ccc(Cl)cc1CN(C(C)C(F)(F)F)C3)C2] |
| 598 | 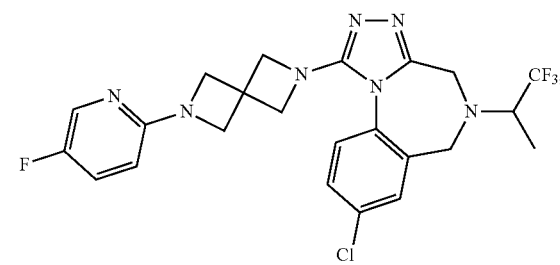 |
| 599 | 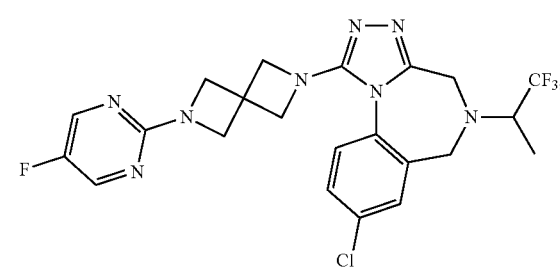 |
| 600 | 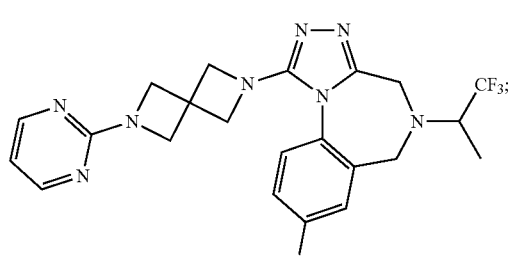 |
| 601 | 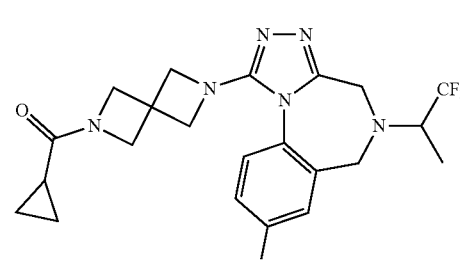 |
| 602 | 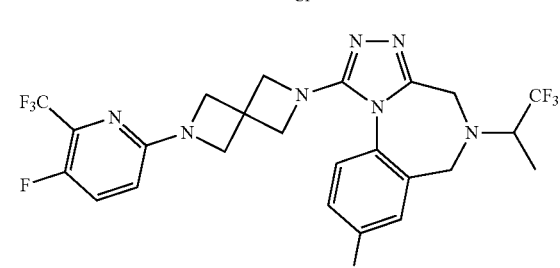 |

| Compound No. | Structure |
|---|---|
| 603 | 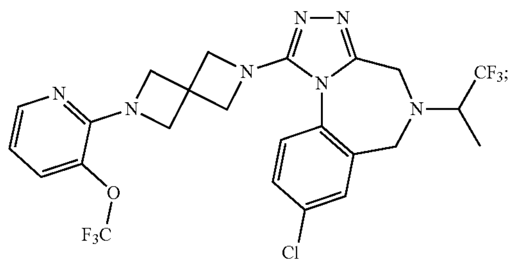 [SMILES: CC(N1Cc2cc(Cl)ccc2-n2c(nnc2N2CC3(CN(c4ncccc4OC(F)(F)F)C3)C2)C1)C(F)(F)F] |
| 604 | 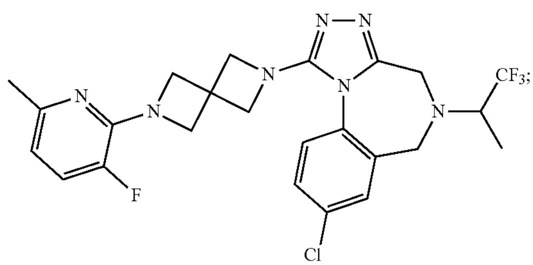 [SMILES: Cc1ccc(F)c(N2CC3(C2)CN(c2nnc4n2-c2ccc(Cl)cc2CN(C(C)C(F)(F)F)C4)C3)n1] |
| 605 | 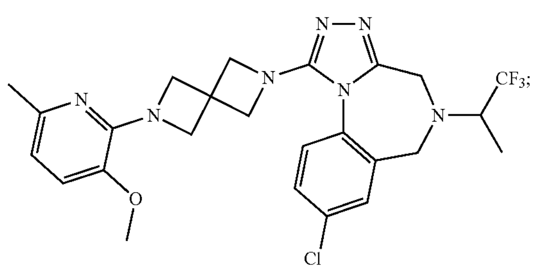 [SMILES: COc1ccc(C)nc1N1CC2(C1)CN(c1nnc3n1-c1ccc(Cl)cc1CN(C(C)C(F)(F)F)C3)C2] |
| 606 | 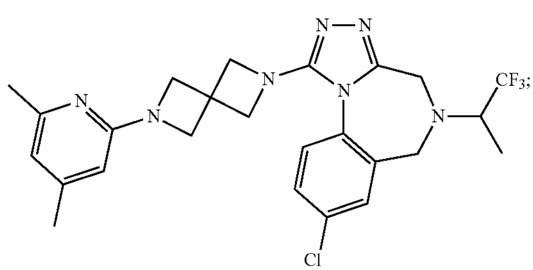 [SMILES: Cc1cc(C)nc(N2CC3(C2)CN(c2nnc4n2-c2ccc(Cl)cc2CN(C(C)C(F)(F)F)C4)C3)c1] |
| 607 | 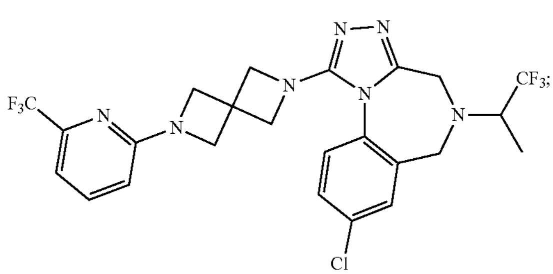 [SMILES: CC(N1Cc2cc(Cl)ccc2-n2c(nnc2N2CC3(CN(c4cccc(C(F)(F)F)n4)C3)C2)C1)C(F)(F)F] |

| Compound No. | Structure |
|---|---|
| 608 | 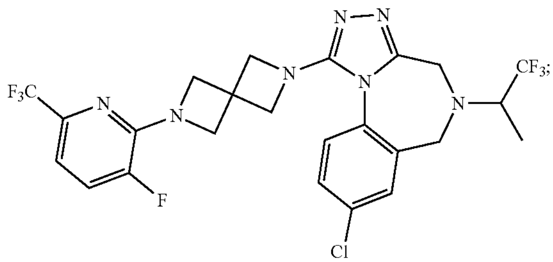 [SMILES: CC(N1Cc2cc(Cl)ccc2-n2c(nnc2N2CC3(CN(c4nc(C(F)(F)F)ccc4F)C3)C2)C1)C(F)(F)F] |
| 609 | 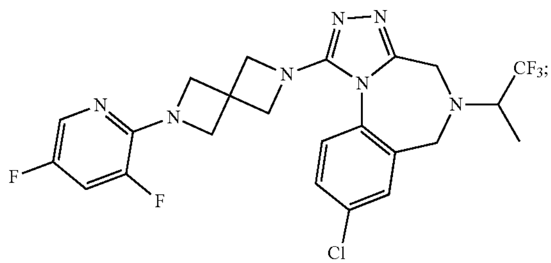 [SMILES: CC(N1Cc2cc(Cl)ccc2-n2c(nnc2N2CC3(CN(c4ncc(F)cc4F)C3)C2)C1)C(F)(F)F] |
| 610 | 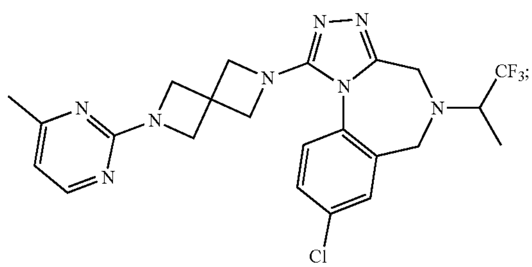 [SMILES: Cc1ccnc(N2CC3(C2)CN(c2nnc4n2-c2ccc(Cl)cc2CN(C(C)C(F)(F)F)C4)C3)n1] |
| 611 | 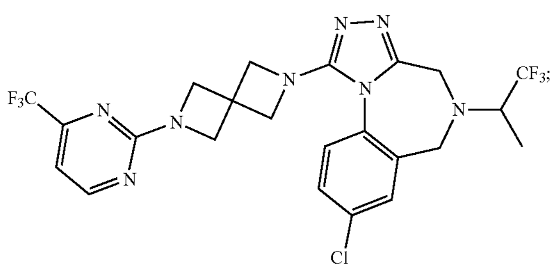 [SMILES: CC(N1Cc2cc(Cl)ccc2-n2c(nnc2N2CC3(CN(c4nccc(C(F)(F)F)n4)C3)C2)C1)C(F)(F)F] |
| 612 | 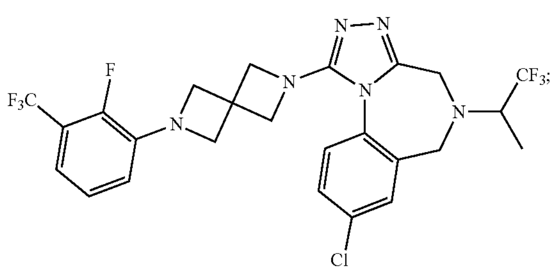 [SMILES: CC(N1Cc2cc(Cl)ccc2-n2c(nnc2N2CC3(CN(c4cccc(C(F)(F)F)c4F)C3)C2)C1)C(F)(F)F] |
| 613 | 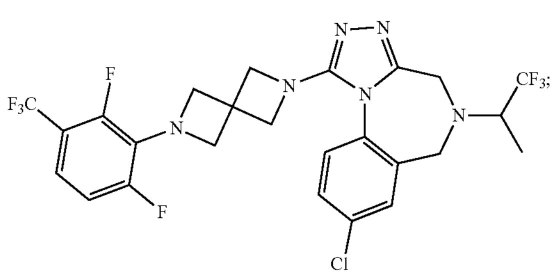 [SMILES: CC(N1Cc2cc(Cl)ccc2-n2c(nnc2N2CC3(CN(c4c(F)ccc(C(F)(F)F)c4F)C3)C2)C1)C(F)(F)F] |

-continued
| Compound No. | Structure |
|---|---|
| 614 | 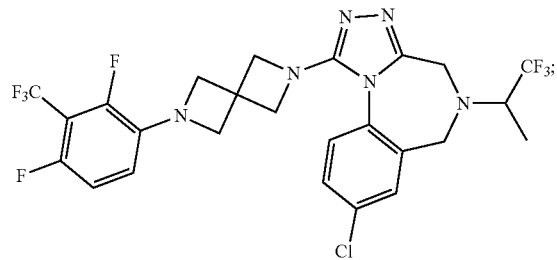 [SMILES: CC(N1Cc2cc(Cl)ccc2-n2c(nnc2N2CC3(CN(c4ccc(F)c(C(F)(F)F)c4F)C3)C2)C1)C(F)(F)F] |
| 615 | 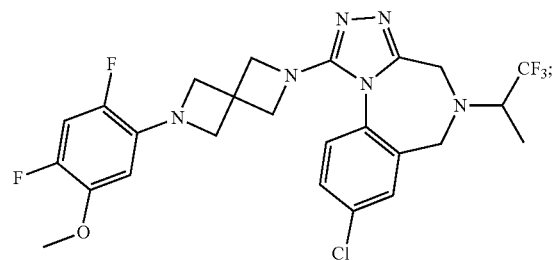 [SMILES: COc1cc(N2CC3(C2)CN(c2nnc4n2-c2ccc(Cl)cc2CN(C(C)C(F)(F)F)C4)C3)c(F)cc1F] |
| 616 | 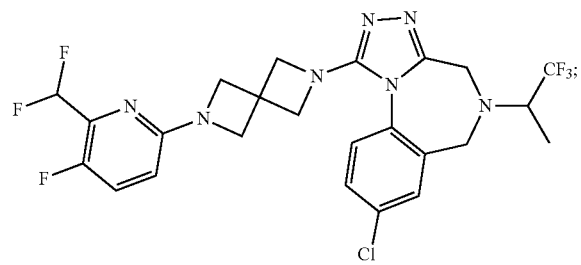 [SMILES: CC(N1Cc2cc(Cl)ccc2-n2c(nnc2N2CC3(CN(c4ccc(F)c(C(F)F)n4)C3)C2)C1)C(F)(F)F] |
| 617 | 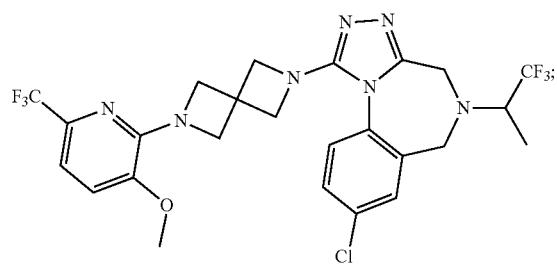 [SMILES: COc1ccc(C(F)(F)F)nc1N1CC2(C1)CN(c1nnc3n1-c1ccc(Cl)cc1CN(C(C)C(F)(F)F)C3)C2] |
| 618 | 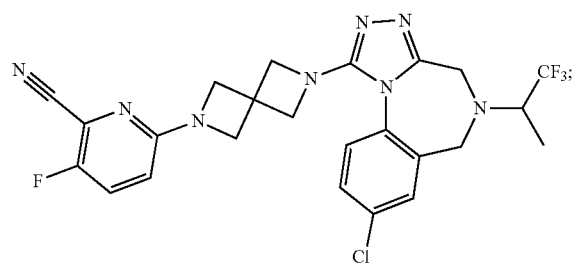 [SMILES: CC(N1Cc2cc(Cl)ccc2-n2c(nnc2N2CC3(CN(c4ccc(F)c(C#N)n4)C3)C2)C1)C(F)(F)F] |

| Compound No. | Structure |
|---|---|
| 619 | 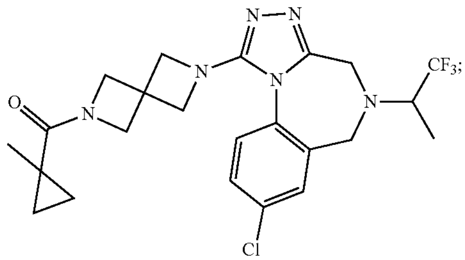 [SMILES: CC(N1Cc2cc(Cl)ccc2-n2c(nnc2N2CC3(CN(C(=O)C4(C)CC4)C3)C2)C1)C(F)(F)F] |
| 620 | 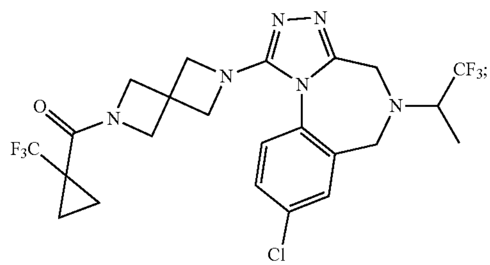 [SMILES: CC(N1Cc2cc(Cl)ccc2-n2c(nnc2N2CC3(CN(C(=O)C4(C(F)(F)F)CC4)C3)C2)C1)C(F)(F)F] |
| 621 | 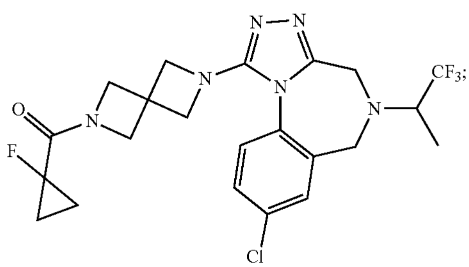 [SMILES: CC(N1Cc2cc(Cl)ccc2-n2c(nnc2N2CC3(CN(C(=O)C4(F)CC4)C3)C2)C1)C(F)(F)F] |
| 622 | 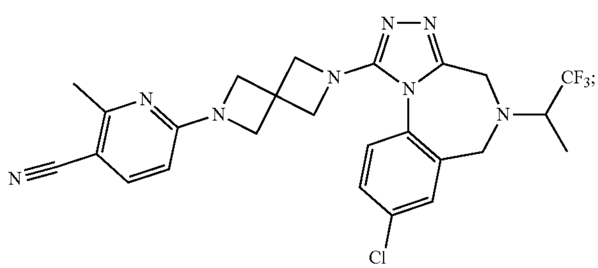 [SMILES: Cc1nc(N2CC3(C2)CN(c2nnc4n2-c2ccc(Cl)cc2CN(C(C)C(F)(F)F)C4)C3)ccc1C#N] |
| 623 | 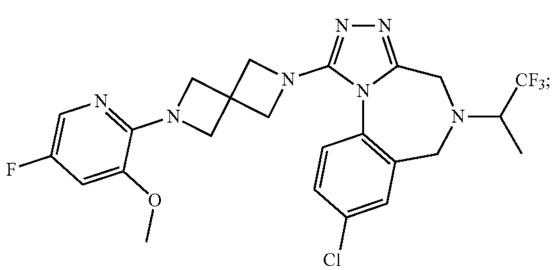 [SMILES: COc1cc(F)cnc1N1CC2(C1)CN(c1nnc3n1-c1ccc(Cl)cc1CN(C(C)C(F)(F)F)C3)C2] |
| 624 | 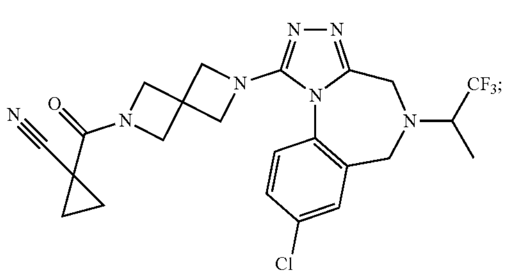 [SMILES: CC(N1Cc2cc(Cl)ccc2-n2c(nnc2N2CC3(CN(C(=O)C4(C#N)CC4)C3)C2)C1)C(F)(F)F] |

| Compound No. | Structure |
|---|---|
| 625 | (structure) |
| 626 | (structure) |
| 627 | (structure) |
| 628 | (structure) |
| 629 | (structure) |
| 630 | (structure) |

-continued

| Compound No. | Structure |
|---|---|
| 631 | 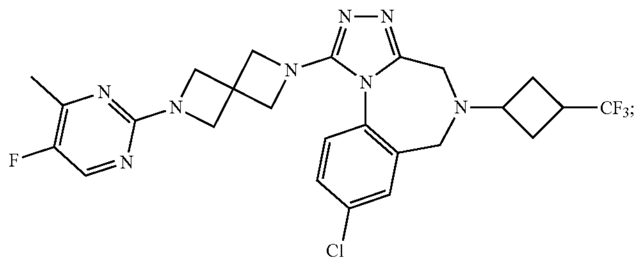 [SMILES: Cc1nc(N2CC3(C2)CN(c2nnc4n2-c2ccc(Cl)cc2CN(C2CC(C(F)(F)F)C2)C4)C3)ncc1F] |
| 632 | 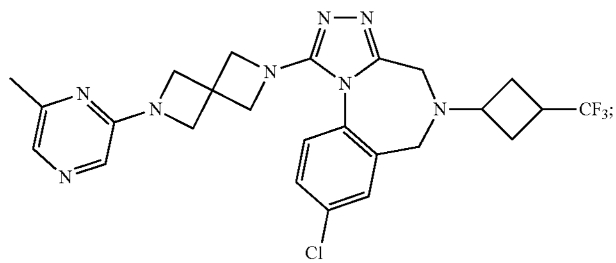 |
| 633 | 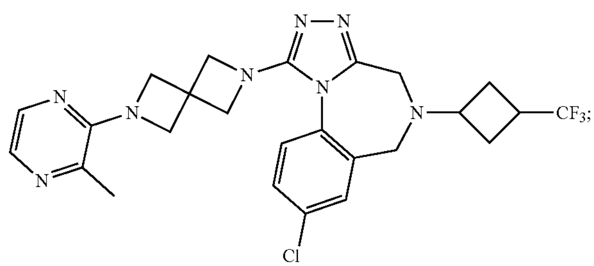 [SMILES: Cc1nccnc1N1CC2(C1)CN(c1nnc3n1-c1ccc(Cl)cc1CN(C1CC(C(F)(F)F)C1)C3)C2] |
| 634 | 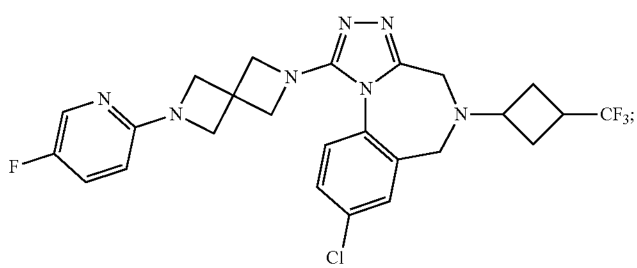 |
| 635 | 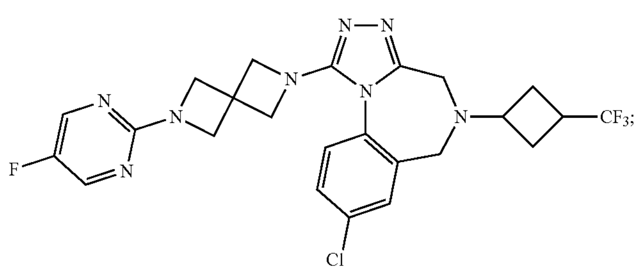 [SMILES: Fc1cnc(N2CC3(C2)CN(c2nnc4n2-c2ccc(Cl)cc2CN(C2CC(C(F)(F)F)C2)C4)C3)nc1] |
| 636 | 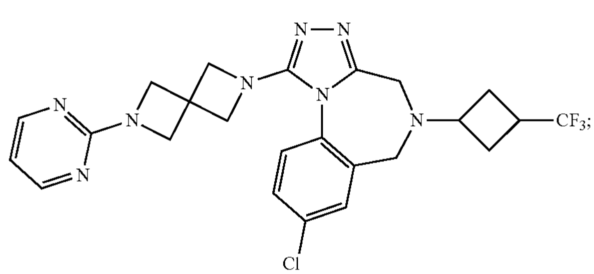 [SMILES: FC(F)(F)C1CC(N2Cc3cc(Cl)ccc3-n3c(nnc3N3CC4(CN(c5ncccn5)C4)C3)C2)C1] |

| Compound No. | Structure |
|---|---|
| 637 | 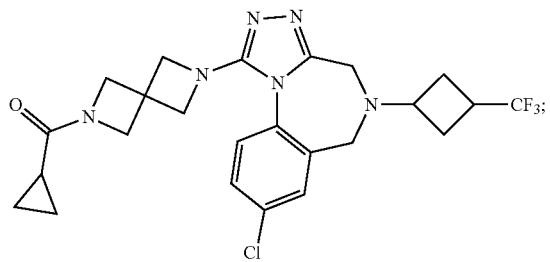 [SMILES: O=C(C1CC1)N1CC2(C1)CN(c1nnc3n1-c1ccc(Cl)cc1CN(C1CC(C(F)(F)F)C1)C3)C2] |
| 638 | 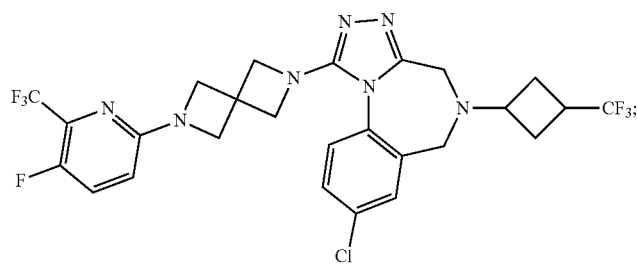 [SMILES: Fc1ccc(N2CC3(C2)CN(c2nnc4n2-c2ccc(Cl)cc2CN(C2CC(C(F)(F)F)C2)C4)C3)nc1C(F)(F)F] |
| 639 | 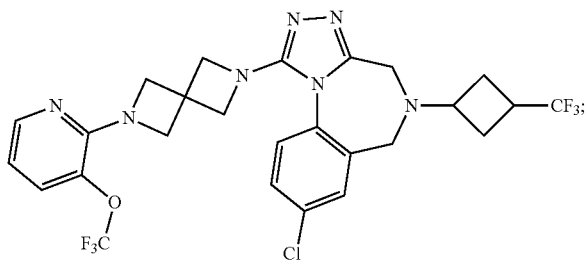 [SMILES: FC(F)(F)Oc1cccnc1N1CC2(C1)CN(c1nnc3n1-c1ccc(Cl)cc1CN(C1CC(C(F)(F)F)C1)C3)C2] |
| 640 | 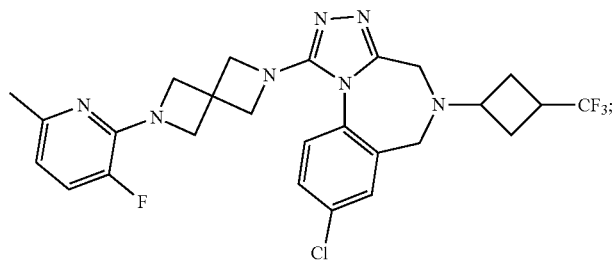 [SMILES: Cc1ccc(F)c(N2CC3(C2)CN(c2nnc4n2-c2ccc(Cl)cc2CN(C2CC(C(F)(F)F)C2)C4)C3)n1] |
| 641 | 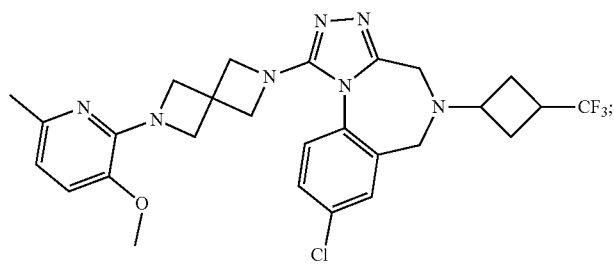 [SMILES: COc1ccc(C)nc1N1CC2(C1)CN(c1nnc3n1-c1ccc(Cl)cc1CN(C1CC(C(F)(F)F)C1)C3)C2] |

US 12,247,037 B2
825                                                                                       826
-continued
| Compound No. | Structure |
|---|---|
| 642 | 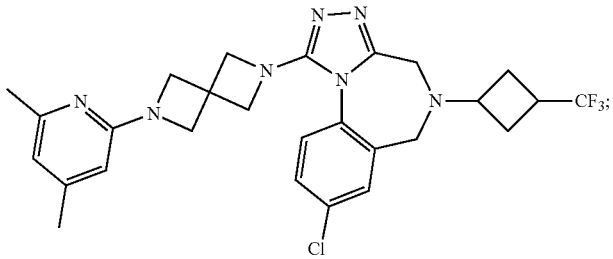 [SMILES: Cc1cc(C)nc(N2CC3(C2)CN(c2nnc4n2-c2ccc(Cl)cc2CN(C2CC(C(F)(F)F)C2)C4)C3)c1] |
| 643 | 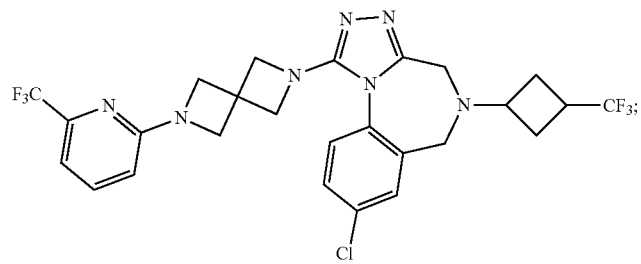 [SMILES: FC(F)(F)c1cccc(N2CC3(C2)CN(c2nnc4n2-c2ccc(Cl)cc2CN(C2CC(C(F)(F)F)C2)C4)C3)n1] |
| 644 | 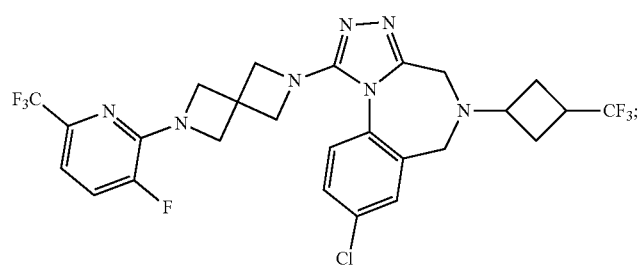 [SMILES: Fc1ccc(C(F)(F)F)nc1N1CC2(C1)CN(c1nnc3n1-c1ccc(Cl)cc1CN(C1CC(C(F)(F)F)C1)C3)C2] |
| 645 | 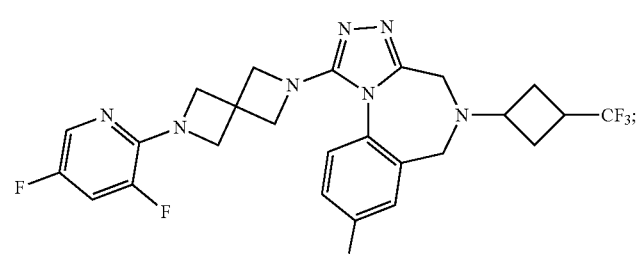 |
| 646 | 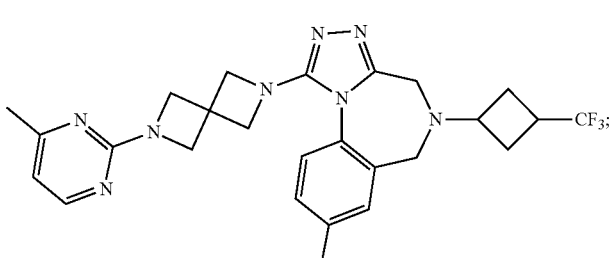 |
| 647 | 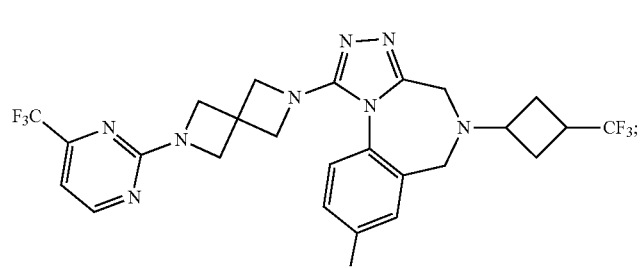 |

| Compound No. | Structure |
|---|---|
| 648 | 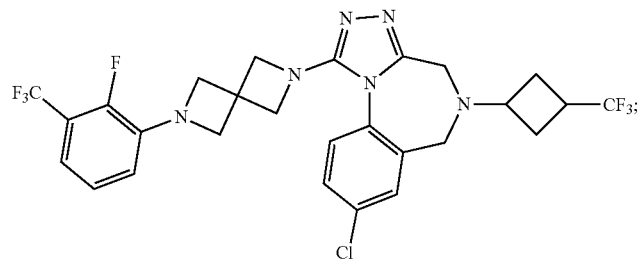 [SMILES: Fc1c(N2CC3(C2)CN(c2nnc4n2-c2ccc(Cl)cc2CN(C2CC(C(F)(F)F)C2)C4)C3)cccc1C(F)(F)F] |
| 649 | 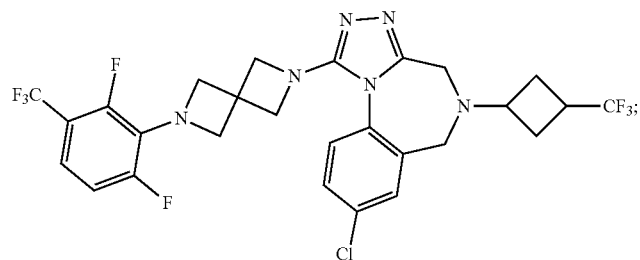 [SMILES: Fc1ccc(C(F)(F)F)c(F)c1N1CC2(C1)CN(c1nnc3n1-c1ccc(Cl)cc1CN(C1CC(C(F)(F)F)C1)C3)C2] |
| 650 | 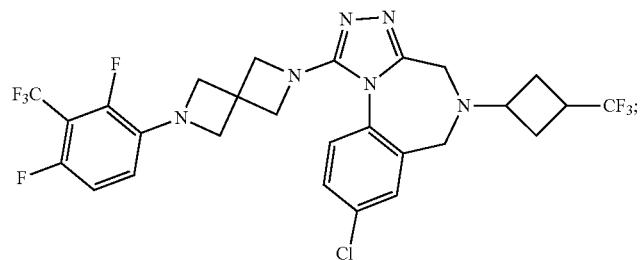 [SMILES: Fc1ccc(N2CC3(C2)CN(c2nnc4n2-c2ccc(Cl)cc2CN(C2CC(C(F)(F)F)C2)C4)C3)c(F)c1C(F)(F)F] |
| 651 | 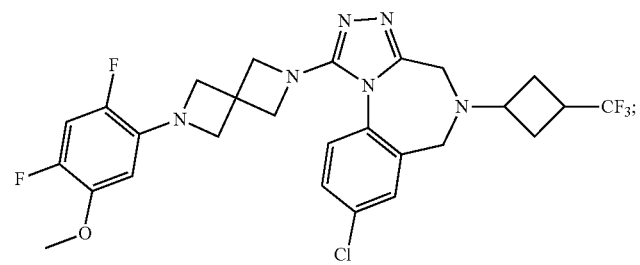 [SMILES: COc1cc(N2CC3(C2)CN(c2nnc4n2-c2ccc(Cl)cc2CN(C2CC(C(F)(F)F)C2)C4)C3)c(F)cc1F] |
| 652 | 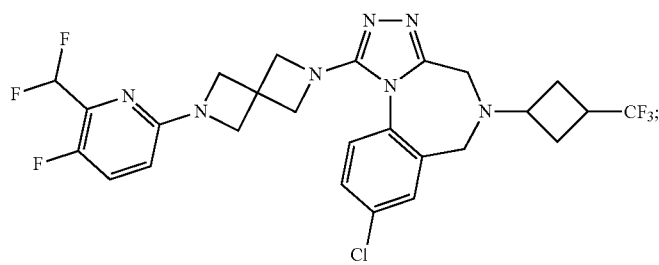 [SMILES: Fc1ccc(N2CC3(C2)CN(c2nnc4n2-c2ccc(Cl)cc2CN(C2CC(C(F)(F)F)C2)C4)C3)nc1C(F)F] |

-continued

| Compound No. | Structure |
|---|---|
| 653 | (structure) |
| 654 | (structure) |
| 655 | (structure) |
| 656 | (structure) |
| 657 | (structure) |
| 658 | (structure) |

-continued

| Compound No. | Structure |
|---|---|
| 659 | (structure) |
| 660 | (structure) |
| 661 | (structure) |
| 662 | (structure) |
| 663 | (structure) |
| 664 | (structure) |

-continued

| Compound No. | Structure |
|---|---|
| 665 | 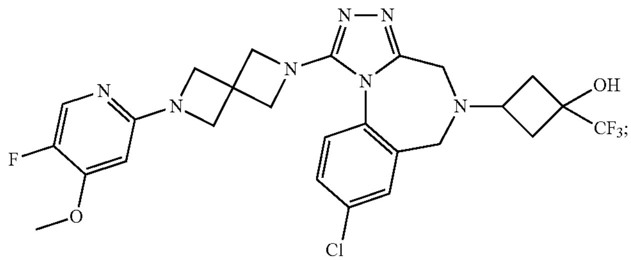 [SMILES: COc1cc(N2CC3(C2)CN(c2nnc4n2-c2ccc(Cl)cc2CN(C2CC(O)(C(F)(F)F)C2)C4)C3)ncc1F] |
| 667 | 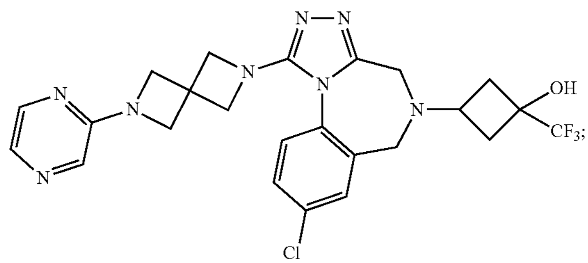 [SMILES: OC1(C(F)(F)F)CC(N2Cc3cc(Cl)ccc3-n3c(nnc3N3CC4(CN(c5cnccn5)C4)C3)C2)C1] |
| 668 | 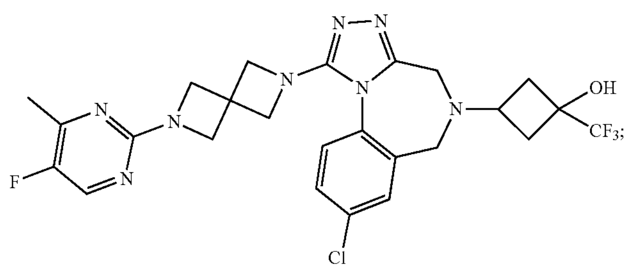 [SMILES: Cc1nc(N2CC3(C2)CN(c2nnc4n2-c2ccc(Cl)cc2CN(C2CC(O)(C(F)(F)F)C2)C4)C3)ncc1F] |
| 669 | 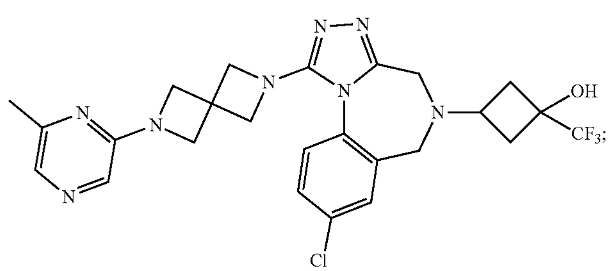 [SMILES: Cc1cncc(N2CC3(C2)CN(c2nnc4n2-c2ccc(Cl)cc2CN(C2CC(O)(C(F)(F)F)C2)C4)C3)n1] |
| 670 | 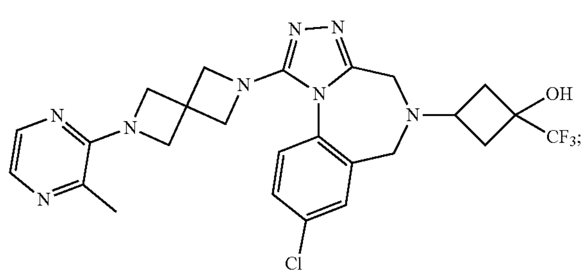 [SMILES: Cc1nccnc1N1CC2(C1)CN(c1nnc3n1-c1ccc(Cl)cc1CN(C1CC(O)(C(F)(F)F)C1)C3)C2] |
| 671 | 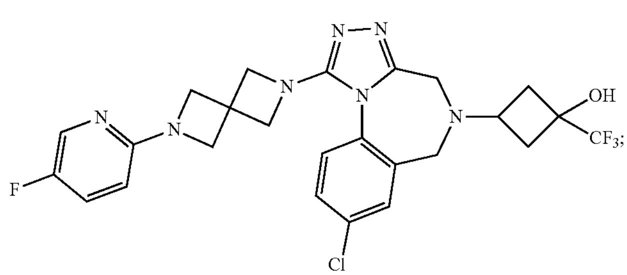 [SMILES: OC1(C(F)(F)F)CC(N2Cc3cc(Cl)ccc3-n3c(nnc3N3CC4(CN(c5ncc(F)cn5)C4)C3)C2)C1] |

-continued

| Compound No. | Structure |
|---|---|
| 672 | (structure) |
| 673 | (structure) |
| 674 | (structure) |
| 675 | (structure) |
| 676 | (structure) |
| 677 | (structure) |

| Compound No. | Structure |
|---|---|
| 678 | (structure) |
| 679 | (structure) |
| 680 | (structure) |
| 681 | (structure) |
| 682 | (structure) |

| Compound No. | Structure |
|---|---|
| 683 | (structure image) |
| 684 | (structure image) |
| 685 | (structure image) |
| 686 | (structure image) |
| 687 | (structure image) |
| 688 | (structure image) |

| Compound No. | Structure |
|---|---|
| 689 | 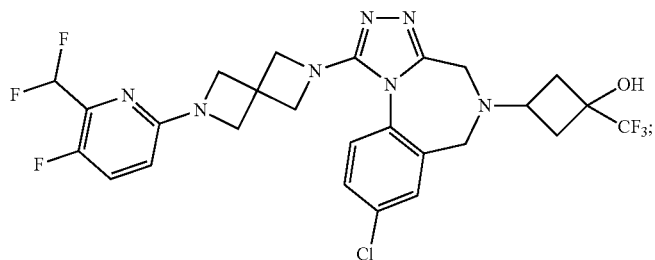 [SMILES: OC1(C(F)(F)F)CC(N2Cc3cc(Cl)ccc3-n3c(nnc3N3CC4(CN(c5ccc(F)c(C(F)F)n5)C4)C3)C2)C1] |
| 690 | 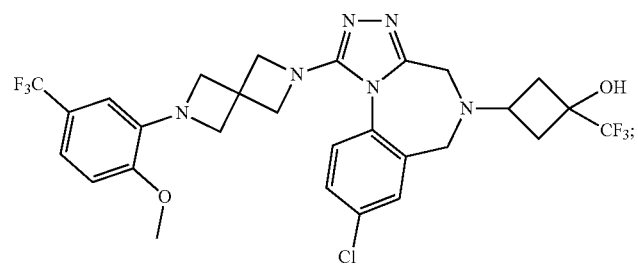 [SMILES: COc1ccc(C(F)(F)F)cc1N1CC2(C1)CN(c1nnc3n1-c1ccc(Cl)cc1CN(C1CC(O)(C(F)(F)F)C1)C3)C2] |
| 691 | 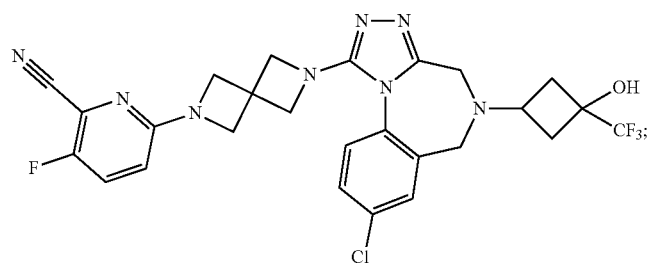 [SMILES: N#Cc1nc(N2CC3(C2)CN(c2nnc4n2-c2ccc(Cl)cc2CN(C2CC(O)(C(F)(F)F)C2)C4)C3)ccc1F] |
| 692 | 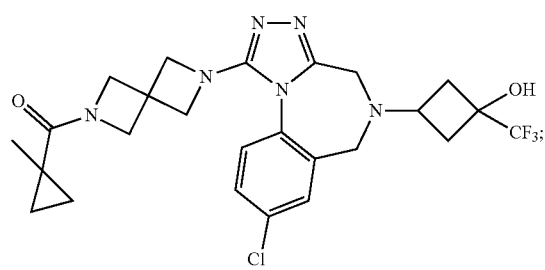 [SMILES: CC1(C(=O)N2CC3(C2)CN(c2nnc4n2-c2ccc(Cl)cc2CN(C2CC(O)(C(F)(F)F)C2)C4)C3)CC1] |
| 693 | 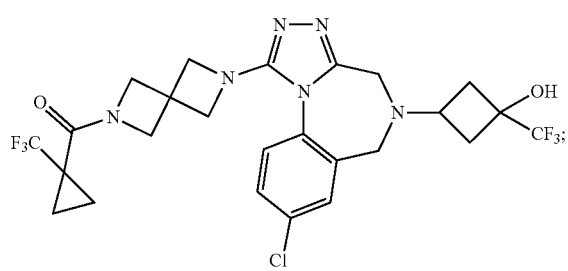 [SMILES: O=C(N1CC2(C1)CN(c1nnc3n1-c1ccc(Cl)cc1CN(C1CC(O)(C(F)(F)F)C1)C3)C2)C1(C(F)(F)F)CC1] |

| Compound No. | Structure |
| --- | --- |
| 694 | 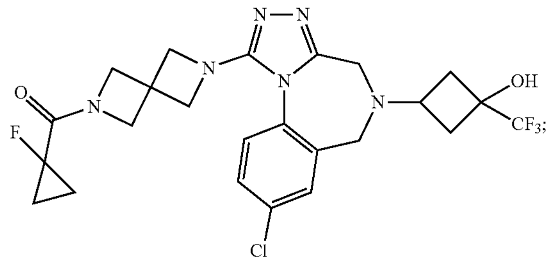 [SMILES: O=C(N1CC2(C1)CN(c1nnc3n1-c1ccc(Cl)cc1CN(C1CC(O)(C(F)(F)F)C1)C3)C2)C1(F)CC1] |
| 695 | 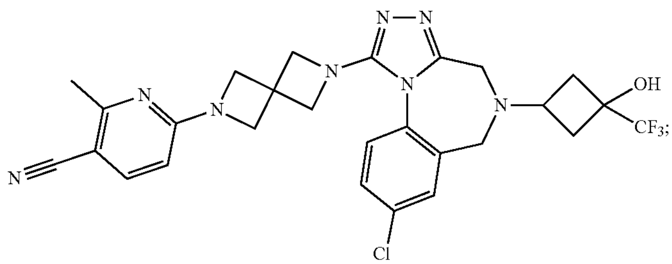 [SMILES: Cc1nc(N2CC3(C2)CN(c2nnc4n2-c2ccc(Cl)cc2CN(C2CC(O)(C(F)(F)F)C2)C4)C3)ccc1C#N] |
| 696 | 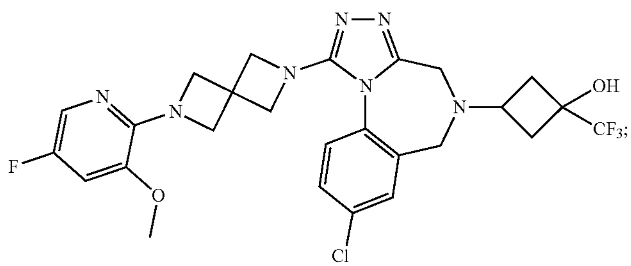 [SMILES: COc1cc(F)cnc1N1CC2(C1)CN(c1nnc3n1-c1ccc(Cl)cc1CN(C1CC(O)(C(F)(F)F)C1)C3)C2] |
| 697 | 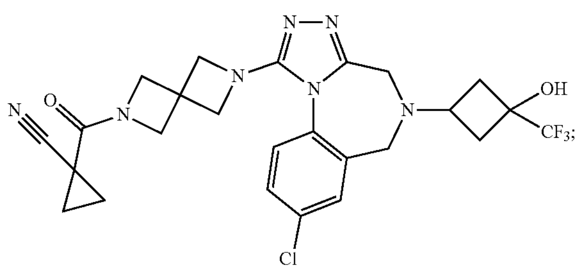 [SMILES: N#CC1(C(=O)N2CC3(C2)CN(c2nnc4n2-c2ccc(Cl)cc2CN(C2CC(O)(C(F)(F)F)C2)C4)C3)CC1] |
| 698 | 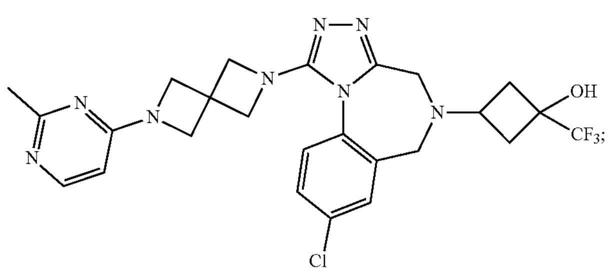 [SMILES: Cc1nccc(N2CC3(C2)CN(c2nnc4n2-c2ccc(Cl)cc2CN(C2CC(O)(C(F)(F)F)C2)C4)C3)n1] |
| 699 | 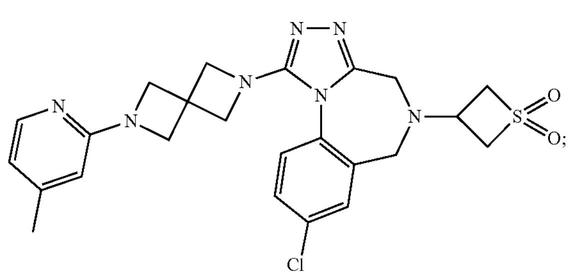 [SMILES: Cc1ccnc(N2CC3(C2)CN(c2nnc4n2-c2ccc(Cl)cc2CN(C2CS(=O)(=O)C2)C4)C3)c1] |

| Compound No. | Structure |
|---|---|
| 700 | 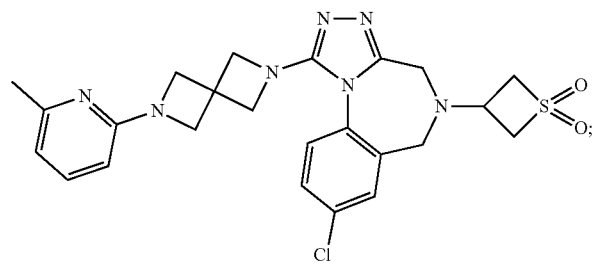 [SMILES: Cc1cccc(N2CC3(C2)CN(c2nnc4n2-c2ccc(Cl)cc2CN(C2CS(=O)(=O)C2)C4)C3)n1] |
| 701 | 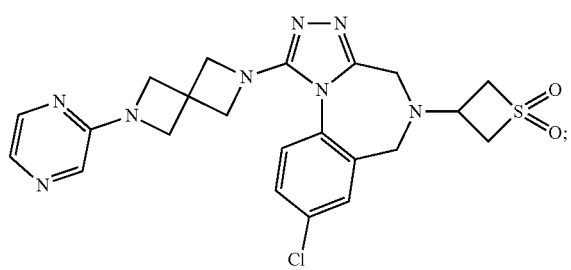 [SMILES: O=S1(=O)CC(N2Cc3cc(Cl)ccc3-n3c(nnc3N3CC4(CN(c5cnccn5)C4)C3)C2)C1] |
| 702 | 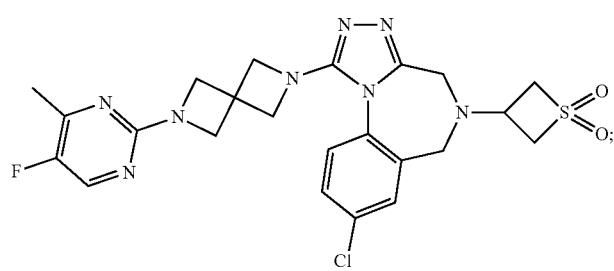 |
| 703 | 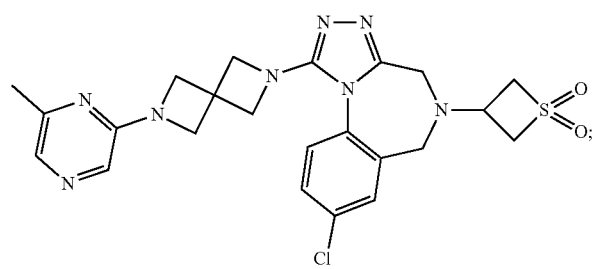 [SMILES: Cc1cncc(N2CC3(C2)CN(c2nnc4n2-c2ccc(Cl)cc2CN(C2CS(=O)(=O)C2)C4)C3)n1] |
| 704 | 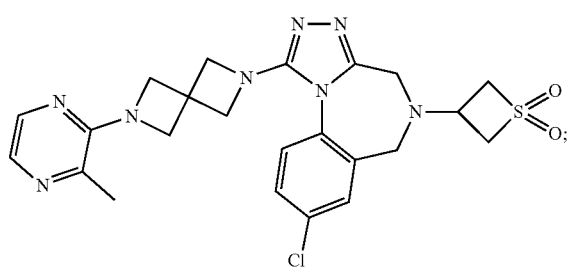 [SMILES: Cc1nccnc1N1CC2(C1)CN(c1nnc3n1-c1ccc(Cl)cc1CN(C1CS(=O)(=O)C1)C3)C2] |

-continued

| Compound No. | Structure |
|---|---|
| 705 | 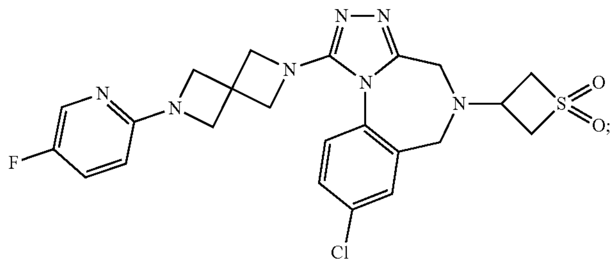 [SMILES: O=S1(=O)CC(N2Cc3cc(Cl)ccc3-n3c(nnc3N3CC4(CN(c5ccc(F)cn5)C4)C3)C2)C1] |
| 706 | 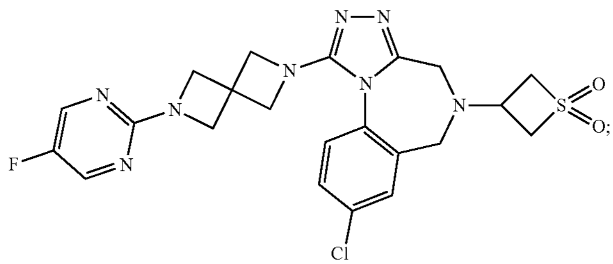 [SMILES: O=S1(=O)CC(N2Cc3cc(Cl)ccc3-n3c(nnc3N3CC4(CN(c5ncc(F)cn5)C4)C3)C2)C1] |
| 707 | 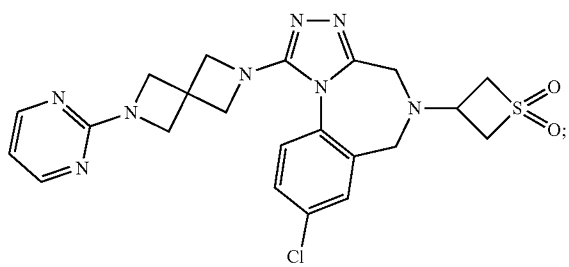 [SMILES: O=S1(=O)CC(N2Cc3cc(Cl)ccc3-n3c(nnc3N3CC4(CN(c5ncccn5)C4)C3)C2)C1] |
| 708 | 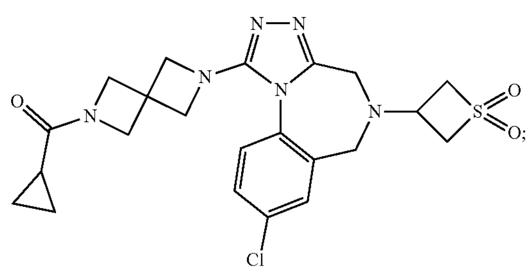 [SMILES: O=C(C1CC1)N1CC2(C1)CN(c1nnc3n1-c1ccc(Cl)cc1CN(C1CS(=O)(=O)C1)C3)C2] |
| 709 | 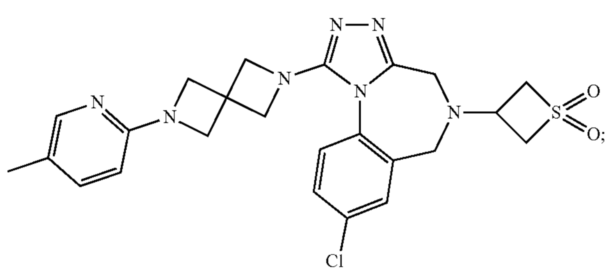 [SMILES: Cc1ccc(N2CC3(C2)CN(c2nnc4n2-c2ccc(Cl)cc2CN(C2CS(=O)(=O)C2)C4)C3)nc1] |
| 710 | 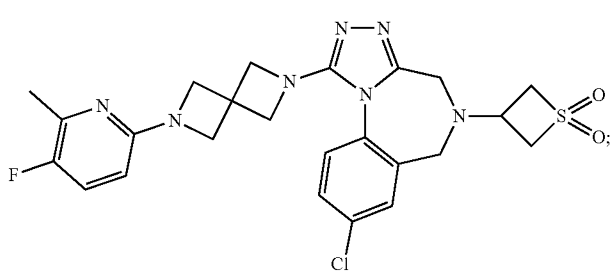 [SMILES: Cc1nc(N2CC3(C2)CN(c2nnc4n2-c2ccc(Cl)cc2CN(C2CS(=O)(=O)C2)C4)C3)ccc1F] |

-continued
| Compound No. | Structure |
|---|---|
| 711 | 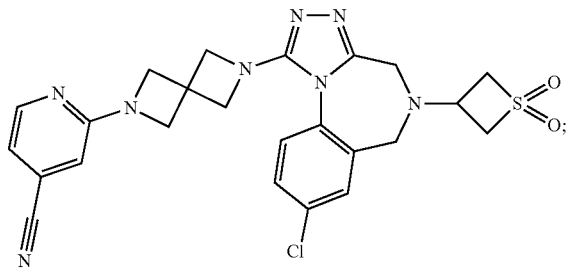 [SMILES: N#Cc1ccnc(N2CC3(C2)CN(c2nnc4n2-c2ccc(Cl)cc2CN(C2CS(=O)(=O)C2)C4)C3)c1] |
| 712 | 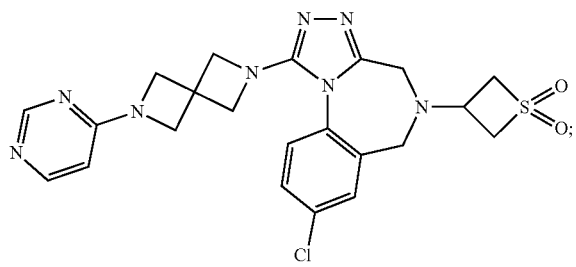 [SMILES: O=S1(=O)CC(N2Cc3cc(Cl)ccc3-n3c(nnc3N3CC4(CN(c5ccncn5)C4)C3)C2)C1] |
| 713 | 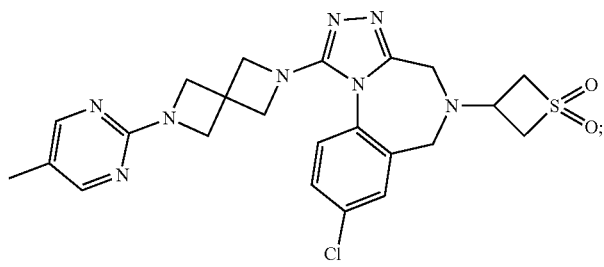 [SMILES: Cc1cnc(N2CC3(C2)CN(c2nnc4n2-c2ccc(Cl)cc2CN(C2CS(=O)(=O)C2)C4)C3)nc1] |
| 714 | 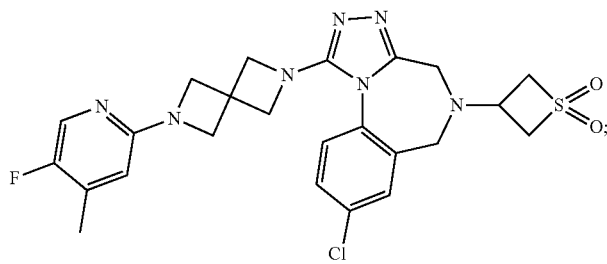 [SMILES: Cc1cc(N2CC3(C2)CN(c2nnc4n2-c2ccc(Cl)cc2CN(C2CS(=O)(=O)C2)C4)C3)ncc1F] |
| 715 | 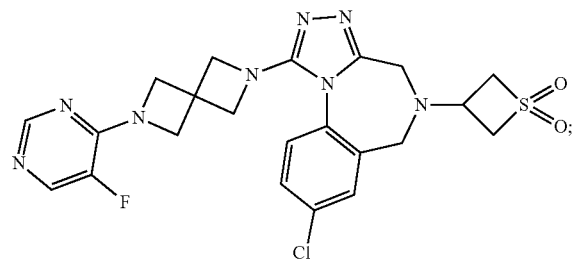 [SMILES: O=S1(=O)CC(N2Cc3cc(Cl)ccc3-n3c(nnc3N3CC4(CN(c5ncncc5F)C4)C3)C2)C1] |

-continued

| Compound No. | Structure |
|---|---|
| 716 | 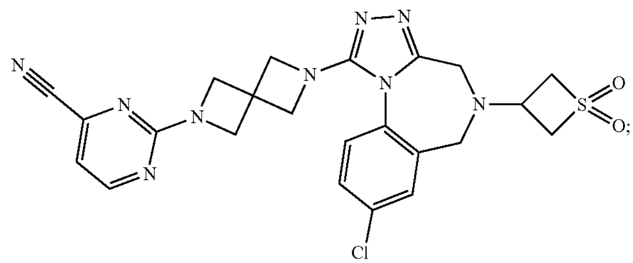 [SMILES: N#Cc1ccnc(N2CC3(C2)CN(c2nnc4n2-c2ccc(Cl)cc2CN(C2CS(=O)(=O)C2)C4)C3)n1] |
| 717 | 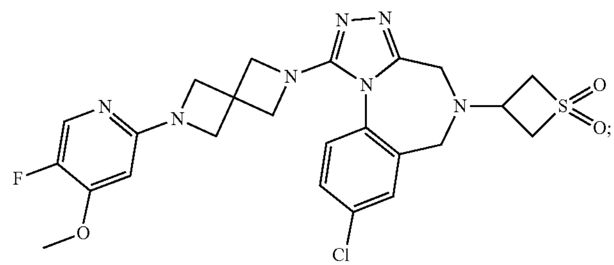 [SMILES: COc1cc(N2CC3(C2)CN(c2nnc4n2-c2ccc(Cl)cc2CN(C2CS(=O)(=O)C2)C4)C3)ncc1F] |
| 718 | 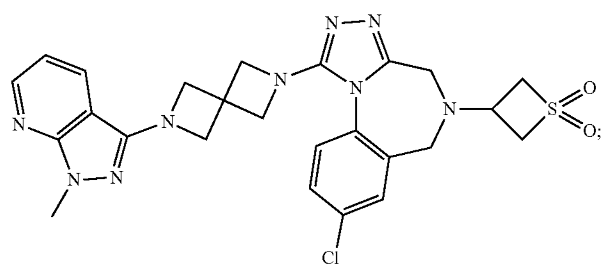 [SMILES: Cn1nc(N2CC3(C2)CN(c2nnc4n2-c2ccc(Cl)cc2CN(C2CS(=O)(=O)C2)C4)C3)c2cccnc21] |
| 719 | 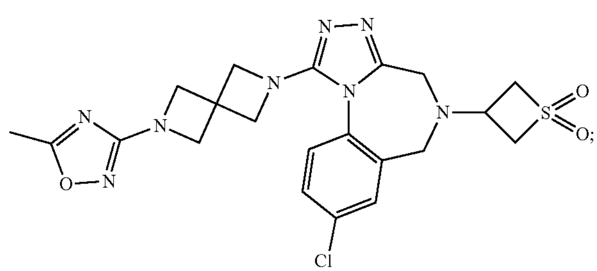 [SMILES: Cc1nc(N2CC3(C2)CN(c2nnc4n2-c2ccc(Cl)cc2CN(C2CS(=O)(=O)C2)C4)C3)no1] |
| 720 | 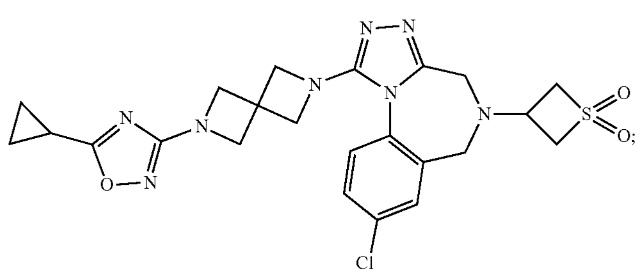 [SMILES: O=S1(=O)CC(N2Cc3cc(Cl)ccc3-n3c(nnc3N3CC4(CN(c5noc(C6CC6)n5)C4)C3)C2)C1] |
| 721 | 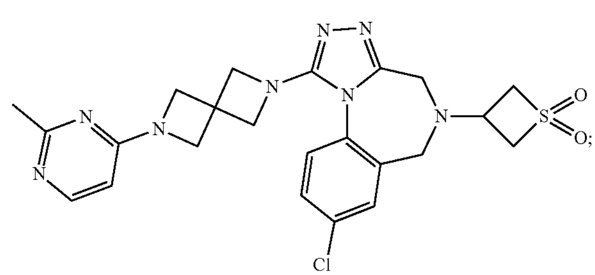 [SMILES: Cc1nccc(N2CC3(C2)CN(c2nnc4n2-c2ccc(Cl)cc2CN(C2CS(=O)(=O)C2)C4)C3)n1] |

-continued
| Compound No. | Structure |
|---|---|
| 722 | 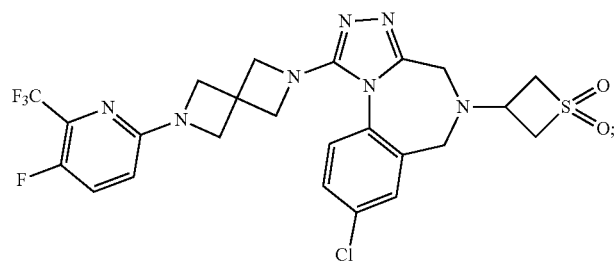 [SMILES: O=S1(=O)CC(N2Cc3cc(Cl)ccc3-n3c(nnc3N3CC4(CN(c5ccc(F)c(C(F)(F)F)n5)C4)C3)C2)C1] |
| 723 | 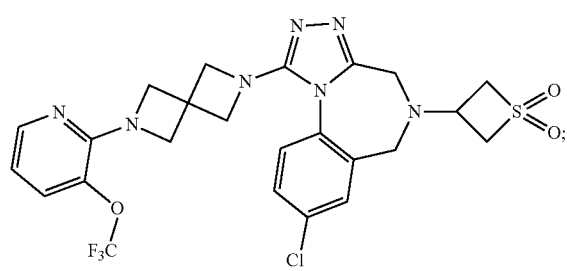 [SMILES: O=S1(=O)CC(N2Cc3cc(Cl)ccc3-n3c(nnc3N3CC4(CN(c5ncccc5OC(F)(F)F)C4)C3)C2)C1] |
| 724 | 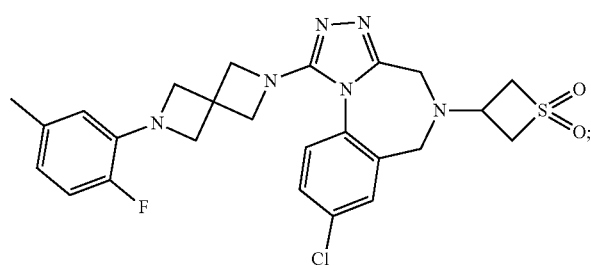 [SMILES: Cc1ccc(F)c(N2CC3(C2)CN(c2nnc4n2-c2ccc(Cl)cc2CN(C2CS(=O)(=O)C2)C4)C3)c1] |
| 725 | 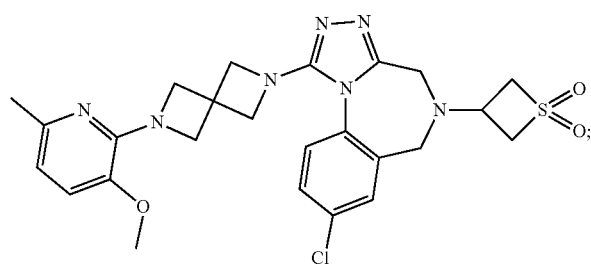 [SMILES: COc1ccc(C)nc1N1CC2(C1)CN(c1nnc3n1-c1ccc(Cl)cc1CN(C1CS(=O)(=O)C1)C3)C2] |
| 726 | 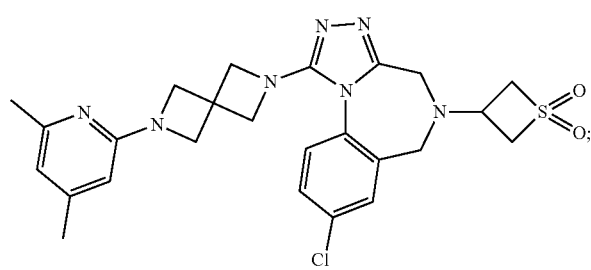 [SMILES: Cc1cc(C)nc(N2CC3(C2)CN(c2nnc4n2-c2ccc(Cl)cc2CN(C2CS(=O)(=O)C2)C4)C3)c1] |

| Compound No. | Structure |
|---|---|
| 727 | (structure) |
| 728 | (structure) |
| 729 | (structure) |
| 730 | (structure) |
| 731 | (structure) |
| 732 | (structure) |

| Compound No. | Structure |
|---|---|
| 733 | 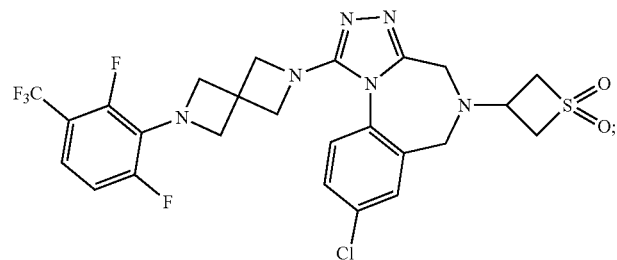 [SMILES: O=S1(=O)CC(N2Cc3cc(Cl)ccc3-n3c(nnc3N3CC4(CN(c5nc(C(F)(F)F)ccc5F)C4)C3)C2)C1] |
| 734 | 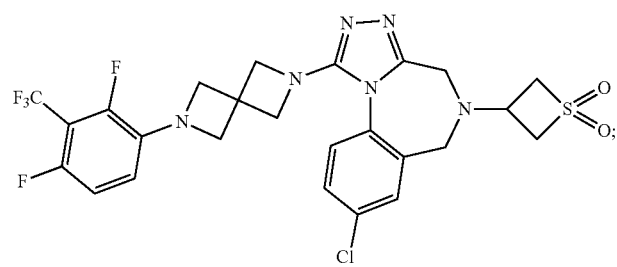 [SMILES: O=S1(=O)CC(N2Cc3cc(Cl)ccc3-n3c(nnc3N3CC4(CN(c5ccc(F)c(C(F)(F)F)c5F)C4)C3)C2)C1] |
| 735 | 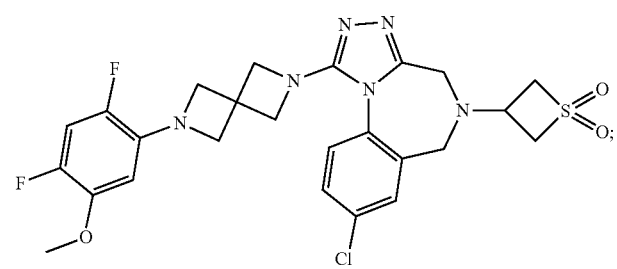 [SMILES: COc1cc(N2CC3(C2)CN(c2nnc4n2-c2ccc(Cl)cc2CN(C2CS(=O)(=O)C2)C4)C3)c(F)cc1F] |
| 736 | 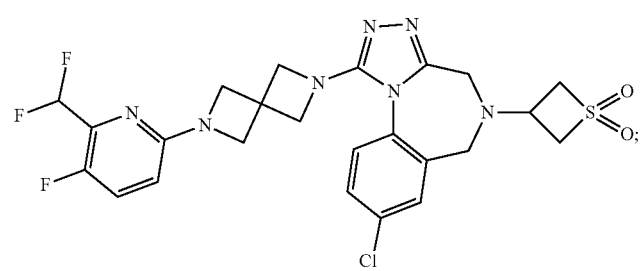 [SMILES: O=S1(=O)CC(N2Cc3cc(Cl)ccc3-n3c(nnc3N3CC4(CN(c5ccc(F)c(C(F)F)n5)C4)C3)C2)C1] |
| 737 | 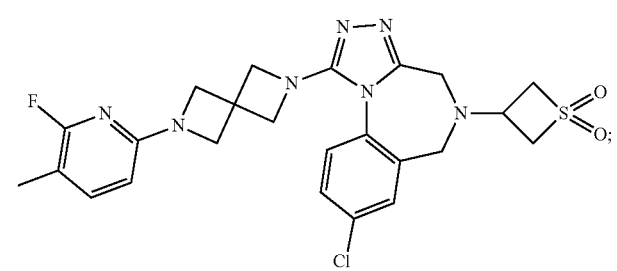 [SMILES: Cc1ccc(N2CC3(C2)CN(c2nnc4n2-c2ccc(Cl)cc2CN(C2CS(=O)(=O)C2)C4)C3)nc1F] |

| Compound No. | Structure |
|---|---|
| 738 | 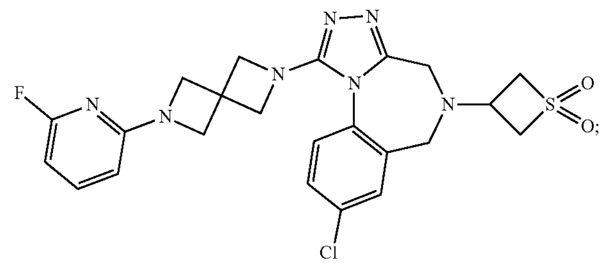 [SMILES: O=S1(=O)CC(N2Cc3cc(Cl)ccc3-n3c(nnc3N3CC4(CN(c5cccc(F)n5)C4)C3)C2)C1] |
| 739 | 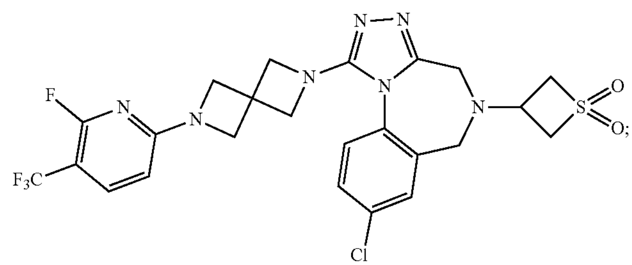 [SMILES: O=S1(=O)CC(N2Cc3cc(Cl)ccc3-n3c(nnc3N3CC4(CN(c5ccc(C(F)(F)F)c(F)n5)C4)C3)C2)C1] |
| 740 | 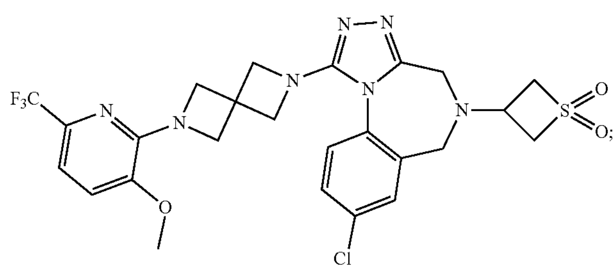 |
| 741 | 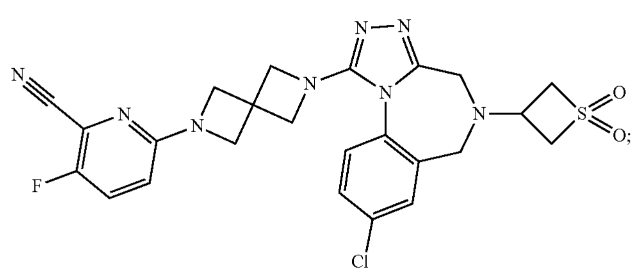 [SMILES: N#Cc1nc(N2CC3(C2)CN(c2nnc4n2-c2ccc(Cl)cc2CN(C2CS(=O)(=O)C2)C4)C3)ccc1F] |
| 742 | 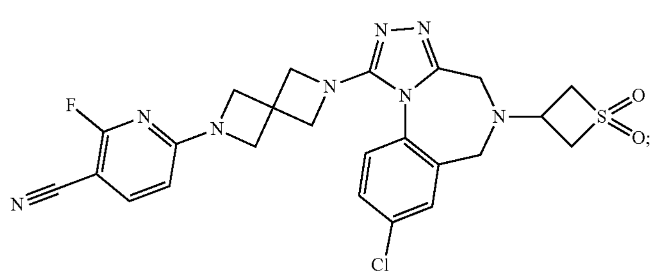 [SMILES: N#Cc1ccc(N2CC3(C2)CN(c2nnc4n2-c2ccc(Cl)cc2CN(C2CS(=O)(=O)C2)C4)C3)nc1F] |
| 743 | 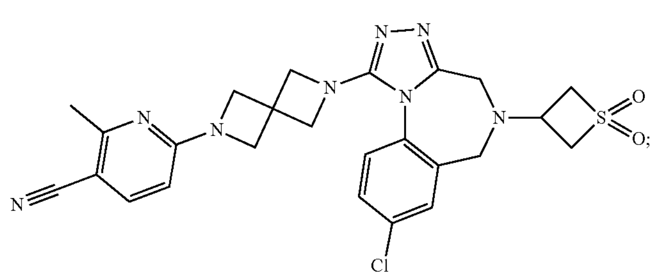 [SMILES: Cc1nc(N2CC3(C2)CN(c2nnc4n2-c2ccc(Cl)cc2CN(C2CS(=O)(=O)C2)C4)C3)ccc1C#N] |

-continued
| Compound No. | Structure |
|---|---|
| 744 | 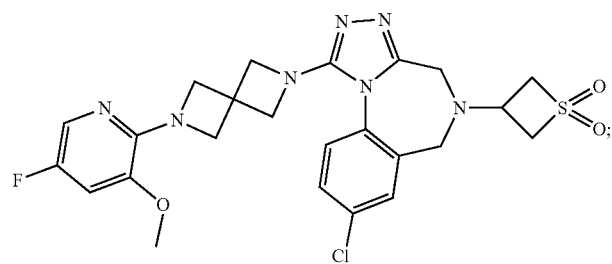 [SMILES: COc1cc(F)cnc1N1CC2(C1)CN(c1nnc3n1-c1ccc(Cl)cc1CN(C1CS(=O)(=O)C1)C3)C2] |
| 745 | 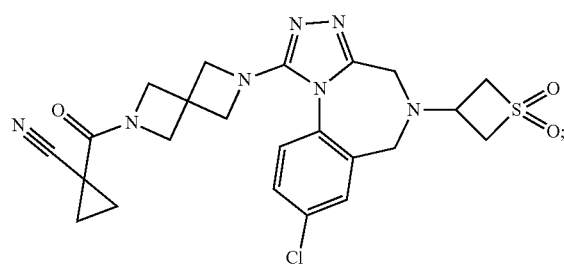 [SMILES: N#CC1(C(=O)N2CC3(C2)CN(c2nnc4n2-c2ccc(Cl)cc2CN(C2CS(=O)(=O)C2)C4)C3)CC1] |
| 746 | 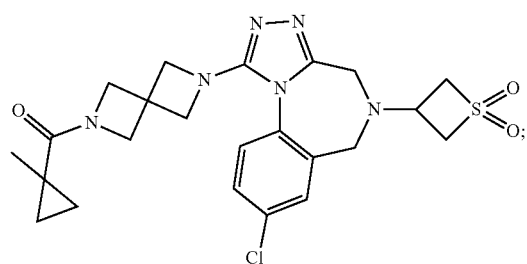 [SMILES: CC1(C(=O)N2CC3(C2)CN(c2nnc4n2-c2ccc(Cl)cc2CN(C2CS(=O)(=O)C2)C4)C3)CC1] |
| 747 | 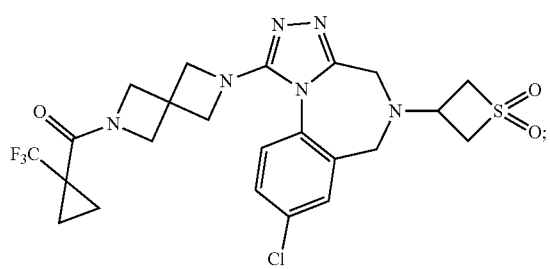 [SMILES: O=C(N1CC2(C1)CN(c1nnc3n1-c1ccc(Cl)cc1CN(C1CS(=O)(=O)C1)C3)C2)C1(C(F)(F)F)CC1] |
| 748 | 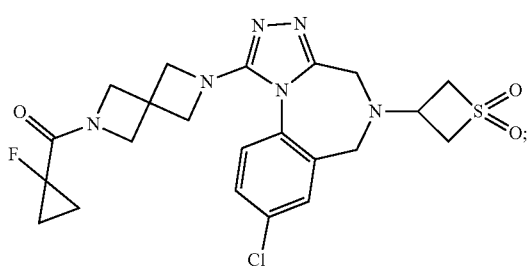 [SMILES: O=C(N1CC2(C1)CN(c1nnc3n1-c1ccc(Cl)cc1CN(C1CS(=O)(=O)C1)C3)C2)C1(F)CC1] |

-continued
| Compound No. | Structure |
|---|---|
| 749 | 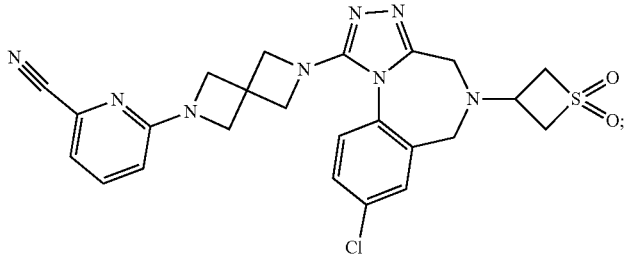 [SMILES: N#Cc1cccc(N2CC3(C2)CN(c2nnc4n2-c2ccc(Cl)cc2CN(C2CS(=O)(=O)C2)C4)C3)n1] |
| 750 | 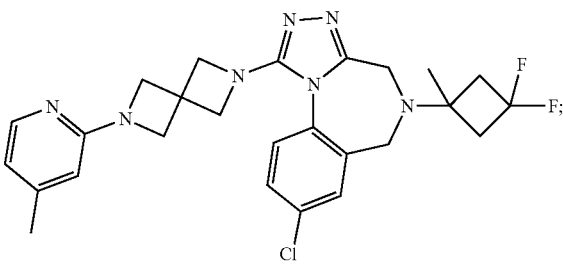 [SMILES: Cc1ccnc(N2CC3(C2)CN(c2nnc4n2-c2ccc(Cl)cc2CN(C2(C)CC(F)(F)C2)C4)C3)c1] |
| 751 | 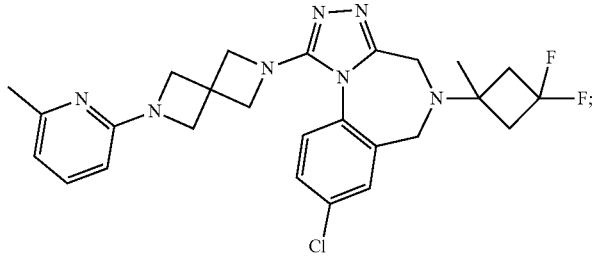 [SMILES: Cc1cccc(N2CC3(C2)CN(c2nnc4n2-c2ccc(Cl)cc2CN(C2(C)CC(F)(F)C2)C4)C3)n1] |
| 752 | 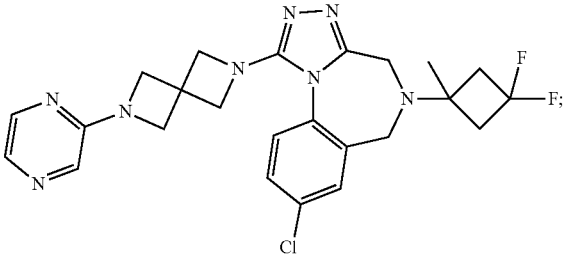 [SMILES: CC1(N2Cc3cc(Cl)ccc3-n3c(nnc3N3CC4(CN(c5cnccn5)C4)C3)C2)CC(F)(F)C1] |
| 753 | 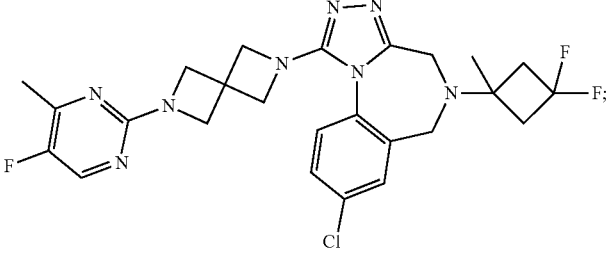 [SMILES: Cc1nc(N2CC3(C2)CN(c2nnc4n2-c2ccc(Cl)cc2CN(C2(C)CC(F)(F)C2)C4)C3)ncc1F] |
| 754 | 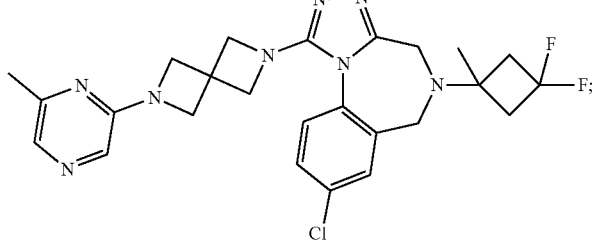 |

| Compound No. | Structure |
|---|---|
| 755 | 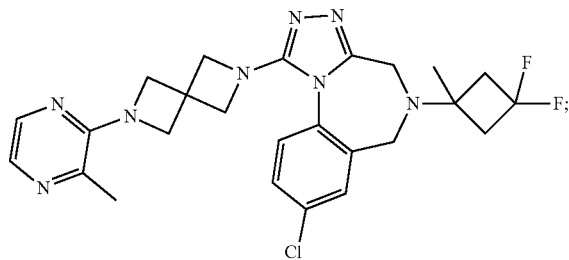 [SMILES: Cc1nccnc1N1CC2(C1)CN(c1nnc3n1-c1ccc(Cl)cc1CN(C1(C)CC(F)(F)C1)C3)C2] |
| 756 | 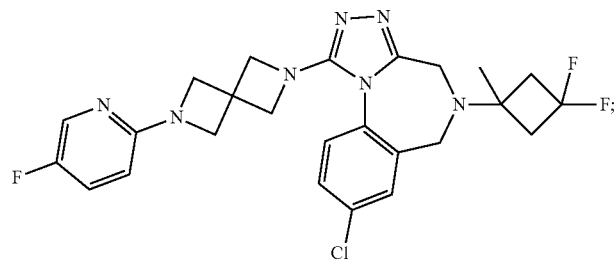 [SMILES: CC1(N2Cc3cc(Cl)ccc3-n3c(nnc3N3CC4(CN(c5ncc(F)cn5)C4)C3)C2)CC(F)(F)C1] |
| 757 | 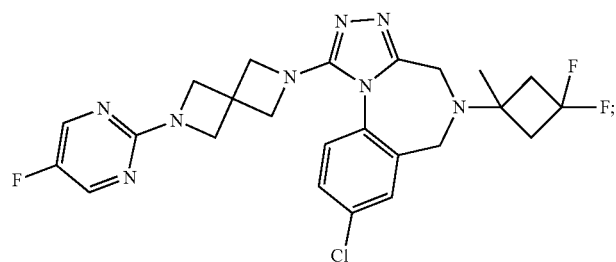 |
| 758 | 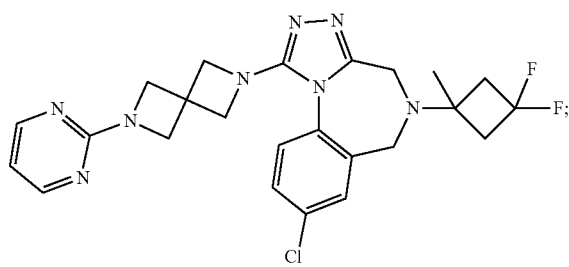 [SMILES: CC1(N2Cc3cc(Cl)ccc3-n3c(nnc3N3CC4(CN(c5ncccn5)C4)C3)C2)CC(F)(F)C1] |
| 759 | 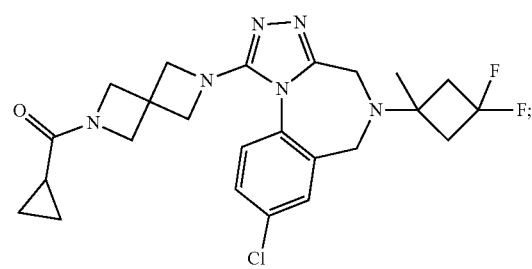 [SMILES: CC1(N2Cc3cc(Cl)ccc3-n3c(nnc3N3CC4(CN(C(=O)C5CC5)C4)C3)C2)CC(F)(F)C1] |

-continued
| Compound No. | Structure |
|---|---|
| 760 | 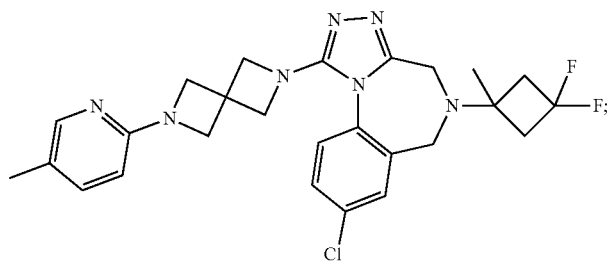 [SMILES: Cc1ccc(N2CC3(C2)CN(c2nnc4n2-c2ccc(Cl)cc2CN(C2(C)CC(F)(F)C2)C4)C3)nc1] |
| 761 | 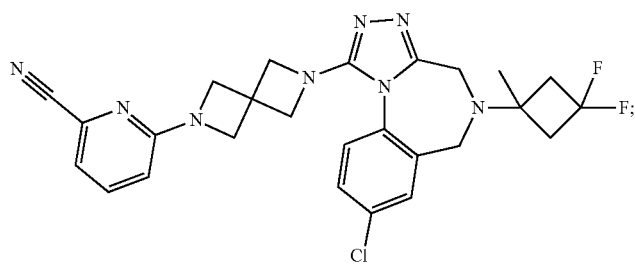 [SMILES: CC1(N2Cc3cc(Cl)ccc3-n3c(nnc3N3CC4(CN(c5cccc(C#N)n5)C4)C3)C2)CC(F)(F)C1] |
| 762 | 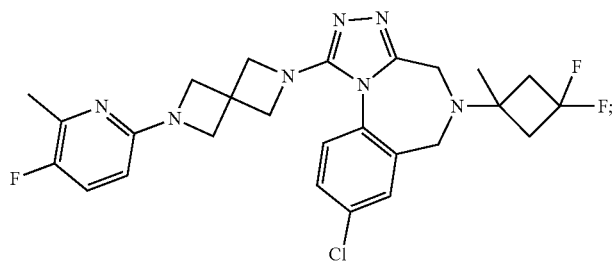 [SMILES: Cc1nc(N2CC3(C2)CN(c2nnc4n2-c2ccc(Cl)cc2CN(C2(C)CC(F)(F)C2)C4)C3)ccc1F] |
| 763 | 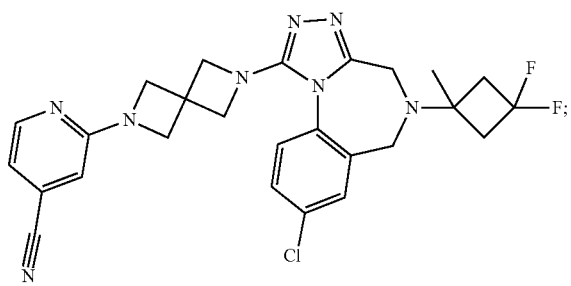 [SMILES: CC1(N2Cc3cc(Cl)ccc3-n3c(nnc3N3CC4(CN(c5cc(C#N)ccn5)C4)C3)C2)CC(F)(F)C1] |
| 764 | 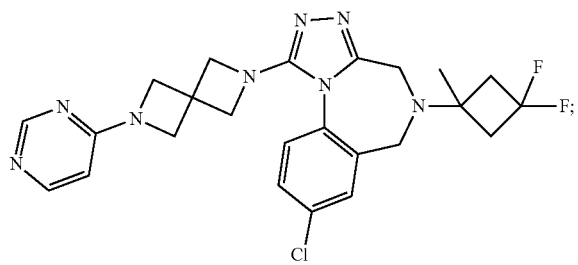 [SMILES: CC1(N2Cc3cc(Cl)ccc3-n3c(nnc3N3CC4(CN(c5ccncn5)C4)C3)C2)CC(F)(F)C1] |

-continued

| Compound No. | Structure |
|---|---|
| 765 | (structure) |
| 766 | (structure) |
| 767 | (structure) |
| 768 | (structure) |
| 769 | (structure) |
| 770 | (structure) |

-continued
| Compound No. | Structure |
|---|---|
| 771 | 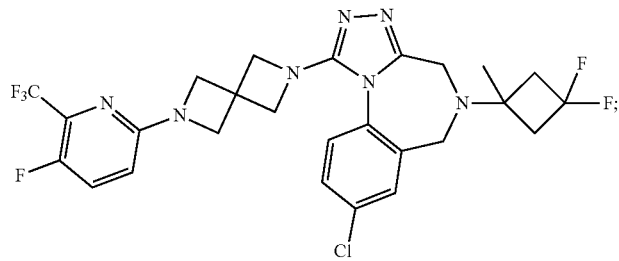 [SMILES: CC1(N2Cc3cc(Cl)ccc3-n3c(nnc3N3CC4(CN(c5ccc(F)c(C(F)(F)F)n5)C4)C3)C2)CC(F)(F)C1] |
| 772 | 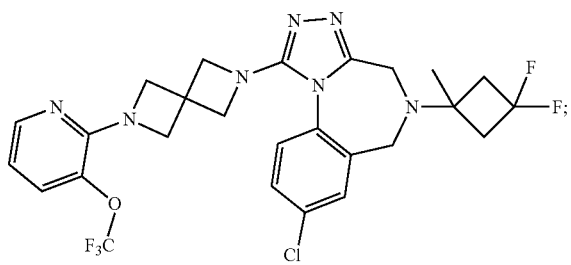 [SMILES: CC1(N2Cc3cc(Cl)ccc3-n3c(nnc3N3CC4(CN(c5ncccc5OC(F)(F)F)C4)C3)C2)CC(F)(F)C1] |
| 773 | 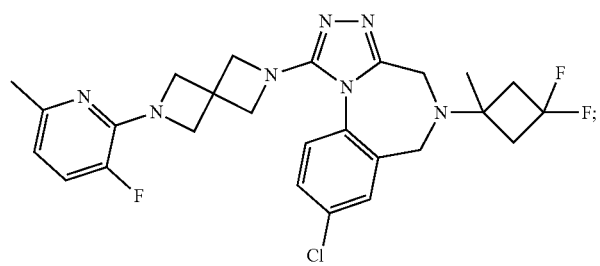 [SMILES: Cc1ccc(F)c(N2CC3(C2)CN(c2nnc4n2-c2ccc(Cl)cc2CN(C2(C)CC(F)(F)C2)C4)C3)n1] |
| 774 | 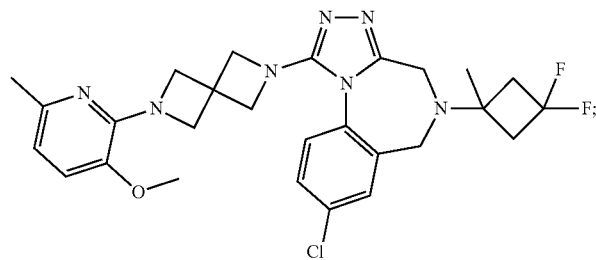 |
| 775 | 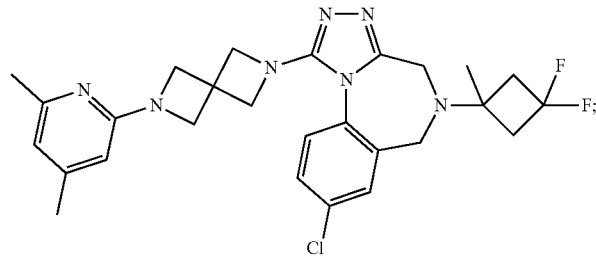 [SMILES: Cc1cc(C)nc(N2CC3(C2)CN(c2nnc4n2-c2ccc(Cl)cc2CN(C2(C)CC(F)(F)C2)C4)C3)c1] |
| 776 | 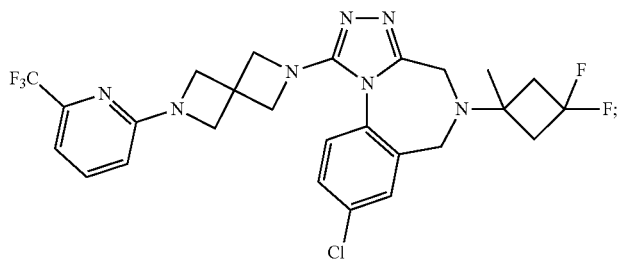 |

| Compound No. | Structure |
|---|---|
| 777 | 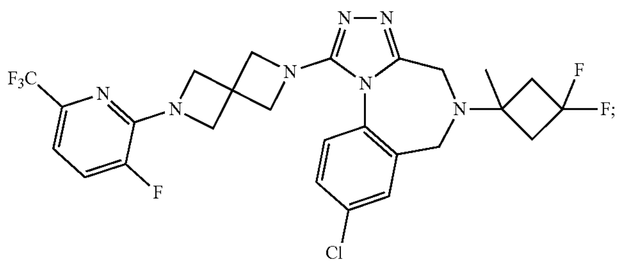 [SMILES: CC1(N2Cc3cc(Cl)ccc3-n3c(nnc3N3CC4(CN(c5nc(C(F)(F)F)ccc5F)C4)C3)C2)CC(F)(F)C1] |
| 778 | 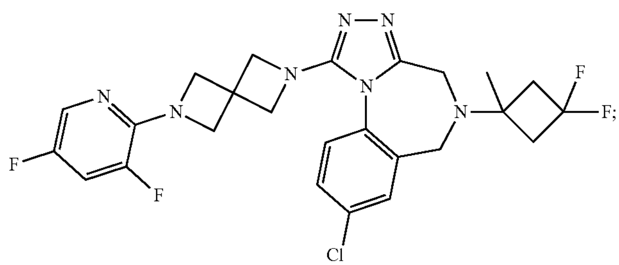 [SMILES: CC1(N2Cc3cc(Cl)ccc3-n3c(nnc3N3CC4(CN(c5ncc(F)cc5F)C4)C3)C2)CC(F)(F)C1] |
| 779 | 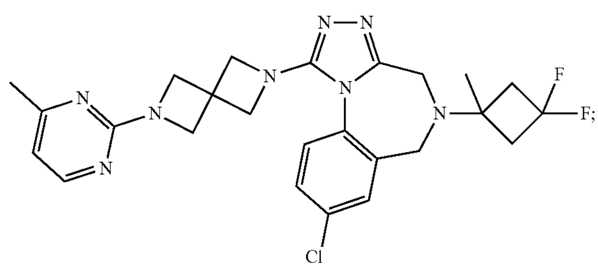 [SMILES: Cc1ccnc(N2CC3(C2)CN(c2nnc4n2-c2ccc(Cl)cc2CN(C2(C)CC(F)(F)C2)C4)C3)n1] |
| 780 | 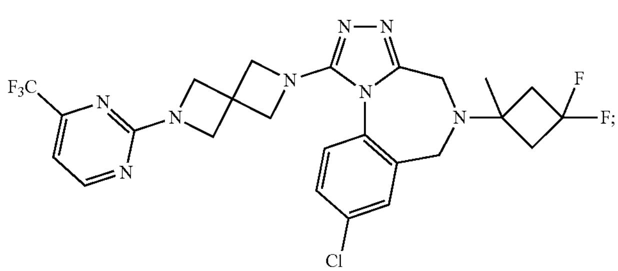 |
| 781 | 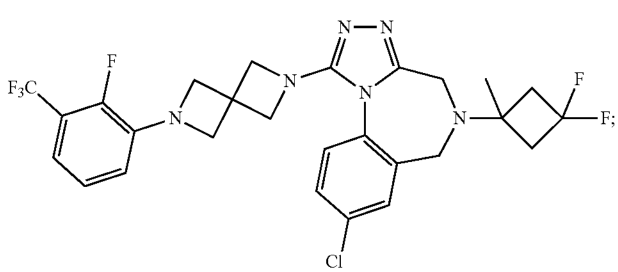 [SMILES: CC1(N2Cc3cc(Cl)ccc3-n3c(nnc3N3CC4(CN(c5cccc(C(F)(F)F)c5F)C4)C3)C2)CC(F)(F)C1] |
| 782 | 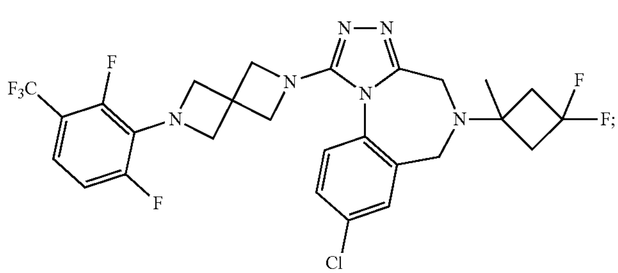 |

-continued
| Compound No. | Structure |
|---|---|
| 783 | 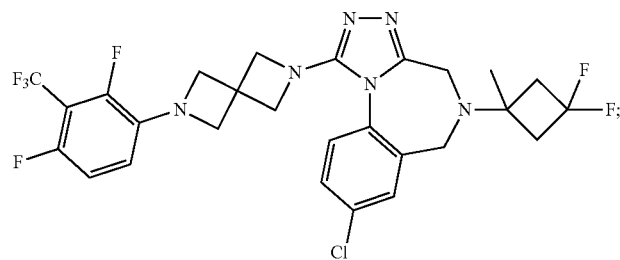 [SMILES: CC1(N2Cc3cc(Cl)ccc3-n3c(nnc3N3CC4(CN(c5ccc(F)c(C(F)(F)F)c5F)C4)C3)C2)CC(F)(F)C1] |
| 784 | 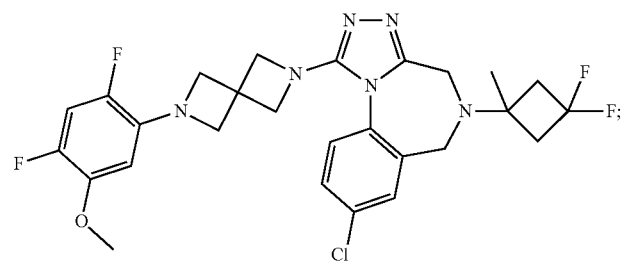 [SMILES: COc1cc(N2CC3(C2)CN(c2nnc4n2-c2ccc(Cl)cc2CN(C2(C)CC(F)(F)C2)C4)C3)c(F)cc1F] |
| 785 | 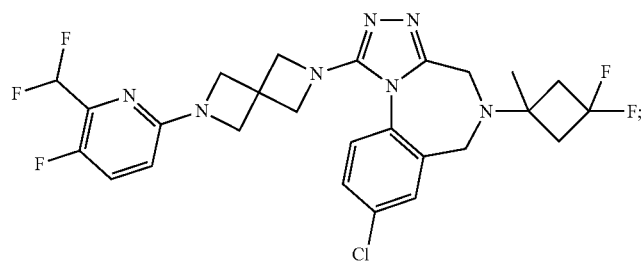 [SMILES: CC1(N2Cc3cc(Cl)ccc3-n3c(nnc3N3CC4(CN(c5ccc(F)c(C(F)F)n5)C4)C3)C2)CC(F)(F)C1] |
| 786 | 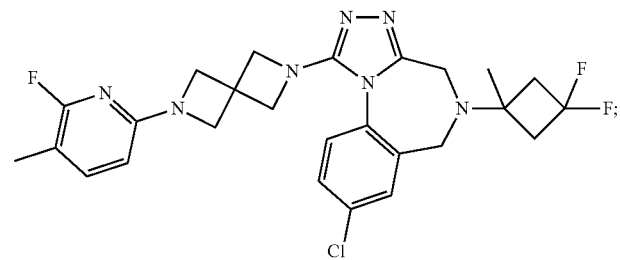 [SMILES: Cc1ccc(N2CC3(C2)CN(c2nnc4n2-c2ccc(Cl)cc2CN(C2(C)CC(F)(F)C2)C4)C3)nc1F] |
| 787 | 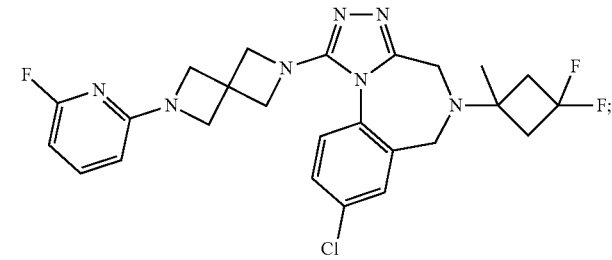 [SMILES: CC1(N2Cc3cc(Cl)ccc3-n3c(nnc3N3CC4(CN(c5cccc(F)n5)C4)C3)C2)CC(F)(F)C1] |
| 788 | 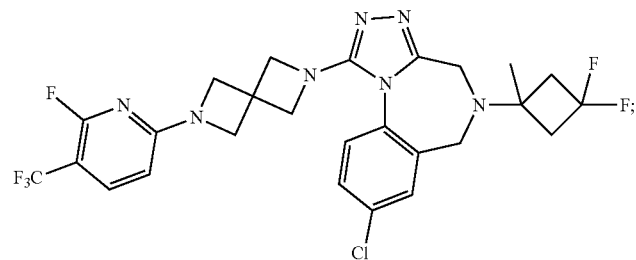 [SMILES: CC1(N2Cc3cc(Cl)ccc3-n3c(nnc3N3CC4(CN(c5ccc(C(F)(F)F)c(F)n5)C4)C3)C2)CC(F)(F)C1] |

-continued
| Compound No. | Structure |
|---|---|
| 789 | 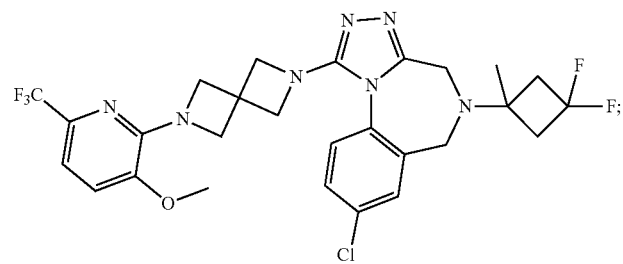 [SMILES: COc1ccc(C(F)(F)F)nc1N1CC2(C1)CN(c1nnc3n1-c1ccc(Cl)cc1CN(C1(C)CC(F)(F)C1)C3)C2] |
| 790 | 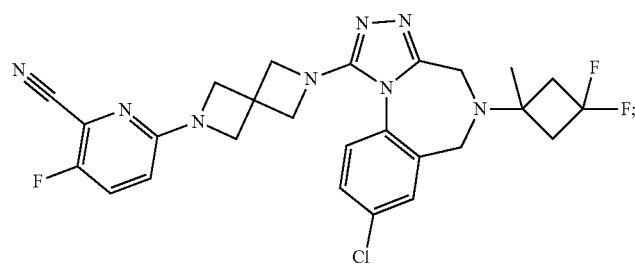 [SMILES: CC1(N2Cc3cc(Cl)ccc3-n3c(nnc3N3CC4(CN(c5ccc(F)c(C#N)n5)C4)C3)C2)CC(F)(F)C1] |
| 791 | 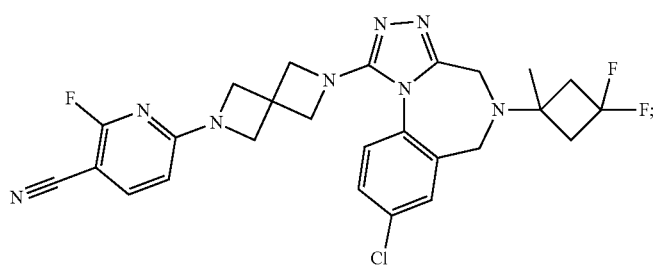 [SMILES: CC1(N2Cc3cc(Cl)ccc3-n3c(nnc3N3CC4(CN(c5ccc(C#N)c(F)n5)C4)C3)C2)CC(F)(F)C1] |
| 792 | 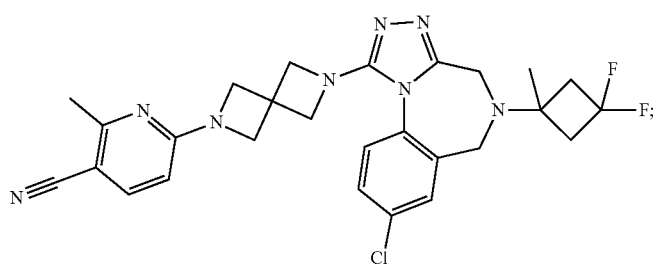 [SMILES: Cc1nc(N2CC3(C2)CN(c2nnc4n2-c2ccc(Cl)cc2CN(C2(C)CC(F)(F)C2)C4)C3)ccc1C#N] |
| 793 | 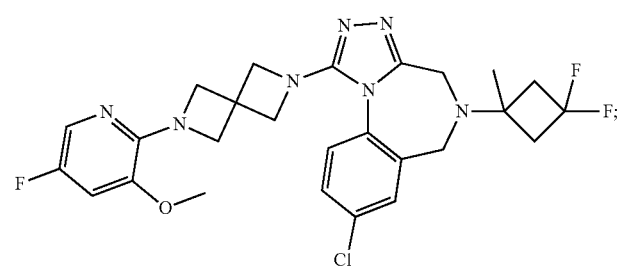 [SMILES: COc1cc(F)cnc1N1CC2(C1)CN(c1nnc3n1-c1ccc(Cl)cc1CN(C1(C)CC(F)(F)C1)C3)C2] |

-continued

| Compound No. | Structure |
|---|---|
| 794 | 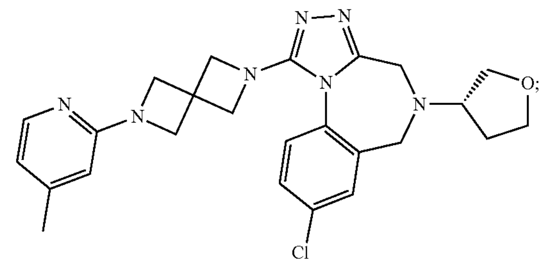 [SMILES: Cc1ccnc(N2CC3(C2)CN(c2nnc4n2-c2ccc(Cl)cc2CN([C@H]2CCOC2)C4)C3)c1] |
| 795 | 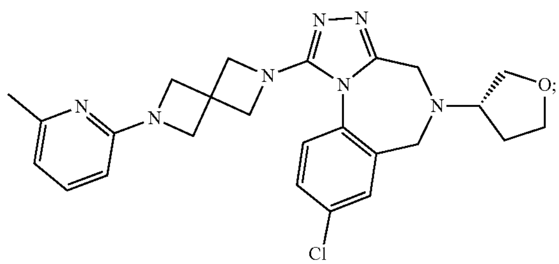 [SMILES: Cc1cccc(N2CC3(C2)CN(c2nnc4n2-c2ccc(Cl)cc2CN([C@H]2CCOC2)C4)C3)n1] |
| 796 | 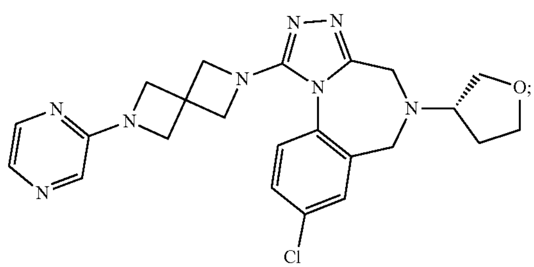 [SMILES: Clc1ccc2c(c1)CN([C@H]1CCOC1)Cc1nnc(N3CC4(CN(c5cnccn5)C4)C3)n1-2] |
| 797 | 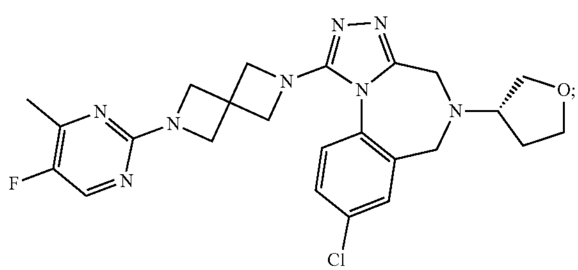 [SMILES: Cc1nc(N2CC3(C2)CN(c2nnc4n2-c2ccc(Cl)cc2CN([C@H]2CCOC2)C4)C3)ncc1F] |
| 798 | 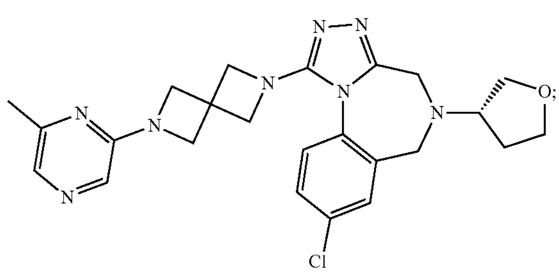 [SMILES: Cc1cncc(N2CC3(C2)CN(c2nnc4n2-c2ccc(Cl)cc2CN([C@H]2CCOC2)C4)C3)n1] |
| 799 | 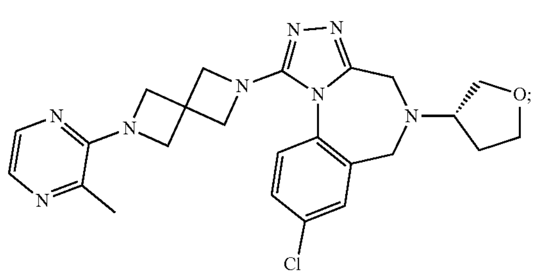 [SMILES: Cc1nccnc1N1CC2(C1)CN(c1nnc3n1-c1ccc(Cl)cc1CN([C@H]1CCOC1)C3)C2] |

| Compound No. | Structure |
|---|---|
| 800 | 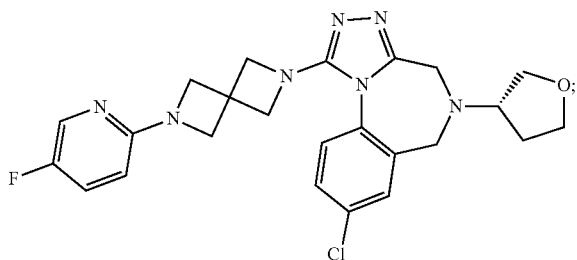 |
| 801 | 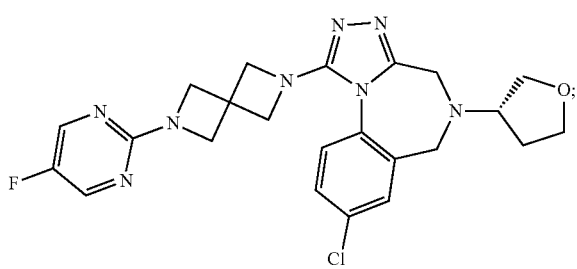 [SMILES: Fc1cnc(N2CC3(C2)CN(c2nnc4n2-c2ccc(Cl)cc2CN([C@H]2CCOC2)C4)C3)nc1] |
| 802 | 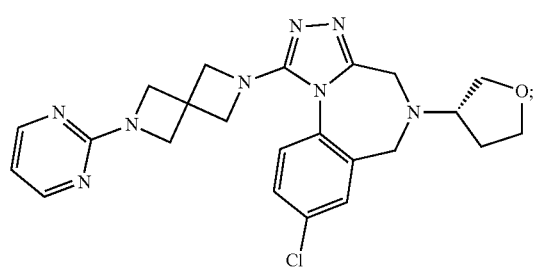 [SMILES: Clc1ccc2c(c1)CN([C@H]1CCOC1)Cc1nnc(N3CC4(CN(c5ncccn5)C4)C3)n1-2] |
| 803 | 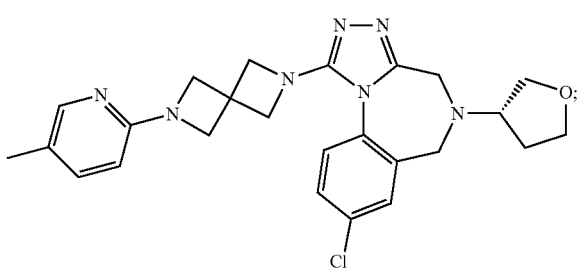 [SMILES: Cc1ccc(N2CC3(C2)CN(c2nnc4n2-c2ccc(Cl)cc2CN([C@H]2CCOC2)C4)C3)nc1] |
| 804 | 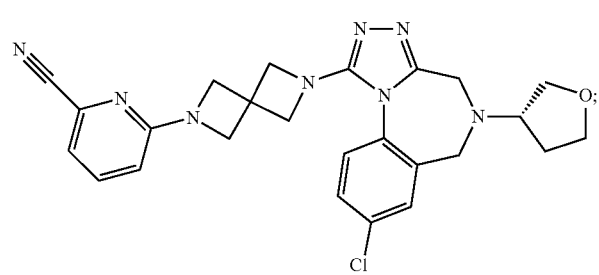 [SMILES: N#Cc1cccc(N2CC3(C2)CN(c2nnc4n2-c2ccc(Cl)cc2CN([C@H]2CCOC2)C4)C3)n1] |

-continued

| Compound No. | Structure |
|---|---|
| 805 | 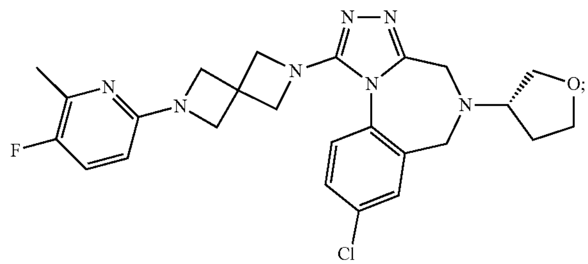 [SMILES: Cc1nc(N2CC3(C2)CN(c2nnc4n2-c2ccc(Cl)cc2CN([C@H]2CCOC2)C4)C3)ccc1F] |
| 806 | 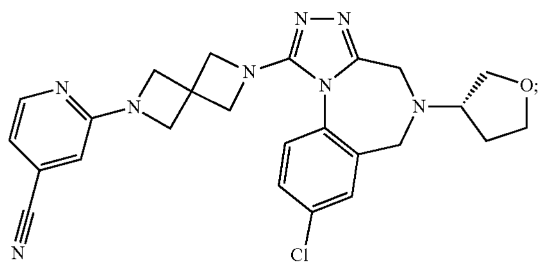 [SMILES: N#Cc1ccnc(N2CC3(C2)CN(c2nnc4n2-c2ccc(Cl)cc2CN([C@H]2CCOC2)C4)C3)c1] |
| 807 | 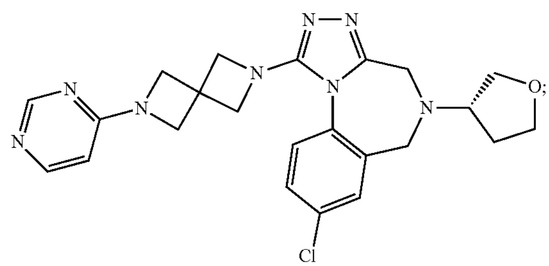 [SMILES: Clc1ccc2c(c1)CN([C@H]1CCOC1)Cc1nnc(N3CC4(CN(c5ccncn5)C4)C3)n1-2] |
| 808 | 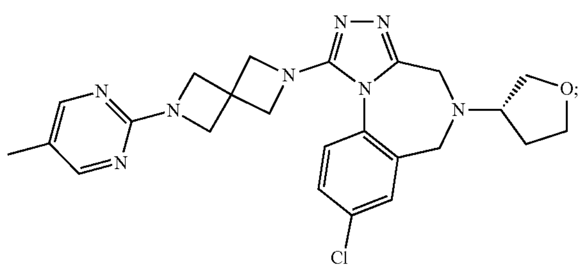 [SMILES: Cc1cnc(N2CC3(C2)CN(c2nnc4n2-c2ccc(Cl)cc2CN([C@H]2CCOC2)C4)C3)nc1] |
| 809 | 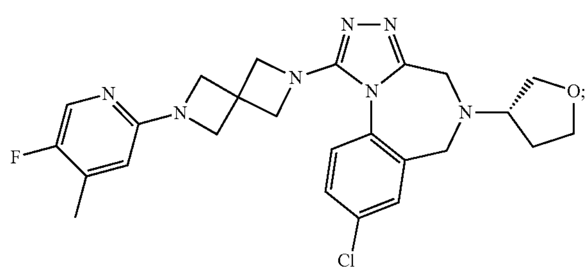 [SMILES: Cc1cc(N2CC3(C2)CN(c2nnc4n2-c2ccc(Cl)cc2CN([C@H]2CCOC2)C4)C3)ncc1F] |
| 810 | 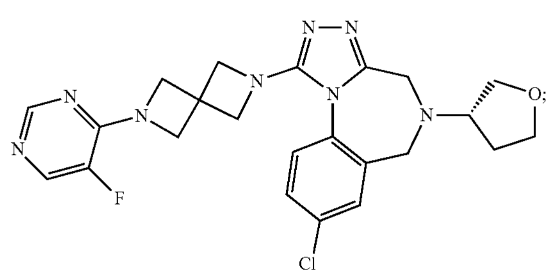 [SMILES: Fc1cncnc1N1CC2(C1)CN(c1nnc3n1-c1ccc(Cl)cc1CN([C@H]1CCOC1)C3)C2] |

| Compound No. | Structure |
|---|---|
| 811 | 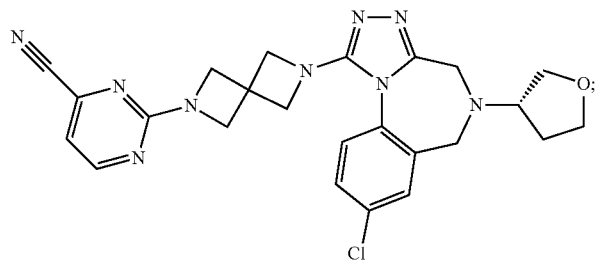 [SMILES: N#Cc1ccnc(N2CC3(C2)CN(c2nnc4n2-c2ccc(Cl)cc2CN([C@H]2CCOC2)C4)C3)n1] |
| 812 | 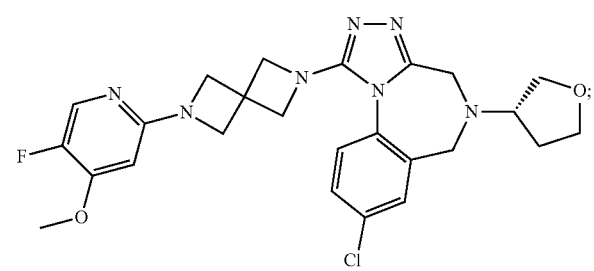 [SMILES: COc1cc(N2CC3(C2)CN(c2nnc4n2-c2ccc(Cl)cc2CN([C@H]2CCOC2)C4)C3)ncc1F] |
| 813 | 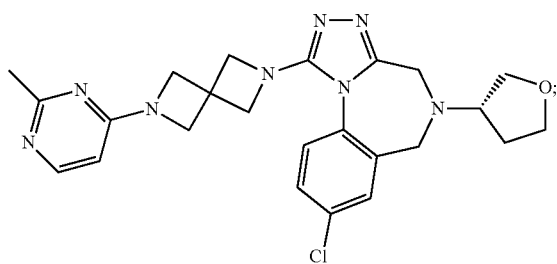 [SMILES: Cc1nccc(N2CC3(C2)CN(c2nnc4n2-c2ccc(Cl)cc2CN([C@H]2CCOC2)C4)C3)n1] |
| 814 | 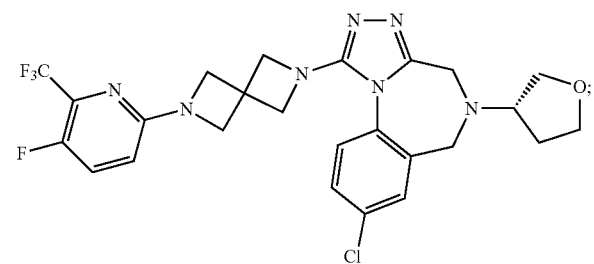 |
| 815 | 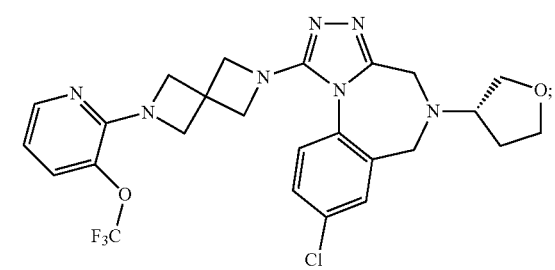 [SMILES: FC(F)(F)Oc1cccnc1N1CC2(C1)CN(c1nnc3n1-c1ccc(Cl)cc1CN([C@H]1CCOC1)C3)C2] |

-continued

| Compound No. | Structure |
|---|---|
| 816 | (structure) |
| 817 | (structure) |
| 818 | (structure) |
| 819 | (structure) |
| 820 | (structure) |
| 821 | (structure) |

| Compound No. | Structure |
|---|---|
| 822 | 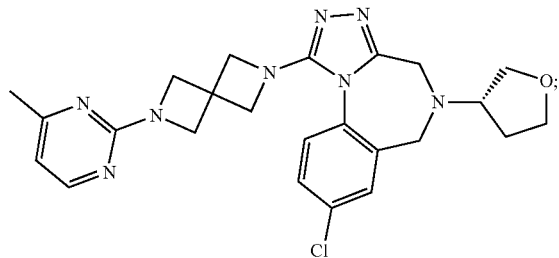 [SMILES: Cc1ccnc(N2CC3(C2)CN(c2nnc4n2-c2ccc(Cl)cc2CN([C@H]2CCOC2)C4)C3)n1] |
| 823 | 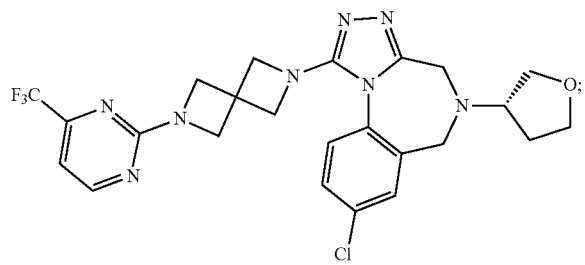 [SMILES: FC(F)(F)c1ccnc(N2CC3(C2)CN(c2nnc4n2-c2ccc(Cl)cc2CN([C@H]2CCOC2)C4)C3)n1] |
| 824 | 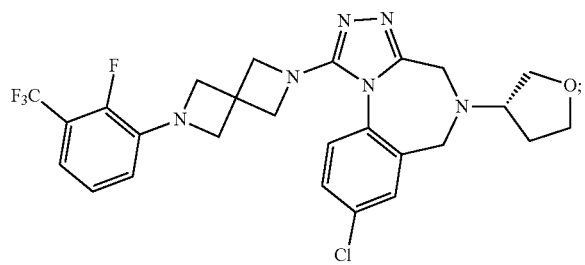 [SMILES: Fc1c(N2CC3(C2)CN(c2nnc4n2-c2ccc(Cl)cc2CN([C@H]2CCOC2)C4)C3)cccc1C(F)(F)F] |
| 825 | 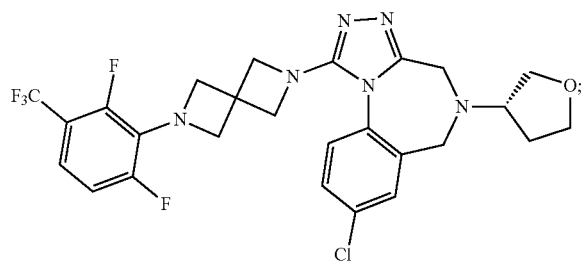 [SMILES: Fc1ccc(C(F)(F)F)c(F)c1N1CC2(C1)CN(c1nnc3n1-c1ccc(Cl)cc1CN([C@H]1CCOC1)C3)C2] |
| 826 | 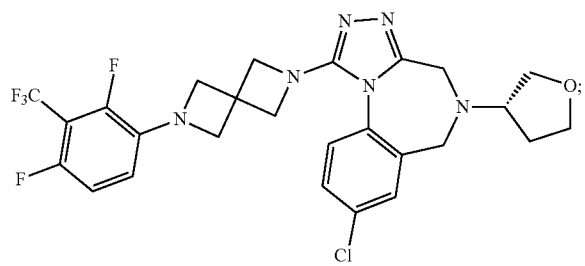 [SMILES: Fc1ccc(N2CC3(C2)CN(c2nnc4n2-c2ccc(Cl)cc2CN([C@H]2CCOC2)C4)C3)c(F)c1C(F)(F)F] |

-continued

| Compound No. | Structure |
|---|---|
| 827 | 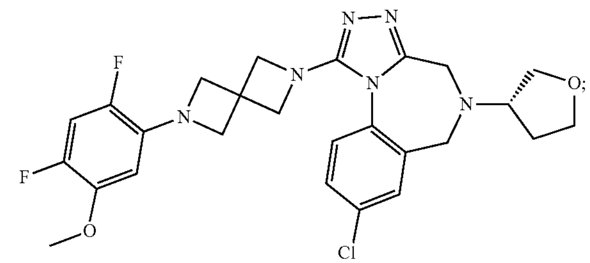 [SMILES: COc1cc(N2CC3(C2)CN(c2nnc4n2-c2ccc(Cl)cc2CN([C@H]2CCOC2)C4)C3)c(F)cc1F] |
| 828 | 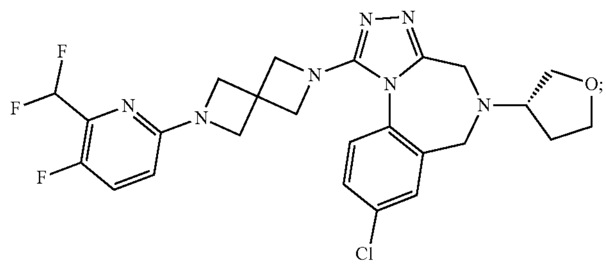 [SMILES: Fc1ccc(N2CC3(C2)CN(c2nnc4n2-c2ccc(Cl)cc2CN([C@H]2CCOC2)C4)C3)nc1C(F)F] |
| 829 | 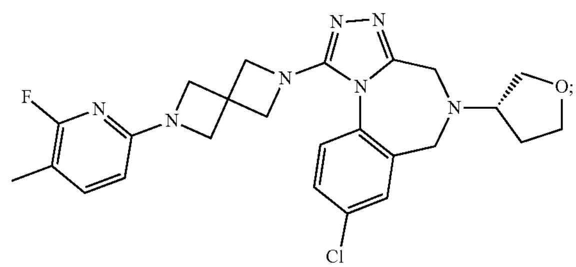 [SMILES: Cc1ccc(N2CC3(C2)CN(c2nnc4n2-c2ccc(Cl)cc2CN([C@H]2CCOC2)C4)C3)nc1F] |
| 830 | 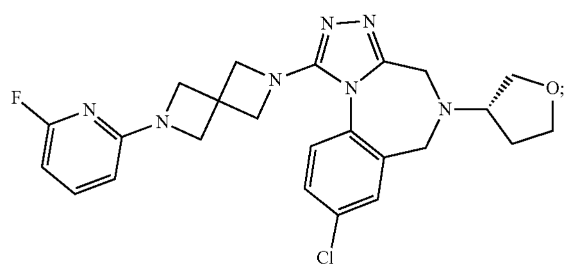 [SMILES: Fc1cccc(N2CC3(C2)CN(c2nnc4n2-c2ccc(Cl)cc2CN([C@H]2CCOC2)C4)C3)n1] |
| 831 | 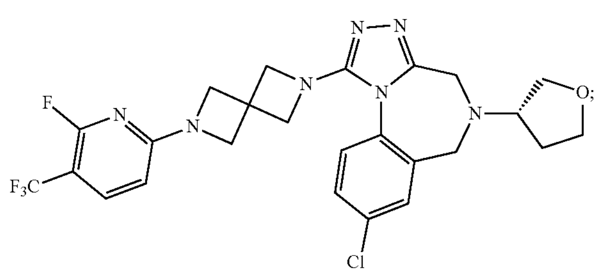 [SMILES: Fc1nc(N2CC3(C2)CN(c2nnc4n2-c2ccc(Cl)cc2CN([C@H]2CCOC2)C4)C3)ccc1C(F)(F)F] |
| 832 | 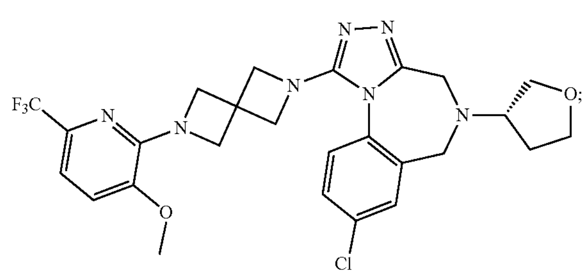 [SMILES: COc1ccc(C(F)(F)F)nc1N1CC2(C1)CN(c1nnc3n1-c1ccc(Cl)cc1CN([C@H]1CCOC1)C3)C2] |

| Compound No. | Structure |
|---|---|
| 833 | 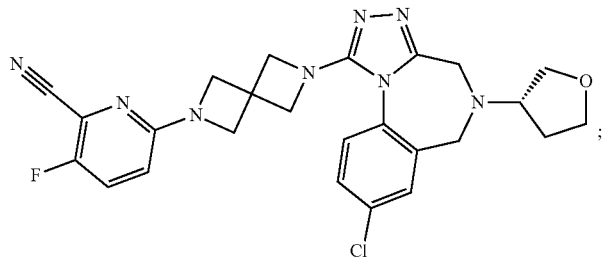 [SMILES: N#Cc1nc(N2CC3(C2)CN(c2nnc4n2-c2ccc(Cl)cc2CN([C@H]2CCOC2)C4)C3)ccc1F] |
| 834 | 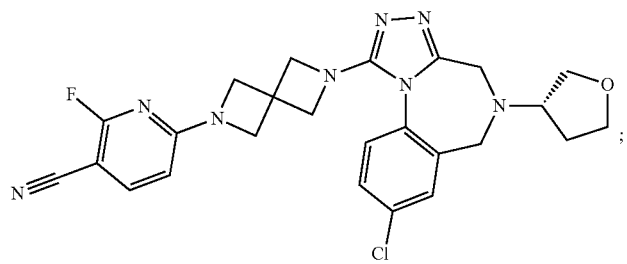 [SMILES: Cc1nc(N2CC3(C2)CN(c2nnc4n2-c2ccc(Cl)cc2CN([C@H]2CCOC2)C4)C3)ccc1C#N] |
| 835 | 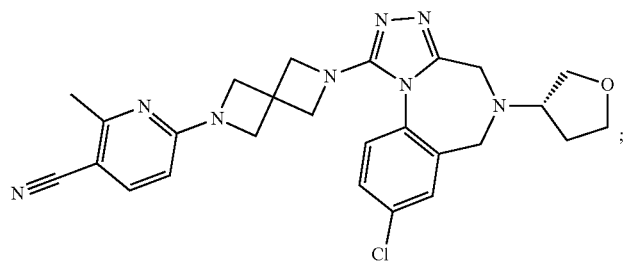 |
| 836 | 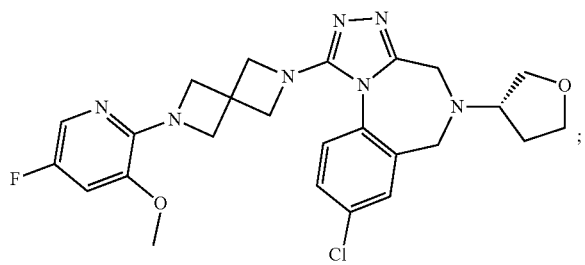 [SMILES: COc1cc(F)cnc1N1CC2(C1)CN(c1nnc3n1-c1ccc(Cl)cc1CN([C@H]1CCOC1)C3)C2] |
| 837 | 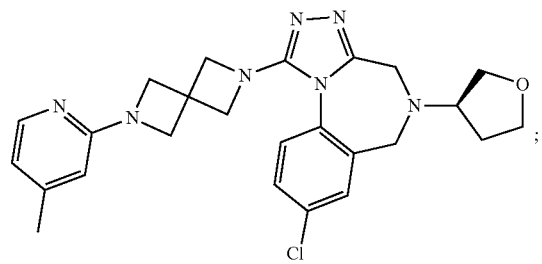 [SMILES: Cc1ccnc(N2CC3(C2)CN(c2nnc4n2-c2ccc(Cl)cc2CN([C@@H]2CCOC2)C4)C3)c1] |

-continued

| Compound No. | Structure |
|---|---|
| 838 | 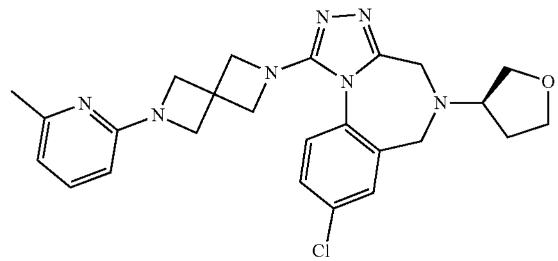 |
| 839 | 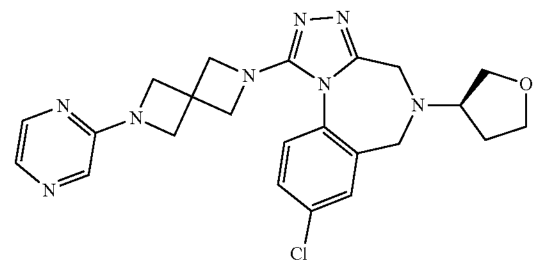 |
| 840 | 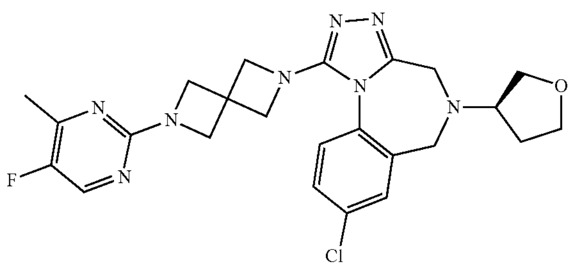 |
| 841 | 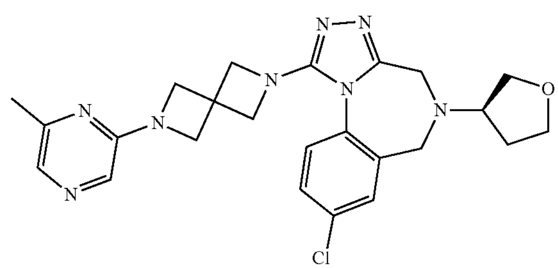 |
| 842 | 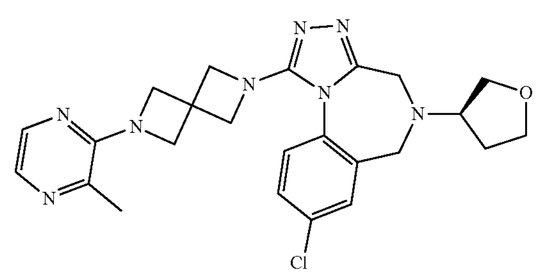 |
| 843 | 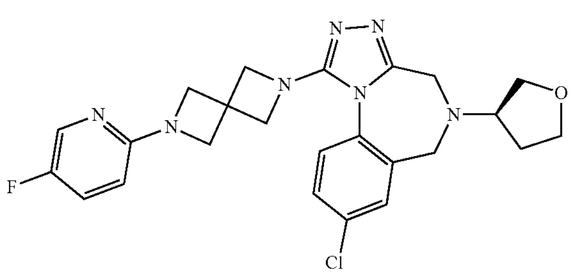 |

| Compound No. | Structure |
|---|---|
| 844 | 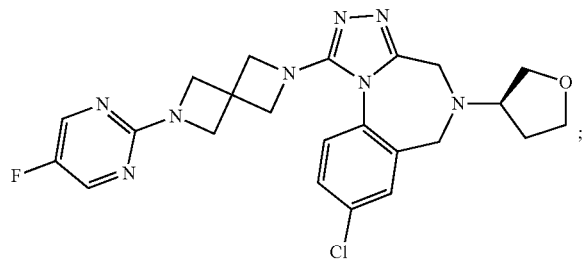 [SMILES: Fc1cnc(N2CC3(C2)CN(c2nnc4n2-c2ccc(Cl)cc2CN([C@@H]2CCOC2)C4)C3)nc1] ; |
| 845 | 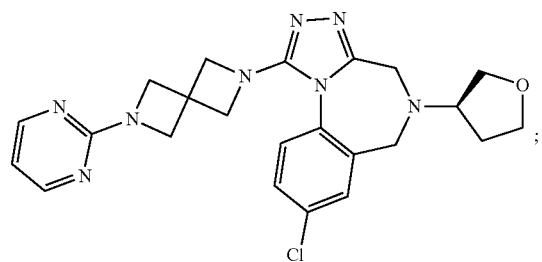 [SMILES: Clc1ccc2c(c1)CN([C@@H]1CCOC1)Cc1nnc(N3CC4(CN(c5ncccn5)C4)C3)n1-2] ; |
| 846 | 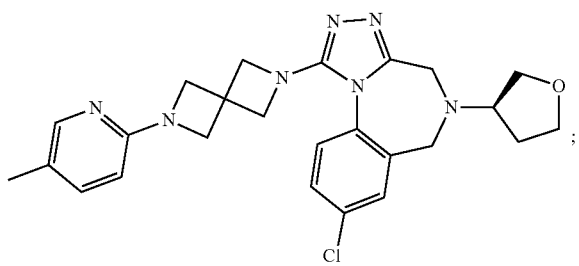 [SMILES: Cc1ccc(N2CC3(C2)CN(c2nnc4n2-c2ccc(Cl)cc2CN([C@@H]2CCOC2)C4)C3)nc1] ; |
| 847 | 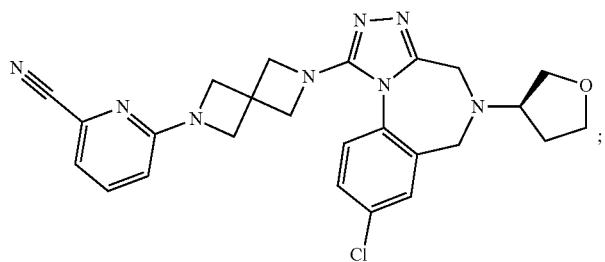 [SMILES: N#Cc1cccc(N2CC3(C2)CN(c2nnc4n2-c2ccc(Cl)cc2CN([C@@H]2CCOC2)C4)C3)n1] ; |
| 848 | 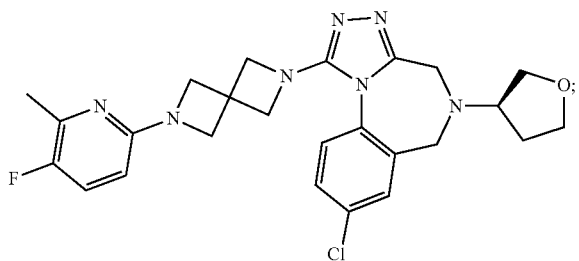 [SMILES: Cc1nc(N2CC3(C2)CN(c2nnc4n2-c2ccc(Cl)cc2CN([C@@H]2CCOC2)C4)C3)ccc1F] ; |

-continued

| Compound No. | Structure |
|---|---|
| 849 | 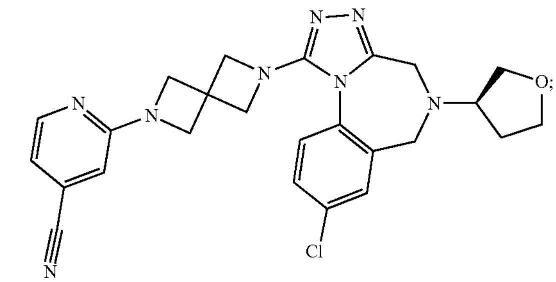 [SMILES: N#Cc1ccnc(N2CC3(C2)CN(c2nnc4n2-c2ccc(Cl)cc2CN([C@@H]2CCOC2)C4)C3)c1] |
| 850 | 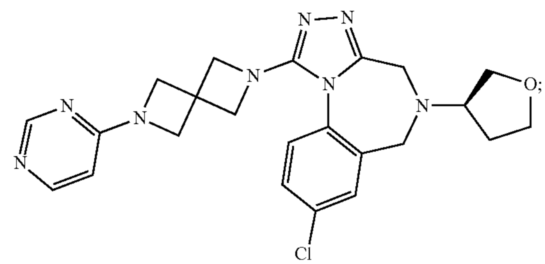 [SMILES: Clc1ccc2c(c1)CN([C@@H]1CCOC1)Cc1nnc(N3CC4(CN(c5ccncn5)C4)C3)n1-2] |
| 851 | 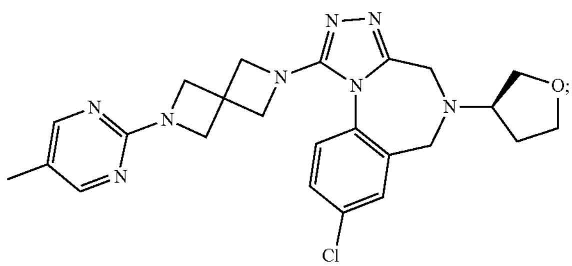 [SMILES: Cc1cnc(N2CC3(C2)CN(c2nnc4n2-c2ccc(Cl)cc2CN([C@@H]2CCOC2)C4)C3)nc1] |
| 852 | 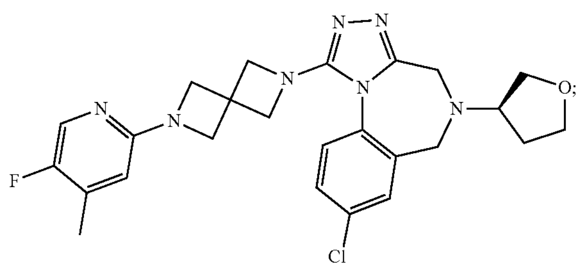 [SMILES: Cc1cc(N2CC3(C2)CN(c2nnc4n2-c2ccc(Cl)cc2CN([C@@H]2CCOC2)C4)C3)ncc1F] |
| 853 | 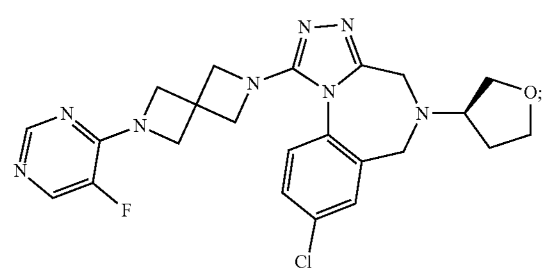 [SMILES: Fc1cncnc1N1CC2(C1)CN(c1nnc3n1-c1ccc(Cl)cc1CN([C@@H]1CCOC1)C3)C2] |
| 854 | 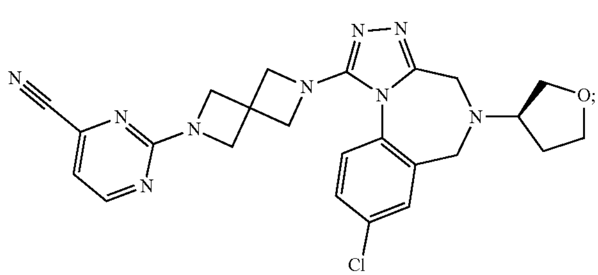 [SMILES: N#Cc1ccnc(N2CC3(C2)CN(c2nnc4n2-c2ccc(Cl)cc2CN([C@@H]2CCOC2)C4)C3)n1] |

| Compound No. | Structure |
|---|---|
| 855 | 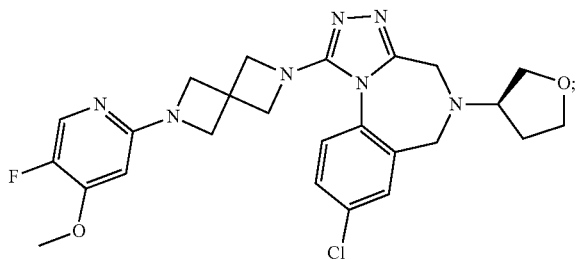 [SMILES: COc1cc(N2CC3(C2)CN(c2nnc4n2-c2ccc(Cl)cc2CN([C@@H]2CCOC2)C4)C3)ncc1F] |
| 856 | 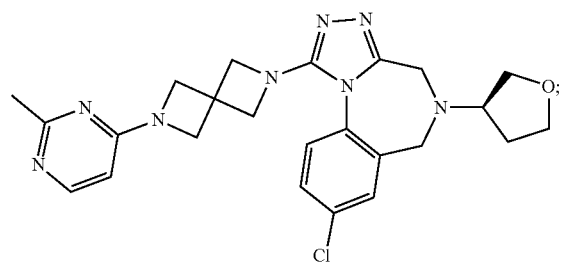 [SMILES: Cc1nccc(N2CC3(C2)CN(c2nnc4n2-c2ccc(Cl)cc2CN([C@@H]2CCOC2)C4)C3)n1] |
| 857 | 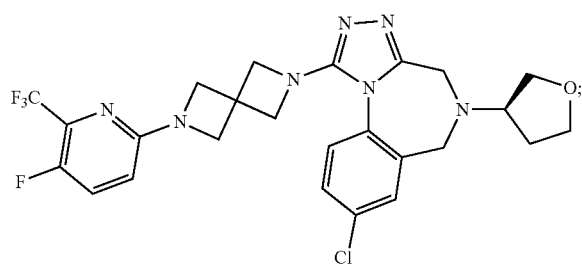 [SMILES: Fc1ccc(N2CC3(C2)CN(c2nnc4n2-c2ccc(Cl)cc2CN([C@@H]2CCOC2)C4)C3)nc1C(F)(F)F] |
| 858 | 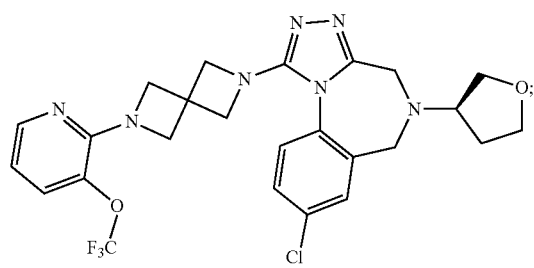 [SMILES: FC(F)(F)Oc1cccnc1N1CC2(C1)CN(c1nnc3n1-c1ccc(Cl)cc1CN([C@@H]1CCOC1)C3)C2] |
| 859 | 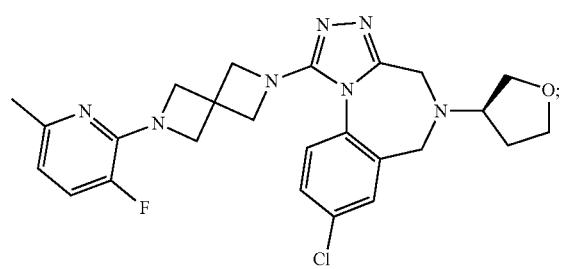 [SMILES: Cc1ccc(F)c(N2CC3(C2)CN(c2nnc4n2-c2ccc(Cl)cc2CN([C@@H]2CCOC2)C4)C3)n1] |

-continued

| Compound No. | Structure |
|---|---|
| 860 | 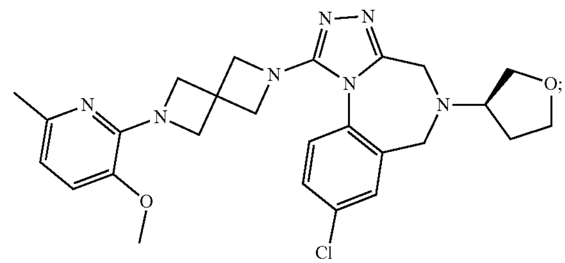 [SMILES: COc1ccc(C)nc1N1CC2(C1)CN(c1nnc3n1-c1ccc(Cl)cc1CN([C@@H]1CCOC1)C3)C2] |
| 861 | 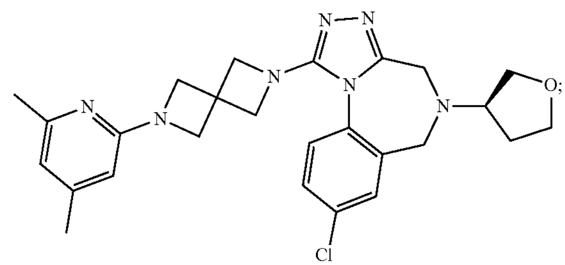 [SMILES: Cc1cc(C)nc(N2CC3(C2)CN(c2nnc4n2-c2ccc(Cl)cc2CN([C@@H]2CCOC2)C4)C3)c1] |
| 862 | 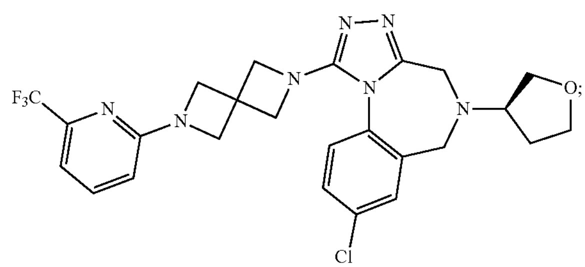 [SMILES: FC(F)(F)c1cccc(N2CC3(C2)CN(c2nnc4n2-c2ccc(Cl)cc2CN([C@@H]2CCOC2)C4)C3)n1] |
| 863 | 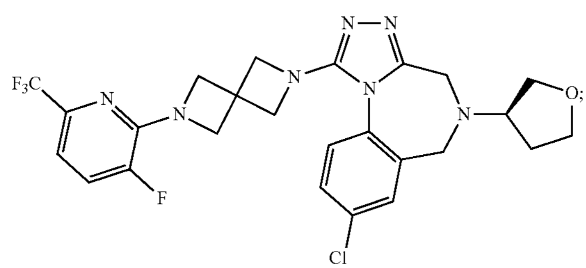 [SMILES: Fc1ccc(C(F)(F)F)nc1N1CC2(C1)CN(c1nnc3n1-c1ccc(Cl)cc1CN([C@@H]1CCOC1)C3)C2] |
| 864 | 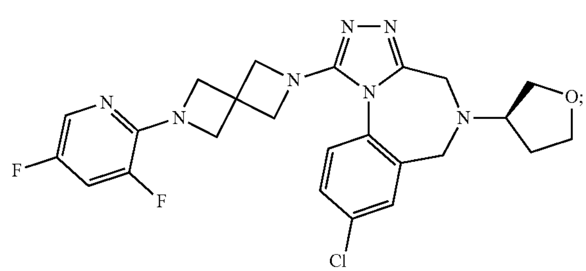 [SMILES: Fc1cnc(N2CC3(C2)CN(c2nnc4n2-c2ccc(Cl)cc2CN([C@@H]2CCOC2)C4)C3)c(F)c1] |
| 865 | 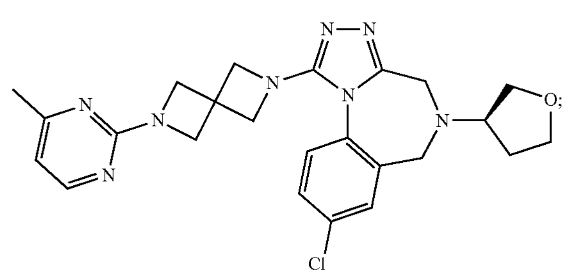 [SMILES: Cc1ccnc(N2CC3(C2)CN(c2nnc4n2-c2ccc(Cl)cc2CN([C@@H]2CCOC2)C4)C3)n1] |

-continued
| Compound No. | Structure |
|---|---|
| 866 | 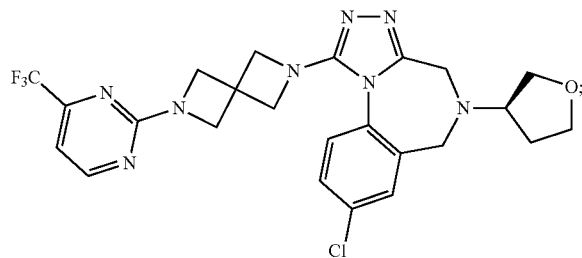 [SMILES: FC(F)(F)c1ccnc(N2CC3(C2)CN(c2nnc4n2-c2ccc(Cl)cc2CN([C@@H]2CCOC2)C4)C3)n1] |
| 867 | 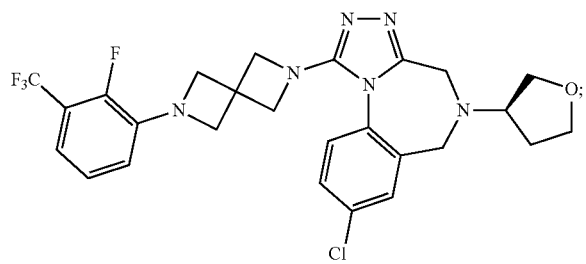 [SMILES: Fc1c(N2CC3(C2)CN(c2nnc4n2-c2ccc(Cl)cc2CN([C@@H]2CCOC2)C4)C3)cccc1C(F)(F)F] |
| 868 | 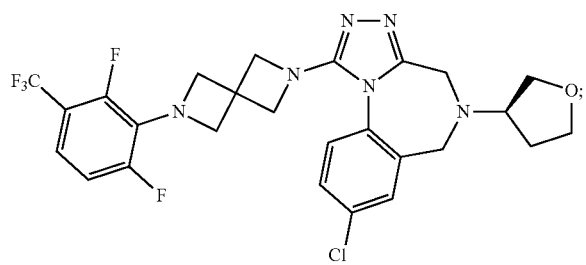 [SMILES: Fc1ccc(C(F)(F)F)c(F)c1N1CC2(C1)CN(c1nnc3n1-c1ccc(Cl)cc1CN([C@@H]1CCOC1)C3)C2] |
| 869 | 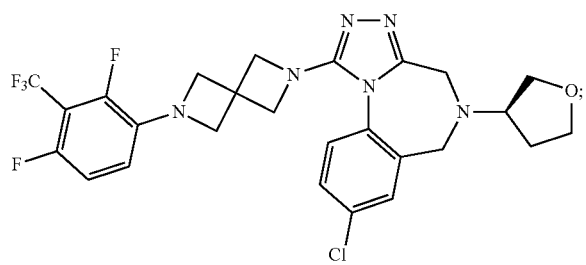 [SMILES: Fc1ccc(N2CC3(C2)CN(c2nnc4n2-c2ccc(Cl)cc2CN([C@@H]2CCOC2)C4)C3)c(F)c1C(F)(F)F] |
| 870 | 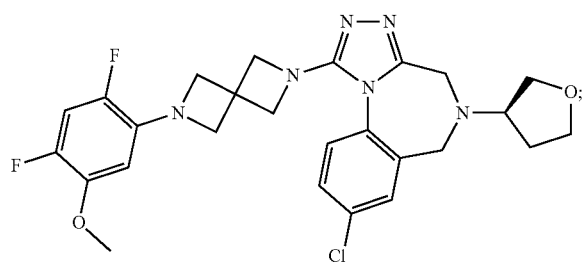 [SMILES: COc1cc(N2CC3(C2)CN(c2nnc4n2-c2ccc(Cl)cc2CN([C@@H]2CCOC2)C4)C3)c(F)cc1F] |

-continued

| Compound No. | Structure |
|---|---|
| 871 | 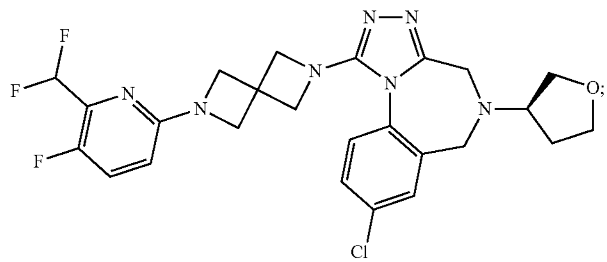 [SMILES: Fc1ccc(N2CC3(C2)CN(c2nnc4n2-c2ccc(Cl)cc2CN([C@@H]2CCOC2)C4)C3)nc1C(F)F] |
| 872 | 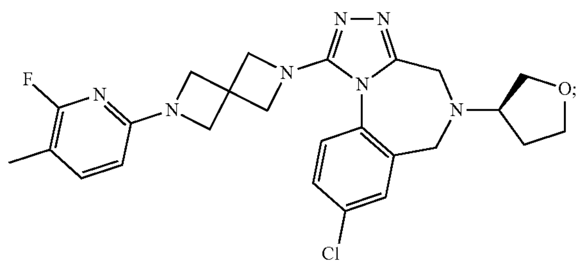 [SMILES: Cc1ccc(N2CC3(C2)CN(c2nnc4n2-c2ccc(Cl)cc2CN([C@@H]2CCOC2)C4)C3)nc1F] |
| 873 | 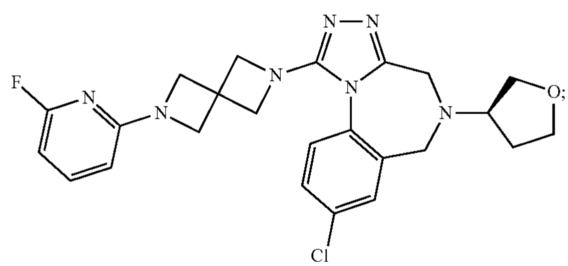 [SMILES: Fc1cccc(N2CC3(C2)CN(c2nnc4n2-c2ccc(Cl)cc2CN([C@@H]2CCOC2)C4)C3)n1] |
| 874 | 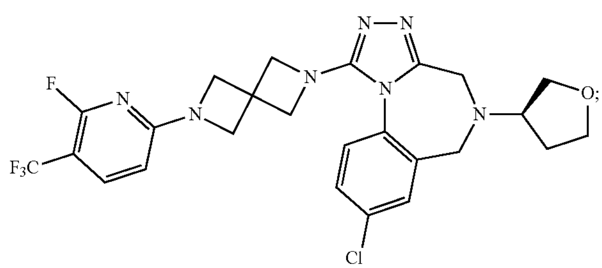 [SMILES: Fc1nc(N2CC3(C2)CN(c2nnc4n2-c2ccc(Cl)cc2CN([C@@H]2CCOC2)C4)C3)ccc1C(F)(F)F] |
| 875 | 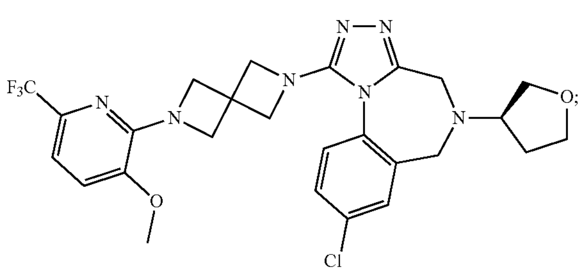 [SMILES: COc1ccc(C(F)(F)F)nc1N1CC2(C1)CN(c1nnc3n1-c1ccc(Cl)cc1CN([C@@H]1CCOC1)C3)C2] |
| 876 | 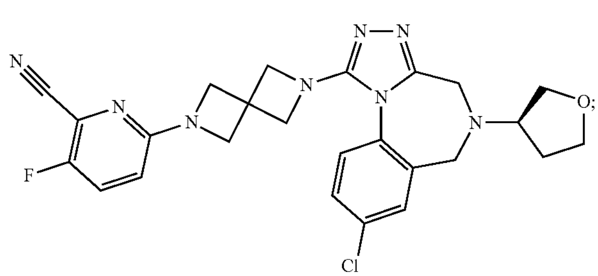 [SMILES: N#Cc1nc(N2CC3(C2)CN(c2nnc4n2-c2ccc(Cl)cc2CN([C@@H]2CCOC2)C4)C3)ccc1F] |

| Compound No. | Structure |
|---|---|
| 877 | 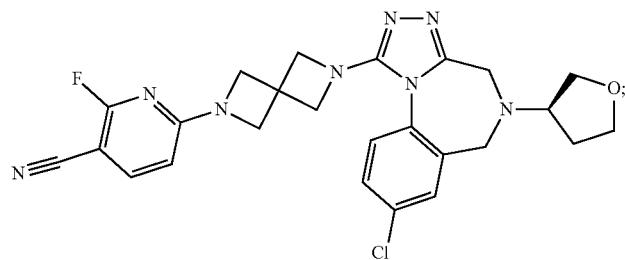 [SMILES: N#Cc1ccc(N2CC3(C2)CN(c2nnc4n2-c2ccc(Cl)cc2CN([C@@H]2CCOC2)C4)C3)nc1F] |
| 878 | 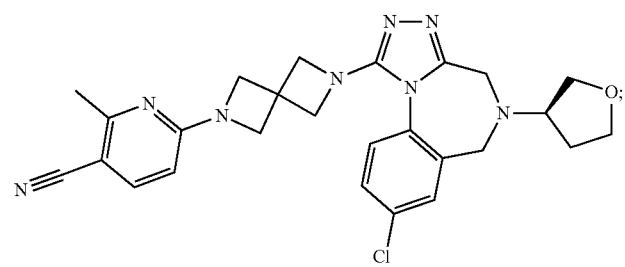 [SMILES: Cc1nc(N2CC3(C2)CN(c2nnc4n2-c2ccc(Cl)cc2CN([C@@H]2CCOC2)C4)C3)ccc1C#N] |
| 879 | 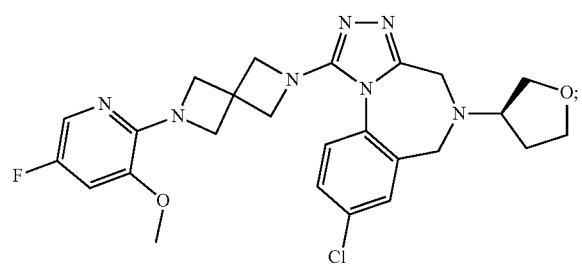 [SMILES: COc1cc(F)cnc1N1CC2(C1)CN(c1nnc3n1-c1ccc(Cl)cc1CN([C@@H]1CCOC1)C3)C2] |
| 880 | 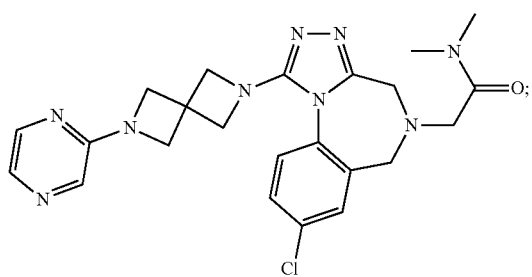 [SMILES: CN(C)C(=O)CN1Cc2cc(Cl)ccc2-n2c(nnc2N2CC3(CN(c4cnccn4)C3)C2)C1] |
| 881 | 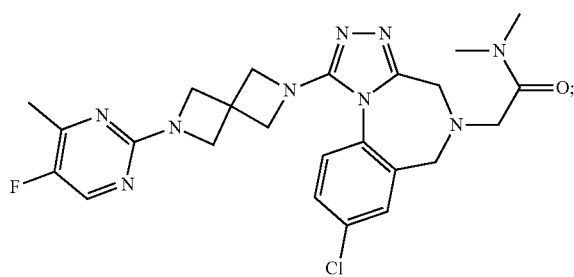 [SMILES: Cc1nc(N2CC3(C2)CN(c2nnc4n2-c2ccc(Cl)cc2CN(CC(=O)N(C)C)C4)C3)ncc1F] |

| Compound No. | Structure |
|---|---|
| 882 | 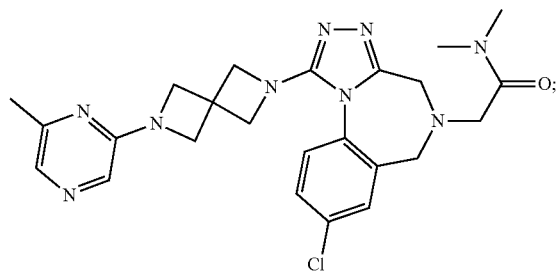 [SMILES: Cc1cncc(N2CC3(C2)CN(c2nnc4n2-c2ccc(Cl)cc2CN(CC(=O)N(C)C)C4)C3)n1] |
| 883 | 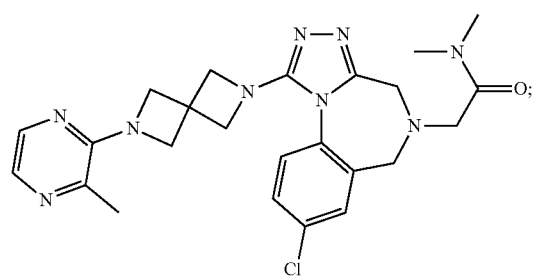 [SMILES: Cc1nccnc1N1CC2(C1)CN(c1nnc3n1-c1ccc(Cl)cc1CN(CC(=O)N(C)C)C3)C2] |
| 884 | 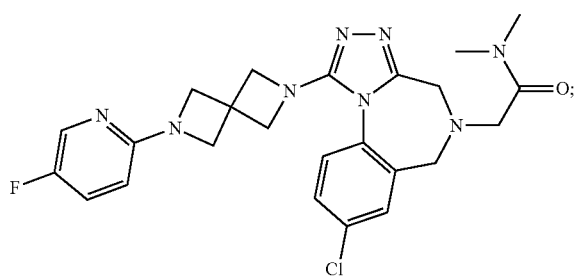 [SMILES: CN(C)C(=O)CN1Cc2cc(Cl)ccc2-n2c(nnc2N2CC3(CN(c4ccc(F)cn4)C3)C2)C1] |
| 885 | 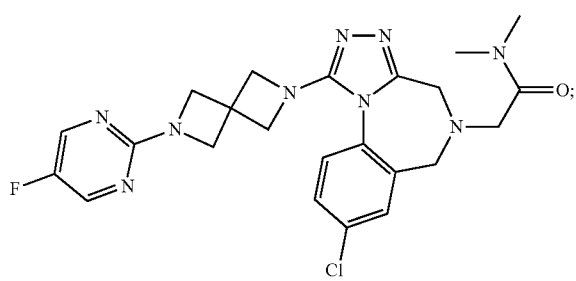 [SMILES: CN(C)C(=O)CN1Cc2cc(Cl)ccc2-n2c(nnc2N2CC3(CN(c4ncc(F)cn4)C3)C2)C1] |
| 886 | 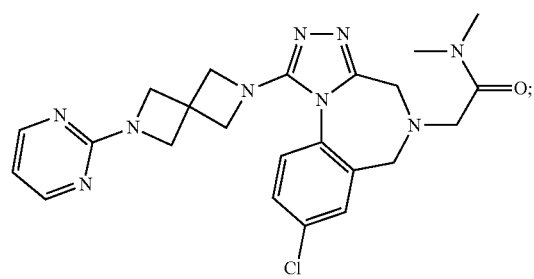 [SMILES: CN(C)C(=O)CN1Cc2cc(Cl)ccc2-n2c(nnc2N2CC3(CN(c4ncccn4)C3)C2)C1] |

-continued
| Compound No. | Structure |
|---|---|
| 887 | 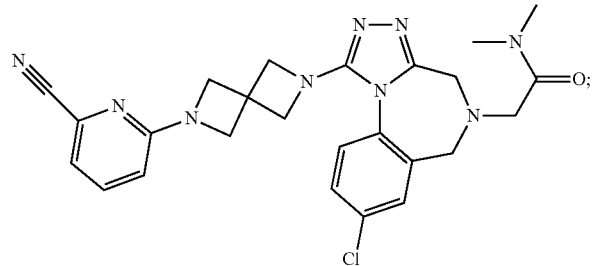 [SMILES: CN(C)C(=O)CN1Cc2cc(Cl)ccc2-n2c(nnc2N2CC3(CN(c4cccc(C#N)n4)C3)C2)C1] |
| 888 | 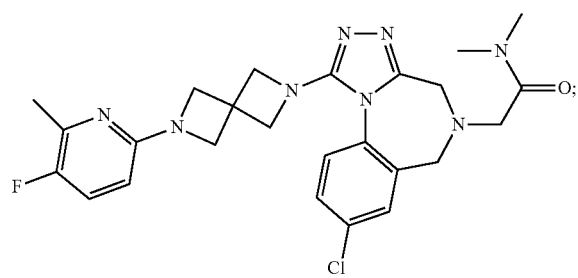 [SMILES: Cc1nc(N2CC3(C2)CN(c2nnc4n2-c2ccc(Cl)cc2CN(CC(=O)N(C)C)C4)C3)ccc1F] |
| 889 | 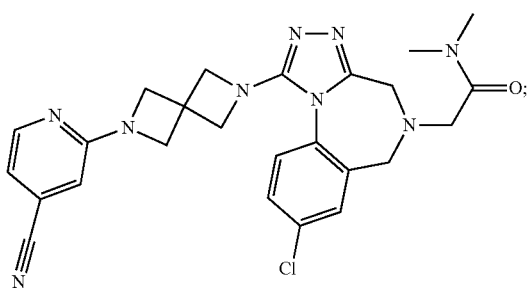 [SMILES: CN(C)C(=O)CN1Cc2cc(Cl)ccc2-n2c(nnc2N2CC3(CN(c4cc(C#N)ccn4)C3)C2)C1] |
| 890 | 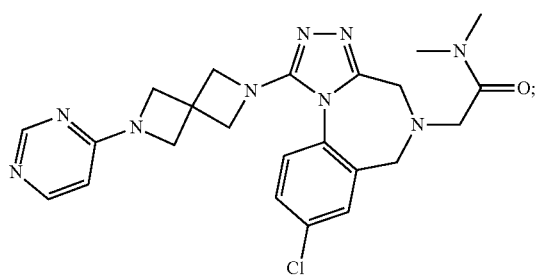 [SMILES: CN(C)C(=O)CN1Cc2cc(Cl)ccc2-n2c(nnc2N2CC3(CN(c4ccncn4)C3)C2)C1] |
| 891 | 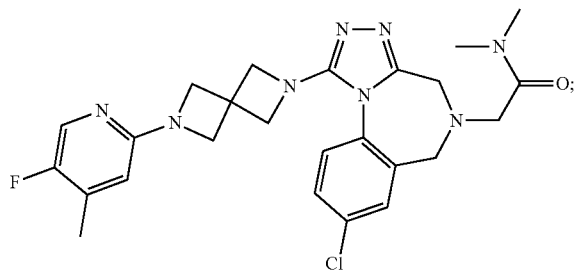 [SMILES: Cc1cc(N2CC3(C2)CN(c2nnc4n2-c2ccc(Cl)cc2CN(CC(=O)N(C)C)C4)C3)ncc1F] |

-continued
| Compound No. | Structure |
|---|---|
| 892 | 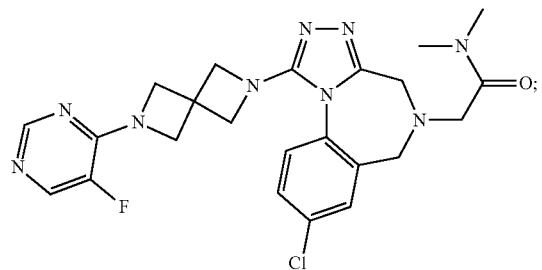 [SMILES: CN(C)C(=O)CN1Cc2cc(Cl)ccc2-n2c(nnc2N2CC3(CN(c4ncncc4F)C3)C2)C1] |
| 893 | 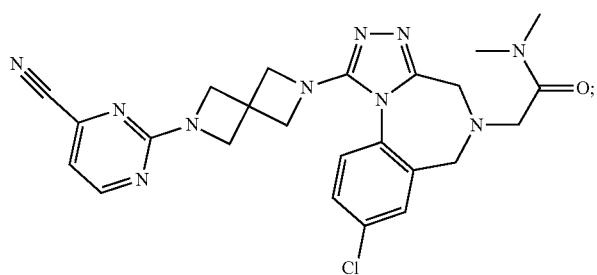 [SMILES: CN(C)C(=O)CN1Cc2cc(Cl)ccc2-n2c(nnc2N2CC3(CN(c4nccc(C#N)n4)C3)C2)C1] |
| 894 | 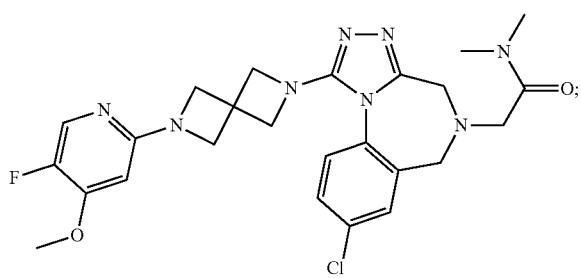 [SMILES: COc1cc(N2CC3(C2)CN(c2nnc4n2-c2ccc(Cl)cc2CN(CC(=O)N(C)C)C4)C3)ncc1F] |
| 895 | 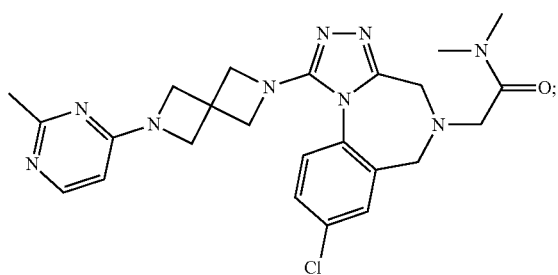 [SMILES: Cc1nccc(N2CC3(C2)CN(c2nnc4n2-c2ccc(Cl)cc2CN(CC(=O)N(C)C)C4)C3)n1] |
| 896 | 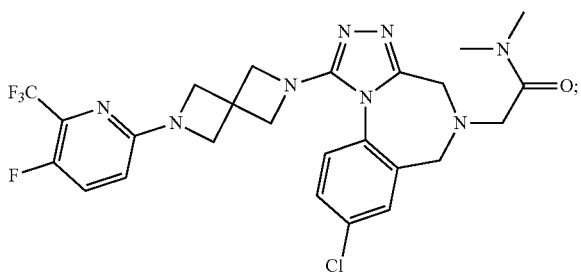 [SMILES: CN(C)C(=O)CN1Cc2cc(Cl)ccc2-n2c(nnc2N2CC3(CN(c4ccc(F)c(C(F)(F)F)n4)C3)C2)C1] |

-continued
| Compound No. | Structure |
|---|---|
| 897 | 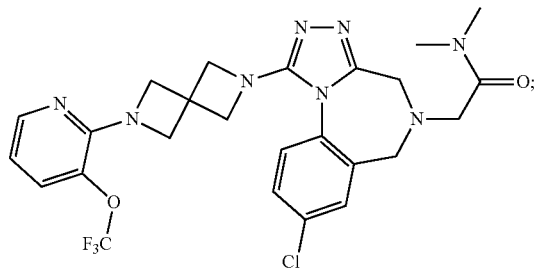 [SMILES: CN(C)C(=O)CN1Cc2cc(Cl)ccc2-n2c(nnc2N2CC3(CN(c4ncccc4OC(F)(F)F)C3)C2)C1] |
| 898 | 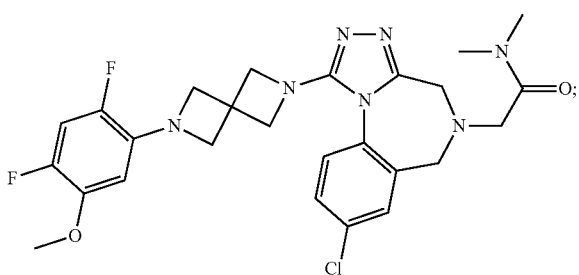 [SMILES: COc1cc(N2CC3(C2)CN(c2nnc4n2-c2ccc(Cl)cc2CN(CC(=O)N(C)C)C4)C3)c(F)cc1F] |
| 899 | 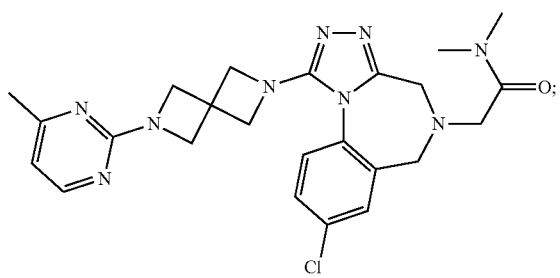 [SMILES: Cc1ccnc(N2CC3(C2)CN(c2nnc4n2-c2ccc(Cl)cc2CN(CC(=O)N(C)C)C4)C3)n1] |
| 900 | 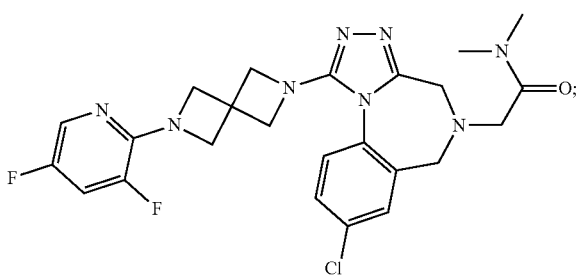 [SMILES: CN(C)C(=O)CN1Cc2cc(Cl)ccc2-n2c(nnc2N2CC3(CN(c4ncc(F)cc4F)C3)C2)C1] |
| 901 | 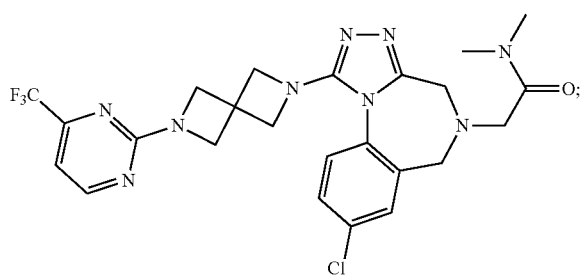 [SMILES: CN(C)C(=O)CN1Cc2cc(Cl)ccc2-n2c(nnc2N2CC3(CN(c4nccc(C(F)(F)F)n4)C3)C2)C1] |

-continued
| Compound No. | Structure |
|---|---|
| 902 | 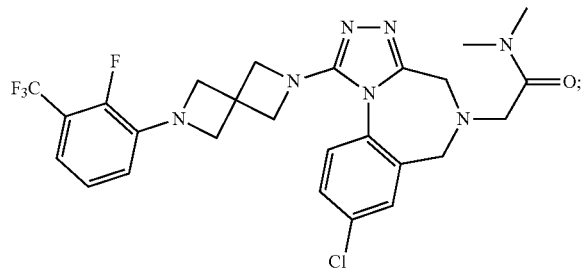 [SMILES: CN(C)C(=O)CN1Cc2cc(Cl)ccc2-n2c(nnc2N2CC3(CN(c4cccc(C(F)(F)F)c4F)C3)C2)C1] |
| 903 | 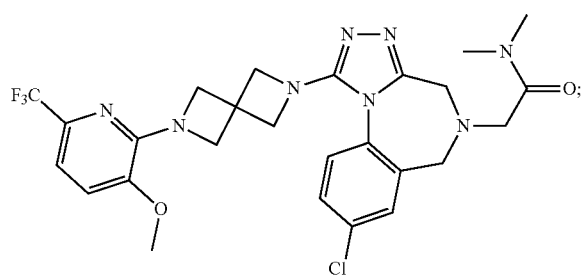 [SMILES: COc1ccc(C(F)(F)F)nc1N1CC2(C1)CN(c1nnc3n1-c1ccc(Cl)cc1CN(CC(=O)N(C)C)C3)C2] |
| 904 | 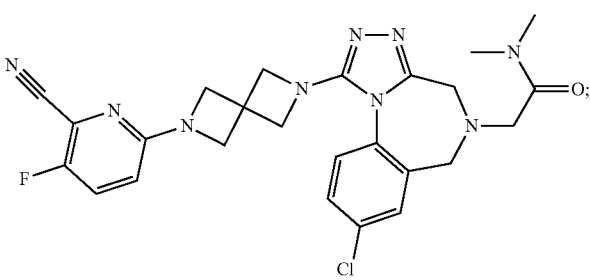 [SMILES: CN(C)C(=O)CN1Cc2cc(Cl)ccc2-n2c(nnc2N2CC3(CN(c4ccc(F)c(C#N)n4)C3)C2)C1] |
| 905 | 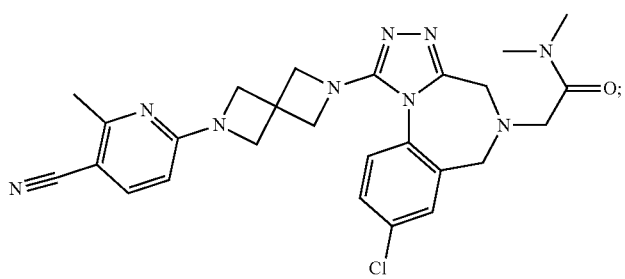 [SMILES: Cc1nc(N2CC3(C2)CN(c2nnc4n2-c2ccc(Cl)cc2CN(CC(=O)N(C)C)C4)C3)ccc1C#N] |
| 906 | 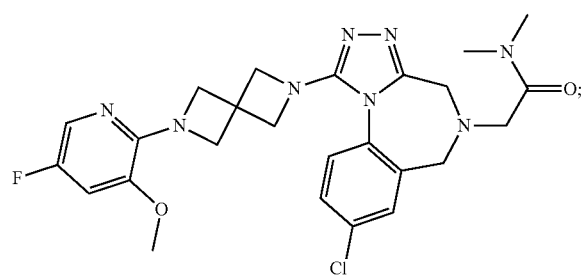 [SMILES: COc1cc(F)cnc1N1CC2(C1)CN(c1nnc3n1-c1ccc(Cl)cc1CN(CC(=O)N(C)C)C3)C2] |

-continued

| Compound No. | Structure |
|---|---|
| 907 | (structure) |
| 908 | (structure) |
| 909 | (structure) |
| 910 | (structure) |
| 911 | (structure) |
| 912 | (structure) |

-continued
| Compound No. | Structure |
|---|---|
| 913 | 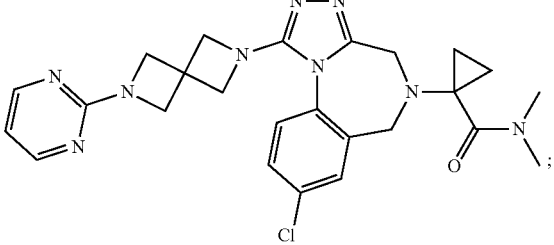 |
| 914 | 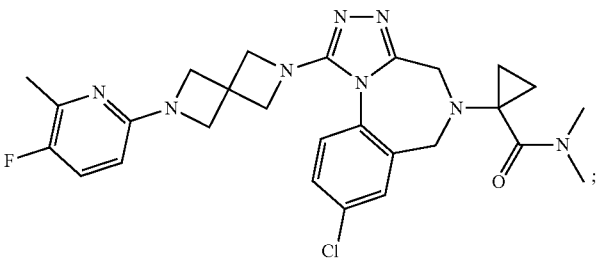 [SMILES: Cc1nc(N2CC3(C2)CN(c2nnc4n2-c2ccc(Cl)cc2CN(C2(C(=O)N(C)C)CC2)C4)C3)ccc1F] |
| 915 | 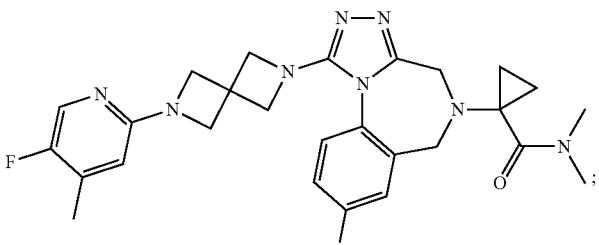 |
| 916 | 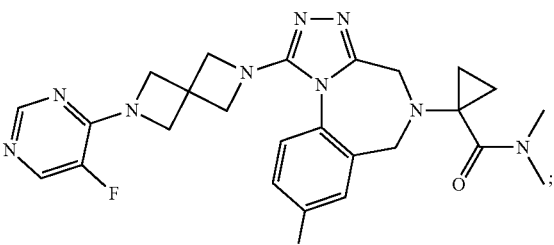 |
| 917 | 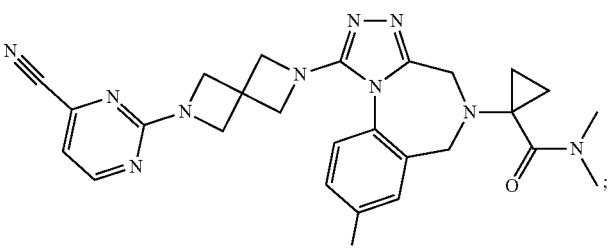 |
| 918 | 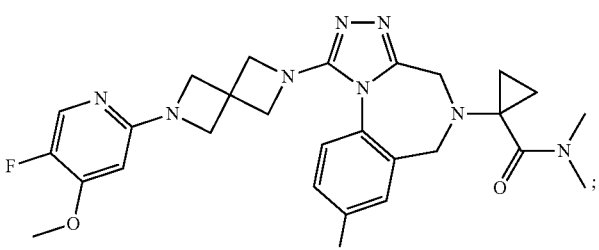 |

-continued

| Compound No. | Structure |
|---|---|
| 919 | 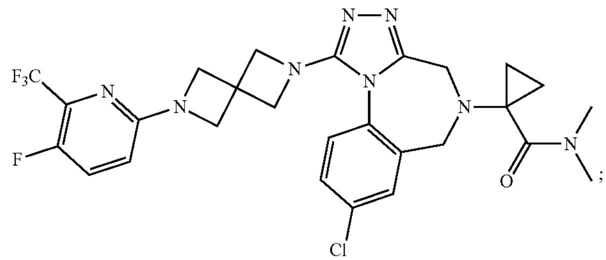 [SMILES: CN(C)C(=O)C1(N2Cc3cc(Cl)ccc3-n3c(nnc3N3CC4(CN(c5ccc(F)c(C(F)(F)F)n5)C4)C3)C2)CC1] |
| 920 | 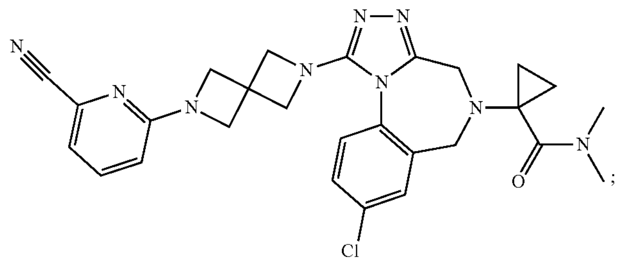 [SMILES: CN(C)C(=O)C1(N2Cc3cc(Cl)ccc3-n3c(nnc3N3CC4(CN(c5cccc(C#N)n5)C4)C3)C2)CC1] |
| 921 | 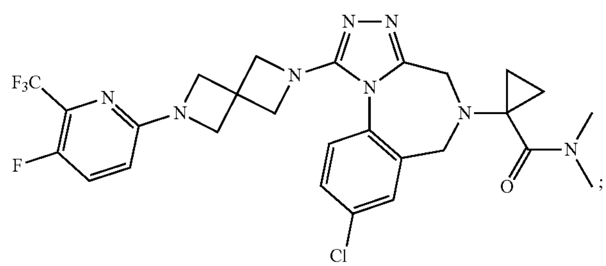 [SMILES: CN(C)C(=O)C1(N2Cc3cc(Cl)ccc3-n3c(nnc3N3CC4(CN(c5ccc(F)c(C(F)(F)F)n5)C4)C3)C2)CC1] |
| 922 | 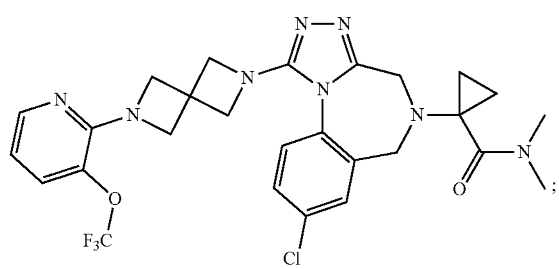 [SMILES: CN(C)C(=O)C1(N2Cc3cc(Cl)ccc3-n3c(nnc3N3CC4(CN(c5ncccc5OC(F)(F)F)C4)C3)C2)CC1] |
| 923 | 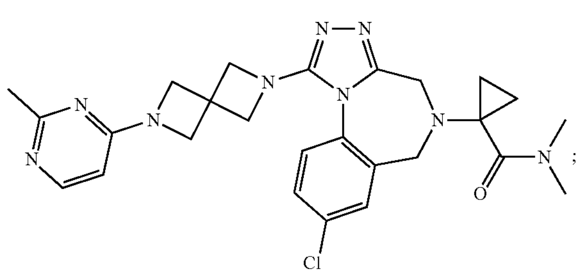 |
| 924 | 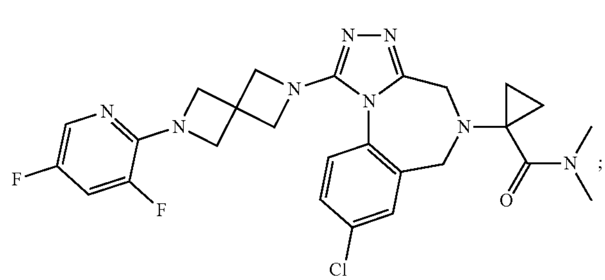 [SMILES: CN(C)C(=O)C1(N2Cc3cc(Cl)ccc3-n3c(nnc3N3CC4(CN(c5ncc(F)cc5F)C4)C3)C2)CC1 ; ";"] |

-continued

| Compound No. | Structure |
|---|---|
| 925 | 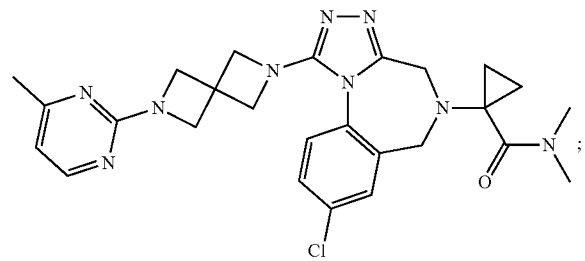 |
| 926 | 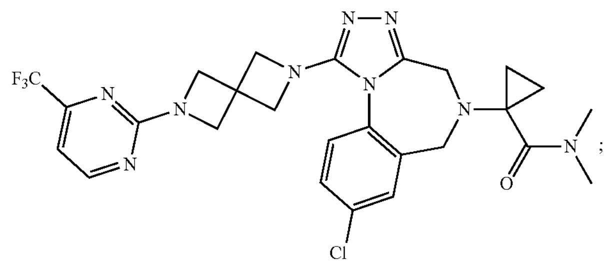 [SMILES: CN(C)C(=O)C1(N2Cc3cc(Cl)ccc3-n3c(nnc3N3CC4(CN(c5nccc(C(F)(F)F)n5)C4)C3)C2)CC1 ; ";"] |
| 927 | 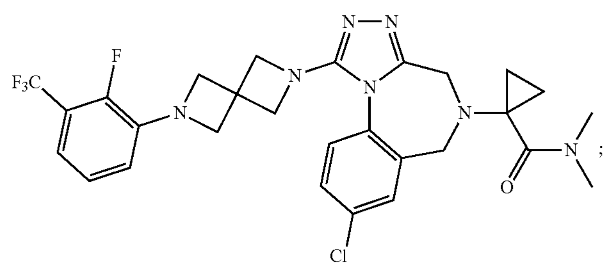 [SMILES: CN(C)C(=O)C1(N2Cc3cc(Cl)ccc3-n3c(nnc3N3CC4(CN(c5cccc(C(F)(F)F)c5F)C4)C3)C2)CC1 ; ";"] |
| 928 | 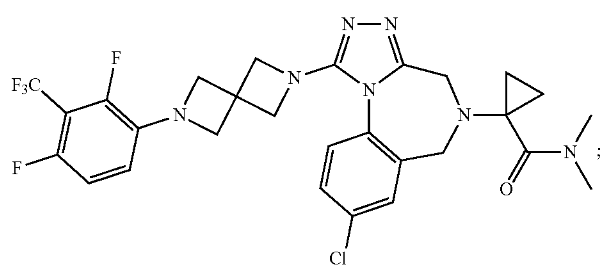 [SMILES: CN(C)C(=O)C1(N2Cc3cc(Cl)ccc3-n3c(nnc3N3CC4(CN(c5ccc(F)c(C(F)(F)F)c5F)C4)C3)C2)CC1 ; ";"] |
| 929 | 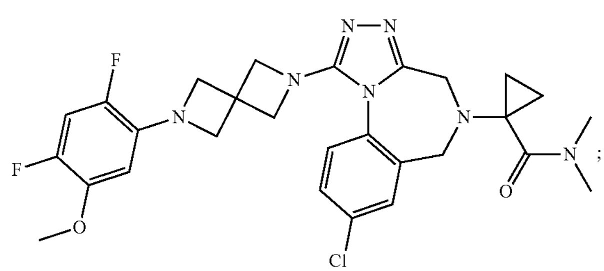 [SMILES: COc1cc(N2CC3(C2)CN(c2nnc4n2-c2ccc(Cl)cc2CN(C2(C(=O)N(C)C)CC2)C4)C3)c(F)cc1F ; ";"] |
| 930 | 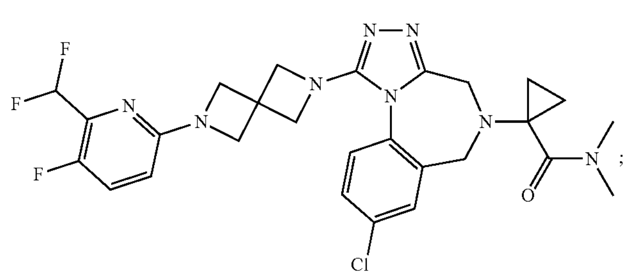 [SMILES: CN(C)C(=O)C1(N2Cc3cc(Cl)ccc3-n3c(nnc3N3CC4(CN(c5ccc(F)c(C(F)F)n5)C4)C3)C2)CC1 ; ";"] |

| Compound No. | Structure |
|---|---|
| 931 | 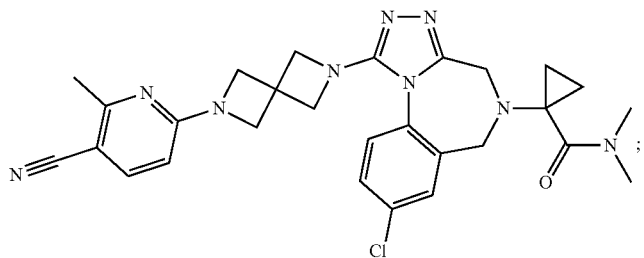 [SMILES: Cc1nc(N2CC3(C2)CN(c2nnc4n2-c2ccc(Cl)cc2CN(C2(C(=O)N(C)C)CC2)C4)C3)ccc1C#N ; ";"] |
| 932 | 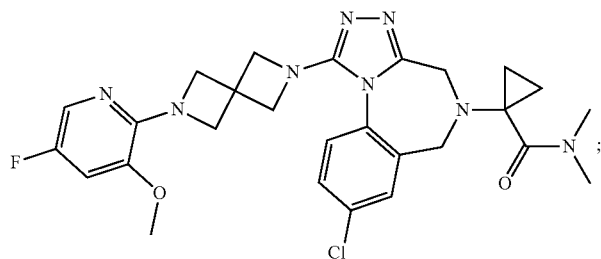 [SMILES: COc1cc(F)cnc1N1CC2(C1)CN(c1nnc3n1-c1ccc(Cl)cc1CN(C1(C(=O)N(C)C)CC1)C3)C2 ; ";"] |
| 933 | 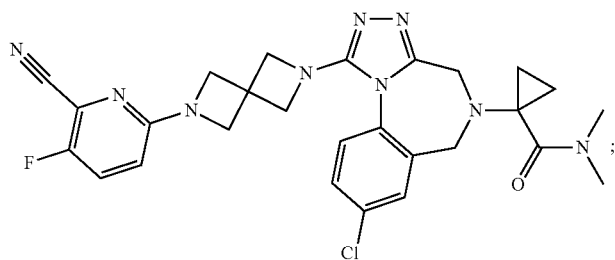 [SMILES: CN(C)C(=O)C1(N2Cc3cc(Cl)ccc3-n3c(nnc3N3CC4(CN(c5ccc(F)c(C#N)n5)C4)C3)C2)CC1 ; ";"] |
| 934 | 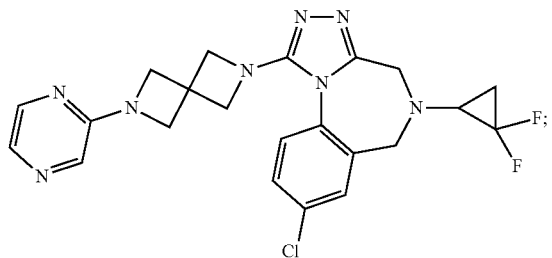 [SMILES: FC1(F)CC1N1Cc2cc(Cl)ccc2-n2c(nnc2N2CC3(CN(c4cnccn4)C3)C2)C1] |
| 935 | 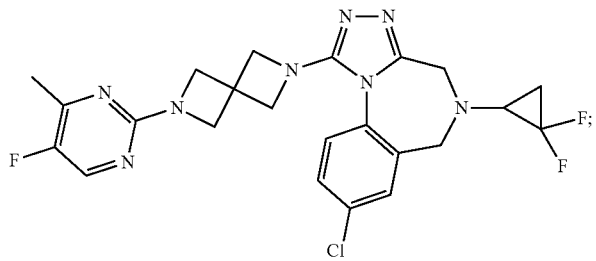 [SMILES: Cc1nc(N2CC3(C2)CN(c2nnc4n2-c2ccc(Cl)cc2CN(C2CC2(F)F)C4)C3)ncc1F] |
| 936 | 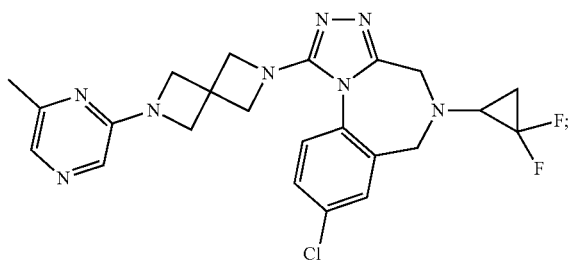 [SMILES: Cc1cncc(N2CC3(C2)CN(c2nnc4n2-c2ccc(Cl)cc2CN(C2CC2(F)F)C4)C3)n1] |

-continued

| Compound No. | Structure |
|---|---|
| 937 | 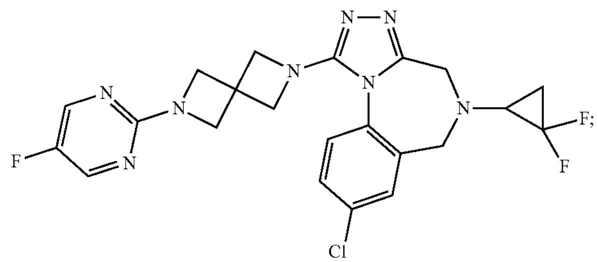 [SMILES: Fc1cnc(N2CC3(C2)CN(c2nnc4n2-c2ccc(Cl)cc2CN(C2CC2(F)F)C4)C3)nc1] |
| 938 | 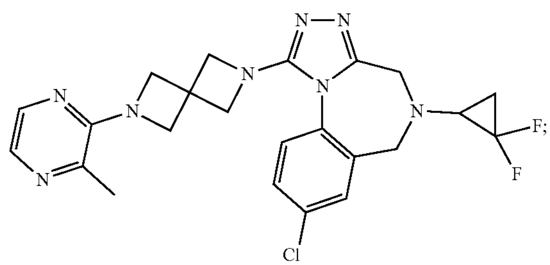 [SMILES: Cc1nccnc1N1CC2(C1)CN(c1nnc3n1-c1ccc(Cl)cc1CN(C1CC1(F)F)C3)C2] |
| 939 | 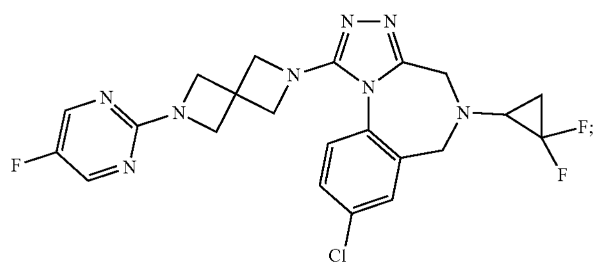 [SMILES: Fc1cnc(N2CC3(C2)CN(c2nnc4n2-c2ccc(Cl)cc2CN(C2CC2(F)F)C4)C3)nc1] |
| 940 | 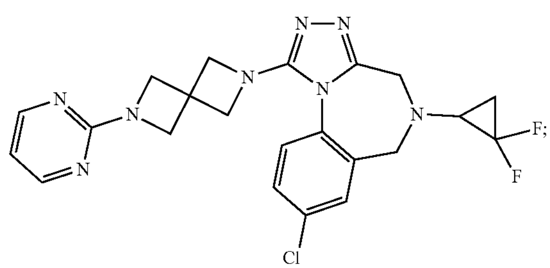 [SMILES: FC1(F)CC1N1Cc2cc(Cl)ccc2-n2c(nnc2N2CC3(CN(c4ncccn4)C3)C2)C1] |
| 941 | 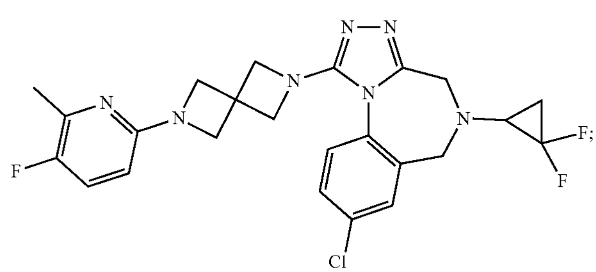 [SMILES: Cc1nc(N2CC3(C2)CN(c2nnc4n2-c2ccc(Cl)cc2CN(C2CC2(F)F)C4)C3)ccc1F] |
| 942 | 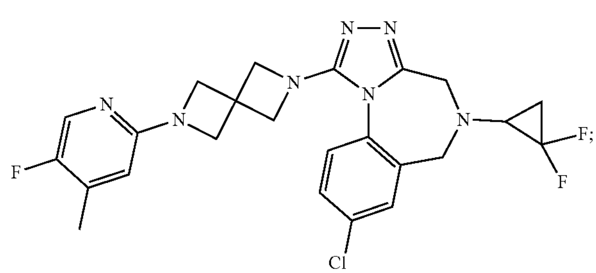 [SMILES: Cc1cc(N2CC3(C2)CN(c2nnc4n2-c2ccc(Cl)cc2CN(C2CC2(F)F)C4)C3)ncc1F] |

-continued
| Compound No. | Structure |
|---|---|
| 943 | 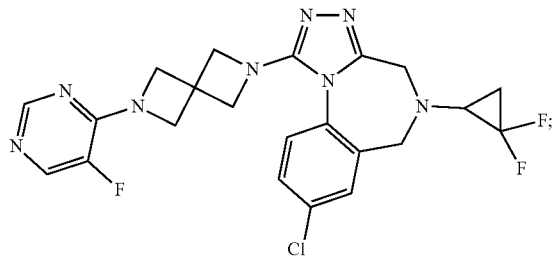 [SMILES: Fc1cncnc1N1CC2(C1)CN(c1nnc3n1-c1ccc(Cl)cc1CN(C1CC1(F)F)C3)C2] |
| 944 | 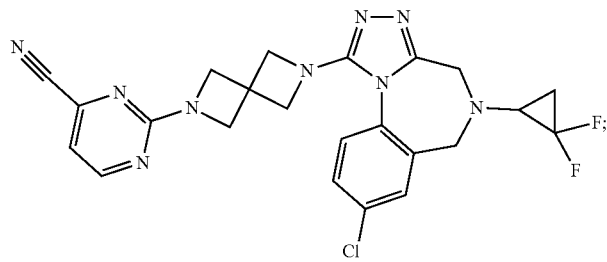 [SMILES: N#Cc1ccnc(N2CC3(C2)CN(c2nnc4n2-c2ccc(Cl)cc2CN(C2CC2(F)F)C4)C3)n1] |
| 945 | 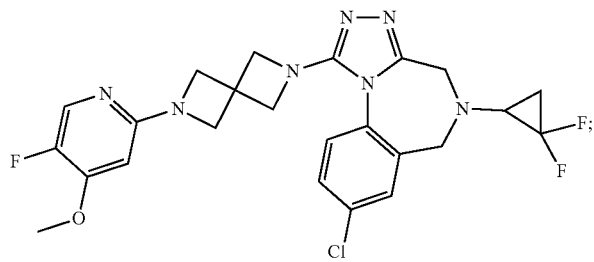 [SMILES: COc1cc(N2CC3(C2)CN(c2nnc4n2-c2ccc(Cl)cc2CN(C2CC2(F)F)C4)C3)ncc1F] |
| 946 | 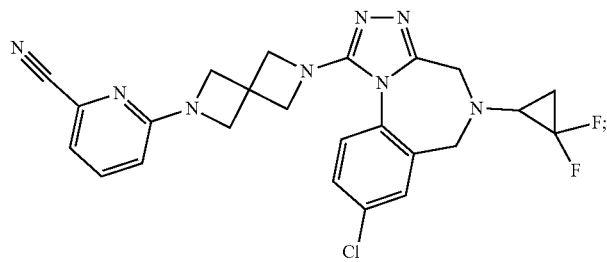 [SMILES: N#Cc1cccc(N2CC3(C2)CN(c2nnc4n2-c2ccc(Cl)cc2CN(C2CC2(F)F)C4)C3)n1] |
| 947 | 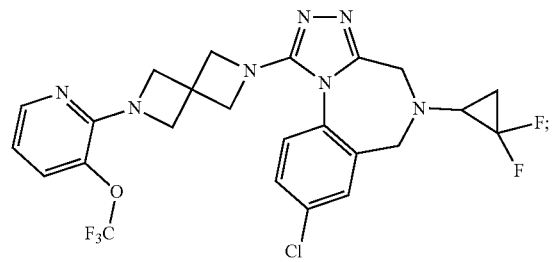 [SMILES: FC(F)(F)Oc1cccnc1N1CC2(C1)CN(c1nnc3n1-c1ccc(Cl)cc1CN(C1CC1(F)F)C3)C2] |
| 948 | 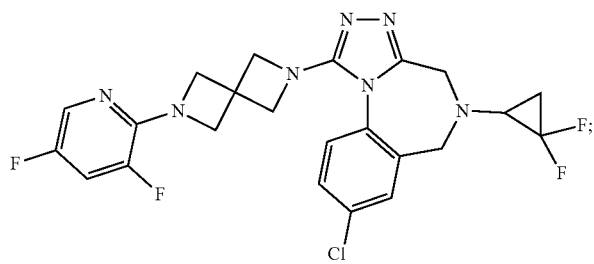 [SMILES: Fc1cnc(N2CC3(C2)CN(c2nnc4n2-c2ccc(Cl)cc2CN(C2CC2(F)F)C4)C3)c(F)c1] |

-continued

| Compound No. | Structure |
|---|---|
| 949 | 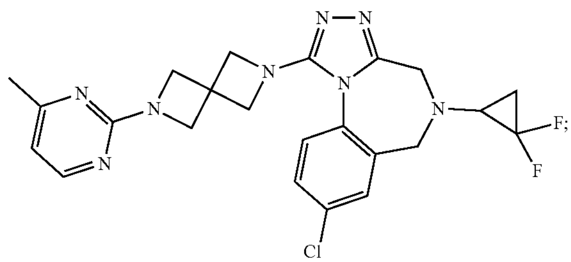 [SMILES: Cc1ccnc(N2CC3(C2)CN(c2nnc4n2-c2ccc(Cl)cc2CN(C2CC2(F)F)C4)C3)n1] |
| 950 | 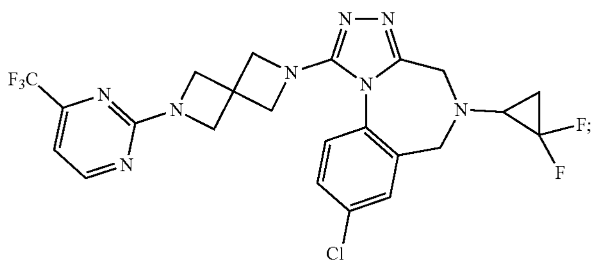 [SMILES: FC(F)(F)c1ccnc(N2CC3(C2)CN(c2nnc4n2-c2ccc(Cl)cc2CN(C2CC2(F)F)C4)C3)n1] |
| 951 | 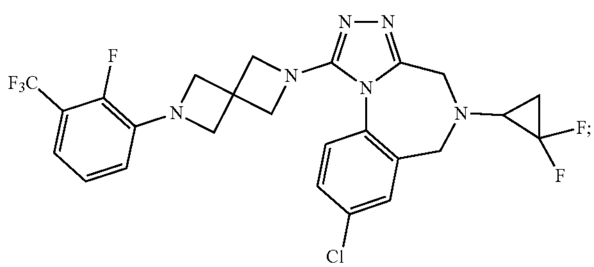 [SMILES: Fc1c(N2CC3(C2)CN(c2nnc4n2-c2ccc(Cl)cc2CN(C2CC2(F)F)C4)C3)cccc1C(F)(F)F] |
| 952 | 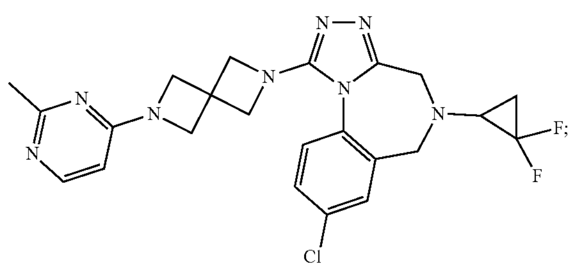 [SMILES: Cc1nccc(N2CC3(C2)CN(c2nnc4n2-c2ccc(Cl)cc2CN(C2CC2(F)F)C4)C3)n1] |
| 953 | 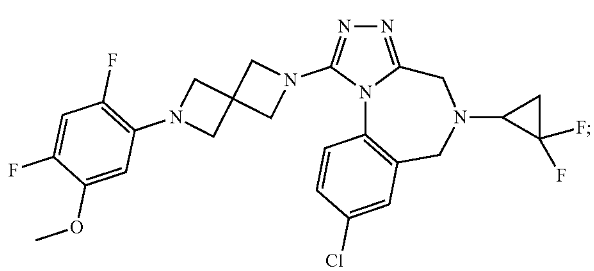 [SMILES: COc1cc(N2CC3(C2)CN(c2nnc4n2-c2ccc(Cl)cc2CN(C2CC2(F)F)C4)C3)c(F)cc1F] |
| 954 | 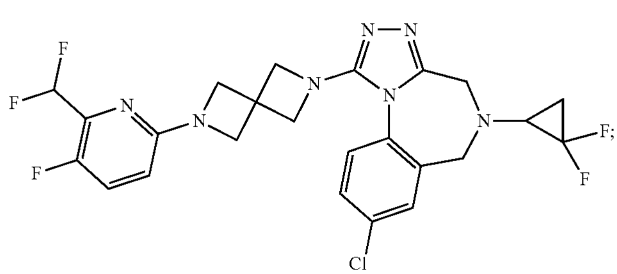 [SMILES: Fc1ccc(N2CC3(C2)CN(c2nnc4n2-c2ccc(Cl)cc2CN(C2CC2(F)F)C4)C3)nc1C(F)F] |

-continued

| Compound No. | Structure |
|---|---|
| 955 | 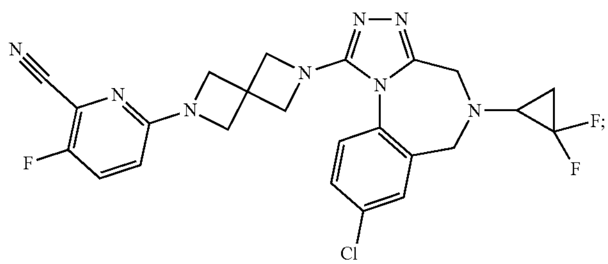 [SMILES: N#Cc1nc(N2CC3(C2)CN(c2nnc4n2-c2ccc(Cl)cc2CN(C2CC2(F)F)C4)C3)ccc1F] |
| 956 | 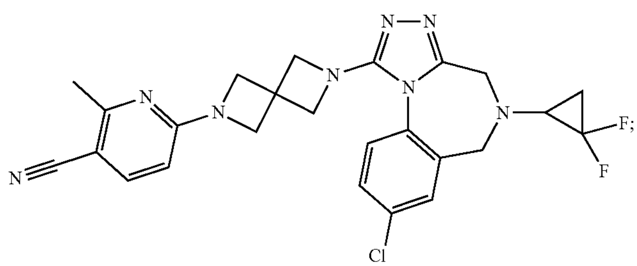 [SMILES: Cc1nc(N2CC3(C2)CN(c2nnc4n2-c2ccc(Cl)cc2CN(C2CC2(F)F)C4)C3)ccc1C#N] |
| 957 | 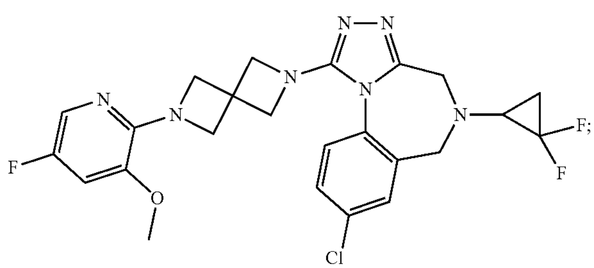 [SMILES: COc1cc(F)cnc1N1CC2(C1)CN(c1nnc3n1-c1ccc(Cl)cc1CN(C1CC1(F)F)C3)C2] |
| 958 | 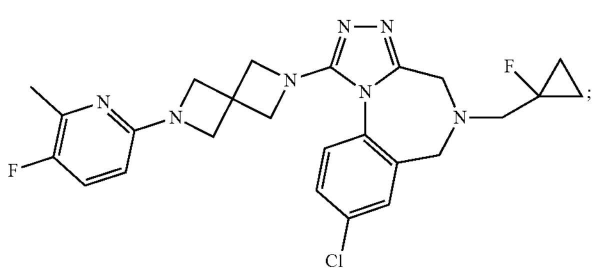 [SMILES: Cc1nc(N2CC3(C2)CN(c2nnc4n2-c2ccc(Cl)cc2CN(CC2(F)CC2)C4)C3)ccc1F] |
| 959 | 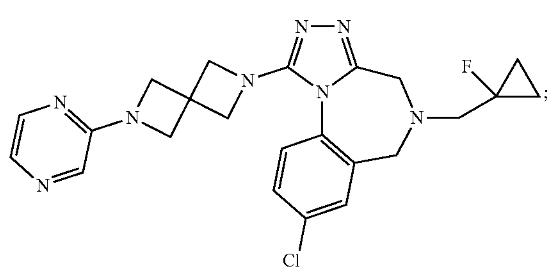 [SMILES: FC1(CN2Cc3cc(Cl)ccc3-n3c(nnc3N3CC4(CN(c5cnccn5)C4)C3)C2)CC1] |
| 960 | 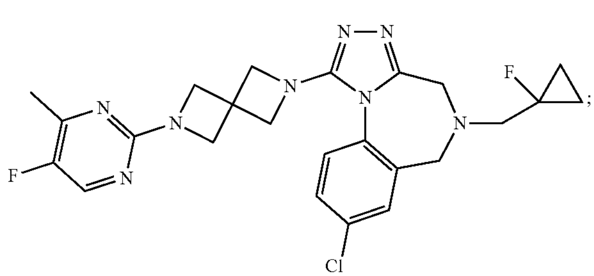 [SMILES: Cc1nc(N2CC3(C2)CN(c2nnc4n2-c2ccc(Cl)cc2CN(CC2(F)CC2)C4)C3)ncc1F] |

| Compound No. | Structure |
|---|---|
| 961 | 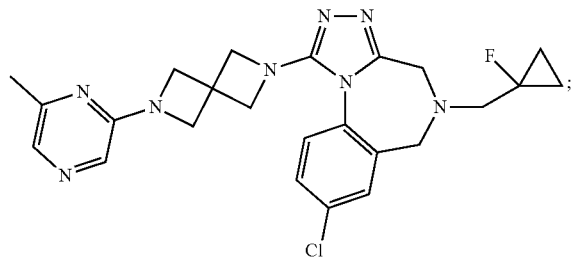 [SMILES: Cc1cncc(N2CC3(C2)CN(c2nnc4n2-c2ccc(Cl)cc2CN(CC2(F)CC2)C4)C3)n1] |
| 962 | 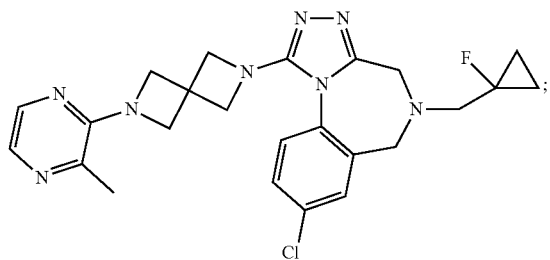 [SMILES: Cc1nccnc1N1CC2(C1)CN(c1nnc3n1-c1ccc(Cl)cc1CN(CC1(F)CC1)C3)C2] |
| 963 | 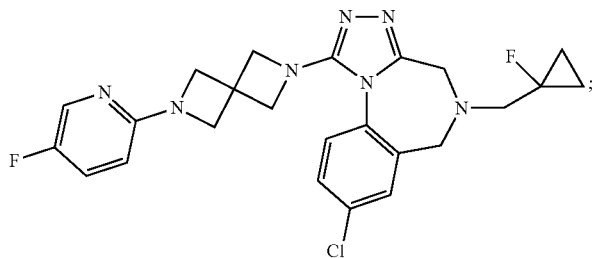 |
| 964 | 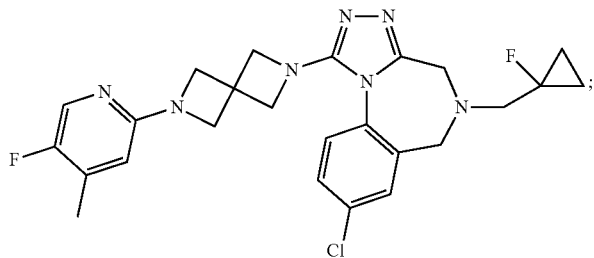 [SMILES: Cc1cc(N2CC3(C2)CN(c2nnc4n2-c2ccc(Cl)cc2CN(CC2(F)CC2)C4)C3)ncc1F] |
| 965 | 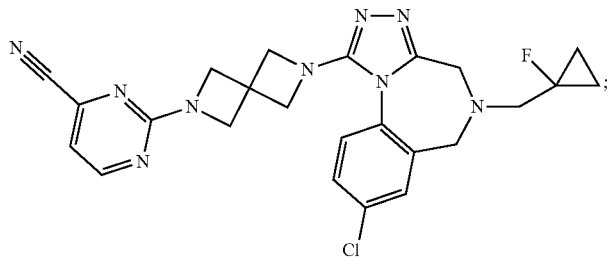 [SMILES: N#Cc1ccnc(N2CC3(C2)CN(c2nnc4n2-c2ccc(Cl)cc2CN(CC2(F)CC2)C4)C3)n1] |
| 966 | 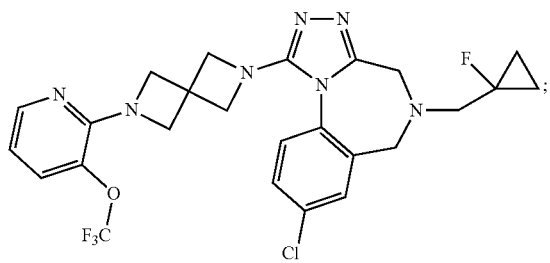 [SMILES: FC1(CN2Cc3cc(Cl)ccc3-n3c(nnc3N3CC4(CN(c5ncccc5OC(F)(F)F)C4)C3)C2)CC1] |

| Compound No. | Structure |
|---|---|
| 967 | 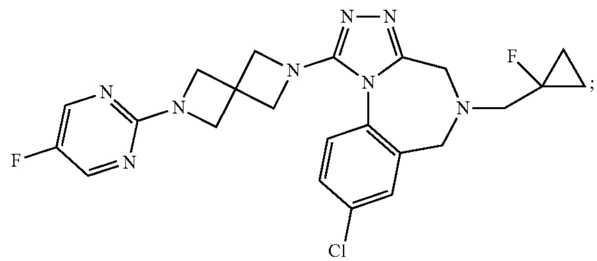 [SMILES: Fc1cnc(N2CC3(C2)CN(c2nnc4n2-c2ccc(Cl)cc2CN(CC2(F)CC2)C4)C3)nc1] |
| 968 | 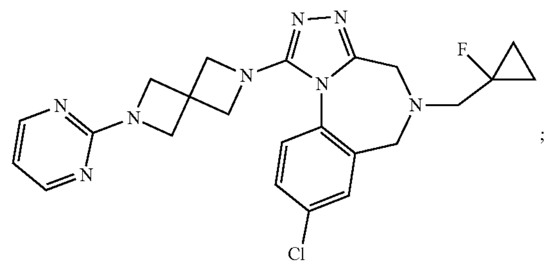 [SMILES: FC1(CN2Cc3cc(Cl)ccc3-n3c(nnc3N3CC4(CN(c5ncccn5)C4)C3)C2)CC1] |
| 969 | 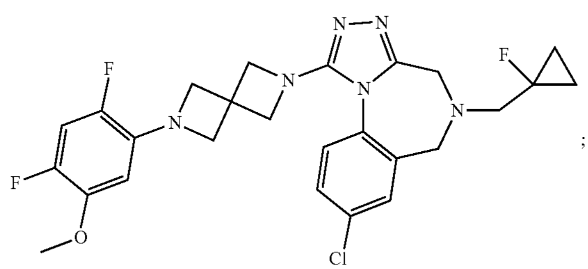 [SMILES: COc1cc(N2CC3(C2)CN(c2nnc4n2-c2ccc(Cl)cc2CN(CC2(F)CC2)C4)C3)c(F)cc1F] |
| 970 | 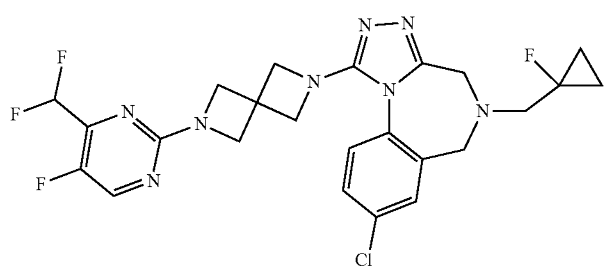 |
| 971 | 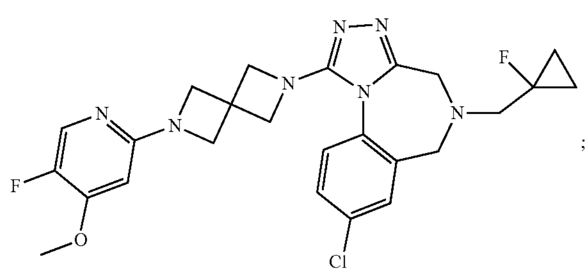 [SMILES: COc1cc(N2CC3(C2)CN(c2nnc4n2-c2ccc(Cl)cc2CN(CC2(F)CC2)C4)C3)ncc1F] |

| Compound No. | Structure |
|---|---|
| 972 | ; |
| 973 | ; |
| 974 | ; |
| 975 | ; |
| 976 | ; |
| 977 | ; |

| Compound No. | Structure |
|---|---|
| 978 | 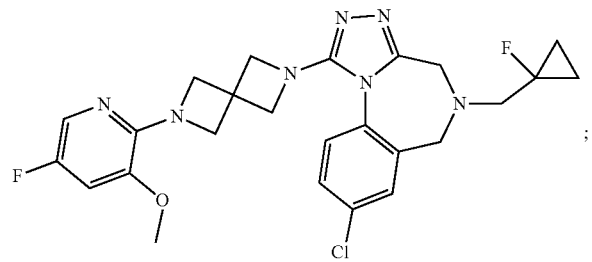 [SMILES: COc1cc(F)cnc1N1CC2(C1)CN(c1nnc3n1-c1ccc(Cl)cc1CN(CC1(F)CC1)C3)C2] ; |
| 979 | 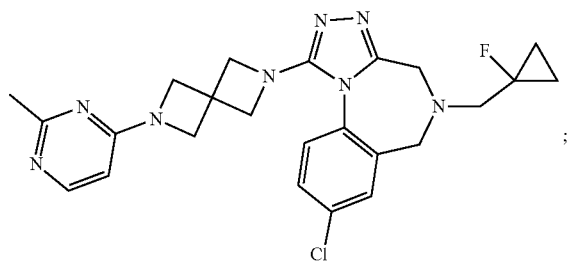 [SMILES: Cc1nccc(N2CC3(C2)CN(c2nnc4n2-c2ccc(Cl)cc2CN(CC2(F)CC2)C4)C3)n1] ; |
| 980 | 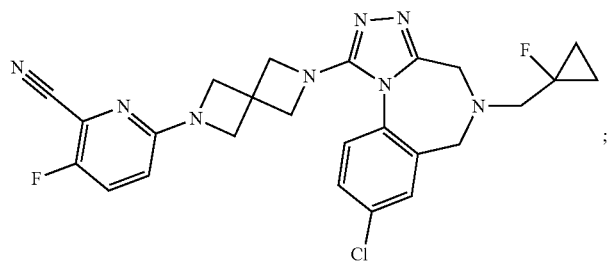 [SMILES: N#Cc1nc(N2CC3(C2)CN(c2nnc4n2-c2ccc(Cl)cc2CN(CC2(F)CC2)C4)C3)ccc1F] ; |
| 981 | 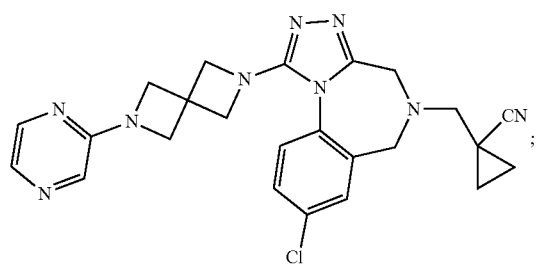 [SMILES: N#CC1(CN2Cc3cc(Cl)ccc3-n3c(nnc3N3CC4(CN(c5cnccn5)C4)C3)C2)CC1] ; |
| 982 | 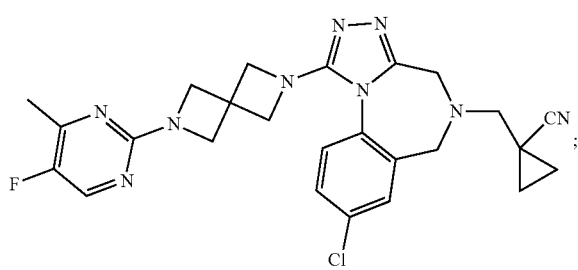 [SMILES: Cc1nc(N2CC3(C2)CN(c2nnc4n2-c2ccc(Cl)cc2CN(CC2(C#N)CC2)C4)C3)ncc1F] ; |

| Compound No. | Structure |
|---|---|
| 983 | 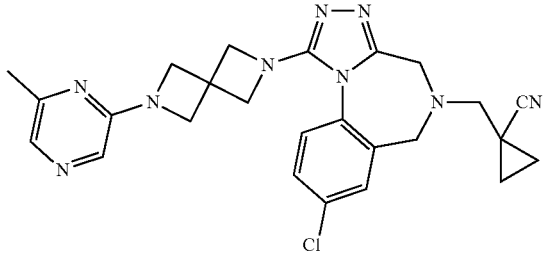 [SMILES: Cc1cncc(N2CC3(C2)CN(c2nnc4n2-c2ccc(Cl)cc2CN(CC2(C#N)CC2)C4)C3)n1] |
| 984 | 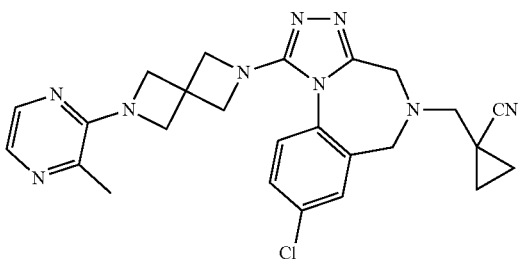 [SMILES: Cc1nccnc1N1CC2(C1)CN(c1nnc3n1-c1ccc(Cl)cc1CN(CC1(C#N)CC1)C3)C2] |
| 985 | 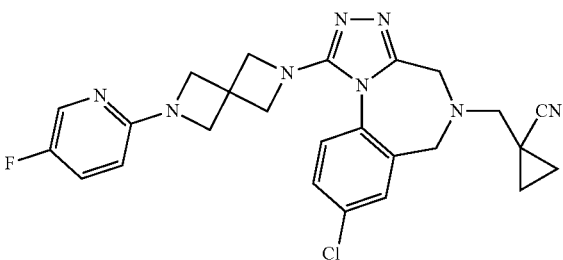 |
| 986 | 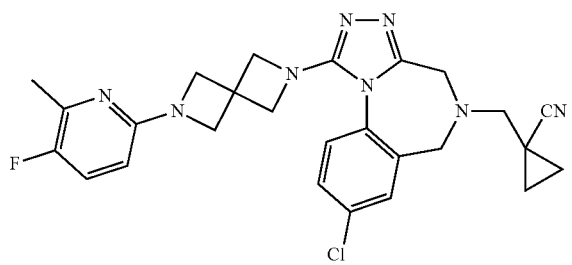 [SMILES: Cc1nc(N2CC3(C2)CN(c2nnc4n2-c2ccc(Cl)cc2CN(CC2(C#N)CC2)C4)C3)ccc1F] |
| 987 | 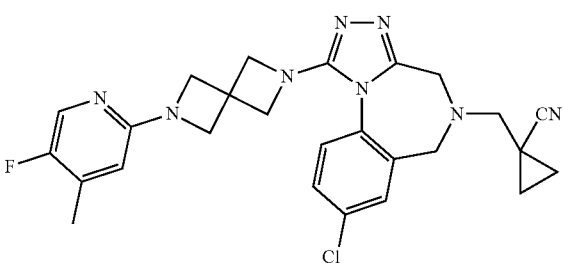 [SMILES: Cc1cc(N2CC3(C2)CN(c2nnc4n2-c2ccc(Cl)cc2CN(CC2(C#N)CC2)C4)C3)ncc1F] |
| 988 | 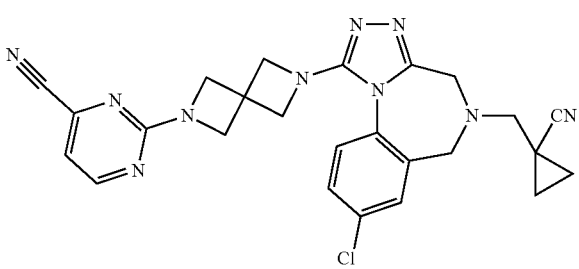 [SMILES: N#Cc1ccnc(N2CC3(C2)CN(c2nnc4n2-c2ccc(Cl)cc2CN(CC2(C#N)CC2)C4)C3)n1] |

-continued

| Compound No. | Structure |
|---|---|
| 989 | 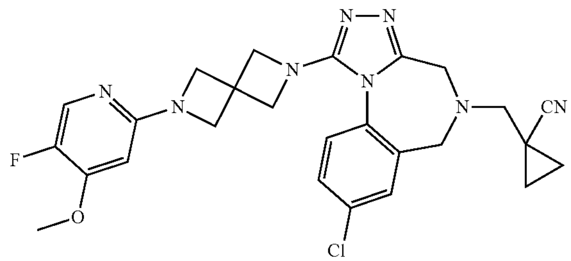 [SMILES: COc1cc(N2CC3(C2)CN(c2nnc4n2-c2ccc(Cl)cc2CN(CC2(C#N)CC2)C4)C3)ncc1F] |
| 990 | 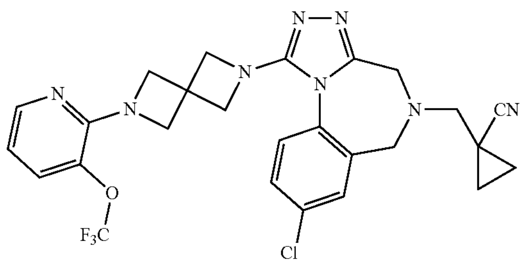 [SMILES: N#CC1(CN2Cc3cc(Cl)ccc3-n3c(nnc3N3CC4(CN(c5ncccc5OC(F)(F)F)C4)C3)C2)CC1] |
| 991 | 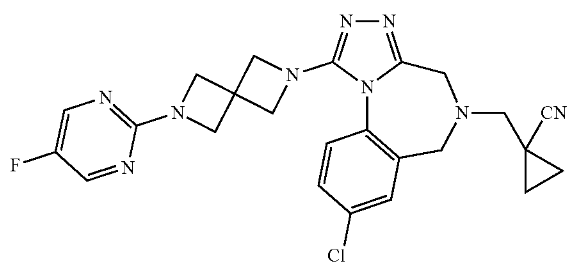 [SMILES: N#CC1(CN2Cc3cc(Cl)ccc3-n3c(nnc3N3CC4(CN(c5ncc(F)cn5)C4)C3)C2)CC1] |
| 992 | 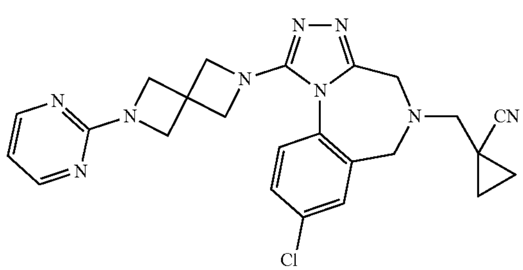 [SMILES: N#CC1(CN2Cc3cc(Cl)ccc3-n3c(nnc3N3CC4(CN(c5ncccn5)C4)C3)C2)CC1] |
| 993 | 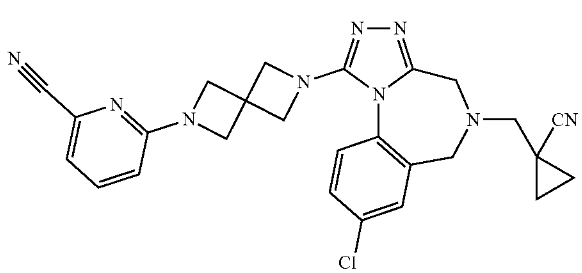 [SMILES: N#Cc1cccc(N2CC3(C2)CN(c2nnc4n2-c2ccc(Cl)cc2CN(CC2(C#N)CC2)C4)C3)n1] |
| 994 | 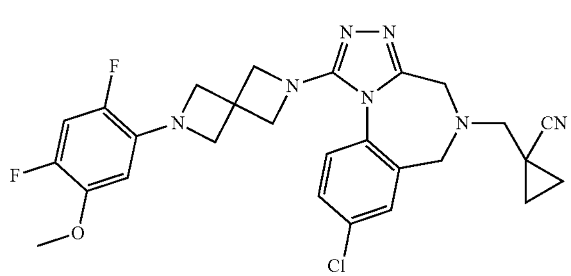 [SMILES: COc1cc(N2CC3(C2)CN(c2nnc4n2-c2ccc(Cl)cc2CN(CC2(C#N)CC2)C4)C3)c(F)cc1F] |

-continued

| Compound No. | Structure |
|---|---|
| 995 | 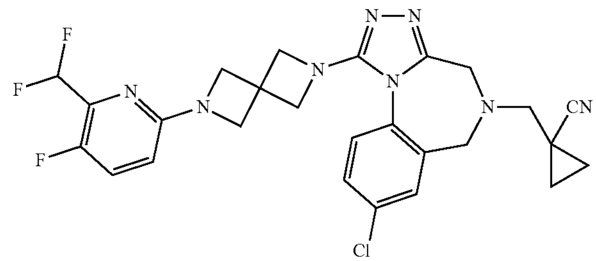 [SMILES: N#CC1(CN2Cc3cc(Cl)ccc3-n3c(nnc3N3CC4(CN(c5ccc(F)c(C(F)F)n5)C4)C3)C2)CC1] |
| 996 | 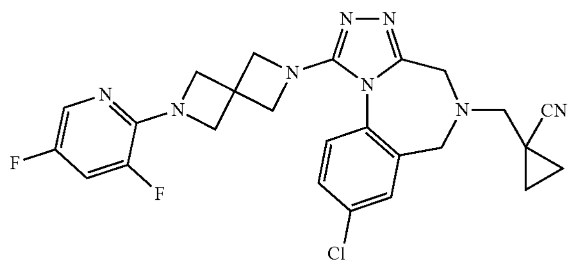 [SMILES: N#CC1(CN2Cc3cc(Cl)ccc3-n3c(nnc3N3CC4(CN(c5ncc(F)cc5F)C4)C3)C2)CC1] |
| 997 | 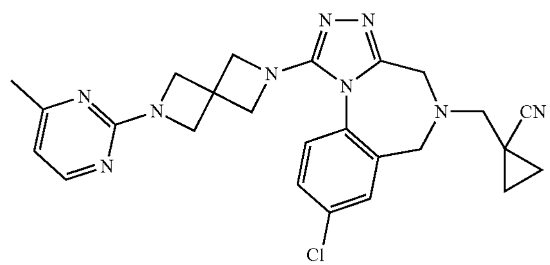 [SMILES: Cc1ccnc(N2CC3(C2)CN(c2nnc4n2-c2ccc(Cl)cc2CN(CC2(C#N)CC2)C4)C3)n1] |
| 998 | 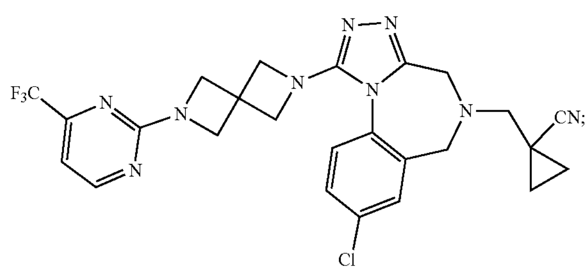 [SMILES: N#CC1(CN2Cc3cc(Cl)ccc3-n3c(nnc3N3CC4(CN(c5nccc(C(F)(F)F)n5)C4)C3)C2)CC1] |
| 999 | 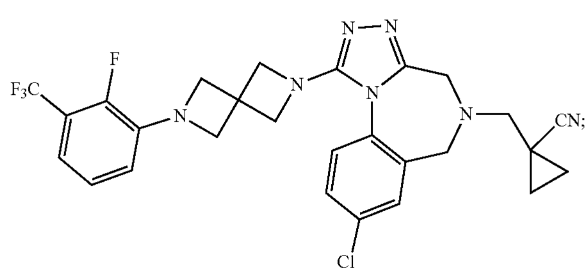 [SMILES: N#CC1(CN2Cc3cc(Cl)ccc3-n3c(nnc3N3CC4(CN(c5cccc(C(F)(F)F)c5F)C4)C3)C2)CC1] |
| 1000 | 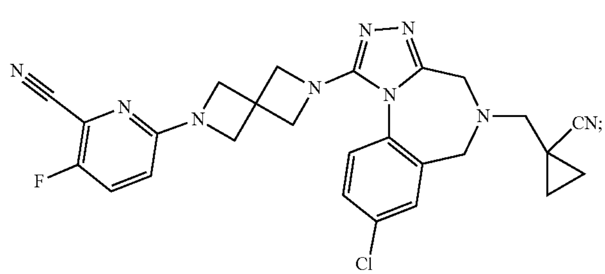 [SMILES: N#Cc1nc(N2CC3(C2)CN(c2nnc4n2-c2ccc(Cl)cc2CN(CC2(C#N)CC2)C4)C3)ccc1F] |

-continued

| Compound No. | Structure |
| --- | --- |
| 1001 | 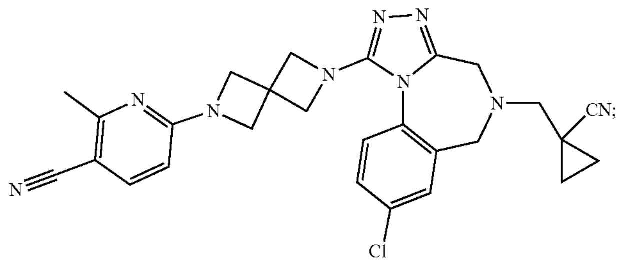 [SMILES: Cc1nc(N2CC3(C2)CN(c2nnc4n2-c2ccc(Cl)cc2CN(CC2(C#N)CC2)C4)C3)ccc1C#N] |
| 1002 | 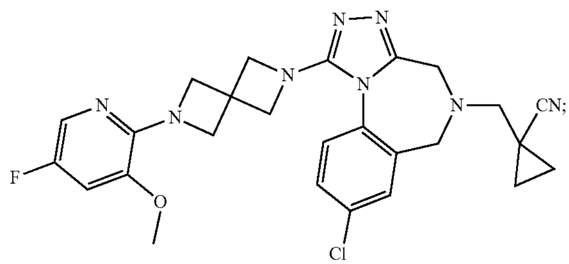 [SMILES: COc1cc(F)cnc1N1CC2(C1)CN(c1nnc3n1-c1ccc(Cl)cc1CN(CC1(C#N)CC1)C3)C2] |
| 1003 | 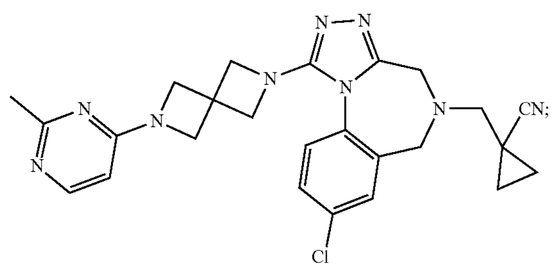 [SMILES: Cc1nccc(N2CC3(C2)CN(c2nnc4n2-c2ccc(Cl)cc2CN(CC2(C#N)CC2)C4)C3)n1] |
| 1004 | 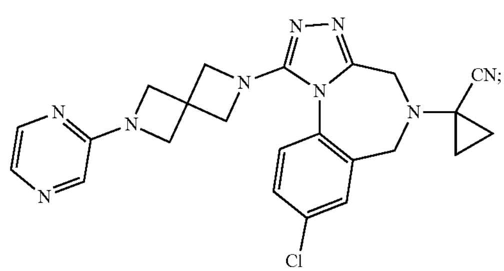 [SMILES: N#CC1(N2Cc3cc(Cl)ccc3-n3c(nnc3N3CC4(CN(c5cnccn5)C4)C3)C2)CC1] |
| 1005 | 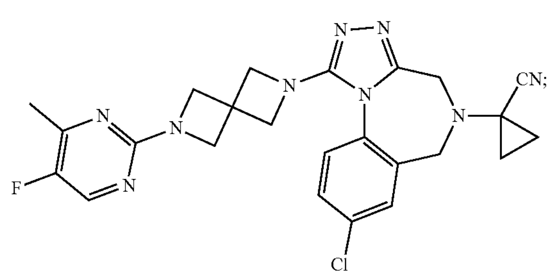 [SMILES: Cc1nc(N2CC3(C2)CN(c2nnc4n2-c2ccc(Cl)cc2CN(C2(C#N)CC2)C4)C3)ncc1F] |
| 1006 | 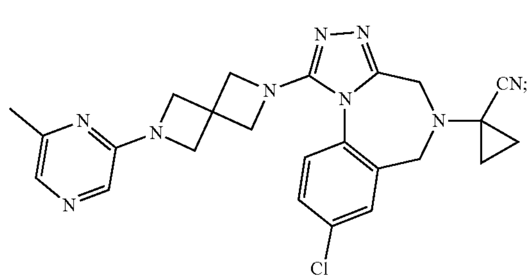 [SMILES: Cc1cncc(N2CC3(C2)CN(c2nnc4n2-c2ccc(Cl)cc2CN(C2(C#N)CC2)C4)C3)n1] |

| Compound No. | Structure |
|---|---|
| 1007 | 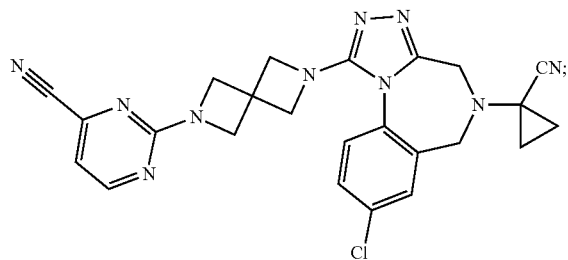 [SMILES: N#Cc1ccnc(N2CC3(C2)CN(c2nnc4n2-c2ccc(Cl)cc2CN(C2(C#N)CC2)C4)C3)n1] |
| 1008 | 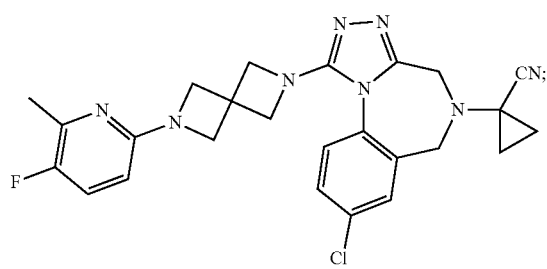 [SMILES: Cc1nc(N2CC3(C2)CN(c2nnc4n2-c2ccc(Cl)cc2CN(C2(C#N)CC2)C4)C3)ccc1F] |
| 1009 | 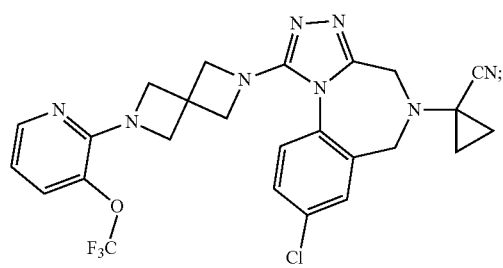 [SMILES: N#CC1(N2Cc3cc(Cl)ccc3-n3c(nnc3N3CC4(CN(c5ncccc5OC(F)(F)F)C4)C3)C2)CC1] |
| 1010 | 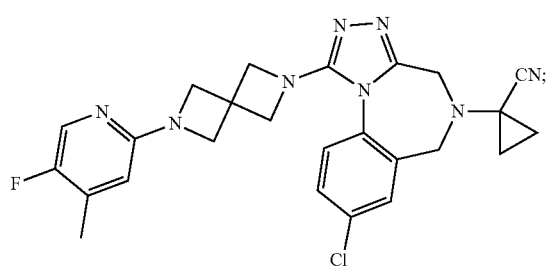 [SMILES: Cc1cc(N2CC3(C2)CN(c2nnc4n2-c2ccc(Cl)cc2CN(C2(C#N)CC2)C4)C3)ncc1F] |
| 1011 | 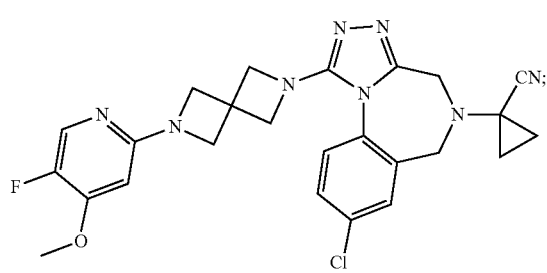 [SMILES: COc1cc(N2CC3(C2)CN(c2nnc4n2-c2ccc(Cl)cc2CN(C2(C#N)CC2)C4)C3)ncc1F] |

-continued

| Compound No. | Structure |
| --- | --- |
| 1012 | 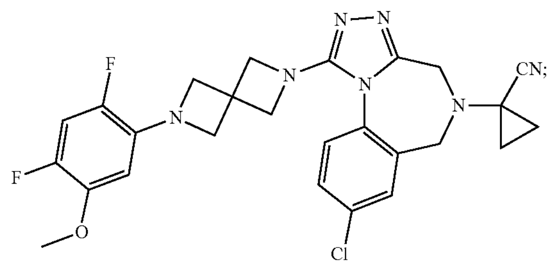 [SMILES: COc1cc(N2CC3(C2)CN(c2nnc4n2-c2ccc(Cl)cc2CN(C2(C#N)CC2)C4)C3)c(F)cc1F] |
| 1013 | 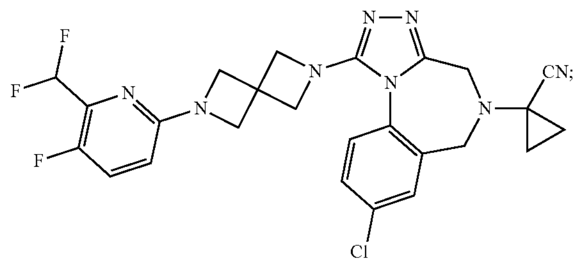 [SMILES: N#CC1(N2Cc3cc(Cl)ccc3-n3c(nnc3N3CC4(CN(c5ccc(F)c(C(F)F)n5)C4)C3)C2)CC1] |
| 1014 | 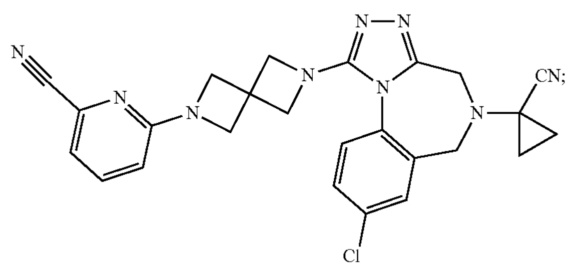 [SMILES: N#Cc1cccc(N2CC3(C2)CN(c2nnc4n2-c2ccc(Cl)cc2CN(C2(C#N)CC2)C4)C3)n1] |
| 1015 | 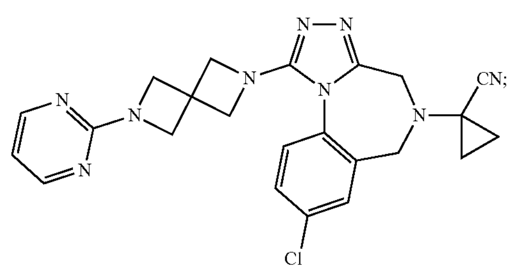 [SMILES: N#CC1(N2Cc3cc(Cl)ccc3-n3c(nnc3N3CC4(CN(c5ncccn5)C4)C3)C2)CC1] |
| 1016 | 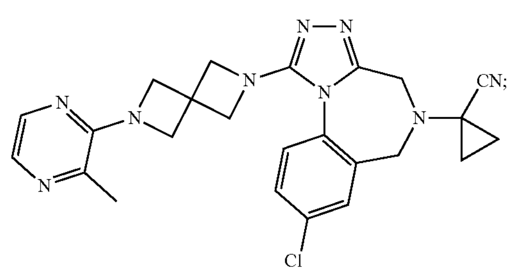 [SMILES: Cc1nccnc1N1CC2(C1)CN(c1nnc3n1-c1ccc(Cl)cc1CN(C1(C#N)CC1)C3)C2] |
| 1017 | 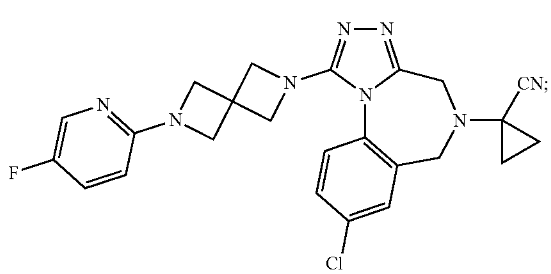 [SMILES: N#CC1(N2Cc3cc(Cl)ccc3-n3c(nnc3N3CC4(CN(c5ccc(F)cn5)C4)C3)C2)CC1] |

-continued
| Compound No. | Structure |
|---|---|
| 1018 | 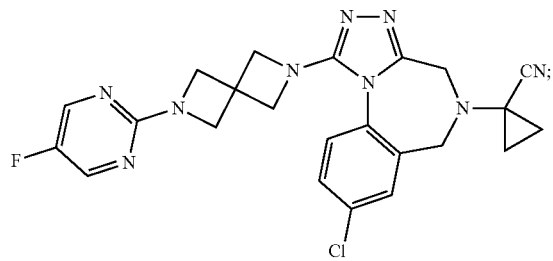 [SMILES: N#CC1(N2Cc3cc(Cl)ccc3-n3c(nnc3N3CC4(CN(c5ncc(F)cn5)C4)C3)C2)CC1] |
| 1019 | 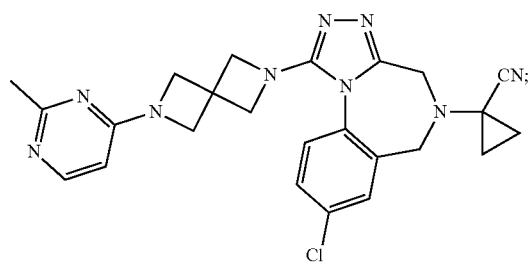 [SMILES: Cc1nccc(N2CC3(C2)CN(c2nnc4n2-c2ccc(Cl)cc2CN(C2(C#N)CC2)C4)C3)n1] |
| 1020 | 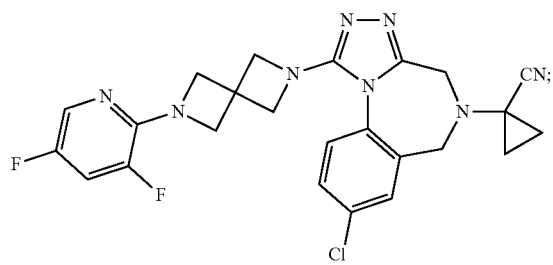 |
| 1021 | 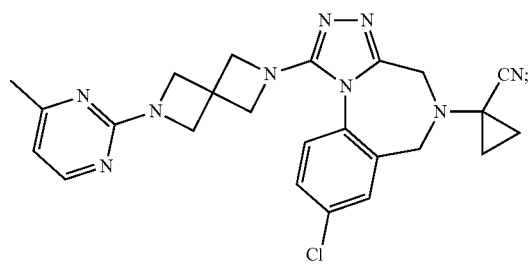 [SMILES: Cc1ccnc(N2CC3(C2)CN(c2nnc4n2-c2ccc(Cl)cc2CN(C2(C#N)CC2)C4)C3)n1] |
| 1022 | 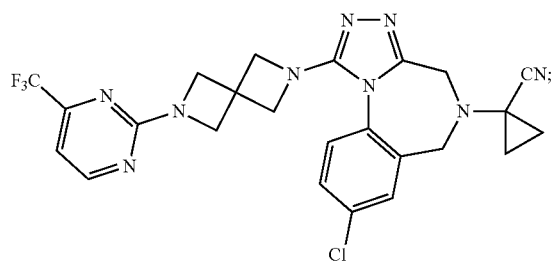 [SMILES: N#CC1(N2Cc3cc(Cl)ccc3-n3c(nnc3N3CC4(CN(c5nccc(C(F)(F)F)n5)C4)C3)C2)CC1] |
| 1023 | 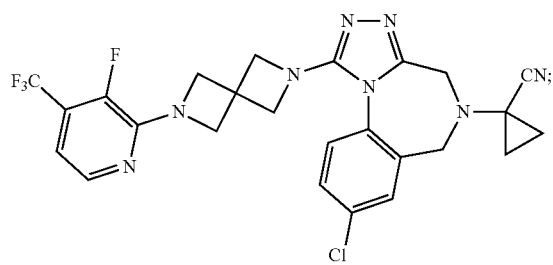 [SMILES: N#CC1(N2Cc3cc(Cl)ccc3-n3c(nnc3N3CC4(CN(c5nccc(C(F)(F)F)c5F)C4)C3)C2)CC1] |

-continued
| Compound No. | Structure |
|---|---|
| 1024 | 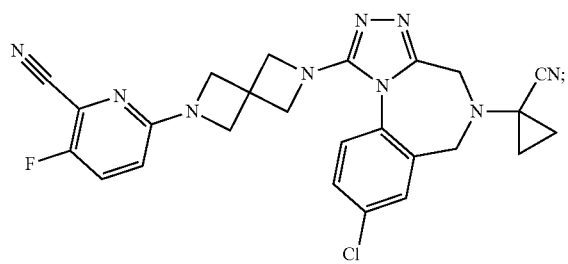 [SMILES: N#Cc1nc(N2CC3(C2)CN(c2nnc4n2-c2ccc(Cl)cc2CN(C2(C#N)CC2)C4)C3)ccc1F] |
| 1025 | 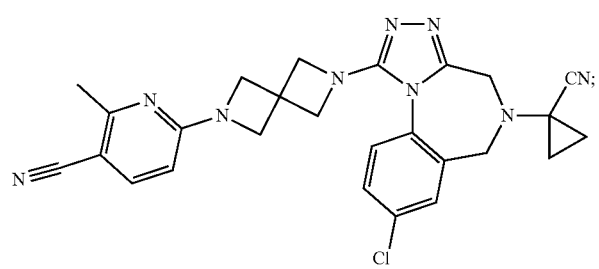 [SMILES: Cc1nc(N2CC3(C2)CN(c2nnc4n2-c2ccc(Cl)cc2CN(C2(C#N)CC2)C4)C3)ccc1C#N] |
| 1026 | 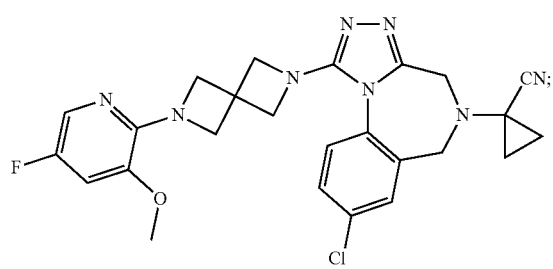 [SMILES: COc1cc(F)cnc1N1CC2(C1)CN(c1nnc3n1-c1ccc(Cl)cc1CN(C1(C#N)CC1)C3)C2] |
| 1027 | 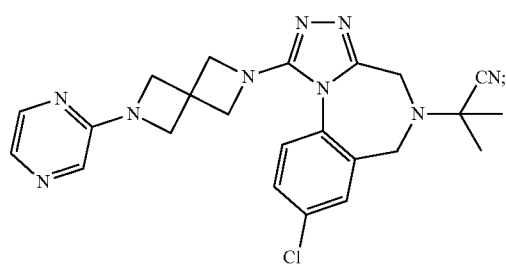 [SMILES: CC(C)(C#N)N1Cc2cc(Cl)ccc2-n2c(nnc2N2CC3(CN(c4cnccn4)C3)C2)C1] |
| 1028 | 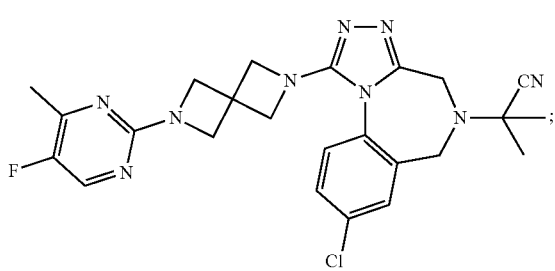 [SMILES: Cc1nc(N2CC3(C2)CN(c2nnc4n2-c2ccc(Cl)cc2CN(C(C)(C)C#N)C4)C3)ncc1F] |

| Compound No. | Structure |
|---|---|
| 1029 | *(structure)* |
| 1030 | *(structure)* |
| 1031 | *(structure)* |
| 1032 | *(structure)* |
| 1033 | *(structure)* |
| 1034 | *(structure)* |

-continued
| Compound No. | Structure |
|---|---|
| 1035 | 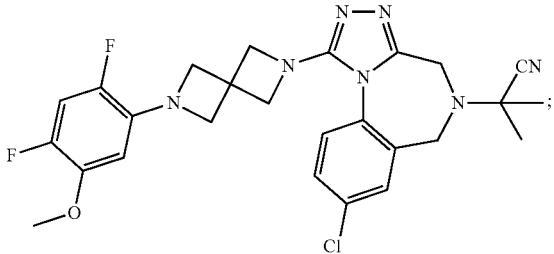 [SMILES: COc1cc(N2CC3(C2)CN(c2nnc4n2-c2ccc(Cl)cc2CN(C(C)(C)C#N)C4)C3)c(F)cc1F] |
| 1036 | 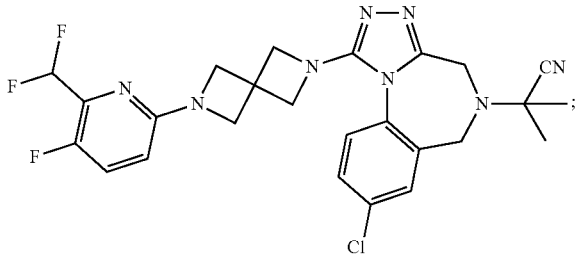 [SMILES: CC(C)(C#N)N1Cc2cc(Cl)ccc2-n2c(nnc2N2CC3(CN(c4ccc(F)c(C(F)F)n4)C3)C2)C1] |
| 1037 | 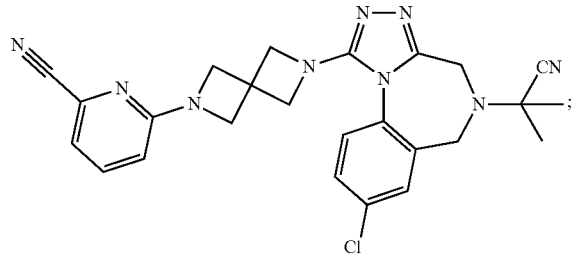 [SMILES: CC(C)(C#N)N1Cc2cc(Cl)ccc2-n2c(nnc2N2CC3(CN(c4cccc(C#N)n4)C3)C2)C1] |
| 1038 | 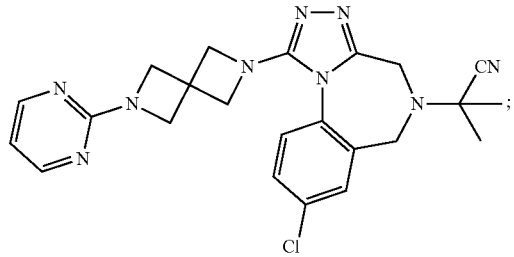 [SMILES: CC(C)(C#N)N1Cc2cc(Cl)ccc2-n2c(nnc2N2CC3(CN(c4ncccn4)C3)C2)C1] |
| 1039 | 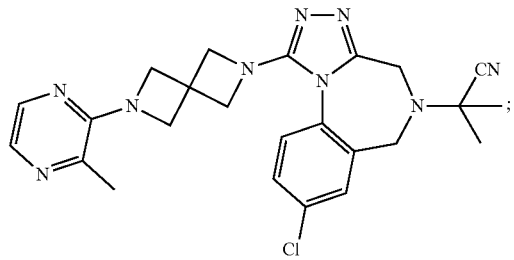 [SMILES: Cc1nccnc1N1CC2(C1)CN(c1nnc3n1-c1ccc(Cl)cc1CN(C(C)(C)C#N)C3)C2] |
| 1040 | 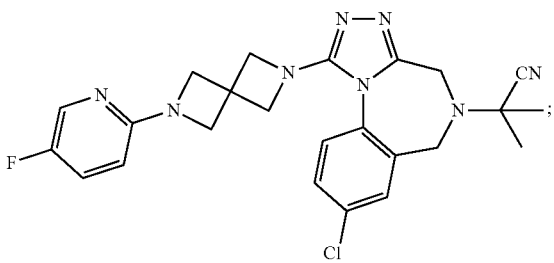 |

-continued
| Compound No. | Structure |
|---|---|
| 1041 | 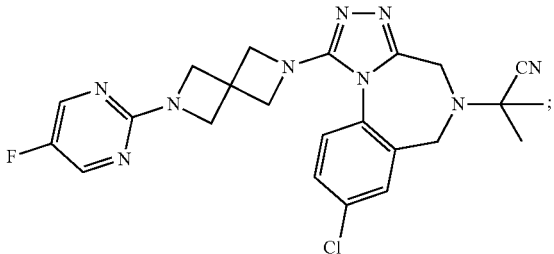 [SMILES: CC(C)(C#N)N1Cc2cc(Cl)ccc2-n2c(nnc2N2CC3(CN(c4ncc(F)cn4)C3)C2)C1] |
| 1042 | 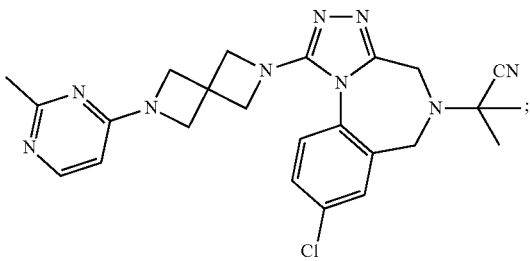 [SMILES: Cc1nccc(N2CC3(C2)CN(c2nnc4n2-c2ccc(Cl)cc2CN(C(C)(C)C#N)C4)C3)n1] |
| 1043 | 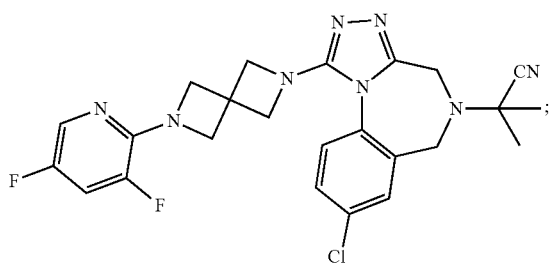 [SMILES: CC(C)(C#N)N1Cc2cc(Cl)ccc2-n2c(nnc2N2CC3(CN(c4ncc(F)cc4F)C3)C2)C1] |
| 1044 | 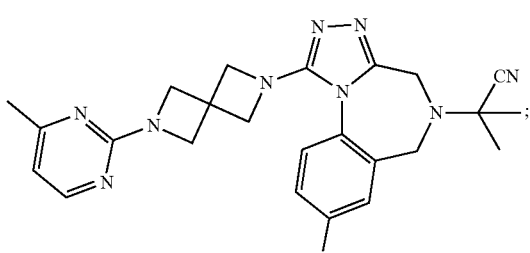 |
| 1045 | 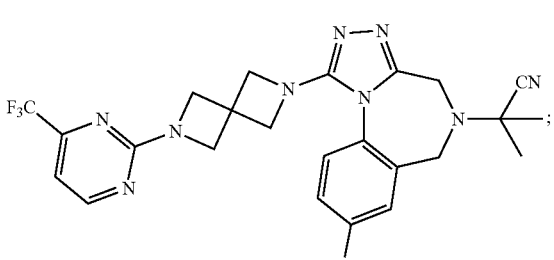 |
| 1046 | 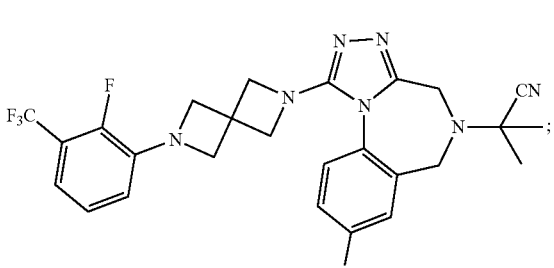 |

-continued
| Compound No. | Structure |
|---|---|
| 1047 | 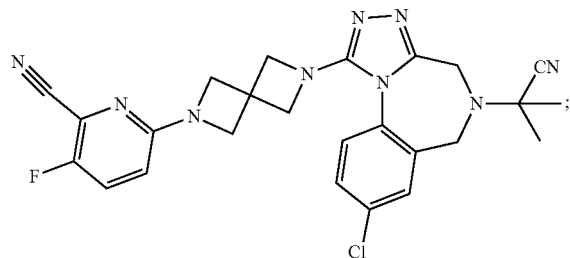 [SMILES: CC(C)(C#N)N1Cc2cc(Cl)ccc2-n2c(nnc2N2CC3(CN(c4ccc(F)c(C#N)n4)C3)C2)C1] |
| 1048 | 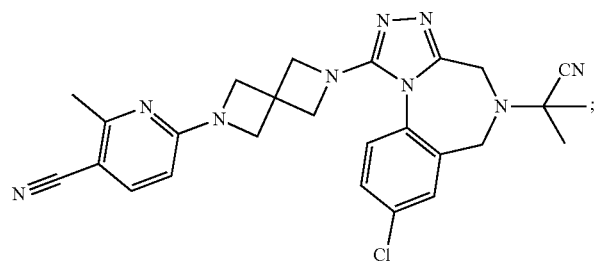 [SMILES: Cc1nc(N2CC3(C2)CN(c2nnc4n2-c2ccc(Cl)cc2CN(C(C)(C)C#N)C4)C3)ccc1C#N] |
| 1049 | 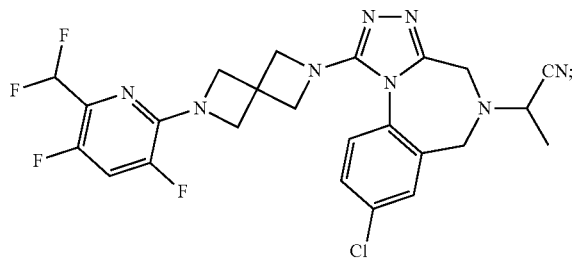 [SMILES: CC(C#N)N1Cc2cc(Cl)ccc2-n2c(nnc2N2CC3(CN(c4nc(C(F)F)c(F)cc4F)C3)C2)C1] |
| 1050 | 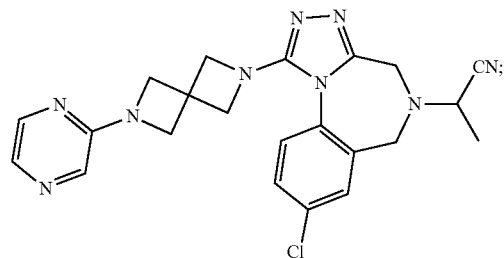 [SMILES: CC(C#N)N1Cc2cc(Cl)ccc2-n2c(nnc2N2CC3(CN(c4cnccn4)C3)C2)C1] |
| 1051 | 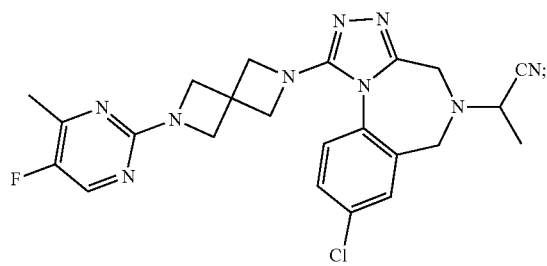 [SMILES: Cc1nc(N2CC3(C2)CN(c2nnc4n2-c2ccc(Cl)cc2CN(C(C)C#N)C4)C3)ncc1F] |

-continued

| Compound No. | Structure |
|---|---|
| 1052 | 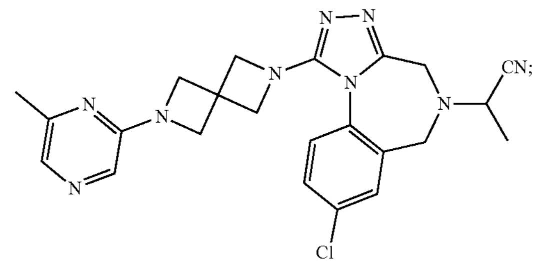 [SMILES: Cc1cncc(N2CC3(C2)CN(c2nnc4n2-c2ccc(Cl)cc2CN(C(C)C#N)C4)C3)n1] |
| 1053 | 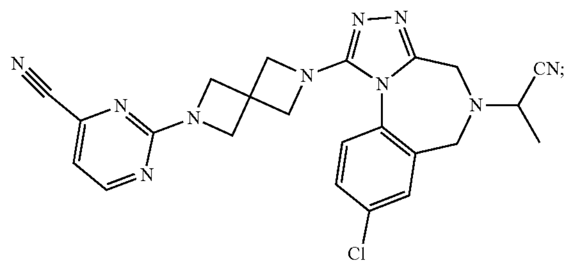 [SMILES: CC(C#N)N1Cc2cc(Cl)ccc2-n2c(nnc2N2CC3(CN(c4nccc(C#N)n4)C3)C2)C1] |
| 1054 | 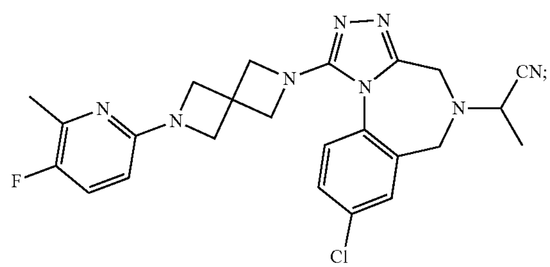 [SMILES: Cc1nc(N2CC3(C2)CN(c2nnc4n2-c2ccc(Cl)cc2CN(C(C)C#N)C4)C3)ccc1F] |
| 1055 | 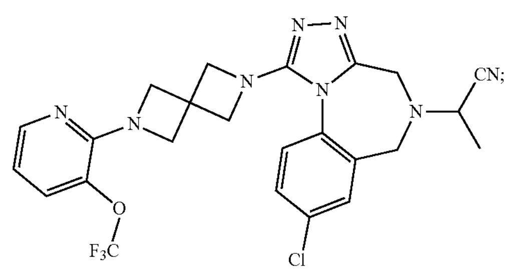 [SMILES: CC(C#N)N1Cc2cc(Cl)ccc2-n2c(nnc2N2CC3(CN(c4ncccc4OC(F)(F)F)C3)C2)C1] |
| 1056 | 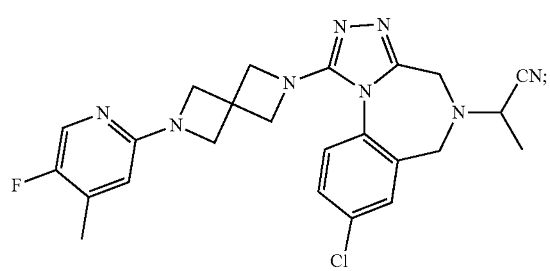 [SMILES: Cc1cc(N2CC3(C2)CN(c2nnc4n2-c2ccc(Cl)cc2CN(C(C)C#N)C4)C3)ncc1F] |
| 1057 | 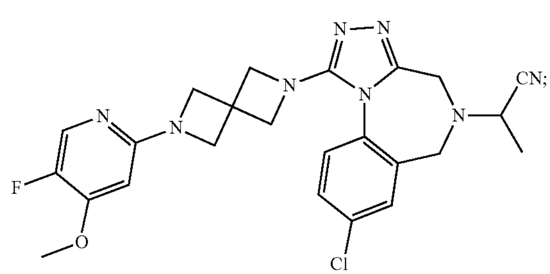 [SMILES: COc1cc(N2CC3(C2)CN(c2nnc4n2-c2ccc(Cl)cc2CN(C(C)C#N)C4)C3)ncc1F] |

-continued

| Compound No. | Structure |
|---|---|
| 1058 | 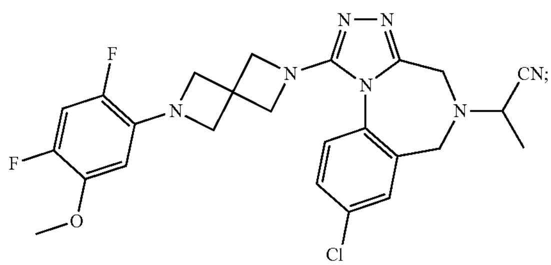 [SMILES: COc1cc(N2CC3(C2)CN(c2nnc4n2-c2ccc(Cl)cc2CN(C(C)C#N)C4)C3)c(F)cc1F] |
| 1059 | 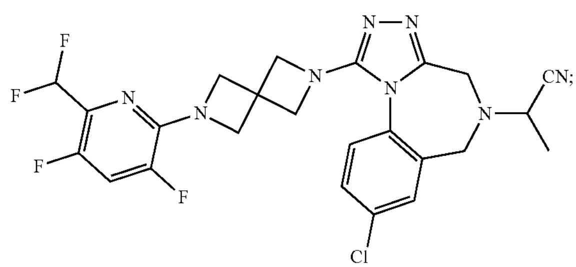 [SMILES: CC(C#N)N1Cc2cc(Cl)ccc2-n2c(nnc2N2CC3(CN(c4nc(C(F)F)c(F)cc4F)C3)C2)C1] |
| 1060 | 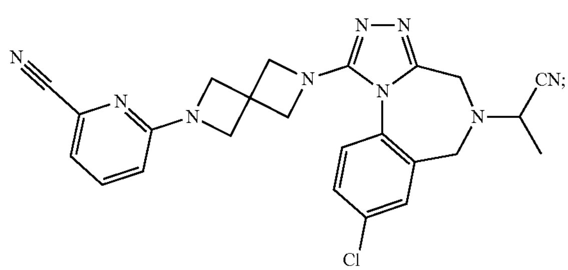 [SMILES: CC(C#N)N1Cc2cc(Cl)ccc2-n2c(nnc2N2CC3(CN(c4cccc(C#N)n4)C3)C2)C1] |
| 1061 | 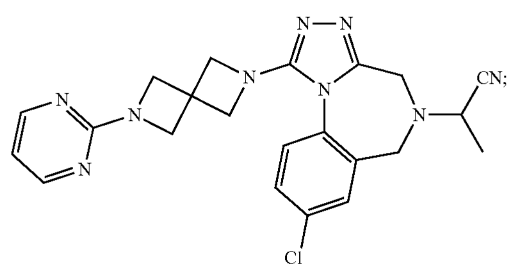 [SMILES: CC(C#N)N1Cc2cc(Cl)ccc2-n2c(nnc2N2CC3(CN(c4ncccn4)C3)C2)C1] |
| 1062 | 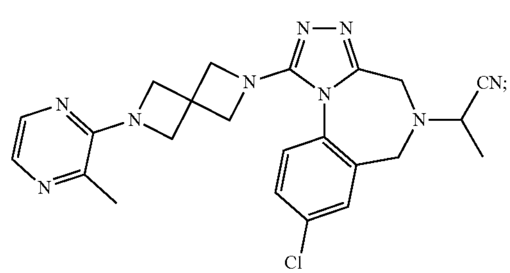 [SMILES: Cc1nccnc1N1CC2(C1)CN(c1nnc3n1-c1ccc(Cl)cc1CN(C(C)C#N)C3)C2] |
| 1063 | 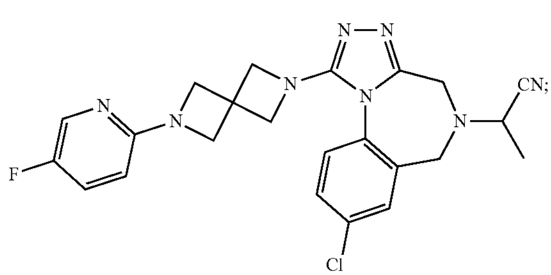 [SMILES: CC(C#N)N1Cc2cc(Cl)ccc2-n2c(nnc2N2CC3(CN(c4ccc(F)cn4)C3)C2)C1] |

-continued
| Compound No. | Structure |
|---|---|
| 1064 | 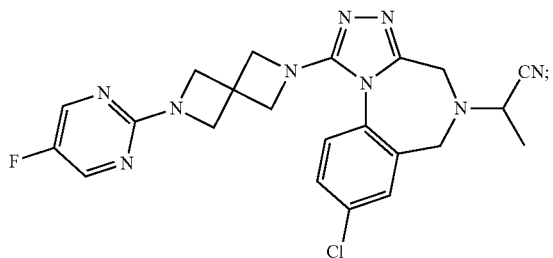 [SMILES: CC(C#N)N1Cc2cc(Cl)ccc2-n2c(nnc2N2CC3(CN(c4ncc(F)cn4)C3)C2)C1] |
| 1065 | 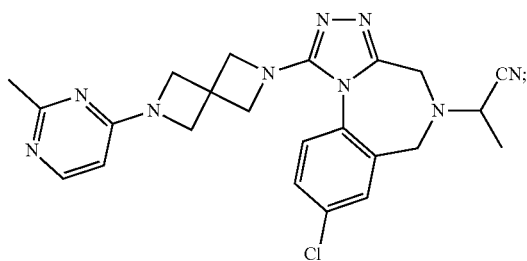 [SMILES: Cc1nccc(N2CC3(C2)CN(c2nnc4n2-c2ccc(Cl)cc2CN(C(C)C#N)C4)C3)n1] |
| 1066 | 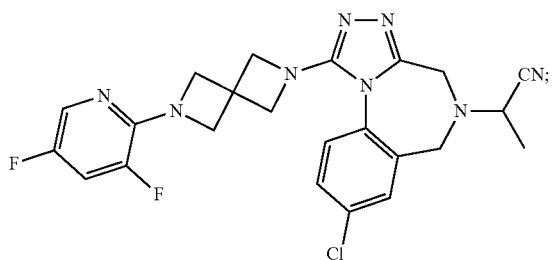 [SMILES: CC(C#N)N1Cc2cc(Cl)ccc2-n2c(nnc2N2CC3(CN(c4ncc(F)cc4F)C3)C2)C1] |
| 1067 | 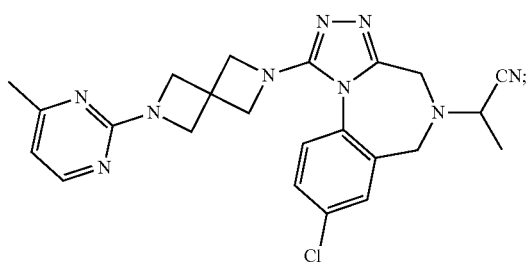 |
| 1068 | 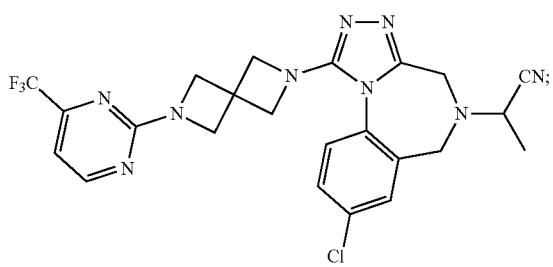 [SMILES: CC(C#N)N1Cc2cc(Cl)ccc2-n2c(nnc2N2CC3(CN(c4nccc(C(F)(F)F)n4)C3)C2)C1] |
| 1069 | 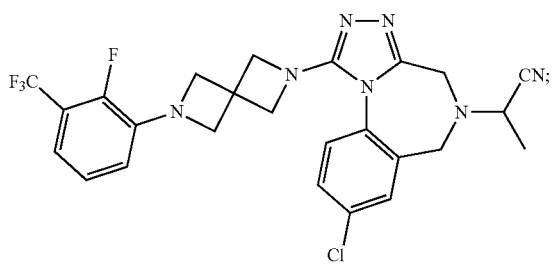 [SMILES: CC(C#N)N1Cc2cc(Cl)ccc2-n2c(nnc2N2CC3(CN(c4cccc(C(F)(F)F)c4F)C3)C2)C1] |

-continued

| Compound No. | Structure |
|---|---|
| 1070 | 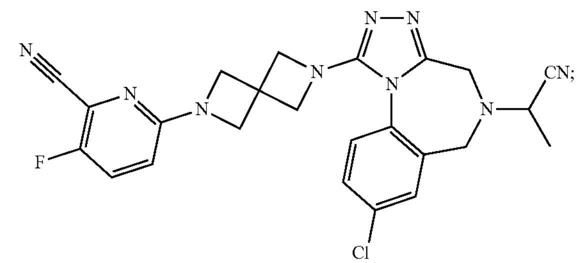 [SMILES: CC(C#N)N1Cc2cc(Cl)ccc2-n2c(nnc2N2CC3(CN(c4ccc(F)c(C#N)n4)C3)C2)C1] |
| 1071 | 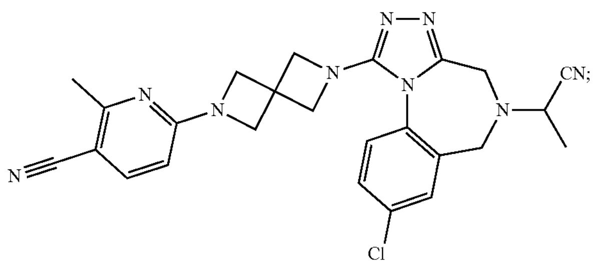 [SMILES: Cc1nc(N2CC3(C2)CN(c2nnc4n2-c2ccc(Cl)cc2CN(C(C)C#N)C4)C3)ccc1C#N] |
| 1072 | 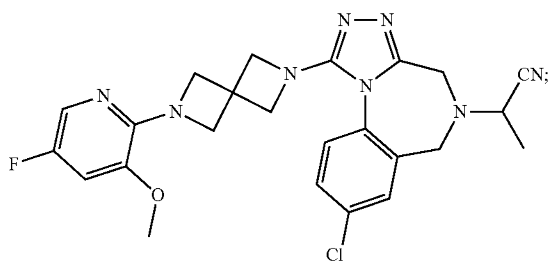 [SMILES: COc1cc(F)cnc1N1CC2(C1)CN(c1nnc3n1-c1ccc(Cl)cc1CN(C(C)C#N)C3)C2] |
| 1073 | 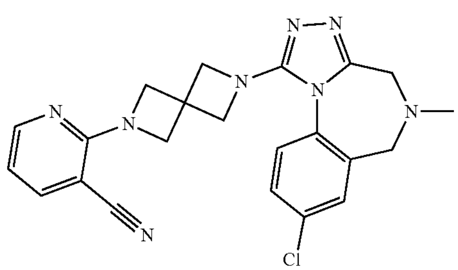 |
| 1074 | 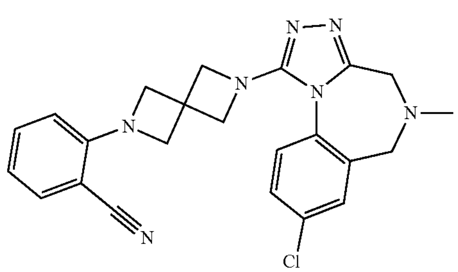 |
| 1075 | 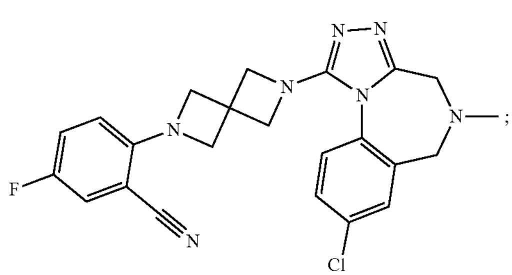 [SMILES: CN1Cc2cc(Cl)ccc2-n2c(nnc2N2CC3(CN(c4ccc(F)cc4C#N)C3)C2)C1] |

| Compound No. | Structure |
| --- | --- |
| 1076 | 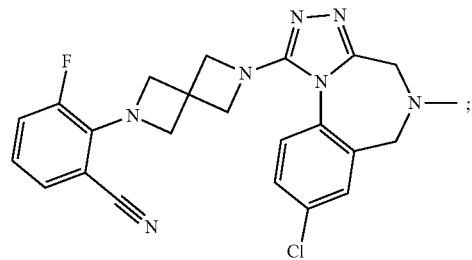 [SMILES: CN1Cc2cc(Cl)ccc2-n2c(nnc2N2CC3(CN(c4c(F)cccc4C#N)C3)C2)C1] |
| 1077 | 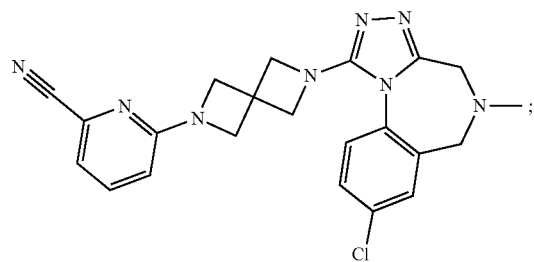 [SMILES: CN1Cc2cc(Cl)ccc2-n2c(nnc2N2CC3(CN(c4cccc(C#N)n4)C3)C2)C1] |
| 1078 | 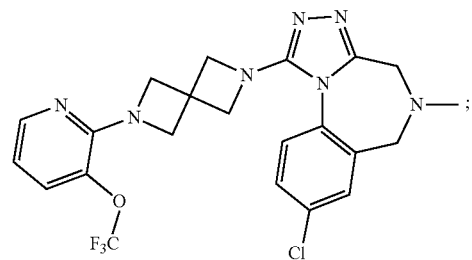 [SMILES: CN1Cc2cc(Cl)ccc2-n2c(nnc2N2CC3(CN(c4ncccc4OC(F)(F)F)C3)C2)C1] |
| 1079 | 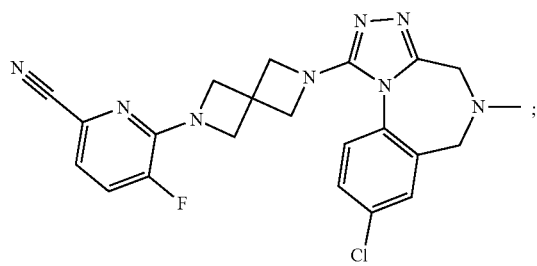 [SMILES: CN1Cc2cc(Cl)ccc2-n2c(nnc2N2CC3(CN(c4nc(C#N)ccc4F)C3)C2)C1] |
| 1080 | 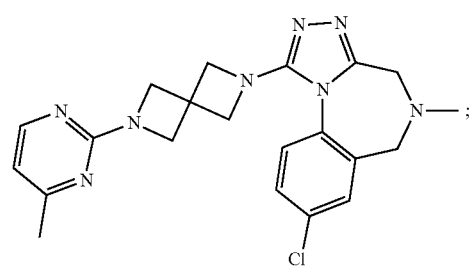 [SMILES: Cc1ccnc(N2CC3(C2)CN(c2nnc4n2-c2ccc(Cl)cc2CN(C)C4)C3)n1] |

-continued
| Compound No. | Structure |
|---|---|
| 1081 | 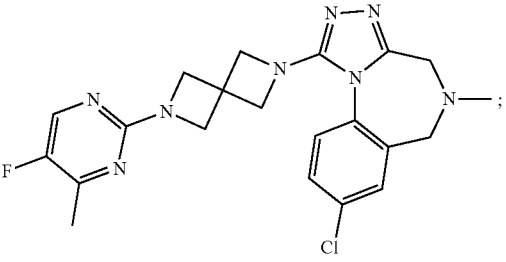 [SMILES: Cc1nc(N2CC3(C2)CN(c2nnc4n2-c2ccc(Cl)cc2CN(C)C4)C3)ncc1F] |
| 1082 | 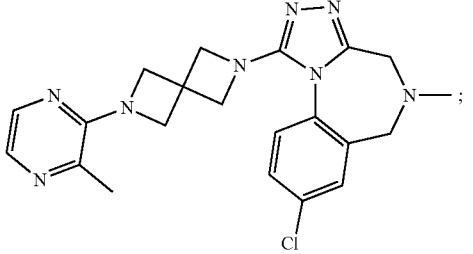 [SMILES: Cc1nccnc1N1CC2(C1)CN(c1nnc3n1-c1ccc(Cl)cc1CN(C)C3)C2] |
| 1083 | 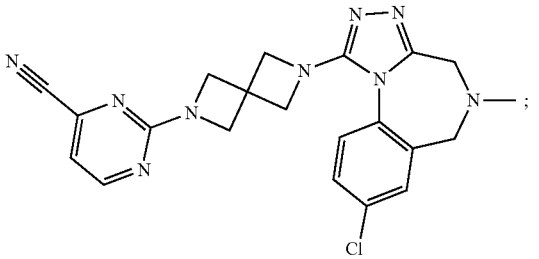 [SMILES: CN1Cc2cc(Cl)ccc2-n2c(nnc2N2CC3(CN(c4nccc(C#N)n4)C3)C2)C1] |
| 1084 | 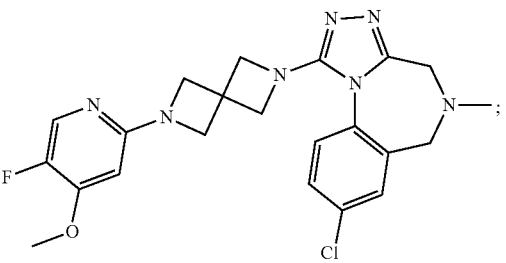 [SMILES: COc1cc(N2CC3(C2)CN(c2nnc4n2-c2ccc(Cl)cc2CN(C)C4)C3)ncc1F] |
| 1085 | 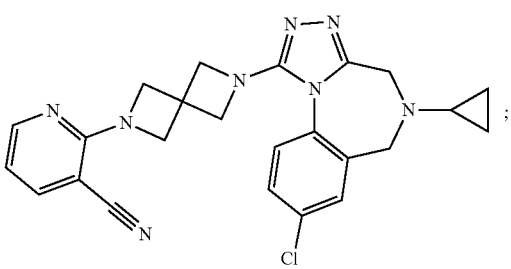 [SMILES: N#Cc1cccnc1N1CC2(C1)CN(c1nnc3n1-c1ccc(Cl)cc1CN(C1CC1)C3)C2] |
| 1086 | 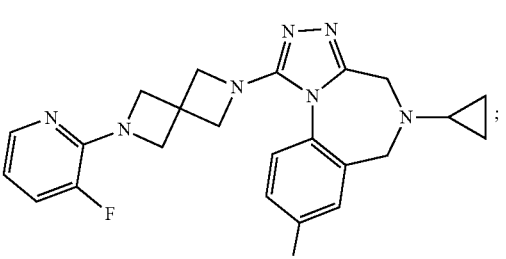 |

| Compound No. | Structure |
|---|---|
| 1087 | 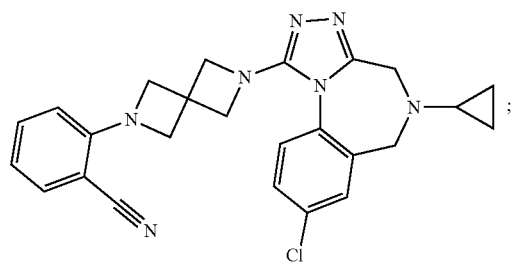 [SMILES: N#Cc1ccccc1N1CC2(C1)CN(c1nnc3n1-c1ccc(Cl)cc1CN(C1CC1)C3)C2] |
| 1088 | 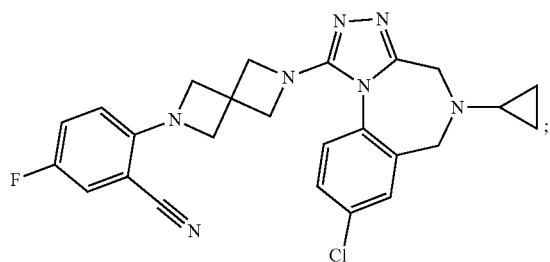 [SMILES: N#Cc1cc(F)ccc1N1CC2(C1)CN(c1nnc3n1-c1ccc(Cl)cc1CN(C1CC1)C3)C2] |
| 1089 | 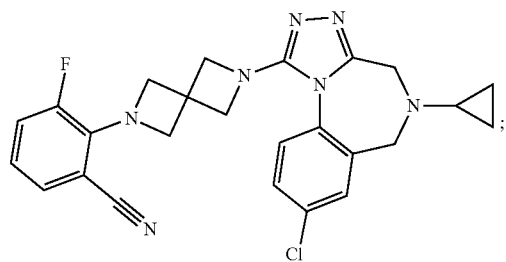 [SMILES: N#Cc1cccc(F)c1N1CC2(C1)CN(c1nnc3n1-c1ccc(Cl)cc1CN(C1CC1)C3)C2] |
| 1090 | 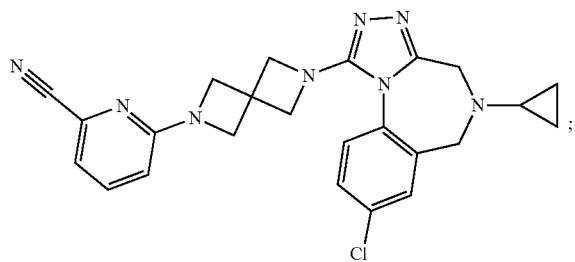 [SMILES: N#Cc1cccc(N2CC3(C2)CN(c2nnc4n2-c2ccc(Cl)cc2CN(C2CC2)C4)C3)n1] |
| 1091 | 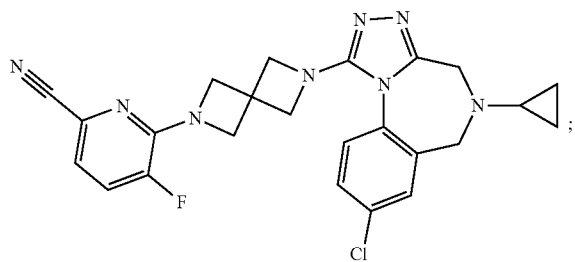 [SMILES: N#Cc1ccc(F)c(N2CC3(C2)CN(c2nnc4n2-c2ccc(Cl)cc2CN(C2CC2)C4)C3)n1] |

-continued
| Compound No. | Structure |
|---|---|
| 1092 | 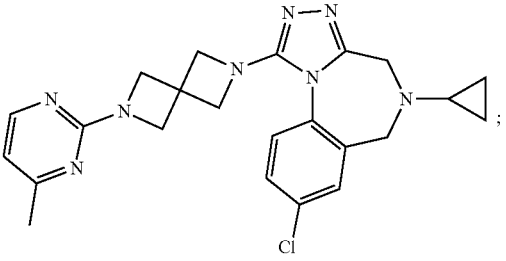 [SMILES: Cc1ccnc(N2CC3(C2)CN(c2nnc4n2-c2ccc(Cl)cc2CN(C2CC2)C4)C3)n1] |
| 1093 | 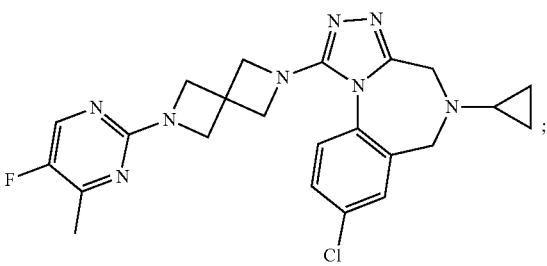 [SMILES: Cc1nc(N2CC3(C2)CN(c2nnc4n2-c2ccc(Cl)cc2CN(C2CC2)C4)C3)ncc1F] |
| 1094 | 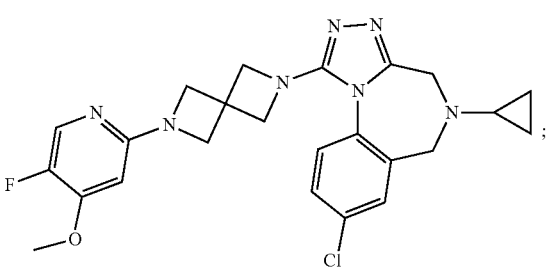 [SMILES: COc1cc(N2CC3(C2)CN(c2nnc4n2-c2ccc(Cl)cc2CN(C2CC2)C4)C3)ncc1F] |
| 1095 | 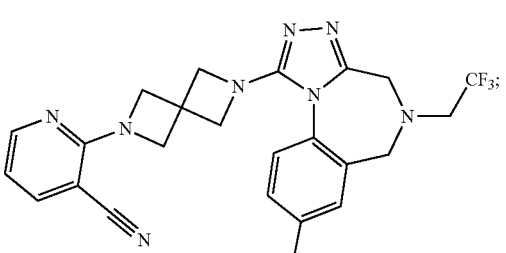 |
| 1096 | 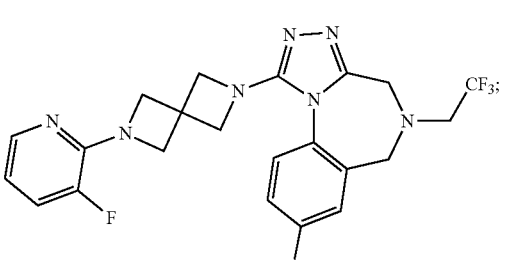 |
| 1097 | 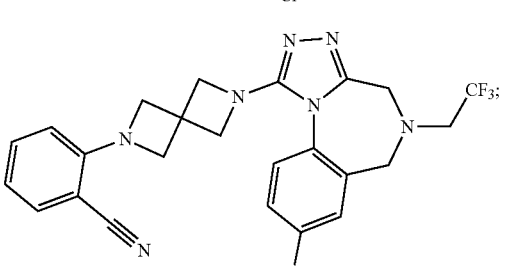 |

-continued

| Compound No. | Structure |
|---|---|
| 1098 | (structure) |
| 1099 | (structure) |
| 1100 | (structure) |
| 1101 | (structure) or |
| 1102 | (structure) |

24. A composition comprising a compound of claim 1, or a pharmaceutically acceptable isomer, racemate, hydrate, solvate, isotope, or salt thereof, and a pharmaceutically acceptable carrier, diluent, or excipient.

25. A method for antagonizing the V1a receptor, comprising contacting the V1a receptor with an effective amount of a compound of claim 1, or a pharmaceutically acceptable isomer, racemate, hydrate, solvate, isotope, or salt thereof, or a composition comprising the same.

26. A method for treating a vasopressin-dependent condition or a condition related to inappropriate secretion of vasopressin, comprising administering to a subject afflicted with a vasopressin-dependent condition or a condition related to inappropriate secretion of vasopressin an effective amount of a compound of claim 1, or a pharmaceutically acceptable isomer, racemate, hydrate, solvate, isotope, or salt thereof, or a pharmaceutical composition comprising the same, at a frequency and for a duration sufficient to provide a beneficial effect to the subject.

27. A method for treating a neuropsychological disorder, comprising administering to a subject afflicted with a neuropsychological disorder an effective amount of a compound of claim 1, or a pharmaceutically acceptable isomer, racemate, hydrate, solvate, isotope, or salt thereof, or a pharmaceutical composition comprising the same, at a frequency and for a duration sufficient to provide a beneficial effect to the subject.

28. A method for treating a circadian rhythm related disorder, comprising administering to a subject afflicted with a circadian rhythm related disorder an effective amount of a compound of claim 1, or a pharmaceutically acceptable isomer, racemate, hydrate, solvate, isotope or salt thereof, or a pharmaceutical composition comprising the same, at a frequency and for duration sufficient to provide a beneficial effect to the subject.

29. A method for the therapeutic treatment of chronic stress related infertility, primary or secondary dysmenorrhea, or male or female sexual dysfunction comprising administering to a subject in need thereof an effective amount of a compound of claim 1, or a pharmaceutically acceptable isomer, racemate, hydrate, solvate, isotope or salt thereof, or a pharmaceutical composition comprising the same, at a frequency and for duration sufficient to provide a beneficial effect to the subject.

* * * * *